US010351906B2

(12) United States Patent
Zimmermann et al.

(10) Patent No.: US 10,351,906 B2
(45) Date of Patent: *Jul. 16, 2019

(54) METHODS FOR SIMULTANEOUS AMPLIFICATION OF TARGET LOCI

(71) Applicant: Natera, Inc., San Carlos, CA (US)

(72) Inventors: Bernhard Zimmermann, San Mateo, CA (US); Matthew Hill, Redwood City, CA (US); Philippe Lacroute, Sunnyvale, CA (US); Michael Dodd, San Francisco, CA (US); Alexander Wong, Mountain View, CA (US)

(73) Assignee: Natera, Inc., San Carlos, CA (US)

( * ) Notice: Subject to any disclaimer, the term of this patent is extended or adjusted under 35 U.S.C. 154(b) by 255 days.

This patent is subject to a terminal disclaimer.

(21) Appl. No.: 15/336,630

(22) Filed: Oct. 27, 2016

(65) Prior Publication Data
US 2017/0145474 A1    May 25, 2017

Related U.S. Application Data

(63) Continuation of application No. 14/538,982, filed on Nov. 24, 2014, now Pat. No. 9,677,118.

(60) Provisional application No. 62/066,514, filed on Oct. 21, 2014, provisional application No. 61/994,791, filed on May 16, 2014, provisional application No. 61/987,407, filed on May 1, 2014, provisional application No. 61/982,245, filed on Apr. 21, 2014.

(51) Int. Cl.
| C12Q 1/68 | (2018.01) |
| C12Q 1/686 | (2018.01) |
| C12Q 1/6874 | (2018.01) |
| C12Q 1/6883 | (2018.01) |
| C12Q 1/6811 | (2018.01) |
| C12Q 1/6848 | (2018.01) |

(52) U.S. Cl.
CPC .............. *C12Q 1/686* (2013.01); *C12Q 1/68* (2013.01); *C12Q 1/6811* (2013.01); *C12Q 1/6848* (2013.01); *C12Q 1/6874* (2013.01); *C12Q 1/6883* (2013.01); *C12Q 2600/156* (2013.01)

(58) Field of Classification Search
None
See application file for complete search history.

(56) References Cited

U.S. PATENT DOCUMENTS

| 5,635,366 A | 6/1997 | Cooke et al. |
| 5,716,776 A | 2/1998 | Bogart |
| 5,753,467 A | 5/1998 | Jensen et al. |
| 5,824,467 A | 10/1998 | Mascarenhas |
| 5,860,917 A | 1/1999 | Comanor et al. |
| 5,972,602 A | 11/1999 | Hyland et al. |
| 5,994,148 A | 11/1999 | Stewart et al. |
| 6,001,611 A | 12/1999 | Will |
| 6,025,128 A | 2/2000 | Veltri et al. |
| 6,066,454 A | 5/2000 | Lipshutz et al. |
| 6,100,029 A | 8/2000 | Lapidus et al. |
| 6,108,635 A | 8/2000 | Herren et al. |
| 6,143,496 A | 11/2000 | Brown et al. |
| 6,180,349 B1 | 1/2001 | Ginzinger |
| 6,214,558 B1 | 4/2001 | Shuber et al. |
| 6,258,540 B1 | 7/2001 | Lo et al. |
| 6,300,077 B1 | 10/2001 | Shuber et al. |
| 6,479,235 B1 | 11/2002 | Schumm et al. |
| 6,440,706 B1 | 12/2002 | Vogelstein et al. |
| 6,489,135 B1 | 12/2002 | Parrott et al. |
| 6,720,140 B1 | 4/2004 | Hartley et al. |
| 6,807,491 B2 | 10/2004 | Pavlovic et al. |
| 6,852,487 B1 | 10/2005 | Barany et al. |
| 6,958,211 B2 | 10/2005 | Vingerhoets et al. |
| 6,964,847 B1 | 11/2005 | Englert |
| 7,035,739 B2 | 4/2006 | Schadt et al. |
| 7,058,517 B1 | 6/2006 | Denton et al. |
| 7,058,616 B1 | 6/2006 | Larder et al. |
| 7,218,764 B2 | 5/2007 | Vaisberg et al. |
| 7,297,485 B2 | 11/2007 | Bornarth et al. |
| 7,332,277 B2 | 2/2008 | Dhallan |
| 7,414,118 B1 | 8/2008 | Mullah et al. |
| 7,442,506 B2 | 12/2008 | Dhallan |
| 7,459,273 B2 | 12/2008 | Jones et al. |
| 7,645,576 B2 | 1/2010 | Lo et al. |
| 7,700,325 B2 | 4/2010 | Cantor et al. |
| 7,718,367 B2 | 5/2010 | Lo et al. |
| 7,718,370 B2 | 6/2010 | Dhallan |
| 7,727,720 B2 | 9/2010 | Dhallan |
| 7,805,282 B2 | 11/2010 | Casey |

(Continued)

FOREIGN PATENT DOCUMENTS

| CN | 1650032 A | 8/2005 |
| CN | 1674028 A | 9/2005 |

(Continued)

OTHER PUBLICATIONS

Ishii et al. (Appl Environ Micro, 2001, 67(8):3753-3755) (Year: 2001).*

(Continued)

*Primary Examiner* — Stephanie K Mummert

(57) ABSTRACT

The invention provides methods for simultaneously amplifying multiple nucleic acid regions of interest in one reaction volume as well as methods for selecting a library of primers for use in such amplification methods. The invention also provides library of primers with desirable characteristics, such as minimal formation of amplified primer dimers or other non-target amplicons.

20 Claims, 290 Drawing Sheets

Specification includes a Sequence Listing.

(56) References Cited

U.S. PATENT DOCUMENTS

| | | |
|---|---|---|
| 7,838,647 B2 | 11/2010 | Hahn et al. |
| 7,888,017 B2 | 8/2011 | Quake |
| 8,008,018 B2 | 9/2011 | Quake et al. |
| 8,024,128 B2 | 9/2011 | Rabinowitz |
| 8,137,912 B2 | 5/2012 | Kapur et al. |
| 8,168,389 B2 | 6/2012 | Shoemaker et al. |
| 8,195,415 B2 | 10/2012 | Fan et al. |
| 8,296,076 B2 | 11/2012 | Fan et al. |
| 8,304,187 B2 | 11/2012 | Fernando |
| 8,318,430 B2 | 11/2012 | Chuu et al. |
| 8,467,976 B2 | 8/2013 | Lo et al. |
| 8,515,679 B2 | 9/2013 | Rabinowitz et al. |
| 8,532,930 B2 | 9/2013 | Rabinowitz et al. |
| 8,682,592 B2 | 3/2014 | Rabinowitz et al. |
| 8,825,412 B2 | 9/2014 | Rabinowitz et al. |
| 9,085,798 B2 | 7/2015 | Chee |
| 9,476,095 B2 | 10/2016 | Vogelstein et al. |
| 9,487,829 B2 | 11/2016 | Vogelstein et al. |
| 9,598,731 B2 | 3/2017 | Talasaz |
| 9,677,118 B2 * | 6/2017 | Zimmermann ...... C12Q 1/6811 |
| 10,081,839 B2 | 9/2018 | Rabinowitz et al. |
| 10,083,273 B2 | 9/2018 | Rabinowitz et al. |
| 2001/0053519 A1 | 12/2001 | Fodor et al. |
| 2002/0006622 A1 | 1/2002 | Bradley et al. |
| 2002/0107640 A1 | 8/2002 | Ideker et al. |
| 2003/0009295 A1 | 1/2003 | Markowitz et al. |
| 2003/0065535 A1 | 4/2003 | Karlov et al. |
| 2003/0077586 A1 | 4/2003 | Pavlovic et al. |
| 2003/0101000 A1 | 5/2003 | Bader et al. |
| 2003/0119004 A1 | 6/2003 | Wenz et al. |
| 2003/0228613 A1 | 12/2003 | Bornarth et al. |
| 2004/0033596 A1 | 2/2004 | Threadgill et al. |
| 2004/0137470 A1 | 7/2004 | Dhallan et al. |
| 2004/0146866 A1 | 7/2004 | Fu |
| 2004/0157243 A1 | 8/2004 | Huang et al. |
| 2004/0197797 A1 | 10/2004 | Inoko et al. |
| 2004/0209299 A1 | 10/2004 | Pinter et al. |
| 2004/0229231 A1 | 11/2004 | Frudakis et al. |
| 2004/0236518 A1 | 11/2004 | Pavlovic et al. |
| 2004/0259100 A1 | 12/2004 | Gunderson et al. |
| 2005/0009069 A1 | 1/2005 | Liu et al. |
| 2005/0049793 A1 | 3/2005 | Paterlini-brechot |
| 2005/0079535 A1 | 4/2005 | Kirchgesser et al. |
| 2005/0123914 A1 | 6/2005 | Katz et al. |
| 2005/0130173 A1 | 6/2005 | Leamon et al. |
| 2005/0142577 A1 | 6/2005 | Jones et al. |
| 2005/0144664 A1 | 6/2005 | Smith et al. |
| 2005/0164241 A1 | 7/2005 | Hahn et al. |
| 2005/0216207 A1 | 9/2005 | Kermani |
| 2005/0221341 A1 | 10/2005 | Shimkets et al. |
| 2005/0227263 A1 | 10/2005 | Green et al. |
| 2005/0250111 A1 | 11/2005 | Xie et al. |
| 2005/0255508 A1 | 11/2005 | Casey et al. |
| 2005/0272073 A1 | 12/2005 | Vaisberg et al. |
| 2006/0019278 A1 | 1/2006 | Lo et al. |
| 2006/0040300 A1 | 2/2006 | Dapprich et al. |
| 2006/0052945 A1 | 3/2006 | Rabinowitz et al. |
| 2006/0057618 A1 | 3/2006 | Piper et al. |
| 2006/0068394 A1 | 3/2006 | Langmore et al. |
| 2006/0088574 A1 | 4/2006 | Manning et al. |
| 2006/0099614 A1 | 5/2006 | Gill et al. |
| 2006/0121452 A1 | 6/2006 | Dhallan |
| 2006/0134662 A1 | 6/2006 | Pratt et al. |
| 2006/0141499 A1 | 6/2006 | Sher et al. |
| 2006/0229823 A1 | 8/2006 | Liu |
| 2006/0210997 A1 | 9/2006 | Myerson et al. |
| 2006/0216738 A1 | 9/2006 | Wada et al. |
| 2006/0281105 A1 | 12/2006 | Li et al. |
| 2007/0020640 A1 | 1/2007 | McCloskey et al. |
| 2007/0027636 A1 | 2/2007 | Rabinowitz |
| 2007/0042384 A1 | 2/2007 | Li et al. |
| 2007/0059707 A1 | 3/2007 | Cantor et al. |
| 2007/0122805 A1 | 5/2007 | Cantor et al. |
| 2007/0128624 A1 | 6/2007 | Gormley et al. |
| 2007/0178478 A1 | 8/2007 | Dhallan |
| 2007/0178501 A1 | 8/2007 | Rabinowitz et al. |
| 2007/0184467 A1 | 8/2007 | Rabinowitz et al. |
| 2007/0202525 A1 | 8/2007 | Quake et al. |
| 2007/0202536 A1 | 8/2007 | Yamanishi et al. |
| 2007/0207466 A1 | 9/2007 | Cantor et al. |
| 2007/0212689 A1 | 9/2007 | Bianchi et al. |
| 2007/0243549 A1 | 10/2007 | Bischoff |
| 2007/0259351 A1 | 11/2007 | Chinitz |
| 2008/0020390 A1 | 1/2008 | Mitchell |
| 2008/0026390 A1 | 1/2008 | Stoughton et al. |
| 2008/0038733 A1 | 2/2008 | Bischoff et al. |
| 2008/0070792 A1 | 3/2008 | Stoughton |
| 2008/0071076 A1 | 3/2008 | Hahn et al. |
| 2008/0085836 A1 | 4/2008 | Kearns et al. |
| 2008/0090239 A1 | 4/2008 | Shoemaker et al. |
| 2008/0102455 A1 | 5/2008 | Poetter |
| 2008/0138809 A1 | 6/2008 | Kapur et al. |
| 2008/0182244 A1 | 7/2008 | Tafas et al. |
| 2008/0193927 A1 | 8/2008 | Mann et al. |
| 2008/0220422 A1 | 9/2008 | Shoemaker et al. |
| 2008/0234142 A1 | 9/2008 | Lietz |
| 2008/0243398 A1 | 10/2008 | Rabinowitz et al. |
| 2009/0023190 A1 | 1/2009 | Lao et al. |
| 2009/0029377 A1 | 1/2009 | Lo et al. |
| 2009/0087847 A1 | 4/2009 | Lo et al. |
| 2009/0098534 A1 | 4/2009 | Weier et al. |
| 2009/0099041 A1 | 4/2009 | Church et al. |
| 2009/0143570 A1 | 6/2009 | Jiang et al. |
| 2009/0176662 A1 | 7/2009 | Rigatti et al. |
| 2009/0221620 A1 | 9/2009 | Luke et al. |
| 2010/0035232 A1 | 2/2010 | Ecker et al. |
| 2010/0112575 A1 | 5/2010 | Fan et al. |
| 2010/0112590 A1 | 5/2010 | Lo et al. |
| 2010/0120038 A1 | 5/2010 | Mir et al. |
| 2010/0124751 A1 | 5/2010 | Quake et al. |
| 2010/0129874 A1 | 5/2010 | Mitra et al. |
| 2010/0138165 A1 | 6/2010 | Fan et al. |
| 2010/0171954 A1 | 7/2010 | Quake et al. |
| 2010/0184069 A1 | 7/2010 | Fernando et al. |
| 2010/0184152 A1 | 7/2010 | Sandler |
| 2010/0196892 A1 | 8/2010 | Quake et al. |
| 2010/0203538 A1 | 8/2010 | Dube et al. |
| 2010/0216153 A1 | 8/2010 | Lapidus et al. |
| 2010/0248231 A1 | 9/2010 | Wei et al. |
| 2010/0255492 A1 | 10/2010 | Quake et al. |
| 2010/0256013 A1 | 10/2010 | Quake et al. |
| 2010/0273678 A1 | 10/2010 | Alexandre et al. |
| 2010/0285537 A1 | 11/2010 | Zimmermann |
| 2010/0291572 A1 | 11/2010 | Stoughton et al. |
| 2010/0323352 A1 | 12/2010 | Lo et al. |
| 2011/0033862 A1 | 2/2011 | Rabinowitz et al. |
| 2011/0039724 A1 | 2/2011 | Lo et al. |
| 2011/0071031 A1 | 3/2011 | Khripin et al. |
| 2011/0086769 A1 | 4/2011 | Oliphant et al. |
| 2011/0092763 A1 | 4/2011 | Rabinowitz et al. |
| 2011/0105353 A1 | 5/2011 | Lo et al. |
| 2011/0151442 A1 | 6/2011 | Fan et al. |
| 2011/0159499 A1 | 6/2011 | Hindson et al. |
| 2011/0160078 A1 | 6/2011 | Fodor et al. |
| 2011/0178719 A1 | 7/2011 | Rabinowitz et al. |
| 2011/0201507 A1 | 8/2011 | Rava et al. |
| 2011/0224087 A1 | 9/2011 | Quake et al. |
| 2011/0246083 A1 | 10/2011 | Fan et al. |
| 2011/0251149 A1 | 10/2011 | Perrine et al. |
| 2011/0288780 A1 | 11/2011 | Rabinowitz et al. |
| 2011/0300608 A1 | 12/2011 | Ryan et al. |
| 2011/0301854 A1 | 12/2011 | Curry et al. |
| 2011/0318734 A1 | 12/2011 | Lo et al. |
| 2012/0003635 A1 | 1/2012 | Lo et al. |
| 2012/0010085 A1 | 1/2012 | Rava et al. |
| 2012/0034603 A1 | 2/2012 | Oliphant et al. |
| 2012/0122701 A1 | 5/2012 | Ryan et al. |
| 2012/0165203 A1 | 6/2012 | Quake et al. |
| 2012/0185176 A1 | 7/2012 | Rabinowitz et al. |
| 2012/0190020 A1 | 7/2012 | Oliphant et al. |
| 2012/0190021 A1 | 7/2012 | Oliphant et al. |
| 2012/0191358 A1 | 7/2012 | Oliphant et al. |
| 2012/0196754 A1 | 8/2012 | Quake et al. |
| 2012/0214678 A1 | 8/2012 | Rava et al. |

(56) References Cited

U.S. PATENT DOCUMENTS

| | | |
|---|---|---|
| 2012/0264121 A1 | 10/2012 | Rava et al. |
| 2012/0270212 A1 | 10/2012 | Rabinowitz et al. |
| 2012/0295819 A1 | 11/2012 | Leamon et al. |
| 2013/0017549 A1 | 1/2013 | Hong |
| 2013/0024127 A1 | 1/2013 | Stuelpnagel |
| 2013/0034546 A1 | 2/2013 | Rava et al. |
| 2013/0060483 A1 | 3/2013 | Struble et al. |
| 2013/0069869 A1 | 3/2013 | Akao et al. |
| 2013/0090250 A1 | 4/2013 | Sparks et al. |
| 2013/0116130 A1 | 5/2013 | Fu et al. |
| 2013/0123120 A1 | 5/2013 | Zimmermann et al. |
| 2013/0130923 A1 | 5/2013 | Ehrich et al. |
| 2013/0178373 A1 | 7/2013 | Rabinowitz et al. |
| 2013/0190653 A1 | 7/2013 | Alvarez Ramos |
| 2013/0196862 A1 | 8/2013 | Rabinowitz et al. |
| 2013/0210644 A1 | 8/2013 | Stoughton et al. |
| 2013/0225422 A1 | 8/2013 | Rabinowitz et al. |
| 2013/0252824 A1 | 9/2013 | Rabinowitz et al. |
| 2013/0253369 A1 | 9/2013 | Rabinowitz et al. |
| 2013/0261004 A1 | 10/2013 | Ryan et al. |
| 2013/0274116 A1 | 10/2013 | Rabinowitz et al. |
| 2013/0303461 A1 | 11/2013 | Iafrate et al. |
| 2013/0323731 A1 | 12/2013 | Lo et al. |
| 2014/0032128 A1 | 1/2014 | Rabinowitz et al. |
| 2014/0038830 A1 | 2/2014 | Srinivasan et al. |
| 2014/0051585 A1 | 2/2014 | Prosen et al. |
| 2014/0065621 A1 | 3/2014 | Mhatre et al. |
| 2014/0087385 A1 | 3/2014 | Rabinowitz et al. |
| 2014/0094373 A1 | 4/2014 | Zimmermann et al. |
| 2014/0100126 A1 | 4/2014 | Rabinowitz |
| 2014/0100134 A1 | 4/2014 | Rabinowitz et al. |
| 2014/0141981 A1 | 5/2014 | Zimmermann et al. |
| 2014/0154682 A1 | 6/2014 | Rabinowitz et al. |
| 2014/0162269 A1 | 6/2014 | Rabinowitz et al. |
| 2014/0193816 A1 | 7/2014 | Rabinowitz et al. |
| 2014/0206552 A1 | 7/2014 | Rabinowitz et al. |
| 2014/0227705 A1 | 8/2014 | Vogelstein et al. |
| 2014/0256558 A1 | 9/2014 | Varley et al. |
| 2014/0256569 A1 | 9/2014 | Rabinowitz et al. |
| 2014/0272956 A1 | 9/2014 | Huang et al. |
| 2014/0287934 A1 | 9/2014 | Szelinger et al. |
| 2014/0329245 A1* | 11/2014 | Spier .................... C12Q 1/686 435/6.12 |
| 2014/0336060 A1 | 11/2014 | Rabinowitz |
| 2015/0051087 A1 | 2/2015 | Rabinowitz et al. |
| 2015/0064695 A1 | 3/2015 | Katz et al. |
| 2015/0147815 A1 | 5/2015 | Babiarz et al. |
| 2015/0197786 A1 | 7/2015 | Osborne et al. |
| 2015/0232938 A1 | 8/2015 | Mhatre |
| 2015/0265995 A1 | 9/2015 | Head et al. |
| 2016/0201124 A1 | 7/2016 | Donahue et al. |
| 2016/0257993 A1 | 9/2016 | Fu et al. |
| 2016/0289740 A1 | 10/2016 | Fu et al. |
| 2016/0289753 A1 | 10/2016 | Osborne et al. |
| 2016/0312276 A1 | 10/2016 | Fu et al. |
| 2016/0319345 A1 | 11/2016 | Gnerre et al. |
| 2017/0121716 A1 | 5/2017 | Rodi et al. |
| 2018/0148777 A1 | 5/2018 | Kirkizlar et al. |
| 2018/0155775 A1 | 6/2018 | Zimmermann et al. |
| 2018/0155776 A1 | 6/2018 | Zimmermann et al. |
| 2018/0155779 A1 | 6/2018 | Zimmermann et al. |
| 2018/0155785 A1 | 6/2018 | Rabinowitz et al. |
| 2018/0155786 A1 | 6/2018 | Rabinowitz et al. |
| 2018/0155792 A1 | 6/2018 | Rabinowitz et al. |
| 2018/0171409 A1 | 6/2018 | Rabinowitz et al. |
| 2018/0171420 A1 | 6/2018 | Babiarz et al. |
| 2018/0173845 A1 | 6/2018 | Sigurjonsson et al. |
| 2018/0173846 A1 | 6/2018 | Sigurjonsson et al. |
| 2018/0201995 A1 | 7/2018 | Rabinowitz et al. |
| 2018/0237841 A1 | 8/2018 | Stray et al. |
| 2018/0298439 A1 | 10/2018 | Ryan et al. |
| 2018/0300448 A1 | 10/2018 | Rabinowitz et al. |
| 2019/0106737 A1 | 4/2019 | Underhill |
| 2019/0106751 A1 | 4/2019 | Zimmermann et al. |

FOREIGN PATENT DOCUMENTS

| | | |
|---|---|---|
| CN | 101675169 A | 3/2010 |
| EP | 0270017 A2 | 6/1988 |
| EP | 1524321 A1 | 4/2005 |
| EP | 1524321 B1 | 7/2009 |
| EP | 2163622 A1 | 3/2010 |
| EP | 2128169 A1 | 12/2010 |
| EP | 2902500 A1 | 8/2015 |
| GB | 2488358 | 8/2012 |
| JP | 2965699 | 8/1999 |
| JP | 2002-530121 A | 9/2002 |
| JP | 2004502466 A | 1/2004 |
| JP | 2004533243 A | 11/2004 |
| JP | 2005514956 A | 5/2005 |
| JP | 2005160470 A | 6/2005 |
| JP | 2006-254912 A | 9/2006 |
| JP | 2011/516069 A | 5/2011 |
| RU | 2290078 C1 | 12/2006 |
| WO | 179851 A1 | 10/2001 |
| WO | 200190419 A2 | 11/2001 |
| WO | 2002004672 A2 | 1/2002 |
| WO | 2002055985 A2 | 7/2002 |
| WO | 2002076377 | 10/2002 |
| WO | 2003031646 A1 | 4/2003 |
| WO | 3050532 A1 | 6/2003 |
| WO | 2003062441 A1 | 7/2003 |
| WO | 0190419 A9 | 11/2003 |
| WO | 3102595 A1 | 12/2003 |
| WO | 3106623 A2 | 12/2003 |
| WO | 2004087863 A2 | 10/2004 |
| WO | 2005021793 A1 | 3/2005 |
| WO | 2005035725 A2 | 4/2005 |
| WO | 2005100401 A2 | 10/2005 |
| WO | 2005123779 A2 | 12/2005 |
| WO | 2007057647 A1 | 5/2007 |
| WO | 2007062164 A3 | 5/2007 |
| WO | 2007070482 A2 | 6/2007 |
| WO | 2007/117256 A1 | 10/2007 |
| WO | 2007132167 A2 | 11/2007 |
| WO | 2007/147076 A2 | 12/2007 |
| WO | 2007147074 A2 | 12/2007 |
| WO | 2008024473 A2 | 2/2008 |
| WO | 2008048931 A1 | 4/2008 |
| WO | 2008051928 A2 | 5/2008 |
| WO | 2008059578 A1 | 5/2008 |
| WO | 2008081451 A2 | 7/2008 |
| WO | 2008115497 A2 | 9/2008 |
| WO | 2008135837 A2 | 11/2008 |
| WO | 2008157264 A2 | 12/2008 |
| WO | 2009009769 A2 | 1/2009 |
| WO | 2009013492 A1 | 1/2009 |
| WO | 2009013496 A1 | 1/2009 |
| WO | 2009019215 A1 | 2/2009 |
| WO | 2009019455 A2 | 2/2009 |
| WO | 2009/036525 A2 | 3/2009 |
| WO | 2009030100 A1 | 3/2009 |
| WO | 2009032779 A2 | 3/2009 |
| WO | 2009032781 A2 | 3/2009 |
| WO | 2009033178 A1 | 3/2009 |
| WO | 2009091934 A1 | 7/2009 |
| WO | 2009092035 A2 | 7/2009 |
| WO | 2009105531 A1 | 8/2009 |
| WO | 2009146335 A1 | 12/2009 |
| WO | 2010017214 A1 | 2/2010 |
| WO | 2010/033652 A1 | 3/2010 |
| WO | 2010075459 | 7/2010 |
| WO | 2011041485 A1 | 4/2011 |
| WO | 2011057094 | 5/2011 |
| WO | 2011/090556 A1 | 7/2011 |
| WO | 2011087760 | 7/2011 |
| WO | 2011146632 A1 | 11/2011 |
| WO | 201283250 | 6/2012 |
| WO | 2012088456 A2 | 6/2012 |
| WO | 20120071621 | 6/2012 |
| WO | 2012108920 A1 | 8/2012 |
| WO | 2012/142531 A2 | 10/2012 |
| WO | 2007/149791 A2 | 12/2012 |
| WO | 2013030577 | 3/2013 |

(56) References Cited

FOREIGN PATENT DOCUMENTS

| | | |
|---|---|---|
| WO | 2013/045432 A1 | 4/2013 |
| WO | 2013052557 A2 | 4/2013 |
| WO | 2013/078470 A2 | 5/2013 |
| WO | 2013/086464 A1 | 6/2013 |
| WO | 20130130848 | 9/2013 |
| WO | 2013/181651 A1 | 12/2013 |
| WO | 2014/004726 A1 | 1/2014 |
| WO | 2014/014497 A1 | 1/2014 |
| WO | 20140018080 | 1/2014 |
| WO | 2014/035986 A1 | 3/2014 |
| WO | 2014/122288 A1 | 8/2014 |
| WO | 2014/149134 A2 | 9/2014 |
| WO | 2014/151117 A1 | 9/2014 |
| WO | 2015/100427 A1 | 7/2015 |
| WO | 2015/164432 A1 | 10/2015 |
| WO | 2016/009059 A1 | 1/2016 |
| WO | 2016/065295 A1 | 4/2016 |
| WO | 2016/138080 A1 | 9/2016 |
| WO | 2016/193490 A1 | 12/2016 |
| WO | 2017/058784 A1 | 4/2017 |
| WO | 2018/083467 A1 | 5/2018 |
| WO | 2018/106798 A1 | 6/2018 |
| WO | 2018/156418 A1 | 8/2018 |

OTHER PUBLICATIONS

Podder et al. (BMC Med Genom, 2008, vol. 1, No. 5, p. 1 of 15) (Year: 2008).*
Carvalho, B. et al., "Exploration, normalization, and genotype calls of high-density oligonucleotide SNP array data", Biostatistics, vol. 8, No. 2, 2007, 485-499.
Ford, E. et al., "A method for generating highly multiplexed ChIP-seq libraries", BMC Research Notes, vol. 7, No. 312, May 22, 2014, 1-5.
Wapner, R. et al., "First-Trimester Screening for Trisomies 21 and 18", The New England Journal of Medicine, vol. 349, No. 15, Oct. 9, 2003, 1405-1413.
Kirkizlar, E. et al., "Detection of Clonal and Subclonal Copy-Number Variants in Cell-Free DNA from Patients with Breast Cancer Using a Massively Multiplexed PCR Methodology", Translational Oncology, vol. 8, No. 5, Oct. 2015, pp. 407-416.
Riley, D. E., "DNA Testing: An Introduction for Non-Scientists An Illustrated Explanation", Scientific Testimony: An Online Journal, http://www.scientific.org/tutorials/articles/riley/riley.html, Apr. 6, 2005, 22 pages.
Tu, J. et al., "Pair-barcode high-throughput sequencing for large-scale multiplexed sample analysis", BMC Genomics, vol. 13, No. 43, Jan. 25, 2012, 1-9.
"Random variable", In the Penguin Dictionary of Mathematics. Retrieved from http://www.credoreference.com/entry/penguinmath/random _variable, 2008, 1 page.
Casbon, J. A. et al., "A method for counting PCR template molecules with application to next-generation sequencing", Nucleic Acids Research, vol. 39, No. 12, Apr. 13, 2011, 1-8.
Craig, D. W. et al., "Identification of genetic variants using bar-coded multiplexed sequencing", Nature Methods, vol. 5, Oct. 2008, 887-893.
Fan, H. Christina et al., "Sensitivity of Noninvasive Prenatal Detection of Fetal Aneuploidy from Maternal Plasma Using Shotgun Sequencing Is Limited Only by Counting Statistics", PLoS ONE, vol. 5, Issue 5 (e10439), May 3, 2010, 1-6.
Fu, G. K. et al., "Counting individual DNA molecules by the stochastic attachment of diverse labels", PNAS, vol. 108, No. 22, May 31, 2011, 9026-9031.
Fu, G. K. et al., "Digital Encoding of Cellular mRNAs Enabling Precise and Absolute Gene Expression Measurement by Single-Molecule Counting", Analytical Chemistry, vol. 86, Mar. 3, 2014, 2867-2870.
Hollas, B. et al., "A stochastic approach to count RN A molecules using DNA sequencing methods", Lecture Notes in Computer Science, vol. 2812, 2003, 55-62.

Hug, H. et al., "Measurement of the number of molecules of a single mRNA species in a complex mRNA preparation", J. Theor. Biol., vol. 221, 2003, 615-624.
Hultin, E. et al., "Competitive enzymatic reaction to control allele-specific extensions", Nucleic Acids Research, vol. 33, No. 5, Mar. 14, 2005, 1-10.
Jabara, C. B. et al., "Accurate sampling and deep sequencing of the HIV-1 protease gene using a Primer ID", PNAS, vol. 108, No. 50, Dec. 13, 2011, 20166-20171.
Kinde, I. et al., "Detection and quantification of rare mutations with massively parallel sequencing", PNAS, vol. 108, No. 23, Jun. 7, 2011, 9530-9535.
Kivioja, T. et al., "Counting absolute numbers of molecules using unique molecular identifiers", Nature Methods, Advance Online Publication, Nov. 20, 2011, 1-5.
McCloskey, M. L. et al., "Encoding PCR Products with Batch-stamps and Barcodes", Biochem Genet., vol. 45, Oct. 23, 2007, 761-767.
Merriam-Webster, "Medical Definition of Stimulant", http://www.merriam-webster.com/medical/stimulant, Mar. 14, 2016, 7 pages.
Miner, B. E. et al., "Molecular barcodes detect redundancy and contamination in hairpin-bisulfite PCR", Nucleic Acids Research, vol. 32, No. 17, Sep. 30, 2004, 1-4.
Munne, S. et al., "Chromosome Abnormalities in Human Embryos", Textbook of Assisted Reproductive Techniques, 2004, pp. 355-377.
Ragoussis, J. , "Genotyping Technologies for Genetic Research", Annual Review of Genomics and Human Genetics, vol. 10 (1), Sep. 1, 2009, 117-133.
Schmitt, M. W. et al., "Detection of ultra-rare mutations by next-generation sequencing", PNAS, vol. 109, No. 36, Sep. 4, 2012, 14508-14513.
Shiroguchi, K. et al., "Digital RNA sequencing minimizes sequence-dependent bias and amplification noise with optimized single-molecule barcodes", PNAS, vol. 109, No. 4, Jan. 24, 2012, 1347-1352.
Taliun, D. et al., "Efficient haplotype block recognition of very long and dense genetic sequences", BMC Bioinformatics, vol. 15 (10), 2014, 1-18.
Cansar, "Hs-578-T—Copy Number Variation—Cell Line Synopsis", ICR Cancer Research UK, Retrieved on Mar. 26, 2018 from https://cansar.icr.ac.uk/cansar/cell-lines/Hs-578-T/copy_number_variation/chromosome_8/, Mar. 26, 2018, 50 pgs.
Chang, H.W. et al., "Assessment of Plasma DNA Levels, Allelic Imbalance, and CA 125 as Diagnostic Tests for Cancer", Journal of the National Cancer Institute, vol. 94, No. 22, Nov. 20, 2002, 1697-1703.
Choi, M. et al., "Genetic diagnosis by whole exome capture and massively parallel DNA sequencing", PNAS, vol. 106, No. 45, Nov. 10, 2009, 19096-19101.
Garcia-Murillas, I. et al., "Mutation tracking in circulating tumor DNA predicts relapse in early breast cancer", Science Translational Medicine, vol. 7, No. 302, Aug. 26, 2015, 1-2.
Jahr, S. et al., "DNA Fragments in the Blood Plasma of Cancer Patients: Quantitations and Evidence for Their Origin from Apoptotic and Necrotic Cells", Cancer Research, vol. 61, Feb. 15, 2001, 1659-1665.
Jamal-Hanjani, M. et al., "Tracking the Evolution of Non-Small-Cell Lung Cancer", The New England Journal of Medicine, vol. 376, No. 22, Jun. 1, 2017, 2109-2121.
Jarvie, T., "Next generation sequencing technologies", Drug Discovery Today: Technologies, vol. 2, No. 3, 2005, 255-260.
Kim, H. et al., "Whole-genome and multisector exome sequencing of primary and post-treatment glioblastoma reveals patterns of tumor evolution", Genome Research, vol. 25, No. 3, Feb. 3, 2015, 316-327.
Leary, R. J. et al., "Development of Personalized Tumor Biomarkers Using Massively Parallel Sequencing", Science Translational Medicine, vol. 2, No. 20, Feb. 24, 2010, 1-8.
Ma, Xiaotu et al., "Rise and fall of subclones from diagnosis to relapse in pediatric B-acute lymphoblastic leukaemia", Nature Communications, vol. 6, Mar. 19, 2015, 1-12.
Margulies, M. et al., "Genome sequencing in microfabricated high-density picolitre reactors", Nature, vol. 437, Sep. 15, 2005, 376-380.

(56) References Cited

OTHER PUBLICATIONS

Margulies, M. et al., "Genome sequencing in microfabricated high-density picolitre reactors plus Supplemental Methods", Nature, vol. 437, Sep. 15, 2005, 40 pgs.
McBride, D. et al., "Use of Cancer-Specific Genomic Rearrangements to Quantify Disease Burden in Plasma from Patients with Solid Tumors", Genes, Chromosomes & Cancer, vol. 49, Aug. 19, 2010, 1062-1069.
Ohsawa, M. et al., "Prenatal Diagnosis of Two Pedigrees of Fukuyama Type Congenital Muscular Dystrophy by Polymorphism Analysis", The Health and Welfare Ministry, 1994, 5 pgs.
Pergament, E. et al., "Single-Nucleotide Polymorphism-Based Noninvasive Prenatal Screening in a High-Risk and Low-Risk Cohort", Obstetrics & Gynecology, vol. 124, No. 2, Part 1, Aug. 2014, 210-218 + Appendices.
Popova, T. et al., "Genome Alteration Print (GAP): a tool to visualize and mine complex cancer genomic profiles obtained by SNP arrays", Genome Biology, vol. 10, R128, Nov. 11, 2009, 1-14.
Primdahl, H. et al., "Allelic Imbalances in Human Bladder Cancer: Genome-Wide Detection With High-Density Single-Nucleotide Polymorphism Arrays", Journal of the National Cancer Institute, vol. 94, No. 3, Feb. 6, 2002, 216-223.
Samango Sprouse, C. et al., "SNP-based non-invasive prenatal testing detects sex chromosome aneuploidies with high accuracy", Prenatal Diagnosis, vol. 33, 2013, 643-649.
Abbosh, C. et al., "Phylogenetic ctDNA analysis depicts early-stage lung cancer evolution", Nature, vol. 545, May 25, 2017, 446-451.
Butler, J. et al., "The Development of Reduced Size STR Amplicons as Tools for Analysis of Degraded DNA*", Journal of Forensic Sciences, vol. 48, No. 5, 2003, 1054-1064.
De Bruin, E. et al., "Spatial and temporal diversity in genomic instability processes defines lung cancer evolution", Science, vol. 346, No. 6206, Oct. 10, 2014, 251-256.
Fan, H. C. et al., "Microfluidic digital PCR enables rapid prenatal diagnosis of fetal aneuploidy", American Journal of Obstetrics & Gynecology, vol. 200, May 2009, 543.e1-543.e7.
Hawkins, T. et al., "Whole genome amplification—applications and advances", Current Opinion in Biotechnology, 13, 2002, 65-67.
Jamal-Hanjani, M. et al., "Detection of ubiquitous and heterogeneous mutations in cell-free DNA from patients with early-stage non-small-cell lung cancer", Annals of Oncology, vol. 27, No. 5, Jan. 28, 2016, 862-867.
Jamal-Hanjani, M. et al., "Tracking Genomic Cancer Evolution for Precision Medicine: The Lung TRACERx Study", PLOS Biology, vol. 12, No. 7, Jul. 2014, 1-7.
Narayan, A. et al., "Ultrasensitive measurement of hotspot mutations in tumor DNA in blood using error-suppressed multiplexed deep sequencing", Cancer Research, vol. 72, No. 14, Jul. 15, 2012, 3492-3498.
Pathak, A. et al., "Circulating Cell-Free DNA in Plasma/Serum of Lung Cancer Patients as a Potential Screening and Prognostic Tool", Clinical Chemistry, 52, 2006, 1833-1842.
Rogaeva, E. et al., "The Solved and Unsolved Mysteries of the Genetics of Early-Onset Alzheimer's Disease", NeuroMolecular Medicine, vol. 2, 2002, 1-10.
Sahota, A., "Evaluation of Seven PCR-Based Assays for the Analysis of Microchimerism", Clinical Biochemistry, vol. 31, No. 8., 1998, 641-645.
Ten Bosch, J., "Keeping Up With the Next Generation Massively Parallel Sequencing in Clinical Diagnostics", Journal of Molecular Diagnostics, vol. 10, No. 6, 2008, 484-492.
Thermofisher Scientific, "Ion AmpliSeq Cancer Hotspot Panel v2", Retrieved from the Internet: https://tools.thermofisher.com/content/sfs/brochures/Ion-AmpliSeq-Cancer-Hotspot-Panel-Flyer.pdf, 2015, 2 pages.
Wikipedia, "Maximum a posteriori estimation", https://en.wikipedia.org/w/index.php?title=Maximum_a_posteriori_estimation&oldid=26878808, [retrieved on Aug. 1, 2017], Oct. 30, 2005, 2 pages.

Wright, C. et al., "The use of cell-free fetal nucleic acids in maternal blood for non-invasive prenatal diagnosis", Human Reproduction Update, vol. 15, No. 1, 2009, 139-151.
Xu, N. et al., "A Mutation in the Fibroblast Growth Factor Receptor 1 Gene Causes Fully Penetrant Normosmic Isolated Hypogonadotropic Hypogonadism", The Journal of Clinical Endocrinology & Metabolism, vol. 92, No. 3, 2007, 1155-1158.
Xu, S. et al., "Circulating tumor DNA identified by targeted sequencing in advanced-stage non-small cell lung cancer patients", Cancer Letters, vol. 370, 2016, 324-331.
Zhong, X. et al., "Risk free simultaneous prenatal identification of fetal Rhesus D status and sex by multiplex real-time PCR using cell free fetal DNA in maternal plasma", Swiss Medical Weekly, vol. 131, Mar. 2001, 70-74.
"Blast of AAAAAAAAATTTAAAAAAAAATTT(http://blast.ncbi.nlm.nih.gov/Blast.cgi, downloaded May 4, 2015)".
"CompetitivePCR Guide,", TaKaRa Biomedicals, Lit. # L0126 Rev. Aug. 1999, 9 pgs.
"db SNP rs2056688 (http://www.ncbi.nlm.nih.gov/projects/SNP/snp_ref.cgi?rs=2056688, downloaded May 4, 2015".
"Declaration by Dr. Zimmerman of Oct. 30, 2014 filed in U.S. Appl. No. 14/044,434".
"European Application No. 014198110, European Search Report dated Apr. 28, 2015, 3 pages".
"Finishing the Euchromatic Sequence of the Human Genome", Nature vol. 431,(Oct. 21, 2004),931-945.
"Fixed Medium, dictionary definition, Academic Press Dictionary of Science and Technology", Retrieved from the Internet: <URL:www.credoreference.com/entry/apdst/fixed_medium>, 1996, 1 pg.
"Genetics Home Reference", http://ghr.nlm.nih.gov/handbook/genomicresearch/snp, Feb. 28, 2014, 1-2.
"Guideline related to genetic examination", Societies Related to Genetic Medicine, Japanese Society for Genetic Counseling, Japanese Society for Gene Diagnosis and Therapy, Japan Society of Obstetrics an, 2003, 2-15.
"How Many Carbs in a Potato?, [Online]", Retrieved from theInternet:<http://www.newhealthguide.org/How-Many-Carbs-In-A-Potato.html>, Nov. 1, 2014, 3 pgs.
"Ion Ampli Seq Comprehensive Cancer Panel, product brochure, Life TechnologiesCorporation. Retrieved from the Internet", <URL:https://tools.lifetechnologies.com/content/sfs/brochures/Ion_CompCancer_Panel_Flyer.pdf>, 2012, 2 pgs.
"IonAmpliSeq Designer Provides Full Flexibility to Sequence Genes of Your Choice,product brochure, Life Technologies Corporation", Retrieved from the Internet<URL: http://tools.lifetechnologies.com/content/sfs/brochures/IonAmpliSeq_CustomPanels_AppNote_CO1.
"Merriam-Webster.com (http://www.merriam-webster.com/dictionary/universal, downloaded Jul. 23, 2014)".
"Multiplexing with RainDrop Digital PCR", RainDance Technologies, Application Note, 2013, 1-2.
"Nucleic Acids, Linkers and Primers: Random Primers", New England BioLabs 1998/99Catalog, 1998, 121 and 284.
"PRIMER3, information sheet, Sourceforge.net. [retrieved on Nov. 12, 2012]. Retrieved from the Internet: <URL: http://primer3.sourceforge.net/>", 2009, 1 pg., "www.fatsecret.com" (printed from internet Nov. 1, 2014).
PRNewswire (Research Suggests Daily Consumptionof Orange Juice Can Reduce Blood Pressure and May Provide Beneficial Effects to Blood Vessel Function: New Study Identified Health Benefits in Orange Juice, Dec. 8, 2010).
The Bump (Panorama Test, attached, Jul. 1, 2013).
What to Expect (Weird Harmony results, attached, May 1, 2015).
Wikipedia (attached, available at https://en.wikipedia.org/wiki/Stimulant, accessed Mar. 14, 2016).
Abidi, S. et al., "Leveraging XML-based electronic medical records to extract experiential clinical knowledge: An automated approach to generate cases for medical case-based reasoning systems", International Journal of Medical Informatics, 68(1-3), 2002, 187-203.
Agarwal, Ashwin. et al., "Commercial Landscape of Noninvasive Prenatal Testing in the United States", Prenatal Diagnosis,33, 2013, 521-531.

(56) References Cited

OTHER PUBLICATIONS

Alkan, Can et al., "Personalized Copy Number and Segmental Duplication Maps Using Next-Generation Sequencing", Nature Genetics, 41, 10, 2009, 1061-1068.
Allaire, F R., "Mate selection by selection index theory", Theoretical Applied Genetics, 57(6), 1980, 267-272.
Allawi, Hatim T. et al., "Thermodynamics of internal C•T Mismatches in DNA", Nucleic Acids Research, 26 (11), 1998, 2694-2701.
Aoki, Yasuhiro, "Statistical and Probabilistic Bases of Forensic DNA Testing", The Journal of the Iwate Medical Association, 2002, vol. 54, p. 81-94.
Ashoor, Ghalia et al., "Fetal Fraction in Maternal Plasma Cell-Free DNA at 11-13 Weeks' Gestation: Effect of Maternal and Fetal Factors", Fetal Diagnosis Therapy, 2012, 1-7.
Ashoor, Ghalia et al., "Chromosome-Selective Sequencing of Maternal Plasma Cell-Free DNA for First-Trimester Detection of Trisomy 21 and Trisomy 18", American Journal of Obstetrics & Gynecology, 206, 2012, 322.e1-322.e5.
Bada, Michael A. et al., "Computational Modeling of Structural Experimental Data", Methods in Enzymology,317, 2000, 470-491.
Beaumont, Mark A et al., "The Bayesian Revolution in Genetics", Nature Reviews Genetics, 5, 2004, 251-261.
Beer, Alan E. et al., "The Biological Basis of Passage of Fetal Cellular Material into the Maternal Circulation", Annals New York Academy of Sciences, 731, 1994, 21-35.
Beerenwinkel, et al., "Methods for Optimizing Antiviral Combination Therapies", Bioinformatics, 19(1), 2003, i16-i25.
Beerenwinkel, N. et al., "Geno2pheno: estimating phenotypic drug resistance from HIV-1 genotypes", Nucleic Acids Research, 31(13), 2003, 3850-3855.
Benn, P. et al., "Non-Invasive Prenatal Testing for Aneuploidy: Current Status and Future Prospects", Ultrasound Obstet Gynecol, 42, 2013, 15-33.
Benn, P et al., "Non-Invasive prenatal Diagnosis for Down Syndrome: the Paradigm Will Shift, but Slowly", Ultrasound Obstet. Gynecol., 39, 2012, 127-130.
Bentley, David R et al., "Accurate Whole Human Genome Sequencing Using Reversible Terminator Chemistry", Nature, 456, 6, 2008, 53-59.
Bermudez, M. et al., "Single-cell sequencing and mini-sequencing for preimplantation genetic diagnosis", Prenatal Diagnosis, 23, 2003, 669-677.
Bevinetto, Gina, Bevinetto (5 Foods All Pregnant Women Need, American Baby, available at http://www.parents.com/pregnancy/mybody/nutrition/ 5greatpregnancyfoods/, Apr. 15, 2008).
Bianchi, D W. et al., "Fetal gender and aneuploidy detection using fetal cells maternal blood: analysis of NIFYY I data", Prenat Diagn 2002; 22, 2002, 609-615.
Birch, Lyndsey et al., "Accurate and Robust Quantification of Circulating Fetal and Total DNA in Maternal Plasma from 5 to 41 Weeks of Gestation", Clinical Chemistry, 51(2), 2005, 312-320.
Bisignano, et al., "PGD and Aneuploidy Screening for 24 Chromosomes: Advantages and Disadvantages of Competing Platforms", Reproductive BioMedicine Online, 23, 2011, 677-685.
Bodenreider, O., "The Unified Medical Language System (UMLS): Integrating Biomedical Terminology", Nucleic Acids Research, 32, (Database issue), 2004, D267-D270.
Breithaupt, Holger, "The Future of Medicine", EMBO Reports, 21(61), 2001, 465-467.
Brownie, Jannine et al., "The Elimination of Primer-Dimer Accumulation in PCR", Nucleic Acids Research, 25(16), 1997, 3235-3241.
Cairns, Paul et al., "Homozygous Deletions of 9p21 in Primary Human Bladder Tumors Detected by Comparative Multiplex Polymerase Chain Reaction", Cancer Research, 54, 1994, 1422-1424.
Caliendo, Angela, "Multiplex PCR and Emerging Technologies for the Detection of Respiratory Pathogens", Clinical Infectious Diseases, 52(4), 2011, S326-S330.
Carnevale, Alessandra et al., "Attitudes of Mexican Geneticists Towards Prenatal Diagnosis and Selective Abortion", American Journal of Medical Genetics, 75, 1998, 426-431.
Chakraborty, R. et al., "Paternity Exclusion by DNA Markers: Effects of Paternal Mutations", Journal of Forensic Sciences, vol. 41, No. 4, Jul. 1996, 671-677.
Chen, E. et al., "Noninvasive Prenatal Diagnosis of Fetal Trisomy 18 and Trisomy 13 by Maternal Plasma DNA Sequencing", PLoS ONE, 6 (7), e21791, 2011, 7 pgs.
Chetty, Shilpa et al., "Uptake of Noninvasive Prenatal Testing (NIPT) in Women Following Positive Aneuploidy Screening", Prenatal Diagnosis,33, 2013, 542-546.
Chiu, R. et al., "Non-Invasive Prenatal Assessment of Trisomy 21 by Multiplexed Maternal Plasma DNA Sequencing: Large Scale Validity Study", BMJ, 342, c7401, 2011, 9 pgs.
Chiu, Rossa W. et al., "Effects of Blood-Processing Protocols on Fetal and Total DNA Quantification in Maternal Plasma", Clinical Chemistry, 47(9), 2001, 1607-1613.
Chiu, Rossa W.K et al., "Maternal Plasma DNA Analysis with Massively Parallel Sequencing by Litigation for Noninvasive Prenatal Diagnosis of Trisomy 21", Clinical Chemistry, 56, 3, 2010, 459-463.
Chiu, Rossa W.K et al., "Noninvasive Prenatal Diagnosis of Fetal Chromosomal Aneuploidy by Massively Parallel Genomic Sequencing of DNA in Maternal Plasma", PNAS, 105, 51 (with Supporting Information), 2008, 23.
Chiu, Rossa W.K. et al., "Non-Invasive Prenatal Diagnosis by Single Molecule Counting Technologies", Trends in Genetics, 25 (7), 2009, 324-331.
Chu, T. et al., "Statistical Considerations for Digital Approaches to Non-Invasive Fetal Genotyping", Bioinformatics (Advance Access publication), 26 (22), 2010, 2863-2866.
Chu, Tianjiao et al., "Statistical Model for Whole Genome Sequencing and its Application to Minimally Invasive Diagnosis of Fetal Genetic Disease", Bioinformatics, 25(10), 2009, 1244-1250.
Chu, Tianjiao et al., "A Novel Approach Toward the Challenge of Accurately Quantifying Fetal DNA in Maternal Plasma", Prenatal Diagnosis,30, 2010, 1226-1229.
Cole, Neal W. et al., "Hyperglycemia-Induced Membrane Lipid Peroxidation and Elevated Homocysteine Levels Are Poorly Attenuated by Exogenous Folate in Embryonic Chick Brains", Comparative Biochemistry and Physiology, Part B, 150, 2008, 338-343.
Colella, S. et al., "QuantiSNP: an Objectives Bayes Hidden-Markov Model to Detect and Accurately Map Copy Number Variation Using SNP Genotyping Data", Nucleic Acids Research, 35 (6), 2007, 2013-2025.
Cossu, Gianfranco et al., "Rh D/d Genotyping by Quantitative Polymerase Chain Reaction and Capillary Zone Electrophoresis", Electrophoresis, 17, 1996, 1911-1915.
Coyle, J. F. et al., "Standards for detailed clinical models as the basis for medical data exchange and decision support", International Journal of Medical Informatics, 69(2-3), 2003, 157-174.
Cross, Jillian et al., "Resolution of trisomic mosaicism in prenatal diagnosis: estimated performance of a 50K SNP microarray", Prenat Diagn 2007; 27, 2007, 1197-1204.
D'Aquila, Richard et al., "Maximizing sensitivity and specificity of PCR by pre-amplification heating", Nucleic Acids Research, 19(13), 1991, p. 3749.
Daruwala, Raoul-Sam et al., "A Versatile Statistical Analysis Algorithm to Detect Genome Copy Number Variation", PNAS, 101(46), 2004, 16292-16297.
De Vries, et al., "Diagnostic genome profiling in mental retardation", Am J Hum Genet, 77, published online Aug. 30, 2005, 2005, 606-616.
Deangelis, M. et al., "Solid-phase Reversible Immobilization for the Isolation of PCR Products", Nucleic Acids Research, 23 (22), 1995, 4742-4743.
Devaney, S. et al., "Noninvasive Fetal Sex Determination Using Cell-Free Fetal DNA: A Systematic Review and Meta-analysis", JAMA, 306 (6), 2011, 627-636.
Dhallan, et al., "Methods to Increase the Percentage of Free Fetal DNA Recovered from the Maternal Circulation", JAMA, 291(9), 2004, 1114-1119.

(56) References Cited

OTHER PUBLICATIONS

Dhallan, Ravinder et al., "A non-invasive test for prenatal diagnosis based on fetal DNA present in maternal blood: a preliminary study", The Lancet, 369, 2007, 474-481.
Dieffenbach, C W. et al., "General concepts for PCR primer design", Genome Research. PCR methods and Applications vol. 3, 1993, S30-S37.
Ding, C et al., "Direct molecular haplotyping of long-range genomic DNA with M1-PCR", PNAS 100(13), 2003, 7449-7453.
Dohm, J. et al., "Substantial Biases in Ultra-Short Read Data Sets From High-Throughput DNA Sequencing", Nucleic Acids Research, 36 (16), e105, 2008, 10 pgs.
Dolganov, Gregory et al., "A Novel Method of Gene Transcript Profiling in Airway Biopsy Homogenates Reveals Increased Expression of a Na-K+-Cl-Cotransporter (NKCC1) in Asthmatic Subjects", Genome Res.,11, 2001, 1473-1483.
Donohoe, Gerard G et al., "Rapid Single-Tube Screening of the C282Y Hemochromatosis Mutation by Real-Time Multiplex Allele-specific PCR without Fluorescent Probes", Clinical Chemistry, 46, 10, 2000, 1540-1547.
Donoso, P. et al., "Current Value of Preimplantation Genetic Aneuploidy Screening in IVF", Human Reproduction Update, 13(1), 2007, 15-25.
Echeverri, et al., "Caffeine's Vascular Mechanisms of Action", International Journal of Vascular Medicine vol. 2010(2010), 10 pages, Aug. 25, 2010.
Ehrich, Mathias et al., "Noninvasive Detection of Fetal Trisomy 21 by Sequencing of DNA in Maternal Blood: A Study in a Clinical Setting", American Journal of Obstetrics & Gynecology, 204, 2011, 205.e1-205.e11.
Eichler, H., "Mild Course of Fetal Rh D Haemolytic Disease due to Maternal Alloimmunisation to Paternal HLA Class I and II Antigens", Vox Sang, 68, 1995, 243-247.
Ellison, Aaron M., "Bayesian Inference in Ecology", Ecology Letters, 2004, vol. 7, p. 509-520.
Ellonen, P. et al., "Development of SNP Microarray for Supplementary Paternity Testing", International Congress Series,1261, 2004, 12-14.
EP06838311.6, "European Communication and Extended European Search Report", dated Dec. 30, 2008, 8 pgs.
EP08742125.1, "European Communication pursuant to Article 94(3) EPC and Examination Report", dated Feb. 12, 2010, 5 pgs.
Fan, et al., "Whole-genome molecular haplotyping of single cells", Nature Biotechnology, vol. 29, No. 1, Jan. 1, 2011, 51-57.
Fan, Christina H. et al., "Non-Invasive Prenatal Measurement of the Fetal Genome", Nature, doi:10.1038/nature11251, 2012, 26 pgs.
Fan, Christina H. et al., "Noninvasive Diagnosis of Fetal Aneuploidy by Shotgun Sequencing DNA from Maternal Blood", PNAS, 105, 42, 2008, 16266-16271.
Fan, Jian-Bing et al., "Highly Parallel Genomic Assay", Nature Reviews, 7, 2006, 632-644.
Fazio, Gennaro. et al., "Identification of RAPD Markers Linked to Fusarium Crown and Root Rot Resistance (Frl) in Tomato", Euphytica 105, 1999, 205-210.
Fiorentino, F. et al., "Development and Clinical Application of a Strategy for Preimplantation Genetic Diagnosis of Single Gene Disorders Combined with HLA Matching", Molecular Human Reproduction (Advance Access publication), 10 (6), 2004, 445-460.
Fiorentino, F et al., "Strategies and Clinical Outcome of 250 Cycles of Preimplantation Genetic Diagnosis for Single Gene Disorders", Human Reproduction, 21, 3, 2006, 670-684.
Fiorentino, Francesco et al., "Short Tandem Repeats Haplotyping of the HLA Region in Preimplantation HLA Matching", European Journal of Human Genetics, 13, 2005, 953-958.
Forejt, et al., "Segmental trisomy of mouse chromosome 17: introducing an alternative model of Down's syndrome", Genomics, 4(6), 2003, 647-652.
Forshew, et al., "Noninvasive Identification and Monitoring of Cancer Mutations by Targeted Deep Sequencing of Plasma DNA", Noninvasive identification and monitoring of cancer mutations by targeted deep sequencing of plasma DNA. Sci. Transl. Med. 4, 136 30 (2012)., 1-12.
Fredriksson, et al., "Multiplex amplification of all coding sequences within 10 cancer genes by Gene-Collector", Nucleic Acids Research, 2007, vol. 35, No. 7 e47, 1-6.
Freeman, Jennifer L. et al., "Copy Number Variation: New Insights in Genome Diversity", Genome Research, 16, 2006, 949-961.
Frost, MacKenzie S et al., "Differential Effects of Chronic Pulsatile Versus Chronic Constant Maternal Hyperglycemia on Fetal Pancreatic B-Cells", Journal of Pregnancy, 2012,, Article ID 812094, 2012, 8.
Ganshirt-Ahlert, D. et al., "Ratio of Fetal to Maternal DNA is Less Than 1 in 5000 at different Gestational Ages in Maternal Blood", Clinical Genetics,38, 1990, 38-43.
Ganshirt-Ahlert, D. et al., "Fetal DNA in Uterine Vein Blood", Obstetrics & Gynecology, 80 (4), 1992, 601-603.
Ganshirt-Ahlert, Dorothee et al., "Three Cases of 45,X/46,XYnf Mosaicism", Human Genetics, 76, 1987, 153-156.
Gardina, P. et al., "Ploidy Status and Copy Number Aberrations in Primary Glioblastomas Defined by Integrated Analysis of Allelic Ratios, Signal Ratios and Loss of Heterozygosity Using 500K SNP Mapping Arrays", BMC Genomics, 9 (489), (doi:10.1186/1471-2164-9-489), 2008, 16 pgs.
Ghanta, Sujana. et al., "Non-Invasive Prenatal Detection of Trisomy 21 Using Tandem Single Nucleotide Polymorphisms", PLoS ONE, 5 (10), 2010, 10 pgs.
Gjertson, David W et al., "Assessing Probability of Paternity and the Product Rule in DNA Systems", Genetica, 96, 1995, 89-98.
Greenwalt, T. et al., "The Quantification of Fetomaternal Hemorrhage by an Enzyme-Linked Antibody Test with Glutaraldehyde Fixation", Vox Sang, 63, 1992, 268-271.
Guerra, J., "Terminal Contributions for Duplex Oligonucleotide Thermodynamic Properties in the Context of Nearest Neighbor Models", Biopolymers, 95(3), (2010), 2011, 194-201.
Guetta, Esther et al., "Analysis of Fetal Blood Cells in the Maternal Circulation: Challenges, Ongoing Efforts, and Potential Solutions", Stem Cells and Development, 13, 2004, 93-99.
Guichoux, et al., "Current Trends in Microsatellite Genotyping", Molecular Ecology Resources, 11, 2011, 591-911.
Hall, M., "Panorama Non-Invasive Prenatal Screening for Microdeletion Syndromes", Apr. 1, 2014 (Apr. 1, 2014), XP055157224, Retrieved from the Internet: URL:http://www.panoramatest.com/sites/default/files/files/PanoramaMicrodeletionsWhite Paper-2.pdf [retrieved on Dec. 8, 2014].
Handyside, et al., "Isothermal whole genome amplification from single and small numbers of cells: a new era for preimplantation genetic diagnosis of inherited disease", Molecular Human Reproduction vol. IO, No. 10 pp. 767-772, 2004.
Hara, Eiji et al., "Subtractive eDNA cloning using oligo(dT)3o-latex and PCR: isolation of eDNA clones specific to undifferentiated human embryonal carcinoma cells", Nucleic Acids Research, 19(25), 1991, 7097-7104.
Hardenbol, P., "Multiplexed Genotyping With Sequence-Tagged Molecular Inversion Probes", Nature Biotechnology, 21 (6), 2003, 673-678.
Hardenbol, Paul et al., "Highly multiplexed molecular inversion probe genotyping: Over 10,000 targeted SNPs genotyped in a singled tube assay", Genome Research, 15, 2005, 269-275.
Harismendy, O et al., "Method for Improving Sequence Coverage Uniformity of Targeted Genomic Intervals Amplified by LR-PCR Using Illumina GA Sequencing-By-Synthesis Technology", Bio Techniques, 46(3), 2009, 229-231.
Harper, J. C. et al., "Recent Advances and Future Developments in PGD", Prenatal Diagnosis, 19, 1999, 1193-1199.
Harton, G.L. et al., "Preimplantation Genetic Testing for Marfan Syndrome", Molecular Human Reproduction, 2 (9), 1996, 713-715.
Hayden, et al., "Multiplex-Ready PCR: A new method for multiplexed SSR and SNP genotyping", BMC Genomics 2008, 9(80), 1-12.
Hellani, A. et al., "Clinical Application of Multiple Displacement Amplification in Preimplantation Genetic Diagnosis", Reproductive BioMedicine Online, 10 (3), 2005, 376-380.

(56) References Cited

OTHER PUBLICATIONS

Hellani, Ali et al., "Multiple displacement amplification on single cell and possible PGD applications", Molecular Human Reproduction, 10(11), 2004, 847-852.
Hojsgaard, S. et al., "BIFROST—Block recursive models induced from relevant knowledge, observations, and statistical techniques", Computational Statistics & Data Analysis, 19(2), 1995, 155-175.
Holleley, et al., "Multiplex Manager 1.0: a Cross-Platform Computer Program that Plans and Optimizes Multiplex PCR", BioTechniques46:511-517 (Jun. 2009), 511-517.
Hollox, E. et al., "Extensive Normal Copy Number Variation of a β-Defensin Antimicrobial-Gene Cluster", Am. J. Hum. Genet., 73, 2003, 591-600.
Homer, et al., "Resolving Individuals Contributing Trace Amounts of DNA to Highly Complex Mixtures Using High-Density SNP Genotyping Microarrays", PLOS Genetics, 4(8), 2008, 9 pgs.
Hoogendoorn, Bastiaan et al., "Genotyping Single Nucleotide Polymorphisms by Primer Extension and High Performance Liquid Chromatography", Hum Genet, 104, 1999, 89-93.
Hospital, F. et al., "A General Algorithm to Compute Multilocus Genotype Frequencies Under Various Mating Systems" vol. 12, No. 6, Jan. 1, 1996 (Jan. 1, 1996), pp. 455-462.
Howie, et al., "Fast and accurate genotype imputation in genome-wide association studies through pre-phasing", Nature Genetics, vol. 44, No. 8, Jul. 22, 2012, 955-959.
Hu, Dong Gui et al., "Aneuploidy Detection in Single Cells Using DNA Array-Based Comparative Genomic Hybridization", Molecular Human Reproduction, 10(4), 2004, 283-289.
Ido, Yasuo et al., "Hyperglycemia-Induced Apoptosis in Human Umbilical Vein Endothelial Cells: Inhibition by the AMP-Activated Protein Kinase Activation", Diabetes, 51, 2002, 159-167.
Illumina Catalog, , "Paired-End Sample Preparation Guide, Illumina Catalog# PE-930-1 001, Part# 1005063 Rev. E", 2011, 1-40.
Ishii, et al., "Optimization of Annealing Temperature to Reduce Bias Caused by a Primer Mismatch in Multitemplate PCR", Applied and Environmental Microbiology, Aug. 2001, p. 3753-3755.
Johnson, D.S. et al., "Comprehensive Analysis of Karyotypic Mosaicism Between Trophectoderm and Inner Cell Mass", Molecular Human Reproduction, 16(12), 2010, 944-949.
Johnson D.S, et al., "Preclinical Validation of a Microarray Method for Full Molecular Karyotyping of Blastomeres in a 24-h Protocol", Human Reproduction, 25 (4), 2010, 1066-1075.
Kaplinski, Lauris et al., "MultiPLX: Automatic Grouping and Evaluation of PCR Primers", Bioinformatics, 21(8), 2005, 1701-1702.
Kazakov, V.I et al., "Extracellular DNA in the Blood of Pregnant Women", sitologia, 37, 3, 1995, 8.
Kijak, G. et al., "Discrepant Results in the Interpretation of HIV-1 Drug-Resistance Genotypic Data Among Widely Used Algorithms", HIV Medicine, 4, 2003, 72-78.
Kinnings, S. L. et al., "Factors affecting levels of circulating cell-free fetal DNA in maternal plasma and their implications for noninvasive prenatal testing", Prenatal Diagnosis, vol. 35, 2015, 816-822.
Konfortov, Bernard A. et al., "An Efficient Method for Multi-Locus Molecular Haplotyping", Nucleic Acids Research, 35(1), e6, 2007, 8 pgs.
Krjutskov, K et al., "Development of a single tube 640-plex genotyping method for detection of nucleic acid variations on microarrays", Nucleic Acids Research, vol. 36, No. 12, May 23, 2008 (May 23, 2008), pp. e75-e75.
Kuliev, Anver et al., "Thirteen Years' Experience on Preimplantation Diagnosis: Report of the Fifth International Symposium on Preimplantation Genetics", Reproductive BioMedicine Online, 8, 2, 2004, 229-235.
Lambert-Messerlian, G. et al., "Adjustment of Serum Markers in First Trimester Screening", Journal of Medical Screening, 16 (2), 2009, 102-103.

Lathi, Ruth B. et al., "Informatics Enhanced SNP Microarray Analysis of 30 Miscarriage Samples Compared to Routine Cytogenetics", PLoS ONE, 7(3), 2012, 5 pgs.
Leary, Rebecca J et al., "Detection of Chromosomal Alterations in the Circulation of Cancer Patients with Whole-Genome Sequencing", Science Translational Medicine, 4, 162, 2012, 12.
Li, Yind. et al., "Non-Invasive Prenatal Diagnosis Using Cell-Free Fetal DNA in Maternal Plasma from PGD Pregnancies", Reproductive BioMedicine Online, 19 (5), 2009, 714-720.
Li, Ying et al., "Size Separation of Circulatory DNA in Maternal Plasma Permits Ready Detection of Fetal DNA Polymorphisms", Clinical Chemistry, 50, 6, 2004, 1002-1011.
Li B, "Highly Multiplexed Amplicon Preparation for Targeted Re-Sequencing of Sample Limited Specimens Using the Ion AmpliSeq Technology and Semiconductor Sequencing", Proceedings of the Annual Meeting of the American Society of Human Genetics [retrieved on Oct. 30, 2012]. Retrieved from the Internet: <URL: http://www.ashg.org/2012meeting/abstracts/fulltext/f120121811.htm>, 2012, 1 pg.
Liao, Gary J.W. et al., "Targeted Massively Parallel Sequencing of Maternal Plasma DNA Permits Efficient and Unbiased Detection of Fetal Alleles", Clinical Chemistry, 57 (1), 2011, 92-101.
Liao, J. et al., "An Alternative Linker-Mediated Polymerase Chain Reaction Method Using a Dideoxynucleotide to Reduce Amplification Background", Analytical Biochemistry 253, 137-139 (1997).
Liew, Michael et al., "Genotyping of Single-Nucleotide Polymorphisms", Clinical Chemistry, 50(7), 2004, 1156-1164.
Lindroos, Katatina et al., "Genotyping SNPs by Minisequencing Primer Extension Using Oligonucleotide Microarrays", Methods in Molecular Biology, 212, Single Nucleotide Polymorphisms: Methods and Protocols, P-K Kwok (ed.), Humana Press, Inc., Totowa, NJ, 2003, 149-165.
Lo, et al., "Digital PCR for the Molecular Detection of Fetal Chromosomal Aneuploidy", PNAS, vol. 104, No. 32, Aug. 7, 2007, 13116-13121.
Lo, et al., "Fetal Nucleic Acids in Maternal Blood: the Promises", Clin. Chem. Lab. Med., 50(6), 2012, 995-998.
Lo, et al., "Free Fetal DNA in Maternal Circulation", JAMA, 292(23), (Letters to the Editor), 2004, 2835-2836.
Lo, "Non-Invasive Prenatal Diagnosis by Massively parallel Sequencing of Maternal Plasma DNA", Open Biol 2: 120086, 2012, 1-5.
Lo, et al., "Prenatal Sex Determination by DNA Amplification from Maternal Peripheral Blood", The Lancet,2, 8676, 1989, 1363-1365.
Lo, et al., "Rapid Clearance of Fetal DNA from Maternal Plasma", Am. J. Hum. Genet., 64, 1999, 218-224.
Lo, et al., "Strategies for the Detection of Autosomal Fetal DNA Sequence from Maternal Peripheral Blood", Annals New York Academy of Sciences,731, 1994, 204-213.
Lo, et al., "Two-way cell traffic between mother and fetus: biologic and clinical implications", Blood, 88(11), Dec. 1, 1996, 4390-4395.
Lo, Dennis Y. et al., "Fetal Nucleic Acids in Maternal Plasma: Toward the Development of Noninvasive Prenatal Diagnosis of Fetal Chromosomal Aneuploidies", Ann. N.Y. Acad. Sci., 1137, 2008, 140-143.
Lo, Dennis Y. et al., "Plasma placental RNA allelic ratio permits noninvasive prenatal chromosomal aneuploidy detection", Nature Medicine, 13(2), 2007, 218-223.
Lo, Dennis Y.M. et al., "Maternal Plasma DNA Sequencing Reveals the Genome-Wide Genetic and Mutational Profile of the Fetus", Science Translational Medicine, 2, 61, 2010, 13.
Lo, Dennis Y.M. et al., "Presence of Fetal DNA in Maternal Plasma and Serum", The Lancet, 350, 1997, 485-487.
Lo, Dennis Y.M. et al., "Quantitative Analysis of Fetal DNA in Maternal Plasma and Serum: Implications for Noninvasive Prenatal Diagnosis", Am. J. Hum. Genet., 62, 1998, 768-775.
Lo, Y.M.D et al., "Prenatal Determination of Fetal Rhesus D Status by DNA Amplification of Peripheral Blood of Rhesus-Negative Mothers", Annals New York Academy of Sciences, 731, 1994, 229-236.
Lo, Y-M. D. et al., "Prenatal Determination of Fetal RhD Status by Analysis of Peripheral Blood of Rhesus Negative Mothers", The Lancet, 341, 1993, 1147-1148.

(56) References Cited

OTHER PUBLICATIONS

Lo, Y-M.D et al., "Detection of Single-Copy Fetal DNA Sequence from Maternal Blood", The Lancet, 335, 1990, 1463-1464.

Lo, Y. et al., "Detection of Fetal RhD Sequence from Peripheral Blood of Sensitized RhD-Negative Pregnant Women", British Journal of Haematology, 87, 1994, 658-660.

Lun, Fiona M. et al., "Noninvasive Prenatal Diagnosis of Monogenic Diseases by Digital Size Selection and Relative Mutation Dosage on DNA in Maternal Plasma", PNAS, 105(50), 2008, 19920-19925.

Maniatis, T. et al., "In: Molecular Cloning: A Laboratory Manual", Cold Spring Harbor Laboratory, New York, Thirteenth Printing, 1986, 458-459.

Mansfield, Elaine S , "Diagnosis of Down Syndrome and Other Aneuploidies Using Quantitative Polymerase Chain Reaction and Small Tandem Repeat Polymorphisms", Human Molecular Genetics, 2, 1, 1993, 43-50.

Markoulatos, P. et al., "Multiplex Polymerase Chain Reaction: A Practical Approach", 2002 Wiley-Liss, Inc. DOI 10.1002/jcla.2058 Journal of Clinical Laboratory Analysis 16:47-51 (2002).

May, Rober M. et al., "How Many Species Are There on Earth?", Science, 241, 1988, 1441-1449.

Mccray, Alexa T. et al., "Aggregating UMLS Semantic Types for Reducing Conceptual Complexity", MEDINFO 2001: Proceedings of the 10th World Congress on Medical Informatics (Studies in Health Technology and Informatics, 84, V. Patel et al. (eds.), IOS Press Amsterdam, 2001, 216-220.

Mennuti, M. et al., "Is It Time to Sound an Alarm About False-Positive Cell-Free DNA Testing for Fetal Aneuploidy?", American Journal of Obstetrics, 2013, 5 pgs.

Mersy, et al., "Noninvasive Detection of Fetal Trisomy 21: Systematic Review and Report of Quality and Outcomes of Diagnostic Accuracy Studies Performed Between 1997 and 2012", Human Reproduction Update, 19(4), 2013, 318-329.

Miller, Robert, "Hyperglycemia-Induced Changes in Hepatic Membrane Fatty Acid Composition Correlate with Increased Caspase-3 Activities and Reduced Chick Embryo Viability", Comparative Biochemistry and Physiology, Part B, 141, 2005, 323-330.

Miller, Robert R, "Homocysteine-Induced Changes in Brain Membrane Composition Correlate with Increased Brain Caspase-3 Activities and Reduced Chick Embryo Viability", Comparative Biochemistry and Physiology Part B, 136, 2003, 521-532.

Morand, et al., "Hesperidin contributes to the vascular protective effects of orange juice: a randomized crossover study in healthy volunteers", Am J Clin Nutr. Jan. 2011;93(1 ):73-80. Epub Nov. 10, 2010.

Munne, S. et al., "Chromosome abnormalities in human embryos", Human Reproduction update, 4 (6), 842-855.

Murtaza, M. et al., "Non-Invasive Analysis of Acquired Resistance to Cancer Therapy by Sequencing of Plasma DNA", Nature (doi:10.1038/nature12065), 2013, 6 pgs.

Muse, Spencer V. , "Examining rates and patterns of nucleotide substitution in plants", Plant Molecular Biology 42: 25-43, 2000.

Myers, Chad L. et al., "Accurate Detection of Aneuploidies in Array CGH and Gene Expression Microarray Data", Bioinformatics, 20(18), 2004, 3533-3543.

Nannya, Yasuhito et al., "A Robust Algorithm for Copy Number Detection Using High-density Oligonucleotide Single Nucleotide Polymorphism Genotyping Arrays", Cancer Res., 65, 14, 2005, 6071-6079.

Nicolaides, K. et al., "Noninvasive Prenatal Testing for Fetal Trisomies in a Routinely Screened First-Terimester Population", American Journal of Obstetrics (article in press), 207, 2012, 1.e1-1.e6.

Nicolaides, K.H et al., "Validation of Targeted Sequencing of Single-Nucleotide Polymorphisms for Non-Invasive Prenatal Detection of Aneuploidy of Chromosomes 13, 18, 21, X, and Y", Prenatal Diagnosis, 33, 2013, 575-579.

Nicolaides, Kypros H. et al., "Prenatal Detection of Fetal Triploidy from Cell-Free DNA Testing in Maternal Blood", Fetal Diagnosis and Therapy, 2013, 1-6.

Nygren, et al., "Quantification of Fetal DNA by Use of Methylation-Based DNA Discrimination", Clinical Chemistry 56:10 1627-1635 (2010).

Ogino, S. et al., "Bayesian Analysis and Risk Assessment in Genetic Counseling and Testing", Journal of Molecular Diagnostics, 6 (1), 2004, 9 pgs.

O'Malley, R et al., "An adapter ligation-mediated PCR method for high-throughput mapping of T-DNA inserts in the Arabidopsis genome", Nat. Protoc. 2, 2910-2917 (2007).

Orozco A.F., et al., "Placental Release of Distinct DNA-Associated Micro-Particles into Maternal Circulation: Reflective of Gestation Time and Preeclampsia", Placenta,30, 2009, 891-897.

Ozawa, Makiko et al., "Two Families with Fukuyama Congenital Muscular Dystrophy that Underwent in Utero Diagnosis Based on Polymorphism Analysis", Clinical Muscular Dystrophy: Research in Immunology and Genetic Counseling—FY 1994 Research Report, (including text in Japanese), 1994, 8.

Paez, Guillermo J. et al., "Genome coverage and sequence fidelity of Φ29 polymerase-based multiple strand displacement whole genome amplification", Nucleic Acids Research, 32(9), 2004, 1-11.

Page, S. L. et al., "Chromosome Choreography: The Meiotic Ballet", Science, 301, 2003, 785-789.

Palomaki, Glenn et al., "DNA Sequencing of Maternal Plasma Reliably Identifies Trisomy 18 and Trisomy 13 as Well as Down Syndrome: an International Collaborative Study", Genetics in Medicine, 2012, 10.

Palomaki, Glenn E. et al., "DNA Sequencing of Maternal Plasma to Detect Down Syndrome: An International Clinical Validation Study", Genetics in Medicine (pre-print version), 13, 2011, 8 pgs.

Papageorgiou, Elisavet A. et al., "Fetal-Specific DNA Methylation Ratio Permits Noninvasive Prenatal Diagnosis of Trisomy 21", Nature Medicine (advance online publication),17, 2011, 5 pgs.

PCT/US2006/045281, "International Preliminary Report on Patentability", dated May 27, 2008, 1 pg.

PCT/US2006/045281, "International Search Report and Written Opinion", dated Sep. 28, 2007, 7 pgs.

PCT/US2008/003547, "International Search Report", dated Apr. 15, 2009, 5 pgs.

PCT/US2009/034506, "International Search Report", dated Jul. 8, 2009, 2 pgs.

PCT/US2009/045335, "International Search Report", dated Jul. 27, 2009, 1 pg.

PCT/US2009/052730, "International Search Report", dated Sep. 28, 2009, 1 pg.

PCT/US2010/050824, "International Search Report", dated Nov. 15, 2010, 2 pgs.

PCT/US2011/037018, "International Search Report", dated Sep. 27, 2011, 2 pgs.

PCT/US2011/061506, "International Search Report", dated Mar. 16, 2012, 1 pgs.

PCT/US2011/066938, "International Search Report", dated Jun. 20, 2012, 1 pg.

PCT/US2012066339, "International Search Report", dated Mar. 5, 2013, 1 pg.

PCT/US2013/028378, "International Search Report and Written Opinion", dated May 28, 2013, 11 pgs.

PCT/US2013/57924, "International Search Report and Written Opinion", dated Feb. 18, 2014, 8 pgs.

PCT/US2014/051926, "International Search Report mailed", dated Dec. 9, 2014, 3 pgs.

PCT/US2014/51926, "Written Opinion", dated Dec. 9, 2014, 5 pgs.

PCT/US2015/026957, "International Preliminary Report on Patentability dated Nov. 3, 2016", Nov. 3, 2016, 3 pages.

Pearson, K., "On the criterion that a given system of deviations from the probable in the case of a correlated system of variables is such that it can be reasonably supposed to have arisen from random sampling", Philosophical Magazine Series 5, vol. 50, Issue 302, 1900, 157-175.

Pena, Sergio D.J et al., "Paternity Testing in the DNA Era", Trends in Genetics, 10, 6, 1994, 204-209.

Perkel, Jeffrey M., "Overcoming the Challenges of Multiplex PCR", Biocompare Editorial Article, NULL, 2012, 1-5.

(56) References Cited

OTHER PUBLICATIONS

Perry, George H. et al., "The Fine-Scale and Complex Architecture of Human Copy-Number Variation", The American Journal of Human Genetics,82, 2008, 685-695.
Pertl, B. et al., "Detection of Male and Female Fetal DNA in Maternal Plasma by Multiplex Fluorescent Polymerase Chain Reaction Amplification of Short Tandem Repeats", Hum. Genet., 106, 2000, 45-49.
Peters, David P. et al., "Noninvasive Prenatal Diagnosis of a Fetal Microdeletion Syndrome", New England Journal of Medicine, 365(19), 2011, 1847-1848.
Pfaffl, Michael W. , "Relative Expression Software Tool (REST©) for Group-Wise Comparison and Statistical Analysis of Relative Expression Results in real-Time PCR", Nucleic Acids Research, 30(9), 2002, 10 pgs.
Phillips, C et al., "Resolving Relationship Tests that Show Ambiguous STR Results Using Autosomal SNPs as Supplementary Markers", Forensic Science International: Genetics 2, 2008, 198-204.
Podder, Mohua et al., "Robust SN P genotyping by multiplex PCR and arrayed primer", BMC Medical Genomics,1(5), 2008, 1-15.
Porreca, Gregory J et al., "Multiplex Amplification of Large Sets of Human Exons", Nature Methods, 4, (advance online publication), 2007, 6.
Price, T.S. et al., ""SW-ARRAY: a dynamic programming solution for the identification of copy-number changes in genomic DNA using array comparative genome hybridization data",", Nucleic Acids Research, vol. 33, No. 11, Jun. 16, 2005 (Jun. 16, 2005), pp. 3455-3464.
Rabinowitz, et al., "Accurate Prediction of HIV-1 Drug Response from the Reverse Transcriptase and Protease Amino Acid Sequences Using Sparse Models Created by Convex Optimization", Bioinformatics, 22, 5, 2006, 541-549.
Rabinowitz, Matthew et al., "Origins and rates of aneuploidy inhuman blastomeres", Fertility and Sterlity, Elsevier Science Inc, 97(2), 2012, 395-401.
Rabinowitz, Matthew. et al., "Non-Invasive Prenatal Aneuploidy Testing of Chromosomes 13, 18, 21, X, and Y Using Targeted Sequencing of Polymorphic Loci", The American Society of Human Genetics, meeting poster, 2012, 1 pg.
Rachlin, J. et al., "Computational tradeoffs in multiplex PCR assay design for SNP genotyping", BMC Genomics, vol. 6, No. 102, Jul. 25, 2005, 11 pages.
Rahmann, Sven et al., "Mean and variance of the Gibbs free energy of oligonucleotides in the nearest neighbor model under varying conditions", Bioinformatics, 20(17), 2004, 2928-2933.
Rava, Richard P. et al., "Circulating Fetal Cell-Free DNA Fraction Differ in Autosomal Aneuploidies and Monosomy X", Clinical Chemistry, 60(1), (papers in press), 2013, 8 pgs.
Rechitsky, Svetlana et al., "Preimplantation Genetic Diagnosis with HLA Matching", Reproductive Bio Medicine Online, 9, 2, 2004, 210-221.
Renwick, Pamela. et al., "Proof of Principle and First Cases Using Preimplantation Genetic Haplotyping—A Paradigm Shift for Embryo Diagnosis", Reproductive BioMedicine Online, 13 (1), 2006, 110-119.
Ricciotti, Hope, "Eating by Trimester", Online]. Retrieved from Internet:<http://www.youandyourfamily.com/article.php?story=Eating+by+Trimester>, 2014, 3.
Roper, Stephen M. et al., "Forensic Aspects of DNA-Based Human Identity Testing", Journal of Forensic Nursing, 4, 2008, 150-156.
Roux, K. , "Optimization and Troubleshooting in PCR", PCR Methods Appl. 4, 1995, 185-194.
Rozen, Steve et al., "Primer3 on the WWW for General Users and for Biologis Programmers", Methods in Molecular Biology, 132: Bioinformatics Methods and Protocols, 1999, 365-386.
Russell, L M., "X Chromosome Loss and Ageing", Cytogenetic and Genome Res., 116, 2007, 181-185.
Ryan, et al., "The importance of phase information for human genomics", Nature Reviews Genetics, vol. 12, No. 3, Mar. 1, 2011.
Ryan, Allison. et al., "Informatics-Based, Highly Accurate, Noninvasive Prenatal Paternity Testing", Genetics in Medicine (advance online publication), 2012, 5 pgs.
Rychlik, et al., "Optimization of the annealing temperature for DNA amplification in vitro", Nucleic Acids Research, 18(21), 1990, 6409-6412.
Samango-Sprouse, C. et al., "SNP-Based Non-Invasive Prenatal Testing Detects Sex Chromosome Aneuploidies with High Accuracy", Prenatal Diagnosis, 33, 2013, 1-7.
Sander, Chris, "Genetic Medicine and the Future of Health Care", Science, 287(5460), 2000, 1977-1978.
Santalucia, J. et al., "The Thermodynamics of DNA Structural Motifs", Annu. Rev. Biophys. Biomol. Struct., 33, 2004, 415-440.
Santalucia, John J.R et al., "Improved Nearest-Neighbor Parameters for Predicting DNA Duplex Stability", Biochemistry, 35, 1996, 3555-3562.
Sasabe, Yutaka, "Genetic Diagnosis of Gametes and Embryos Resulting from ART", Japanese Journal of Fertility and Sterility, 2001, vol. 46, No. 1, p. 43-46.
Schoumans, J et al., "Detection of chromosomal imbalances in children with idiopathic mental retardation by array based comparative genomic hybridisation (array-CGH)", JMed Genet, 42, 2005, 699-705.
Sebat, Jonathan et al., "Strong Association of De Novo Copy Number Mutations with Autism", Science, 316, 2007, 445-449.
Sehnert, A. et al., "Optimal Detection of Fetal Chromosomal Abnormalities by Massively Parallel DNA Sequencing of Cell-Free Fetal DNA from Maternal Blood", Clinical Chemistry (papers in press), 57 (7), 2011, 8 pgs.
Sermon, Karen et al., "Preimplantation genetic diagnosis", The Lancet, Lancet Limited. 363(9421), 2000, 1633-1641.
Servin, B et al., "MOM: A Program to Compute Fully Informative Genotype Frequencies in Complex Breeding Schemes", Journal of Heredity, vol. 93, No. 3, Jan. 1, 2002 (Jan. 1, 2002), pp. 227-228.
Shaw-Smith, et al., "Microarray Based Comparative Genomic Hybridisation (array-CGH) Detects Submicroscopic Chromosomal Deletions and Duplications in Patients with Learning Disability/ Mental Retardation and Dysmorphic Features", J. Med. Genet., 41, 2004, 241-248.
Shen, et al., "High-quality DNA sequence capture of 524 disease candidate genes", High-quality DNA sequence capture of 524 disease candidate genes, Proceedings of the National Academy of Sciences, vol. 108, No. 16, Apr. 5, 2011 (Apr. 5, 2011), pp. 6549-6554.
Shen, Zhiyong, "MPprimer: a program for reliable multiplex PCR primer design", BMC Bioinformatics 2010, 11:143, 1-7.
Sherlock, J et al., "Assessment of Diagnostic Quantitative Fluorescent Multiplex Polymerase Chain Reaction Assays Performed on Single Cells", Annals of Human Genetics,62, 1, 1998, 9-23.
Simpson, J. et al., "Fetal Cells in Maternal Blood: Overview and Historical Perspective", Annals New York Academy of Sciences, 731, 1994, 1-8.
Sint, Daniela et al., "Advances in Multiplex PCR: Balaning Primer Efficiencies and Improving Detection Success", Methods in Ecology and Evolution, 3, 2012, 898-905.
Slater, Howard et al., "High-Resolution Identification of Chromosomal Abnormalities Using Oligonucleotide Arrays Containing 116,204 SNPs", Am. J. Hum. Genet., 77, 5, 2005, 709-726.
Snijders, Antoine et al., "Assembly of Microarrays for Genome-Wide Measurement of DNA Copy Number", Nature Genetic, 29, 2001, 263-264.
Sparks, A. et al., "Non-Invasive Prenatal Detection and Selective Analysis of Cell-Free DNA Obtained from Maternal Blood: Evaluation for Trisomy 21 and Trisomy 18", American Journal of Obstetrics & Gynecology 206, 2012, 319.e1-319.e9.
Sparks, Andrew B. et al., "Selective Analysis of Cell-Free DNA in Maternal Blood for Evaluation of Fetal Trisomy", Prenatal Diagnosis, 32, 2012, 1-7.
Spiro, Alexander et al., "A Bead-Based Method for Multiplexed Identification and Quantitation of DNASequences Using Flow Cytometry", Applied and Environmental Microbiology, 66, 10, 2000, 4258-4265.

(56) References Cited

OTHER PUBLICATIONS

Spits, C et al., "Optimization and Evaluation of Single-Cell Whole Genome Multiple Displacement Amplification", Human Mutation, 27(5), 496-503, 2006.
Srinivasan, et al., "Noninvasive Detection of Fetal Subchromosome Abnormalities via Deep Sequencing of Maternal Plasma", The American Journal of Human Genetics 92, 167-176, Feb. 7, 2013.
Stephens, Mathews. et al., "A Comparison of Bayesian Methods for Haplotype Reconstruction from Population Genotype Data", Am. J. Hum. Genet.,73, 2003, 1162-1169.
Stevens, Robert et al., "Ontology-Based Knowledge Representation for Bioinformatics", Briefings in Bioinformatics, 1, 4, 2000, 398-414.
Steyerberg, E.W et al., "Application of Shrinkage Techniques in Logistic Regression Analysis: A Case Study", Statistica Neerlandica, 55(1), 2001, 76-88.
Strom, C. et al., "Three births after preimplantation genetic diagnosis for cystic fibrosis with sequential first and second polar body analysis", American Journal of Obstetrics and Gynecology, 178 (6), 1998, 1298-1306.
Strom, Charles M. et al., "Neonatal Outcome of Preimplantation Genetic Diagnosis by Polar Body Removal: The First 109 Infants", Pediatrics, 106( 4), 2000, 650-653.
Stroun, Maurice et al., "Prehistory of the Notion of Circulating Nucleic Acids in Plasma/Serum (CNAPS): Birth of a Hypothesis", Ann. N.Y. Acad. Sci., 1075, 2006, 10-20.
Su, S.Y. et al., "Inferring combined CNV/SNP haplotypes from genotype data", Bioinformatics, vol. 26, No. 11,1, Jun. 1, 2010, 1437-1445.
Sun, Guihua et al., "SNPs in human miRNA genes affect biogenesis and function", RNA, 15(9), 2009, 1640-1651.
Sweet-Kind Singer, J. A. et al., "Log-penalized linear regression", IEEE International Symposium on Information Theory, 2003. Proceedings, 2003, 286.
Tamura, et al., "Sibling Incest and formulation of paternity probability: case report", Legal Medicine, 2000, vol. 2, p. 189-196.
Tang, et al., Multiplex fluorescent PCR for noninvasive prenatal detection of fetal-derived paternally inherited diseases using circulatory fetal DNA in maternal plasma, Eur J Obstet Gynecol Reprod Biol, 2009, v.144, No. 1, p. 35-39.
Tang, N. et al., "Detection of Fetal-Derived Paternally Inherited X-Chromosome Polymorphisms in Maternal Plasma", Clinical Chemistry, 45 (11), 1999, 2033-2035.
Thomas, M.R et al., "The Time of Appearance and Disappearance of Fetal DNA from the Maternal Circulation", Prenatal Diagnosis, 15, 1995, 641-646.
Tong, Yu et al., "Noninvasive Prenatal Detection of Fetal Trisomy 18 by Epigenetic Allelic Ratio Analysis in Maternal Plasma: Theoretical and Empirical Considerations", Clinical Chemistry, 52(12), 2006, 2194-2202.
Tong, Yu K. et al., "Noninvasive Prenatal Detection of Trisomy 21 by Epigenetic-Genetic Chromosome-Dosage Approach", Clinical Chemistry, 56(1), 2010, 90-98.
Troyanskaya, Olga G. et al., "A Bayesian Framework for Combining Heterogeneous Data Sources for Gene Function Prediction (in *Saccharomyces cerevisiae*)", PNAS, 100(14), 2003, 8348-8353.
Tsui, Nancy B.Y et al., "Non-Invasive Prenatal Detection of Fetal Trisomy 18 by RNA-SNP Allelic Ratio Analysis Using Maternal Plasma SERPINB2 mRNA: A Feasibility Study", Prenatal Diagnosis, 29, 2009, 1031-1037.
Turner, E. et al., "Massively Parallel Exon Capture and Library-Free Resequencing Across 16 Genomes", Nature Methods, 6 (5), 2009, 315-316.
Vallone, Peter, "AutoDimer: a Screening Tool for Primer-Dimer and Hairpin Structures", Bio Techniques, 37, 2004, 226-231.
Varley, Katherine Elena et al., "Nested Patch PCR Enables Highly Multiplexed Mutation Discovery in Candidate Genes", Genome Res., 18(11), 2008, 1844-1850.

Verlinsky, Y. et al., "Over a Decade of Experience with Preimplantation Genetic Diagnosis", Fertility and Sterility, 82 (2), 2004, 302-303.
Wagner, Jasenka et al., "Non-Invasive Prenatal Paternity Testing from Maternal Blood", Int. J. Legal Med., 123, 2009, 75-79.
Wang, Eric et al., "Gestational Age and Maternal Weight Effects on Fetal Cell-Free DNA in Maternal Plasma", Prenatal Diagnosis, 33, 2013, 662-666.
Wang, Hui-Yun et al., "A genotyping system capable of simultaneously analyzing >1000 single nucleotide polymorphisms in a haploid genome", Genome Res., 15, 2005, 276-283.
Wang, Yuker et al., "Allele quantification using molecular inversion probes (MIP)", Nucleic Acids Research, vol. 33, No. 21, Nov. 28, 2005, 14 pgs.
Wapner, R. et al., "Chromosomal Microarray Versus Karyotyping for Prenatal Diagnosis", The New England Journal of Medicine, 367 (23), 2012, 2175-2184.
Watkins, N. et al., "Thermodynamic contributions of single internal rA •dA, rC • dC, rG • dG and rU • dT mismatches in RNA/DNA duplexes", Nucleic Acids Research, 9 (5),, 2010, 1894-1902.
Wells, D, "Microarray for Analysis and Diagnosis of Human Embryos", 12th International Congress on Prenatal Diagnosis and Therapy, Budapest, Hungary, 2004, 9-17.
Wells, Dagan, "Advances in Preimplantation Genetic Diagnosis", European Journal of Obstetrics and Gynecology and Reproductive Biology, 115S, 2004, S97-S101.
Wells, Dagan, "Detailed Chromosomal and Molecular Genetic Analysis of Single Cells by Whole Genome Amplification and Comparative Genomic Hybridisation", Nucleic Acids Research, 27, 4, 1999, 1214-1218.
Wen, Daxing et al., "Universal Multiples PCR: A Novel Method of Simultaneous Amplification of Multiple DNA Fragments", Plant Methods, 8(32), NULL, 2012, 1-9.
Wilton, et al., "Birth of a Healthy Infant After Preimplantation Confirmation of Euploidy by Comparative Genomic Hybridization", N. Engl. J. Med., 345(21), 2001, 1537-1541.
Wilton, L., "Preimplantation Genetic Diagnosis and Chromosome Analysis of Blastomeres Using Comparative Genomic Hybridization", Human Reproduction Update, 11 (1), 2005, 33-41.
Wright, C. F. et al., "Cell-free fetal DNA and RNA in maternal blood: implications for safer antenatal testing", BMJ, vol. 39, Jul. 18, 2009, 161-165.
Wu, Y. Y. et al., "Rapid and/or high-throughput genotyping for human red blood cell, platelet and leukocyte antigens, and forensic applications", Clinica Chimica Acta, vol. 363, 2006, 165-176.
Xia, Tianbing et al., "Thermodynamic Parameters for an Expanded Nearest-Neighbor Model for Formation of RNA Duplexes with Watson-Crick Base Pairs", Biochemistry, 37, 1998, 14719-14735.
Yeh, Iwei et al., "Knowledge Acquisition, Consistency Checking and Concurrency Control for Gene Ontology (GO)", Bioinformatics, 19, 2, 2003, 241-248.
You, Frank M. et al., "BatchPrimer3: A high throughput web application for PCR and sequencing primer design", BMC Bioinformatics, Biomed Central, London, GB, vol. 9, No. 1, May 29, 2008 (May 29, 2008), p. 253.
Zhang, Rui et al., "Quantifying RNA allelic ratios by microfluidic multiplex PCR and sequencing", Nature Methods, 11(1), 2014, 51-56.
Zhao, Xiaojun. et al., "An Integrated View of Copy Number and Allelic Alterations in the Cancer Genome Using Single Nucleotide Polymorphism Arrays", Cancer Research,64, 2004, 3060-3071.
Zhou, W. et al., "Counting Alleles Reveals a Connection Between Chromosome 18q Loss and Vascular Invasion", Nature Biotechnology, 19, 2001, 78-81.
Zimmermann, et al., "Noninvasive Prenatal Aneuploidy Testing of Chromosomes 13, 18, 21 X, and Y, Using targeted Sequencing of Polymorphic Loci", Prenatal Diagnosis, 32, 2012, 1-9.
Anker, P. et al., "Detection of circulating tumour DNA in the blood (plasma/serum) of cancer patients", Cancer and Metastasis Reviews, vol. 18, 1999, 65-73.

(56) References Cited

OTHER PUBLICATIONS

Ashoor, G. et al., "Fetal fraction in maternal plasma cell-free DNA at 11-13 weeks' gestation: relation to maternal and fetal characteristics", Ultrasound in Obstetrics and Gynecology, vol. 41, 2013, 26-32.
Bianchi, D. W. et al., "Genome-Wide Fetal Aneuploidy Detection by Maternal Plasma DNA Sequencing", Obstetrics & Gynecology, vol. 119, No. 5, May 2012, 890-901.
Chan, K.C. et al., "Size Distributions of Maternal and Fetal DNA in Maternal Plasma", Clinical Chemistry, vol. 50, No. 1, 2004, 88-92.
Chen, X. Q. et al., "Microsatallite alterations in plasma DNA of small cell lung cancer patients", Nature Medicine, vol. 2, No. 9, Sep. 1996, 1033-1035.
Dodge, Y., "Bayes' Theorem", The Concise Encyclopedia of Statistics, 2008, 30-31.
Geiss, G. K. et al., "Direct multiplexed measurement of gene expression with color-coded probe pairs", Nature Biotechnology, vol. 26, No. 3, Feb. 17, 2008, 317-325.
Gunderson, K. L. et al., "A genome-wide scalable SNP genotyping assay using microarray technology", Nature Genetics, vol. 37, No. 5, May 2005, 549-554.
Jenkins, S. et al., "High-throughput SNP genotyping", Comparative and Functional Genomics, vol. 3, Dec. 5, 2001, 57-66.
Kwok, P. Y., "High-throughput genotyping assay approaches", Pharmacogenomics, vol. 1, No. 1, 2000, 1-5.
Lander, E. S. et al., "Initial sequencing and analysis of the human genome", Nature, vol. 409, Feb. 15, 2001, 860-921.
Levsky, J. M. et al., "Fluorescence in situ hybridization: past, present and future", Journal of Cell Science, vol. 116, No. 14, 2003, 2833-2838.
Palomaki, G. E. et al., "DNA sequencing of maternal plasma to detect Down syndrome: An international clinical validation study", Genetics in Medicine, vol. 13, No. 1, Nov. 2011, 913-920.
Quinn, G. P. et al., "Experimental Design and Data Analysis for Biologists", Graphical Exploration of Data, 2002, 64-67.
Tebbutt, S. J. et al., "Microarray genotyping resource to determine population stratification in genetic association studies of complex disease", BioTechniques, vol. 37, Dec. 2004, 977-985.
Yuan, X. et al., "Probability Theory-based SNP Association Study Method for Identifying Susceptibility Loci and Genetic Disease Models in Human Case-Control Data", IEEE Trans Nanobioscience, vol. 9, No. 4, Dec. 2010, 232-241.
Deutsch, S. et al., "Detection of aneuploidies by paralogous sequence quantification", J Med Genet, vol. 41, 2004, 908-915.
Illumina, "Patent Owner Illumina's Preliminary Response to Petition", dated Oct. 17, 2018, 75 pgs.
Illumina, "Plaintiff/Counterclaim Defendant Illumina, Inc.'s Amended Patent L.R. 3-3 Preliminary Invalidity Contentions for U.S. Pat. No. 8,682,592", Oct. 30, 2018, 22 pages.
Illumina, "Plaintiff/Counterclaim-Defendant Illumina, Inc.'s Patent L.R. 3-3 Contentions for U.S. Patent Preliminary Invalidity Contentions for U.S. Pat. No. 8,682,592", Oct. 9, 2018, 81 pages.
Mamon, H. et al., "Letters to the Editor: Preferential Amplification of Apoptotic DNA from Plasma: Potential for Enhancing Detection of Minor DNA Alterations in Circulating DNA", Clinical Chemistry, vol. 54, No. 9, 2008, 1582-1584.
Minkoff, E. et al., "Stem Cells, Cell Division, and Cancer", Biology Today Third Edition, Chapter 12, 2004, 10 pages.
Natera, Inc., "Defendant Natera, Inc.'s Invalidity Contentions Under Patent L.R. 3-3; Document Production Accompanying Invalidity Contentions Under Patent L.R. 3-4", Aug. 20, 2018, 17 pages.
Natera, Inc., "Exhibit 8 Ehrich Invalidity Chart", Aug. 20, 2018, 16 pages.
Natera, Inc., "Petitioner Reply Per Board Order of Nov. 2, 2018 (Paper No. 10)", Nov. 9, 2018, 8 pgs.
Wang, T.L. et al., "Digital karyotyping", PNAS, vol. 99, No. 25, Dec. 10, 2002, 16156-16161.
Alaeddini, R. et al., "Forensic implications of genetic analyses from degraded DNA—A review", Forensic Science International: Genetics, vol. 4, 2010, 148-157
Hornak, M. et al., "Aneuploidy Detection in Pigs Using Comparative Genomic Hybridization: From the Oocytes to Blastocysts", PLoS ONE, vol. 7, No. 1, Jan. 2012, 6 pages.
Lo, Y., "Noninvasive prenatal detection of fetal chromosomal aneuploidies by maternal plasma nucleic acid analysis: a review of the current state of the art", BJOG An International Journal of Obstetrics and Gynaecology, vol. 116, 2009, 152-157
Lu, I. et al., "Establishment of a system based on universal multiplex—PCR for screening genetically modified crops", Anal. Bioanal. Chem, vol. 396, Oct. 24, 2009, 2055-2064.
Shen, R. et al., "High-throughput SNP genotyping on universal bead arrays", Mutation Research, vol. 573, Feb. 11, 2005, 70-82.
Wang, D. G. et al., "Large-Scale Identification, Mapping, and Genotyping of Single-Nucleotide Polymorphisms in the Human Genome", Science, vol. 280, May 15, 1998, 1077-1082.
Zimmermann, B., "Noninvasive prenatal aneuploidy testing of chromosomes 13, 18, 21, X, and Y, using targeted sequencing of polymorphic loci, Supplemental Information", Prenatal Diagnosis, vol. 32, 2012, 7 pages.

* cited by examiner

| | | |
|---|---|---|
| The sequencing-adaptor sequence is located inside the primer sequence and flanked by target specific sequence on both sides. 10 bases are target-specific at the 3'-end of each primer. Primers were tested successfully in real-time PCR. For sequencing this reduces the number of primer bases that need to be sequenced. | | |
| rs8130564 | int-tag 1.10 | AACTCACATAGCACACGAGGCTCTTCCGATCTTGCAAGCACA |
| rs2832093 | int-tag 2.10 | TCCTCTGTGACACGAGGCTCTTCCGATCTCCCTGCTCTT |
| rs12011281 | int-tag 3.10 | tcctctctctACACGAGGCTCTTCCGATCTCGGGCTGTCA |
| rs6719561 | int-tag 4.10 | TACATCCTTGAGACACGAGGCTCTTCCGATCTGCTGTGCAGT |
| rs10187018 | int-tag 5.10 | tttgcttgagctACACGAGGCTCTTCCGATCTcgggagtttc |
| rs10460481 | int-tag 6.10 | gtcttatggtggACACGAGGCTCTTCCGATCTcaaagccagt |
| | | |
| The sequencing-adaptor sequence is located inside the primer sequence and flanked by target specific sequence on both sides. The internal tag is formed into a hairpin structure by 10 complementary bases on either end. This brings the target-specific ends of the primer into close proximity and hinders unspecific binding to the "internal tag". 10 bases are target-specific at the 3'-end of each primer. Primers were tested successfully in real-time PCR. | | |
| rs8130564 | loop-int-tag 1.10 | AACTCACATAGCtgatcggtACACGAGGCTCTTCCGATCTTGCAAGCACA |
| rs2832093 | loop-int-tag 2.10 | TCCTCTGTGtgatcggtACACGAGGCTCTTCCGATCTCCCTGCTCTT |
| rs12011281 | loop-int-tag 3.10 | tcctctcttgatcggtACACGAGGCTCTTCCGATCTCGGGCTGTCA |
| rs6719561 | loop-int-tag 4.10 | TACATCCTTGAGtgatcggtACACGAGGCTCTTCCGATCTGCTGTGCAGT |
| rs10187018 | loop-int-tag 5.10 | tttgcttgagcttgatcggtACACGAGGCTCTTCCGATCTcgggagtttc |
| rs10460481 | loop-int-tag 6.10 | gtcttatggtggtgatcggtACACGAGGCTCTTCCGATCTcaaagccagt |

FIG. 12

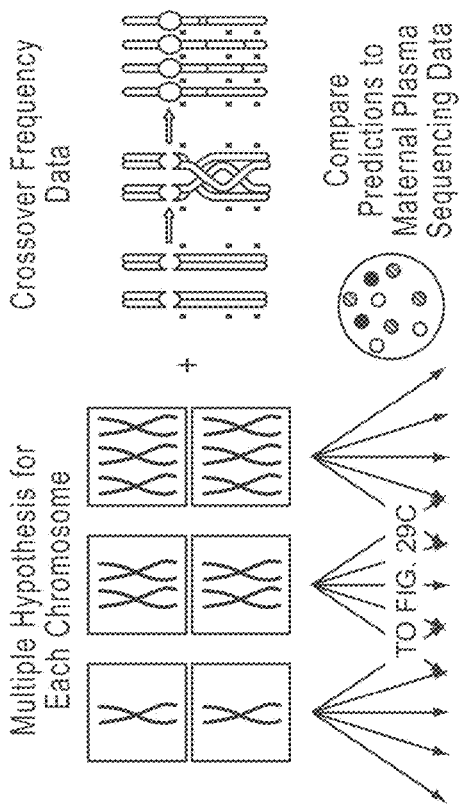
FIG. 29B
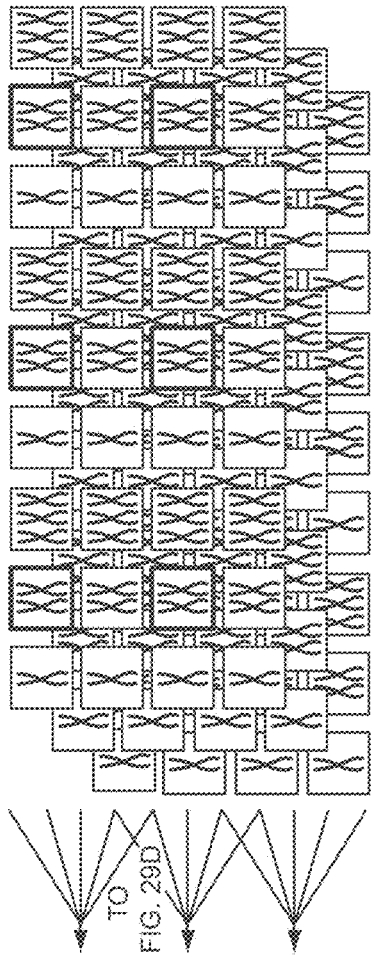
FIG. 29C
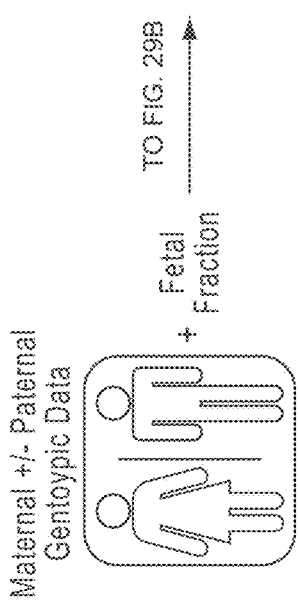
FIG. 29A
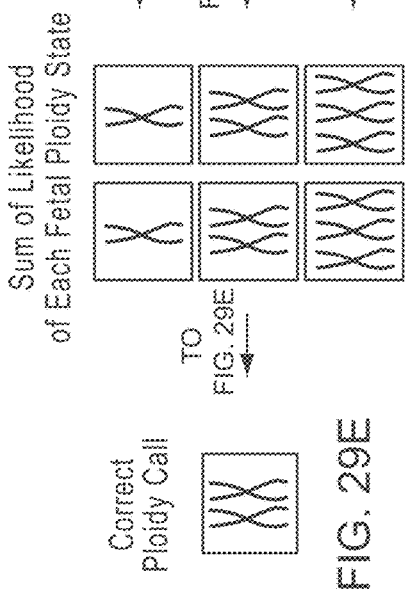
FIG. 29D
FIG. 29E

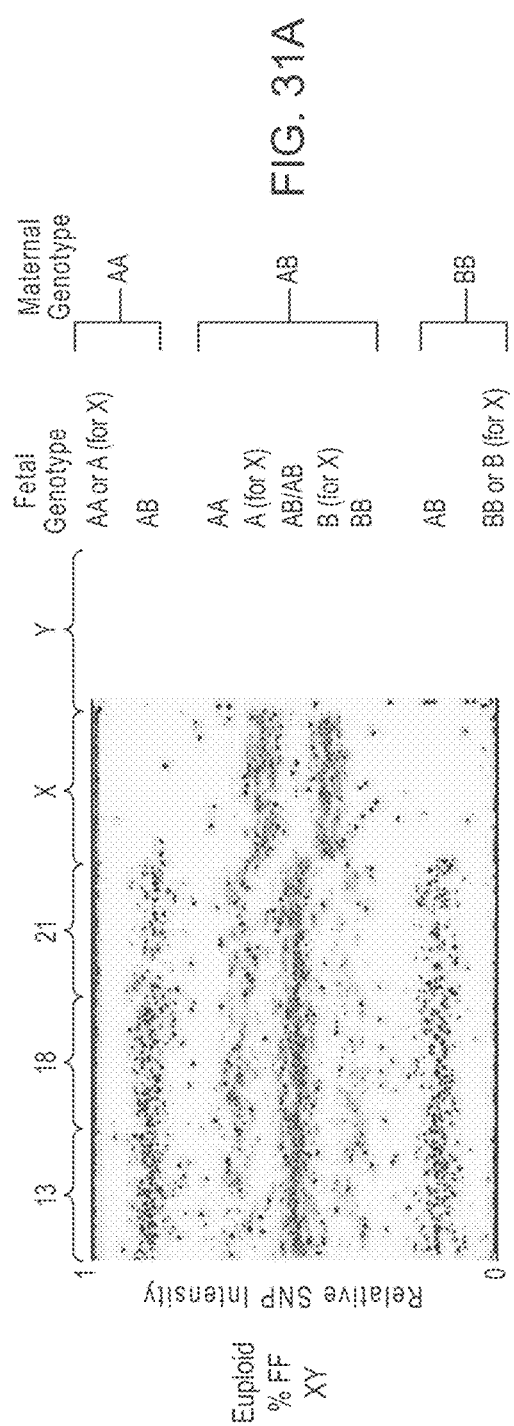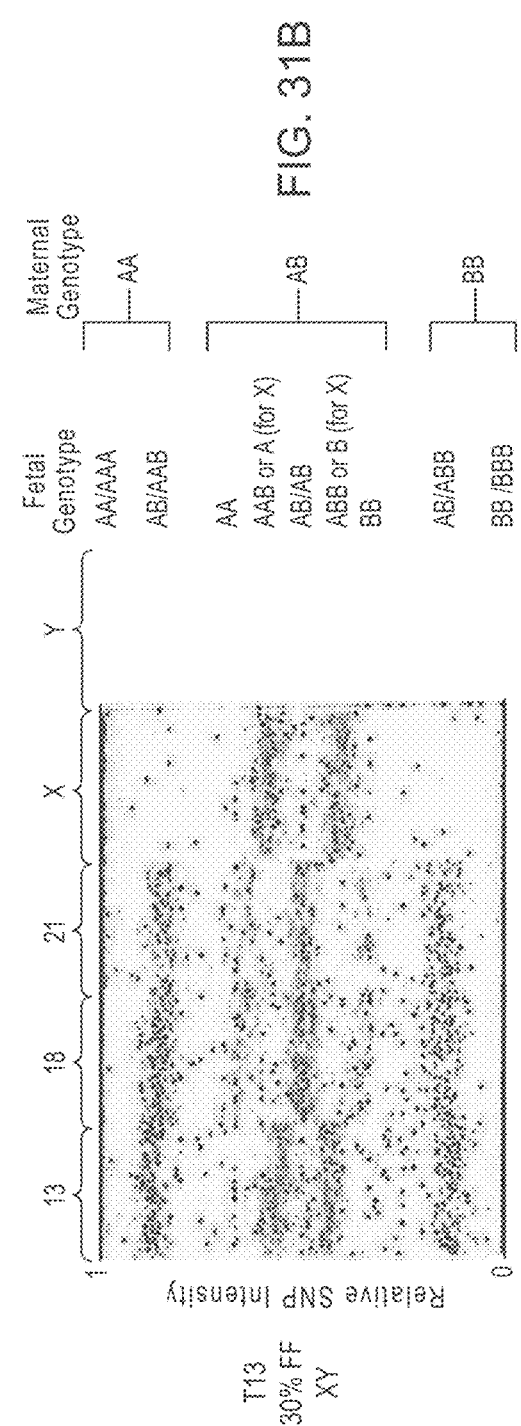

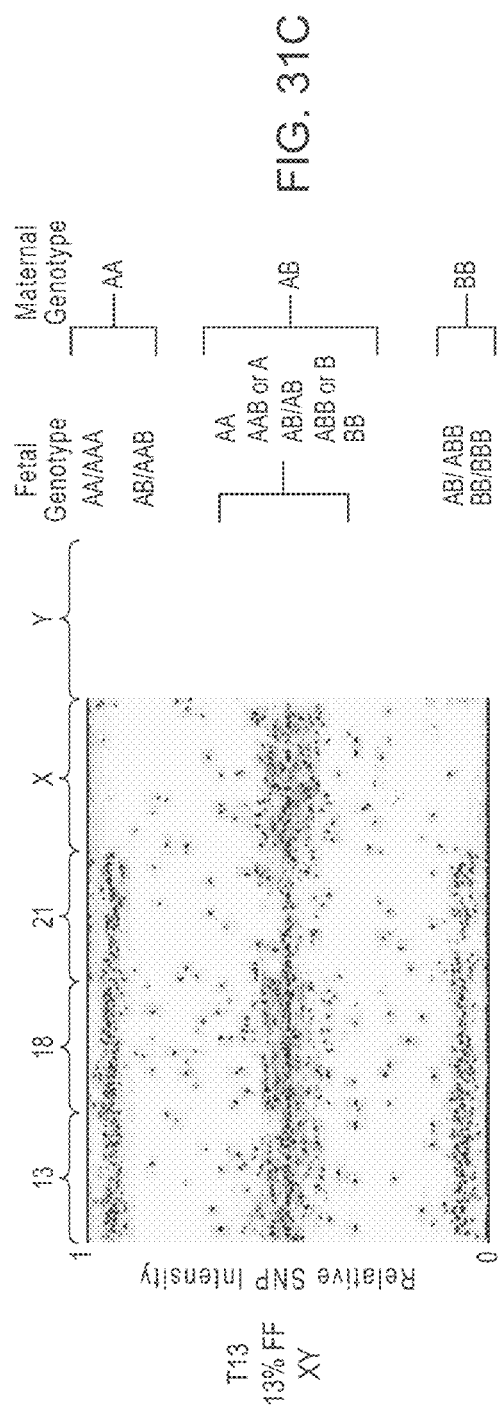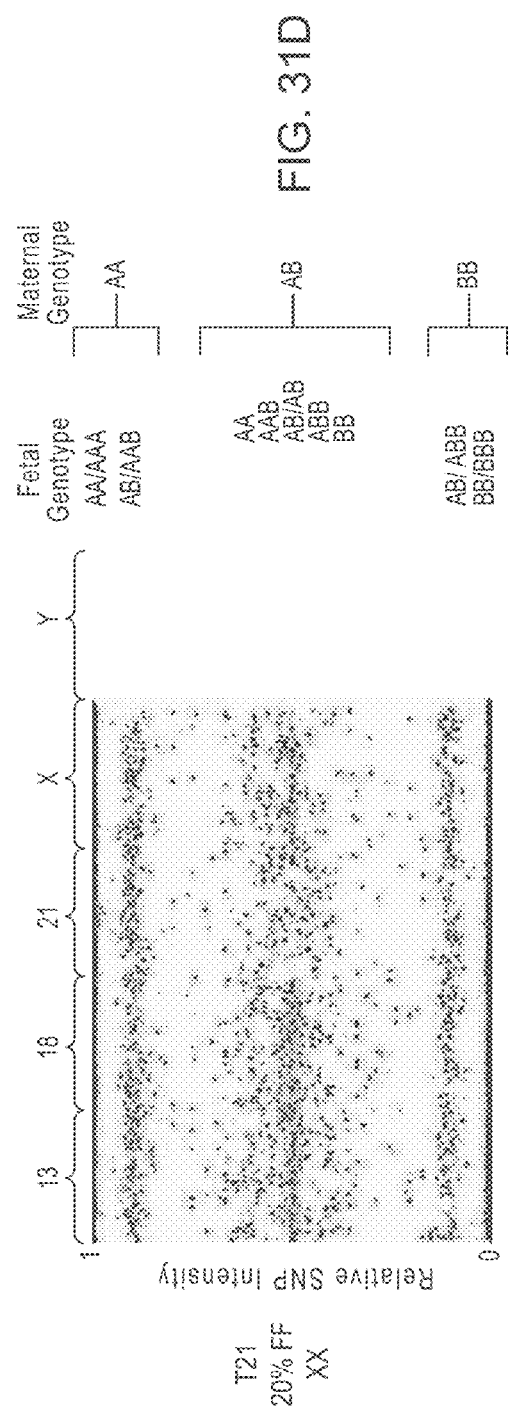

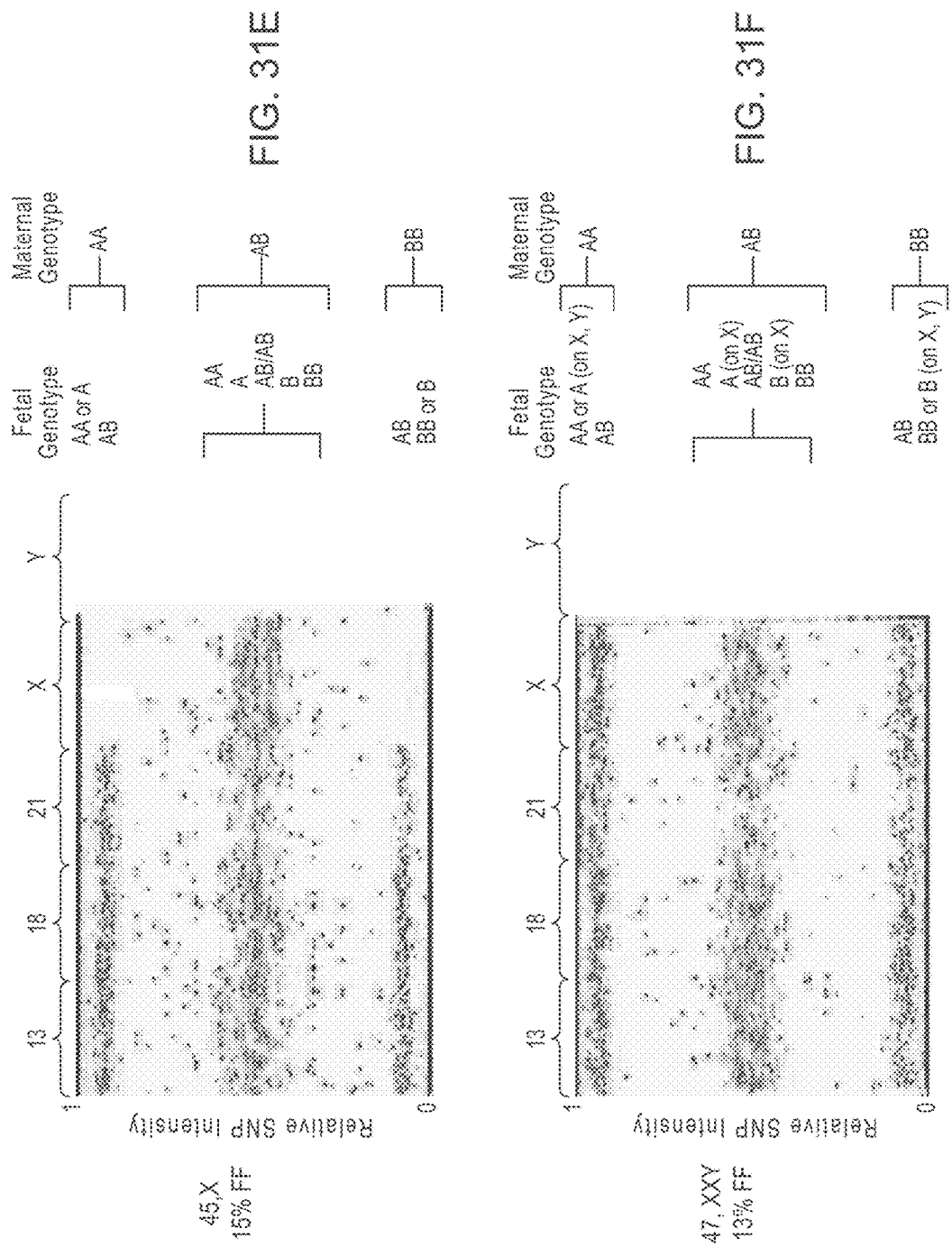

$$\Delta G = \Delta G_1 + \Delta G_2 + \ldots + \Delta G_x$$

To FIG. 33F

| Target No. | Pool A Sequence (5' to 3') | SEQ ID NO. | Pool B Sequence (5' to 3') | SEQ ID NO. | Pool C Sequence (5' to 3') | SEQ ID NO. |
|---|---|---|---|---|---|---|
| 1 | GGCACAACATTTGGGAGACAAA | 1 | CTCACTAAACTTTTCCCCAGAACTCA | 1201 | GCTTAAGCCACAGAAAGGCACAAC | 2401 |
| 2 | CCTGGAACCTGAAAGCTTGCAAAAAG | 2 | CCTCTGAAGGGAGACTGAAACAAC | 1202 | CGAGTGCCCTGGAACCTGAAA | 2402 |
| 3 | ACAGGGTGCTCTCCTCTTGA | 3 | GCAAGAATGCTTGGCTGCAA | 1203 | AGCCACCACTCCTGCTTCTGA | 2403 |
| 4 | GGAAGCAAACAGGTAGAGCCTGGTA | 4 | GTGGCATTTCACTGCCCTTTG | 1204 | TTGGGACCCCTGGACTAAG | 2404 |
| 5 | CTACAACAACAGAGCTCCAGGAT | 5 | GCAGCTTGTTCAATTGTGGTTCA | 1205 | CCTCCCCAGTATCTTACCACTACAAC | 2405 |
| 6 | TGTCCTTGGTCCTATGTGAGACA | 6 | GTGAGGATGAGTTTTCACTGGCTATC | 1206 | CACCAAGCCCTCAACTCCTAAA | 2406 |
| 7 | GCAGGAACTGGCTTGCCTTT | 7 | CCCTCGACAAATGTAACAGCCAAAGT | 1207 | GAAGTGAAAGAAAATGGCAGGAACT | 2407 |
| 8 | AGCTTTCGGCTTTAGTTGTGTGA | 8 | ACCTAGCTATCCTTCCAGCATTTC | 1208 | GCTGGTATTGTTTTGGGGATAGAGGTT | 2408 |
| 9 | TGTCTGCTTCTCCCCGCCATTC | 9 | CCTGGACAAACTTCCTGCTGTCC | 1209 | GTGGGAGCAAATTAGATGTCTGCTTCT | 2409 |
| 10 | GTCCCTCACACCTTTCTACCAGAAG | 10 | GCCAATAGCTGCTTGATGCAAT | 1210 | GGGCAAGTCCCTCACACCTTT | 2410 |
| 11 | GGCTGCAGGAGTAGAGGTCTAAATG | 11 | TAGTTGCCCGGGATTCCCAAGA | 1211 | TGAGGTCTGGCTGCAGGAGTA | 2411 |
| 12 | GGCAAGAAGAAAACTGGAGCCAAGA | 12 | GGGAGAGGCTGGTCCTGAGT | 1212 | CTGAAGCCCAAGTGGCAAGAAG | 2412 |
| 13 | CAGCCTGAGTTCTTGATCACTACA | 13 | GTTTGTGAAAGCTCAATGTGAGGAA | 1213 | AAGTCCTGAGCCTGAGTTCTTG | 2413 |
| 14 | CCTGGAAAAGCCCGGTAGA | 14 | TCCTCGGGAGCTCACAACCTTA | 1214 | TCTCAGGGTGCCTGGAAAAG | 2414 |
| 15 | GCAATGGTCCAGTGAGACTT | 15 | TCCCACTGATGCCAGACCAA | 1215 | GCACTCCAAAAGAAGACCCTATTG | 2415 |
| 16 | GCCCTTTGGAACCTGACCAA | 16 | CCCAGCTTAAGCAAAATAGGGCAAGTA | 1216 | TGGGAACCAGCCCTTTGGAA | 2416 |
| 17 | GGCCTTGATTTGACCCTTCTTTTTC | 17 | TGGCCAGTAGTAAGTTGAGAAGACTA | 1217 | GGCTTCACTATCAAGAAGGGCCTTGATTT | 2417 |
| 18 | CCACCCGCTTCTGAAACAGATC | 18 | CCGGAACCTTCACGTTCTGT | 1218 | AAGCAGGCCACCCGCTTCT | 2418 |
| 19 | TGCCCCTAAAGCCCAAACA | 19 | GGAGGCAGAGCTCCATCTCTGA | 1219 | TGGAGCAGGCTGGCGCTAA | 2419 |
| 20 | CCTTCCCCGCTTCTGGATATGAAA | 20 | CCGGCAATAGGACTCAGCAA | 1220 | CCGAAAACCTTCCCCGCTTCT | 2420 |
| 21 | GTCAGGGTTTACGCCTATTGAGT | 21 | TACGGCAGGTGTCCTCTGCAT | 1221 | GGAAGGGCAATTTCTCAGCGTTTA | 2421 |
| 22 | GCATCTCCAGTGCCCTCTGT | 22 | GTGAACCAAGCTATACTACCTGCTTTTC | 1222 | GCAGTCTCAGCCTTTCCTTTGCAT | 2422 |
| 23 | CATCTTCCTAGACATGCACACAAC | 23 | GGCTTCTGTGCTCATAGTTCACACT | 1223 | GTTGGGAAGCATCTTCCTAGACAT | 2423 |
| 24 | GTCCCAAGTCAACTGCCATCT | 24 | GGGCACACGGAGGTCAAAAGT | 1224 | GCCTATTTTGGAGTCCCAAGTCAA | 2424 |
| 25 | GCCTCAGCACAGCTAACACA | 25 | CGGGAGCCCGTTATACCAGCTTAG | 1225 | TGGGCCACGTTGCCTACT | 2425 |
| 26 | TCACAATGGGCAGGGAACATTCAA | 26 | GCTTCCTATGACCAAGTCCCTTT | 1226 | CCTCTTATTACTACCTTCCTCTCACAATG | 2426 |
| 27 | GGTAAAGCCTGGTTCTAAAGTCCACAT | 27 | GTGTTGGCCAGACCCACTGT | 1227 | ACTGAGGCTAAAGGCTGGTTGT | 2427 |
| 28 | CCGACTCAATGGGCAACTCCTACT | 28 | GGGCACTTTGAGTTGGGCTTTG | 1228 | AAGGCTCCTCCCCGACTCAAT | 2428 |
| 29 | TCCTTACACCTTGGGGCGTCTA | 29 | GCAGCTCGGTGCCTAATGGTT | 1229 | AACAGGGCGTGAGTTTTCCTT | 2429 |
| 30 | GGGCATTTCTAAGACACTTGGACAGT | 30 | CAGACCTGGCAGGATCAGAATAGT | 1230 | GGAGAGGGCAGGGCATTTCTAAG | 2430 |
| 31 | CACTGTATCTCAAAGGGCAAAACAA | 31 | TGCAATGCAGAGGAGAAAGGTT | 1231 | CAGCCTGCTAGGAACACACTGTA | 2431 |
| 32 | ACTTGTCTCTGCACACAGTTTCA | 32 | AGTCACAGGTATCCTGACTCTCATA | 1232 | GGTGATTCTGGCCGAACTTGTCT | 2432 |
| 33 | GGCCTCTTCCTGCCTCTGTT | 33 | GGAGCAATCAGCCTTGCAGAGA | 1233 | TGGATCGGAAACACCAGACTCA | 2433 |
| 34 | GCTAGAGAAACAAGACAACATCCAAGTTC | 34 | TGGCGCCCGGAAAACCAT | 1234 | CCTGAGACCGTTGCTAGAGAAACAAG | 2434 |
| 35 | GCCGGGCATAGAGAAGGAAAT | 35 | TTCAAGACATCCTTCCGCTAT | 1235 | TGGGATGCGGGCATAGAGA | 2435 |
| 36 | GGCTTCAGTCCTTCACCTCTTTG | 36 | ACCTTGAGAAGGTGGTATTTGTGT | 1236 | TCTCCCAGGCTTCAGTCCTT | 2436 |
| 37 | TCAGAGTCCTAGGCCAGCAT | 37 | AGAAAGACCCCAGGTAAGAACCAT | 1237 | CCAAGTTATGCCTGCTGCTCAGA | 2437 |
| 38 | GGTTCCTCATGGAAGACTGGTTTG | 38 | CACTCACACATCCACAGGAGACA | 1238 | GGGAACCTGGAAAGACCTTTACTT | 2438 |
| 39 | GTTGAGAAGGGAGTAAGATCAGACAA | 39 | GACGCAGTATCCCACAGAGCATT | 1239 | GGTGGGATAGTTGAGAAGGGAGTAA | 2439 |
| 40 | CTCCCGCCTCTAAATGAATGGAT | 40 | ACCAGCTCTGAGTCAGGAAGT | 1240 | CCTCAGCTCCCGCCTCTAAA | 2440 |
| 41 | CATTCCCTCCCCTACCCTGGAAA | 41 | CCCACAGTCCGACGAGTGTTTT | 1241 | GGATGAGCATAAGCAGTGGTTCA | 2441 |
| 42 | GAGACTCAATCCTGGCACTTGT | 42 | TCACTCCACTTTACAGGCACATATT | 1242 | AGGAGTGAGAAGGGAGACTCAATC | 2442 |
| 43 | CCCCGCTGCCATTTAAGACCAT | 43 | ACGAGGATCAGACAACTCACAGA | 1243 | TCAAGTCCCGGCTGCCATT | 2443 |
| 44 | GATGAGGGCTGAGTATGGTCAAG | 44 | CCCATGACCCCAGGTTGGATTG | 1244 | GACAGACAGATGAGGGCTGAGT | 2444 |
| 45 | CCCTTTCCTGAACCCCTTCATT | 45 | CACTCTGTGCAGTTGCTGGTT | 1245 | AATTGCCAGCTGTATTCTCCTTCT | 2445 |
| 46 | GGGGCACCAAAGAAAAGACAAG | 46 | GTCGTGTGGAGCACACCTTGGAA | 1246 | ACAGAGGATGGGCACCAAA | 2446 |
| 47 | CATCACTACCCCACATAGCTTTAACT | 47 | GCCTTTCCACTGAGCCATGA | 1247 | GCATGAGGATGGAATGCACTCATCA | 2447 |
| 48 | GGAGCTCAGTATGAGTAGAGGGGAAA | 48 | CAGCCTGCTTGGTTAGATTCTGT | 1248 | GACCTTCAAGGGGAGCTCAGTAT | 2448 |
| 49 | TTGTGCACGACGCTGGAATG | 49 | CTTATCTGTGGCTTTGGCTTCTTG | 1249 | TCTGATATGGAACCCAGGGATTGT | 2449 |
| 50 | TCCCTAGGCCATTCCTCCTGTT | 50 | GGGGGCTGAATCAGACAAGGAA | 1250 | TGCACCATCCCTAGGCCATT | 2450 |
| 51 | CACGACACCCTTAGATAATGTTGGAT | 51 | CACAGCTTGGAAGGCCTGAA | 1251 | GTCAGTTCACACGACACCCTTAGA | 2451 |
| 52 | TGGCACAAGCCCAGGTCAT | 52 | CTCATGATGTCAAATGCTGCTCAA | 1252 | AGCCCTGGAAAGCTGGCAAA | 2452 |
| 53 | GCCTCCTCTGCCATCTCTGAACCAA | 53 | GTTCTCGTGACAGCAACCTTCCT | 1253 | TTCCCAGCCTCCTCTGCCATCT | 2453 |
| 54 | TGCAGCGATCCCTTCACCTT | 54 | TGAGCAGCACAGTCCAATTCT | 1254 | CTCAAAGGGGAAGAACGTCAGT | 2454 |
| 55 | TGGTAGTCAGGCCTAGTGACTT | 55 | CCCCTGGGAAAGTTACTGTCGAT | 1255 | TCTGCGTCTCACTTCCTGGTA | 2455 |
| 56 | GAGGTCTTCCAAAGGCTATTCAGA | 56 | GTCAGTCAGCTGCCAGTTTTC | 1256 | AAGGTGACAGAGGTCTTCCAAAG | 2456 |
| 57 | CCTGAGCCTGTCACACTATTTCT | 57 | TCCCAAATCCTGAGCCTGTCA | 1257 | TCCCAAATCCTGAGCCTGTCA | 2457 |

FIG. 34A1

| | | | |
|---|---|---|---|
| 58 GAGAGCAACAGGCGTTGAGA | 58 GCCAACCTATAGACACAACTTTGGTTAC | 1258 GGAGAAAGAGTGGAGAGCAACA | 2458 |
| 59 AGCCCTACAAGGTCAAGTTTTCA | 59 GTTGACTTCCGGCAGTAAGTGATGA | 1259 GACTATACGATACCAAATAGCCCTACAAG | 2459 |
| 60 GGAGGCACTTCACTCCTCCTA | 60 ACTGCCACATTTCTCACGTTATCA | 1260 GTCACAAGGAGGCACTTCA | 2460 |
| 61 GTTGGGGTCAACTTTCCCTGAAG | 61 GGAATCCAGCCCATCCTCACATC | 1261 AGAGCTGCCCTGGAACTGAA | 2461 |
| 62 GAGGTTTGGCTCCATCATCAGA | 62 ACTGCACCACCACACGGAAA | 1262 GGAAAGGTACCCCAGAATGAGGTT | 2462 |
| 63 CAGGGTCATCTCTCTTCACCCTTAG | 63 CCTTCAAGGGCTTTCTCTCACA | 1263 GGTGGTAGAGGGCTCATGTCTCTT | 2463 |
| 64 GTTGCTTCCCGTTATCCTCACT | 64 ACTTCCACATGGCTTAAACAGAGA | 1264 TCCCCAAATCCTTTGGCAATGT | 2464 |
| 65 GGGCCTGTTCTTGTTGATAGTGTT | 65 TCGTGAAGAAGATGGAGAGGAGTTA | 1265 GTGTCAAAGGGCCTGTTCTTGT | 2465 |
| 66 CTTTGCTGTTACTGAATCCCGAATCT | 66 CTGGGACCAACCCATTTCACA | 1266 CTCTCATCAGCTGTTTGCTCTTAC | 2466 |
| 67 GCACATGTAAAAATCCTCCCTACTGT | 67 AAGGAAGTGGGGTATGGACTGA | 1267 GACCTCTTTCTCCCTGCACATGTAA | 2467 |
| 68 CCTCTGGTAATAGCACCCAGGATAC | 68 TGTTGGCCACATACATTGTTCTCA | 1268 CCTTCCTTGAACTTGCCTCGGTA | 2468 |
| 69 CTGAGGTCCAGAATCCAGATGTTCT | 69 CTCCTGCCTTCGGGGATGT | 1269 GCTGTCACCAAGACTGAGACTGA | 2469 |
| 70 GGACAACAGGATCGGGGATGA | 70 CACAGGCCAGAGATTCACCAT | 1270 TGAAAGCTATTCGGACAACACGGAT | 2470 |
| 71 CCATGTGTAGGAAGCCCCTGTGA | 71 TGGGAAGCCTACCCTTGACTCT | 1271 CAGGAAGATAAGTACTCAGCCATGTGT | 2471 |
| 72 GCGACCTCACTTTTCCAGTCAT | 72 AAGCCCCTCAGAATCTAAAAGCAA | 1272 GCACATGTCTGCGACCTCACTTT | 2472 |
| 73 GTGCTATTGTGGCTCTGTAGGTTGA | 73 CGACAGGGCCTCCCAATTC | 1273 CAGCAGAGCAGAGTGCTATTGT | 2473 |
| 74 GTTTCAGCCTGAGAGGGCAAGA | 74 AGGTAGACACGGAAGTAATCACA | 1274 GCTGTTGCACTGTGAACTTGT | 2474 |
| 75 GAGATGAAGCGTGCGACCCAAGT | 75 TCAGGTAGAGGTCGCCAAGGTT | 1275 GCAGCAGACAGCTGGAGATGAA | 2475 |
| 76 TGGCTCATCTCTGCCCCTCTTT | 76 GGAGGCTATGAGAAGTCAGGTTTG | 1276 CTCTGTGTTCCCTCACCTGTAA | 2476 |
| 77 TCTCAGTGCCTTTGGAACGAAA | 77 GGGCCGGTTAAAGAGCTTCAGAGA | 1277 TCTGGCTTCTCAGTGCCGTTT | 2477 |
| 78 AGGTTTCCCTGGACACACATTC | 78 TGGTCTTCTTTATGCCCAACAAAC | 1278 TGTCAACGGACTAACTTTCTAGCTTTC | 2478 |
| 79 AGGAGACAGGGACAGTTTCAATG | 79 CTCACACGGGCTCACATTCT | 1279 GGCTCATGCTTGTGATAGGAGACA | 2479 |
| 80 TGGGTTGGAAACACGTCCTTTA | 80 CCTGCTCACCGATGCTCAA | 1280 GCCGAGGAGAATATGGCTTGGAAAC | 2480 |
| 81 GCCCTTAGCACAGCTGCAT | 81 GGTCACAACACGAGCCTGTAAAAC | 1281 GCATCTTGTGCTTGCCCTTAGCAA | 2481 |
| 82 GCAGACACGCCTCTGGCAAAT | 82 CCTGAGACAGAAGCAGTAGCGTCTT | 1282 GTCCATTGGGCAGCTTCT | 2482 |
| 83 GCCAAAAGTGACAGCAACACA | 83 CGCAAAATGGGCTCCTCCTT | 1283 CCTGATGCTCCCTCTCCCAAAA | 2483 |
| 84 GCACACATCCAATCCTTCAGTAAATC | 84 GCCGGATTAGGGGTGAACTTTG | 1284 GGCTCATTCTCGCACACATCCAATC | 2484 |
| 85 TCCTCATCCAAGCTCCTTCTCT | 85 GGAGGTATTCTGGCTTCCCTAAGA | 1285 GCCCTTCCTCTTGCTGAACAGT | 2485 |
| 86 CGCACTTTCCACCCAGAACTTAAC | 86 GGAAGCCTGAGTTTAGCACAATGGTT | 1286 ACCTGAAGCCAGGCACTTTC | 2486 |
| 87 AAGCCCACGTTGTGCTCTTG | 87 CCCACTTGCACAAATGCAAAGA | 1287 TGGGAGAAAAAGCCCACGTT | 2487 |
| 88 CTCAGTAGGGTGAAAGGATGGAAGT | 88 AGCTGTGCTTTTCCTGTCTCA | 1288 GCAAGGCTCACTAGGGTGAAAG | 2488 |
| 89 GCTGGATCTACAGAAACCAGCAAA | 89 TGTGTGTCTTTAGCAAGGGATTTC | 1289 GCCAAACTGCTTCTTCCTCCATCT | 2489 |
| 90 TGGCTGCAGATGCTTGTCA | 90 CGTTTGGCAACGGAGATGTCT | 1290 GGAAAGGCCGGTGGTAATGTGGTT | 2490 |
| 91 GCCTCTCAGCCTCACGTTCTTA | 91 TGCCCACCCTTTTCTTTTGCTT | 1291 TCTGACCAAGTCCGCCTCTCA | 2491 |
| 92 TCCTTGACTCACGCCTCTGA | 92 GGGCTATACATTTCTCGGCTCAA | 1292 CCTCACACTTTCCTGTCCTTGACT | 2492 |
| 93 GGAGGACATGGTGTTTGAGGAT | 93 TACATTCCCCTCTCCCGCAACA | 1293 CAGCTGATCTATGCATTGGAGGACAT | 2493 |
| 94 CTACAGTTAGAGTCACACGTCACA | 94 CCAGCCAAATCAGGATCATGGACAGA | 1294 GCATCTACCCAATCACTACAGTTAGA | 2494 |
| 95 CATGCGGAGGGACTTAGCAA | 95 GGCCCATGACTCTGCTGGAT | 1295 CTCATCAGACACAGGCAGCTT | 2495 |
| 96 GCTTTCCAGAGTAGAGGCGTTTC | 96 GGAGGCATCTCCGGCTACA | 1296 AGGGCAAAAGCTTTCCAGAGTAG | 2496 |
| 97 TGATGGTCAGAATTGCTACGATA | 97 AGTGCAAGGTTGGAGAATGAAAAG | 1297 GCAAAGTTTCATGGCCAAGTGTCA | 2497 |
| 98 GCTGAAATGGACCCACAGAGA | 98 CGAGTTGGCCTCCTCTTACCAA | 1298 TGCTGCCAGGCTGCTGAAAT | 2498 |
| 99 TGCTCCAACGATGGCTCTTC | 99 CGTGGCAGCTGGCTTTAGAATC | 1299 TCCCCAGGCACCTGCTCCAA | 2499 |
| 100 AGGTGAAAGCGATGTCTGCTTAG | 100 TGGTGCAGCCAGCTCTCTTATC | 1300 TCACCTACCTAGGATTAAAGGTGAAAG | 2500 |
| 101 GCCCTGACCTCACCATTGGAA | 101 CTCTGGCACATGCGTTAGTTC | 1301 GGACAGCCTTGCTGCCAGATT | 2501 |
| 102 TGGGGCAATTGCGGGTATT | 102 GGGGCTTTGGATAACACCAAGGTA | 1302 AAGGAGGTCCTGGGGCAAT | 2502 |
| 103 GCATTACAGGAGAGTGAAGATGGAT | 103 TTCCAACCCCTCCGACATTC | 1303 CTTGCCTAGGAAGCCCATTACA | 2503 |
| 104 GGAGGAGAAAGGTGGTACACTTG | 104 AGCAGAAGTTCACGGGACCAA | 1304 GTTGCAGCCCTGGAGACAAA | 2504 |
| 105 GGAGACAATACAGGTTGGGTGGTT | 105 AGAGCTGCTATCATGATGTGGAAA | 1305 GCTGGTCAATTCTGTTAAATCAAGGAGACA | 2505 |
| 106 GCCGGATCTTCCTTACCTAGTCTGA | 106 AGGGTGAGTCTGGAAGAGGTT | 1306 TGGGTGAGGGCGGATCTTC | 2506 |
| 107 GGATACTGTGTAGGAAGGCAATACA | 107 CCCCACTCCCCTCAAGGTATGT | 1307 CCCAGAGAGGCTGGATACTGTGTA | 2507 |
| 108 CAAACTCCAACCCCAGCCTTTTG | 108 GTCACCCTCTGAGGTACACACT | 1308 CCTGTGGCTCCTGAGAGAGAAATCAA | 2508 |
| 109 CAGGCCAAGAATGACATACCGACTT | 109 ATGACAACATCACGGACAGAGAA | 1309 TGGGACACTTCAGGCCAAGA | 2509 |
| 110 GGCTGCAAAATGAGCACTGTGGAA | 110 TGACAAAATGCGGAAGGGATTCT | 1310 GCTCTAGGATGTGTAAAGGAAGGCAGTACA | 2510 |
| 111 GGAAGGCAGTACAAGAGCTTACT | 111 CTATGTTTCAGCCACACCCACATTC | 1311 GCTCAGATGTGTAAAGGAAGGCAGTACA | 2511 |
| 112 GGCGATTCCTGACATTTGATTGCAT | 112 CAGGCTTGTTCGGGAAATACAAG | 1312 TTCCCGGTGTTCTGGCGATT | 2512 |
| 113 GGGGTTTGTTGGGTCAGAGA | 113 GCCGAGGTTTCAAGGCTCCAA | 1313 GGCATGTAAGGGTGACAAAGGAGTTG | 2513 |
| 114 CTGCAATATTGGCCATTTCTCTTCA | 114 TGCTCAACTCAAACAGGACACT | 1314 CCCTCCCAGGCTTCTCATCT | 2514 |
| 115 AGTGTGCACGGCTGGTTGAA | 115 TGCGGCGATGTGCCTGTA | 1315 CCTGCCTACGGTGCTAAAGTGT | 2515 |
| 116 CCCCAGCTCCTTCACAAAGACT | 116 CAGAGGGTGGATGGATACAGTTC | 1316 TCCCTCAAACCCCAGCTCCTT | 2516 |
| 117 TGGAGCTGAGGAGGAAAGAACA | 117 CGTGGCCTCCTGCACTGAT | 1317 GGCATGCTTTTCATTGTGAGTGA | 2517 |
| 118 TGGGTCATAAAGTGACTCTGTAACATC | 118 GTGCAGGCTCAAGTTGCTTCT | 1318 GGATCTTCCTTCTGGGTCATAAAGT | 2518 |
| 119 GCTGTCAATGTTACATGGCAGGAT | 119 GCTTGCTTGGAACCGATTTTGAT | 1319 GCTTTTAAAACCCAGCTGTGAATG | 2519 |

| | | | |
|---|---|---|---|
| 182 TGCTTCTGTCTGGCTGAGAAG | 782 TCTGGAGAAAGTGACAGGGTAAGA | 1382 ACAACCTCACCTTTGCAGACA | 2582 |
| 183 CTCCTTCTGTGTATATGAGCAGCTT | 783 GAAAGGCTGGGTATTTTTGAACCAA | 1383 GTCATTTGCTTTCATGACCCTCCTT | 2583 |
| 184 GCCCTTTTCCTTAAAAGCAGGAACA | 784 CACAACCTCACATTCTCCAGGTTA | 1384 AGTGCCCAGCCCTTTTCCTT | 2584 |
| 185 GCGCAGGAAGAGCAGTTTGATG | 785 GAGCCCACGTATCAGCTCCACCA | 1385 ATGGCGAAGCGCAGGAAGA | 2585 |
| 186 GGTTCCCCAGATTGGCTCAAAAG | 786 ACTCCAACCTTTTTGCCTGAGA | 1386 TTGCCAGAGGTTCCCCAGATTG | 2586 |
| 187 ATCCGGCCAGCCGCCCAATA | 787 TCTCACCCGTTGGTCAGAGT | 1387 CAAATAAAGCCCTCCTTCAACAAC | 2587 |
| 188 CCAAGTCTCAGGTGTGAGGAGTTAC | 788 TCTCCAGCCCTCAGTCCTTCT | 1388 CAAGGAGGAGGACCAAGTCTCA | 2588 |
| 189 CACACTGGGTTTTCTGGTTTCAGT | 789 TGAGAGGTCACCACACACAGA | 1389 GCATCTGTATGCACACTGGGTTT | 2589 |
| 190 CAGGCCAACTCAACGGCAAAAG | 790 TCATCCCAGCATCATTTGTTGAGAA | 1390 AAGGTGCCAGGGCAACTCAA | 2590 |
| 191 AGCTGGTCACTGTGGAGAACA | 791 CCGCCTCTCCACCCTTTGAACTT | 1391 GTTCTGCAGCTGGTCACTGT | 2591 |
| 192 AGGCTCAGCTCTGGGATTG | 792 CGACAATTTAAGGCGAGACATGGAA | 1392 TGCTGCACCCATGCTTCCTA | 2592 |
| 193 GGCTGGCTCCATCGTTTGAGAT | 793 GCACATTGCCACCGTCCAGAT | 1393 AGAAGCGGCTCGGCTCCAT | 2593 |
| 194 CAGGGAAGCTTTGACAGAAGAGATA | 794 CCCGTCCTTCAAGTCGTGGTT | 1394 GCCTTCAGGGAAGCTTTGACA | 2594 |
| 195 AGGATACAGCTTGGAAAGCAAGATT | 795 ACCCGGTGGAGTCAGGATTTGA | 1395 GCAGCACCGCTCTCTAGTTAAG | 2595 |
| 196 GTGCGGCTGTCATCAACATTCAAC | 796 TGGATGGGTTGGCTTGGTACT | 1396 GACACTAAGTGCGGCTGTCATC | 2596 |
| 197 GGAACGGGAGTCAGGTCAAACA | 797 GCTGTGTATTTGTTGAGCCTTGT | 1397 GCTACCAGGAACGGGAGTCA | 2597 |
| 198 TCCCTCTCTCAGTCTGGGTCTA | 798 GGGGTGAGGTACTGCAGTTAAACAT | 1398 ACCCTGTTCCCTCTGTCAGT | 2598 |
| 199 AGCCGCAGTCCACAAACA | 799 ATCGGCGCGAGCCAGGATT | 1399 GCCCAGCTTTAGCCGATGAAGT | 2599 |
| 200 TGCATATTGTCCAAGGCTGCTT | 800 GCAGTCTCTCAACTCTGCTGTTGT | 1400 GCTGCGCCCATTTGCTTTGCAT | 2600 |
| 201 GCCCTCTGCATCTAGCCAAT | 801 AGGGATGTCCTCCCCAACTT | 1401 GGCACAAAGCCCTCTGCAT | 2601 |
| 202 TGGTCCATCCAAATGAGGCAAT | 802 GTCAGCACCATGTAGCAGATGT | 1402 TGGGCCCATGGTCCATCCAAA | 2602 |
| 203 GCCGCTCCTCTTTCTGTTCCTTAAAAA | 803 CCAGGCATTGGGGCAGCTTCT | 1403 TTGCCGCTCCTCTTTCTGTT | 2603 |
| 204 CCAAACCAGGCTTTTCTTGCATA | 804 GCCCTTTAAGGAACCTTGCTACA | 1404 TCTTCCCCAAATCGGACCTTCA | 2604 |
| 205 CCATCTGGCTATGTGACGGATGT | 805 TCCAGGTCCACTACTGTGTCG | 1405 CCACATAGCTCTCCATCTGGCTAT | 2605 |
| 206 CAGTAAAAGCAAGCTTTGACGTTTGT | 806 CCCTTGGGTCCCTCTTCTTCA | 1406 GGACTTTCCGAAGGCAACAGT | 2606 |
| 207 TTAAATACTCCCATCCCCGGAAA | 807 GCCCGGTATTGTGCCTGACA | 1407 TGCTGGCCTAAGGGGTGTTT | 2607 |
| 208 GGTTCTGGAGACAACGGTTCCTA | 808 CCATTCTGCCAAATTTCTGTGTGT | 1408 GTGCTCAGCGTTGTGAGACA | 2608 |
| 209 GCTGTCTCTCCCTAGGTCAGGTT | 809 GGGGAGCACAAGGGATTTGTCACT | 1409 CTCTTCAAGCAAGGCTGTCTCT | 2609 |
| 210 ATGTGTTGCTGAGAGTCCCTTTAC | 810 CAGCTACTCAGGCAACCACAGA | 1410 GTGTACAGTCAAAGGCCATCTGTTC | 2610 |
| 211 GGGACATAGCACAGGACTGGAT | 811 AGGCAGATCACTAACTGGTTCTAAG | 1411 TCCATGGCTCAGGAGGGACATAG | 2611 |
| 212 CAGCTCTACAAATTGTTGCCATCTTC | 812 TCAGTAGAGCCTTGAGGTAGCTT | 1412 ACCACGATCACACCTTCCTAAC | 2612 |
| 213 GGCTCTGGAAGTTGCCAGTCA | 813 GCTGCCCTACCAACCCACATT | 1413 TTGGCTGCAGGGCTCTGGAA | 2613 |
| 214 CCAAGATTTTGGAAGATGCGAGGAT | 814 CCCTCTGCTTTTGCTTCAGATA | 1414 GCACCACTGGAGCCAAGATT | 2614 |
| 215 GGCTGAAGCTGTAATCCACACA | 815 AAGCCAAGCTAAATCTTCCCTGAA | 1415 GCTGGAACTCTGTGCATAGGCTGAAG | 2615 |
| 216 CAACCACGATCGCCCTAGAAAA | 816 AGGCCTTCAGCCTGAGACA | 1416 AGTGGGAGTGGTCTGCTCAAC | 2616 |
| 217 AACCCAGCTACGGAGAGGATGA | 817 TCTTCCTGGGCACGTTCTTC | 1417 ACTGGAGCGCTTGAGGTAGA | 2617 |
| 218 ACCCAGCTTAATGGTTCCAAATAGT | 818 GGGATCTCTGCAGCATGACTTG | 1418 GCACACCAGAAGATAACCGAGCTT | 2618 |
| 219 TGCTCTCCTTTCTTCCAGTTTCA | 819 TCAACACCTTTTTCGGTGACAGT | 1419 GGGCATTATTGAATGCTCTGCTTTCTT | 2619 |
| 220 CCTTCCAAAGGGAGGGATGTTTTC | 820 CCGCGCTCTACCCTCTTGATTTA | 1420 ACCCTGGAGCTCCCTTCCAAAA | 2620 |
| 221 GCATTGAAACACCTCGTTTACTTCA | 821 TCTCTTCTTGAAGATCGCAGTGA | 1421 ACCCTCCTGGTCGTTGAAAC | 2621 |
| 222 TGCTTGACACCTCTCTTGATTGT | 822 GCACTAGGTGGAGGGTGTTC | 1422 GTCCATACACTTGACTGCTTGACA | 2622 |
| 223 GCCAGCTAGAACCCTATACCGAAA | 823 AGACCTTCCTGGCTTCCTTTTG | 1423 TGTAAGTGCCAGCCAGCTAGA | 2623 |
| 224 GTGAAATGCTCTTGCCCTTCTGCATC | 824 ATGGGCCTCAGGCAGATTGT | 1424 GACCTCAGTGTGGTCAAATCTCT | 2624 |
| 225 CACCACCTACCCAAGCTCAA | 825 GCAAGAGGAAAGACCAGCATCA | 1425 CAGGGTGCCTCATCTCAGGAT | 2625 |
| 226 GATGACTGGACCGCATGTCTCT | 826 CAACCCTGGGCTGGACTGT | 1426 AGCTGAGGCTATGGGGATGACT | 2626 |
| 227 CTCGTTCCTGCTGTGCTTGTAG | 827 CAGCCGGCAAAGACAGCCTAA | 1427 GCTTGTTTCACCCACCTCGTT | 2627 |
| 228 TCCCTTTGGTCCCTCACACAAG | 828 GAACACACCAGGTTCCACTAGAT | 1428 GCTGAGTCCCTTTCTGCCTTT | 2628 |
| 229 GAGAACCACGGAGAGGAAGT | 829 CCCCCCTCTCTGTCCCATCA | 1429 AGTGACAGAGTATGGGGTGAGAA | 2629 |
| 230 CCCACAGTTAGTACATGGCAGAGTTT | 830 ATGGGAGTCACAGCACTTG | 1430 GCTTCCCAGATCCCACAGTTAG | 2630 |
| 231 CCTGGGAGCCATGTCTGAAACT | 831 CTGAGAGAGCAGTCTATCTTCCTTGA | 1431 CCCAGGACTGTCATTCCCAAGA | 2631 |
| 232 GGGCACCTTCACATTCTGAGA | 832 GGCCAAGGGTGAACTGGAGAA | 1432 GGGTTATGGCACCTTCACA | 2632 |
| 233 GGACCCTGGTCTTTACTTCCGATT | 833 CCCCGCCAGGTACTGTCTCA | 1433 GGCAGACACAACTTGGGGAAA | 2633 |
| 234 AGCACCAAGCGCTGAAGGAAAG | 834 GGACCAGGCTGCGAGAAA | 1434 GACGTGCTCAGTGGGATTTCT | 2634 |
| 235 GCAACACAGATCCACTGAAGACA | 835 CTGGGACATCTTATGATCCGCTTAG | 1435 GCAATAACCCATCGGTGGAGCAA | 2635 |
| 236 GCCTCTCCATAACCAGTCTCTGTA | 836 TGACTGTCTAAACATGGGCACATAC | 1436 TGGTGAGATCTTGGCTCTCCAT | 2636 |
| 237 TTCCACTGGCCCACTGTACT | 837 AGCCTGCCCTACCCCAATCT | 1437 GCCCTCTTTCCATTGCCAGAA | 2637 |
| 238 GCCCATCAGTCTCCCCTGCTA | 838 TGACTATTTGACTGGTCCTGGTAAC | 1438 GTCTCTGTCTGCCCATCAGTCT | 2638 |
| 239 CCAGTCATCCCGGCACTT | 839 GGGACTTGACCTTGCTTCCACAA | 1439 GCAGGGAAAGCCCAGTCATC | 2639 |
| 240 GTGGAATCCAATCACTCAGCCTTCA | 840 AAGTACCGCCCTCCTCTGTT | 1440 CCCCACATTTCTTCAGACAGTGGAATC | 2640 |
| 241 CGCCCACTGCTATCTCTACCATTC | 841 TGCCATGCCCTGTTGGATCT | 1441 TCCCGCCCACTGCTATCT | 2641 |
| 242 AGTGCCTGGCCATCTGCTGTA | 842 AGAGACCCTTGGCAGGTCAT | 1442 TGTCTCGGGGTGCCACACA | 2642 |
| 243 GTGTTCATCCTCAGGGCCAATG | 843 CACATTAGTCTGGGAGCTTGGTT | 1443 GCACGTGGACAGTGTTCATCCAT | 2643 |

FIG. 34A4

| | | | |
|---|---|---|---|
| 244 GCTAACCTTGGCACTGTGGAT | 244 CCCCAGTACTCAGGGGACTTTGT | 1444 TGAAATGAACAGACCAGCTAACCTT | 2644 |
| 245 GCTGTCATCCATGGTCCAGACA | 245 GATGGGCCATGTGGCTTCT | 1445 CCTGGGCTATGCTGTCATCCAT | 2645 |
| 246 CCATGCAAGGGGAGATGGAAGT | 246 TCTCCCCAGTCGAGCTTATGT | 1446 GAGACTGCCTGAATACCATGGAAGA | 2646 |
| 247 CCACCTCTTGGGCCCTTTG | 247 CACCAACAAGCTGGCTCTGA | 1447 TGGGAGGGTGCCACCTCTTG | 2647 |
| 248 CACAGAATATGGGCTGAGAATCCAAGA | 248 CGGCTCCAAGTTCCCACAT | 1448 CTTTTGTTGCAGGCCCACAGA | 2648 |
| 249 GAGTCCCCACCAGCAAGAAG | 249 TGTCCAAGGTTGAGGGGTTGT | 1449 GGCTGCCTTCGGACACATCT | 2649 |
| 250 GTGATGTGGCTACTGCTTCACT | 250 CTGGAATGGCTGTTAGGCACCTT | 1450 GCCAGGAACACTGCTTGTGATG | 2650 |
| 251 GCTTCCCTCTTCCAGTGCTT | 251 GCACATAACTCTACCTCCTAAGCCATA | 1451 GAGAGGGGTTTGCTTCCCTCTT | 2651 |
| 252 CTGCACTGTGATTCTGGCATAGT | 252 GGGAAAGCAATCCTGTGTCTTTATG | 1452 AGGGGCCTGCCACTCTGATT | 2652 |
| 253 CCCCTCCACTAACGGTGCATTA | 253 TCCCACAGTCAGGCCAACCAT | 1453 CCATCAGCAGATTCACACTCAGA | 2653 |
| 254 CAGGGATGAAAGACAGAGAGCATTTG | 254 ACAGCTGGACCCAGGGAAGTT | 1454 CAGGGAAAACAGGGATGAAAGACA | 2654 |
| 255 CCCCTCGAGGCTGTTTTAGTGA | 255 CCTGGTGGCATAAGGGATGCTT | 1455 CTGCTGTGAAGCTGGAGACTTTTTAC | 2655 |
| 256 CCAGTCTCAGGGCCGAGTAG | 256 GATGGTTGGTACTCGTTCTCAGT | 1456 TCGCGCGTTGAGCAGTGT | 2656 |
| 257 TGCTGCTTTACCCCCAGTCA | 257 GGGTTACTAAAGGGCAGTTCTGTTC | 1457 GGACAGGGTACTAGGTGCTGCTT | 2657 |
| 258 GACCAATGGGTGTCAGCTT | 258 TCCTAGGCTGACCAGTGTCAT | 1458 GAAGCCCGTTTAACTGGTGTTG | 2658 |
| 259 AGGCTATGGGAGGTGGGAACA | 259 GCCTTTCCCCAGTCCATTTCT | 1459 CAGCAGGAGGGAAAAGGCTATG | 2659 |
| 260 CTGTGTATGTGGGTCTGAAGCTCAA | 260 TGTCTTTCACCAGCCCAGACT | 1460 CTCAAAAGGCAGGTGCTTGACA | 2660 |
| 261 GGGGCTCAGATCCCTTGGTT | 261 CGTGTGAGAAAAACCTCTCCTACTAC | 1461 TGGTTCCCAAGGGGCTCAGAT | 2661 |
| 262 AGCATCCGTGGAGGCTTTTAAT | 262 TGTCCAACAGCTTTACATAGCACAT | 1462 GTGGTGAAAGTAATGGCATCAAGCAT | 2662 |
| 263 ACGATTTCTGAAGCAGTCTTGGTA | 263 CAGAAGCAGTGAGCTGTGGTT | 1463 TGCTGTGCTGTCGTCATTTGT | 2663 |
| 264 GGGCATTAGCTGGCCTTCACA | 264 CTGGGCCTGCAGAAATGCTA | 1464 TCCCACTGCAAGGGCATTAG | 2664 |
| 265 TCCCACTTACAGGCCCGTTCT | 265 CACTGAGGCGATGCTCTGATCT | 1465 AGGCTGGCCTCCCACTTAC | 2665 |
| 266 TTTCAGAACTCCTGGAACCAAGA | 266 TGGCCTCCTTCTCTAAAAGCATTC | 1466 AGACTAAACTTGGAAGGATGGGTTTC | 2666 |
| 267 CATGAAAGCACTGGGCTTCTCT | 267 CACTCAGAACTCCTTTCCCAAGT | 1467 GCAATCCCTGCCACCACAT | 2667 |
| 268 CGAGAGAGGAAGACACTGGCAGTGAA | 268 GCGTGGGCAAAGCCTCCAT | 1468 AGGGCAAAGTCCCTGTGAAC | 2668 |
| 269 CCTTCCTCCACACTAAGTGACTGGAAA | 269 ATCCACTGCCCTGACCTTGT | 1469 GGATGAGATTCCCTTCCTCCACACT | 2669 |
| 270 CAGCCCATCCTGGGCATCT | 270 ACTCCAAACCCCACCTGCTA | 1470 GCTGTTTCTGTGTGCCTCCTT | 2670 |
| 271 AGGCTGGCAAATGGGCTCAA | 271 GGGTCCTAACCCTCAGTCTTGT | 1471 GGGTGCTGGGAAACATGAGGAA | 2671 |
| 272 GCTGAGCCGACCAGTCTT | 272 ACAGGGCTCCTGGTTCTAACT | 1472 CAGCCTTCTCTCCACTCCTTAG | 2672 |
| 273 CCTGGCTGGGCTACATCTTACTT | 273 CTCTAGGAGCATGGGTCACCAAA | 1473 TGCTTCCAGAGCCCCACACT | 2673 |
| 274 GCATGGGGACCTGAGACTTTCT | 274 AAGCCGGCAGGCTGAGTT | 1474 CACTCCGCATTGTTGTGCAT | 2674 |
| 275 GGGCCCATGAGCAAGTCAGTT | 275 GGAGCCACAAGGAATGCAGAGT | 1475 ACACCCTGTGGGCCCATGA | 2675 |
| 276 CCTCCCCGAAAGGAAACAGAGCAT | 276 CAAGACCCTGCCACCTCTCT | 1476 GTGGTAGTTAGACCTCCCCGAAAG | 2676 |
| 277 TGGATGGTGAGAAGAGCCAATG | 277 GGTGCAGCCTTGCTCACT | 1477 GGGCAGAAGTGGATGGTGAGA | 2677 |
| 278 GCCTGGTCACCATCCCCTTT | 278 GCCGAAGGCTGGAAGAACCTTT | 1478 GCCCCTACCTCTTCCTCCAT | 2678 |
| 279 GACACTCACAGGCTCAGAGAAC | 279 GGGCACACTGAAGTCTACAAGCAA | 1479 ACTTCCAGGAGCACCTTTGAATAG | 2679 |
| 280 TGAGCACTCCTGGGTCAAGA | 280 TGGGCCCATCTCTTGACTTTC | 1480 CCATCAAAGAGGTAACAAGCCAGTGA | 2680 |
| 281 CTTGCCTGGTCGTCCAAGA | 281 GAAGGATGACCCGATCCCTCTA | 1481 AACCCCGCTCTTGGCTCGATT | 2681 |
| 282 CCAGAGCAGCCAGGTCTTCA | 282 GCAGTACTTGGGGTCCTATATCTGT | 1482 GCTACACGCTGGGCACCAA | 2682 |
| 283 TCTCCTCGCCCAAGATCAGA | 283 TCCACCTACCTGTGGGCAATC | 1483 GCCCTATGGCAAAGGCTCACTA | 2683 |
| 284 CCTCAGCCCAGGCACTCACTTTTAG | 284 CCCCGGCTACAACAGTCACCTT | 1484 AAGCCTCTGGCTGGTCTTTC | 2684 |
| 285 TCCATGACGGGCAGCTGTA | 285 TCTCCGGAAAGTCCGGTTCTA | 1485 CCTGTGGTTTTGGGCAGGTT | 2685 |
| 286 CACCCTGGGATCAAGTCCAAGT | 286 CACCCAAGCTCTCACTGTTACT | 1486 TGGTTACCACCCTGGGATCA | 2686 |
| 287 TGCATGCTGGGACACAGAGA | 287 GGGCCAGCTGACCAACTAC | 1487 TCTGCTACTCCAGGGTGCAT | 2687 |
| 288 AGGGGCTGCTGGGGCTTGTA | 288 CTCCCTGAAGCAGCAGCAAA | 1488 TGGATACACCGGGCTTGTCT | 2688 |
| 289 GCCGCTGCCTAGTGACATTGGTT | 289 GCTGTCAGACTGACCCTGGATT | 1489 AAGACACCCGCGTGCCTAGT | 2689 |
| 290 TCGTGGTCCTCCCCAGTAATGT | 290 GCCATGCTCAGAGCCTCTGT | 1490 TCCAGAGGCAGGAGACAATCA | 2690 |
| 291 CCCTGCTGGGTTTCAGTGAA | 291 GTCCACGTCTGGAACATGTTATT | 1491 CCCGCAATTGGAGCTGAATTCTTAAATC | 2691 |
| 292 CCCACTTAGAGCCCCAGGAAA | 292 GCAAGGAGCTGATCTCATCTGTGT | 1492 CCTTGGGGTTGGCCCACTTAG | 2692 |
| 293 CGATCGGCTTTGCAGGCTTT | 293 CAAAGCGGCTCCTTCCCCACAAA | 1493 TTTTCCCTGACCATCGGCTTT | 2693 |
| 294 AACCAGATCGTGTCTCCCTAGT | 294 GGGAAGCCTTTGAGGGTTGT | 1494 GTCAGGGAGAACCTATGGACCTA | 2694 |
| 295 CCAACAGCCTGAGGCTTCTGA | 295 TCTGCACCCCTGCCCTGTGT | 1495 CCCCAGACAGATGTAAGTCCAACA | 2695 |
| 296 GCCTGGAACACACTGTACTCTGA | 296 TCCCCAGTGCACAACTCCTT | 1496 CTGCATGCCTGGAACACACT | 2696 |
| 297 TCCTGCCCGTCTGCTCAA | 297 GTTTTGGCTGCACGTAGAGAAAAG | 1497 CTGGGACTGCTCACTCTGGAACT | 2697 |
| 298 TGAAACCAGAAGCTTTCACCTCAT | 298 GTTGGCACTGGGGCCTTCT | 1498 TGCCCGAACAGGCATGAAAC | 2698 |
| 299 AGTGCAGGCTGTCTCTTCCATGA | 299 GACTCAGTCAGTACGAGGGAGAA | 1499 TCTTCTCCAAGTCAGGGTGTCT | 2699 |
| 300 CAGCAAAACAGCTGTTCCAGAGAA | 300 CGTGGGCAGGGCAGACCACTT | 1500 GCAGTGCCAGGAGCAAAAGA | 2700 |
| 301 CCTTCTACACAGGGATGGGATGACT | 301 TCTTCTTTTGACAGACTGGGAACAT | 1501 AGCCTTAAAAACTGCCTTCTACACA | 2701 |
| 302 TGAAGGGTTCCCTCCAAAGT | 302 ACCTTCTGAGGTTTGGGGTAGA | 1502 GGGATTCACTAGTGTTGTCGATTGA | 2702 |
| 303 GCCTACATGTCTATCCCCTGAAG | 303 TGTAAGGCTAAGCCGCATTTTG | 1503 CCAATGGTGGAAACAGCCTACA | 2703 |
| 304 GCTGGAAACCATGCGGGAGTT | 304 TGACCAGAACCACTCGGACAGA | 1504 GCTAGATCAGGAGGCTGGAAAC | 2704 |
| 305 GGGGCAGTAGCCAGGAGGAA | 305 ACAGGCCCACTGCCCTGTCT | 1505 CCTGGATGTGGCTGGCAGTA | 2705 |

| | | | |
|---|---|---|---|
| 368 GGTGCTGCAGAGGGTGGAAA | 368 CCGGCCACTGGCTGCTATAC | 1568 GTGAGAGGATGTGTGCGTTCCAT | 2768 |
| 369 AACTACCCTCCCACCCAACA | 369 CTCTGCATGTGGAGCAAACCAA | 1569 CATTACCCCAGTTGGCAGAAAC | 2769 |
| 370 GTTGGGTGGACAGTCTTTTTCATCTTTG | 370 AGGTAAGGGGAGGCTGCAGAA | 1570 GACAAGTTGGGTGGACAGTCTT | 2770 |
| 371 GTGCTCTCCCTTGAAATGAGGAT | 371 GCTAGATAATGCTGGCTGCTTTG | 1571 AAGGGGTGCTGTCCCTTGA | 2771 |
| 372 GATGGTCGAAACCGACCAACT | 372 CTGAAAAGATCACTACCAGGATGCTA | 1572 CCCCGTGAAATGATGGTGGAAAC | 2772 |
| 373 TGCAGGGTGGCAGCATGA | 373 AGACAACACGCGTTGCTTGAGTA | 1573 GGTAATCAACCCTCAGTCTCTCATC | 2773 |
| 374 GCCCTCTCACTTCACTGACCTACT | 374 AGGGAGAGCCTCTGATGAAAAGT | 1574 AGGCCAGCCCTCTCACTTC | 2774 |
| 375 TCCGGTTCAGGTCCCCTTATC | 375 CCAGTGTACGGCTCACATTCTGT | 1575 GCTTGGGACTCTGGGGTTGA | 2775 |
| 376 CCCCTTCATCTGCCTGGTAGT | 376 CCCAGGAGTCTCTGTCCATTGT | 1576 CCTGGGCTTTGCCCCTTCATCT | 2776 |
| 377 CCTCTGCACCTTGGCCTACATT | 377 TCCTGGTGTGGACGTCTCTCAT | 1577 AGCCAGCCCTCTGCACCTT | 2777 |
| 378 GGCGGAAACCAAACCCTCAGA | 378 CGTCAGGGGTCCCTTCTTTTTG | 1578 CCTCTGAAACGCGGAAACCAA | 2778 |
| 379 GGGCCCCTCCCACATACACA | 379 GCCAGAGCCTTCATTTGGGAGAAA | 1579 AGTGGCCAGCAGGAGCAA | 2779 |
| 380 GCCCATGCTGAGGACTAACCTT | 380 TGGGCCTCCTCAGCCTTT | 1580 CCAGGGCAGGACTCTAACCATTG | 2780 |
| 381 CCCCTAAGGTTGGGTCGAGTTG | 381 GTTTTCCCAGGCCTCTCTTCTTC | 1581 GTTAGGAAAGGGTCCCCTAAGGTT | 2781 |
| 382 CAGGGTCCCAACGGGTTTCTA | 382 GGGATGTACCCAAAGCCTTCTCT | 1582 GGTGGCTTGCATTGCCTACT | 2782 |
| 383 GCCCCAGCATTCACACTGCAT | 383 GGTGCTTCACAGGGTTCACAGT | 1583 TCCACCCTGGCCCCAGCATT | 2783 |
| 384 GCAAGTAGCTGGGCCTTGTCA | 384 AGCCAGCAGGTGCCATTCAT | 1584 CGTGGAGGGGAGGAAGTCTTG | 2784 |
| 385 GCACCATCAGGAGATGCAGACT | 385 GGGAAGTAAACATCCCAGCTTCA | 1585 ACCGATGGGAGGCCACCATCA | 2785 |
| 386 CTCTGTCACTTTCTGACTGGGATGA | 386 GCAGTTCTCCCTGCACGCTTT | 1586 GAGTTGCACTTGTACTCTCTCAGT | 2786 |
| 387 GAGGCCTCACTCTCCCCTAT | 387 CTTCCCGTATTGCTAAGGAACTATTCT | 1587 GGCTTTTTGGCTTTCCAGCGTTCATG | 2787 |
| 388 TCATGCTGCTTGGGTAATGTTCT | 388 CTCTGCAGCAGAGGCAGTTATG | 1588 CCCGCAAGGGTTGGGAAAT | 2788 |
| 389 CTGGCCCATCCTCCTGTCT | 389 GGGCCTCGAAAGCCAGAAATC | 1589 TCCAACACCATCGGCTCTTC | 2789 |
| 390 TGGAGACTGGGGAGGAGCTT | 390 GCATCCATCCGGCCACTTTTCA | 1590 GTGGGTGCCACAGTTGAGATTC | 2790 |
| 391 GGAGCATGCCGCCTTGTTACT | 391 GAAGAGCAGGAGCTACTTCTATCCAT | 1591 GGCCGGGAAAAGGGGAGCAT | 2791 |
| 392 GTCTCTTCCCTGAAGTAGGGTTGT | 392 GACCCCAGACTCAGTCAGTAGATC | 1592 GTCTTCCCCATACTTAAGTTCTCTCTTC | 2792 |
| 393 TCACTCACATCATCATGGTTGCAT | 393 CAAACTGGAAACCATACCCACTTC | 1593 GCAGCTACCGCATACAAATCACTCACATC | 2793 |
| 394 GGAGCAGGCATTGCCTTCGTT | 394 TGGGGCTCCACCAGCAGAA | 1594 ACTGGACTCAGGGAGCAGCAT | 2794 |
| 395 GCCTCGCATCACCCACTTTT | 395 GCCTCTAACAGCCTCACCCAAT | 1595 AGGCCACTGCCTGGCATCA | 2795 |
| 396 CCCGTTTGAAGAAATGATAGCTCGAA | 396 CTGGTGGGAGTGGGCTTATTT | 1596 GCACTTTTGTTTTCCCCGTTTGAAG | 2796 |
| 397 GGGTGCTGTTCTGGCTTTGA | 397 GCAAGTGTTATCAGAAGTCCACCTTAGT | 1597 TCTAAATGTTCTCTGGGTGCTGTTC | 2797 |
| 398 GGCTGTGGTTCTTGACAGAGT | 398 TGAGCCAAAAGACTTTCCCTCTATT | 1598 GGGGTCTAATGGCTCTGGTTGT | 2798 |
| 399 CCCTGTGGAACAAAGTGGGAACT | 399 GCAAGACGCAGGCCTAGTAA | 1599 GGCTGTTAGCCCTGTGGAACAA | 2799 |
| 400 GCAAAGGCTTGTCTGACAGTGA | 400 TGGCCACCTCCTCTCCACTA | 1600 ACGGCAGGACAAAGGCTTGT | 2800 |
| 401 CAAGAGGACCTTGGGAAACTTTGA | 401 ACAGCAGGCTTAATCCTAGAGGTA | 1601 GGACAAGGCCCTTTAATTCATACCAACA | 2801 |
| 402 AGGCACACGCAGGTCTCATC | 402 CCCAGAGTTGCAGTAGGACACAGT | 1602 AGCCCAGAGCAGCGTTCA | 2802 |
| 403 GTGTAGAGGGCCAACTCCTATCTTG | 403 CTCCTTGCCCCGACCTCTT | 1603 TGGTAGTGTAGAGGGGCAACT | 2803 |
| 404 CAGACTACAAAGCTGTTTGCTCTTTGT | 404 TGCCCGGCTCAGTTTGAAT | 1604 GGGCCAAGCGTTCAGACTAC | 2804 |
| 405 CTGCCTTGTGCCTACTCTGT | 405 CTGCCTTAGGGATCTGGGTGATG | 1605 ATGCTCAGGCTGCCGTTGT | 2805 |
| 406 GGTGTCCCGCACTTAGCAT | 406 GGCTTTGGAAGGAGCCATCTGT | 1606 TGGCTCCCTGAGGAGTGTTTG | 2806 |
| 407 CTGAAGCAGACACAGCAGTAATCA | 407 CCAGCGTTCAGTGTGCACCAA | 1607 CACAAAAGTCTAGTGAACCCAGACA | 2807 |
| 408 CCAGGGTGAACAAGGCAAAGATG | 408 CCTGAGAGCTGTACTGTTGTCGAA | 1608 GCAGCAACTGGAGGAGGCGAAC | 2808 |
| 409 ACCTCCAGGAGCTAGTTAGAGA | 409 TTTCCTCACTGGGTGGGATCT | 1609 ACATACCTGCTGTACCCCAAATG | 2809 |
| 410 GCTTTCACTCCCCACTTGTGA | 410 GCCGGCAATTCCACATCTGA | 1610 GCAATGAACAACGACAGGCTTTCA | 2810 |
| 411 GTGAGGCAGGAAGGATGAGTTT | 411 CCAACTCAGGGCAAGTGGTTCT | 1611 GACTGAGCCTTGTGAGGCAGGAA | 2811 |
| 412 GAGCTTTGGAGACAGTGGGGTAAC | 412 GGTTCCAAAGTACTGTGGAATAAAG | 1612 GCATACTAAAGGAGCTTTGGAGACA | 2812 |
| 413 CCAGCATCAGGTCACAATGAAC | 413 GAGGACTTGGGCCTTTCCTATC | 1613 GCCCAACCAGGCCAGCATCA | 2813 |
| 414 ACTGAGGGCGGCATTGCTTA | 414 TCTGCGATCGTTCCTCTT | 1614 ACAGACGCGGTACAGCGGAATC | 2814 |
| 415 GCGGGCAAGGAGGGTTGTAA | 415 GTGAAGCTTGGGCTGGTTTG | 1615 GAGAAAGTGAGCATTTGCCATGAAAG | 2815 |
| 416 TCAGAGTTCTGTCCTAATGGACGAA | 416 CCATACAAAGCAAGAGTGGGAACT | 1616 GGTCTTACCTTCACAGTTCTGTCCTA | 2816 |
| 417 CACTAGTCTGGAAAACCAGCACCAA | 417 GGGAGGGGTTTCCCCACTAAGA | 1617 GGGGAACATTTCAGACCAGATAACACT | 2817 |
| 418 AATCCTGGAACACTCTTGCCTAAA | 418 CATCTTCCAATGTGGAGCTGTCA | 1618 AGGGCCAATCCTGGAACACT | 2818 |
| 419 GTGTGAGCGTAGTTCCTTCTGCTCTTC | 419 CAGCCGCTGACTGCCTCAT | 1619 CCTTGCCCAAAAATGAAGTGTGAGCTA | 2819 |
| 420 CAACTGCAGCCTGCTGATTTTA | 420 CGAAAAGGGGATGGTGCTTTC | 1620 ACTGCCAAGTGGCTGCAA | 2820 |
| 421 AATCGGCCACAGCCCCAGACA | 421 CCCCTGCTGCTGGTCTGTTC | 1621 CACAGCTGAACCTCAGGCAATC | 2821 |
| 422 GGATCTTCTGAACACCACATCCTT | 422 GGGCCTGGGTTCTCCTTCA | 1622 CAACAGCCCGGATCTTCTGAAC | 2822 |
| 423 ATCCAGTTCCCTGGCTGTTCTCACACT | 423 CAGTGCCTGTGGTTCTCACACT | 1623 GGGCCTAGGTGTGTGTCATCCAGTT | 2823 |
| 424 GTTTCTCACCAACACACCTTTCT | 424 GCTTACACTGACCGTGCAACTGA | 1624 CCTGTGGAATGTTTTCTCACCAA | 2824 |
| 425 AAGGGGACTCGGAGGACAAGA | 425 TGCCCTGCACCTCTGATCT | 1625 GGGTCTAAGGACACGGGTCTA | 2825 |
| 426 GGGCCAATGTGTCCTGGTTTGT | 426 GGAGGCCACCACACCTGCTA | 1626 TTTCCGGTGGGGCCAATGTGT | 2826 |
| 427 TGCCATGGCCTTTGCCTATAC | 427 TCTCACCCGACTCAGATCACT | 1627 GCATTGTCAGGCTTCTCTCTTTG | 2827 |
| 428 CCTCTCAGGGAAATCATCCATTTG | 428 CATTCTGGAGTGTGGGTGGATT | 1628 CAGAAATCAGAAGCCTCTCAGGGAAA | 2828 |
| 429 CCTGGGATTTACCATGTCCCATAA | 429 ACGGTGAAAAATGAGGCTGTGT | 1629 ACTCTTTTGCCTGGGATTTACCAT | 2829 |

| | | | |
|---|---|---|---|
| 492 TGTGAGCTCTTCTTGCCATGT | 492 GCAGAGTCCCTTGGTGGTGTAAG | 1692 GCAAGTTTGGCCATCTCTTGTGA | 2892 |
| 493 GTGTTACCTGGCGCCTGAATGT | 493 CAGGCCCACATTCTCCACAGA | 1693 CGTCCATGAAGGAATAGCTGGTGTT | 2893 |
| 494 AGCTAAGTTTTCCAGGCGATGT | 494 TGCAAACATGCACGGGTTTGAT | 1694 ACCCGGCTATACGAGAACTCTTT | 2894 |
| 495 GTGAAAGAGCCATGATAGGTCTGA | 495 GTGTTGCAGCACTAAAACATCACA | 1695 GTTCATGAAAGTGAAAGAGCCATGA | 2895 |
| 496 GATGCCCGCACCTGCTAGA | 496 ACAAAGGGAAATCCAATGGTCACT | 1696 GGGACAAAATCGGCTCCTTCAGA | 2896 |
| 497 TCGCCCTTGTGGATCCAAGT | 497 GCTGGGAAGCTCTGCCTCAA | 1697 ATGCCCTGAATCGCCCTTGT | 2897 |
| 498 AGGGGACCTCTCCCAGGTT | 498 TGGGAAGTCCACCCACTCCAA | 1698 CCCACACCTCTTGCCAAGGAA | 2898 |
| 499 ACCCTGCATCGCGTCTCA | 499 CCACGGGAGGAAGAACCAGAAGT | 1699 GCCCATGGGTAAGGCAGGAA | 2899 |
| 500 GTCCTGTTCCCGCAAGGTGA | 500 ATCACCCGGAGGACCCATGT | 1700 ACTGGCCGGTGGTCCTGTT | 2900 |
| 501 GTGTTGTTCCTCTTCCCAAGGAAT | 501 AGGGGCCTAAGTGGGCTCTTC | 1701 CGCTGTCCTGGAAGTGTTGTTC | 2901 |
| 502 GTCTCAAGAGATTCCACAGGCTACA | 502 GAAAAACGGGTTAGGGCAGAGA | 1702 TGGCCCACAGAAAGGGTCTCA | 2902 |
| 503 ACAGATGCCAGATGCAGAAGAAA | 503 CGGAATGGGATGCCTTGGAA | 1703 TCTCTGGTTAACAGATGCCAGATG | 2903 |
| 504 GGCTCTGACCTCATCTCTGTATCA | 504 CACTGTCCCCCTGCAGAT | 1704 CCCAAAAGGCTCTGAGGTCATC | 2904 |
| 505 CAAGTCCCTCCCAGCAACAA | 505 TGTCACAGATCAGTTGGTGAATGT | 1705 GGACATGACTCCCTGGGACAA | 2905 |
| 506 CGGCTCTGTCCTCTGTCACTTT | 506 CCAGGACCCGAGATGGTCTGT | 1706 TGTCTTAGCTGCGCCTCTGT | 2906 |
| 507 GCATACCAACCCCGCCACAA | 507 ACACACCAAGGCTTCTCTCTAA | 1707 CCCAAGCCCAGCTCCCATA | 2907 |
| 508 CCATCATCTGGTTATGCTACAGTCT | 508 GAGGGGAGGTCAATCCACGAGAGA | 1708 CCTTTCCAACTCCATCATCTGGTTA | 2908 |
| 509 CTTGATGACTCCACTTCTCCATCA | 509 AGGGCCACCACGGTGAGAAA | 1709 CCTGCCTGATACCTTCTTGATGACT | 2909 |
| 510 GCCAAGGAGTGAACCAGGTTTG | 510 AGAGAGCCCATCCTCCCTTCAA | 1710 GGCCTAAAGGCCAAGGAGTGAA | 2910 |
| 511 CGACCTGTGTTAGGGGTTCAGT | 511 ACTTCTGAGCAAGTGTGATGTGA | 1711 CACTGCTTAGCGACCTGTGT | 2911 |
| 512 GTGGCCCAGAAGGCTGCTT | 512 GGCGACAGTTCCTCTGGACTTA | 1712 TGGTCAGCGTGAAGCTCTGT | 2912 |
| 513 CACAGGAGGTCATTAAGGTTCAACA | 513 CAGATTGGGCACCCACCCTTAT | 1713 AGGCTCCACAGGAGGTCATT | 2913 |
| 514 GCAGACATTGTATGTCGGTGAACA | 514 GGCCTTTCCTAAGCTGATGGTTGA | 1714 TGTGAAAGAAAGGGCAGACATTGTA | 2914 |
| 515 TGGGTTCGCACGGCTGTT | 515 GCTGGCATCTAATGCTGCCATGTT | 1715 CCAGTGTGGGATCTCAGGCATT | 2915 |
| 516 ACCACCACACCTAGCTCCAAAG | 516 GCTGCTCAGAGAGAAACTGCAT | 1716 CAATTTACTCTGACCACCACACCTA | 2916 |
| 517 TGTCCCTGGGCCCACTGAA | 517 GATCCGCCTGAGAAGGAACAAG | 1717 TGCTGTGTGCAGGGACTGT | 2917 |
| 518 GTGCGGTAACAGCCGCAGGTAT | 518 ATGCCCTCGACACCAGCTAGAA | 1718 TCAGGTGACAGCTCGGGTAACA | 2918 |
| 519 CTGCCCGGAGACTATGCTCAGTA | 519 GAGGTTTGGGCTGCCAATGAT | 1719 GAAACCAACTGCGGGAGACT | 2919 |
| 520 GTCACCCAGGCCATCTGAACTT | 520 GCAGAAGTTGCTGGTTCTGTT | 1720 AAGGAAGTGGCGCAGTATG | 2920 |
| 521 GGGCCATGTCATTGCTCTGTAG | 521 GGGCAGAGGCAGGACCATTG | 1721 AGGCGCTGGGCCATGTCATT | 2921 |
| 522 CCCCAAGATGTCTGCCATAGTTC | 522 GCTGCTATTTTCGTTTCTGCATGT | 1722 GGTTAGTTCCCTTTATTGCCCAAGAT | 2922 |
| 523 GCAGTTGGTAAAGGCAAAGCTTAACGAAA | 523 TTGCCCCTCCTCCCCTCAA | 1723 GTGTGCAGTTGGTAAAGGCAAAG | 2923 |
| 524 AGACTAGCCAGGCTACACACA | 524 ACATCCCTACACCCAAAGTCATC | 1724 GTGATTTTCCAGCACCTCCCACTA | 2924 |
| 525 GTGAGCACAAATTTCGATCGAGTCACA | 525 TGCCTGGAGGAAGGAAGTCA | 1725 CGGAAACCCTGTAATAACTCACTCTGT | 2925 |
| 526 GAGTCGTAGCCTCAAGACACA | 526 CCTTCCCTCTGGATTTTGGGTTT | 1726 GTCAGTGCTTTTCATGGCATCTT | 2926 |
| 527 GTGTGGGAAGGAGGATTCCATGT | 527 AGCTCCTCACCCAGCCTCAA | 1727 AAATTACTCCATGGTGGGAAGTGT | 2927 |
| 528 ATGGTAGCTCACACCCAGAAGT | 528 ACACCTCTGGACCATCTCTGA | 1728 GCCTGATTGAACCCCTACAACA | 2928 |
| 529 CGTCCAGGAGACAGTTAACCTCTTG | 529 GCCCCAGGGTATGCTTGACCATT | 1729 CGGCGTCCAGGAGACAGTT | 2929 |
| 530 TTCCAAGAGCATTCAGGTGTCTT | 530 ACCCAGCCAACCCACGAAATC | 1730 CCAGGGTCTTTCCAAGAGCATTC | 2930 |
| 531 AGCAGCTCAAACTATGCCAAACA | 531 GGAGACCAGAACATGACACTCCAAT | 1731 GTTTCTCAGCATAAGCAGCTCAAAC | 2931 |
| 532 AGTGCCAGAGCCCGCTAGAAA | 532 CTGGGCACCTTGCAGCTTTT | 1732 TGACCAGGCAGAGGGCTGAT | 2932 |
| 533 ACCCCTGTGCCTAAGCTGAAGT | 533 AGGCCCTGTTTCCCTGGAATG | 1733 TTGGCCACCCAGAGCAGTCAT | 2933 |
| 534 CTGTGCTGCTGCTCTTCA | 534 ATCTGCCCAGCCAGGTCACTT | 1734 GCAGTGATGCGATGTGAGTCT | 2934 |
| 535 GATGGGTGTTGCAAGGCAAAG | 535 GGTTTTGCCCACCACCTCTGA | 1735 GAAACCTAAGGATATCAAAGGGCTGAT | 2935 |
| 536 GGCCCATTTACCCTTTCTATCATGT | 536 AAGGTTGTGCTTTCTCTCGCTAT | 1736 CAGGCCCAATAGGCCCATTTAC | 2936 |
| 537 CAAGTGGATTGTGGTGGACACT | 537 CCTTAGCTCGGTCGCCTAAACT | 1737 CTGGGTCAGCTCAAGTGGATTG | 2937 |
| 538 TGTGTCACATTCCTGGTGCTAAA | 538 CCCACTATGGCAAAGATCCATCA | 1738 TGTGCCGCTGTGTGACATTC | 2938 |
| 539 AGGCAGGCCATGAGCCAAAT | 539 TGGCACCCAGTCATCTGCTA | 1739 GCCCAGGCATCCAATCCCTAAG | 2939 |
| 540 GTTCCAATCACAGGACAGGGTAT | 540 CATCCCGGTGTTTAAAGCAAAG | 1740 TGATGTGCCTCTCTTGTTCCAAT | 2940 |
| 541 GGAGATGCAATCGGCCCATAA | 541 AAGGACGTACAATTTCGGACTCA | 1741 AGGAACTCTGGGGAGATGCAA | 2941 |
| 542 TGTTGGCCAGGGGTTAGGTT | 542 TCCTTCCCTAGCTGGGCCTTT | 1742 CGTTGCTGCAATCAAGGCTGTTG | 2942 |
| 543 GTCATGGGACCTGGCATTGCTA | 543 GGGGGCGATAGGCACACACA | 1743 GACACCTCCTCTATCCTGTGGAATG | 2943 |
| 544 GCCACATGGACACCTCACACTT | 544 CTGACATAGGTGGCTGGAGTGA | 1744 AAAGGTAATGTCCATTCGGCTAGAT | 2944 |
| 545 GGTTTTCCTATCGGTCGTTTGAGGTCTAC | 545 CCCCAGACAGAGAAGCAGTCTA | 1745 CGGAGAAAATTGGTTTTCCTATCGGTGTT | 2945 |
| 546 CAGGGTGATAAGTCCACAGCATTC | 546 GACTGCCCGCAGCTCTTGTAA | 1746 GCACTAAACCCCAGGGTGAT | 2946 |
| 547 CAGCACCCAGAGAGCAGTT | 547 GCCATGGTTAGGGTCCTGGAT | 1747 AAAGGGGACCTGCCACCTTCA | 2947 |
| 548 GCCCAGGCCCAGCATTATT | 548 CTCCCCGCTAGAGCAGTGA | 1748 TGGTGTCAGCCTCGTTCCTTCT | 2948 |
| 549 CACGACACCACACGGCATTCA | 549 CACTGGGCCTTCCCTTTACCAT | 1749 CACCACACAGGTGCATCACA | 2949 |
| 550 TCCCATCAGCACCAGTAGAGGAGGTT | 550 CCGATGGCCCAAAGGCTCTCAAA | 1750 CCCATTGCCAAAAGCAAACTGT | 2950 |
| 551 GGGAGATCATACACAGAGAGGAGGTT | 551 ACACACTTCATCACAGCCTTGT | 1751 AGGGCCACAGCAGAGGAGAT | 2951 |
| 552 TCAGGCTAAAGACATTGCTGTAGGA | 552 TCCTTGATCTCCCACTCCATTTTC | 1752 CTGCCGTTTGTGTTCAGGCTAAAG | 2952 |
| 553 CCCTGCTCTTCCATGCTGCTAA | 553 ACCTGGCTGCCCACTTCTCA | 1753 ATGTTCCCAGGCCCTGCTCTT | 2953 |

| | | | |
|---|---|---|---|
| 678 CCTTAGTCCTACTTTTTCCCTTGCAT | 678 GGATGGAGACGGCAGGAATG | 1878 CATGCCTATCTCCCTTAGTCCTACT | 3078 |
| 679 GACCTTGCAAGAACGGAGTCA | 679 GGACAGAGAATCAGGTCACGGTAT | 1879 AGTCAGCTCAGGGGTGACCTT | 3079 |
| 680 GACTGCCATCTGGCATTGAGAAC | 680 ACCTCGGCCTCAGGACTTCT | 1880 CCACAGCACTGACTGCCATCT | 3080 |
| 681 AGCCGCTCCTGCTTTTTCA | 681 TGCTCACAGCCTCGGAGATAGT | 1881 ACATGCTGAAAGCCAAAACCTCTA | 3081 |
| 682 GCCAAAAGTGCAGAGTTATTTCAGT | 682 AGCAGTCAGGTGCTCCTCCTT | 1882 CAGAATAGCACACAGTGTCACAGA | 3082 |
| 683 TATTGGCCGCCAGCACTGT | 683 TGGTATGGGGCCGGCAGTGA | 1883 CGCCATCCTGCCATAGGACGTA | 3083 |
| 684 GAGCCCCTAGTCAGTACTTTGT | 684 CCCAGCTGACACAGGCTCAT | 1884 TAGGGCAAAGAGCCCCTAGT | 3084 |
| 685 GAAGCCAAGTTGGTGGAGGAT | 685 GTGTCCAGTCTCCTTGAGTCATTTG | 1885 GGAATTCTGTAAGCTAAGAAGCCAAGT | 3085 |
| 686 GAGAAGGGAGAGATGCATGGGTTT | 686 GGAGGCATGCCCCATCTCA | 1886 GCTCCCAACCCAGAACACT | 3086 |
| 687 CGGCCACCCCTGTGCATCTTTA | 687 GTGGTGCTTCTTGCCACTGT | 1887 GGCATTCCAGCAGTGACCCTAG | 3087 |
| 688 TGAATGGTGGCCGAATTGTGT | 688 GGGCAGTGATAGAACTGACATTTG | 1888 CCATGGGCACAATCCAAGCCTAT | 3088 |
| 689 GCCCTTTCTGGAGGTACTTGAGCTTAT | 689 GGAACGTCAGTGGTCACCTT | 1889 GGGGCCCTTTCTGGAGGTA | 3089 |
| 690 GCAGTCTCCAGTGCTCTTCTTC | 690 TGTCACCCTCTCTCCTCATAAGT | 1890 AACGGCAGGTGACCAGTCT | 3090 |
| 691 CTTCACCCACAGCCAGAAATGT | 691 GTTCCATCCCCAAGGACACAGA | 1891 GTGGTTGCTTTCACCCTACTTCTTC | 3091 |
| 692 CTGGCTTGGAACAGAAACCATGACT | 692 GGGACTGGACCAAGAGGGTATG | 1892 CACTCCTGGCTTGGAACAGAA | 3092 |
| 693 AACGCTTGAGACGTGCTTGT | 693 CCATGGCAGAAGCTCAGGAAAC | 1893 GCAAAGATGACATAAGCAAAGGCTTGA | 3093 |
| 694 GCTGCAGTGAGCCACGAT | 694 GGTCTCGCTCTGTGACACCATT | 1894 GGAGTATCACTTTAGCACTGGAGTT | 3094 |
| 695 TGGCTGGAGCACAGTGAACA | 695 GCTTCCCCGTGACTGTCTCCTAT | 1895 AGGATCGGTCAGGCCAGTGT | 3095 |
| 696 CCGCCATCAGGGGTTGATGTAA | 696 GAGAGGGTACTGGTAGAAGCATTTC | 1896 TCCAAGCCACCGCCATCA | 3096 |
| 697 AGGGATCAGGGCCATCTTCA | 697 AAGTCTGGGGCCCTCCTAAG | 1897 CCTCCACTCTACCAAAGCTTATAACA | 3097 |
| 698 AGTCAGCAGGCTGGAAAAACT | 698 GCAGCTGCTGTCTCTGCAATTC | 1898 TACGCTGACCACCCTGACACT | 3098 |
| 699 CTGTGCAGGAAGCAAGGTAGAT | 699 CCTTGTCCTGTGCATCTCTGT | 1899 GTGGGTACTACTCTGTGCAGGAA | 3099 |
| 700 TGAGTCAAGGTGATACTTGCTTCTT | 700 CAAAGGCAAAAAGTGGCATCTGT | 1900 TGAGGCATTTGAGTCAAGGTGATAC | 3100 |
| 701 ACCTATAACAAAGGGGAAGTCAGGAT | 701 GAGCCTACCTCTGTGGACTTCA | 1901 TGCCTGGGTTAAGGCGCATA | 3101 |
| 702 CCTTCCCCACCATCTTCTACA | 702 GGAAAACCCTCTGAGCCTCACATT | 1902 GGGGAACCTTACTCATCACTAGTACAAAC | 3102 |
| 703 CACATGCCCAGTAAATGGAACAAA | 703 CGGCCCCTTAGCTTGAGTTAGT | 1903 CTCCTGACACATGCCCAGTAAA | 3103 |
| 704 CACCTGGAAGCTGAAGCCAAAG | 704 GAGGCTGCCTAGAGAGACAGA | 1904 AGTGTGGGGCACCTGGAA | 3104 |
| 705 AGTGGGCGAGCGCCCCTTAT | 705 GGGCACGCATGGGCATTTG | 1905 ATGTCCGGTCGGAGGTACAGT | 3105 |
| 706 AGGCCTGCTGCGTGGACAA | 706 GGGGCTCGCGTCTCTGTTT | 1906 AATACTGCCCTCCCCGGACTACA | 3106 |
| 707 CTTGGGAACTAAGTGAGGGCAAAG | 707 CTGTCGGATGTCCTGGAACTAC | 1907 CACTGCAGCCAAAGGCTTTCAAC | 3107 |
| 708 GCAGCTTTTCCTGGTGTCTTTC | 708 CTTCCAGAAAGGCTTGGAGATACT | 1908 CTCAGCTCTGTGCCTGGATAATG | 3108 |
| 709 GGGGTGGTTAAGTATGGGCTAGCAA | 709 TGGCCCTCAAGGAGCTGTA | 1909 CTGATGAATTGCTGGGCTGGTTAAG | 3109 |
| 710 AGTGAGGACATACAGCTTCTCAGAAAT | 710 GCACCCAGCCAGCAATTGGATA | 1910 GGTTTAGGTCCTCCATACTGAGCATA | 3110 |
| 711 GGATCTAAGCAGTGCATCTCTGTGT | 711 CCCCGATTCTGGTGTTTGCTT | 1911 CCGGTTCTTTCTTGACAGGGGATCT | 3111 |
| 712 GGTGACTGTGCACGCGTTAAT | 712 AGAACCCGGTCCACATGCTAAC | 1912 AGGCTTCCCCTGGTGACTGT | 3112 |
| 713 GCTCAAGTACTCCCTGGCTTCT | 713 CCAAGGCCCTCCTCTCTCTAAG | 1913 AGAGCTGGCAGGCTCAAGTA | 3113 |
| 714 CAGGATCTTCTTTGTTTGAAGGAGCTT | 714 CACAGGCAGTTAGGGTAGGTTCT | 1914 CTGGGGCCTGCAGTTTGATT | 3114 |
| 715 GGCAGACAAATCAGCCCAGTT | 715 TCCCCACGATGGCAGTGAGTT | 1915 GCAGCCTGAATCTTGGCAGACA | 3115 |
| 716 GTCATTGAACTGCGCTTCAT | 716 TGGAGCAATATGCTGCACTGTT | 1916 GAGCTGTCCACTAACCATTAATTAGGTCAT | 3116 |
| 717 GGGACTACAGATAAGCACCACTGT | 717 CACTCTGTCAGTTTTGCCGTCTT | 1917 TCTCACCTTAGCCTCCAAGT | 3117 |
| 718 CAAAGAGGCCCTCATGCTCAGT | 718 GCAGGCATGACAGACTTTCCTT | 1918 TGGCTGCCCTCCTTCCATGAT | 3118 |
| 719 TTGGTCCTACAACCAAGCAACT | 719 GCGTTCCCATGGCATGTCTAAA | 1919 CCCACCAGTGTATCTTGGTCCTACA | 3119 |
| 720 GCCAGAGATGAATCGTTTGCGAATG | 720 TTGGAGTGGACGTCTTCCTATTTC | 1920 GCGGATTTTGAAGCCAGAGTGA | 3120 |
| 721 CCTCTGCTATAGAATCAGCACTCT | 721 CAGGGCTCCCTCCTCCATTT | 1921 CCCCATCCCTCCCCTGTGCTA | 3121 |
| 722 TGTGTGTTGTCGAGAGGGAGAT | 722 CAGCACTGAGTTCATTGCCTCAAAAA | 1922 CCGTGGTCGAGATGGTGTTT | 3122 |
| 723 GAAGCTCCTTACATTAGTGCCAGGTT | 723 GCCATACGAGAGACCCTGAATCT | 1923 TGGCTCCTGGAAGCTCCTT | 3123 |
| 724 TGCACTCAGAGGAAGTTAAAACA | 724 GACTGCAACAGAGGCTCACCTA | 1924 TGTAAACAGGGAAGATGCACTCA | 3124 |
| 725 GGATCAAAGTTCAAGGAGTTAGTGTGA | 725 TGCCCTGCCTGGTCTTCT | 1925 CCTCCTCTGAGGATCAAAGTTCAAG | 3125 |
| 726 CGGCACCAGCATTTCAGTCTTG | 726 CAGCAGAGACCTGATAGCCCTATGT | 1926 GGAAAATGGCCACCAGCAT | 3126 |
| 727 CCGGCCAAGAAGGTAGCAA | 727 GCAACAGGTTTTGTCCTCTGGTT | 1927 AGCAGTCAGTCAGTTCCAGCTA | 3127 |
| 728 CGGCTTTCTGCCCAGATCAA | 728 CCTGGTCCTCCTCCCATCCAAA | 1928 CCTCAATGATTACCGGGGCTTTC | 3128 |
| 729 GCCACAGGTTGGAGGCAAGA | 729 CTGGAAACGGCCCCAGAGT | 1929 GGCTCTCTTGGCCACAGGTT | 3129 |
| 730 AGTGCCCTGCTCAACCAATAC | 730 TGGTGGGGACATTTTCCTGAAG | 1930 CCCCCAGAATCAAGCCCAAAG | 3130 |
| 731 TCCCTCTTGTTTCCAGGTTTTTGT | 731 CTGGTTGCACTGTGGAGCAT | 1931 CCTCTTAGCTGTCCCTCTTGTTTC | 3131 |
| 732 GGAGGCTCCATCCACAGTCA | 732 TCAGATGCTCAACCCGCCTAT | 1932 ACACACCCCACAGCTTCTTC | 3132 |
| 733 GGGCAAATCTGTGTCCTCCAGATA | 733 CGGCCGACTACTGCAGGCTTT | 1933 GGCTGGAGGGCAAATCTGTGT | 3133 |
| 734 GGGTTACAGCTTGACTCTGGGATT | 734 AGGTAGCCCAGCAGTTCTCCAT | 1934 GCCATCACAGAGGGCTTACAGGTT | 3134 |
| 735 CCTAGCCTACAAGCGCACTCT | 735 TGGCCTGCCTCACTTGCTTA | 1935 TCACTAAGTATAAGGCCTAGCCTACAA | 3135 |
| 736 GAGTACTGAGGCAGGGAAGCTTT | 736 TCCGGAAGACACGAGAGGAAA | 1936 GGGTCCAATGTGAAAAGCACAGT | 3136 |
| 737 CCAATGAGTTCTAGACCTCAGATTCT | 737 ACATCGGTTTTGAGTCAGCCATT | 1937 CAACGCCCATAAGCCCAATGACT | 3137 |
| 738 GAGGGGTGCTAGTCAACTGTGT | 738 GAACCTTGGCTCTTTGCAAGTCATC | 1938 CCTGAGCGTGAGGGCTGCTACT | 3138 |
| 739 AATGCCAAGCCACCCTGGAA | 739 TGACTCACTGGGCCTTCAGA | 1939 GGCATGCTCTTCAGGGACAAGTTAG | 3139 |

FIG. 34B2

| | | | |
|---|---|---|---|
| 740 AGGAACCCACAGCGGTAACTGA | 740 GGCAAGGCAGCCAATAAAGGATGTA | 1940 TGTCCCCAGCACCAGTAAGTTC | 3140 |
| 741 TGCGAGCTGAGTGCAGCAT | 741 GGGCCTGTTGGGCTTGTTTTG | 1941 GCGGGAATTGGACACAGACTGGTA | 3141 |
| 742 CTCCAAGTCCAGGATATATGAAGCAA | 742 CAAAGTGGTGAGTTCCTTGGGTTT | 1942 GGCTTCTTCAACTCCAAGTCCAGGATA | 3142 |
| 743 GCACAGAAATAATCGTGCAGGAAA | 743 TTGCCCTCCCAGTGGCTTCA | 1943 GGGCTCCATTGTGTTCCTCAAC | 3143 |
| 744 GGCAGCAAACCTCTTAGCGAACACA | 744 CCTGCTCTACGGGCTCACA | 1944 CCTTCTGACCGACCAAACCTCTT | 3144 |
| 745 TTTGGGGTTTTGGGATGAGGATAA | 745 CAGTGAGGAACGTATTCAGCCTAT | 1945 ACCCTCTTAATTGCTTTGGGGTTTT | 3145 |
| 746 TTCCTCCGCCCAACCCTCTTT | 746 GGCATCGCTCACCCAAGT | 1946 CGTGGAGAGGTATTTTGGCAGTGT | 3146 |
| 747 GCTACCCTGAGTGCTGATGGAT | 747 AAAGAAAGAGGCCATGTGGTACA | 1947 GGCTGATTTCTGCTGTCCTCAAGCTA | 3147 |
| 748 CTTGATCTGTCAAGGGAGAAGAGAGA | 748 TCTGCCCACCTGGCGATTT | 1948 CAGTTGCCTGCATCTTGATCTGT | 3148 |
| 749 GCAAAGCCAGTGATGGGAGATGA | 749 GACATGACCCACAAGCCCTTCCTT | 1949 GCACTGGTGGAAGAGACAGCAAAG | 3149 |
| 750 CCCGACTCTTGCTGGGTTGAA | 750 TGGCTGACCTCCATGGAAAC | 1950 ACCCATGACAGCCGACTCTT | 3150 |
| 751 TGTGTTCCTAGAGACTCTGGCTTT | 751 GCCCATGTGAGGCATAGACTT | 1951 CCTTAGAAGGCCTCTCTTCTCTGT | 3151 |
| 752 ACCAGCTGTGTCAGCTAAGTTG | 752 AGAAACCCGACCCTCAGACA | 1952 CGGTCTGAACGGAAACTGCCATA | 3152 |
| 753 TTGCCTTTCCCTGTCTTTGGAA | 753 AGGCCAAGCTAGCTGATATCCTTTC | 1953 ACCCTGGTCTGCCTTGCCTTT | 3153 |
| 754 GCAGGACTAACAATGGCTCAGA | 754 GGTGGACTGACCCAAACCTTCA | 1954 GCTCAATCGAGGCAGGACTAAC | 3154 |
| 755 CAGGAGCCACCTGGGAACT | 755 GGGCATCCTTTCAATATATCCTCCTACT | 1955 CCAGTTGGCCCACAACTTCCAT | 3155 |
| 756 TGGAGAAGAGCAAATCCATGTTGT | 756 CCGGGAAACCTGGGAAGTCA | 1956 CTAAGGGCTTGGAGAAGAGCAAA | 3156 |
| 757 CCAGGACCCAGAAGTACTCCCTAT | 757 CCTGGTGAGTAACGGAGAGTCA | 1957 AGCCAACCAGGACCCAGAAGT | 3157 |
| 758 CCTACCATATGCAAGGCACCAT | 758 CAGGCATGGGCACTTTCTTTTATC | 1958 AGACACATTTGCATCCCTACCAT | 3158 |
| 759 AGAAGTCCAGGCTTCCCACTTG | 759 ACCCTCTGCTTCTGGTGTCAGT | 1959 CACTCCATTAAAGCCATTTGGGAATAGAAG | 3159 |
| 760 GGGCTTGTTAAATGAACCCGAGAAGT | 760 ACGCCTACAGTGAGCGGAAA | 1960 GCAGCCAAAAGGGCTTGTTAAATG | 3160 |
| 761 GCCACAGTAAAACAAAGTACACAGT | 761 GGGGCATGGAATCAGGAACTT | 1961 TGGGTACCAGTTAAGCCACAGT | 3161 |
| 762 TGTGCAGTGAATGCAGAGACTAT | 762 TTAGAGTGGGAGCGGAGACCTT | 1962 AGAGGGACTTATGTGCAGTGAATG | 3162 |
| 763 CTCACAAGCCTAGAAGGGTATGTT | 763 GCAATGATCAGTGGCGTTTTCAGA | 1963 GCTGGTTTTCTCACAAGCCTAGA | 3163 |
| 764 ATGGGACACCTCCCTGCTGAGT | 764 ACCACAGGGTTGGGCAATGA | 1964 AGACTGCCTGCTGTTTCATCA | 3164 |
| 765 GGTGTAGCAGGGAGAGAGATTGGTT | 765 ACGGTGCCCGGCCATTTCT | 1965 GCAGGGGCTGTAAAGGGTGTA | 3165 |
| 766 GGCCTTCTTGCCTCTCCACTTA | 766 GGCATCTGCCTTTTCTAACCAT | 1966 CTGGGTCTTCTATGGCCTTGTTG | 3166 |
| 767 CACTTCATAGTGTCACCCTGGTTGT | 767 GCCCACCTTATACCTCGCTCAACT | 1967 GGTGCCTCACTTCATAGTGTCA | 3167 |
| 768 AGAAGCTGCTTTCTGCTTGTCA | 768 CCTCCTGCCACCACATCTATCA | 1968 AGATGGAGGGCAGATTTCAGAAG | 3168 |
| 769 GATTGTTTGTGCTCCAGAAAGAAGA | 769 TGGTGACGGAGGATGGCAGAA | 1969 CACACAGAGCCTGGGCTTATATC | 3169 |
| 770 GAACAGTTGGCGATAGGCTGAA | 770 TGGCATCCCAGCTGTCTATGACT | 1970 GCCTGGGCATCTCTCAAGCAACAGTTG | 3170 |
| 771 GGCCCTATACTGCCTTCAGAGA | 771 AGGCAGAGTTCTGCCTTCTTG | 1971 CCCTTTGTAAAGCATGGCCCTATAC | 3171 |
| 772 CACAGGTGATAGCAACAACCTACCAT | 772 AGGCTGCGAGTTTGGCAGAT | 1972 TTCTCATACACAGGTGATAGCAACA | 3172 |
| 773 CCTTGGGTGGAACCTGTGATTCAA | 773 GTCCTGCTGGTGCACTT | 1973 CCTCTTTGCCCTTGGGTGGAA | 3173 |
| 774 AGGCACCATGCTCAGCTCCTA | 774 GCACTATGCAGCAGGAACCTAAG | 1974 GTTGTTGGCCAGGCACCAT | 3174 |
| 775 GCTCAAAGCCTTGGGGTTCTAC | 775 ACAGGCCTGGTTGGCCTTTGT | 1975 CCCTGGCTACTCCCCATGTTT | 3175 |
| 776 GCTCCAATGTCAGTCCCTTCA | 776 CCAGCTGCAGGGTATATTATGGAAACA | 1976 GCCTTGCCTGTCAGCTCCAATGT | 3176 |
| 777 GCTGGAGTTCCAGGTTGGACTT | 777 CCGTTGGCCACTCATTCAAGA | 1977 CATCTTTCTGGGGCTGGAGTTC | 3177 |
| 778 GGGGCACCCACCATTGGAA | 778 GGGCTCACTTGGATGGTCCTAAAG | 1978 GAGCCCACATCCCGTGAACA | 3178 |
| 779 GCCAGTCTCTGGTGTTCATTGT | 779 CCAAGTGTGACAGTGTCTTTGTTT | 1979 GAATGTGTCCGCCAGTCTGT | 3179 |
| 780 CACCCTGGGAAGCTGACTGTA | 780 CGATACAAGTGGATGGCTCTTCATTC | 1980 CCTGGAAGCCAGCTAGAAACCAT | 3180 |
| 781 GTGGCATCTGAGGTGAGCTTTC | 781 CATCTCACCAGATCTTGACTCCTAA | 1981 GGACAGGAAGACAGTGCCATCT | 3181 |
| 782 GCCGGTAGTTGTGACAATAGGAAA | 782 AGGGTGGAGCTGCCATCTTGA | 1982 GGGTGAATGCCGGTAGTTGTGA | 3182 |
| 783 GGGGCGTACTTCCTTTTTCATTCTA | 783 AGACACAGTTAGCCAGACCTATTG | 1983 AGCGGGGCTACTTCCTTTT | 3183 |
| 784 TCTAGGCTGCACTGGACACCAA | 784 CACATGTCCCGGAGCCTTAATCGAAC | 1984 GCTGTATGTCTGCAGGTCAAGT | 3184 |
| 785 GAGTTTCCTGTGTCTGGGTATGGGTTT | 785 CCTGCCTAAAGGTTTGCAGACAA | 1985 TCCTCACATGAGAGTTTCCTGTTC | 3185 |
| 786 GAGACACCTGGAAGGACGAACA | 786 CCACCCAGATGGACTCCCTTTTA | 1986 CTCCAGCATCTGGAGGAGAACA | 3186 |
| 787 GCTTGCCTGAGAAATGCCTGTGA | 787 CCCCTGTGTGACTGCCCTTA | 1987 CGGGACGCCTTGCCTGACAAA | 3187 |
| 788 CCCACACACAACTGCTCACA | 788 GAATTCTGCCGTCTGGTTCTTTC | 1988 TAGGCCAGCTCCCACACACAA | 3188 |
| 789 TGGCAGGACAAGGGGTTTG | 789 ACCCAATGTCCTTTGCCAGTAG | 1989 TGGGCGTAGCACAAGAAATCA | 3189 |
| 790 CCTATTCCCATGGAGCCATTGTTC | 790 GGCTGCAGTACACCCAGACT | 1990 TGGGCTTGCTCTTTGCTGTTCAA | 3190 |
| 791 ACCCTTGCTGAGGGAGCAGTA | 791 GTGTTTGGGGTAATCACCCACAGTTAAA | 1991 GTGGCAAACAACTCTGAGGCTAAC | 3191 |
| 792 CAAGGCAGATGGGAGAAGAGCAA | 792 CACACACCTTTTGCCCCTTTTG | 1992 GGGAAGAATGCTGTGTCCTCACAA | 3192 |
| 793 CCAACCTTCCAGCCCCTTGA | 793 TCTGCAGGGGTAAAAAGCTCACT | 1993 ATTTCCTGCCGTGCCACCTT | 3193 |
| 794 GCAACATCCTGGGGCACAGA | 794 GTAGGACCAAAACATGGAGACTGT | 1994 CACAGAAAGCTGGGGCAACA | 3194 |
| 795 TCCCAACACAGGTGGCTAGA | 795 CACTAAGTGCCCGAGTCAGGTT | 1995 CCAGTACATGCTTTCCCAACACA | 3195 |
| 796 GCCAGTGCATCCAGAGTCTTTCTTTC | 796 CAACCATTCGTGCCCCAAAAC | 1996 CCTTTTTAAAGGAGTGCATCCAGAAGT | 3196 |
| 797 GTACACTAGCAAGTACCGGTGAGA | 797 GACACGACATCTCTATCCCTACTT | 1997 GAGCCCCAAATGTACACTAGCAA | 3197 |
| 798 TGAGGCTTCTTTCCGCATGT | 798 AGAAACCAGACTGTGAGGGAAGA | 1998 GCCCAGTGCTTTTCTTAATTGCTTTGA | 3198 |
| 799 ACTGGACTACACTGGACTACTTTGAT | 799 AGGGCAAGGCTCCCTCATTT | 1999 CCACTGGACTACTGGACTACACT | 3199 |
| 800 CCAAGAGCCCACCTGATTCTCT | 800 ACCTTAGGGTACCAGCTCAGACA | 2000 CAATAGCCAGGGTCTGAATTGCAT | 3200 |
| 801 TGATAGGCAAACAGCAGACAGT | 801 AGGGCTCTTGAGACCAGCAA | 2001 GAGTGCAGAAGAATGGGTTCTGA | 3201 |

FIG. 34B3

| | | | |
|---|---|---|---|
| 802 CCCGCGTTACAATGCAACTT | 802 GTGTGGATTGTTGCAGGAGGAA | 2002 AAGCCCTAAACCCGCGTTAC | 3202 |
| 803 CACTTCCAAAAGGCAGCTACAATC | 803 CAGCAAAGACTGGATTCCTACTCA | 2003 AGCAGAAATCACACAATGGCAATAC | 3203 |
| 804 TGCCTGGTGATCCTCCATCA | 804 GGCATCATTCATTCAAAGACATTC | 2004 TGCCTTCACTGCCTGGTGAT | 3204 |
| 805 GCTGCAAACGACAACTAAAGCAT | 805 CACCCATGCCCACCTTTCTT | 2005 ACCCCTCCCCCCATCAAGTA | 3205 |
| 806 GCCCTATGCACATTGGCTTGT | 806 CCTCTCTGATCATTTGGCAGGAAGA | 2006 CGTCTTTCTCCAGTTTCTGAGCCCTAT | 3206 |
| 807 AAGGACTGAGCAATGGCTGTT | 807 TCATTGTAACTAGGGACTCCACGTA | 2007 GGTCAGCTGTGTCAATAAGGACTGA | 3207 |
| 808 GGCCCCAGAGACCTCAACTTT | 808 CATATTACCCTGGGAATCACAGCAA | 2008 GGAAGCAGGTGTCAGTGTGA | 3208 |
| 809 GGAGTCTGCAGTTTGAGGTTTATATG | 809 TTGGCCTGCCACATCCCCTAT | 2009 GGTCTGCTTCTGGAGTCTGCAGTT | 3209 |
| 810 CCTGTTTCAGGATTAAGGGCTTCT | 810 CCCAAATGGCAGAGGCTGTGT | 2010 CACACTGGTTCCTGTTTCAGGATT | 3210 |
| 811 AGCTTTGGGCTCCCTCACTAT | 811 CCTGATTCCCTTCAGTTCTGTTCT | 2011 ACACCCATCCCAAAGGGATTAAAAG | 3211 |
| 812 AGATCAAATCACCCCAGCTTTGT | 812 TGCACTAATGTCTTAGAGGAGCTTTC | 2012 CCTGTCTCCCTTGCCAGATCAA | 3212 |
| 813 CACACATGTCCCTGCAGTTTG | 813 CAAGGCCACACAGGATGTGTCT | 2013 AGGGCTTCCCTGAGCAGAGATATT | 3213 |
| 814 GCCTCTGACTCATGTCCTGTT | 814 GGGTCCAGGGTATAGGTGGAAGA | 2014 TCTCTGGCTCCAGCGTCTGA | 3214 |
| 815 CCGGCTTCTTTACCCCACTTAG | 815 GCGCCTCTGGAAAGGTGAGATT | 2015 AGGGATATGGCCGGCTTCT | 3215 |
| 816 CACCCCAGACCCCAAGTTC | 816 GGCCTGGTGTAAATTTCTACCTACATA | 2016 GTGGTGGTGGTTGTGCTACT | 3216 |
| 817 AGCCTCTCTGCCCACCTGAAA | 817 TGCAGTCAAATGCAAAGGCTGCTA | 2017 CCTTCCTTTTCACTAAGCCTCT | 3217 |
| 818 GGAGCGCAGCCGACCGTCAT | 818 CACCTGGATGATTGCCATTGCTT | 2018 GAGAGATTGGAAGCGGGAGAGATTG | 3218 |
| 819 GCACTGGACTAGTATTCGGGAGAT | 819 GGTCAGTGACAGATCCAGGACTA | 2019 GGTGGAGTAAAAACAGCACTGGACTA | 3219 |
| 820 CTCTTCTGGCACAAGGTGTGTCT | 820 TTTCAGGCCCTAGCTCCAGGAT | 2020 CCTTCAGGGCAGTGAGTTCTCTTCT | 3220 |
| 821 CACCAGCAAAGAGGGAAGTTAGA | 821 CAGCCTCTTTCCTAGGGTTGTGT | 2021 TCCAGGAAAAGGAACTGCAACA | 3221 |
| 822 GATGTCAAGGTACTGACTCCAACA | 822 GGCAGTTATTGCAGCAAGGAAATCT | 2022 CGCATGTGTACCTTAATGATGTCAAC | 3222 |
| 823 CCACCACCTTCATTGCTCTCT | 823 CCCACCCTAAGTGCTCATGT | 2023 CCCTGAATCTTCCACCAGCTT | 3223 |
| 824 GGGATGGTTATCATGCCCCTCTTC | 824 CAGGACAAGGTGCTCAGAGTTTC | 2024 GCCTCCAGAGCTAGGGATGGTTA | 3224 |
| 825 GGTTCTAGATCCCGCTCTCTTCT | 825 AAGATGGAGCCCGGCAGTTC | 2025 TGGAGGGGACCGGGTTCTA | 3225 |
| 826 CTCTGGTACCTGAACCTTCCCATT | 826 GTTGAGGCTCAAGCCCCATCA | 2026 CCTGGATTTGTCTCCTCGTCACTTC | 3226 |
| 827 TGCTTCGAGGAGAGGTAGTGA | 827 CCACTTAGCATTGCTTGTCATCAA | 2027 GGGGACACGTCTTACTGTAGTCTT | 3227 |
| 828 GCACTTGACTCACAGGGAGAA | 828 TCCAGGAACAACGGCACAGT | 2028 TCAGCAGGAAAAGCACTTGACT | 3228 |
| 829 GTTATGGCAGCTGACACCAGTA | 829 GGAGCCCCAAGAACCTTGGATT | 2029 GTTTCCTTCCTTGTTTGCAGAGTT | 3229 |
| 830 GTCACAGATTCAGGGAGAAGCAA | 830 GGCTATCGAAGCCTTCATGTCTA | 2030 CCATACCAGACACAAATACAGTCACA | 3230 |
| 831 CAGCCTTTTCCCTAGGCAATGT | 831 GTGACAACTGTGTGGGTCAGTA | 2031 CCTGACTTTCTAGTTCAACTCAGCCTTT | 3231 |
| 832 GCTCTGGCTACTGCTATTGGTGTCA | 832 TGGGACACCTCACTCATGGAT | 2032 GTTGATGCTCTGGCTACTGCTA | 3232 |
| 833 ACACAAAGAGTTCGATGGCCTTT | 833 AGTACTCATTTTCGGCAGCACGTA | 2033 CAAGGGCTATTCAGGACTCACAAA | 3233 |
| 834 TCTTTCCAGACAAGCCAACAAGT | 834 CAGGCTGCTCAAGGCATTAGT | 2034 CACTGCATACCACAAATCAGTTGT | 3234 |
| 835 GCCAGAGCAGCTTCTTTCCCATCT | 835 GGTTGTTGTTCGGGGACTCTGAATA | 2035 ACTGCATGGCAGACAGCAGCTT | 3235 |
| 836 GTCCAGCCTGGGAGCAAAA | 836 GGATTGAGGAAGGTAGCGCTTT | 2036 GCAGAGCTCCTCAAAGGGAAA | 3236 |
| 837 TCACTATGAACCCTACCACCACTA | 837 GTGGTAGTAAAGCTGGTGATGACA | 2037 CCACCACTACCATCATCACTATGAA | 3237 |
| 838 CCCCTGCCTCCTGGTAGTAA | 838 CCCAGCACCAAACCCATGAA | 2038 GTGAGTGAATGGCTGGGAGGTA | 3238 |
| 839 AAGGCGACCCTCCGGACA | 839 CAAATTACGGCAATGACGCACATAG | 2039 CATGTGCTCTAGCAAGACAATCAAA | 3239 |
| 840 AGGCGGAGCTCTAAGCACTA | 840 TCTGCCCACTTTAACACCTCATT | 2040 GGAGACCACAATGCACAGGTCTAC | 3240 |
| 841 ATGAGCTCTGCAGTCATTGAATTG | 841 GGGTCATGCTTCGCTTGATACTGT | 2041 AGCTCTGTAGGAGGGCAAGGAT | 3241 |
| 842 CTGGCTGCTATGCACTCAGA | 842 TCTCTACCCCACCCCAGCAAAT | 2042 TCCATGGCTCTGGCTGCTAT | 3242 |
| 843 GGTTCCTGCTTTTACCTGACTGT | 843 CACCCAGACCCTCATTCCTAAAC | 2043 CCCTGACTAGTGCTTCCTGCTT | 3243 |
| 844 CCAAGGACGACCCTCCCAGAGA | 844 GGAGGGCAAGGGCATCTCA | 2044 GGACCAATGCCTGGAAGACCAA | 3244 |
| 845 GGGGTTACTTACCGGTCAGACAAATTC | 845 CTCCCCTGTGCACTCTTTCACT | 2045 CAGAAGTGTGGTGGGGTTACTTAC | 3245 |
| 846 GCAGAAGCATCACTGCCTAATATC | 846 GTGCTAGATAGACCCCGCTAGACT | 2046 GGCTGTTGCAGAAGCATCACT | 3246 |
| 847 ACCATCCTCCCCATCTCAGTAAA | 847 GGTCCTGAGCAACTGGGTAAA | 2047 CCAAACCTGCTCCTCCACCAT | 3247 |
| 848 CGCTCTCCATTTCTGTATCCCTCTCAA | 848 GAAGATGGGACAGGCGTTGT | 2048 GCCCAGGTCTCCTCTCCATT | 3248 |
| 849 GTGGGTAACGGTTTAGGAGTTC | 849 GGGTAAGGTGTGCCCTTGTTCT | 2049 TGAGCCTTGCAGTGGCGTAAC | 3249 |
| 850 CCTTAATTACTGCCCATTGCCTGTT | 850 CAAGCGGAGCACAGAACTGA | 2050 GCATAGCTCTTTGTAGAAACTTGACCTTA | 3250 |
| 851 AGCCTGGAGAACAAAAGGTGAAA | 851 GCAAGATCCCAACCTCCAGGAGAA | 2051 CCACAGTGAAGCCTGGAGAACA | 3251 |
| 852 CCAGGCAATTTCCCCTCCAA | 852 GGAGACATCCTCCCTGACCTA | 2052 GGACATGGGCGAGGCAATTT | 3252 |
| 853 GAGGTGACATGCCTGTTGTCAT | 853 GGCCTGAGCTAAGCTTTTTCTTTGCTA | 2053 ATCCCAGGGAGGAGAGGTGACAT | 3253 |
| 854 GCCCTTCTAGTGAATGTTTGGGTCA | 854 CGCCAGCATTCTGCTGCTT | 2054 CGCTGCCCCTTCTAGTGAATGT | 3254 |
| 855 CCAACAATCTCTGTCCCTCTACT | 855 ACACTGGTGCCCAGTGTGA | 2055 CTGCAATTCCCCAACAATCTCTGT | 3255 |
| 856 CCCTGCCTAAAGGTCTCCAAAAC | 856 GCAGAATAAACAGGTTGTTGTGTCA | 2056 GGCTGTCCTCCCTGCCTAAA | 3256 |
| 857 TGAGGGCTATCCTCGACCTTT | 857 CCCAATCAGCCCCAGACATTTG | 2057 GCTGTGGGGTTTGAGGCTAT | 3257 |
| 858 GTGGTAGCTACTGAATCAGCCCTAT | 858 TGCTCTCTCTCCACCTCTGT | 2058 CCCTGAGAGTGGTAGCTACTGAA | 3258 |
| 859 TCCAGGTGAAAGCAGGTCAAG | 859 GTGTGTGGCAGGTGTGTCT | 2059 GCCAGATCAAATCATTCCAGGTGAA | 3259 |
| 860 GCAGATAAAGCAAAGGGTGACTT | 860 AGGTGGGATTGGAGGTTGAA | 2060 CACAGAAGGGCAGATAAAGCAAA | 3260 |
| 861 TCCAGCTCACTGCCTCATAGAT | 861 CAGGCAGAGGAAGCCAA | 2061 GCCATGTGCGATTTCCACGTCACT | 3261 |
| 862 TGTGGGAGGAGAGGTCACCAT | 862 CCTGCCTCCCCAACAGTGA | 2062 CGCTGTAGCTGAAGCACTGTCCTA | 3262 |
| 863 AGGGCCTACCCGTCAACATT | 863 TCCCTTAACAAGTCACCCACTTC | 2063 CTGCTGATTCAGGACCACAGAA | 3263 |

| | | | |
|---|---|---|---|
| 926 GAGGGAGGTGCTTTGCTGTCAA | 926 TCCCTTGAGCCTCCTCTGTTCT | 2126 GGAAAGGGAGGGAGGTGCTT | 3326 |
| 927 GGCTCTGTGAGGATGGAGAGAGT | 927 GGGGACAGTGGGAGGATGTCA | 2127 GCTCTCCTGGCTCTGTGAGGAT | 3327 |
| 928 GCCAGGGGAAGTGGTGTTTAAG | 928 ACTGGCTAGCTCCCAGTGATG | 2128 ACAACCTAGTGCCAGGCGAAGT | 3328 |
| 929 GTAGACTCCACACCTTCCTACCTT | 929 CGCCACCTCCACAGGAAACA | 2129 ACAAGCCCCACAGGGTAGACT | 3329 |
| 930 TCTCCTGGAAATGTGAACAGGATTG | 930 AGGAATCCTCAGGCCAGGAAAG | 2130 GAACCAGTTTCCTTTCTCCTGGAA | 3330 |
| 931 CTCGCTGCATCTCAGTGAGT | 931 GCCTCTGTTACCTTTCTCCCATT | 2131 GGAAGCCACTCGCTGCAT | 3331 |
| 932 TGGGATGCTTCCTGGGCAAAC | 932 AGCTGCTGGGCAGTCGGAAA | 2132 TGGGTGGCTCGGATGCTT | 3332 |
| 933 CAACCGCTCAGGCTGTGAA | 933 GCCCAGTGAAAGGGCAAAACT | 2133 GCTCATTAATGCACGCAGACACA | 3333 |
| 934 GATGATAAGCCTGTCCCTGAGATG | 934 GGTCCGTGCAGACTGGACAAT | 2134 GGTGGTACAGAATACAATGGCTGTGATG | 3334 |
| 935 CACGGAGGCAGAAAGCTTTGGAAGA | 935 TCCATCACATGCTGGTGAAATGT | 2135 TCTCCTAGCAGGAGGGACAAAG | 3335 |
| 936 CATCCGTCTCTTCACTAGCTCTTAAAT | 936 TCTATGCTCAGGGCCTAACACT | 2136 GGATGTGTTCATCCGTCTCTTCACTA | 3336 |
| 937 GTCCCTCTGCTTCCTGCCATA | 937 CACCTTCCCACGTTGCCTAT | 2137 AGACATGGGTCCCTCTGCTT | 3337 |
| 938 GCTGTACTCCTGCGTGACATTC | 938 TGAGCTACCCATCAGGGTTATTTTT | 2138 CCTGGTACCTGATATGATGTTAGCTGTA | 3338 |
| 939 AGCCCTCTGATTCAGGTAACA | 939 GCATTGAGTTTCAACTGGGGTACA | 2139 GGTCCACCCATAGCCCTCTGA | 3339 |
| 940 TCGATGGCAGAGACAAATGACA | 940 GCCTCATCAACGACCCGATTCA | 2140 GGTAGGCATTTTTCGATGGCAGAGA | 3340 |
| 941 CAGGGTCACACACTCGGGTATT | 941 ACCAGGACCCCACTGGTT | 2141 AGTAGAGGCAGGGTCACACA | 3341 |
| 942 CTCCAGCAGACAGCATGCAAAC | 942 AGGTCTCAGCCCTGACTGTT | 2142 ACTAAGGAAGCCTCTTGGGTTCT | 3342 |
| 943 GCACACCTGAAGCTCAAACGAACA | 943 TGGTTTACCCTGAATCCACTCTGA | 2143 CTCTTCCCTGAAGACAACCAACTT | 3343 |
| 944 GTTCATGCTCGCATTCCAGATGTA | 944 ACCATATGACCGTCAGGCTTCT | 2144 CCTTCCAGGTTGATGGTCGCATT | 3344 |
| 945 TGTGGCCTGGCTCAGACATA | 945 CCAGGGGTTGGCGTGAAAG | 2145 CACTGCCCAGATGGCAGAAG | 3345 |
| 946 TTGCGGGCACTCTCACTACT | 946 CAAACAAAGTGCCTGGTAGAGTTTCA | 2146 CGTGGCTGGCCATCTGATCCTTTC | 3346 |
| 947 CAAATCCTTTGTGGGTGTTAAGTGT | 947 CCTCCACCTGCCCCATCAGT | 2147 TGTGAGAGGCCGTTGGGAAA | 3347 |
| 948 TGCCCTGATGGATAGGTGGAT | 948 GTAGCCAGGCATGCATTTTTGA | 2148 GGAAATGTTTGACTCATGCCCTGATG | 3348 |
| 949 AGAGCTCCAGGCTCATCCCTAT | 949 CCCAGCTGTCCAAAGGACTTCA | 2149 AGTCAGCCAGATGCCCAGAA | 3349 |
| 950 CAGAGTCCCTTGGATCTGTTCTCA | 950 CTGTCCCGTGCCTTCCAA | 2150 AGCTCAGGACTGCGTTCTTC | 3350 |
| 951 CTGGGGCAGGACCAGGAAA | 951 GCCACCTCCCTCCCAGCTAA | 2151 CCATGTACCCAGGAGAGGTGATGA | 3351 |
| 952 CAGTGGAGCTTGCTGGTTGACT | 952 GCACTTTGCCTTTGATGCCTGAAATA | 2152 TGTGTGCTGCAGTGGAGCTT | 3352 |
| 953 GGGTACCTTCTCTCAAAGCAGCATCT | 953 CCCCACAGGTAGCACCTCTGTAAG | 2153 GGCGTAACATTAGGGTACCTTCTCT | 3353 |
| 954 CATCCAGCACCATGGCATCT | 954 GGCCTCCTCCTCTCCCATT | 2154 GGGTCTGGGAGAGGGATAACTTCA | 3354 |
| 955 TGGCAGAGACTGGCAGGAA | 955 TCCCACCCGGTCGGATCCCCATA | 2155 GTGGTAACTGCCACCAGGACAAAG | 3355 |
| 956 TTCCTGAAGGGTTGTACCAGTTG | 956 GAAGGACATGGCCATCAGCAA | 2156 GGAGCCTCTTGGTTCCTGTGT | 3356 |
| 957 AGGGGCCCTGCTGAACACTGAA | 957 AGGCAGAGGGGGGTGTCTT | 2157 AAGACCTCTCGCAGGCCGATT | 3357 |
| 958 CATCTCCAGACCGCTGGTGTTC | 958 GGTCTGCCTTCCTGGGTTT | 2158 AGTGAAGGCCCTCTCCTGAA | 3358 |
| 959 CTTCGCCTTGGCACTGTCTCTCT | 959 AGGTGACCATGTGACCACAGA | 2159 CCTCGATTCAGTCTGGGGACATTC | 3359 |
| 960 ACTGGCACAGCCCAGGATT | 960 GGGTAGCTTATTGGGGTTCAGTCT | 2160 TCACTTTCCACCTCTCGAGGAA | 3360 |
| 961 CAGGACTTCTGGAAACCCACTCT | 961 GCCGTTATTGCAGGCACAATCT | 2161 AGGTGAAGCAGAGCAGGACTTC | 3361 |
| 962 CATCCCTGCGCCTAACTCTAAG | 962 AAGCAGGCAGGAAGGAGACA | 2162 GCCTCCTCATCTCATGGGTTTCA | 3362 |
| 963 TGCACATGGCGGCTAAACA | 963 TGGACCAACTCTCACAGCAGAT | 2163 AACCCCTTTGGTCTTGCACAT | 3363 |
| 964 GGAGTTCGCATGGTACCTCCCTTA | 964 CAGGCCAATGGACAGTGGTGAAGCTA | 2164 GCTGCTATGGTGGTATCAGGGAGTTG | 3364 |
| 965 AGCCATGCCGATTGCCTCTT | 965 GGTGGCGAAGGGGGTAGTGAAA | 2165 GCAGGGAGCAGGCTTTAGCTGACA | 3365 |
| 966 TTGGTCTTCAGGTCCGGAGGTT | 966 ACTTCCCGGGCCTGGCTTCT | 2166 CTCACACTTGGGCACTCCTT | 3366 |
| 967 GGCTTTTCTTGGAAGCACAGAA | 967 GCTAGGAACCTTCCAGGCATTTTA | 2167 GCTCCCCAGTGATGGGCTTTT | 3367 |
| 968 TTGAGTCCTGGGGCTCTCT | 968 GTTCTGACTTTCTAGTAACCACCGATT | 2168 CCTCTGTCTACACAGTGAACAGCATTG | 3368 |
| 969 TGTGGATGGCCAGGATGTCT | 969 TCCACAGCCGTGCATCTGA | 2169 AGCACCCCTGAGCATGTGGAT | 3369 |
| 970 CCATGACAGACACCCAGGATCT | 970 CTGATGCCAACTTGGGCCTATGA | 2170 CCATGCAGGCCATCACAGACA | 3370 |
| 971 CCTGCCTCAAACAGGGAACTCTA | 971 GCTGAAAGCTTTGCTGGCTTCT | 2171 ATAATCAGCCTGCCTCAAACAGA | 3371 |
| 972 CACTGAGCAATCATGGCATTTGT | 972 CAATGGGTAACTAGGCAAGGGAATTAT | 2172 GCTGCCAAGACAAATGGGACACT | 3372 |
| 973 TCCATCCCCTCTCCCAGCTCCTA | 973 CCCCGCCTCCTTATAATGGGAAACA | 2173 CCCATCTCAAACTCCCCCAATC | 3373 |
| 974 GGAACAGCACCCTAACTCATGT | 974 GCCAGTTCTGGCGATGGCTAA | 2174 GCAGCTTGCATGCTTTGGAACA | 3374 |
| 975 GTAAGAAGGAGCCGTCGGAATC | 975 TTCCCTACCCCTTCCCCAGAAC | 2175 GTGAATGGAAGGTCATGTAAGAAG | 3375 |
| 976 TGCTGGGTCTTGCCCAACAT | 976 GGAAGAAAGCCCTCTCGACAA | 2176 GGGCAGAAACATAATGCTGGGTCTT | 3376 |
| 977 GCCTGGAGATCAAGCTGCAAA | 977 GAACTAGCCACCTTGATGTCATCTGT | 2177 GACAGACCAAGCCTGGAGATCA | 3377 |
| 978 CACCAGGGTAGGTATCCAATACTGT | 978 TGCCCACCAGTGAGACTAAAC | 2178 GCTTCACTAACACCAGGGTAGGTATC | 3378 |
| 979 CCAACTGAATGCACGTGTGTGA | 979 GCAGCTGCTAAGTGTCCTGCTT | 2179 GCTGGAACTGCCATTTCACCAA | 3379 |
| 980 GGACCTTAGAGCAATGACCTTCA | 980 GAGTTCCTTTCCCTCCAGTTTCTTG | 2180 GTCCATAACAGGACCTTAGAGCAA | 3380 |
| 981 GGAGTAGCTGGAAACAAACTGCTTCT | 981 GCCAGCTGAGGACTCCTCTT | 2181 GCTCTTGGGAGTAGGCTGGAAC | 3381 |
| 982 GAAGCAGTCAGCAGTGCTCACA | 982 CAGTGCCATGCGGAATCCCAGAT | 2182 GGTTTTGGGACCTAGAAGCAGTCA | 3382 |
| 983 GCAGTCTCTCCTCCTCCAGCAA | 983 CTCAGCCTCCCTGAGAACAAAC | 2183 GGGATAGCAGGTCTCTGTTCCAA | 3383 |
| 984 GAGCTCTACCCAACTCTTGGTCCTA | 984 CCCATGCCCTTTCCAACCTT | 2184 CTCTTCTGAGCTCTACCCAACT | 3384 |
| 985 CCCTGAAGAGCTCAATCACAGACA | 985 ACAGACTGCCTGTCCTGCAA | 2185 CCCTTTTTCCCTGAAGAGCTCAA | 3385 |
| 986 AGGAAGGCTGTAGGAACTGCAAATAC | 986 GATTACGAACGTAGGGCACAAAC | 2186 GGACTGGTCAGGAAGGTGTAGGAA | 3386 |
| 987 CCTCAACATACGGGCTACCAAA | 987 CCAGGGGTTCCTGAAGTCAAAA | 2187 GCAAAACTCCGGGATCCTCAAC | 3387 |

| | | | |
|---|---|---|---|
| 1050 CTGGAAGTCAGCAAAGTACAGTTCTA | 1050 ACCTTTGTGCCTGCTGAATCT | 2250 GGCCCTGGAAGTCAGCAAAG | 3450 |
| 1051 GGTTGTCCTGGTTCGCAGAGTT | 1051 GACTGGCTGGCACCAAGATT | 2251 CCAGCCTTGGTTGTCCTGGTT | 3451 |
| 1052 GCCTGATGGGAGAATCAGAAACT | 1052 CCTTCTACAGACATTGCAGGTCATC | 2252 GGAAGGTAATACAGCCTGATGGGAGAA | 3452 |
| 1053 CGCAAATCAAAGCCTGCCTTTTC | 1053 GGACAATGATTTTGAGCTACGGTGTA | 2253 GCAAGCAGTGTCTGCCAAATC | 3453 |
| 1054 AGTGTCGGCCCTACCTGTGATT | 1054 AACCCACAGGGTCCCTAACA | 2254 CCAACTGCTTCCTGCTGACTGT | 3454 |
| 1055 TTTTGCCGCTGCCCCTGAT | 1055 CACTGCCAGGGGAAGAAACTGA | 2255 GGTACTAATGCCGCTGATGCTT | 3455 |
| 1056 GGACTGTGTTGGGTGCAATAAC | 1056 GTCTATGCCAGTCCTAGAGGAAAC | 2256 GTCGGTTTAAGTGCGGACTGTCTTG | 3456 |
| 1057 ACCCGATGCCCCATGACT | 1057 GGGGACCATCAGTGCCATCT | 2257 TGACGGAGGTCGGCACCTAAA | 3457 |
| 1058 CCCAGTGAAGCCCACCTTTAG | 1058 CCGCCAGGCTTCAGACCTT | 2258 GGACCAGGTCCCCAGTGAA | 3458 |
| 1059 GTGGCAGACAAGGACAGTGAGT | 1059 TGGCCCTCCCCTGAACAA | 2259 AGTGCTCAGGGTGCCAGACA | 3459 |
| 1060 CCATGGCAACTCCATGCTTCCAA | 1060 GAGCAGTCAAGGAATCGAGGATGA | 2260 GTTCTCAAATCAATCCATGGCAACT | 3460 |
| 1061 GCTTCCCAGGATACCCACCCATTA | 1061 GGTAATGTGTAGACCCCACAGTTCA | 2261 CCTTCTCCAGCTTCCCAGGATAC | 3461 |
| 1062 GCTGTCTCGTCCTCGTTAGT | 1062 TGAACCCACAGCCCCATCTCA | 2262 AGGCGATGGCACGCTGTCT | 3462 |
| 1063 GAGCCGATTTTATATCCATGCCTGTAG | 1063 ACCTGCCGCAAGATCTCAGT | 2263 CAACATCCAACAGAGCCGATTTT | 3463 |
| 1064 CCCAGAAACGAGCCATGGAAAG | 1064 TGCTGGGTCCCTGGATGGAT | 2264 ACACAAGGGGCACCCAGAAA | 3464 |
| 1065 AGGTGGCCAGAGTGCTGTGA | 1065 ACTCTCCACCCAGGCATCCAGAT | 2265 GCTTCAGGGGAGATAAGGAAATCAAGA | 3465 |
| 1066 CCAAACCCAATTGCAGCTGTGTAAC | 1066 TCTGAGAGAGGCTTGGCTACCT | 2266 GCAATCACCCAAGCAACAAACCCAAT | 3466 |
| 1067 GCTGCCTTCTTGAGCTCCTGATTT | 1067 AGCCTGAGGACTTGGCAGTCA | 2267 CAAGGGCCTGCCTTCTTGA | 3467 |
| 1068 CAGCCTAGAGGCAGCAAAACTGT | 1068 TCGGCAACTGCTCCTCTGT | 2268 TGCCCCATTTCCCTCAGAGT | 3468 |
| 1069 GCAAGTGTCAGGTCCCTCTAGTCA | 1069 GGGACAACTTTGGGGCTTGA | 2269 TTTGTGGAGAAGGCAAGTGTCA | 3469 |
| 1070 AGCCAACTGAGCCAGGAACA | 1070 GGCCAAGCTTTCAGCCTTTC | 2270 GCCTGTGCCATCAGCCAACT | 3470 |
| 1071 CCTGCATGCTTGGGTTAATTCTTG | 1071 CTGGATGAGAATGGTTGGCCTAAT | 2271 AACCAGATACACCTGCATGCTT | 3471 |
| 1072 AAGGGGAGCTGTGTGTCCTT | 1072 AGCCAGCCCTGCAGCAAGA | 2272 ATGCCGGGGAAAGCCAGAA | 3472 |
| 1073 CCAATCCTACGACGGGACCAAA | 1073 CAGAGCCAGGGCTCTCATTGTCT | 2273 CCATCTGTGCTGGCCAATCCTA | 3473 |
| 1074 TGCTCGATTGCCTGTGTTGCTA | 1074 CAGGAAATCCAGGGGACAGAAGAA | 2274 TTCCCACCCATCCGAGACTTTG | 3474 |
| 1075 GGGAACACTGACCTGCACCAAAA | 1075 GGCCAAACACATCAGGGGAGCAA | 2275 TGTGCCCTGGGACACTGA | 3475 |
| 1076 GGACCCTTCTAAGCCACTGATCTCT | 1076 TGGGGCTGCTGGGAGAGGAA | 2276 GCTGGGTCTGGACCCTTCTAA | 3476 |
| 1077 CTAACCCAGCTCAACCTCTTG | 1077 GGGTGGCAACCCTCAGATTC | 2277 GGTGTGCTGGACCCAGATTCTAAC | 3477 |
| 1078 GTGACACAGGCTGCTTCTCATC | 1078 CTTCGTTTGCCAGATTTACCTGTGT | 2278 TGCACGCACTCTCCCTTATG | 3478 |
| 1079 TTGCTGTAGGCACCAGGAGAT | 1079 GCTTGTGGTCCTGGGTGTCA | 2279 GCAATGCTGCCACTTGGTGTAG | 3479 |
| 1080 CCTCTTACACCCACTGTTCCACTAAG | 1080 AAGGCGAGGTCACCTGACTAAG | 2280 ACACCCACCCATCTCTCCTT | 3480 |
| 1081 GAAGCATTCTGGGCTGAGAGAGA | 1081 CCAGAAGAGGTGTGGCCTGAAAG | 2281 TGCCCCAGGCCAGAAGCAT | 3481 |
| 1082 GGAAACCTGGTCCAAACCACAA | 1082 CAGTCAGTAGACCGCGCTCTT | 2282 CCGACGGCAGAACCGAAAC | 3482 |
| 1083 AGGCACTGTTTGCCGAATG | 1083 GGATGGGAATGGCTAAGGCACAGA | 2283 AGGGCACCAGAGGTGACA | 3483 |
| 1084 GCTGTCAGAACCAGCCTGAGTAT | 1084 GGAGCTTTTGACTGGGGTTCACT | 2284 TGGCAGGTGCTGCTGTCAGA | 3484 |
| 1085 GCGGGTAGGATGTTAAAGGCAGCTT | 1085 CCAAGGTCCCTGGTCTGGAAGT | 2285 TGTTCCCTGCGGTAGCATGT | 3485 |
| 1086 GGTTCAATCTCAGGCTCACACT | 1086 GGGCAGAGCAATAGCCGAAA | 2286 GCCCTTGTGCTTTGGGGTTCAA | 3486 |
| 1087 GCATGGATCTGCGTGGACACA | 1087 GGCCCACGTGGTCAGATTGTT | 2287 TCCTTACTGCTCAGCATGGATCT | 3487 |
| 1088 CAGAACTGGGTGCTGTCGTTTTG | 1088 CCGAGAGCCTCAGCATGTACAAAT | 2288 GGAAACCTCCTATAGTACGGCCAGAA | 3488 |
| 1089 CAGACCACTTGAGAGCAGGTT | 1089 GTTATCTTCCACTGTCCTGTTCCTTAG | 2289 CACCAGCCATGGACAACAAGT | 3489 |
| 1090 GCTACCAAGGAGGTCTCTTCT | 1090 GCTTCTGCCCAGTGCTCAAGAT | 2290 GCCTCCTGCTATTCCTGTGCTA | 3490 |
| 1091 GAGGTGGGTAACAGACCCATCA | 1091 GGCTCTGTAGGGCTTCTAGAATGTT | 2291 CCCGGGAAATCAGAGGTGCCTAAC | 3491 |
| 1092 GGAAGCAAGCACATACTCACCAT | 1092 GGGTGTAGAGCAGCATGGGTTA | 2292 GTCCATCAGGAAGCAAGCACAT | 3492 |
| 1093 ACTGCGTAAGCGGTGGCATA | 1093 GTCCCGAAACCCACACTGTATTC | 2293 CCAGCAAGAGGAAACTGCCTAA | 3493 |
| 1094 GGTATCAGCAGTGTGGTTAAGGAT | 1094 CCCAAAACTGACCTGGCAGCTT | 2294 GGCACGCTTACTTCGGGAGCACTGT | 3494 |
| 1095 CTCGGAAGTCCCAGCAGATCTTTC | 1095 GTGACCAGTCTAGCTGACAA | 2295 GTGCCTTACTTCGGGAGCTTTG | 3495 |
| 1096 GGTGAGGTTCACACCCTCCTTTC | 1096 TTCCGGAGGTCAGATCCCAAGA | 2296 TGCTGCGGGTCAGGTTCA | 3496 |
| 1097 CTGCCACTCATGGCTGTGCAA | 1097 CAGCTCATCCGCCCACAGA | 2297 CCCAATCGGAGCTGCAGTCAT | 3497 |
| 1098 CCCCTGCCTGTGCAGCTTATATT | 1098 AGGGAGCAGCGCGACTGAA | 2298 TCCTCCATCTAACTCCTGCTCAT | 3498 |
| 1099 GGGCATTGCCACAATGGTTT | 1099 GGCAGTGGGGTCCATTTCAAACA | 2299 CTGCCTTGATAACTCTGGGCATTG | 3499 |
| 1100 GTGGCAACGGACAGGGATT | 1100 TCTCCAGAAGCCTCGCCTTGA | 2300 CTGGGGTACCCAGCCATGT | 3500 |
| 1101 TCTAGGACCAGGAGCCATCAGA | 1101 GCCCCATGTCTCTACTTCTTCT | 2301 TGGGCCAGGGCTGTAATCTA | 3501 |
| 1102 CGAGGGGTCTTTGAGGCAAACTT | 1102 AGGCCCAGCCAGCTTTAGTCT | 2302 ACCGGCCGAGGGTCTTTGA | 3502 |
| 1103 TCCCCACCCTCTCTTTCTTTAGAGTAT | 1103 TCAAGATGGAGCACAACCACCAA | 2303 TCCCTTCCCCACCCTCTTTC | 3503 |
| 1104 CCAGAAAGCCACCAATGCAA | 1104 GTGTTGAGCAGGCAACTTGTGA | 2304 CCGAAAGCTCTGCCAGGAAA | 3504 |
| 1105 GGCTGATATAATGGAGGCAGCTTAG | 1105 ACTCATCACCTTGGCATGCTT | 2305 GTGCCAATTTTGTGGGGCTGATA | 3505 |
| 1106 CCCCTGTCCTGACTGACATTCT | 1106 TCACCCAAGAACCTATTCTTGGAA | 2306 CCTCTCCACCAAGCACAGCAT | 3506 |
| 1107 TCTTTGGCCACACAGATTTACTCTAC | 1107 CAATGCAGGAGCTTCTCCACAAA | 2307 CTGCCACTGTCCATCCACATCT | 3507 |
| 1108 CAGAGTAGCTGTGCCCGTAGGA | 1108 CCCACCCAAAGGCAGCCAATTCT | 2308 TGCAAAGTGCATGGCACAGA | 3508 |
| 1109 CGCTGTCTCTCCATCCAAGTGTT | 1109 CTTTGCCCTGGCATCTGAAAC | 2309 GGTGGCGCTGTCTCCCAT | 3509 |
| 1110 CGGAGCCTTGGAGCTAGGTGATTA | 1110 CTCTGGCACCTGGAAACACT | 2310 TCCTGGCATCAAGACTGTGAAC | 3510 |
| 1111 CAGGGTTCCTAGCTCTTTCCTCTTC | 1111 TCATCCATCCTGAGCCAAATTCT | 2311 GTCTTTGTTTACCTCCAGCGTTCCTA | 3511 |

FIG. 34B8

| | | | |
|---|---|---|---|
| 1112 CATTCCCAAATGGATCTGGCTACA | 1112 AAATCCAGCCACAGGATGATACAA | 2312 CCATCTCTGCATTCCCAAATGGAT | 3512 |
| 1113 GCTCCACTTTCGCCCTCACTT | 1113 GCACCAAGGAAGCATCAGGTACT | 2313 CCCTCTGTTTTCAGCTCCACTTTC | 3513 |
| 1114 CTTTGCTCTTGTCTGCACTGACTA | 1114 CTGCTCAGGGGCCAGACTTC | 2314 CAGACTTCACCCACTTTGCTCTT | 3514 |
| 1115 TTGAGCTGTGCAGGCTTGT | 1115 GAAGAGCAGTTTCACTTATGTGTCA | 2315 TGGGCTGAGCGGCTTTCTTA | 3515 |
| 1116 TGTGGCTACTTTCCCACAGTTTG | 1116 GCCTCGGATCTGTTGCTAGTGA | 2316 GGGATAGCCCTTGTGGCTACTTTC | 3516 |
| 1117 CAAAGGACAATCACAGAGCTGTTC | 1117 AGGGGAGCCTCAGCATCCTAAA | 2317 TCCCATTGGAAAGTATGGACTACAAAG | 3517 |
| 1118 GGAATGGACCAACTTTGTCTTGATT | 1118 CGGCTGACTGCACTTCTCT | 2318 GTTCAGGAGTAAGGAATCCACCAA | 3518 |
| 1119 TGGATGTGGCCCCATTTGT | 1119 TCGCTTCGGGCTTTCAGCAA | 2319 ACTTGGCAGGAAGGGTGGAT | 3519 |
| 1120 CCCCTGCCCCAAATAGCATTTTA | 1120 GATCAGAACTCCTGGCATGATCA | 2320 TCCACCCCTGCCCCAAAT | 3520 |
| 1121 ACCAAGCACTGGGGAAACTAAA | 1121 GAGAGCCCCTCAGGGCTCTTG | 2321 GGCAGACGGGATTCAGTTGCTA | 3521 |
| 1122 GGCATGCTCCGCACCAAGA | 1122 CCCCAGGAGAGCTGGTGTATGA | 2322 ACCAGCCTGGCCCACAGT | 3522 |
| 1123 CAGGCCATCTAAACGACTCTCA | 1123 ACTCTCCTGTTCCACCCTTCA | 2323 GGGACTTTCCCAGGCCATCTA | 3523 |
| 1124 TGCTGAATCCTTTCCTCAGTTTG | 1124 AGGGCCCTACTACCACTTTAG | 2324 GTCTTGTCCTGAATCCTCAATGCTTT | 3524 |
| 1125 TCCAGTCACTTACCTGCTCAAATG | 1125 GACCAGGGAAGAAAGACCTCTGAA | 2325 CCTGGCTCCATGGGTCACT | 3525 |
| 1126 AGCAAGCGACGGTCCTCCAT | 1126 TGGACACTGCCGTAAGGTGAAG | 2326 TCTGGGGTGCCACCAGCAA | 3526 |
| 1127 ACCTGCAGAACTGAGCCTCTCT | 1127 GCCTTTCCACCTCGATGTCTTC | 2327 GCCTCTTCATACCTCCAGAACT | 3527 |
| 1128 AGTGTCAGGAGGGGAAACGAA | 1128 TTCCCATGGCAGATGCTGTT | 2328 GCAGGTGGAGTCTGAAGTGTCA | 3528 |
| 1129 CCACTCCTTCCCTTATACCCTGTA | 1129 GGGGATAAATGTCACAAGCTGGAT | 2329 GTCCTGATTATCCACTCCTTCCCTTA | 3529 |
| 1130 CCAAAGATTGCTCCCGTTCA | 1130 GGCTTACTATGCCTGCTAAACATTAC | 2330 AGGCTGCAGAACAGCAAAGAT | 3530 |
| 1131 TGGACAAGAATGGAGAAAGACCTT | 1131 TGGTACCTGATATGCAGCCATTG | 2331 CTGGTGGGCCTTATGGACAAGA | 3531 |
| 1132 GCCTTTCCCAGGACTCAACAGT | 1132 AGGCAGGGCAAATGGTGTATC | 2332 CTGGGGCCAGAGTCTGATTCTTAG | 3532 |
| 1133 CTGCTTTGAGGCAGATAGGAGCTT | 1133 GCAGACCTACTGACCCCTTTGGTT | 2333 GCACTGGAGATGAGCCTGCTTT | 3533 |
| 1134 CCTGCACAAAGTGGCTGTCAAC | 1134 CAGTACTGAGTCCCTTGTGTTTTG | 2334 TTTCTGCCCACCTGCACAA | 3534 |
| 1135 GCAGGAAACCACAAACATCACCTA | 1135 CATCACTCCCCTCTGCTGCTA | 2335 CCAAAACTATCTCAGCTGCAGGAA | 3535 |
| 1136 GCTTTCTCTCCCCTAGGACATACAGT | 1136 AGGGCACTGCCTTCTACCTT | 2336 CCTCTGGCAAAGCACCCATTCA | 3536 |
| 1137 AGCCTGGCTCCCTACAGCATT | 1137 ACGAGGGGCTGGCACCGAAA | 2337 AGAGCCAAGAGGGCTGCAACA | 3537 |
| 1138 TGCCTATTGGGGCATTGGTGTT | 1138 GACAGCTTGCAGTCAAGACCTTCT | 2338 GCAGTGAGGCAGTAGCCTTTTG | 3538 |
| 1139 TGCATCCCGTTGCTGTCAAG | 1139 CATGGGGAATGGGTCAGTACAGT | 2339 GCTCCAAGGTACTAGTGCTGCAT | 3539 |
| 1140 GACCTGTGTCCCTTGTCCTTAG | 1140 GCCAGTGGAGGTAGTAGCATTTAC | 2340 GGGCCAAACCTCTGTACCTTCAGT | 3540 |
| 1141 GCTTTGCCCTTCCAGAGTCTCCTT | 1141 GTTACAGCATCAAGTGCAACAGT | 2341 CACTTCTCAGTCTCTCCCCTTTG | 3541 |
| 1142 GCCTGGTACTCTCCCAGTTTTAG | 1142 TGAGGATTTCCTGGGACACAGA | 2342 CTCCTGGTTTGCCTGGTACTCT | 3542 |
| 1143 GGGACCAGTCAACTTTGCCAGATT | 1143 AGCGGCTGTGTCAGAATCA | 2343 AGGGACGGACCAGTCAACTT | 3543 |
| 1144 ATTCCCATTCCTAAAAGCCGTGTA | 1144 ACTGCCTCCAATGACCCAGGAT | 2344 GCCCTACAGGTTTACATGCAAAGATATTC | 3544 |
| 1145 TCCAGGCACGGCACTCTGAT | 1145 TCCCTGCGTTGCTTCTCACT | 2345 GCTGTCCATGCAGAGCTAAGT | 3545 |
| 1146 GGCAGGCATCTGTGCAGTCATT | 1146 TTGGACTCCAGTGCTTTGCAT | 2346 GAATGAACTGGCAGGCATCTGT | 3546 |
| 1147 TGCCCACATAACCCCTTCCTT | 1147 TCTTTTGGCACTACGAGCTATGAA | 2347 GGCTAAGCGAATGCCCACATAA | 3547 |
| 1148 CGCCAATCTCAGTCGTTGGAAT | 1148 CCAAAGCACATTAGCCTGTGATG | 2348 GCCAGAAGGGAATCGCCAAT | 3548 |
| 1149 CGGAGCAACTTCCCATGTTAATACA | 1149 TGGCCCAGGTCCATTCTCT | 2349 TTCCATCCCCGAGCAACTT | 3549 |
| 1150 GTGCCAGCCTTTCTGTAGTTCA | 1150 GGAAACAACTTGTCCCTCACTTTG | 2350 TTGAAGGAAGTGGCAGGCCTTT | 3550 |
| 1151 GCTCGTTAAGAATTAGCCCCACATC | 1151 AGGAGGGTACCTCCGTCTCTA | 2351 GCCTTCCCTGGAGCTCGTTA | 3551 |
| 1152 CACCCAGCTAGAAACCTCCTGTAGT | 1152 GTAGGCTTCCAATGCAAGAAATG | 2352 CTGAAATGGCAGCCTTTATGTTCATC | 3552 |
| 1153 GCTGCTTTGCGGCGACCTT | 1153 CTCAGCCATGGACACCTATCTTC | 2353 TTCCTCGGAGTGCTGCTTTG | 3553 |
| 1154 GCAGGAGCTCAGTGACAAGTGTA | 1154 AGCTCCCACTCCAACTCAGA | 2354 TGGAGCTGGCAGGAGTCAGT | 3554 |
| 1155 TGTGTCAAGCAGATTTGAAGCTAAC | 1155 GCAGGCGAGACTCCCCAAAC | 2355 GGGCTGTGAGGTTTGTGTCA | 3555 |
| 1156 TGCACATTCCTTCCTTGCTGAT | 1156 TGCACTCTTGCCGAGGAAAA | 2356 GCTCAGGGCTTGCACATTCCTT | 3556 |
| 1157 CCTGCATTGCAAGCCGTTT | 1157 GCTCAGGCTGGCTTGAACA | 2357 TGCCCTAACTTCTCCTGCATTG | 3557 |
| 1158 ACCTGCCTGTGTGGTATGGAA | 1158 GGGCTGGACAGTTGGTTGCTGAT | 2358 ACCAGGCCTTCTTCTAGTCA | 3558 |
| 1159 GAGCCGAATGTTCACTTATGGAGTT | 1159 AGATCAGCCACCCTGACGAA | 2359 GGCTGAGCCGAATGTTCACT | 3559 |
| 1160 CTGAAGCCTAATCGGATCCAGAA | 1160 AGGCACCCCTTACTGTGAGA | 2360 GCCAGCCAGAGAGGTATCAACT | 3560 |
| 1161 AAATAGCCTGTCCCATTCTGGTTGT | 1161 CCAGGATCGAGAATGCACACA | 2361 GCTACTTTGCAGCTACCACTGAA | 3561 |
| 1162 TCCCCGGATTTCCACAGTAGT | 1162 AGACCAGAATGGATGGAGGTGTA | 2362 CTGAAGTATCATCTCTTCCCGGATT | 3562 |
| 1163 GGGTAGGATGCATGAGAGACTGAT | 1163 GGCTACCTCCTCAAGCCAGAAA | 2363 CAGGGGGAGGTAGGATGCATGAGA | 3563 |
| 1164 GCCAGCTGAGGAACTATTAGACACT | 1164 TGGCAGCCCTCCACCATTTT | 2364 CTGATGCTAACCTCCTTCTACTTG | 3564 |
| 1165 CTGCAGATCTAGCCAATGAGCTT | 1165 TGGCAGCCTGACAAGCTCAATTT | 2365 GGCAATAGGAGCCTGCAGAT | 3565 |
| 1166 GGCCAAGATTTTCTGTTCAAGTAG | 1166 AATTCCCTACGGAGTGAAACACAA | 2366 GGGGCTGTTGGGCCAAGATTT | 3566 |
| 1167 ACAGCTGCGAATCGGCTAAT | 1167 TGTGTAAGGGCAGGATAAAAGAACT | 2367 CCCAACTATTTTTGGGTTAGGAAGAAC | 3567 |
| 1168 GATCTCATGGCTACCGACATCAAG | 1168 ACCTCAACCTCTGTGTCTGTC | 2368 GGGTCACACCTCAGCGTTCTGA | 3568 |
| 1169 CCTCCTGGGAAACTGGCAAGTAAAG | 1169 CCACAGTGAGGGTGAACAATCAT | 2369 CCCAAAATGCCTCCTGGGAAAC | 3569 |
| 1170 GTACATGGTTATGGCTACCAGGAA | 1170 CCTCACTCCCTCCTGTCTT | 2370 GGAACATCTCATGGTCACGTATTTG | 3570 |
| 1171 TGGTCAGTGCTCCCAGAGTT | 1171 ACAGCTCTGAGTACAAACCTAGAGA | 2371 GGTCTAGGGTCTCAATTTGCTCAGT | 3571 |
| 1172 CGGACATGTCTCCGTGTCACT | 1172 CATTCTCTGTACATTGGAGGGAACT | 2372 CCCTTTGGATGACTCTTCGCACAT | 3572 |
| 1173 ACCACTGACAAACCTGTGCAT | 1173 GGTGGGACCAGTCAATCACTAAG | 2373 CCACTGCCACCACTGACAAA | 3573 |

FIG. 34B9

| | | | |
|---|---|---|---|
| 1174 CAGGGATGAATAACCCTCATGAAAGA | 1174 CAGCGTGCCCAGCCTGTAA | 2374 GAGTGGTTTCCCATCAGGGATGA | 3574 |
| 1175 ACTGCAACACTGTGATTGTCTTCA | 1175 GGCATGTTAGCGAGCATTTTACA | 2375 GGCAAAACTGCAACACTGTGA | 3575 |
| 1176 TTGGCTCCCCAGAGTGTTGT | 1176 GTTCTCGTTCAGACAGTGGTCT | 2376 TGCAGGTTTCTCACATAACTCCTT | 3576 |
| 1177 CAGTCGAAAGAGTGGAAAGGATCA | 1177 CAGGAACCTCATCCTGAGTTCATTT | 2377 TTCTCTCCAGCAGCACTCTTTATT | 3577 |
| 1178 TGAAGCATCTGGCCTGTCTGA | 1178 TCTTGCTGGACCAGAGTGTGA | 2378 CTGTGGCCCATGAAGCATCT | 3578 |
| 1179 TTCGGGGTGCATCCTCACAT | 1179 AGGGCCGAGGGAGTTTGTTTG | 2379 TGTCTGCTTCCTAGCCTCTTC | 3579 |
| 1180 CATCCACACCTGTCTCCGTCTA | 1180 GGCCCTCAAAGTGGTGAAGACT | 2380 CACACATTTCAGGAGCTTGATCTCATC | 3580 |
| 1181 TTCCAGGTTGTTTTCTGCAAAGTAG | 1181 CCTTGCCTGAGCTGGTATTTCT | 2381 GGAACCATGTTCCTTTCCAGGTTGTT | 3581 |
| 1182 TCCCAGAGACACAGCTAGTTAAAAAC | 1182 TGTGGCTACAACTCAGGCAAA | 2382 TCATCATCCCAGAGACAGCTA | 3582 |
| 1183 TGCTGCTCCTACAGTGGAAAG | 1183 GACATTGCTTGACTTGGGTGCT | 2383 CCTTGTCCTGCTAACCATGAGACT | 3583 |
| 1184 GGAGCAGTATCATTTTGGTGCATTG | 1184 CTCACGGCTCCCATGAATGAATC | 2384 GGACCCTAGTGATTCTCCCATCAT | 3584 |
| 1185 CGGTGGTGCCTTTCTTTTAACT | 1185 TGTGTGCTGACAGGTTTGTGA | 2385 CACACTTTTGGGTGGTGCCTTT | 3585 |
| 1186 GGAGAAGGAATGTCAGGAACCAAAC | 1186 GCAACAGGAGCTACTTGCCAAA | 2386 AGGAGCCAAGAACAAGGAGAAG | 3586 |
| 1187 AGTAGGTGTGATGGCCAGGAT | 1187 GCCCCTGTTGTTGTGCTCAT | 2387 TGGCCATAACAGAGTAGGGTGTGA | 3587 |
| 1188 TGTCTTCCTAGCCTCATCTCTCA | 1188 GGCTGCAGCATAAGGAATGTGA | 2388 TAGCCCCACGTGTCTTCCTA | 3588 |
| 1189 GCTACCGGATACTGAGTCCTGCAT | 1189 GCAGACCATTGCTTGGAGGAGATA | 2389 ACTTGTTCACTTGCTAGGGGATAC | 3589 |
| 1190 CCCAAAGACTCCCCATCTGGTT | 1190 CTGAGCTGGGAAGACTCAAACT | 2390 CAGAGAGAAGGAGGCCCAAAGA | 3590 |
| 1191 AGACCTAGGCGGCAAACAAA | 1191 GCAACTTTAGGCCAGCTGAGTT | 2391 TGTCAGTAACGGTGGAGACCTA | 3591 |
| 1192 AGTTTCCTGGAAGCCAGCTATTAAA | 1192 AAGACAGGGTGCCAGATCTAGT | 2392 GCCTTTTAATTAGCCTTGCAGCTT | 3592 |
| 1193 CGTAAGCATAGGGGCTGCAGTA | 1193 CCTGGATTTGGGCATACGTGAA | 2393 AGTGGGAGCCTCGTAAGCAT | 3593 |
| 1194 GCAGTTGAGGGAGTTCAACTAAAGA | 1194 TTCCCTGAACTCTTGCTGGTTT | 2394 GGAATAGGTAGGTGCAAGCAGTTG | 3594 |
| 1195 CCTAGGCTAGAAGCCCACAAAAC | 1195 GGGTTGAAACTGGAGGCTTCTTC | 2395 ATCCACAATTTCCCTAGGCTAGAAG | 3595 |
| 1196 CCTTCCCTTTGTCACACACATC | 1196 ACTCTGTACCGGGTATTTCACACT | 2396 GCCTAGGGTTCTCTTCCTTCCCTTT | 3596 |
| 1197 CCTGTGTTCAGGAAGAATGAGGAT | 1197 GCCCATCCAGACCCTTCTAATTC | 2397 TGGTTCCCCGAGCTCTTTTC | 3597 |
| 1198 GAACGAAACTGACTTTGCAGCTTAAC | 1198 CAGCCTCCTGCAGCAGTTG | 2398 TGGGTCTACAAACGAAACTGACTTTG | 3598 |
| 1199 AGGGAGAAAATCACACTCTTGCAT | 1199 AGAACCCCATACCTGCATTACAAA | 2399 GGGCTCAGGGACAAAATCACA | 3599 |
| 1200 GGGGACGAAGTCAAGGTGTAG | 1200 TCCCCTGGAACCTCCAAAACT | 2400 TGAGTCTTACGGGGACGAAGT | 3600 |

FIG. 34B10

| Target No. | Pool A Sequence (5' to 3') | SEQ ID. NO. | Pool B Sequence (5' to 3') | SEQ ID. NO. | Pool C Sequence (5' to 3') | SEQ ID. NO. |
|---|---|---|---|---|---|---|
| 1 | GTGTCCTGCCTGCTAGGTATT | 3601 | TCGTGAATGCTGAGGAAAAGAG | 6287 | CCTCTGCTGAGCTCCTGTCT | 8973 |
| 2 | TGTGCCAGGCCCAAAAGCTT | 3602 | GAGCCCTCTCCGTTTGTCACA | 6288 | GCCTCACCACCACTACACA | 8974 |
| 3 | TCTGCTTCTGCCGGCATTC | 3603 | GCTGGACAAACTACTGCCTCTT | 6289 | GTGGAGGAAATTAGATGTCTGCTTCTG | 8975 |
| 4 | AGGAACTGTCAGATTGCAACCA | 3604 | CAGCTTCCCTCTTTTGCTCTGT | 6290 | CACACACACAAAGGAACTGTCAGAT | 8976 |
| 5 | CCACCAGGTGCTCTCAACTCT | 3605 | GAACTCAAATGGCTGTGTGAAGTC | 6291 | AGGGCCTGCTGACTCGTTCT | 8977 |
| 6 | TCCCACACACGTGTCTGTATCT | 3606 | CAACGGATGGAGATGCAACCAT | 6292 | AGTTCTGTCCCAATCCCACACA | 8978 |
| 7 | AGAAGGCAAGGAAACATAACCTT | 3607 | ATCTGGGGCCTCATCCTTTGG | 6293 | GTTTGAAAGAAGGGCAAGGAAAC | 8979 |
| 8 | CCACTCCTGGCCCTTTTCTCTTTT | 3608 | GCCTGGAGAAGAGGTAGATGTG | 6294 | TCCCCACTCCTGGCCCTTT | 8980 |
| 9 | AACTTGGGGCCACTCTCTA | 3609 | GGAGTCCTTCTTTCACCTCTTTCC | 6295 | ACTGGGATTTGACTCTGGAACTTG | 8981 |
| 10 | CCACGATGAAAACAGAAACCAAC | 3610 | AGCTCCATGCTCTGTGATGGT | 6296 | CAGCTAGAGCAACACGATGAA | 8982 |
| 11 | GGTTGCAAACCCCTCCTCTTT | 3611 | CTCGCCAGCATGGTGACA | 6297 | GCCTGAAAGGTAGGTTGCAAACC | 8983 |
| 12 | GCCTTTGTGTAGACAGCCACTT | 3612 | TCCACTGGGCCCATCTCTCT | 6298 | AGAGTCATAAACCAAGCACCAACA | 8984 |
| 13 | TGTGTGCATAAAGGGTCTTGAAGA | 3613 | GGTCCACAAGGTGGAAAAGCCT | 6299 | ACACGCCCTTGTGTGCATAAAGG | 8985 |
| 14 | ACCCTTCCCTGCCACTGTTT | 3614 | CTAGTCTTAAGAGTATAAGGTAGGGTGAGA | 6300 | TCTGCACCAGTCTCAGGTCTTC | 8986 |
| 15 | TACCGTAGCTCAGATTCCTAGCCT | 3615 | TTTGCCCTTCCCACACAAGACA | 6301 | TTTCCAGAAAGGGGTCAAACC | 8987 |
| 16 | TCATGGTGCCCTGGCCTCACT | 3616 | CCACGGAGCTCCTCCTGTCT | 6302 | GCCAGGCAGCCTCATGGT | 8988 |
| 17 | CTCCAGGCCACAGAACTCAACATG | 3617 | TGCAGGGAGGACTGTTGTC | 6303 | TGCCTCCAGCCACAGAAC | 8989 |
| 18 | GGCTCACCATGGCTCTGATC | 3618 | TCACCCACCATTCATGCAAGAG | 6304 | GGTACCAGGGCAGAAGGT | 8990 |
| 19 | CCAGGTCCCCCAAACAC | 3619 | GGGAATACATGCAAAGCAAGGA | 6305 | AAAGCCCAAGCTCCTCAACAG | 8991 |
| 20 | TCCAGTGCTCACTCACTCTCCTT | 3620 | GCGCAGTAGAGAAGAGGCTTTTAG | 6306 | TGAAAACCTAAACCCTTCATCAACCT | 8992 |
| 21 | GAGTAGTGCATGCACACAGTGA | 3621 | CAAGCTAATTCTGCAGCAAGTATGA | 6307 | AAGCCCAGAGTAGTGCATGCA | 8993 |
| 22 | TGGGCCTCATTCTCAAGTTC | 3622 | ACTCTTAGTTAACACAACCATGTAT | 6308 | GTTGACAAAGATCTACATAACAAGGAGTCA | 8994 |
| 23 | GGCTTCTGCAGAATAACATCCTGATT | 3623 | ATTGTGGAGGGCTGAAATGCT | 6309 | TCAGTGGCTTCTGCAGAATAACA | 8995 |
| 24 | TCCAGCCTCAGCCTGGTT | 3624 | GGGCTGTTTCCATAATCATCCTACCT | 6310 | GGAGTCAGACACAAATAAATGGGTTCAG | 8996 |
| 25 | TGCATGGCCAGACAATATGGT | 3625 | TCACAACCAGTTTTCACCAACCA | 6311 | GGCTGGGAAACTGCTATGCAT | 8997 |
| 26 | GAAAGTTGTGTTCCCAAGGCTTTG | 3626 | GAGCTGAGTAAAGCCATGTGTCA | 6312 | CAGATACATGGAGGTGAAAGTTGTCT | 8998 |
| 27 | GTATGACTCCCCTAAGGATGAGAAC | 3627 | GTCACCCATCCCACCTATTTACTTG | 6313 | CACTGTCTATGACTCCCCTAAGG | 8999 |
| 28 | AGCAGCATGATGCCGAACGAA | 3628 | AAGGAAATAGACCCATTTAGCTTCAGT | 6314 | GCTCCAAAATAGCTGGCAGCATGATG | 9000 |
| 29 | GGCTCATCTTTGTCAGTTATTTCCA | 3629 | GGAAGTTCTGGCTCTGTGACCTGAAA | 6315 | ACAAGACTACAAGAGGCATTGAACT | 9001 |
| 30 | GCTGTTCCATGGAGCAATCACTT | 3630 | TCCTGTGCTCACCTTGACT | 6316 | AATGTGAGGATGGAGGCATTG | 9002 |
| 31 | AAAAATGGCCCAGTTTTGCAGAA | 3631 | GTTTTAGTCCTTCCTTATAGCCCATTGG | 6317 | GGCTGAAACTAAAAATGGCCCAGTT | 9003 |
| 32 | AACAATCCCCTCCCCAATCCT | 3632 | TTTGGTCACCAGCATCGGAGT | 6318 | AGGTCACGGATGACACAATCC | 9004 |
| 33 | TGCCCAGGCTTTCCCCAAT | 3633 | GCCAGTGGTGGATTCAAAAAGCA | 6319 | TGCCTGGCACACATGATGT | 9005 |
| 34 | TGCTCTCTGCCTCAGGATGA | 3634 | GCTGGTGCCCTTATGCTGAAG | 6320 | TGTTCCATCTCTTGCCATCTC | 9006 |
| 35 | GTGGGACACAGACCCTTGTT | 3635 | AGTCTCTCAAAGCCTGACGTTTC | 6321 | TGCCAGGGTGGGACAGACA | 9007 |
| 36 | GTTTTCCTGTTCAGGTGACCTAGTC | 3636 | GTGGAATAAGATGGAAGCCACACT | 6322 | CTGGTGAACCACAAACAATTAAATGTT | 9008 |
| 37 | GAGACGTATACAGAATTGTGTGGCTTTTC | 3637 | AATATTACTAGCCACACTGCTATTCCTT | 6323 | GGTTGCCTGAGAGCTATACAGAATTGT | 9009 |
| 38 | CCCGCAGTGCATTCCAACATAGA | 3638 | CCAGGACCCACCACAGTCT | 6324 | AGGCACCCACTGCATTCC | 9010 |
| 39 | TGCAAACATCCCACCTGAACT | 3639 | GAGTGGGATAAATAAAGGCTGTAAAGAG | 6325 | ACTGGCAGCAAAACTCAACCT | 9011 |
| 40 | AGCTGGGCTCTGAATGTGA | 3640 | TCCAATCCCACCTCTGACAATG | 6326 | TCCTCTACCCTGGAGGCAGTAAA | 9012 |
| 41 | CCTAACTGCCCCTCTCACTA | 3641 | CCTGCTTAGTGGCCTATGTGATCA | 6327 | GCTGCAAGGCCCAACTGT | 9013 |
| 42 | CTGGTTTGAATGTCTTGGATTGCTTAG | 3642 | TTGTCCCCCAACCCATTCA | 6328 | GAGGACTGACAGGAGATGTTAGTAAGA | 9014 |
| 43 | TCAACAGGCTACCATTCTTTGGAT | 3643 | GGAACACTCGGCTTCACTATT | 6329 | AGTACGTATTCAACAGGCTACCATT | 9015 |
| 44 | TCCCCAAAGAGGAACTGCTT | 3644 | GGTAGTAAGATTAAGAGCTCTGATTCCA | 6330 | ACTGGAGGCATTTTCACACCTT | 9016 |
| 45 | GGAATCCCCTCCCTCTATTTATTG | 3645 | CCAGGAAAACACCCACCATACA | 6331 | TGTGCTAGCCTACCCAATGG | 9017 |
| 46 | GAAATGTCCTCTCTGGTCCAAGAT | 3646 | GAAATGGTTGGTATCTAGGCATCACT | 6332 | GGAGAGGACACCAAAGAAATGT | 9018 |
| 47 | TGGGCTACTGGCACTGATT | 3647 | GAGTGCCAACAGTCAGCTAAT | 6333 | CCTAAGTGGGTGGCTACTG | 9019 |
| 48 | CACGGTTAAGTTGCACCCAAAC | 3648 | GCATCAAACTCAACTCAAATGGATGT | 6334 | TGTCTCAGATAATGTCACGGTTAAGTT | 9020 |
| 49 | AGCAGGTCGTGAGTGCAGAGAA | 3649 | TCCACATCCCCTTTCCACTTT | 6335 | AGCACCCTTGGTTTCATAGAGCTT | 9021 |
| 50 | GCTGGGCGAGCTCTTTGG | 3650 | AGGCACCCACCTCTAGACACTA | 6336 | AGCACACACGCAGGAACCT | 9022 |
| 51 | ACAGTGAGGAGCAGAGACTTCA | 3651 | CAGTCATGGTCAGCCAGTTCATAT | 6337 | AACCACCCTGGGACTAGGAAT | 9023 |
| 52 | TAGGCAGAGGCATGCTCGAAT | 3652 | TGCTTCCTGGGCCTGTTTGT | 6338 | CATGAGTCCAGCGCCACCTA | 9024 |
| 53 | TTGGGTGCCAGTTGGACCAA | 3653 | TCGGCAGGGAGGGAAGCTTT | 6339 | AGGGGTTGGGTGCCAGTT | 9025 |
| 54 | CCCCAGCTGTCTTCACTGTT | 3654 | CCACGGTGCACTCTCTTCCT | 6340 | TGATGGCCCAGCTGTCT | 9026 |
| 55 | GTGTGCTCAGTGGACAAGCA | 3655 | AGCCCCTGCTGAGCTTATCCA | 6341 | GCCCCAGGTGTGCTCAGT | 9027 |
| 56 | AGGACAGGGCAGGGAGTAAT | 3656 | CACACCTCTTATCACACTCTTCCTAGT | 6342 | GTGGAGCCCTCGGGACAT | 9028 |
| 57 | GGAACCACTTATCAGAACCACAA | 3657 | AAGTAGCCTAGCATTTGCCTGCTT | 6343 | ACTGCAGATGGAACCACTTATCCA | 9029 |
| 58 | GAGGCTGACTCCTGTTGCAT | 3658 | ATTTCCTCGAACCACTCGCTAAA | 6344 | TTGGTGTGACTGCCGCTTTT | 9030 |
| 59 | TGGAAAGCTACATTCAATTCAGAGACAAA | 3659 | CAAGCCCTCCTTGACTTGCTT | 6345 | CAGAGCTTAAGATGGAAAGCTACATTCAA | 9031 |
| 60 | CTCCAAAACTGATCCCGGCAA | 3660 | TTGGCTGACCTAGGCTGTAGT | 6346 | AGAGGGGTGTCCTTGGAATT | 9032 |
| 61 | TGATAAGGGCTGTGCTCTTCTAAG | 3661 | TGCCCTTAGTCTAGCACAGCTT | 6347 | CCACACTTGCCCCAACTTGATAAG | 9033 |
| 62 | ACATACCGAGTCGGTTTATTCTTCTC | 3662 | CCCATCAGGAAGCCTGAGATG | 6348 | GCCAGTTGTAGATACCGAGTGGGTTT | 9034 |

| | | | |
|---|---|---|---|
| 459 ACCTTGCCTGCTATGGGTTCAA | 4059 CCAAAACAGGCAGACCATGTCCTT | 6745 TGCTGTCACCTTGCCTGGTAT | 9431 |
| 460 AATAAAAGTCCTCTGCCGAAGACA | 4060 AACGGCAGGGGAGGAAAGG | 6746 AGGTACAGGGCAGGATCGG | 9432 |
| 461 CCTCTTCCCTTGCCTACTGTGCACA | 4061 TGCCAATGGGAGGATAGGGATACT | 6747 ACCAGGTTCCTCTTCCCTTTCCT | 9433 |
| 462 ATGAATCCTGCCATGTAGGTGTAG | 4062 GCTGCTCCAGAATTCATGGT | 6748 AGGCTTTGCCTCTATTCATAGCT | 9434 |
| 463 CAGTGTATAGCCCTTCCTCCTTTCTT | 4063 GGGAACCCCAGGCAGTGTGA | 6749 TTCTGTCTCCATTTCCCTTTCTCA | 9435 |
| 464 CAGGCATGGGAATTTGGGTAGACA | 4064 CCCATGTGTGCCCATTTGC | 6750 CCCCATTCGTCAACGCTCTAC | 9436 |
| 465 GGTCTCAGACTAGGCAGAATTTGG | 4065 TGCTCCTGCCATCCGTCAT | 6751 GAGGTGAGGCTGGGTCTCA | 9437 |
| 466 TGTCACTTTGTTTGAATGGAGACTGA | 4066 CCCATAAAGAGATGGTGCCAGTT | 6752 GCTCTCCAAACACAATGTGGACTTTA | 9438 |
| 467 TCTGCAGGCCATCTCTGCAT | 4067 CHGAGGAAACCACAGGGTCCTT | 6753 CATTTGCCAGCCTTTTCTCTTAATGG | 9439 |
| 468 ACCAGAGCCCTCCATTCCTAAACT | 4068 GCTTCGTGCCTTTACCTGACTGT | 6754 GCCACCAGAGCCCTCCATT | 9440 |
| 469 CTAGGAGGCGGAATCAC | 4069 ATTCCTGCCTCCTGGTAACGT | 6755 GACTGCACGAATGTGTGAAAGC | 9441 |
| 470 CTGATCAAATTTAGTCTGGATGTGACCAA | 4070 CCACTAAAAGGCAGCTCTGACTTGGA | 6756 AACAAACGCTTGTCCTAGAAAAATCATATT | 9442 |
| 471 TAGTTGCTATGGGCCAGACA | 4071 GCCGGATACAGTGAGATTCGTAATC | 6757 ACABACATGCAGGCCTGCAB | 9443 |
| 472 GCAGAGGCTCTGTGCTATGT | 4072 CTCACTGTTCTCTGTCACTCACTTTT | 6758 GGCACTTTTGTGTGTAAGGAACAG | 9444 |
| 473 TGGGGAATGAATGGAAGATGAG | 4073 GCACTGGAGGAGTGCTACATAACCA | 6759 GAGAGGGTCATATATGGGGGAATGA | 9445 |
| 474 GACTACCCTTTGCCAATTGGAAGCA | 4074 TCCAGTGGCAATGGCAGACT | 6760 CCAAAGGCAAAGACTACCCTTTG | 9446 |
| 475 CAACAGACCTGCCTAGGCAGCTA | 4075 TTTCTAGCTGGTTGGTTGGAACT | 6761 TGTTGCCTAGTCTTGCCAACAGA | 9447 |
| 476 AGCCCTCTGGTGCCAAAC | 4076 TGCTCATGTCCTAGAAGACGGGTACAG | 6762 GAAATTTCTTGGAAACGCAAAACCA | 9448 |
| 477 CTGCATGAAGTATTCTGCACTACTG | 4077 CCTAGTCTCCTCACTGGGAAATAGGA | 6763 CCTGCACACTGCATGAGCTATTCTG | 9449 |
| 478 CAAACTCCCTTTGGCTAGGAGAGAA | 4078 ACTGCCCATAGCTACAATCTC | 6764 CCTCTGAATTTCAAACTCCCTTTGG | 9450 |
| 479 CGCTGGGTTAGATCGCCAGTTT | 4079 CCTTGATACTGAATAAGTTCTGATCCACTT | 6765 GGCATAAGATTACACACTGGGTTAGATC | 9451 |
| 480 TCCTGGTGATGTGGGGAATAT | 4080 CCAAAATGTTACCCATAGTAAAGACGTT | 6766 TGAACACTCTTTCCTGGTGATGTG | 9452 |
| 481 GCTAGGATTCCTGGGTGTGTGTT | 4081 GTGAGTGGTCCAAAGTGACTTGAT | 6767 CTGGCTTGCCTAGGGATTCCT | 9453 |
| 482 TCTGGGAGCCCGAAATTCCTTCT | 4082 AACCAAGGCTGGATTCCTGTCT | 6768 CCAAAGGCAAAGACTCGGAGCCGAAA | 9454 |
| 483 GAACTTACCAAGGTAGCCAGATGT | 4083 CTCTCAGGGTTGGCATTACAG | 6769 CGCTGGTAAAGTTGGCTGCTTATTTCAC | 9455 |
| 484 CAAGATGCTCACCCCATACCTT | 4084 TGGGTAGTGGTGGTGAGGAA | 6770 CCTATCCTGGACCCAAGATGCT | 9456 |
| 485 CCCGGCCATCCTGAATTTTATTGC | 4085 TGGGTAGCCCTAGACCTTTACTTC | 6771 ATGCCCGGCCATCCTGAAT | 9457 |
| 486 AGAGGACTGGGCTCTTCCTATT | 4086 AGGATTGCAATGACTCCCATATGG | 6772 AGGTGGAGGAGGCCTTGAG | 9458 |
| 487 CTGGGCCAGTCATCCCTAT | 4087 TGGAAACAGCCAGGATGGTACAT | 6773 GGAGCGGAAGTGAGCATGT | 9459 |
| 488 TGATCAGGGTCGGCTATCA | 4088 TCTGCCAAGCCGACAGTGT | 6774 GATTTTGGAGCGACAGGAAATTAAGCAG | 9460 |
| 489 TGCTCAGTTCCACCCAAACC | 4089 TGCCTAGTGCTCTTCGTGTCT | 6775 CTTGCCTAGTGCTCTTCGTGTCT | 9461 |
| 490 AGCCTATATGAGACCAGGCTAAGCT | 4090 AGTGCTACAGAGCATTGTTGCT | 6776 GGGTGTGGGAAGGCTATATGAG | 9462 |
| 491 GCAACGGGAGGGAAAAGTTTCT | 4091 CTTGAAATGACCCCCCATTCCT | 6777 GGTACCCGCATGTGCTATGG | 9463 |
| 492 TCCTACCTCCTGTCTCTTGAGCA | 4092 GGGGTTGTGGCCGTGCTT | 6778 ATCCCTTCCCAGCTACAACT | 9464 |
| 493 CCCATTTGGCCATAACTCAGCTACA | 4093 CCCAAACTCCTTTGCAACTAAATGG | 6779 CTATCTACATCCCCATTGGCCATAACT | 9465 |
| 494 GGGGCCATAACTTCTGGATTGTGT | 4094 CCATGGCAATGACCTCCAAGT | 6780 AGGGAAGGGGCCATAACTTCT | 9466 |
| 495 ACCTCTGAGGCAAGGACCTT | 4095 TGGAGAGCAGGGGGACACAAT | 6781 CAGTTAGGAAGCCGATGAAAATTAGTTT | 9467 |
| 496 CTAACTGCACAGAGAAGAGCAAATG | 4096 GGAAACGGAGGCACAGTTCATT | 6782 CAACCTACTAGCTGCACAGAGAAG | 9468 |
| 497 CGCTGTTCCTGAATGCCATTAG | 4097 GTACCAGTTTCATTAATGGGAAGCA | 6783 CTCTGACGCTGTTCCTGAA | 9469 |
| 498 CTGAGTAGGACAGTGATGTGTGTCAGA | 4098 GCATGCCTGGATTCATCATCAAGGA | 6784 GGAGCCACTGCAGCTTTCT | 9470 |
| 499 AGACCTCTTCGCCTCTTGTTC | 4099 GGAGATGGGACCTGCTTGCT | 6785 AGGCATGGCAAGGCTACCT | 9471 |
| 500 GCAAAATGAGAGTGAAAATGCTGCTGAA | 4100 ACACAGAGAGCAGAGGGGTTT | 6786 CTCTCGATTCTGTTTTCAGCAAAATGAGA | 9472 |
| 501 CCTCCTAAAAGCCAGTCCCTCTT | 4101 CAATAGCCCCCTTCTTGAAACAC | 6787 CTCCCCTGCCTCCCAAATTAA | 9473 |
| 502 AACCCAGAGACACACCTATCCT | 4102 TCCTATGATGCCCCATGTGT | 6788 AGACCACACTCAACCCAGACA | 9474 |
| 503 GCAGGCTATGGCAATCCTACCCACAA | 4103 CAACTGGCCAGCCTCTCA | 6789 TCCATGCATAAGCAGGTCTATACAATCC | 9475 |
| 504 TCCCTCCTTGACGCTTAACT | 4104 TGGAATTTCTGCCCCTGGGGTATGC | 6790 AGCGGGCATCCCTGTCCTT | 9476 |
| 505 CACAGGGTAATAAGTGGCCCCTTA | 4105 GGCACTGCTGCTGCTACA | 6791 GCTGCCTAGCTGGGTAACCT | 9477 |
| 506 ACCCACGTGGTCTCAGAGTCT | 4106 ACCTTTTTCCTCCATGCAGCTAAT | 6792 GACAATCGATGAGGAGCAGATAC | 9478 |
| 507 AAGCATTCCCTTCCTCCTGCAA | 4107 TCTCCAGTCGAGGCCAAAACT | 6793 GGABACTGAGGAGGCCATTCTCA | 9479 |
| 508 ACCCCTCACTTCCTACCCTTTTG | 4108 GGGAGCTACTGTTACAGGTGTTAG | 6794 CACAGAATTGACCCCTCACTTCCA | 9480 |
| 509 CTGGTGGCATGAGCAACTTATAGT | 4109 CCACAGAAAATACCACTGCTCTGAAC | 6795 ACTTTCTGGTGGCATGAGCAA | 9481 |
| 510 CTGACTTCCTCCCCTCAATTTCT | 4110 GCTGGAAAGGTAATGGTGTCACCTA | 6796 AACCCACCAAAATCTGACTTCCT | 9482 |
| 511 AGGAAACGTCCCCTGCTCACTA | 4111 CACAAATCTCCAGTATCCTGTTGCT | 6797 GGGGGAGGGAGGAGAAACGT | 9483 |
| 512 GAGTAGAATTGCAACGGGCAAACAG | 4112 CCCCAAATGATTGACACAGCTTTCT | 6798 GTGCTATGTGGGAGTAGAATTGGAA | 9484 |
| 513 CTGACAAACACTCCCAGCAAGT | 4113 ACCCCAGATCCCTTCGAGTGA | 6799 CTCTCGCGTCAAAGTTGCC | 9485 |
| 514 GGATGAAGGCAGGCTGTAG | 4114 CAGAGACATTCATGCCTTACTCT | 6800 CCCACTCCTCATAATAGGGTATTGAGGAAA | 9486 |
| 515 CGCTTAAGTGTTCATTGCTATAACAC | 4115 CCATAACCCCGGTTGTAAGTAAACA | 6801 CAGGTATTACGCTTAAGTGTTCATTGC | 9487 |
| 516 CCTCTCCTCAGATGCCTGTTCT | 4116 ATGGGTCCAGTGGGTAAAGGT | 6802 CCAAGGATTTCTCCTCTCCTCAGAT | 9488 |
| 517 AGACCTACTGATCCCTTGCCTAGA | 4117 CAAGCACAAATACAAATATGTGGTTTG | 6803 TCCCTCAGCTCTGAAGACCTACT | 9489 |
| 518 GTTCAACATGCTGCTAGCTTAGAC | 4118 GTGCACTGTGGAACTCCTTTCA | 6804 GCTTGTGAATCAAACTGGAAAGCT | 9490 |
| 519 ACAAAGGTAAGTATATGATCATGTGTCT | 4119 AGGGTGAAGCCACGGGATCAGT | 6805 GTGGTCCAACAACGGTAAGTGT | 9491 |
| 520 AAGTTGGTCAGGGAGGCAGAT | 4120 CGCTTCCTTCCCTTACTGCATTTAGG | 6806 GGAATGGGGCTCTATGTGGAAAGA | 9492 |
| 521 CTTGGCACTGTCCCAGTTCTAA | 4121 GGACTAAAGGGGTTCCTGACACA | 6807 CCCCAGTTTCTTGGCACTGT | 9493 |
| 522 CATGACTCATAGACCCTCTACTCAAC | 4122 AGGTGCCTACAGGACATTGG | 6808 GAATTTCATTCATGCCTACGACTTCA | 9494 |
| 523 GCAGGCTTCTGACGTCAAGGA | 4123 CCAGCCAGAGCCAGCCATACAATAGA | 6809 CCTTGCTAGATGCAGGCTTCTTG | 9495 |
| 524 ATGGTGACTGTGGGTCAT | 4124 TCTCTCTCCACCCTGTCTGTTT | 6810 AGGTGGGGTGATGGTGACT | 9496 |

| | | | |
|---|---|---|---|
| 855 GGTCCAAGATGACTCCAAGA | 4455 TTGAGAAACGTCTGTGGACACA | 7141 TGCCCATGGGTCCCAAGAT | 9827 |
| 856 CAGTCACTCCTTGAACACCATGT | 4456 GGACATTTGGGTTTAACCACCCTAATTC | 7142 CCAAGATACTGTGCTCTGTACTGAGA | 9828 |
| 857 CCCAAGTTCTCTTGCCCATTTGA | 4457 TGTACCCAGGCTCCCATCTCA | 7143 ATGCCCACCCAAGTTCTCTTG | 9829 |
| 858 TGCACTGCTGAGCCACAGA | 4458 CCTATGTACTCTTCCTTGGATCCAA | 7144 GCATTGGTACAGGCCGTTCA | 9830 |
| 859 CACACACAGCTGCACAGATTG | 4459 AGCCTGCTTGAGACTGGATGGA | 7145 TGGCAGCTCCCACACACA | 9831 |
| 860 CCTGCTTATCAGTGCCTGGTGAT | 4460 GGGCCAGGCTTTTGGGAAATA | 7146 AGTTGGACATCCCTGCTTATCAGT | 9832 |
| 861 GCAAATGCAAAGGTTCTGAGGCAAA | 4461 CCCTGTCTCTTGGTTGTTCCTT | 7147 GGCAGAGAACAGCAAATGCAAAGG | 9833 |
| 862 TGAGCAGTCCTGGTGCTGTA | 4462 CCCCTGCTTAACTAACTTTCAGTCAAC | 7148 AGGGCAGGTGTCAGCAGAA | 9834 |
| 863 AGAGGAGCAGTGAGTCCTAGCTTG | 4463 TGACTGTAGTGAATGGAATGAGCATT | 7149 TGACTCCTAGAGCAGCAGTGAGT | 9835 |
| 864 CACCGTGAAATGAATTGCCTTCTGT | 4464 AGGGGCGTCTACGATCACT | 7150 GCTTGTTGCTGCAACACAGTGAT | 9836 |
| 865 GCCAGGACTCTCTGACTTAAGC | 4465 GTGCACAGCCGGGATGGA | 7151 GCTGAGCTGTTTCTTCTTAAAGCAACA | 9837 |
| 866 TTCCACCTCACATTGGCTTCTG | 4466 CAGAGCTCTGATTGCCCAAGATTCG | 7152 TTTGGCCTGCTCCTTCTGTCT | 9838 |
| 867 GTTGAGGTCTGCTGTGGTCTAA | 4467 CATGCCCAGCCACTGCTTATTA | 7153 CAGCCAAAATAGGAGGATTCTATTCTGT | 9839 |
| 868 CCAAAGTGAGACATTATCACCATATATCG | 4468 CAAGACTCCTTCAGCAGTGACA | 7154 CACTGACGAAAGTGACACATTATCAG | 9840 |
| 869 GAAGAATGGGGCAGACATGGA | 4469 GACTCACCTCCCTAAGCTAATCTTACC | 7155 GCTCCCACCTATTCCTCAGGCT | 9841 |
| 870 ACTCCTGCAGCTCTCTAGTCA | 4470 TGCCCTGGCACTCTCTGCTT | 7156 GAGTAGTGGGAAATCATTCTGATCCA | 9842 |
| 871 TGGCAATACAGCAGGGCTTCAA | 4471 TGAGAAGTAGACCCAGCCTGTAAC | 7157 AGTAGACGGGGATGGCAATACA | 9843 |
| 872 CCCGTGAAAGTCAAGCTATTGATTGC | 4472 CAGTGGGCAATAGATTCAGCAGAT | 7158 GGATTTACCCGTGAAAGTCAAGCT | 9844 |
| 873 TGCTGTCCTGGAGCTGTTGAA | 4473 GTCAGCCACCCATTGGATTGTTG | 7159 GTTCCATTGCCCTATGTGCAATCT | 9845 |
| 874 TGGTCGCCTAAACTTCATCACA | 4474 CTGTAACATGCTCTTGGGATGAACAG | 7160 TGGTGTGGGCGCCTAAACT | 9846 |
| 875 GACATGCATCACTTCTGCTCACA | 4475 GCTTTGGCTACATAACTGCTTTGG | 7161 CTTCATCCCAGAAGTGACATGCA | 9847 |
| 876 CTCCCCGAAACACCTCTCT | 4476 AGCAAGTCTCATTTCCCCTTTGG | 7162 GGGTCACCTCCCCGAAAC | 9848 |
| 877 AGATAAGGACTCCACAGGGACTCT | 4477 TCACTGGACACCTGTCATTTGG | 7163 ASCCPCCCGATGAGATAGGA | 9849 |
| 878 TTGCCCCTGTTTCAGTGATGCT | 4478 AAGTTTTCGCAGTCACCACTTTAC | 7164 GCAAGAGTACTTCAGACGTGATACA | 9850 |
| 879 CCTGGCACAACTGACACTTT | 4479 GAGACTCCTGGGTCAGAGATGAA | 7165 AGCTCCCTGGCACAAGCT | 9851 |
| 880 GTGGTAGGCGATGCATCTCAA | 4480 CTGAATTCACCAGCCTGTGTCA | 7166 GTCAAGAAGGTGCCTGTGGTA | 9852 |
| 881 AAGCGGAGGGGCTTTCTCT | 4481 ATGCTACGGAGGGAGGTGTATACA | 7167 GCACAAGCTTGATCTAATGCCTATTGG | 9853 |
| 882 GCTGGGTAGCACTCCCTTACT | 4482 ACCCATGGGCACACATTCA | 7168 GCCCATGGGTTCTGCTTATTG | 9854 |
| 883 GAGAGCGGACTTTCTCCCAAT | 4483 GTGACAATAGAGAAAGCACCATCATC | 7169 CACTGGTCCCCTTTCTACATAGTTG | 9855 |
| 884 AGTATGCGTTGTTAGATGTTTCAATTCC | 4484 CCTGAGGCTGTTTCTTCCAGACAA | 7170 AAATCTCATAGTTCATTAGTATGCGTTGTT | 9856 |
| 885 CATCATGGTTCATCATGGTTCTCCTT | 4485 GCCTTGCTTCAATAGCTGAGCTACT | 7171 CACCACTTCATCATGGTTCATCA | 9857 |
| 886 CACTAAGTCACCTTCTCCCTTG | 4486 GCAAAACCACAATGACAAAAATCAGGTAT | 7172 GGGCTGAGGAATTTTGGCTATTCA | 9858 |
| 887 CTCCCTCTTAACCAAGGATACCA | 4487 GCAAGGGGCAGCTGTATTGTT | 7173 CAACTGTTCCTTACTCCCTCTTAACC | 9859 |
| 888 GGCTACCCTGACAACTTAAACAGTCT | 4488 GTTCAAATTCAACCCCACTGAGA | 7174 TTGGATGCAGCCCTGGTTCAT | 9860 |
| 889 ACCTGTGAAAGACCACTGCATACC | 4489 GGGGCCAATATTTACCAGAATTATGATGGT | 7175 TCTTGGCCACCTGTGAAAGAC | 9861 |
| 890 AGCTAGACAGAGCTGCACAAGATG | 4490 GAGGTGAGGCAGTGAAACCAAT | 7176 CCTGCTACTGCATCTTTCACAGTGAA | 9862 |
| 891 CAAACCTCATGGCTGGCATGT | 4491 TCAGTCTGGAACACTCCTTGACT | 7177 AACAAGAGTGGCTGGTCAACCT | 9863 |
| 892 TCTTCACCCGCCCATCCA | 4492 GGTCTGGGGCTAGCAATTGC | 7178 AAGCCACCCCTCCTCTTCA | 9864 |
| 893 GCTCTTCACCCTTGACAGATGTACGT | 4493 ACCCTCTATCCTCGGCCTGAATCC | 7179 GCTAATTCTATCCTGGTCTTATCTTTGG | 9865 |
| 894 GCTCACACAAACTTGCCCCTAT | 4494 AATTGAGATCATGCTGTTCTTCATTCG | 7180 GCCAATATGAAAAGCTGCTCCACAAA | 9866 |
| 895 AGCCCCCTAGTCAAACACAA | 4495 GGAGCGTCCAGGTCACAGAT | 7181 CTGTGTGGGTCTCATGGAAAG | 9867 |
| 896 GTGCCAAACAGAGCTTCAGG | 4496 AGGGTGACATGTGCCCAATTGCA | 7182 CACAACTCAGGGCCAGTCAAAT | 9868 |
| 897 CTAATCTGGTACTTAGCTGACAGTAAGT | 4497 GAATACCAACCAGACAACAGACACA | 7183 CTAGGTGCCCACTTCAAATATTCAAA | 9869 |
| 898 ACAGACGACCACAATAACCTTATCC | 4498 GAACATGCAGCAGTTTGGTGAT | 7184 GCAGAAAATGCCAAAGAAACAATGHT | 9870 |
| 899 CAGAGATTGGCACTCTTCCCTCTT | 4499 GGTCATTTTTTTTTTGCAGTGGAGGATGTG | 7185 CCATTAGACAGAGATTGGCACTCT | 9871 |
| 900 CTGCTGAGGCCTGAGCACTG | 4500 GGTGCACCAGTACTTGATCATGG | 7186 GCCCACTATTAATCTGATGAAACACAC | 9872 |
| 901 ACCCTGCCAGTTGACAATTGC | 4501 CAAGGCCAATGTCTAGTAAGAGCA | 7187 CACTTTTTAACATTACCCTGCAGTTGA | 9873 |
| 902 GGGAGAGGAAGTATATGAGTGTGAATTAGG | 4502 CAGCCTGCATTCACCCCTCATACTCT | 7188 GAATGTGTGTGCATATGGGAGAGGGA | 9874 |
| 903 CCAACTACAAGTCCCTAGCTCTTTTCTC | 4503 GTCGTTGCTTGCTGTTTAACTGT | 7189 GGCAGAATGGAAATACAGCAAACAGTT | 9875 |
| 904 ACTAATATTCACTGGCCAACTGTGA | 4504 GGCTAAGCTAACGATATCCATCTCTCA | 7190 GAGTACGCAGCAAGTAAAAGTAAACT | 9876 |
| 905 ACCCTGTAGCTCCCTGAGCAGAA | 4505 GCTATCCATGTTGTGAAAGGTCTGT | 7191 GTGTGTCTGTCTTCCCTCTAAGCC | 9877 |
| 906 AGAGATAGCCCATCCCAGTTGT | 4506 GAGGGAGACTTGTAAACAATCCA | 7192 CAAGGATTTACCACCTCTAGAGATAGC | 9878 |
| 907 GTCAGTAGGCATGCTTCATTGAATC | 4507 GAGTCTGGGAAATGCACAATTATGGT | 7193 CAGACACTGCTGTGAGTAGCAT | 9879 |
| 908 TGGAGAGGGTCGCTTGCT | 4508 AGGCTCAGGTCTCAACCACAGT | 7194 CAGGACGTTTCTTCACCACACAA | 9880 |
| 909 AAACAAATGTCCCTGCACTCAAG | 4509 CCACATGGCACTTCATTTTTGACAGT | 7195 TGTATCTGTCAACTCATTGCCTCATC | 9881 |
| 910 GACATGACCAGGAAGCATCTTTCA | 4510 GCTTCATGCTGCATTGCTT | 7196 GCCTCCGGGTGCTTACATGCA | 9882 |
| 911 ACCCGTCCACACACACAA | 4511 TGGTTCAACACTATAGCAGAACTGT | 7197 GAGTCCGTGAACAAATACAGTGTGTAAT | 9883 |
| 912 AGGCCTCTCATTGATCTTTTGCT | 4512 GCTCAATAACCAAGCAGCACAGA | 7198 TGGGGCTCACCCGCTTATGG | 9884 |
| 913 CCGAGGAACTATACCCACTTGGTT | 4513 CATTGGCAAATTGGCTCACTTTG | 7199 TGGAGGTGACCGAGGAACTATAC | 9885 |
| 914 CGTCTCACTGCTGTCTTCTGT | 4514 GGAAGGACTCCCACGGAAACA | 7200 GCCAAGCATGCCCGTCTCACT | 9886 |
| 915 GCAACCCCTCTTTAACTTTGC | 4515 AGACGTGTGAGGGCTCTGT | 7201 CACTGAAAGTTGAGGGGAAGCA | 9887 |
| 916 AGGGGATGACCAACCCTGATCATA | 4516 TCTTGTTGCTCTTGAAGGCATTG | 7202 TGGAATATGAATGTGGAGGGGATGA | 9888 |
| 917 CCCAGGTTAATGAGTAGTAAGTGTCA | 4517 CAGAGAGGCCTGAATTCAAACCT | 7203 TTCCTCCCAGGTTAATGAGTAGT | 9889 |
| 918 GGCTTCATTCATCAGTGACTCTCTGA | 4518 GGCTTCATTGCTGCCTTCCA | 7204 GCTCTGGCCTTCATTCACACA | 9890 |
| 919 ACGTGGCTGCCTTCATCCT | 4519 TCAGTCCACGCACTCACCAT | 7205 CCCTTCCCTCTTCTCACAGATGAC | 9891 |
| 920 CAGAGAAAATAGCTGTCCCCATTGG | 4520 GGGGAGTAATCTGCTCTTACGTT | 7206 GCAAGTCTCCCATCAAGAGTTTAGA | 9892 |

| | | | |
|---|---|---|---|
| 1119 GCAGTCTCTATGGGGTCATAGTTG | 4719 TGGCTGGAGGTTGTGATTTGG | 7405 AACAAGGCAGCAGTCTCTATGG | 10091 |
| 1120 ACTTTTCTGCAGTGATCTCCATCT | 4720 TGTCGCGGCTAATGGTTTCCT | 7406 CCTTGCCATTTACCTTGTATTTCACT | 10092 |
| 1121 GCCCAGTCAGTCTGTACCCTTT | 4721 GGAAGGAATCACTAGTACTTCTAGCTAT | 7407 GCTACCATGCCCAGTCAAGTCT | 10093 |
| 1122 CCCCATTTGGAGGTGAGGAAATGTAGTC | 4722 AGCATACAAGCAACCAGGTGAA | 7408 GTTTCCCATTTGGAGGTGAGGAA | 10094 |
| 1123 TGGAGCTGAAATCAACACTGCTT | 4723 TGGATAGACCGTTCATGCCATATCTA | 7409 GGCAAAACCCAAATGGACGATGA | 10095 |
| 1124 ACCTGGGCCTGCCTGTATGA | 4724 GGATAACAAGGGGCCAGATAGTG | 7410 CCACACTCAGGGATTCTTGGAACA | 10096 |
| 1125 TCTCCAGTTTATAGTGGGTGAGACT | 4725 GCGAGGGGTCTACTCAGA | 7411 AATTTGTGACAGGCATATGCACAAT | 10097 |
| 1126 GGTCACTCTATGTGCCTCTGTGTA | 4726 CATGAGAAATAATAAGTCATTGCTGCTTCA | 7412 GTTTGTGTCTGCAATGATTATGCAAAA | 10098 |
| 1127 GCTCAGCTGTAGGGAGATTGTTCT | 4727 GGTGGAAGAATGAGGCTGTACCTT | 7413 CAACTCCATCAGCTCAGCTGTA | 10099 |
| 1128 ACTGTTTCTGTCAGGGCCAGAT | 4728 CAAAGACTGTATCTCCATAAAGCCTAA | 7414 TGCATATATCTTGCAGTAACTTCCCATT | 10100 |
| 1129 CCTTGCTTTTGGTCTGGTTTGG | 4729 ATGTGAAGGTAGAAGCATGTGTCT | 7415 CCCAGAAGGCTTCCAATTTGAACAATA | 10101 |
| 1130 TGGCCTGGGCCGTGTTAGAAG | 4730 TCCCTCGCTCATCCCACTT | 7416 TTCCATGGCCTTGGAGAAAATAAC | 10102 |
| 1131 GGTAGGTAGAGGGTAGGTTTTGTACA | 4731 AGCTTTTGACAGGACCTCATTCAA | 7417 GCAGGGAAAACTGAGGAAGTAGATG | 10103 |
| 1132 GCTTTAGGAATGCCTGGGATGCA | 4732 CCGATCCAAGTTGCCATCCT | 7418 GCACTAACCTGCTTAGGAATGC | 10104 |
| 1133 CCAAACTCTTCCCCTAGGTTTATTTGG | 4733 TGCTGCAGGGTTTTGGTGATA | 7419 TCTCCAAACTCTTCCCCTAGGTT | 10105 |
| 1134 CTCTCTAGAAACCTGTCTTCATGGGTTA | 4734 TGAGCAGTGACATTGTAGTTAAAGCT | 7420 GGCCATTTTTTCCCCTCTAGAAACC | 10106 |
| 1135 GGGTCCAATGGCATTTCACTGA | 4735 AGGGACTGAGGAACAGCAGTAATG | 7421 GTATGGATAAATAAATGAAGGGTCCAATGG | 10107 |
| 1136 CCTCAGGGACTAAGTTCTCATTTCC | 4736 GGCAGCTTCCAGGAGTAAAGAG | 7422 AGCTCCCTCAGGGACTAAGTTCT | 10108 |
| 1137 GTGGGAAGGAAATGGAACGT | 4737 TGATGGTCACACAGCTCTCATAGG | 7423 CTGTTTGTCACACTGGGAAGGA | 10109 |
| 1138 CTCTGTTCTGCCTTGCTGAAAGT | 4738 TGACTGCAGGGTGTGACTGT | 7424 CTCTCCCACTGCTCTGTTCTG | 10110 |
| 1139 TGGGGTCACTTGGAAGATTGGA | 4739 CCACATGCTAGGCTGGGTAGA | 7425 GGGCATGGGGTCACTTGGA | 10111 |
| 1140 TGTAGCCATTTCCCCTATCTAGGT | 4740 CCAGATGGAGTGGGGTAAAATCAC | 7426 GAAAGTTTCCAGTTTGCTAGCTTGTA | 10112 |
| 1141 CTTCAGGCTTGGACTAGAAGTACAC | 4741 CAGTTGGCAAGCTGGAGACT | 7427 TCTGGACTTCAGGCTTGGACTAG | 10113 |
| 1142 CCAGATCTTCATTGCGCCCTCTGAT | 4742 TTGTCCCTGAGTCAGTGGCTTA | 7428 CCACTGAATAGGGGAAAATGGT | 10114 |
| 1143 CCAACCAGCTATGCTACCATTTCTAC | 4743 CCTTCAAGCCCTCTTAGTAGGCATAA | 7429 GCTTAGACCAACCAGCTATGCT | 10115 |
| 1144 GAGAGATGGTTCCTATCTCTCAAGCT | 4744 CTGGTCCAGCTGTTTCCTTTCTGT | 7430 CCACTGCAAGAGAAGATGGTTCCTA | 10116 |
| 1145 CTGTTGATTGGTGTGAATGGTAGGA | 4745 CCCTGTCCTTTACTCCTAAGAGTCT | 7431 TTTACAAAGTTAACAGAGCTTTCTGTTGAT | 10117 |
| 1146 CACAATACCTGAGGCACCTAGTG | 4746 TCACAGTTCAGCTCAGTCACT | 7432 TTTCCAAGAAGAGCCACAATACCT | 10118 |
| 1147 GCTGAGGCACTGCCTCACA | 4747 CACTGCTCCATTTTGCCTTAGCTTTT | 7433 TCCACATGCAAGCAAAGAAGCT | 10119 |
| 1148 AGGCCATCGTTGAAGCCAAT | 4748 CCTGCTGAACACCTTGTTTATAGTG | 7434 TGAGGTACTAACTCAGGCCATCGT | 10120 |
| 1149 TGGAAAACCCTTCATTCAAAGTCTGA | 4749 TGGGTTCTGGGGATTGGAGAGA | 7435 GCCCTAGGAATATTGGAAAACCCTTCA | 10121 |
| 1150 CACCCGGAGCTGTTGTTTGGA | 4750 CGGTGCAGAGGATGGTGTGA | 7436 GCCTGTGTTCTCACCTGTGAAATG | 10122 |
| 1151 CTGTCTGCTCAGCACATGGT | 4751 TTCTGTCACCCCACACACTTG | 7437 GGCCCATGTAGTGCCTGACTTTTG | 10123 |
| 1152 CCTCTCTGGGCCTCAGACCAT | 4752 CGATGGAGGCAGATTGTAGCAA | 7438 CACCCACTTCATACACAGGGTTGAG | 10124 |
| 1153 ACAGATCCACCACAGAGATTCAT | 4753 CTGTTCCATGTTGCTTGAGGCTAT | 7439 AGGCCACAGAGTTGGGGAATTACA | 10125 |
| 1154 ACCGTACTGCACTGTCGTT | 4754 CAAAACTTGCAGGTCTGACCTTCAT | 7440 CTTGACTTTGGGCATTGCATCCA | 10126 |
| 1155 GTGAACAGTGTCTAGGCGTTTTGGT | 4755 TCACACACCTGAGAAAGACTGTTCA | 7441 CATGAGGCTCTTCTAGTGAACAGTGT | 10127 |
| 1156 CGGCTCCTCTCTCACCACCTAA | 4756 GACTCTCCAGTTAGATGGACCAAGAG | 7442 GCCAGGCCTCTCTCTCA | 10128 |
| 1157 AGCAAGCAAGCAGCACACT | 4757 GGTTAAGGAGACAGAATGTTACCAGTT | 7443 ACGCTTCTAACAGCCTCTTCTC | 10129 |
| 1158 AGGTGCAGCCCCAAGTGA | 4758 TGGCATGGCAGTGGCAGAA | 7444 AGGAGAAGAGTCCAGTCTGTCTT | 10130 |
| 1159 GTCTTCTTCTCACCCCTACT | 4759 GTTCCCAGACAGTGCTTTATACTCT | 7445 CACACTTGACTCCTGTCTTCTCTCTC | 10131 |
| 1160 TGCTTCTCCGTCACAGCTAAG | 4760 CCTCTCAGAATGCAAATGGTAGGA | 7446 ACCCGGAGCTGTATCCCCATATGG | 10132 |
| 1161 GCTGCCCCTTTAAATATCCCAGAGA | 4761 TGCAACGAACTTTCTCCTCTAT | 7447 CTCCACCCTTCCCCTTGACATTT | 10133 |
| 1162 TCCAGCAGCTAGTAGGGAAGCA | 4762 AAGTCACAGGGGTTGGTTTCCA | 7448 TGCAGGGTCCAGCAGCTAGTA | 10134 |
| 1163 TCCCCATGCACACACCCTCTA | 4763 GCAAAGTTCCTTACGAAGTGAGATGGA | 7449 TTGGCCAGGAATTCTCCCTTCCT | 10135 |
| 1164 TTACATTGACAGCAGGGAACAGAT | 4764 GGCTGTGCATCTTAGGGTCATGATA | 7450 GTGCAAGAGGATCGTATTCATTGACA | 10136 |
| 1165 CCGAATGGCGTCATTGATGATTT | 4765 CTTAGTTGGACCAGCTGTCT | 7451 GGAAAAGGAATCCTGTTAAAGCCCAAT | 10137 |
| 1166 AAACCTGAAGAGTACGTTTGGTTTC | 4766 ACCAACATGCAACAAGGACACA | 7452 AACATGCTATCAGTGAAAACCTGAAG | 10138 |
| 1167 GAGCCCCAGTCTCCTCCTTCT | 4767 TCACCGCAGCCTATGAGTAGGT | 7453 CACCTCTCACCCCAGTCT | 10139 |
| 1168 GAGGCACTATCTTGCTAGGATGTAG | 4768 GGCTCTATCCCTTGCCCCAAT | 7454 GCAGGAAGAGGCACTATCTTGCTA | 10140 |
| 1169 AGGTTGAATAGTCTCTGTAGTTTGCA | 4769 AACCCACAGAGCCTGACTTG | 7455 GCGTTTGAGCTGGGACAACCTACTA | 10141 |
| 1170 GCTTCCATATAGGCTTAGCATCTCT | 4770 TCTGTCACAGTCTGCCAACCTA | 7456 GGTTTTTGTTCTCTGTTCTCATTATAGG | 10142 |
| 1171 GGAGAGAATGATCATCACTTCTTCTC | 4771 GGCCATCATCCAATAGGGTTTG | 7457 TCCAATCAGGGAGAATGATCATC | 10143 |
| 1172 CTGTCACTGACAGTGCTTTCCT | 4772 CAGTGTTATCTTAATGGGAGCACCTA | 7458 TGGGAGCTCTGTCACTGACA | 10144 |
| 1173 TCCAGCATAGGGGTGCCATTGCA | 4773 CCCAGCTGTATCTCAACAGGTAAGAAG | 7459 TCCAGGCTGCATGTCCTTTTT | 10145 |
| 1174 GAGTTCTGAGAAATGGGCCTTGCT | 4774 AGGACTCCAGCACTCTGAGGAA | 7460 GGCCCCTGACCCACACAGTAACTTCCT | 10146 |
| 1175 TGATTGTGCCAGCTGACTGT | 4775 GGACTGCAAAAGACTGAATGATAAGGT | 7461 CTCAGTTTATCAGCATGGGAGTGA | 10147 |
| 1176 TGTGTGTCTCTGTCCAGAGTCA | 4776 AGTGCTTATAGGTCCTAATGCA | 7462 TCTCCCTGGTGTGTCTTCTGT | 10148 |
| 1177 GGAGAGTAGGGATTTTACCTTTGTGATC | 4777 TCCGTTTTCAGGGCTGGGATAA | 7463 GCACAAGGAGAGTAGGGATTTTACCTT | 10149 |
| 1178 GTCATTGACATGGCCACAGAGATTAATA | 4778 CCTCGCTAAGCTGTCAGTAGCAT | 7464 GAGCACTGACTGTCATTGACATC | 10150 |
| 1179 GATATTGCCAAACCTCCCTCAGT | 4779 GTTCAGAGCTTTGCCTAGATCTCA | 7465 CCTCTGTGCCCCTCAAGTTG | 10151 |
| 1180 CAGTGAATCCAATGGGCCATTG | 4780 GCAGGGCAGAAGCTACACGA | 7466 CCAAGCCTCTCAGTGAATCCAA | 10152 |
| 1181 TGTCTCTGTCAATGCTAATGTC | 4781 ACAAACTACATGTAAAGCACAGATAGTAC | 7467 GATGGAAAAACCTATGAGTTCTAGGT | 10153 |
| 1182 AGGAGTTAAATAACTGCCTGAGCTA | 4782 CAAATTGCCTGGCTTCACATTGG | 7468 TGAAACCAAGGCCTAGAGGAGTT | 10154 |
| 1183 TGCTCCAACCCCACAGTAAAGTC | 4783 TCTCACCTCACTGTCATCTCTGT | 7469 CTTATCAGCAGGTACTACGCTCCAA | 10155 |
| 1184 GCAGACAAGGATCCAGTTGCAA | 4784 TCAGGCCTCACTGACACATCA | 7470 CCTGCCTTCATTTCTGTGAACAG | 10156 |

| | | | |
|---|---|---|---|
| 1251 CCAAACCATTGGCCTGTAAACTTTCT | 4851 AGAGGTGTAGAGTTATTTGCACTGTATC | 7537 CCATGCTATGAATTCTACCAAACCATTG | 10223 |
| 1252 GACAATGGACTGCCATTGC | 4852 ACCTCTGGGGCTTGGTATACAT | 7538 GCTGAGAATGACTTCCATCTTCTTG | 10224 |
| 1253 GACTACCTTCAACATCATGGGATCA | 4853 GATGGAGAGAGATGGTCCAAAGAC | 7539 CTGGGACCATCTACCTTGATCATC | 10225 |
| 1254 GGGGGTGTAATCACAGCTCTGAAT | 4854 GTAAGCCTGCTGGAGGATGAA | 7540 AAACCAGGAGGGGGGTTAATCA | 10226 |
| 1255 TCTGAGACATCTTCCTCGTTTGG | 4855 CCCTTCCCTTGAATGTGTTGAAAGTG | 7541 CCTGGTGTGGTGGTGTTTTC | 10227 |
| 1256 GGGTGAACCTGGGGACACA | 4856 TCAACCCCATCTGAGGACATTGAG | 7542 TCCTTCATATCACCCTGCTGACA | 10228 |
| 1257 TCCCTAGCTCTGAGGGTGAATGT | 4857 GCAGAGAAGAGAACAGCTGCTTTC | 7543 CCCCATCTTCCCTAGCTCTCA | 10229 |
| 1258 CCTGGCTGCTCCAGGTTAA | 4858 CTGTAGGACAAGCATGGAAGCA | 7544 AGCCAAGCGGGTTCCTTTC | 10230 |
| 1259 CCTACCAGAGTCCTGTGTCTCAG | 4859 TCAGGGTTTCAGCTGCTGGAA | 7545 ACTGCTGAAGACAAGGGATTCAC | 10231 |
| 1260 TGTGGACTTTGCTGAGCATAACTAG | 4860 CCAAGATTGTGATGGAAATTCCCAAA | 7546 GTGGGTTTCACTATGTGGACTTTG | 10232 |
| 1261 AGTGGGTGGATAGTCAGGGANGA | 4861 CTGGGATAAAGTGGGGAGCTTAAGG | 7547 GCACAAGGATTAGTGGGTGGNATAG | 10233 |
| 1262 GGGAAACTGAGAGAGAAGCTGAGT | 4862 GCTCTGTCTCCAATGTGTTTTTGTG | 7548 AGGGCTTCATAGAGGGGAGGAAACTG | 10234 |
| 1263 GTTCTGGCCTACCCTTGTCA | 4863 AGCACGCAGCTGCACGAGTCAAA | 7549 TCCCCTTGCCAGGAGGTTGT | 10235 |
| 1264 GCTCACAGGTACACGGAAAATGG | 4864 TGAGCCCTTGAATTACAGGAGAGA | 7550 CCAGAACTGCTCACAGGTACAC | 10236 |
| 1265 AGAGGAGGAGAGAACAGGACAGT | 4865 TCCTCCCTTGACCCATGTTCT | 7551 GTGGAAAGAGCACACACGAAACA | 10237 |
| 1266 AAATGCCCCTCTTGCCTATGCA | 4866 GGCCTGAAGGTAATGATTCTTATCACA | 7552 TTTCCACCAAATGCCCCTCTTG | 10238 |
| 1267 TGCTCTGGGCTGTCCTAAATT | 4867 ACACAGCAAAGGCAGGCTCTT | 7553 AGGCCCACTGCCATTTGCT | 10239 |
| 1268 GCAGTCCTGTCATCCCTCTGTTAATG | 4868 CAGAACCTGGAGCTGTGAATTCA | 7554 AAATGCCGCAGTCCTGTCAT | 10240 |
| 1269 AAACCACCCAAGCCAACCT | 4869 ATCCCATCCGGACTCAAAGG | 7555 GCTGTTTCTTCCACGAAAGGAAACC | 10241 |
| 1270 GGTGTGAATGGCAGCCCTCTAAATG | 4870 TGCCAGGTTGCATACTACACAAC | 7556 TGTACCAATCTGTCTAGGGTGTGA | 10242 |
| 1271 TTGGAGGGGTGGCCCTTTGCT | 4871 GGGTAACAAATGGGTCAGGTATATTGG | 7557 CCAGTGAGGACCTGCATGATAAATCA | 10243 |
| 1272 CCGGCATTTCTGAACACTGCT | 4872 CCTCTAAATGGGACTTGATGGGCATTTAA | 7558 AGCTTGTATAACTCAGTTTCAAATGAAGAC | 10244 |
| 1273 CTGCAGCCCACTAGAAATTACACCTCAT | 4873 GCTCCGTCTGTCGCCTGTCATCT | 7559 ACAAAACTCCACAAAAATTCAACACGAT | 10245 |
| 1274 TGGTGAACTTCTCCAGCAGTTG | 4874 GATGTGAATGATGTGTTACCGTAACC | 7560 ATAGGGGCCGCTACTACA | 10246 |
| 1275 TGTGTCCCGGCAGACATT | 4875 CGCCTGTCTGTCGAGTAACAG | 7561 GGGCCCAAGAGCTACTGTGT | 10247 |
| 1276 GAATGATAGTAACATAGCCCCATTGT | 4876 ACAAGCTTGGGATGGTCTGCTTGATT | 7562 TTGGGCAAGAGATGATAGTAACATAGG | 10248 |
| 1277 CTCCAGACCCCATTTGATTAGTC | 4877 CAGAGAAGCGCBAGGCAGAAGTTCA | 7563 TGCCACTCCAGACCCCACTTT | 10249 |
| 1278 ATCTTGGTGTGGCCCTTCT | 4878 AAACTGGGTCTGAACTTCGAATCT | 7564 TCCAGGCTTCTCAGGTTTGC | 10250 |
| 1279 CCTTGCTGGACCCACGAATTAACA | 4879 ACAAGCCAGTGTGCCCATTAA | 7565 CTTACTGTCCTTGCTGGAACCA | 10251 |
| 1280 CACACAGCTCAAATTATTGCCAGAGA | 4880 TTGAGCTCAGGAATCCCAAGTTC | 7566 TCAGCCCCAGAGAGGTTCATTC | 10252 |
| 1281 AGGAATTCAGGTGAATATGTTCCAACA | 4881 TGAACTGTGCCTTCCACTGACA | 7567 ACCTAGGAAAGGAATTCAGGTGAAT | 10253 |
| 1282 AGTTGAAAGAATCTCAGGTCTGGTT | 4882 CAGTGGGTTCTTCTTTGCAGTAGCT | 7568 CCTTTGGTTTGTAAGCTGAGGTTTTCA | 10254 |
| 1283 AGTCTCCCTCTAGCCAAGTATTCC | 4883 GCCACCAAAGACTTATGGACTGT | 7569 CCATTATGGGTAAATAAGTCTCCCCTAG | 10255 |
| 1284 CCAGTGTGAGGGTTCCTTTTCTT | 4884 AGGCCAGATTGGATCTCCATGAGA | 7570 TGTCCCAAGGATCAGTGTGA | 10256 |
| 1285 GACTCATCAGTAAATGCAGTCAACTGA | 4885 TCTCGTGCACTGGAAGCAAA | 7571 AGCCTCCACTTCTGGATTCCA | 10257 |
| 1286 GTCTCACTTTTTATGCCGTGGTTAA | 4886 AGCAGTAGCATCTCCTCTCTGT | 7572 CTACGGACTTGTCTCACTTTTATGC | 10258 |
| 1287 CCATCTCACTGCGGAGAAGTTT | 4887 GCCGACTCATTCTCCCTATGCA | 7573 TCACAGCCTGTCCATCTCACT | 10259 |
| 1288 TCTGCTAGGAACGGCTGAGTT | 4888 AGAAAGCAAGCTGCATGGACAT | 7574 TGGCTCTACCTGGAATATCTGCTA | 10260 |
| 1289 TGACCCAGAAGCAGTTGGAGTTG | 4889 GCCTACTTCTCACATCACAGCTCTCTA | 7575 GAGCTTTCGTTTTGACCCAGAAG | 10261 |
| 1290 CAACTTGGGCATCACAGAGCAA | 4890 ACTAGAATGTGGAAACCCTAAATTCAGA | 7576 CCTTACACCTTAGGGGAAAAAATGTAC | 10262 |
| 1291 CTTGGGGAAATACAGGGTCATTCT | 4891 GCTTCCAGGAATCTAACCCTGTA | 7577 GCTGCTTAATGGGATGTTTTGCA | 10263 |
| 1292 CTCTTATGCCTTGGCCATACTCT | 4892 ATCCTGGGAGTTGAGTTCTGAG | 7578 CTCTCATCCTACCCTGACTCTTAGC | 10264 |
| 1293 CCATCCTCGTGACTGTTCCTTTCA | 4893 CCATGCTTCAGGCTGCTGTAAGA | 7579 CCATCAGGCTGATGCCAGAGCTGCTTATAG | 10265 |
| 1294 TGCTTCTTCCTTCCTAGCTACCA | 4894 AGGGTGAGAACCGAGTGCAT | 7580 GCTCCTTCTAGTTTCGTGCCTTTCT | 10266 |
| 1295 AAAAAGAGAGAGAGGAAGCATTGG | 4895 GCACCTCACCTTCCCCATCATT | 7581 GATTACCCTCATGAATCCTTTTCCAA | 10267 |
| 1296 CTTGGTCTTGCGCTGAGAGA | 4896 GGCTGTGGTATTGAACCTCCAA | 7582 CTGTACGCACTTTATAATACCTTGGTCTT | 10268 |
| 1297 GGACCCTAAACCGTTTATGAATCCCTAA | 4897 GGTGAACAGGTCATGTCGACTTGA | 7583 TGGGGTGTCCACAGTACTCA | 10269 |
| 1298 TGGTGGTTTGCTGTGTGTTTAC | 4898 TGTCCCTCTGTCTCAGCCATGTG | 7584 GCCCGACAGAACAACCT | 10270 |
| 1299 AGAACCTACCCTGAGCACAGA | 4899 TGCTGTCAGGCCCACTCT | 7585 AGCCACTCTCAGAGAAGCTA | 10271 |
| 1300 TCTGTTTTGAGGATGGCTGACA | 4900 GCTCAGCAGGGGATTATTCTACA | 7586 GCCAGATTGCAGAGTTTCTGTTT | 10272 |
| 1301 GGTCTCTCAGGTGTGCTCAGTAGA | 4901 TGAAGCCTGGGTGTAGCCTTG | 7587 AGGATGGACTGGTTGCCCCGTA | 10273 |
| 1302 AGTGTCAGCTTTTCCCATGGT | 4902 CCAGCACAGGGTTGGATACC | 7588 CTCATGTACACAAGTGCAGCTTTT | 10274 |
| 1303 ATGAGTACAGGGTGGGGACAT | 4903 GCCTTGGCTCACAGAGTCATCT | 7589 GCCAGTATGACATTTAGAGATGGTCT | 10275 |
| 1304 GGTGAGGCCCCTTGATCCTTTT | 4904 AACCGGTGTGAGGCAATACC | 7590 CCTGAGGTGAGGCCCCCTTT | 10276 |
| 1305 GCCTCGGAAACTGTCAGATGGT | 4905 CGAACGCTGGTTCTTCTTTGC | 7591 CGTGGCCTCGGAAACTCT | 10277 |
| 1306 GCTACTATGTAACATTTCATATGGCAAAGA | 4906 GGATTCGGCTTCGGCTATCT | 7592 GGGTCCCACACAATACCCTTTAGT | 10278 |
| 1307 TGTCTGAATCTAAGCTTTTCTGCATAGA | 4907 GTGGCTTGGGGTAGATTGCA | 7593 GAGTTCACATGTCTGAATCTAAGCTTTT | 10279 |
| 1308 CAAAACAGCTGGTGCTGCTCATC | 4908 ACACACAGACAAGCAATGTTCATTGA | 7594 ACTTGCTGGAGCCTCCCTAA | 10280 |
| 1309 GTGGCAGGTCCAGGGATCT | 4909 TGGGGTCAGGGGAATGTGGAT | 7595 CACATGTCAGTAGGGCACCAT | 10281 |
| 1310 AGGCCTCCTAACAGGTATTCAGA | 4910 GGACACACAGCACTCTAAAGCT | 7596 GCTGGATCTCCACTCTCTTTGAA | 10282 |
| 1311 GCCACCACAAATACACTTAGAACTC | 4911 CCAGTGAGTGGTATCTGTTGGAA | 7597 GACTTGCAGCCACCACAAATACAC | 10283 |
| 1312 CCTGCTGGGTATCTGTAACAATGCA | 4912 CCCTTTCGGAGTCTGACTTCC | 7598 CCTGCCTGCTGGGTATCTGTA | 10284 |
| 1313 AGGGATTGGCTTATCTCCTCTGA | 4913 GATGCCTTCTCCTGCTAGCAA | 7599 TGAAATGCTTAAAATAAAGGGATTGGCTTA | 10285 |
| 1314 ACAACAAAATAGGGCAGGTCCTA | 4914 TCCACTCCCCTACCTTTCCAT | 7600 GGTGTACACAGAGTATACATGCA | 10286 |
| 1315 TGNTAACTGTTGACTGTTAATTCCACAGA | 4915 GCCAGTTTGCAACCTCTATGCT | 7601 AAACTCCAGTGAACTTTCGATAACTGTT | 10287 |
| 1316 AAGCAGGCGGCAGAACTAGAT | 4916 GCGTCGGCGCTGGATGTCA | 7602 AGGCTACAGCGCGGCAAA | 10288 |

| | | | |
|---|---|---|---|
| 1647 AGGGAAGGAGTGTGTGAGATTCCA | 5247 CCAGGAACTCTAGGGAAGACAGAA | 7933 TGCTCAAGGGAAGGAGTTGTG | 10619 |
| 1648 TGAACTGGAATTGCAGTAACAG | 5248 CACCCAGATAACACACTCTGGAA | 7934 GGGAATAGGAGTTAGATGAACTGGAATTC | 10620 |
| 1649 GCAAAGCCTTCTCTCGCACATT | 5249 CAGCAAGCCTTCTTTCTGGTCAA | 7935 AAGAGGGAGCAAAGCCTTCTC | 10621 |
| 1650 CCTGTCCATTTGTATTAGGTATGAGCTT | 5250 TGCCAGCGAACCCTAGAAGGA | 7936 CAGCACCTGTCCATTTGTATTAGGT | 10622 |
| 1651 GGGTTACCTAGGAGTCAGTATTACTAAGC | 5251 ACCAGCCCAATATTATCCCCAATATG | 7937 CCTGAGCATTTCTAAATGATTGTGGAAT | 10623 |
| 1652 GGTGGTTCCAAAGAAGGGATCAGA | 5252 AGCCCAGATTCCTGAGGGCTTTA | 7938 TGGGAGGGTGGTTCCAAAGA | 10624 |
| 1653 GCAGACACTCAGTGCATGTTTGTG | 5253 TGCTCCACTTCAGTGACTAGGT | 7939 CATGCCACTTCAGTGACTAGGT | 10625 |
| 1654 CCTCAAGCCAGTGGTCTCTTC | 5254 AGAGCTGTGCTGCCTTCTG | 7940 GTTCTGGTGTTCTGACCCTCAA | 10626 |
| 1655 TGGCCTAAAAGTGGCCTGCTAT | 5255 GCTCCTTCTATTTTGAGGGTCAAGGTT | 7941 TCCAAGCCCTGGCCTAAAAGT | 10627 |
| 1656 CTGCTAGTCCTTCAAGGGAGAAGGA | 5256 CCTCTTGGGAAACAGCTCTTGG | 7942 AGCAGCTCCTGCTAGTCCTTGAA | 10628 |
| 1657 GAPGTGCTGAGAAGGGTTCAGA | 5257 CCTCTCTCTCCTGATACATTCCT | 7943 GTGAGAACCAAGACCTTCTABTCAGT | 10629 |
| 1658 GCAACTTGTGCTTAAACCTGAAGT | 5258 ACGGCTCTTCCACCCATCA | 7944 GCAGGAAGCAACTTTGTGCTT | 10630 |
| 1659 AGGCGGGAGTGCTAGCAT | 5259 AGGCCCATGTCTGAGCTGGTAA | 7945 CCAGAGGGGATTAAGCACAAAGTG | 10631 |
| 1660 CCTCCTCATTGGTATGTGGTT | 5260 TCACTGTGCCCAGTCTTTGAA | 7946 ACCAACACCTGCCTCATTGGT | 10632 |
| 1661 GCTGAGATTTTGCCCAGTACGT | 5261 ACTACAGGATTCGGACAGGGAAAC | 7947 CTCTTCAGTTGCCCCTTTTGAG | 10633 |
| 1662 TGTATCTTTTGCAGTTACCTCTTAAACC | 5262 GGAACGCTTGTCTTTGCATTCC | 7948 AGCCATTGTATCTTTTGCAGTTACC | 10634 |
| 1663 AGGACCACAACCTGATGAAGTC | 5263 GAAAGGATGTTCATAGGGGACTGAT | 7949 GGAACCTTGAGAAGTCTTCATCATTTC | 10635 |
| 1664 ACCTCATGCGGTCAGGACTCA | 5264 AGGCTGGAGGAGGACACATTT | 7950 TGCTGCCACTGTGACAAAGCA | 10636 |
| 1665 TCTGAATCCCTGTTACATTCTTTCCA | 5265 TGTCTTCATGTGTATGGCTGTGT | 7951 CTGTTTCCCTATCTGATCCCTGTTAC | 10637 |
| 1666 CCAGAGTATTTGTCTCCAAGCTATCC | 5266 GGGTCAACAGATGCATGTGAAG | 7952 AAGAAACAAACAAACAAACATTAAGCTGTCTT | 10638 |
| 1667 GGCAGTAAGGAGGCCCTGCTA | 5267 CACCACACCTGGCCTATTTTCCT | 7953 AGAACACTAGCAGGCAGTAAGGA | 10639 |
| 1668 AACCTCTATTCGCTGCGTGAGT | 5268 ACCAGGTGGCTGGGTGACAT | 7954 CCAAACCAACTGAAAACCTGTATTGG | 10640 |
| 1669 AGTTCTGCTCTGCCGCTACCA | 5269 CCTAGCGATCATGATGAACTGCTA | 7955 CAGGAGCCGGGTTTCTAGTTTCTG | 10641 |
| 1670 GGGTCTAGAATGGATTGCAGCTGTT | 5270 CTGTCTTATTTAGGTGCATAGGGTTATG | 7956 TTAGTGTATGGGGCTGAAATGGATTG | 10642 |
| 1671 AGGCCAAGTCCCAGGTCAA | 5271 ACTTCCCAACCCACTCT | 7957 GCCTCTATGCCAGGCCAAGT | 10643 |
| 1672 TGGGCCCAAGCAGGACTGT | 5272 CAGCTCCACGAATTGCTCTACT | 7958 TGGGAGCATGGCCTGATGGA | 10644 |
| 1673 TCAGTGCATGGCCTCTCTCT | 5273 ACCTGGGTCTTCATTCTGGAGAGA | 7959 TGCCATTCCTCACTCAGTGCAT | 10645 |
| 1674 TGTGGCCTTCGAGACAATTACTG | 5274 BCTCTTTCCTGCTTCAACTGCAA | 7960 CCATTGACATGTGGCCCTTCGA | 10646 |
| 1675 CCTGCAAACCGTTGACAATTAGG | 5275 CCCTAAAACACAACCTTGATCATGCT | 7961 AGCACCTGCAAACCGTTGA | 10647 |
| 1676 AAAATCCACATAGATTTCCAGTGTGAGA | 5276 CCTTCCCTCAAATCACTGCTTGCTT | 7962 GAGGAGCACGAGAGATGAATCTG | 10648 |
| 1677 CCATAGGGATGCTGACATTTGCT | 5277 AGGAGGAACCCAGCAAAGTAGG | 7963 AGTCAAGCCCCTCTTCCATAGG | 10649 |
| 1678 CTGCAGGCTCAAAGTGATACAGCTA | 5278 AGTCAGGGCCTGAGTTCTAGTC | 7964 GGACAGACAATATTGGTCCCCATT | 10650 |
| 1679 GAAAAGAACAGAGCTCCCATGCT | 5279 CCTGGAAGACAGAAAGCTCATTCC | 7965 GGAGAAGGGTGAGAAAAGAACAGA | 10651 |
| 1680 CACGAACATCAAACTGACCAGCTA | 5280 TCCCCCATGCCTTCCAAATC | 7966 GGTGGAAGCTCACCAACATCAAAC | 10652 |
| 1681 GGPTGTAATGGAAATACAGCTTCAGTTG | 5281 CTCTTGTTGATTGGACTCTGCTAGTC | 7967 CATAAAAGTAGGGTTGTAACGAAATACAG | 10653 |
| 1682 CTGGCTTCAAGCTCTTTCGAA | 5282 TGGAGGGACCTGGAATTCCATGT | 7968 GCTGGCTGGCTCCAAGCT | 10654 |
| 1683 AAGGTCTGCCTGGTTTCTATGG | 5283 GGGATCCATAGTTACCCTTCTCCTA | 7969 GTACCCTTTCCCCAGAGCTTAAA | 10655 |
| 1684 AGAGTGAGACTTAGGAATCATTCATTGG | 5284 CCCTACCTCTTAGCCCAGAAACT | 7970 AGCTGTAGAGTGAGACTTAGGAATCA | 10656 |
| 1685 CCCTCAGTTTATATATGGGTTAGGA | 5285 CTGCAGTGTCACTTTACTTCTCTGT | 7971 TTCCTATAACTAACTCGCTCAGTTTACA | 10657 |
| 1686 AGAAGTGTCCTGACGACAAG | 5286 TCACTCTGTCCACTCCTCAGTT | 7972 CTGGCTTCACCATTTAGACAACGT | 10658 |
| 1687 GAGCTGGGGGTTTGTGATCATA | 5287 CCAACCATGGCTTGAGATCTTCAC | 7973 TGTTTACAGAGCTGGGGTTT | 10659 |
| 1688 GGACCAGGTTCTAGCAGTGAGA | 5288 ATTTCACGGCAGAGGTGTGT | 7974 CCTGTCTGTAGGACCAGGTTCTA | 10660 |
| 1689 GCAGACCTGTCAAGAAGACAT | 5289 GGCTGGTACTGTGGGTGATTACAA | 7975 ACACAGCTCCAAGTAAATGATAGGAA | 10661 |
| 1690 GCCATGCGCCCTCTGAAAGCA | 5290 GAGAAGGCCTGCGTCAGATCCT | 7976 GGGGGCTTAAGCAAGAAACACT | 10662 |
| 1691 CCAGCGATGTTCAGGGATGTAA | 5291 GCTCTTTCACATGTGGGAGTAGCT | 7977 GTCTCAAACACACCATGTCTTTTC | 10663 |
| 1692 GTGGTCCTTCCATGACTTGTCA | 5292 CCAGGTCATGCACAAAGACCTA | 7978 TGCTCCAGTGGTCCTTCCA | 10664 |
| 1693 AATGGACCCAAGGCCACATG | 5293 CGAAGCCATGTTTAGTCACTTAGT | 7979 AGCAGTGGTTGAGGAATGGA | 10665 |
| 1694 CTGCAGGGGATTAGGGAAGA | 5294 CAGTGGTTCTAGGGAAGTACACTT | 7980 TGTTCAAACATACAGTAGTCTCACATGGT | 10666 |
| 1695 CGCTTCCACCTCTTTTGACTGATTC | 5295 CAATGCATGTTTTGGAGACTGGAGGAT | 7981 AGCCGCTTCCACCTCTTTTG | 10667 |
| 1696 GGCTGGTGCAGTAGGAAATTAACC | 5296 CAGCCTTCCACAACATGAACCA | 7982 AAAGATGGCTGGTGCAGTAGGA | 10668 |
| 1697 CACCTACCTTCAGCCTTTTTAGCA | 5297 CCACTTGCAGAAGAGGTGCAT | 7983 CAGACTCACCCTCCCTCCTTAC | 10669 |
| 1698 CTAGGCAGCCCCCTTCCA | 5298 GTTCCCACACAGTTACCAAGCT | 7984 CGATTATGAGGCCCACCAAGCTA | 10670 |
| 1699 GCTCCTTCCTACTGGCATTCCT | 5299 TGCACTAAGGAAAAGGGAACAC | 7985 GCCCATCTGCTCCPCCTACT | 10671 |
| 1700 TTGATGTGTGCACTGGKAGATG | 5300 CCAATTGGGGATTCAATGCTACTT | 7986 GGCACAAAACATTGATGCTGTGACT | 10672 |
| 1701 TGGGACTTCAGACCTGCATGGT | 5301 CAGTTACGCTCACTCGATGGT | 7987 AGTCAGCCATGGGAAGGAA | 10673 |
| 1702 CATTACTCCACCAGTGCAAATCTCT | 5302 GCATGAGGACTACTCTGGGTCTATTG | 7988 GAACCCTCCTCTGAACCTGAATAAG | 10674 |
| 1703 CAGCAGCTGGCACTCACACA | 5303 CCTCATGGGAACAGGCATTCTT | 7989 CAACTGAAAAGGACTAGAGGTAGCA | 10675 |
| 1704 CCCAATCAAGCAGCCCTGAAAT | 5304 CAAGCAGCCTGAGGTAATCTCT | 7990 TCCTCCTTGCATCCCAATCAAGCA | 10676 |
| 1705 CCAAACAGGAGGCAGAAAATGTACCC | 5305 CCTTACTGTGGGAGTGACATGGT | 7991 CCCCCAAACAGGAGGCAGAA | 10677 |
| 1706 AAGGACTTCAGGGCAAGTG | 5306 AGGTAACCGAGGCTGGGAGTT | 7992 CCATCTCCATGTTCAGAAGGACTT | 10678 |
| 1707 CAGTAGCTGTCAAGTTTTTCCAGAAC | 5307 TTGAGCAGGACCATCTCCTTTG | 7993 CGTGCTAGAGATACAGTAGCTGTCAAG | 10679 |
| 1708 GTTTCCCCCTTTACCAGGAATCA | 5308 TCAATAAATGGCAGCCACCATCA | 7994 AGGATCCCGCCACAAAGGA | 10680 |
| 1709 AACTGCCCAGAACTGCCACAGAG | 5309 TGCCTGCATCTCCTCTTT | 7995 ACACATTGGAGACCCTCTTCCAGAAC | 10681 |
| 1710 CTATGCCGAGCACCACATTCTT | 5310 GGAGGTCAGACACAGGACAAACAA | 7996 AGTGGGGAACATCGGCTATGG | 10682 |
| 1711 GAAGGAAGAGACTGGGCATT | 5311 TCCCCACCCACCTCAACA | 7997 CAGTGTGCAAAATATATTCAAAGATACA | 10683 |
| 1712 AGTCCCAGTACTATCCCAAGA | 5312 GCTGCCBGTGTTAAAAAACCATGGT | 7998 ATCTCAGCGTCCTGCAAGGA | 10684 |

| | | | |
|---|---|---|---|
| 1845 GGGTACAAGCTCAAGTTAGAAGTACAG | 5445 GGCTGAACCTGAGGTTTTCACT | 8131 AGTCTGGGTACAAGCTCAAGTTAG | 10817 |
| 1846 GGTAAGACAGTTTTCCCTACTCTTCTC | 5446 CCAAAAGAGATCCCATCCTTCCA | 8132 GGTAACCAAGAGGTAAGACAGTTTCC | 10818 |
| 1847 TGATGGCAGAGCAAACCACAAA | 5447 AACCCTTCCTCTTCCCAGATGA | 8133 CATCTTGATTTGATGGCAGAGCAA | 10819 |
| 1848 CAGGGGCCTCATACTTCCAT | 5448 TGGGGACATTTGCATCTCACAT | 8134 ACCAGATGATCAGGAGCACAGACA | 10820 |
| 1849 AGCTGCAGTGGTTGGAATTGG | 5449 GGTTCCAGAACTGTTCGAATCCT | 8135 TCAATCCCAGCTGCACTGGTT | 10821 |
| 1850 ACAGGGTGAGGAGACTTTCTGA | 5450 GGTTCCCTAACGCATCCTTTCAC | 8136 GCTCCACAGAAGCTACCTAGGA | 10822 |
| 1851 CGGCAAGAACATCAGCTATGTTACCC | 5451 CTCCTGATGGTTAAATCGTGGAAGAC | 8137 CATTTGTGTTAAFAAACGGCAAGAACAT | 10823 |
| 1852 GCCCAGATCCTAGAAAGAGATGTG | 5452 CCAATCCCCGCCAGTCT | 8138 CCTGAGCCTTGTGATCTTCTGGAT | 10824 |
| 1853 TGAGTTGAGAGCCTCAGACTTCT | 5453 GGCAGGAAATGTTTCTGCCTAAGC | 8139 TGGGCCAAGTCATGTAATGAGTT | 10825 |
| 1854 AGAGCCCCTCTACCCCTCTCT | 5454 TGGCAGAACTCAAGGGCCAAAA | 8140 GGCGAGAGAGCCCTCTAC | 10826 |
| 1855 ACCAAGAAGGACACTGACGTTCAC | 5455 TGCCAACTCTGTAATCTTGGCAAA | 8141 TGAACTATGCTCATTTACCAAGAGGA | 10827 |
| 1856 ACTGTCCCCTCTGCATGGTAT | 5456 CAGAGGATGCCTAAGAGTTTTCTAGGT | 8142 CCACCAACACCCTTCTCTACTGT | 10828 |
| 1857 TTGGCTGCTGGGGAGCATTTA | 5457 ACCCCTGGTCTATCGTATGCT | 8143 TGTTGGTTTCCTCAAGTTGTCTGA | 10829 |
| 1858 AGGACAGGACAGAGCTTTTCAG | 5458 GTGGCCCACACGAAGGTT | 8144 CCCTGTCTTCATCCATAGCGTTT | 10830 |
| 1859 TGTGCATTCATAGAGGTGAGGATAAA | 5459 CTGTGTGCACCTCACCGTATC | 8145 GGTCACACTCAGAACAATGTGCATTC | 10831 |
| 1860 TTGGGCATGAACAGCCTACCT | 5460 GACTTTGGGCCCTTTTTGATTTCA | 8146 TCTTTGCCATAATTGGGCATGAAC | 10832 |
| 1861 GCAGCAGATGGCACAATGTAGAGG | 5461 GGACACCAABAATCTCAGCAAGTT | 8147 AGCAACAGAGGAAAGACAAGCT | 10833 |
| 1862 GTGGAATCCATTATAGGGTGTGATACCT | 5462 AGGAATGTGTAGGTGGCTGAGA | 8148 GCCCTTGATGCTGTGGAATCCATT | 10834 |
| 1863 TCAGAGCGTGCTGGCTATGTTA | 5463 GGGGAGTAAGGGTTGATTTTACTTTCGT | 8149 GACTATGTCTGGTGCATTTAAATTGGA | 10835 |
| 1864 GCACAGAACTGTTCAGCTAGAGGAT | 5464 GGACATAACCTACTCGTATGGCAAA | 8150 CAATGGGCACAGAACTGTTCAG | 10836 |
| 1865 CCCTCATCTCCAGATGGCAGA | 5465 CCCAAAAGCCATATGCTCTGTTG | 8151 CCAGCAGGGGGCCATTATAGC | 10837 |
| 1866 GTCCAGTGATCTGTTAGAGAAAGG | 5466 GCCCTGATTACCCTAAGCCAAT | 8152 GCCTTAAGTCCCAGTGATCTGTT | 10838 |
| 1867 GCCCCAATCCTAGCTAATCAGGATCA | 5467 CCAATAGGCAAAGAAATTACTCTGTTGGA | 8153 CCATTGTATAGCCCCAATCCTAGCT | 10839 |
| 1868 CCCTACTGTGTGGCAATGAAGAGA | 5468 TCCCAGGATCACCAGACCAT | 8154 GAGTGCCACCTCTAACTTAGATAATGCT | 10840 |
| 1869 AGCTATGGCAGAATTATCACTGCTT | 5469 TGCTTGGGGCATGGGTTCA | 8155 CAGGAAGTGAAAGCTATGGCAGAATT | 10841 |
| 1870 GCGCACTTCCCTCTCAAACACACT | 5470 TGCTCCCGACCTTGTCAGAGCCA | 8156 CCAGATATGCCCACTTCTCTCTCA | 10842 |
| 1871 GGCCTGGAAGACGGGGTTT | 5471 GGAACTACAATCACCTGAGCTGAA | 8157 AGTGCTGGGCCTGGAAGA | 10843 |
| 1872 TGTCTGATAATTACAACATCTGTGTCATCT | 5472 GACAATTGCCAGACACCAACAG | 8158 GGGGGCATTTTATGGATAGCTGCTTTTC | 10844 |
| 1873 AGTGGCTGTGTGGAAATCCA | 5473 AGGTGAGCTGGGTCAGACAA | 8159 CCTGTTTCACAGACGTGGAAAGG | 10845 |
| 1874 AAACAGGGCTCTTGGGAATGG | 5474 CCACTGCTCTTGAAAAGGCTGAA | 8160 GGCTCAGAGGCCTGTGTTTAGAAAC | 10846 |
| 1875 TGTATGTGGACTGCAAGGTTAGG | 5475 GGAATGAAGAGGGCTTCTCACA | 8161 TCAGTAGCTGGGGCTTGTATGT | 10847 |
| 1876 CCTCCCTGAAGCCCAACACA | 5476 GAGTCTGCACTGCTACATCTCTACCA | 8162 CACAAGTAATGCTTCTGGCTTTCC | 10848 |
| 1877 GGTTTTTGTTTGATCTCACCTGGAAA | 5477 GGGGGGAATAGCACAGAAGGT | 8163 TGCTTTCCTGATCATGTTGATTCCT | 10849 |
| 1878 AAGGCAGGCCTCAGAAGCCA | 5478 GAAAGATGGGCAGAGTTCTTTGG | 8164 GTACAAGACAAAGCGGCCTGATGT | 10850 |
| 1879 TGGGAGTCCAGGGAGAGA | 5479 GGACGCAGCCTTTTATGAG | 8165 CAACCTCCTTCCCTCAAACATAAC | 10851 |
| 1880 CTGATTTACACCCGTGTAATGGA | 5480 GCAGTGAAATGGGCATGCAT | 8166 GAGGTTTCTTTGGGAAGCAAGGTCA | 10852 |
| 1881 CCACCAAGAGGCCCAATGC | 5481 GGTTTGGGTGGGCTAGAAAGC | 8167 TCCAGCCATCCCCACCAAGA | 10853 |
| 1882 CTGAGATCTGTGAGAGGAGATATGTG | 5482 TGCATCTGCTGATCCTTCAGTTC | 8168 GGGTACCTTGACTCTGGAACTGAGAT | 10854 |
| 1883 TGGACAGGGCTGCAATCT | 5483 AGCTGTTGGAAGGGTCAAGCT | 8169 CCCCACCCTTCCAAGACATCA | 10855 |
| 1884 GCTACAAATAATCTTGGATTCCTGACATCA | 5484 CAGCTAGATGATAAGGCCACAATGG | 8170 GCAAGGAGCTACAAATAATCTGGATTCC | 10856 |
| 1885 TCTGCGAAGCTCTCCCCTATGC | 5485 ATGGCTGCAGAGGCCTTGA | 8171 CTCTGCAGCCATGTCTGGAA | 10857 |
| 1886 GAGCCCCCAGCATTCAGTGTT | 5486 ATTTCCCTCCCCCAACATGTCT | 8172 TGTTAGAGGAGCCCCAGCAT | 10858 |
| 1887 TTTCCTCCTGGGTGAAGCAAGA | 5487 AGCCACCCCCTCGACTATTCAA | 8173 AGAACCATAGTGCCTGGAATGC | 10859 |
| 1888 GGGGCCAATCAGCAAATTCCAT | 5488 GGTGCTGAGTGCAAAGAGCAT | 8174 GGGGACCAAAGTCAAGGCATGT | 10860 |
| 1889 CTCATCTGAGGGCTTGAAACCT | 5489 GCCTTGTACCCTGAAAACCTCCAT | 8175 GCCCGAGCTAGGAATCTTCTCA | 10861 |
| 1890 AGGCAGGGGAAACAGAACCA | 5490 CACTCTTCAGGGATCATTACTGTAACT | 8176 TGGGGCAAAGGGCATCAG | 10862 |
| 1891 GTGCTACAGTCAGAGACCTGGGAAA | 5491 CTTGGCCACAGCACTGGAA | 8177 TTTCCCAGGTCACCTTGACTGT | 10863 |
| 1892 TGCTCCCGGGAGTCCATTG | 5492 CCACAGGGGGGTTGGGACTAAA | 8178 TCCACCCCGTCCTCTTGCT | 10864 |
| 1893 CACTAGGATGTTTATCACTGCCATCA | 5493 GCCTAATAAGAAAGTTAGGGTACAAGT | 8179 AGCCCAACACTAGGATGTTTATCAC | 10865 |
| 1894 GCAGGGAGCCATCGAAGGTACT | 5494 GCTTGCAAGGGTGAGTAACTGA | 8180 TCACTCTTGGGACAGAAGGA | 10866 |
| 1895 TGGAAGGGGATGATGGAGTGT | 5495 GTGATGCATGACTATACTTCTACACACA | 8181 AATTGCCTTGCTGGGACCCTTA | 10867 |
| 1896 CTGTCACTGCAGTACTCAAATTG | 5496 GTTGTTATGGTATGGGTGTCTACAA | 8182 CCACCTCATTTTAGAAACCCTGGCAT | 10868 |
| 1897 AGGTCTCACCAGACACAGATTCCA | 5497 TGCTCGTGGTTCTGCAGATT | 8183 CACCCTGTGAGCACTGACTT | 10869 |
| 1898 TGCCTGGGACTTCAGCTAGCA | 5498 GAAGAGGAGTCAGGTAGATGTTCAAG | 8184 CACATGCCTGGTGGTTAATGCT | 10870 |
| 1899 CACTGCTTTATTGTGTCCAGTTGT | 5499 GCTGAGGGAGCCAAGCTTACA | 8185 AGGGGCCCCAGTGCACACT | 10871 |
| 1900 GGGTGCCAAGCTTACAAAGGAAT | 5500 CACGAGACTTGTTGCTTGCTTAGGAGGTAGGA | 8186 ACAGGTTTCCTGTTTAGGAGGTAGGA | 10872 |
| 1901 CCAATGGCCACTCAATATCCT | 5501 GGGAAGATGACCTTAGTTCACACAGA | 8187 TCAGAGCCTGGGATCAATCA | 10873 |
| 1902 AGACCCGAAGCACTGGTAT | 5502 ACCCCTGCCTCCTGCTCTT | 8188 GATGGCCACCGCTGAGAAG | 10874 |
| 1903 TTGAGCATGTACCTAGGGCAAA | 5503 CTGCTCACAACTAGAGATGGACATG | 8189 TTTTGCTTGGACGATGTACCT | 10875 |
| 1904 AGGCCACCATACCACATGCT | 5504 GCCTGTAGCAGGTGGTATGGT | 8190 ACCATGCTACAGGCCACCATA | 10876 |
| 1905 GGCTACACAGTCCATGTCATAAATGC | 5505 AGTGTTTCCAAATACATAGACCACCAT | 8191 CATTAAATGGCTACACAGTCCATGTC | 10877 |
| 1906 AGACTGGGGACAAGATGCCATA | 5506 ACAAAAATCTTCACATATCATGCCACTT | 8192 TGGGGGGGTGATATTACAAGACT | 10878 |
| 1907 GGCCACTGTTAAAAACCAAGTTATGCA | 5507 CACAAGGAAGTGAGGTGATCCA | 8193 GCTGGCCACTGTTAAAACCAA | 10879 |
| 1908 GTTTCCCCTCTTCTCCTTGCCTAA | 5508 GCTCTGTGGTGCACGGGATCTAAT | 8194 AATTCATTGTGTTTCCCCTCTC | 10880 |
| 1909 GCTTGGCCGTTGTTGATTGGT | 5509 TCACCTCCCTGTCCCATGT | 8195 GGGTTAGAGTTTAAGGGTTTGGAA | 10881 |
| 1910 TTCTACAGGGCCTTGGGAAT | 5510 AGGTCAGGGACTACTAGACATGCT | 8196 GCCACAACCAGCTTCTTTTACTT | 10882 |

| | | |
|---|---|---|
| 2241 TCACAGCCAAGCATACCTCTGT | 5841 AGCCAGGTGCAGTATGGGAAA | 8527 AGGACTTTCTTCCCCCTTTATCCTA 11213 |
| 2242 AATCCTGGTAAGATCCTCAGATC | 5842 CTCATGCTTGCCTCTGGACAA | 8528 CAGTCTAGGAATCCTGGCAAGATC 11214 |
| 2243 GCCCATCTCAAGTGGCTCTT | 5843 GACCCAAAACTGAAACTGAGATGCA | 8529 TGCAAGGGCCCATCTCAAG 11215 |
| 2244 ACCGACTGCAGAAGCTCACA | 5844 GGCAAGCATTCTTCCATCCTT | 8530 AACGACTCACCGACTGCAGAA 11216 |
| 2245 CTGTTGAATCCAAGACCAAACC | 5845 CCCCAGGATAGAACATTTCAT | 8531 CTGGAAATCAAAGATTTTACTGTTGAACC 11217 |
| 2246 GACTATACTCACACACAAATTGCTTTG | 5846 TCCAATGCCCACAAGCTTCTT | 8532 CACCTTCTGACTATACTCACACACAAA 11218 |
| 2247 GCAAAAGCAAGATGACTAAGTGTTCGT | 5847 GCTCCCCTGACATCCCACTTTT | 8533 GCAGGTATAGCTTAGCATAATGAGA 11219 |
| 2248 CCTCCAGGGTAGTAGACATATGTGT | 5848 AGATGTTGGGGTTCATAAGGGAAAC | 8534 CCACAAACAAACCTCCAGGGTAGTAG 11220 |
| 2249 AGGAAGCCTTAGGCCTTGTTAGC | 5849 GCCATTATCTCTCCAGGTGTTTACTGT | 8535 GAGCTCTAAAGTAGAAGAGGAAGCTTAG 11221 |
| 2250 GGATGCAACTCACGGAGCAAA | 5850 CCAGGTTGACTGCACACACA | 8536 TGGTGCAGAGATTGAGGCATCTG 11222 |
| 2251 AGGCCTGACTGGGGATGTC | 5851 CTGGACCTTGCTTAAGCACTGA | 8537 ACCTTGGAAGAGGCCTGAGT 11223 |
| 2252 CACCAAGAGATCCTGTCCTCAAAG | 5852 CTGGGTTCTAGTCCTGCTTGTG | 8538 GGTGCTTTGACACCAAGAGATCGT 11224 |
| 2253 GGGAACTCCATCAATATTTGTCCTCGTT | 5853 GCAAGAGGCTGCTACTCAGATTCA | 8539 CCGCAGTTGGTGGGAACT 11225 |
| 2254 AGGTCTCTAAAGCCCAGTTGCAT | 5854 AGTCAAAAGGCAGGAGGCAAA | 8540 ACTAACATTCCCTAGGTCTCTAAAGC 11226 |
| 2255 AATGCTGTATGTAGGTGGAAGCT | 5855 AGAAAGGGCCCACTGGTCTT | 8541 GTGCGGCTGAAAGAAATATACTCT 11227 |
| 2256 GTGTTGAGAAGCTCAGTCTCACA | 5856 CCAATCCACTCCACATACCAGTGT | 8542 GTCTGGACTGTGTTTGAGAAGGT 11228 |
| 2257 CCTTCTGTTAAAGCCACAACTGTCT | 5857 CTCTAAAGTCTCTGGTGTCAAGGT | 8543 CACAAACACAAACTACAAAATCCTTTG 11229 |
| 2258 CCCCCAATATGGGCAACGTT | 5858 TGGTCCTGGCTTCTCTGGCA | 8544 GCAATCAAGACAACTTCAAAGCGAAAC 11230 |
| 2259 CTAAAATAGTATGTGAGCTGCATTGGT | 5859 GCATTCCGAGCACTGAATTGTTAAGTG | 8545 ACAGCTATGAACTCATGACCAGTTG 11231 |
| 2260 TGTAGGTAGTTCCCCCAAACTTTC | 5860 GACTCAGCTTGGGGAATTCTCTT | 8546 TCCTGGATAAGGGTTCTAACATTTTGTAG 11232 |
| 2261 GTGAGGGAGGTAGGGTTTCAAG | 5861 GAGGGGCTACTAGAAGCAAACC | 8547 CTGAACAGGGTCAGGCAGGTA 11233 |
| 2262 CAATCTGGTCTCATTGACGTGTC | 5862 CAATGCCCCTGATAAGCTTTAATGATG | 8548 TCTCCATCCAACCATAAAATCCTATCA 11234 |
| 2263 CCCACATTTTACGGGTGCATGTTC | 5863 CACAAGAGCACCAAATACATCA | 8549 ACCTCTTCCAGTTCACATTTACG 11235 |
| 2264 CTATGGAGTTTGGCCCACAGA | 5864 CAGCAAATGGTCCCACAGGATT | 8550 TTTACAGTGTGTTCTATGGAGTTTGG 11236 |
| 2265 ACTGTTCCTCCGATGGGCAAGTG | 5865 GCCCAATTCAATATTTCCGAATGCA | 8551 ANGGAGCACTAGGCCTCCAAAA 11237 |
| 2266 GGCAATCTACTAGTAGAGGTAGTTCAG | 5866 AAAAGGGATGTGGTGGCATCT | 8552 GGAGACAGGGCATCATTTAGCA 11238 |
| 2267 CCTATTTCCTGCTTGTGGTTACG | 5867 AGGCAACAGGTGGTCAAATGA | 8553 AGATGCCCACAGAACTAAAGCTT 11239 |
| 2268 ATCCACAGCCAGCAAACAGT | 5868 GGCATTACTTCCCATCCTACCAA | 8554 GAGTGCTATCTCCTAAGCATCGTGT 11240 |
| 2269 AGGTTCTGCTCTGGCATTTGG | 5869 TGCCTGTCAGTCTGCATCTGT | 8555 TTGCTCACTGCACCAACGTTCTG 11241 |
| 2270 AGAGATGATGGCAGGGACAGA | 5870 ACAAGATCCAGGGTTGCTCTGT | 8556 TGACGTGATGGGAGATGGT 11242 |
| 2271 GCATGCTCCCCTATTCTGAACA | 5871 TTGGGGTTGTCACCTGTTGCA | 8557 TGACCAGCAATGCTCCCCTAT 11243 |
| 2272 CCCAGGTGCAAAACCCAAAATGTTATCC | 5872 AAGAGGGTACAAGGGAGGCTTCC | 8558 GCACCAGGTCAAAACCCAAAA 11244 |
| 2273 CCTCCCTTACCCTAGTGAGTACCA | 5873 AGAGGAGAAGTGGAGACTATTACAGT | 8559 CCCAGCCACTGATCTCCATTT 11245 |
| 2274 GGCAGTCATTCAAACCTAACTCTGT | 5874 GCACAGTAGGAAAAGCTCTGTTGTC | 8560 GCTCCTAAATGCAGTCATTCAAACC 11246 |
| 2275 TGGTAGGAAGTAAGAGGCAGGTTAGG | 5875 AAGACTCACCTCTCCTTCTATCCTT | 8561 AGGGAGGTGGTAGGAAGTAAGAG 11247 |
| 2276 GCCTAGTGGGTTCAGTCAAGCT | 5876 TGAACCTAGTTCCTGCTCCTATGAT | 8562 CCACACGCCTACTGGGTTCA 11248 |
| 2277 CTGGACTTCAAAGACCCTGATG | 5877 ACCCCTTTCAAGCCAGGATGT | 8563 CCCAGGTATGTGACTGGACTTCAAA 11249 |
| 2278 AGCCCCACACTACTCATCTCA | 5878 GGGAAACCCAACCTCCTGACTA | 8564 CAGCCAGCCCCACACTAC 11250 |
| 2279 CCCAGAACACATGTTAAATTCCCCTTA | 5879 CCTAACCTGCTCTCAAGCTTTTGC | 8565 GGAGGTATTCCCAGAACACATGT 11251 |
| 2280 ACCTGAGCCTTAACCTCAACTCTCAG | 5880 AACCTGGCCACTCCACCATA | 8566 CCAGCAACCTTAACCTCAGCCTACA 11252 |
| 2281 TCTCCAACTGAAACCAATCTAAGGT | 5881 TGGTGGGTATAGGAGGGTGTT | 8567 GAGTCTCTGGCTGTGAAGAAAACA 11253 |
| 2282 GCAAAACCCTGAGGCCTTCA | 5882 TGGAAGAGGGGGCATCTG | 8568 CCTTTCTCTACTTTACCTGCAAAACC 11254 |
| 2283 GCTGATTTCCATTGGCTCACA | 5883 TGTTGGTTGTGTCTCCCATGCA | 8569 CCTGAGTGTGAGCTGATTTGCA 11255 |
| 2284 GTGCAGGAGCATGGGAGATTACA | 5884 ACCTGCATCATGGCCTGACA | 8570 AGGGCGAGGTTAGACATGAGA 11256 |
| 2285 TGCTAGATTCGGAGGCTGGAA | 5885 AGGAGCATGGGCCTCAGA | 8571 TTTGAACTCCCTCTGCTAGATTCC 11257 |
| 2286 TGGCATGCCTTTAAAGCTTGGA | 5886 CCTTAGAGGAACAAGGCCCTGACT | 8572 CATCCCGTCTTTCTCCTGCAT 11258 |
| 2287 GCCTGGTGGATGGCAAGCT | 5887 CAAGACAGTTCCCATCCTGACA | 8573 GGCATGCTGGCATCTTGCT 11259 |
| 2288 CCAACCTCACAAGTGCAGATCTG | 5888 GCCTTGCTCCTCTGCCATTGG | 8574 AGCGCCAACCTGACAAGTG 11260 |
| 2289 ACGAACCTCACATCAGCCAGTA | 5889 TTTGCAGCCCTTGGACATGGT | 8575 AGAAGACACACGAACCTCACATC 11261 |
| 2290 TCCTGCTACCTATGAAGGGTAGGA | 5890 ACTGGTCCAATTTAGTCACCATGAT | 8576 GCAAGACAGTTCTGAAATCACAGACTTC 11262 |
| 2291 TGTCCTGGCTGATAGGAGGCA | 5891 GCTCATTCTTGCCCTCCTGTAAGTAC | 8577 TGGCTTTGTCCTGGCCTGATA 11263 |
| 2292 TGATATCCTGTGTCTTGGTCTTAATACAG | 5892 GCTAAGAGGCTCTAGGTAGCAGTAG | 8578 ACCCAGGGTTCAACAGAACTGAA 11264 |
| 2293 GGACTGCAGGTAAATTTTTGGCTTTG | 5893 GCTCTGGCTGTTTCCTGCTA | 8579 GTGTTTTCTGTAAAGCACTGCAGAGT 11265 |
| 2294 AAGTGTTGCAGTAAAAGACCATACAG | 5894 CTCCTCCCTCTAGTTCTTCGTGT | 8580 GCATAACCAAAGTGTTGCAGTAAAAG 11266 |
| 2295 AGGATGCTGTTGATTGTATGTAGCA | 5895 CCTTCCCTCCTCCTCAAAAGCGT | 8581 CCTTGTTTCCTAATTCAGGGATGCTGTTG 11267 |
| 2296 CACAAGCTCACCTCACTGCTTA | 5896 GACTCGATTGGAAACAAAGCCAAGAG | 8582 CTTCCATCCTTCAGCACCATTTCAC 11268 |
| 2297 TGTACCCCCTTCTTCCCTACAGCTA | 5897 CCCTCTTTTATGGGCATGCATTCT | 8583 CAAGTGTTTCTTTACCTCCAGCAAA 11269 |
| 2298 GCTGTTATAGTCCTGGTGGTTCTG | 5898 AGCCACAGCTCTGACAACAG | 8584 TGGCTGCTGGCTGTTATAGT 11270 |
| 2299 TCCTCTGCTCACTCCCCATTC | 5899 CAAGCAGAACACAGGATAAGAGGAA | 8585 GCTGGAAGCCTCTCAAAGATGCT 11271 |
| 2300 CTAGGAAAGGCCCTACACTGTTC | 5900 AACTTTTGCTCACCGACAGGGTGA | 8586 TCCCTTCTCCTCCCATAGC 11272 |
| 2301 AACTGAAAGCCCACTGCAA | 5901 CACCTGTTTACCTTCCTAGCCTCTT | 8587 TGCAGAGGCTGTAGGATAGCA 11273 |
| 2302 TTCCTGGTGGCTGCAATGCT | 5902 TCCTTGTCTACCTATTGCAGATG | 8588 GGCATGGCTCTCCCTTCCT 11274 |
| 2303 GGCTCAGCTGACTGAACGGTCTAGAC | 5903 GGAGCCCTTGCACCTTGGA | 8589 CCGGTACAATTGGCTTGACTGAAC 11275 |
| 2304 AGCTCAGCTCTTCGCCAGGTA | 5904 ACTTCGAGGAGATGAATCTTGA | 8590 GAAACAGGACAAGCGTCACT 11276 |
| 2305 GCTTCAGCAGCATCACCAGGA | 5905 CTGCCTGCCTGAAGTTCTGA | 8591 GTCTGCAGCAAATACAGCTTCAG 11277 |
| 2306 AATGCCTGGAGGGGTGTGTCA | 5906 GCACGCTCTTCAAATCAAAACTTC | 8592 GGCAAACAAACTGAACACTCATTGG 11278 |

| | | | |
|---|---|---|---|
| 2373 CCTCCATGCAGATTAGACACTGTG | 5973 TCCTGTTGCCCAGTTCTGCTT | 8659 GGCAACAAAATTCTTCACACCTCCAT | 11345 |
| 2374 TTACAGGCGTCAGCATTGT | 5974 CTTCGCTCACTTGAGTCAAAA | 8660 CCCATTTGGCTGACAAAGTACTG | 11346 |
| 2375 CAGGGGATCAGGGAAGTGAGCAAA | 5975 GCACCCTATCATCAGCTTTACAGA | 8661 ACCTTTGAAAGCAGGGGATCAG | 11347 |
| 2376 ACTGGTTGGTTGCCTGGTTT | 5976 TCCTCACCCCAATCTAAGGACACA | 8662 TCTCAAACCCGTCTTTTGTTAACAG | 11348 |
| 2377 GGTGAAACTGTTGGGACGCTTT | 5977 TGTTTGTCGACCATCTGGGAAT | 8663 GTTCAGACTACGGTGAAACTGTTG | 11349 |
| 2378 CAAGACTCTTTTAGAAACGGGATTACA | 5978 ACAGAAATATCTTGTCCTTCAGAGAACT | 8664 GGATTTCCACACAGACTCTTTTAGA | 11350 |
| 2379 AAAAGATCTGTTCTATCAGTACCAAGGT | 5979 CACACATGCCTCATTACCATTAACATC | 8665 CTCCAGGTATCAGAGAGGCTTCA | 11351 |
| 2380 TGGTAATGAGGGTTATCTTAACAGTTCA | 5980 CCACTGATTCAAGGACTTTTGCCTAGA | 8666 ACCGGCTGTTTTGAGAGACAGT | 11352 |
| 2381 CCCTGCACATGTATTCATTCTCAAGCA | 5981 GGGCAAGTAGTCAACGTTACTGA | 8667 CCCCCTAGTACCCTGACAATGTATTCA | 11353 |
| 2382 GCAGGTAGGCCTTTGAGGTGTGAAT | 5982 CCAAGCAAGTTCTATGACTCTGAAC | 8668 GGCAGCACGTAGGCCTTTGA | 11354 |
| 2383 GGACTGGGGAGGTGTGTCAAT | 5983 TTCCCACGTTGGTTCCTTTT | 8669 GGCTTCCTAAGTCAGTTAAGAAACC | 11355 |
| 2384 TGAGCTGTATGGCTGCCTAGTA | 5984 CAGGGTAGGGGCATTATCTTCAG | 8670 TGTCAAAGCTGGGGCTAGATCA | 11356 |
| 2385 GGCTCGTTCTGCCCACTTG | 5985 TGGGATCCAGGCCAGTATTATACG | 8671 CGCCTTTGCCTGAGTTTTCTT | 11357 |
| 2386 TCTGTTAAAAATCTGCATGTTGGGTCA | 5986 CTGCAGTTTGACCCTTTCTACCA | 8672 GCTCGCCTTGGGTTCTGTTAAA | 11358 |
| 2387 CCCGATGGTTTCCTTTGCTCTT | 5987 AGCTCTGGGCTCAGGAAGT | 8673 TCACGTCCCGATGGTTTCCT | 11359 |
| 2388 CTGGCATGAATGTCACTCAGCTT | 5988 CCTCCTCACAGTTAGTGTACACCTT | 8674 GTGTTTCACTGGCATGAATGTCA | 11360 |
| 2389 GTGAGACCATCAAAAGAAAGGAGTCT | 5989 GACTGAGTGCAAACTAATGTTGACTT | 8675 TTGTCCCCTGTGAGACCATCAAAA | 11361 |
| 2390 CTGCCTATTGTTGCCATCAACTTG | 5990 CAGCACTGCTTGGCATGAAC | 8676 AGGAGCCATCTGCCTATTGTTG | 11362 |
| 2391 GGCAAGAAATGACTTCCAATGACATTGTA | 5991 AGGGGAAGGGCAGCTATACTTA | 8677 CTTTTTGGCAAGAAATGACTTCCAATG | 11363 |
| 2392 TGCGAGAGTATAGGTACAGGCATTTG | 5992 TGCTTGCCGGCTTAAGTGTCAT | 8678 CACCAAAACTGCGAGAGTATAGGT | 11364 |
| 2393 TGTTCGGAGGTTGTCTGAGATCAC | 5993 GAGTAATTCAGTCATCCTGCTCTAG | 8679 CGGGTGAGGGAAGACTCCTT | 11365 |
| 2394 GAGCCCCAGTTACTGGTTAATAGT | 5994 CAACTTCTTGCCCCTTGTTTCGT | 8680 ACGTTGAGCCCAGTTACTG | 11366 |
| 2395 ACGAGTCTGTTGGGTCCCTTA | 5995 CAGTCTGTAAAATGGCTCAGAAATTTCC | 8681 GAGCAACATGAGGATGTCTCTTG | 11367 |
| 2396 GGGAGTAGCATACTTCCTTTCAGGAT | 5996 TGCACAGACAGAGGCCAAATTC | 8682 AGGCTGAGAGGGAGTAGCATACTT | 11368 |
| 2397 CATGGACAAAAGCCTTGATGGAAGTATT | 5997 GTGATTCTCATTGCACATTCTTTCTCT | 8683 GTGAAAPCATGGACAAAAGCTTGATG | 11369 |
| 2398 GTTCAGGTAAGTCAAATGGGTCTGA | 5998 CAGACTTCCACTTCTCTAAGTAAGG | 8684 TCCTCCTTTGTTCAGGTAAGTCAAA | 11370 |
| 2399 GCCTTGGCAGGTGTGAATGTGAT | 5999 TGGGACATGGTTGTGACAAGGA | 8685 CACCAAGGCCACCACACA | 11371 |
| 2400 GTTCTTCCAGGCACCGTTGT | 6000 TACTTGCTTCCCAGACAACATC | 8686 TCAGGGCTGCAAGTCTTCCA | 11372 |
| 2401 CTCTGAACCTCCCTGAGACACA | 6001 ATGGCAACCCACTCCTCCCTTT | 8687 CTGGAGTTCTTCGGCCATCAG | 11373 |
| 2402 TGGGACCAGGAACAGGCATT | 6002 TCGGGACACACTCTAGTTTCTCA | 8688 TGCAGCTGGGACCAGGAA | 11374 |
| 2403 TGCCTGGCCGAGGGGTTCA | 6003 CTTTTCCTGAGTGCGCGTTCCTT | 8689 GCAATCCCTTGATCCTGGTTAGGA | 11375 |
| 2404 CAGACCCACAATGCAGCAATTTAGG | 6004 TGCCTCCTCAGGGAAGCAT | 8690 CTTGGTTCAGACCCACAATGCCA | 11376 |
| 2405 TCACCCATCAGCGTGTAGTCA | 6005 GGGGAGCCAAATGCTTCT | 8691 TTTGGCTGGCATCACCCATCA | 11377 |
| 2406 AGCACTGTCAGGCCAAACAT | 6006 GTCCTGCACAGTGAGGACATGTCA | 8692 GCACGATACTGCTAACTGATCTTTTTC | 11378 |
| 2407 TGTGTGGGGACAGCCTCTCTT | 6007 CGCAGCTCTCGTACACTAACG | 8693 GAGGCCAGTGGCACTGTGT | 11379 |
| 2408 CGGACCTTAGAGACAAGCTAGACA | 6008 ACTGCAACTCCTTGAGGTCAAG | 8694 GCCCTCGGACCTTAGAGACA | 11380 |
| 2409 CCCATTTGTTCTCAGAAAGCAAGT | 6009 TCCTTGACCTGGGGATGATGGA | 8695 CCATTTGAGCCCATTTGTTCTCAGA | 11381 |
| 2410 CTGGCCTTGGATCTCTTCAGT | 6010 AAGAGCCAAGCTTGTCAACCA | 8696 TGTGCAAATCCTGGCCTTGGAT | 11382 |
| 2411 TGGAGTCTTCCCAGTCTGTGA | 6011 CATGGACCCAAGACCTAGGATTCT | 8697 GGACACAGATGTAGCAATGGAGTCTTC | 11383 |
| 2412 GAGTTCGAATGGGCTAGGTACTTC | 6012 GTCCCATCTAGGGACCTAGGA | 8698 AGTGACACCAGAGTTCAATGG | 11384 |
| 2413 CCTTTCAGTTCCAGCAGCCA | 6013 AGAAGAGGCAGTGAGAACCTAACT | 8699 TGTTTGCATTGATCTCTCCTTTCAGT | 11385 |
| 2414 GCTGAGGCACACCTGAGAACATA | 6014 CCTAGGTCGCTTAAGTCACAAAGC | 8700 GCTGCACACCAGGAAACAACCT | 11386 |
| 2415 TGTGTGCAAAGCAGGAGACA | 6015 AGTGAAGGCACAGTTTTATCCAGTT | 8701 GCTAGGTGTGGTGTTTCTTGATAGTT | 11387 |
| 2416 GACTCAGTACCAGTTCTTTTCCA | 6016 TCTCTGGGCTTAAAGGGAAAGC | 8702 GAAAAATTGAAAGCACTCTTCCACTCT | 11388 |
| 2417 AGGATGCCTCGGCTAAGGAGA | 6017 GGGAAGTGGGCATAACCTTGTT | 8703 CCTCAGTAGTCATCCCCTTGAGGAT | 11389 |
| 2418 TGGTACCCCTAATGACTGTCAGAA | 6018 GCAGCAAAAATGGTTCTCATCCT | 8704 CCCTCTTCCATATTGGTACCCTAA | 11390 |
| 2419 GTTCCTCTGTCCAGATCTGTGT | 6019 CCAACCTCCAGTAAAGTATCAACTC | 8705 AGTTAGGGCTGGTGAGAAAGGT | 11391 |
| 2420 CAAGGATAGTCGTTCAACACTAGTGA | 6020 ACCCAGCACTGACCTTCCTAAT | 8706 CACTGGTCAAGGATAGTGGTTCA | 11392 |
| 2421 GGGACAGGTCAGGCTTCCT | 6021 CCTCCTTGTCTTCCCACTGCTTTT | 8707 AGGAAGGAAGCCAGCCTTTG | 11393 |
| 2422 ATGGAACAATGAAACATGATGATCAACA | 6022 GGGAAAACAGATCTCCCTTGA | 8708 GACAATGACCATCGTTGATCTCATCTTG | 11394 |
| 2423 ACAGTGCGCGCCACCCCATT | 6023 GTAAAGCTTCAGTCAATCAGTGTCATT | 8709 CAGGAAGTGACCCCAGTTGG | 11395 |
| 2424 CAGAACTCCTGGAACCACTACTTTG | 6024 TGGAGGATTTGGTGCCAGAGA | 8710 ATGACTACTACTGAAGCCACAACTG | 11396 |
| 2425 AGGAACAGAGCGGCAGAGA | 6025 TGACACCCTGCTGCTGTCTA | 8711 CACAAGTGGCTGAATGTCAAGAG | 11397 |
| 2426 ACAATCAGATCTACCACCAACAG | 6026 GTTCTGAAGGGCATATGGCTTCA | 8712 AGATTTCATCCTACAGACAGATCTAC | 11398 |
| 2427 GTGGTGTATCTGGGCATTGATTCT | 6027 CAGCAACCCCCACCATGATAAA | 8713 CCTTCATGGCTTTAATGAGAGAACATT | 11399 |
| 2428 GAGATCTCCTTTCAGCTCCTAATGG | 6028 GGGGCCATGTCAGAAGAAATGT | 8714 TCCCTTGATGGCTGTCATCTGA | 11400 |
| 2429 CCAGCCACCAGTAGCAATATTGTG | 6029 TCCCCACCATCAACTCTGTCTA | 8715 ATAGCCAGCCACCAGTAGCA | 11401 |
| 2430 TCACCAGCAGAGATCTCAGATGGT | 6030 TCCTGCTACAGCTTCAGATGGT | 8716 AGCTGAGCTGCAGGCAACCA | 11402 |
| 2431 TGGGTCTGCTTCTGGGAACTG | 6031 GCACCCTTTAAPGTCCAGACATACA | 8717 GGCTCATTTGGCGCCCAGTGT | 11403 |
| 2432 TCGTCCCTACATTGAGGGCTCTA | 6032 TTCAACACGAGGGTGATCCTAA | 8718 CACCTGGGATGACATAGTGAAACC | 11404 |
| 2433 TCCAGGGCTTTGGGTGTTCAAT | 6033 ATGTGCTGGTCTTGGCAGTT | 8719 ACTACTTGTCCAGGGCTTGG | 11405 |
| 2434 ATGGCTCACCTCTTCTCCAATG | 6034 ACCCTCCTCAGCACAAAGCA | 8720 CAGCCCAGTACAGACAGCTTTATG | 11406 |
| 2435 CAGGGAATTCATTCTGCGATTGATT | 6035 GCCCCCTTCTTTCTTAGGATAGGT | 8721 GGGCCTTCATCTTGCACCCTTAGAT | 11407 |
| 2436 AGGCCCATCCTCTCACTAGAC | 6036 CCAATGGGCAGCAAGACA | 8722 ACTGGGAACATCTGTCCTTTAGG | 11408 |
| 2437 TGAGAACTGGAGTGTGCAAGCA | 6037 CTGCTGACACCAAACAGTTG | 8723 GGCTTCCACTCTCAACTTCACAGATG | 11409 |
| 2438 CTGGCCCAGGTAATGTCCATAAA | 6038 TGAGTCCAGGCTTAGAGCTCT | 8724 TCCCCTCTGGCCCAGGTAAT | 11410 |

| | | | |
|---|---|---|---|
| 2505 CCACATTTTCCATCTGCTCCTGGAA | 6105 CCTTGGCCAGAACTCAACCAAA | 8791 GAGCCTGACCACATTTCCATCT | 11477 |
| 2506 ACTCAAGGCCATAGACCCTTTCA | 6106 GGCAGCTCAAACTGTAGCTGAAG | 8792 GGCTTGACAATGACTGCATGCT | 11478 |
| 2507 TGTGGAATAAGGGACCGATTAAGG | 6107 CTGGCCTGGAAAGATTGACCTT | 8793 GTCCTGAGATATTCACTTCCTCTACA | 11479 |
| 2508 TCAGATGGACTGCCAAGGTCAA | 6108 CATAAAGTACATTCCATGGTGGCATATT | 8794 CCCTGTTGGATTGACCATGGAAT | 11480 |
| 2509 GCCTCATCTCATGGGCAAGAC | 6109 CCTTGGGCTGGCTTTTGGA | 8795 GTTCAGATTTAATTTCCTCATCTCA | 11481 |
| 2510 CTAAACCTAGGACTCAACAGTCGTT | 6110 GGGTTGGCAGAGTTTCAAGATAGA | 8796 GGAAGCTTGGGTAAATTCTAAACCTAGGA | 11482 |
| 2511 GTTGTATCAGTGGAGGGAAAGTCT | 6111 CACACATGCCTTCCATCCATCT | 8797 CAGGTGGTGGCACTCTCCTTAGG | 11483 |
| 2512 TCTTTGCTATTGGGCTAGTTATTCCA | 6112 GGTTACCTTGGTACTCTGAAACC | 8798 AATGGAGCTCCCAGGGAAAGG | 11484 |
| 2513 AACTAAGGAGACTTGGCTTTCAAATCG | 6113 CCGTGATCACACAGCTGGTTTA | 8799 AGGACTTCCTTTGAGAAGTAACCATATT | 11485 |
| 2514 TCCACCAGTCACGGAGTCACA | 6114 CCTGGCAAGGAAAGCCTCTTTACA | 8800 ACTCGATGTCTCTCCAGGGAGTCA | 11486 |
| 2515 TGGGTAACTACACCTACTACTTTCAAG | 6115 TGTAGTGTCGGGCCTAAATCAG | 8801 TGGGAAAGTACAATTGGGTAACTACAC | 11487 |
| 2516 GTATAAGGCATGCTTAGCCATTGC | 6116 CTCTATCTCTGTCTCGGTTCAGAGTC | 8802 GTTTTGCTGTAGTATAAGGGCATGCT | 11488 |
| 2517 ACAGAAATGGAGGAGCAGGAA | 6117 ACCCTTTGTCTGTCTCACTCCCTCT | 8803 GTGTGCAACTATTAATCGGTCGT | 11489 |
| 2518 GCAGACACATGTCTTGCAAAGCTTT | 6118 CAACTGGCACAAATGAGGCATT | 8804 GACTTCCTGAGTACCACTACTTGGATTAT | 11490 |
| 2519 TTCTGGCTCCTGCTAAGTTGGA | 6119 GAAAATTACTTGCAACTGTAAGGGCATT | 8805 GACAAACCCACTCACCTTTTCAAG | 11491 |
| 2520 GGTTGTCAAAGTCAGGGATGATAAG | 6120 GCAAACCCTTCCTCCCTTTCGT | 8806 GCTCACATGCTCTCTATTGTTCCA | 11492 |
| 2521 CTTGCTGTTTCTAAGGTCGTGAAG | 6121 TCATAGCCTGTGGAAGTGTAGCAA | 8807 CCGGCTCCTTGCTGTTTCTAAGG | 11493 |
| 2522 GGAACACAATGGAGCTGAGGTT | 6122 GGCACTCAAACCACACGGAAATAC | 8808 TCTAGGCACTGTTTAGGGAGAGTAAAAG | 11494 |
| 2523 CTCCCGAATGGATCAAAGCTTACTG | 6123 AGTTTTGCCCCAGGGATACAG | 8809 TCTGGCTCCCGAATGGATCAAA | 11495 |
| 2524 GGGAAAAACATTTCTCTGTGCTCATTTC | 6124 GCAAAGTACCCTACCTAACCACA | 8810 CCTCTCCCAATTTCATCAGAGTAGTT | 11496 |
| 2525 CCTCCATTTCAGGCCATAGCTT | 6125 TCCCTTCTGGCTCAGGATATGT | 8811 ACAGGATAAGGCACCCATCATG | 11497 |
| 2526 CAATTTCTGCAAAATCTGGCTCCAA | 6126 GTAAGTTTGCCAAACCCTGCTAAA | 8812 GCATGCTTACCCTTGCAATTTCTG | 11498 |
| 2527 TGGGAAGGATTCACTCCCAACCT | 6127 GCCACAAGGGAAACAAATCTGACAACAG | 8813 GGTTCGACTGGGAAGAATTCACT | 11499 |
| 2528 GGCTTTCTTCATAGCCCAGTACA | 6128 CCCAACCAACATAGTGCACTTGA | 8814 GAAGGTGGCTTGGCTTCTTCA | 11500 |
| 2529 GCAGAGAGCCTGGAATTAACAAGACT | 6129 TTTGGGAGTCTGCCTTCTCCTT | 8815 TGCAGCAGAGAGCCTGGAATT | 11501 |
| 2530 CAGCGTTATGACTCATCCTGAATTA | 6130 CCTCGTGGAAAAATACCTCTGTTAG | 8816 GCCAGCAGCGTTATGACTCAT | 11502 |
| 2531 TGTTCTCGGTTTATACTTTGATTGC | 6131 GTCAACTGCTCGTGTCAGAGTTTG | 8817 CATTCTGTTTTGGCTGCAGTTTATAGT | 11503 |
| 2532 TGCATCTGCAGCCTTCATTCC | 6132 CCCTGGAACATGTTAACAGACTTAATTAC | 8818 TTAAAGTCAGCCAATTAGCAACTTTTATTC | 11504 |
| 2533 ATGGCCAGCTGTTGGGTTGA | 6133 ACTCTTCCAGCTCAGTTTCCTAAAC | 8819 GCTTCCATGCTGGGTTCATCCTT | 11505 |
| 2534 TCAACTGGGCGCATAGTTCAA | 6134 ATACTTATAAACCCAAGCTCTGTCACT | 8820 GGGGAGTCCATATTATCTGCAACTG | 11506 |
| 2535 GTGGTCAGCAAGACAAGACCAT | 6135 GTTCCTTAGCCCACATGTCGTT | 8821 GAATAAAACTAGGTGGTCAGCAAGAC | 11507 |
| 2536 GACATGCTCACTCAGTGCCATT | 6136 TGAGCTTGTGTGGAAGTGATTCA | 8822 GCAAGCTATTAGCAAGCGCATATTTTGC | 11508 |
| 2537 AACAGGTTTCCGGCAGAGTTT | 6137 GGGTTCCCAATGCATACAGAAATCC | 8823 GGCTGCACTTCAAACAGGTTT | 11509 |
| 2538 CTTCAGGAATCAGTGATGATCAA | 6138 GTCACCTTTGACCTGTTCTTGTCT | 8824 TTCAGAAAACACTCAGGAATCAGT | 11510 |
| 2539 CCCAAGGAAGATAGTCAGACTCTTCTC | 6139 AGGGTGAACAGGTGACCAACT | 8825 GCATGGCTACTACTTCCCAGCGAA | 11511 |
| 2540 TCCAAGGAAACGTCACCAGGAA | 6140 ACCCTAGGACAAGGCTGTGT | 8826 CCACTGGGGCTTCAAGGAA | 11512 |
| 2541 ATGTGGAGGAGGGCAAAACC | 6141 ACAGCCCTGTAAATGCCCCTGCTTT | 8827 CGTCAACAAAAGTTACTTCTGAGA | 11513 |
| 2542 GGAGGACTGATAACAAATGCCATTT | 6142 AGACTCCAAATATCAAGCCTCAGAAT | 8828 GTARCACCTGGAGGACTGATAACAAA | 11514 |
| 2543 GCAGGTTTTAGCTGCAGGTCTT | 6143 CTACAAAGATGAACATCCTGACGTTCA | 8829 CCAAATCTGCATTTGCAGGTTTTACCT | 11515 |
| 2544 GTGGCTCTGTTTCATGGAAGA | 6144 GGTTAGTCCATCAGACATTCCTTCA | 8830 TGCTGAACTGCTGCTGTTTC | 11516 |
| 2545 AGCAGGAAAATGATAATTTGTAGGCAAA | 6145 ACACATTCCCATCTGCTTTGAGAT | 8831 GTGTGCATGGCCATAAGCAGGAA | 11517 |
| 2546 CCAAGGAAAAGGTCATGGTAGTTTGT | 6146 AAAGCTGCAGAGATGAGACA | 8832 TCTCTATTGGATTGTGATGTGCAATG | 11518 |
| 2547 GGCTCACAGAACAGATGGTTTGG | 6147 GATTCCTTATCACCACCCTTTATTCTTT | 8833 AGAAGAGTCCTGGGCTCACAGA | 11519 |
| 2548 AGCCTTGATAAAACGTCATCTCCAT | 6148 GCTCTACAGTCAAGGTTATCCTTCTC | 8834 TCATGCTCAGAAGGTGAGAATTGA | 11520 |
| 2549 GCTCACCTAAACACGCCAATCTC | 6149 GCACCCCATTCAATGCACACAAA | 8835 AGCTAGCTCGCCCTTTCACA | 11521 |
| 2550 CTGAATTGGTAAACACAATGGATGCA | 6150 ACTTCTTCTGGCATGCCACTCT | 8836 GCCTATTTTCAACGCCTTGATAAAATC | 11522 |
| 2551 TGTGTTTTATGGTAAACACGAAAGTAGGA | 6151 GTACGGGCTTCAGACTCATTACAC | 8837 AGTTGGGTTAAACCATCTAAAACATCAAA | 11523 |
| 2552 TGCTTTTGACCTCATCTTCTTTCC | 6152 GGGAGATGGAGGTTGTGGGATTAA | 8838 TTGTAACATGCATTGCTTTTGGA | 11524 |
| 2553 CTTCCATTGTAGAGTGGTAGTCTAATTTC | 6153 GGCAGAGATGATTGATACGGACTAC | 8839 GCTCTTGTATTCCGGACATACTCT | 11525 |
| 2554 CAGAAGTTTCTCTGCCATAGTCATTG | 6154 GCCTACTAAGAACTGCTCTCAACT | 8840 TGTAATGTAGATTACAGTCGCTGTGT | 11526 |
| 2555 GCCACACCCTAAAATTCTAATAATGCA | 6155 GATAGAGAAGAAAAGTCAAGGACCAT | 8841 AACATTAAATTCTTGCCACACCCTAAA | 11527 |
| 2556 TCTGGTGAGTGCTCCTCTCTAT | 6156 CCCTCTGCAAGATGCAGTTACAG | 8842 ACACACAAGCAGGTTAGGTATCTG | 11528 |
| 2557 CTGAGTCTGTGTTAGGAATGAACTAG | 6157 CGACTGCATCGTGCCTGTA | 8843 CCTATGGTTATCTGAGTCTGTGTTCAG | 11529 |
| 2558 AGCCACTTCCAAGGTGAGCTA | 6158 GGAGAGGCTGTGTCTCTAGTAATGAG | 8844 ATGAGTCCCAGCCACTTCCAA | 11530 |
| 2559 CACCAGGCAGATAGCACTAAGCAA | 6159 GCAGGTATTGAATCACAAGTTCTGGTT | 8845 GGACCTGATACACCAAGCAGATAGCA | 11531 |
| 2560 CCATTGCTGCCACCATTGCT | 6160 GAAAACAATCAGGCTCTTCTGTTTCCT | 8846 AGGATGGAGCTCCCAGAGACAA | 11532 |
| 2561 GTCTTCCAACTACCTGAATCTGAAGC | 6161 CAGGAGAACTTCAGGCAGGTT | 8847 GCAACTTTTTGTCTTCCAACTACCTGAA | 11533 |
| 2562 CTATGCCCAGTTCTGCCTTAGG | 6162 GCAGCTTAGACCCATAAGGACTAC | 8848 ACCCTAGTCCACTGTCCTATGC | 11534 |
| 2563 CATGCCCCTTCTTTAAGGTGCTT | 6163 ACATATGCTGCTTCATTCTGACTGAA | 8849 AAGCACCCGAAAAGACATTTAGTC | 11535 |
| 2564 GGAGAAAGCCAACAAATGAATTCTCCTT | 6164 GTCATCAGGGTTGTGCTTCCT | 8850 TCAGAAGCTGAGAAAGCAACA | 11536 |
| 2565 GTTCAGTAATGGAAATGGTTGTCAGT | 6165 CCTGAGGGTCAGATTCCTGCACATT | 8851 TGGCCATAGTTTCAGAGAAAACACT | 11537 |
| 2566 CCATTATAAAAACAATCAATGAGGCTTGTAGGTTCC | 6166 ACACCCTAGCTGCTTCTAGTCA | 8852 AGGATTATACACTCATCAAAAGTGGTGTT | 11538 |
| 2567 CATGCTGCCCTATACTAGCCTTTCAC | 6167 CCAAGCTAGTTGAAGCACACCATACC | 8853 TGAAAAGCCTATACTAAAGCATCAGTTTT | 11539 |
| 2568 CCCAAAAAGAGGCAATCAGACCAT | 6168 CCCACCCACAATCAGATATAAGG | 8854 CAAGGCAAAACTGATCTCTAGAAATTAAGG | 11540 |
| 2569 GGTAATGAGAATCTCAGCTGGGACTT | 6169 GCACCTTGCTCCATCAGGTAT | 8855 CAGGTTAGCTCTGGGGAATAAGGT | 11541 |
| 2570 CATACAATTTATCATTGTCACACCACCTA | 6170 GACTTCTGAGGAACGCACTTACA | 8856 GGGCATTAAGCCATACAATTTATCATTGTC | 11542 |

| | | | |
|---|---|---|---|
| 2637 CTTGCCACTGTGAGTTCAAGTG | 6237 GTGGCCTAGACAGCTCTTAAAGT | 8923 CCACAAACCTTGCCACTGTGA | 11609 |
| 2638 ACAAACTAAATAAACGACCCATTCTGTTAT | 6238 TGGCGGAAAGTGTTTAGCTGAA | 8924 CACCTACAGATTAACTGAAAGCTTTTGA | 11610 |
| 2639 TGGAGACAAGTGGCACGTAAAA | 6239 TGCAATCATGTCTTCATTGTTTCCA | 8925 AATAAAAAATCCGGATGGAGCAAGTG | 11611 |
| 2640 GTGTCCCTCTAAATACAACTATTGCTTACC | 6240 GTGATGCCCTTTATCAGCAACACA | 8926 GCTCCCTTACCTACTCAGAGATGA | 11612 |
| 2641 GTCGCCGAAGTACTGAGATGAA | 6241 AGGGGCGGAGAGACACAATGA | 8927 CATAAATCCTGTCGCCGAAGTACT | 11613 |
| 2642 AAAGCTGCCTGGGAGGGAAAA | 6242 CAAGTATTATTTTACCTCCCAGACATCAGA | 8928 AGAGCTTTAAGTGCACAATGGAAAG | 11614 |
| 2643 CTCCTAGCAAACCTGTGAGGAAA | 6243 GGCAGAGATTCTGAGCCTTATTTGT | 8929 GAGCATTTTACAATTCACAAAGCACAT | 11615 |
| 2644 GGCATTGCTAAGAGTGTAACTGTT | 6244 AGCTCTTTCCACATGCAATAGTGTATC | 8930 TGATTGTGTGGCATTGCTAAGAGT | 11616 |
| 2645 AACATCTGTCAGACTGTAATCACCAT | 6245 TGAACATATGCAAAACCATCTGAGTCAAGA | 8931 ATCCCTGCTCTGCCGTGCTTT | 11617 |
| 2646 TCCTGCTCCACTCTCACTCTGT | 6246 TCCTCTCACAGCTGAGGAAATC | 8932 TGTCTGTGACAGAGTGTTCTTTCT | 11618 |
| 2647 GGTTGGGTAGAATACTTTATCCTTTGATTC | 6247 AATTATATGCAGGCTCCACTATTCCA | 8933 CGACTTTTCCTGAAAATACACCTATGG | 11619 |
| 2648 GGTCAACACTCAGGAATTGACCCTGAT | 6248 ACCAGGAAAAAGACACCCCAAA | 8934 TGCTCAGGGCTCAACACTCAGA | 11620 |
| 2649 GTGATAGATAACCCTCTTCCTCATTGT | 6249 GGTCTTTGCTCTCCTAGTCATTT | 8935 CTGCTTCTTAAGTGATAGATAACCCTCTTC | 11621 |
| 2650 ACTGGATGTCCTCCCATGCTAAA | 6250 AATCTATTCACAACTTGAGAGTTTTCCAA | 8936 CCAGTGAGGTTTTCTACTGTAGTGTGA | 11622 |
| 2651 AGAACTTATTCCCAGTAGGATACAAA | 6251 TGCCTCTACCACTGCTATGATTCA | 8937 GTATATGGGTGGTCTTTCTCTCACA | 11623 |
| 2652 AAGCTGTAATAAAACTCTGCCAGTAATG | 6252 TCAGCAGTTTGATAAAAAATCAGGTCCTA | 8938 CACACCAAGCGTAAATTAAGAAACCCAATA | 11624 |
| 2653 GCCTTTAAAGCAGGTCTGTACCAATG | 6253 CCTGATCAATTCCACCTGCTTTAAATAG | 8939 TGGGTGTGCCCTTTAAAGCA | 11625 |
| 2654 CCTGTAGATAGACCCTAACCATTCTTAACC | 6254 AGTCTGACCTCCCTGCTTACC | 8940 GGACCTGTAGATAGACCCTAACCA | 11626 |
| 2655 CTAAGCGATAAGGCGCAAAC | 6255 AGGAGGCCCCTTTCGTGTTA | 8941 TGAAAGAGCAGCCTAAGCGATAAG | 11627 |
| 2656 GCGATGTGCTTTTCAGATAGATGGTATC | 6256 CCCCTTAATATCTTCACTTAACCCTACAT | 8942 TCCTTTGCCGATGTGCTTTCAG | 11628 |
| 2657 CCATGGAACTAAGACAGAGACCAACT | 6257 AGCTTCTGCAAAACCCCATTCC | 8943 GTGAGGTCTTCCATGGAACTAAGAC | 11629 |
| 2658 GTCCCTAACCTCTGCAATTGCC | 6258 AGGGAAGGCTACCAGCTCTATGA | 8944 CACAGGTGTTGATGTCCCTAACCT | 11630 |
| 2659 AATACTTATCCAAGCTTTTCATGAAACG | 6259 GACATAATCTGAACCACCAGGTAGT | 8945 ACCTCACACTTGTTCTTTAAATGTTC | 11631 |
| 2660 AGAAAGGCTGCCTGCAGATG | 6260 GCAGTTACAACTCAGGTGTCTACCA | 8946 GTCACCCTGGAGCTGATCAGAAAG | 11632 |
| 2661 GGCTTTGAGTTAACCTTTGAAGTCTT | 6261 TCCTTTGACACAAGACATGAGACGAGGTT | 8947 GCAACATCCTTTAGGCCTTTGACTTAACC | 11633 |
| 2662 GGAAAGTTTGACCACAAATTGACAATC | 6262 TGTTCTTTCTTGCCTTGTTCCTTGA | 8948 GTGCTAAGAGGGAAAGTTTGACCACAA | 11634 |
| 2663 GGCTGATTACCCTGGGTAAAGGTATC | 6263 GTCCAGTCTGCCATCAAAAAGAACT | 8949 TGATGGAAGTGGTCAAATGTAATCAAC | 11635 |
| 2664 GCTTGAATAGTGAAAGCAATTCCTAATCC | 6264 GACAGGGAATGTCATGCTTCCA | 8950 TCTGCACAATTCAACACTATTCCTATCA | 11636 |
| 2665 CTGTGTTGTGTTTCTTTTGGTTGACA | 6265 TGGTGTCTTTTCAGTCCATTTTCTTG | 8951 TCACATGCTATAGTTCATTCACACAAATC | 11637 |
| 2666 GGCAGAAGAGTAATGGACTGCAT | 6266 TGGCTCACTGTGCAGCTT | 8952 AGCCTTGAAGCTAGGAGGCAGAA | 11638 |
| 2667 CTCAGTTCACACAAAGGATCTTCCA | 6267 CTGTGCCTAAATCCCTTCTACATC | 8953 GCCATATTCTCTCAGTTCACACAAAGG | 11639 |
| 2668 TGTGATTACCACGCCAGTAAGAAAGAAC | 6268 ACATTTGCCTTCAGGAAGATTCCTTAG | 8954 CCTTTCACAAAAAGCTTGTGATTACCA | 11640 |
| 2669 AACTGAGCTGATGGCAGTTAGG | 6269 ACAAGTGGATTCTATGTGACTCTATCA | 8955 ACAGGACAGGGAGATTATTCACTAAC | 11641 |
| 2670 CTATTGGCAGGATCTTTCTGTTTGTAG | 6270 TGGCCTCAAACGCACACTGT | 8956 CCTGAAAAGGAAAATCTGGCCTGAT | 11642 |
| 2671 TTAATCTGTCTTACACTCTCTGACA | 6271 CGGTGATCCTGTACATGGTAATC | 8957 GGGATGCTAGCTGCTCTTCTCTTTGG | 11643 |
| 2672 GGAGGCCCTCCATTCTTTGTT | 6272 GCCCCATGGAGAGGCCTATA | 8958 TGCACGGAGGCCCTCCAT | 11644 |
| 2673 CACAATAATAGCTTCTTACTTGTGCATTTC | 6273 CAAGTAAGGTTAAGCTAGTGATCAG | 8959 GCTGAACTCACAATAATAGCTTCTTACTTG | 11645 |
| 2674 AGCCTTCCAGATCCCTTGTT | 6274 GCAGGAATGTTCAATCGCTTCCT | 8960 AAGCTCTGCAGCCTTCCAGAT | 11646 |
| 2675 CCAGTTGACTACCATCACAGATACAAGATG | 6275 GCTTTGTTACCCATATGGCTAGTTG | 8961 ATCTTTGTTCCTCTCCAGTTGACTAC | 11647 |
| 2676 GCATATAACTGTGCTGGGTAATTGTC | 6276 CAGTATTTCAAGTGACTGCAGTTATACAG | 8962 CCAGTTATAAGCAGATGAGGTGTATTCAT | 11648 |
| 2677 CCACTAGAATACAAATCCACTTCTGACA | 6277 TGTAGCCATGACTGAGCCTAT | 8963 CCCAGGCAAGCCACTAGAATACAAATCC | 11649 |
| 2678 AGGGTGACAGCTTCACAGATC | 6278 ACTGATTACTGAATACTGGCCTTAATCT | 8964 ACCAATGATGCAGGGTGACATG | 11650 |
| 2679 AGGTTAGTAGTCAAGGCCTATCTTTTAC | 6279 AGGAAGGGATATGAAACATGGCTTAA | 8965 CTCCAAAGCTTGTTCACTTCCTACT | 11651 |
| 2680 GCAACCTATAGCAGCCTGGATT | 6280 CAGGGTTCCAATATGGCCAACA | 8966 GCTTGCCCTTTTTCGTTCATTGT | 11652 |
| 2681 AAAGGCCCCAAACCCTTTGCT | 6281 CCAACATATGCTTTCAGAAGCAAAA | 8967 TGGTGAAAATTAACACGGAAATTCTAAAGT | 11653 |
| 2682 CCCTCATTCTATCGTATTGATTCCACAA | 6282 ACATGTTGCTGTGCGCACAGA | 8968 TCTCTGTCCCTCATTCTATGGTATTGA | 11654 |
| 2683 GGCCATCACAAACTGTCATTCTG | 6283 CCCTGGCCATCAAGGAGCTA | 8969 ACCTACTGGGGATCACAAACTG | 11655 |
| 2684 GCATATATTCGGATACTACAACCAGACGAA | 6284 GGAATATGGCCTGTAGTTTCTCTCCTT | 8970 TCCAGGACCTGATGACTTCACT | 11656 |
| 2685 TGAAAGACAATTGCCGGTATGTTAC | 6285 GCAATTGCTGGACCCATAATGAGACAA | 8971 GCATAATGTGTAGGCACTTTGAAAGA | 11657 |
| 2686 CCTGAGGTCCCCATGAAGAGCTATAA | 6286 GGCAGAGTGATCATTGATTGATAACCA | 8972 AACACCCATTAATCCTCATGTTTTCC | 11658 |

FIG. 35E1

| Target No. | Pool A Sequence (5' to 3') | SEQ ID NO. | Pool B Sequence (5' to 3') | SEQ ID NO. | Pool C Sequence (5' to 3') | SEQ ID NO. |
|---|---|---|---|---|---|---|
| 1 | GGCACAACAPTTGGGAGACAAA | | 11659 CTCACTAAACTTTTCCCCAGAACTCA | | 22643 GCTTAAGCCACAGAAAGGCACAAC | 33627 |
| 2 | CCTGGAACCTGAAAGCPTGCAAAAAG | | 11660 CPTCTGAAGGGAGACTGAAACAC | | 22644 CGACPGCCCTGGAACCTGAAA | 33628 |
| 3 | ACAGGGTGCTCTCCTCTTGA | | 11661 GCAAGAATGCTTGGCTGCAA | | 22645 AGCCACCACTCCPGCTTCTGA | 33629 |
| 4 | GGAAGCAAACAGGPAGAGCCTGGTA | | 11662 GTGGCAPTTCACTGCCCTTTG | | 22646 PTGGGGACCCCTGGACTAAG | 33630 |
| 5 | CTACAACAACAGGPAGAGCTCCAGGAT | | 11663 GCAGCTTGTTCAATTGTGGTTCA | | 22647 CCTCCCCAGTATCTTACCACTACAAC | 33631 |
| 6 | PGTCCTTGGTCGPATGTGAGAGA | | 11664 GTGAGGATGAGTTTCAGTGGCTATC | | 22648 CACCAAGCCCTCAACTCCTAAA | 33632 |
| 7 | GCAGGAACTGGCTTGCTTTT | | 11665 CCCTGGACAAAAPGTAACAGGCAAAGT | | 22649 GAAGTGAAAGAAAATGGCAGGAACT | 33633 |
| 8 | AGGTTTCGGCTTTAGTTGTGTGA | | 11666 ACCTAGCTATCCTTCCAGCATTC | | 22650 GCTGGTATTGTTTGGGGATAGAGGTT | 33634 |
| 9 | TGTCTGCTTCTGCCGGCATTC | | 11667 GCTGACAAACTACTGCCTCTTC | | 22651 GTGGAGGAAATTAGATGTCTGCTTCT | 33635 |
| 10 | GTCCTCACACCTTCTACCAGAAG | | 11668 GCCAATAGCTGCTTGATGCAAP | | 22652 GGGCAAGPCCCTCACACCTTT | 33636 |
| 11 | GGCTGCAGGAGTAGAGGTCTAAATG | | 11669 TAGTTGCCCGGGATTCCCAAGA | | 22653 TGAGGTCTGGCTGCAGGAGTA | 33637 |
| 12 | GGCAAGAAGAAAACTGGAGCCAAGA | | 11670 GGGAGAGGCTGGTCCTGAGT | | 22654 CTGAAGCCCAAGTGGCAAGAAG | 33638 |
| 13 | GAGCCTGAGGTCTTGATCACTACA | | 11671 GTTTGTGAAAGGTCAATCTGAGGAA | | 22655 AAGTCCTCAGCCTGAGTTCTTG | 33639 |
| 14 | CCPGGAAAAGCCCPGGTAGA | | 11672 TCTTCGGAGCPCACAACCPTA | | 22656 TCTCAGGGTGCCTGGAAAAG | 33640 |
| 15 | GCAAPGGTCCCAGTGAGAGTT | | 11673 TCCACPGATCCCAGACCAA | | 22657 GCACPGCAAAAGAAGACGCTATTG | 33641 |
| 16 | GCCCTTTGGAACCTGACCAA | | 11674 CCAGCTTAAGCAAAATAGCCCAAGTA | | 22658 TGGGAACCAGCCCTTPGGAA | 33642 |
| 17 | GGCCTTGAPTGACCCTTCTTTTC | | 11675 TGGCCAGTAGTAAGTTGAGAAGACTA | | 22659 GGCTTCACTATCAAGAAGGCCTTGATTT | 33643 |
| 18 | CTACCCCGCTTCTGAAACACATC | | 11676 CCGAAGCPTCACGPTCPGT | | 22660 GAGAGGCCACCCGPTCT | 33644 |
| 19 | TGGCGCTAAAGCCCAACA | | 11677 GGAGGGAGAGCTCCATCTCTGA | | 22661 TGGAACAGGCTGGCGCTAA | 33645 |
| 20 | CCTTCCCCCGCTTCTGCATATGAAA | | 11678 GCCCAATACAGCACTCAGCAA | | 22662 CCAAAAACCTTCCCCGCTTCT | 33646 |
| 21 | GTCAGCGTTACGGCTATTGAGT | | 11679 PAGGGCAGGTGTCCTCTGCAT | | 22663 GGAAGGGAATTGTCAGCGTTTA | 33647 |
| 22 | GCAPTCCAGTGCCCTCTGT | | 11680 GTGAACCAAGCTATACTACCTGCTTTC | | 22664 GCAGCTCCAGCCTTCCTTTGCAT | 33648 |
| 23 | CATCTTCCTAGAACATGCACACAAC | | 11681 GGCTTCTGTGCTCATAGTTCACACT | | 22665 GTTGGGAAGCATCTTCCTAGACAT | 33649 |
| 24 | GTCCCAAGTCAACTGCCATCT | | 11682 GGGCACACGGAGTGAAAAGT | | 22666 GCCTATTTGGACTCCCAGGTCAA | 33650 |
| 25 | GCGTCAGCACAGCTAACACA | | 11683 CGGAGCCGTTATACCAGCTTAG | | 22667 TGGGCCACGTTGCCTACT | 33651 |
| 26 | PCACAATGGGAGGGAACATTCAA | | 11684 GCTTCCTATGACCAAGTCCCTTT | | 22668 CACCPTATTCCTCCTCPCACAA1G | 33652 |
| 27 | GGTAAAGGCTGGTTGTAAAGTCCACBT | | 11685 TGTTTGGCCAGACCCACTGT | | 22669 ACTGGGGTAAAGCTGGTTGT | 33653 |
| 28 | CCGACTCAAPGGGCAACTCCTACT | | 11686 GGGCACTPTTGAGPTGCCCTTTG | | 22670 AACCCTCPGCCCGACTCAAT | 33654 |
| 29 | TCCTTACACCTTGGGGCGTCTA | | 11687 GCAGCTCGGTGCCTAATGCTT | | 22671 AACAGGGCGTGAGTTTTCCTT | 33655 |
| 30 | GGGCATTTCTAAGACACTPGGACAGT | | 11688 CAGACCTGGCAGGATGCAAAAGT | | 22672 GGAGAGGCCAGGGCAPTTCTAAG | 33656 |
| 31 | CACTGTATCTCAAAGGGCAAAACAA | | 11689 TTCAATGCAGAGAGAAAGGTT | | 22673 CAGCCTGCTAGGAACACACTGTA | 33657 |
| 32 | ACTTGTCTCPCGAACAGTTTCA | | 11690 AGTCACAGGTATCCTGACTCTGCA | | 22674 GGTGATTCTCCTGACTTGTCT | 33658 |
| 33 | GGCCTCTTGGTGCCTCTGTT | | 11691 GGAGCAATCAGCCTTGCAGAGA | | 22675 TGGAPCGGAAACACCAGACTCA | 33659 |
| 34 | GCTAGAGAAACAAGACAACAACATCCAAGTTC | | 11692 PGGCGCCCGGAAAACCAT | | 22676 CCPGAGCACCGPTGCTAGAGAAACAAG | 33660 |
| 35 | GGGGGCATAGAGAGAAGGAAAT | | 11693 TTCAAGAGCATCCTTGCCCTAT | | 22677 TGGCATGCCGGCATAGACA | 33661 |
| 36 | GGCTTCAGTCCTTCACCTCTTTC | | 11694 ACCTTGACAAGGPGGTATTTGTGT | | 22678 TCTCCCAGGCTTCAGTCCTT | 33662 |
| 37 | PCAGAGTCCTAGGCCAGCAT | | 11695 AGAAAGACACCAAGGPAAGAACCAP | | 22679 CCAAGGPTATGCCTGGTGCTCAGA | 33663 |
| 38 | GGTTCCTCAPGGAAGACTGGTTTG | | 11696 CACTCACACATCCACAGGAGACA | | 22680 GGGAACCPGGAAAGACCTTTACTT | 33664 |
| 39 | GTTGAGAAGGCACTAAGCATCAGACAA | | 11697 GACGCAGTATCCCACAGACCATT | | 22681 GGTGGGATAGTTCACAAGGGAGTAA | 33665 |
| 40 | CTCCCGCCTCTAAATGAATGGAT | | 11698 ACCAGCTCPGAGTCAGGAAGT | | 22682 CCTCAGCTCCCGCCTCTAAA | 33666 |
| 41 | CATTCCCTCCCTACCCPGGAAA | | 11699 CCCACAGTCCGACGAGTGTTT | | 22683 GGATGAGGCATAAGCAGTGGTTCA | 33667 |
| 42 | GAGACTCAATCCTCGGCACTTGT | | 11700 TCACTCCACTTTACAGGCACATATT | | 22684 AGGAGTGAGAAGGGAGACTCAATC | 33668 |
| 43 | CCCGGCTGCCATTTAACCAT | | 11701 ACGAGGATCAGACAACTCACAGA | | 22685 TCAGTCCCCGCTCCATT | 33669 |
| 44 | GATGAGGGCTGAGTATGGTCAAG | | 11702 CCCATGACCCCAGGPTGAATTG | | 22686 GACAGAGAGATGAGGGCTGACT | 33670 |
| 45 | CCCPTTCCTGAACCCCTTCATT | | 11703 CACTCTGTGCAGTTHCTGGTT | | 22687 AATTGCCACPCTGTAPTCTCCTTCT | 33671 |
| 46 | GGGGCACCAAAGAAABACAAAG | | 11704 GTCTGTGGACCACACCCTGGAA | | 22688 ACAGAGGATGGGGCACCAAA | 33672 |
| 47 | CATCAGTACCCCACATAGGTTAACT | | 11705 GCCTTTCCACTCAGCCATGA | | 22689 GCATGAGGATGGAATGGACTCATCA | 33673 |
| 48 | GGAGCTCAGTATGAGTAGAGCGGGAAA | | 11706 CAGCCTGGTTGGTTAGATTCTGT | | 22690 GACCTTCAAGGGAGCTCAGTAT | 33674 |
| 49 | TPGTCACGACGCTGAAGTT | | 11707 CTTAPGCTGPGCTTTGGCTTTG | | 22691 TCPGATATGGAACCCAGGGATTGT | 33675 |
| 50 | TGGCTAGGCCAPTCCTCCTGTT | | 11708 GGGGCTGAATCAGACAAGGAA | | 22692 PGCACCCATCGCPAGGCATT | 33676 |
| 51 | CACGGACACCCTPACATAPTGTTGGAP | | 11709 CACAGCTTGGAAGGCTGAA | | 22693 GTCAGTTCACACGGACACCCTAGA | 33677 |
| 52 | TGGCACAAGCCCAGGTCAT | | 11710 CTCATGATGTCAAATGCTGCTCAA | | 22694 AGCCTGGAAAGCTGGCACAA | 33678 |
| 53 | GCCCTCCTCTGCAPCTCTGAACCAA | | 11711 GTTCPGGTGACAGACAACCPTCT | | 22695 PTCCCAGCCPCCTCPGCATCT | 33679 |
| 54 | TGCAGCGATCCCTTCACCTT | | 11712 TGAGCAGCACAGTCCAATTCT | | 22696 CTCAAGGGGAAGAACGTCAGT | 33680 |
| 55 | TGGTAGTCAGGCPGTAGTCAGT | | 11713 CCCCTCGGAAATAGTGTGCAGAT | | 22697 TCTCCGTCTCACTTCCTCGGTA | 33681 |
| 56 | GAGGCTPCCAAAGGCTAPTCAGA | | 11714 GTCAGTGAGCTGCCAGTTTTC | | 22698 AAGGTGCAGAGGTCTTCCAAAG | 33682 |
| 57 | CCTGAGCCPGTCACACTATTTCT | | 11715 TCCAAATCCPGAGCCTGTCA | | 22699 PCCCAAAPCCPGAGCCTGTCA | 33683 |
| 58 | GAGAGCAACAGGCGTTGAGA | | 11716 GCCAACTTATAGACACAACTTTGGTTAC | | 22700 GCAGAAGAGTGGGAGACAACA | 33684 |
| 59 | AGCCCTACAAGGTCAAGTTTTCA | | 11717 GTPGACTTCCGGCAGTAAGTGATGA | | 22701 CACTATACGATACCAAATAGCCTACAAG | 33685 |
| 60 | GGAGGCACTTCACTCCTCCTA | | 11718 ACTGGGACATTTCTACGTTATCA | | 22702 GTCACAAGGGAGGCACTTCA | 33686 |
| 61 | GTTGGGGTCAACPTTCCCTGAAG | | 11719 GGAATCCAGCCCATCCTPCACATC | | 22703 AGAGCTGCCCTGGAACTGAA | 33687 |
| 62 | GAGGTTTGGCTCCATCATCAGA | | 11720 ACTGCACCACCACACGGAAA | | 22704 GGAAAGGTAGCCCAGAATGAGGT | 33688 |

| | | | |
|---|---|---|---|
| 258 GACCAATGGGGTGTCAGCTT | 11916 TCCTAGGCTGACCAGTGTCAT | 22900 GAAGCCGGTTTAACTGGTGTTG | 33884 |
| 259 AGGCTAGGGAGGTGGGAACA | 11917 CCCTTTCCCCAGTCCATTTCT | 22901 CAGCAGGAGGGAAAAGGCTATG | 33885 |
| 260 CTGTGTATGTGGGTCTGAAGCTCAA | 11918 TGTCTTTCACCAGCCCAGACT | 22902 CTCAAAAGGCAGGTGCTTGACA | 33886 |
| 261 GGGGCTCGATCCTTGGTT | 11919 CGTGTGAGAAAAACCTCTCCTACTAC | 22903 TGGTTCCCAAGGGGCTCAGAT | 33887 |
| 262 AGCATCCGTGGAGCGTTTTAAT | 11920 TGTCCAACAGCTTTACATGACACAT | 22904 GTGGTGAAAGTAATGCATCAAGCAT | 33888 |
| 263 ACCATTTCTGAAGCAGTCTTGGTA | 11921 CAGAAGCAGTGAGCTGTGGTT | 22905 TGCTGTGGTGTCGTCATTTGT | 33889 |
| 264 GGGCATTAGCTGGCCTTCACA | 11922 CTGGGCCTGCAGAAATGCTA | 22906 TCCCAGTGCAAGGGCATTAG | 33890 |
| 265 TCCCACTTACAGGCCCGTTCT | 11923 CACTGAGGCGATGCTCTGATCT | 22907 AGGCTGGCCTCCCACTTAC | 33891 |
| 266 TTTCAGAAGTGCTGGAACCAAGA | 11924 TGGCCTCCTTCTCTAAAAGCATTC | 22908 AGAGTABAACTTGGAAGGATGGGTTTC | 33892 |
| 267 CATGAAAGCACTGGGGTCTCT | 11925 CACTCACAACTCCTTTCCCAAGT | 22909 GCAATCCCTGCGACCACAT | 33893 |
| 268 CCAGACAGGAAGCACTGGAGTGAA | 11926 GCGTGGGCAAAGCCTTCCAT | 22910 AGGGCAAAAGTCCCTGTGAAC | 33894 |
| 269 CCTTCCTTCACACTTAAGTGACTGGAAA | 11927 ATCCACTGCCCTGACCTTGT | 22911 GGATGAGATTCCCTCCTCACACT | 33895 |
| 270 CAGCCCATCCTGGGCATCT | 11928 ACTCCAAACCCCACCTGCTA | 22912 GCTGTTCTCTGTCGCTCCTT | 33896 |
| 271 AGGCTGGCAAATGGGCTCAA | 11929 GGGGCCTAAACCCTCAGTCTTGT | 22913 GGGTGCTGGGAAACATGAGGAA | 33897 |
| 272 GCTCAGCCCAGCAGTGTT | 11930 ACAGGCTCCTGGTTCTAACT | 22914 CAGCCTTCTGTCCACTCCTTAG | 33898 |
| 273 CCTGGCTGGGCTACATGTTACCTT | 11931 CTCTAGGAGCATGGGTCACCAAA | 22915 TGCTTCCAGAGCCCACACT | 33899 |
| 274 GCATGGGACCTGAGACTTTCT | 11932 AAGCCGGCAGGCTGAGTT | 22916 CACTCCGCATTGTTGTGCAT | 33900 |
| 275 GGGCCGATCAGCAAGTCAGTT | 11933 GGAGCCACAAGGAATGCAGAGT | 22917 ACACCCTGTGGGGCCGATCA | 33901 |
| 276 CCTCCCCGAAAGGAAACAGAGCAT | 11934 CAAGACCCTGCCACCTCTCT | 22918 GTGGTAGTAGACCTCCCCGAAAG | 33902 |
| 277 TGGATGGTGAGAAGAGCCAATG | 11935 GGTGCAGCCTTGCTCACT | 22919 GGGCAGAAGTGGATGGTGAGA | 33903 |
| 278 GCCTGGTCACCATCCGCTTT | 11936 GCGAAGGTGGAAGAGACCTTT | 22920 GCCCCTACCCTGTTCCTCCAT | 33904 |
| 279 GACACTCACAGGCTCAGAGAAC | 11937 GGGCACACTGAACTCTAGAAGCAA | 22921 ACTTCCAGGAGCACCTTTGAATAG | 33905 |
| 280 TGAGCACTCCTGGGTCAAGA | 11938 TGGGCCCATCTCTTGACTTTC | 22922 CCATCAAAGAGGTAACAAGCCAGTGA | 33906 |
| 281 CTTGGCTCGATTGGTCCACA | 11939 GAAGGATGAGCGGGATGGCTCTA | 22923 AACCCCGTCGTTGGCTCGATT | 33907 |
| 282 CCAGAGCCAGCCAGGTCTTCA | 11940 GCAGTACTTGGGGTCGTATATCTGT | 22924 GCTACACGCTGGGCACCAA | 33908 |
| 283 TCTCCTTGGCCCAAGATCAGA | 11941 TCCACCTACCTGTGGGCAATC | 22925 GCCCTATGGCAAAGGCTCACTA | 33909 |
| 284 CCTCAGCCCAGGACTCACTTTTAG | 11942 CCTGGGTACAACAGTGACCTT | 22926 AAGCCTCTGGCTGGTGTTTC | 33910 |
| 285 TCCATGACGGGCAGCTGTA | 11943 TCTCCCGGAAAGTCCGTTCTA | 22927 CCTGTGGTTTGGGCAGGTT | 33911 |
| 286 CACCCTGGGATCAAGTCCAAGT | 11944 CACCCAAGCTCTCACTGTTACT | 22928 TGTTACCACCCTGGGATCA | 33912 |
| 287 TCCATGCTGGGACACAGAGA | 11945 GGCCAGCTGACCAACTAC | 22929 TCTGGTACTCCCAGGGTGCAT | 33913 |
| 288 AGGGGCTGCTGGGGCTTGTA | 11946 CTCCTTGAAGCAGCAGCAAA | 22930 TGGATACCACGGCGTTGTCT | 33914 |
| 289 GCGCTGCCTAGTGACATTGGTT | 11947 GCTGTCACACTGACCCTGGATT | 22931 AAGACATCGCCGTGCCTAGT | 33915 |
| 290 TGGTGCTGGTCCCAGTAATGT | 11948 GCCATGCTGAGAGCTCTGT | 22932 TCCAGAGGCAGGAGACAATCA | 33916 |
| 291 CCCTGGTGGGTTTTGACTGAA | 11949 GTCACCTGTGGAACATGTTATT | 22933 CCGCAATTGCAGCTGAATTCTTAAATC | 33917 |
| 292 CCCACTTACAGCCCCAGGAAA | 11950 GCAAGGAGCTGATCTCATCTGTGT | 22934 CCTTGGGGTGGCCCACTTAG | 33918 |
| 293 CGATCGGCTTTGCAGGCTTT | 11951 CAAAGGGCTTCCTTCCCCACAAA | 22935 TTTTCCCTGACGATCGGCTTT | 33919 |
| 294 AACCAGGCGTCTCTCCCTAGT | 11952 GGAAGGCCTTTGAGGGTTGT | 22936 GTCAGGGAGAACGTATGGACCTA | 33920 |
| 295 CCAACAGCGTGAGGCTTCTCA | 11953 TCTGCACCCCTGCCCTGTGT | 22937 CCCCAGACAGATGTAAGTCCAACA | 33921 |
| 296 GCCTGGAACACACTGTACTCTGA | 11954 TCCCAGAGTGCACAACTCCTT | 22938 CTGCATGCCTGGAACACACT | 33922 |
| 297 TCTTGCCCGTCTGCTCAA | 11955 GTTTGGCTGCACGTAGAGAAAAG | 22939 CTGGACTGCTCACTCTGGAACT | 33923 |
| 298 TCAAACCAGAAGCTTTCACCCTCAT | 11956 GTTGGCACTGGGGCCTTCT | 22940 TGCCCGAAGAGGCCATGAAAC | 33924 |
| 299 AGTCAGGTCGTCTCTTCCATGA | 11957 GACTCAGTCAGTAGAGAGGGAGAA | 22941 TCTTCTCCAAAGTCAGGGTCTCT | 33925 |
| 300 GAGCAAAGAGCTGTTCCAGAGA | 11958 CGTGGGAGGGGAGGAACCACTT | 22942 GCAGTGCCAGGAGAAAAGA | 33926 |
| 301 CCTTCTACACAGGATGGGATGAGT | 11959 TCTTCTTTTGACAGACTGGGAACAT | 22943 AGCCTTAAAAACTGCCTTCCTACACA | 33927 |
| 302 TGAAGGGTTCCCCTCCAAAGT | 11960 ACCCTCTGAGGGTTTGGGGTAGA | 22944 GGGATTCACTAGTGTTCTGGATTGA | 33928 |
| 303 GCCTACATGTCTATCCCCTCAAG | 11961 TGTAAGGCTAAGCCGCATTTTG | 22945 CCAATGGTGGAAACAGCCTACA | 33929 |
| 304 GCTGGAAACATGGCGGAGTT | 11962 TGACCGAACCACTCGGACAGA | 22946 GCTAGATGAGGGAGGCTGGAAAC | 33930 |
| 305 GGGCCAGTACCCAGGAGGAA | 11963 ACAGGCCCACTGCCCTGTCT | 22947 CCTGGATGTGGCTGGCACTA | 33931 |
| 306 CACAGGGCATGAGCACCACCAT | 11964 GCTCACGGCTGGAATCATCT | 22948 CATTGGCAACCCAGCTCACA | 33932 |
| 307 TGGCAGAGTTGTCAGGATTCAA | 11965 AGCTCAGGTAAAAGGTCAAAGACA | 22949 AGCCCGAGCCTCCTACAACTT | 33933 |
| 308 AGGCGAGTGTCCCAAGACAA | 11966 GCAGGCCAGTAACGTCAATTC | 22950 ACAGGCCTCAGGCGAGTGT | 33934 |
| 309 GTGAACCAGGGACATCTGGACAAG | 11967 AGTGCTTCAAGCCTGACATTGT | 22951 TGGGAGGTGAACCAGGGACAT | 33935 |
| 310 TCAGGCACAGCCAGGTATAC | 11968 CTCCGTTCCCTCCTTCTCCAT | 22952 CGGCTGCACAGATAAGCTGTT | 33936 |
| 311 CGGGACGCAGACGGAATTACT | 11969 GGTGACCGATGGCACTGAATGT | 22953 CGTCACAGCCAGTTCTCACACA | 33937 |
| 312 GGCAGTTTGGGGAGCTGTGT | 11970 CACCCTGATCACCTGGGAAAAG | 22954 TCTGACCTGCGGGCAGTTTG | 33938 |
| 313 CTGACATTTGCGGGCTGTTG | 11971 TGCTGTCAGCCACTCTACACA | 22955 GCGAGAAACACCACTGACATTTG | 33939 |
| 314 CTTCAGGTCAATGGAGCCAAGCTATG | 11972 TTCCCTTAATGCATGGAGGTCAA | 22956 CCCAATGGTAGCTGGCATGCTT | 33940 |
| 315 CTGGCTGGACCCTTCCTGAT | 11973 CAAGCTTGCTCCCTGACACT | 22957 ACCTCCCCAGGGACACTCACT | 33941 |
| 316 GGGCCCTGGCTGTGTGAA | 11974 AGGCAGTGCCAGGTCCTGAA | 22958 AGGCAGTGGCTCCTCTTGTA | 33942 |
| 317 TTCCTCGTGGACCCTACTGTGT | 11975 TCCTTCCAGGGTTCGTTCTTT | 22959 GTGCCGGTGGATCCTCACTT | 33943 |
| 318 CGTTGGCTCCTAAAGTCAGCTA | 11976 GCAGTTACCAGGGACATTACTGAA | 22960 TGCAATTGATCGTTGGCTCCTA | 33944 |
| 319 GTGTAAGGGCGGTCTAACTGA | 11977 GGACCTGAAGTGGATGAGCTTTGT | 22961 GGCCGCTTTCTAGGGTGTAAG | 33945 |
| 320 ATCAGACCAGGGCGGAACCAA | 11978 AGTCCTGGACAGATTGAGA | 22962 GGTGAAGGTGAGGAATCAATCAGA | 33946 |
| 321 GGAGACCATCTGGGAACCCTTCAAC | 11979 GCAGAAGGAGCACCTCTCCATA | 22963 TGTGCCTTCTGGGAGACCAT | 33947 |
| 322 GGTCCTGTCGTTGAGGTAGTCA | 11980 GTCACAGCCATCCAGTCCAA | 22964 GGTTCTCCAGAATGTCCTGTCGT | 33948 |

| | | | |
|---|---|---|---|
| 388 TCATGCTGCTGGGTAATGTTCT | 12046 CTGTGCAGCAGAGGCAGTTATG | 23030 CCCGCAAGGGTTGGGGAAAT | 34014 |
| 389 CTGGGCCATCCTCCTCTCT | 12047 GGGCCTGAAAGGCAGAAATC | 23031 TCCAACACCATCCGCTCTTC | 34015 |
| 390 TGGAGAGTGGGGACGAGCTT | 12048 GCATCCATCCGGGCAGTTTTCA | 23032 GTGGGTGCAGAGTGAGATTC | 34016 |
| 391 GGAGCATGCCCCTTGTTACT | 12049 GAAGCAGGAGCTACTTCTACCAT | 23033 GGCCGGAAAAGGGAGCAT | 34017 |
| 392 GTCTCTCCCTGAAGTAGGGTGT | 12050 GACCCAGACTCAGTCAGTAGATG | 23034 GTCTTCCCATAGTTAAGTTGTCTCTTC | 34018 |
| 393 TCACTCACATCATCATGGTGGAT | 12051 CAAACTGGAAACCATACCCACTTC | 23035 GCAGCTACGCATACAAATCACTCACATC | 34019 |
| 394 GCAGCAGCATTGCCTTCGTT | 12052 TGGGGCTCCACCAGCCAGAA | 23036 ACTGGACTCAGGAGCAGCAT | 34020 |
| 395 GCCTGGCATCACGCAGTTTT | 12053 GCGTCTAACAGGCCTCACCCAAT | 23037 AGGCCACTGCCTCGCATCA | 34021 |
| 396 CCCGTTTGAAGAAATGATAGCTCGAA | 12054 CTGGTGGGAGTGGGCTTATTT | 23038 GGACTTTGTTTCCCGTTGAAG | 34022 |
| 397 GGGTGCTGTTCTGCGTTTGA | 12055 GCAAGTGTTATCAGAAGTCCACCTTACT | 23039 TCTAAATGTTCTCTGGGTGCTGTTC | 34023 |
| 398 GGGCTGTGTTGTTGACAGAGT | 12056 TCAGCCAAAGACTTTCCCTGTATT | 23040 GGGGTCTAATGGCTGTGGTTGT | 34024 |
| 399 CCCTGTGGAACAAAGTGGGAACT | 12057 GCAAGACGCAGGCCTAGTAA | 23041 GGCTGTTAGCCCTGTGGAACAA | 34025 |
| 400 GCAAAAGGCTTCCTGACAGTGA | 12058 TGGCCACGTCCTCCTCCACTA | 23042 ACAGCAGACAGGAAGGCTTGT | 34026 |
| 401 CAAGAGGACCTTCGGAAACTTTGA | 12059 ACAGCAGGCTTAATCCTAGAGGTA | 23043 GGACAAGGCCCCTTTAATTCATACCAAGA | 34027 |
| 402 AGGCACACGCAGTCTCATC | 12060 CCCAGAGTTGCAGTAGGACACGT | 23044 AGCCCAGAGCAGCGTTCA | 34028 |
| 403 GTGTAGAGGGCAACTCCTATCTTG | 12061 CTGCTTGCCCCACCTCTT | 23045 TGGTAGTGTAGAGGGGCAACT | 34029 |
| 404 CAGGCTACAAAGGGTGTTGCTGCTTTGT | 12062 TGCCGGGCTCAGTTTGAAT | 23046 GGGGCAAGGCGTTCAGACTAC | 34030 |
| 405 CTGCGTTGTGCCTACTCTGT | 12063 CTTCCTTAGGGATCTGGGTGATG | 23047 ATGCTCAGGCTGCCGTTGT | 34031 |
| 406 GGTGTCCCGCACTAGCAT | 12064 CGCTTTGGAGGGAGCCATCTGT | 23048 TGGCTCCCCTGAGGAGTGTTTG | 34032 |
| 407 GTGAAGCCAGACAGCAGTAATCA | 12065 CCAGCTTCAGTGTGCACCAA | 23049 CAGAAAAGTCTAGTCAAGCAGACA | 34033 |
| 408 GGAGGGTGAACAAGGCAAGATG | 12066 CCTCAGAGCTGTACTCTGCTCGAA | 23050 CACAGACAACTGGAGGGTGAAC | 34034 |
| 409 ACCTGCAGGAGCTAGTTAGAGA | 12067 TTTCCTCACTGGGTGGGATCT | 23051 ACATACCTGCTGTACCCCAAATG | 34035 |
| 410 GCTTTCAGTCCCCACTTGTGA | 12068 GCGGCAATCCACATCTGA | 23052 CCAATGAACAACGACGGCTTTCA | 34036 |
| 411 GTGAGGCAGGAAGGATGAGTTT | 12069 CCAACTCAGGGCAAGTGCTTCT | 23053 GACTGAGCTTGTGAGGCAGCAA | 34037 |
| 412 GAGCTTTGAGACAGTGGGGTAAC | 12070 GGTTGCAAAGTACTGTGGAATAAAG | 23054 GCATACTAAAGGACCTTGCAGACA | 34038 |
| 413 CCAGCATCAGGTCACAATGAAC | 12071 GAGGCACTTGGGCCTTCCTATC | 23055 GCCAACCAGGCCAGCATCA | 34039 |
| 414 ACTGAGGCGGCATTGCTTA | 12072 TCTGCGATGCGTTCCTGTT | 23056 ACAGAGGCGGTACAGCGGAATC | 34040 |
| 415 GCGGCAAGGAGGGTTTCTAA | 12073 GTGAAGCTTGGGCTGGTTTG | 23057 GAGAAAGTGAGCATTGCCATGAAAG | 34041 |
| 416 TCAGAGTTCTGTCCTAATGCAGGAA | 12074 CCATACAAAGCAAGAGTGGGAAGT | 23058 GGTCTTACCTTCAGAGTTCTGTCCTA | 34042 |
| 417 CACTAGTCTGGAAAACCAGCACCAA | 12075 GGGAGGGGTTTCCCCACTAAGA | 23059 GGGGAACATTTCAGACCAGATAACACT | 34043 |
| 418 AATCCTGGAACACTCTTGCCTGAA | 12076 CACCTTCCACAGCTGGACCTGCA | 23060 AGGGCCAATCCTGGAACAC | 34044 |
| 419 GTGTGAGCCTAGTTCTTCTGCTCTTC | 12077 CAGCCGCTGACTGCCTCAT | 23061 CCTTGCACCAAAAATGAAGTGTGAGCTA | 34045 |
| 420 CAAATGCAGCGTGCTGATTTA | 12078 TGAAAAGGGCATGCTGCTTTC | 23062 ACTCCCAAGTGCCTGCAA | 34046 |
| 421 AATCGGCCACAGCTCCAGAGA | 12079 CCCCTGCTGGTGGTCTGTTC | 23063 CACACGTGAACCTCAGGCAATC | 34047 |
| 422 GGATCTTCTGAACACCACATCCTT | 12080 GGGCCTGGGTTCTCCTTCT | 23064 CAACAGCCGGGTCTTCTGAAC | 34048 |
| 423 ATCCAGTTCCCTGGGTGACCT | 12081 CAGTGCCTGTGGTCTCACACT | 23065 GGGCCTAGGTGTGTGTATCCAGTT | 34049 |
| 424 GTTTTTCCACACCAACACACCTTTCT | 12082 GCTTACACTGACCCTGCAACTCA | 23066 CCTGCTCCCAATGTTTTCTCCACCAA | 34050 |
| 425 AAGGGGACTCGGAGGACAAGA | 12083 TGCCCTGCACCTCTCATCT | 23067 GGGTCTAAGGACACCGGGTCTA | 34051 |
| 426 GGGCCAATGTGTCCTGGTTGT | 12084 GGAGGCCACACACCTCCTA | 23068 TTTCCGGTGGGGCAATGTGT | 34052 |
| 427 TGCCATGCCCTTTGCCTATAC | 12085 TCTCAGCCGACTCAGATCACT | 23069 GCATTGTCAGGCTTCTCTCTTTG | 34053 |
| 428 GCTCTCAGCCAAATCATCCATTTG | 12086 CATTCTGGAGTCTGGGTGATT | 23070 CACAAATCAGAAGCTCTCAGGCAAA | 34054 |
| 429 CCTGGGATTTACCATGTCCCAAAA | 12087 ACGGTGAAAAATGAGGCTGTGT | 23071 ACTCCTTTGCCTGGGATTTACCAT | 34055 |
| 430 CGTGCTCCACTTTCCTGGCAA | 12088 GGHGACAGAGGCATGAGA | 23072 ATCTGCCCCTGGCCCACTT | 34056 |
| 431 CAGCGATGAGCCCGCTGTTTCTA | 12089 TGCCACTGCGTCATCTGTCA | 23073 AACACCTGGGAGGGCAACA | 34057 |
| 432 AGACTTCGGGCCTCCAGACA | 12090 GGHCCGGGGACTTCATT | 23074 AGGCAGGGACCACAGAGAT | 34058 |
| 433 GCATAGTCCACAGTAGGAAAAATGCAA | 12091 CTCTGGCCCCACAATCAATGT | 23075 GGTTTTGGGGCATAGTCCACAGT | 34059 |
| 434 GGCAGCTGCAACAGTATGTCT | 12092 ACCCTGTCCCAATACCCTGTATC | 23076 CCTCCCCTCCCAGCATGAAG | 34060 |
| 435 GGTCTGTCTGATTCAGCTGATAC | 12093 GCCTGACCTATGACCTTCAGTAAC | 23077 TCCCTGGGTGCTCTGTCTGATT | 34061 |
| 436 CTCAGTGGGCTTAGAATAAACCTGAAT | 12094 GAGCCACCACAGCACTGT | 23078 CCCCATCCCATTGCTTCTCAGT | 34062 |
| 437 GGAGGTTGGCTGGGTCTTT | 12095 CCTCAGCCCTAACAATGATCCAAA | 23079 TGGCTTCAAGGTAGGGAGGTT | 34063 |
| 438 AGGGGGTCCCAGGAAACA | 12096 TGAGCCTCCTGCCTGCTA | 23080 GGAGGGTGGCAGTGTGGTA | 34064 |
| 439 ACAAGGGCCTGACTCAGCTT | 12097 GTGCCCTTGGCCACCAT | 23081 GCTGTATCCAGGGACGTGACAGG | 34065 |
| 440 CCTGCGTGCTCTCCCTTGAA | 12098 GCTGGATGGGAGACAGGAAA | 23082 CCTGCGTGTCAAATACTCCTTTCTA | 34066 |
| 441 CCTCGGTGGACACTTGGTCTTG | 12099 ACACGGCCGTCCAGTCAGT | 23083 GCTGTTGTGCTTAAGAGCCTGGAT | 34067 |
| 442 GGAGATAGAAAGTCATGGAGGGTAA | 12100 TGCGTGACAGGGAGAT | 23084 ACCAGGCATAGTGGAGATAGGAA | 34068 |
| 443 AGTCTCATGCAGGCTGCTT | 12101 CCACCAGGACTCGGGTCTTCT | 23085 TGCCGGCCTCCCAGTCTCAT | 34069 |
| 444 AGAACCCTTGCACCCTCTTTCT | 12102 GGACTTCCCTGGATGAAGATGAGA | 23086 TGCTCGGGCAGGGTGAGAA | 34070 |
| 445 GGCCTTAATTGACACCCTAATCTTG | 12103 GGGGACACCGATGGGAGACA | 23087 GGCACCCGTTTGGCCTTAATTG | 34071 |
| 446 GGAGAGGGCTAAGGGAAACAGA | 12104 GTGGAATGCAGGACTGTCTCT | 23088 TGGTGGGCAGGAGAGGCTAA | 34072 |
| 447 ATCGGTGGTGGCTGTGCGATT | 12105 CCAGACCCCTTGACTCTATCCAA | 23089 AAGTGGGTGCTACAGAAGCATT | 34073 |
| 448 TTGGGTCATAGGGCGAGAATG | 12106 TCCACCTACGGCCAAGAATG | 23090 GGGCTAAGAATGAGTGATTGGGTCATA | 34074 |
| 449 ACACGAAACCGGCGCTCAGAA | 12107 GTGTGTGATTGGCCGGATCT | 23091 TTCAGGCTCTGACACACGAAAG | 34075 |
| 450 TGGCCTTCTGGGTTCTAGATGT | 12108 AGAAGGGATCACCCCACCTT | 23092 ACTCCTGACCTCAGGCAATGT | 34076 |
| 451 GGAAACCATCCCATGTCTACTGTGT | 12109 CTCCGGCCTCAAGTACCTTCAATTT | 23093 CCCAAAGGCAAACCATCCCATGT | 34077 |
| 452 TCCCACTTACTACGCTCCAAGA | 12110 GCTTGGACTCATGGTACACGTT | 23094 CACAGGTTCCCTCCCACTTACT | 34078 |

| | | | |
|---|---|---|---|
| 713 GCTCAAGTACTCCCTGGCTTCT | 12371 CCAAGGCCCTCCTCTCTCTAAG | 23355 AGAGCTGGCAGGCTCAAGTA | 34339 |
| 714 CAGCATCTTCTTTGTTTGAAGGAGCTT | 12372 CACAGGCAGTTAGGGTAGGTTCT | 23356 CTGGGGCCTGCAGTTTGATT | 34340 |
| 715 GGCAGACAAATCAGCCCAGTT | 12373 TCCCCACTGATGGCAGTGACTT | 23357 GCAGCCTGCAATCTTGGCAGACA | 34341 |
| 716 GTCAGTGAACTCGCTTGCAT | 12374 TGGAGCAATATGGTGCACTGTT | 23358 GAGCTGTCCACTAACCATTAATTAGGTCAT | 34342 |
| 717 GGCACTACAGATAAGCACCACTGT | 12375 CACTCTGTCAAGTTTGCCCGTCTT | 23359 TCTCACCTTAGCCTCCCAAGT | 34343 |
| 718 CAAAGAGGCCCTCATGCTCAGT | 12376 GCAGGCATGACAGACTTTCCTT | 23360 TGGCTGCCCTCCTTCCATGAT | 34344 |
| 719 TTGGTCCTACAACCAAGCAAGT | 12377 GCGTTCCCCATGGCATGTCTAAA | 23361 CCCAGGAGTGTATCTTGGTCCTACA | 34345 |
| 720 GCCAGAGATGAATGGTTTGCGAATG | 12378 TTGGAGTGGACGTCTTCCTATTTC | 23362 GCGGATTTTGAAGCCAGAGATGA | 34346 |
| 721 CCTGTGCCATAGAATCAGCACTCT | 12379 CAGGGCTCCCTCCTCCATTT | 23363 CCATATGAGCCTCTCCCTGTGCTA | 34347 |
| 722 TGTGTGTTGTGGAGGGGAGAT | 12380 CAGCACTGAGTTCATTGCCTCAAAAA | 23364 GCGTCGTGCAGATGGTGTTT | 34348 |
| 723 GAAGCTCCTTACATTAGTGCCAGGTT | 12381 GCCAGAGGAGAGACCCTGAATCT | 23365 TGGTCTCCTGGGAGCTCCTT | 34349 |
| 724 TGCACTCAGAGGAGAAGTTAAAACA | 12382 GACTGCAACGAGAGCTGACCTA | 23366 TGTAAACAGGGAAGATGCACTCA | 34350 |
| 725 GGATCAAAGTTCAAGGAGTTAGTGTCA | 12383 TGCCCTGGGTGGTCTTGT | 23367 CCTCCTGTCAGGGATCAAAGTTCAAG | 34351 |
| 726 CGCCACCAGCAGTTGAGTCTTG | 12384 CAGGAGAGACCTGATAGCCCTATGT | 23368 GGAAAATCGCCACCAGCAT | 34352 |
| 727 CCGGCCAAGAAGGTAGCAA | 12385 GCAACAGGGTTTGTCCTCTGGTT | 23369 AGCAGTCAGTCAGTTCCAGCTA | 34353 |
| 728 GGGCTTCTGGCCAGAATGAA | 12386 CCTCGTCCTCCCATCCAAA | 23370 CCTGCAATGATTACTGGGGCTTTC | 34354 |
| 729 GCCACAGGTTGGAGGCAAGA | 12387 CTGGAAACGGGCCCAGAGT | 23371 GGCTCTCTTGGCCACAGGTT | 34355 |
| 730 AGTGCCCTGCTAACCTAATAC | 12388 TGGTGGGGACATTTTCCTGAAG | 23372 CACTCCCAGAATCAAAGCCAAAG | 34356 |
| 731 TCCCTCTTGTTTCCAGGTTTTGT | 12389 CTGGTTGCAGTGTGGAGCAT | 23373 CCTGTTAGCTGTCCCTCTTGTTTC | 34357 |
| 732 GGAGGCTCCATCCACAGTCA | 12390 TCAGATGTCAACCCCGCCTAT | 23374 ACACACCCCACAGCTTCTTC | 34358 |
| 733 GGGCAAATCTGTCTCCTCCAGATA | 12391 CGGGCGACTACTGGAGGCTTT | 23375 GGCTGGAGGGCAAATCTGTGT | 34359 |
| 734 GGGTATCAAGGTTGACTCTGGATT | 12392 AGGTAGCCACAGACTTCTCCAT | 23376 GCCATCACAGAGGGGTTACAGTT | 34360 |
| 735 CCTAGCCTACAAGCGCACTCT | 12393 TGGCCTGCCTCACCTGCTTA | 23377 TCACTAAGATATAAGGCCTAGCCTACAA | 34361 |
| 736 GAGTACTGAGGCAGGCAAGGTTT | 12394 TCCGGAAGACACGAGAGGAAA | 23378 GGGTCCAATGTGAAAAGCACAGAGT | 34362 |
| 737 CCAATGAGTTGTAGAGCTCAGATTGT | 12395 ACATGGTTTTGAGTCAGGCATT | 23379 CAAGGCCTAAGCGCCAATGAGT | 34363 |
| 738 GAGGGGTCCTAGTCAACTGTGT | 12396 GAACCTTGGCTCTTTGCAAGTCATC | 23380 CCTGAGGTGAGGGGTGCTAGT | 34364 |
| 739 AATGCCAAGCCACCCTGGAA | 12397 TGACTGACTGGGCCCTTCAGA | 23381 GGCATGCTCTTCAGGGAGAACTTAG | 34365 |
| 740 AGGAACCCACAGCGGTAACTGA | 12398 GGCAGGCAGCCAATAAAGGATGTA | 23382 TGTCCCCAGCACCAGTAAGTTC | 34366 |
| 741 TGCCAGCTGAGTGCAGCAT | 12399 GGGCTTGTGAGTGCAGCAT | 23383 GCGGGAAGTTGGCTTGTTGTTTG | 34367 |
| 742 CTCCAAGTCCAGGATATGAAGCAA | 12400 CAAAGTGGTGAGTTCCTTGGGTTT | 23384 GGCTTCTGAACTACAAGTCCAGGATA | 34368 |
| 743 GCACAGAAATAATCGTGCAGGAAA | 12401 TTGCTTCTCCCAGTGCCTTCA | 23385 GGGCTCCATTGTGTTCCTCAAC | 34369 |
| 744 GGGAGCAAACCTCTTAGGAAGACA | 12402 GGTGCTCTAGGGCCTCACA | 23386 GGTTCTGAGGGGAGCAAACCTCTT | 34370 |
| 745 TTTGGGGTTTGGGATGAGGATAA | 12403 CAGTGAGGAACGTATTCAGCCTAT | 23387 ACCCTCTTAATTGCTTGGGGTTTT | 34371 |
| 746 TTCCTCTCCCAACCGTCTTT | 12404 GGCATCGCTCACCTAAGT | 23388 CGTGGAGAGGTATTTTGGCAGTGT | 34372 |
| 747 GCTACCCTGAAGTGCTGATGGAT | 12405 AAAGAAAGAGGCACAGTGGTACA | 23389 GGCTGATTTCTGCTGTCCTTCAAGCTA | 34373 |
| 748 CTTGATCGTCAAGGGAGAAGAGAGA | 12406 TCTGGCCACCTGGGGATTT | 23390 CAGTTGCCTGCATCTTGATCTGT | 34374 |
| 749 GCAAAGGGAGTCATGGGAGATGA | 12407 GACATCACCCACAAAGCCTTCCTT | 23391 GCACTGGTGGAAGAGACAGCAAAG | 34375 |
| 750 CCGACTCTTGGTGCGTTGAA | 12408 TGCCTGACCTCCATGGAAAC | 23392 ACCCATGACAGCCGACTCTT | 34376 |
| 751 TGTGTTCCTAGAGACTCTGGCTTT | 12409 GCCCATGTGAGGCATGACTT | 23393 CCTTAGAAAGGCCTCTCTTCTCTGT | 34377 |
| 752 ACCAGCTGTGTGAGCTAAGTTG | 12410 AGAAAGCCGAGGCTGAGA | 23394 CGGTCTGAACGGGAAACTGCCATA | 34378 |
| 753 TTGCCTTCCCTGTCTTGCAA | 12411 AGGCAAGCTAGCTGATATCCTTC | 23395 ACCCTGGCTGCCTTGCCTTT | 34379 |
| 754 GCAGGACTAACAATGGCTACAA | 12412 GGTCAGTGACCCAAACCTTCA | 23396 GCTCAATCAGGCAGGCAGGACTAAC | 34380 |
| 755 CAGGAGCCACCTGGGAACT | 12413 GGCATGCTTTCAATATATCCTCCTAGT | 23397 GGAGTTGGCCCAGAAGCTTCCAT | 34381 |
| 756 TGGAGAAAGAGCGAATCCATGTTGT | 12414 CCGGGGAACCTGGGAAGTGA | 23398 CTAAGGGCTTGGATAAGAGCAAA | 34382 |
| 757 CCAGGACCCAGAAGTACTCCCTAT | 12415 CCTGGTGAGTAACGGAGAGTCA | 23399 AGCCAACCAGGACCCAGAAGT | 34383 |
| 758 CCTACCATATGCAAGGCACCAT | 12416 CAGGCATGGGCAGTTTCTTTTATC | 23400 AGACACATTGCAGCCTACCAT | 34384 |
| 759 AGAAGTCCAGCCTCCCACTTG | 12417 ACCCTCTGCTTCTGGTGTCAGT | 23401 CACTCCATTAAAGCCATTGGGAATAGAAG | 34385 |
| 760 GGGCTTGTTAAATGACCCCAGAAGT | 12418 ACCCCTACAGTGACGCGGAA | 23402 AGGGCCATGGCTTTGTTAAATG | 34386 |
| 761 GCCCAGTAAAACAAAGTACACAGT | 12419 GGGGCATGGAATCAGGAACTT | 23403 TGGGTACCAGTTAAGCCACAGT | 34387 |
| 762 TGTGCAGTCAATCCAGAGAACTAT | 12420 TTAGAATGGGAGCGGAGACCTT | 23404 AGAGGGACTTATGTCCAGTGAATG | 34388 |
| 763 CTCACAAGCCTAGAAGGGTATGTT | 12421 GCAATGATCAGTGCGTTTTAGA | 23405 GCTGGTTTTCTCACAAGCCTAGA | 34389 |
| 764 ATGGGACACCTCCCTGCTCAGT | 12422 ACCATAGGGTTGGGCAATGA | 23406 AGACTGCCTGCTGTTCATCA | 34390 |
| 765 GGTGTAGCAGGGAGAGAGATTGGT | 12423 ACGGGTGCCGGCCATTTCT | 23407 GCAGGGGCTGTAAAGGGTGTA | 34391 |
| 766 GGGCTTGTTGCCTCTCCACTTA | 12424 GCATGTGCCTGTTTCTAACCAT | 23408 CTGGGTGTCTCTATGGCCTTGGTTG | 34392 |
| 767 CACTTCATACAGTCTTCACACCTGGTTGT | 12425 GCCCACCTTATACCTCGCTGCAACT | 23409 GGTGCCTCACTTCTACTGTCA | 34393 |
| 768 AGAAGCTGCTTTCTGCTTGTCA | 12426 CCTCCTGCCACCACATCCTATCA | 23410 AGAAGCGAGGGCAGAATTTCAGAAG | 34394 |
| 769 GATTGTTGTGTCCAGAAAGAAGA | 12427 TGGTGACGGAGGATGCAGAA | 23411 CACACAGAGCCTGGGCTTATATC | 34395 |
| 770 GAACAGTTGGCGATAGGCTGAA | 12428 TGCATCCACCTGTCTATGACT | 23412 GCCTGGGATCTCTGAAGAACAGTTG | 34396 |
| 771 GGGCCTATACTCCTTCAGAGA | 12429 AGCCAGAGTTCTGCCTCTTG | 23413 CCCTTTGTAAAGCATGGCCCTATAC | 34397 |
| 772 CACAGGGTGATAGCAACAACCTACCAT | 12430 AGGCTGCGAGTTTGGCAGAT | 23414 TTCTCATACACAGGTGATAGCAACA | 34398 |
| 773 CTTTGGGTGGAACCTGTGATTCAA | 12431 GTCCGTGCTGGTGCACTT | 23415 CCTCTTTCCCCTTGGGTGGAA | 34399 |
| 774 AGGCACCATGCTCAGCTCCTA | 12432 GCACTATGCAGCAGGAACCTAAG | 23416 GTTGTTGGCCAGGCACCAT | 34400 |
| 775 GCTCAAAGCCTTGGGGTTCTAC | 12433 ACAGCCCGGTTGCTTTGT | 23417 CCCTGGCTACTGCCCATGTTT | 34401 |
| 776 GCTCTCAAGTCAGTCCCTTCA | 12434 CCAGGTCAGGGTATATTATGGAAACA | 23418 GCCTTGGTTGTCAGCTCCAATGT | 34402 |
| 777 GCTGGAGTTCCAGGTTGGACTT | 12435 CCGTTGGCCACTCATTCAAGA | 23419 CATCTTTGTGGGGCTGGAGTTC | 34403 |

| | | | |
|---|---|---|---|
| 1168 GATCTCATGGCTACGGAGATCAAG | 12826 ACCTCAACCTCTGTGTGTTC | 23810 GGGTGACACCTGAGGTTCTTGA | 34794 |
| 1169 CCTCCTGGGAAACTGGCAAGTAAAG | 12827 CTACAGTCAGGCTGAACAATCAT | 23811 CCCAAAATGCCTCCTGGGAAAC | 34795 |
| 1170 GTACATGGTTATGGCTACCAGGAA | 12828 CCTCACTCCCTCCTGTCTT | 23812 GGAACATCCATGGTCACGTATTTG | 34796 |
| 1171 TGGTCAGTGCTCCCAGAGTT | 12829 ACAGCTAGTCTGGATAAAACCTAGAGA | 23813 GGTCTAGGGTCTCAATTGGTCAGT | 34797 |
| 1172 CGGACATGTCTCGTGTCACT | 12830 CATTCCTCTACAGTGGAGGGAACT | 23814 CCCTTTGCAATGACTCTTCGCACAT | 34798 |
| 1173 ACCACTCACAAACCTCTGCAT | 12831 GGTGGCACGGTCAATCACTAAG | 23815 CCACTGCCACCCACTGACAAA | 34799 |
| 1174 CAGGGATGAATAAGCCTCATGAAAGA | 12832 CACCGTGCCCAGCCTGTAA | 23816 GAGTGGTTTCCCATCAGGGATGA | 34800 |
| 1175 ACTGCAACACTGTGATTGTCTTCA | 12833 GGCATGTTAGCGAGCATTTTACA | 23817 GGCAAAACTGCAACACTGTGA | 34801 |
| 1176 TTGGGCTCCCAGAGTGTTGT | 12834 GTTCTCGTTCAGACAGTCGTTCT | 23818 TGCAGGTTTCTCACATAACTCCTT | 34802 |
| 1177 CRGTCGAAACAGTGGAAGGATGA | 12835 CAGGAACCTCATCCTGAGTTGATTT | 23819 TTCTCTCCAGCAGCACTCTTTATT | 34803 |
| 1178 TGAAGCATCTCGGCCTGTCTGA | 12836 TCTTGCTGGACCAGAGTTGTGA | 23820 CTGTCGGCCCATGAGACATCT | 34804 |
| 1179 TTCGGGGTCATCCTCACAT | 12837 AGGCCGAGGGAGTTTGTTG | 23821 TGTCTGCTCTCCTAGCGTCTTCKC | 34805 |
| 1180 CATCCACAGCTGTCTCCGTGTA | 12838 GCCCTCAAAGTGGTGAAGAGT | 23822 CACACAATTCAGGAGCTTGATCTCATC | 34806 |
| 1181 TTCCAGGTTGTTTTCTGCAAGTAG | 12839 CCTTGCCTGAGCTGGTATTTCT | 23823 GGAACCATGTTCCTTCCAGGTTGTT | 34807 |
| 1182 TCCCAGAGACACAGCTAGTGAAAAAC | 12840 TGTGGCTACAACTCAGGCAAA | 23824 TCATCATCCCAGAGACACAGCTA | 34808 |
| 1183 TGCTGCTCGTACAGTGGAAAG | 12841 GACATTGCTTGACTTGGTCTGT | 23825 CCTTGTGCTGCTAACCATGAGACT | 34809 |
| 1184 GGAGCAGTATCATTTTGGTGCATTG | 12842 CTCACCGCTCCCAGAATGAATC | 23826 GGACCCTACTGATTCTCCCATCAT | 34810 |
| 1185 CGGTGGTGCCTTTGTTTTAACT | 12843 TGTGTGCTGACAGGTTTGTGA | 23827 CACACTTTTCGGTGGTCCCTTT | 34811 |
| 1186 GTACAAGGAATGTCAGGAACCAAAC | 12844 GGAACAGGCAGCTACTTGCCAAA | 23828 AGGAGCCAAGACAAGCAGGAAG | 34812 |
| 1187 AGTAGGTGTGATGGCAGGAT | 12845 GTCCCTGTTGTTGTGCTGAT | 23829 TGGGCATAACAGAGTAGGTGTGA | 34813 |
| 1188 TGTCTTCCTAGCCTCATCTCTCA | 12846 GGCTGCAGCATAAGGAATGTGA | 23830 TAGCCCCACGTGTCTTCCTA | 34814 |
| 1189 GCTAGGGGATACTGAGTCCTGCAT | 12847 GCAGACCATTGCCTTGGAGGAGATA | 23831 ACTTGTTCACTTGCTAGGGGATAC | 34815 |
| 1190 CCCAAAGAGTCCCCATCTGCTT | 12848 CTGAGCTGGAAGACTCAAACT | 23832 CAGAGAGAAGGAGGCCCAAAGA | 34816 |
| 1191 AGACCTAGGCGGCAAACAGA | 12849 GCAACTTTAGGCCAGCTGAGTT | 23833 TGTCAGTAACGGTGGAGACCTA | 34817 |
| 1192 AGTTCCTGGAAGCCAGCTATTAAA | 12850 AAGACAGGGTGGGAGATGTAGT | 23834 GCCTTTTAATTAGCCTTGCAGCTT | 34818 |
| 1193 CGTAAGCATACGGGCTGCAGTA | 12851 CCTGGATTTGGGCATACGTGAA | 23835 AGTGGGAGCCTCGTAAGCAT | 34819 |
| 1194 GCAGTTGAGGGAGTCAACTAAAGA | 12852 TTCCCTGAACTCTTGCTGGTTT | 23836 GGAATAGGTAGGTGCAGGCAGTTG | 34820 |
| 1195 CCTAGGCTAGAAGCCCAGAAAAC | 12853 GGGTTGAAACTGAAGGCTTGTTC | 23837 ATCCACAATTTCCTAGGCTAGAAG | 34821 |
| 1196 CCTTCCCTTTGTCACACACATC | 12854 ACTCTGTTACCGGTATTTCACACT | 23838 GCCTAGGGTTCTCTTCCTTCCCTTT | 34822 |
| 1197 CCTGTGTTCAGGAAGAATGAGAT | 12855 GCCCATCCAGACCTTCTAATTG | 23839 TGGTCCCCCGAGCCTTTTC | 34823 |
| 1198 GAAGGAAACTGACTTGCAGCTTAAC | 12856 CAGCCTCGTCAGCAGTTG | 23840 TGGGTCTAGAAGGAAACTGACTTTG | 34824 |
| 1199 AGGGAGAAAATCACACTCTTCCAT | 12857 AGAACCCCATACCTGCATTACAAA | 23841 GGGCTCAGGGAGAAAATCACA | 34825 |
| 1200 GGGACCAAGTCAAGCTGTAG | 12858 TCCCCTGGAACCTCCAAAACT | 23842 TGACTCTTACGGGGACGAAGT | 34826 |
| 1201 CCAGAGAAAACAGAGGGCATTGGTT | 12859 GCGGGTCGGGACATGTTGA | 23843 GATGACCTTCCAGAGAAAACAGA | 34827 |
| 1202 TGGTCTCCAGCGTTTGCATTTC | 12860 AACGCCACCCGCCTGAAAG | 23844 GCAGGGCTCCTGGGCTAATG | 34828 |
| 1203 GAAAGTACAGCCTATAGCTGCATGGAT | 12861 GTTTGTCCCALACACCCTATTG | 23845 CCTCTGACCAAAAGAAAGTACAGCCTAT | 34829 |
| 1204 GGCCATTGTGCTGGTCTCTCT | 12862 CGGTGCTGTTATAGTGAGTTCCAACA | 23846 AGGAACACGGGCCATTG | 34830 |
| 1205 CTGTGAAAACTGGGACTAGCAAAG | 12863 GGAGTGCTACGGCAGCTT | 23847 AGCATCTCTCTGCCCTGTGA | 34831 |
| 1206 CTCCTTGTAATCCCAGTGACAGAAA | 12864 GAGCAAAGGAACTCTGGTGAA | 23848 GGTTTGTGGTCAGTGACTCCTTGTA | 34832 |
| 1207 GGGTGGGAGCACAAAGTATGTTG | 12865 CAGGGCAAAGCCACGAAGTT | 23849 AGGTGGGTGGGAGCAGAA | 34833 |
| 1208 ACAAGRACGCAGAGCTGTCA | 12866 TGGGCAGGAACCTCCTGGTAAAA | 23850 GGCACTTGGCAGGCAAAACA | 34834 |
| 1209 TGGAGTCTGCTCCAGTAGCTAAG | 12867 GCCAGGTTGCTTGTGTAAAAC | 23851 TCTGGGAACAGCAATGGAGTCT | 34835 |
| 1210 GTCACAGTGAGTGTCTGCAAA | 12868 GCAAAACCACCTGAAGTACTCGTT | 23852 TGCCCAAGTCCACAGTGAGT | 34836 |
| 1211 TCCCTGGCCTATAGCTTCGTA | 12869 GCTTCAGCAGCAAACAGAG | 23853 GGTCAATGCCTTCGCCCTAT | 34837 |
| 1212 TCTTGGGATTCTGGGGCTTTC | 12870 CCTGCTGTTCAAGGATTTCTGAGCTA | 23854 CTGAGAAAGGAGGCTTCTTGGGATT | 34838 |
| 1213 CGTCTGCGCCAGACCTTT | 12871 CTCCAGTCGTTACTCCGTCAGT | 23855 CGCCTCCCATGACGTGAAC | 34839 |
| 1214 GGCCTGTCTATCTCAGCATGT | 12872 GGCACAACCAACAGTGGACCAA | 23856 TTCCCGCATGGCCTGTCATC | 34840 |
| 1215 GAGGAGTGCGCTCCAGTGGAGATAC | 12873 AGGGCAAGCTTCCCATTAAACT | 23857 AGGGCAAGCTTCCCATCTAACT | 34841 |
| 1216 GGCTGAGTTGCTTTGGCATGTAA | 12874 AGCACCACACCTGATCCAT | 23858 CTCTCTGTGTAGGCTGAGTTCTTTC | 34842 |
| 1217 GACCCTTGCATAGTTAGAGAGTGGTT | 12875 GGGGCCTGTGTGGACTCTAG | 23859 CCATCTGTGACCCTTGCATAGTTAG | 34843 |
| 1218 GCCCTAAATAACCCTCTACTCACGGGATTT | 12876 CCTCCTGGCTTGCCTGGTTT | 23860 AGAAGTTCTGCCCTAAATAACCTCTAC | 34844 |
| 1219 ACCCAGTGCTTGGTGTTCA | 12877 CTGATCCATTTGCCCACACACA | 23861 TCTCACTACAAAACCCAGTGCTT | 34845 |
| 1220 GCCCCATCCATGACTGGTCAA | 12878 GTCCTTAGCTGGACGCATAGTTG | 23862 GTTCAACAATGACCCCATCCAT | 34846 |
| 1221 GGGGCCTGGGTCAAAGAA | 12879 GGGACTTGGAAAAGCCCTCATAG | 23863 GGGCATGCAGCCTCTCTGT | 34847 |
| 1222 GCCAAGAACCTACCCTGCATTG | 12880 CCTTGGTCTGTGTACCCTGTTC | 23864 CCTGGTGAAGCCAAGAACCTA | 34848 |
| 1223 TTCCCTGGCCCTGTTCTCT | 12881 CCTGGGAGCCAAGAAGAAAGTTAATGA | 23865 CCCCTGCTACAGAATGCAGCTT | 34849 |
| 1224 CCCACTTTGCTGGTCTATAGCTT | 12882 CAGGTTTTTGAGTAGCAGGAGGAA | 23866 ACAGGGGATGTAAACCCACTTTG | 34850 |
| 1225 CCTGAGCATGTGGGTGTGGTTT | 12883 TGGGAACCACTGGACCTTCA | 23867 GCATATGCCCTAGAACAACCTGAGCAT | 34851 |
| 1226 CCCTCAAAATGGGAGCCAGCGATA | 12884 GTCACAGTGGGAAGGGCATT | 23868 CCTACTATATGCCTGGGGACCTCAA | 34852 |
| 1227 GACATAGGGAAAAGTCTGTCTACTTCA | 12885 ACTTCGGGCGCCCACTCTA | 23869 AGTCGGGACATACGGAAAAGTGT | 34853 |
| 1228 AGATCTCAAGGTAGGCAATGTGTCTCA | 12886 CCAGCCACTCTGACCTCTGTGA | 23870 CCATGGGGAATCTGGGCAATCA | 34854 |
| 1229 GGCAGGTAGAAAGGACACATCCTAT | 12887 TGGCATTGGGCCTGGTTGAT | 23871 CCATGTCTAGTCAAGGCAGGTAGA | 34855 |
| 1230 TGACTCCAGCTCCAGAGTTACA | 12888 CAGTCTTCCCTGGGATAGCAA | 23872 GTGTTCAAATTGCAGTGCTCTGTT | 34856 |
| 1231 AGGCAACGGCACACACCATT | 12889 CCCCTGGAAGGGACAGCAT | 23873 TCTGTCTGAGTCAAGATGGAGACA | 34857 |
| 1232 CAGGGATACCATGGAGAAGTTGGTA | 12890 GAGCCGTCCTTGCACACA | 23874 GCACCAGCCAGGGATACCAT | 34858 |

| | | | |
|---|---|---|---|
| 1363 CAACAGGATGTATCTCAACCAAGTCA | 13021 GATCACAGCGTACCTCTTCATGT | 24005 GCAATCCTAACAGGATGTATCTCA | 34989 |
| 1364 TCCCCATTCACCCCACCAA | 13022 GTGCCAGATGAGAGTCAGGTTT | 24006 AGTGAGGCGTCTCCCCATTC | 34990 |
| 1365 CGGGGATTCCTCATCCAGGTTGT | 13023 CCAACTGTGTCAGCTTCACA | 24007 GTAGAATAGCCGGGGATTGTCAT | 34991 |
| 1366 CGTTCTCACGGAAGACAACTTCT | 13024 CCCTCTTCACCCCATTCTTTGT | 24008 GTCACCATCAACACCTCTGACAAC | 34992 |
| 1367 CTCTGTCACAACTACTCCATTCT | 13025 GTTTCCTCTAGCTGCTTTGCATTG | 24009 GGCCATACAGTCTCTGTCACAAC | 34993 |
| 1368 GTTCCCACAATCAATCCCACCTA | 13026 GTGCTTCTCTCCATCAGGAT | 24010 GGAGACTCTAAATGGTTCCTACGAAT | 34994 |
| 1369 AAGGACCTGCCCCTCCTCAGT | 13027 CTCTGGAAAGGGCTTGAAGCAAATGT | 24011 CCAAGCTTATGGTGGGAACAGGAA | 34995 |
| 1370 CCTATCAAAAGATGAGGCACTGGAA | 13028 CAGGGTCTTTGCACGTGGATCT | 24012 GTTGGGTGGGATTGTTCCTATCA | 34996 |
| 1371 CACTGTTACCTCGGGATTGCTTTG | 13029 GCCTTGGGACAGGCATGCGT | 24013 CTGATGCCTGACCTGACTGTTAC | 34997 |
| 1372 GGGAAGGCTTGGGGTGTTCATTG | 13030 CCAAAGCCCCTCGTACTCACAT | 24014 AGCTAGGCGAGGGAAGGTT | 34998 |
| 1373 CCCCAGCTGATTGCCAGGAGAGTT | 13031 GTTCCTCTTCCCTGTGCTGTAG | 24015 GCCAAATGATTGCCCCAGCTT | 34999 |
| 1374 GCAAGGATTGAAGCCCAAGTCA | 13032 GCATAACAGTCGGTTTCAGA | 24016 GTGAGTAGTCGAGCCAGGAGTTC | 35000 |
| 1375 TCCATGCACTAGTGGTTTCTTACA | 13033 GGGGACCCATACTTTCTCTGAAC | 24017 ACCCAAGGATCTCCATGCACTA | 35001 |
| 1376 CCTTTCTAACAGACTCTGGCTCAA | 13034 GCTTGGAAAACCTTGGTGAGGAA | 24018 GCAGGGCCTTCCTTCTAACAGA | 35002 |
| 1377 AGCACTCTGCTATCCTGTGA | 13035 TCAGTACCCAGTGCCAATGA | 24019 AGCCCTCTGAAGCAGCACTGT | 35003 |
| 1378 GCTGCCTGAGTCGAATTTCAAAAC | 13036 GGTGTCTGAAGAGCCCCAATTC | 24020 AGAAGGTGAAGTCCCAGGAA | 35004 |
| 1379 TAGGGTCTGCGAGGCACTGA | 13037 GAGGAGGGTCTGAGCTTCTGATGT | 24021 GCAGCTCTGCCTGGTCTCA | 35005 |
| 1380 CATGACATTGCAACTCCCTCTTT | 13038 CAGCCCTGTGTTAAGCAGGTAA | 24022 CCTCCTCTTCCCTCCCTCCTTAT | 35006 |
| 1381 GAAAACGCGGTAGGATACAAGGTT | 13039 CCTGCATTAACTGGCTTCTACTTACT | 24023 GTGGAATGGAGGGTAGGTGAGAAAA | 35007 |
| 1382 TGACCTGGTTAGAGCACGTTT | 13040 GTCTCTCACTGTAGACAGGAAAGCAA | 24024 AGTATGCTACAGTTTGAGCTGCTTAG | 35008 |
| 1383 ACATGGGGTATTCAGCCAAATGT | 13041 CATGTGTCAGAGCCCGAACT | 24025 GCCTATGTACACAGGGGTATTCA | 35009 |
| 1384 AGCAACTCCGTGGTCAAGGAT | 13042 CAACATCTGGGAAAAGGTACTTCAA | 24026 TGCCTGCACCAGCATTTTCA | 35010 |
| 1385 CACAGTGACCTGCATTTAACCTTT | 13043 TGCAGCCTAGGAGGAATAGT | 24027 GAGACATCACAGTGACCTGCAT | 35011 |
| 1386 GCTCAGGTCAGCTGGTCTTCA | 13044 TGACGTCCCCGGTCACAGTAATA | 24028 CCCTTCCTTCCCTGTGAGGAATG | 35012 |
| 1387 GTCAGACTAAGAGGTTAAGTGCCTTGT | 13045 GTAGGCTGGGATTTCCCTGATG | 24029 GATACTGGAAAGTCAGACTAAGAGGTT | 35013 |
| 1388 GAGCAGCAAACGTCCTCAAC | 13046 AGGAGGGACCTTGGAGCAA | 24030 GAAGCCAAGGAGCAGCAAAC | 35014 |
| 1389 CCACAGAGGGCTGCAAAA | 13047 CCGAGGTGGCTGTGTATTAACT | 24031 CCAGTGCATTAGGCTGGAAGGAA | 35015 |
| 1390 GGCCTCGAACACTATACACCAAA | 13048 GTGGTTTTCTCAGCTGTCAAGATG | 24032 GGTGTCTGGCCTCAGAACACTA | 35016 |
| 1391 GCCTCCAGAGACCGCAAATACA | 13049 CAGCCAAGAATCCTACCACTGT | 24033 TGCCTGCTGGGAAACCAAGA | 35017 |
| 1392 AGGCCTCCATCTGCTCTTCGT | 13050 GCGAGGACAACTCCAACTCTTTCT | 24034 TGGGCAAGGCCTCCATCT | 35018 |
| 1393 CCTGCAGCTCCATGTGGACATTAC | 13051 GTGACTGCACTCCGGGATGA | 24035 ACTCCTGCAGCTTCCATGT | 35019 |
| 1394 CCTGTTTGGTACCAGCTTCTTTC | 13052 GTGTGACGGGAAAAATCCAGGAT | 24036 CCTCCTGCTTCCTGTGTCGTA | 35020 |
| 1395 TGGAGGGCAAAACCAAAAGGAT | 13053 GCTCAGGCCACCAAACCATCTA | 24037 TGTCAGAGTATTTGGAGGCGAAAA | 35021 |
| 1396 CCTCCTCCATGTGGCCATATTAC | 13054 GGATAAAAGCAGCATTCTGCAAA | 24038 TCTTTCTTCCCCCTCCTCCATGT | 35022 |
| 1397 CCTAACCGCTAGACCAGATGGAAGT | 13055 TCAGTGGGTCACCGCAGTT | 24039 CCAGGAATCCTAACCGCTAGACCAT | 35023 |
| 1398 ACCGTCACCACCAACTGT | 13056 GACCGTGGCTTCAAGGAAGCAT | 24040 GGCGTGCCTGGTCTAGGAGACA | 35024 |
| 1399 GTTCAATAGCTCCAGTGGGGTTAC | 13057 GCTGGTCGTAGCCCATAATATACTCA | 24041 CAGGTGCCTTGGTGTTGAGTTC | 35025 |
| 1400 CCCCAGATTCCCCACTGTCA | 13058 CGGGCTAGAGACAAACCCTGAA | 24042 TCACACGGACTCCCCAGATT | 35026 |
| 1401 GACCTGAAGATGGTAGATGCTCTTG | 13059 TTTCCTGCCCACCCTGCTAT | 24043 GAGAGGATCATACATTTACAAGACCTGAAG | 35027 |
| 1402 TGGGTCCTGTCTTCTCCACCTT | 13060 TGGGTACGACTATTTCCGGTTGA | 24044 CCGTAGGGGCATTTCTATTTCCAT | 35028 |
| 1403 TGTCGTGGAACGGGTACAGGAT | 13061 CCCCATCAGGGTCAGGTCTCTT | 24045 AGTGATAAGGACCTGTGGTGGAA | 35029 |
| 1404 AGAAACATTACCCACCCAATCAA | 13062 GGGCAAAAGTCCTCCTCAGT | 24046 CCGTGAACCCACTAATTAGAAACACTTAC | 35030 |
| 1405 CCAAACCAGCATGAAGCATTTACAGA | 13063 TGGGAGGCAGAGGGACTCAA | 24047 TGCCCAAACAGCATGAA | 35031 |
| 1406 CCACCTAGGACATGAGGAGTCA | 13064 CCACAAACACCGACCCTGTTC | 24048 CGTGTGCTTTCACCTAGGACAT | 35032 |
| 1407 GCCGCTAGAACTAAGTGCCAACA | 13065 TCAGGAGTCACTGGGGTGAAA | 24049 CCTGCCCGGCTAGAACTAA | 35033 |
| 1408 ATGGATCGCTTTGAGAACAATC | 13066 CTGTCAAAGGGCATGGAAGT | 24050 GGAGAAGCTCATGGATCGCTTTG | 35034 |
| 1409 GGGTAGAAAGCAGTTGTAGGGGTTA | 13067 ACTCTCCCAGGAAGGAAGTCA | 24051 GCACCGTAAGGGTAGAAAGCAGTT | 35035 |
| 1410 GCGAGCACCTTTGACTTTTCTT | 13068 CCTGCTCCCCTGTCCTTATAGA | 24052 TGCGTGCCAGCAAACCTT | 35036 |
| 1411 AGCCATCATGTCCACATTCAT | 13069 TGCTCTTCCCCTCACTCAAGTTTT | 24053 GGCTGTTGCATACTCAGCCATCA | 35037 |
| 1412 GTTCTGTCAGAGGGTGTGCTTCA | 13070 GTGAGGCCAGTGCTTGTGGAT | 24054 TCTTGACCATGGAAAGTTCTGTCA | 35038 |
| 1413 GGAAGGCTTAGTCAACACACCACATTT | 13071 GCCGCTGAAAACCAGCATTC | 24055 CCCAGCCAAGAAAGGGAACCCTTAG | 35039 |
| 1414 GCTGAAAGGGCCAGGTTGT | 13072 GCAGTTGGAGCCTTAGCAGTCA | 24056 CTCTGGCCAGTGTTGCTGAAAG | 35040 |
| 1415 CATGACCGGCTTCTGTCTAGTT | 13073 GCAAGAGGGAAATGGCTTAAGATG | 24057 CAGCAGAACTTACAAAGCTTCCATGA | 35041 |
| 1416 CAGACCGCTATCACCAGTTT | 13074 CCAGTTCAGTTGGGGCTTGTT | 24058 TCAGCCCCAACTGTCAGCCGCTAT | 35042 |
| 1417 TGACAGTCAGCAAGTGCCTTAG | 13075 CCTCTTACACCTGGTGGCAAT | 24059 GGGAGGCCAGCCTGAACTA | 35043 |
| 1418 GCAGATGCACTGTCAAGCTGTACT | 13076 TCATGGACGGCTCCGTATG | 24060 GGAACAACACTGACCCTTGCAGATG | 35044 |
| 1419 CGATGGGTGTGGTTCAGGTCAAA | 13077 AGCGAACTTCGGCAAACTTTC | 24061 TGGGTCGATGGGTGTGGTT | 35045 |
| 1420 GGCTCCCACCCACTGAGTTTT | 13078 TGCCTCTTCCCATTGAGGTGAAA | 24062 CAGACTTCCATAGTTGCCTTTCTCT | 35046 |
| 1421 CACCCTGTAAACATGCATTTTGCATGA | 13079 CACACACAGCTCTGTCCTT | 24063 CCCGAAATTCACCCTGTAAACAT | 35047 |
| 1422 TTCCTGCACTTGGAGGATCGTT | 13080 GCCAGGGGAACTACAGGTGCA | 24064 GGCTGACTCTGAAGAGCCTTT | 35048 |
| 1423 CCTTCATTCAGCCACTGTCCTGTA | 13081 GCTGCCAATGTCCTGAAGCCATA | 24065 CCACACAGGCACTTGTCCTTCA | 35049 |
| 1424 GCCCACCTCAGTCAGGCAACATA | 13082 CCTGCTAGAAGCCTGGCTAA | 24066 GGACAAATAGGCCCACCTCAGTCA | 35050 |
| 1425 GGAGTCAAGCAAAGGCAATAGTCA | 13083 GTAGTTTTCCTTGTGGAGGGCTAA | 24067 TGGGTTTAAAGCAATGGAGTCAAG | 35051 |
| 1426 CGGCTGTGGAAACCACAAATG | 13084 CAGCACACCCCTACCAAAAGGAAA | 24068 GGGTCAAATGGCTGTGGAA | 35052 |
| 1427 ACGAGAGAGGTGAAGTCACAGA | 13085 TCCCTGAAGAGGGCCAAGGAT | 24069 GCCTTACCATTGCCTCCCAAA | 35053 |

FIG. 36C2

```
1428 AGCCCTGAAGGTCTTCCCATA        13086 GGAAATAAATGGCCTGTTAGGCTGAA    24070 GACCATCTCCAAAGCCTGAA         35054
1429 CCTTGAGCCTGAGCTGAAGCAGTT     13087 GCTCCGTGTTTCCACAGAACCTT       24071 AGGCAGCAGGTCACCTTGAA         35055
1430 TCAGGCTTACATCCCTGGAGTAG      13088 GGCAGCAACGTCAGGGAAAA          24072 GGCTTTGTCAAGCAATCAGTCTTAGA   35056
1431 GCTGCTTATAGCACAGGCACCAA      13089 TGCCAGTACAGTGCAATTGGAAA       24073 CCTCCCACAAAATCTGCTGCTTTA     35057
1432 TGTTGGGACCCACCTCTGCAA        13090 GACGTGAATTGCCCATAGCTACA       24074 GGCCTCACAGTCATGGTGTTG        35058
1433 GCTGATCTGCTGGGGAGGTT         13091 GGGGAAGAAGGAATGGAGTGTGA       24075 TGTCTCCCATATTGGGCTGATCT      35059
1434 CACATGGCCTTGGATGGTATTCT      13092 CCAGCTCACAGATCCTGTAAC         24076 TCTGGCCCTTGGTGCACAT          35060
1435 GGTGTTTGAGCCACTCAGTCAAG      13093 CAAGGTAGGATCTTCCCTCTTGTGT     24077 GCCAGCCCCAGGTGTTTGA          35061
1436 CACGGTTTCCAGGCATCGTGCA       13094 TCTTGCTTCCCCACCTCAGT          24078 GCCCTTATCTTCCCAGTAACAGGTTT   35062
1437 CAGCAGCCCAAACTCGCTTT         13095 CGGAGCAGTGCCAATGGAAATC        24079 TTCCTCGCCTCCTACTGTGAGA       35063
1438 GCAGAACTCAGGCCCTCTGTAT       13096 CCTCCTTGGGGAACCACAAACT        24080 ATTTACCAAAGGGGCAGAACTCA      35064
1439 GCTGCCTGAATGGATTGGAGCTTG     13097 GGGCTGACAACATGACTGCTT         24081 GCCACAATTGCTGCCTGAATGGAT     35065
1440 GTGTGGAAAATGGCAAGACAGTTCT    13098 CTATGGACCTGTTCCAACCACAT       24082 TGAATGATCCCTATCAAGTGTGTGT    35066
1441 CCTCACCTTCAGGCTCAAGT         13099 GCAGGATAAAGCCACAGGTAA         24083 GCTGGCCTTCCCTCACCTTTCA       35067
1442 TTTACCCAGGCTGTGGACAAG        13100 CAGATAAGTGTGCTCAGCTCTCA       24084 AGGCCAGGGATTCAGGGCTTTAC      35068
1443 GAGGGTAGGGACTGTGTTGATCT      13101 GTGCCAGCCAGTGTGCTAAATC        24085 GCCCACTGGAACCTCTCTTTGA       35069
1444 GCTGGGACACTAAGTCATGAAGCTA    13102 CCTAAGCAACAGGGCAGTCCTT        24086 GCGTGATGCTGGCACACTAA         35070
1445 GACTGATGCACATACCCTCTGA       13103 AGGCTGCTGCCTCCACACT           24087 GCCTCCTCAGTGCATGCTTGACTGA    35071
1446 CTGGTCCCACGGATTTGTTTCTTG     13104 AGAGGGGAACAGGATTATGCTTCTA     24088 GCCACTGAGGTTACTGAGTCATTG     35072
1447 CTGCCAAGCAACAATGGCTATG       13105 GTGGAGGTATTTCAAGCTCAACTTC     24089 AGTGGGCTCTGCCAAGCAACA        35073
1448 GCGAGGGAAATTCAGCTAGAT        13106 CCAGACATCTAAGCGATTTGGAAGT     24090 GGCATTGTCTGATAGCGAGGGAAA     35074
1449 GTCCTGGGCTCGAACACACT         13107 GTGTGGTTCTGCAAAGCAGTGAT       24091 ACCGGGTGAGGCTCCTACTT         35075
1450 GGAACAGACTATGTGGGCATCA       13108 TGTTGACTCCAGGTGCAAAATCT       24092 GTTACTGTCATAGCTGGAACAGACT    35076
1451 ACCTCCCGTTCCTCTCTACCTT       13109 ACCCGTGTGGCTGGAGAAGAAC        24093 GGACAACTCCCTGATCTATTATCTAAC  35077
1452 CTGAAACATCTGCACTGTCTAGGAA    13110 TCTTGCCTTCATGCAGCTCAAATA      24094 GTCCTCAAAACTTCCTGAAACATCT    35078
1453 CCTCTCTTCAGCAAGAAGCAGATG     13111 CAGCAGCATCCAATCCAACCATCA      24095 CCATCCCCTGTATTCCTGTCTTC      35079
1454 TGCTTGCTCCCTATGGAAAATGT      13112 GAATTGGCTCACTAGGCCAGAATGT     24096 CCTGAGCCATTCCTCTTGCTT        35080
1455 ATGGGAAGGGAGGCTGCAGTT        13113 GTCCTCGTCCTCAGCAGATGTT        24097 GGATATGCTGTTGTACGTCTGTGTCTCA 35081
1456 TCCCCTCTTCCTGTCATGGAAAGA     13114 TGCCAAAGTTATGGGCTGCTA         24098 CTTACCCTCTTCCCCTCTTCTGT      35082
1457 CCCAGGCTTCTTCACCCTTTTG       13115 CCACCATCCAGTGCCCTGTTGA        24099 GGCTGGGAGTCCTGACACTACAT      35083
1458 CCTAAACAAAGGCGAGCATGATGA     13116 GGCCATGCTGGATGATAGCAA         24100 GGCAAGAAGTGAGAGTAGAATTCCTAAA 35084
1459 AGTGGACTGGCGATTCAGAACTCA     13117 CCTACGTTCAGATTGTCCACTTA       24101 GGGCTTAGAAACAGCTGGACGGCATT   35085
1460 GCAGGGAAGTGTTGTGGTTGAAGA     13118 GCTCTGTACGTGGAGCTTTGACTA      24102 GTGAAAGTGGAGGGAAGTGTTGT      35086
1461 GGTGTGAACTCTCCAGCTGATC       13119 TCGGGATGGGACAATGGTACT         24103 GTGTGAGACTTGGTTTGGTGTGAAC    35087
1462 TCATCTGCACAGCTTTCCCTTGA      13120 CGTCCCTCACCATCCAGCAT          24104 GGTGACTGCTGTCATTCAGATCA      35088
1463 CCCTGGACCTGTAAGTGGCTTTTC     13121 CCCTGTGCCCCTTAAGCCTACAA       24105 ACCCATGCCCTGGACCTGTAA        35089
1464 GCGGAGATCTGTAGAAGAGGACAA     13122 CTGCCCACTGTAACGCATTTC         24106 TCAGCAGCGGAGATCCTGTAGA       35090
1465 GGCTACTTCCATGGAGTTAGTCA      13123 CGGAGAACCTTTGCCAGTGAGTGA      24107 ACCTABATTCGGCCACTTTTCCAT     35091
1466 GCCCTGGAATCTAAAATGCCAATCACA  13124 CCACCTCCACACCCTCATCT          24108 TGTAGTTTGAGCGCCTGGAATC       35092
1467 TACCTCCGGACCCTCCCACAGT       13125 CCATGGCCAGCATTACCTCTT         24109 AGTTGGGGCACCCACCACTA         35093
1468 TTGCCAGCCGTGAGTACA           13126 CAGCCAGATTCATGCCTGTT          24110 GGTGGAACACAGTCACAGTTTG       35094
1469 CTCTCACCTCAAGCCCTTCTTC       13127 CAGTGGTCAAAGCTGGGGAAAC        24111 GTTCACCAATTAGCTTCTATCTCTCA   35095
1470 CCTCTGAGGGCCAGATGGATTTTTA    13128 TGGCCCTCCTGCTCCTGGAT          24112 GTACTGTCAAGGCATGAGTTCAAGT    35096
1471 GTTCAAATATAGTGCCTGGGGTTAC    13129 GTTGCCCTGGGACTCAAACATAG       24113 GAACGTAGGATACCTGGGTTCAA      35097
1472 GCTCCTTCCCCACAAGACAGAGAA     13130 GTGCAGGAACCCATCTATATGTGAA     24114 TCTTACAGGTCCTTCCCCACAA       35098
1473 GCTTTTCCGACTCCAACCATCACT     13131 TCCAGAGGGTTGACAGGTCAGT        24115 GATGGTTGGAACATGGTGCTTTT      35099
1474 GAAAAGGTGGACCACCTGAGCA       13132 GCTGCATGTTTACTCACTTTCCTTT     24116 AGCTTCAGGAAGGCCTCACA         35100
1475 CCTTTCTTTAGAGCTTCCTTCCAAT    13133 AATTTCTTGGACCTCAGGTTT         24117 CTTGGTAATTTCCAGCCTTTTCT      35101
1476 GCTTGTTCAGCTTGCATGTGT        13134 CAAGTGCTCGCTCTGCATTG          24118 CCTCCTGGTTCTATCAGTTAGGCTTCTTC 35102
1477 AGGGCTGGCCCTTATTGTTG         13135 TCTAACACAGCGTGTTTCTCA         24119 GGGAGAAGGGGACACAATGAAG       35103
1478 CTGACTGATAGCAGTTTGCCTCTCT    13136 GGGGTGGGGCATGAGAGATT          24120 GCTCAGCGCTGAATACTGATTGATAG   35104
1479 ACGCAGCCTCAGCCCTCAGTAA       13137 ACAGGGTAAAGGGGGCTAA           24121 CTCAAACCACAGCCAGTGCAG        35105
1480 CAAAGGGCATGTGTAATCTGTAGGTA   13138 GCCCAAAACACAGTGTGACAAGTA      24122 AGGAGGCTGAGTTAGCTCCAA        35106
1481 TGACTGGTGTAGGATTGACTCT       13139 TGTTTGCCTCACCGACTCTTG         24123 TCCCCACGTGAGCTGGTGTA         35107
1482 CCAACATGCAGGCCATATGTGA       13140 TGCTCAATGTCTATGCCAGAGCT       24124 ACTTCAGTCTATCCCAATCAACA      35108
1483 CACTGGTGCACTTGGCGATGA        13141 GTCCCTGGGGACATAGGTGACA        24125 TGGGGAGGCTTCTCATGCTTGA       35109
1484 GCCAAGATCCACCTATCTCAACA      13142 CTGGAGAGAGAGGGCCTTGGAA        24126 GGGCCTTCCCAGCCAAGCAT         35110
1485 CCCTAGTTCCAGCTTCCTATTCATC    13143 CACCCTGAGATCATCATCGCCACTT     24127 CAGTTTAAGTTACCCCTAGTTCCAGCTT 35111
1486 CCTAGAAATGGGTGGTACAGCAA      13144 AGGTCAGAGGAGCCATCTTTTTG       24128 GGCTCAGCTTTTCACAAGTTTTACA    35112
1487 ACAAGTGGTGGAGGGTATCA         13145 CTTGACTGATAGCCAGTTCCCTATG     24129 AGAAGAGTCAGGATCTTAAGGACAGA   35113
1488 GCCCTGGATTCTGGCAGTCATT       13146 GGTTGCATGCCTCACATCCAT         24130 GGTGATCAGAGACGCCTGGATTTC     35114
1489 CGCTTCCTTAATGCCCACTTACT      13147 TGGAGAGGAGTTGCAAGGTAA         24131 ACAGACACCCACGCTTCCTT         35115
1490 TGCTGAGACGTGGTCACAGC         13148 CTGCTTCTTCATCTAGGAGGAAA       24132 AGCCTCAGACTGCTGCATCTCT       35116
1491 AGCAGTGCTACCTATCGCTCCAA      13149 ACAAGGACTGTCATGGAGGGAAA       24133 TCTGGGAAGCTGCAGTGCTA         35117
1492 AGCTGGTGAGTGTCTCTTTG         13150 TCAGGAATGTCATGGAGGTTACTCT     24134 GCTGGAAAAGCTGGTGAGTTG        35118
```

| | | | |
|---|---|---|---|
| 1558 GTGGTGCTTTAGGGAAATCCAATC | 13216 AGCCTAGTAGCCACTGAAACTAGA | 24200 GACAATTCTCAGGAGTGGTGCTTT | 35184 |
| 1559 GPGCTTCCTATAATGATAATGGCTCACT | 13217 TCTGGCACATGTTGAGTGCCTT | 24201 CGACACGGTGCCTCCTATAATG | 35185 |
| 1560 CACGAGTGTGTCTATCCAACGCTAT | 13218 CAGATCTTCTCCTGCCCCAACA | 24202 GTGCATTAAATCCAGGAGTCTGTGT | 35186 |
| 1561 GGCAAGGTCTACCCAGGATCAA | 13219 GGGCTGGGGTTGGAGAGAAG | 24203 TTGCGTCTCTGGGCAAGGTCTAC | 35187 |
| 1562 TGCCTGAGAGGATCTGGTGACA | 13220 CCTTTGACGTCTAGCATCCTATGT | 24204 AGGCTCACTGCCTGAGAGGAT | 35188 |
| 1563 GCAGACAAAGTACCAACTGGAAA | 13221 CCCCAACACCCTAGAGCCTTTT | 24205 GGCAACAAAGTTTAGGCAGACAA | 35189 |
| 1564 GGTTCAGGGACACAGGCTTT | 13222 GCAGGTGGGTAAGGTCTCTGA | 24206 GTCCTTCCCCTTCCCAGGTT | 35190 |
| 1565 GCAAGCTCAAACCCCAGAAGT | 13223 TTGCCCCTCCTGGTCAGT | 24207 GCCAACCTAAAGCAAGCTCAAAC | 35191 |
| 1566 GGTGCCCAGCTCTCATGAATGT | 13224 TTCTCCTCAGGCTGACTGGAA | 24208 TGCAAGGGCCTGTCTCCCATT | 35192 |
| 1567 GCAAATCAGCCACCCTCAGCAA | 13225 CCCCTCTTGCCTGGGAATACA | 24209 GAGACCAGATGCTGGGAAATCA | 35193 |
| 1568 GGTACTGTAGGTGGTTTATGAGTCAA | 13226 GCCAAGGATTGGGTCTGTGTGA | 24210 GGGAGGTGGTACTGTAGGTGGTT | 35194 |
| 1569 CCAGCATGGTGGGTTCTGTTG | 13227 AGCACCCTCAACCTGGAAGA | 24211 CAAAGATCAGGGTGCCAGCAT | 35195 |
| 1570 ACTCCAGGATGCACAATTGTCT | 13228 CTCTTTTCCTTGGGTGGATCGATTT | 24212 GTCCTTCCCAGACTCCAGGAT | 35196 |
| 1571 GCACTCCCAGCTTCACTGACAAG | 13229 AGAGTCTGACCTCCCTTTCACA | 24213 AAACCGGGCCACTTCCAGCTT | 35197 |
| 1572 GAAGGAGGATTTCCTCCCATTGCTA | 13230 CCCATGGGGCTAACTTTGACTGA | 24214 GGAGGAGGAAGGGAAGGAGATTTT | 35198 |
| 1573 GCCAGACTATCGCTGATGTTTCTT | 13231 CACAAGCTGACTGAACAGTCCTT | 24215 CCATGGGGAGTACTGCCAGACTAT | 35199 |
| 1574 TGAACAGCCCCAGAGTCTCA | 13232 CCCTGTCATGGGCAAGGTGTTA | 24216 AGTCCAGCTGCTGTAATGAACA | 35200 |
| 1575 GCTGCTGAAGTGAGTATCTCTGTTG | 13233 AGGAACCTGGGCCCTTGAAT | 24217 CCAAGGAAAGCTCCTGAAGTGA | 35201 |
| 1576 GCTGACCCATACTTGGGTAGGAA | 13234 GCTATGGGTTGGGAAGGACAAGT | 24218 AGAGGCACAGCTGACCCATACT | 35202 |
| 1577 GCCAATGCAAAGACCCTGAAG | 13235 GGCCCAGGTCCTCAACCAA | 24219 CTGAGGGAAAGGCAATCCAAAG | 35203 |
| 1578 CACTCTGCGCTTATGCTTACACTT | 13236 ACTGACAGGGTTTTGCTGATGGAT | 24220 GGAGTCATTTTTCACTCTGCGCTTA | 35204 |
| 1579 GCCTGTTACTGTATGTGACAAGGATAGT | 13237 ACGTGGTTGCAAGCTACTGA | 24221 CCCTTTCCACTGCCTGTTACTGT | 35205 |
| 1580 GTGCTGTGCAATCTGCGTTTG | 13238 AGCGCTGGGTGTAGGATGTT | 24222 ACTCTGGGTGCTGTGCATTC | 35206 |
| 1581 CCCTGACAGGTTCTCCTTCATTC | 13239 CTGCCTCACCGAAGCATTCA | 24223 CCCCAAGTCACACGTTACTTATCATC | 35207 |
| 1582 AGTGTGGGAAGGGAAGTGGATA | 13240 GCATGTTCCCTGAAGTTCCCTTAC | 24224 AGAAGAATGGAATGCATGAGTAATTAG | 35208 |
| 1583 GGGAGTCTAGGATTGTGGAGTTCAGT | 13241 TGAGGCTGAGGGTGCAACA | 24225 TCATCTGTTGGGAGTCTAGGATTGT | 35209 |
| 1584 AGGCTTTTCTCCCTGGGTTGA | 13242 GAGCTACAAAATGGAAGGAGACTGA | 24226 CTTGCCCAGTGAATAAGAGGCTTT | 35210 |
| 1585 TGGTGGCACCCAAAGGCATTC | 13243 ACAAGGGAGGAGGCTTGCGTT | 24227 TGTGGTTAGGCGTCTGACCTAGT | 35211 |
| 1586 GATGGCTTGGACATGAAGGATGCTA | 13244 GCCACAGTTATACCTGACTCTCTT | 24228 CCCCATTGATGGCTTGGACATGA | 35212 |
| 1587 CCCAAAATGCAACACACCATCA | 13245 GGCTGACCATTAGGTTTACTGTCA | 24229 GTGCCTCATCTCACTGACCCAAA | 35213 |
| 1588 GTGTCGGCCTAAGTCCCGAGTTC | 13246 AGCACGGGCAGCAGCAGAA | 24230 GGGTCAGAGTGTTGGCCTAAGT | 35214 |
| 1589 GGGAAGCTGACTTGACATCCAT | 13247 CCTGGTGCACACTAGGAATAACA | 24231 CTGCTGTGAAAGGGAAGGCTGACT | 35215 |
| 1590 TTTGCTCCCAGGCTCCTCCTA | 13248 CCCTCAGCTACATGCCGAGAAA | 24232 GTCCAGGGATAGTAAGGCAGTTTG | 35216 |
| 1591 CTCTCACGCCCAGCACTCT | 13249 AGCACGCGGATGTCAAGGAA | 24233 ACCCACCGGCTCTATCTCACA | 35217 |
| 1592 CGTCGCAACAATTCCCTCTATCTCA | 13250 TGGGTCTCTGGCCTCACTT | 24234 TGTAGGAGCGTGCCAACAAT | 35218 |
| 1593 GGCAGTGGTACAATCATAGCTCCAT | 13251 GGTCACCTGTGCCTAGGAGTT | 24235 CTGGACGGCAGTGGTACAATCA | 35219 |
| 1594 GATCCCTTAGGCGTGCGAAAG | 13252 GTCTAGGGGCGGTAGGATACACT | 24236 GGCCTTGTGCAGAACTGAGA | 35220 |
| 1595 CACTGTTTCTAGTCCCAGTTTCTGT | 13253 GGAACGGGGTGGGAACTTTCCTT | 24237 GTCACTTGACTGCTTTCCTAATCACT | 35221 |
| 1596 GCCCAGTACCTCGGGCATA | 13254 AGCCAGGCACCAAGCATGCA | 24238 TCAGTGCCTGCCGCAGTA | 35222 |
| 1597 CCTCTGGATTCTGGCTGAGGATTTG | 13255 GGCATAGCGTGGTGAATGACT | 24239 GCCCTTCTTAGTCCTGTGGATTC | 35223 |
| 1598 GGGCTCCACACAGTTCCACCTTAC | 13256 GAGCAACTCAGACTCATGGAGCAA | 24240 CCAAAATCAATATGGGCTCACACA | 35224 |
| 1599 GTCAAGAAACTGACTTCACTCCTA | 13257 CACCAGCGGGAGCATCATTA | 24241 CCCTGCCTGTCTCAATCAGGTCAA | 35225 |
| 1600 CTGAATCACCATCACACGAACCAT | 13258 CCCGGCAAAGCCTCCCTAAT | 24242 GGGGAACAGGATATAGACCCATGA | 35226 |
| 1601 CGCTGTGTATCAGGCATACCATA | 13259 GAGTCTGAGCAAAATCCTTCACT | 24243 CTGCTGATCAGAAGCTACGCTGTGT | 35227 |
| 1602 AGAGGGAAAGACTCTGAAATCGAAC | 13260 ACTGAAAAGCCGGTTGCTTATAGA | 24244 TCTTCACCCAGAGGAAAGACT | 35228 |
| 1603 CCAGCGTGTGTTTCAAAGGCAAATG | 13261 TGTAGGCAGGCTGGTCGTGATA | 24245 TGGCATACCAGCGTGTTTCA | 35229 |
| 1604 AGGGGCCTAGAGGACGAGTCTT | 13262 GCAGAATCGATAGGCACACCACAT | 24246 CCCAGAGGAAGCATGGAACTGAAG | 35230 |
| 1605 CCTCCTCCCATGTGGTTAGAGAGT | 13263 GGGCTCTGGGACTAACCTCTT | 24247 GCCACACCCCTTCCTGTTCTT | 35231 |
| 1606 GGATTAGTTACTGTGAGAGTGGGTTGT | 13264 ACATGAGGGGCAGCTTCACT | 24248 GTGTTCTTGCTTTTGAAGGACAGGAT | 35232 |
| 1607 GCAACACATTTGTGTAGCCTTTTCAGA | 13265 AGGGTATGCTTGAGGCACACA | 24249 CCCTGCCCAGGCAAGACATTTG | 35233 |
| 1608 TCCCAATGTAATTTGACGCACAACA | 13266 GCCTCCAGCTCCCCATATC | 24250 GCTCAGAGAAGCAGTCCCAATCT | 35234 |
| 1609 GGGGTGAAACAACAACCACTAC | 13267 GGCTTCCACACAGGAAATAGTGT | 24251 TGGGGTCATGTGGGTGAAA | 35235 |
| 1610 GGACTTCGGAGGATGTAGGTA | 13268 GGGGTGAGGTTGTGGGAAGCATAAG | 24252 TTATGGCAGCTACATGAAGGACTT | 35236 |
| 1611 CGCACAAAAGACCTGGCACAGA | 13269 GCTCCCAGGCACCCTTTATTGA | 24253 AGCCAGCTCCGCACAAA | 35237 |
| 1612 CCCAGTCTGCTCCCTTTGGAATCTTG | 13270 CCTGCTCCGGATACACAGAAAC | 24254 TCCTCCCCAGTCTGCTCCTTT | 35238 |
| 1613 TTCCAAGTGTAAGGCTGAAGAAGT | 13271 GGGATTCTTCCTCGAAATTGGCTTTG | 24255 GCTAACGGTCCTGCTCAAGACTTCCAA | 35239 |
| 1614 GGCTGGAGAAACTAGTCCACAGA | 13272 GCCAGAAGCCGAGTCAATCTCT | 24256 ACACATTTGACTTTGGCTGGAAA | 35240 |
| 1615 GTGGACCACGTGCAGAAGTCA | 13273 ACATGCGGCTTCGGTGTT | 24257 TCTGCCTAAGCTGGGATCA | 35241 |
| 1616 GCATGGTAGGACAGTGGACGAA | 13274 AGACAGCGGCCAGGTGAAT | 24258 AGTGAAGACGCTCCTGCAT | 35242 |
| 1617 GGGATGCAGAGCCGTTTCA | 13275 CCAGGAAGCTTCTCAAAGTCAAGA | 24259 AACCTGCCAGCTGGCTTAC | 35243 |
| 1618 CCCATGCCTACCAAGAGCTAGT | 13276 TGCTTCCTTGCGCACACA | 24260 TCGCACTCCCAGCCTGAAT | 35244 |
| 1619 AGGGCTCTGACCTGCAAGAATTTC | 13277 CCPAAGACACATCCCAGGAAAAA | 24261 CCTTGTCCAGTGGGCCAAAA | 35245 |
| 1620 TTCTCCATCAAACTCGGGATGAAT | 13278 ACAGCCTGCGAGACCCTGAACA | 24262 GGTGATGAAGGTTTGTGCTCTTTCT | 35246 |
| 1621 CCTTCTACCAGGTTGGACAAAGTCT | 13279 CCTTGAAACCCAGACGACTCA | 24263 CCACTTCAAACTCTGCACTTTTATCCTTCT | 35247 |
| 1622 CAGGGAATCCTCAGATAGGAGGTAGA | 13280 GACTAGGACCTCTGCTAGGATGTA | 24264 CCTATGAATGGACTTTGTTCTGTTC | 35248 |

| | | | |
|---|---|---|---|
| 2468 AGCCAGTTGCCATAGGCTTT | 14126 TCAGCTGCTGGGGAGCTTTC | 25110 TGTTCAAACAGACCCTACTTGGAA | 36094 |
| 2469 GGGCCACACACTCAGAGTAA | 14127 AGACAGGGAAGTTGTGGGTATATGA | 25111 AAAGACTGCACCAAGCTGGAA | 36095 |
| 2470 ACTGGGCTGACCCTTTTGATTTC | 14128 TTGCCGCCTTGCACCAAAAC | 25112 TGTCTGCAGGGGACTGAAAC | 36096 |
| 2471 CGAGGGACATGCGGGTCTA | 14129 CAGGCCCGGAACCCTCTCT | 25113 CGCACGATCCGAGGGAGAT | 36097 |
| 2472 ACCACAGTTCTCCGTGCAT | 14130 ACTGTCACACGCTTCCTGAAT | 25114 CATCTTGCTGTAACCACCACAGT | 36098 |
| 2473 CCAGGGAGGGAGGTCACACA | 14131 CCTGGCCGGCTGTTACAGACT | 25115 AGGGGATGGGTGGGAAACA | 36099 |
| 2474 GTCAGCATAGGGCAGTTGCAAAG | 14132 CCTAGGACTGTCCAGGACCTCTGTC | 25116 GTGTGGGTGTGTCTGACCATAG | 36100 |
| 2475 GGAAACCTTAGCTGGGGTCTTTTC | 14133 TCACTCGCTCTGTCCTGTGA | 25117 GGACTAGGGGATCTCTGGAAACCTT | 36101 |
| 2476 AGAGGTTCCCACTAGAGAGGTCATC | 14134 AGGCCACAGTGTTGCTCTGTTC | 25118 GCCCTAGATGAAGAGGTTCCCACTA | 36102 |
| 2477 GTTGAGACCGAACACTGGCAAAC | 14135 TTGCTCTGAGGCCCTACACT | 25119 GAATCTGACTGGGGTGTTGAGA | 36103 |
| 2478 CCAAGGACATGACTTACCCAGTTT | 14136 GTACCTGCTGGGATATGTGTTTT | 25120 GGCAGGAATGCAACCAAGGACATGA | 36104 |
| 2479 GCTTAGGACCTATCTGGAGTCACAGT | 14137 AGGAGAACCATCCTGCATGT | 25121 CACAGATGCGTAAGGGACCTATC | 36105 |
| 2480 CCAGGGAAGTGAGCAGGTTCTAG | 14138 GGCTACTGGGGAATTTAATACAGTCT | 25122 TCTGGGCCATCAGCAAGTGA | 36106 |
| 2481 TGTCTGCGTGGCAAGGTTTC | 14139 CCTTCAGCAGTGCCTGACAAAC | 25123 GAGGTAAGCCAGAGGAAACGAA | 36107 |
| 2482 GGCCCCAAGAGGGTTCATTTC | 14140 CCAAAGCATAGGCTGTTGTGAGT | 25124 AACGTGTAGGGGTCAGAGTTTG | 36108 |
| 2483 TGGCACAGCATTGCAGTTAGA | 14141 GTCCAGGAGGTGCTCCTAGTATCT | 25125 CAGATGGCTAATGGCACAGCATT | 36109 |
| 2484 CAGAGCGAGACATCATCCTTTCA | 14142 CAGGGCCAGTGTTCTTCCAAAC | 25126 AGCAGATTCAGAGCGAGACATC | 36110 |
| 2485 GCTGCTCTGAGGCGTTACTT | 14143 GGTTACTGTTGGGGCTCAGGAAA | 25127 CTTGGCCTCTAAGGCTGCTT | 36111 |
| 2486 GCAACTGCTAGCAAAGGCATGA | 14144 GTGCCTTCCGAGAGCTGTGA | 25128 GGCTTCCACACACAAGGAATG | 36112 |
| 2487 CCTCCCCAGTTACCCTGCAT | 14145 TTGAACACCTCTGCTCAACACA | 25129 GCAACTCACTCCTCTTCCTAAGAAAT | 36113 |
| 2488 CCATCCTATAGTCTGGGGCTGTTTG | 14146 ACCAGGCCCACCCAGTAAA | 25130 GGCTTCGAGATTCAGTCACAA | 36114 |
| 2489 CAACAGCAAGACATTCAGCATAG | 14147 CAGCCCATACCCTCCCTGCTA | 25131 GGACCCAGCAACAACAGCAAGA | 36115 |
| 2490 CCTCCACCTCATTGAGTCGTTTCT | 14148 GCCTGTGCTACCCTGGGAAGA | 25132 ACCCCTTCCCTCCACGTCAATTG | 36116 |
| 2491 AGGTGCCTCTCTCAGCAGGATT | 14149 GGGTGCCAGGTACAGAACAAGT | 25133 TCAGGTGTGAAGGTCCCTCTCT | 36117 |
| 2492 CCCTGTCCTGACCTTAACT | 14150 CTTTGGAATTCTCCCTGGGTATG | 25134 AGCGGCATCCCTGTTCCCT | 36118 |
| 2493 GTCAGTTCCCATGGACCCAGAA | 14151 ACCTCAGGCTAATGTCCACTTG | 25135 ACCTCTGTGCCAGGTCAGTT | 36119 |
| 2494 CTGAGATTATGCCAATGCCTGCTA | 14152 GTGCATCAGGATAGGGGCTCAA | 25136 GGGACCGCTTAGATTATGCCAAT | 36120 |
| 2495 CTATGGACGCAGCCCTCTA | 14153 GTCTCTATCCGGGTCTATCCAGCAT | 25137 CGTAGACCTTCTCAGATGCCACTACT | 36121 |
| 2496 TGGCCTGTTTTTATCCCATTGT | 14154 TCTGCCCTGTTTGCTTCAGT | 25138 CCCATGAGTTGGCCTGTTT | 36122 |
| 2497 GGTCATGCAGAGAGGACTGGAATTA | 14155 GGTTTGCCCTCTGCCTGTTCT | 25139 AGGTCCTGCCGAGGTCAT | 36123 |
| 2498 CCCACTGTGGCCACATGT | 14156 TTCCGCCCATGCCCTACA | 25140 GGTGTGGACTTAGGCCCACTGT | 36124 |
| 2499 TCTGCTTGTCCCAGCTAGT | 14157 GACCTCACCATGTTTCCTGTAGTTG | 25141 GCTCTACCCTCCTGTCCCTCAA | 36125 |
| 2500 ACAAAAGGGCAGGCTTGCTTA | 14158 CTCCCAATGAATCCTCCTCCTTCA | 25142 CAGAGCCAGGCCTTCTCTTAAA | 36126 |
| 2501 TTCGGCACAGGTGTGTCCTT | 14159 AGGTAGGGTTCCCCAGTTC | 25143 AGGAATGCGGGCCACTCA | 36127 |
| 2502 ACACACCCTATCAGCCACCAT | 14160 GGCTTCCTCACTGTGGTGTTC | 25144 CTATCTGAGGGAAACAGACCCTATC | 36128 |
| 2503 CCTCACAGCCTCCTGATCTCCTT | 14161 CCTCAACCCCTTCATCTACAGCTT | 25145 TGCCTCCTCACAGCCTCCTT | 36129 |
| 2504 CCGTAAGCAGAACATAGTTCCCTGTTC | 14162 TGGTCTCTGCCTGTAGACTGT | 25146 GGGTGCTCTGCATTCCAACTA | 36130 |
| 2505 CAGGGCTAGACACGAGTCAACT | 14163 GGTCGGGTGGGAGGTTTTGAT | 25147 TTTCCTGAAACACAGGCAGACA | 36131 |
| 2506 GGGTGGTGAAATGGCAGAGA | 14164 CAGGCCTAGCAGTGGTAAATCA | 25148 GCCCACAAAGGGTGGTGAAA | 36132 |
| 2507 GCTTGCTTCCTTGCTTCTTTG | 14165 CCATGGCTGGCCCTTTGAAACA | 25149 GCTTGCTTCCTTGCTTCCTT | 36133 |
| 2508 AGCCTGCAGGCAGTTCAGGAA | 14166 CCCAGGGCATCTGTGATACAA | 25150 GCTAGCAAAAGCCTTGCTAGCTT | 36134 |
| 2509 GTGGCTCCTACATTACTACCAGTGA | 14167 TGCCTCCCTCCTCACA | 25151 TGATGACTTGCTCACCCTGTTCT | 36135 |
| 2510 CCCTGTCTGTCTCAGGAGGAGAAAA | 14168 TGGAGGATGGCGCTTTGGAT | 25152 GAGACTTTCACCCTGTCTGTCTCA | 36136 |
| 2511 GGACATGGTGCTGCAGTATC | 14169 TGGGCCCACCAGTCACTTCT | 25153 CCCACAAAGGCCATGGGACAT | 36137 |
| 2512 CAGGGAAATCCGGCCATCCAT | 14170 TGGTTAGTGCACAAGCACTGT | 25154 TCGGCCAAGAACAGGGAAATC | 36138 |
| 2513 ACCGTGAGTCCCAGAGGTTCA | 14171 GCAAATCTGGGCGACTCTGA | 25155 AGGACAGGTGACCGTGAGT | 36139 |
| 2514 GGCAGGGAGATTATTCCTGCTAA | 14172 GGCTCCAGCTCCCAGACTCA | 25156 CCTGCAGGCAGGGAGATTATT | 36140 |
| 2515 CCAGTGCTATAGAAGTAGTGGAGTGA | 14173 TCTAAGGCACGGGGATAGGAA | 25157 TGTGCTTCGGGGAGCTGATA | 36141 |
| 2516 TGCTCCCTGCAGCATTCGAA | 14174 TGAACAAGGTCACAAGGTGACT | 25158 CAGGGATGTGCATGGCAACT | 36142 |
| 2517 TTCACCCTGGKGCTCTTCA | 14175 CTAGGACATGATCAAACCTGGATTG | 25159 GAGCAGCTTCCATCTTTTCTGT | 36143 |
| 2518 TTGCTCGGACCTACCTTCCAA | 14176 GGACCTTGGCAGGAGGCTAA | 25160 CAGAGAGTCCAACCTGTCCCCATTG | 36144 |
| 2519 CTCATTAACACCTCAGCCCGTGAA | 14177 GAGCCTGAGGAGGCCATTTGA | 25161 CCTGGAGAGCTTGGTGTTTGGAT | 36145 |
| 2520 TCCAGTGTGAGGTGGCTTTATG | 14178 TCCGCACAGGCGCTTTT | 25162 GAGGCAACATTGCATTCCAGTCTGA | 36146 |
| 2521 GCCCAAATCCAGAACCAGTCCTA | 14179 GGGAGCTGTCCATAGAGGCAAT | 25163 AGCTCCCTGGCCCAAAT | 36147 |
| 2522 CATGGTGCTAGCTTCACTCTCA | 14180 TGCATGCCTCTTGCCAGAAAA | 25164 GGCTTATATTCCTTCATGGGCTA | 36148 |
| 2523 CCCCTGGGGACCTTGGCATGT | 14181 GAAGATGGAGCCTTGGCATGT | 25165 GATGGGCAGATAGGGACAGAGT | 36149 |
| 2524 CTACCAAAGCTGTATGCTCTGTAAAAC | 14182 GCAAAGGGCCAGAGAGTCAA | 25166 CAGGCAGGCCTGTGTTGTTACT | 36150 |
| 2525 CATTGGTGCTCACCCACTGACT | 14183 GGCAGGATGCATTTGGGCCATT | 25167 TCCCCATCCTAGATTTTCTACTTCTTG | 36151 |
| 2526 CCAGCAAGACACGCTGGAA | 14184 GGTCCTCATGAGCTTCAGGTTATT | 25168 AATGTAGTGTGAGCGAGCAAGA | 36152 |
| 2527 GGATGGTGCAGCAACGAATGA | 14185 GTCGGCCAGCCCTTCACAT | 25169 GGAGAACGTGATGCCCTATTTCT | 36153 |
| 2528 AGGGGCCAAGAACCAGGAACA | 14186 GGGCTACCAAGGACATTAGCAT | 25170 TGTGGAAAGAGGGGCCAAGA | 36154 |
| 2529 AGGCTTTGGGGTGGTTTGTT | 14187 CTGTTTGGTTGCGTGGT | 25171 TGTCTGAAGAGTAGGCCTTTG | 36155 |
| 2530 TCATTCCTCGGCTCACCCTCT | 14188 GGGCCATTATAACAGGAACGGGAAC | 25172 CAACATGAATCAGATGCGGTCATTC | 36156 |
| 2531 GGTAACTGATCAGACTCGGGAGTTC | 14189 AGAATCTGGCAGCCCCTACA | 25173 GGAAACATCTCCCTTTCCTCGTTCA | 36157 |
| 2532 CCTGGGCTCCTTCATGTGTCT | 14190 TCCAGCCCAGCTGTCACTAACT | 25174 TTGGTTCCCCTGGGCTCCTT | 36158 |

| | | |
|---|---|---|
| 2598 GGGATTCCTGCACTAAAGACCTTAC | 14256 GGCACACGACCCACCTATCT | 25240 CCCCTTAGGCATTCCTGCACTA 36224 |
| 2599 CTCATTCCATCCTTCCCTCTCCAA | 14257 GGAAGGGCATAGAGACCATCT | 25241 GCCCAGACAAGACTCATTCCATCCTT 36225 |
| 2600 CAGAAGCCATGGTGGAGATTTGA | 14258 ACTAATGCTGACATTGGTGGAACA | 25242 TGGGCTTCTGGGGCAAAAA 36226 |
| 2601 AGATGGTGGCACCCCGTCAT | 14259 GTGCCACACCATCCTCACCTA | 25243 GCAACTAACCACCCTCCAGATC 36227 |
| 2602 CCAGAACAGCTTCCGAAACAGT | 14260 GGCAGTCCCTTCAATGTCA | 25244 GGTGGGTATCTCCAGAAGACTT 36228 |
| 2603 GCTCAGTGGTTGCTGCAGATGT | 14261 TTCCCTGCCCTTCCACCTTTC | 25245 GCTGGCTGAAGCTCAGTGGTT 36229 |
| 2604 GCTCAAGCCCCATGAATAAGGTT | 14262 AGAATTCAACCACCATTGGCAGAT | 25246 GGGGTTTCAGCGGACTGTGA 36230 |
| 2605 GAGAGACAACTGCATGCTCAGA | 14263 GCTGGTCCCTGGAAGGGGATA | 25247 AGCCTCTGCCCTTGAGAGACAAC 36231 |
| 2606 GATGGACTGCTACTCTCTAACCCAAT | 14264 CCATCCCTGCAGGAGGAGGACAT | 25248 GCTGCCTGATGCACTGGTACTCT 36232 |
| 2607 ACTGCTCAACCAACATCTGTTCA | 14265 TTCCCTCCCCAAAGCCACAA | 25249 GGGACACACTAACTGCTCAACCAA 36233 |
| 2608 GGGCCATGGCACTAGGGTAA | 14266 CTCCTCAGCAGGAGGAGTTTGT | 25250 GCAACACACAGCCTGGACATTC 36234 |
| 2609 CAAGGGAGGCTGAAGAACGTCAT | 14267 AGCACAGGGCTCACAGCTA | 25251 GCCATATCTTGTTCAAGGGAGGCTGAA 36235 |
| 2610 TCACCCACTCCACAGCATGTTC | 14268 GCTGCCTCAGAACCTCTTCA | 25252 GGTGCTTGGAATTGTTCACTTGT 36236 |
| 2611 CTTCCCCAGTTGACAAGGACAAAG | 14269 GCAAAGAGCACAGCCAAACACA | 25253 GCGTCCTTCCCCAGTTGACA 36237 |
| 2612 TGGTGATGGGGAGCCACTCTT | 14270 ACAGAGCTCCTGGAGGCAAGAT | 25254 CAGATGGCCCAACTTGGTGATG 36238 |
| 2613 GGTGCCTGCTTGTCCCTGAATA | 14271 GGCTGCTCAGCCTTGCCTGTA | 25255 AAGCTGGTGGTCCCTCTTCT 36239 |
| 2614 GATCCTCCCCAAGGGTTAAGAATG | 14272 CCCCGGTGGAGACAAGGAA | 25256 CGTTTACCAACGGGCGAAGA 36240 |
| 2615 GCCACAGCTGTCTGAGGGTTA | 14273 CACTGCCAGGGTGGTCAATC | 25257 GGAGGCAGGAAGAAGTCCACAT 36241 |
| 2616 CCTTTCCATGGACTGTGCAACT | 14274 TGGGACCGTTGTTGCTGCTAT | 25258 CGGTGCAGTTTGTTGCGTTCCTTTC 36242 |
| 2617 GGTGACTCAGATCAGGGGTTCCAA | 14275 GGGCTAGGGAGTGTTTCTCAAAG | 25259 ACCAGTCCCTGGTCACTCAGAT 36243 |
| 2618 GGTGTGTGTGGAAGCACTGTGA | 14276 GATGCTACCCTGAGGCTTGAAA | 25260 GGTGAGGGTGTGTGTGGAA 36244 |
| 2619 GAGGAAGGAGATATTGGAGGTGTCT | 14277 CCAGCCAGCAAGCATCCTGAA | 25261 ATCCCACCCAGAGCAGGAGATA 36245 |
| 2620 GCCAGCCTTGAGTCCAGTGA | 14278 GGGGTGACTTGTAAACCATCTTGT | 25262 AGCCATCTCCCAGCCTTGA 36246 |
| 2621 AACCTCTCAGCTTCAGCCAAA | 14279 AAAACTGGCTACCACATTTGTAAAG | 25263 GGCAGATATTTAATCCACCTAACCTGTCA 36247 |
| 2622 TGCTCTGATTATTAGTGTCAGGTT | 14280 CCCTGCCATGAGCCCTTCA | 25264 TCTATAAGCGCTGCTGATTAT 36248 |
| 2623 CACTTCACCCTTCAGCAAATGAACA | 14281 GCCCCTCTGCTCTTCTCACA | 25265 GGTGCTTTGAAGACCGATGAGTTC 36249 |
| 2624 ACACTGATCTCCACTCCCAGAT | 14282 CAATCCTAGCATAGGGTGCTTCA | 25266 CTCCTATGTCAGCCACACTGATCT 36250 |
| 2625 AGCCTCGAACCTCCGCAAA | 14283 CGTGTCGCTGCCAGACAGAT | 25267 TGACAGTGGAGCCTCGAA 36251 |
| 2626 GGGAAACCAAAGGCCCACAGT | 14284 GCTTAAACCTCAGCTCCACCACTA | 25268 CCAGTGAAGGACGAGAAACAA 36252 |
| 2627 GAAGAAGAGAAGGCATTGCACCAT | 14285 TGTGGCCCTCTCTCTCCAAT | 25269 GACAGACGAGGACGAAGTCAACAT 36253 |
| 2628 AGCCCACCCGCTTTCTCCAT | 14286 TGAACTGCTGTCCAGGGTCGAT | 25270 GGCAGGTCAACCTTGGCTCTTAC 36254 |
| 2629 CCAGAGAACACGGCTGTTT | 14287 TGCATCGCTTGGAGAGGAA | 25271 CAGCAGGGTCATTTCCAGAGA 36255 |
| 2630 CCCCAGTTCCCCTGCTGAGTTTAGA | 14288 TCTGCCCACCATCTGACTGT | 25272 GGGACTCAAAAACTGACATCCCAGTTC 36256 |
| 2631 CACCCTGAACTCCCTGCTAAAT | 14289 ATGCTAATTGCTGGGCCCTATT | 25273 GCATATTCTGCACATTCCACCCTGAAC 36257 |
| 2632 CCTTCACAGCCCGGTGCATA | 14290 CCTCGAACACAAACCAGAAGTCAGA | 25274 CCCTCATCGATGCCCCTTCTTT 36258 |
| 2633 GTGACAATCAGGGTGCCTTGCTCT | 14291 TCCCAGGCTCCCACACTT | 25275 CCCCAGCCTAAGCAGTGACAAT 36259 |
| 2634 TGAATGACTGATGAGATCGTTGT | 14292 TCTCCACACCCTTGCCAGAATG | 25276 GTGACAGGGAGCTATTGAAPGACTGA 36260 |
| 2635 TGGCAGGAGATGGCTTGAGA | 14293 TGAGCCTGCTGCACCTTT | 25277 GGGTAGAACATGGCAGGAAGAT 36261 |
| 2636 AGCCAGTAAGGGATGGCTGAT | 14294 TGGGCTCCTCCCTCGAAAATAC | 25278 AGGCTCGGGCTTCAGTGGAT 36262 |
| 2637 TCTTCTCCCTCACAGCAAATCTCTT | 14295 GCAACATGGCTGGTACACATTTC | 25279 GCCATTGCTTCCTCCATTGTTC 36263 |
| 2638 CTAGGCATCTGATTCAGTGTCAA | 14296 GCAGGGTTTGCCTTCTGCTCTA | 25280 GTCTCAATGACCAGGCATCTGATT 36264 |
| 2639 CCTGCAATGGGCTACCGCATCA | 14297 GGAAACAGGCCCAAGGTGCAT | 25281 CTCATAAACTCCTGATTGCCTCCAATG 36265 |
| 2640 ACAGGGCCCTTTTGCCTTTGT | 14298 TGCTAGACAACCTGGCTAGTAACA | 25282 GCGGTAGGATTGGTCTGGGAAT 36266 |
| 2641 GGAGGCCATCCAACTCAAGAATTC | 14299 TGCTCCTCCTCCGGAGGTAAAGA | 25283 CCTGAGGCATAACCATTTGATCTTC 36267 |
| 2642 AGCCAGTCAAGCCCAGAGTAG | 14300 CACAGGCAACCTCTGCTCAT | 25284 TCTGTCGCTTTGGGCTCTTC 36268 |
| 2643 GTGAAACCCTGTCTTGGTTGA | 14301 CACGGACGCCATGAAACAA | 25285 CAGGATGTAAAGTGAAACCCTGTT 36269 |
| 2644 AAGGAGGGCACCAACTTACAGA | 14302 TGTGTCCTCGGCGTGTGCT | 25286 TGGCCATAAGAGGCTGTTCTA 36270 |
| 2645 GGGCTAAAGTCATCTCACCCTAAAG | 14303 GGGAGATCTGGCTCACGTT | 25287 CTCTGTCAATTGGGCTAAAGTCAT 36271 |
| 2646 CTGCCCCATTGACAGAGGTTCT | 14304 GACCTCCAACTTGTGGCAGACA | 25288 TGGCTCCTCTGCCCCATTGA 36272 |
| 2647 CACCTCCTCACCCGCTATTGTA | 14305 GGGCACAAAACCTCTGGATGCAA | 25289 TGTGGCAGGGGACACCTTCT 36273 |
| 2648 GATGTAGGAGTCATGGGATCTTC | 14306 AGCCGTGCCTGTCCACAT | 25290 GTGGTGGCGGACACACAAAA 36274 |
| 2649 GAGCTACAGTATAGCACTGCGTT | 14307 TCCTGGTTCCTCCCACTGCAT | 25291 TCTCCTCTTCTTGGCTAGCAGTAT 36275 |
| 2650 CAAGCGGGTGCAACAGATGA | 14308 CAGTTTTGTGGGGCTCTGTCT | 25292 TGTGTACCTGGAGGGCACAG 36276 |
| 2651 CACCTGGTTCCCTGCAGTCAT | 14309 GCCATCCATCTCTCTTTCCTACA | 25293 GCTGGATGGCACATTGAAC 36277 |
| 2652 GCCTCAGGAGAGAATCAGGGGTTCT | 14310 TGGCCACCTCAAACTTAACACA | 25294 CACCTCGGCCTGAGGCAGAAT 36278 |
| 2653 GCAGTGGTGATTGCCTTGGAGTT | 14311 TTGGGCCAACTCCCACCTCTT | 25295 CCACGCAGTTAGGGGAGACTTTG 36279 |
| 2654 CGGGAACAAGCTTCTTTGGTAAATG | 14312 TCCTGTATCCCTGACTTGACTAGAA | 25296 CTGGAAAAATGCCCGGCAACAAG 36280 |
| 2655 ATACCCTGGACTGGAGGAGGCAGAT | 14313 GAGATATGCACGGAAGCAGAAGA | 25297 CAACCTGCCTGCTCGGTAA 36281 |
| 2656 GAAACCTTGGCAGCTGTATTGACTCT | 14314 TCACTCATAAATGGCTGTGAAACA | 25298 CCCAATAAAATGGCCTCTGAAACTT 36282 |
| 2657 CCACTAGCCTGTAGCGTAAAGTTC | 14315 GGGCTTCATTTGCCATACTCAGA | 25299 CCCACCCAGCCATCATTTCTTCT 36283 |
| 2658 CCTTCCCCTCCAATCTATCTGACT | 14316 AGGCCACAAAATGCTTCAAGTTC | 25300 GCTAAATTCATTTCCTTGCCTCCAA 36284 |
| 2659 GACCAAAACCACCAGGAACA | 14317 GGACATGGAGCAGGTAGCTAGCCA | 25301 GCCTCCCTGCTACTTGAGCAAA 36285 |
| 2660 CTGTAGACAGAAACCTTGACCCAGAT | 14318 GCACCCAGACCCATTCTGA | 25302 GGGGTAGTTGGTGTAGACAGAAACCTT 36286 |
| 2661 GCCTGAGCTGAGCCTTCTT | 14319 CCCAATGTTTCAGTCTCAACCTGAAG | 25303 TCTGACTGCCTCAGGTGGAA 36287 |
| 2662 CCCTGGATTTGGCCTTCTCT | 14320 GTGGAAGCCACTGCCTGTTG | 25304 CCTATCCTTGGGCCTGGATTTG 36288 |

| | | | |
|---|---|---|---|
| 2858 TGACCAGTTCCCACCCTCTGT | 14516 AGGGGCCTGTTTGGGACAATG | 25500 GCCTGGACAGACAACAGCTACT | 36484 |
| 2859 GGCCATGTGAAGATGACAGA | 14517 GACAGCCAGGTGAATGTTCTACACA | 25501 ATGTCTNGGCTGTGGCTGTTG | 36485 |
| 2860 GGTTTGTCGGATCAAGACCTTCT | 14518 TTGCCCACTCCTGACCTAGT | 25502 CCCTGAGCTAGGCCTTGGCTTT | 36486 |
| 2861 TGTCTGTCCCCAAGCCACACT | 14519 GCAGGGACCATACAGACTCCAA | 25503 GCCACAGCCACAAGAAACATA | 36487 |
| 2862 GCCCATCTAGCCTGTGTTAGGAAGA | 14520 CCTCCACTCCCATGGTGCTTAG | 25504 GGCAACAGACACAGCCCATCTA | 36488 |
| 2863 GGCTGATTGGATCTGACTCTAC | 14521 GCTTGGGATTGCACGGATCA | 25505 GTAAAGAACTGGAAGCAGGCAACT | 36489 |
| 2864 AAGGCTGTTGGACAGACACAA | 14522 AGCACAGGGTGAAGACTGT | 25506 GGATAGGCTGGTACCATGAGAAG | 36490 |
| 2865 TGGCCCATGACGAGGGATA | 14523 AGCCCACGATGCCCACTA | 25507 TGGACAGGCCTTAACACTTGATC | 36491 |
| 2866 GCCTGCCACCCACAGAACTT | 14524 CCATCCATCCCCAGGTGTTC | 25508 GGCTCCAAGGATTAAGGTCCCAGAA | 36492 |
| 2867 GGAGCCTGTACTCTCACTGA | 14525 CGTGAACTCTGACTCCTTTTCTGGAT | 25509 GGTCAATACTTAGGGAGCCTGTACT | 36493 |
| 2868 GTGGCGGGAACAGCAATATGA | 14526 TCTCACCAGCTGTCCCTAAATTC | 25510 GTTTCCTAAGTGGCGGGAACA | 36494 |
| 2869 GGCCCTAGACTGGAGCCAAAAAG | 14527 AGGGGAAGACGTTTGGGGTAA | 25511 TTGCCCCTTTGGCCCTAGACT | 36495 |
| 2870 AGGACTCCATCTGCCCTGTTTC | 14528 CCAGGGAGCCTGCACACAT | 25512 TGTTCCCACCAGGACTCCATCT | 36496 |
| 2871 CACCAGCCTCACCCTTTGGATT | 14529 GTGGCATAGGCTGTCCTGCAT | 25513 ACCAGGCTGGGAAGTCA | 36497 |
| 2872 CTCCTCTGTCCTTCTGCCAA | 14530 CTCTCTAGCATGCGGTGGGTAA | 25514 GAGCCTAGTGATGCGGGTTCT | 36498 |
| 2873 GTTGCCAGACCTCCCGTTAC | 14531 GGAAGGCAGTGGGACGGTAATTG | 25515 GCCTGATGTGTTCCCAGTGTTG | 36499 |
| 2874 CGAAGTGGTCGGACGGACAA | 14532 GGCCTTCCCCTACTTTACTGTCGAA | 25516 CTGGGAAACTGCATGGGAAGT | 36500 |
| 2875 ACCAGGAAGTTGGATGGGACTTA | 14533 GGAAGGAGCCACGCTTACCAA | 25517 GACACAGACTGAAAACCAGGAAGT | 36501 |
| 2876 CGCAGGCAATTATCTCCTATACTTGA | 14534 AGGAGGAATACTCACTCCTGTTC | 25518 GTGCGTCTGCAGGCAATTATC | 36502 |
| 2877 TCACCTCCTATTCACTCCTAACA | 14535 TGGAATGGAGGACAAATTCCTGAAA | 25519 CTGTCCTTCACACCTTCAGCTCCTA | 36503 |
| 2878 CAGAGCCTTCCATTTCCTTGCAT | 14536 TGCCTCTCCGCCAGTCTATG | 25520 GCAGGCCACTCTGCTCTCA | 36504 |
| 2879 TCACCTATGTCACATCCTGTCT | 14537 GAGGGCTTGGACAAGGTGGAA | 25521 TGGGCACCTCACCCTATGTCA | 36505 |
| 2880 CATCAACAAGGTGGTCACCTGACA | 14538 CTGTGGATGTGCTGTGAATGTTGA | 25522 GAAGAAAAAGGGCCGTTCTACCAT | 36506 |
| 2881 CGTGCGGAAGGCAGTTCAAT | 14539 GAGTTGCTGGGTCACGGAGTTT | 25523 TCACTGGCTGACGACTCCAA | 36507 |
| 2882 TGTCTCCGGCACAGGTTTG | 14540 CCCCGAGAAAACCTTCACCACAA | 25524 CCTACTCGAGTTTGGCTTGTCT | 36508 |
| 2883 AGGTCCCAGCCACCTGGTTCATC | 14541 AGATACCCATCCCAGCACA | 25525 CACCGAGACGCCACCACCA | 36509 |
| 2884 TGAGTGGTGTTTCAGATCATCACA | 14542 ACAGCCTTTGCCCTCCTATCT | 25526 CCCTGATGCCTCTGAGTGGTGTTT | 36510 |
| 2885 CACCTTCCCCACTCCAAGTTTTG | 14543 TAGCCACCCTTCCTCCACTGTCA | 25527 GATAGAGCACATAACCTGAGCAATTC | 36511 |
| 2886 GGAGCCCTGAATGAACCATGA | 14544 TTGGGCCTGTGAACCTGCT | 25528 CACAGAACTGGAGCCCTGAAT | 36512 |
| 2887 GAAGCCCTCCAGAGTCAAGAGA | 14545 GGGTTCCTCCACGCACTTGT | 25529 TCACGCTAGGTGGTGGTGAA | 36513 |
| 2888 GGAAGGGCCTCAACCATCCAAA | 14546 GGTGCCTCTGGGCTCAGTTTT | 25530 AGGACATGGAAGGGCCTCAA | 36514 |
| 2889 TGGGCCACCATCTCTGCTGTCA | 14547 CGTGTCCCGACTAGCCAAT | 25531 CCCATGGCCGATGAACAGT | 36515 |
| 2890 TCCTGGCCACCATGACGTATCT | 14548 TGGCCATTCGCCCTACTGT | 25532 TGGCAGTCCTGGCACCAT | 36516 |
| 2891 ACAGAGCCAGCAGCCCCATA | 14549 GTGTTAGGTCAAAGCCAGGGTTCT | 25533 GAAGCCTTGGCAGACACAGA | 36517 |
| 2892 CCAGTTCCACCTGGTATGT | 14550 GTTTAGTGGGTTGGCTTAGGTCATT | 25534 CAGTGTCAGGGTGGACTCA | 36518 |
| 2893 GCTTACCAAGGAACGCGTAGA | 14551 ACCATCCAGTCCGAGTGCTT | 25535 GGAGGAAGAACCTGCTTGCTTA | 36519 |
| 2894 CGTGTCTCTGGCTTGTCCACT | 14552 GGACGGGCAATGTCCATGT | 25536 ATGCCCTGTGCCGTGCTCT | 36520 |
| 2895 CAGCCGTCACTTCGTCTGTCA | 14553 CAGGCCACACCCCTTTATCT | 25537 CCCTTGGACTTGACCAGTCA | 36521 |
| 2896 TCCCTTGCACTTAACGCTCTAGT | 14554 CTGGAATCCCTCAGCAAAGTCT | 25538 GCCCCTGCTCCTTTGCACTTA | 36522 |
| 2897 CCACCAAGGGCCTTGACA | 14555 GGCATAGCAGACACTGCCGATT | 25539 CCTAGGGTAGCTGCCACCAA | 36523 |
| 2898 GTTGGCGGGAAAAGCAAATTC | 14556 CGCCTCCATCTATCCATTCCTATTC | 25540 GCAAATGAGTGTTGGCTGGAAA | 36524 |
| 2899 CAAAAGACCCCTGACCACTCAAG | 14557 ATCTCCTCTGCTGCGTGACAAG | 25541 GCTCACACCCTCTTCACCACAA | 36525 |
| 2900 GTGGTGCTTGTGCGTGCT | 14558 CTGTACATGTGGCTCGAACAGA | 25542 ACAGCCCATCTGTGGTGCTT | 36526 |
| 2901 CAGAGCCACCATGTAGGCAACGT | 14559 TCCAGGACGTGGCACAAAGT | 25543 CCTCACGCTGGCAGCAGT | 36527 |
| 2902 TGCCCAGCTGGTGGACACT | 14560 CTCTTCCCGTCCTCCTGCAAAC | 25544 TGTCAGCTGAGGGATCAGT | 36528 |
| 2903 GTGCCCTGTGCAGACATCACT | 14561 TCCAATCGCCGTCTGTGTTC | 25545 CATCGACATTGCCTAAAACCTCTTG | 36529 |
| 2904 CCAGAGAGTCGGTCCACAAGGTA | 14562 CCTCACATTGCCATCCAAGCAT | 25546 AGGCCTCACGTGCCAGAGGT | 36530 |
| 2905 AAACCCAAGAGGACCTTGAAC | 14563 GTCCACGTGGGTTTAAATTCAGCTA | 25547 GGCCAGGGAAGAAGCAACA | 36531 |
| 2906 CCAAATGAACCGAGCCCTTCACT | 14564 CACAGACACAGCCCCAAACACA | 25548 CAGACCAGTTACGCCCCAAAG | 36532 |
| 2907 TGCTGCCAGAAAGAAGAAGTATGTT | 14565 TTGGCCAAGGGGTCCCAAGAA | 25549 GGGCTTTTGCCTGCCAGGAAA | 36533 |
| 2908 CCTGGATGGCAGAATATGCCTTT | 14566 AGTGTTGGCCTGGAGGTCTCT | 25550 CCGACTTCAGTGGGGACAA | 36534 |
| 2909 AGCGGAACGCTCACGGAGATA | 14567 CAGGCAGGCTGCACACAA | 25551 TCGCTGCCACAGAGGGTGAA | 36535 |
| 2910 GCCAGCTGTTCTCGGTTTGGAA | 14568 CACGCGCACATGCACAGT | 25552 CACCTCTGATGCCAGCTGTTCT | 36536 |
| 2911 TGCGGGCGTTGGGTGGTTT | 14569 TGTGCCTGCACTCCCTGAT | 25553 CGCTTAGGCACACGGATTGA | 36537 |
| 2912 CAGTCACTGAGATCAGGCAGTGTA | 14570 ACCCTGCCCTGCTGGACTA | 25554 GAGGCAAGAGACAAGTCAGTCA | 36538 |
| 2913 AGTGTGCAGTGCCCGAGAGT | 14571 GGGTGCTCTTGCCATTCGTTCA | 25555 GAACACATAGAGCCACAGAGT | 36539 |
| 2914 GGAGACAACGGCCCTCAAACA | 14572 TCCACTCCCTGCGCCTCACA | 25556 ACGCCCAGGAGGAGCAAC | 36540 |
| 2915 CCAGGCAGGCTGGAGTTTCA | 14573 CTGCCGTCGGGAGTCATGT | 25557 AGGAGAGCTGAGGACCAGACA | 36541 |
| 2916 TGAAGCCCACAGCCATCCAA | 14574 TGCGCCATGCTGCAAGATGT | 25558 ATCTCCTGTGCGCTGAA | 36542 |
| 2917 CAGGTGATGCGCTGAGATTC | 14575 ACATGGAGGCAGAGTCAGA | 25559 TCCCCAGCCAGCCAGGTGAT | 36543 |
| 2918 CTGCCCTCTGGGACGAA | 14576 AGGCCTTCCTGAGCCTTCGAT | 25560 CCCATGCCAACAGGACATCT | 36544 |
| 2919 TCTTGCCTCATCTGCCTCATGT | 14577 GCCCAGTGGGTGGAGGGTTCT | 25561 GGACCCCGGATCTCAGTCATCC | 36545 |
| 2920 CCCGCAAGTACTCATGGCTCTTC | 14578 GGTGCACTTGGAGTCACAGACA | 25562 TGGACCCCTGCAAGTACTCA | 36546 |
| 2921 CACACACACTGAGGACGCTTTC | 14579 GCCACCACGCCAAGAAAGCAA | 25563 CCCCTGACCCACACACTGA | 36547 |
| 2922 TGTCTTGGCCGATGACACAA | 14580 GGCAACCCAGTGCTCAGGAAT | 25564 GGCCTGCCCTTTGATCTAGTTG | 36548 |

FIG. 36E5

| | | | |
|---|---|---|---|
| 2923 CCCTGACCGCTGATACAAGCAA | 14581 TGCTCGCCGTGTCTGCAA | 25565 CGTGCAGTGAAACCTGGAGTGA | 36549 |
| 2924 TCGGGATGGACAATTCCAAGAAC | 14582 GTGCTTCCCTGCCGGACTAC | 25566 AGGAGGCTTCGGGATGGACAAT | 36550 |
| 2925 CCCTCACACAAGCCACCTGTTT | 14583 AGGGGTGTGGCTGAGCATATC | 25567 GCATAACCTCAGTGCCCTCACA | 36551 |
| 2926 AACCCAGGACTGTGAGAGTGA | 14584 GGAGGTCCTTCCTTGCCTCAAT | 25568 TGGGGCTTTATTTGGCAAGTGTAAA | 36552 |
| 2927 TCCACCCCTCTGCGTAACTTTG | 14585 GTGGGCCCTTTATTGACCAGGTT | 25569 CTCTTCCCAGGTCCCTTCTTTC | 36553 |
| 2928 ACCCACCCAGCTCCCCTTTCA | 14586 GCGGCCTCAGGAAAACCTT | 25570 GCTTTTGCTCTGGCCATGTAAG | 36554 |
| 2929 GGGCGCATAGCCCAGGAATGA | 14587 ATGCTCCCCTCCCTGTCCAT | 25571 TTTGGGAACCCGGGGCATA | 36555 |
| 2930 GGAGACGGGATGCTGGAGAAT | 14588 GCGAGTCCCATCTGCTCTTC | 25572 GGCCAGCTAATTCCAGCAGACT | 36556 |
| 2931 TCGCTGCCAAGCAGTGGAT | 14589 AGGCTCTGGGCTCCTTGT | 25573 AGACAGAGCAAGGGGCTGAT | 36557 |
| 2932 TGGCTCCCAGAACTGCTGACT | 14590 GACTTCAGGGCCTCCAACCATT | 25574 GCTCCACAAATGGCTCCCAGAA | 36558 |
| 2933 CTGTCACGCTTTGTCACGCTTTG | 14591 TCCCCTGCCACCACTTCTCAGAT | 25575 CGCTGTCTGTCACGCTTTGT | 36559 |
| 2934 TGCCCGCCCATTCCATCAT | 14592 TGGGTGCTGGGTGCACAGT | 25576 AGGGAGTCAGCGGACGTT | 36560 |
| 2935 CGAAAGCCACAGGACGTGCTTA | 14593 GGAACGCCCTGCCAAAT | 25577 GTGGGTCTGTGTGGAGATGGATAC | 36561 |
| 2936 GCAAGATCAGCACTTCTAGGACGTT | 14594 AGTGAGCGTCCCGTGGTT | 25578 TTGGGAGCAGGGCTGGAA | 36562 |
| 2937 CCCCGAGGGGAATCAGCAT | 14595 GTGGCAAGGACAAGCTGTATCT | 25579 CCCCTCCAAGGGGTGATTGT | 36563 |
| 2938 CGTCCAGCTTCATGCTCAGAGA | 14596 AGCCACCCGTGCTCTCAAC | 25580 GCCACAGCGTCCAGCTTCAT | 36564 |
| 2939 ATCCTCCCTCCAGCCCATGA | 14597 CCTGTGCCTCCTCTGGACTTTATC | 25581 ACACGACTCCAGGCCACAT | 36565 |
| 2940 TACCTCCACCGCAGACAGAA | 14598 GGCTTGAGCTTGCAGTCTTG | 25582 TGAGCACGTCAGCGTCTCTAC | 36566 |
| 2941 GGTTTGGCATGGCCTGGAAGT | 14599 GCTCCCTGAAGGGCAGTGAAG | 25583 CCCAAGGTGGGGAAGAAGGCTTTG | 36567 |
| 2942 GCCCATTTCCACCCTAACTGTGT | 14600 GCTCTTCTGGAGAAGGAGACAGA | 25584 GGGTATAAAACTCCCAGAGCCCATTTC | 36568 |
| 2943 TTCTCTGGGGAGCGGAAGTT | 14601 TGCTGGGGCAACCTCGAT | 25585 GGAGGCAAGACTCCTCACTTTGTCT | 36569 |
| 2944 GCCTGGTTCCCCTGACATTCT | 14602 TGCACTGCCCTAGAGCTGCAT | 25586 TTGAACCGGGGAGGCCTGGTT | 36570 |
| 2945 CCACTAGCGTGGGGTACTGAA | 14603 ACCCCGCCTCACTCGGATGT | 25587 GGTGATTACATCCCCGCCACTA | 36571 |
| 2946 CCATGACCAGAGTCCACCTTTC | 14604 TCCTCTCTCCCCTGTGCAGTTTA | 25588 CTGCCCCAATCTTCATTTCCTTTC | 36572 |
| 2947 CACTGACATCCGTGTTCCCAAACT | 14605 TCGCACGTCCCTGCTACAAG | 25589 CCAGGGCTCTTGTTTCCACTGACA | 36573 |
| 2948 TGCCGTGCATGAGTGCAGAT | 14606 CACAGTGGCAGTTCCGGATGA | 25590 ATTTGCCGTGCCGTGCAT | 36574 |
| 2949 AAAGGGTGGGACCTCTCGAA | 14607 TGACGAATCAGAGAATATGACCTGTAC | 25591 TGCCCATTGGCTTCCCCTAA | 36575 |
| 2950 AAAGGGCCGTGTGGGACACAT | 14608 GCCAGGCTCAGACTCATCATCTTG | 25592 TGAGGAAGGCCCCAAGGAAA | 36576 |
| 2951 CATCACTGCTCCCTGCTTGTTC | 14609 TCGATCAGGCCCTCTTCTGT | 25593 TGGGCTTCCTGGCATCTTCA | 36577 |
| 2952 CCAGCCATTCTATCCTCCTCCAA | 14610 TCCAGCTTCCTCAAGGCACTCA | 25594 GTTGACTTTCATCACCAGCCATTC | 36578 |
| 2953 TTTGGACGGTGGAGGTGAGT | 14611 CCAGCCAAGAAGCAGCAACA | 25595 ATGCCCTTGCGTAGGGTTTG | 36579 |
| 2954 CACACTCAGTTTCGGGCACAGT | 14612 CACGGCCTTGCTTTCCTGAGA | 25596 TTAGCAGGAGCCCCACACTCA | 36580 |
| 2955 GCTTCCCAGCACCTCCTCTAAG | 14613 AGGCCCCGGAGGGAAAAGAA | 25597 CCACCTATTGCAGGGAGCTGTT | 36581 |
| 2956 ACCATGGTGGAAACTCCATTCATT | 14614 GAGGACTGTGCCAGGGAAGTA | 25598 GCTGTGTACCATGGTGGAAACT | 36582 |
| 2957 TGGATCTGCCCACACCCTTAGA | 14615 TGCTGGACAGACGCCCAGTT | 25599 GCTGCAGATGAATGTCTCTGGATCT | 36583 |
| 2958 GCCGAAGGACAGGCACACTT | 14616 GTCCTCAGGTCCCAGTCGTAGTA | 25600 GCCAGCGTACACATCCCTGAA | 36584 |
| 2959 GAGACAACCCAAACCCTTCCCAAGT | 14617 GTGCTTCCCTTTTTGCCCTCTA | 25601 CCCATCTCTCCCTGAGACAAC | 36585 |
| 2960 TACCTCCGGCCTGACCAATCA | 14618 GGAGAGGGGCTTGGGAAGTGA | 25602 CAGAGGACATTAAGAAAACTCCCTCTGA | 36586 |
| 2961 GCAGCTCAAGGGTGTTCGGAAAT | 14619 CTGCCAGCACACCTATGTGATA | 25603 GTAACTAATCACAGGGCAGCTCAA | 36587 |
| 2962 TGCCCTGCCCTTCTCAGTCT | 14620 GAAGTTCCCCAGTGCTCACCAA | 25604 CTGCCTGCCTTCTCTCCTTTCT | 36588 |
| 2963 TCCCATGTCCCGATCCGACTTC | 14621 CCTCACCAGCTCCCAACGTTTT | 25605 CTTGTCAGAACTGCTCCCATGT | 36589 |
| 2964 CTGTTACCATCCACTGGACCAA | 14622 TCCACACCGGCCCCATCAT | 25606 GGGCCTGAGGAACTGTTACCAT | 36590 |
| 2965 GCCTGTGAGGAGGACTTTTCCAT | 14623 TGAAGCACAGGTGGGAAGAAG | 25607 ATGTGTCCTTGGGCCTGTGA | 36591 |
| 2966 GACTCTGTGTGAGAACAGCACTAT | 14624 AGAGAATGGAAGAGAACGGACTGT | 25608 TGTGCCAGACTCTGTCTGAGA | 36592 |
| 2967 GTCATGGTGAGTCAAAGACTACGTTA | 14625 AGAGGCTCCACCCGTCTTCTT | 25609 GAGGCTTTGTCATGGTGAGTCAA | 36593 |
| 2968 CGCTGTGAGCCTCCACTGATTT | 14626 TGAACAGATGGCTACGAATGTATGA | 25610 TGCCTGCCATAGGGGAGCATA | 36594 |
| 2969 CACACGCAGGTTGTCTCTATTTACACTT | 14627 ACCCTGCTCAAGAGGGAACTCA | 25611 CCAAACACACCAGGTTGTCTCTA | 36595 |
| 2970 AGCCTGGTGGTAGAGGGAGAAG | 14628 CAGCCTGGCTTGCCCAAAG | 25612 AGCTTCTCAGCCTGGTGGTA | 36596 |
| 2971 GGCAGTATCCAAGGCAGGTGTAG | 14629 TGGCAGGTTCTGGGCCTTCATC | 25613 GAAGGCTGGAGAATGTGGTACA | 36597 |
| 2972 CAGCCACTACCCTGCAACCAT | 14630 AGGGGATGGCCTCTTGAACACA | 25614 TGGGGTCTTCTGCAGCCACTA | 36598 |
| 2973 CCTCATGTACTCCTGGTCTCACA | 14631 TGGAGCTGTTCTCCTAGTGTCT | 25615 ACTGCCTCACTCCTCATGTACT | 36599 |
| 2974 CAGCCCCAACCTCATTAGTCAGTTA | 14632 GCCTGTCAGCAGGCAGACTT | 25616 AGGGCAGCCCCAACCTCATT | 36600 |
| 2975 CACAGGCAGGTTAGAGACGCTTTC | 14633 CCTTTGGCTGTGTAGGCTTCGAT | 25617 CCAAAACCACAGGCAGGTTAG | 36601 |
| 2976 TCAGGCCTCTCTCAGTCGAA | 14634 GGTGGGTCTCCAGGTCACTGAA | 25618 AGGGTCGGGACGTGTAGTCA | 36602 |
| 2977 GATCCTCAAAGCCTGTAGGAGAAG | 14635 TGAAGACAGCCTCCCACTCTCT | 25619 GCGAAACGTGGTGATCCTCAAAG | 36603 |
| 2978 GTATCCTGGTTTCAGACACTGAACTT | 14636 GCCGGGCCCAACTATTTGCTA | 25620 GGGCTCCAAAACGTATCCTGGTT | 36604 |
| 2979 GCCCTCAGAGAGCCACAAGA | 14637 GCAGGGAGCAGGGAAGCAAGT | 25621 GGAGGTGGGGCAGAATGGAATC | 36605 |
| 2980 TCGGGACCTATCCGCTGCATT | 14638 CTGGGGCAGCTGAGGAATACTT | 25622 CCAAGCTGTCTCGGGACCTAT | 36606 |
| 2981 GCCTGGACTTTTGATTACCCCTTA | 14639 CATGAACCTGCAATTTGGCTGAT | 25623 CCAGTTCCTATGCCTGGACTTTT | 36607 |
| 2982 GTTCCCTCTCTCCGCTGACAATC | 14640 CCAGCCCAGGTTGCTGAATGT | 25624 CAAGGCCCTGTTCCCTCTCT | 36608 |
| 2983 GACCTTCACATTCCATGTGGCTTT | 14641 TCAGTCCTGAGCTGGAAATACCTA | 25625 GGGGACTGCAGAGATATGAGCTT | 36609 |
| 2984 TTGAGTCTCCCCATCTCCCTTT | 14642 CCCACACCCATCTTGGGTCTTT | 25626 AGTGAAGTTGGAAACCAAGGTTGA | 36610 |
| 2985 GAGCAAGGCTGATGTCTTCACA | 14643 AAGGCCCAGCAGGGAGCAA | 25627 TGGGCAGAGCAAGGCTGAT | 36611 |
| 2986 CGCAATGCTGACACACATCCTTT | 14644 GGCATGTTTGTCGTGCGATGT | 25628 TAGAGCCGCAATCTGACA | 36612 |
| 2987 GGAAATTCTGCAAGGAGGGAGACA | 14645 TCTCAAACTGAGCATTAGCTCCTT | 25629 GTGCTGAAGGCCAAGAGGAAA | 36613 |

| | | | |
|---|---|---|---|
| 3053 AGCCTGATCTGGTGGACAAAG | 14711 TTCCGCACCACGTCCACAAC | 25695 GCAGGAATCTTGACGAAGCCTGATCT | 36679 |
| 3054 CACAAACCCAGTGTTTTAGGAGCATGA | 14712 TCCGACAGGACGCACACA | 25696 GTCCCTTCACAAACCCAGTGTTTTA | 36680 |
| 3055 CCCTCCATTCCCACCCATGA | 14713 CCGGACAGCCAGGGTCTGATC | 25697 TCCCTACCCACCCCTCCATTC | 36681 |
| 3056 GTATCCCCTATCAGCCACCAGAT | 14714 TGGAGGGCCTCTGGTCACTTC | 25698 ACCCCAGCTTGTATCCCCTATC | 36682 |
| 3057 GGGAATCACCACACTTGTGTCT | 14715 GCAGAGATTAGTGCCACCATCAAG | 25699 GAATGGGGATGTGGTGGGAATC | 36683 |
| 3058 CCAGTCATCTCCAAAAGGTCTGATTC | 14716 AGTGACTSTGCATTGTGGGAAA | 25700 TGCCAGTTTAGACGCAGTGT | 36684 |
| 3059 GCACACATCCACATTCGTTCTTG | 14717 CAAATCCAGACCAATTGAGCAAAGA | 25701 AGCAAAGCTTTAAGAGCACACATC | 36685 |
| 3060 GTGATGTGCTTTTGGTTCCTT | 14718 GGGAGGAAGGAGGGAAAGAGATTTTG | 25702 GGCAGGTGAGAACGTTCAGT | 36686 |
| 3061 GGGGCATGATTCCACCTGTAAC | 14719 GCATAGCTGGGCCTATTTCTCT | 25703 GTGTCCTGCCCTGAGGTTTG | 36687 |
| 3062 TGACTCACAGGTCACCAGTCT | 14720 GCGGGATGGAGTGACAGTGTTT | 25704 TCAGATCCGGCTGACTCACA | 36688 |
| 3063 AGACCCCTGGTGCCTCAGAT | 14721 GGCACAGCAGCTCCAGAAT | 25705 GCCCCTCATCCCCACCTTCA | 36689 |
| 3064 CTCCTCCGCCCTCATGTGAA | 14722 TTCCCACCGCCGACTTCCAA | 25706 CTGAAACCCTGCAACGAGACT | 36690 |
| 3065 AGGTCTGCTCCAGCCTCATC | 14723 CCAAGTAGCAGGGCTGGCTAAA | 25707 CACTTATCAGCTGGGCCTCACA | 36691 |
| 3066 CCCAGCTAAGCACATGCACAAT | 14724 AGCCCAGGCTGACTGGTTTG | 25708 CTCAGCTTAAAGCCCCAGCTAAG | 36692 |
| 3067 TGAAAGCGGATCCCGGCTAGA | 14725 AAGCTGGGGTGGACTCCGTTA | 25709 GCTGCTAGTTGGCTCCTGAAA | 36693 |
| 3068 CGGGCAGGGAGAAGACAGGATA | 14726 AGGCAGGGCTGGCTGCAAA | 25710 CCGCAGGGAACAATGAAGGTT | 36694 |
| 3069 GAGTCTTCGTTTGCACCTCTGT | 14727 GGACAGCAACCGTTCAGAGACT | 25711 TGTGGGTGGAGTCTTCGTTTG | 36695 |
| 3070 CAGGCATAAGCCAAGGGACACA | 14728 TGGTGGTGGCTGGCACAGTA | 25712 AGACTGGAGTAACACAGCCATAAG | 36696 |
| 3071 CCCTCCCTTTTCACCCTGGAT | 14729 AGCCATCGTGGGGTCTCTTAC | 25713 AGTCAGAGGCTCCCTCCCTTTT | 36697 |
| 3072 GTGGTTTGTGTAATCTCGCTCCAA | 14730 GTCTTTCCATTTGCCTGGCATT | 25714 AGACACAGTGCACACCACTTC | 36698 |
| 3073 CAACTTGCCAGGGGCAACAAC | 14731 AGCTCCGCCTCTTAACCCTAA | 25715 GCTTAGAGACGCTGAGCAACTT | 36699 |
| 3074 GCAGCTAGGAGTAGTGACCAAGAAG | 14732 CAGTGGCATTGCAGGGCTTT | 25716 AGCCGTGCAGCTAGGAGTAGT | 36700 |
| 3075 CAACCCCTCTAGCCATGTAGTCT | 14733 AGGAAAAGGCCATCCCAGGAA | 25717 TCGCCTTTGCCAACCCCTCTA | 36701 |
| 3076 CTGAGGTCAATCCCGATTCCCACATC | 14734 TGGAGGGAAGAGGTGTGTGT | 25718 GTCCCTGCATCTGAGGTCAA | 36702 |
| 3077 AATTGATAGCAGGGGTGAATCAAGA | 14735 GGGGCCACAGCAAAGCAT | 25719 CTGTGGCAGCTGCAGGTTTT | 36703 |
| 3078 GGGTTTGGTGACAATGGCTCTTTC | 14736 ACCTTCCTGTGCACCCACAA | 25720 CTGGCTGGGTTTGGTGACAA | 36704 |
| 3079 GACTTTGATCTGGGTGCTTCTTC | 14737 CAGAGATGACCTCAGAGCCTTTTG | 25721 GCCGGCCCTGACTTTGATCTT | 36705 |
| 3080 GCGATGGAGTAAATTAAGGCACAA | 14738 GCACAGGCACTGGGCTAAAC | 25722 CCACCTCCTATGGCGATGGAGTAA | 36706 |
| 3081 ATCCACCCAGGGGTCAAGAGTAG | 14739 TTGGTGGCGCCTCAGATG | 25723 CTCCTAGTTGGACCCTGGGTAA | 36707 |
| 3082 AGCCCATCTCAGGCATCTAGT | 14740 ACTGCCTGGCTCAGTGACA | 25724 GGACATGTTGCAGCCCATCTCA | 36708 |
| 3083 GACAGTGACGGCATAACCCTGAA | 14741 GGGAGGGCAGCAATAATAACCTCTGA | 25725 GGTGCTGTGCATGAAGACAGTGA | 36709 |
| 3084 CAGGCACTTTCCTCTCTGTGTTTT | 14742 CAGAGCCACAAACCTAGGGAGTGTT | 25726 TCCAGCCATCAGGCACTTTC | 36710 |
| 3085 TCACACCAGACCCCTAAGGAA | 14743 AGGGTGTATGTGTGTCTGACAAG | 25727 GCTCCCTTGGAGTCTGCATCTT | 36711 |
| 3086 ACACAGGTGTAGCCAGTGTTTG | 14744 CACTGGGTAGGGGACGGATACT | 25728 TGGCATAAGCCTGGCACACA | 36712 |
| 3087 GTGGACTTCAGAGCACAGCAT | 14745 GACTATGAAAATCTGCCGCTGGAT | 25729 GCTTGCAGCTTTGCCTGTCA | 36713 |
| 3088 CCCTTCCCTCCTGGTTTCTTCA | 14746 TGGACTGACCACGTCAGGAT | 25730 GGTGGTGTTGGCTTGCTCTTC | 36714 |
| 3089 GACTGCTGATCTGGCCTCCAAA | 14747 TCCTCTGCGCCCCATCTGAA | 25731 TGGAGCCCTGACTTTGATCT | 36715 |
| 3090 GCCTAGCAGTTGCTCAGTGT | 14748 CTCGGGGAACCATGGGCTAA | 25732 TGAGCAGGGGCCTAGCAGTT | 36716 |
| 3091 CACACCTTGGTGCTCGGTATG | 14749 TTTGCCCTGAGAACTGAGACTT | 25733 GATGTGCCAGCCACACCTT | 36717 |
| 3092 GCCCATCAGCTGCTTGAAAC | 14750 CCCCGGAAGCAGCACATGAGATAA | 25734 CCCAGGTTGGCTCCACATTCT | 36718 |
| 3093 TCCTCCCCTTGAATATCCTCAACTGT | 14751 CTGCCTGAGGGTAGCTTTGCTA | 25735 GCTGTCAACTTCCTCCCCTTGAA | 36719 |
| 3094 AAGGGGACCTGGTGGCTTTA | 14752 CATGTCCTAGCACACGTCTCT | 25736 TGGGATGATGGATTCATGGGTTATTG | 36720 |
| 3095 CCTGCGACACTTCCGTCACTT | 14753 AGTGCCGAGACCTGGAAGTT | 25737 ATCTCCCCCTGGCGACAGTT | 36721 |
| 3096 GCTCACACGGGCATGACCTAAT | 14754 CGGACGGCTCGGGTACTTT | 25738 AGCCCCTTTCCTGGCTCACA | 36722 |
| 3097 TTCAGGGCATGAGCGCCTTA | 14755 GGGGCTCCCAGGAGACATCA | 25739 GTGCCATGAGCAGACTTGGTTTC | 36723 |
| 3098 GAGACAATCCCTGAGTGTCTGAT | 14756 TGTCTGAAGTTTCCTACCCATTTGT | 25740 TGTCCTCAGAGACAATCCCTTGA | 36724 |
| 3099 GGTCCGCAGAGAAGGAAAC | 14757 AGTGAGTCACACCGACTTCTGA | 25741 ATAGGCACAGGTCCGCAGAGA | 36725 |
| 3100 TTGTTCAAGAACTTGCCCTGGTA | 14758 GCACGGCCAGCTCATTCA | 25742 GTCACTTCCCATGGACTTACATTTTTG | 36726 |
| 3101 CCTCAGTGTTCTCAGGGCATCT | 14759 ACTCCCGGCTGGTGCTCACA | 25743 CCCTTGTGTGCTCCTCAGTGT | 36727 |
| 3102 ACCCACAGCCATAGGACACA | 14760 TCACCCAGCTAGGAAGGATTTTG | 25744 TCTCGGTGGACAGTGGAGATC | 36728 |
| 3103 TGGTCCTCAAGCAGGGCTTTTGTT | 14761 GGGTTTCTCCAGGCCGTAAAG | 25745 TGAGGCATGTGGTCCCAAGA | 36729 |
| 3104 GCGGAACGGCCTGTGAAGT | 14762 GGCGAGTTCCACTCATAGCAA | 25746 ACCCACTGCTGAGCCTGTTTC | 36730 |
| 3105 GCCATTCATACACCGTTGTCTTT | 14763 CGCTGGCCTTGTGCTTTCAA | 25747 GCCTTTTCAGTTTTGCGCATTTC | 36731 |
| 3106 GAGTTTGCGGGGCTGTTTCTAC | 14764 TTGGGCGTGCGCATTCACT | 25748 ATCGGTGGCCGCTTGAGTTT | 36732 |
| 3107 AGGAGCGCATGCTGTATTC | 14765 GGTGCCCATGGCATGACTGT | 25749 AGGGTGCATCTGCAGGAGTT | 36733 |
| 3108 TGCAGAGGGATGGAGGACTATG | 14766 GGTGGGTGTGTGCGTGTA | 25750 ATGCCCCTTCCGACTGTTG | 36734 |
| 3109 CTGTATGTTCTCGGGCCTCAGT | 14767 GGCAGATTCTATCCCCATGTCACT | 25751 CAATGGCACATGCTGGCTGTA | 36735 |
| 3110 CTCCCGAAACCCTGCAGAT | 14768 CACCCACTCTTATCTCAGCAGGAA | 25752 TTCTTCCCACCTCCCGAAAC | 36736 |
| 3111 CCTCTGGTTCGGATGGAGGGTTTG | 14769 AAGGCTGGGCCTGCTGCTTG | 25753 GGAACACTGTTGACCTCTGGTT | 36737 |
| 3112 TGGTCTGGAAACCTGGTGATTC | 14770 TGCACCGGGCACAAATGA | 25754 GCCTGGATGGCAACCAACACTT | 36738 |
| 3113 TTGCCGGCTGACGTCTTAG | 14771 GTCAGTTCTGCTTCACGGGTTTC | 25755 AGCCAACCCAAGCGTCTTT | 36739 |
| 3114 GCTGCATCACCTCAACAGT | 14772 AGATGCACATCAAGGTGGCTAGTTC | 25756 TGGGTCTCAGGCTGGCATCA | 36740 |
| 3115 GGCTTTGGCCTGAGACTGTTG | 14773 CGGACAGCATAGACCTGTTCAGT | 25757 AGAGCGAGCCCAGGCTTTG | 36741 |
| 3116 GCTAAGAATTCAGCAAGTAGGACAACA | 14774 AATGGGACCAGAGGGTCTAAGAA | 25758 GCACCACTGTGTGACAGAGCTA | 36742 |
| 3117 CACCCAGACAGCAGCTGAA | 14775 CGGGTAAGAACTGGCTGAACATAAG | 25759 AAGCTCCTAGCCACCCAGACA | 36743 |

| | | | |
|---|---|---|---|
| 3183 GCCAGACGAGTCATCTACCCTTGT | 14841 TGCCTTGGATGATGAGTTGAGAAG | 25825 CTCTTTCAAGCCAGACGAGTCA | 36809 |
| 3184 CAGTCACTATTACTGTACCAGGAGTGAT | 14842 GCCTGTTTGCGCAGGTCTGA | 25826 GCTGATGTGTGCACAGTCACTATT | 36810 |
| 3185 CACCCAAACATTGCCTTTCTTCCAA | 14843 GACGTCCCTGCATTCCCAACCT | 25827 CCACGGATCCTCACCCAAACAT | 36811 |
| 3186 GAGGCACTGCTTTTGCAAAAACAACA | 14844 ACCTACCCAGCGACACGTT | 25828 ACAAAAGGGATGAGGCACTGCTT | 36812 |
| 3187 CATGGTGCCCACCCACAAG | 14845 GACTGATGAGTCTGGGTTCACATC | 25829 AGGTGCAGGGCTCACAGTAA | 36813 |
| 3188 GAGGGGAGAATACAGTCCATGTTTCT | 14846 GGCTGCCAACCACCACTAGA | 25830 GCGGCTCTGAGGGAGAATACA | 36814 |
| 3189 AGGCAGGGAAAACTGGTGAGGTA | 14847 CACCTCTCAACACTGCTCTTTCT | 25831 TTGTTGGAGGAGGGAGGGAAAC | 36815 |
| 3190 GGCAAAGTGGAGAGATCCAGAACA | 14848 AGAGATCTGGGCCAGCCAAAG | 25832 GCAGGGTTCAGCCAAAGTGGAGAGA | 36816 |
| 3191 CTGAGACAGAAAACTGATGCTTCTT | 14849 TAGHCACTGCAGCCCTTTCA | 25833 GAGAAGCCCACTHTCTCTCTGA | 36817 |
| 3192 GGTAACCACCAGTGGCCATTCT | 14850 TTGCCACGCAAGGCTACTT | 25834 GAAGGAAGACTTAAACTGGTTGGGAAC | 36818 |
| 3193 TCTGAGGGGCTGGGAACTCA | 14851 ATGGCTGGCTGCCCAGGTAA | 25835 TGTGGTCTCAGCTTGGTCTGA | 36819 |
| 3194 CCAAGTGGTCCCAGTTCCCCTTA | 14852 CTCTGCTGGTAGGGGTGATTGAT | 25836 ACATACTCTTCCTTCCCTCCAAGT | 36820 |
| 3195 CGTGTTGCTGCAAAGGTAGGAT | 14853 GGTTGTCAAATCCCAAGTCCAGTCT | 25837 AGATGAAGTTAGGTGTTGCTGGAA | 36821 |
| 3196 AGGAGGGTCACCTTTGTGTCT | 14854 GCCTTTCAAATCCAGTGGTGACAAAC | 25838 CCCACCAATCACCATAGCCAGTA | 36822 |
| 3197 CCAGAAACCGTGAGTCCTGTCA | 14855 GGACCCAGCCTACATCACAGTC | 25839 GGACATGGAACTGTGACCCAGAAAC | 36823 |
| 3198 GAACCCCATAGACCAGTCTACCTA | 14856 TTGGGACACTGTGCAGCAA | 25840 CCCCACAAAGAACAGCCATAGA | 36824 |
| 3199 TGGCATCAACTCCCTTTCTTCAA | 14857 CCTACACAAGGAGGGAAGAGTGA | 25841 GCAAGCACATGTTGCCATCAACT | 36825 |
| 3200 TTGTCCCTGCCTGAAGGACTCA | 14858 GAATTCCCAGGTTGAGGAAACCTA | 25842 CTCACCCCGAGACCCTTGT | 36826 |
| 3201 GGAGCAATGTCTACAGGATGAGATG | 14859 AAGCCCCAGCCCACTGGAT | 25843 GAGGGAAATCAAGAGGCAATGTCT | 36827 |
| 3202 GGCACACAGTCATCGTAGAATAAACTT | 14860 GTCTACAGCACCTTTCCCACACA | 25844 GTGGATGGCACACAGTCATGGTA | 36828 |
| 3203 CAGTGACCAAGTGGGAGAGAAG | 14861 TCCACCCAAGGTGCCTTCTTA | 25845 CATGGCACACAGTGACCAAGT | 36829 |
| 3204 CACGAATTCCGGGAGATGAACTGA | 14862 GCCTTCACAGTCAACACTGA | 25846 GCCCGGGAGCTATGACAAAT | 36830 |
| 3205 CTGCAGCACAGGTTTGCAAGT | 14863 TCCTGCTAATCTGGCTTTCGTT | 25847 GGCAAAACTTTTCCTCAACCCTCTTAG | 36831 |
| 3206 GACAGGACTTCCACAGAGCATGA | 14864 CCCACAGGAACTGTCCATCCAATC | 25848 ACACCAACAGGGACAGGACTTG | 36832 |
| 3207 GATGACAGACACGCAGGAAGA | 14865 CCTGTCCCCAGGCATTGAAGT | 25849 ATGGTCAAGGTGATGACAGACA | 36833 |
| 3208 ATATCCGCCCATCTCCTCAGT | 14866 CCCAAAGAACCCCGTGTGGTT | 25850 TGTTTGTAACCCCTCCCTCTCT | 36834 |
| 3209 CAAACCCAATGCTACACTCCACTT | 14867 CCACCACCAGATGGAAACGTACT | 25851 CCTGTTTGAACAAACCCAATGCTA | 36835 |
| 3210 GGTCCTTGCCTCCAAGAGTTA | 14868 APGTGCCCCTAGGCAGGCAGAT | 25852 CAGGGCCCTGGGGAATACAGA | 36836 |
| 3211 GTCGGCAGTTCTGGGCATGA | 14869 CTCTGCCCCTGGACACTGAA | 25853 TGGGAATACGGTCGGCAGTTC | 36837 |
| 3212 CTCACAACCCAGAAGCCCTTGA | 14870 TTTCCCACGGCTGCTCACT | 25854 CACCTATCCTTCCCCTCACAAC | 36838 |
| 3213 GCGGCTTCCTTCCTCCGTTT | 14871 CAGTACACAAAGTCCTGTGGGAACTA | 25855 TGTCCCCGCCCCTTCCTT | 36839 |
| 3214 TGCTGGCCAGACCCTGCAT | 14872 CAGGGCTCGTAGCCTTGTTCTA | 25856 GCCACAGTTGACTCTGCACTCCTT | 36840 |
| 3215 GCTTTGCAGACCACCAAACAA | 14873 AGGGCAGATTGCTGACTTTTGA | 25857 CTAGCCCATTTGAGATAGACCTTTG | 36841 |
| 3216 GGGCCATCTGGGGTTCAGTT | 14874 GCTCCACACTGCCGCAACA | 25858 AACCCCTTGACGGCCCATCTT | 36842 |
| 3217 CCAAGGGCAGGCAGTGTTTTG | 14875 ACAGCCACCCTTGGCAAAC | 25859 CCAAAGGGTCGCTACACCAA | 36843 |
| 3218 CCATCCTGGAATTTTGTCCAATCT | 14876 ACAACATTGACGCTTTGGTATG | 25860 CCAGATGCAAAAGCTATCGTGGAA | 36844 |
| 3219 GGAGAACTGCACGGTTGTGAAC | 14877 GCCATGGTCCCTCCCAAGTTAC | 25861 ACGAGGCCCAGCTGAACAA | 36845 |
| 3220 CCTGTTGAAGCCACTAGACCAA | 14878 AGACTTGACCAGCTGGGAAAA | 25862 CCTCAGCTTCCCCAGATACCTGTT | 36846 |
| 3221 GTGTCATCTGTGCCTTCACA | 14879 TCACTGCACCTGGCCTGTTTT | 25863 CTAGGACAGGCATTGATGTGA | 36847 |
| 3222 AGTTCCCTGGGTCAGGAACAA | 14880 GCCTCTGGTTCCCCTTCTGT | 25864 TCCCTCAGATCCTCCTGTTAC | 36848 |
| 3223 GTCCCAAAGAAGCATGGACA | 14881 GCAACACGACCATGCCCATT | 25865 CCTGCTGACTCTGCTATTGT | 36849 |
| 3224 GGTGCAGTCAATGGTGGCCTTA | 14882 GCTGCCCAGCGTTCAATATC | 25866 AGAAATCAATGGGGTGGCAGTTGA | 36850 |
| 3225 CCTCCTGCCACCACCTAA | 14883 CGGAAGCCATAGGTAAGCACTGA | 25867 GGCACTTCCCCATCACTCTTTCT | 36851 |
| 3226 GTGAGCAAGACACCTGACTGA | 14884 CAGGGATCAAGCTGTGGCTTAG | 25868 GGGTGGCCTGAGCTAAGAGT | 36852 |
| 3227 CACTGCACCATGCTGTTCATGT | 14885 AGGGAGGCAGTAGTAGGTTTGA | 25869 AGTCACCCCACTGCACCAT | 36853 |
| 3228 GATGGCTGGAGCAGAAGT | 14886 BAGGGCTTTCCCCGCTTTTG | 25870 GGCAGAGGGCAAGCAAACA | 36854 |
| 3229 TCAACCTCCGGAGCTAACATGA | 14887 TCTCCCCTACCCAGGAGTCTAA | 25871 TGGGTTGCTGCAGAGTCAAC | 36855 |
| 3230 CATGGAATCACTCAGTGTCATAGTCA | 14888 GGTAATTTCTGGCTGACAAGGTT | 25872 TTGACTGCTACTCCATGGAATC | 36856 |
| 3231 TGGACACACAGTTGGAAGATG | 14889 CCACAGGGCATTGAGGTTTAC | 25873 CTGAGACCTTAAACTGGACACACA | 36857 |
| 3232 ACTCAGTGGTTCTGGATCTGA | 14890 CCCCTGCCCAGTTTCAAAAT | 25874 AGGAACTTCCCTCTCCTTACTCA | 36858 |
| 3233 CCACCTAGAACCCACGACAAA | 14891 GCAACTTGACTCACCTCACTGACAA | 25875 TGGGACACCTAGAACCACTAGA | 36859 |
| 3234 CTCACAAGGGCTACAGGCATT | 14892 CGATGAGGAGACTTTCCTGTCTCA | 25876 ACCAGCCCAGACCTCACA | 36860 |
| 3235 GGATAGCAACTCTCAGGGCAAAT | 14893 GGGTCCTGCAGACAAACCTT | 25877 GGCACACAAATGAGGATAGCCAACT | 36861 |
| 3236 CTGGCCGATGGGGTTCATC | 14894 CTCCCAACTGAGATTTGCGATATAATCTTC | 25878 CACTTCCCAGTTACCCCTCAGTTC | 36862 |
| 3237 CTGGGCTCAAAGAATACTTCTACCCTAG | 14895 CACCTGTGGTCCCAGCAACT | 25879 CCTCAACCCTCTGGGCTCAAAC | 36863 |
| 3238 GAGGGACTAGCACAGGCAATACAAAG | 14896 CCACCTCCAGGCTAAGAAATC | 25880 AGAGGTAGGCACAGAGGGACTA | 36864 |
| 3239 ACACCAACAGCCCCTGATAGA | 14897 ACTTCCTCCCTGCCTGATGT | 25881 GGCCTTAGGGACACCCAACA | 36865 |
| 3240 CCCTGATCTTGCCTAACCCTTCAGA | 14898 CACCCAGTGCTCCTTCCCATCAGA | 25882 CACACATGCCCTGATCTTGCCTAA | 36866 |
| 3241 GCCAAGATCCACTGTTAGACCAAGA | 14899 GCTGAAAGCTGTGGGTTTGGTTTTG | 25883 CACATTAGGCCAAGATCCACTGT | 36867 |
| 3242 GGAAAGCTCTTGAGCTGAAAATG | 14900 AGCCCCAGTTCCCACAGCTAA | 25884 GTTGATCATCATGCAGTGGGAAA | 36868 |
| 3243 APGTGATGGCTTTGGACCAGAT | 14901 TGCTGTTGGAACTGGAAAGAGTT | 25885 GCCCTTTTCAGCTGTAATGTGATC | 36869 |
| 3244 GGAGACAGTTAGGGTGTGGACAT | 14902 CCATCCCGCGCCAACTCA | 25886 GGACGTGAAGAGAAGCGGGTTT | 36870 |
| 3245 GTCCACCTGACTTGCATTCTTTCTCT | 14903 CCCTCTGAAGCTTCTGTCTAGTT | 25887 CCCACATGCTCACCTGACTTGCAT | 36871 |
| 3246 CCCTCCCAACTCTGAAGTTTGT | 14904 TGTATCTGCGGCTGAATTGAGAA | 25888 AACCAGACCCTCCAACTCT | 36872 |
| 3247 GCTGTGTCAACCCTCAGAGTTCAGA | 14905 GCTTTGGTCTGTGGCTGCATAG | 25889 AGGCGGAAGAGCTGTGTCAAC | 36873 |

FIG. 36E10

| | | | |
|---|---|---|---|
| 3248 TGACTACAGCTCACTGCTCTTG | 14906 CAGTTAAAGTCCGAGGAGGTGATC | 25890 TGGGCTGACCACTGACTACA | 36874 |
| 3249 GTCATCCGAAGTTAAGCCGCATCT | 14907 GCAACTGAGCATCCACACT | 25891 CCGAAGTCGTGTCATCGTCAAGT | 36875 |
| 3250 CCAATGTAGGAGTGGATGGCTTT | 14908 CCTTCAGCAACTGTAGCTCCTCTAC | 25892 GCTGGATTAGAGTAGGGGCAATG | 36876 |
| 3251 GGGTTTCAACAACTCAGTGCAA | 14909 CGGTTGCCTCTCTCTTTACTGAT | 25893 TCCGTCTCAGGAGGGTTTCA | 36877 |
| 3252 CTGGAAAATCACCTAATTCAAGCCCAAATC | 14910 GGTCCGAGGAGGGGTTTGT | 25894 CTGCCTCCTTCGATCTTCTGGAAA | 36878 |
| 3253 CCAAGCATATCATTTACTCCCCATTC | 14911 GAAGTTCCCCGTTCCACACA | 25895 GTCCCCAGCCAAACTTTCCAA | 36879 |
| 3254 CTGGCAAGGGTTGGAGACACAT | 14912 GCTTGCCAGCCAACCTGTTA | 25896 CAGGTAGTTTGTCGAGAGCAAGTCA | 36880 |
| 3255 TGGGGACTTGTGTGGTGCCTTTC | 14913 CCAGTTGGTCCATGGCAGTTA | 25897 ACAGACCAGAGTGGGGACTTGT | 36881 |
| 3256 CGGGAGATTAAGCGGCAGTTAC | 14914 GGTGGGCCATTAAGACAGTTC | 25898 TCCTCCAGTTTCCACAGGAGAT | 36882 |
| 3257 GCATAGCTGGTCACACTCT | 14915 GGAGGAGAAAGCCTTGGCATTTG | 25899 GAGTCTCTTCAGGCACTTAGCAT | 36883 |
| 3258 GGCTCCATCCTCAGGGTTCA | 14916 CCAGGAAGCTGCAATATGGAGTGA | 25900 GGACGTTCAAACCCTGATGAAAG | 36884 |
| 3259 CGAGGTGAGACGCTATCTATGCAA | 14917 GCCGTGGCTGTCAAATGTT | 25901 ACAATCCTCCCGAGGTGAGA | 36885 |
| 3260 CCCTCCTGCAGGTCTCTGT | 14918 TGACTTCTGTGAGTCCGTGAAG | 25902 ACTGATGGAGGTGGCCTGAA | 36886 |
| 3261 CAGGCTATGACATCAAGGCTTTCT | 14919 AACACGATCGTCGTCATGATT | 25903 CAGCTAAATCAACAGGATGTATGACA | 36887 |
| 3262 GCCTCAATGGGAGCTTCTCAAC | 14920 CCCACATCCAGGATACTTGGCTTTT | 25904 GCCAAGAAAGGTCGCCTCAAATG | 36888 |
| 3263 GAGGACCAGGCAGTGGAATGAAGT | 14921 TCCGACCCTTCTCCCACATT | 25905 GCCATCACTGTATCCTCCCATCAGT | 36889 |
| 3264 CTGCCTGGAATGCTCTTTCTCTAGATTT | 14922 GTCTGCGTGGAGGGAGAGA | 25906 GGGTCCTTCTGCCTGGAATC | 36890 |
| 3265 CAGTGTCAGGAAATGTGCCTTGT | 14923 TCCCGTCTCCCATCACACAT | 25907 GCCCCTGCAGTGTCAGGAAAT | 36891 |
| 3266 GGATGGCTGATGCTTCCGATT | 14924 GGTTACATTGCGGTGATCAAG | 25908 GGACAAAACAGAGTGGGCTGAT | 36892 |
| 3267 CGCGTCCCTACATTGGGTGCA | 14925 CTCCCTCGGCTCTCATTCTCT | 25909 GCGAACGCGTGCCTTACA | 36893 |
| 3268 TCGGCTTGACCAACTACAAATTCT | 14926 GAGCCTGGGGAGAGGATCA | 25910 CCACACTTCGGCTGACCAACT | 36894 |
| 3269 TCGCAGTGCCTGGTCTCTGA | 14927 GTATGTGAAGATGGTTGCTTGGAATC | 25911 GCCCTTGCCTAACCACATGTTC | 36895 |
| 3270 AGTTGCTCTCCCAGCCAAGA | 14928 CCCAAAGCACTAGAGACTGGGTCAT | 25912 CTCCCTTAAGGAAACCCACAGTTG | 36896 |
| 3271 GAGGACTGACAGGTTCCTGCTT | 14929 AGGCCTGGGTTGCCTGAAAC | 25913 CTTGACTTGCTGAGGACTGACA | 36897 |
| 3272 CCGAGAGACAATGTAAGATGTTC | 14930 GCCCAAGCAAGGTGGAAATCT | 25914 GGGAAGGTCCGCAGAGACAAT | 36898 |
| 3273 AGCCACACTGCCTCAGCAAA | 14931 TGTGGACAGCAGGTCTCTAAG | 25915 GACATGGAAABAGGCTGGAATGTAG | 36899 |
| 3274 CCTCAAACCTCCCTGTGGCTAA | 14932 GGTCATGAACATGGAAGGAACAAGATT | 25916 TGCTGATCCACATACCTCCTCAA | 36900 |
| 3275 CATGACCCTGCTCACACCTT | 14933 CTGAACTCCAACAGGCATCTCA | 25917 CTTCATTCGAATCTCCACTGGGAACA | 36901 |
| 3276 TCCCAGTGTTCCCTCACTCA | 14934 GACTTCCTTTCTACCTTGTTGCTGAT | 25918 TCCTGGTCTTCCCCAGTGTT | 36902 |
| 3277 CCCCAAACCCTTTTCTGGTGTT | 14935 CACCATGAAGTTCAGTCCATAGTCA | 25919 CCAAAATAGCTCCCCAAACCCTTT | 36903 |
| 3278 GCCCAAATCAGGGACAACA | 14936 CCCACCGTCCTGCATACTCA | 25920 AGCCCAGGACCCTGCCAAA | 36904 |
| 3279 GCCGGCTGGTTCCATCACT | 14937 ACGTAAGTGGATGAGGGAGAACT | 25921 TTGCCCCTTGCTGGTGCTGAA | 36905 |
| 3280 GAGCTGGGTTCAAACCAAAAGT | 14938 TCACTGCACCATTTCCCCAAT | 25922 CACTGACTGGAGCTGGGTTCAA | 36906 |
| 3281 GTGCATTCTCCATCATGGCATTGAAA | 14939 TCCTCAGGGCCTTGGGAAACAT | 25923 ACGAGCCCACAGACATCCTTAAAAA | 36907 |
| 3282 GCTTGGCCTCTTTCTGAACCTACTA | 14940 AGCCTGCCTCACATTATCCTTTC | 25924 CTCCAACTGCTTGGCCTCTT | 36908 |
| 3283 GCTTCCCAGCATGAACCCTTT | 14941 GGCAGGGAGGTCCTGACTGAA | 25925 ACTTCTTTGAGCTTCCCAGCAT | 36909 |
| 3284 CCTTCCCTGACAATAGCCACCTGTT | 14942 CTGGGACAGGACCAAATCCAACTAC | 25926 AGAAGAGATGTCCTTCCCCTGAGAAT | 36910 |
| 3285 ACACTCGTACAAGCATCTTCAGA | 14943 GCTAAACTCGACAGGCTAAGTGCTA | 25927 GTGGCANTTGAAGACACTCGTAAC | 36911 |
| 3286 TCTCTGGCCCTCAGTCCTTTGT | 14944 ATTGGAAACCCATGAAGGACTCCTA | 25928 GHAATCTACACCACTGCCTCTCT | 36912 |
| 3287 CAGCCTACATGAGTCCTTTCAGAT | 14945 GCCAGATGGTGCTTGGTTCA | 25929 CACCCACACTACAGCCACATAGT | 36913 |
| 3288 TCTTGCCAGGTAATAGCCTCAAC | 14946 GGGCAATGCCTGACAAATGGTA | 25930 GTCTCAGGAGAATAGCATGTCTTG | 36914 |
| 3289 ACCAGGAGAAGACTAAGAAAAACACTTTTG | 14947 TCCAACTGGGCTTTTGGAACA | 25931 CTGTGTAAACTATACAGGGAGACTAAG | 36915 |
| 3290 CATCCCTTCCCTACTTCTCCATTC | 14948 TCAGAGGCATGTTACCCTCTCT | 25932 CAGCTACTTCATCCCTTCCCTACT | 36916 |
| 3291 CCCGTCCAGTTGGTGCTCAT | 14949 GATGGCACAGAGAGATGCTCAGA | 25933 CAGCAAGCCCGTCCAGTT | 36917 |
| 3292 GCCTCAAACCAGGGAGGATGACA | 14950 GGGCCTTTTGGCCACAGACTAA | 25934 GCTCAGCCCAAAGCCTCAAAAC | 36918 |
| 3293 GGCAAATAAACTCATTGCACGTAT | 14951 AGGTTCTGTCCCATACGTTTTG | 25935 GCTGCCATTCAAGAACAGCAAT | 36919 |
| 3294 GCAACGGGAACTTCACTCACT | 14952 CGCTCAGCAGCAGTTGTAACTA | 25936 GAGATCGAGTTATGCATGGATTCT | 36920 |
| 3295 AGGAACCAGTAGGGCTATCACA | 14953 AGCTGCAGGTTGCAGTTCA | 25937 GCCATCACCATGATGAGGAAAG | 36921 |
| 3296 GGCATGCAAGGAGAGACAGGAAA | 14954 ATCGCATCCTTAGTACCCTTAPGCAA | 25938 CAGACAGGAATGGGCATGCAA | 36922 |
| 3297 ACCCACCCTGCCTGTTATGT | 14955 GTAAGGTACGGTCAGTAGTGTAGAAG | 25939 TTAGCGATCCCAGTTCACGTAAC | 36923 |
| 3298 CCTTAACTTCCTGCACAGCTTCAAT | 14956 TCAGGACCCCTTGGCTGATCT | 25940 GCAGCTCAAAATCTGCCACCCTTAACT | 36924 |
| 3299 GTGGGCTCAAGGTCCCTTTAC | 14957 TCCTTCTGCCTGAGAAAGCAA | 25941 TGCAGGACAGTGGGCTCAAA | 36925 |
| 3300 CTCGACAGCCCTAGGTAATGA | 14958 AGAGCCCTAGGGAGCTCATGGTA | 25942 GCACAGGAATGCATGAAGCGAAAC | 36926 |
| 3301 GATTTCTTTCCTGAGTGAGGTCCAA | 14959 TCACTGATCCAGACCCCAAGA | 25943 GGACTTGCCCTCTGATTTCTTTCCTGAGT | 36927 |
| 3302 GGGCATCTTCGCCACAAGGAA | 14960 THCCAGTCCAACCAGCATAC | 25944 GTCTCTATCCTCAGTCTAAGGGATCT | 36928 |
| 3303 CCTTCAACCAAAGTCGCACAC | 14961 CCCAGTGGGCAGAACTTTGA | 25945 CACACATTGGTCATTTCTCTTCAAC | 36929 |
| 3304 GCCGATAGTCCCAGCTGTTT | 14962 GGGCTCAAGTGATCCTCCCATCT | 25946 TCGTGGTGCATGCCGATAGT | 36930 |
| 3305 TGGTTTACAAGCACACAGCAT | 14963 TGCCCTACAGCAAAGGGTATATTTC | 25947 CAGCTGCAAGCTGCATGGTT | 36931 |
| 3306 AGCCTTCGTAAGCGCCATTGATT | 14964 GTTCCAGGCACAGGAGTCA | 25948 GGAAACCTGCAGCGTPGGTAAGA | 36932 |
| 3307 AGGTGGGCTGGGGTCATGT | 14965 TCTGCTGCTCCCGCTCCATT | 25949 GGTGTGCTGTGTGAACAGGCAAAT | 36933 |
| 3308 TCAGCAGGCACTCCCGAATC | 14966 GGGCACTTGCCCGTGTAATTCT | 25950 GGATCCTGTGTGAACAGGCAAAT | 36934 |
| 3309 GGTTCTGAGGTTCTATCCAAATGTCTTC | 14967 GCTACTAGCCCTCCATCTCAAGC | 25951 CCTTCTCGGGTATTATGGTTCTGA | 36935 |
| 3310 CTCACAGGGATGGTCGAATG | 14968 CTGTGGGCACAGGGATCATCT | 25952 GGCTGTGTGTCCGCTGTGAA | 36936 |
| 3311 TCAGGTGTAGCGGGCAGTTAGT | 14969 AGCACATCAGGCAGGTTCAAGT | 25953 CCGTGGCTGTCTGAGAGACACT | 36937 |
| 3312 CACCTTTCCTCAAGTGGCCTTT | 14970 CCTCTGTGTGTTGTGCTTGGAA | 25954 CGTCAAGTTCAAGTCTCACCTTTC | 36938 |

FIG. 36F1

| | | | |
|---|---|---|---|
| 3313 TTCCACGGAGAGGAGAACACA | 14971 GCCAAGCTCCGTGCTGGTAA | 25955 TGCTGTCTGCCCACAGACTT | 36939 |
| 3314 ATGGCTGCTGCTGCCCTAGA | 14972 CAABCCGAAGCAGACATAGTGAAG | 25956 GGGCTGCTGTCTCTGGAAAT | 36940 |
| 3315 CTGTCCCAAAACAAACAGCATCTGA | 14973 GCAAGATTGTGTCTCGGAGGTTCA | 25957 CACAGAGTTCCTGTCGCAAAACAAAG | 36941 |
| 3316 TCTCAAAGACGACCAAGTGATTCTT | 14974 CGGTGAGCTTTGGAGAGTTTTG | 25958 CATCGCAGCGAGCTCTCA | 36942 |
| 3317 CCTCCTGAATCTGAGGCCTTT | 14975 TCCTGCCTGGGACATGGAA | 25959 CCAAGCTCGCACACCTCCTGAA | 36943 |
| 3318 GGAACAATGCCCAGCCACACT | 14976 ACACCGGGCATTCACAGA | 25960 CACTCTCCAGCATCTTAAGGAACAA | 36944 |
| 3319 AGGCTTGGTCAGTGGCTCTA | 14977 GATGGAGAGCATCTGGGTCCTT | 25961 GGGAAGCTTCAGGCTTGGTTCA | 36945 |
| 3320 ACTCCGCTGCTGAGGACTA | 14978 TGGGTCCACATGGTGGAATGA | 25962 GCATCAGAAGCATTCCTGTCA | 36946 |
| 3321 GAACTGAACATGCACTCACACTA | 14979 TCTTGGGGTGGATTCGGGACTT | 25963 TTGGAGACAGGTTTGACCATCT | 36947 |
| 3322 GGACCACATGCCTGGTACTCA | 14980 ACAGTCAAGCAAGGGGTTGTTATG | 25964 CGTGTACGCTGGACCACAT | 36948 |
| 3323 GCCACCAGAGCTTGACACTGTT | 14981 CTGCCCACTGTCACTACTGCAT | 25965 GGAAATGGGCACCAGAGCTT | 36949 |
| 3324 GAGAAGTAGGGCATGTGTGTGA | 14982 CAGGATGGAGTCACACGGATAACTT | 25966 AGAGGAAGAGGGTGGAGAAGTAG | 36950 |
| 3325 GACCACAAGCACAGATTGATGAGA | 14983 CCAGCCACCACAGTCCATCA | 25967 GCGGGAAAATGACGAGCAGAT | 36951 |
| 3326 GGAAAAGCTACAGCCTACCCCAAA | 14984 CCTTCCGGAGGCAAAGGAAACA | 25968 CTGGGCAACCGTCAGGATTATG | 36952 |
| 3327 TGAACACCAACAGTAAGAGGACAA | 14985 GTCTTGACAAGTGGCTCGCATTT | 25969 CAAACCAAAGTGAACACCAACAGT | 36953 |
| 3328 ACGGATTACCTGTGTGCCATT | 14986 GCATTGCCCGTAATACCTATCTTG | 25970 TCACAGTGTGCCACCGATTAC | 36954 |
| 3329 AGCGTGCGCACCAGTTTG | 14987 GCCCTTTGCATCGTTGGTGGCATACT | 25971 CCTTGCACACAGCCGGAAGGAT | 36955 |
| 3330 GGACTTCAGGGAGCTTCTACTCA | 14988 CATGTAATGCCTGCTCCCTTTG | 25972 TCTGCTTCCACTGGGGACTT | 36956 |
| 3331 CTTCCAACACAGGGAATCAAAGTTCA | 14989 GATTTGCTTGGCCTGGTAAGT | 25973 CCTCACTTCCAACACAGGGAAT | 36957 |
| 3332 CACCACGCTAGTTGGTGATAGAAC | 14990 GGAGCTGAATGCTGCCTGGAT | 25974 CCTGAGGTCACCACCCTAGTTG | 36958 |
| 3333 GCCTTGCTGTCCTCCAAACT | 14991 GGTGGTACTGATGCTTTGGTCTGA | 25975 CCGTCACCCAACCCTCAAAAGT | 36959 |
| 3334 GATGCCACTGTCATTCCAGACA | 14992 CCCGTAGCTTTGGGCTCCTT | 25976 ACCAGCACCTAGATGCCACTGT | 36960 |
| 3335 AACGTCTCGCCACTCCCTGTCT | 14993 CCCATGGCTCAGGCTCAAG | 25977 TGCATGATCCAGGCGGTCAAC | 36961 |
| 3336 GTGGTGCTGGATGGGAGGAA | 14994 CCCGGACACCCTTGGAACA | 25978 GACTTAGGGAGGTGGCTGGAT | 36962 |
| 3337 CAAGACACCCATGCCCTCACTT | 14995 GAGCCAGTCCAATGGTCTCCTT | 25979 CCCCAGCGCTGTAGCAAGACA | 36963 |
| 3338 GCTTCAGCAAGTCATCCTGATCT | 14996 CAGCACCGACAGCAACGAAA | 25980 GCCTCCACTGAGCCTTCAGCAA | 36964 |
| 3339 CCTCGAGGAGCTTCGCCTTT | 14997 CGGTTCTGAAACAGGGAGTCTT | 25981 AGCCGCTCCCTTCCTTTTC | 36965 |
| 3340 TCAACCTCTCAGGCTCAGTGAT | 14998 TGCTGTGGTCCCAGCTACTT | 25982 ACTGCAGCCTCAACCTCTCA | 36966 |
| 3341 TCTGCTTCACTCAAAACGAA | 14999 TGTCAGCAGAAATGTACAGTGCTA | 25983 CCAGAGTCAGCAGTAGGAAGGAGTTC | 36967 |
| 3342 CCACTCACAGAAGTGCCACTGTTTC | 15000 TGGCCACCTCTCCATCTCAA | 25984 GCCTTTAGCTCTCCACTCACAGA | 36968 |
| 3343 GCACCCAAAATGGACATCCAACA | 15001 GCCTCTGGCCAGCCTTCAAAAT | 25985 GACTCGGTTGCACCCAAAATG | 36969 |
| 3344 GGCCAGTCTTCACTGCAT | 15002 GGGACACAGAAACTCACTGTTCAA | 25986 GCAAGACACAGGCACTCTGATG | 36970 |
| 3345 GCACTAACACCAGCCTGAGTGAATG | 15003 TGACCTGGTCCTCAGACAAGT | 25987 TCCTAGGATCTGCACTAACACCTA | 36971 |
| 3346 TGCTGTGGTTGCGGGAGAAG | 15004 CAATGAGCCTTCCCGTCCCACTT | 25988 GGGGAAGGAATTCAGGGAGACA | 36972 |
| 3347 CCATGGTGCTAGGCAGGTAGT | 15005 CCAGCCCAGGGCTGTTAGGATA | 25989 GGCTTGAGGCCATCCTGCTA | 36973 |
| 3348 CCTCCTTACCTTCCAGCTCCTTGCAT | 15006 GAGCCCGATAAGAAGTGGAGACA | 25990 CCCTGTGAGGCTACCCCTCTTT | 36974 |
| 3349 GGTGCCGAAGACCACAGTAAAG | 15007 CAGAGCCGAAGAAGAGTCAAGTT | 25991 RAGGGGCAATGCTGGCCAAGA | 36975 |
| 3350 GGAACTTCGCACTGGAGCAA | 15008 GGTGGCAAAGCAGATTCATTTTCTCCCTAA | 25992 CTCCCCACTAAGGATGAGGAACT | 36976 |
| 3351 TCCCTGCAGGTGAAATCTGTT | 15009 ACCATGAGGAAGAATTGGCCTTT | 25993 GGCTGGCTAACAATGGGTTATCTCT | 36977 |
| 3352 GGGACATTTGACCAGAGACAGAA | 15010 GCATAGCATCCTGCTCCAGTT | 25994 AGAGAGGCAGAGGCACTTTGA | 36978 |
| 3353 TCTCCACGTACCCCTTTCTAG | 15011 GGACTAGGGAGCCCATGTGGAAGT | 25995 GCATTCAGAACTCAAGCACATCTTCTCCACCTA | 36979 |
| 3354 TCTGGCAGGGCTGGAGTAGA | 15012 TCCAGTCTCATTTTGCACTGTTCT | 25996 GCATTCAGAAACTCAAGCACATCT | 36980 |
| 3355 CCCAGCAGCAATGTGGAACA | 15013 GCTTCCTGGTTGGTAATACTCTGT | 25997 CAGGTTAATTCTCCCAGCAGCAA | 36981 |
| 3356 TGTTCCGCTCTGCCCTCTCT | 15014 CAGCGGTTGCTGCTTGATG | 25998 CCAGGCAAGTGACCCTGTGTTA | 36982 |
| 3357 CCAAGACACGGAAACTCCTCAT | 15015 CCAACGTAGGTCTGGACTGATG | 25999 GTGCAATCGTCGTTTCCAAGACA | 36983 |
| 3358 GGATCACTTGACCACGAGGTT | 15016 TGATGCGGAACATGGCTCACT | 26000 GGTGTGGCTGCAAGATCACTTG | 36984 |
| 3359 GATCTAGCTCCTGCCTACTTCATGT | 15017 CTGGGGCAGACGAAGCTGGAAAA | 26001 TCCTCTAAGGAGTGGCATGACTA | 36985 |
| 3360 CTGTGTGTCCTACTGAACGTTGTACTGA | 15018 GGCTCCTAACCACTAAGAACACA | 26002 TGCAAGTCTGTGTCCTACTGAAC | 36986 |
| 3361 GCATCACTGCCTTCCAACTCA | 15019 GGGAGGGACAAGAACTGTGACA | 26003 CCCTTTGCTCAGCCATGCATCA | 36987 |
| 3362 GGAAAAACAACCCTGGGAACA | 15020 GTTTGAGATGGTGCTACTGACTTAAC | 26004 GGCATTGACACAGTGAGACTGAA | 36988 |
| 3363 TTCCTGCTATGACCCTGAACTTG | 15021 TGCTCCAGAGTGCTCACA | 26005 CCTGACATGGAAGGGTTCCTGGTA | 36989 |
| 3364 CCTGGGACATAGGGAGCACAT | 15022 CCCAAGGACAGGCAGACCCTAGT | 26006 CGCTAATGAATTGCCTGGACATA | 36990 |
| 3365 CGGTTGAGAGGTATATCTTAGGCCTGTTA | 15023 GCCCGGCTGAAAAGCAACCAT | 26007 CCCTACAGAACGGTGAGAGGTT | 36991 |
| 3366 TGTGGCTGGAGCATGGAGATCA | 15024 CTTTTCTGCATGTGGCTTCCAA | 26008 GTCCTCCTTATTCCTTTCTGCTCTTG | 36992 |
| 3367 TCAGCCACACAGATTAACCCAACT | 15025 AGAGACCGACTGGGAGGATACA | 26009 TGGCAGTTTTCAGCCACACA | 36993 |
| 3368 TAAGCCGGTACAGGGGTGACT | 15026 GAGCTGCTGAGATGCTCCTCTTTC | 26010 TGGGTGCATAAGGCGGTACA | 36994 |
| 3369 GCAGTTTGACCTCGGTGAAG | 15027 CACGCTCCAGTGACAGAAG | 26011 GTCACTCAGGTGACAGGTTCAA | 36995 |
| 3370 CAATACCCCAGGTCTTGTCAGT | 15028 GACTGGTTGCATCTTCACCTGTGT | 26012 GCTCTTCACCATTTTCAGGCATT | 36996 |
| 3371 CCCATGAAGTTCTTGGCTTTG | 15029 CACCACTGACTCACCCTTGAT | 26013 GTGGAGCTTAACCCATGAAGGTT | 36997 |
| 3372 LACCCTTGGATGCTGGTAGTGT | 15030 CCCCTCGGGTCTCAAGGATTT | 26014 CCACAAGTTGGACACCCTGGAT | 36998 |
| 3373 GGTTGGGATTGTTTGTGGCTATTT | 15031 TCCAGCCAGGAAGGCAAGT | 26015 CTCTGCCCTGGTTCGGATTGT | 36999 |
| 3374 GCAGACCTGTGTTTGAGACCTA | 15032 CTCAAAGCCATATCGGAGCAT | 26016 ACTGTTTTCAGCAGACCTGTGT | 37000 |
| 3375 TCTTGGTGAGGGCCTTGCAATTT | 15033 AGCTCTGAGGTTGCTGGAA | 26017 GCCTGAATGCTGCCATGAGTT | 37001 |
| 3376 GGAAGCATCTGCATCCTAGTAGTT | 15034 CACTGCCAACCAAGATCCTTATGT | 26018 CCTCCCATGTTGAGGAAGCAT | 37002 |
| 3377 CGATACAGCTCGTGTCTCCAGAA | 15035 CTGATCCATAGGCCGAAGTCACAA | 26019 GGGGATCAATAAGCCATCGATACA | 37003 |

| | | | |
|---|---|---|---|
| 4223 CCTTGAGGCAAACACACTGCTGCT | 15881 TGGCAGTTCTGAGTGGGATTTG | 26865 GGCAGCCAACGATTGGTACT | 37849 |
| 4224 TCCAGCTTCATGCCACTCCTA | 15882 CACAGCTCCAGGGCCATCATA | 26866 TCCTCACCTCCAGGCTTCAT | 37850 |
| 4225 CAGAGCCCCGTTACTCTTTCTTGTAG | 15883 AGTGTACAGGAGTGGCTTCAGT | 26867 GAAGAATTCCAGAGCCCGTTAC | 37851 |
| 4226 GGGGAAGGAGATGGTAGAGA | 15884 GCCTCTTCAGGTCCCTGTTCT | 26868 GGCTTAATTCGAGGGGAAGGAGAT | 37852 |
| 4227 CCGAGCCTTGTTCAGTCTGTTC | 15885 CTTAACAAGGCGCTGAAGGAAGA | 26869 CAATCAGTCCCACGGTTCATTC | 37853 |
| 4228 GGGTTTGTCTTACCTTCAGCTTCT | 15886 AGTGLAGACAATACCCGAGACA | 26870 GCCTCTATTTGAAAGGGTTTGTCTTAC | 37854 |
| 4229 TCAGCCAGCAATGTTAAAGACAAG | 15887 GGGGCTGACTTATTTGGTGCTT | 26871 TGAGGCTGGCTTCCAAATTTCA | 37855 |
| 4230 GGTATCGTTCTAAGCAGGGAAAAGA | 15888 GCCCAGGTGAAGCAGAACTTTG | 26872 AAGTGAAGGCATAAGGTATCTTCT | 37856 |
| 4231 GCAGGCCTAACTTGGAGAACT | 15889 GGACTCACAGAATGTGACCAGATAG | 26873 CGGAAGTCCAGCACGCGTAA | 37857 |
| 4232 AGGACAGACAGGTCAGGAACCTT | 15890 GGGAAGCCCCACTTTAGGAGTT | 26874 GGGAAGCCTGGGCTTTGCTA | 37858 |
| 4233 CCAGGTGCATCTGCCAACCTATTCT | 15891 CCTTTTCCTCCCCAGGACTTC | 26875 GCCAAATCCAAAAGCCAGGTGAT | 37859 |
| 4234 GACTTCTGTACATGCCCCTCACTT | 15892 AGGCCCATGTGGCTGATGTAG | 26876 CGGCCTCATCCAGACTTCTGTTAC | 37860 |
| 4235 GGCAGGAAACCTGTAGATGGGAGTA | 15893 GTCCCCTGTCCATAGGAGAGACT | 26877 CACACTGAGCTATAAGGCAGGAAAC | 37861 |
| 4236 GCTGGGGAAGAGTCTGTAGACTTAG | 15894 TGTCATCTACCAGCAGCATTATT | 26878 TGCCAGCTCAGGCAGAGT | 37862 |
| 4237 GCATAATGAAGCCATTCCCAACCTT | 15895 GCACCTGCCGAAACGTGGAA | 26879 GTGGATGGGATCTGTCTGAGCAT | 37863 |
| 4238 CCAGGACCACAGTTGGAATCCTAT | 15896 TGTTACAGGCAGAAGTGCAAGT | 26880 TGACCCACCAGGACCACAGTT | 37864 |
| 4239 AGGAGTGGCACCTCCCAAGA | 15897 TGGCACAGCCCACCCGAAA | 26881 TAGCAGGGGCCACAGCCTTAG | 37865 |
| 4240 GTACTAAGACAAGCAGGTCCAT | 15898 CTCTCCACTAAGTTCAAGTCTCTGT | 26882 GCACTGTTTTTACACACGGAAGACA | 37866 |
| 4241 GTGCTTGGAAATGGGTAAATTGT | 15899 TCAGCAGAGCCTGAAGCAATG | 26883 ATGGCGCTGCTGCTTGGAA | 37867 |
| 4242 AGGATCGGGCTGCTGATGTTA | 15900 AGCCTCAGAGCTGCATGAAG | 26884 ATAGGGCATGGCTCCCAGAGA | 37868 |
| 4243 GGGAATTGCCCTCAGCAAATACTAAC | 15901 GCCTGGCCTGCACTGACTT | 26885 CTGACTACTGCTAAAGAGTTAGGGAAT | 37869 |
| 4244 GCCAGCTCAAAGGCCATACA | 15902 GGCTATAACACCCTGCTGACAT | 26886 GAGTCACCTGTAGCCAGCTCAA | 37870 |
| 4245 GGAGTTTCTTGCAAAGGAGCTATG | 15903 CAAACAGGGCACGTCCCAAAG | 26887 CCAGTTGAAGCTCTCTGATGGTT | 37871 |
| 4246 CGTGGCCAGGACCTTTCACA | 15904 TGAGGACTAGAAAGAGGCACTGAT | 26888 CTCACAGGGCCCATTCATTACA | 37872 |
| 4247 ACCGAGGTTTAAAGAAGGCAAGT | 15905 CATGAAGTGCTACTACCACTCTTAACT | 26889 CCCAGCCCTTACCGAGGTTTA | 37873 |
| 4248 AAGGCAGGAATGTTGCAGGTA | 15906 GTGGACAACCGCTCAGATTC | 26890 GCCTGTTAATACTCAGTGAGGAGAAG | 37874 |
| 4249 GCCGAGAAATGCGGCCAAGA | 15907 CGCGGGACTGTCCACTGAT | 26891 CACAACCTGAGTGCCGACAA | 37875 |
| 4250 AGGAGGGGTACACATGCCCAAA | 15908 CCTCCTGCTGCACATCTTTCT | 26892 TTCCTCCCACGAGGGGTACA | 37876 |
| 4251 CCCCCGCTGTTCCCTTCATT | 15909 TCAGCTCCTGAGGCATGTTTG | 26893 TCAGGCACCCCCTGTTT | 37877 |
| 4252 ACACTGTCCTTGACTCCTTTGTT | 15910 TTGAGGATGCGTGGGATGTAC | 26894 GGCCAAAAGGTGAAACACTGTCCTGA | 37878 |
| 4253 GGTGACTAAGCAGCAATTCCCTTTAC | 15911 TGGGCCTCGTCAGGTCTTTAT | 26895 CTTGCCAAGCAAATTGGTGACT | 37879 |
| 4254 GTGTCCTACTTCAGGAAGGAATGTTCA | 15912 CAGCAGCAACCATGCTGCAAA | 26896 CCAAGATTTGGAGTGTCCTACTTC | 37880 |
| 4255 GTTGCCAGCACAGTCAAGCTTTT | 15913 ACAGCCGGACAAGGTGGTGAA | 26897 GCATGCTCCCCTACTTGTCA | 37881 |
| 4256 ATGCCCAGCGAGACGCATGT | 15914 GTCCCATGGATGAGTGGCTTTG | 26898 CCCAGTGGCTTCCACAAGTGA | 37882 |
| 4257 GCCCAGAACCCACTGAAATTATTC | 15915 AGGCTAGGCAGGCTTAGGATTG | 26899 GGACAACTACGGACAGCCTCTCT | 37883 |
| 4258 GAGGGGTTCATGAGAGCAAAGT | 15916 CTGCAGAGCAGAACCTCAT | 26900 TCAGCAGTGTGAGGGGTGATG | 37884 |
| 4259 GCCGCATTAAAAGTCCCATATCTAAGT | 15917 AGCTCAGGGAGGCGGAAGTATT | 26901 TGAGTCACGTCCGGCATTA | 37885 |
| 4260 CTGTGCAAACATCAAGGGATTAGAAG | 15918 CCCACTAGGGCACCCTCCAT | 26902 CAGTGTAGACTCCTTTCTGTGCAA | 37886 |
| 4261 CAGCAAGCTCAGCTGGGGAAAA | 15919 GACACAGATCTCTGGTAATTCAGAGCAA | 26903 TGTGTTCTCAGTTGTCTGGGTAAG | 37887 |
| 4262 CATGTCTCTGGGACGTTGCATGT | 15920 CCAACACAGTTAGGCAAATG | 26904 CCAGGTACCTCCATGCCATAGACA | 37888 |
| 4263 CTCTGCAAACCCAGCCAGGTAT | 15921 GTACCACTCAGACCAGGAAAACA | 26905 GGGGAACACTCACGCTTGTGACA | 37889 |
| 4264 AGGAGTTGCTGAGGCAGACT | 15922 CTCCCCACCTTCGTCTCTGA | 26906 GAGGATAAATGGAAGAGGAGCAGTT | 37890 |
| 4265 TCTGCCCTTCGCACAGACCTT | 15923 AGATACAGATGCTGCAACGTAAGA | 26907 GTGACTCATTCCAGGTGTAGAGGAT | 37891 |
| 4266 CACCTTGGATGGCAGCGTTGCT | 15924 GTGCAAGTTGCTGTTGTCTCACT | 26908 AAAAGTAGGGCAGTGTTGATT | 37892 |
| 4267 CAGTGGCCTAGGCCCTGAGA | 15925 TCAGGAACGTGGACTCTTTTTCA | 26909 ACGTGCAAGCAGTGCGTTAG | 37893 |
| 4268 GCTCTCCACATTGATTGGCTTCA | 15926 GCTGCCATCTTGCCACTTGTA | 26910 CCTGGCTTTCTCTTCCACATTG | 37894 |
| 4269 GGCATGGTGACCAATGGGTGT | 15927 CAGTGCCCACAGCCTTCATTGT | 26911 CCTGCTTCACTCTGTGGCATA | 37895 |
| 4270 GCTCCTCTCATCATTTCGGTATCA | 15928 CCACCGCACCAGCTATTATGT | 26912 GGGAAAAACATGTACAGCTCCTCA | 37896 |
| 4271 GGCCTCAGCCTAAGTTCTTCT | 15929 TGGCTGTGCCGGCAACATAG | 26913 TGGAACAGGCCTAGGCTAA | 37897 |
| 4272 ACAGCAGTGTTGCCACCGT | 15930 GCTCTCCATTATGCCGTTATAGTGA | 26914 GCACCATAGGACAGCAGTGT | 37898 |
| 4273 CTGTGTTAACCGTGTGATGACTCT | 15931 CCCCTTTCCATACTGTGCTCTT | 26915 GCCTAACTCTTCCCTTGTTCTGTGT | 37899 |
| 4274 CCATCAAGATGGCTCCTCCCATTT | 15932 GGAGCCCAGACCCCAACAAG | 26916 TCCCGGCTGTCCCCATCAAGA | 37900 |
| 4275 CCACTCTGTCTGAAACGTGTTACT | 15933 CATTCACACCCAGCCTCTGT | 26917 TGGGCTAATCCACTCTGTCTGA | 37901 |
| 4276 GGGCTTGAAATGCAATATCCCTTTCTGA | 15934 CCCTAGGGGCTGCAAGGTAC | 26918 CAAGCTAACTCAGGGCTTGAA | 37902 |
| 4277 CCCTCACGAATTCACAGGAGAGACTA | 15935 TCTGCTTCAGCCGCACCAAT | 26919 GGTGACTGTTTTCCTCCTCAGCGAA | 37903 |
| 4278 GGCTTAGGTCAATGCCATCAAGA | 15936 TGTGCCCACCATCGGATCA | 26920 GCCTTCTGAGGCTTAGGTCAATG | 37904 |
| 4279 CATTCAGCACCCCACACACATT | 15937 GCACTGTCCTGTCCTGGTTGAA | 26921 AAGCCATCCCCAGCCCACATT | 37905 |
| 4280 TGGGGTCAGGGAATGTGGAT | 15938 GGTCCAGGGATCTGGACACA | 26922 GGAGAAATGGGACCAGGAGAT | 37906 |
| 4281 CTCTCCCTTGTGGGTGTGCTT | 15939 GCTGCACACCACTGACCAAT | 26923 CCCCAGCACCACCTTATTGT | 37907 |
| 4282 CCCCCGTGTTCTTCCCTTCAGT | 15940 GAGGGAAGGAGCCGCATCGTATAAC | 26924 TCTCCGGCCGTCCAGCTTT | 37908 |
| 4283 GCAGGTGGCGTTAGAGCACAT | 15941 GCCCTGTAACGTAGCAGAAGT | 26925 TGTTCAGCTCCTAAAATGGCATCA | 37909 |
| 4284 ACCAGCTGCCAAAACATTAGGAT | 15942 AGAGAGAGCCTTCTTCCCTTAGA | 26926 GGGAAGAACACCAACAGCCTGCCAAA | 37910 |
| 4285 AGTTGGAAGCTTCTGGGATACA | 15943 CAAAGCATGCCACTACTGTGTGT | 26927 GGATCCCCTAGCTGAGTTTGGAA | 37911 |
| 4286 CAGAATCACCACGTAAGGCAGAT | 15944 GTCCCTGTGGAACTCCTGATCACT | 26928 CCCCACAAAACTGGCACTGAGA | 37912 |
| 4287 TGGGTGCCCACAGTCAAG | 15945 ACAGGGGCTTGGTTCTTGCTTT | 26929 GGGGCTGTGCTTCAGAATCAGT | 37913 |

| | | | |
|---|---|---|---|
| 4353 AGTCAAGCTGGGAGATGAGGATA | 16011 CAAGCAGATAGGAGCCGATCAGA | 26995 GGACTTCCCGCAATACGAAAC | 37979 |
| 4354 CAGTGTCTACTGCTCCAGTGCTT | 16012 GCTCATCACACTCACCCCAGCTA | 26996 TCCATCTCTCTGTACAGTGTCTACT | 37980 |
| 4355 GGGAGGGTGGACTCAAAAG | 16013 TGAGGGTGGCAGCGTCAT | 26997 AGCCCTCCTCGGACCCATGT | 37981 |
| 4356 GCGTAGTGTGTGTGAAAGACTCAGAT | 16014 GCACAGCACTCTGCCCTTCA | 26998 GAAGAGGCTGTTAGAAGCGTAGT | 37982 |
| 4357 CCATGGCTGTTACTCCCAATC | 16015 GGTCTGGGCCTAAGGCAGCATTGA | 26999 GCAGTAGTCCAGCCTGAGTTTC | 37983 |
| 4358 AGCCACAGCCTTCGCCTCACA | 16016 TGCCCTGGGCGCAGGTTATTA | 27000 TGCCGGCCTCAGCCTCAGTA | 37984 |
| 4359 CACCACACATCTCCTAAGCATGTA | 16017 CACCAGGACAAGTGCTGTCT | 27001 CCCCAGCCATAGCTCTCTGATTC | 37985 |
| 4360 GTAGCTGAGACATGGTGTCCAAAC | 16018 GGAGTATCGCTCAGCTCTTCTT | 27002 CCTGGCTCTCAGCCTTAGTCA | 37986 |
| 4361 CCTCCTGAAGACGAGTCCAACT | 16019 CCGCCTTGACAGCAGGAAGT | 27003 AGTGAAGACAAAGTCCTCCTGAAG | 37987 |
| 4362 CCCTGGAAACTATAAATGGCTGCTA | 16020 ATGCAACTTCCCTGAAAGGAGTAA | 27004 GGCAAGGAATTATAACTTAGGCCCTGGAA | 37988 |
| 4363 TGACTTCCTGGCCAGTCTAT | 16021 CTGCCTTGCTGGGATGGCAAAATG | 27005 TCCCAGGGCACATATGACT | 37989 |
| 4364 CTGTCTGACCAGACCTCAGACT | 16022 CATTGGGAGCCAGCAGGTGGTA | 27006 ATTTGTACCCAGTGTCTGTCTGA | 37990 |
| 4365 GGCCAGAGAACATGTCTGCATC | 16023 GGGCTAGGAGCCCAATATCATTT | 27007 TGCAGGAGGCCATAGAACAT | 37991 |
| 4366 GCTCTATCTCGCCCTCTTTG | 16024 CCCATCTCCCTTCCCATCTGTCT | 27008 GCCCCATCCCTTTGCCTTATCTTC | 37992 |
| 4367 GCTGAGAGGTTTCACACGGATAC | 16025 CAGGAAGCTCCACACAAACACA | 27009 GTGTCACACGCTGAGACGTT | 37993 |
| 4368 CCCAACTTGTTCAACTCTAAGTGTCT | 16026 CAGTGCCCTCCAGCCAAAG | 27010 CCTGCAACAAGAGATAAGCCCAACT | 37994 |
| 4369 TGAGGGTGTCCAGGCAGTTG | 16027 GTCACCGACACCCTGTGGAT | 27011 TGAGCCACTGTGCCTGGATA | 37995 |
| 4370 GCTTAGCCAGTCTTCATTCTACAAC | 16028 ACAAGAGCCCTAGAATCCAAGT | 27012 CAGTTTAGATATGCTTAGCCACTCCTTCA | 37996 |
| 4371 GHCCTTTGGCTTCCTCATCAT | 16029 GGCGGACTCCACCTGAACA | 27013 TCACCTCACCTTGGCTTTG | 37997 |
| 4372 AGGCCTTTGCTGTCCTGCAA | 16030 CCATTCTCGTGGTCCATTTGTCT | 27014 CAAACACATGCTTTCCTCAAACAAG | 37998 |
| 4373 GCATGGGGATATAACTGTTCAGTTTG | 16031 CATCAGGTTGCAGTCTCAGCAT | 27015 CAGGATACTCGAGGCATGGGGATA | 37999 |
| 4374 CTCCTCAAAGCCACTGCCTTGAAA | 16032 GGCAGTAGAGAAGGGTCTAGGAT | 27016 GGCATGGGGAGGAAGTACACAT | 38000 |
| 4375 GCCTTGTGGGTCAAAGAAAGCAT | 16033 TCACCAGATGGCATTTGTCTTCA | 27017 TGAAAAGGCCTTGTGGGTCAA | 38001 |
| 4376 CCAGGCTCGAATCCCTCTGT | 16034 ACTGAACTACCTGGACATCTGTTTT | 27018 AACTACTCCCAGGCTGGAA | 38002 |
| 4377 GCGACACGAAAATACAGCAAAC | 16035 GCAGGCACACGGAATGCAAA | 27019 GAATGCTTCATCGCACACCAAAA | 38003 |
| 4378 GGCAGACTGAAAGGAGATACAGA | 16036 ACAGCCCTCCCGGCTGACTT | 27020 CCAGCTGTCATTTAGGGCAGACT | 38004 |
| 4379 CCCTGTGTGTCTCTGAAGCTGATG | 16037 CAGTGGTGACCTGTGGGAAAG | 27021 CCCTGAAGCCCTGTGTCTTCT | 38005 |
| 4380 GTCTCTTTGCCCCTAGAAAAGGTTACT | 16038 CCCGACCCCTGATACTTCACAA | 27022 GGAGTTTGTGTCTCTTTTCCCCTAGAA | 38006 |
| 4381 GGCAGGCAGCTTTTCAAAATGAAGT | 16039 GAGGCAGTTCTGGCCATAGGAT | 27023 CTTGATCTGGCAGGCAGCTT | 38007 |
| 4382 CACACGTCGATTTATGGGAGCAAAG | 16040 TGCCATCTTCTTCATTGCAGTTG | 27024 ACAGAACCCTTTCACACGTGATT | 38008 |
| 4383 CAGGTCACTTCTTCCAGGTCCTT | 16041 GCACAGGCAACATCACAGTTC | 27025 GCCTGTATGGTATTCAGGTCACTTCTTC | 38009 |
| 4384 GGGAGAAAGGAGCAGGCTAATTG | 16042 GGAGACCCAACTGTGAACAAGA | 27026 GCCAACCAGTTCTTTGGGAGAA | 38010 |
| 4385 GGGGACTCATGCTTCTCTCA | 16043 TCATGCCTGGGACCAAATTCTAAG | 27027 GAAACAGCCAAGGATTACAACCTA | 38011 |
| 4386 GTGTACCCTCGGCTATGTTTACT | 16044 GCAGCTGCCTCTGAGTGTTTG | 27028 TCCTGCCTGTCCCCAGTGTA | 38012 |
| 4387 AGAGAGGCCACCAGCTCCAA | 16045 TCCCTGGCTCCGTGTGCTT | 27029 GAGAGGGTCAGACGGTAGAAAC | 38013 |
| 4388 ACAAAAGCCTCCGGGCTACT | 16046 TGCCGTTGTTTGGGAAGCACTA | 27030 CACCTGAAGCCTTTTCATCCTGTTCA | 38014 |
| 4389 GGCCACAAGCATTGTAGGTGTT | 16047 AGGTTACAACCTTGAAAACCCAAAC | 27031 AGTGCGGCCACAAGCATT | 38015 |
| 4390 CAGCTCTGCAAAAGCATTCTCTA | 16048 GGGAGGGATGGGGTGAAATC | 27032 GCACATCTTCTACAGCTCTGCCAAAA | 38016 |
| 4391 GCTTCCAATGCCTCCCCTTAT | 16049 AAGGGTCGGCGGGGTCAGA | 27033 CTGTACTGCCCTGTGCTT | 38017 |
| 4392 CCCACAACACCCAGGTTCTGA | 16050 GCTGATTAGGTGACTCTGTCCAA | 27034 ACCAGTGGCTTCCCCACAACA | 38018 |
| 4393 TGGTGGGCTCAGTAAGTTCAAAG | 16051 TGGCAGCACTGGGCACAT | 27035 GGACTTCTGTGGGATGAGCATT | 38019 |
| 4394 CCCAACCTCTCCTTGGATTCTAAC | 16052 TCCTGGAGCACAGCCTTCAT | 27036 AGCCCTTCACCACACTCTCCTT | 38020 |
| 4395 TGCTAGGCCTCAGAAAGCTA | 16053 GGGACCTGAGCCTCTGTTTTGA | 27037 TGCCCTCTGCAGGGAATGGTA | 38021 |
| 4396 CTCAAGCTGCTAAGTGTTAGGGTTC | 16054 CCACCACAACCACTTCCAGTT | 27038 GCAGCCAGGAGCAACTTGTACTCA | 38022 |
| 4397 GACCACAGGTTTCCATCTACATTACT | 16055 TGCCCTGAGGGTTTGCGTAGT | 27039 CTCTTTCTCTAGACCACAGGTTTCCAT | 38023 |
| 4398 CATCTGTCGCAGCTGCATTTTC | 16056 GATTCTGCAGCAAGGTGCTATG | 27040 GTGCGAAAGACTGGAGCAATC | 38024 |
| 4399 CACCAACTCTGCTTCAGACAGAATC | 16057 TGGAAGGGCGAGGGAAT | 27041 GGACAGGACCAACTCTGCTT | 38025 |
| 4400 GGGCACAGGAGATTAGTACTATG | 16058 ACTGGGCTCATTCGTCTCACT | 27042 AGCATTAGTGGGCAACAGGAGAT | 38026 |
| 4401 AAGAACCTGGGCCCCTGATG | 16059 GGCAGGCCTCACAGTTCCAT | 27043 GATAGTTGAGCAGAGAAACAGGAAGA | 38027 |
| 4402 GGGACAATAAGGAGGAAGAGCAA | 16060 AGGAGCTTTGGCTGTGTCAA | 27044 TCATAGGCATCTGGAGGGACAATAA | 38028 |
| 4403 ACCATGCTTCAGTGTGCAAGA | 16061 CCATCTTGGTGACTGTTTCCTTCA | 27045 GCATGACGTCAGAACCATGCTTCA | 38029 |
| 4404 GGTAGGTGCCTAGAAACGTTCA | 16062 GAGCCGAACAACGTTTCTGT | 27046 GTGGAAACCCCATTCCCTTTGGTA | 38030 |
| 4405 ACACCTGTGACTGGCTGAGT | 16063 TGTGGCAGTGGGGAAGGTGTAA | 27047 TGACCAAACCAAAACACCTGTGA | 38031 |
| 4406 CCCTGGTGCTAGTTTCTTACAACA | 16064 GTGCTGTTTCCTCCCACCTTCT | 27048 GTGGTCTCCCTGGTGCTAGTTT | 38032 |
| 4407 GTGGCGTCGATGACCTGTCT | 16065 AAGCCCTGCCCACCACTGA | 27049 CGACACCCGATCCCTGAAGT | 38033 |
| 4408 CGCCATGTTTCAGGCCACCTT | 16066 GCTGCCTGGGAATAGACGTTCA | 27050 ATAGCCGAGCCGCCATGTTT | 38034 |
| 4409 CAGAGCAGTTCCAGCCTTCACA | 16067 AGATGCTCTGTCCTGGATGATGT | 27051 GGTGGCAAAATGACCAGAGCAGTT | 38035 |
| 4410 CCGGGTAAAGTCTCAGGGAAGTGA | 16068 CTCCCTGACAACGTCTGGAATG | 27052 GGGCTCCGGGTAAAGTCT | 38036 |
| 4411 GGCACTTGGCAGTGTGATTT | 16069 GCTCTCATCACACTTGACCTTGA | 27053 TCCACCAGGCACTGTGTTAG | 38037 |
| 4412 CCAGGGAGAACAAACCCATCCTT | 16070 TGTAGGGTGGGTTGACAGATTT | 27054 CACACCCTTCCAGGGAGAACAA | 38038 |
| 4413 TCCAAGGGGCCTTCAGGTTTCT | 16071 GCCGTTGCTGCTCCTCCTAA | 27055 CCATGAAGCTCCACCTCTGTCCAA | 38039 |
| 4414 TCACTGGGCTCAGGTGGAGTAAG | 16072 GCACTGTGCTCCTGCTGTTTG | 27056 TGGGGTGGTGTGGGACCAAT | 38040 |
| 4415 AGGGCTTCAGACCGGTTT | 16073 TGCCAAGCCACCACAGAAA | 27057 GAGGATGAAATGATATAGAGGGCTTCAT | 38041 |
| 4416 GGCAAAGTGCTTACGAAGTGAGATC | 16074 TCCCCATGCACACACCCTCTA | 27058 CACTCAGAGTACAGAACGCAAAGTCCTTAC | 38042 |
| 4417 GCTAACTCCCCTAGACAGGAAAAAG | 16075 AGGAAGGCAGATGGTGTCAAC | 27059 CCCCAATGCTAACTCCCCTAGA | 38043 |

FIG. 36G8

| | | | |
|---|---|---|---|
| 4418 GCCAGTGCCCACTGAGGAA | 16076 GGGCCTTGCCTCCCAGAAAT | 27060 GCCTCCACAATCCTCCCAGGTA | 38044 |
| 4419 GTCTACACACACGCCTGAATAGT | 16077 TTTCCATTTCTCCCTCGCTTATTCT | 27061 GCACTAAGGACGTTGCTTTGTGTCTAC | 38045 |
| 4420 CGGAGAAGGGCCCTCTATTTCTGA | 16078 AACTGTTCCTGCAGCCCTTT | 27062 CCCAGCCATTCCCTCCAACAT | 38046 |
| 4421 TCCCTCAAAACCCACGTATTTGT | 16079 TCCAGCGACAATGGCCTGTCT | 27063 GCATATCCCCTGACTGTTCCCTCAAA | 38047 |
| 4422 CACAGCCCTGCTTTAGGAAGA | 16080 GCCTTCAGTATGTCTTGCGTCTTG | 27064 TGCCAGTAGGGAGTCACTGAGA | 38048 |
| 4423 TTTGAGCCCAGGAGGTGACTCT | 16081 GCAGGGCAGTGGCACAATCATA | 27065 CCAAGGCAGCAGGATCATTTG | 38049 |
| 4424 TCCCTACACACTCCCATGAAGA | 16082 AAGGGTGGCACCGAAGTCAGA | 27066 CTTTCCGGTCTCCCTACACACT | 38050 |
| 4425 ACCTGAGACTGGCCTCCAATTC | 16083 GGCCAAGGTGGAAGGATTGCTTA | 27067 CATAGATGGGGCATCACTGTGT | 38051 |
| 4426 GTGGCCTCGAGGAAGCATGA | 16084 AGGTGAAGCTGAGCCACTTG | 27068 CCAGTAGACCCACCATGTCTGT | 38052 |
| 4427 GTGCATGAGTTTCACATGTCTCTCTT | 16085 CTACCAAGTCTGCTGTCCCAAA | 27069 GCAGAGAGTGCATGAGTTTCACA | 38053 |
| 4428 TGTGGGCTGTAGGACACAA | 16086 CCCACGCTGATTAATGCTCCTTTG | 27070 GTGCGTGAGAATAGATGCTGACAT | 38054 |
| 4429 GGGGTCAACTCCCATCACCTTTC | 16087 GAGAGGCTTTGAGGCATTGAGA | 27071 GGTGGTGGGGTCAACTCCTA | 38055 |
| 4430 GTGGCAGGGCTCTTGTACTTC | 16088 GGCAGTTGGGAGGAAGGTAT | 27072 TAGCCTCACTGTGGGAGTGT | 38056 |
| 4431 GCCAGAGACGCTACAGTAGCCAA | 16089 GCAAGGCTGGACCAGGAATCT | 27073 AGGCCCTGTTACTGGCAGAGA | 38057 |
| 4432 GAGACCCTTCCTTCTGCTTGA | 16090 AACACAAAGTCCTCCCCCACTCT | 27074 GCTGCACAGCTCGTAGCTCTAA | 38058 |
| 4433 GAACAGCACAAGGTGGGACAAAC | 16091 ACACAGGCAGCGTTTGCTT | 27075 TGCCTTCCACAGGGAGGAGAA | 38059 |
| 4434 CTGTTGTAAGGTCTCTGGGTATCA | 16092 ATTAACCCCCATGGTGGTATC | 27076 CCAGGACTAAGGGAGTTGTCTGT | 38060 |
| 4435 CACCATCACAGCTGGGGTCTTT | 16093 CAAAGTCGCCCGTCTCACT | 27077 GCACCAGGGCCACCATCAGA | 38061 |
| 4436 GGATGTGAAAGCTGGAGCACTGT | 16094 CCTCATCCAGAGATTGCAAGGTT | 27078 GGTGCACAGCAGAGGATGTGA | 38062 |
| 4437 GACATCTGTGTGCTTGTTAAGGGAATGA | 16095 CTACCTGCCTGCACTGTAGATG | 27079 GGGGTGGACATCTGTGTGCTTGT | 38063 |
| 4438 TCCAAGTTCAGTCCCAGTTCTATC | 16096 AGCCTGCTCATGCAGGACTTG | 27080 GGGATTCAACTCCACATCTTTTGATTC | 38064 |
| 4439 TGCCTTGGCCTTGCCTTTT | 16097 GCGAGACTGATTACAGACTGAGCTA | 27081 ACCAAGATCCACTCCAGCAAGA | 38065 |
| 4440 CAAAGGGAAGACACGAACTCCTT | 16098 GCGTGAAGTGTTGCATTCTGT | 27082 CACAGAGCTTAAAGGGAAGACA | 38066 |
| 4441 CGAGTTGGCGGTATACAGTGTTG | 16099 TGGCCCAGGGTGTGAAGGTA | 27083 TGCAGTCGATGTGGCGGTAT | 38067 |
| 4442 CGCTTCACTGGCCAGAACTTG | 16100 CCAGCTCCCCTTGTGGTTAAA | 27084 TCAGTTTTGCTTCACGCTTCACT | 38068 |
| 4443 GCATTGTTCATTGTGCGTGTGT | 16101 GGCATGGCTTTCCACCTAGT | 27085 GCTCTATGTGCTAGTGTGTGCAT | 38069 |
| 4444 AGGGATAGAATTGCTGACCAGATAGA | 16102 AGCCTCCACTCCCTCCTTCT | 27086 GCACAGTCAGTTGTCAGGGATAG | 38070 |
| 4445 CCAGCCGGACAGGCAGTTCATTA | 16103 GCTCCCCGAGCTGTCAGTAA | 27087 GCAACACAACACCTACAGGAGACA | 38071 |
| 4446 CGTGAACTGCCTCCTCACA | 16104 GGCCTGCACAGTGTCCGTGTT | 27088 AGAGGACGTCCAGCGTGAA | 38072 |
| 4447 GCAGCTGAGGAGTTCAGGGTTCAA | 16105 AGCCCCAGCTCTCCCATGT | 27089 TCTCTGGGCAGCTGAGGAGTT | 38073 |
| 4448 CAGGCTTGGAAACTCAGGGACTT | 16106 TCGACTGCTCTGTGCCCATCT | 27090 CAGCCACAGGCTTGGAAACT | 38074 |
| 4449 CCCACATGGGAGACGCTAA | 16107 GGTGAAGGCAAAGTCCTCCTT | 27091 GGTTCCTGGTGAGGGAAGATGT | 38075 |
| 4450 GCTGTGGCTTTATGCTCCCCTAAAC | 16108 ACAGCCCTGCTCCTCCTT | 27092 CACCCCTGACTTAGCTGTGGTT | 38076 |
| 4451 ACCGGCTGGTTCCTGATTCT | 16109 CACACACAGTCCTAGGCCATAC | 27093 TTGCTCACTACCGCCTGGTT | 38077 |
| 4452 CGGGGGAGGGCTAGAGTTAAGTTC | 16110 TCTGGGTCGCGTAGCTCCAT | 27094 TGCAPAGACAGGGAGGCCTAGA | 38078 |
| 4453 GGGGGCTCCCCTCTCGATGTA | 16111 GCTGGGGAGCAGTTCGTA | 27095 GGTCCACGAAGCCCCACTA | 38079 |
| 4454 CGGGGCCACCTGGAGAAAGAATAG | 16112 AGGCAGCCTGGCCTTACA | 27096 TGGCCCCACTACTTCCTGAAC | 38080 |
| 4455 ATGGGTGGCTTCGGCTCAA | 16113 ACGCTTGGCAAGGCATCA | 27097 GAGTGTGGCAGTCGGTACTAAG | 38081 |
| 4456 GCCAAGTTTTTCAGAGAGCAGTCAGAT | 16114 AGTCGTGGGCTGTGTGCAT | 27098 TCTGATGGCCAAGTTTTTCAGAGA | 38082 |
| 4457 CCCTCGCTCACCTTCTCTTC | 16115 TGCCTGTTATGCACAAGCACTA | 27099 CTCCAGGAAGCATCTGTTGACT | 38083 |
| 4458 TGACACTGACCGGTGTGGAT | 16116 GGGGCAGCTGGACACTGGAT | 27100 TGGGGACTTGGTGTCCACTGA | 38084 |
| 4459 CCTATCCCATTCCTCACAGCCATT | 16117 AGGGAATGGGGAATATTGAATGCTT | 27101 TCTGGTTGACGAAGCCCCTATC | 38085 |
| 4460 TGGCTGGAAGCTAATTTGGTTTG | 16118 GGGTGGGGCTCAGTGTTGA | 27102 CAAGCAGCTCTTGGCTGGAA | 38086 |
| 4461 GAGGCCACCTACGGTATTCAAAC | 16119 GCAGAGCAGGGTGAACAGT | 27103 CATGTTACCCACAGCCCACCTA | 38087 |
| 4462 GACTCCAGAACAGAAGGGCTTC | 16120 TGCCCAGGCTTCTTGGTGTT | 27104 GGAGGGGACAATTGCTGTGTGA | 38088 |
| 4463 AGAAGCCTCCCTCCCTCTGT | 16121 AGGAGGATGGGGACGAAGGAT | 27105 CCTTCCCTAAAGTCCAGGAGAAG | 38089 |
| 4464 GTGGCTAGAGCTTGAGCCTATC | 16122 GTTGCTGACAGGTCAGTGTCT | 27106 TGTTGTCCAGTGGCTAGAGCTT | 38090 |
| 4465 CCAGCTGCCCTGACACTCAAA | 16123 CCCTAGGCCACTGCAGCAA | 27107 CGGATGCTGCAGCTGGAATCT | 38091 |
| 4466 GTCCTGGCTGGCTAAAGGTTGT | 16124 GACAAGCCTGGGGAAACTGT | 27108 CCCACAGAGCTCGGCCAGAAA | 38092 |
| 4467 GGGCTTCCCAAACACACAATC | 16125 ACGCAGCACCCAGAGGTAAT | 27109 AGGTGACTAGGGTTCCCAAA | 38093 |
| 4468 ACAACAGATTACAGGAGCACAGTTA | 16126 TGTGGCCACCTCTTTTTGAA | 27110 CAGGTTTCGACTTGAGTCAACAGA | 38094 |
| 4469 GGTGGATGAATCCCCTGTCAAC | 16127 CCCTTTTGTGCAGTGGTCAGCAT | 27111 TGGCTGACGGTGTCATGAATG | 38095 |
| 4470 TGTGGGCCCCTGGAGCTACT | 16128 TTAGGCCCCACTGCAGATCA | 27112 CCGAAGGCCCTCTGGGCTTTA | 38096 |
| 4471 GCGTCGTGTCACTAATTTTCTTG | 16129 GGGGAACCACCAAGGGTCTTT | 27113 GCATGGCGTGGTCCTGTCACT | 38097 |
| 4472 TGCCCTTCCTGAAACCACATTC | 16130 AGTGGGCACTTCCACCTGTGA | 27114 TCCAGTTGCCCTCCTGAA | 38098 |
| 4473 CATGGCTCGAATGACTCAAGTGCTA | 16131 AGACCTCAGAACGGAGTTGTTC | 27115 AGGGATATCATGGCTGGAATCAGT | 38099 |
| 4474 TGACTCCTGGGAAGCTAGACTAAA | 16132 AGACGCCCAGAAGTGACTGT | 27116 AGGCTGGCACAGGTATGACT | 38100 |
| 4475 TCTGATTATCAACCAAGGCTGTT | 16133 CACGAGCACCAGGCATCA | 27117 GCGAGGCTGGGCAGTCTGATTA | 38101 |
| 4476 CTCCCTGTCTGCATCTTTCCTTAT | 16134 GGGCAAAGCTCTTGAGACCAGAA | 27118 GTTGCATCTTCATCTCCTGTCT | 38102 |
| 4477 TGAGTGACCATCCACTGACAAG | 16135 AGTCAACGCTGTGGGTTTGTT | 27119 TGGTGGATGCAGCTGGTTG | 38103 |
| 4478 GAAGTCTCACATGTAGCCACTGAAT | 16136 GCAGAGCCTGGGGTAGTTTTTG | 27120 CCAAGACACTTCTCGCTGAA | 38104 |
| 4479 GCTCTGTGCTTTGGGAGACTGT | 16137 AGTGTTCCGCTTGGCTGGTA | 27121 GATATGCTGAGCTGTGTGCTTTG | 38105 |
| 4480 GCCTGGAAGCATCATCAGACA | 16138 GAGGAACGGACAACTTTTCCCAACA | 27122 GACTCGATCTAGCCAGGAGCAT | 38106 |
| 4481 CCCACTGCAAAGCCTCCATGAATGA | 16139 GCAGCCTCCACAGAGAACAT | 27123 TGCCTGTGTGCCACTGGAAA | 38107 |
| 4482 GCCAGGACTAGCTTGCCTCTTT | 16140 CCTGCAGCCAAGTGCTTACTCT | 27124 TCAAGAGGAAAGGCCAGGACTA | 38108 |

| | | | |
|---|---|---|---|
| 4678 GACCACACACCATTCACATATGAGAT | 16336 GCCTAGGTTTTCACTGGACCAT | 27320 AGAGATAGGACCACACACCATTGA | 38304 |
| 4679 AGTGGTTAGAGCCCAGCACTGA | 16337 GCTAGGGACCCTCCCGTATGA | 27321 TGGTGGGGTCAGTGGTTAGA | 38305 |
| 4680 CCTCCGTGTAGGCCAGCAT | 16338 AGCCTGGGCCTGTTTCTCA | 27322 GCAGCGAGTCCTCCGTGTA | 38306 |
| 4681 CCACAGCATCTCTGGGACTCA | 16339 GAGCAAACCCTTGGCTCCTAGT | 27323 CAGGCCCAGTGGGAAGTTG | 38307 |
| 4682 GGAAGCCAAGAGGCCAAAACGTA | 16340 CTCCTCATTCCACCACCCTCTT | 27324 CACCAGGACTAGCACTAGAAGGAA | 38308 |
| 4683 ACTTCTCGATCTCTGGGTCTTTCT | 16341 GCCCTGTCCAATGAGTGACCTT | 27325 TCACCCCAGCCTGACACTTCT | 38309 |
| 4684 GCACAACATCTTGCATCCTGCGTAT | 16342 CCACAGCTCCCTGTCACTCA | 27326 GACGACGCACAACATCTTGCAT | 38310 |
| 4685 GCTTTGGGTGGGTCATTTCCTT | 16343 TGCAAATACCCCATAGCCAGATG | 27327 CCACCTATGTGCCAGGAAGCTTTG | 38311 |
| 4686 GCGGAAATCCGTGACCACAACA | 16344 GCAAGATCTGCCTCCGCTAAAG | 27328 GGGATTGTCCCAAAGCGGAAA | 38312 |
| 4687 AGTTTCACCCTCCACCCCATTC | 16345 CCCCTTCACTATCGGCCAAGGTAA | 27329 TTCCCTGCATTGTTACTACTCAGTT | 38313 |
| 4688 TGCTGAGCCCGTTTGTGT | 16346 CAGCCTGGACCCTGTGGAT | 27330 GGCATGGCAGTGAGAAGCAT | 38314 |
| 4689 AGGCAGCGGAGGCTCTTG | 16347 CAGTCACTGGGAGTTTGACTCATC | 27331 AGCCAACACCACCGGAAGAT | 38315 |
| 4690 TGGCTCTTCCACTGCACAAACA | 16348 TCTGAGGAGCTCACCTTCCTT | 27332 GCAGTCCGTCCTCTTGGTCTTC | 38316 |
| 4691 AATCGAGCCCAGCAGCTACA | 16349 GGGTTGGACACCTTTCTGCTGTT | 27333 GCCAAGGCCGAGGTGCTAAAAA | 38317 |
| 4692 CCCGCTTGAAACCTAAGCATGAGA | 16350 TGGGGCCATACCTGTCTTGTGA | 27334 ACCACCCCGCTTGAAACCTA | 38318 |
| 4693 TCCAGCTCTGACACTTGGTAAC | 16351 CCAAGTGCGTCGCTCCTTTAC | 27335 GGGGTGAATTCCAGCTCTGACA | 38319 |
| 4694 GAGGCTGGACGACTTGAAATACTCA | 16352 GCACCTGGCTTCGTGCTAAT | 27336 GCAAACTGAGGCTGGACGACTT | 38320 |
| 4695 TCTGCTGAGTGTCTCCTCCAT | 16353 GTTACACAGTGCAGGGAGATTAGA | 27337 CCCTCAAGCATGGATGCACAGTT | 38321 |
| 4696 GGCCAAGTACCTGCTTACCTAAC | 16354 GTTCTGGAAAAATCTGGCCTTCTTC | 27338 GCCCCACCTATCAGCCAGACTTTA | 38322 |
| 4697 CCACCGTGCTTTGGATAGATAAGA | 16355 AGACGGTGACAATGCCCAAT | 27339 TGGTCTCCACCGTGCTTTG | 38323 |
| 4698 CCCTCTTGTCCAGTGACTCT | 16356 TCCCTCGCCTAACTGGCAGAT | 27340 TGTCTGCCACCCGCTGTTCT | 38324 |
| 4699 TCCCCAACCCTTTCCTTCTCAT | 16357 ATGGAGGCAGTGGTTACTTTTCA | 27341 CAACCATGTCCCCAACCCTTT | 38325 |
| 4700 TGGCTCATCCCACTCCCAAAC | 16358 GTGCTGTGGGTGAGCACAGT | 27342 GAGGCCACACTCTCAGATCAA | 38326 |
| 4701 GCAGCTGCCTCGGAATAAGCAA | 16359 TGGATGTGTCATGCCCAGTTC | 27343 GTTGGCCTCAAACACCTTCACT | 38327 |
| 4702 GGTCTTCGTCTGCTCGGTATT | 16360 TGGCCCAGCATCGACCAAT | 27344 GAGTCACGCCACCTAATCCATTC | 38328 |
| 4703 CTCCCCATGTTTGGGTTAACTCCTT | 16361 GTCAACCCAGGCGAGACATTC | 27345 AGCCCGTCTCCCCATGTT | 38329 |
| 4704 GTCCTGCTTTCATGTCCCCTTTAG | 16362 GGTGATTGGGTGGCCCTTAGA | 27346 CCCCTCTAGGAAGTCCTGCTTTCA | 38330 |
| 4705 CCAGAGCCGCCTGAATCTCAT | 16363 GGGCAGCTGTGAGAAGTGATGAT | 27347 CGCATGCAAGAGACTGGTGTTTG | 38331 |
| 4706 TGAAGGCCCCAATCTAGTCTTAGT | 16364 CCCAGCAGCACCTCAAGGAT | 27348 GGACCTGAAGGCCCCAATCT | 38332 |
| 4707 TCAGCCCCGGCTCCAGTCT | 16365 AGGGGCTCCTGCTAACACCAT | 27349 CCAAGGGAACTAACTTCTGGCTAGT | 38333 |
| 4708 CAGGTCTCACCAATGCCATCAAGT | 16366 CCGCCCCGCATTTCCCTAA | 27350 GCAGAGCTCAGGTCTCACCAATG | 38334 |
| 4709 AGCCTCCTCTTAGTGGTGGAA | 16367 GGTTGAAAGGGGCTCTCTAACA | 27351 CTGCTGAAGGTTAGCCTCCTCTTA | 38335 |
| 4710 GGCCAAACGAAAGAGGACTGA | 16368 TGGTGCCACCTGATGAACAAACA | 27352 GGAAGTCAAACGGCCAAACGAA | 38336 |
| 4711 TCCTTCAGCCTGCACGTACT | 16369 CCCAAAGCTGTCAATGCGTCTTC | 27353 CCCCCACAGTTTAAACATTCATCT | 38337 |
| 4712 CAGGGAAAAGCCCACCTTCGAT | 16370 GAGAGGCTCCTTGCTCAGT | 27354 GCCCTGTGCACTGATGACAAA | 38338 |
| 4713 GGATACATCCCCAGGGAGCTGACA | 16371 GATGAAATGAGCTGCTTCACTCGTT | 27355 TGCCCCTGGCGGGATACAT | 38339 |
| 4714 GACGAAAACTGCTCACTTATCGGTAA | 16372 AGCCCTGTGGCCCATTTG | 27356 CAGGAGAGGAAAACTGCTGACT | 38340 |
| 4715 GACTGAGACACCCACTTCTTTTACTTG | 16373 TGGTCTCCCACTTGGACTGA | 27357 GACAGAGTGAGACACCCACTTC | 38341 |
| 4716 TGCCATCAGCCTCAGTGAAC | 16374 GAGGGATCCACTTCCAGAGTGAAC | 27358 TCGAAGGCTACCTCTGCCATCA | 38342 |
| 4717 GAGTCGAACACAGCGCTGAAAAAC | 16375 AGAACCACAGCGATGATGATGTTA | 27359 TGTGATGACGAGTAAGTGAGGAAGA | 38343 |
| 4718 GGCCTTGACACAGTCCAGATGA | 16376 AGGGAGGGCTGGCTTAACT | 27360 GCCTAACCTTGGCCTTGACACA | 38344 |
| 4719 CAACTGACCGCGACGACGTGCT | 16377 CCAGGCGGGAAGACAACT | 27361 GCCTGGGAATCATGGCAACT | 38345 |
| 4720 CGCAACTTCCCAACCTCCTT | 16378 GCCTATGGTAGTCTCCCCACAT | 27362 GCCGCCCTTGACCCATTGTAT | 38346 |
| 4721 AACTGGACGGCTGTGACTGA | 16379 GCCAGAGCTCCTGCAACCTTAT | 27363 GGCGTATGAATTGGAGTCAGTAAGT | 38347 |
| 4722 TCAGTGCCCCTTCCCCAAT | 16380 GGACGTGGCACCATGAGTTG | 27364 CAGGCACCAAGTACATTCATCAGT | 38348 |
| 4723 GGGTCTACACCTGCAAGGACTGA | 16381 TACGCCCCCACGTGCTAGAAAA | 27365 GCATGCAGTATGAGGGTCTAC | 38349 |
| 4724 CACACAACACTTCCGCCCACAT | 16382 AGTAGGGCATGTGACTGAGTT | 27366 TGGAAGGGGCACACAACACT | 38350 |
| 4725 CAAGCAATATCCCCAGCCACTT | 16383 CATCAAGCCTGAACGAAGCAAA | 27367 GCTCCCATCAGTGCCAAGCAAT | 38351 |
| 4726 CTCTGCCACTGAGGACTGGTTCA | 16384 CTCTGCACAGCACAGGGAAT | 27368 TGGGAGGCTCTGCACTGA | 38352 |
| 4727 TGCCTGACATGTAGGAGGTTCT | 16385 CGAAGCCTATCCATTTCCACTTAGTAGT | 27369 CGCACACAGIGCCTGACAT | 38353 |
| 4728 CACAGTCTCCCCACCTCGTT | 16386 CCGGATGCCACTCGACCAAA | 27370 GCCCCGTAACTCTACTGCTCAGA | 38354 |
| 4729 ACTCCCCAGGGAGCCTTATCTAC | 16387 TCGCTAGGCAGTGACTCAGA | 27371 CCTCCCCACTATTCAAGTCCCAACT | 38355 |
| 4730 GAAGGTTCCTTGACATAACAGGTTTC | 16388 TGCCGTACCTGGGAATCCAT | 27372 AGCAACTAAGAAGGTTCCTTGACA | 38356 |
| 4731 CCCTCTGTGTCTTCGTGCTACTT | 16389 GAGTCAGAAAGGATGACCTGGAGTA | 27373 TGCTGCTCCCTCTGTGTCTTTC | 38357 |
| 4732 CCCTGAATTCTCCCTTGCCTAAC | 16390 CTGCTCTGAATGGAAGCAGGAAGGAA | 27374 CTGAATGGAATCTGAAGTTACCCTGAAT | 38358 |
| 4733 GCCCCAAAGTGGCAGAGTTTTG | 16391 GGAGGGGAAGGCTTTGCTTCTCA | 27375 GAAAGCACAGATGCCCCAAAG | 38359 |
| 4734 GCCGGACTGAGAAATGCCTGAA | 16392 GTGCCCATCTGCCGGATCT | 27376 TTCTCTGGGCCCGGACTGA | 38360 |
| 4735 GGATGCCTACGTTCTGGTGAGA | 16393 CCCTAGCCAGGTGCTGTTTGT | 27377 CCTGGTGGGATGCCTACGTTT | 38361 |
| 4736 GGCGTCCTAGAGGGACGTAA | 16394 TGGTGCTGGAGTGGGAGTGA | 27378 TGGGTAGGTAGGCGTCCTAGA | 38362 |
| 4737 GCTGCTGGAATTGCACCTTTAC | 16395 CAGCTCAGTCTGAAGTGCAAGA | 27379 TGGCAGAGCTGCTGGAATG | 38363 |
| 4738 TGGTGGTCATCCCCACTTCT | 16396 AAGGAGCAGGGACCTAAGGGA | 27380 GGTGTCTTCTGGIGGTCATC | 38364 |
| 4739 CTCGATGCTTGTGGTTTTACTGTTC | 16397 AGGCCTGGCTCCTGCATCA | 27381 CGCAGGTTCTCGATGCTTGT | 38365 |
| 4740 TCGGGAGTTAACCCAAATAGTAAAC | 16398 TTGGAGTGGGTCTGGAAGGAT | 27382 GGTGTTTCCACTTCGGGAGTT | 38366 |
| 4741 CCTCCACTGCCTGAAGTTTGAAC | 16399 CAGCCCACACACCCTTTCT | 27383 GAACTTTCCCATGCCTTCAAAC | 38367 |
| 4742 TCCGCTCTCAGGGCGTATC | 16400 TGCTGGCCAAGGAGACAGATG | 27384 CCGAGATCTGGACTTGTGTCTATC | 38368 |

FIG. 36H3

| | | | |
|---|---|---|---|
| 4743 AGGAAGGACCCCATGGCTCTA | 16401 GCATTCGACCTTAGGTTTGGAAAG | 27385 GGAAGGGATGGGCCCAGGAA | 38369 |
| 4744 TCGTGTTTGATTGACCCATGTTACT | 16402 GGTGCCACTGGACTATCTCTACA | 27386 CCAATGCTATGTCCTCTTTGATTCA | 38370 |
| 4745 GGGACCAAGTCAAACCAAGAGTCTTTC | 16403 GCCTCACACTTGGGACACAAA | 27387 CAGCTGCTAAGGGACCAAGTCA | 38371 |
| 4746 GCTATGGAAAGTTTCTGGTGGAGTT | 16404 AAGCCTTCGCACTCAGCTT | 27388 GGACAGCTAAATCAGAGAGCTATGGAAA | 38372 |
| 4747 CCTCAGAGACAGATGCCATTGAATTA | 16405 CGTTCCATGAGCCAGACTCTTCT | 27389 ACAGTGAATCAGCACTCCTCAGA | 38373 |
| 4748 CTTCTGGAGGCACTTGGGTTGACA | 16406 CTTGCCACCTAGCCCAAATGT | 27390 ACTGATACCATCTTCTCGAGGACTT | 38374 |
| 4749 CCCTTTCTTGCCAGACTAACAGT | 16407 CAGCCCCGAACACAGTTTTGA | 27391 GGCGTCCTTACTCCCTTTCTTG | 38375 |
| 4750 GCAAGGTGCTGAAGCTATTCAAG | 16408 GCACTACTGTCAGGCTGCAATC | 27392 AAGGGGCAAGGTGCTGAAG | 38376 |
| 4751 ACCAGCTAGCAGAGGAGGATGTA | 16409 TCCAGCGGACCCTGAAGGAA | 27393 CCATTAATCACCAGTTCCTTGATAC | 38377 |
| 4752 GCCCCTTCAGAGTCTTGCAGGAAA | 16410 CCCTCCCATGGCCTTTCTATCA | 27394 TCCCAGTCAGCCCCTTGAGA | 38378 |
| 4753 TCCGTGTGTAGTCTCTCAGTAG | 16411 GCCATCCTCAGGAGCCTGAAT | 27395 TCACCTGTCACTCCGTGTGTAG | 38379 |
| 4754 CACTTGCCAGTCCCGTCTAA | 16412 GCAAGGACAGCTTAGTGATTAGGTA | 27396 TCAATGCATCCTAGAGCCACTTTG | 38380 |
| 4755 GGTGGTTGGCAGTCACCTACTGA | 16413 AGGGCCCTGTCTCCAACTCA | 27397 GGCTTTGGGCCTGGTGGTT | 38381 |
| 4756 AGCCTTGGCCTGGGAGAT | 16414 GGAAGTCAGCATCAAACCCTTGACT | 27398 CCCTTGCCCATCTCAGTTACAAG | 38382 |
| 4757 ACATACCCTTTGCCGAGCTGGTT | 16415 GGCCAGCCTAGTGAAGAAAAC | 27399 CCTCCCCATTCAACCCCATCTT | 38383 |
| 4758 GGCTTAGACCAGGAGTGGAATGA | 16416 TCTCCATCAGGCCTCTAAGAT | 27400 GCTCAGAGATCCACTGAAGCCTA | 38384 |
| 4759 CGGGATAGGAGACTTTGGTTGGTT | 16417 TCCCTGCCTGATGTTGGAAAC | 27401 GTGCCCCTGATAGGAGACTT | 38385 |
| 4760 CTGGAGCCATCACTGATACCTTT | 16418 CGCAGCGACAGCAGTCAGA | 27402 GGCAGCAGAGACCACCAGTT | 38386 |
| 4761 CCTGCTGTGAAGGTGGTGAGA | 16419 TGAAGTGCCGAGCCCTGTGA | 27403 TGGAGGTCACCTGCTGTGAA | 38387 |
| 4762 GCCCTTGTGTAATTCTACGCACCAGAT | 16420 TGTGCACACCATGTCACCATAG | 27404 GTGGGTGTTTTAGGCTTGTGTTGTAATTCTAC | 38388 |
| 4763 CCAACGTGTCAATATGCTGTTGATT | 16421 TTCCCTCTCCCGCCAACAT | 27405 GCTCGGCTCCAACGTGTCAATA | 38389 |
| 4764 GGGGCTTGCATCCCCTTT | 16422 GAGGTGGGAACGTGAGACACT | 27406 ACTGGGACAGCAGGGAAAGA | 38390 |
| 4765 GGCACTACCTCACTTCCTTTGT | 16423 GGTAGGGCTGGCTGGAGGAA | 27407 GGAGACTCATGTCAAAGTCCTGTCA | 38391 |
| 4766 GTGGTTTGCTGGCTTTTGGAGGAA | 16424 AGTAGTGCCTCTGTCTTCTGTGA | 27408 GGCCCTATGCTAGGTGGTTCT | 38392 |
| 4767 CTCTCCCTCCCTCAAGTACACAGA | 16425 CTGGAGCAGAGGTAAACAGAGGTAAA | 27409 CTTCCCAAGTTGCTGCACTCT | 38393 |
| 4768 ACCCAGGCATGTTAGTGTTTTCTA | 16426 CCAGAGCACCATTCCCCATAG | 27410 CCTGAGACCCAGGCATGTTAGT | 38394 |
| 4769 GCCTGCTTGGCCTCCCTCTTCTTC | 16427 GCTGTGCATGCTTGCTTCAGATTG | 27411 TCACCAGCCATCTCAGTTACAAG | 38395 |
| 4770 CTGAAAGGACTAGGCTAATAATGACT | 16428 GGATGGGCTCGGACTTCCTAA | 27412 GAGAGGACAACAGAAGTCTGAAAG | 38396 |
| 4771 TTCAGAGTCGGCACTCCATAG | 16429 GCCAGCGTCAGGACTTGTTCATTC | 27413 TTGGGAGGTGGGCTTTCA | 38397 |
| 4772 GCTCTGGAGAAAGACTTGAGTAA | 16430 GGCACACGGCCAAATTCAGA | 27414 GCCTCACTGGGCCCGATTTT | 38398 |
| 4773 CCAGGGCCTCAGCCTGTGTT | 16431 CGAGGGATGAGGCAGGTGTTT | 27415 CGAGCCTTGGATGCTCCCTTTC | 38399 |
| 4774 GGGAATGCATCTTCCCCAACTGT | 16432 TGGCAGCACCCTTTGGGTTT | 27416 GCCTATTTCCTTTGAGGGAATGCATCTT | 38400 |
| 4775 AATCTAAAGTCCAGACGCACCAGT | 16433 CCCTCGTTCCCTGCAATGTCA | 27417 CCGACTGCCATGCTGGCAGAATCAA | 38401 |
| 4776 GGAGCCGAAAGAAGGCTTTTAGA | 16434 GCCAGGAGGTGGAGGTATGA | 27418 GCAAATCTCTTTGATATGGAGCCGAAAC | 38402 |
| 4777 TGGGCACTCGAAAGTAAGTTG | 16435 CCCAGTAGTGAGGTCTTCCACAAT | 27419 TCTAGCTTGGGCATTGGAA | 38403 |
| 4778 GGGCCCTTTCTGACTGTGTTC | 16436 ACAAAACCCTGAAGGATCCCAGTAT | 27420 ACATCCTTAGGGGCCCTTTGT | 38404 |
| 4779 GCCAGACAATGTCAGGTGCTCAT | 16437 GTAGGCCCTCCTGCAGTGCGTAT | 27421 GGTGTGGGCCAGACAATGTCA | 38405 |
| 4780 TGGGTCGGGATGGCTAACA | 16438 CTGATTAGGTCCTGCCGTCCCTT | 27422 CCAGAGTGGCTGAAGCACAGAT | 38406 |
| 4781 GCGAGACAAAAGGGCGATATTCAG | 16439 CCCATTGGCTGAAATAGGGGAAA | 27423 AGACTTAGAGCTGCGAGACAAAA | 38407 |
| 4782 CGAGTAAGTCAGTTCTTCCAGATC | 16440 GGCCTTGCTGGTGTTGTCAA | 27424 CCAGTGTCATGTGGCCGAGTA | 38408 |
| 4783 GCGGATGGCATCATTGTGAGA | 16441 CCAAGCCCTTCAGCCACTTCA | 27425 GGAAACCATGCCAGCTCTTTG | 38409 |
| 4784 CTGGGAACGACAGAGAATCACA | 16442 TCCTCACACCCTTGGCTGAT | 27426 CCCAGCATCAGCTGCTCATATGTAA | 38410 |
| 4785 GGATCATGCAGAGAGAGCTGAGACA | 16443 TGTCCCAGAGGACAGGGACAA | 27427 GTTCCTAAAAGGATCATGCAGGAGACA | 38411 |
| 4786 GAGCCCTGGCTCTGTCACT | 16444 GGCCAAGCCCTTACCTGAAGAT | 27428 TGGTGGCAACTAGGGATGTGA | 38412 |
| 4787 CACTCCTTCTCCTGTGGGGATTTG | 16445 CTCACCCCTTCCGAACTCTTAACAT | 27429 GTGGACAAAGTACTCACTCCTTCT | 38413 |
| 4788 CGGTAGAATCTGATCCTGGAACTTCT | 16446 AATCGACACCCCATTACTGT | 27430 CCACATGACCCTAAGACGGTAGA | 38414 |
| 4789 CCTTGCTGCTCATTGGCTTCT | 16447 TCCACAGGGCTCCCGTGACA | 27431 CCTTGCAGGAAGGTTATCTTTTGT | 38415 |
| 4790 CTCTTCATCTTAGCCAGTCCACTT | 16448 TGTCCTTCTAGGCTGTCTGTGTT | 27432 CAAGGGCCTGGCTTCTTTGT | 38416 |
| 4791 GGCTTGTCCAGGTCCATGATA | 16449 TGGCCCACTCCCAACAAAG | 27433 CTGGGCGAGAGACACTAAATG | 38417 |
| 4792 TCCAGGGAGGGCTGGAGACT | 16450 TGCGGTCAGACGGGCTCAGA | 27434 ATCAGGGCTTGGTCCAACA | 38418 |
| 4793 GGGCCACGGAATTTCCTGTGA | 16451 AGTTCCCTGGGTTGCACAGT | 27435 CGAACGCTACACCTAGGACATTG | 38419 |
| 4794 GTAGTGGGGATCTGACCTAGGAA | 16452 CATCCACTGCTCGCTTTTTC | 27436 GAAGGCAAAAGTAGTCGGGATCT | 38420 |
| 4795 CCACCATCGGCCCATGTCA | 16453 GCAGGCTGCTCTCTCTCTT | 27437 TGCCTGCACCTCCACCAT | 38421 |
| 4796 ACGGGACGGCAGTCAGCTT | 16454 CGTCCTCAGGAGGTGGAAATCATC | 27438 GGCACCAGCTCTTCCATCTGTAG | 38422 |
| 4797 TGGTGGTGTGTGCCTGTAGTTC | 16455 GCAATCTTCCCACCTCAGCTT | 27439 GCTGGGCATGGTGGTGTGT | 38423 |
| 4798 CCCCACACACAGAACGTGGAAAC | 16456 GGGGCCTGCCCATCTCCTTT | 27440 GCTGATGGCCCCACACACA | 38424 |
| 4799 GAAGAGCAGAGGAGGCAAGAA | 16457 ACACTTGGTCAGGTATGGATCACT | 27441 GGTGCCCACACAGAGGAGA | 38425 |
| 4800 GCCAAACTGGCTGGGTTACATC | 16458 CCAGAGCCACCTGGAGTAGGTA | 27442 GCCTGTCCTCAGGAGCCAAA | 38426 |
| 4801 GTGCGTAATGACAGCAACTGAGA | 16459 CATCGTGAGTCATGTGTGCACT | 27443 CAAACAGGACTGGTAATGA | 38427 |
| 4802 GGCCCTGGGAAGACTTCAACAA | 16460 AGGGTGGAGCCTCCTCGTTT | 27444 GGTGAGCAGTTCCAGTGCAAGT | 38428 |
| 4803 CCAGAGGCCTTGCCAGAACATT | 16461 GAGGACCTCCCTCCTCTCA | 27445 CCTTTGTCCTCCTCAATGAGCTGACTGT | 38429 |
| 4804 AACCCAGGGAGACTCAGGGTCTGT | 16462 TGGCTTCTCTCCCACAGTGAT | 27446 GCCTGAGGCTCTAAGGGAGATGAAC | 38430 |
| 4805 GCGGTTGTGAGAAACACACTGA | 16463 GCCCTCAAGTCCATTCTTTGGATTTG | 27447 TTCACTCTGCGGTTGTGAGAA | 38431 |
| 4806 ACTATCATCGCTCCCGAGGAA | 16464 CGGCTCGGCATGGCTGCTTAATA | 27448 CCCCACTACCTAGTTCCAGAATACTATC | 38432 |
| 4807 GCTGAGCCTGGACGGCTGT | 16465 CCTCAGTCCTCACAGGAGATTC | 27449 TCTGGAGAGGTGGGAGAGGTTTG | 38433 |

| | | | |
|---|---|---|---|
| 4938 AGCTCTGGACGGGCAAAC | 16596 GAGCTCTGGAAGCAGCATCTAAGT | 27580 CCCAGTGAATATGGGCCTGATG | 38564 |
| 4939 TGGAACAGCCCCTCTCTGTGTA | 16597 TGATCCAAAACAGAGGAAGGAACA | 27581 GCACACAGGAGGCTCTTCCAT | 38565 |
| 4940 ACTTTCCCTGCACCTTTATACACTTTC | 16598 GAGTCAGCCTCCTCTTCGTTAG | 27582 CAGTCTCACTTTCCCTGCACCTT | 38566 |
| 4941 CACAACCCACCCATCAGTCATTG | 16599 GACGAAGGTTGGGAGTCAGAAAC | 27583 CCAGCAGATTCACACTGTAGACACA | 38567 |
| 4942 CCAGAAACCATGCCATTATGCAA | 16600 GACAAGGTAAAACAGGCACTTCCTT | 27584 GAGAATGGCCAAGGTGTGGAA | 38568 |
| 4943 GAGCAGCCAATGCACAGTCA | 16601 GACAGACCCAAATTTCTGCCACGT | 27585 AGCAAGGTTGAGTAGCCAAT | 38569 |
| 4944 TGTTCAGACCTCTTGGAAATTGCAT | 16602 CCACCGTGCCCAGTGCACATA | 27586 GGAGAGATGTTCTTATTGTTCAGACCTCTT | 38570 |
| 4945 CCCTGGCTTGGTTTCCTTTCA | 16603 GGAGAGAAGGTCTAAGCGGAAGT | 27587 ATCCCTCATCCCCTGGCTTTG | 38571 |
| 4946 ACGCACGGGAAGCTGAAA | 16604 CTGCAGACCGTGCAACT | 27588 AAGGGAACGCGGTGGGTTAG | 38572 |
| 4947 GAACCTTGACGCTACAGCTTTGA | 16605 TGACTTGCAGCTCATGCAATTTTG | 27589 AGACAATTAGGGTCAGGAACCTTGA | 38573 |
| 4948 CTGTTGGTCTGACATGCCCTGAT | 16606 ATCGTGGAGACTGGCTGGAT | 27590 TTGCCCCTCTGTTGGTCTGA | 38574 |
| 4949 AGCTAGAATAGCCCCTGAGTGT | 16607 CTGACCGCTAGCCCTGTTAG | 27591 CCATACAGTGAGCTGTGGAGCTA | 38575 |
| 4950 GTTCCAAAGTGATAAGGACGGATGA | 16608 GCTGCCACCATGACTTCTCT | 27592 CTGTGGGAAGGGAAGGCTGGATAGCTCCABAGTGA | 38576 |
| 4951 GGATGCAGCAAAGGCAGATCTAAG | 16609 CCCCAGGCAGAGCCATATCT | 27593 CCAAAACGTTCGGATCCAGCAA | 38577 |
| 4952 CTTGCTGGATGCTCAGCTTGT | 16610 CCTCTGTCCATGCAATCCCAAGAA | 27594 CACCCAAATGTCACTTGCTGGAT | 38578 |
| 4953 ATCAGTCCAGTGGTATGTCAAG | 16611 TGGTGGAGCCAACAGCATAGAT | 27595 CAGGAGGTTCTCAGCTCTGTTG | 38579 |
| 4954 GGAAGGGCTGATAACAGCAGTTTGTGA | 16612 CCCAGTCGCCTTCTCTCAACTT | 27596 CTGTGGGAAGGGAAGGCTGGATAA | 38580 |
| 4955 CTGTCTGGACACGGACCAGATAA | 16613 GGGTCCACATATTCAGGTCAAC | 27597 AACCTTTCTTTCAACGGCTGTCT | 38581 |
| 4956 TGGCACCAAGCCAAGGGATCT | 16614 CAGGTAGGAGGGTGTTCTGGTCAAG | 27598 GACTGCCAGGATGGCACCAA | 38582 |
| 4957 CATAGATTCCCCACTTCTAGGTT | 16615 GGGCCTGACCGAGACCTAATA | 27599 CAGCTGGGGAAGCTTTGT | 38583 |
| 4958 TCTCACCGCAGCCTTCCTA | 16616 CCTGGTGCAGTGGTATGCAA | 27600 TGACTTCCAGGTTGAGCGAAT | 38584 |
| 4959 TGGCAGCTAGCCCACGTT | 16617 GACTCTAACCACTTATCACCTCCATTG | 27601 GCAGCAGATGAGATGGAGCTA | 38585 |
| 4960 TACCCAGTCCACCTCCAACACA | 16618 GGGAGGATGAATTCAGCCTTGT | 27602 GGCTCACCACATACCAGTCCTT | 38586 |
| 4961 GCTCTGGGAGAAAACATAGGCAATG | 16619 GGTTGGACCAGGGAAATCAGT | 27603 CAGCCAGCTCTGGAGAAAACA | 38587 |
| 4962 ATAGGCCGGTCTGAACCAGGAA | 16620 ACCCCAAGCCACCCTCCAT | 27604 GTGTCACATGCCATGACTGAGA | 38588 |
| 4963 CTGCCATTTCTTTGGGACTGATG | 16621 ACTGGAGCAGCCTCTGAGACA | 27605 CCATGGTTCCTCCTCTGCCATT | 38589 |
| 4964 CCTCTCCTTTGACATATTTCCTTCAGT | 16622 TCACAGGCCCAGATGAGTCA | 27606 CCTGAGAGCCACTGAAACCTCTCCTT | 38590 |
| 4965 CTTGGTCAAGTGCCATTGGTTAGA | 16623 CCACAAGGCGCATCTCATGT | 27607 CCAGTAATGATGAGGCAGATGTCTTG | 38591 |
| 4966 CTGCAGGGATGAGGGGAAGAACT | 16624 CCTGCACCTGTTGACCCATT | 27608 TCTTAGCGGCTGGAGGATGA | 38592 |
| 4967 ACCCCATCTCTGCCACTGTT | 16625 ACACCCCAGGACACACCAAT | 27609 GGAACCATGCTTAACCCCATCT | 38593 |
| 4968 CCTTCTGCCTCCCCTTGAAAT | 16626 GTGGCTTGATGGGACTCA | 27610 CCAGATGGCTAGCATTGACCTT | 38594 |
| 4969 GTGGCTTTCAGACCTCCTGGAT | 16627 GCGCAACGGCCCCTCATTTA | 27611 GGCACTGATGCTAGTGCTTTG | 38595 |
| 4970 CAGAGAGAGTCATGTGGGTATGTTT | 16628 CTTGAGCCCTGCACCTTTAATTCT | 27612 GCTTCCCAAAGTCAGAGAGTCA | 38596 |
| 4971 AGTGAGCCCATGCATAACTGATAC | 16629 GCCCATGCAACAAAGTAGCCATGA | 27613 GGGGAACTGCATGATCCTGAGTGA | 38597 |
| 4972 GTCCTTTGCTGGCCTGCTGTA | 16630 GATTGCATGGCACCCAGTCT | 27614 TGACTCTCCGGTAATCTCTTGCTT | 38598 |
| 4973 CTGCTGCTGTTAAAAGATGGGAACA | 16631 GAGGGAAGGGAAGAGAGCCTTA | 27615 CACATGACCACTGCTGCTGTT | 38599 |
| 4974 TCTACCTAATGGACAGGCTGAGAT | 16632 CCTTGCACATCCCAGGCTCAAGT | 27616 GTGCGCACATCTGGCATTT | 38600 |
| 4975 GGGGCAGTGAGTATGTCTAATGA | 16633 CCAAGCCGAAAATGGAAGCTATG | 27617 GGCATGGGGCAGTGAGTATT | 38601 |
| 4976 GCAGCTGTGCCATGTGTGA | 16634 CCTGGCCAAGAGGCCAACAA | 27618 GGGTTGCATTGCTCCCTTATTCAGT | 38602 |
| 4977 GCTTCCTCATCATCGTTCCGGTCTTTG | 16635 AGGCCCACAGAGAAGGTGACAT | 27619 GAGCTGGCTTCCTCATCATCTT | 38603 |
| 4978 TCTTCTGGAACAAGCCCAACAA | 16636 CCAGAAGTCCTGCTCTGCTTCA | 27620 GCATTCCTAGGCAGGTCAATTCTTCT | 38604 |
| 4979 GGTTGTGAGGGGCAAAGCTTGA | 16637 GGCTGGGAGTCAAAATTAGGGTATC | 27621 CTTGGTGTAGACCAGGTGTGA | 38605 |
| 4980 GTCAGCTCCCTGGGCCATA | 16638 GGACTGAAGTCCTCAGAAGCAAA | 27622 GGCTGAATGTACCCAGCCAAGTCA | 38606 |
| 4981 CCGTAAACCATTTGCACAGCACATT | 16639 GCCCTGGGATCCAGAATTCCTA | 27623 CCACTCCATCCGTAAACCATTTG | 38607 |
| 4982 CCATGCTTGCCCCTCTGGTAATG | 16640 CAGGAGTTCACCCCACTTTACA | 27624 GGTTGCACAGGCCTCAGTTG | 38608 |
| 4983 AGGCCACAGTGACCGAGTCT | 16641 CAGGGCTGGTCCACAAAGGAA | 27625 GCTATTTCCCAGGCCACAGT | 38609 |
| 4984 TCCGAGCCGGGATCTTTAG | 16642 GGACAACCAGCACCCAAAGGAA | 27626 GGAGGTCTCAAAACCGGTCAGATG | 38610 |
| 4985 GGCATTGCAACTACCCTGTGTGA | 16643 GACAATGACGTGGCTCCACCAT | 27627 ACACAGAGGACTTTTTGGGCATT | 38611 |
| 4986 CCTGGGCTTTGCCTTCTTCA | 16644 ACCAGGCCAGGCACTAGGAA | 27628 TGATGGAAGGTCCTGGGCTTTG | 38612 |
| 4987 CTGCTCTATGCCATGGGTCTGA | 16645 AGCAGGGAGCCCATTGATGT | 27629 TGCTTCCACCCCTGCTCTATG | 38613 |
| 4988 TGGCAGGCTTCCTCAACATG | 16646 CCCCGACCTCCAAGCTACT | 27630 TGCTGCTGCCCCCTCT | 38614 |
| 4989 ACCTCCATTCAACGGATGAGAAAA | 16647 GGAGAAGTTACTTAGCCACACTGA | 27631 GCAAAATAGGCATTACCTCCATTCAAC | 38615 |
| 4990 GATAGCCAGCCAGTGTTCTCA | 16648 ACATCCGTGGTGTCTCTAACAT | 27632 GGGTGGGAGGCCTGAAGAT | 38616 |
| 4991 GGAGCCTCTGCCTAGAGTTT | 16649 GCAGCTGTTGCACTGTTTTGTT | 27633 ACACCGAAAGGGCAAGAAAGT | 38617 |
| 4992 AGGACCTCAGAAGGGAGCAACT | 16650 CCTCGAGGAAGCCTCCCCTTA | 27634 GGTGGAGACAGTAGGACCTCAGAAG | 38618 |
| 4993 GGGAGGGTTGCAAATTCTAACTCA | 16651 GCTTTATTTCCTGCACATCCAGTT | 27635 GGGTAGGGGAGGGTTGCAAAT | 38619 |
| 4994 GGATGAAGGCTCTGGGAGGA | 16652 GCTTAGAGCTCACACGTTGA | 27636 GAGATCTGCAGGGTAGGATGA | 38620 |
| 4995 GGATGGCTGCTGCCCTCTTA | 16653 AGTGGGGACTGTGGAGGACACA | 27637 AGTCCAGGCTGGCTGGAT | 38621 |
| 4996 CCATTCATGGGCATGACGAA | 16654 CACTGTGCAAGAACAGATGGTTCAGA | 27638 GCGTTTGCAGTTCCCATTTCA | 38622 |
| 4997 CAACATAGCCCCAAAAGACCCAT | 16655 CCCAAGGTTCCAAGAGAGACAA | 27639 ACAGAAAACCAACATAGCCCCAAA | 38623 |
| 4998 ACTTTGATTGTGTCACTGCTGTCT | 16656 GAAACACGGTCTCACTCTGTCA | 27640 TTGGCCAATAAAAGGACAGTGAAC | 38624 |
| 4999 TGTGTCCGGACTGTCAAC | 16657 GCGGTTGCAGCTGTACTCTGA | 27641 CCAGAAGCCGAAGTTGTGT | 38625 |
| 5000 GCTGGCTGTAGCAGAACTGA | 16658 TCGCCCTCCATTCTTCT | 27642 GTGGATGACCAGCTGGCTGAG | 38626 |
| 5001 CCCATACAATGTGGGGACTGAT | 16659 GGAGGGCCAGTGACATTCAA | 27643 CAGGGACTCACCTTAGTCCCCATACAA | 38627 |
| 5002 CCTCCCCAAGCGGAAGCATTTT | 16660 GCCCAAAGAGAGGGTGCTAGT | 27644 GAGAAGGGACCAAGCCAATTTCA | 38628 |

FIG. 36H7

| | | | |
|---|---|---|---|
| 5003 TCTGGGAGCTTCTGCCTCATC | 16661 TGATTTGTGGGGCAGAGACA | 27645 TGGCCTTACATTACAGCCATTCT | 38629 |
| 5004 CTGGTTCACACGATGCAAGATG | 16662 TGGCCTTGGTTGGACACACT | 27646 TTCCACCACCACTCCCAGTGA | 38630 |
| 5005 CTGAAAGCTATGCGTGTACTGCAT | 16663 GTGTAGGGTGTTAGTTGTCCACAGT | 27647 AGGTAGGCCCTGAAAGCTATG | 38631 |
| 5006 GGAAAGAGGTCAGGCTCTATGTGA | 16664 CCCAGCAACTGTAGCACTGA | 27648 CCCAGATCATATTTTGGGAAAGAGGTCA | 38632 |
| 5007 GGATGTACCCCATGCATCCTAAC | 16665 TGAGCCAGGGAATGCCTGAA | 27649 CTGAAAGCCACTAGGCAAGCATGT | 38633 |
| 5008 CCCACCTCAACCTTGCAAGTAAC | 16666 AGGGCATGGTCACACACAAC | 27650 GGGATTCTCCCACCTCAACCTT | 38634 |
| 5009 CCCAGCGTGAAGGCAAAAAG | 16667 GAAGGTCATCTTTCAGGGATTACAGA | 27651 CCCTTTGCTCATTCAGCATGGTA | 38635 |
| 5010 CAGTCAGAAGGAACAAAGGAACCAA | 16668 CCAGCCTGTCCTCCTCTAA | 27652 CAGGAGTTGGTGTTCAGTCAGA | 38636 |
| 5011 TGAAAAGTGCATGGTCCTGTTGA | 16669 GTTGTGTAGTCCAGAGTCTGAA | 27653 CTCCAGAGTCTTTGAAAAGTGCAT | 38637 |
| 5012 GCTGGAACTCAGTCACAAGCAA | 16670 GTTGCCAACAGTTATTTCCACCTA | 27654 GTGAAGCCATTTGCTCGAACTCA | 38638 |
| 5013 TGGCCTCAATCCAGGCCCTAC | 16671 TGCCTCAATCCTAGCATACAACAATC | 27655 CTCTCTTTCTCTCTGGCCTCAATTC | 38639 |
| 5014 GTGGTTGTAGTGACGAGTTTGACT | 16672 GCTTCACCAAGCGTTCCCTTGT | 27656 CCCTTGTGTTGGACTGTGGTTGT | 38640 |
| 5015 CAAGACAGCACAGGTATAGAGGAACA | 16673 AGCCTCTGCCTCACCTCTTG | 27657 GACCATACAAGACAGCACAGGTA | 38641 |
| 5016 GCTACTTCACAATCACTAGGAATC | 16674 CCCCAGACTCACAAAGCTATTCT | 27658 GTGCTAGATTCTAGCTACTTCCACAATC | 38642 |
| 5017 GCGACCAGGATGACAGGTGTA | 16675 ACACTCTGCATAGCTCAGAACAA | 27659 TGTCAGAAGGCGACCAGGAT | 38643 |
| 5018 CACTTTGCCTGCATGAAGATTGT | 16676 CTGGAAGAAAACGGGTCTGATAAC | 27660 GAGAATCAACCACTTTGCCTGCAT | 38644 |
| 5019 CCCAGTTACATCTCCTTCTCCATTC | 16677 CCACTAGTAGCCGTGTGAAGAT | 27661 GGGCTTTCAGCTCCCAGTTACA | 38645 |
| 5020 TCCTCCGGGCTAAGGGAACA | 16678 GCCTCAACGTCCCCTATCAAGACT | 27662 ACCCCAAAGCGGCAAGAAGT | 38646 |
| 5021 GATCCAGGACTGCTCCAGATTG | 16679 AACCGCCACCGTTTGTCT | 27663 ACCTGGGCCTTTGTGGTGAT | 38647 |
| 5022 CTGCAGGGATTAACGGTCATTATCA | 16680 AGGGCCTGCAGAACACACATC | 27664 AGGGACAGCTCTCCTAGATCTAACTATC | 38648 |
| 5023 CCCAGGCAGTGTTGACTACAA | 16681 GTGGGTGTCTCACCATTGAAGA | 27665 ACAAACAAACCCAGGCAGTGT | 38649 |
| 5024 GCCTGCTGAAGCATGACAGAT | 16682 CCATCACATGAGTGCCTTAGTTCT | 27666 AGCTGGAGCTAGGCTGCTGAA | 38650 |
| 5025 CTCTCTCCACTGAAGTTTGACATTA | 16683 GAAACAGCCAAGGTCTGTGCAT | 27667 CCAGAACCACTCTCTCCACTGA | 38651 |
| 5026 GCCTGGAGCCTAGCAACTGTA | 16684 CCCATAGCCAGCATGTTTAGAGA | 27668 TGACTGGATCCCAGTGCTGTTG | 38652 |
| 5027 CATAGAGCACCAGTCCACACTT | 16685 GCAGCCAGCACTTTCTGTTTC | 27669 CGTTTGGCAAAACCTTAATCCACATAG | 38653 |
| 5028 AAGCACACAGCAGGAGAGTCA | 16686 CCCACTCCAAGCACCAAACA | 27670 TCCTGGTCAGATGCCCACAAG | 38654 |
| 5029 ACCTTTGCCAGACATGGGATTG | 16687 TGCAGGTGGCCTGAGTTTC | 27671 GGGACATTCCATAGTCCATACCTTTG | 38655 |
| 5030 ATCTGGAAGCCAGGGAGGAAA | 16688 TTGGCCCCAGCGGTGAGCATA | 27672 GAATGTGTGAGGGGAGACAATC | 38656 |
| 5031 GCTCAGGACACACCCATCCTTTC | 16689 GAAAATCACCCACACTCCAGAA | 27673 TGAAGGGGCTGAGGACACA | 38657 |
| 5032 CCTCTCCATGACCACAGGAA | 16690 CGAGCTGCTTTCACACACTGTGATT | 27674 TGGCCCATGCCTGCTCCAT | 38658 |
| 5033 TGTCCACACGTTGGCCTAC | 16691 GTGTAACGAGTTACTGCCGATAATG | 27675 AGGGATGCAACCCGACTGT | 38659 |
| 5034 GAGCTGACTCCTCCCACATA | 16692 CCCAACACTGTCAACTCACAGA | 27676 GTAATACAAGCTGTCCCTGAGCCTCACT | 38660 |
| 5035 GCAAAATCCACCCGTGACAGA | 16693 TGGGAGTGACGTGCCCACAAA | 27677 GGACAGCCAATCCAGATCACCTTCT | 38661 |
| 5036 GCCTGGTCACCTTCATCTGCTT | 16694 GGGAGTGAAGTGCAGTCCTGAAA | 27678 CTAGGAGCCTGGTCACCTT | 38662 |
| 5037 GAAGCTGGACGTGGGTCAA | 16695 CCATATCTTCTCTCAGGCCCTATCT | 27679 GGTGAGGTCCAAGAGCTGGAA | 38663 |
| 5038 CCTGAGGTTAGGCACCTCCAA | 16696 TGGGTGCCACGTGTGATGGTA | 27680 TCTCCAGAGGGCTGAGGTTAG | 38664 |
| 5039 CTATGCTGCCATGTGGGTCAAA | 16697 AGTGGAAGAGCTTTGTGTGCTAAG | 27681 GCTTTCCACATCCTCCATAACCATT | 38665 |
| 5040 GAAAGGTGGGCTTCCACACA | 16698 GTGGACAGCCAGGAAACAGTCA | 27682 CCCACAGTGTCTCCACGTGTCAGA | 38666 |
| 5041 CTGCCTTGCATTGCGACAGA | 16699 CTGAGAAGCCTTCTGCATCCTA | 27683 AGGTGTCCCTGCCTTGCAT | 38667 |
| 5042 AGCTGTCCCGGGACTTGAA | 16700 AGAGGAAAGTATCTGCCCAAAA | 27684 TCCGAATTCTTGACACCAGTCTTAG | 38668 |
| 5043 AGCCTTGCCTGTTGCCTTTC | 16701 TGCCCCCAGGGGAATAAAAC | 27685 GTGCAGCCTACTACTGTTTCCTT | 38669 |
| 5044 TTGCCTCTGCAGGGCACAGAA | 16702 AGGGCCAGGGCTCCAAATC | 27686 GACGGAACCAAGATGTTCTCCAT | 38670 |
| 5045 GCCTCGGGTCCTTGTGACATAAT | 16703 ACTATAAGGCGCACTGT | 27687 TATTTCCCTGGGGTCTTTG | 38671 |
| 5046 CTCGGCTGCAGTGTCTCAGTAT | 16704 TTGCCCAGTGCGTAGCAA | 27688 TGGTGCCCTGCAATTATTGAACT | 38672 |
| 5047 GGGGAAGAAGCAAGCATCAGT | 16705 GAAAAGCAGGACAGGCTCACT | 27689 GCAGACCAACTTTTGGGAAGAAG | 38673 |
| 5048 GTACCAAGGTGCCATGGTGCTATAA | 16706 GACTGCACCCCCTTCGGATTTA | 27690 GATTCAGTACCAAGGTGCCAT | 38674 |
| 5049 GGCATGACCCAAGCAGCTACA | 16707 GTGGGGACTGGGCTCTCAAAAT | 27691 CCAGAGGAAGTTTGTGCCATGA | 38675 |
| 5050 ACACTTGCTGCCCCTGACTTC | 16708 ACCTCATTCCTCCTGGACACA | 27692 CAGACGTTAGCACCCACACTTG | 38676 |
| 5051 TTGGGGCTCAGCCTCAGTGTT | 16709 CTGACACAGAGGGAAAATCCTA | 27693 GGGCTTCAGCATAGTTTGAATTG | 38677 |
| 5052 ATGCACCTCCCACGTCAGAA | 16710 GGGATGCTTAGAGCAGGCAGTT | 27694 CCTCCGCACAAGTTGCAAGG | 38678 |
| 5053 GGAACAGAGCATGAGGGTTTTG | 16711 CTTACGCACGTGGCAGAAATC | 27695 CAGCTAGCTCTAAATGACTTTTGGACACA | 38679 |
| 5054 AGCCGTTGGACTGAAGCTAGTA | 16712 GGGCAGGTCTGCACTGTCTAA | 27696 TACTGAGCAGCCGTGGACTCA | 38680 |
| 5055 CTAGGACCCACTGCAGCCATTAG | 16713 GGGAGGTGCAGTGCAGGAAAT | 27697 CCTGTTATACAGGGCCAGATGTCTTC | 38681 |
| 5056 CCCCTCTGGCCTCTTCTTGATG | 16714 CTGGGACTTTGGGTTGGCACATT | 27698 TGCAGACCCTGTCTCCATCTT | 38682 |
| 5057 GTTCCCCCTGCTTCCCTTGTCA | 16715 CTCTCCTGCTTCCCAAAGCAT | 27699 CCTGTGAGGTCTCCCGTTCTT | 38683 |
| 5058 ATGCAGCAGCTGGGTGGCAGAA | 16716 TTCCCACCCACCAACCAGAT | 27700 GTGCCTCATGGTGGCAGTAA | 38684 |
| 5059 GAGGTTGTTCCAGGCTGATGT | 16717 CCAGGAATGTTCCGGCCCTTAG | 27701 AGGGATGGGTCAGAGGTGTTC | 38685 |
| 5060 CCACCTGAAGATTGGCAGTTACA | 16718 ATGGGAAGGCCTGGGAGGTAAT | 27702 AGACAATCCAGTAATAACCACCTGAAG | 38686 |
| 5061 TCCACATCGCCTTGCCTTCA | 16719 CGCCGCACCAGGACTTGAT | 27703 GACAGGGCTTAGCTTCCACATC | 38687 |
| 5062 TTTCCCCTTTCGGGCTGAAG | 16720 GGTGAAGAGCAGCTGAAGTGCTTA | 27704 CACCGGGCACTGGTCTCTATTTG | 38688 |
| 5063 AACTGCACCTGCCCCATGT | 16721 TGGTGGGAGTCAGCCTGCTA | 27705 TGCTGCAGGAGCCCTGTCCTTCA | 38689 |
| 5064 GCCACCACCACAGTAAGAAGT | 16722 GCTGCAGAGAGTTTCTGTGGAA | 27706 TTCAAGACCTGAACACGAAGTGA | 38690 |
| 5065 ACTGCTTCCTACTTTGACTATCTTC | 16723 GGTTGTCCAGGCAGTTCACTA | 27707 GACTTAGAACAGCTGCCTCCTACTTTG | 38691 |
| 5066 TCTTGAGACTTAAGCAGCTACAACA | 16724 TGTTGAGGGCAGGGTCTAA | 27708 GTTGGTCCCTCACACTTCTT | 38692 |
| 5067 ACCTCCTACTTCATACAGGGAAT | 16725 TGAGGTGGAAGCCAGGTCTCT | 27709 GCCCTCTGAAACCTCCTACTTC | 38693 |

FIG. 36H8

| | | | |
|---|---|---|---|
| 5068 CCAGCAAAGCCAGCTGCACTCA | 16726 ACCTGGTCACCTGTGTCCTT | 27710 GCCCGGTGTCTTTCCCTTT | 38694 |
| 5069 AACTCCAGCAGAGCCAAGA | 16727 AGACTCCCAGGAGCCAAACT | 27711 CCCAGCAAGCTGGACATAAAACT | 38695 |
| 5070 CCCAATCCCATGCTGGTCCTT | 16728 GGCAGGGCTGTCACAATGACT | 27712 GCTCTAAAATGCCCATTCCAACGT | 38696 |
| 5071 GAGAGACACAATGCTTTGAACAGAA | 16729 ACACAACTAGTGCAGGCCAAA | 27713 GGGCAGTCCAGAGAGACACA | 38697 |
| 5072 CACCCCTCTCAAGACTGAGGAA | 16730 CCAACACCCAGGCAGCTCAA | 27714 AATACCAGAAAACACCCTCTTCAA | 38698 |
| 5073 CAGGAAACCCACAGGCAGTTGC | 16731 GCTGCCTTTGCCCCTGTCTT | 27715 CCACTGCCGTGCAGGAAAC | 38699 |
| 5074 GCAAAAGATCACTCTGGCCACTTC | 16732 TCCACCCTGCCCTCTCCATC | 27716 TCTGCCTCAGCAAAAGATCACTCT | 38700 |
| 5075 TTGGGGCTGAAGCCAGGAA | 16733 GAGGGCCACCAGTAAGAACCAGAGA | 27717 GGCTGAATTGACAGCCAGGGTTTG | 38701 |
| 5076 CAGTGCCACTGGCAGTGA | 16734 CCTGGGCCAGACAACTGA | 27718 CCCAGCCAAAGTATGTGGGTACT | 38702 |
| 5077 TGAACCCATTCAGGCAGGAT | 16735 CCCAAATGCACTGAGCTCTCA | 27719 CTCTTCTGTTAACCAATGAACCCATTC | 38703 |
| 5078 TGTCACTGCCTGCTCCTTCT | 16736 TTCTTGGGCCAGTGAAGAGAAAA | 27720 CGCAGCCAGTTGCTGTCA | 38704 |
| 5079 TACCACAGGCCTGGTCTGAGGAT | 16737 ACCAGAATCTTCACAGAGTTTGTCT | 27721 TCAGGACAGTCATTTCTGCTCTAC | 38705 |
| 5080 ACTGAGACACTGGGGTGCTT | 16738 CAGTGCAATGCTTTCAGGCATGT | 27722 TGAGGGATGGGCTTATCACAGA | 38706 |
| 5081 ACAAATGCATCCTCCGCTTACA | 16739 TTTCTGTGCCAGCTGGTTTG | 27723 GTTGTTTCTGCCCACCTCTTCACAA | 38707 |
| 5082 GACTAAATTGGCTAGAGGGGCAGAAG | 16740 CCTCCCTGAAGTTGCCTTCTCA | 27724 GTGTCCTGGAGACTAAATTGGCTAGA | 38708 |
| 5083 CAGAGGGCTGTGGCCATATTTTC | 16741 TGAAGGGATTCCATTTTCTGGCTTT | 27725 GCAAGCAGGGTTCATCTACTCACA | 38709 |
| 5084 GGGTCCTTGTATAACCCAAAACT | 16742 TCAGTCCCTGGCCCCTGAT | 27726 CAGCAGGGTTAGTAACAGGAGACAAG | 38710 |
| 5085 ACATATCACTTTGAGTTCGGTCAGA | 16743 GCAGATCTCTCTAGGCTTTGTGT | 27727 GGTGTATCCCTCATGACCTTGA | 38711 |
| 5086 GCCTCAGGTAGGAACCTAAAGTCTCA | 16744 ACTACTCTAGTGCCCCTGAA | 27728 GCATATGCTCCAGCCTCAGGTA | 38712 |
| 5087 CCTTCACTGTATCTGACGGGAAAC | 16745 GAAGCGAGCAGCAGTCA | 27729 GGGCCCCTCTGTTTCTGTCCTT | 38713 |
| 5088 GCCCCCGTAAGAACCCATAGACT | 16746 ACAGAGTGTCCACCGTCTT | 27730 GGCATGGCTTATATAGGCGGTCTGT | 38714 |
| 5089 GGCTCACTGGTCCCACCTTC | 16747 CCCCTGGGAGTGACAGTTCAA | 27731 ATCCCCAGCACGGCTGACT | 38715 |
| 5090 GCTTAGTGTGCATTTGCTGTGT | 16748 AGAGGGTGCTGAGGGTTTAGA | 27732 CAGGCAACTTGCTTAGTCTGCAT | 38716 |
| 5091 TGTGTCTACCTTCGGGGAAAAG | 16749 CTCGGAACTCCTGCCAAGAAG | 27733 AGCCTAGGCCAATCAGGATCAAG | 38717 |
| 5092 GCTGCCGCGAGCAACATTTCGAA | 16750 CTCAGGTTCAAAATCAGGCAGGTT | 27734 GCAACGTGGGTGGAGCABCA | 38718 |
| 5093 GCCATCCAAAAAGGAGCTTAGATTT | 16751 GCTGCCTCACTGTCTGATGT | 27735 GCCAGGTCTTGCCCATCCAAA | 38719 |
| 5094 GGTCCGTGCAAGGATTGAATG | 16752 GGCCCTGTTCGAAGCAGTTT | 27736 TACCTCACAGGTCGGTGCAA | 38720 |
| 5095 TCTCTGGCCCACTTAGCACACA | 16753 GACTGGGAGCTCTTGCTCAT | 27737 GCATTTCTGGTTTTCAACGTGTCT | 38721 |
| 5096 GCCCCTGGATCAGCTCCATTTT | 16754 ACCAGTGCGGTCGGGAACA | 27738 CCCCATGCTCCATGTGCAA | 38722 |
| 5097 GAGCAGAAGTGTTCTTGTCACAT | 16755 GGAAATGGCACACTGGTTCTCA | 27739 TGACCACTTGTTACCACTGAACAT | 38723 |
| 5098 GGCAGACATCCGTTCAGGTA | 16756 GCTGAGCGTTGGAAGCCATT | 27740 GTGCTGACCAAAAGCCAGACATC | 38724 |
| 5099 GACCGCCTCTGGAAATGTGTGT | 16757 CACCCCTGACATGTGTGGTACA | 27741 AGAGATACACCTCCCAGCATGA | 38725 |
| 5100 TGCCCAGCCTCAACACCATT | 16758 GGACAAGTAGCGATCCACTGACA | 27742 GGTTAGCCTCACCCACCTGTTC | 38726 |
| 5101 GACAACACCGGCACATCTCA | 16759 TTCCACCTGGCTCCTATCTCTT | 27743 GCAATGAGCTCTTGATCCATCTGA | 38727 |
| 5102 CTGGGGCCTAGGCTGAAGA | 16760 CAGTGTATCTTGCGCAGGGTTTC | 27744 GAGGGTGGAGAAGAACGGTACACT | 38728 |
| 5103 AAGAGGCTTAGGAAGGGTTAGAACTAC | 16761 TGGGGTCCTGGGAGCCAAAT | 27745 CCCAGAAGGGTTAAGAGCCTTAGGAA | 38729 |
| 5104 CCAACTTCGACCCCACGTGAT | 16762 CCGGAGTGGAAGGGCAACAATA | 27746 GGAAAGGCGACCCCGAACTT | 38730 |
| 5105 GTCAGCTCTAAACCACTCTCTTTCA | 16763 CTGATGCCAAGCCCGTATATCAT | 27747 GCAGAAGCATTAGCAGTCAGCTCTA | 38731 |
| 5106 GGTGGGTACAGTGAGGTGAAATG | 16764 CAGATGCCTGCTGCTTCTGT | 27748 AGGGCAGGTGGTTACAGTGA | 38732 |
| 5107 TGGCTCCCAGCAACAACAAA | 16765 GAGACAGGGTTTGCAGGAGGGAA | 27749 GCAGAGGCAGATAAGGAAAG | 38733 |
| 5108 GCCACCATACCTTACCCACAGTA | 16766 GGCTGGGGTCACTGTACTTTCTT | 27750 GAAGCAGAGCCACCATAGCTT | 38734 |
| 5109 GGTCAAGGACACACAGAGATGT | 16767 CPTCPTCCCCACAGACCAPTG | 27751 GGGCCAACTTCTGTGATTCTAGGTCAAG | 38735 |
| 5110 GGAAGCTCTTTCCTGCTGAGAGTTAG | 16768 AGCTGGGGACCAGGATGAAC | 27752 CCCAGGTAGAGTCACTGCTTCTGT | 38736 |
| 5111 GGACCCCATTGATCAGGGTAGATG | 16769 GGTTGTGACAAACACGCACACA | 27753 AGACTTCCAGAGGGACCCATTC | 38737 |
| 5112 CTCCCCACCACCTTCTCAATTTTC | 16770 CACTTCTTAGGGCTTCCGGTTTC | 27754 ACCCTTCCCCACTACCTTCT | 38738 |
| 5113 AGGCACCTGGCTGTGCAA | 16771 CCGGGGGCCCTTCAAACAT | 27755 GCAGTTGACAGGAAGCAGAGA | 38739 |
| 5114 CTCGAGTCCCTGTTGGTGTGT | 16772 CACCCACCCTTGCCAACCATAA | 27756 TCCAAACAGACCTTCCCCTCAGA | 38740 |
| 5115 ATGGGGACCCACATGCTCCTTA | 16773 CCAAAATGATGGCAAGCAGCTACCTA | 27757 ATCCCAGTTGGCCCCTTGT | 38741 |
| 5116 TGCTATGGTCTGCGGGGTAAG | 16774 GTGCTCACCAGCCACATTCT | 27758 CCCAAGACGGGGCTGCTAPG | 38742 |
| 5117 GGTCTGGTAACCTTCCAAGGAAGTAAG | 16775 CAACAAGTGCCACCCTCAGA | 27759 GCCCTAATTAATGGTCTGGTAACCTTC | 38743 |
| 5118 CTCCGCATGCCACAGTCTGTTA | 16776 GCAATGGTCATGGATGGAGCTT | 27760 GGAGTCAGGTGTTAGCACTGT | 38744 |
| 5119 TGACCGGCCCATTGGATGA | 16777 GTGCGGGGCCTCTGAACATA | 27761 AGGCTGCAGGTCCTTTCTGA | 38745 |
| 5120 GGCATCCCCACTTGCAAGAAATCAAG | 16778 GCTCCAAGACCAGCCATACCTA | 27762 CCCAGCATCCCCACTTGGAA | 38746 |
| 5121 CTCACCTCACTCTGTCAATGGTAAAC | 16779 CTTTGCTGCTAGGTTGGGATCA | 27763 CGAGCTGCACCTGCTGGTCA | 38747 |
| 5122 ACTGTCCCCAACCCAGTTCA | 16780 AGGGACAGCTGCCCAGGTT | 27764 TGCCTCCCACCTCTACCCTATT | 38748 |
| 5123 ACGCAGGTCATGACCACAGA | 16781 GCTGCACAGCTGAGAATCCTT | 27765 TCATGATAGGTAGATACGCAGCTGAT | 38749 |
| 5124 AACCCTAGCGGCCGGTGTGT | 16782 TCGGTCCCGATGGTCCCTTAGA | 27766 GGACCGCTTCGGTGTGGAA | 38750 |
| 5125 AGGACCCCAAAGCCCATGAAGA | 16783 CCCAGGTCTGAGCCACTTACTCT | 27767 TGGGCAGTAGGACCCCAAA | 38751 |
| 5126 GGTACCTGATGGCCCTCTCTTG | 16784 GCCCCATGCCTATAACCTCCTA | 27768 AGTGAGCCCCGGGTACCTGAT | 38752 |
| 5127 CCTGTGCCTGGCGATAGATAAGCAA | 16785 CTATGAAGCAGCACCTTCTCTT | 27769 AACAGCCCTCTGCCTGCATA | 38753 |
| 5128 TTGCTTCCCTGGGACTCA | 16786 GTGTGTGAGGGAAGAGAAACTTG | 27770 TCTCCTCTTCCTGCTGTTT | 38754 |
| 5129 AGAGCAGGAACACTGGAAAACTT | 16787 TCCCTTGGCCAACTCCCTT | 27771 GTCACAGTTAAACAGCAGGAACACT | 38755 |
| 5130 CAGGTGAGAGGACACAGTGAT | 16788 CCCCTCTCTGACCATCCATATCT | 27772 AGAGGCAGTGGCAGTCAGAC | 38756 |
| 5131 GCAAACCCACACTTTCTCTGACT | 16789 CCTGGGGCTGAGTGTGCTTAAG | 27773 GCAACCCAAGGTCAGCAA | 38757 |
| 5132 GCAGAGGGAGAAACAACCAGAA | 16790 AAAAGATTGGCTGAGGCTTCTGT | 27774 GAGTAGGATTAGGCAGAGGGAGAAA | 38758 |

| | | | |
|---|---|---|---|
| 5393 GAACAAACCGTGTGGGCAAT | 17051 GCACGGGCTGGAACTCTCACTTC | 28035 TGGGGTGGAAGAGTGAACAAAC | 39019 |
| 5394 AGGCAGGGGAAACGACAGAA | 17052 GAGCAGGAAGCCTGAGTCTTGA | 28036 GGCTGATGCGAGGTGAGTGAAA | 39020 |
| 5395 CAGCCTTACAGGTGAGCCTTTC | 17053 CTCCTCTGTTCCCTTTTGTGGAT | 28037 GGCAGTTTGTCCAGCCTACA | 39021 |
| 5396 AGTTGCTAATGTCCAGTGTCAA | 17054 AGGACAATGCCCTGGAAGCAAAT | 28038 TGTCTCACACAGAAGTGCTAAT | 39022 |
| 5397 TCAGTTAGGTCAATCAAGCAA | 17055 GCAGGGGTTGGGTTTGCAGTTGA | 28039 TTCCAGGTGTCAAATACACGAGTT | 39023 |
| 5398 CTCAGTGACTAGGTTTGGGTCTGTA | 17056 TGCCTCCACTCCAACTTCTTTAG | 28040 GTACAGTGCTCAGTGACTAGGTTT | 39024 |
| 5399 TGGGAGAGGAAGCTGCAACA | 17057 CTCCTGCAGTGTGTCACCTTGTTG | 28041 AAATGGCGCTGGGAGAGGAA | 39025 |
| 5400 AGACTAACTGCCACCCTGAGA | 17058 GGCCAATGCACGTACTATTGCTT | 28042 GGGATGCTTCCTAATGCTTCTTAAGACTA | 39026 |
| 5401 GGAGCCATGAAGGGAACTCAAAG | 17059 AACCTGCACACCTGCCAATC | 28043 TGTCCTCAAGGAGCCATGAAAG | 39027 |
| 5402 CACCATAGCTCCTTAAATCCAGAA | 17060 TGGAGCGAAGTCATGTCAGTCT | 28044 GCTCTACCATACACCATAGCTCCCTTA | 39028 |
| 5403 GTGAGGGAGGTAGGGTTTCAAG | 17061 GGAGGGGCTACTAGAAGCAAAC | 28045 CCTGAACAGGGTGACGGAGGTA | 39029 |
| 5404 CTGACTTCTTAGCCACCGTACA | 17062 TGCCTGGCAATGTAGAAAGGAT | 28046 GCTGGACAATTTTCTAGGTGCTGACTT | 39030 |
| 5405 TCACTCCGGAGGAAGACAAAG | 17063 CCGGCCTCTCTCACCATGT | 28047 GGGCTCAGCCTGCTTTCACT | 39031 |
| 5406 GGTCAGTGGCAAGAGGAATCGAA | 17064 TGGCATGCCCATCCACCCTAA | 28048 GCTGATGCATTGACTGGCTGTGA | 39032 |
| 5407 ACTCCCCTCTTTCCCAGCTT | 17065 CCCCTGTGTTTCGGGTGAT | 28049 AGAGGCCCTCACCATGTAAGA | 39033 |
| 5408 GGTGAGGAAAGAGTGGTCCCTGAA | 17066 GGTTGCCAAACTGTCCCAACT | 28050 GCTCTCAGTAAAGGAGGGTGAGGAA | 39034 |
| 5409 GGAATGGCTGCAGAGTTGTGA | 17067 GBCACAGATTCTGGTAGAATGGAA | 28051 CAGGATTCTGAGGTCATGAGGAAT | 39035 |
| 5410 CTCTTCACCAGGACCATGTACCTAGAA | 17068 CATTTCCCCTCACAAGCCATT | 28052 CTCAGCTCTTCACCAGGACCAT | 39036 |
| 5411 CCAGGTAGTGTTCAGGCTTTTGACA | 17069 GACTCAGCCCGGAATTCGTT | 28053 GGACATCGACCCCAGTTAGTGTTC | 39037 |
| 5412 TCCTCCCATCGGCATCA | 17070 CCAAGGTATGGCAGGAGTTTGT | 28054 CCCAAAGTGCAAGGCTGTCA | 39038 |
| 5413 TGGGGATGCATGTCCTGACT | 17071 TGCAGTGCTGCTCCATGTGT | 28055 GTCCCATGTTTGGGCATAGCAT | 39039 |
| 5414 CAGAGCTCGTGAGTGATCTGCTT | 17072 ATCCTAGGCCCCCGTAAGTCA | 28056 TGGGTGCCTCATTCTCAGTACA | 39040 |
| 5415 GTGCAAATGCCTGAGATCAAAG | 17073 CGTGGCTTGGAGAGAGATAATTCA | 28057 AGACCTTGGACTTGGTGCAA | 39041 |
| 5416 TCGGGCCCCATAGGCAACA | 17074 TCAAACCCACCAACCCTACA | 28058 ACTCTGCCTAGTGTCCATCTTTCT | 39042 |
| 5417 TCTGAGTTCAGTAGCAGACAGTGA | 17075 CCCAGGGTTGGGGTTCCTT | 28059 GGTACCAACCACCGATTCTGAGTTC | 39043 |
| 5418 GTCTCAAAAGCCTGAGGTCTGA | 17076 CCCATCTTTTGTCCAGGCACTT | 28060 GTCAGGGTGCAAGGTAGCTAAG | 39044 |
| 5419 GCCAAGTCTACTGGCTTGACA | 17077 CTGCCAGCCTTGAACTCTGT | 28061 GGTTAGGCAGGAAGCCAAGTCT | 39045 |
| 5420 GCATTGTCAAGACCCTGCAATTCTTC | 17078 CCCACAGCATGCATGACAAAC | 28062 GCAGGGAGAAGCATTGTCAAGA | 39046 |
| 5421 GCACAGCCTTAGTTCCACCCTTGT | 17079 ACCAGGCAGCTCCCATCTTC | 28063 GGTTTGACCCACAGCCTTAGT | 39047 |
| 5422 ATGAGACAGCCACCTCTCTAATTG | 17080 CAGGAGCCAATAGAAGTCGGGAATA | 28064 GCCCTGGAATGTGAGTCTATC | 39048 |
| 5423 ACCAGCCATTCAGTTCAGA | 17081 GGTGTACCCAAGCATAAGGTTT | 28065 GAAGTAGCCACTCTTTGCTTCCAA | 39049 |
| 5424 TCTATCTGCTCCTTCCTCAAG | 17082 AGATGTGGGAGGAAAGGATGTTC | 28066 CCACCTTCTCAGGTGCATCTCATC | 39050 |
| 5425 GCTTTGCACAGGGTAGGAT | 17083 GGTGCCTCTGGAGTTGTGAAGT | 28067 CCCCACAGAGCACTAGAATAACA | 39051 |
| 5426 TGGCCATCCATATTACCTGCAA | 17084 GCCAAGTTCCCAGACAATGAATC | 28068 GCTGCACATTTGTGCTGGATTG | 39052 |
| 5427 GCCTCCGCCTATGCTGGAATTA | 17085 GCCAGATAGGGCGAGTTC | 28069 CCATCTTGGCCTCCGCCTATG | 39053 |
| 5428 ACCAACCTGGAGGCCCTGTA | 17086 AGGAGAAATGCATTCAGGACACT | 28070 GCTGTTCTCTGAGCTGACACCAA | 39054 |
| 5429 GAGGATGAAAGAAAGCCAAGTTGT | 17087 CCACTTGTTAGCCCTCAAAGCAA | 28071 AGCCCTCACACTGGTAAGA | 39055 |
| 5430 GAGATGCCTGTGGGAAGAAGT | 17088 TGGGCTTGACCTACCTGCTT | 28072 CGGCCTGGAGATGCCTGT | 39056 |
| 5431 TGCCCCTTGTGGGACAGTGA | 17089 AACCTGCACCGTGGGACTCA | 28073 CCTTTGGGCTGCCCCTGT | 39057 |
| 5432 GGGTGTGAGAGCGACGTTTT | 17090 GGTTTGACCAGGCATGTCACTCA | 28074 GCATACTAGAAGGCTAGGGTGTGAGA | 39058 |
| 5433 TCCCGGGGCACTTTCCACTT | 17091 TGACTGGCTGCACCGTCAA | 28075 ATGGCAGGAGGCACCTT | 39059 |
| 5434 CCTTGGGGATTATGAGCTTCCATT | 17092 ATGGCCTCCGTGCCTGATC | 28076 TGACGGGCCTTGGGGATTATGA | 39060 |
| 5435 TCCCTCATCTGAAATTGTGCATGT | 17093 CCCAGGAAACCTAGAGGAGGATT | 28077 TTCAGGGAGCTGTCCCTCATCT | 39061 |
| 5436 GAGGATGTTTCATTGGCCACAGTCT | 17094 TCATGCAGGGCCACTCTTTG | 28078 GTGACTCGCATAGAGGATGTTTCA | 39062 |
| 5437 TCCACAGCACGGTGTGGTT | 17095 CTCTTTGGCAACTAGAGACACAACTT | 28079 CCCAGGCAACTGCACCAATG | 39063 |
| 5438 GCTTGTAGCCCATGTAGTTCA | 17096 GGAATATTGGCTCAGGTCCAAGAA | 28080 AAGAGGGCCTCTGCTTGTAG | 39064 |
| 5439 AGGCTGGCTCCTTCCAGATATGA | 17097 CCCCGGCCTTGAAGTGGTCTTT | 28081 AGACCTCAGGCTGCTCCTT | 39065 |
| 5440 GAGGCAGCAGTGCTTTGGGT | 17098 AGGATGGCACCACTGACACT | 28082 TGGTCTCCCATCCCCTTCACA | 39066 |
| 5441 GGTTCCTACTGCCAGTGGATAGA | 17099 GAGGGGCCCTAATGTCTCTCTT | 28083 GGGAGAAGGAAGCAGGTTCCTA | 39067 |
| 5442 GCTGATGGGCATGGAGATGAA | 17100 GCTGTATCTCAATCTTTTCCAGGAGT | 28084 CGGCAGGCACAGGATTCAA | 39068 |
| 5443 TCCAAGGAGCCAGGAACA | 17101 GCCTCCTCCAGACAAATCCAA | 28085 AGCAGAAACTCCCTCCTTCTTC | 39069 |
| 5444 CCAAGATACTCATCGTTGTCTGAACT | 17102 GTCCCTGGATGAACCCTGTTTG | 28086 CACCAGCTCTGTGAATTCTGTGA | 39070 |
| 5445 GTAAAAGCTCAGGGAGTACAGT | 17103 TGAGTGCTGTGGGACTGA | 28087 GGGTCCCAGGCAAGCAGTGAA | 39071 |
| 5446 ACACCTGGCATTATCAAGACGTAA | 17104 ACTGCGCATGCTGCAAATGT | 28088 CCAGACAGAAAACACCTGGCATT | 39072 |
| 5447 CAGGTTTGGTTAGCGGAGGACTT | 17105 CCTCCACCTCATGCACACCCTTT | 28089 GGGTAGATAACGACAGCAGGTTTG | 39073 |
| 5448 GTGACAGTAGGGCCTGAAGGAT | 17106 CCTGGGGATGAGTAGCAACCAA | 28090 GGCACCTGTGTGAACATGGTAGT | 39074 |
| 5449 TGGTGTGGACAGTCCACTT | 17107 ATTGACCCCACGGTGTCTC | 28091 GCATAGGCTCCTTCTCAAGTCGTA | 39075 |
| 5450 TGGGACCTAGGTGCTGGTGTT | 17108 GTGGAGGTCTACGTCCTCAGTTG | 28092 TGCTAATGCAGGGTGGGACCTA | 39076 |
| 5451 CCCCATCTGAGGCCCTGAA | 17109 CPGTGCAAAATCCTTCCGTCTTG | 28093 AGGCCCTGTTTACCCCATCTGA | 39077 |
| 5452 TCTGGCCCTCTACCGCTTGTTA | 17110 GCCAGAATACCGAGGTCTTGGTAG | 28094 CACCACATTTCTGGGGCCTCTAC | 39078 |
| 5453 GATCGGGAAACAGGGTCTGAAG | 17111 CCATGTGAAGTGAAGATCGGGAAAG | 28095 GGGTTGAAGTGAGAGTCGGGAAAG | 39079 |
| 5454 TGTCAATGGTGATCGGAGGTTTC | 17112 AGGAGAAAATGGTGCTTGTGGAA | 28096 GCAGGAAAGCAGAGTGCAATG | 39080 |
| 5455 CCTGCCACTTGCATCCATCTCT | 17113 CACCAGCCCCAAAGCACAAA | 28097 TTGATCCAGTCCTCCGCCACTTG | 39081 |
| 5456 CAGTGGGAATACTCTCGGCATCT | 17114 AGCAGGAGGAAAGCAGGTCTTG | 28098 AGTAGGGCCACAGTGGGAAT | 39082 |
| 5457 GTCCTGTAGTGAAATAGCCAGATTCTA | 17115 TGATTGGCAACACTGTAGGTGAT | 28099 TGACACTGGGGAGTCCTGTAGT | 39083 |

FIG. 36I4

| | | | |
|---|---|---|---|
| 5458 TCAACCTGAGAGGTCCCGAGAT | 17116 AGTCTGAGCATCCCTTGTCTGA | 28100 GGGAGAGGAGTTCAACCTGACA | 39084 |
| 5459 GGGCTGATCTGCTGATTTCCTTGA | 17117 TGCAAGTCCAGTGCTGCTT | 28101 CCACACTTACTTTTAGGGCTGATCT | 39085 |
| 5460 GGAGAAGGCAGCCTCTACACTA | 17118 TCCTCCCCAGTCCCCACATTTT | 28102 GGAGTGCCAGTCCAGGAATGTT | 39086 |
| 5461 TGGCCAGTGGTCTGTACT | 17119 GTGGGAGAGGCAGGTACTTCAGA | 28103 ACCCCTCCTTGGACCATCTGT | 39087 |
| 5462 AGGCCTCTGTGCCACTCTTTG | 17120 GCTCCCAAGCCACTGGTAAAGT | 28104 ATGCTAAGGCAGGGCCTCTGT | 39088 |
| 5463 GTCTGCCCTTGACACCTCAAAGA | 17121 GGCTTGGACAAAAGGGCTGACAA | 28105 GGATGGGAGTCTGCCCTTGA | 39089 |
| 5464 GAAGGAGAAGCTGGGGACTCGGTT | 17122 ACCAGCCCCAGAGAGACATT | 28106 GCACAGCTCAAGGGAAGGAGAA | 39090 |
| 5465 CACAGCCAGCACTAGAGACAATC | 17123 GCACCTGGAAAAGGGAGTGTGA | 28107 GGTCCCTGCAGCTTTCATCA | 39091 |
| 5466 TCCAGCCCTTGAGTCTTTGTCAT | 17124 ACAGGGTCCCCATGGTCATCAA | 28108 GGAGCTCTTCCAGCCCTTTGAGT | 39092 |
| 5467 CAGGCACACTGAGATGCCCATA | 17125 CCAGTGCCCCTGCACAGTATT | 28109 TGTCCAGCCAACTGCCTTTC | 39093 |
| 5468 CCACTTTCACATCCAAGAAAACTGT | 17126 CAGCACGGTGTCACTGAAATG | 28110 AAGAACCTACCACTTTCACATCCAA | 39094 |
| 5469 GCTTCCCAGTCACACATAAGA | 17127 GGTCCAGGACCCTTCAACACCTA | 28111 TTGTTTTACCCTCCCCTTGCTT | 39095 |
| 5470 CATGTGGCCTTTAATGTGTGGATAAG | 17128 CTTTGGCAGGGAGGCAGAAA | 28112 CCCAGGCACTGCAATTCTCCAT | 39096 |
| 5471 GGAAAGCCTGTGCAATGGATAC | 17129 AGGGTGAGTTGGGGACTGAA | 28113 GGAGGGATTGGCATATGTCAGTGTAAG | 39097 |
| 5472 GACCCTCACCAATGCGAAGGAA | 17130 CACCGTGCAGCCACAAAACT | 28114 GGCTGGAAGTTTGGCTGTCA | 39098 |
| 5473 CGAGCAGGCTGAGGGAAGTCT | 17131 AGGGGAAAGGTGAAAGCTAAGTAAG | 28115 GCTCAAGAGCTTCACCACACA | 39099 |
| 5474 GTGCGAGGCAGTAAACCCAAGT | 17132 GCACTTAAGGCTGAGCTTGTGA | 28116 ABCGACAGTGCGAGGACATA | 39100 |
| 5475 CATTCACGTTGCTAGTTCTCTCTTC | 17133 GGAGCAGCTACGTTCATGTCT | 28117 GTTTCCCATCGTTGATACTTGCATTC | 39101 |
| 5476 GACTTCCAACCTGGACTTAGACAT | 17134 TCCACATGCCTCAAAAAGACACA | 28118 CCTTCAGCCTCACAAGAACCTGACT | 39102 |
| 5477 CTCGCAAAATCCTCAGATCCTTTGT | 17135 GGATGTGTTTGTGAGCCGAACAAG | 28119 AGGACCCCTTTCCCTAGAGTTC | 39103 |
| 5478 GCAGACACATGGGGCTCTACTTAC | 17136 ACCCCTCGGGAGGACGTGTCA | 28120 AGGACACCAGGAGCAGACCAT | 39104 |
| 5479 CTCCCACCCACATAAGCAAAGACT | 17137 CCCACACTGTCACCCATCAT | 28121 TGTCGAAACCTCCCACCTACAT | 39105 |
| 5480 CACTTGCAGCCGACTTTGGTA | 17138 GAGGACAAGGGAATGCACCTA | 28122 CACAGGCTGGCAGTAAAACAGA | 39106 |
| 5481 ACCTCCCTATGTAGTGAGCTGTTAG | 17139 TGACAGACCCACTGAGCTGACT | 28123 AGGTTTGAGAACCTCCCTATGTAGT | 39107 |
| 5482 GCAAAGGTCTTCATAGGGCAGAT | 17140 GCTTGGCAGTAGGACAGACCAAA | 28124 CCCAGCCCTCTAGCCAAAGGTCTTC | 39108 |
| 5483 GACCAGAGCTGGCAAATTCTACA | 17141 AACTGGCCTTCACTCTGGAAAG | 28125 GGTTACAACAGCTTGTAGGTCCTTGA | 39109 |
| 5484 GCCTGGAATGTGATCCATCAATGTT | 17142 GTTCCCTTTCTCCTCTACCTAGCAT | 28126 AAAAAGAGGGCCTGGAATGTGA | 39110 |
| 5485 GGGGAAGAGAGGTTAGGGAAGTGTT | 17143 GCTGAGCTCAAGCCCTCTATCT | 28127 AGAGCCTGGGGAAGAGAGGTTA | 39111 |
| 5486 GGCTACTCCTCCCAGTCTGTTGT | 17144 AGGAAGGGGATGAGCACGAA | 28128 CCTCTGTGCAGGATAGAATGGCTACT | 39112 |
| 5487 CCACCCTGTGGATTTACTTTCTTCA | 17145 TGAGGACTTCCCCTGCTGTGAAAC | 28129 GCCTTCCACCTGTCTGGATTT | 39113 |
| 5488 GGGAATCATGTGGGGTGGAATTC | 17146 TCAGGTCCACCACTGTGAAAC | 28130 CCTCCAAACCTGCAACAGGGAATC | 39114 |
| 5489 AGTGAGGGCCTTACACAGTGA | 17147 GGGATGTCGGAGCTGCTAGGTT | 28131 CTGCATCCTAATGTGCAGGAGTCA | 39115 |
| 5490 GAGCAGAGACAGCAGTGTTGTAA | 17148 GGGACCATCCCTGACTCTTACATT | 28132 CGGAAGAGACCTAGAGCAGAGACA | 39116 |
| 5491 GCTGCTGTGATTGGGAGTTG | 17149 ACCCGGCCATCTTTGGTTACA | 28133 GGGATTCACTGGCTGCTGGGAT | 39117 |
| 5492 CTCCCCTGGTACTCTGGAATTGA | 17150 GCTATAGAGCCGTCTGCATCCAA | 28134 GGCCTTACTCCCCTGGTACT | 39118 |
| 5493 GTGCAGGGTAGAGAACTGATTCTCA | 17151 CCATGGTGCCAGAGGTTCAGGTAGAAG | 28135 GCCAAATTCTGTGCAGGTAGAAG | 39119 |
| 5494 CCCCTCTGTCCTTGCTTCTC | 17152 GGCTGGACACGTTCAACCTAC | 28136 TCACTTGCACCCGTGTGTC | 39120 |
| 5495 ACTCTCAAACGCTGTGCTTT | 17153 AGGTAGRTGGCAAAATCTGTGGAA | 28137 CCATCAGTGTAGTTCCTCTAACTGTCAAAC | 39121 |
| 5496 AGTCAGCAGGAGGACTTGGAT | 17154 GATGGAGCCTGAGGCATTAABCA | 28138 GGCAGAAGACTGCAAAAGTCA | 39122 |
| 5497 GGACAGAAGCCCATTTTAAGCAT | 17155 GGCCATGGGACAGCATTTCT | 28139 GGCAGGAACCACCTGGACBA | 39123 |
| 5498 ACTCCGACCAACCCAGACCAA | 17156 CAGACCAGAACCCCATGCTTTG | 28140 ACAGCACCAGACTCCGACCAA | 39124 |
| 5499 CTCCAATGCCATTAGCTCCAGAAC | 17157 GAAGTCCTCTGCTGCTGGAGAGA | 28141 ATCTGACCTCACTGCTCCAATG | 39125 |
| 5500 GCTATGTGCCCTCTTGGGGTTAC | 17158 ACAATCTAGGGAAGGCAATTTGTCA | 28142 CTGGATTTCAGGCTATGTGCCTCTT | 39126 |
| 5501 AGACAGTGCTGACTCTGTGAGTA | 17159 CCACTGTCTCCCTTCCTGAATG | 28143 CAGACTTAAGCCAGCCAATTACACA | 39127 |
| 5502 GCTCTGCTGACTCCTCATCTCTTC | 17160 CAACTTGGCCTGGAACCAGGAT | 28144 CTGCTGTCTGCCTGCAATG | 39128 |
| 5503 ACTCGAAATCATGGCTGATTCTGT | 17161 ATGGAGCCCACTACCGAAGTA | 28145 GCTCCACCATCCTTACCTTAACTCGAA | 39129 |
| 5504 CACCAGCAACTACAATGGCAAA | 17162 CAACCAAAGTTGCAACGAACT | 28146 GACCCTCACACCAGCAACTAC | 39130 |
| 5505 GCCCTGACTCAACTTCCCTCTGT | 17163 GGGCATGGTGGAAAAGCTTGA | 28147 GGTTTCCATGCCTTGACTCAC | 39131 |
| 5506 GCCATGGCCTGTGATCTCACTTA | 17164 GCATGGAGCCAACAGTCAGT | 28148 CCAGAATGCCATGGCTGTCA | 39132 |
| 5507 CAGTGCAGGCAGGATGTATGTGT | 17165 GCCACCGCACCTGGACTATTT | 28149 CAGCAAGTCAAGGCACACAGT | 39133 |
| 5508 CTCTCTGCCTCAGTAGTTGT | 17166 CTTTATTGGCACCATCTCACATC | 28150 GGCCTGGGACATACTTAATC | 39134 |
| 5509 TTCTATCAGCACCCGCCAGAA | 17167 CGTTCCCTCTCTCTCCAACTTTAC | 28151 TGGCTGCCCTTCCTATCA | 39135 |
| 5510 GGTTGGAATAAAGGGCACAGCTT | 17168 TGTCGGATCCGAAGAA | 28152 GCTGGAAGACTGGGTCAAT | 39136 |
| 5511 CCCTCCCACTTGCTGTGTTATGA | 17169 GCCCCATTGCCTACCTTTTCAGA | 28153 CGTAGGCCTGATTAACTCCAGA | 39137 |
| 5512 GGGATTCAACAGTCATCAAACA | 17170 TGKCTTCCAGGTCAGCATCA | 28154 CCTCCCAGCAGGAGATGAACA | 39138 |
| 5513 GCGGGGTTAACATTTACTCAGCAT | 17171 TTCAGCAGGTGGCTGACACA | 28155 GCAAAGCCTCTTCCATCTGCAT | 39139 |
| 5514 GAAGTTCAGTGGATATGCCCTCATT | 17172 ACCTCCACATCCTCTGTCAGA | 28156 GAGGCAAAGGAAGTCCAGTGGATA | 39140 |
| 5515 ACTCGCAGTCCCTTCCTAAT | 17173 GTGTGGCCAAAGGTTGTAGA | 28157 GTGGGACACAGGGAACAACA | 39141 |
| 5516 ACCACATTTGACTCAGGGTGTT | 17174 CCAAGAAAATCACGTTTGGAAAGA | 28158 CCCACCGCTGGTGTTTGGAAAA | 39142 |
| 5517 GCCCCAGTGATTTCCTTTGACA | 17175 CACCAGCCATCCGTGTGT | 28159 CTGCACAGCCCCAGTGATTT | 39143 |
| 5518 GAAGGTCCAACCCACATCTTG | 17176 GTCTCAGGCAGAAAGTCA | 28160 ACACCAACCAGGAAGGTCCAA | 39144 |
| 5519 AGCGCCCCTTCCTCTTTCTA | 17177 GTGGTGTGCACTGAGTGGAT | 28161 TGCAAACAGGTCCCTGGAA | 39145 |
| 5520 CCACTCCCTGTGTGGTTGGTTATC | 17178 GCACCCACAGCACCACAT | 28162 GCACGGCTGCTGGGTTATG | 39146 |
| 5521 AGGCTCGTGGCTGGAATCATCT | 17179 GCACCAACTAGCTGACCTGTGA | 28163 GGCATCACCAGCGGTGATTTGA | 39147 |
| 5522 GTCGTTGCCCTCTGGCCCTTATC | 17180 GGGAGGGTGCAAGGAGAAAGACA | 28164 CCTTTTCTCCCAATTGCTACTGTGT | 39148 |

| | | | |
|---|---|---|---|
| 5588 TCCAAGCAGGAGACAAAATTCACT | 17246 CTCTGGTCCATGAACTCATTCCATTTC | 28230 GAGAGACTTTCCAAGCAGGAGACA | 39214 |
| 5589 GGCGAAGAGCCCAGTCATCA | 17247 GCAGTGTGGATCAGCCTGTACT | 28231 ATAGAGGTACAGGGCTGAAGA | 39215 |
| 5590 GGTGCTTGGAGCATCTTCAGAAA | 17248 CTCAGCAAGAATCAGTGACTTCCAA | 28232 ACTCAGGGTGCTTGGAGCAT | 39216 |
| 5591 GCACCAGAAGCCCTGAAATCAAC | 17249 CCATTCCACAGCCAGCACAGA | 28233 TTGGGCAGCACCAGAAG | 39217 |
| 5592 GGAATTTGCAGCTGCCTGATCT | 17250 GGAGAGTTAGAGCCATTGGGGAACA | 28234 GATTAATCCTCCCTGCCTGGAATTT | 39218 |
| 5593 CAGCATTCATCCCCTCTAAACGAT | 17251 CAGCTGTCTCTGCTTCCAACA | 28235 CCATGTGAGGACACGCATTCATC | 39219 |
| 5594 CTCCAAATCCAATACCCCATGGAA | 17252 GTGAGAATTGCCTGCACAAAC | 28236 CCTCTTTCTTCTTCCTCCAAATCCAA | 39220 |
| 5595 GCTCAGACAGCATGAGAGTAATACAGT | 17253 CAGTGCATAGGTTTCACCAGGAA | 28237 GACCTGATTGCTCAGCAGCATGA | 39221 |
| 5596 GCCCTTTCCTCTTTTGGCAGTAG | 17254 GGATGGAGATCACACAGACCCTAT | 28238 GGGAGTAATGAAGCCCTTTCCTCTTT | 39222 |
| 5597 CCCCTCACAATGGAAAGAGATTTG | 17255 CGGAGCACTCACTATTCTAGACCTT | 28239 CCCAACCCCTCACACATGGAA | 39223 |
| 5598 CAAATGCAAAGGTTCTGAGGCAAA | 17256 CCCCTGTCTCTTGGTTGTTCCTT | 28240 GGCAGAGAACAGGCAAATGCAA | 39224 |
| 5599 GCACAACCCCGCAACTGAAACA | 17257 CCAGCTTACTGACTTGTAAGGATGGTT | 28241 GCAACCAGCAACAGGTGCACACA | 39225 |
| 5600 CCCTGAAACCCACACATTGCAT | 17258 TGTGAAGGGAAGCCTTGGAATCA | 28242 CAAGTCCAGGCTCCCTGAAAC | 39226 |
| 5601 GGAGAGCAAGCAGGCAACACAA | 17259 CACATGGATAGTTCAGTCCCACACA | 28243 GGGCGAATCACTGGGAGACAA | 39227 |
| 5602 GGGAACAAAATGTTCCCAGTCAAG | 17260 GTCTGCTTCCATGAACGTACAGA | 28244 CACACAACCTCCATGTGGGAACA | 39228 |
| 5603 CAGCCTAAAGCAGAAGCCAAGTAAG | 17261 GAGACCTTGTGCCCTTATGCATCTT | 28245 TGACCTTCAGCCTAAAAGCAAAG | 39229 |
| 5604 GCCACCTACCCACCCACTCA | 17262 GAGCATAATCCGAAATCTCTCTGT | 28246 AGGCAGTGAGAAGCCACCTA | 39230 |
| 5605 GGCAATCCGAATCACTTCCTACA | 17263 GTGTTATGTGTCAAGCCTTCTGTTC | 28247 GGAACAAACTGTCGCAATGCCAATG | 39231 |
| 5606 CACCACCAAAAGCCTGATAAAGTGAA | 17264 GTCTGTGAGAGAAACATTCCGTCAATCAAT | 28248 GCTATGGAACAAAAGACACCACCAA | 39232 |
| 5607 CCTGAGGCTCCATGCTTTTAATAACT | 17265 CCTGGGTTCACATGCGTGGTGTA | 28249 TCCATCCTGAGGCTCCAPGCTT | 39233 |
| 5608 CACTTTGATCTCCTATGCTGCTAGT | 17266 GCCAAGTGGGTGTCATCTT | 28250 GGCTGGGTCACTTTGATCTCCTAT | 39234 |
| 5609 CCTTTCTGAAACTATAGTAGCACAGAGTTG | 17267 AGACACGTCGGTTCTGGAAT | 28251 CCAGGGGAAGAATGACATTGACCTTG | 39235 |
| 5610 CTTCCCACTCTGGTTATAGGCAAGA | 17268 CTTAGCCAGGGACTTAATTACACA | 28252 GATCACTCTTCCCACTCTGGTTT | 39236 |
| 5611 CCTGGGTAATAACTCAGATGGGATCA | 17269 GGGGTGTTGCATCTGTGCAT | 28253 TCACTTAGGCACTTCCTGGGTAA | 39237 |
| 5612 CCCTTCATAAGTAGCGTCACTCAA | 17270 GCAGGAAATAAAGCAAGGGGATTTG | 28254 TTTCAGAAAGGCCTTCCCTTCA | 39238 |
| 5613 GGAGGTTATTCACAGCGGCTTCAGA | 17271 GCTCATTGGCTTCCTTACTGTGA | 28255 CTGCCCGCATAGGGAGGTTATTC | 39239 |
| 5614 TCAGACACCTGCTGTTCACTACT | 17272 CCTCAAGCACTAGCCTGCTCAA | 28256 TCTCAAGTCAGTCAGTGTGTGTTC | 39240 |
| 5615 CTCACCTGTACTTTCTACTCTTGCAT | 17273 TGCATTGCTTGGTATGAGGAATTAG | 28257 CCAGTGTCAAGGCTCACCTGTA | 39241 |
| 5616 GCTGCTCAAGTCTAAGTTGCGAATTCT | 17274 CTGCTTTCCGCTAGAGTCTTGTTC | 28258 GAGAACTGCTGCTCAAGTCTAAGT | 39242 |
| 5617 ATGCACTAGGATTGCCTTCTGTT | 17275 GCACGGAAAAGCAAAAGCTGATAAC | 28259 TCCAAGTCATAAAGCACTAGGAT | 39243 |
| 5618 CCACAGTTAGGATCCTTAAGCTTTTC | 17276 TCTCAGAACGGCACCGGAGAT | 28260 AGGGCTGCCACAGTTAGGAT | 39244 |
| 5619 CCCTGTCTCACTGAACAGCTGTAG | 17277 GAGAGCCTGATGACCACAGGAA | 28261 AAGGGCCCTGTCTCACTGAA | 39245 |
| 5620 CCCGGCCTCAACAGTTGTGCTA | 17278 GAACCTGAAACGCATTCAACGTAACA | 28262 GCAGCATCCAGCCGGCTCAT | 39246 |
| 5621 GGHCCACTTACTCAAAGCTTCTTG | 17279 GTCAATATGCATGACCAGGACCTAGA | 28263 TGACCACTTCAGGCCCACTT | 39247 |
| 5622 CCTGTTCACATAGATCCCAGGTCAAG | 17280 CAGCTGGCTAGAGTAGCCTGCAT | 28264 GCCAAAGGAGCCCTGTTCACAT | 39248 |
| 5623 AGGGTGAAAAGCTCAAGTGTGAGT | 17281 CCTTCCTTGCCGTGCAGTAGAT | 28265 GTGAGAGACAGGAAGTCAAAGGGTAAA | 39249 |
| 5624 GCCCTTAGACGAGGTGAGTC | 17282 CCCCTGTCGCCAATGATCCTA | 28266 GGCTGAGGAAGCAGCCCTTA | 39250 |
| 5625 GTTGCACTACAAGGTAGATTGGGTTA | 17283 GATTGGCCTACTGCTAATTCCCTAT | 28267 GGTCGTTAGTCAGTCTGTTGCACTAC | 39251 |
| 5626 AGCACGGAAGCGGATTTCTTTG | 17284 GGTGGAACTTCCTTACAGCAGACA | 28268 TTGCCCCTCTGCCTCTTCTAAA | 39252 |
| 5627 GGCTAACCTGACAATTACCTCAATG | 17285 TCAGGAGGGAGATTTGTGGAAA | 28269 CAHTGAGGAGCAGATGGCTAAC | 39253 |
| 5628 CCTTAGCGGGGAACCATAATTTTC | 17286 TGTGAACTGTTAGGAAGCTGTCTTT | 28270 GGTGGGCTGCTGTAGCCTTA | 39254 |
| 5629 CTGCCTGCTATTTCCCAACTGT | 17287 CCCGGCCACAATGGCATCT | 28271 CCGCTGGAACTGCTGCTATTT | 39255 |
| 5630 CCTGGCCACATGTGTCTGAAC | 17288 GCAACTGCTCCCCTTCTCT | 28272 ACCTGGATCCCTGGCCACAT | 39256 |
| 5631 CCCATCCTACCTCTAAACACAGA | 17289 GCTTTGTCCTCCACCTCCTAAG | 28273 GCTTTCAAGCAATCCCCCCTTA | 39257 |
| 5632 CCTTCTGCTTTTCCACCATGTTAAG | 17290 GCAGCAGCTTCTGGTGCAA | 28274 GTCCTCCTGTCCTTCTGCTT | 39258 |
| 5633 CTCTGTACTGCTCCCCACATTG | 17291 GCTTGGAGATAAAACACGTGTAGGATTG | 28275 CACCTTCTCTGCCACTCTGTAC | 39259 |
| 5634 ACGCCCCGTGATACTGTTCCTA | 17292 ACAGGCGGAATGTAATATCGTTCT | 28276 TGCACACGCCCCGTGATA | 39260 |
| 5635 TCTCGGACCACTTGACGTTTC | 17293 GCCCAGCCAGTGAGCTTATTC | 28277 GCCTGACTTGCCGATCCTCT | 39261 |
| 5636 GGCTGGGTTCAGAAGCATCA | 17294 GCCGCTTGGAAATCAATACACTTTG | 28278 TGCTTCTGTGGGCTGGGTTCA | 39262 |
| 5637 CATGCTCAACAGCACCATGT | 17295 ACCCAGGAGTTCATCACAAACTGT | 28279 TGAAACCGATCATGGCTGAGA | 39263 |
| 5638 GGGCACAACACTGAAGCTCTGA | 17296 CCCTGACTGAGAACCAAGCACTGA | 28280 CCTTGTAGAGGGGCACAACACT | 39264 |
| 5639 GGGTAGATTCACAAAGCAGCTATCA | 17297 ACAGAAGGTAACAGTCTTTCACAGT | 28281 GCTCCCCTGTAGGCGTAGATTCAGA | 39265 |
| 5640 GCAGGTGAGTGTACTGTGAGCTA | 17298 CCAGCTGGTGGATGGCAGATA | 28282 AGCTGTTTTCCAGGTGAGTGTA | 39266 |
| 5641 CAGGCAAGATGTACGCCTTCAA | 17299 GGCCTCCCCTTTCTGCTTCTT | 28283 CGGCCCACAGGCAAGATGT | 39267 |
| 5642 GCAACAGGGAACCATGGAGACAGAA | 17300 AGTTCCTAGCTGTGCAGTCTA | 28284 CCAGGCAACAACAGGAACCATGA | 39268 |
| 5643 GGGCATGCTGCAAGGACTGT | 17301 GTGCAGAGATTGAATTCCCTCAGT | 28285 GTTTTGTTAGCCAAGAAAGGGACAT | 39269 |
| 5644 GGGCCCTGTAAAGGAGAGAAATTG | 17302 GAACCCTCCACTGTCCTTGTAG | 28286 CTCATTGGATTGGCCCCTGAA | 39270 |
| 5645 GTGGCCGAATCCCACCAAAA | 17303 GTGAGGGATGACCAGAGGCTCTTT | 28287 GTGGTAAAGAAGGCTGCCGAATC | 39271 |
| 5646 ATACACAGAGCCGCCATCA | 17304 CGTGGGAAATCGGGAAAT | 28288 CATCGTCTGCCGGATACACA | 39272 |
| 5647 GCCATACCTGAAACCACGTTTAC | 17305 GACTGACCACTGATACTTCCTCGTTAAATCA | 28289 CGGCCTCTCAATTTTGCCATAC | 39273 |
| 5648 AGGTGTAGCTACGGTCGAA | 17306 TGCAACTTTGCAGGTAAGACGAT | 28290 CCAGAAGGAGGCGAGGTGTAG | 39274 |
| 5649 CCTGCCTCCAAACTCCAGTAGA | 17307 GGGATAGGCGAAGAGTAGACAGA | 28291 AACAGAGCCGCCTCCAAA | 39275 |
| 5650 CTTAAGGCCTGGATGTCTGTTTGA | 17308 CAGGTGGATTCCAAGACAGGAA | 28292 CTGCTGACTTCTTAAGGCCTGGAT | 39276 |
| 5651 CCCATTGTCCAACAGGGCTTTTTC | 17309 TGGGCTTTTGTAAAGCGACAT | 28293 GAATCTTCCCCATCTCCCATTGT | 39277 |
| 5652 CAAGGCTTCCTTTTCAGTCCTAGT | 17310 AGGATAGAGAGGGGCCAAATGT | 28294 CCCTCACCAATTCAAGGCTTCCTTT | 39278 |

| | | | |
|---|---|---|---|
| 5913 AGGGGAAAGACCTGCCTTGT | 17571 TCACCTGCTTTCCCTCTTGAAAAA | 28555 ACAACCCCTCTGGGCTCCAA | 39539 |
| 5914 TGGATACCTCTGAGAAGCTGATGAT | 17572 CCAGTTTCATGTGTTTGCCTGCTTT | 28556 TTCTGTAAGGGGCACATGGATAC | 39540 |
| 5915 CAGGACTGGAAGTGAGGGTATTC | 17573 CCAGTCCTAACCTTCGGCTCTCT | 28557 GGGGCCATCAGGACTGGAA | 39541 |
| 5916 GGGGCCTGTCAACGTATTAGTTG | 17574 GTTCACAGAAATGGCTTGCCTTTAG | 28558 ACCTCTCTGCGGCGTGTCAA | 39542 |
| 5917 CCAGTAGGGTCACAGCAGAAGAAAA | 17575 CAGGATGACACTGGAGTTAGCTT | 28559 CCTTTACATTTCTCCAGTAGGTCACA | 39543 |
| 5918 GTGGGTATGTCACCTTAGGCAAGA | 17576 GGGTCCCAGTCAGACCATCT | 28560 CCTGAAAGTCTAGCAATCAGTGGGTAT | 39544 |
| 5919 ACTGTGCCCGATGCTAGGTA | 17577 AGAGAAACAATCAACTGGAAGTGA | 28561 AGCTACGACCTGACGATCACA | 39545 |
| 5920 GCTACAATTAGGCACTGGATCTGGTT | 17578 GCCTGAAGGTTCTTTCGTCACTTC | 28562 GTGTGTTGCTGTGAGGGCTACAA | 39546 |
| 5921 CCTTACCATCAGTTCAGTAGAAGCATAGAT | 17579 GGCACCGTGTATCATGTTACTGCTCCT | 28563 CCCTGCCTTTAAAACCTTACCATCAGTTC | 39547 |
| 5922 GCCGGCAGGCAAATGTGGAATC | 17580 CCTCAGAAAACGAGAAGCAATGAT | 28564 TGTGAGGAAGCGGGAGGAAA | 39548 |
| 5923 GAGCCCTAGTTAAAATGTCCCTGTAAG | 17581 GTGGAGCTCACTGCTTAATTGTGA | 28565 CCCATACAACTCCAAGTCCTAGTTT | 39549 |
| 5924 CTGAGCCCAGAAGACTTATTTTCCAGTTT | 17582 GGAGGCTGTCCCTGTGGCTTTC | 28566 GCCTCCAAAGGCAAAGACTGA | 39550 |
| 5925 GGGTCTTCATATTAGGCTGTCAGATAGTCT | 17583 CGCTTGGTTCATACAAAACCAACT | 28567 GAAGTCTTCAAAGGCTCTTCAT | 39551 |
| 5926 GGCTTAAACCTCCGTTCTTGTTC | 17584 CACGTCCCACTAGGGGTTAAGTTC | 28568 CACCTTTGCACCGAGGCTTA | 39552 |
| 5927 CTGAAAGCCTGGATCTTTCATGGGATAG | 17585 GTGTGTTTCAAGACAGCAAGGAAAG | 28569 CCTGCCTGAAAGCCTGGATCTT | 39553 |
| 5928 CCCTCCAGGTTGTATATGGTTCCTT | 17586 CCCAGTTAACTCCTAGAGCCAAAC | 28570 GCACAGCCTGCAGGTTGGTA | 39554 |
| 5929 CCAGCCAGAAGTGTTAGTGAGAAG | 17587 GGCAACATCCCTCACAGCTTCTT | 28571 CAGCACCAGCCAGAAGTGT | 39555 |
| 5930 CGGCATTTGTTGAGCACAGAG | 17588 GCCTGGATCTTGTTTGCCTTGA | 28572 GGCTGAGAGTCGGCATTGGTT | 39556 |
| 5931 CCAGAACCTATGGCAGCTAAAAC | 17589 GCAGTTGGAAATGGAGCAGTAAAG | 28573 TTTGCCATCTTTGCAGAACCTATG | 39557 |
| 5932 GGATCAGAGAGAACCAGACTCACTT | 17590 TCTCAGGAGCCGGTTTGTTATG | 28574 GGCAAAAGGTGAAAGGATCAGAGA | 39558 |
| 5933 CTGAGTTATGTACAGGGCAGAGATG | 17591 TGAGTGTGTTTGTAAGTGCAGGAT | 28575 GCGGGACCGAAACTGAGTTATGT | 39559 |
| 5934 AGGAGGGCACCTGTAGATTAAAAC | 17592 TGCCCACACATTCAGCTGTT | 28576 TGTGAAAGGAGGCACCTGTA | 39560 |
| 5935 GGCAAAAACATTATCATTGAGCCTGGATTC | 17593 ACACCAGTGAGGAGCCATA | 28577 GGCTGGGAGTGGCAAAAACA | 39561 |
| 5936 ACTGTAGACTCCATCCACCATTACA | 17594 GGTCTGAGATGTTACTTGGTTTCCCAAA | 28578 CCAGAGGGTCTGAGTTCTACTGT | 39562 |
| 5937 TTGTTGGGTGATGGCTGTCT | 17595 AACTGCCCAGCCTGTACCAT | 28579 GAGCCTTCAAGTTGTTGGGTTGA | 39563 |
| 5938 GGTGTGGCTTGGTTTCTTTTTGAAG | 17596 GGAGACCAAATGCCTTTCCTCCTT | 28580 GAAAGTTTTGGTGTGGCTTGGTT | 39564 |
| 5939 CCATGGGCTAAGAACCAGGTGAAAG | 17597 CAGTGAGCACAGACAAAGCAAGT | 28581 CGAGCCAACCATGGGCTAAGAA | 39565 |
| 5940 AAAACTGCTGCTGTAACCTGAATC | 17598 TCTGGGGCTGTCGGGTGTCT | 28582 GGCAGTGAAAACTGCTGCTGTA | 39566 |
| 5941 CCCCAGCCAATCTAACTCACCCAGAA | 17599 GGGTGCATTGCATTGTCTTC | 28583 GGGGTCCCCAGCAATCTAACT | 39567 |
| 5942 GAGCCGTGTAAGAAGGAAGGATCT | 17600 TGTGTTCTCTCTACCTAGACAAAATG | 28584 CCTCTCTGTGTGAGCCGTGTAAG | 39568 |
| 5943 GTGGGGCTTAACAGCCAGTAGA | 17601 CCCCAGCTGCCAGCCTTATTT | 28585 GACAGACCTTGTGGGGCTTAAC | 39569 |
| 5944 GGAACCACAGATCCAGTTAGCTT | 17602 CTGTTTCCTGCCGAGGTTCAACT | 28586 AGGAATGACTGCAACCAGAGA | 39570 |
| 5945 CAGTAAGATGTGTGCCTTTGGATCT | 17603 AGCCCACCAAACCCTAAGA | 28587 GGCATGGTTTCATCTGGTCAGT | 39571 |
| 5946 TGTGTCTGTGTCCCTAGGTTGA | 17604 GCCTCAGTGACCTGTGCAT | 28588 GGCCAAGGACTGGTATGTGTCT | 39572 |
| 5947 CCTCCTGCTACTAGGCTTTGAAC | 17605 GGGAAGCCTTACAAATATGTCTACAGAAG | 28589 CCATGCTTCCTCCTGCCACTA | 39573 |
| 5948 GGGTCGACAAGATGTAAAAAGCTCAAC | 17606 GGGCTAGTAAGACAGATTCAGGAGGAG | 28590 GGGTCTCCGGCTGACAAGATGTA | 39574 |
| 5949 GCAAGGGAGTCTGACCTACATCA | 17607 CCCTAAACTGTTTTCCCACTCTACT | 28591 GGAGAGTACAGCAAGGGAGTCTGA | 39575 |
| 5950 GGTTCCTTCTTACCTTGGAGTGAA | 17608 AAGTCCCATTCCATGATAGTTCAGA | 28592 TACCCCTGCTCCCTCTGCTT | 39576 |
| 5951 CAGCCTTGCTCAAGATGCTGAGA | 17609 GCTCCACTGCACCTGGTTAGTT | 28593 GTAGTTTGAGACCAGCCTGCTT | 39577 |
| 5952 CTCCAACATCAACTCCTACAATTCTCTTC | 17610 GTGAAACTGGCATGTCCAGAGA | 28594 TGACTCTGGCCTATTCTCCAACA | 39578 |
| 5953 CCCACCAGCTACACAAGGAGATTC | 17611 TGAGCAGTTTCAAAATCGTGTCA | 28595 CCAAGATTTCCCACCAGCTACACA | 39579 |
| 5954 CAGCAGCTCTTTCCCCTCTTTC | 17612 GGAAGCATCCAAGCTGTTTGA | 28596 GGTGTTTCTCTCAGCAGCTCTT | 39580 |
| 5955 GCAGAAATCAAAACTGGCTACCAA | 17613 CCCTTCCTTCATCAGCCAGAATC | 28597 CACCAACGACAGAGCTAGAAATC | 39581 |
| 5956 CAGCTAAAAGAGGCTGGAAAGAA | 17614 GGAGGGAAAACATTCAGCTGTGTT | 28598 CAGCATCCTCCAAGGTTCAGCTA | 39582 |
| 5957 GGAAACAGGGAATGAGGGTAGAAG | 17615 CTGAAACCATCGTGCACAAAATTC | 28599 GCTCCTATGGGAAACAGGGAATG | 39583 |
| 5958 GCTAAATGGCAAGTGAATCCCTAGA | 17616 CTGCCTTGCTCTGCATCTCT | 28600 CCAACCAGGAGCTAAATGGCAAGT | 39584 |
| 5959 GGGGAAGAGTGCACTTATCTGTGTTT | 17617 CTTCCAGAAAGTAGGCACAGTTG | 28601 CCCAAACACACTGGGGAAGAGT | 39585 |
| 5960 CGGCTGAGCTGGGAGATATCATAAGT | 17618 CTGTTGATCCCCTTTGCACATCT | 28602 GGGATTAAGATGGGTGAAGCTGGGAAT | 39586 |
| 5961 CCCGTCTTGTGGGTAAACTGTCAT | 17619 CACTGGAAACCATGCCATGCAATAA | 28603 ACCACTGAGTCCCGTCTTGT | 39587 |
| 5962 CAACATGGAGAGACACTGTTCCTA | 17620 CCCTCTAGTTGAAGCTGCCATAACTT | 28604 CCAGATTTACCAACATGGAGAGACA | 39588 |
| 5963 CCAGTTGTCTGGTCTCAGGGACATAA | 17621 CCTCTCCTCATTTGCTAGAGAAGGTA | 28605 ATCCCTGCCACCAGTTGTGT | 39589 |
| 5964 GGGGAACTTGAACTACCACGGAAAG | 17622 CTGCAACTGCTTTTCTCCACAACTAC | 28606 GTTCCTCAAGGGAACTTGAACTAC | 39590 |
| 5965 CATCAGCCTATTGCTATGACGACTGT | 17623 CTCTTTTGCAACACCCTTTCTTTG | 28607 GCAAGGTCACAAGACATCAGCCATA | 39591 |
| 5966 CTGTCCCACTTCATCTCCTTTCTCTT | 17624 CCAGATCCGTAATACCTGGAAATGGTA | 28608 GTCCTCCAAATCCTCCACTTCATCT | 39592 |
| 5967 GGATGGGACCAGATATGCCTGAGA | 17625 CAAGCACTTGTGGCTGTCTGA | 28609 GCAGACCAGGATGGGACCAGATA | 39593 |
| 5968 ACTGCCCCTTCTGACTGAAAACA | 17626 CGACGGAACAACACACTGGGATT | 28610 GATTATGCTGAAAACTGCCCTTGT | 39594 |
| 5969 GGACTGTCTCCTCTCTGGATGTAG | 17627 CGTGCACACGACTTTTTGGAA | 28611 ACCAGTGTGTCCCTGGACTGT | 39595 |
| 5970 TCTCTTCTTCCACCAAACTGACA | 17628 AGTGAGCAGGACCTTGCAAAT | 28612 CAACAATGGGCTAACCTTTCTCTTC | 39596 |
| 5971 CTGCTCCTTCCTTTGGGTCTGA | 17629 GAGCTGTGGGAATTCCATCCTTCCT | 28613 TGCTCCTCTGCTCCTTCCTT | 39597 |
| 5972 AGGGAGGAGTGAGCAAGAAGT | 17630 GCCCTTGCATGGTGTGGTTA | 28614 TGGGGTTTAGGGAGGAGTGA | 39598 |
| 5973 GTCCAAACAGAGCCCTGGAAAA | 17631 CATGCAGGGATGTTTAACTCCAATC | 28615 GGCATATACCGTAAACCTTAGTCCAAAC | 39599 |
| 5974 CCCTCAATCCCTTTCCTGCTT | 17632 GGGTTCTGTAATCAGGGCCATACA | 28616 CACACACGCTTTCCCCTCAATC | 39600 |
| 5975 CCCCTGAACCCAAATTCTGAGATACT | 17633 GGGTTTGGGGTTCACCACATT | 28617 GCTGCTTCTTCCCCTGAACCAA | 39601 |
| 5976 CCCAATGAAGAAGATGCCAGTCA | 17634 GCAGCTGCCAAGCAGATGTT | 28618 CAGTGTTTTCAATACCACCAATGAAG | 39602 |
| 5977 CGTGCTTTGTCAGAATGGTGGAA | 17635 CACATTAACCTTCCACTGCTGCCATTA | 28619 GTGGCTTTGTTCTGACGTGCTT | 39603 |

FIG. 36J2

```
5978 ACGGTATCACACAGTGGAGACAT          17636 CAATTTGGGTGGAGTTAGAGAGAACA    28620 GAGGCATTAGTGTTAGAGGGTATCACACA   39604
5979 GTCGGGGAAAGTGAAAAGAAGTTG          17637 TCCTGTGACCCTATTATCTCCCATT     28621 GTGPAGGAGTCGGGGAAAGTGA          39605
5980 GGTCCAATAAAACCCAACAGT             17638 CBAGGTCTGCTCTCAGAAGABAACT     28622 CCCAGGTAGGTTAGGCTCCAAT          39606
5981 ATGCTGAAAGCTCACCCTTCAA            17639 CTTCTCTGGCATTGGGCTCCTTGT      28623 GCCAAATCCTCTGCAATATGCTGAA       39607
5982 GTGTTTGTCTTCCCACTTCCTA            17640 GGTGAGTTCGAAGCACATGTGGAA      28624 CGTGCAAGAACTAGCTGTTTGTCT        39608
5983 TGTATCGTAGTTGCCCATTGTTCAT         17641 GGTCTGGGCATTAGTGCCATT         28625 GGGAGACAGATGTCAGTATCGTAGTTC     39609
5984 GGCCATTCAGGCCAGTCATACA            17642 CCATCAAGAGCATACAGGGGTCTTC     28626 TCCCACCTGCCTTTTTCAACT           39610
5985 CCTCTTCTAGATACAAGCCCCAATCA        17643 GGCCCTTGGGTCAGAGCTT           28627 CTGGCACTGTTACCTCTTCTAGATAC      39611
5986 AAGTGGGTGTCGGTCTCTCT              17644 CAGCCTCTTCCCCTTTACCTTTG       28628 CCCAGGCAAAGTGGGTGTCT            39612
5987 GCAAGGGTGAAGATACTCACTGT           17645 AGTACCTGCCAATGTCTATCAGTCT     28629 GGCCAGCAAGGGGTGAAGAT            39613
5988 GGGCTGAGAAGGGAGTATGTACTAG         17646 AATCACCTGTGGCACTTCTTAAG       28630 TGAATCCAAATCTTGGGGTGAGAAG       39614
5989 TCTCAATCTTCCAGCTTCTCATTGT         17647 GCTAATAGCTGGCATCTAGGGGABA     28631 CTCCATGTGTTTCTCTCTGCAATCTTC     39615
5990 CCAACCCCAAAGCCACTTCAGT            17648 GCAGATGCATCCTCAGACCATTAC      28632 TCTACCCGTCCAACCCCAAA            39616
5991 CTGCATTCTGCTCAAGGAAGAATAG         17649 AACTCTGATGGAGTGATTTGCCTTA     28633 CCTCATTTATCAACTGCATTCTGTCTCAAG  39617
5992 AGTCGGTACTTGGATACTTCATCA          17650 GCTGCTGATCACAACAGAATGAAAAC    28634 CCTACTTCTCTCCCTTAGTGGGTACT      39618
5993 GCXACTGTTTCTGCTCAATGAAG           17651 GCTCTTTGGACTCTGCCATTTC        28635 CAGGTGTGAGCCACTGTTTCT           39619
5994 GPCGTAGTTCCTCTGAAGCGGATTATTTGT    17652 ACTGTGGTTTTTACTGAGGAAAGT      28636 CTCCACATGTGAGTCAGTAGTTC         39620
5995 TGAGTGAAAGATGGCACTGATCTAC         17653 GGGGACTGAGGGACTTACTTCAAC      28637 TGCATAAGGCCACTTGAGTGA           39621
5996 CCACCTAAGCAGTTCCTGCATGT           17654 CAAGGATGCTGAGTCCAGGTTCA       28638 GCCCAGTTTTCTCATACCACCTAAG       39622
5997 TTCTGTGGGGCTCAGTTTTGT             17655 GGCAGAAGCAAAACCCTTCAGATG      28639 GCTGTTCAGCCTTTCCACATTCTGT       39623
5998 GCAAAGCTAGGCAAATGTCTAATGGATTG     17656 AGCAGTGAGCAGCCTCCTT           28640 GGCCTGAGTGGATGCAAAGCTA          39624
5999 GCACCGTGAGTCTACCAGAAAC            17657 GCCACAAAGCCAAGTGCAAG          28641 TTCCCTAGCACCGTGAGTCT            39625
6000 TGAACATGGGGTCATCACACTTG           17658 GAAGCCCTGGCCAGCTTTCGT         28642 GCCTTGGCCTGTGATGAACA            39626
6001 CTTCAAGGCAGTATTCTGGCAAGT          17659 CCTTCAGCCCAAGACAAGAATTTATCA   28643 GGTTCTGGGCATAGAGACTTCAA         39627
6002 GCAACTAGCTAACTGGCCACAA            17660 GCTGTGTGGGGTACAGTAGACACT      28644 CCCAGGCAACCAAGGTTTTGCAACT       39628
6003 CAACTCCATCAGGGTGGTCTCT            17661 GACTTGGACTAGAGACATGGAATCTT    28645 GCCCTCCCTCAACTCCAATCA           39629
6004 CCACTGTAATCACCAACCACGTT           17662 GGGGATGGTTCAGTAATAACCTACTCTGT 28646 CCAGAGCTGCCACTGTAATCA           39630
6005 GCTTCTTAAGCACATTCTGGCAAAC         17663 CACACTGATGGAGACCACAGT         28647 GTGAGATTTGCTTCTTAAGCACATT       39631
6006 CAGTAGGGTAAAAGAAGGGATTTGTGGATAG   17664 CCAAGTAACTGCTGCAAGAAAACACA    28648 CTGGCTCAGTATCTAAAAGGAGGCATT     39632
6007 GCTTTTGCAGTGTTGCTGCTAAAA          17665 GCATCTCATAAAACCTAACTCTCTGACA  28649 ACACAGAGCTTTGCACTGTTC           39633
6008 GGGAGTTGATCTGTGTGGACAA            17666 GCACCATATTTAGAGGGTATCCGATTTCTGA 28650 GCTCTGTGTCCTGGCAGTTGAT        39634
6009 CCCAGGCAGTTCTGAGGTACA             17667 CAGTGCATCTAGCTATCAAGTCCCAAA   28651 AGCAAGAACCCAGGCAGTT             39635
6010 GCATGTCTAAGCCTCAGTGGTT            17668 CAAGAGAGGAAAGCTCTACTGGAA      28652 GATGCTGCTGTTCGGCAATG            39636
6011 ACXACAACTGGCTTGATTTCCTT           17669 CCATCCTGGCCTAGAAAATGTTA       28653 GGTGTGGCGTACCACAACT             39637
6012 AGAAACTGTAGAAGGAGGAGTCA           17670 ACTTGCTGGGAACAGGATGA          28654 GTGGGTCTCTTGGGAGCATAG           39638
6013 GGGTGTGCATTCTTCACCTCCCTAAG        17671 GACTCGTCAATCCTTCTCCTATC       28655 CGCAGCCTCAATTCCTCTGATTC         39639
6014 GGAGTGTCTTATAGGGGCAAGAAG          17672 TCTTACTTGGCCTACTGCAAAG        28656 GGGCAGGTTACAAGCAGTGTCTT         39640
6015 CCACCAGTTAGCAGAGAATACAGTCT        17673 AGCCTCCACCCTTCTCCAT           28657 TGCCCTACCAGTAAGCAGAGA           39641
6016 GCCTCTTCCCTGCATTCTTCCTTTC         17674 GCTGGTAGGTCACTGTCGTGT         28658 GGGTTGCCCTCTTCCCTGAT            39642
6017 AGCATCAGACACTCGGTGTAC             17675 GGAAATCACCTCGCTAGGAACTTG      28659 TCCAGACCAGCATCAGACACT           39643
6018 GTCCCTTCCTCCATCATGAACTGT          17676 GGCCATTCCTAACCTGACCCATG       28660 TGTGCTGCCCTTCCTCCAT             39644
6019 GGAGTTTGTGTTAGAAGCAGGTAAGA        17677 CAAAGTTTGTGCAAAGAGGGAAGA      28661 GGATGAACTGAGTTGAAAGGAGTTTGTGT   39645
6020 GTGGATGCTTTGAAGGTTGGCTTT          17678 CGCTCCAGTCAATGGCAATGT         28662 GGGAGAGCTGTGTGGATGCTT           39646
6021 CACAGATTCTCATCCTCAGTGGTAG         17679 ACTAAABAGGTCCTTCACACAGAGTTC   28663 TCTCCTCATTTGCCACAGAGTTC         39647
6022 CTGCATGATCGTATTGAGTGGTT           17680 CTGCATGACTGGAAGAGCCAAAC       28664 CCACAGGAACTGCATGATCGTA          39648
6023 GCTCAGAATCCAAACACCATAGCTTTC       17681 GGTTCTGCACACTGGCAATA          28665 CAGCTGGTTTGCTCAGAATCCAAAC       39649
6024 CTGACTGCCTAACTGGGCTCA             17682 GAAACCACACAAAGCAAGAGGAATC     28666 GTCTGCTGACTGACTGCCTAAC          39650
6025 GGGGCTGACTTACCACTGACTCTA          17683 GGAGGTTAGACTCAGAGACATACA      28667 AATGGAGACGGGGCTGACTTAC          39651
6026 GCCAGGGACTAAAGTCAAAAGCCTTA        17684 GCCAGCACAGTCTAACAGA           28668 CTTTCCAGGAGCCAGGGACTAA          39652
6027 GGGAGCCAGGATTTTGAACTCT            17685 ACTTCCTTTACCTGATCCCTCTCA      28669 AGTAACGGGGAGCCAGGATT            39653
6028 TAATACCGCCCGCAGCCTCTT             17686 GGCGTCCAAACTTGAGTTACTT        28670 CCAAGTCGCTGCAAACGCTAA           39654
6029 CCCAGGCAGCTTTCTGGACTGT            17687 GAGAAACCCTGAGTTAGAGGAGATGAAAT 28671 GTGAAAAGCACCCAGGCAACT           39655
6030 CATTTTGATGCATACCACCCTTGT          17688 TGAAACCCTTACACCTGAGTTCTTG     28672 CTGGGTGGTTCCAACAGTTTGATG        39656
6031 CGAGGCTGCTAAGGGAACACAAT           17689 GGCAGGTCATTCAAGGGAAATGAATGT   28673 CTTGCCAAACGAGGTGCTAAG           39657
6032 CCCCATTCCCAGAATTGAGAGAATAAGGTGTA  17690 CCACAGCACCTTCCTCTGTGTAT       28674 CATGATCCCATCCCAGAATTGAGA        39658
6033 GCCCATGCCATATACAGTGCCTTC          17691 CTACAGCCGGTTTCTCTGAACA        28675 CCTGCTTTGGCCTCATCCCTAT          39659
6034 GCCCACAACCACACAGTGCTTGATC         17692 CGCACAGGGGGAGACCTCAGT         28676 CCAGCCCACAAACCACACA             39660
6035 GAAACCCAGTGAACATGAAGGAAGA         17693 TCTCTGTGCGTTCATCGTCTGTGTAAA   28677 GCTGAGTAGAAACCCAGTGAACA         39661
6036 CCAGTTCCATGCTTTGTTCCAATC          17694 CCCAGTGCACAGCCATATTCCAT       28678 ACCTTCATCGAGTTCCATGGTTT         39662
6037 CAGTTGCCTTTGTGTGTCAGACATAC        17695 CCAAGCCTCAGCAAGTCGTGCAGT      28679 CTGCAAACAGTTTGCTTCGTT           39663
6038 CCGATTCCTTCCAGTGTGACTTG           17696 GACTAAGCCTGCTATCTACCACCACTT   28680 AGCACGCCACCGATTCCTTG            39664
6039 GTTGCCTGTTGGGAGATCACT             17697 CCAGTCTGCCCTCTCCAAACCTA       28681 GTCGGACGAGTTGCCTGTTG            39665
6040 TGCCATTACTCATGCTGTCACT            17698 CGTCCATGAAAACACAGCCAAT        28682 CCTCAACCAGCAAAGTGCCATTA         39666
6041 CTCCAGGTGAACACACAAAAATCATGT       17699 CAGCCTTTCTTCAGCTCCTCCAA       28683 GGAACTCTGCAGGTGAACAGACAA        39667
6042 GGGAGGAGCTGACACAGTTCTCTA          17700 AGATTCCCATTGCCTTCTTGGAT       28684 GCATGGGGAGGAGCTGACA             39668
```

| | | | |
|---|---|---|---|
| 6368 GTTAGAGACTGGAAGATGCCATACA | 18026 GATGTACACACCCACATGTAGCAA | 29010 GACACACATCCTCAAGTTAGAGACT | 39994 |
| 6369 CCTCTTGAGTCTTTACCTGTGTGT | 18027 CTGCGTCCAATATGTGTACTGTTCT | 29011 CCTGTTTCCACCTCTTGAGTCTTT | 39995 |
| 6370 GCATTGGGTGCACGTTGAGA | 18028 TCCTTTGCAACTCTGAGCTTTGT | 29012 GCACTGTGCGAGGCATTG | 39996 |
| 6371 CCGAAGATGGCAATGACGTTGA | 18029 GACTGCTCAATACTTGTTGAGTCGTT | 29013 TTCCCGTCTGCTACCGAAGATG | 39997 |
| 6372 CCCAGCCTCTGCAATTCTTTACT | 18030 CCAGCTTCTTCCACAAACCTAGA | 29014 AGAACACCCAGGCTCTGGAA | 39998 |
| 6373 GACCTTGCCCACAAAAGTCAATGTTC | 18031 AACATTCGGTGCAGCTATGGTA | 29015 GAACAATTAGACCTTGCCCACAAA | 39999 |
| 6374 TGGGTCTCAAGTGGCCCAAA | 18032 ACCTCCCATTGCCACTCGAT | 29016 CCTCCTTCCTTTGGGTCTCAAG | 40000 |
| 6375 GTGGGGATTATCTGGGAGTGTGA | 18033 GACTAGGAAGTGTCCTCCTCTGA | 29017 AGAGCTGAGCAGTGGGGATT | 40001 |
| 6376 GGGCAAATAGCTCCTTTCGATCCTA | 18034 TCTTGGACAAGGCATGTTTTGATG | 29018 CTGCTAGGTTTTCCAAGGGCAAA | 40002 |
| 6377 GGGCAGGTATGAGGCTGACA | 18035 CCTGACCACATGCCTTCATATCTCA | 29019 GGGAGCAAATGGGGCAGGTAT | 40003 |
| 6378 GGCTATGGCCTCACTCCATCTTTC | 18036 GACTGTTTGTTCAGCCTAAGTCCTAGA | 29020 GCAGGTTGGCTATGGCCTTCACT | 40004 |
| 6379 GTTGAAGTTCCCTGCATTTCACA | 18037 GGCTGACCTCTCTCCCTGTGTT | 29021 GTTGGGACAAGCTGAGTTGAAG | 40005 |
| 6380 GACCCTGCAGTAGTACTTTTGTTCT | 18038 AGCTCATCAAAATCACCTGTGTCT | 29022 TCATGGATAATTGACCCTGCAGTAG | 40006 |
| 6381 GCCTCATGTAACTCTCTGGGTATGA | 18039 AGTCATGAGACCTATTGCTACCCTTA | 29023 GCAGATACTGCCTCATGTAACTCT | 40007 |
| 6382 CCAATGCCTCAATTTCTCCAGGAAAC | 18040 TGCCTAGCCTGGAGCATGAA | 29024 GACTCAGCCAATGCCTCAATTTC | 40008 |
| 6383 TGATGCTTCTAGTCCACAGACTTTC | 18041 GCTTGGGCTGTGGTTTTCTCTA | 29025 AGCTCCCAGATGATGCTTCTAGT | 40009 |
| 6384 GGTCGCTGGAAGTTTGTTGAAGA | 18042 CCACTCACCACCTCTCACCAGAT | 29026 GCAGTGTTGGTGGCTGGAA | 40010 |
| 6385 TGTTTGTCATCAGTCTGGAATGCTT | 18043 TCACCCATTATCTTGGACCCTTTTC | 29027 GGGGAGGGTGTTTGTCATCAGT | 40011 |
| 6386 GGAACCGCATTTAGGTCGTGTTG | 18044 CCCGTTTTGCCGGGAGATG | 29028 GAGATGCACGGAACCGCATT | 40012 |
| 6387 CTGAACCAACTAAAAACAGGTGGTGTTG | 18045 GGGATATGAATTGCCTTCTTCCCACATA | 29029 AGCAGCCTGAACCAACTAAAAAC | 40013 |
| 6388 CCCCCCCATACCTGCAAAT | 18046 CCAAACTTTTGCATCACGTCACA | 29030 CCGAGCCAGCCCCTCTTCAAT | 40014 |
| 6389 CCCTGCTTTCCTAAGGGCAGATTT | 18047 GGAGAAGCAGTTTCCAAGACATCA | 29031 AGTGGGATCCCTGCTTTTCCTA | 40015 |
| 6390 GCCCGGTGCTTTGTTTTACTCTGA | 18048 AGGAAGAGGGACTTTGTCTTTCAACT | 29032 TCTGCCCGGTGCTTTGTT | 40016 |
| 6391 GGGTCATGGTTTCAAGGAAATGGATTG | 18049 GCTACAAGCTCTACTCCACTCAGAT | 29033 CTCAACTGGGGTCATGGTTTCAAG | 40017 |
| 6392 GGCTATGGGAGAAACAGTAGCGTT | 18050 CCAGAAGGCCATGTATGCTCTGAA | 29034 CCGTGAATCCTGGGCTATGGGAGAA | 40018 |
| 6393 CCTCCCCTGTACTCTTCCTGTCT | 18051 CAGGGAAAAACCGAACATTTCAGGTAT | 29035 AAAGGCTCCCTGCCCTGTACT | 40019 |
| 6394 CTGCCCTGTGTTTTTAGGCCATTT | 18052 ACTCAAGGCCCTGGGTTCAAG | 29036 ACCCCACCCACCTTTCTCT | 40020 |
| 6395 GGAAAGACAGTTAAGGCTGGCTCTA | 18053 GCCCAAAGGCAGACCACTCTA | 29037 CCCTGCTAAGGGAGGAAAGACAGT | 40021 |
| 6396 GGGGAGTAGGTTGCCTTCTTGCTA | 18054 GGCTGAGGTTCAGAGAAGAGAAAA | 29038 GTATCTCCAGATCTAGGGAGTAGGTT | 40022 |
| 6397 CCTGAAGAACGCGATTGACCCATT | 18055 GGTGAAGAAGACTTAGGAGTGACAT | 29039 CCTCGCAAAGCACCTGAAGA | 40023 |
| 6398 CTCACCTGCTTGTTGATTCTCCTTA | 18056 CTCTATCTCAGCTTTGGAGGCAACA | 29040 GGTTAGGATCTCACCTGCTTGTTTG | 40024 |
| 6399 GCGGAATTCAGTCAGACAGTGAAC | 18057 TGAAGCCAAGTCTATAAGGACGTTT | 29041 TCCCCGCGGGAATTCAGTCA | 40025 |
| 6400 ACACAGGCTGAAGGAAATGATGT | 18058 CCCTGGTGAATCTGTTTCCATCAAA | 29042 GTGCATGAAACACAGGCTGAAG | 40026 |
| 6401 CGGTTATCAGCCAAGAAGGGGTTT | 18059 CCCCACCAGCTGTTTCTGACA | 29043 CCCTGCCGAATTTGCGGTTATC | 40027 |
| 6402 GGGTGATGGAAGGGATGTGA | 18060 CTCAGAATCTGTTGGCAATGATTTCTCCAT | 29044 CCTCAGGGTATTGACGGTGGAT | 40028 |
| 6403 GTACCAACCCTCGTAAGTTCCTTAG | 18061 GTCACTCAGGAAATGGGTTGAACA | 29045 GCTTTTCTGAGTACCAACCCTCGTA | 40029 |
| 6404 GCACCAAGACCACGACCAA | 18062 CCAGCCTGGTCCATTCAACAGT | 29046 ACTGCTGTAATCCAAGCACCAA | 40030 |
| 6405 GCCCTTGGCTTATTTTCCCCTTTC | 18063 GCAAAAAGTCACCTGGCAGTTTTG | 29047 GCTCCTACAGCCCTTGGCTTAT | 40031 |
| 6406 GGGCTCCCTATTTTCCAAAGATCAGA | 18064 GGTGGGAACAGATATTTCTGGTGAA | 29048 AGAACTTACAAGGGCTCCCTATTTTC | 40032 |
| 6407 GTTCCCTGAGATGTTCACTGT | 18065 CAGTAAGCACTGTAAACACCCTTCCTA | 29049 GGGGCATCATAGTTGCCCTGAGAT | 40033 |
| 6408 GGCACAAGTGAGCTGAGTTTCAGA | 18066 GTAGCTCCTAAACACAAGTACCAT | 29050 AGGAGGACTTGGTAGGCACAAG | 40034 |
| 6409 GCTAGGAGGTCCGAATTCTTTTGAAC | 18067 CCTCACACCATAGTCCTTTCCTCTA | 29051 GGAGAAGCTAGGAGGTCCGAAT | 40035 |
| 6410 TGCCCCTGGAAAGACTACAGA | 18068 TTGTGGTCCCAAACAGGGTATATTT | 29052 CAGCTTGTTTGCCCCTGGAA | 40036 |
| 6411 GGGAAGTTCAAATTGCTGAGCTTGTAG | 18069 CCCAGCCACCTCCTAATGGACTA | 29053 CCCCAAAGCTAAGCATGGGAAGT | 40037 |
| 6412 CCAACCAGCTATGCTACCATTTCTAC | 18070 GTGGAAAGTCCTCAAGCCCTCTTAG | 29054 CCACTGCTTAGACCAACCAGCTATG | 40038 |
| 6413 GCAACAGGAGATTTTTGGTCTTG | 18071 GTGCCTAGCCAAGGAATACACT | 29055 GTGTTACTGAAGTGCAACAGGAGAT | 40039 |
| 6414 TGTGTCAGGTTTTAGGCTGCTT | 18072 TCAGGAAGCCATGGTTTTTGAGAT | 29056 GCTTGCTCAAGTACATTGTGTCAGGTT | 40040 |
| 6415 AGGCCACAAAGCCTCACATC | 18073 GTGTTTAGGATTCAGAAAGAGCTGAGT | 29057 AACAAGCCCAGGCCACAAAG | 40041 |
| 6416 AACAGGGAGTAGCACAAAGCCAAA | 18074 GCCTCCAGAGATGATACCTGACCTT | 29058 TGGGGTATGTCTATCAACAGGAGTAG | 40042 |
| 6417 CAGCAGCTTAAACAACCATGAGAAGT | 18075 CCAGGTGAGATTTTCCTTGTCACT | 29059 GACAGTGAATCAGCAGCTTAAACAAC | 40043 |
| 6418 CCTTCATCATTGGTAGCCTAGTGTA | 18076 ACTTGCTGTAGGGGCTGAGT | 29060 GCCAGTGCTGTTTGTGTCCTT | 40044 |
| 6419 GTCAACCCGAATAGCTCCTTTCT | 18077 ACAAAAGGAGAGGTAAACCCTGTTC | 29061 CCCAGAGAACTTGTCAACCCGAAT | 40045 |
| 6420 CCCCACATCACAGGGCTTTAGA | 18078 AACCACTATAGCCTGGCAAACAA | 29062 CCCCTCAACCCCACATCACA | 40046 |
| 6421 TCCCCTCAAGCGTCCAAGT | 18079 GTTACCCCATGACAGCAAAATCAAG | 29063 GACTTATCATTCCACTCCGCTCAAG | 40047 |
| 6422 CCTGGAATGGTTTTATCTGACAGGTT | 18080 CGCCCAGCCAGACTTATTCTCA | 29064 CTCCAACTTCATCCTGGAATGGTT | 40048 |
| 6423 GCCCCTGACTTTGCTCAAGAT | 18081 TCCTGCCTGCCTTCTCTCT | 29065 TGGGCTTGGCCTCGACTTTG | 40049 |
| 6424 CAGGCGTTATCAACTTTCCCACTT | 18082 CATAAACACTCCTTTGCCTCAGTCT | 29066 CGGAGGATGACACAGGCGTTA | 40050 |
| 6425 CCCTCTGAATCACTGTCTGCTCTTCA | 18083 TGGAGACATCCGCCCATATCA | 29067 GCCCACTTGTGTCCCTCTGAAT | 40051 |
| 6426 GCTGTCTTCTCTAACACCCAGTCT | 18084 GGTTCTGAGGACCTGGGTTTTCTT | 29068 TCTGGGTTGCTGTCTTCTCTAAC | 40052 |
| 6427 CAGGCATGGTCAGAAGGGTTAAG | 18085 CAGGAGGTAAACACCATCCCTGAT | 29069 CAGATTCACAGGCATGGTCAGA | 40053 |
| 6428 GATCCTCTTAGGCATGGAAGT | 18086 GGGGTGAGACCCATGAGTCACATT | 29070 GCTTACATTCCCTGTGATGCTCTTAG | 40054 |
| 6429 TGTCTGTTTCTGCTCCTTCCTT | 18087 CCACTAGTTTATCCCACCTGTGTAAC | 29071 CCAGGTTTTGTGTTGTGT | 40055 |
| 6430 GTTTTCCTGTGCCTTGACTCACA | 18088 ACCCAGACAACAGTCTCATCTGT | 29072 GCCCCACAGTGTTTTCCTGTT | 40056 |
| 6431 GGGGCTGTTAAATAGAATCCACTCCTTTG | 18089 TGCGAGTGGCAGTTGCTTAG | 29073 CCAAGCTCACTGGGGCTGTTA | 40057 |
| 6432 GGCTTCTGTGAGGGCGATGTT | 18090 GCATTAGTGACAGGGATCCAGGAA | 29074 TGGGACTTCAGGCTTCTGTGA | 40058 |

FIG. 36J9

| | | | |
|---|---|---|---|
| 6433 GGGGTGGAAACGTTGGAAGCTA | 18091 CCGATCCGTGACAGCTTTCA | 29075 AAGGGCTGGTGGGTGGAAA | 40059 |
| 6434 GGACACTCTCAGGTTACTGAGGTT | 18092 GCTCTAGAGACAATGGTTCTCACTGATG | 29076 GGTGATTGGACACGTGCAGGTT | 40060 |
| 6435 CCGCCTCCTTCACATTTCCACTAC | 18093 TTGGATGCGTGGTGTGAGAGAAG | 29077 CTGAAAGCTCAACCGCCTCCTT | 40061 |
| 6436 GTCACAGGCTAAGGCTTCTGAAG | 18094 CTGGGCCTCCATTGTTTTGTCA | 29078 GAGGCAATGAGTCACAGGCTAA | 40062 |
| 6437 GTCGAGCTAAGAAGCTTGTGGAAAAG | 18095 GTTTCATCCGTTTTCCCTGTAGTT | 29079 GCCTGTCGAGCTAAGAAGGTT | 40063 |
| 6438 CTGGTTCTGAATGGAGATGTGCTA | 18096 TGGAGGGACCGTCTTTGGAGTT | 29080 CACGTAAAATGTGCTGCGTCTGA | 40064 |
| 6439 TTTGATACAATCTGTCTGGGGATGA | 18097 GGACTGGTCTGTGCTGGTGTACA | 29081 CTCACCCAGTTCCTTGGCTTT | 40065 |
| 6440 GCAGGGATCTGAAGAAGGGGTCTA | 18098 GTAAGTCGTCAAGTTAAGGTACCTAGT | 29082 GGCGTTGGTGCTTCGGAAGGGATCT | 40066 |
| 6441 CCAGTCTCACTCACACCCAGATAGT | 18099 CTGGAGGAATCGCAGACAGTTTCA | 29083 TGATCCCAGTCTCACTCACA | 40067 |
| 6442 GGGCATCTGAATTGCTCTGGGAAT | 18100 CTCATTAAACAGTTCAGGACAGGTAA | 29084 GCAGCAACTAGGGGCATCTGAA | 40068 |
| 6443 GGTCTCATAATTCCATCCTCCCATCA | 18101 GGGTCCAACTGCTTATTTCTTGGTG | 29085 AAGGCTCTGGCTCATTAATTCCAT | 40069 |
| 6444 GGGGTGGCATAAATTGCTCTTC | 18102 CTCATACATTTAGGGCTGTGTGTTCA | 29086 TCTTTGTTACTAGGGGTGGCATA | 40070 |
| 6445 CCTCCAGTTACCATTTGAACCTCTT | 18103 CTTTCTTGGCCTGTGGGACTA | 29087 GGAAAAGATAGCTTTGATACCTCCAGTTAC | 40071 |
| 6446 GGTGACTGGCAGCTCTTAGTGGAA | 18104 GTGCTCTTCAGGAGGGTGAATC | 29088 TTCTGGAGGTGCTGGTGACT | 40072 |
| 6447 GCACCTCACTTGCCTTACCTT | 18105 AGGGACTGCAGTGGGAGAAA | 29089 ACATAGAGATAAGCACCTCACTTG | 40073 |
| 6448 GCTTCTCAGAGGGCTACAGTTG | 18106 TGTTGCTGATGGGACATTGAGTAT | 29090 CAGCTACCACTAAGTGCTTCTGA | 40074 |
| 6449 CACACTCTGGGCAATGGTGTT | 18107 GGAGGCTGAAGTCACTCGTTCAA | 29091 GTTGTGAAGGTAGCACACACACTCT | 40075 |
| 6450 CACTCCTGAATCCTCCTCCCTAACA | 18108 GGACGCGGTACAACGAACTTG | 29092 CCATTCCTTCCCACTCCTGAAT | 40076 |
| 6451 GCACTTCAATTCAGCATGTCCAA | 18109 GAGGACTTAGGTTTAGGGTGGAATG | 29093 GGGGTTTCTAAGGCACTTCAGTT | 40077 |
| 6452 CATGCAGATTCATAGCCACTCCTAGA | 18110 CCCACTCCTTACAGCTGGTCTTC | 29094 GGGACAAAGTCTTTACATCCAGATTC | 40078 |
| 6453 GGGCAGATTTTGATAGGTGTCTTAG | 18111 CCAGTCTTCTATGGGTGTCCCAGTT | 29095 GGTTAGGATTGAGTTGGGCAGATTT | 40079 |
| 6454 CAAGCATCTACATCCTTTCCAGAGA | 18112 GGACACCACCCTGTAACTCTGA | 29096 GCCCACACTCAAGCATCTACATC | 40080 |
| 6455 ACAGACAGAAGCATGGTCTTAGGTA | 18113 TGGGTCATGGTAAGGAGCTTAC | 29097 TTGGACAACTACAGACAGAAGCAT | 40081 |
| 6456 CCACGAACCTTGTCTTTGCCATT | 18114 CCCCAGAAACTGCATGTCACATTAC | 29098 AGGCACACCACGAACCTTGT | 40082 |
| 6457 GCAGCAGTCGAAAAATCCCACATC | 18115 GCGCTGGTTTGTTTGAGGGTCAA | 29099 GCATTCCACAAGAGCAGCAGTCGAA | 40083 |
| 6458 GCACAGCTTTTCCTCGCTCTT | 18116 GGAGCAAAACACGAATCATCTGCAA | 29100 TGGGAGAGGGCACGCTTTT | 40084 |
| 6459 GGTACCCAGGAGATAGCAAGCTCTTC | 18117 GAACAGTGGGATTCTTCTTCACATCAA | 29101 TCTGAAGATTTGGTACCCAGGAT | 40085 |
| 6460 GGTCACCACATTATTTCCGTCTGATCTCTT | 18118 GGAGCAGAGCAGTTGGCTTCA | 29102 CTCATACCCTCTTGGTCACCACATT | 40086 |
| 6461 GCGGCAGCTTTGCCATCACATCT | 18119 CCTTCCATAGGCTCCAGTATCCAA | 29103 AAGCCAACTGGGGAGCTTTG | 40087 |
| 6462 AGCCAAGACACATAGAGCAA | 18120 CTGATTGAGCAGCTGATGGATACAAGAGATAC | 29104 CGTTGCTCCAAAGCCAAGACACA | 40088 |
| 6463 CCAGGTTCCTTGCTGGAAGTAT | 18121 CCCAGAATCTGAGAGGGACATGAAC | 29105 TGGCCTTGGGTTGCCAGGTT | 40089 |
| 6464 GCATTGTCTGGGTTCTGGTTCT | 18122 CCATGCAAAACACCCACTATACCTACA | 29106 CCTGGAGGCTGGCATTGTCT | 40090 |
| 6465 CCTCCGACCAGATTGAGAACTTG | 18123 GGGTGGGGATCAATAAGAGGAAAG | 29107 GCTACAAGTTAAATCTTCCGACCAGAT | 40091 |
| 6466 GGAACACCTCTGGGCACTTG | 18124 CTGGCACAAGCATCACTGTCA | 29108 CCAGCTCCAAACACAGGAACA | 40092 |
| 6467 GCAAACTGGCAGGAGTTGGAATG | 18125 CACTGCTTGTACTTGGTCCCTTTG | 29109 GCTTCAAAATGCTGCCTGCAAACT | 40093 |
| 6468 GGGTTTCGCTGTTAAGAAAGGACCAAA | 18126 CCAAGATTCAGTGCGTGCCATTCT | 29110 CTGCAGTGTGCAGGCGTTCGCTGTTA | 40094 |
| 6469 GGGAAGTATCTCTCAAGCATTACT | 18127 CAGTCCTGCCTCTTCTCCTT | 29111 TGCCTATTCTATGGGAAGCTATCTCT | 40095 |
| 6470 CCCACATAAACATAGCCACAGAGGAT | 18128 GGGACAACGGCTCATTGGAA | 29112 ACAGCCAGAATGCCACATAAACA | 40096 |
| 6471 GTGTGGGGTCTTCATGATTCACT | 18129 TGCCAGCCAGACTGCCTAA | 29113 TGCAGGGAATGGGTAAGGAA | 40097 |
| 6472 ACCTGACCTTCTTGCTTGTTTG | 18130 CCATAATTCAAATTCAGGCCTCAGGAATG | 29114 CTTTGAGGCTAGAAAAACCTGACCTT | 40098 |
| 6473 GAGGGGAGCTACTTGATCGTGAGGTT | 18131 CCCATACTGTGGGCTAGAGAT | 29115 TGTCGTTCCTGAGGTGACTTCA | 40099 |
| 6474 TCATCTGTGAGCAATCCTGCTT | 18132 CCTGGTGACACAATGGGTAAGAATGTTAG | 29116 GTCCCTCTAAGCTTCATCTGTGA | 40100 |
| 6475 GCGTGAACACGTTAGGGACCTT | 18133 AGGGCCAAGGCTACCAGTGAA | 29117 TTTCCTCTTGGAGCGTGAACA | 40101 |
| 6476 CCAGGTGCCGTCAATCCCATTT | 18134 GGGGACTGGAAGTCATTTCTGATG | 29118 GCAACCTGATGCCCTCTCCTT | 40102 |
| 6477 GCATTCACAGGACAAAGACCATTAG | 18135 GGTGTCAAGGTGCCTCACA | 29119 GCTCAATGCATTCACAGGACAAA | 40103 |
| 6478 TGACAGCTCCACCATAATTACTTGA | 18136 GGTACCTTCCTTTGAGGATTGCTACA | 29120 GGGTGTAAATGACAGCTCCACCAT | 40104 |
| 6479 CCTGTTGTAAGGCCACAGCAAAA | 18137 CGTCTTTCCAGCACGTCTGT | 29121 CCCTTTCACTCCACCCTGTTGAT | 40105 |
| 6480 GTGGCAGCCATAGCTGAAGT | 18138 GGGGACAACTACTGATGGATAC | 29122 TGCCCAGTGGCAGCCATA | 40106 |
| 6481 CAGCTCGTTCACGTCTCAGTCA | 18139 AGGTGAGAAGCAGGGCAAAG | 29123 TGGACTTCCCAGCTCGTT | 40107 |
| 6482 CCCTGCTTCTCTGGTGCATTG | 18140 CCCATGCATGCAGACACTCTTTC | 29124 GGCAAACATCCCTGCTTCTCT | 40108 |
| 6483 TCCCACTTTGGTGAGACAGGAA | 18141 CTGGAGAAAGACATTGCTGCCATCA | 29125 TGCATAGCTCCTTATCCCACTTTG | 40109 |
| 6484 GGCAGTAGTAGGGTGCGATTC | 18142 GACCTGGACATAGAAGGAAGGTTCT | 29126 TCGTGGGCCAGCAGGTAGTA | 40110 |
| 6485 GGTTGCCATAGTGCGTTCCTCAA | 18143 TCAACAAGGAATTAGAAGCTCCACATA | 29127 CCTGGAGCTTCTGGTTGCCATAG | 40111 |
| 6486 CACAGTGCTGTGCCTAAGAATGGT | 18144 GAGCATCACAGTTCCCATGTTCA | 29128 CAATTAAGCATCACAGTGCTGTGCCTA | 40112 |
| 6487 GTGGGCCACTTGCCTCTTT | 18145 GACCACTGACAAATGCGTGAAG | 29129 TGTCCAGCTGCGGTCAGT | 40113 |
| 6488 GCTCCTGATCTGAGAGACAAAGTGTGT | 18146 TCCGTAGTGCTCCCTCCTGTATC | 29130 GCCAGTGGCTCCTGATCTGA | 40114 |
| 6489 GTGGTGAAGTGGATTCCTCTCTGAT | 18147 GGGTGCTCCAAATGCCTGAA | 29131 GCTCCCCTGAGATTGTGGTGAA | 40115 |
| 6490 CCTCCAAGGCCTCAAGGACCAAA | 18148 CCTCAGCTGACATTGTGTAATGCTA | 29132 TCTTCAATTGCCTCAAGGCCTAA | 40116 |
| 6491 GCCCCTCCTCCTTACATGGATAAC | 18149 CCATGCCCGGCCCGTTTGTA | 29133 CCAAGTAATTCTGCCCCTCCTCCTT | 40117 |
| 6492 CGCAACCAAACACCCTTATTACTAGAGA | 18150 CCTTTAGGGAGCATGGGGAATC | 29134 CCCTCGCAACCAAACACCCTTA | 40118 |
| 6493 GGAGTCTATGTTTGAAAGGAAGCCAACAT | 18151 GCACAAGCAGCAACATTCCTT | 29135 TGGTGTTCGGAAGTCTATGTTGA | 40119 |
| 6494 CAGGTTGTAGGTAAAAATGGGGTCAGA | 18152 TTGTCATACCATGCCCTTCGTA | 29136 GCTGAGTAGAATAGCTCAGGTTGTAGGTA | 40120 |
| 6495 GCCCATCCCATTTAGGATCACA | 18153 GCTTGGAAAAGGCAGCAACCTACT | 29137 TTCACAGCCCATCCCATTTA | 40121 |
| 6496 GCTAATCTTACAGGAGAGTATGGGAAAC | 18154 GGACAGGCACTGAGGGACAACGAGTA | 29138 GAAGCCTGTCAAACTGCTAATCTTAC | 40122 |
| 6497 GTGAGCCATTTGAGACTGGAAAAA | 18155 TGAGATGGTCACATCCTGTTCTCTAA | 29139 GGAGCATGTAAGCTAGTGAGCCATT | 40123 |

| | | | | | | |
|---|---|---|---|---|---|---|
| 6563 | GGGGCTGTACGTGGCACAA | 18221 | GGGGCTGCATGATATGCTGGTA | 29205 | CACCTCTATGTGGGGCTGTTAG | 40189 |
| 6564 | GAGAATAACCATGATGAGGGGAAA | 18222 | TCACAGAGACTGGCTCGATCT | 29206 | GCTTAGGTGAAGGAGAATAACCATGA | 40190 |
| 6565 | GGTTCCCCAGATCAAAGAATCGAAGA | 18223 | AGCAGAGAACAGAGTAAATGACCTATC | 29207 | TCAGAGGGTTCCCCAGATCAA | 40191 |
| 6566 | CTCTTATGCCCTTGGCCATACTCT | 18224 | GATCTCTGGGAGTTCAGTTGTTCA | 29208 | TGTCTCTCATCCTACCTTGACTCTTA | 40192 |
| 6567 | CCTGTATTGGCTGCGTGAGT | 18225 | ACCAGGTGGCTGGGTGACAT | 29209 | GGACCCAAACCAACTGAAAACCTGTA | 40193 |
| 6568 | GGGTAGAGGGACTGGTCTACCAAA | 18226 | ACTGACTCCAGGAGTTTCATCT | 29210 | AGAGGCAGGGTTTGGGGTAGA | 40194 |
| 6569 | CCACTGTTTCTCAGACCTTCACTT | 18227 | TGGCCTGACTCTCCCGATTTC | 29211 | TTCACTCCATCCTCACTCTTTTCT | 40195 |
| 6570 | GAGTTGATCTAGGATTCTGTATTTG | 18228 | CCTGGGGCTTGCATTTGTTCCTA | 29212 | TTCAGTGGCAGGGAGAGTTGA | 40196 |
| 6571 | GCTTCTCCAGCATCACGTCTCT | 18229 | CCTCACTCAGGAAGAATGTGTCCTT | 29213 | CCAGATGACTGCTCTCCAGCAT | 40197 |
| 6572 | GACCAGGTTAATCAACTACCTCTGACATT | 18230 | GAACCTTTGGTAAGGCAGACATACA | 29214 | GGAAAGACAGAGGACGAGCTTT | 40198 |
| 6573 | ACCAGGGGACTAAGATGACAAG | 18231 | GGTGGGTAGCCACTCAGGGCTTTTG | 29215 | GCTGGAAACCAGGGGAACT | 40199 |
| 6574 | GGGGAAGGCCTAACACTAAGGTGAT | 18232 | CCCAGGAACAGTAAAGCATCATTC | 29216 | TGCAGACATGGGGAAGGCCTAA | 40200 |
| 6575 | TTCCTTGGTCCTCCGAGGCATA | 18233 | TTCTGGGCCTGCCTTTGACT | 29217 | GCCAAGATTGAGCAGCCATTTCCTT | 40201 |
| 6576 | AGATTATCTCTGCTGGATACCGATTC | 18234 | GCATTTCACTAGAAGATGTCGGGCTTCA | 29218 | ACAAACACTTGCTACACTGAGAGA | 40202 |
| 6577 | GGTGGTTCGGCCTGATCTT | 18235 | GCACAGTGATCACTAGGCTGTT | 29219 | TTCGTCACACATCGGTGGTGTT | 40203 |
| 6578 | GCGACTCTGAACCAAAACCCATAG | 18236 | CACACCAGTCTGCCTGAGTACA | 29220 | CCACTTGGGAACCACTCTGA | 40204 |
| 6579 | GTGGGAGGATGACTTTGGAGCTATG | 18237 | CCACAGAGCTAGGAAACTCGTGAA | 29221 | GGCAAGTACTATTCTCTGGGACGAT | 40205 |
| 6580 | TGATAAGTGCCTTCTGCAGGTTTT | 18238 | GCCTTCCCCAGAGGAATGTGT | 29222 | TTTGTACGGGGTTGGTACTATGATAAG | 40206 |
| 6581 | CGACTCAATAGAGCGATGGCTTGA | 18239 | CGACCAGCCATCCCTCGTTTT | 29223 | GCTGAGCTTTCACATTGGGGCTGA | 40207 |
| 6582 | GACCCCGTTAGTCCTAACCTCAATC | 18240 | TGTAAGCCGAGGAGGACGAT | 29224 | GCTGCGGACCCCGTTTAGT | 40208 |
| 6583 | GCCCTACTTTGGACAAGAACA | 18241 | GCCCTAAAGATTAGGGTGAGCATGT | 29225 | GCTGCCTTTATTAAGCCCCTACTT | 40209 |
| 6584 | GGATACAGAAGATGGGAGGCATAG | 18242 | CAGTCTTCCTTTGCTCCTAACAA | 29226 | GTTAGCACAGCTGACCTAGGATAC | 40210 |
| 6585 | TGTACTGGCGAACAAACAGAAAAGT | 18243 | GAAATTCCCCTGACCTTCTTTCCAA | 29227 | AGAGAAGAATGTACTGGCAACAAA | 40211 |
| 6586 | CCGGACTAACAGGGCTTGGTATCT | 18244 | GCTTCCCGTCTCCCCAACAA | 29228 | TGCCAAGGGCCGGACTAACA | 40212 |
| 6587 | GGCCTGCCTGTGTTTACTGTTG | 18245 | CATGTGTCTGGACTGTCAGATGT | 29229 | AGTATCGGGCCTCTTTGTGT | 40213 |
| 6588 | CAGCCCAGTGATTGTCCATCTTC | 18246 | AGCGGGTAGGCCATGATAGACA | 29230 | GAGGCAAATATCAGCCCAGTGA | 40214 |
| 6589 | CTCACCTGTCTTTGCAACTTTGGTT | 18247 | GGCTGTAAACAGAGGCATTTCCTA | 29231 | TGGGAGCCTCACCTGTCTTTG | 40215 |
| 6590 | CAGTGTGGGTAGAGGGCAAGAA | 18248 | GGAAAGGGTAGTATTGGGATTACAGA | 29232 | CATTTCAAAGGCAGTGTGGGGTAGA | 40216 |
| 6591 | TCCACTGGTCTATGGCCTGACA | 18249 | GCACCCGTGTAAGAGCAAAC | 29233 | CCTTCCACGTCATTCCACTCGTCTA | 40217 |
| 6592 | CCAGGGAAGCTACTGATGTGGATTA | 18250 | TGGGGAGGAGCCAAGAGCT | 29234 | GGACTTCCCAGGGAAGCTACT | 40218 |
| 6593 | GCCAAGGACAGATGTGATCTGATGTA | 18251 | AGTCGTGCTGTGGGACAGT | 29235 | ACATAAAGCCAAGGACAGATGTGA | 40219 |
| 6594 | ACCTCTGCAACAAGGGATTGA | 18252 | GCTGGAAGATTTTCTGCCTTTTGA | 29236 | GCAGCAGCCCAGGGTAAA | 40220 |
| 6595 | CTCCTAACCTACAGAGGAGTCT | 18253 | TCTTTTCCCTCTCTGGGGATCA | 29237 | GCCACAAACCTCACTCCTAAC | 40221 |
| 6596 | GCTGGTTCGTCCCCTBTTCATC | 18254 | AGCCTTCCAAGGAAAAGAAAGGAA | 29238 | CCTTCTAGGGCCTCTAAGCTGGTT | 40222 |
| 6597 | GAAACAGCCACAACACTCACCAT | 18255 | GCTGGAACAAAGAAAACCACGAGAA | 29239 | TCCTCCACGTGAAGAAGAAACA | 40223 |
| 6598 | GCCCCAATAGGTGCTGACCTT | 18256 | CCTGGGTTTCCCTCTAGCTGTT | 29240 | CCTCTCTGGAAAACTGGGCCAATA | 40224 |
| 6599 | AGTTGAGAACTGGACATTAAGCTATG | 18257 | AATAGCCATTCCCTGAGCTT | 29241 | GTCCTGGGGCAAAAGTTGAGA | 40225 |
| 6600 | CCAGTTTCAGGATCACAGTGACA | 18258 | TGGACCTCCCACCCTGGATAA | 29242 | GGAGCTTCGCCATTCACTT | 40226 |
| 6601 | GCACCAGGATGTATGATGGGAGGTA | 18259 | GCCTGCAGCTGGCTCTCTCA | 29243 | ACTATGGAGCACCAGGATGTATGA | 40227 |
| 6602 | CTGGAGACATGCACGCCATTCA | 18260 | GCCCTTAGAGTATACTGGGCTCTTTC | 29244 | TCGACGACACCACTGGAGACA | 40228 |
| 6603 | CCCTTGAACTTCAGCCCTTCCAA | 18261 | GTCAAAGCTGCAAAAGGGAGATAAC | 29245 | CTGCACGTGCCCTTGAACTTG | 40229 |
| 6604 | ACCTTCCTGGTGCCTGTGATG | 18262 | TGTAAGGCTTTCTGGGAATAAGGAGAT | 29246 | GCTTTAGCTACTGTGCTCAACTT | 40230 |
| 6605 | GCGTGGAGATCTGGGCATTAAG | 18263 | CCACCCCAGGATGTAAGGTACTCA | 29247 | AGCCAGCAGAGCGTGGAGAT | 40231 |
| 6606 | GCATCCACCCCATCCTGAAACTTC | 18264 | GACGTCAGGCATAGTGATGGAT | 29248 | GCCAAAGCCATCCACCCCATCTT | 40232 |
| 6607 | GCTACCAGATGGATGGCTATTCT | 18265 | GAGGCCAGTGCTGATCACCTAA | 29249 | TGGCCCTCCACCAGATGGAT | 40233 |
| 6608 | AGCTTCTGTGATGAGGACACT | 18266 | AGGCAGACGGAATGAACTTTCT | 29250 | GGGGAGAAATTCCAGCTTCTGTGA | 40234 |
| 6609 | TGAGGAAGAACCAGCAGACTCA | 18267 | AGGTCCCCAGGAGAAGGATCT | 29251 | AGCCATATCTCTTTGAGGAAGAA | 40235 |
| 6610 | CCCATGTCACTCCTTTTCGTTCCTA | 18268 | GCATGTGCCAAGGCCTGTAAC | 29252 | CCCCTACTCCCATGTCACTCCTT | 40236 |
| 6611 | GAGTCCCCTGTGTAGAACCATCTTC | 18269 | CACAGCCTGTCGGCATTCTA | 29253 | CCCTTGTCTAAGAGTCCCTGTGTAAG | 40237 |
| 6612 | CAGTCATGAGGTCCTGTTTCATCT | 18270 | CCTACGTTGATCCCAGGTGTTG | 29254 | CTCCCACTATCACTGGGAATGAGT | 40238 |
| 6613 | CCCTCTGATTATGACATCTAGGGAACA | 18271 | CTGTGGAAGGGTATCCCTCAGAAG | 29255 | GCCCACATTTCTACCCTCTCATTATG | 40239 |
| 6614 | GCTCTTCCAGTCATTTCTGGGTCATTC | 18272 | GGGTGCTTTCTTATGGGCAGAG | 29256 | GATAGTAATCAGCTCTTCGAGTCA | 40240 |
| 6615 | GGGCCAATAGGGCTGGTGTCTT | 18273 | CAAACGTATCAACCTAAAGTCCAGAAG | 29257 | GCCCAGATTCAACTGCCAAGA | 40241 |
| 6616 | TGGGACCTGAACAAACCAGGTA | 18274 | CAGCATAGATTGAGGTGGCATTTC | 29258 | ACAACAAACATGGGACCTGAACA | 40242 |
| 6617 | CCTGAGCGAGTTGAGGAATTGTGT | 18275 | CTCCTGAGTTCCTGCTTCGTT | 29259 | AATAGGACCTGAGCGAGTTGAAG | 40243 |
| 6618 | CCCAGCAGCTTTGCTTAGTAGGTA | 18276 | ACCAGCTGTCTTTTTGGTGTAAACT | 29260 | TCACCCAGCAGCTTGCTT | 40244 |
| 6619 | GGCTAGTCCACTGCAGACTGA | 18277 | AAGCAAGACTGGGCAGAGAGGTA | 29261 | CACACACACCCCAGGCTAGT | 40245 |
| 6620 | GTGCCCAACCTTGAGAGTGGTA | 18278 | CTGGCTCACCAACTCACCTAT | 29262 | TCTAGCCTGTGCCCAACCTT | 40246 |
| 6621 | CTGGGTCTGTGACCTTGCTGTA | 18279 | CCATTCAAGTCTGCCGCTTTGTGT | 29263 | GCACCTTAAGAGCTGGGTCTGT | 40247 |
| 6622 | CAAACCCCAAGTCCTCGTTTTC | 18280 | TGGGACCCTTCCACACCAA | 29264 | TCCCACACCCAAACCCCAAGT | 40248 |
| 6623 | CCCTCCTAATTGGGTTGCCTGAA | 18281 | CAACCAGGTTGAGAACTACTCAGTTG | 29265 | AGGCTTCTTGGTCCCTCCTAA | 40249 |
| 6624 | CCACTTCTCAGAGCTAACCTGCTGTA | 18282 | GGGAATGGGACCTTGAGTTCA | 29266 | TGTCTACCTCTCTGCCACTTCT | 40250 |
| 6625 | CTGCAATGGACCCGGATAC | 18283 | GGGAATCGGAGAATGATGAAAG | 29267 | AGGGTGTGGGGCTGCAGAT | 40251 |
| 6626 | CAAGGTCTGCTTGCTGTGTGATG | 18284 | GCAAGTGGAAAACTAAAGCTCAGAGATG | 29268 | CTGTGTCTGAGCAAGGTCTGCTT | 40252 |
| 6627 | GGACTGGAGTTCTTCATAGTAGTTG | 18285 | CCAGAATCCACTCACCAGAAAAATG | 29269 | CCAGCAGAGATGGACTGGAGTTTC | 40253 |

| | | | |
|---|---|---|---|
| 6823 TGCTGAACCTCACACAGTGAT | 18481 ATGGCCCTGGAACTGGAAA | 29465 TGGGGACTGAAGATCCTGAAC | 40449 |
| 6824 GCAATCTTGCTAATGAGACCATTT | 18482 CATGGCTTCTGCAGACCATTTT | 29466 GCCCATGGCAATCTTGGCTAATG | 40450 |
| 6825 GCCCTTCTATTCTACACTGACGTAAA | 18483 GTGATATGTGTCAGHTTCTCTGTT | 29467 CAGCTCTGAATTGGCCCTTCTATTCT | 40451 |
| 6826 GGAGAAACAACCACCATGCGAATGA | 18484 TGAATGCTGCAAGAGGAAATGGAA | 29468 GGAGCAAACACCTGGAGAAACAAC | 40452 |
| 6827 CACAGTGCTGACTTCCTTTCTACT | 18485 GACGCCATGTGCGTAGATTACT | 29469 GGCTTGATCACAGTGCTGACTTC | 40453 |
| 6828 GGGCCACCTGGATGTAGACTTTG | 18486 CCCACAGACTGATTCAGAGTCGTTAC | 29470 TCAGGGCCACCTGGATGT | 40454 |
| 6829 GGGACAAATCTTCCTACCCCATTC | 18487 GAGGCCGAGCAGCATTTGAT | 29471 CGGAGTTATGGCTGGGACAAATC | 40455 |
| 6830 AGTACTGGCATTGCTACACAGAAG | 18488 TCAGTCGTCCAGCATGCTTAG | 29472 TTCAGCACAAAGTACTGGCATTT | 40456 |
| 6831 GGGGAGGTATCAGAGCCTTTTCTGA | 18489 GGCTGGCACAGATATGAGGGAACA | 29473 GGGGTCCTGGGGAGGTATCA | 40457 |
| 6832 CCATGAAACTCAATGACACTCTTTCTGTCA | 18490 GCACAACCATGTACCTTTGGAAATC | 29474 GCCCTCCATGAAACTCAATGACACT | 40458 |
| 6833 CTGATCTTGTACTGCTAGCCCTTATAG | 18491 TGCCTCATACAGACCCGACAT | 29475 GCCCCTTTGAAAACTGATCTTGTACTGCTA | 40459 |
| 6834 AATGGCAATGACCCAACATGAAG | 18492 ACATTTGCCACTCCCTCCTT | 29476 GGCTGCTTCCCTAGAAAGACAACA | 40460 |
| 6835 CGAGGAAACAGGGATCATTGT | 18493 GAGGCAGTGCCAAATATGAACTGATAC | 29477 TGGACACCCGTCAAGGAGGAAA | 40461 |
| 6836 CTGTGCCTCAACGAGACAGTGA | 18494 GAGATCCCAAATGCCCTCCAACA | 29478 ACGCTGCTGTGCCTCAAG | 40462 |
| 6837 CTGCTGTCAACAGCCAGTGAAA | 18495 GCTTCTTGAGCGTAGGCTTGGAACT | 29479 TGGCCTACAGACTGCTGTCAAC | 40463 |
| 6838 ACTTCGGGAGCCACAGTCCAA | 18496 GTGTGTTGCATCTCCAGCTAATG | 29480 GGACAGCAAAGGCTGCTTGACT | 40464 |
| 6839 CCACCTTGTTTTAGATTTGGKCTGA | 18497 CAGCCTCCAAGTTGAACCTAGT | 29481 GTGGGATCCCCACCTTGTTT | 40465 |
| 6840 CAGACAGGCACCTTTCAAACTCTTCT | 18498 AGGGCCACCTCTCTGGGTTTA | 29482 CCCCATCACGCAGGCACCTT | 40466 |
| 6841 TGCTGATACACTGACTCGGTACT | 18499 GCATTATGGGGTTGTGGGTTGT | 29483 GCAAGACACCTGAGATGCTGATAC | 40467 |
| 6842 GGGAGCCAGTCATTAATCGAAATGT | 18500 CCCGAGGAAGCATTTGTGCTGTGA | 29484 ACAGCATGGGAGCCAGTCAT | 40468 |
| 6843 GTGCCTTACCTTTGCCAGTTCTGT | 18501 GGCATGGTTCTTCCAACTCCAAGT | 29485 CCTGCAGACAGTGCCTTACCTT | 40469 |
| 6844 CTGAGACTCGATTGGGATAAGGAGATG | 18502 GCCTGGCCACCTATCATTGT | 29486 GGCATGGTAGACTGAGACTGGATTG | 40470 |
| 6845 GGGCACTTCATCTCCTTGGAA | 18503 TGTGGCAGTGGCAAATCCCAAA | 29487 CCTTCTGCCCACCAGGCCATC | 40471 |
| 6846 GCATGATAGGAAGTGTGCGTGATAG | 18504 GGCAGCACTCCACAAATGTTAC | 29488 GCCTGATAGGAAGCCTGCAT | 40472 |
| 6847 CACCTCCTGGTTAGAGGCATTC | 18505 TGCAGTTCCATTTCCAATAGTCACA | 29489 AGAGAGGCTTTCACCTCCTGGTTA | 40473 |
| 6848 ACACTCGAGGCACAGAACTACTGA | 18506 CCCCAAACTGGATGTTTTCCCTCAT | 29490 GCTTCCGAGAGGTACTGATACACTGA | 40474 |
| 6849 GTGAGTCTGGTTAGTACCTCCTAATCTT | 18507 CCCACCCATGTCTGTTCTCTATTT | 29491 CCAATTGATCCAGTGAGTGTGGTTAG | 40475 |
| 6850 GTCTGCCATTCCAGGGAGATT | 18508 TGAGGGAACTCCCCTGACCTTT | 29492 CCCACCATGCCTGGCCATT | 40476 |
| 6851 CAGCCTTGTTGCTGGAGGGAAT | 18509 CCACCTGTTCAGGGCCACTA | 29493 AGTTGCACGCAGGCTTGTTG | 40477 |
| 6852 CGAAATTAACAGAGTTCTCTCTGGTTCCAA | 18510 CTTCAACTCTACATTTCTGAGGGTCAT | 29494 GGGCTCCAAATCCCCAAA | 40478 |
| 6853 CTGGCAGCAGGAAGGCTTGTTAC | 18511 CCCCTACACACCCATACAGACA | 29495 ATCCAATGAAACTGGAGCAGGAA | 40479 |
| 6854 GTGTTCCTGGACATGTGTTGATACCTA | 18512 GCAATTTGCTTAAGGACAGGGATTGTATC | 29496 CGGTGTTCCTGGACATGTGTT | 40480 |
| 6855 ATGGCCCAGCCTCTGAGTGA | 18513 CTCCCTCAAAATTCCCTGGTTCT | 29497 GTGGGCAACACCGAGAGATC | 40481 |
| 6856 GCACCACGAGCTTGGACTTTCA | 18514 GCCTCAGCCTCCAAACAA | 29498 CCCACAGGCACCACGAGCTT | 40482 |
| 6857 GCGATGCTTCTGGATCTGCAA | 18515 TCCCTGGTGTGGATCTTATTTTCATC | 29499 CAACCGCTGGAGGTGCCTCT | 40483 |
| 6858 CCAGCCTCGAAGGAATTGGTCTATG | 18516 GCTTCCTCGGAGACCACAGT | 29500 CCTTTTCCAGCCTCTGAAGGAA | 40484 |
| 6859 TCCCCTGATGGAGAGTTGCAT | 18517 GGGTCTTCGACTTAGCATTTAGTCT | 29501 TCCACAGGGAAACCTCCCCTGAT | 40485 |
| 6860 GCAGTGGAAGATAGGCAGAGGAA | 18518 GCTAGCTCCTGTTTCCATCAGCAT | 29502 CTTTAGCAGCAGCAGTGGAAGA | 40486 |
| 6861 CCAACAGGATTGTCGGTGAATTG | 18519 GCTTGGTCCAAAACCTCATTGATTTAC | 29503 GAAGGAAGAGCCAACAGGATTG | 40487 |
| 6862 CCACCCTCGAATTTCTAGGTGTGAAC | 18520 ACACGGTTGCTACATCCGTAAGA | 29504 AATACCCCTTCCACCCTGAATTTCT | 40488 |
| 6863 GCTCACTACGAACCTGAGACCTA | 18521 GTGTGGAGGAAGGGGAAGAGTTC | 29505 CGGAGATACCAGCTCACTACGAA | 40489 |
| 6864 GACCAGGAACACTTCTTGAGAGTTAAG | 18522 CCCCTTGCTTTCATGGTGACACTT | 29506 GAGAGATGACCAGGAACACATCTTG | 40490 |
| 6865 CCTGCAACTAGCAAATTCCGCTTTT | 18523 GTGCCTCCTTTCACGTAGTTGTTT | 29507 GCATGCCCTGCAACTACCAA | 40491 |
| 6866 TGAGATTCACCACTCTTCCTGAAC | 18524 GGACATGGGAGCAGATTTACACT | 29508 CCCCAAAACCCTCTCTGAGATTC | 40492 |
| 6867 GCTCCAACAGACGAGACGAATCTA | 18525 GCACACTAGGGTTCTCAGTGAT | 29509 TCCAGGGTGCAACAGACTCA | 40493 |
| 6868 GAAGCAGCTGGGCTGAGATAGGATCAT | 18526 CCCCTAGAAGCCATTTCGCTTCTTC | 29510 CGGTGCAAGCATGGGTGAGAT | 40494 |
| 6869 AGTGAGGCTCACTGCCATCTTG | 18527 ACATGCGATAGAAGGTCTGCCTTAATG | 29511 CATGCTTTGGTGTGCAAAGGGATGA | 40495 |
| 6870 GGGCCTTTCCAACCTGAATTGAGTA | 18528 CAGCTTGGCCCATGCTATG | 29512 AGTTTGTCTTGGGCCTTTCTCAA | 40496 |
| 6871 GGTCCCATGTAGGGAAGCTCTT | 18529 CAGAACCCCTCCTGAATAATGGAAGT | 29513 TGACCTGCTGTGTCCCATGTAG | 40497 |
| 6872 AGGCAGACAGGGACCAGAT | 18530 ATCAGGCCACTCCTTGTGT | 29514 GGGAGGTCAGAGACGCAGACA | 40498 |
| 6873 CGAATTTCAAGCAGGGACTAAG | 18531 GGCTTTCTTGGATGGACAAACAGAT | 29515 GGATGGCAAGCTTTCAAGGAACA | 40499 |
| 6874 CAATGCTGGGATCTTCCTCCAA | 18532 AGAATCCTGTCTATTTACAGGGGTAGA | 29516 CACACTTCCTTCAATGCTGGATCT | 40500 |
| 6875 CCGTTCGGTCAAAGGACATGCAA | 18533 CAGTTGGCCCAGTCAACCAA | 29517 GCCAAATAGACAACCGTTCGGTCAA | 40501 |
| 6876 GCTACTCTGGGTGGTTGTAACTGTTG | 18534 CTGGCAGTGAGTCTCTTTCTCGT | 29518 TCAGGCTACTCTGGGTGGTT | 40502 |
| 6877 CTGCAATAGCTAGGCGAGCAT | 18535 CCCACAAGACACTAGCCACTTCCA | 29519 GTGTTTGCCCTCTGTCCACATAG | 40503 |
| 6878 CCAGGTTAGCATACAGAAGGCCAAT | 18536 CTCAGGAACTTTGGAGCTATAGATCA | 29520 GGCATCCAAGAAGTTTCCCAGGTT | 40504 |
| 6879 CCCCCTAGTGCCTGGTGCTA | 18537 CATGAAGTTACGGAGGAAGGGAAA | 29521 CTCCAACCCTCCTCCAGTGCTT | 40505 |
| 6880 CGGATTTGGAGTAGTGGCAATG | 18538 GGCATGTTACTCACCAACAACA | 29522 CCCACTTGGTTGGATTGGAGTAG | 40506 |
| 6881 CCCATCGGAGAATACACACT | 18539 CCTTCAGAACTGAGCTGCCAAA | 29523 GTGTTCAACCCATCGGAGAA | 40507 |
| 6882 GGGCTCTGAAGAGACTAGGCAAAT | 18540 GCCATCTGCTGCTGTTACCAT | 29524 AGCGCCTAGGCTCTGGAAGA | 40508 |
| 6883 CCGTATCTCCTCCAGTCCATTACTGT | 18541 GACCTAGGCAAAGAGGTAACACAAAC | 29525 TCAGTTGGACTCACACCCTATCT | 40509 |
| 6884 ACACCTTTGCTGCAGATTACTTGCTACTGT | 18542 GAGAGTCAGTTTAATGAGAGTTGACCTT | 29526 GGGCACATTCCATCAACACCTTT | 40510 |
| 6885 CTGTTCCTGCAGATTACTTGCTACTGT | 18543 TGGAGATACAGTGCTTGTGTTTGA | 29527 CAGTGCTGCTCTGTTCCTGCAGATT | 40511 |
| 6886 CCTGCGGTCAAGCCTCAAT | 18544 GCTTCTAAAGGATACGGTGAAAGCGTAG | 29528 CTCATCCTAATACTGACCTGTGGTTCA | 40512 |
| 6887 AGATCAGGTTCTAAGGGTCATACCAA | 18545 ACAGTCGTAGAGATGCAGAAGATC | 29529 CCCATACCCAGTCAAAGATCACGTT | 40513 |

FIG. 36K6

| | | | | |
|---|---|---|---|---|
| 6888 | GGAGAGAGGCTAACTGACATATACTGGTAA | 18546 GAGGTTCAAATAACCAAGTGGACAAG | 29530 CTGAGGAGAGAGGCTAACTGACA | 40514 |
| 6889 | GCCCAGTGTCTGATGTGTAGAAAG | 18547 CCCAGATTCAGTCCTGTAGTGTAAC | 29531 GGGAAAAGCCCAGTGTGTCATC | 40515 |
| 6890 | GAACAAGGGATGTCTCCTCTTCAA | 18548 GGGTGAGACAAACATAGGTTCTTTACTTG | 29532 TGGCATTTGCAAGGGGAACAA | 40516 |
| 6891 | GCAAGCACACAAGCGAAGACACT | 18549 TCGGGACCAGCCATCACT | 29533 AGGGACGAGGCAAGGACACAA | 40517 |
| 6892 | GCACCATGGGTTTGCCTCTACT | 18550 GCACTGTTCCAATCTCCAGGTT | 29534 TGTGGGGCACCATGGGTTT | 40518 |
| 6893 | AGCCTCCTATGATTCCCAGAACT | 18551 CTGGGAGTAGGCATTAACCCATTG | 29535 CCACCCACAACAAGCCTCCTATG | 40519 |
| 6894 | GCAGAGGTTCAGAGGGAAAGATGTTC | 18552 TCCAGCCCCTACAGAATTCTATTTTTC | 29536 AAGGAAGGGGCAGAGGTTCA | 40520 |
| 6895 | GTCATCATGTGCACAACCTGTGACT | 18553 GCTCAAGAGCCACACAATCT | 29537 CCATTGAGCCCAGGTCATCATGT | 40521 |
| 6896 | GGCACGACTAAGTGTGTCTGA | 18554 GGGCTGTCACCTCTTCTGTGA | 29538 GGGGTGAAAGGCACGAGTAA | 40522 |
| 6897 | GCCCTCCATGGGTCACTATT | 18555 ACGCTTCATTCCCTCAGTCTCA | 29539 GCACTCACATGGCCTGCAT | 40523 |
| 6898 | CCAGTCTGTCCTTGAAAACAACACA | 18556 GTCTGGTTGCCCAGTGAACA | 29540 CCGAGACTCATCCAGTCTGTCCCT | 40524 |
| 6899 | GCATCCGCCTTAGATAAACAAAGAA | 18557 GCCCTGCTACCCTCTTTCCTATT | 29541 AGCCTTCTGCATCCGCCTTAG | 40525 |
| 6900 | CACATTGACTTCTTTCCATGCCCTAT | 18558 GGCCATGCCAGGAGAACATCCTGT | 29542 CCTACTCCGTTAACTCACATTGACTTCT | 40526 |
| 6901 | CCCTGAAGTGCAGTAGGAGCTGTA | 18559 TGGCCACACAGCCTACCTT | 29543 ACCTGCTGTGTACCCCTGAA | 40527 |
| 6902 | TGCCATCCCATTGAGGAGTGA | 18560 CTACCTAAAACCTCTAATCACCTAAGACTTG | 29544 AGGGCCACTTGCCATCCCATT | 40528 |
| 6903 | CCATCTTTCTAGAGTGGGAATGTCT | 18561 CCAGAGCCATGAGAGGAAAGGGATT | 29545 CGGGCATCACTACCATCTTTTCTAGAGT | 40529 |
| 6904 | CCTGGCCTCTGATTCCATCCAAAC | 18562 GGGTGATGTCAGATTCCCCTAACTCT | 29546 GCCACCCTGGCCTCTGATTC | 40530 |
| 6905 | GGGTTTTGCTTGTGGTGGTGTTG | 18563 GCACTCTCAAGGCGTAAGACCTTT | 29547 GTGGCAGAAAAGATGGGTTTTGCTT | 40531 |
| 6906 | AGGGCACCCATTCCTGTCACTTG | 18564 ACATAAGCGTGCCAGGATAATAAG | 29548 GCCCTTTCCAGGCACCCATT | 40532 |
| 6907 | CGAATGCGTATCGATGTCCTTGA | 18565 CCAACCAGCCACTCCAAAAG | 29549 CCTCCCAAGTCAACGAATGGGTATC | 40533 |
| 6908 | TGACTGCGTTCAGCTTAGAAGTTA | 18566 GTCAGGCTGCGTCATTGCTA | 29550 GTGACAAGTTCAAATCACTGCGTTGA | 40534 |
| 6909 | GTCCAAGTCCAGCCTTCACA | 18567 CAGAAGAACGAGGAAGAACTGT | 29551 TCCTGAGCTGTGTCCAAGT | 40535 |
| 6910 | GCTGGGAACCTTGCCCTGTATATC | 18568 GGAGGAGCTGGTAAGAACTAGTCA | 29552 AGGCCCACCCTGCCCAACCTT | 40536 |
| 6911 | GCTTCCTGTTTCCACGTAGGCTTTC | 18569 CCACCAGACAACTTTCTCCTCTT | 29553 CTTCGTCCTTGCTTCCTGTTT | 40537 |
| 6912 | GGCTGGAAAGGATGGTGGTGCTAT | 18570 GAGCAAAGAATGTGCTATAAGGGAGAT | 29554 GCTGTCACCCTTTGGCTGGAAAG | 40538 |
| 6913 | GACTGGCTAACTGTCCTAAATTCAAA | 18571 GCATCTGGGTTTTCCAGCAAAT | 29555 CAAGACAGGCTCTGAGTCGCTAAC | 40539 |
| 6914 | GCCTCAAACTCCTGGGCTCAA | 18572 ACTGTCCTTGCTACTTGAGAGACT | 29556 CCTCACTGCCAGCCTCAAACT | 40540 |
| 6915 | CCCTCTGGCAGTGTGTTAGCAGAT | 18573 ACAGGTTTCTTTCAAGCAGGATTTC | 29557 TGGGTCCCCTCTGGCAGTGT | 40541 |
| 6916 | GGGTTACACTGCCTCTGAGATAC | 18574 GCCAAGCACATAAGCCATGCTA | 29558 AACGCCTTCAGTCGGCTTACACT | 40542 |
| 6917 | CCAGACTTCCCTCTTTGGGAATGA | 18575 TGCCTGGATTCTTCCAGGATTAC | 29559 TCCCCTCCAGATTGCCCTCTTTG | 40543 |
| 6918 | CAGGACTTGTGTCTGTGGCTAAAC | 18576 GCCCAGATGGAGACACAGCTT | 29560 GAGCTGAAAGGCACAGGACTTG | 40544 |
| 6919 | GCTTCTCGTGACTCATTCATGTTT | 18577 GTCACAGCCTGCTTGCCTAT | 29561 AGGAAATCAATTGCTTCTCGTGACT | 40545 |
| 6920 | CCCTTGTCTCCAAGTGAGCTATTC | 18578 CAGAAATAGGACCTTTGGGGTTCATTC | 29562 TCTGACTTCCCTTGTCTCCAAGT | 40546 |
| 6921 | CGTGGCCTAAACTTTTCCAAAGACAT | 18579 GAGTGGACACAGATCCCACACA | 29563 CCACCACACGTGGCCTAAACTT | 40547 |
| 6922 | GGTGATGGCTGATGAGTGGTT | 18580 GCCTCCTGTGTGAAGGTGAAA | 29564 CAGGTTCAAGCCCAGAGGTGATG | 40548 |
| 6923 | GTCACTTGCTCACCCCAATGA | 18581 CCTGCCCAAACCCTCAAAGA | 29565 TGCCCCTGAGCTTGCACTTG | 40549 |
| 6924 | CCTGTGTGGGACAGTAAATGTAGGTA | 18582 TAGGTGCCCGAGGCCAAAC | 29566 TGCCTTCCTGTGTGGGACAGTA | 40550 |
| 6925 | CCTTCAGGTACTGAGGGTGTCTCT | 18583 GGAGGACAAAAGGAGCTCTATTCAA | 29567 GCTGCCTGCCTTCAGGTACT | 40551 |
| 6926 | GTGAAGGCGACTACTGAAAACTGAAGA | 18584 CCTGGAGTGTCGGCAGGTATTTTTC | 29568 TTTTGGATGTCAAGGCGACTACTGAA | 40552 |
| 6927 | GGCTCCATCTAAGATTTCAGGAGTCA | 18585 CTGGTGATCACTTTACCCTTCTCTGA | 29569 GTCTGGCTTGATAGGCTCCATCT | 40553 |
| 6928 | GTGTTCCCAAAACAATTCCCAGTT | 18586 TTCAGAGTCCCTTGAGTTATCCTA | 29570 TGGGGTGTGGCACAGTGTTC | 40554 |
| 6929 | GCAACTCTCCATTCGGAGTACGCAAGTCA | 18587 CAGTTAAGCCTCTTGATGGGAATG | 29571 GGCAGATTGATGGAGCAACTCTCCTA | 40555 |
| 6930 | GGTGAAATCTCAGCTCAGTTCTTTCAGATT | 18588 TCTTAGGGGAGGCCAGACCAA | 29572 GGTGGGCAGCAGGTGAAATCT | 40556 |
| 6931 | AGACCTAAGACTATGTGGCAAA | 18589 GGTGGAAGTCTGTGTGGAATGTTAGTGA | 29573 GCAAGCTGGAGACGTAAGAGCTA | 40557 |
| 6932 | GCTTTCTGTGATTGCCAATACCATT | 18590 ATGAGACAAGCAGCTCCGTTTA | 29574 CCTAAGACATCTAACGCTTTCTGTGA | 40558 |
| 6933 | GCACACAATATGCCATTTCCTCTGAA | 18591 CACCAGCTGCCCTCTAGGAA | 29575 CAGGGAAAACACACAATATGCCATT | 40559 |
| 6934 | TGGGAAATGGTGTGCCTCATAG | 18592 GACTTGAACATTGCTCTCCTACCTA | 29576 GTGCACAGAATGGGAAATGGTGT | 40560 |
| 6935 | CTGACATGCAACGCGCCCAAAA | 18593 CTGTTTCAATCCTTGCACTGTGTCT | 29577 TCCTACACGTGGGCCTGACAT | 40561 |
| 6936 | GGCAAAGACCTGAAGAATGACGAT | 18594 ACCCCTTCCCTGCTTCTTGT | 29578 AGGAGATAGAGCCAAAGACCTGAA | 40562 |
| 6937 | CGCAGCTACAACATAAGCCAAA | 18595 GTCCTCTCAACATGCAGACCTTGAT | 29579 CCTGTACTCAGAAACGCAGCTACA | 40563 |
| 6938 | CGCACATGCATCCTCTGGGTACT | 18596 GGGAGGAGTAGGAGTTGTAAA | 29580 GGTGGCAAAGCCGCACAT | 40564 |
| 6939 | GGAAACTGTGCATCCTAGTTCTGA | 18597 GCCCACCGGACTATTTGCTCT | 29581 GGGCTATGGAGTCAGGAAACTGT | 40565 |
| 6940 | AGCTGAAACCTGCAGGAGGAT | 18598 CCCTAATGGCCCAGCCAACATAC | 29582 GGAGGAAAAAAGGCTTAGGAAGCTGAAG | 40566 |
| 6941 | TGCCTCCAGATCTAGTAATACTGCTT | 18599 AGCGCTTGTGAACTCAGGAATG | 29583 TCCTGTGGTTGTCTGCAGAT | 40567 |
| 6942 | CCACAACCCTTAGACTGACGTCTT | 18600 GTAGTCCACCCATCCTGATAAGGTTAAG | 29584 TGCCGATTGCAGACCCACA | 40568 |
| 6943 | GCAAAGCACTGCCCACATTG | 18601 CCTTATACCCCACCTCCACGAA | 29585 GCCTTCCAAGTGACAAGCAAAG | 40569 |
| 6944 | CACACTGGTAAAAGTGGCATGTATGA | 18602 GCGCAAAGGATTTTGTTCCTTCACT | 29586 ACCTCACTATGACACACTGGTAAAAG | 40570 |
| 6945 | GGAAAGCAGCTGGCACTCATGA | 18603 CAGCACAAGCAAATTGTCTATT | 29587 GAATGTTCTGCCATCTTGGGAAAG | 40571 |
| 6946 | CTCCCTTCTATAATACCTCACAGATAG | 18604 CACCAGTGTGTAGTGGTAGCAGAT | 29588 GCGAAGCAGGAGTTCTCCCTCTATAATAAC | 40572 |
| 6947 | GCCGTGTTTACGCTCTTCTTG | 18605 TGTCCTTGGGAGGAGAGCTAGT | 29589 TCTTGAATGCATTGCCGTGTTAC | 40573 |
| 6948 | GCATTACACCGTTCACAGTT | 18606 AGCTACGGCCCATGACAAGA | 29590 CTACTGCAGGTGCCATTTACA | 40574 |
| 6949 | CCGACAGGCACAGACCAATGAGAA | 18607 CTAGCTTAGCCCTAAATAAAGCACAGT | 29591 CAGAGTCCGAGAGGCACAGA | 40575 |
| 6950 | GGATAGTGAGTTCCTCGTGGATCA | 18608 GGTGTGGGACCATGGAGACAAAT | 29592 CCATACCTCCTTTACTGGATAGTGAGTTC | 40576 |
| 6951 | CCTGCCCATCCTGAGGCACTCTTA | 18609 CAATGCAGTAAGGGAGAACACAAAC | 29593 TGCCTTGACCTCCCCATTCTGA | 40577 |
| 6952 | GCCCAGGAGTTGACCCTTCAAT | 18610 GGCCTTATCATCATCATCTGAGCATGAAGTTT | 29594 CTGCAGAAATGCCCAGGAGTTG | 40578 |

FIG. 36K7

| | | | |
|---|---|---|---|
| 6953 AGGAGTATAGTAAGTTCTCGGTAGCAT | 18611 GTTGCAATCTACTGGCAGTTTCTAAGG | 29595 GCGTTAGGTGACTCTAGGAGTATAGTAAG | 40579 |
| 6954 TGAGCTTGTTCTGGTCCTTATCTTT | 18612 GATTTGTTGTTAGGTCACTCCAACTTC | 29596 GCCCCTCAATTTGCTATGAGCTTGT | 40580 |
| 6955 CGGGTAGTAAGCACACAGCAA | 18613 CGCTCTGAGACAGGCATACAGTTG | 29597 TGGCAACGACGGGTAGTAAG | 40581 |
| 6956 GGACAGTGAAAGCCACCATCTAAGGGGTA | 18614 CCAAGGTCACTGCCTCTCATGT | 29598 ACTGTTCTTGTCACCAGGAGAGTA | 40582 |
| 6957 AGGGGTACTTCCAAAAACATAATCT | 18615 CAGCTCGTCCTTTCATTCTTACA | 29599 GGCATTCAGGGGGCTCTTCAAA | 40583 |
| 6958 CTGAGAAACAGTCATTACCAACATAC | 18616 CTTGTCTGCTGGGCTGTTCTA | 29600 TTCTCTGACAAAGACTGGGAAACA | 40584 |
| 6959 GTAGTGACAAGAAATTAGGCCAAGTCTA | 18617 CAGGGATCAGACAGAGACATTGTT | 29601 GTTCCTTGCAGCAGTGACAAGA | 40585 |
| 6960 GCACACAGTCAGTTCATGGCAAAG | 18618 AGTACAAGACTGTGAGTCACGAGAT | 29602 TGCTTGGCAGCACACAGTGA | 40586 |
| 6961 TTCCTCCTGAAACGAAAGAATGA | 18619 GTGAAGCCAGAGGTGCTCTT | 29603 GGAGGCATCTCACTTCCTCCTGAA | 40587 |
| 6962 TGGAACCCTAATCCTGTTCAGGTA | 18620 CCTGAGCAACAGAATTCCCACAGAT | 29604 CACCCTACAACATAGATGGAACCCTAATC | 40588 |
| 6963 CTGTCTTAGGTGTCAGAATACCAACTCT | 18621 CTGTGCCACCGTCTATGTAATTTATGT | 29605 GCATCCCTATTACTGTCTTAGCTGTCACA | 40589 |
| 6964 CAGTGCCACAGCACTTCTCA | 18622 CAACAAGATTCAGTGCCAGGAACA | 29606 GAGAGTTTGGCACTGGTGAT | 40590 |
| 6965 GCTACTCTCACTGCCCTCTTCTA | 18623 GAATATAGCGGCCAGAGTGATGA | 29607 GCCTCCAGGGTGCTACTCTCA | 40591 |
| 6966 CCTCTCAACGAAGGCATAATGCTA | 18624 AGAGGACGTGGTTATCTTGTCAATG | 29608 TCATCTCCCCCTCTCAACGAA | 40592 |
| 6967 GTCACCATTTCTGGCATAGTCTGAGGAA | 18625 GGCTTCATAGGCATCTTCAAGGACCTA | 29609 ACTTTCACAGTCACCATTTCTGGATAG | 40593 |
| 6968 TGACCCAGAAGAGTTTGGAGTTG | 18626 CCTCACTTCTCACATCACAGCTCTCA | 29610 GCTGAGCTTTCGTTTTGACCCAGAAG | 40594 |
| 6969 AGTGAATTGAAGAGGGCACGAAAT | 18627 CAPTAAGAGCCCTTCAGATCCTGTCT | 29611 AGCCAGATTCCAGTGAATTGAAGA | 40595 |
| 6970 GTGGCAGTGGCAAAAGAACACAA | 18628 CGAGTCCATGTGCAGAAAGAAC | 29612 GTAGTGGTGGCAGTGGCAAA | 40596 |
| 6971 GGTCTGTGCTCGCTTGGTTA | 18629 GGCTTGTCCTGCTTCAAAACACT | 29613 CTGCCTCATTCCAAGCTCTCT | 40597 |
| 6972 GAGTAGTCCAGGTTATCCTCAGAGTCA | 18630 GGAGAAATCCCTATTCTCCCTGTTG | 29614 GAGGGAAGAGACTAGTCCAGGTTAT | 40598 |
| 6973 GCTTCACTTGGCAGCTGTTTC | 18631 CTGTGTAAGGAGGACACCACGATCT | 29615 GGTTTGGACACCAGGTGCTTCACTT | 40599 |
| 6974 GCTGGGGACATGTCTTGGATTTTC | 18632 GAAACTGGTCCTGAGGATGACA | 29616 GAACTTTGCTGGGGACATGTCTT | 40600 |
| 6975 GCATGGCAGAAGCTAGAAAGAAGGAT | 18633 AGGGACAGGCAAATAAGTATGCTGTAAC | 29617 CAGGCAAGATCATGGCAGAA | 40601 |
| 6976 CCTAAGTGGTTGGTTCAGAATTCACT | 18634 AGGAGCTAGTATGGTCTTTAGAGTAA | 29618 GGGCATACGGACCTAAGTGGTT | 40602 |
| 6977 TGAGCATGTAGCCTTGCCAAA | 18635 CCTAAATCGTCTGCTGGTGTCCAT | 29619 CAGGTTTGGGTTATCAGCATGTAG | 40603 |
| 6978 GCCCATTATTCCCCACTACTCTCT | 18636 TCCTCCTCCCACCTCCTTAAAA | 29620 TGTCCTGACTCCTGCCCATT | 40604 |
| 6979 CCAGCTAGACCTGGAAGTACAGGAT | 18637 CACCACCAATCAGAGAATTGGCCTTT | 29621 TGCCTCCAGCTAGACCGGAAA | 40605 |
| 6980 TGCTGCTCAAGTGTTTCCTTCT | 18638 TGGAGACTGGTCATGTACACACA | 29622 CCCTTCTGACCATTGCTGCTCAA | 40606 |
| 6981 CCTTTCTAGAGTGGTGCCATTATCTCA | 18639 TGGTTTTCCATCTGCTCACTTTTC | 29623 CAAGGACTTTGGCTCCCTTTCT | 40607 |
| 6982 GGAGGCCTTTCTGAACCATGCTT | 18640 GAATGGTGGAAGGGTAATGTCAATG | 29624 TCATCTTCTCAAGGAGGCCTTTC | 40608 |
| 6983 CTGTTGTAGGCCTGAGGCATTG | 18641 GTGATAATCTGCTCCTAGCTGAACA | 29625 ACTGAGCCTGGCCCTGTTGTA | 40609 |
| 6984 GGGCTACACTGGATCACAGCTT | 18642 GCACAGGACAGAGGATTCATGCTAATG | 29626 AGAGCCCTTGGGGCTACACT | 40610 |
| 6985 GCTTTGGAATTTGGGGTGACCTTTC | 18643 AGACTGGATGCTGAAATCCTTGA | 29627 GGAGAACCACATCTGAAGCTTTGAAT | 40611 |
| 6986 GCCCTTGTTCATGGATAAAGAGCATTTG | 18644 TCATGGCTCCCCTCACTTCCTA | 29628 GAGCAGCCCTTGTTCATGGAT | 40612 |
| 6987 CCAGATGCCCATGGATACTCCTTTTC | 18645 CCAGGCCAGTTCTGAGAGGAAACA | 29629 GAAAGTGACCAGATGCCCATGAT | 40613 |
| 6988 GAGGTTCATCGAAATGGTAAAGCAA | 18646 GGGTGACAGCTGTTCCTAATCGT | 29630 TGGTGATGAGTATGAGGGCTGAT | 40614 |
| 6989 CCCTCGGTTACAGCAACAGTTC | 18647 GCATCCAGTTATCCAGAGAGCATGAT | 29631 GTGTGTGTAGAGTTCCCTCGGTTAC | 40615 |
| 6990 GGGGATCAACGAGAGCCTACAGT | 18648 GTCAAGGGACACTAGTAAGTGGGCTT | 29632 TAGCACCCACACGGGGATCAA | 40616 |
| 6991 CCCAGAGATAGTTCCTACTGACCACTT | 18649 CAGAGACAAAATGTGATCGTCT | 29633 CTGAGGACAGACACCCAGAGATAG | 40617 |
| 6992 CGCCAACAGGGTTGGAGTAGT | 18650 CAGGCCTGAGAGAAATTCACAGTTG | 29634 CCTTGTCAGGGTTTCGCCAACA | 40618 |
| 6993 CCTGACCATCTTTGCAAATCAGGCTTTA | 18651 TGCAGAGGACCCACTAGTCCAA | 29635 CCTGACTGCCCTGACCATCTTT | 40619 |
| 6994 GGGTACCAGTCCTTCCACTTTTG | 18652 GTCGTTAGGCGATGCATGATTGTAA | 29636 GCCCTGGGTACCAGTCCTT | 40620 |
| 6995 GCTTGGGGCAAGAGTTGTTTAC | 18653 GCGGTTTGAGGGTATAAATGGAAGTGA | 29637 ATTGCCCTGCTTGGGGCAAGA | 40621 |
| 6996 CAGGGTGACTGACATGGGTTT | 18654 GACATGAAGACTCGCTTGCAATTGTATTC | 29638 TCGTGCCACAGGGTGACTGA | 40622 |
| 6997 AGGACTTGCTCTCTGGGTCAGTT | 18655 GGCACTAGAGCGTTAAGCACAACTT | 29639 AAGCCTCCGTTTCCTAGGAGTTG | 40623 |
| 6998 GAAGATTGGGCATGGTTACATCCATATAC | 18656 GGTTTAGGAGCCTCTCTCTCCAA | 29640 AGTGAAGAGTTGGGCATGGTTACA | 40624 |
| 6999 CCTGCCTCACTGCTCCTTCT | 18657 GACAGTTTTCACTTTGCAGGAAGTA | 29641 TCAGGGTCCTGCCTCACT | 40625 |
| 7000 GGGAGGAACCAAGCTTCCCATTG | 18658 GGCCAAATTATTGGTGGCTTAGCA | 29642 TACCCCTCCTGGGAGGAACCAA | 40626 |
| 7001 CAGTATCACAAGCCTCACTTTGGTTC | 18659 GGTACTGGGCATTCTACTTGACT | 29643 CAGAGGAAGCTACCAGTATCACAA | 40627 |
| 7002 CAGAGTGTCATTCTGGGCATGAAC | 18660 GCTTCCATGAGCTGTCCTCAATCT | 29644 CTGCAGTTGGATCAGAAGTGTATTC | 40628 |
| 7003 GCTGCTACTTCTCTTTTGCTGACTACTTC | 18661 ACCCTCTCCCAGCCCTGAAAA | 29645 GGCCTGATTCATGCTCTGCTA | 40629 |
| 7004 CTCACACAGCCTTCTGGGATCA | 18662 GGGCTCTCTGAGTGAAGGATGT | 29646 CACTGAACTAGTTGGTTCTCACACA | 40630 |
| 7005 CCATGTAAGGTGGGTGGAAGGAA | 18663 GTGGCCTTCCTCTGAATGAAGT | 29647 AGCAATGGAAAACACCTCCATGT | 40631 |
| 7006 GGGATCTCTCACTCACACAGT | 18664 GACAGAGCAGAGGTAATGGGTATACTTG | 29648 TGCAAACATCTTTGGAAGGCATCT | 40632 |
| 7007 GGCCAGGTTAGGAAGGCTTA | 18665 CCATCCATGTCCCAATCCAGAGTT | 29649 GGATCTAGTGATTGTTAGGCAGGTT | 40633 |
| 7008 GGAGGCTGTAGTTGCTCTCATGTA | 18666 GCACAACAACACTACCCATTTTCGA | 29650 CCCCACAACGTAGGAGGCTGTAGT | 40634 |
| 7009 CAGCTTGGTAACCACCATAAAATACTCAAC | 18667 CGATTGTATTGCCTTTGCTCCTTTGT | 29651 TCAAAACAGCTTGGTAACCCACA | 40635 |
| 7010 CCATAACCACACAGGAAGTCTGATG | 18668 GGCCACAGAGTAGCATCCTCTGAAT | 29652 GGAATGTCCACTCCATAACCACACA | 40636 |
| 7011 GAGGAGCCTGGAACTGACCAA | 18669 CGAGCCTGCTGCCCCTTACA | 29653 GCCCCAGGGAGAGATTGAAGA | 40637 |
| 7012 GGGAGGAATGTTACTTGCCTTGACA | 18670 GCCTCCAAAGTGACAGGAGTGA | 29654 CCGTAGCCTGGAGCAATGTTAC | 40638 |
| 7013 ACTGCTATGCTTTTCATGTTTGGAT | 18671 GGTGGGCAAGGAGCTACTCAA | 29655 CCATTGCAGAAAACTCGCTATCCTT | 40639 |
| 7014 GCAAGAGGAATGGCAAGTAGAGAAG | 18672 CCTGGGCAGTTCAGCTGTTGT | 29656 GTCAAGACTTGGCAAGAGGAA | 40640 |
| 7015 CTTAGCGTCACACAGCAGACA | 18673 TCTGCCTAGAAACGGGTCGA | 29657 GTCTCAGCTGTCTTAGCGTCACA | 40641 |
| 7016 GACCTCACCATCATCCATGTGTTC | 18674 CCTCAAAAGACCCTCACAGATT | 29658 TCTCGGTCTGACCTCACCAT | 40642 |
| 7017 TGCTCCCCTGAGATGGAGACT | 18675 GCTCCTGACCTCACAACAACTTCT | 29659 TGGTGACGGGAGTTGGAATG | 40643 |

| | | | |
|---|---|---|---|
| 7408 GTCCTTGCTCATGACTCAGAACT | 19066 CGAGGGAATGGCGCTTTTCAAC | 33050 GAAAAAGGCAAAAGTCCTTGCTCAT | 41034 |
| 7409 GCTGGTGACTGCACATTTTTCA | 19067 ACTTCTCAAGGACAAGTGTTCTCTTC | 33051 CCTGTAATTCCATTTGCTGGTGACT | 41035 |
| 7410 GCTGAGTATCTGCGTGTCTGT | 19068 CTCTTGACCACATCTGGAAGTAGAAAC | 33052 GTGGTGTCTCCTGAAGCTGAGTATC | 41036 |
| 7411 GCTTGGCCTTACTGTACTTCTCT | 19069 GACCAAGGAAAGGTTGGCTAATAGT | 33053 CCTCTCACAACTTGCTTGGCCTTAC | 41037 |
| 7412 GGAGCAAGTGGGTATGTGAGAAG | 19070 GCCTCCATTTCTTGCTGGTTGTT | 33054 GGCCTCTGAGGGACCAAGT | 41038 |
| 7413 GGAGGACCCGTTTACATTCCTGATG | 19071 ACCTTCTCCAGATGCTCTACT | 33055 CTGTGTTTTTGGAGGACGGGTTTAC | 41039 |
| 7414 GCATTAGCCTCTTASTCGTTCCTT | 19072 TGTGGCAGGGACAGAGCTTCT | 33056 CATGGGAGCTCTGTCAGTGCAT | 41040 |
| 7415 ACAACACTTACCTCCCATCCATTT | 19073 GGGCTCCTAGGGGTGGTAGATTGT | 33057 AAGCCCCTACCAAACAACACTT | 41041 |
| 7416 CACTGTGACTGGCCTGTTCGTT | 19074 CCTCATCCTTACTGGGGAGTAACAGAT | 33058 ATAGGTGTGAGCCACTGTGA | 41042 |
| 7417 AGCCGTTTCGGAAAAGTGGAA | 19075 TCTCATCTCGAGACACCCAGAA | 33059 AGGAGGGACCAGAGCCGTTT | 41043 |
| 7418 GTCCCTAAGGTAAGGATGGAAAATCT | 19076 GCATGTATACTTGAAGCCACACAGA | 33060 GCCAGTGTTTGTCCCTAAGGTAAG | 41044 |
| 7419 GCTTTCGAAGGGCTGTTCTTTTC | 19077 AGGCCATGGCTCTTCTTCCTT | 33061 GCCTGGCCTTTGCTTTTGCTT | 41045 |
| 7420 CAGCTCGTTGTGGAGAAGCATCTTTAC | 19078 GTGAGATGCTATCTAGGTCACTGCTT | 33062 CCAGCCCTTTCATCAGCTTGT | 41046 |
| 7421 CTGTTTGACACCGAAACACTGCAT | 19079 CGAATTGCTATAGCCAAAAGCCATACA | 33063 GCTCGAGGCGTCGACAGAGTGTTTCT | 41047 |
| 7422 GTGCCTCTGTTGTGTCCAGAGTT | 19080 GCTCTGTTCTTCAGGTGGAAAG | 33064 AGCCTGTGGAGTGCCTCTGTT | 41048 |
| 7423 GGGCAAAACAACTGCAAATGCAACA | 19081 CCGTGATGCTGGATCAGCCAAT | 33065 GGTGCAAGCCAGATTGGGCAAA | 41049 |
| 7424 TGCAGCAGAGACTGTCCACTA | 19082 TCTCAGGGCCAGCCCCACTT | 33066 GCCAGAGCCGCAGCAGAGA | 41050 |
| 7425 TGGACATCACATCTGCATGAA | 19083 GACTCACGAGACTGCAATGTCT | 33067 GGCTTATACTTAAGGCATCTGCACATC | 41051 |
| 7426 GCTATCCCTGGACTTCTCGGTTA | 19084 CTGGCTTAAGCAAAAGGGGAATTT | 33068 AGTTCTACCTGAAGCCGATGCTATC | 41052 |
| 7427 GGCAGCCTTAATTCCCACCACAA | 19085 AGCTCCCTCCTCATGCTACA | 33069 AGGCCCTTGGCAGCCTTAATTC | 41053 |
| 7428 CGTAAGAGCTTGACAGGTGCTAT | 19086 TCTGGAAGTAGGAAGATCCCATTCT | 33070 ACGTTAAAACACCGTAAGAGGTTGA | 41054 |
| 7429 TGGCTCCTACCACACCTTGT | 19087 CCGCTATGCCTGGCTTAACTTC | 33071 CCTGAGTCTCACTCTGGCTCCTA | 41055 |
| 7430 CACACAGATGCTACTGGAGTAAAC | 19088 CGTGTCATTTAGACAGCCCTGTTTTC | 33072 GCCGGGGAAATCTTCTTCACA | 41056 |
| 7431 AGGTCCGTCTTCCCAGCTAGA | 19089 AGGTGACCCTATCTTCAGTGCTA | 33073 GGCCTATCTCTCAGGCTCGGTCTT | 41057 |
| 7432 CGGGAGAGTTCCTTCTCTTCA | 19090 CCGGTCAGCCAAAGGTCTTCTA | 33074 AAGGCCATGGCGGGAGAGTT | 41058 |
| 7433 GAGGGAACACCATTCCTCACA | 19091 GGGTTTGAGGGTGTGGGATTGT | 33075 CCTCAGAAGGGAGGGAACACCAT | 41059 |
| 7434 CCACAGTGAGGTCAAATGGATCA | 19092 CCGCCTCGGATGAACAAGAAAC | 33076 AAACTTGGCCTAAACCACAGTGA | 41060 |
| 7435 CATCAACGAGACTCCAAGGTAATTCT | 19093 CCTCCCTCCCTATGGCTACTT | 33077 GGCACCATGACATGAACGAGACT | 41061 |
| 7436 CTGTAAGTAAGCTTGACTCCCTGTAT | 19094 CGTGCATGATTTGAGACGAACGAA | 33078 GTGACTTCCTCGAGTTACCAATCTGT | 41062 |
| 7437 CTGGACAATATAGAGCTGCCACAGT | 19095 CACCTTTTAGCTCAGAAGATGCAGAT | 33079 CCACGGCTTTTTCGGAAGATACA | 41063 |
| 7438 GTGGTTTACCAACTGCACTACCAA | 19096 CAAGGATATGGAGGACCAGGATTC | 33080 CCAAAGACCTCACCATAGTGGTTAC | 41064 |
| 7439 TGACGCCCTGCACTTACTGA | 19097 GGTCCATGGTGTTGAGGGAATTG | 33081 CCCCACTAAACCTCCCAGTGA | 41065 |
| 7440 CAGCTTCCTGGTTACTGTGTCA | 19098 CAGCTAAGGGAAAGTCAATTCAGGTTA | 33082 GCCATCACAGCTTCCTGGTT | 41066 |
| 7441 GTGTGCCCAAGACCCTCTTC | 19099 TGCACGGGGAAACTCACATTC | 33083 GGCTGCTGTGTCCAGTGTGT | 41067 |
| 7442 GGAGCAGATCGTCTCAGGAGGATA | 19100 TGAAACATACCGCCCTTAAAAGT | 33084 CTGCTTATAAACCTAGGCAGCAT | 41068 |
| 7443 CCCCAAATGGTAGTGACTGCTGCAATA | 19101 TGTGCACCAACTTTCTGTCACAT | 33085 TCCCCTGGCTCTTCCCCTTT | 41069 |
| 7444 TCTGCTCCAGCTGCTAGACTTT | 19102 CCAAAAGGAGCATGGCTGCT | 33086 TCCCCTGGCTCTTCCCCTTT | 41070 |
| 7445 CTGTACAGCATCAGCTACCTAAAC | 19103 AACGCCTACTTTCCCTGTCTTC | 33087 GCGGAAGGTACTGTACAGCATCACA | 41071 |
| 7446 GATGTGTCTCCAGTATTGTGTCTGT | 19104 GACAACACGGCTGTTCCACAA | 33088 CGAACCAAAGATGTGTCTCCAGTAT | 41072 |
| 7447 GGAGGAGACAGGCAGAACTGTA | 19105 CGAATAGTGCTGGGAATCTCTGA | 33089 CCGGGAGCTAGGAGGAGAGA | 41073 |
| 7448 GCGGTTAGCGTAGACAACA | 19106 GCTTCTGATCGTTGGACATTTGGTTCAT | 33090 GAGGGACCAGTTGCGGTTAG | 41074 |
| 7449 CCCAGAGGTTCTGCATGTTTG | 19107 CCAGTAAACCTTTTCCATGAAAGCCTGA | 33091 TCGGGGACCCCAGAGGTTCT | 41075 |
| 7450 CCCCAGACAGTAGTCCTGAGATT | 19108 TGATTGGCTCCCAGAAGTTGTAAT | 33092 CCCTTTGACCCAGACAGTAGT | 41076 |
| 7451 GCTGCAAAGATAATCGTGAGGCCAAA | 19109 CTCTGAAAGATCGTGTCTTCCTTGT | 33093 GCCCAATTGGCTGGAAAGATAAT | 41077 |
| 7452 GGCGGTTGACAGAAATGCTACA | 19110 TGTCAGCACTGCCTTCAAAATG | 33094 TGACAGTGGCGGTTGACAGA | 41078 |
| 7453 AATTATCTCAAAACAGCGGGGTTA | 19111 CCCCAAAACATGCAACCTTTCCTTATC | 33095 GCAACTGAGGGTGTGGAAGT | 41079 |
| 7454 GCCGTAAAGTCCTGCCAACTAC | 19112 AACAAAGGATACCTCCGGGTAATATG | 33096 CATGGGAGTACACTGCCGTAAAG | 41080 |
| 7455 GCCCGGGGTTTTGCATAGCCTTCA | 19113 GCTCAAAGAGGATTAGGCTGCTTCA | 33097 TTCCAGGAAGGCCGGGGTTTT | 41081 |
| 7456 AGTGACTATCAGTGCCCACAAAC | 19114 CACCTGCAGACTAGCACAAGA | 33098 GCCATCTCAGGGTCAGTGACTATC | 41082 |
| 7457 TGTCTTGCTTGAGTCACTCTTTG | 19115 CTTGCTTCAGGCCAAGCAAA | 33099 CCATCTCCTATGTCCTTGGTCAGT | 41083 |
| 7458 TGGATCAACTCTCCCCTTGACT | 19116 GTCCATAAGGGCATATGGGTCTTTC | 33100 TCTGGTACCCTTCAGTAATGGATCA | 41084 |
| 7459 AGGACAGAAGTCCTAGAGGCACACA | 19117 AACCGAGGCGAGTCCCAGTT | 33101 GGGAACTGGATTGTGGGCTAG | 41085 |
| 7460 GTCCTTGTTCACAATCCAAGGAGAT | 19118 GCCAACCTGGTTCCTCATCATT | 33102 CACTCGAACTCCAGTCTCTTGTTC | 41086 |
| 7461 GAGGATCTATCGGAATCCTCTGTCT | 19119 GGCAGCTCCTTAAGCTGAGTGACTGT | 33103 CAGCCGAACAAGGATGAGGATCT | 41087 |
| 7462 TCCAGTCAAAGGCTACTTCTGTGAAA | 19120 CAGCTCCTCTCCTGTCCATTT | 33104 GTGGGCTGTAACACTTCCAGCAA | 41088 |
| 7463 CTCTCCAGCGTTACCCGATTTC | 19121 GGGGACTCCACACCTGAAAACT | 33105 CTGTCGGTTCTCTCCAGCGTTA | 41089 |
| 7464 CGTTCCCTCTCTTCTTCCCCTTT | 19122 TGGGGAACCTTAGAGAGCTTGT | 33106 CCTGTTGAGTCTAATCGTTCCCTCTCT | 41090 |
| 7465 GGTAAAGCAAGTAGAGGGTACTAACATGA | 19123 GCAGGTAGACGGATTCAGCTT | 33107 GGGAGAGAAAATGGGAAAGCAAGTAG | 41091 |
| 7466 AGCACCGTTCTGCAGCTGAT | 19124 CAGGATAGCTCCCTAAGGCTCAAATC | 33108 CCTTCAACAGGATAGCACCGTTTC | 41092 |
| 7467 GAGGAGACAGGCAATTAGCACAT | 19125 CTCCAGTGCCATACCCAGTTGT | 33109 GCAGATCTTTCACTGGAGGAGACA | 41093 |
| 7468 CCAGGTGGGACTGCTTATCTCT | 19126 GCTAAACAAGTGTGTAGTCTTGGGATCT | 33110 TTGCCTCCAGCTGGGACTGT | 41094 |
| 7469 TCACACCTCGGAACCCTGCTT | 19127 GAGGCAACAGCAGACATCCATCA | 33111 AGCACCATCCATCGGTCACA | 41095 |
| 7470 CCCTACTCACTCCCTTCTCAGT | 19128 TCGGATTCCTTGTTCTAGACCTTTC | 33112 TCCCTGGGGAGACCCTACTCA | 41096 |
| 7471 CCCGCCAAGCTGGAGGTAATAGTAG | 19129 AGGCTCTGTCCCCATGACCTAA | 33113 TCTCACCCGCAAGGCTGAA | 41097 |
| 7472 GCTAGCAGTTGATGAGAGTGGATTTC | 19130 ATCCGTGACAGGCCACACAAC | 33114 CATAAGCACCCAAGTGCTGCTA | 41098 |

FIG. 36L5

| | | | |
|---|---|---|---|
| 7473 GGGGCCACAAATGGGGAAT | 19131 CCCCAGCAGAGAGGAGACCATATT | 30115 AGCTGGGATGTGGCTGTTTG | 41099 |
| 7474 GGGTGGTTTGCGCTTCTTATCACA | 19132 GAGATCAGGACAGACAGGTCTAAAG | 30116 GAGACAAATGTAACAGGCTGGTTTG | 41100 |
| 7475 CTAGCAGCTCTTAACAGATGATGTTG | 19133 GAGTACAGTCAGCCTCTTGTTTCCTT | 30117 AACCATGCCAGCCTGCTCTA | 41101 |
| 7476 GGTGGTGTGAGGGCTGGATATT | 19134 CCTTCCTCATCATGGTAGCATCTCA | 30118 GGGGATTGTTCAAGGTGGTGTGA | 41102 |
| 7477 CTGGTTGGCATTATTTGCTCCAA | 19135 GCAGAGCAGCATTGACGAACA | 30119 AGAAAGGGCTGGTTGGCATT | 41103 |
| 7478 GTGTCTGCCTCTCCACATGTCTTG | 19136 TAGCGGCACCCTGTGCTT | 30120 GGGACCTCCCCTGTGTCTGT | 41104 |
| 7479 CACACCCTGAAGTCACTATCCTTTC | 19137 AGCCATGGTCCCAGGATACA | 30121 GGTCCAGCACACCCTGAAGT | 41105 |
| 7480 GCTCGAATTCACTACTGGGCTAAA | 19138 CGTGCAATCCGTGGTGGCAA | 30122 CTGCCATCGCTCCGAATTCACT | 41106 |
| 7481 CCATCTTCTTTGCCATGCAGCAAT | 19139 AGCTGGCCGCATTCCAGTTT | 30123 TCGCTGGCCCTTCATCCAT | 41107 |
| 7482 CTCAGAAAATCACCTCCTCCCTGAAG | 19140 ACTGAGATTCTCGCCCTGAAAATG | 30124 CGAGGAAGACCTGACTCAGAAATC | 41108 |
| 7483 GCTGTTCACCGCACATTCAGT | 19141 GCAGAGAGGTTAGTTCACTAATAGAAGCAT | 30125 ACGCAGACCTGGCTGTTCA | 41109 |
| 7484 CTCTGTCTCCTGTCCCTGGAATAC | 19142 GGGCTTCAAAAGGCAGGACTGT | 30126 CAGTTTCTTGTATCTGGCTTCTCTGT | 41110 |
| 7485 GGCTCTTGCACTGCTCCTATTTG | 19143 CCTTGGACCAGAGACTATGTGAA | 30127 AGGGTTTGGCTTGGCTCTTG | 41111 |
| 7486 TGACCCCATGTTCCAGCTACT | 19144 TCCCTGTCTACATGAAGCAGATAAAG | 30128 CCCAGTTACACTCTTGACCCCATGT | 41112 |
| 7487 CATCTGTGAGACAACTGGTGAACT | 19145 GCCAGAAATCTGCCCTCTAGGTT | 30129 GCAGAGTGCATCTGTGAGACAAC | 41113 |
| 7488 GTGCAGTGAGAGGCGAAGTACA | 19146 GGACAGGCTCCAGATGCTAACAA | 30130 GCAGGATTTGCCTGTGCAGTGA | 41114 |
| 7489 GAAGTACATAGGGGTGACCATGAAA | 19147 CTCCCCAGACAGAGAGAACTGA | 30131 AGGTGCTTCGACAGAAGTACATAG | 41115 |
| 7490 AGCGCTCTGCGATTTCCTT | 19148 GTCACACACAGGCATGGCTACA | 30132 ACAGCGTGGCATGCTTTCT | 41116 |
| 7491 TCACACCACCCATCTGGAGTCA | 19149 AGGGAGGGGCATCTGCGTAT | 30133 TCTAGAAGCCTCCCTCCTCACA | 41117 |
| 7492 GGAGGCAAGGAACATAGTCTTTAAC | 19150 CCTTTGCTTTTAGCAGGACACTTG | 30134 TCTCTGAAAAGGAGGCAAGGAAAC | 41118 |
| 7493 CAGTTTTCAGGCCACGTTCTAAACAAG | 19151 CTGGGACACCAGGGAATGATGTTC | 30135 CTCATTATCAGTTTTCAGGCCACGTT | 41119 |
| 7494 GCAGGCATGGTATAAAACCCATTCCATT | 19152 GACCATGTGGCTTGCTGCAAAGTT | 30136 GGGTGAATGTTGCAGGCATGGTATAAAAC | 41120 |
| 7495 CCCTCTGTGGGGTACTTGGTAGA | 19153 GGTCCTGATAGGAAAGCCAAAGT | 30137 TGGAAACCTCCTTACCCTCTGT | 41121 |
| 7496 GGTGAGAAATGCTGTTATCCACCTTTAG | 19154 AGTGCCCCTCAGCACATGAAG | 30138 CTGGAAAGAGGTGAGAAATGCTGTT | 41122 |
| 7497 GCGCAGATCACCTTGTTCTCCAT | 19155 GGTCGCCTTTGGAGCAGAGA | 30139 ACCAGGGCCCAGATCACCTT | 41123 |
| 7498 GGAAGGGGCTGTCCTTCCTCTA | 19156 CAGACACCAGCATCCTTCCTGGAT | 30140 TCAGCGCGGTTGAAGGAGGAA | 41124 |
| 7499 CCACACCAAACGGGTGTGAAAC | 19157 GCTGCGTCTTTCCTGGATGT | 30141 GGCAACCACCACACCAAAC | 41125 |
| 7500 TGGATCGTATATGGCTTTTTAAG | 19158 GCCCCAGTTATCACCTAATGAACACA | 30142 GCAGTTGGCTTGATTGGATCGTGATA | 41126 |
| 7501 GGGTTTTGGCTTAAAGCAGTCTGAGT | 19159 AGTTTGTCTCCCATAAGCTCTGTAG | 30143 GTAGCCCTTGGGTTTTGGCTTA | 41127 |
| 7502 GGGAAGAGGACAAAGTGGGACTGT | 19160 CCACCCTTAAAAACTCCTCTCATCAAC | 30144 ACAAGTTTGGTGACAAGGGAAGA | 41128 |
| 7503 CCTCCCAATCCCTGACCTGTAA | 19161 CCACACTTCAAGGCTTCAAATCATCCTT | 30145 TCTGTGCCTGTCCTCCCAAT | 41129 |
| 7504 ACACCTCCATCTCGGCCACA | 19162 CCCGGCCACAACTGCTTTCTA | 30146 TGGCTCCCACACGTCCATCT | 41130 |
| 7505 GGAGTTTTACCCACTCCACCTGATTC | 19163 GATGGAGACCCCTCTCTCCACTA | 30147 GGCTCTGTGAATACCAGGAGTTT | 41131 |
| 7506 GGCAGCATGTGTGTGTTTCCATCT | 19164 CCCATTTCCCACCCACAGGAA | 30148 GGGAAAGGCAGCATGTGTGT | 41132 |
| 7507 CCTGAATGCCAACTGGAGGGAAT | 19165 CTCACAGCCTTTCTCAGCCTTTC | 30149 CAGACGCCTGAATGCCAACT | 41133 |
| 7508 TCTCCAGTTCTGACGGGACATTT | 19166 GCTAGGCTTGGTCTCTGCAACT | 30150 AGGGTGTATTGCTTTCTCCATTTCT | 41134 |
| 7509 CCAGGACCCAGACATAGGTGAT | 19167 CACGGTTCATGTAAAAGAGCGAAT | 30151 AGGTCCCAGGACCCAGACA | 41135 |
| 7510 GCTCAGACACACTCCTGGAACA | 19168 TGTGGCGGACGCCATTATCA | 30152 ATGCTGGGCCTCAGACACACT | 41136 |
| 7511 CAGTTCACCTCTGAGCATTGATTTC | 19169 GTTTGGTGCTGGCTTTTGGTT | 30153 GGTGAGTGCTCAGTTTCACCTCTGA | 41137 |
| 7512 GGTTTCTACAGTTGCCTGTTATAGAGAAG | 19170 CAGCTCCAGGCTTGAGACATTCA | 30154 CACATGGTTTCTACAGTTGCCTGTT | 41138 |
| 7513 AGGACAACCAGAGAGGAACAATG | 19171 CCAGGCCAACCTTAGCCATATT | 30155 GGGCTGTGTGAGAAGGACAA | 41139 |
| 7514 GAGAGGCCACTTTCAGCCACTA | 19172 GGAGATGGAGGGAGCTTTGTGA | 30156 GGCTGTTAGTGAGAGCCCACTTT | 41140 |
| 7515 GGTAGCTGGGAGAAAAGAAGGTTAG | 19173 GTCCTGCTTTAGGAGCTTTTGCACTTAC | 30157 CCAAGCAGGTAGCTGGGAGAA | 41141 |
| 7516 GGGATGAAGATCGAAAATAGGACCAA | 19174 GAATGGGGTTGTCCACAATTAGTATG | 30158 TGGAACAATGGGATGAAGATCGAA | 41142 |
| 7517 GCCAACGGGAAACACATTGAA | 19175 CCACCAACCCGATCAGTGCAAA | 30159 CCTCAATGTATGCCAACGGGAAA | 41143 |
| 7518 GTGACTTCCTCACACTCCTGGATTC | 19176 ACTTTTTCAGCAGCTCTCTTCATCT | 30160 CTGGGAGTGACTTCCTCACACT | 41144 |
| 7519 GTGGAGCCAAACCAAGCCAAT | 19177 TCTTCCATTCTCCCCTTCCAAAATG | 30161 CACACTGTACAATAGTGGAGCCAAAC | 41145 |
| 7520 CAGGGCTCAGTTGAGGTGAGGTT | 19178 GCTGACAGACTTGCTTTCCCAGTA | 30162 AGACAGCAGCAGGCTCAGTTG | 41146 |
| 7521 GCAAAATGGCCAGGTACGATGT | 19179 CACCAGGTTGGATGTGCTA | 30163 GAAGACATGGGCAGCAGAGCAA | 41147 |
| 7522 GTTTCCAGTCTCTGCTCATTAGGAA | 19180 TCTGTGGGTGTAAGGAATACACAATG | 30164 ACTTCCAAATGTGTTTCCAGTCTCT | 41148 |
| 7523 AGATGGGCTCTTCCTGCTCATC | 19181 CTGAGGCTAAAGATCACCCATGGTA | 30165 ACCCACACAGATGGGCTCTT | 41149 |
| 7524 CCAGCCCTTGATTCTTTGGAATCTGTTAC | 19182 GCTCCTCACGGATGGTCTGAAA | 30166 CTGTCCAGCCCTTGATTCTTGGAA | 41150 |
| 7525 TCCATCCCCTGGGCCTCAAATCT | 19183 CTCACCAGCCTGAGAAAGGAAAC | 30167 TGTCGTGTTTCTCCATGTTCCAT | 41151 |
| 7526 GTGTGCCAGTGTACTTCATTCATCTGT | 19184 CAGGGAGTCGTCCCCTTGCATAC | 30168 GAGTATCTGTGTGCCAGTGTACTTC | 41152 |
| 7527 CCTTGCGGACTGACTTCAGTGTTG | 19185 GCATCTTGTACCAGGGACCAGAAAC | 30169 GCCTTGACACTTGCGACTGA | 41153 |
| 7528 ACGTCCTGGAAGTCAGTGTAAC | 19186 TGGGAAGTGGCGTGTGTTCA | 30170 CCAAGATGACCACGTCCTGGAA | 41154 |
| 7529 GACCACCCAAAAGAGAACTGTTG | 19187 CCAGTCCAGGCCCCTGGTTA | 30171 GCAGAACTGTCTGACCACCCAA | 41155 |
| 7530 GGGAACCAAAACAAGCACTAAAGTGTCAT | 19188 GTGGAGGGAATAGCCCTTTGAGA | 30172 TCTGGGAACCAAAACAAGCACTA | 41156 |
| 7531 GGGGATCTTGCACTCACTTGT | 19189 GGCCAGTCCCCACTCTTTCTTA | 30173 GGTCCCATACAGAGGGGATCTTG | 41157 |
| 7532 GTCCTGTAGCATCAGACCTTTAAGACA | 19190 GACAGCAGAATGCAAGTGACCTT | 30174 GCTGAAACAAGTCCTGTAGCATCA | 41158 |
| 7533 CCCTGCCATCTTTCAAAGGCATCTTTC | 19191 CTGTTTCTTCGCTGGCTACAGTTTG | 30175 GCTGTTGACACAGTCCCTGCAT | 41159 |
| 7534 CCAGTCAAGGGCAAAGGCTACT | 19192 CTCCCCTGGAAACAATAAGTCGATGA | 30176 AGTTTCAGTCTCACCCAGTTCAAG | 41160 |
| 7535 GTGACTCCTAATGAAGGCAGACTCCTA | 19193 TGTGCCCAAGAAGTAAATTGGGATA | 30177 ACGCTATGTCTGTGACTCCTA | 41161 |
| 7536 GTGGGCTTTGCAGTCAGGACAT | 19194 GGTGTGGCCTTCACAGGTAAGA | 30178 CGGTTTAGAGCATGTGGCCTTTG | 41162 |
| 7537 GAAGAGGGGATTGAATAGTCAGGTTAC | 19195 CCTCAAGAGCATGCTACACACT | 30179 CTTCCCATTTGAAGAGGGGATTGA | 41163 |

FIG. 36L6

| | | | |
|---|---|---|---|
| 7538 | TGCCTCTAGAATGGCACTGTTTAG | 19196 | TGCTGGACACCACAGAACTTT | 30180 | GTGCTGGTACCTGTTGCCTCTA | 41164 |
| 7539 | GTGTCAGGGGTAGTGAGTTTGGTTT | 19197 | GTAACATTCACACTCAGGACCTT | 30181 | GCTCATGGTGTCAGGGGTAGTGA | 41165 |
| 7540 | TCCTGTGGACATACCCAGTTGA | 19198 | PGTCTTCCATTAGCTCCAGACTCA | 30182 | GCCCCTTGAATATTCCTGTGGACAT | 41166 |
| 7541 | GCCAGCAGATGAGTCATGGAGTAT | 19199 | CCATCCTCTTCACGCCCATCAGATA | 30183 | GGTCAATGCCAGCAGATGAGT | 41167 |
| 7542 | GTGGGATGCCAAGAACTTGACTTTG | 19200 | TGCTCCCTTGCTATTGAGACTTG | 30184 | GGCTAAGTGTGGGATGCCAAGA | 41168 |
| 7543 | GAGCAATGAGAGACAATGCGTTAT | 19201 | CCACCAGCATCACCAGCAGCAATG | 30185 | GTGCAGCATCACAGAGCAATG | 41169 |
| 7544 | GCCACAGGGAATCTGTGTTTGAAG | 19202 | GGAGAAAGGTTGAGTCTGGGGAATG | 30186 | GAGGAAAAACAGCCACAGGGAATC | 41170 |
| 7545 | CGTGCTGACTAGGCAGATTTTG | 19203 | CCACATACCAAGGAGAGTTGACAGAT | 30187 | CTTTCAAGACCTACGTGCTGACT | 41171 |
| 7546 | GCCAACAAAAGTCCTCGCTTTG | 19204 | GACGTCATTTAGCTCGGGTGAA | 30188 | CCAGGCAGGTGCCAACAAAA | 41172 |
| 7547 | CCAGGAAAAGAGGTGACTGCAT | 19205 | GCAAAAGATCCTGCTCTGTAGGGAAA | 30189 | GTGCAATTCAGATGGCCTCTTC | 41173 |
| 7548 | CTCAGCATGTTCTAAGGGCAGAGA | 19206 | CCCTCGATAAGGCAATGTATACTCACA | 30190 | TGCAGAATCACTCAGCATGTTCTA | 41174 |
| 7549 | GTCCTCTGLCCATGAGTGAAC | 19207 | GCCCCAGAATATGAAATTGGAACAGAAG | 30191 | GGGGCCTCGTTTTGGAGTTG | 41175 |
| 7550 | CCCTGGAAATGCATCCACGAT | 19208 | CAGAATGGATGCGTCCGCTAA | 30192 | GCCTGCGAACCCTGGAAATG | 41176 |
| 7551 | GGCTTGAGTGAAATGGTAGTACTCAAA | 19209 | GTTCAGGGTTCTTCTTCTCTCCAA | 30193 | AGTCTTGGCTTGAGTGAAATGGTA | 41177 |
| 7552 | GCCTAGTGTAGGCAAAGGAAGTCT | 19210 | GATTTCTTAAAGCCGGTTTGTCGAT | 30194 | AGGGGCAGAGAAGCCTAGTGTA | 41178 |
| 7553 | TGGGCCCTGTAGAGTGCATTTC | 19211 | CCCTATGGAAAGACAGCACCCAAA | 30195 | TCTTTCAGGATGGGCCCTGTAG | 41179 |
| 7554 | GTGTCCTGGGTGTGTGTTCA | 19212 | CCTCCTAGTTCCTACTCAGCCTCTAAC | 30196 | TTGCAAAGCCCGGGAGTGT | 41180 |
| 7555 | CTCCTACTTGGGTGGAGGAAGTCT | 19213 | CATGCCTGAGGTAACACCTACTCF | 30197 | GACCATAGATCCCCTCTCCTACTTG | 41181 |
| 7556 | GTAGCAGTACAGATGAGTGACATAGAT | 19214 | GTCTTGTCATTCCTACCCTTCAAATG | 30198 | GGACGAAGGTGGTAGCAGTACAGA | 41182 |
| 7557 | GGGGTTCCTGCAAAAATGGAGAGCTTTTT | 19215 | GCTTCATGCCTGCCATCCTT | 30199 | CCTTCACTCGGGTTTCCTGCAA | 41183 |
| 7558 | CAAACCAAGCACTTCTCCAAAACT | 19216 | ACTGGAGCTTCATCCTTTCATACAA | 30200 | TGTGAAGTACAAACCAAGCACTTC | 41184 |
| 7559 | GCCCCTCTTTCTCTGCATCTGGTA | 19217 | CAGAAAGTAACAGGTCAGCTCAGAACTA | 30201 | TCACCCTGCCCCTCTTTCTCT | 41185 |
| 7560 | CCTTTCAGCCACACACTGTCTTTG | 19218 | CAGGCTCATGGCAGAACTGT | 30202 | GCACTGCCTCAGCTCCTTTCA | 41186 |
| 7561 | GGAGACTGTATCCAGGCAGTGTGT | 19219 | CTCAAATAGGCCCTTGGCAGAAAAG | 30203 | CATCTCCTAGAGCTGGAGACTGTAT | 41187 |
| 7562 | GCCCCTCTCTTGCTGGCATT | 19220 | GGTTTGCCATCTAGATCAATGCAGACTT | 30204 | TGACACCAGATGCCCCTCTCTT | 41188 |
| 7563 | GTAGCCCTTTTTGCCAGGAT | 19221 | CAATCCCTGTTAAATTACCCCATCCAT | 30205 | CATGTCTGTACAGCAGCCCTTT | 41189 |
| 7564 | GAGCTTTGGGAAAGGGGAAAGAGA | 19222 | CTGAGGACCCTGTGGTTGAGTT | 30206 | CCACATCCAAAGAGCAGAGCTT | 41190 |
| 7565 | TGGCCTCGGGTTTAGATGAAC | 19223 | GGCTGCTTGCTAATTCCAGAGA | 30207 | GCAAAATATAGGATGGCCTCGGGTTT | 41191 |
| 7566 | GCACCTTACAGTGCCAACTGTTTC | 19224 | GCCTCTGTAGAGAGCAGCATTC | 30208 | TTGGGGAGCAAGCACCTTAC | 41192 |
| 7567 | CCACTTCTCTGTGACCATTTGTTGGTA | 19225 | GTCCTGGATTGTACTTAGAGGAAGAAC | 30209 | CACACCACTTCTCTGTGACCAT | 41193 |
| 7568 | TGGGCAGGTCACACCCTGAAT | 19226 | ACCTCGAGTCGGAACCTCTT | 30210 | TAGGTCGGGGAGCTGAGACA | 41194 |
| 7569 | CACTTGTCCACGCTGCGTTT | 19227 | ACCTTTCGGGCCCTGCATT | 30211 | AAACCAGCCCGTCACACTTG | 41195 |
| 7570 | CCATCTTCAGCTCTTGCTTTGCTT | 19228 | GCAACAGGTCTGTGGCAAATG | 30212 | CCCCAAACCATCTTCAGCTCTT | 41196 |
| 7571 | GGGGTCTCCTTAGTATCATCCCTTT | 19229 | GTTTAGGACCCCTTTCTGGTAACAT | 30213 | TTTGGGTCAGGGGTCTCCTTT | 41197 |
| 7572 | CCTTCCTGGATGTGCCTTGAAGT | 19230 | ACCTTCTCTGCATGTGACTGT | 30214 | CAGGTGCAAATTTCCTTGGATGT | 41198 |
| 7573 | CCGGGTCACACCAACCATCT | 19231 | ACCATGGTAACATTGGAAGGTGAA | 30215 | CAATAAAACCTTTTCCGGGTCACA | 41199 |
| 7574 | GGGTCCCACTGTTACCAACTCTTG | 19232 | GGCTTGTTCAGTAAGGTTGTCAGAA | 30216 | ACTGAATGGGTCCCACTGTTAC | 41200 |
| 7575 | GTGTGGAGTCAAACACTCCTGGTT | 19233 | CCCCAAATCACCACTTAAATGGAATCAGA | 30217 | GCTCAGGGTGTGGAGTCAAACA | 41201 |
| 7576 | GGATGAAAAGAAACCCAGACAGAGACTTT | 19234 | CGAGGTTCCATCCTAGTCCCAAGT | 30218 | CGTGTCCTTTAGGAGGATGAAAAGAAAC | 41202 |
| 7577 | TGGGGTTGTCTCAGTGGTGCTA | 19235 | TGCCCAGTGGATGACGGAAT | 30219 | TCCAATGAATGTCAATGGGGTTGT | 41203 |
| 7578 | GGGGTTCTGCTGTAGAATTCCTGTTG | 19236 | CGAAGCACTGGGAGTGCAGTAAA | 30220 | CTGGATTTCAGGGGTCTGCTGTA | 41204 |
| 7579 | GTTTCTGGAAGACAAATCGGCATTAC | 19237 | TGTGTATGAACACACAGACAGGTT | 30221 | GCTGTTCACAGTTTCTGGAAGACA | 41205 |
| 7580 | CCCTGCATCATATTCTGTGAAACACTTTG | 19238 | ACAGCATGGTGTAAGCAAGAAACT | 30222 | TCCAGCCATTCCCTGCATCA | 41206 |
| 7581 | GGGCAGGCAATTTCCCCTAAGA | 19239 | GCGGAGAAGAGAGTTCAGTTTTCATC | 30223 | TGTCAGTGTGGGCAGGCAAT | 41207 |
| 7582 | CTCTCTGATAAGGCCCCGGTTT | 19240 | CCATGCCTGAAATGCGGCTAA | 30224 | GTGGGGCCCTTCTCTTCTCT | 41208 |
| 7583 | CCACCAAGGACCCCTATGAGCAGTT | 19241 | CCCTAGGGTTGTTCCCTTCTCAGT | 30225 | TGGTAAGGGCTAGGCCACCAA | 41209 |
| 7584 | TCCCATCCAGAGTCCGACCAT | 19242 | GTCAACGACAACCAGCAGACA | 30226 | GCAGCTGTTCCCGTGACTGT | 41210 |
| 7585 | GAACCAGCAGAGTTTGGGCTAT | 19243 | GCACACCTTTGGAATCAGCTACT | 30227 | TGCCTGAAGCCCCATGAAC | 41211 |
| 7586 | GGGCCCGCTGTTTTAACACTTTG | 19244 | GGGGTAAGGAATGTGATGTAGTTTCATTG | 30228 | TTGCATAAGGGCCCGCTTT | 41212 |
| 7587 | GAGAGTAGTTGTGGATACCCGAGAAA | 19245 | GGGGAAACCTTGAGAACTGAGAA | 30229 | GGAACAGAACAAGAGACTAGTTGTGGAT | 41213 |
| 7588 | TGCTCAAAACCAGTAGCACTTTCA | 19246 | AAGCTCCCTAAAAGTCAGCAAAGA | 30230 | GCAACGCAGCAATATATGCTCAA | 41214 |
| 7589 | CCAACCTAGACTTCCACGCTTAAG | 19247 | CCTGGGCTTCGGACAGAGA | 30231 | CACCAACCCCAACCTAGACTTC | 41215 |
| 7590 | GCAAAGGGCCCCAGTTTTGCT | 19248 | CAGTCACCAGAGTGAGCACTCA | 30232 | TACCCTTGGCATGCAAAG | 41216 |
| 7591 | GCCTTGCAGAGAAACACATTTTTGGAT | 19249 | GCCATGGGGAATAAGCACTCA | 30233 | GCCAGCCTTGCAGAGAAACA | 41217 |
| 7592 | GGGGAGTATCATTTTCCAGTCCAA | 19250 | CACGCTACTCAAGCTGAAGCAA | 30234 | CTACAGTCCTAAATGGGCAGTATCA | 41218 |
| 7593 | GTGTGTCCGTTGTGTGCAACT | 19251 | CCTGTGGCCAAGGAGGAAAG | 30235 | GGTGGGCTCTGTGCTGTGT | 41219 |
| 7594 | AGCCGTGTAGCCGTCTGA | 19252 | TGCCAGGCTGCTCCTGCAT | 30236 | CCAGGTGCAGAGCGGTGTA | 41220 |
| 7595 | CGCTGAAGGACCCTCCTCAAAG | 19253 | CCCAGGTCCTCCCCTAAGCAT | 30237 | AAGCCCTGGCTGGCGCTGAA | 41221 |
| 7596 | AGAGAGGCCCTGAGGACTTG | 19254 | GACACTGTCCTGCCAACCATTTC | 30238 | AGGAGCCCGGGCATTCAGAGA | 41222 |
| 7597 | TGTAACTAAAGTGTAGGCTGCGTAT | 19255 | GACCTTGAAGCCAGGTCCTATG | 30239 | GAGGATCCCTTTCCTGTAACTAAAGTGT | 41223 |
| 7598 | GACCAACGATGTGTTGCTCTT | 19256 | GACTCCCAGGCAAAGATCTGAGAA | 30240 | GTGTATAAAGCCAGACCAACGATGT | 41224 |
| 7599 | GGTGTCCATGCGGCTTAGTA | 19257 | CCACAACAGAAGCATGGTGCATAC | 30241 | TGGCAGGACGTGGTGTCCAT | 41225 |
| 7600 | CTCCGGGATTGGGAAATCACTCT | 19258 | CTGGAGCTGAAGTTCATCCAGAT | 30242 | CCGCAACCTCTCGGGGATTT | 41226 |
| 7601 | CACGATGGAGAGGTCATCTTG | 19259 | CGCCTCTCGTTGGCAAATCAA | 30243 | GGAGGCCACCATTCCACGAT | 41227 |
| 7602 | GCCTTTGGCGACATCGTCTTC | 19260 | GATGGAAACCAACCCTTTTCACCTTCT | 30244 | GATGCCAACCGATGCCTTTG | 41228 |

| | | | |
|---|---|---|---|
| 7668 CCGCCTCAATACCAGGACTCTTAG | 19326 TGGAGGCTGAACGTGCCTTT | 30310 TCCCTGACAGCCGCCTCAAT | 41294 |
| 7669 GCTATTGTTCTCACCTATGCTGTGTTG | 19327 CACCCTAGGATGATGGGATGACTGAA | 30311 GGGACTCACAAACTGCTATTGTTC | 41295 |
| 7670 GCTGGCTTTAGAGCTGGGCATA | 19328 TGAAGAGGAAGTGGCAGAGTTG | 30312 GCTCTGCCAAGAGCTGGCTTTA | 41296 |
| 7671 GGATTTTCCTCTACAGAGTGGTTTCT | 19329 CAGGAGGGCTCACAGAGAGGCTTA | 30313 TCCAACCTCTACGATTTTCCTCTACA | 41297 |
| 7672 CTGCTTGTGAGAAGGAGACCAA | 19330 GGGAGAGGCCAGGTGCAAGT | 30314 GCTGGCAACTGCTTGTGAGA | 41298 |
| 7673 GCTTGGGCCATGTTCTTGGAAGCTA | 19331 GGGCTGGAATGTTGTCTGGCAAA | 30315 AGGCTGCTTGCCCATGTTCT | 41299 |
| 7674 GGTTGCTTCTGCACAAATCCAAGT | 19332 CACCAATATGGAAGACGGTTCAGCAT | 30316 CCCTTGAAAATACCTGGTTGCTTCT | 41300 |
| 7675 CCCGCTCTGTTTGACTCAGTGT | 19333 GTTGCAGAGGGATTTAAAGAAGCTGTT | 30317 GAGAAGAATGCCCGCTCTGT | 41301 |
| 7676 AGAGGAATTGCGAAACCATGACT | 19334 TTCAGCGAGACCTGCCCTTTC | 30318 CCCAGATGGAGCTGAAAAGAGGAATTG | 41302 |
| 7677 TGACCGTGGAGATGGTGATG | 19335 GGGAAAAATCCTGGGTAACTACTTCTTC | 30319 GGGGTCCAGCACTATTCTCTTG | 41303 |
| 7678 TCGGAAGGGACTTTCTAGTCTGT | 19336 GCACAAAGACAGACGTAAGATGAAAC | 30320 CGAGGTTGTCGGAAGGGACTTT | 41304 |
| 7679 CTCCCAGCACCTTCTGACAAAC | 19337 CCAAGCAAACAGTGTACTTCAGACAA | 30321 CCAAGGACTCCCAGCACCTT | 41305 |
| 7680 TGACCCGCACAGCATCCTTG | 19338 GCCTCCCTGCTTCCTTCTGAT | 30322 AATGTCAGGCAGCCCAGAGA | 41306 |
| 7681 GGATCCTGCTTTCCAGTCTGTCA | 19339 GACCCTCCTTCAACTCGTGGTA | 30323 AACCGGTGGATCCTGCTTTC | 41307 |
| 7682 GGACTTCTTTGCTCCGTGTCTGT | 19340 GAGTAACCACAGCTCATCCTCATAG | 30324 AGTCCCTCCCTGGAGTTCTTTG | 41308 |
| 7683 GTGGTGGTGTTATGGCTAGGTTAG | 19341 GATCAAGCAGAAAGGTCCCTTGTTTA | 30325 TGGAGAATTTGTTGTGGTGGTGTT | 41309 |
| 7684 CTTCCAAACCCCAGATTCTTTAGTCT | 19342 CCTGGCTATAGCATAAAGGTTGAGAGTCAT | 30326 AAGTTACATCTTCCAAACCCCAGAT | 41310 |
| 7685 TCCTGCCCTTAGAGTGCAGAAAGA | 19343 TCTTCAATCCCTTGTGTGCCAATA | 30327 GACAGAATCCAAATCCTGCCCTTAG | 41311 |
| 7686 CCCCTGATTGACAGCCAGCAA | 19344 GCAATTCCATGGGGCTGTAGCATAG | 30328 CGAGGGTGACCCCTGATTGA | 41312 |
| 7687 GTCTTCTGTCTACTTGGACCTTTAAGTCA | 19345 GAAGGAAGGGATGGCCATTAGGAA | 30329 CCAACTGGTGTCTTCTGTCTACTTG | 41313 |
| 7688 CCTCAGGACCTTTGAGCAGTCCAA | 19346 CACCACCCCAACCAATCCCTTT | 30330 GCTTCTGTCCCTCAGGACCTTTGA | 41314 |
| 7689 CCAGCTGCTGTTTCAAGAGTGCAT | 19347 CACAGCCAAACCATATCAATAGGTGAA | 30331 TCCTTCTCCAGCTGCTGTTTC | 41315 |
| 7690 CCCAGGTGTGTGTAACAAAAGTTC | 19348 TGCTTGAACTCCAGATCAGCAAA | 30332 CTCTCTTTTCCCAGGTGTGTGT | 41316 |
| 7691 GGAGACAAACAAGACAGAGGAGAT | 19349 CTGCACTGCGTTTCCAGCTA | 30333 GGGTAGAGGCCATGGAGACAAAC | 41317 |
| 7692 GGACCTGTGTGATAGCAAGCAT | 19350 GTGCAATACACTGGGTTTGCTGTAG | 30334 CCATAAGAAAGAAGGACCTGTGTGA | 41318 |
| 7693 GGACTGGTCTAAGTGGGTGTCACT | 19351 ACTGTGTGTAGAGAGACCTTGTGA | 30335 GCCCAGCTTTGGACTGGTCTAAGT | 41319 |
| 7694 CAGAGCAGGACAATGGCTCTAC | 19352 CTAGCACATTGACTGAAGGAGATAGAA | 30336 TCTGGGTCAGAGCAGGACAA | 41320 |
| 7695 GCTTCGGACTGATTCTGCTGTGTT | 19353 GACAGAATGGAGCAGGTGCTAAGA | 30337 CCTGCTGCTTCGGACTGATTTC | 41321 |
| 7696 GCAGTAGCGAGTTGACTCCATCA | 19354 CTCACAGTCAATATAACCATCGCTAACCAA | 30338 CGTTACACGCAGTAGCGAGTTG | 41322 |
| 7697 CCACAGTCCAAGGTCAATTCAGACT | 19355 CCGCCATGCAGTTTCTCTCTTG | 30339 GCCCAGGAACCACAGTGCAA | 41323 |
| 7698 GGCTGGTCTTCCTTGCTGTAA | 19356 GCTCAGTGGAATTGATTTGTCGGTAA | 30340 CCTACAAGGGTGCCTGGTCTT | 41324 |
| 7699 GCACTGGCATTTCCCTTTGCT | 19357 AGCTGAAGGGGTTTCCACAATG | 30341 TGCTGTGGCACTGGCATTT | 41325 |
| 7700 GTCCAGAACCACTAGGGCATGA | 19358 ACTCCGGCAGAGACTCGAA | 30342 GCTCTAGGCCTCATGTCCAGAA | 41326 |
| 7701 GAAGCAAAGAGGAGTATGTGTCTTCATC | 19359 GACCAACACATAGGTTAGGGTCCTTG | 30343 TCTCAGAAGAACGAAAGAGGAGTATGT | 41327 |
| 7702 CTGCTTCTCTTCGCTTTTGCATTTC | 19360 CAGGAACGGCAGGAAATAAGAGATTT | 30344 TCCTGTGCGACTCTGCTTCTCT | 41328 |
| 7703 GCTCCCCGGCTCATCTCTCTCT | 19361 GAATAGGGAATTGAGGAGGAATGTTGA | 30345 ATCGATGGCTCCCCGGTCATT | 41329 |
| 7704 CCCCGGCTATCCAATCTATCA | 19362 CAGAAACCTGCCTAATACAAAATCCCTTTC | 30346 ACTGTCACATCCCGGGCTAT | 41330 |
| 7705 CTGCCTCTTGGAACACTAACAGT | 19363 CGTCTGCTTTTGGAGGATCTGAAC | 30347 GATCACACTACTGCCTCTTGGAA | 41331 |
| 7706 GCTTCACCCCGAAATCAGAGACA | 19364 GGACTCCGACCAGTTCCTCTCT | 30348 ACAGAGAGCCTCACCCCGAAA | 41332 |
| 7707 GTCAGACTCCATAAGTACCGTTTACA | 19365 TGTCAGGTAGGATTGCGATGGTT | 30349 TCCCAGATTGTCAGACTCCATAAGT | 41333 |
| 7708 CCAGAGCATGCTGACGCGTATTT | 19366 GGGAGGCAGGACACCTTTTCTT | 30350 GCGCCAACACCAGAGCAT | 41334 |
| 7709 GGTTTGTGGTGAATTGTCAAGCATGT | 19367 AGGGAGGGCATCCCCTGAAG | 30351 GGGTCACCTGACTTGGGTTTG | 41335 |
| 7710 GCAGCCCAAGATCACTGGAGTT | 19368 CAGCCATTAGAGAACCACAGACT | 30352 GGTGGGTGGCAGCCCAAGAT | 41336 |
| 7711 TCACCTGTGCCGGGTACTGAA | 19369 TGACAAAACCCCCTCTTCTAATC | 30353 GGGTCTCAGCTCGTTCGTTTCA | 41337 |
| 7712 CGTACTACCACGTATCCAACTCTTTG | 19370 TCAGGGAGTGGTAAATAAGGCTAGA | 30354 GGCCCTTTCGTACTACCACGTATC | 41338 |
| 7713 AACTTGGAGTGGAGATGCAGAAA | 19371 TGGGGTGCAGGGACTCCTTAAA | 30355 CACCCTGCCTGCCTCTAAAA | 41339 |
| 7714 AACCAGGCCAAGACCTTTCTTT | 19372 CCTCTGATCTCACTCCCTGATTCACT | 30356 TTCTGCTTAAACCAGGCCAAGA | 41340 |
| 7715 GCTTGACTGCCAGTGTCCAA | 19373 TCCCCGGCCTTTTGCTGGAT | 30357 GGCCACGAAATGCATGCTTGA | 41341 |
| 7716 CGCTGTCCAGTTTTCCCTGTGT | 19374 GAATIACTCTGGCTCACGCTCTT | 30358 GTTCCATCCGCTGTCCAGTT | 41342 |
| 7717 AGCCTTGAGAGAGGTGTGATGAT | 19375 GCAGCTACAGGTTTACGCTTCTCT | 30359 GTCACCAGTACCTTCTATAAGCCTTGA | 41343 |
| 7718 CAGGTAACATGCGTTCCCTTTG | 19376 GTCTCTTATCCATCCACAGCAAGAA | 30360 GGATGAACCCCTTCTACAGGTAACA | 41344 |
| 7719 CAACAGCGCACTACAAAGCTAT | 19377 TCCATTCTAGGGACCAATGCTACT | 30361 ACCAAATTCAACAGCGCACTAC | 41345 |
| 7720 GACTGCAGAATACAGAGGACGACTT | 19378 CAGCCAAGAGCTCGCATTCA | 30362 CCACACCCTCAGTCCCTGTGA | 41346 |
| 7721 CTTCCTTAGAAGGTGGCATCAAGT | 19379 AGCAAGCAGCAAGCCATTTTAC | 30363 GCTCTGCACTTCATCCTTCCTAG | 41347 |
| 7722 CATTGTGGGCAAAAGAGCAAAAC | 19380 GGGTCAGTTATTGCCAAGAGTGATTT | 30364 GGGCCTTCATGCTGTGTCATTG | 41348 |
| 7723 CCTGGGACAAAACCTCTTTCTCTGAAT | 19381 GGACTTTCAAGGAGATGAATCCCAAAGA | 30365 TCTGGAGTTCCTGGGACAAAAC | 41349 |
| 7724 GGAAGACAGATGTTGGGAGGTA | 19382 CCTGTTTCTTTTCAAGGAGGCTAT | 30366 GGCAGCTGGAAGACAGAGTGT | 41350 |
| 7725 GGGACAAAGGTAGGGGTGTGATAC | 19383 CTCAATAGTATTTGACACGCTCTCCT | 30367 GCACAATCAACAGCGGACAA | 41351 |
| 7726 GCGGAATTCCTCAAGGCACAGA | 19384 TCTGGGTGGGGCTGTGAGTAAA | 30368 TCCTCCACTGGACTGCGGAAT | 41352 |
| 7727 CCACTGGTTTATCCCACTGGCATTT | 19385 GCTCATCTGGGGAAAGATGTCACTA | 30369 CCTGCTCTGCATTTCCACTGGTT | 41353 |
| 7728 GGGCTATTGGTCTGCCACACAT | 19386 GTCTCATGGAAAGCAAGTCACATTGTTC | 30370 TTTCAGGGACTCATGGGCTATTG | 41354 |
| 7729 GGTGGGTGCTTCCACTCATCAT | 19387 GGTGATTTAAGAGCAAGGGTTAGCTT | 30371 ATCCTGTCGGGGTGGGTGCTT | 41355 |
| 7730 CTGGCTGTTAGACTGTGATGAAGA | 19388 TTAAGCCCCAGGCTGCTAATC | 30372 TGACCTCATCTATTCTGGCTGTTAGA | 41356 |
| 7731 GCAGCTTGGCCTTAGAACCTTTC | 19389 TGTGTGCCATCTGCTTTCACAA | 30373 CAACACTGCAGCTTGGCCTTA | 41357 |
| 7732 GGGAAGGCTATTTTACTGACCCAAA | 19390 CTCTTGCTTCCAAGGCTGAAATC | 30374 TGATCTAGAGAAAGGGGAAGGCTAT | 41358 |

FIG. 36L9

| | | | |
|---|---|---|---|
| 7733 CACCCATACTTGCTGGGTTCAACA | 19391 CTGGTCACACGGCTTTCTCCTT | 30375 AGCCTGCCTATCACCCATACT | 41359 |
| 7734 GAAACCAACCTCTCAATCCATCAAG | 19392 CCTGCCCGCCTTTTAGATAATGT | 30376 CTCCATGGAAACCAACCTCTCAA | 41360 |
| 7735 GGGCTCCAAGCTGTTCTATGCCTAAC | 19393 GGCCATGCCCTCTCCATGTAT | 30377 TCTGGGGCTCAAGCTGTTCT | 41361 |
| 7736 GACCTTACCCAGCAGTTCAAGCAT | 19394 AAGGGCTGACCCTCTTCAGT | 30378 GAGAGTGAGGAAAAACCAAGACCTTA | 41362 |
| 7737 GCCATAATTTCAGGGAGGACGTA | 19395 AGAGCCTCAGCCGGACCTTT | 30379 GGGCTGTGCTTCCATCTTGCCATA | 41363 |
| 7738 ACCTGGCCTCAAGTGGTCCAT | 19396 CGATTCTTGTTCGAATGGAAGGTAATG | 30380 TCTCACACACCTGGCCTCAA | 41364 |
| 7739 GGTCTGTCTTGCTTTTAACTGGATTG | 19397 CAGGTGTTAGTAAACATAGTCCTCTCCAAA | 30381 CCAGCCTTGGTCTGTCTTGCTT | 41365 |
| 7740 TCCTGGCTCTGTGAGCAACTAC | 19398 CTCACGTGGGTTGCTCTCTGT | 30382 AGCACCTCCAGGTCACAAATC | 41366 |
| 7741 GGGCAAAGCACAGTCAGTCATC | 19399 GGAGAAACTGATCAGGTCCCTATTTCT | 30383 TCCGGGACTGTGGGCAAA | 41367 |
| 7742 GCTGACAATGTCCTGTTGCTGACA | 19400 GCGAATCACCAAAGGAAAACACACTTG | 30384 GGTGTTTCTGGAGGGCTGACAA | 41368 |
| 7743 GCTGAGTGTCCAGAAGCTAAG | 19401 CAGGTGAAGTTTCCCGGCATGA | 30385 CTTCATACACCTCCATTTGCTGAGT | 41369 |
| 7744 GCCTGACTTTGTATGCCTGGAT | 19402 CCAGACCTGGGACCAAGAACA | 30386 CCAAGTTGCCAAAGAATGCCTGACT | 41370 |
| 7745 GCTGCTTGGTTCACATGCTTAC | 19403 CAGGGGCTAATTGGATGCGAA | 30387 CCTGCTAGTGCTTGCTTGGTT | 41371 |
| 7746 GCAGGGAGTCTGCTCCTTCA | 19404 GGCTGAGAGTAAATGGTGACTTTCACA | 30388 CATGTGCTTTGCAGGGAGTCT | 41372 |
| 7747 CTAGCCTCTGTTCCAGCTTTACA | 19405 AGTCCTGGATCCCGTTCAGT | 30389 TCACGGCTCTAGCCTCTGTTTC | 41373 |
| 7748 GGGCCGTCAATTGCAACTCTTC | 19406 CCAAATCTGATGGGGTAGGCAACA | 30390 TGGCCTTTGGGCGTCAAT | 41374 |
| 7749 GGGATTGGGGACCTCCTTCAAA | 19407 GCACAGCACAGATGCTCCACTA | 30391 CCTAGTAAGGAGGAACGGGATTG | 41375 |
| 7750 ATTCCCAGATGCATAGGACACT | 19408 TGGGCACGTTTGTCCAAGAT | 30392 CAGCTCAGAAGTAAGACTCCAGAT | 41376 |
| 7751 AAGGTTTGGGGACGGTCTCA | 19409 AGGACGGACCCAGGCAAA | 30393 GAGGACAGCACTCCAAGGTTT | 41377 |
| 7752 CACTGCAACAGTCACAGTCTAACA | 19410 GGACCAGGATTCGAGGAGTTAAG | 30394 TGTAGCACACTCGAACAGTCA | 41378 |
| 7753 CATCCACAGTTCCAGGAATAGGATTTT | 19411 CCAGGTTGTCTTTAAAGGGATGGAATG | 30395 CTCACTACATCCACAGTCCAGGAA | 41379 |
| 7754 GCTTTGTTCTAGGACATTGGCTGTTC | 19412 GTAAGTGACTTTCAGGGACATTGAATG | 30396 TCCTTCAGAGATCAGAGAAGCTTTG | 41380 |
| 7755 GAGCCAGTGTTAAAATGGCATGAGA | 19413 GCAAAGACAATGAAAGCACCATCATC | 30397 GGTGCCTGAAAGAGCCAGTGTT | 41381 |
| 7756 GGCACCAAAATTCCAACAGCAA | 19414 GCAACTGCCTAGAGAGCTGATT | 30398 GACATCTGAGTTAACTGGCACCAAA | 41382 |
| 7757 CATGAACTTGGGGCTTGTGTCA | 19415 TGCCCGGGACAGACCCAGAT | 30399 CACACGACACACATGAACTTG | 41383 |
| 7758 CTTTGGGCAAACACACAGACAAG | 19416 TGCAGCAGCTGGTGGTTGT | 30400 GGCCCACATCACTTTGGGCAAAAC | 41384 |
| 7759 CCAATCTCCAGCCCACAAA | 19417 ACGGTGACACTTGTGTTGTGA | 30401 ATGCAGGCTGACCTCCCATCT | 41385 |
| 7760 TGCAGCCAAGTAACTGACTCTTC | 19418 TGAAGGAATAACCATACCTTCCTCATC | 30402 GAACAAATGCATGCAGCCAAGT | 41386 |
| 7761 GCAGACCTCTTACATGAAGTGAATG | 19419 GCTCTCAGAATGGGGTATCGTTGT | 30403 CCACCCTGCAGACCTCTTACAT | 41387 |
| 7762 CTGTCTCAGGCAAAGCTGGAT | 19420 GGACACCCCTGCCGTAGACAT | 30404 AGGGACTGGAAGAGCACTGT | 41388 |
| 7763 GGCAAGAATCAGATAGCACCCACAAA | 19421 GACATGGGCCTTTCATTGAACTCTCT | 30405 ATCAAAGACCTGGCAAGAATCAGA | 41389 |
| 7764 GGCCTAAGGCATCCTGTATCCCAAA | 19422 CTCTTACTGGAAATGATGGCTTGTCT | 30406 TGCTGGCACCAGGGCCTAA | 41390 |
| 7765 AGATGCGGGACCCACTGA | 19423 GGTTTCACGGGATGCCTTTG | 30407 CCCTCCTGTCTGTGAGGGAGAT | 41391 |
| 7766 GCCCCATGACTATCGTGTGAGGTT | 19424 AGGGGCTTTGCTGAAATGATATGAA | 30408 AGCCACAGCCCCATGACTA | 41392 |
| 7767 GTTACCGCAGCAGCATGTTTAC | 19425 GTTGATGCCACTGTCAGCAGTT | 30409 CGCACGTCTCAGGTTGGTGAA | 41393 |
| 7768 CCCTACAAATGCCAGCAGCTTTC | 19426 TCCTTGCGAGACTTTGTGGTT | 30410 GTCAGTCCCCTCTCCCTACAAATG | 41394 |
| 7769 CCCGGATATTATTAGCCAGTTAGCAA | 19427 GGGACTGCACAATGTGGTA | 30411 CGCCCCACAACCCGGATATTA | 41395 |
| 7770 GCATGGAAACAGAAATCTGGTGTGGAT | 19428 CTCCATTGATTTAGAGCTGATCCACTGA | 30412 GGGTTTGTGTGCATGGAAAGAGAAATC | 41396 |
| 7771 CCTGGCAGTGTATGAAGAGGCATT | 19429 CCAATGTACAGGCATGGCTTCT | 30413 GCAGCATTTCCTGGCAGTGTA | 41397 |
| 7772 GGGGAGTGTGACTGAAGGAAAAAC | 19430 CCAAGCAGGGTGCTATTTCTCA | 30414 AGCAAAGGGGAGTGTGACTGA | 41398 |
| 7773 GCCCAAAATGGACCAGTTCAAAAC | 19431 GGGGATAGGACTGGGTTTCAGA | 30415 CAGAACCAAATCCATAGCCCAAAATG | 41399 |
| 7774 TCCAGGCTTGCCCCTTCTCA | 19432 GCCTTAAGGAGCAGCGTTTG | 30416 CTGATGCCTCCCTAAATGTTCT | 41400 |
| 7775 GGGTAATGCCGAGTAGAGAATTGA | 19433 GCTCCTTCATTGCTATCCTGTGTT | 30417 GGTACTAAGGGGTAATGCCGAGTA | 41401 |
| 7776 TGTCCTTTTTCATTGGAGGGTACA | 19434 GTATGTTGCCATCTGTAGCCAATG | 30418 CCTCACACCAGAGCTGTCCTTT | 41402 |
| 7777 TCCCCTCTTCCTCCCTGCAAATA | 19435 CAGGCACCACCAATCGTT | 30419 TCGGGTCCTGCCTTTCTCTTG | 41403 |
| 7778 CCTCCCAGTCACAGTGTTTC | 19436 GCTGAAATTAGTCACCGACCACCAA | 30420 GCATCTCTGGTTCTTCCCAGTCA | 41404 |
| 7779 GTCATGTCCCGCTGTTCTGATGT | 19437 GCTCTTCCAAGAAAGGCAAGTGAAAG | 30421 GCATCTCTGGTTCTTCCCAAGTCA | 41405 |
| 7780 ACCTGGAAGTACCAGTCTTTGAAC | 19438 CAGCTTTCACGGCTCAGTGT | 30422 GACGCTGATGTAACCTGGAAGT | 41406 |
| 7781 CTGGAGGTAGAGCCTTGGACTTTC | 19439 CCATTACCACAATCTGGGCTGTTTC | 30423 TGGTGTCATTCTAATCTCTGGAGGTA | 41407 |
| 7782 TCCCAAGAGATGTAGCTTTTCTAC | 19440 TGCCTGGTACAGGTGAGGCTTA | 30424 CAAGGGTATCCCAAGAGATGTTAG | 41408 |
| 7783 CGGACAGGTTCATGCGAGTA | 19441 GAGACCCAGGAGTCTTCCTTGTTAC | 30425 GACTTACTAGCGGACAGGTTTCA | 41409 |
| 7784 GGTGTCTTTCCAGAGCTTTCTCTTC | 19442 GTTACAAAGAAGGGAGAGGTTCACA | 30426 GCTGTAGACATGCTCTTGGCGTCT | 41410 |
| 7785 CGATCCAGAGAGATGCTGGCAAAA | 19443 CCTCCCTTTAAGGTCCTTTCCAGAAGT | 30427 GGCCAGCGATCAGAGAGAT | 41411 |
| 7786 GAAGCTGTGATCCTAAGAGCACTTTC | 19444 ACGTGCAGCAGTCGGATGCTA | 30428 CTCAACAGTGAAGCTGTGTATCCTAAG | 41412 |
| 7787 GGCCCTGAAATCCAGCAAGATG | 19445 GCCAGGTGATCTTAGACCTGCACTA | 30429 AATCCCAGGAGGCCCTGAAATC | 41413 |
| 7788 GGAGCAGATAACGGTGCAATG | 19446 GCATTACTTACCTTGCTCTTAGCTTGTTG | 30430 GGCTAAACGCACGAGCAGAT | 41414 |
| 7789 TGTGGAACGGGGAAACTGA | 19447 GTGGAGGCTTATAATGAGGGCTTGTATAG | 30431 CTCAAATCCTCCTGTCTGTGAA | 41415 |
| 7790 GGCCTATGGTAGCAACCACTGCTATAA | 19448 CCTAGCAGCTGTTGGCAGAAG | 30432 GGAAATACAGGGCCTATGGTAGCAA | 41416 |
| 7791 CTCTCCGGCGATGTAATTCTGGAT | 19449 GCCTGATGTGATGCTGGAAAC | 30433 CGAGCTCTCCGGCGATGTAA | 41417 |
| 7792 TGCTATAGAGAGGACAACTTGAGAT | 19450 GCATGACAGCACAGGCTCAT | 30434 GAGGAGGGACTATGAAGGATGCTA | 41418 |
| 7793 CCACATCAGCCTAGCATTCAGA | 19451 CTGAAGAGGACTTCTTGACTTTGGTAAG | 30435 CTGGAATTACATGCCACCACACT | 41419 |
| 7794 CGTTAAATCCTCACACAGTTGCTT | 19452 GACATTGGCATGTGATGTCATT | 30436 GGCTGCAGAAGTTCATACGTTAAATC | 41420 |
| 7795 GGCGAACTCCCTGTGGTATTGT | 19453 TAACGCGCCTGGGCTCTCCTTT | 30437 TTTCGGCTCCAGGCGAACT | 41421 |
| 7796 CACCCTTGCCCATGCCAACATTC | 19454 GCCGATGAACTGGGTTTGGAAATG | 30438 GGAGCCAGTTGGCATGCACCTT | 41422 |
| 7797 AAGCAGGAGGAATAAGTGTGAATGA | 19455 TGATCTTCTTTCGTGGCAACAGATT | 30439 ACTAGGAAGGTAAGCAGGAGGAA | 41423 |

| | | | |
|---|---|---|---|
| 7863 GCCTGTTACTCTTGGAGACAGAGTT | 19521 GTTCCATATAGGCCTTGTTCTTCTACAAAG | 30505 AGGGTGTGGAGCCTGTTACTCT | 41489 |
| 7864 CACCCAGGGCTTTCTGGCAGATT | 19522 GCGTATTCCTAGGGCCTGAAGT | 30506 ACTCCACTCACCCAGGCTTT | 41490 |
| 7865 CGTGCCACAATAGTTTTTAGAGGGTTT | 19523 GACCAAATGGAATGCTCAGCTACA | 30507 CTTTGCATTCGTGCCACAATAGTT | 41491 |
| 7866 TTACCGCGTCCGGAACTTCA | 19524 GGAATGTGTAAGAGGTAAGATCCCATTTC | 30508 ACACTTGCCGTCTTCCTGTTAC | 41492 |
| 7867 GCCATGCAAGTCAAGAGTCAAG | 19525 ACGATGTTATCTGCCAAGCATGAT | 30509 CAAGACCTAAGCCATGCAAGTCA | 41493 |
| 7868 AGTAAGAGAGGGAAGGGATATTGCAT | 19526 ACCACTTGAAAGCAGGGTAGTTG | 30510 CCCTTACAACTCCATCAAGTAAGAGA | 41494 |
| 7869 GCCCTCTACCCCTCTCTGCAA | 19527 GGCAGAACTCAAGGGCAAAAC | 30511 CAGTCGGAAGGCGAGAGAGA | 41495 |
| 7870 GGAATTCAGTCTGTACAAGGGATCA | 19528 CCTGGCAACCTTCATTTAACCCAAA | 30512 CGGTTGATCCCATGGAATTCAGTCTGT | 41496 |
| 7871 GCACGTCCAAATCTTGCTCAATC | 19529 GCTTTGTGAAGGGTGTCCTA | 30513 CCACATCCTTGCACGTCCAAATC | 41497 |
| 7872 CCACACTGCATTTGGAATTTGGTATTG | 19530 GGAAAAAGAAGTGGACTGACATCGGAAT | 30514 CCAACTTTGCTCCACACTGCAT | 41498 |
| 7873 GACACCTGACTCCCTAAAAGAAACTTGA | 19531 AATCCCAACCCTCTGTGCTTTT | 30515 GGGAGAGACACCTGACTCCCTAA | 41499 |
| 7874 GGCCCTCCAGAATAAGTGTCAAGA | 19532 CTGCATCTGCTGTATCTCTAGTGTCT | 30516 ATCCACTTGGCCCTCCAGAA | 41500 |
| 7875 CCACTTCTACCTGGCCGATTTC | 19533 GAAAAGGAAGGGAATGTACCCAGTA | 30517 GCCATGTCCCGTACCCACTTCTAC | 41501 |
| 7876 AGAGGGCTAGAGGGCTGAAAT | 19534 CCCCAGGCCTTTTGCTGTTATAC | 30518 AATGAACTAGGAGAAGAGGGCTAGA | 41502 |
| 7877 AGTGTCCATCCAGTCCACGTA | 19535 CCTAAGAATGCACAAGGCTATTGAAGATG | 30519 GCGTAGGCCACCAACAGT | 41503 |
| 7878 TCTTCCCACACGTTTATGGACAAT | 19536 GCCCTGCATCAGTGCTACTAAG | 30520 TGGTGTTTCTTCCCACACGTT | 41504 |
| 7879 CAAAACAGACAGGCAGCCAATAG | 19537 GCCGGCCAAGATCATGACTTTTAT | 30521 GGCACATCTGGGGCAAAACA | 41505 |
| 7880 CCTGTCGTGCTAGACTCACCAGTAA | 19538 GGAAGGCCGCTATCATCCTTATTCA | 30522 CAAGCCTGTGCTGCTAGACT | 41506 |
| 7881 CCCTATACGGGTTCACCAAAAAGT | 19539 GTGGACAGTGCCTTCTGAGTA | 30523 GCATCTCCTTACCCTATACGGCTTCA | 41507 |
| 7882 GGCAGTTCTCAACTTGCAGTAATAG | 19540 GGCATTGCCAACCTTTACAGACCTATC | 30524 ACCCAATTGGCAGTTCTCAACTT | 41508 |
| 7883 GCATGAAAGGGGCTAAGGTCCTAGT | 19541 CCCTGGGAGTCAACATCAGAGTTTTGT | 30525 CCTGGCATGAAAGGGGCTAA | 41509 |
| 7884 GGCATTGCACCATCCCCTAAGA | 19542 GTGGAGTGCACTAGGCTGACCAA | 30526 AGTGCTGCAGATGGGCATT | 41510 |
| 7885 CAGAGGCAGCTTGGAGTACTGA | 19543 CTCCTTTATTCCCCAGATTGGTTGA | 30527 TACCTCCACAGAGCAGCTT | 41511 |
| 7886 CTGGGTTTCTGGGTTCCCTTTC | 19544 GCAGAGTCATCAAAAGCCACTTTC | 30528 TTTGCTGGCATACTGGGTTTCT | 41512 |
| 7887 GGGTTTAGGGACAGAATTCAACTTTC | 19545 GGGCCTCCAAACATCATTAGTCCAAA | 30529 GTCGGTGGGTTTAGGGACAGAA | 41513 |
| 7888 GGGAGGCTAAGTGATACACACACA | 19546 GGCCTCCCTTGAAGAATCGTTGT | 30530 GCTGGAGGGAGGCTAAGTGA | 41514 |
| 7889 CTCCACCAAAGCGATTAGGAGACT | 19547 GGCTCACCAGAATCCTAGCAAAA | 30531 CCACTTCTGTACCGTCTCCACCAA | 41515 |
| 7890 GGGTGACCAAAGACGGAAAGTAGA | 19548 TTGCTATAACCACTCAGTCCTTTGT | 30532 CCCTCAAAACTAGGGTGACCAAA | 41516 |
| 7891 CTCCAAGAGGTTTCCCTAGTTGTGA | 19549 GGGAATGTCTCTGCAAGGGATGTT | 30533 CCCACAGAACTCCAAGAGGTTTC | 41517 |
| 7892 GTCCTGCCTGGATTGGGCTTTT | 19550 GCATTACCATGCCCTGTGATTAAG | 30534 CCATTCGTAGTCCTGCCTGGAT | 41518 |
| 7893 GGTGGGCTTCATGCTAGGGTTTT | 19551 GGGGACTACTACCAGTGTTAAGTGAGA | 30535 ACCTACTGATGGTGGGCTTCA | 41519 |
| 7894 TGATAGTGAGGAGCCAAGATCACT | 19552 TCCAGGCTGCTATCATCTCTTCT | 30536 ACAAAGGACCACATAAGGGAGTATG | 41520 |
| 7895 GCAAAAGATGCCTGTGGACAAAGA | 19553 CCCTTCAGTGTCAACCTTATGGATCTTC | 30537 GGCAGCAGGTCTCTGCAAAA | 41521 |
| 7896 TGCATTCTTCCCAGTGGAGAAAC | 19554 GCTCATCTTCCATCGGAGCAACT | 30538 CCCCACACCCCTTGCATTCTT | 41522 |
| 7897 CTCGTACAGTACTCTTGGGTGTAAAAATTG | 19555 AAKAAAACGCCTCCAGAAAAGT | 30539 GGACACAGATAAGTTGCCATTCTCGTA | 41523 |
| 7898 TGGGTGTTTAGTCCCTGAGAGT | 19556 TCACAGGCAGAGTAGGGCATA | 30540 TCAGCAGAGTCTGGCACTCA | 41524 |
| 7899 GCTGGGAGAAGGGTTTGTGTCA | 19557 AGAGAGGACATCAGGGGAACAA | 30541 AGGCTCTGGGCTGGGAGAAG | 41525 |
| 7900 GGCCTAATCAGGAATGGCTTCTTC | 19558 GGCCATGGCAAATAGGAAAAGGTTTG | 30542 GTGGAAGACACATGGCCTAATCA | 41526 |
| 7901 GCCAGTCACTCACACTTGGGCTAT | 19559 GCCCAGAAACCAGGAGATGATG | 30543 TGACAGAGGCCAGTCACTCA | 41527 |
| 7902 AGGGGAAGTCCTTGCCCTTGA | 19560 CATGTACCCACGCCTGAATCT | 30544 CTCTTTGTTGACAAACAGGGGAAGT | 41528 |
| 7903 GGTGGAAAGGTGACTTGTGTGTCTGA | 19561 GCAAAGATTCAGGCATGGAATAA | 30545 ACCAACAGGTGAAAGGTACTT | 41529 |
| 7904 CAGCATTTCTAACCTTGTTTCCCAATC | 19562 TGGAATTGGCAGGGTGTCTTCTCT | 30546 CATGCTAAGGGCAACAGCATTTC | 41530 |
| 7905 AGCCTGTGAGCTGGGTTTTG | 19563 CAGACGCACCTAGAGTTGTCCTA | 30547 AGGAGCCACGAAGCCTGTGA | 41531 |
| 7906 CTGCCATGACAGCCCATTCTCA | 19564 CCAGAGTCGGTATTTTCAATCACCAAA | 30548 AGGAGGGGTGGCTGCCATGA | 41532 |
| 7907 GGACGCGCAAAGGTGTTTC | 19565 GTGTGTCATATTCTCCCCTAGGACTT | 30549 TTCGGTGAAGGACGCGCAAA | 41533 |
| 7908 CGGCAGCCAAAATATAGCAGAGA | 19566 CCCAGACATGCCCTTGACCTTT | 30550 CAGAAGATAAGTTAAACGGCAGCCAAA | 41534 |
| 7909 ACCAGAAGATGCTGGCAAAAA | 19567 GCCTAGAACTGAAAAACGAAGACCTGTA | 30551 GGAAAGGACAACAATTGCCAGAAGA | 41535 |
| 7910 TGAGCTGGTACTGGTGTCTCT | 19568 TGACCAGGGTTCACACCTCAGA | 30552 AGGAGGTCCTGTTGAGCTGGTA | 41536 |
| 7911 ACAATTGCCCTGAAGTGTGTGTCA | 19569 GGGCTATCACCAGTTTGACTATTCTGT | 30553 GTCCCCTCACAATTGCCCTGAA | 41537 |
| 7912 CCCGCTGATTCAGGGACTCT | 19570 CCATGTTAGAGGGTTTAAGTCATGGAGTTC | 30554 CACACTCAAGACCCGCTGATTC | 41538 |
| 7913 GCGTGTTTCAACCAACACTCGA | 19571 GTAGGTAAATTGGTAACAGGCAGTTG | 30555 CCCGTAAAATGCCCTTATGCGTGTTTG | 41539 |
| 7914 GCCCTAACACCTACAAACCCCTTTT | 19572 TCCAGTGGCGAAATGTTTCTGT | 30556 TCTGTGGCCCTAACACCTACA | 41540 |
| 7915 CCTGTGGTTAGCTTCTGTGTTCAT | 19573 CCAGACTAAGATGTCAAGGAGACTTGGTT | 30557 TCTACTCTCTGTGGTTTAGCTTCT | 41541 |
| 7916 GCAAACCAGAAACTAGAGAAAGGTATC | 19574 TGATTGCCACTTCCATGCCATT | 30558 GGACTGGAAGCAAACCAGAAACTA | 41542 |
| 7917 GTCATTGCTCTTCTGTAATCCTCAGTTTTC | 19575 CCACGTGTAGGCTGTGTTATTC | 30559 TGCCAAGTCATTGCTCTTCTGT | 41543 |
| 7918 CCACCATCAGGGAGAAGGGATA | 19576 GCCCAAAACCTCTCTCTCAGAA | 30560 TCAAAGCCTGGCCACCATCA | 41544 |
| 7919 CGTCCCTAAAACCATCTTCCTTCTTCA | 19577 TCAGGATTTTGTGAGTGTTCGGTTA | 30561 GTCCCGTCCCTAAAACCATCTT | 41545 |
| 7920 CCCTCTGCATGCGTGTCTATC | 19578 AGKCATGGAGCTCTTCTTGA | 30562 TGCCCAACGATCCCTCTGCAT | 41546 |
| 7921 GCCACAGTGTTAGTAGGACAAGT | 19579 CCTTTGTGTGAAGATCCTTAGGCCAAAAC | 30563 GAAGGCAGCCAACAGTGTAGT | 41547 |
| 7922 CTTTGCTAATCAACCCTCAGCAACT | 19580 GGCCTAGAATAGTCACCCCTTATCTGCCT | 30564 CGGTTGCACTTTCCCTCCTT | 41548 |
| 7923 CCAGACTCCCTCCCAGCTAGA | 19581 CTGTCCTACCTCCTGGTAAAAGTTC | 30565 ACCCTCCCTTCCCAGACT | 41549 |
| 7924 CTCAGTCCTGAACAGGTCACCATT | 19582 TTTCCCTGAAATGATGGCACTACA | 30566 CCAGCCTCTCAGTCCTGAACA | 41550 |
| 7925 GACCACCACACTGATGTCAAGAGA | 19583 AAGGCTGGCTTCGGGTAGAGA | 30567 GCTTGTGACCACCACACTGA | 41551 |
| 7926 CCTAATGGACCTAACTCAAGAGTCATAG | 19584 GGTACTGCTACCGTGCTGTT | 30568 GCCCATGGAGTTACCTAATGGACCTA | 41552 |
| 7927 TCAGCCATGCAGAAGCAAATCTA | 19585 AGCACACTTGGCATGAAAAGAAAG | 30569 GACCGGGTCACTTCACCTTTT | 41553 |

| | | | |
|---|---|---|---|
| 8058 GCCCCAGGCTGTTATTCCAATG | 19716 GCACGCCAAGTTCTCGGATGT | 30700 TCACTCTGCCCCAGGCTGTT | 41684 |
| 8059 GTGTCCCTGCTACCCTGGATTTAC | 19717 CCATGGGATGGAGCCACTACAGAA | 30701 AGAGTTCACAGTGTCCCTGCTA | 41685 |
| 8060 CATCCTTTCTCCTAGACTGGCAAAGA | 19718 GAGCCAGGGAGGTGGAAGAAAT | 30702 GGAACCCACCATCCTTTCTCCTAGA | 41686 |
| 8061 TGCATAAAGGCGGCAGTAG | 19719 GAAGTGAACAGAGAGTTTCATGTCAGA | 30703 GACTCAGACCCTCTCCTGCATA | 41687 |
| 8062 CTGTGTTTGCATCCACTCCCTAA | 19720 GAGGGGAGGAGGCTTTATTTTCTTG | 30704 AGCTTACCTTCCCATCTGTGTTTG | 41688 |
| 8063 GTTAAAGTGCCGTGAGCGATTAG | 19721 ACCGTTCCCCTTCTCCCTTGT | 30705 CACCTATGTCTGGGCTTAGTAGTTAAAG | 41689 |
| 8064 GGCAACACTGGTAGCACCGTAA | 19722 CCATAGGTAGGTGGGCAAACACA | 30706 GGAGAAACAATGGCAACACTGGTA | 41690 |
| 8065 AGTTGGGCAGATTGAAGTAACCTTAG | 19723 GCAGTGCTGTGGCTGTGAAG | 30707 GCTGCAGCCTCTGGGAAGTT | 41691 |
| 8066 AGCTCGATTCCCTGTGCAGTTC | 19724 GGGCTTAGATGACGACATTGTTGGT | 30708 CCATGTCTAATGACCAGCTCGATTC | 41692 |
| 8067 AGGGCCAATTTTGTTCCACTACT | 19725 CCAGAGCACTGGGTAAAATGCTTAG | 30709 GGCAGCCTTCAGTTTAGGGCCAAT | 41693 |
| 8068 AGAAAGGCAAGCATTCCAAGCTA | 19726 TTGGGATGCCTCTCCTTGGTA | 30710 CACACTTCTGAAGAAAGGCAAGCAT | 41694 |
| 8069 AGCGTCGAACACACCACAGA | 19727 CCCTCCCATTAAGCAGAGGTGAACT | 30711 GGACACCCAGCGTCGAACA | 41695 |
| 8070 GGCATCCAGGGAGATGTGGGAAAT | 19728 TGCAGTCTCCAGTAGGCTGTGA | 30712 AACGCAGGCATCCAGGGAGAT | 41696 |
| 8071 CCCAGCCCAATCAGGCTAAACT | 19729 CAGTGCTGAACACACCTGAGA | 30713 CCGACTCCCAGCCCAATCA | 41697 |
| 8072 CCTACAGAACTACTGGCCAAGGAT | 19730 ATCATGCCCCTCCTCTATCACT | 30714 GGACAAACCTACACCTACAGAACTAC | 41698 |
| 8073 TTCTTAATGTGTCAGCAGAGAGTCA | 19731 GCCCCGGTAACGAGGTTTTCT | 30715 TGCATAGGAATTGGGCTCTCTTTC | 41699 |
| 8074 GCACTGGAAAGCAGCTTGGTAGA | 19732 GGTCATACGTTAAGGACATGTTTCACT | 30716 GGGAATGCAAAATGATGCACTGGAA | 41700 |
| 8075 CTGTGGAGGGCTAAAGTAGGGATTCT | 19733 CTTCACATTTTCCCAGCTAGACTGAAT | 30717 CCCAGATATGTGTGGAGGGGTAAAG | 41701 |
| 8076 TCCCATTGTGTTTCTCAGGAAAGAT | 19734 GGTGCCTCCAAAAGCCTTGTA | 30718 CTGGCTCCAAATATATTGTCATTCCCATTG | 41702 |
| 8077 CGATAATCCAACCCAAAGCAGAAACT | 19735 GCCCACCTGATCACAACCAT | 30719 GCAGTTTAGCGATAATCCAACCCAAA | 41703 |
| 8078 TGTAGTGCTCCTGGCTCAGA | 19736 GAGTGTGTAGCTGACTAGACTTCA | 30720 GGGTGCACATTCTTCACAGGTTGTAG | 41704 |
| 8079 CCCTGAACCCCATCAAGCCAAT | 19737 GCACAATGCCATGTGGGAGGAA | 30721 GGGGTAGCATGCCCTGAAC | 41705 |
| 8080 GGCCTCATGGGAGTTCTTTTGGAT | 19738 AACCAAGCCTGAGTCCTCTCT | 30722 GCATCTATGGCCTCATGGGAGTT | 41706 |
| 8081 TGTGTGACATGTACAGGTGAAAGTT | 19739 AGGCAGACATCCAACTGGAGA | 30723 GGCCTTGCTCTGTGTGACAT | 41707 |
| 8082 GCCAGATTTGGTTTACCTCTAATCATC | 19740 CTGGGGCTTACTACAGCTTGAAAAC | 30724 TCTCATCTGTGCCAGATTTGGT | 41708 |
| 8083 AGCTCAGTCATCCCAGTTTCTCT | 19741 CATTGGACACACTCAGGTAGGTT | 30725 CTTGAAGCCCAGCTCAGTCATC | 41709 |
| 8084 GGGGCCCCATTAGGACACATTAC | 19742 AGTGTGGGCCTTCTGTATCACT | 30726 GGAGGGCAGTGGCTGAAGTTA | 41710 |
| 8085 GCCAGCCATTGCTCAGTTTTTC | 19743 GCCCCACTGAGGGAAATGTTTTG | 30727 GATATTTTGAGTCAGCCAGCCATTG | 41711 |
| 8086 GGTGGCTGTAATCCATCCTCA | 19744 TGTGTTATGGACCTGTCTATCTCTGA | 30728 CCAAGAGGCAGGTGGCTGTAAT | 41712 |
| 8087 CTGTGTGGGACAAAAAGCACTTG | 19745 GTGTGTGTCCTCATTTTCCTATTGGTTT | 30729 CATGAACTGATCTGTGTGGGACAA | 41713 |
| 8088 GTGCCGTTGGGAAAAGAAGTAG | 19746 GGCTGTCTCCAAAGCAAGGTGAAC | 30730 GCTGTAGTGGCGTTGGGAAA | 41714 |
| 8089 GAGGGAGAATGGCACACATCA | 19747 GGACAAGACCCACTCTGCAA | 30731 TTTGCTTTGGCTGAGGGAGAA | 41715 |
| 8090 GGAAGTGAGGAGGGAAGAACAGTCT | 19748 TTGCCCCTCTCCATGCTTTC | 30732 TGTGGACCAGGTGGAAGTGA | 41716 |
| 8091 CCTGTGTGTTCCGCATCCATCTCT | 19749 GAGCACCAAGCCCCATTAGT | 30733 GGGTGCAAGCTTTCCTGTTG | 41717 |
| 8092 GTGCCTGCTGTTTGGTTGAGTA | 19750 CCTGCTGCAGCAGGAAGTCA | 30734 CACTGTCTGCTGCCTGCTGTT | 41718 |
| 8093 GACCTACTCTTGGGTGATGACAGTAA | 19751 CCTTTTCCTGTCTCTCAGGCCTATTC | 30735 CCAAGACATAAGGAAATGAAGACCTACTCT | 41719 |
| 8094 CCTACCTCCCAGGTTTGCTGTATG | 19752 AGCAGGCCCTTCTGGACTAT | 30736 TTGCCTCCTACCTCCCAGGTT | 41720 |
| 8095 CCTCTCCACTTTGTCCCCACTTC | 19753 GAGGGGAATGGTTTACCTTCGTCAA | 30737 CCCACACTCTCCTCTCCACTTTGT | 41721 |
| 8096 CACACCGACCTTGAACTCCTCTTC | 19754 CCTGGTGCAGGGAGACATTTAC | 30738 GAGAAACTCCACACCGACCTTGA | 41722 |
| 8097 GGTCGCTCACAGAGAGAGTTTAG | 19755 GGGCTGTGCACATTCCAGTA | 30739 CCCAGGCTCAGCCCACAGA | 41723 |
| 8098 GTCCAAGGAAGATAGTCTGGGGTTCATG | 19756 ACACATAAATGGTCTCCCTGATCCTT | 30740 GCCTGACAAACTACTCCAAGGCAAGATA | 41724 |
| 8099 AGGCCTTTCCTGCCCCTCAA | 19757 GCAAGTAAGAATGGGTTTGAGTCAGT | 30741 CCAGAAGATGTGGGAGGCCTTT | 41725 |
| 8100 AGGCCAAGTTTAGCTGTGTGT | 19758 CCCACAGCAATATGTCAGAAACCATAA | 30742 GACCAGTGTTTAAAAGGCCAAGTT | 41726 |
| 8101 TCATCCAGTCCAACCTCTTCCTT | 19759 TGCTGAATCTTGCTAGGATTGACTT | 30743 CCAGAAGGGACCCCTCAAATCAT | 41727 |
| 8102 AGGCAGAGACAGAACACAGAA | 19760 CACATGAAACACACAGACTGATTC | 30744 AACCTGGCAGAGGACAGACA | 41728 |
| 8103 CCAAACCAGCACACTCAACT | 19761 GGTCTGGGGACAGCCAAGT | 30745 CACAAGTCAAGGTCTCACTTCCAAAC | 41729 |
| 8104 ACCTCTTCCCCTCATCCTTTATGT | 19762 GCACAGAGACATAGGACTTGGTGTT | 30746 CCTGGGGTCATCTTTACCTCTTC | 41730 |
| 8105 CTGTGTTATCTAGGATTGCACCTTCT | 19763 GATGCCCATCTGCACGTGAT | 30747 TCTGGCTAGCTGTGTTATCTAGGATT | 41731 |
| 8106 CGGCCACATTGTGAGTCTGT | 19764 GCCCTGCCTCAGAAAAGTCCATTC | 30748 AGCTCGAGACGGCCACATTG | 41732 |
| 8107 CAAATGTCTGGCCCTTGGATATCA | 19765 GCCAAATGCTTGAGGTTTGCTT | 30749 CGGCTGCCCTACAAATGTCT | 41733 |
| 8108 TGGGGTTTGGAGTCCATGTTAC | 19766 GCCGTTGCAGTGATTGTAATTCT | 30750 AACAAGTTCCTCAACTGGGGTTT | 41734 |
| 8109 CCAGGAAGCATGTAAAGAACAAGAAG | 19767 ACTAGGAGCCCTTCTCTTTCCAA | 30751 GGAGGGAGCAGGAAGCATGTAA | 41735 |
| 8110 CCTGTGGAAGGTGGTTGTCAGA | 19768 CCACTAGCATAGGACAGTCATTCT | 30752 AGCTGGGTGCACCTGTGGAA | 41736 |
| 8111 GAATTGTCAATCCCAGCAGTCAGA | 19769 CTCCTGTGGTGGTGATGCTT | 30753 CCTAGCCAGAGGGAATTGTCA | 41737 |
| 8112 AATGGGTGGTGTTCTGGAAGATT | 19770 CCCCAGTCTCGGTCTTTTATTTACA | 30754 ACATGTTTGAAATGGGTGGTGTTC | 41738 |
| 8113 GGGTCTGAAAGGGGCAGATTG | 19771 CCCAGAGAATGGACAGTTTACAGA | 30755 TGTGAGTAATCGAGAGGGTCTGA | 41739 |
| 8114 GGGACACCAATCTGGGACAGAA | 19772 GCATGGGCTTCCCATCCACAT | 30756 GGTACCATCCTGGGACACCAATCT | 41740 |
| 8115 ACGCTGGTAGAGGTTCTTCATTT | 19773 GGTATTTGCAAGTTCCCGAATCAA | 30757 ATTGGCCACGCTGGTAGA | 41741 |
| 8116 GCACAGAGTCAGGCACGGAGACA | 19774 CTGCCTCCCATAGGGCTAGT | 30758 CACTTTGCCCAGCAGGAGTCA | 41742 |
| 8117 CCAGCATAGTGGTAGCCCTTCA | 19775 CACTTATGTCCCCTACCAAACCCATAC | 30759 AGTGGACCAGCCAGCATAGT | 41743 |
| 8118 CTCTCAAACACTTAGCTGGCAAAA | 19776 GGGTGGGAGCGCCTATTCTTG | 30760 GGACAACTCCTCTCTCAAACACTTAG | 41744 |
| 8119 GCTCCAAAGCCCTCCTTCATC | 19777 GCGTTCGAAGCACTCTACACACT | 30761 TCGTGCTCAGCGCTCCAA | 41745 |
| 8120 CCGTGCCTATCAGTTCTCCATTTG | 19778 CACTGAGTTGCCACCAGTTCAAACA | 30762 TGGACCTCGTGCCTATCAGTT | 41746 |
| 8121 TCCTACAGTCCTCCTCGCTCAAG | 19779 TCCAGCCCAACACCTCATCA | 30763 TGGTACCTCGGGGTCCTACAGT | 41747 |
| 8122 CTGACATGTGCTTTTAAGTCCCTGCTA | 19780 AGTGACAGCCCCATCACTGT | 30764 CAACCTCCCTGACATGTGCTT | 41748 |

| | | | |
|---|---|---|---|
| 8383 TGCCATGTCCTACTGCTTCCTA | 20041 GGAGCCAAATGAGAGTCAATTTCCTTTCT | 31025 GCCCAACCTGCCATGTCCTA | 42009 |
| 8384 CCCACCCTTAGATCAGGGATAGT | 20042 CCTCTGCCAGGCTATTCGTGTATTTC | 31026 CCCTTCACATATTCCCACCCTTAG | 42010 |
| 8385 GTTGGATGTTTCTCTCCCATGCAA | 20043 CCAGTGGGTGCAAACAAACACA | 31027 TGGTCAAGGTTAGAATGTTGGATGT | 42011 |
| 8386 CTGAAGGGTTAAGGTCGGCTGTCA | 20044 TTGGCTCCTTTCCCCTAGACA | 31028 CTCCTGGCTGAAGGGTAATGT | 42012 |
| 8387 CCTGGAAGCAAGGTACATTCAA | 20045 GCACACGTGGCCACAAAGAAA | 31029 TGCCATCAGCTGTACCTGGAA | 42013 |
| 8388 TGTGCCGATGGGAGGAAATG | 20046 TGAAGACGGGTGGGGTCCTTTA | 31030 CGGGGAGTATGTGGGGATGT | 42014 |
| 8389 GTGCCCGGACAGAAAAGACTTTCA | 20047 GGCAGGATGAAGTATGGACCTGAGA | 31031 CCACTGTGCCCGGACAGAAA | 42015 |
| 8390 TCAGCTCTGTTTTATGGGTGACAA | 20048 CACCTACCTCACTAAGACCCAAGAT | 31032 GAAGGAGAAAGCATCAGCTCTGT | 42016 |
| 8391 AGGGAGGGTAGCTGGGGTTTAC | 20049 CCCCAAGCTGCTCTCTGTAAG | 31033 TTGCAGTGCATTTGAGGAACAAC | 42017 |
| 8392 GCCGGCTTTAGCTGGAAGCAA | 20050 ACTTAATGAAGAAGGGTTACCAGAT | 31034 CGGATTCACCTTGAGCGGCTTT | 42018 |
| 8393 GGATCCCAGCTCCTTCCATCATGT | 20051 CAGGGCTTCAACTGAAGGACTCTAAG | 31035 TTCAGGGATCCCAGCTCCTT | 42019 |
| 8394 GCTCTTGTCGTCGCTTTTCTTC | 20052 CCCACTCATCCACCCTGACT | 31036 GGTGCCCTTCCAGCTCTTGT | 42020 |
| 8395 TGGGGAAAGGGATGCAGTTTTCA | 20053 GAAGTGTCAACTTCTCAGCAAGTAAG | 31037 GGAGCTGGGGTTTGGGGAAA | 42021 |
| 8396 CGTCCTTTGTTGCAATCTCAACTT | 20054 GCCTCGTAGTATAGCTTGGAAAGTA | 31038 GGCAACTCCTGTACTACCGTCCTT | 42022 |
| 8397 GCCGTTATCAGTACGAGAGTTGT | 20055 CGTTGAGGAGCACCTGTATCAA | 31039 TGCCTCCTGCCGCTATCAGTA | 42023 |
| 8398 CCGGGATCTTAACTGGAATGACCTT | 20056 TGGTCAGCCCCTAACTGT | 31040 GACTTGCGGATATCCGGGATCTTAAC | 42024 |
| 8399 GGTCTCTGAGGTCTCCCTTTGA | 20057 TTGTGGAACGGAGGGAAGAGTATG | 31041 ATCCAGTAGCTGAAGGTCTCTGA | 42025 |
| 8400 GCTTAAAAGAATGTCCTGGGTTCA | 20058 GCTGCTGGGTCAGTCTTGAACATT | 31042 GCAAACTGCCTGTCCCTGCTT | 42026 |
| 8401 CAACATGAAACATGGGCTCCAAATCT | 20059 CCCTCTGTTCCTATGGTCCTGGTT | 31043 GGTAGGAGCTGGTTCCAACATGA | 42027 |
| 8402 GAGGTGGGCAAAGGAACACGTA | 20060 CCTGCCCAGCCTTTTATGGGTAGA | 31044 ACTCTCCCAGGTGGGCAAAG | 42028 |
| 8403 TGAAGGCCTTAGGTCTTCCTT | 20061 AGGGAGGTCTTTTCAAACCCTTTCA | 31045 ACAGCCCTTATGGAGGCCTTAG | 42029 |
| 8404 CAGGGAGGAACAAGTGGCATGA | 20062 CAATGACGAGGCAAGTCAATATCTCT | 31046 AGCTGGTCTCAGGGAGGAACAA | 42030 |
| 8405 GGCCCTGAAGTATGCTCTTAAAGT | 20063 TTCCCTGTCCCTGTCACTCCTT | 31047 AACCCGACCTGAGGCCCTGAA | 42031 |
| 8406 AGGGGTTATATCTGGCCTGAA | 20064 GCTGATCAAAGAGGGATATTCTATGCATT | 31048 TGAGGGTTTAAGGAGATAGGGTTA | 42032 |
| 8407 GACTCTTCTCCAGTTCCAGGAAAAT | 20065 GCACATGGCTCCCTTTCTGA | 31049 GGCCAAACCCTGTGACTCTTCT | 42033 |
| 8408 GCAGTGATGGAACTGCCACCTA | 20066 CTGGAAGAAGCAACCCTGGATATG | 31050 GGCTCAAGTCGACCAGTGATGGAA | 42034 |
| 8409 CCTGTAGGTCCCAGGAAGGTAAA | 20067 CAGAGTACTTCTTCCTGACCCTAAC | 31051 GGGTTCGTCCAACTTCCTGTAG | 42035 |
| 8410 CCAGATACCATTTTGCCTCATGTCA | 20068 TGAATTACACAGCTTCAGGCCTTT | 31052 TGCCTTTCCTGACCAGATACCAT | 42036 |
| 8411 GTGTCGTTAGCACGAGCAGT | 20069 TGCTTGCCTTTTGCAGTAAATGTAG | 31053 GGTCCCCTCCTAGGTGTCGTTTA | 42037 |
| 8412 CCTGTGGTTGCTACCCTCTCTTCT | 20070 GGAAACCTCAATGTGAACTGCTCTCT | 31054 CCCAACTGCCTGTGGTTGGTA | 42038 |
| 8413 GACCAGAACCCTGCTGCTTTGT | 20071 CGAGTCAGCCACTTGTGAAAC | 31055 GCGCTTGCTGCTGGTTAAGA | 42039 |
| 8414 GCTTCTAATAGAGACCATTCTCCTGAA | 20072 CACTGTATCTGGCCTGCCAATTT | 31056 CAGGTTCTAGAAAGPGTCTGCTTCT | 42040 |
| 8415 GGCAAGTAAGTCTTCCCTCCTTTG | 20073 GGCACAAAGCTAGACTTCCAGTA | 31057 GCCATGCCACAGCCAAGTAAGT | 42041 |
| 8416 TGGGCTGGAATCCTGACTCT | 20074 GCAAAGGTGGTTCAAAGTCACA | 31058 AGAGGCTGCCTGGGCTGGAA | 42042 |
| 8417 GTTGGGCGTGATGAGGGACTT | 20075 GGAAACATTCCCTGCCATCTCCTA | 31059 TGGGCTGCTTTCCCCAGTTG | 42043 |
| 8418 CAAGTGAGGCTTGTGCCTTTTC | 20076 AGTGCAGGCTTAAGGAAAGGTT | 31060 TGGGAGAAGAATACAAGTGAGGCTTTG | 42044 |
| 8419 GAGAAAAGAAAGGGGCAAGAATTGA | 20077 GTGGTGAACATAGTCCCCAGTAAAT | 31061 CTGGGGAATTCAAAACAGGAGAGAAAG | 42045 |
| 8420 TCGCTCTTTGGTAAAGTGAGACA | 20078 GGAGGGAAGAGGCTAGATTAAATACCTTAG | 31062 GGGCTCTATCGCTCTTTGGTAA | 42046 |
| 8421 CAACTTAAGTGCCTCAGGCTGTCT | 20079 GCTGACATTGAAGACCAAGCGATC | 31063 GTGAGCTACTAAGAGCACCAACT | 42047 |
| 8422 GCCCAAGAACCCACAATCAATC | 20080 CAGTGAGCGCAACCATTCCAATC | 31064 AGCAGCAGAAACCCCTCTTG | 42048 |
| 8423 CCGTCACAGTCCAAGTAAAAGCTA | 20081 CCAGATCACATAGGGCATTTTAGACCAT | 31065 CCCAATGTCTTCCCGTCACAGT | 42049 |
| 8424 GGGAGTTAGAAAGGGCCTCTAACAGTTT | 20082 ACTTATTCACTGTGGCCACCTTTC | 31066 GTTGCAGCTTGGGGAGTTAGA | 42050 |
| 8425 CGCTAAACACTCTTCAGACAGACA | 20083 CTCGATCAAATGCAGTGGTCAAATGT | 31067 ATGTGGTCATCGCTAAACACTCT | 42051 |
| 8426 GGGGCTACTGATGAAGCACATATAG | 20084 CTCAGCCTTTTATCCTGTTCTGTGT | 31068 CGAGCAAGGGGCTACTGATGAA | 42052 |
| 8427 GGCCCTGTTGAACCTTGCTAGCTT | 20085 CCCACCCCACCTTCTCCTTTTTG | 31069 GGGAGAATATTTGGCCCTGTGA | 42053 |
| 8428 CCGTGCCAGGAAAGTGACAGT | 20086 GGTCCTTGAGTTCGGGGTTAGGAT | 31070 TGGTGACCGTGCCGAGGAA | 42054 |
| 8429 GGGAGAGTCAGTCACCAAAGTATG | 20087 GTCATCCTGAAAGTCTCCGCTACA | 31071 CTGGCAGTCTGGGAGAGTCA | 42055 |
| 8430 CGAGGAGATGAAGGGACAGAAAT | 20088 ACTGCCTCTTTTGGCCACGTA | 31072 CGAGCTACACAGGAGGATGAA | 42056 |
| 8431 AGACCTTCAAGAGGAAAGTGAGAGT | 20089 GAACCACTGCCTTAGATCAAACAAA | 31073 CCCACTCCAAGACCTTCAAGAGGAA | 42057 |
| 8432 AGGACTCAGAATCCACTCCCTATG | 20090 CCACAGCACCCTATGCCAAGTGA | 31074 GCACCTTGGCAGGACTCAGAAT | 42058 |
| 8433 TGAGGTGGTCAGAATGAACCTACT | 20091 GGACAGCCCAGGTGAGTCAT | 31075 CCCCTTAGAAAAATGAGGTGGTCAGA | 42059 |
| 8434 CCCAGTGCTTCCTGTTTCCAA | 20092 GGCCTAGTCTCCCTAAGCCTAATG | 31076 GCTTCAACAGCCCAGTGCTT | 42060 |
| 8435 GGTCAGGTGGGGTTTTATTCACCAA | 20093 CCCAGGAGTAGCCCTTAACCAATTAC | 31077 AACTTGGTCAGGTGGGGTTTTT | 42061 |
| 8436 GCTGTCAAAGCAAGTGGGAAGA | 20094 CCAGAATTGGAATTGGGTTCCAGTA | 31078 TCGGGGCTTCTGCTGTCAAA | 42062 |
| 8437 GCCAGATAGAGAGCTTGTGGGTTCT | 20095 CAACCAGGCTTGGGAGAAACA | 31079 CAGTGTTGCCAGATAGAGAGCTT | 42063 |
| 8438 GGTTAAATGACATCCACTAGGCCAAAAC | 20096 CATGGTTGGATTGTCGGTTGTTCTTC | 31080 CCAGGGGTTCACAAGACAAGGTT | 42064 |
| 8439 GGCAGCATAGGTAGGTTTGGAATTG | 20097 GCCTTTTATCCCTGAGCCATTGA | 31081 AACAAGTGTGGCAGCATAGGTA | 42065 |
| 8440 CACTCACATCCCATTGTGCATATCT | 20098 GCCTCATCCTTCTTCAGAACATT | 31082 AGGTGACCCTTCCACTCACATC | 42066 |
| 8441 CCACGGGACAGTCAGCATTA | 20099 GGACTAAAGTAAAAGAGGCAGTGAGATGA | 31083 TTGCTAGCCACGGGACACA | 42067 |
| 8442 CTGACACAGTCCTGCCAGATGA | 20100 CAGGGTCATGGTCCAGAATCCTT | 31084 TGCCCCATCCTGACACAGT | 42068 |
| 8443 CTGCCGTTGAAGGTGACTGGAT | 20101 GACGCCCACTGTGATTGGT | 31085 CAGCAAACCTACCTGCGTTGAAG | 42069 |
| 8444 GTTCCGCAGGCATTCTACCAT | 20102 AGACAAGGTCGGCTGCAACA | 31086 GGATGAGCTCCTTGTAGTTCTTGTTC | 42070 |
| 8445 CCCATCTGCTTCACAGGGTTATAC | 20103 CCAGCATAAGGAGCCTGTGATTTTT | 31087 GCCATCAATCCCATCTGCTTCACA | 42071 |
| 8446 CCGATGCTTCAACCACACCTAGA | 20104 ATCTCAGTCCCAGGCCAACT | 31088 AGGAACCCACCGGATGCTTCAAC | 42072 |
| 8447 GCAGGCTCCTGTAAGGAAGGAGTT | 20105 CCTTCCCAGTCCAACTCCAAAG | 31089 ATGTCTCGCAGGCTCCTGTA | 42073 |

| | | | | | |
|---|---|---|---|---|---|
| 8513 | CCATCTTTGAACCCCTACTGCTCAT | 20171 | GTGTTTTGAAAGGCTAACTCTGGTT | 31155 | CCCCATAGTTTCCTGCTTCCATCTTTGAA | 42139 |
| 8514 | ACTAAGGCAATGCTGAGTGGAAA | 20172 | GCCCTTGTTGGGGACTTTGTGTA | 31156 | CCCTGTGGAGCCGACTCTACTAA | 42140 |
| 8515 | TGGGAAGGTTCCAGGCAGTT | 20173 | TTAGGGCCTGGAATGGGGTTTC | 31157 | AGGCAAGGAGCTGGGAAGGTT | 42141 |
| 8516 | TGGCAGCTACTGGAGACTCGTA | 20174 | GGCTTGAACCACTTGGCTCTCT | 31158 | GTGGTCAGTTCTTATGGCAGCTA | 42142 |
| 8517 | CAGGAGATGTACCTTTCACCAAAAC | 20175 | GGGATCCTGGGACTTCCTGTAATC | 31159 | GGACGGTCCAGGAGATGTACCTT | 42143 |
| 8518 | GGGGTAGGATGGAGATAGGTTTCAGA | 20176 | CCTCTTCAAGGTCCCCAAATATTCTTCA | 31160 | GGGACAATGGGGTAGGATGGAGAT | 42144 |
| 8519 | CTCAATTTTGGAGGGTCTGAATTGGTTT | 20177 | GGGCATATGAGATTATAAGGGCTAGTTTTG | 31161 | TCTGTGTGCCCGTCCTCAAT | 42145 |
| 8520 | GATCCAAGCCAATGGGGTATTTTC | 20178 | TGTCTGCTGATACTGTACTTGTT | 31162 | GAGTGCCAGATCCAAGCCAATG | 42146 |
| 8521 | GCCATCTTAGATCACAGGAGGGAAA | 20179 | GAGGGGAAATGGAGATAAGTGTTCTAAG | 31163 | CGGTAAGAGCTGGAGAAGCCATCTT | 42147 |
| 8522 | CACCATATCCCCTTAGGGTCTTGACA | 20180 | CCAATCCTCCCTCTTGCAGTTTC | 31164 | CCAGCCATAGATCACCATATCCCCTTAG | 42148 |
| 8523 | GGCAAACAGGGAGAATGGGAATAC | 20181 | GTGAGCCATTTCCCCACCACTT | 31165 | GGTGGGAGGGACAGGCAAA | 42149 |
| 8524 | GTGCAAGGAGAGCTGAATTCATGT | 20182 | TGAACCACAGCAAGGCAGATAC | 31166 | GCTAGAGGCTGACTGTGCAA | 42150 |
| 8525 | GTGGTGGGGTTTGTTGGCATTC | 20183 | TGAGCCCTGCAGACACCAA | 31167 | AGGTGGTGGAGTGGTGGGGTTT | 42151 |
| 8526 | CGCAACCCTGTTTGTTCAAAGATTC | 20184 | GCCTTCTTAGTTCCTAGTAGCTGATT | 31168 | GGCTTTATTCATTCGCAACCCTGTT | 42152 |
| 8527 | GGGGTAGAGGGAGACTTCAGTAGTTGTCA | 20185 | GCTGCTGCCCTGATTCTAGCTT | 31169 | GGCAGTGGGTAGAGGGAGACTTCA | 42153 |
| 8528 | CTTTTTCTCATACCTGCGCACTCT | 20186 | CTTCCAAGTGCTGCCATTTAGTCA | 31170 | CCTCGGCCAGATTTCTACTTTTTC | 42154 |
| 8529 | AACCACGGAATGCGGGACTT | 20187 | CTCTACATAAGTGCATCCCCAGAA | 31171 | CCATCACAGCCTAACCACGGAAT | 42155 |
| 8530 | TGACCTGGCTATGCCTGTTTAAT | 20188 | CCTGCTGGACAAGCTTCCTT | 31172 | AGTTCAAGTTTTCTGACCTGGCTAT | 42156 |
| 8531 | GTCTGGGAGGAGGAACAGGAAA | 20189 | ACCCTCCTCCACTGGTTTCA | 31173 | TGGAAGAGGGAGGCAACTCTGT | 42157 |
| 8532 | GCTTGATGCAAAGGAAGGAAACT | 20190 | CCCCATTGATGCCAAGACATCCTAAG | 31174 | GGCCACTGCTTGATGCAAAG | 42158 |
| 8533 | GCCCAATGCCGTTAAAGATCTGA | 20191 | GCTGAGCATGAAGTCAGGAGAAAC | 31175 | ACAACAAGCCCAATGCCGTTA | 42159 |
| 8534 | CTCTCCCAGTTTAGCACCAGCATA | 20192 | GAGAGGAAGAAACTGACAGGTACTCAAG | 31176 | CACATGAGGTGTTTCTCTCCCAAT | 42160 |
| 8535 | CCCTAACTAGGCCAGGGAGCAA | 20193 | CTCCTCAGAATTTGCCTCAAGTTT | 31177 | CCTCATGGCCTGAAACAAACCCTAAC | 42161 |
| 8536 | GGGGCTTCCCATAGCTAGGATTGT | 20194 | GAGAGAACCCTAGGACTTCACATTTC | 31178 | CAAAGGTTTAGGGGCTTCCCATAG | 42162 |
| 8537 | AGGGGAGTACAAAGCCATCATTG | 20195 | GCTGAAGCATAGTGGTCCAGAT | 31179 | TGCTACATTCAAAGGGGAGTACAAAG | 42163 |
| 8538 | CACTCTCAGTGGGAAGGGAATTAG | 20196 | CCACAAAGTTTTTGACACTCCTCTCT | 31180 | GTCATTACATCTGACCCACTCTCAGT | 42164 |
| 8539 | TGTCTTGAACAGCTCGTCACT | 20197 | CACGCAAGGGCAGTGTGTTGTCCTA | 31181 | CAATGCTCAGTCTCTGTCTTGAAAC | 42165 |
| 8540 | GAGACCCAATAATGCTCTAGGGATTTTA | 20198 | ATGGGCACAGAAGCCACTTT | 31182 | GGCACAGAGTGTGAGACCCAAT | 42166 |
| 8541 | CTCACCAAGGTCACCAATTTTCAT | 20199 | GTCAAGCTATAAACTACGACCCATCTCT | 31183 | GCTCTCCCAAGAATTATCTCACCAA | 42167 |
| 8542 | CTCCATCCAATCTTGCTGACCTAAGAAC | 20200 | CTCATGGAGTTGAAGGCTTGGTTTG | 31184 | GGGCCTAAGCTCCATCCAATCT | 42168 |
| 8543 | ACTGCTTCTAGCATGTCACCAA | 20201 | GAAGTTTGAAAGGCCACTAGGTGTT | 31185 | CCATCACATTGCTCAAACTGCTTTC | 42169 |
| 8544 | GGGAACAATCCTTGCAATAACTCCTA | 20202 | GGCCTCAATATGGAACTACATTGTT | 31186 | AGGACGTGCATTGGGAACATC | 42170 |
| 8545 | GGGCTCCAGGTTTAGTTAGCAGAT | 20203 | CGAGGGAGGTAATGGGAGCTAGA | 31187 | CCAAGCAAGGGCTCCAGGTTTA | 42171 |
| 8546 | CGCTACGTGACTTCTGCTTAGT | 20204 | TGCATCCCAACAGGGCTTTC | 31188 | CTGGATCATAAAACGCTACGTGACT | 42172 |
| 8547 | CACCAAGATGGCTAAGTGACGAA | 20205 | TGTCCACGGTATCCACACTGA | 31189 | GGCTTTTTTCCATCTAATCACCAAGATC | 42173 |
| 8548 | GCCTGGGTAAGTGATGGCATAG | 20206 | GGTTCCAAGGGCACCACATTT | 31190 | AGCTACACAAAAAGCCTGGGTAA | 42174 |
| 8549 | GGTCAACTATAGGCTTGCACGTGAT | 20207 | CTGATACACCAGTGTCCTAATTTCCAA | 31191 | CCTGCCACTGGTGGTCAACT | 42175 |
| 8550 | CGCTCGATCCAAGTTTCTCTATTTG | 20208 | CTGATCTTAAGCCCAATACTGTAGA | 31192 | GATTAAAATGCGCTGACTCCAAGT | 42176 |
| 8551 | GGGTGTGCTGTTTACGTGGAT | 20209 | CACCAAGCCAGTCCTGGAGATA | 31193 | CCGTGGTGGGTGTGCTGTT | 42177 |
| 8552 | TGTTGGAGGTCAGTCAGGTTGT | 20210 | GAATGATGGGAGCTAGGCTCTAAG | 31194 | GGCTTAGACAGGGGAAGCAACT | 42178 |
| 8553 | GTAGGGCAGATCAAAGGAATGAGA | 20211 | ACTCCCCTCGCTGGGTGAT | 31195 | AGAAGGTTCTAGGCAGAAACAGTAG | 42179 |
| 8554 | CCTGAGCCCAAACCATGCATCTG | 20212 | GCTTCTGGACCTTACTCTTGTTTCA | 31196 | CCTCCTGGCCTGAGCCCAAA | 42180 |
| 8555 | AGGTTAGGTGGTCCTCAGCTATG | 20213 | CTTGCTAGCTCTTGGGTCTCATTC | 31197 | ACAATTACAGCAGCCCATCTAGGTTAG | 42181 |
| 8556 | AGAGCACTCCTCAACCAACTTC | 20214 | CTGGGAAGCAGTCTTGAGACCAA | 31198 | CCCAAAGCCAGGGATCCAAA | 42182 |
| 8557 | CTGGCACACCTGTGATGTTGAAG | 20215 | GGCTAGCCTCCATGTCAGCAAA | 31199 | TTACCCTGGCACACCTGTG | 42183 |
| 8558 | GGCTTCACAGAAGAGGTGGTATGA | 20216 | CTCCACCTGCCAAAATCCTACT | 31200 | GGGAAATCAGGTAGGCTTCACAGA | 42184 |
| 8559 | GCTAGGCGCTACCCGTAGAAG | 20217 | TGTGTGTTTGAGACCCTTGCATCT | 31201 | ACAGCGACACACCACTACTGCTA | 42185 |
| 8560 | CCTGGATGTAGCAGATAGGGTTTTC | 20218 | CTACCAAAGCTGTTGACCAAAC | 31202 | GCTTGTCCTGGATGTAGCAGAT | 42186 |
| 8561 | CCCACTGGAAGGAAGCTTAAGATG | 20219 | CCTTTGCCTGTTTCCTGCAGATT | 31203 | CCTCAATCTCCCACTGGAAGGAA | 42187 |
| 8562 | CTAGCTCTCTCGTATCATTCAGACTAC | 20220 | AGTTTTCCCTGAAAGGAGTGACAT | 31204 | TGATGTGGCTAGCTCTCTCCTA | 42188 |
| 8563 | TTCACACAGCTGTCACACACAA | 20221 | TGTCTGCCTCCCACATCTCT | 31205 | GCCTCTCACGTACCATTCACACA | 42189 |
| 8564 | CTTGAGGTCTGATTGATGAAGTGA | 20222 | ACAGGACCATCCAAATCACCTTGAA | 31206 | GTGGGCCAACTTGAGGTCTGAT | 42190 |
| 8565 | CACGTCCACTAAAATTCCTGCTCTTG | 20223 | CCTAAACACTGGACTCTTTACACATCT | 31207 | CGCTTGAAAACACGTCCACTAAA | 42191 |
| 8566 | CCAGAGGCAAAGGGAAGACTCA | 20224 | GCACATCACCCAGTTGGGAAAC | 31208 | CTTACTACTAGTGTCCAGAGGCAAAG | 42192 |
| 8567 | GCCCATAGATAACCTGATGAACACAAG | 20225 | GGGATTGGGTGTTGACGATGA | 31209 | GGCCTCTTGCCCATAGATAACCTGAT | 42193 |
| 8568 | TGAACTTGATTCTACAGGCAGTGAT | 20226 | GACGTGTGTCACGTTCTCTTCA | 31210 | GGACAGCCCAAAGAATTTGAACTTG | 42194 |
| 8569 | TGGCTGCTACACCAAATCGTT | 20227 | CCCCTTGCATTTGGCACAGA | 31211 | TCCCAGGATTGGCTGCTACA | 42195 |
| 8570 | ACAGTGCAAACAGAGGTTTAAA | 20228 | CTGGGAGGGTGTTTTCAAACCCAAAC | 31212 | CCCCTGGGACAGTGCCAAGAA | 42196 |
| 8571 | GGCTTTGTGACTGCTTTGACTAACAGA | 20229 | GGGCCTGAAAACTGGCATGA | 31213 | AACAGGCTTTGTGACTGCTTTG | 42197 |
| 8572 | CCGCCAATCCTCTCCAACTTGT | 20230 | TCGTCAACCTGTGCAGGTAAG | 31214 | CACTTTATCTTCAGGTCCGCCAATC | 42198 |
| 8573 | GGTCTGTTCCTAAAGGTCGGAGACT | 20231 | GCAATCAGGACGATCAGACAAAAGAAG | 31215 | CCTGAAGTCTGGTCTGTTCCTAAAG | 42199 |
| 8574 | GGGGATTGAAATTCAGCACCACCAA | 20232 | CTCTGCCTTTTGCAGGGGTTGT | 31216 | TGCTGCTGAGTGGGGATTGA | 42200 |
| 8575 | CGGAGTAAGTCTTTGTCTCAAACAGCAT | 20233 | ACCCAAGGAGACAAGAGCATCA | 31217 | GTGGCGACGGAGTAAGTCTTTGT | 42201 |
| 8576 | AAGGCAGGTGCTGCTCCTAT | 20234 | GAGGACTGGAAGTGGTAAGTCACA | 31218 | AGCTGGCCCTGTGGGAGGAA | 42202 |
| 8577 | GGGGTGCAGTAGCCCTCTATGAA | 20235 | GCCCAAGACTGGCATTCTCA | 31219 | ACCTCCTCAGGGGTGCAGTA | 42203 |

```
8708 CCCTTAGTTGTGAAGGATGGTTCT        20366 TCCTCCTTGGCCCAATCAAAG        31350 GTCCTCTTGTTTCCCTTAGTTGTGAAG    42334
8709 GCTGGCATCTACTGGCACACA           20367 ATTGGCTAAGCAGGCCAATCT         31351 TGTTACTACTTCAGCTGGCATCTAC      42335
8710 GGACTGTGTCGTGGTTTGA             20368 ACCTGGTGTTCTAGTCTACTGTGA      31352 GGAAAGAGTGGGAAGGACTGTGT        42336
8711 CAGTAAGTTCTGAGGTCCTGTGTT        20369 ACTTGGGGAACAGAAAGATGTCAA      31353 GGCAGTAATGGGCAGTAAGTTCT        42337
8712 GAGGGAAAGGGTGGCCATCATCA         20370 CCACCCAGGAGCTCAGTTGTGTT       31354 CGACTACCAAGTTCTGGAGGAAAG       42338
8713 GCTGCACAGGATTTTCCACAATG         20371 GTGGTTACTGCATCGGACAGT         31355 AGGGGCTGCTGCACAGGATTT          42339
8714 TTGCTGGGCTTTTGAGGTATT           20372 GGGAAATGCTTCGGGACCTT          31356 GCTTTTGTTGCCTGGGCTTT           42340
8715 CTGCTCTTTGCTCCGTGACA            20373 CTTTGGGCTGGTTGGTCTGA          31357 TCCCCTGTCCTCCTGCTCTT           42341
8716 TCAGACTGGCCTTCGAGACA            20374 AGTGATGGCTCCTGCCCAAAC         31358 ACAGGCCAAGCCTGCTCAGA           42342
8717 GGACCCAGTCACTGCATTTCA           20375 GCCCTCCCAGGCTAAGAATATC        31359 CACATTTGCAAAGGACCCCAGTCA       42343
8718 GCAGATCTTGGAGATGACCCATAATTC     20376 CCTAAGGCCTTCTGCAGCTGAAAT      31360 CCTCCGCAGATCTTGGAGATGA         42344
8719 GCAAAGAGCCAACTTCTGATCGT         20377 GTGAAGCAGCTGGAAGTCTCT         31361 GGCAAACCAATAGCAAAGAGCCAACT     42345
8720 AGGTAAGGAGGGCAGTTTCTATGA        20378 ACTGCCTCCCGTTCCATTTTCT        31362 TGCAAACAACCCAGGAAGGTAAG        42346
8721 CGTGGTAACACTGCACTCAAG           20379 CTTCACTACCTAGATGCCATCCTATT    31363 TTGTGGCGGCGACGTGCTA            42347
8722 GGGTCCAAAGGACATTTCAGACTA        20380 GACCCTCTGTGTCTTGTGCAT         31364 TGACCTGACAGAGGGTCCAAAG         42348
8723 AGGGCTGTGTGAGGTTCCAT            20381 AGCTGCCTCCGAGAGAAGAT          31365 GATGGCATTATATCAGGGCTGTGT       42349
8724 GCCTTGAAGTTGCCTTCAAAACACT       20382 AGTGCGCTGTGGGGAAAGGAA         31366 TGCCCCTAGCCTTGAAGTTG           42350
8725 GCCTGACCAATTCTGTGGCTCTT         20383 GGCTTCACGGCTGAAAGGAT          31367 CCACCGTGCCTGACCAATTCT          42351
8726 GGTCTCATCTCACTGTGTCTCAAC        20384 TGCAAGGCATCCCCAAGA            31368 CGCTTTCCCAATGTACCAGGTCTCA      42352
8727 CGGGCAATGGATAACCAAGCTTTCTTC     20385 GTTTCTGCCAGTTAGGCAGCTAGT      31369 GCTCTAATAGCTACGGGCAATGGAT      42353
8728 GTGTCATCCACATTGAGTGAAAACT       20386 GGACTCAGAAGCTTCAGACAAC        31370 GGTTTGACCCTCAACATGTGTCAT       42354
8729 CCCTCCTCAGCTTTTCCCACTCT         20387 GGCAACAGAACAAGCCTGGTCAA       31371 GTCGAATCTACCCTGTCAGCTT         42355
8730 CTTGGTCCTTGGTGCCTTATTTAGT       20388 GCACGAAGACCATTTAGGAAACA       31372 TCTCTCCAGGCTTGGTCCTT           42356
8731 CGTGGGCCTAAGTTTTCAACTCATT       20389 CTATAACTTCCAGTAACTGTGCTCCTT   31373 TGTGTAGAATTTTACGTGGGCCTAA      42357
8732 TGGAGACCTATGCTGTCAGGAA          20390 CCCCACCTAGCCACTCTCTAC         31374 GTGTGCTGGGGTAGTCACAGATG        42358
8733 CCAAGGGAGGCTGAATGAAGTGAT        20391 GGGGAGGCAAGAAGAAGCATAATGTCA   31375 CATACCAACCAAGGAGGCTGAA         42359
8734 TGAAGAACTATTGCTGCTCCGTGAT       20392 GGACCTGCTCCTTTCTGCTCAA        31376 GCAACTATCAGGAGCTGAAGAACCATTG   42360
8735 TCCATCACCTCGGTCTCCAAA           20393 GCCACCTTTCAGGACTTGCTAA        31377 CTCCTGGACTCAAGCAATCCAT         42361
8736 AGGGTCATTTTCTGGCCTTTGA          20394 CCGTTTCAGGCCATAGCTCACA        31378 TTCCTTCAAAGCAGAGGGTCATT        42362
8737 GTGTTCTGGACACGGACGTAAG          20395 CTGGTTCTCAGGTCCTGCCTTT        31379 TGCCCCAAGGCTAGTGTTCT           42363
8738 GTGGATCTTTGCTCTTGGTGAAGATGTA    20396 TCCAGGGCAGTGCCTCCTTT          31380 GGCATTTTGACTGTGGATCTTTGCTCTTG  42364
8739 TTGGGGCATGCCGTCACT              20397 GCTTTCCTTTTACTCCGCCTTAAGATT   31381 CTTGGCTGCTTTTGGCCAAGT          42365
8740 GACAAGGTTGGTCCTCAGATAGATTACA    20398 TTCTCTGGCCAGCCTTTAAGTTT       31382 ATCTACCTGGCCTGAAAGACAAG        42366
8741 AGTGTGCTAACTTGGCTGCAA           20399 CTCAAGGCCAGTCAGCTCTGT         31383 GCACGGCTGGGTGGAAATAAGT         42367
8742 GGCAGTGGACTTAAAATATGGGGAAGAT    20400 CTGTTCATGGCATCCCCTAATGT       31384 GCATGAAGGTGGCAGTGGACTT         42368
8743 GCCAAAGGTTGTCTAACTGGTAGT        20401 CAGCCTAGTGTTTTGTGACCATCTGT    31385 GGAAAGATTTGCCAAAGGTTGTCTA      42369
8744 CCTGCACCGTGCCTTCTCATT           20402 GCCAAACAAAGGGAGCACTGCTT       31386 GGCTTCTCTGCACTCTGGAA           42370
8745 CTGGAATCAGCTGCTGTGGTATG         20403 ACTGCAGCAACTATGCATCACA        31387 GTGTTGGGACGGTCTGGAATCA         42371
8746 GCAGCTACACATCCCTCTCT            20404 GGCTTCTCTCCCTACCCCAGATT       31388 GCCAGCAAGCAGCTACACAT           42372
8747 CCTCTCCATTTCTGGGCTCCTT          20405 AATGGGGAAGGCTGTGAGTAG         31389 CACCGCTATGTCCTCTCCATTTC        42373
8748 GCAGGAGTCAGAAAAGTTAACACAAA      20406 CTTCCCTATCCAGCTGGTCACT        31390 CCAGACGAATGCAGGAGTCAGA         42374
8749 GTGAAGGGGCTGAGCCAAAATGAAC       20407 GCACAGCTGATAATGCAGAATTC       31391 ACTCTGTGAAGGGGCTGAGT           42375
8750 CAGTGGTTTTCAGGAGCCCTAATC        20408 ATCTGTCCGCAGAGGGCTTT          31392 GGGTGAGATAAACTGTTTCAGTGGTTTTC  42376
8751 GTGTGCATTTGCTCGTTGCCTTT         20409 GGAATCCCATGTAAGCTACTTGCTGTT   31393 AAAAGTTCCTGGCTGTGTCAT          42377
8752 GGTGGGGCACAAATTCAGTTAC          20410 GTGGGCTTAGATTTGGGATATTGTA     31394 GGAGGTAGGTGGGCACAAA            42378
8753 GCACTTTACACATCCTGATGTCTCTT      20411 AGTGGGGTTTGCAGCCTATC          31395 GGATCCCAAAGCACTTTACACATC       42379
8754 CCAGGCTTTGGGAACACCAT            20412 CCTGGAAACACCAGGCTTTG          31396 GCTAAACAGGATTCAGGGCTTTG        42380
8755 GCCCTGACATTTTTCCTAGAGGGAGAT     20413 GAGAAGACGACAGGGTTCATTTGCTTTG  31397 CTGAACACAAACCTGCCTGACA         42381
8756 AGAAGGGAACTCAGAGGTTACCAA        20414 GCAGGGCATGACTGACTTCT          31398 CCAATGTCAGAACTAGAAGGGAACT      42382
8757 GGCTTCAGCAGGGTCAGACT            20415 GTGTCCATGCCTCTAGGACATCAT      31399 TGTAGAGTCCCTCTGGGCTTCA         42383
8758 CCCACTACACCATGAGCTCTTCT         20416 CCAGTAGTGCAGTTCCAGTCTGAGT     31400 CCTTCTCCTACCCTCCCACTACA        42384
8759 CCATGTGAAAACTGCTTCCCTCT         20417 CGACTAACCCTCCTGCACCATGT       31401 GTGACTCTGCTTCCACCATGT          42385
8760 GCTCAGGGGTTAGCCTTCTTTG          20418 CTCCACCATCAAGACGTTCT          31402 TTGCAGCTCAGGGGTTAG             42386
8761 CAAGAAGGAGCCAAGTTTGTTATG        20419 GGGCAGGGGATGGATAGGAGAAA       31403 TTGAGGGCCTTTGCTCAAGAA          42387
8762 CACAGTGCTGATGGTTGTCATGGTT       20420 CCTGTTTCTCATGCATACTTAGCCATGTT 31404 GGCGTCAGATCCTGATGGTT           42388
8763 CACAAGACAAGATCTCTCCCAGATG       20421 CTCCTGACAAAATAACGGCTGGAA      31405 CTGCTTGGCCACAGAAGACA           42389
8764 GTCTCCTTTGACACTGGCAAAA          20422 AGCTTGAAGTAAGCCCTTTGA         31406 GCCCAGGGCTGTCTCCATTC           42390
8765 TCAACACACATGGGGTTGCAT           20423 CCTTAGTCAATGCAATGGGAAAGCTA    31407 CCTTGGAAGATACCTAAATCAACACACA   42391
8766 GGACCTAGTCTTATTCGACTGGGAATT     20424 GGAGCTGGTAGAGCCAGAATTCAA      31408 GACTTCCTAAGAGCAAGGACCTAGT      42392
8767 CGCCCGGCCTTATATAGTATTTTCACT     20425 AAGACTGCCAGGTGGAGGTT          31409 CGCGGCCGGCCTTATATAGT           42393
8768 CTCTGGCCTTTTTAGTTTACAGAGTTC     20426 GAAACAACATCCCACACAGATGA       31410 AAGACCCTCTGGCCTTTTTAGTTT       42394
8769 TGCTCATTCACTGGGATTTGAA          20427 GAGAAGCCTTTGACTGTCTTTACTGT    31411 GTGGGTTTCCACTGCTCATTC          42395
8770 CCATCACCTGCAATGCCCATTAGT        20428 GTGAGGAGTGTTGTGAGCTTTAG       31412 CGGTCTTCCCATCACCTGCAAT         42396
8771 GGCACTGGGGATTACTAGAGGAATAA      20429 CCAACAGGTAGTTTCCAGCTCTT       31413 GGAACAGAGGCACTGGGGATT          42397
8772 TCTCTCTTCAGCCCAGATGTAATTG       20430 GGCAGAGTAGCATTTCTGCAAAC       31414 ACCTCACCGTACTGTTCTCTCT         42398
```

| | | | |
|---|---|---|---|
| 8838 GTGGACTTGATTTTAAGGACACCAACA | 20496 GGGCCACTTTGTACGTGGCTAT | 31480 GGCCAAGTGAGTGGACTTGA | 42464 |
| 8839 TCTCATCTCAGTGGCTCACATTTATC | 20497 TGGACTTAGGGTACCATCTACTCTTG | 31481 GGGTAAAAGTGAGTCTCATCTCAGT | 42465 |
| 8840 GGATTTTAGCTGTCAGGAGACAACA | 20498 TCCTCTAACACCTGTGCCATTTG | 31482 CCCATGTGAAAGTGGGATTTTAGCTGTCA | 42466 |
| 8841 AGCCCCTCCTACCACAGCTAAC | 20499 CAGATGGAGGACAAAGCCTCAGA | 31483 AGAAGCCATTAAGCCCCTCCTA | 42467 |
| 8842 CCCAAGCAAGACATTATCAATGCTTCA | 20500 ACCAACCTCCTTAAGGGAAAGGAT | 31484 CCTTACTCAATTTACCCAAGCAAGAGA | 42468 |
| 8843 GCAGCAATTGGTAACAAGGTGCATA | 20501 GTGGCAAGCCAGGACAACTGTA | 31485 GCTTGGAAAAGCAGCAATTGGTAA | 42469 |
| 8844 GGAAACCAGTTCAGAAAAGGGAGGAAA | 20502 AAAGGAATATGGGTTCTTGGCTACA | 31486 CCTAGCAACAGGAAACCAGTTCAGA | 42470 |
| 8845 GAAGCAAGACACCTTCACAAGACA | 20503 TGGTAGTTCCTCCTGCGTTCAT | 31487 GGTAAAGAGGAAGCAAGACACCTT | 42471 |
| 8846 GAGTCTTAGGGCCTTGAGTGAACA | 20504 CCATTACCTAGTTGTAACCAATACCTGACT | 31488 GCCACCTGCTGATTGTAGAGTCTTAG | 42472 |
| 8847 GCCTCAGCAAGTCTGCTCTT | 20505 CTGCCAGCACGGCTAAAATG | 31489 GAAGACCAGAAGCCTCAGCAA | 42473 |
| 8848 GGGGCTTCTAGAGCCACTTTAC | 20506 GGAGCATAAACTCCCAGGCACTTC | 31490 CAGCTGGCTTGGGGCTTCTA | 42474 |
| 8849 GGTGGTGAAGGAGCTTCTAAG | 20507 CTTCCTAGCTCTTTAATCCTTTACTGT | 31491 CCACTTGTAGTCTGGGTTGTGAAG | 42475 |
| 8850 TTCTAGGGGCCCTCACTTATTATCCTA | 20508 GGCTGATAACCGGGTGATTATACAACT | 31492 GCCTACATTCTAGGGCCCTCACT | 42476 |
| 8851 TGGTCTGCCAACTTTGCTGTT | 20509 TTCCCCGAAGCCCACAGTCTA | 31493 TGGAGTGCTTAGGGGAGGATTG | 42477 |
| 8852 ACAAGGCCACCCAGGAACCTA | 20510 TGGGCTCACGGCAAGTTCA | 31494 AGGGAGGAGAAAAGGCTGAAGA | 42478 |
| 8853 CCCAAGGAATTCTGCTAGGACCTAAAAAC | 20511 TGCATGCACCTGCTGTGA | 31495 GCTGCTGTCCCTAACCCAAGAA | 42479 |
| 8854 TGAAGACCCCAAGGAGCCTACT | 20512 TGTACCCTAGGTACCAGCTCATC | 31496 AGCCTAGGCCTGGACTTGAAGA | 42480 |
| 8855 GGTGGGACAAAAGCCAGATCACA | 20513 TCCACTTCTCACCTCTCCTTCA | 31497 CAGCAGAGTGTGGGACAAA | 42481 |
| 8856 GAGACAAAACTGCAAGCCAGTGA | 20514 GGGAGGCTCGAGTGGCTTATG | 31498 AACACCAGGCCAGAGAGACA | 42482 |
| 8857 TCCATACAGCTGGCTCACAGA | 20515 CACGTGTAAATGACAGGACACATC | 31499 CAHTCACCAAGTCCCTCCCATACA | 42483 |
| 8858 CACAACTGTGCTATGCTAGGGGTAT | 20516 GCTTGGGAGGGTACACAGTGAT | 31500 GGCTGCTTTTCCTTGACACAAC | 42484 |
| 8859 GCTACAGGCAGTGAATTCGTGATG | 20517 CTGGAAGGAGGAAAATGACATAGGAT | 31501 ATCAACGCTACAGGCAGTGAA | 42485 |
| 8860 GGTCATGCTACTGTCTAAGGTGCAA | 20518 ACCTAAGAAAAGCAGAGGAAACAGT | 31502 GCTCTATCCACTGTGGTCATCCTA | 42486 |
| 8861 CTGAAGTCAACTGATGTGGAGTCA | 20519 TGCCCCAGCTAGTGGAAAGT | 31503 CCAGGTGGAGTCTGAAGTGAACTGAT | 42487 |
| 8862 GGTCATGCCAGTGATTACAATGGAGTAA | 20520 CACCAATTATGCCCTAGCCTAAGAAG | 31504 GAATCTGGTCATCCCAGTGATTACA | 42488 |
| 8863 ACTGGGTCAACTGGAGGGTAGA | 20521 GTGCCACTAGGGTTGAATTTATCATGTTC | 31505 CCTGTGCTAGGTACTGGGTCAAC | 42489 |
| 8864 GCAACATGGCAAGTCAGGGTAATCTTG | 20522 TTGCTCCCACAGCTCCATTG | 31506 AGTGGAACTTAGCAACATGGAAGT | 42490 |
| 8865 GGCCTCAGCTTCCACTTTTCAA | 20523 ATCTGTTCCACGAGATGTTGATGA | 31507 TGGGGATGGCCTCAGCTT | 42491 |
| 8866 TGCCCTTCACCCTACCAAACT | 20524 CTCACAGCCAGTGCAGAAGT | 31508 CTCAGTAATGGTGGATGCCCTTCA | 42492 |
| 8867 CCACTAGACAGTGCATCTGGATT | 20525 GTGCCTTCACCCCATCTGACAA | 31509 CTCATGGGGTATCTCAACCACTAGA | 42493 |
| 8868 GTGCCTTACTCTCACCTCAGTCA | 20526 GTCTAAGGTGTGAGCACGATGTTG | 31510 TGGGGAATATGTGCCTTACTCTCA | 42494 |
| 8869 GCTGCTTGGATGACTCAGCTGTTTT | 20527 CCTGGTCTGTTTGCACTCTCCAA | 31511 GGCCACCATCCTTTGCTGCTT | 42495 |
| 8870 GCCCCAGTTTTCATGCCAACATAC | 20528 GGGTGGAAGTTTTGAGATTATCTGGTT | 31512 CCTTCTTGTGGCCCCAGTTTTC | 42496 |
| 8871 CCAGAGGAAAGAATTGTGTGGTCCAT | 20529 ACCCATTTGTTCCCAAGTTGTTG | 31513 TCCTTGTCTCCAGAGGAAAGAATTG | 42497 |
| 8872 GGCATTGTTCCACAGAAGCAAGT | 20530 GGTGGTTGGGTGCAGTAAAATAGTCA | 31514 GGTGGTCACGTGGCCATTGTTC | 42498 |
| 8873 GAAATTTAAGCGGCATGGCTTGA | 20531 TGGATACCCTTTCGGTGACATCT | 31515 TCTGTGGGGCAGACAACATAGA | 42499 |
| 8874 GCCTGTACTAGTCTCTCCCAGGAA | 20532 CTCCACAACTGGAGGAAACACATGAT | 31516 CACTGTATGCGTAGGTACTGTACT | 42500 |
| 8875 GGTCAGAAATACCCCATCTGTGATGA | 20533 TCACATAGCCGCAGAGGTAGAAATG | 31517 TCAGCACCACAATTGGTCAGAA | 42501 |
| 8876 GGCGCTAATCTCCATGCATTTTACT | 20534 AGCTCACCTAAACCAAGTGCAA | 31518 CCFATTTCCACATGGCGCTAATCT | 42502 |
| 8877 TGTGGTCAAGGATGGTGAGATTG | 20535 CAGGAGCTCTTCCCACTGATCTTG | 31519 CTGCTACCACCTCTTGTGGTCAA | 42503 |
| 8878 ACTTACCCAAGGATAAACCTACCAAGA | 20536 GGTGCTGTTGCTAAAGGCTCACA | 31520 TGGCTCAACTTACCCAAGGATAAAC | 42504 |
| 8879 CTTCTCTCCTGGGGCCTACTTT | 20537 CCAGAGGTCCTTTTCCCAACAGAT | 31521 CAGGGCCCAATCCTCTTCTCT | 42505 |
| 8880 CCACCTGACTTCTTAGGAGCACAA | 20538 GCAGAGAGTACAAATAGCAGTAAGCAGTT | 31522 ACAAGAACCTCCCACCTGACT | 42506 |
| 8881 GGGAGGAACCAAGGTGGACAAG | 20539 GACTCCCTGTGACCTTGAACAGAT | 31523 TTCGGGTGGGAGGAACCAA | 42507 |
| 8882 TGCCAGTGTGAACTTACCAAGT | 20540 CTGATCCAGCTCGLAGAGTCTA | 31524 CTCGGCATCTTTTCTGCCAGTGT | 42508 |
| 8883 GGCCTGCCCATCTCCTTTATGT | 20541 CATGGATCGTTAAATGTAGCAGGATCT | 31525 GTGTTATGGCCTGCCCATCT | 42509 |
| 8884 CTGCCTGTGTTTCTAGGCTCTTC | 20542 GGCTTAGCAATTTCCACTCGGATT | 31526 GGCAATTTTCTGCCTGTGTTTCT | 42510 |
| 8885 CTGGAGGCAGCTAGGTAGCAGAAATAG | 20543 CAGTGGAGACTTGGGTCTTCATAG | 31527 CCTATGCATCTGGAGGCAGCTAGGTA | 42511 |
| 8886 GGGCTGGGTGTTGGGGATATAA | 20544 TGAGCCTCCTTGACGACAGGAAT | 31528 TGLAGAATGGGCTGGGTGTTG | 42512 |
| 8887 CAGAGTGAAGACCTCTTTGACTATGATTG | 20545 TGFCTGGCCTCCTGTTCCAT | 31529 GGCTCAGAGTGAAGACCTCTTTGA | 42513 |
| 8888 CTTCCCCTAGATAGCTGGCTTTG | 20546 GTFCCTCTGAAGCAAGAGACTTC | 31530 CTTACCTGCCTTCCTCCCCTAGA | 42514 |
| 8889 CCCAAGTAAACCCACTAATTTCACACTTG | 20547 CCCCAAAAAGGCTTACACAGTTAAA | 31531 AAGGGCTTGTGTTTCCCAAGT | 42515 |
| 8890 CCCTTACACAATGGATGAGTGACTGGAT | 20548 CCAGACAGGCATTGACAAACTATG | 31532 GCTCACAAACCCTACACAATGGAT | 42516 |
| 8891 ACCAGGAGAGTGTGATGTTATGGAT | 20549 GCTGTAGACCTTATGCTTCCTGTAT | 31533 GGGTGAGAACCAGGAGAGTGTGA | 42517 |
| 8892 GGCTCAGAGAGCATTGTATTTCTTCCAT | 20550 CCTTCACACAACAGGAGAGGCATT | 31534 TGACTAAAACAGGCTCAGACCATT | 42518 |
| 8893 GGCCAAGACAGTCTACCTCATGTGT | 20551 CTCCTCAGTGCCAGCTATGTCA | 31535 GGACAAGGCCAAGACAGTCTAC | 42519 |
| 8894 CTCCTCTTCTCCCATATACAACTGGAAT | 20552 CAAGGATTTGAACGCATTTAGGAGGTA | 31536 GTCATCCACGGATCTCTCCTCTTC | 42520 |
| 8895 GAGTGGATGCACACGCAATGCAA | 20553 GGGATGTTTTAGGGACTGTGCAA | 31537 GCCAGTCTGTTGTGAGTGGATGA | 42521 |
| 8896 GTCTACCCCAGAGATTATTTCCCTCATACT | 20554 GGTTGGCTGCATTGCTCAAA | 31538 CCCTACTTGTTAAAGTCTACCCCAGAGAT | 42522 |
| 8897 GCTCAAGGGCAGGGAATGA | 20555 AGGGTGGCCCTCATGATTTCT | 31539 ACATGTCCTGCCAATGCTCAA | 42523 |
| 8898 GGAGCTGGTTACAGAGGGCTTT | 20556 CTGCTTTCATTGGGAACAGATGGTCTA | 31540 GGGGATTGTGGGAGCTGGTTAC | 42524 |
| 8899 CCCTTGTGGGTGTATGAGGGAAGT | 20557 GAGAGAGAAAGGTTCAGGGGTCAGA | 31541 CCCATATTTGACCCCTGTGGGTGTA | 42525 |
| 8900 GAGGCAAGACAGTGAGGCTTTC | 20558 GGGGTAGCCCTGTAACCAGTGATTC | 31542 TGATCAGCCTTGAGGCAAGAGA | 42526 |
| 8901 GTTTGTGTAGACACCCTCTGCTT | 20559 CTGCTTTCTTCCTGGAGTCTGGAAT | 31543 GGGGTTTGGTATTCAGTCTGTTTGTGTAG | 42527 |
| 8902 GGAGCCAGACAGGTAAGAAGTAAA | 20560 TGGTTTGCTCCTTTTGGTGGTT | 31544 ATGCCTACTGGAGCCAGACA | 42528 |

FIG. 36N7

| | | | |
|---|---|---|---|
| 8903 CAGCCTTCCTGAACTGAACAGACA | 20561 CTCAAACTGTAGCTGTCTTGGTTTTC | 31545 GCATAGCAGCCTTCCTGAACT | 42529 |
| 8904 GCCAGGAGACTCAAGTGGAAGAGAAG | 20562 GCCCACAAGTCTCATCCCTCTCA | 31546 ACAGTGCAGCCAGGCACTCAA | 42530 |
| 8905 GTTGGCTTCAACCTGGGATTGA | 20563 GCTCTATGCCCAGGCCAGATT | 31547 CAGGTGGGTAGTTGGCTTGAAC | 42531 |
| 8906 TCCCCTTTCCCTCTCACCAT | 20564 GGCAACACAATTTGCTTCTGGTAA | 31548 GTGATATGTGCCCTTCCCCTTTG | 42532 |
| 8907 GAGAGCCATTGCCCATCTGT | 20565 GGAGAGTCCACCAAAAGATAAGCGT | 31549 AGCACCAGAAGAGGCCATTG | 42533 |
| 8908 ACCGAAAGACAGAGTTTGTCAGAT | 20566 GCTTTGGCCTATGGTTGGGTCTT | 31550 AACATACCAACCGAAAGACAGAGT | 42534 |
| 8909 TCTCCGTCCCTCCCTCTCAAA | 20567 GGATATCAAAGTTACAGGACAGCAATC | 31551 TAGCCCATGGCTCTGTCTCT | 42535 |
| 8910 AGCAACCCAGCTAGTTCTGAAAA | 20568 TCTGGTGCCTTCCATAAGACTAGA | 31552 GCTCCCATAGCAACCCAGCTA | 42536 |
| 8911 CCTCTGGTTGCCCCTAAATTCT | 20569 GGCTTAGCCCACAAGTGTTCTT | 31553 GCAGTTTCTTCTACCTCTGGTTTG | 42537 |
| 8912 GCTAGAAATGTGAGGCTTGAGT | 20570 TCCTCTCCCTCAATTCCAACCAT | 31554 TGGAGTTAAAAGGGCTAGAAACTGT | 42538 |
| 8913 GTCCGTGCTTATCCAGATCCAA | 20571 GGTGCTGGTGGCTGGAAGTTA | 31555 CCTGTAGTGGGTAATGTCCGTGCTT | 42539 |
| 8914 CTGGACCCTTCTAGCATCTTCTCT | 20572 CCATGGAGGTGGGCTTCTCA | 31556 GTCAGCTCACTGGACCCTTTCT | 42540 |
| 8915 CCACCAAGCATTCCCTGCAAGT | 20573 AGACAGGCAGGCCTTGAACT | 31557 CCACTCTCTCCACCAAGCATTC | 42541 |
| 8916 CGTAGAATCTCTTCTGTATGGTGAGAGT | 20574 GGTGTAATCTAGCCTAACTTGACTGA | 31558 GCCTATGGGATTAGTTTTGAACGTAGA | 42542 |
| 8917 GGAGGTGAAGACTGAGGCACAA | 20575 CCAAGCTCCAAGATGACAAGCTCAA | 31559 TGCTATGACTTGGAGGTGAAGACT | 42543 |
| 8918 TCCACCCTCTTGCACCTTTCT | 20576 GGATCTGTGGCTCAAGCTCAGT | 31560 AGGCTGAGTTCCACCCTCTTG | 42544 |
| 8919 GTTTTGGAAAATGCAGCACTCAAG | 20577 AACTACAGCCCAAAGTGAGAAAATG | 31561 GCAGGTAATGGGTGGTTTTGGAA | 42545 |
| 8920 TTTCTCTTACCACCCAAGAAAGCAT | 20578 TCCTAAGGGCATCACTTTGACTTAC | 31562 CTGTAACTCTGCCCCTTTCTCTAC | 42546 |
| 8921 CCAGGAAGTGTTGAAGTGACTGAA | 20579 TCTCTGCTCTGCCCATGCTA | 31563 GGACTGTCAACCAGGAAGTGTTG | 42547 |
| 8922 GGGAAATCCAAGCCAGAGGTT | 20580 AGCCCTTAGGCAGTAGCCTTGT | 31564 GCACAGGAGACAAGCTGGGAAATC | 42548 |
| 8923 GGGGATAACCAAAGCTATTTGCAT | 20581 CCTCATGGCTGGGCCATTTAGT | 31565 GGAACAACAAGAGGGATAACCAAAG | 42549 |
| 8924 CCTTGCATCTGCATCCCTTAGA | 20582 TGTAACATGCCTCTGTCATAGCAA | 31566 GAGCACATTCCCCTTGCATCT | 42550 |
| 8925 CAGATGTTCAGGCACCTCTCA | 20583 ACTGGCTTGAATTCAGGGCTTTA | 31567 CGGAAGCACAGGGCATTTCAGA | 42551 |
| 8926 GGGGTTGGGGAAATATCCTGCTT | 20584 TGCTGTGGTTTATGAATCCATGTTC | 31568 ACCTGTGAAGGGGTTGGGGAAA | 42552 |
| 8927 GGGAGGTAGCCATTTGAACTAAGTCTTG | 20585 CTTGCACCTTCCAACCCCTATC | 31569 CCCTCAAACTAGGGAGGTAGCAT | 42553 |
| 8928 GCCACTCAAGCTAATCCTGAAATTGGAA | 20586 GGGTCACAGAGGCAGTGATGAT | 31570 GCTCAGTCAGCCACTCAAGCTA | 42554 |
| 8929 TGTCCTTTCCTACCCATGAATGAAAC | 20587 TGAGACTTGGTAAGCTATGGACTCT | 31571 CAAGTCATGCTGTCTTGTCCTTTCCTA | 42555 |
| 8930 GCATAGCATGAGAAATACCTTGCAGTT | 20588 CCTGGCTAGTAGGCACCTAAAAC | 31572 CTGCCTGCCATAGCATGAGAAATAC | 42556 |
| 8931 GGGAAAGTGTACCACGATTTGTTCAGA | 20589 TGTCCCACAGAGGACAGCTT | 31573 CCAGGGAAAGTGTACCACGAT | 42557 |
| 8932 CAGGGAACATAGTCAATGCCTGAGTTAAT | 20590 CCTGACTGATTGGTCATGTGGTCTT | 31574 TGAGTCAATCCAGGGAACATAGTCA | 42558 |
| 8933 CAGCTCCTTTGCCACAGCATA | 20591 GGACCCACCATAGTCAGAACTAAGA | 31575 ATGTGGTCCTCAGCTCCTTTG | 42559 |
| 8934 GGGGCCAAATGTGCTAATTGTTCA | 20592 TGGACAGAATCCAGTTTGATGGAA | 31576 CCCTGTTTTAATGGGGCCAAATG | 42560 |
| 8935 ACTTTACTCTGTCCTCACCCTAGT | 20593 GACTGGAGCACAGGTTACTTTACA | 31577 TTGTCCACTTCAGCACTTTACTCT | 42561 |
| 8936 GAGCAAGAATTACTGCCTCCAGATA | 20594 GTGCAGACAAGTTCACTGAGTAATTC | 31578 CTCAAGACGCCAAGAGCAAGA | 42562 |
| 8937 CCTGAAAAGCTGCTAGTGGATGTTG | 20595 GGATCTGTTGCAGAGCTTTCTTTTG | 31579 CAGGGTTGACCTGAAAAGCTGCTA | 42563 |
| 8938 CCCTCCCTTGCAATTTGATATAGTCCTAAG | 20596 TTACTTCCACTTACATTCCGTGACA | 31580 TTCACCCTCCCTTGCAATTTGA | 42564 |
| 8939 GGACATTGTGATTGACCGAACCTA | 20597 GAGCAAACTGGTAAGCTAATTCTT | 31581 CCCAAAAGAAAGCCTAGGACATTGTGA | 42565 |
| 8940 CTGTTGGGAGGGAGTTGGATGAA | 20598 GGAGGAGATCTGAAATAGGAAAGACAGTGCA | 31582 ACAGCCCTAGATGGCCCTGTT | 42566 |
| 8941 GTTACGCTCGGTGAAGAATGTTTAAG | 20599 GGAGAACTTAGGGAAGTCCAGTTG | 31583 CTCCAAGTTACGCTCGGTGAAG | 42567 |
| 8942 CTGTTTTCCTGGCCGGCATCT | 20600 GAGCAGTGACGCCCTCCATTT | 31584 CCCCTGCCTGAAATGCTGTTT | 42568 |
| 8943 TGTAACAAACATGGACCAGAACAGT | 20601 GGGAGCTCTGTTTTCACTGTGTTA | 31585 GGTCAGCTTGAGCTGTAACAAACA | 42569 |
| 8944 CTGAAGGCTTCCTGACTCCAGAAT | 20602 CACTGGGACAAGTAGCATGACA | 31586 CCAGAACTGGAACTGAGGCTTTC | 42570 |
| 8945 GGTGCCTTGCTGCATAGCATAGTAG | 20603 CTTCTAATGCAGGGGTTTTTGTCTT | 31587 AGAACGGTGCCTGCTGCATA | 42571 |
| 8946 GGTCTCCTTGATCTCTGACTACTCCTA | 20604 AGTGGGGTAAAACCTGTGTTTCT | 31588 TGGAGGGTCTGCTTGATCTCT | 42572 |
| 8947 GTGTGTCATGCTAAAGGGCTAATGGATA | 20605 GGTTGAGAGACAAGCCTTAGCAT | 31589 TCACCTGGGAGTAAAGTTGTGATG | 42573 |
| 8948 CAGAGGGCCTTAGCTCACTTCGTT | 20606 CTCCATTCTCAACTCATTCAACCTCTAAG | 31590 GCCCAGAAGAGAAGAGTATTTCAGA | 42574 |
| 8949 GGCTCAAGCAATCTTCCTGTCT | 20607 GGCATCTACTCTGTACTCCCAGCTAT | 31591 CAGTTCCTGGGCTCAAGCAATC | 42575 |
| 8950 GTTTCTGCTTTCAATGTCCAGACTTC | 20608 GGTGATTGACACACTGAGGATCCAA | 31592 GGTATGGCATCAGTTTCTGCTTTCA | 42576 |
| 8951 TCCCCACAATCTCCCTGGTACT | 20609 CCCTACTACCCCGATTAATAATAC | 31593 GCTACAAATGAGTTTTCCCCACAATCT | 42577 |
| 8952 GCTTCCAGTGTGGGGATCTGA | 20610 CCAACACAGGGAAAGGTTAAGTGA | 31594 CAGGGATTGCATCGTTCCAGTGT | 42578 |
| 8953 GCTCCAATTTCTGAGCTGGAAAAGTC | 20611 GCAAACAGGAACACCTGGTTGTCT | 31595 GCTTGGAATGACCTGCTCCATTTTC | 42579 |
| 8954 GAGTGAGAGAATCCAAGAGGACAAG | 20612 GTCTGTTCTCAAACCTTCCTTCTGT | 31596 GGCCAAGGGAGTGAGAGAATCCAA | 42580 |
| 8955 CCACCAACAGAGGACATCAGAACT | 20613 CACAACACAGGCTAAGAAAACCTAATG | 31597 GGCAATGAAGAATACCACCAACAGA | 42581 |
| 8956 GGTGGGGACATCATTTCTGACCAGTAG | 20614 GGAGTTGGCAGGAGCATCAGA | 31598 GACATGACCTGGTGGGGACATCA | 42582 |
| 8957 CGCTTCATCCCATTGGCCTACA | 20615 GGGACCTTTTGAGGCTTGCAGTTC | 31599 ATGCCTGGGAGCGCTTCATC | 42583 |
| 8958 GTATTGACAGGTGCTTCTGCCTTCTA | 20616 CAGAGGCAAATGAAATGAGCTGTTAG | 31600 GGGCCTTCAACTATTGACAGGTCTTC | 42584 |
| 8959 TGCTTATGGTCCCAGCTCTTG | 20617 AGCACAAAGCACTTGGTCAGA | 31601 CAGACAGAGGGAGGTGCTTATG | 42585 |
| 8960 GACTGACAGGCAGAATACCTGTGT | 20618 CCACAGACCCTGACCCAATGATG | 31602 AGGTGGACTGACAGGCAGAA | 42586 |
| 8961 CTGAACCCTGCTCTACCCATTAAGAAG | 20619 GGAAGTTAACTGGAGAGCATAG | 31603 ACTACTGAACCCTGCTCTACA | 42587 |
| 8962 GCAGATGGACTACCATGCCTTGTT | 20620 GCCCATGTTGAGATAATGGCTACCTT | 31604 GGGGCCAGATCCTGCATTG | 42588 |
| 8963 GGAAGCATCACAGCAGGACTGTA | 20621 AGGATGGGGAAGCTAGAAGTCAA | 31605 GGACTGACTCCATACTGTCAAGGAA | 42589 |
| 8964 AGGATCCTGCTAGCTGCTGAAT | 20622 CATTGGCTTGACCCCACTAAGA | 31606 CCTGGAGTGTAGGGCTGTAGGAT | 42590 |
| 8965 GCAAAAACCAATCATGCCCAAAAC | 20623 GGGGAGGCAATGAAGAAAAGCCTAA | 31607 GCCCATCCTACAGCCTAGCAAA | 42591 |
| 8966 CGGGGACCAAATTTACAGGGACAA | 20624 TGCCCAATGTCCAATGTCTTGA | 31608 AGATGGAGTAACGGGACCAA | 42592 |
| 8967 CCCGGGAGGGTCTTAGAGTTTGT | 20625 GAGTCTGTCTTCCTTGCCTCTCA | 31609 ATGGTGCCCGGGAGGGTCTT | 42593 |

FIG. 36N8

| | | | |
|---|---|---|---|
| 8968 CCCCTGCTTCATGGGCTCAAA | 20626 TGAAAGGCATGCAAACAGTCTTC | 31610 TGGGTACTGCCCCTGCTTCAT | 42594 |
| 8969 ACCACATCCAGCTCACAGA | 20627 GGTGGGAGCTTCTCTTTAACTTTTC | 31611 GACCACACACTCTACACCACAT | 42595 |
| 8970 GGGCATTAATGAGCACATTCCTTTTC | 20628 GCTTCCAACGTCCCTATCTTAGTGT | 31612 GGCCCCAGTAAAAACAGTGGGCATT | 42596 |
| 8971 GTTGTTGGCTCAGTCAATGAGAAG | 20629 GCCATTGACATGTCTGGCTGAAG | 31613 GCCTGGGCAGGTCATGTGTT | 42597 |
| 8972 CGGCTCTGATTCTAATCCCACTATTAC | 20630 GCCTTTGACTTTGGTGTGAACCTA | 31614 AGGGGATCGCTCTGATTCT | 42598 |
| 8973 GGCTACTGGTCTCAGACAAAGATAC | 20631 CTGGTCAGCTATTTTCCACTGGATATG | 31615 ACAGGGTGCCTACTGGTCTCA | 42599 |
| 8974 GCCTGAAGGTGAGACAATCAGAAA | 20632 TGAAAAAGTGGCCTCTAGTGTGT | 31616 GCTTAACTTTGCCTGAACGTGAGA | 42600 |
| 8975 AGTGGGGTATGCCTGCAGTTG | 20633 GGGAGAGAGAGTTTGTGTCTGTTC | 31617 AAAGCAGACTCAGTGGGGTATG | 42601 |
| 8976 GTGTCGACTCGAAGAGGATTGTTGA | 20634 CCACTACCAGCAGGCAACCTT | 31618 CACCATGTGTGTGGACTCGAA | 42602 |
| 8977 GAGCACGATCCTGAACAGGTTA | 20635 CCTGGAATAAACTTTGCCCAGACA | 31619 GCAGGTGACATTTGAGCACGAT | 42603 |
| 8978 AGTCAGTCTGGCCCAGCAGTA | 20636 CTCAATCCTGGACTACAATTTCTGTCT | 31620 CTCACCAAGGCATAAAGTCAGTCT | 42604 |
| 8979 CCACCTGCCAAATGCAGTTAAAGT | 20637 AATCTGCTCCTTTCCTGGTCTTC | 31621 TGGACTCCACCTGGCAAATG | 42605 |
| 8980 GGGGTAATACGGCTTAGGAGGAACA | 20638 GACACTCAAAAGGCTAAGGCTAAC | 31622 CCAGGAAGGGGTAATAGGGCTTA | 42606 |
| 8981 ACAGGGCTGAGACCAGCACAT | 20639 CACAGTGGACACATGACTCAGA | 31623 AAGGGGAACACAGGGCTGAGA | 42607 |
| 8982 CACTGCTAGTACAGGTTGTAAATTGGTATG | 20640 GAAATGGTGCTAACTTGCTCTCCAA | 31624 CTCATTCACTGCTAGTACAGGTTGT | 42608 |
| 8983 GGTGCTGACTCCAACTACTGAAAC | 20641 GGCTGCCCCTGTCAATGATGA | 31625 CTTGTGTAGGTGCTGACTCCAA | 42609 |
| 8984 CTTGGCTGCTGATTGGAATTGTT | 20642 GGGTCAGCTGCAGATTATGTCATT | 31626 GCCCCTACTTGGCTGCTGATT | 42610 |
| 8985 CCAGCCAGTAAAGCCTTGTATGA | 20643 CAAGGCGAGAAGGTGGGAGACA | 31627 CCAAATGCTTTTCCAGCCAGTAAAG | 42611 |
| 8986 GCTCCTTCATTCCCTTGGCAAGTA | 20644 AGTCCAAAACCGTGACAAGACA | 31628 CAGCTGTCAATGAATGGCTCCTT | 42612 |
| 8987 GGAAGGCATCCTGGGGCTCTAAG | 20645 ACCGGACTTTGCTCCAGTCATC | 31629 CCTCGAGGGGAAGGCATCT | 42613 |
| 8988 AGGGCATCCTCGAGCCAAAT | 20646 GACACTTCTGGTTGCCACATACA | 31630 AAGCACCTGTGACTTTGTCTGA | 42614 |
| 8989 GGATGTATCCAGATGGTGTGTGAAAG | 20647 GCTCACACACAGTCCCAAACGTA | 31631 GGTTGGAGGAGAGTGTGGATGT | 42615 |
| 8990 GGGACTAGTGTACCTTCTGGCTA | 20648 GTGGTCATTTGCCAAGGCTCTA | 31632 TGGGGCTGTGGGACTAGTGT | 42616 |
| 8991 GGACGTGGTTTGCTAAGGTGTT | 20649 GTCACACCCTTCATTCTCCCATCT | 31633 GTGGTGACAGGACGTGGTTT | 42617 |
| 8992 ACTGTGTCCCCTGGCACCTA | 20650 GTGGTCAATGTTAGGGGTTCAGTCT | 31634 ATCCGAACTAACCATTCACTGTGT | 42618 |
| 8993 GGCAGGATCTGCCAGCAAAA | 20651 TTTGCAGCGCAGCCTCAGCTT | 31635 TCTCTCACAGTGGGCAGGAT | 42619 |
| 8994 GTCCTTCCTGTCTGCTCTTGGTA | 20652 CCTGGTTAAAGGAAGAGTGAGTCTCAGAA | 31636 GCTGCAGTAGTCCTTCCTGTCT | 42620 |
| 8995 CCCAGACATACCAGTGAGCGTTGA | 20653 GGCTAGGAAAAACCCACATTCAACA | 31637 CCAGGCAACTTTCCCAGACA | 42621 |
| 8996 GTTGAAGCCAGATCATGGAAGACT | 20654 GCTTACCAAATAAAGTCTTCACCCCTTAG | 31638 CCAAAAGTGGGGTGAAGCCAGATCA | 42622 |
| 8997 TCTGGAAAGCAGTACAGCATCTTT | 20655 CGAATGTCCCACTACTTATGGTGAA | 31639 TGCCTGCACATCAGTGATTCT | 42623 |
| 8998 CAAGATCTCTGCTATTCGTGTTTG | 20656 CCTTGAATGATGCTAATCCTGAGCGAAA | 31640 GTGGCTATTAATCAAGATCTCGTGCTA | 42624 |
| 8999 CCATCTGCCATGATAGTATTCTGTCT | 20657 GGTTTTGTGACTGGAGGAACCAAAATG | 31641 CTGCCTCCCATCTGCCATGATA | 42625 |
| 9000 CGGTGTTTGGGGTCCCATGTAT | 20658 CCTAGCAGTAGCAATTACAACCATCT | 31642 AAAAGCCCCAGCGGTGTTTG | 42626 |
| 9001 GGCTTTGTTAGGACAGACCCAGTTC | 20659 GAGGGAAAGAGCACTAGACTTC | 31643 GCACAGTACTGGGCTTTGTT | 42627 |
| 9002 CCTGGCCCTGTATTAGCTGTGGAT | 20660 CTGGACAAAAGGACTACATAGCAGAATTAGA | 31644 CAGACAGTATTCCTGGCCCTGTA | 42628 |
| 9003 CCTCCAGCCTGCCTCATAC | 20661 TGCAGGCCTGGACCCTGAT | 31645 CAGGCTGCTACCTACCGATTGA | 42629 |
| 9004 GGGGAGAAAACATTCCACCCATAAGATA | 20662 GCCTTCTGTGTCAACCAGTGT | 31646 CCTCTTTAGGTTTTGGGGAGAAAACA | 42630 |
| 9005 GTCAAAGCCAGGAGCCATGAGA | 20663 AGCAGTGCAAAACAGACTAAGGTAT | 31647 CCCAGCCAGGAACTTTGTCA | 42631 |
| 9006 TGTCATATGAGCACACAGTGTTTGA | 20664 AGATGGTGTCTTGAATGCTGCTT | 31648 TTTTGCCCTTCTGTCCCTTATGT | 42632 |
| 9007 GGACATTATATGTCAGGGAGTGCAA | 20665 GGTGTTGGGTGTGTGGGATCAA | 31649 GCTTGCTCACAGGGTGGACATT | 42633 |
| 9008 GAGAGGCAGGTGTGAGAAATCATTG | 20666 ACGTGGTCAAGGCCATGTGT | 31650 TGATCAGAGAGCAGGTGTGA | 42634 |
| 9009 CCCATCTTTGTGTGGAAAGTTAGTGA | 20667 GCTTGTGGCCAGGGAAAGGTT | 31651 GCATCTCAGTCTCCCATCTTTGT | 42635 |
| 9010 GTCCAGCTGTTCATGGAGTCAAC | 20668 TCCCCTCAGGCCTGGTGAT | 31652 CAGGGGATTTGAGTCCAGCTGTTCA | 42636 |
| 9011 TCAGGTTAGTGGGTTCCCTTCT | 20669 GACCCTAGGTCTTGGATGACATTT | 31653 GGCTTGGTTTTTCACTTCAGGTTAG | 42637 |
| 9012 CCTTAGCAACACCAAGGAACAAAG | 20670 CTGGCAGGCAACAGCAAATG | 31654 GGACATCCTCCCTAGCAACACCAA | 42638 |
| 9013 GGAAAGAATACGGTAGGAGCGTTCTCT | 20671 AGTGGTTGGCAGATTGTCTGAAG | 31655 GGAACTCAGACCCTATGGAAAG | 42639 |
| 9014 TGGCAGAGAAAGTCTGAGAGTAAATG | 20672 GGTTGGTGAGGGACAAAGTGTAG | 31656 CCTTCTATTGGCAGAGAAAGTCTGA | 42640 |
| 9015 ACCCTCTCATAACCTCACTTGACA | 20673 GGAAGCCATTTGGGGCTCCTT | 31657 GACAGGTTGCTTGAAATACCCTCTCA | 42641 |
| 9016 GGGCAGGTAGCATCTACAGCAA | 20674 TGTCCTGCCTGGGAGTGAAA | 31658 GTGACTGATGGGCAGGTAGCAT | 42642 |
| 9017 GGCCAACACACCAAGAAGTGCTTA | 20675 CACAGGGAGGTCTTGCACATCA | 31659 GGGAGAGGCCAACAGACCAA | 42643 |
| 9018 CCAGGAGCTCTAGGATGAACTGAA | 20676 GGGCAACCAACATCCACTCAGA | 31660 GCTCCAGGGAGCTCTAGGAT | 42644 |
| 9019 GGAAGTGGGTCTTTGAAGAGATCATGT | 20677 GTCCATCATTCAGCGCTTCT | 31661 GGGCAAGGAAGTGGGTCTTTGA | 42645 |
| 9020 GCTGCCAGGATGAAACCAGAGA | 20678 GCCCTCCTCTGGGTAAAACCTACT | 31662 TGCAGGACTGCTGCCAGGAT | 42646 |
| 9021 GTTTGGTGTTTAATGGGCGATAG | 20679 GGTGTTACTGGGGAAAAGCTAGT | 31663 GCTGTGGCAGGTTTGGTGTT | 42647 |
| 9022 GTTCAGTGGAAAACTGATGCAACT | 20680 GGATCTGAGTCCTTGCAGGTGAT | 31664 GCACTCCCAAGTCCAGTTCTAAAG | 42648 |
| 9023 CCCATCTTTCTGGCTCATTCTATCT | 20681 GTCCGCCATGCGTGAAGTGATG | 31665 CTTTCCACCCACTTCCCATCTTTCT | 42649 |
| 9024 GCTTTAGGACCAAGTTGCTGAATTG | 20682 GGCTGCTCGTTTTAATGAGATGT | 31666 CTGGAGTAAAATGCTTTAGGACCAAGT | 42650 |
| 9025 GGGGCTCAAACAGGTAAAGTT | 20683 GTGTCCTCAGGCCAGACTACTCTAA | 31667 AGGTAAGAAAATTGGGGCTCAAACA | 42651 |
| 9026 CCCAGCAAAGCCATGCTACAGT | 20684 TCCGCTAGTGCTTCAGTAGTCT | 31668 AGCAACCCCTATCCCCAGCAA | 42652 |
| 9027 GCCTGAAACAACCAAATACCAGGAAA | 20685 CTGGTTCTAGTGTCTTGAAAACTGTTG | 31669 CCCTCCTGCCTGAAACAACCAA | 42653 |
| 9028 CACCCTGGAACCTATGGGAAGAATG | 20686 TCAACGGGCTGCCTTCTCTT | 31670 GGGTTGTTCACCCTGGAACCTA | 42654 |
| 9029 AACCTGCAGAAGCACATCGGT | 20687 GCACCTGACTTTGCACATTG | 31671 GAGGGGACTTTAAACCTGCAGAA | 42655 |
| 9030 CAAGTTAAGTAGTGTAGAAATCGGGAGTAG | 20688 GCACCCTCTAGCATGCTTTTGTCA | 31672 GGTGAAGTCTATGCTGACCAAGTT | 42656 |
| 9031 CCCAGACCTTATCCTGTAGCTGAATG | 20689 GCAGAAGAAAGCACAGGATTTGCATAG | 31673 GCTTTAACTTGCCTCCCAGACCT | 42657 |
| 9032 AGGTAGCCTCTTGGCATCTGT | 20690 CGGGCCTTTAAGGAAACCAGGAA | 31674 CCATCTACAGACACTAAGGTAGCCTCTT | 42658 |

FIG. 36N9

| | | | |
|---|---|---|---|
| 9033 GGGCCTCAGAAAACTACTGGAACT | 20691 TGGTGGTGTGGTGGGTCTAT | 31675 CCCTCTCTTGGGCCTCAGAAAACT | 42659 |
| 9034 GAAAGGCATAAACCCCACAAGCTA | 20692 CCACCACAGGCTCCTTTTCACT | 31676 GACTGATGATGCAAGAAAGGCATAAAC | 42660 |
| 9035 TGCAAGGTCGATCGAGTGAT | 20693 GTCCAGAATCCCAGAACTGTCAGA | 31677 CCCCAGCTGTATGTTGCAAGGTT | 42661 |
| 9036 GGAAGAGCTGGATCAGAGGGATGATAA | 20694 GGAGGAGCTGCATCCATCTTTTC | 31678 CCAGAGGGAAGCAGTTGGAAGA | 42662 |
| 9037 CTGGGATAGATGGTGTCCGACTT | 20695 CCCTCCTGAAAAATAATGCTTACCCCATT | 31679 TTTGAAATGGCAGTGTCTGGCATA | 42663 |
| 9038 GGCCCTACTGAAACAGGAGAGTT | 20696 CCACAGCCCTGTCGCATGT | 31680 GCAAATCCTGGCCCTACTGAAAC | 42664 |
| 9039 GCCTATCGGCTGGTAGGATGAA | 20697 TGGTGTGGTGCTTGGCTCTTC | 31681 CACCTGGGCCTGAACATCAA | 42665 |
| 9040 GCCATACATAAACAAGCACACAATC | 20698 CCCCTGCCCAAGTATTTTAAAGCAA | 31682 CACTGAAGCCAAAAGCCATACACA | 42666 |
| 9041 GGCGCAGATACAGCGGACTTA | 20699 CCATTGCTCTCTTCAGATCCAGTAG | 31683 GGCTGTGGGCGCAGATACA | 42667 |
| 9042 GGGAAGACAGAGATATGTGACCGTTT | 20700 CAGGTTGCCCATTACAGCTATTTTGA | 31684 CAAGAATCCTATCCTGGGAAGACAGA | 42668 |
| 9043 GGGCAGCTTGAAGGAATGTGGAA | 20701 CCAGTCACAAGTGAGCCTTCTT | 31685 TCCACATGGGGCAGCTTGAA | 42669 |
| 9044 AGCTTGTGTGGCAGGTGTGT | 20702 ACACGTGTCAGTCACATCACATA | 31686 ACGGGTGTGGAGCTTGTGT | 42670 |
| 9045 TGTCCCTTTTCCTTGGCCTGT | 20703 GCAGTACCCATGATTGCTTTTCAAG | 31687 CCACAATGTCCTTTGTCCCTTTTC | 42671 |
| 9046 GCTGTTTCTTCTGGCAACAAAGTTTC | 20704 TGAAGCTGGGGACACTGAATTTG | 31688 CTGAGGATGGGAAGCTGTTTCTTCT | 42672 |
| 9047 GGCCCTCCATTCGAAAGTCAAC | 20705 GCAAAAGTAGGGCCAGTCAAGACA | 31689 GTTATCATTCTTTGGCCCTCCATTC | 42673 |
| 9048 GCCCAGACACCTATTGACTGGAAA | 20706 TGCCAGGCCATCTTGCCTTT | 31690 GGGGCAATATAGTAGCCCAGACA | 42674 |
| 9049 GCCCATGCACTGATGACTCCAA | 20707 GATGTGCAGCCTAGGAAAGAAGA | 31691 ACCTACTGCCATCCACTGA | 42675 |
| 9050 CTGATTCCAGAGCTTGGGGAGAA | 20708 CCCAGACCCCTGCTCCAAA | 31692 CTGGTCACAGCAACCTCTGATTC | 42676 |
| 9051 GGGGCCCATTTCAGCATTAGAACTCATC | 20709 CCAAAGGTAGGCTAGGCCACAA | 31693 CTCTGGGCCCATTCAGCATT | 42677 |
| 9052 CACAGGGAATCCAGAGCCACTATG | 20710 GACAAGTATTTAGCTGTAGGGAAGAGA | 31694 TGACATTGCCATCTTCACAGGAAT | 42678 |
| 9053 GACTGATTCATTGTGTTCCCGAGTT | 20711 GGGGTGCATCTGTGTCTGTGT | 31695 GGCAGTTTCATTTAAGGCTGACTGATTC | 42679 |
| 9054 AGCCCTACCAATGCATTCATTCAA | 20712 GGACCAAAATCTGTTAGGTACTCAGGAA | 31696 GCCTGTCCAAGCCCTACCAAT | 42680 |
| 9055 GGAGAAGTTATTGCTCCAAGGTGAT | 20713 GATCTGAATTGAAATCCCAGCTCTTTC | 31697 ACCGAGGTTCAGAGAGGACAAG | 42681 |
| 9056 CCTGCTTTTGGCATGGTCTTC | 20714 GGACACCAAATTTTAGGTCAGCATTTGACT | 31698 GGTCTTGCTTATCCTGCTTTTG | 42682 |
| 9057 GTCCTGTGGTCCAAGTTCAACTCTT | 20715 AGCTAGCTGTGTGGGTGTTG | 31699 CCCATGTGAGTCCTTGTGGTCCAA | 42683 |
| 9058 CAAGTGGGCATTTGGGGTCTCT | 20716 GGGTCCAACATGTCTGTCCAA | 31700 CCACAGTGGGTTAGAGCATCAA | 42684 |
| 9059 AGTTGCTGAACTAAGGCAGCTATTT | 20717 CTGCAAACATAGTCGGAGGTATAAGAAG | 31701 CTGGCATGGATTGTAGTTGCTGAAC | 42685 |
| 9060 GGGAAACCCCACCTAAGTCACTTTC | 20718 GGGTACCGTGATTGCCTCCATT | 31702 CTTCTGGGGAAACCCCACCTAA | 42686 |
| 9061 GGCTGGTTTGGTGTTTTCCTTTC | 20719 CCCTCCATCATAAGGTGAGCTTT | 31703 ATGTGAGGGAGGGGCTGGTTT | 42687 |
| 9062 CAGTGAGGGAAATTTGCTGTGTAG | 20720 GCCACCACCATGATGATGCAA | 31704 AGTCCAACAAACAGTGAGGGAA | 42688 |
| 9063 GCTGTTAAAACCAGATGACCCAAAC | 20721 CGCTCATGGTCACAGTGGTACA | 31705 CAGAACACCAGGACTTTCTTCCTGTTA | 42689 |
| 9064 GGAACATCTGAAGATCATGTTCTTGT | 20722 CACCAGTAAGACACTCCCTGAGAT | 31706 TCATGCCCACCTTGGAACATC | 42690 |
| 9065 TCTTGGTGTAATGGGGTAGGTCTAAT | 20723 CATCCTTGCTTCCTGTTAGAGACT | 31707 GGGAGGTGAGGGTCTTGGTGTAA | 42691 |
| 9066 GAGGCAACCAACAACCCTTTG | 20724 AAGGTCAGCAGGGGCAGAACT | 31708 GTGCTTCCAGAGGCAACCAA | 42692 |
| 9067 CCAGATGTGGTTTCATTCTGTGAGCAA | 20725 GAGTAGCTGCGTATCAGTACCAA | 31709 GCTGCAAATCTGTCCAGATGTGGTTTCATTC | 42693 |
| 9068 TCTGGGATGGGGAAAGGATATTAGT | 20726 CGGGCCCGGTCATGAGATAAA | 31710 GCTCCATTCTGGGATGGGGAAA | 42694 |
| 9069 CAACCCTGGCTCTCCTTCCAAA | 20727 TCCAACCACTACCACCCAAGA | 31711 GTCTGAAGCTTGGTGCTTACAAC | 42695 |
| 9070 GTATGCCAACTCAAGACCAAGAGA | 20728 GGCACACGAGCATTCTGTCTCTA | 31712 CGGGGAGTAGACCTGCTTGTAT | 42696 |
| 9071 GACTGGGACTTCTACTTTCACTGGAAAC | 20729 GCCATTGTCTGCCTCAGAAGTGTT | 31713 GACCTTTGATGGACTGGACTTCTAC | 42697 |
| 9072 TTTCGATTGGCCCCTGGCTCTA | 20730 GCACTAGAGCAGGGCTTTCTTC | 31714 CCAATCAGGTCTGTGTTCGATTG | 42698 |
| 9073 GAACTACCACTGCTAGCATCTCAACT | 20731 GGGGTATACAAAGGTAGTGAGGCATGA | 31715 GTGCCATTACAATGTAACTACCACTGT | 42699 |
| 9074 TGGCTTGCTTGAGCCCATATT | 20732 CCAGCCCAACAAAGCCCAGATT | 31716 CGCTGTATGAATGGCTTGCTTGA | 42700 |
| 9075 GTTTGCACTCAGTTGCACATACTT | 20733 CTCACCCTTGATCAGCTCCCATTC | 31717 GGGATAGAGGGTTTCCACTGACTT | 42701 |
| 9076 GAGGGCAGAAATGGAAATCAACTCT | 20734 GCCACTGGAACTCAGAAGAGTCAA | 31718 GACAAAAGGCTAAGAGGGACAAATG | 42702 |
| 9077 CCAGGCTAGAAAGGCCTGGTAA | 20735 CTCTGGTTCCTCCTGCAACCATT | 31719 AGGGTGGCCAGGCTAGAAA | 42703 |
| 9078 CATGTAGGCTTCCTGTCCCTATAC | 20736 GTGGTTATCCAGAGAGGTGGAACA | 31720 CCCTTTGTCCAGCCCCAACAT | 42704 |
| 9079 GGCAAAAGAAAGCAAGATGCCTATG | 20737 CCCAGCTCCAGTGGATGAAG | 31721 GGGAAGGCAAATCTCTGGCAAA | 42705 |
| 9080 GTCTACCCAGTGCTGCAGTTTC | 20738 CCTGCCCTTGTCCCAACAATGTT | 31722 CCAGGGATATGGGCTCTGTCTAC | 42706 |
| 9081 GCAAGGAAATACACTGTCACTACTCCTA | 20739 GCACTGGCTAGGACTTCCAGTATG | 31723 GGGAAGAAGGCAAGGAAATACACT | 42707 |
| 9082 GGGCCAAATTTCAAAGTCAGATGGAT | 20740 TTTCCCGCTATATCTGTGCAAGT | 31724 CCAGGGACCTAGGGGCAAATTTCA | 42708 |
| 9083 CCAACTCTGCTTTGGAAGTCTGTTA | 20741 GGAAGAAGGCATCCCATTTGAAACA | 31725 CGCTTCCTTTACACTTCCAACTCTGCTT | 42709 |
| 9084 CTGTCAGCTCACGAGTGTGTTT | 20742 CACCCAGGTCCTAATATAACATGA | 31726 GGACTTTCTAATATGTGTCGGCTCTGT | 42710 |
| 9085 CCCAGGAAGAAGCAGAGGTAGTTG | 20743 CAAGATAAGTGCCATGGTTGTCTCA | 31727 CTTTAGTAAAAACAGCCCAGGAAGAAG | 42711 |
| 9086 GACTTGGTCATAAAAATCTCTCCTGCAT | 20744 AGTTGCACAGAGAAAGTGTTTG | 31728 GATGTGTGCAGACTTGGTCCAT | 42712 |
| 9087 GGGGCAAATTAGGCTGACCTTTG | 20745 GTCTGTGCAGAATAAGCCCAAACT | 31729 CTGGAGGGGAGAGGGGCAAATTA | 42713 |
| 9088 CAGTCTCCTTTGCCATTCTGCTACA | 20746 ACCAGGCAGGCTTTGCTGAA | 31730 GACTGTGCATTCAGTCTCCTTTG | 42714 |
| 9089 ACACCATAGGTAGGGCTCACA | 20747 TCATCCTCCCAAGTCGACTGT | 31731 GAGTCCTGTCATCCTAACACCATAG | 42715 |
| 9090 TCTGTTGCCTCAGCTCTTTTCA | 20748 TGTCAGAACCTTGTTGAGTTGTGA | 31732 AGGCTTTTCTCTCCCTCTGTTC | 42716 |
| 9091 ACTTGGCAGTTGGTAGGTGTCTTTAG | 20749 GACTCAACCATCTGCTGCCTAAAATAG | 31733 CCACCCCTTTACTTGGCAGTTGGTA | 42717 |
| 9092 GCAATGCGCAGAGAAGGTAGTCT | 20750 TGCTGGGGAGTTAAAGGAAATTGT | 31734 CTCAGTGGAGATGAGTTTGCAATG | 42718 |
| 9093 GTGGGGAGACTCTAGACTGGAT | 20751 CAGGACCACAATTGATGCCATTT | 31735 GGTGACTGAGAGTGGGGAGACT | 42719 |
| 9094 ACCGTGTCGCATGGTCTCT | 20752 AGTAGGACAGAGGGTTCTATGCAT | 31736 TCCTGGTGCTGCCTGGAAC | 42720 |
| 9095 GAGGAAGAGCAAGATGGCAGAA | 20753 AACTTGGTGTCTTCTGGGGTTA | 31737 CCAGAGACAGGAGGAAGACAA | 42721 |
| 9096 GTCAGAACCAGGTATCACTGAGCTA | 20754 GGGGTGGCAATAGGAGCACTTT | 31738 CCTCACTGAAGTCAGAACCAGGTA | 42722 |
| 9097 TCCGAAAAGCCATTGTGTTTACCTA | 20755 CATGCCAAGCTGTGCTGACT | 31739 ACAGGTCCGAAAAGCCATTGT | 42723 |

| | | | |
|---|---|---|---|
| 9163 TGGCAGCACTACCTGAGAGT | 20821 CACCAGTTCCCATGGAAAACCATAAG | 31805 GCAGAGTTGTGGCAGCACTA | 42789 |
| 9164 GCCCCTTAGGTAACTGCTGATAG | 20822 CCTATTTGCTTCCATCCTCCTAGTAGATTT | 31806 GATTATCTGGATGCCCCTTAGGTAAC | 42790 |
| 9165 TGCTCTCTGAATTGACTCACTGTT | 20823 GCCTTTTGGTAACCCAGACAAAG | 31807 GCTTTCTATGGCTGATGCTCTCT | 42791 |
| 9166 TTGATCACCATCACTCTGCATGT | 20824 TGCCTCATGCCTGGACTAATTT | 31808 CTGCTGGGTGTTTGATCACCAT | 42792 |
| 9167 CCTGCTCAAACTGATTTCTCACTCTCT | 20825 CGAAGGTAAGACTCTGGCAAGTGAAG | 31809 GCCACATCCACACCTGCTCAA | 42793 |
| 9168 GAGGTGCCTGTTTCCTTTCTGGAT | 20826 GGAGCAGCCTCAAGGACCTTAT | 31810 TGTGTAGACAGAGGTGCCTGTT | 42794 |
| 9169 CCCTTTCGACTCTCAAAACTTCCTTAC | 20827 GCAGCTGTTATATGTACCTCTGTACT | 31811 GCCACCTCAATACCCTTTCGACTCT | 42795 |
| 9170 TCCTCCCAGAAACCTGGTGCTT | 20828 AAGGACAGGGTAGCABAGTGTAG | 31812 TCCACTTCCTCCTCCCAGAAAC | 42796 |
| 9171 GCCTGCCACCATTTCATGGTTA | 20829 TTTCTGTAACCCAGGAGTCTCA | 31813 GCTAAAAAGTTAGCCTGCCACCAT | 42797 |
| 9172 CTGTGACACCAAAGGCAGAAACA | 20830 TGGGATATTGGCCTGAAGTTTTCTT | 31814 CGGCATCACTGTGACACCAAAG | 42798 |
| 9173 GGTCGGAATGATGACCCCTGTT | 20831 AGGCATCAAATACCTCTGTGCTT | 31815 CCTTTATGTAAGCAGGGTCGGAATGC | 42799 |
| 9174 GAGCATTCCAGCAGAGGTCAGT | 20832 CACCATAGCAGTAGTGCTGGTCTA | 31816 GAGATGGGCCACAGAGCATTC | 42800 |
| 9175 CCAGGAGCCAGACTTGAGAATCA | 20833 GCCTCATTGCACCTTTTCTCCTGTA | 31817 GTGTGTTTCCAGGAGCCAGACT | 42801 |
| 9176 GGGTAGAAGCCATTGGTATAGTTCA | 20834 GGGCAAGGAGAGGGGTGTTTTA | 31818 ACTCCGATGGGTAGAAGCCATT | 42802 |
| 9177 GTGCCAGTCCTTGTGTTAGGTTCT | 20835 GCAGCCTCTGTAACAGGGTTTGAT | 31819 GACTAACTACTCTGTGCCAGTCCTT | 42803 |
| 9178 ACCAGCCTCTGTACCCGCAAT | 20836 GGCTTCCTTTACTGGACCTACTTTC | 31820 AGATGGCACCAGCCTCTGT | 42804 |
| 9179 GCTCTGGGATCATCACACAACA | 20837 CCCACTGGTTCTGGCTCTTTGT | 31821 GACTTGGCAAGCTCTGGGATCAT | 42805 |
| 9180 TGACCCTTCTGTTTCCAACAGTTA | 20838 CTCAGCTTAAAAACCAGTGTCCTAGA | 31822 CTCATGTAGCATGACCCTTCTGT | 42806 |
| 9181 CCTCTCTGTACTTTTGCACTCACTGT | 20839 CAGAGAGGAGCAGGACATTCCATAC | 31823 AGTGGTTCGCCTCTCTGTACTT | 42807 |
| 9182 CCTCCCCTCTCACACAGGAAGA | 20840 GGCCAAGGCACCTTCTCATTGT | 31824 TCCCTTCTCCTCCCCTCTCA | 42808 |
| 9183 CACATTTCCCAAACCAGACTGTAGAGA | 20841 AGGTTCCAGGCTGCAGTGA | 31825 AGACAGGGTCTCGTCACATTTC | 42809 |
| 9184 GATTCCAGCAGCATGAACAGACA | 20842 GCTCTGCGTTCCCCGGAAGT | 31826 GGCCTTGGTTGATTCCAGCAGCAT | 42810 |
| 9185 GGAAAGGGTACTGGGATTTTTGTTTAG | 20843 CATTCTGAAAGTAGGGAGGGACTAAG | 31827 GCTAAATAAGGAAAGGGTACTGGGATT | 42811 |
| 9186 CCTGAGCTAGCCTTTCCACACT | 20844 CACCTTCCCAAATGAGGACAT | 31828 TGGGCATGAACCCTGAGCTA | 42812 |
| 9187 CCCTCAGGTTTGGGAATAGTCATC | 20845 TCAGGCCCTAGGTTCAGTCTGT | 31829 GATCTTCGGTCCCTCAGGTTTG | 42813 |
| 9188 GTCGTCACTACAAGGGGCTCAA | 20846 GGGGTCTGCTCTGGGGAACAATC | 31830 GGGCTTCGATCTTTGTCGTCACT | 42814 |
| 9189 TGGGGTCCTCACAAGGAAATGT | 20847 AGAACAGAACTCACTGGAATGACAA | 31831 GTGGGCGCTTTTGCTTCTTG | 42815 |
| 9190 GTAGAAGACTACTGCTCTGGCAAA | 20848 CTGACTGTATGTGACTGACTGGAATTG | 31832 TCCGGGCAGGGAGTAGAAGACTA | 42816 |
| 9191 GAGCTGGGAATTTGGTGGTTTG | 20849 CATCGAAGTGGCAGGAAATGAAG | 31833 GAAGGCTAAATGAGCTGGGAATTTG | 42817 |
| 9192 CACCACAGGTTTCTTGCCAATC | 20850 GACAAGTCCAGCTCAGAGAATGAA | 31834 TGAGATGCTTATCACCACAGGTTTC | 42818 |
| 9193 CCCTGGAGGTCAGACAGAGAAGT | 20851 CCTTGACTGACAGGTAACTCACAAA | 31835 ACATGCACCCTGGAGGTCAGA | 42819 |
| 9194 GAGGAGTGTGGTGGTTGGAAA | 20852 TCTGAAGAACACCTCAGTGTTG | 31836 GGCTGTGCGACGAGGAGTGT | 42820 |
| 9195 TGTGCTGCCTGACACTTTG | 20853 TTCTCCAAAGAGGATTCTGCTCTAC | 31837 TGGCATCCCTTGCAGTCTGT | 42821 |
| 9196 CTCTCCAGGTACAACCCCAGTA | 20854 GAGCTCAGCACTGGATGAGACTTA | 31838 GCACTCCCTCTCCAGGTACA | 42822 |
| 9197 CCGTCTTCAAAGCCAATGCTAAG | 20855 GCCGATTCAGCAAGTGAGTTCTCCTA | 31839 GAGTTTTCCCGGTTACCGTCTTC | 42823 |
| 9198 GGAGGGCAGCATGGGATAAAGAA | 20856 GGACTTTTCCCAGGGCCTCAAA | 31840 TGGTGAGGAGGGCAGCAT | 42824 |
| 9199 TGTTGCCAAAAGTTGCTCAGTAAG | 20857 GACTGCAGGGGTTTCACTTGT | 31841 GTGTTAAGCATGTTGCCAAAAGTTG | 42825 |
| 9200 CACACACGTAAAGGCAAGAAAAC | 20858 GTCATCCCATGTGGCCTGTAGT | 31842 TCCATTCTCCCACACGTAAAG | 42826 |
| 9201 GCCCTCTACCCTTTCCACTAAC | 20859 GGATGTCACTTGTGGGCAACT | 31843 TTCTGTTGCCAAGCCCTCTAC | 42827 |
| 9202 CTGCCTTTCACCAAGTTCCCTTC | 20860 GAACCGGCTCACTCATTTG | 31844 TCTGCCCTGCCTTCACCAA | 42828 |
| 9203 GCCGATGGTTGCATTCTTACT | 20861 GGCGCCAGTGCTTTATGTCT | 31845 CATCCTGGTTTGCCGATGGTT | 42829 |
| 9204 CCACTGGGGTTGAGAGAGAACA | 20862 GGAGGATTCTCATCTTCCTGGTATCATC | 31846 TGAGGCCACTGGGGTTGA | 42830 |
| 9205 CCATTCCCTGCCGTGTCACT | 20863 AGGGGTGGTCTCCTCCCTTAT | 31847 AACTTCCCCTCCTGCCCATTG | 42831 |
| 9206 GACCACCTTTTCCTACAGATGT | 20864 TGTGCAGTGGGCAGGAGA | 31848 CCTACTCACCCACCATTTATGACCACCTT | 42832 |
| 9207 AGTGGAGCTGTTTGTTTTCTACCCTA | 20865 CAAACAACCCATAGGTCCTTTCTCTCA | 31849 GCAATGGAGTGGAGCTGTTTGT | 42833 |
| 9208 GGGGTTCTGAGGTGCACATAGTTAAG | 20866 GGCTCTTAGTTTAGAGCGTCACTTCGTT | 31850 TGAGGGTAAACAGGGGTTCTGA | 42834 |
| 9209 CTCTACTCGCAAGGGTCTGGTT | 20867 TTGAGGAGGGGAGAGGCAAAAG | 31851 CAGTAACCAGAAGCCGCTCTAC | 42835 |
| 9210 GCCTGTCCAGTCTCATCTAGCATT | 20868 GCAAACACAGTGTAAGGTAGTAAGAAC | 31852 GTGTTGCCTGTCCAGTCTCA | 42836 |
| 9211 GTAGTGGAGCACCCAAACACTT | 20869 CTTTCTCCAGCAAGCTCTCTTTTTAC | 31853 AAGGATATGAGGTGCATTGTAGT | 42837 |
| 9212 AAGAGAGAGCTGTCCTCCTTGA | 20870 GCTGCGAGGACTCATGTGAT | 31854 TGAGCTCAGGGAAGCAAGAGA | 42838 |
| 9213 CTTCTTTAGGGCTTGGTGTCACT | 20871 CCAGGATGGCCAACACATTCTTC | 31855 ACCCCAGGTTGAGAATAACTTCTTT | 42839 |
| 9214 GCTGCTTTGGTCTGGCTGTTG | 20872 CAGCCGTACTGCCTTTCACA | 31856 GGCTTAGCTACTTTGAGCTGCTT | 42840 |
| 9215 CAGTTTCCCCTGGGAGCACTTT | 20873 GCAGACCCTGAGATGGAGATTG | 31857 TTCTCCTGCCCCTTACCAGTTTC | 42841 |
| 9216 CGAGTTATCTAATCCTCCCCTACAATG | 20874 CTGCTTGCTCAGGGTTGTGAAAA | 31858 GCGATGGGACAGTTTTCGAGTTATC | 42842 |
| 9217 CCTCCCTGCAAAGACATTACA | 20875 CTCCAAGCCGGCTCCTTTACAT | 31859 GAAGGTTCATTTCCTCCTCGCGCA | 42843 |
| 9218 TGCAGCTGTACTTTATGGATGACAA | 20876 GTTTGGAGCTCTCCCTGAACAATAAA | 31860 CCCACACTTCTGCAGCTGTACT | 42844 |
| 9219 TCTGGCTCTATCACCTGGGTTT | 20877 TGACTTCAAGTGAATTGTGGAGCTT | 31861 CCCCATCACTCACTCTGGCTCTA | 42845 |
| 9220 AAGGGGAGTCGCATGGGTTA | 20878 GGCCCAGTGTCGAGTTTGTCTA | 31862 TGGGCAACGTGGGGTCAA | 42846 |
| 9221 AGCGCGAAAACCTGGCTAAGA | 20879 GTTCACGTGGCTGAGACAAAC | 31863 GGTGCATGGCATAGCCGAAA | 42847 |
| 9222 GGCAGAGTGTGACGTTAGTGAGA | 20880 GGCATACAGGAAGGGAAAGGATGACA | 31864 GCTGAGGAAAGGCAGACTGTGA | 42848 |
| 9223 GCCATTGGAACTTAGAATTCTGTCTGT | 20881 TGCGGGATGCAGAGCAAA | 31865 GACACTTGCCTGGCAGAACCTAGAA | 42849 |
| 9224 CCACACTACTCCATGCCAGGATCT | 20882 GAGACTGAAAAGCCTCCAGACA | 31866 TTCCAGGGCTACACTACTCCAT | 42850 |
| 9225 AGTCACAGAACTCCCCAGAAATATAC | 20883 GTCATTGTGGGAAGTGCATTTGTT | 31867 GTCTCTGTCATCACAGTCACAGAACT | 42851 |
| 9226 CACCCTTGGCTATAGCTGCTAATTTC | 20884 CCAGGACACCTATTTCGTACCCATT | 31868 CACACCCTCTCACCCTTGGCTAT | 42852 |
| 9227 GCCTTTTGGGAGCCCGAACTAT | 20885 GACGGTGATTGTGATCTGCTACTA | 31869 TCCCAGGAAGCTGCCTTTTG | 42853 |

FIG. 3602

| | | | |
|---|---|---|---|
| 9228 CCAGTTCCCCACAGAGGAGGAAAA | 20886 CTGCACCATCTTAACCCCACTTC | 31870 CCCTTCCAGTTCCCCACAGA | 42854 |
| 9229 CCTGTCAACATGATGGTCGTAGTAAC | 20887 GGGCCTAACAATCCACCAAAACA | 31871 GGAATCTTGCAGCTCATCCTGTCA | 42855 |
| 9230 CCTGTGTAACATGACTTGTACTCCTA | 20888 CCAGCTTTCTATGACATTGGGCTAT | 31872 GTTAGTGAAGCAGTCCTGTGTAACAT | 42856 |
| 9231 GAAGAAAAGCAGTTCATCCCAAACA | 20889 CCAGTTACTACCCTGCGCTTAATG | 31873 GATGGCATACGACCAGAAGAAAAG | 42857 |
| 9232 GGGAGCTTGCTTTCTCTCTTACTCT | 20890 TGGAGATGGCTGCTCTTCTCATTTT | 31874 GACCTAAGGGAGCTTGCTTTCTCT | 42858 |
| 9233 CCTGGTTGGGTGTCTTTGTGT | 20891 GCACAGGATGGACATCAGGTTCACT | 31875 CCCAGTGGACAAGTACCTGGTT | 42859 |
| 9234 AGAAGAGAGGTCCTTCTGGTATGT | 20892 CCCAGGCTCTGTGCTTTGA | 31876 TGGGCCACAGCTCCCAGAA | 42860 |
| 9235 GGGCAAAGGAGTGGCATAATCT | 20893 GTGCACAGCCAGAATCATCCTT | 31877 GAGACAGGAGCCACTGGAATTTTG | 42861 |
| 9236 GGCTCATGGTAGCTACACCTTTC | 20894 GCAGCCTGGTGGACTATTGGAT | 31878 GTACTGTGTGTGGCTCATGGTA | 42862 |
| 9237 GGCTTTCAGTAGAGTAAAGTAGGAA | 20895 GCCCCTGCCTGGCATCTCTA | 31879 AGGTCCTCAAGACTGTGGCTTCA | 42863 |
| 9238 CCAACTCTCCTCCAAACAGTGATTC | 20896 GGAGGGGACTCAGGGACCTAAAAT | 31880 TCTTGAGACCAACTCTCCTCCAA | 42864 |
| 9239 CAGATTACACGCGATTCACAAATCA | 20897 AGTCAGTAGGGTTGCAGAAAGTATAAC | 31881 GCGCTCAGATTACACGCGATT | 42865 |
| 9240 GAAGGAAGTAGAATCACCAGATCAAC | 20898 GGCCTCTGTCCCTTCTCTTTAC | 31882 ACAGCCTGTGAAGTATTGAAGGAA | 42866 |
| 9241 GGAGGAGGAATCAATGATGGTGTAGAT | 20899 CTCCCTGCAACACCCTCTTATC | 31883 GGAGCAGGAGGAGGAATCAATG | 42867 |
| 9242 GTCTGCTAGGGTTAAACAGGGCTTT | 20900 CAAGGTGGTAACCTGTGATTTGGTT | 31884 GCCCAGGTCTGCTAGGGTTAAA | 42868 |
| 9243 CAGCACAGCCATCATTCTTCCAATG | 20901 GGAGGAATAATGTTTGCACCAGGGAAT | 31885 CCATCCTCAGCACAGCCATCA | 42869 |
| 9244 GAGATGTGCCTATACTGCGTTTGAAG | 20902 GGCCCCTCCCTCTTTACAACT | 31886 CAGACAGGTTGAGATGTGCCTATAC | 42870 |
| 9245 TGGGAGGGAATGAGGTGTATCT | 20903 CCGGGTTCGGGTCACCTTT | 31887 ACGACAGTAATGGGAGGGAATGA | 42871 |
| 9246 GAGACAAAATCCACTGTCAGGATAAC | 20904 AAGAAGACCCACCCCTCAGACA | 31888 GGGAATGGCTGATGTTAAGAGACA | 42872 |
| 9247 GGCACAGAAGTAGAGGCTGTAG | 20905 AGTGGGGCCTGTCCTCAAGT | 31889 TTGGGAGAAGCAGGCACAGA | 42873 |
| 9248 ACACCCCAGGTCCTGACTGATA | 20906 AAGCACGGCGCAGTGAGGAA | 31890 ACGCTGGAGCTGGTGAAACA | 42874 |
| 9249 CCPCTPGTTGCCCCAAGCTTTC | 20907 GGTCACTCCCPCATCAGCTTAG | 31891 GTGGCAAAATTGCCCTCTTGT | 42875 |
| 9250 GCTTTTCAAGAACGGGAGACACACA | 20908 CCCTGAGCCTAGGGTATTGTAATTT | 31892 GGACCACGGATGATGCTTTCA | 42876 |
| 9251 CCAGGAAGCAATGTTTTACCTCTTC | 20909 GGTGCAACTGATGGCTGTAGT | 31893 ACCACATAAAACCAGGAAGGAATGT | 42877 |
| 9252 GGAGTGGCCTTCATTACCCTCAA | 20910 GAGGAAGTTTGAGCACTGGGTTA | 31894 GCCCTACAGGGAGTGGCTTTCAT | 42878 |
| 9253 CCTGGCTTAGTATATGCCGAGACA | 20911 CTTGGTTCTGAAGTTTTCAGGTCAAPC | 31895 GGCACAAGGAGTCCTGGCTTTA | 42879 |
| 9254 GCCAAATCCACTTAAGAGCAGAAA | 20912 CCCCATAAGCTCCCACTTAGTGTAT | 31896 CTCTCATGCCCAAACTCCACTT | 42880 |
| 9255 AGGCTCCAGTTGGGGACACA | 20913 CTGCCCAGTGCTGTATCACACAT | 31897 CGACAGCACAGGCTCCAGTT | 42881 |
| 9256 CACTTCCATCCACCTGCAACA | 20914 GTCCGTCCAAACAAAAGGTTGACT | 31898 GCACTGCGGATCACTTCCAT | 42882 |
| 9257 GCAGCTCCTCCTTACAACAAGA | 20915 ACACAAAAGACTTGGACTTCCTTCT | 31899 CCTGTCPTTTGCAGCTCCTCCTA | 42883 |
| 9258 CTGCCTGTTGGAGAGACTTGACA | 20916 GGCTCTTCTACATAATACTCTTCTCTCATC | 31900 CCTTGCAGATAATTCTGCCTGTTG | 42884 |
| 9259 CCGTGTTTGCCCCTCCTTTT | 20917 TCCGGCCCACTGGGGTAAAT | 31901 CAGCCAAACATAAAGCCGTGTT | 42885 |
| 9260 GCCCTACAGGGAAGATGCAGAGA | 20918 CTAGGGACCAAATTCCAGTAGAAATC | 31902 TCTTTGGCCACTGCCCTACA | 42886 |
| 9261 CCTCAGGGGTATATCAACTTTGTGTCA | 20919 GCAAAAGGTGATCCAGGTCTCT | 31903 CTGTCCTACCTCAGGGGTATATCAAC | 42887 |
| 9262 CTACTTGGAAACTCCCTCTTCCTTAG | 20920 AGTGGGGAGACACCAGGAAA | 31904 AGACAGTCTTGACCACTTTCTACTTG | 42888 |
| 9263 TTGCCGAGACAGGGATTTCAA | 20921 TTCCCAGGACTGAGCTCTTCA | 31905 TGGTCCCGTTTGCCCGAGACA | 42889 |
| 9264 GCCTCTCTGACAATGACCATAACCCTTA | 20922 GAGAATGACTTCCTGCACAATTGGTT | 31906 GGCAAACAGCCTCTCTGACA | 42890 |
| 9265 TCACTTCCCAGTGGTGATATGAGT | 20923 TGGCTTGGAGGAGACCAGGTA | 31907 AGCTTCTTCCCAGAGTTTGAATCACT | 42891 |
| 9266 CCTCCTGCAAGAGCAGCATTGA | 20924 GCCTGTGTAAACTGATCTTGGACTTG | 31908 TGTCTTGGGCCTCCTGCAA | 42892 |
| 9267 GCTGGGCCTTGTGATCTGGCTTTGA | 20925 GGAGGGCCCAGAATGCCATTTCA | 31909 TCCTTTGAAATTAGCTGGCCTTGT | 42893 |
| 9268 GGAGGCAAAGGGAGGATAGTCA | 20926 GCACTGAAAGCCTTGGAACTGA | 31910 ATGGCAACAGGGAGGCAAAG | 42894 |
| 9269 GCTTGTCAAGTCTCTCTGATGCAA | 20927 CCTGGCTTTCCTCCTTTGACATACAA | 31911 GGCAGATTTCTCCAGCTTGCA | 42895 |
| 9270 ACTCACCATGGGTGGGTCAA | 20928 ACCCTCACCATCCTCAGTTGAT | 31912 GTGGCAGCAGTAGACTCACCAT | 42896 |
| 9271 CGGCAAATCCGAGAAGGACGTT | 20929 TCCTTAAATGCCTGAAGCCAAAAG | 31913 CCCTACTCTGAATCAAGCGGCAAA | 42897 |
| 9272 CCATTGCAGAAAGATGTGGTCTTG | 20930 CCACATGTAGCTGCTTTGCAATTA | 31914 CAGCAGCCTCATTTTAACTTCCATTG | 42898 |
| 9273 CCCAACATTACCGAAGTAGCACATT | 20931 TCCTTCTGAAATCCTTCCATTGGTT | 31915 TCAGGCAACCTCCCACCATT | 42899 |
| 9274 CCCTGGGCCTTAGTTTTGCTT | 20932 GTCTTCTACCCAGTTCCTTCTCACT | 31916 CATCATCCTCCCTGGGCTTCTA | 42900 |
| 9275 ACACACCCCGCTCCATTACT | 20933 AAGCCTTGTGCCTGGAGAGT | 31917 GGTGTTGGGTGGCTGAAAGACA | 42901 |
| 9276 CCTGCCACACATTTTTGGTGAA | 20934 CAAGATGGGTCTATGCTGGAACA | 31918 CTTTGTGGCTTGGGGAGTGA | 42902 |
| 9277 GGCACTGGCTGCTAATTAAGGCAAT | 20935 GGGCTTTCTCCTTCAGCAAAGA | 31919 GGAAGGCACTGGCTGCTAAT | 42903 |
| 9278 GCCACTACTGGCATCTTAGCAA | 20936 GCAGAACCAGAAGGCCGAAT | 31920 TGGACCACTGCTGCCACTACT | 42904 |
| 9279 TCTGAGACAGCTTCTTTACTTGACTTC | 20937 GGGGCAAAACCTGGAGTCAGATG | 31921 GCACTTGCTCGTCTCCTTCT | 42905 |
| 9280 GGAGCCTGGTGCTACTTTGTTC | 20938 ATGCTGAGCTGCACCGTACT | 31922 GGTCTCAGGAGCCTGTGGTA | 42906 |
| 9281 CGGGAATCAGGCAAGAGATCCAA | 20939 GAGGCATCCAACCAACAGTTTTC | 31923 AGAGGGCAGGCGGGAATCA | 42907 |
| 9282 GGGCCAGTAGGAACAPCTGTGAA | 20940 CTGAAGACTTAAACCAAAGTTGGCAGAAC | 31924 TCTGCCTTCAGGGCCAGTA | 42908 |
| 9283 GTTAGGAGGGTGTAAATCTGTGAATGA | 20941 ACTTTTAGCTCAGGGTCATGCTT | 31925 CCTGCATAGGTGGTTAGGAGGGTGTA | 42909 |
| 9284 GCTGTCACCTTCCGGTTGGAT | 20942 AGAGCCACGAGGGCTCAAA | 31926 TGGAGATCCTGGCTGTCACCTT | 42910 |
| 9285 GGTCAGACACTGGCTTGTCCAT | 20943 TCCTGAGTGCCCTACCTTGT | 31927 CCACCAGGGGTCAGACACT | 42911 |
| 9286 GGGTCGCGTGAAGAGAAAACA | 20944 GCCATGTTAAACTGCATCACCTCTAA | 31928 TGGAAAAAGGGTCTGCCTGAA | 42912 |
| 9287 GTCTTCCTTTTACAACCTACGTGACA | 20945 CACCACTGTGGAGAGGAAGGTA | 31929 CCCTGACAGACAACCGTCTTCCTTT | 42913 |
| 9288 GCTGCTTCGTTCCTTTGTTGT | 20946 CAGGTTCTTGGCGTTTTGAACA | 31930 TCTGCTTTCGCTCTTCGTT | 42914 |
| 9289 CTGCCCCTGGTTAGAATCAACT | 20947 GCATTGCAAGTGTTGTGACAGA | 31931 TGCTGTGCTGCCCCTGGTTA | 42915 |
| 9290 GCTGTGACTCATCCACACTGTCT | 20948 TTTCCTGGAGGCCATTTTGTCA | 31932 GGGTGATGGCATCTGCTGTGACT | 42916 |
| 9291 GGGCAGGTGGATGCTAAGTTTG | 20949 TCCAGAGTCCCTTGCTTCATCA | 31933 TGGCTGAATGGGCAGGTGGAT | 42917 |
| 9292 CCTTACATCAAAGAGGGTGAACTGT | 20950 CACTGCCAGAGCAACAAGAAAC | 31934 GTCCCCACTGCACCTTACATCA | 42918 |

| | | | |
|---|---|---|---|
| 9358 CAGAGAACTGTGGATCAAGACTGA | 21016 ACAGGAGGTGCTGATGTCTCA | 32000 GGCAGAGAACAGAGAACTGTGGAT | 42984 |
| 9359 GGATCAGTCTGGCTTCTGATTTCT | 21017 GCTCCATTGTCTTCTGCTTTGAA | 32001 GGGCAGGTAGGTAAAAGGATCAGTCT | 42985 |
| 9360 GAAACCCAACTCTGACACACTGA | 21018 GTGCTGAAGAGGCTCTGAGTCAT | 32002 TGCTCTGAATGAAACCCAACTCT | 42986 |
| 9361 CCCATAAGACAGGAACTGAGCTTTGA | 21019 GAGAGCTGCAGGGTGTTGAGA | 32003 CAAGGTACACTTTCTCCCATAAGACA | 42987 |
| 9362 CGTGGGGTAACTCATGGTCTCT | 21020 GTCAGGTATCGCGCTGGAAGTT | 32004 TGAGTCTAATTTAGCGTGGGGTAAC | 42988 |
| 9363 GACCAAAGGCAATCCAGAGTGTA | 21021 AAAAGAAGGCCTTGGAGAGTTCTAA | 32005 AGGAAGCCGACCAAAGGCAATC | 42989 |
| 9364 GTTTAATGTTGGTTCTCTGCCTAGACT | 21022 AGGTGCCTCTGTAGCTGAGT | 32006 CCCCGAGAGGAGCAGAGTTTA | 42990 |
| 9365 CCATAATTGCTAGCCACAGTTTGCTTAC | 21023 GGGAGCCAAAGGTTTTCAGGAAT | 32007 ACTCAACCACTGCCATAATTGCTA | 42991 |
| 9366 GCACAATCATTGCTATTGGCCGTAA | 21024 GCTGATGCATCATGCAAAGACTACA | 32008 CTGATCCAGAGTAGGTGCACAATC | 42992 |
| 9367 TCCACACATCAAACTTGGAGCAT | 21025 ACCTCTGGACAGGCAGATGA | 32009 AGGGTGGCCTCCTGTGTCTA | 42993 |
| 9368 CCTCATCTCAGACTGCCGTAGAA | 21026 GCAGAATGGATACAGCTTGGCTACT | 32010 GACAACAGGGAACCCTCATCTCA | 42994 |
| 9369 GGATGTGATAGCTGGATCCTGAAG | 21027 CCACCCCACTCCCATTGTTTGA | 32011 GGCTTGCCAGAGAAGGAAGGAT | 42995 |
| 9370 GTTCCAAGGCCTATTTAGCAGTTG | 21028 AGGACCAGTGCTCCAAGTCA | 32012 CTGGTTTCAAATGTTCCAAGGCCTATT | 42996 |
| 9371 GCCCTCTCTTCCTTTGAACTTTGT | 21029 AGCCCAACACATTTGAGCATTACTA | 32013 ACCCGCCCTCTCTTCCTTTG | 42997 |
| 9372 GGATGACAGCATAAAGTCCAGACCAA | 21030 CCCTTCTTCGCGTGTGTTGT | 32014 GGCTCTGTGGGATGACAGCATA | 42998 |
| 9373 GTCACCACCCATTGGATTGTTGT | 21031 TGCTGTCCTGGAGGTGTTGAAG | 32015 TTGGCTGTCACCACCCATTG | 42999 |
| 9374 CCACCCCATTCTCTGACCAATC | 21032 GGAAGGGCAGTGGTACCTATTCA | 32016 GCTCAGCATTCCACCCCATTCT | 43000 |
| 9375 CCAAACAAAGTGCCTCTTCTTTCA | 21033 GAGGGTTTTCCCTCACAACCTCTA | 32017 CCAAGACTCCTGCTTATTTTCTCCAA | 43001 |
| 9376 CACCTAAGTCAGCTTGTGCTCTTC | 21034 GGACACCCTTCCAAATGGTTTTCTTC | 32018 CACTAGTGGGACACCTAAGTCAGCTT | 43002 |
| 9377 GTGTTGTTTGCCCCATAAGGTATGT | 21035 GGAAGCTGGTGATCCACATTTTG | 32019 CCCGTGCACATGTGTTGTTTG | 43003 |
| 9378 CACCACACATGCCAATGCTCATATTC | 21036 GCACTCATGTGCTATGAGGGAGTT | 32020 CGTTCACCACACATGCCAATG | 43004 |
| 9379 ACTGTGCATTCAGGCAAGGTT | 21037 GGCTGTAGCCTGAGTCTCTGTTTG | 32021 CCAGTGGCTGAACTGTGCAT | 43005 |
| 9380 GTGTTTGTGTAGAAGGTTGAGTGCTA | 21038 AGCCCACTGTGGTCATTTAAG | 32022 GGGAGTTTACGTGTCTTGTGTTTG | 43006 |
| 9381 CGACAACTGTACTGCTCTGAA | 21039 GTGATGAGGATCATGCGAACGGAATAAA | 32023 CTGCTCATCAAGCACTCGACAA | 43007 |
| 9382 CCATGCCCTGGGCTGATTGTT | 21040 GAGCTCCACCCTAGAGCAATGAAG | 32024 GCCTGAAATGCAGCCACCAT | 43008 |
| 9383 GCTTGGCTGATGTTAAAGCTTACTCCGT | 21041 TGGAAGAGGACACCCCTCAAA | 32025 TTCTGTCAGCTTGCTGATGTTA | 43009 |
| 9384 GGTTTAGTTCCTGGATCTCACACTGA | 21042 GCCCTATTTTAGTATAACCCTGGAGCAT | 32026 CTGGTTCTTAGGTTTAGTTCCTGGAT | 43010 |
| 9385 GCATCTCAGGACTGAGTGACTCTAC | 21043 CCCGCAAATCAAGCATCAGCTTAC | 32027 CACGAAGCAAAGACTAGCATCTCA | 43011 |
| 9386 GACATGGGTTATGCAATGAGGCAAAT | 21044 TCACAGACCTCACGCCTGAAT | 32028 CCACGTTAAAACTAGAGAAGACATGGGTTA | 43012 |
| 9387 GCAGTTTCTCTGTTGTGGGAAGA | 21045 CCCCACCCATGATACGTTGTTC | 32029 GCTCCTGTCTTGCAGTTTCTCT | 43013 |
| 9388 CCTCCCACAATTTTACCCATGTCTTC | 21046 CTCATAAAGTAAGAACAGACGTTACCAATG | 32030 CCTGGGCTTCCTCCCACAATTT | 43014 |
| 9389 CCCGTCACAAGTCTGAGTCTTCT | 21047 CCTAGATTCTGGAACGCCTTGTTC | 32031 GGTGCTAAATTTTTCCCGTCACAAG | 43015 |
| 9390 TCCCACATGGAGGCAAACTTTCT | 21048 GGGCAGTGCATTTTTCTCCATAG | 32032 TGTTCCCCATCCCACATGAAG | 43016 |
| 9391 AGGGTGAGAAGGAGTTATCCAACTT | 21049 TGCTCACCTCCAGGAAGACT | 32033 CCAAAGTCAAAAGGGTGAGAAGGAGTT | 43017 |
| 9392 CCCACACTGGTTGTCCACAT | 21050 GGAGTCCTAGGCTGTCAGAAAC | 32034 TGTCTGTCCACTTCCCACACT | 43018 |
| 9393 CACGTCCACCTACATCTCCCTTAC | 21051 GACACAATGACTGGAATTTGCTTCA | 32035 GATCTGCACGTCCACCTACAT | 43019 |
| 9394 GGTTTTCAGATGGTAAAGTGGTGTCAA | 21052 CATTGTGCAACCAGAACTGAGATT | 32036 GCTGCAGCCAGAGGTTTGCAGA | 43020 |
| 9395 CCAAAGTTGAGGCAAGCATGACA | 21053 CAGAGTAGGCACCACCATCTATC | 32037 CCTCAAGCATGACTCCAAAGTTGA | 43021 |
| 9396 TCTAGGTACAGCCTGAGCATTCA | 21054 TGCAGCCACCCGAATGAGAT | 32038 CTTCTAGAGTGTGGACAATCTAGGTACA | 43022 |
| 9397 GGCCTGACTTTGTCATGGAAGGAT | 21055 CTTTGTGCTGCAAATCTGATCTTCT | 32039 CTGGCAGGCCTGACTTTGT | 43023 |
| 9398 CTGTGGCTTTAGCTGAGAGTTCA | 21056 CACTGGAGTGCTTACTGAATGAAAACA | 32040 CCTGGTTCTCAGTCTGTGGCTTTAG | 43024 |
| 9399 GAGGAAGAGTTGCAATACAGCCAAT | 21057 AAACCTCAGGGCTGGAGACA | 32041 AGGAAGGGAGTTGCAATACAGCCAGTT | 43025 |
| 9400 GGGTAATCCCAGCATGAAATGAGGTAAA | 21058 GCAGGTGCTAAGGACTGTAAGAAGT | 32042 CCTCAAAGGGTAATCCCAGCATGA | 43026 |
| 9401 GGACAGCCACTCCTTAGTTGTTGA | 21059 CACCCCTTTAGAGCTAAGGAAACAAG | 32043 TTAAAACTGGACAGCCACTCCTT | 43027 |
| 9402 GGGTCATGCTCCATCCAGTGA | 21060 GAGACAGAGGTCAGAGGTGTT | 32044 CCCATGGGTCGGGTCATGTCT | 43028 |
| 9403 CCAGGAGTGTCAAATCAGCTCTT | 21061 TGTCAGTCATAACCTTGGATGCTAA | 32045 GGTTCCTTTCCAGGAGTGTCAA | 43029 |
| 9404 CTCCTCTCCCTCATCCTCAA | 21062 GGAACCAGAGCTGAGGCTGTTA | 32046 GTCTTGAAACTCTCTCCTCATT | 43030 |
| 9405 CGCATGTCCCTAATGCGTGGAT | 21063 ACTCTGGGTGTGTCGGCATT | 32047 GTCCTTGGCCTGCCCGATTCTT | 43031 |
| 9406 GCACAGCCAGCATTCCCATAGT | 21064 ACCCTCGTGGCATCAGAGATGA | 32048 ACCTCTCTGCACAGCCAGCAT | 43032 |
| 9407 CGTTGCCTACAGTTCTCCTCTATC | 21065 AGTGGGCCCAGTGCAGGAA | 32049 CACACTTGAATTCGTTGCCTACAGTT | 43033 |
| 9408 CCGAGAATGTCACTTCTGCTGTATC | 21066 GTGGGCTGGGCTTAATGGTATG | 32050 CCATAGAAGTCCGAGAATGTCACTT | 43034 |
| 9409 GCCAAGTCTGTGGCTAGAGGAAGT | 21067 CCCAGTACGCTAGGCAGAAGA | 32051 CCCAAATAGCTCAAGCCAAGTCTGT | 43035 |
| 9410 GGCTGCCCGATTCTTAAATCATTC | 21068 CTGCCAAGCTCACTGAGGTAAC | 32052 CCATCTTGGCCTGCCCGATTCTT | 43036 |
| 9411 ACCGGAAGCCTTAACCAATTTTTG | 21069 GCCAGGTCGACACGTAACAT | 32053 AGGCACCCGAAGCCTTAAC | 43037 |
| 9412 CCCTGGAACCCTACCTGTCTTAT | 21070 CCACCCTCTTTCTCATCACAGTT | 32054 CCCATGAGCTTAACAGCCCTGGAA | 43038 |
| 9413 GCCCACAACCCACTGAGCAT | 21071 GGACATAAGACCCATCCACCAATG | 32055 GGTTTTAGCCGAAGCCCACAAC | 43039 |
| 9414 GTATTTACCCCAGATGGGATGTTCA | 21072 GGTCTGTAAAGTTGCCATGAATACTGA | 32056 GACCAGAAGCTGTATTTACCCCAGAT | 43040 |
| 9415 CAGGGCTGTCCTAACCTGTGATGAGT | 21073 TGTCCTTGGGAAGAAGTGAGGTTTAAG | 32057 ATGGAGGGGCAGGGCTGAGTT | 43041 |
| 9416 TCCCACTATCAGAACATTACCTGGAT | 21074 CCCTGAAAATAATACCCAGCTTTCATC | 32058 CTTCTAGCATTCCCACTATCAGAACA | 43042 |
| 9417 GTGGAGCTTCACGTGATCCTT | 21075 CATCTGAGCTGAGGTCATGTTCTTC | 32059 CGTGTGGAGCTTGTGGAGCTT | 43043 |
| 9418 GTTCCTACCCATAGGATCAAGATG | 21076 GGGCAGGTGCTTTCAGGAAGT | 32060 GCCTAAGCAGGTTCCTACCCCATA | 43044 |
| 9419 CTGAATGGTGAACAGGACAGTCT | 21077 AGTAACTATCTCAAGTCACAGGAGTCT | 32061 GTCCTAGCCTTACTGAATGGTGAAC | 43045 |
| 9420 TCAGCCTTCGACATCTTTCATTGT | 21078 CATAGTTGCTAAATAACGGGAGCTACT | 32062 GAGTCATAGAATTTTCAGCCTTCGACATC | 43046 |
| 9421 GGAAAGGGCTCACAGAAAATTAAGAGA | 21079 GGTCATTCAGACCAGCTCCAATAA | 32063 TGCCTAGGAAAGGGCTCACAGA | 43047 |
| 9422 GGGCTATTTCCATTGTAAGCACTTT | 21080 GGCCAGTGCCACATTAGCAAAC | 32064 AACAGAAGAGGGCTATTTCCATTGT | 43048 |

| | | | |
|---|---|---|---|
| 9553 CCAAGGAAGGTGTGAAGTATTATTCAGT | 21211 TGTTCCTCTCTAAGAACCTTCTAGTCT | 32195 TCACAAGCAGGTGTCCAAGGAA | 43179 |
| 9554 GGACATATGTTGCAGGTAGAGCTAGGGA | 21212 CTTTCCTACACCCTCATTCAGTTGT | 32196 GCAGGGACATATGTTGCAGGTA | 43180 |
| 9555 GCTAGACCAAGGATCCCTCTGATG | 21213 AAGAGCGTGAGCCTTCTGTTATC | 32197 GACCCTGACGTTACTGCTAGA | 43181 |
| 9556 TGCAGTGGATTCAGGCTTGCTA | 21214 TGCCATTCTTTAATCCCTTGGAGTTAG | 32198 CCCAACGACATATGTTGGAGTGGATTC | 43182 |
| 9557 CCTTCAACAAAGGTTAGGCCACAAA | 21215 TCTAGGAGGCCCGTCACACT | 32199 GTCTGGTAGGACAAAAGATCCTTCAAC | 43183 |
| 9558 AGCCAAAGAAGGAGGAGCTTATG | 21216 ATGCAGCTCCTATGTAATTGCTACT | 32200 GAGACCTGGCTTCTAGCCAAAGA | 43184 |
| 9559 GGTCCTGGGCATACAGTGATTT | 21217 TTCCTCCACTGGGTGGTTAATTG | 32201 GGGCCTTTTTAAGGTCCTGGGCATA | 43185 |
| 9560 CTGAACACGTACACTCTATCTTCCCAAA | 21218 GCGGCAGCTAGGGTATTTTGA | 32202 GTGGCTTCCTGAACACGTACACT | 43186 |
| 9561 GTGCCTGCTGATAAAAACTCACTAC | 21219 GTGGTATGGTGTTTGCATTATGCTGTA | 32203 GTCAGTAAATGAAGTGCCTGCTGAT | 43187 |
| 9562 GCCAGTGCATCAGTTCCTCTT | 21220 AGCCCAGCTCAGGTCAACT | 32204 ACAGAGCAGGCAGTGCATCA | 43188 |
| 9563 GACCAGGGAGCATATTACTGGATCA | 21221 TGGGCCATAATGGACAAAGATG | 32205 CAGACAAGGACCAGGGAGCAT | 43189 |
| 9564 GCTGGGAACAGGGTTTCACA | 21222 GGAGGCCAAAGGAGCTTATGGTTAC | 32206 AGCCAGTGCTAGCTGGGAACA | 43190 |
| 9565 CAGCTGTGGTAGGGCTATAGAA | 21223 CACCATAGTCCACABAAGCACTCT | 32207 TGACCCTGGACAGCTCTGGTA | 43191 |
| 9566 CCAABACCTCCAAAGTCGTGAAG | 21224 GCCTTCGAACACAGACTGAGCA | 32208 AACAAGCAGCCCACTTGGAGTT | 43192 |
| 9567 CTAAGCTCAGAAGCCATCCAATCT | 21225 AGAGCTCTTTTGCCTAAACTTGTTC | 32209 AGCGGGGATAATAAACTAAGCTCAGAAG | 43193 |
| 9568 CTGAAACAGTTAGGAACTCAAGGTGCAA | 21226 CCAGGGCCCTTGGATTTTGA | 32210 CCTGGAAGCTTCTGAAACAGTAGGAA | 43194 |
| 9569 AGGACAAGGCTGTTCTGGTACT | 21227 CAAGAGGACGTAAGTCCAATGTTAAGT | 32211 AGCCTTTAAGGACTCAAGAAGGACAAG | 43195 |
| 9570 GGGGAAGGATAGAGCAGTGCAA | 21228 GCCTTCCCTAGCCACCCATCTAA | 32212 GGAAAACATGACGGGGAAGGATAG | 43196 |
| 9571 GTGTGTAGGTCAGCCTGACCAAAG | 21229 TGTTCGGTACCGTTGTCTTTTCT | 32213 TGCTGGGAGCTGTGTGTGTA | 43197 |
| 9572 GGCTACCAACTAGCCAGTGCTT | 21230 CAGAGATGCCTCAATCTCATTGCAT | 32214 GTTGTCAGTGAGAAATGGCTACCAA | 43198 |
| 9573 AGGGCAGAACGATGTAAAAACAAC | 21231 GGTACAAAGGCAAACGTGTTCAT | 32215 TGTTTTACATCAGGGCAGAACGAT | 43199 |
| 9574 TCCTACCTAATCTAACCCTCATGCTA | 21232 GGCTCCTGATTCTTAAACAGAGCTT | 32216 GCCCAGCCAAGAAACTATTCCTACCTA | 43200 |
| 9575 GCCGTGAACAGGCTTACTCTCA | 21233 GGTGGCTCTGATGCTCCCTAAAG | 32217 AGCCGTCCAGCCGTGAACA | 43201 |
| 9576 CCTCTAGGAATTTAACTCCACCCACAAC | 21234 AATGTGGGAAGGGTCTACTTTCAAT | 32218 GCCGATGACAAACAGACCTCTAGGAA | 43202 |
| 9577 ACGTTCCTACCAGTGTTGATGA | 21235 CTGGTTAGGAATCTGCAGGAAAAACAAC | 32219 CCCACTGCAGAAACGTCCTA | 43203 |
| 9578 GGGAGGTGGAAGACATGATGGATA | 21236 CGTATAGTCTTCCATGCCATCTTCACTA | 32220 CAGAGTTGGGAGGTGGAAGACA | 43204 |
| 9579 GTTGAGTGATGGCAAAATGGGTGAA | 21237 TCTCAGGCTCAGGGAGAGTCAT | 32221 GGCAGAAATCTTTGCTGTTGAGTGA | 43205 |
| 9580 CCCAGTCCCCTTTTCCACTAGA | 21238 AGAGTAAGCACTTTGCCATAGGTT | 32222 TTGGGCTTCCCAGTCCCCTTT | 43206 |
| 9581 GCCTGTTTGCTCTCTATACCCATACCTA | 21239 CAGGGTTCAGGATGAATTCTACAACA | 32223 CCAGTAAAGCCTGTTTGCTCTCT | 43207 |
| 9582 GGCTTTGCCACTTGTCATGCTAAC | 21240 GCAGCAGCCACTAAGAATCACAACTTT | 32224 CTGCTGGCTTTGCCACTTGT | 43208 |
| 9583 GCTGTGGATAGCAGTAGCAACACT | 21241 TGGCCCCAGAGGCATCTAAA | 32225 TGGCATGGACGCTGTGGATAG | 43209 |
| 9584 GGAGCCTCTCTCTGGGTTCTATCT | 21242 CACAGGAAGTCACCTGCAAGGAA | 32226 AAAGCCTCTGGGAGCCTCTCT | 43210 |
| 9585 GCCCAACCCCTAAAGACTGACA | 21243 TGGCTGTTTAGGGTGCTTTCAA | 32227 GCATCCAGCCCAACCCCTAA | 43211 |
| 9586 GTGGCTGCTGTTAGACGTGTTAG | 21244 CTCATCATACGAGCTCAAGAGAACAAGA | 32228 CCTGCAAATGTGGCTGCTGTTAG | 43212 |
| 9587 GCCTCACACAGGGAATGAGAGA | 21245 GTTGGAGAAGGCAGTGAAGTCT | 32229 CCAGCTGAATTCTAAGCCTCACACA | 43213 |
| 9588 CTGGCGTTCAAAGCTAATTCTGCCATT | 21246 CCGACTGCTGCCAAAATTACATCTCT | 32230 GGACCCTCTGGGTTCAAAGCTA | 43214 |
| 9589 AGCCTCTGAACTGTAAGATGCAAA | 21247 CCATCAACCTTCCTTCCACACA | 32231 GGTGGCAACTTTAGCCTCTGAAC | 43215 |
| 9590 CACACAGCCAGCCAGTCCTATT | 21248 CCGCTGACCTCAAAGCAACA | 32232 GAGGCCATGTCTCAAAACACACA | 43216 |
| 9591 CCGGATCCTCAACCCAAGAAG | 21249 CCCCATTCCACGGACAGAATC | 32233 CACGTTTCCCGGATCCTCAA | 43217 |
| 9592 AGTGGAATGTCTTGAAGGACAGATG | 21250 GCTCTAGATAATCTGATGACACGGTGATG | 32234 CTGGGTACCAGAAAAGTGGAATGTCT | 43218 |
| 9593 GGGAGAATGAGTGACTGCTGACAT | 21251 GCCACTGGACCTGGCACAA | 32235 AGGTCCGGAGGCAGAATGAGTGA | 43219 |
| 9594 GTTCTGGCCAACCTTACTGTCTTC | 21252 TGATTGACATCCTTTTCCCTGTGA | 32236 GTGAGGCAACGCCTAAGTTCT | 43220 |
| 9595 CCGAGTTCCAGGCTAGGAGTAT | 21253 CTCCAGCACCTACACTACCCTAA | 32237 GCCTCATTCTCTTTCTTTCAAACCGAGTTC | 43221 |
| 9596 CCAGTGGAGACTTTCACCCCATA | 21254 CCCCAGAAGGCAGCAAGTCAAT | 32238 ACCCCGACCAGTGGAGACTTT | 43222 |
| 9597 CCTCAATGTAGACAAGGAAGATGTCA | 21255 GCTTTGTCACAGCTGTTTAGGAA | 32239 CAGTCACCACAACCTCAATGTAGA | 43223 |
| 9598 GTGAAGCCTGGGTGTAGCTTTG | 21256 GGGTCTCTCAGGTGTGTTCAGTAGA | 32240 GCTTATGGCACAGGGTTTTGTGAAG | 43224 |
| 9599 TGTACCAGGTGGCTGCTCTTG | 21257 GCAGGCCTAGGACTATTTCTCTGA | 32241 AGCCTCCCTCCAACCTTAGTGT | 43225 |
| 9600 CGGTTTAAGTTCAGCAGGAAAAAGT | 21258 GAGAGTGAGCAAGGACAGTGTTTA | 32242 GACAGCAGCTGACGGTTTAAGTTC | 43226 |
| 9601 TGGCTCAGAGATCGTCCCTTCT | 21259 CTGACAGAATATTGGAGTGGGTGATG | 32243 GAGAGTGCTTTTGGCTCAGAGA | 43227 |
| 9602 GGTTCAAAGACAACTGTGAAGCGATGA | 21260 TGAGACCAGAGGTCTGTATGTATGA | 32244 CCCAGGGAAACTGGTTCAAAGACA | 43228 |
| 9603 GACCTATGGGCTTTACAATTGGAGTAGA | 21261 GACCAAGTGTGCTTGTAGCTCAT | 32245 TGGGGAGACCTATGGGCTTTAC | 43229 |
| 9604 CCAGAAGGCTTTGAGCCATTCA | 21262 CTCTGTGTCCACCTGCTACACT | 32246 GGAGTGAACCCAGAAGGCTTTGA | 43230 |
| 9605 CTCTCTGAGCAGCTGAAGTCTGT | 21263 GGCATCCATGCCACCTTCT | 32247 ATGCCCACTGCACTCTCTCT | 43231 |
| 9606 CACCGGCATATGTGCCAAGAA | 21264 GGTAGGTCCCAGTCTTCACCAT | 32248 ATTTCTTCCTAACCACCGGCATA | 43232 |
| 9607 GAATCCTTTGAACCCAGGACTTTG | 21265 GGAGGACAGTGGCATGAACA | 32249 AAGGGGCTGAGGTGGGAGAA | 43233 |
| 9608 GGTGTAGCCACGTCCCAATTCT | 21266 GCAGAACAGATGCCTCATTTTGCTA | 32250 GGGATGTACTTCGTGGGGTGTAG | 43234 |
| 9609 CCAAACGGATGTATGTAGGACACCAA | 21267 GTGTGTGCCATTTGTGTTTGAAAAG | 32251 TGAGCAAACCAAACGGATGTATGT | 43235 |
| 9610 CTTCCTGTGATTGCTTCCCTTTGA | 21268 GCTCCACAATGCGTTGCATGT | 32252 GCTGTGTGATTGACAGATCTTCCTGTA | 43236 |
| 9611 GACAGTTGGCTGACGATATTCTCCTT | 21269 GCTGTGCTCCTTGAAGTGGCATT | 32253 GTGATGACAGTTGGCTGACAT | 43237 |
| 9612 CCCCTTGAAACTGGCTTATACTCT | 21270 GGAAAATGAGGGCATTCCAGGTA | 32254 TGATCGTCTCTACCCCTTGAAACT | 43238 |
| 9613 GGTCACCAAGGGTAGGTATGACA | 21271 GCCCCGTGGCTTCTGTTCT | 32255 CCTCTGCCACAGGTGACCGA | 43239 |
| 9614 GGAACTGACCAAGCTGACATGGAA | 21272 GCTGTGATCCCTCAATGCTGTAACT | 32256 AGACTCAGTAATGCTCTGGAAGTGA | 43240 |
| 9615 CCGTGGAGTTGCTTTGAGGGAGAT | 21273 GGGACGTAAACTAGGAGAGGCACCAT | 32257 CCTGGCCGTGGAGTTGCTTT | 43241 |
| 9616 CGCCCAGGGTACAGAGGATCCAT | 21274 AGGGATGGACAGGGGAAAGCAT | 32258 TCCCATCGTCCAGGTACAGA | 43242 |
| 9617 CCACCTGGTGAACTTGAGCTTGA | 21275 GGTCATCACAGTTGGTATGACACTCT | 32259 CCATCTGGAACCACCTGGTGAA | 43243 |

FIG. 36O8

| | | | |
|---|---|---|---|
| 9618 GATCCCAGTTGTGTGCCCTTAG | 21276 AGAGCTCTGCTGGCACCTT | 32260 CCCAGTTTTCAGATCCCAGTTGT | 43244 |
| 9619 GGGTGGTGAGGAGATCAGACTGTA | 21277 CTCATCTTCCTCCTGGCCCTTA | 32261 GGGTGGGTGGTGAGGAGAT | 43245 |
| 9620 CACACACAGAGAAAGGTCACTTC | 21278 AGGGCCACCCTCTCACTATG | 32262 CCAGGGCTTTACACACAGAGAA | 43246 |
| 9621 GCAAGCCTAATCGGATTTTAGCTCTT | 21279 GATAAGGCCGCCATTTTCTGAAC | 32263 TTAGTGGTCTATGCAAGCCTAATC | 43247 |
| 9622 GGAGAACAGAGCCACATGCTAAC | 21280 AGCTGCTTGGGATGATTATGTTGA | 32264 CGATGTAAGGGTGCAGGAGAACAGA | 43248 |
| 9623 GCTCCTCGTGGAATCCGAAATG | 21281 CATGAGGCAGGACTTGGAAAACA | 32265 TCCCATGCTCCTCGTGGAAT | 43249 |
| 9624 GCCCTCTGACAGTAGTCAGGAAACTA | 21282 ACTTTGAGGCCCAATAACCATGT | 32266 CTGCAAATGACGCCCTCTGA | 43250 |
| 9625 GCTGGTATGGAGAACAATTCCTGACA | 21283 GCGTGCCATTTGCAGTCTGT | 32267 GCTTTGAGCTGGTATGGAGAACAA | 43251 |
| 9626 CCCTCTCTTGCCTGGTCTATTTT | 21284 AGAAACCTAGACAGCCCTTGTTC | 32268 GACCTTCCAGAAGACCCCTCTCTTG | 43252 |
| 9627 CCCTGCATTCCTTCTTCTTGGAT | 21285 GGGTACAGAAGCTTCAATCACATCA | 32269 GCCGATCACCCTGCATTCCTT | 43253 |
| 9628 GCAAGGAATCTTGTGTCTCTATGATTG | 21286 ACCAGCCTCAGATTTGTCTTTTACT | 32270 GCCTGAAGAGGACGAACTGTTG | 43254 |
| 9629 CTGGAGGAATACCAATCAGACGACAA | 21287 TGGGGTGGTCTGTGCAGTT | 32271 GGGTGCCTGGAGGAATACCAATC | 43255 |
| 9630 ATGCAAGGGTGATGAAGAAGGAA | 21288 CTGTAACAGTGTCTGGTACCAAATG | 32272 GTGCAAGCTATGCAAGGGTGATG | 43256 |
| 9631 GGAGTTAAGAGGGGAGTTGAAGTCAAAG | 21289 GATGGAGTCCTGTGAAGATGGTAAC | 32273 ACAGAAAAGGAGTTAAGAGGGGAGTTG | 43257 |
| 9632 ACTCTGCCTCTGAGATTCTAGATAGT | 21290 CACTAATTGGTGCCATTATGCATCT | 32274 GAGCTTAGAAAACTCTGCCTCTGA | 43258 |
| 9633 TCCTCATTCCTCAGAGCTGACA | 21291 TGAGTACACCTAATGGCAGGTTTT | 32275 AACAGACTCCTGCTTCCTCATTC | 43259 |
| 9634 GACGGGTACTACGGGTCCAT | 21292 CACCATGCAGCACCAGTGA | 32276 AAGCCACGGACGGGTACTA | 43260 |
| 9635 GACTGCCTCTATGAAGCCATTCCTA | 21293 CCCTGAGGAGGGGTTGATTGT | 32277 TGTCCACTCTTGACTGCCTCTA | 43261 |
| 9636 CAGCCACAAGGAACAATCTCAAAA | 21294 GTGTCTGCAGGTGTGGTTGT | 32278 GCATGCAGCCACAAGGAACA | 43262 |
| 9637 TGCCAGCCTGCCTCTCTAA | 21295 ACGAGACTCATCCTTATCCCTAGAA | 32279 TGACCTCCTCAGCTTGCTTTG | 43263 |
| 9638 GAGTAGGACTTCTTACATGGCAGTTG | 21296 TCCAAATTGCCCTTCCACAACA | 32280 GCTGGTTCCAGAGGAGTAGGACTT | 43264 |
| 9639 ACAGTCACCTCTGCCTGTCT | 21297 AGATCGGCCTCCAGCTTCTA | 32281 GCAGGCTGGCTGATTTCCAACA | 43265 |
| 9640 GGGTCTGATCACCCCAACATTC | 21298 AGAGTGACTACCTCCCCAGCAA | 32282 GCCTGTTAATAAGGTGTTGGGTCTGA | 43266 |
| 9641 CCCAGGAACTTAAATGAAATGGGATAC | 21299 TGCAATAGGCTGAGTCTACAATG | 32283 CTCCAAGGCTCTTATCCTAGGAA | 43267 |
| 9642 TCCGACCTGTCTGGGAAGTT | 21300 GCAGTCGCTTCTCCACCATGT | 32284 CCCCGACTTCCGAGTACAGAT | 43268 |
| 9643 CCACATGCCTCCTATATGCTTTGT | 21301 GCTCAGTCTAAAACAATAGCCTCCCATA | 32285 TCCAGTTCCACATGCCTCCTA | 43269 |
| 9644 CAGCACCACTTTGCACTACTTC | 21302 GCTACAAGCCACTGTTACGTTTC | 32286 GACAGCACAGCACCACTTTG | 43270 |
| 9645 AGTTCTCTCCAGTCTCTTCCAGTT | 21303 ACTGAAGGAATGTGGTCATGAAAGA | 32287 CAGATCACTGTAGTCTCTCAGTCT | 43271 |
| 9646 GCCCTGAGTCCATTCCAAGTCT | 21304 AGGGTGGGAGTGCAACACTAAC | 32288 CCAAGGAAGCCCTGAGTCCAT | 43272 |
| 9647 CGCAAACTGGTATCCCTGGTCAC | 21305 GCAGCCAAGCAGGCTATTCA | 32289 GCACATCCAGCGCAAACTGGTA | 43273 |
| 9648 GACCAATGGAAGCAACTACAGAAACTTTG | 21306 GGCCCTTTTCTCTGAGTCACTA | 32290 GGTGTGGGCGTGAATATAGACCAA | 43274 |
| 9649 AGCGCTCTTGGCCTTTGTT | 21307 GCACATGCTCTTTGCAGGACAA | 32291 CCTCACCGCCGTGTCATTTGAA | 43275 |
| 9650 CCTCCAACATTCCTCCTCTACAAC | 21308 CACTGAGGTAATAACCAGCAGACA | 32292 GGCAGTTACCTCCTCCAACATTC | 43276 |
| 9651 AGGGAAGTCCCTGGCTCCTAAAG | 21309 TCAGGAGGGGAGGTGGAGTAT | 32293 GGAACCACAGGTGAAATAGGGAAGT | 43277 |
| 9652 CAAATGGCCCAGCTATATCTGATTG | 21310 TTTTCTGCTGCTCATAGGGGATAG | 32294 GCTTTGTCAAATGGCCCAGCTA | 43278 |
| 9653 CACCCAAGGAGGGCTGTAATCA | 21311 AAGCCCTCCCTCTCCAGCAA | 32295 GGAACATCCCTCAGCCAAACA | 43279 |
| 9654 CCAAAGAGATCTAGGACACAGACATAACT | 21312 CCATCCTTCTTCAAAGTGGCAGATA | 32296 GCTTTCCAAAGAGATCTAGGACACA | 43280 |
| 9655 TCCAGGTGCCATTCCCCATTG | 21313 GTCTTGCTCTTACTACCTGTTGAACT | 32297 GGTTCTCTCACGGGACCCTTTC | 43281 |
| 9656 CCAATTCTCTTGGTTCCATTAGCCAGAA | 21314 AGCCCTAGATTAGTGCTGAAAATGA | 32298 CTCCAAGGAGGACCAATTCTCTTGT | 43282 |
| 9657 GTGGCTCTTCCCATTGGCTTT | 21315 AGCAGTGTGGACAGAGGCTAGA | 32299 CAATGACTGGATGTGTGGCTCTT | 43283 |
| 9658 GCACCTGACCATACTTGCTCACACT | 21316 CAGTCCTTAGTGTTGTCACACTGGAGTTAT | 32300 GAGAGAACTGCACCTGACCATAC | 43284 |
| 9659 ACCCAGATCTCTGCTTCTAAAACTTG | 21317 GTCCCTGGAAGCAGCTAATCTAATG | 32301 GCAGAGCCAACTTTTAAACCCAGAT | 43285 |
| 9660 CAGAGCTCTATACTGAGCTTTCCCTCTAT | 21318 CTCAGCCATACAAAGTGACTGTCTT | 32302 TGCATGTCCCAGAGCTCTATACT | 43286 |
| 9661 CCATGCCTGCTATTGCCACTAT | 21319 GCCCACTGCACCTCTGTTTG | 32303 CCCCACATTCCATGCCTGCTA | 43287 |
| 9662 ACATGCAGGAGCTTAGAGACTGA | 21320 GTGAGGATTATTGAGAGGCGATTGT | 32304 CCAGGACATCTACATGCAGGAGCTT | 43288 |
| 9663 ACTGCACCCTTAGTTCCATCCATAG | 21321 GACCACGCCACACTTGGTATGA | 32305 AACAACAAGAACTGGACCCTTAGTTC | 43289 |
| 9664 GCATGGCAGAAAAACTACCTTTGTCA | 21322 GCTCCTGAGAAGCAAACACACA | 32306 GTTAACTTCAGCATGGCAGAAAAC | 43290 |
| 9665 GCATGTACACAGTGCATACCTCTGA | 21323 GGAACAAAAATCTGCTGTCTGCATTTT | 32307 TTATGGAGCGGCATGTACACAGT | 43291 |
| 9666 GTGACTCACACCAATGACAGTTACA | 21324 GCCAAATAGAGAACTAACAGGCACACT | 32308 GCCCCAGTCACTCACACCAAT | 43292 |
| 9667 CCGACGTTGTCATCTCACATTATC | 21325 CTCCTGCCCTGAGTCTGAAAC | 32309 CCAGGACCGACGTTGTCATCT | 43293 |
| 9668 GCTCTCTGCAAATGGGAGGATGGTA | 21326 TGTGCCACGCTCAATGCTAAAGT | 32310 CGCTTGCTTTGCTCTCTGCAA | 43294 |
| 9669 CTCTTGGTTTCCAGGCAGACA | 21327 GCCCATCACGCCCTTCAGTA | 32311 CGGTCAGGCCTTCTCTTGGTTT | 43295 |
| 9670 GGTGGTTGTGTGGGTCTGA | 21328 GAGGGAAGCCGTGTTCTGATTG | 32312 CACTTTCAGTGCAGGTGGTTTG | 43296 |
| 9671 CCTTTGTGAATGCCTGATGCAA | 21329 GCTGTCCCCTTGTGAATGAGT | 32313 GGAGCAGCCACAGATCCTTTGT | 43297 |
| 9672 GGCAAACTCCACTTCAGCAGGAT | 21330 ACATGTACACTGGGTCAGAATTTGT | 32314 GTCTTTCAAAGGCAAACTCCACTT | 43298 |
| 9673 TCCACTCTGGATTCCTGAACAAC | 21331 GCTCTCCATGTTTCTGCTGCTTGT | 32315 GGTCAGCTTATCCACTCTGGATTC | 43299 |
| 9674 AGGGAACCAGCAAAACCAATGA | 21332 CTGGTTCTTGGGCCTTCCAA | 32316 TGCAAACTAGGGAACCAGCA | 43300 |
| 9675 GCGGCAGTGTTTCCTCTGTT | 21333 TTCGTGGGAGAGAAGTTGATAAG | 32317 CCCTGAGAAGCGGCAGTGTT | 43301 |
| 9676 GTCTAAGGAAGTCTGTAGGCTGAATAC | 21334 TGGAACAATAGCCACAGCAGTT | 32318 GGAGTCAGGTCTAAGGAAGTCTGTA | 43302 |
| 9677 AGCACTTCCCCTTTGATCCATTC | 21335 CCAGGGCCAGAGTAGCAAGT | 32319 GGCCAGAAGAAGCACTTCCCCTTT | 43303 |
| 9678 GGGGACATAGGCAACAGGACAA | 21336 GCCCACACGCCATGTAAAGA | 32320 AGGGCAGGGTAGGGGACATA | 43304 |
| 9679 GAGCTTCTCACTGTCCCTGTA | 21337 GTGTCCCAGAAAGGAAATGAGACA | 32321 TCCCTTCCTCAGCTTGTTGAGCTT | 43305 |
| 9680 TGTCCAAGGAATGGGAAGGGTAA | 21338 GGCACCTGTCAGATAGGGTTGGAT | 32322 TGGCAAGTGTGTCCAAGGAAT | 43306 |
| 9681 CGCCCCAACAGAAGAGGAAGTT | 21339 CTGGCAGTGACCCTTTGGTGACTTA | 32323 TCTCCACCCTCGCCCCAACA | 43307 |
| 9682 ACGCAATGCCTTTTCAGAGCTA | 21340 GGTCATGATGCATGGGACTAACAGGTA | 32324 GTTGTTAGCCCAGAAACGCAATG | 43308 |

FIG. 3609

| | | | |
|---|---|---|---|
| 9683 CTCCATTCCCTGTCTTCAGAGT | 21341 AGTGACAGGGATCCTTTTTCATGT | 32325 CCTGTTGGACTCTGCTCCATTG | 43309 |
| 9684 GGAACCACAACAATCTCACTGAAG | 21342 CTGGTTGTGCGGGAACTATGTCTCA | 32326 CAAGGTTCTTGGAAACCACAACAA | 43310 |
| 9685 CACCCTCCAGTTTCTGGTTTCA | 21343 GTCTTCCATGCCAGACAGACATC | 32327 AGTAGAGAGACACCCTCCAGTTT | 43311 |
| 9686 GGCTCACTCCAAAGCCCATATTC | 21344 TCTGGGCTCCACACTCCAAA | 32328 GAACCCTATAGGCTCACTCCAAAG | 43312 |
| 9687 GTTGGCATCAGACAACTCTTACCTAT | 21345 CAGTTTATCCTGCCAGCCCATA | 32329 CCCAGCCATGTTGGCATCAGA | 43313 |
| 9688 CGCATATTGCAGGAACCAGGTAGT | 21346 GCCTGCAAATTAATTATGGGTCAGCAT | 32330 CAGGGGAGGTTTTACTTTCGCATA | 43314 |
| 9689 CGAGGAGGGACCAACCAAGATTAACA | 21347 CCGTAGCCTACAGAGTGTTGTCATC | 32331 TCGACCCGAGGAGGGACCAA | 43315 |
| 9690 AGGGCTTACCAGGGTGAGGTATC | 21348 TGACAAACCAAGCACGTTCAGT | 32332 ATCGCTGAGGCCAGGGCTTAC | 43316 |
| 9691 CTGTGACACCCGTTTTCCTGAGA | 21349 GGGGAAGGGAGGTGAGTTAAAG | 32333 AAGCAGGCAGACAGGCTGTGA | 43317 |
| 9692 GTCTTCACTAGACTAGGCCTGCAGTA | 21350 CCTAGGATTATGCTGCCAACAACT | 32334 CAACGGCCAGCGTCTTCACTA | 43318 |
| 9693 CACAGGTCTATTTAGTGCAGGGAACT | 21351 CCCCTGCTTGTCTGAGTTCATGT | 32335 GGCATTGCGGACACAGGTCTAT | 43319 |
| 9694 ACTGATTGCATATGGGGTTTGACA | 21352 CGTCAATGCCAGAAGGCTAGAAG | 32336 CTCCTGTAGTCAACAACTGATTGCAT | 43320 |
| 9695 AGCCTGCAGTACCCCTCTTGT | 21353 CATGGCTGGCACCTTTCTGT | 32337 CCCGGGTAAGCTGCAGTA | 43321 |
| 9696 TGGGGTTCTTTCATGCTTTGTGT | 21354 CGGCAGTGTGAAAATGGACTGA | 32338 CTCCATGGTTTCTGGGGTTCTTTC | 43322 |
| 9697 CTGAGTAGGACAGTGATCCAGAGT | 21355 GCCAGCCTGGACCACATCA | 32339 AGGCCACTGAGTAGGACAGTGA | 43323 |
| 9698 CCAAGCTGCAAAGTAAACTTGGAT | 21356 GGATGGGTTTTGAGAGCACTAATTTTG | 32340 CATGCCAACCAAGCTGCAAAG | 43324 |
| 9699 GCCCACCTCTTTATGGAACGTA | 21357 CCCAGGCACAGGCAGAATTG | 32341 GCCCTGTAGCCCACCTCTTTA | 43325 |
| 9700 CAGCAGAGCTGGTATTTAAGTATTCTGGTT | 21358 AGTCTTGTAACGGACAGACCTCTA | 32342 CCAGTACACAGCAGAGCTGGTATTTAAG | 43326 |
| 9701 GGTCCAAGATGGAATGGGTTCT | 21359 CTCCTGTTTCAGCCCCTTCTAC | 32343 CTCAACACAGGATCTGGTCCAA | 43327 |
| 9702 GAGCTTAGGCTGTTTCTATCCAGTCA | 21360 GGTGAACCGTAGGCAACTGAAC | 32344 GGGGCTCAAGAGCTTAGGCTGTTTCT | 43328 |
| 9703 CCTGAAACTTGCAAAGCCTCACAGA | 21361 GCTAATTTTAAAAGCCAGCCTCAAACT | 32345 GGAGCACACACACCTGAAACTTG | 43329 |
| 9704 TGCAGTGTCAAGCTTGTCAGA | 21362 GGAAGGAAAAACTTCTCCCTGAGGTAT | 32346 TGCCAGCCATGCAGTGTCAA | 43330 |
| 9705 GCCAGCACTCACAACTAGACTT | 21363 GGTTCGGTCTGGGGAGAGATTG | 32347 TCAACAATGCCAGCACTCACA | 43331 |
| 9706 TGTGTGGGCTTTCACTCTCAAG | 21364 CGGTGGCCCAGAGGAATGAAATAGT | 32348 AGGAACCAGGAGGCATGTGT | 43332 |
| 9707 TGCATGGATCTTCATAGTCCTACTCT | 21365 GGTGTTAGAAAGAGTTCAAGGCACTTTC | 32349 CAGAGAGGGATTGCATGGATCTTCATAG | 43333 |
| 9708 GAGTTCTTCTCTTCCTCCACCTAAAA | 21366 CCTCTTGAGCTGGGGTCTTGGAA | 32350 CCTGTGGTTTCTACTGCTTAGAGTT | 43334 |
| 9709 CGTGAGCATTAGTAGCAGTGACA | 21367 GCACGTGCGTTACTCTCTGTGCTT | 32351 GAAACCTGAAACGTGAGCATTAGT | 43335 |
| 9710 GACTGTCAGCAAGCAACAATACAAG | 21368 TCCCCAGGGTGTCATTTCTTGA | 32352 CAGTACCCTGGACTGTCAGCAA | 43336 |
| 9711 CTGAGATCAAGCGAGCTGTACAAAG | 21369 CTCCTTTCCTGGTCCCAATTCTGT | 32353 GTGAAAACGAGGAAACTGAGATCAA | 43337 |
| 9712 GGAGGTTTGGAACTGGTAGAGAGA | 21370 GCCTCCATAGCAGTCTGTGAATC | 32354 CTGTCATTGGGGAGGTTTGGAA | 43338 |
| 9713 GGCTGTTAGGTTGGGAGAGGAT | 21371 CTCCAATGCAGGACAGGAACATC | 32355 GGGACAGTTGGCTGTTAGGTT | 43339 |
| 9714 CTGCCTTCCATAGTTGCCACCAA | 21372 CAACATATGGCATGCCTGAGAAC | 32356 AGAGCTCAGCTGCCTTCCATAG | 43340 |
| 9715 CTCTGGAAAAGGCTGAGAAAACTCCTA | 21373 CGTGTGTCAGCAACTTAACACTTTG | 32357 CACGTCCCCAGTTTCTCTGGAA | 43341 |
| 9716 GTTGAGGGCTAGAGGGCTAAGA | 21374 CTGTTGACAAATACTCTCTCCACCTA | 32358 GTCCACTGATTGTTGAGGGCTAGA | 43342 |
| 9717 AAGGCTGGAGCTAGGAGTCACA | 21375 ACTGAGAACCAGTTGATGAGAGAGT | 32359 CCAACACCATAGGCTGGAGCTA | 43343 |
| 9718 GCCATGCACAGTTGAGTCACACAT | 21376 GGGAAGAACCAGAATCACTGGAA | 32360 CCTGCCTGAAAAATTAAGCCATGCACGT | 43344 |
| 9719 ACTGCATTCCCACCATACCAAA | 21377 TGGGGCGATAGCGAGTCT | 32361 CCCCAATACCACCACTGCAT | 43345 |
| 9720 TGAAACCTCAGTAGGGATCTTCCAT | 21378 GCTGGTGTATTCCCTGGACAGAA | 32362 CAGAGGAACAGAATGAAACCTCAGT | 43346 |
| 9721 GGTTGTGAAGCCGCACTTGGTT | 21379 GCGGGTACTGGTGGTGTTTTC | 32363 TGAATCGTGTCCTGGTTGTGAAG | 43347 |
| 9722 GCAAGAGGATTGGGCATACTGGTAA | 21380 CAGCACTGAGAAACCCCTCTT | 32364 GGCTGCATGCAAGAGGATTG | 43348 |
| 9723 GCGCAGCCAGAAATGATGAAC | 21381 GCACCACACATGGAGAGGAGAAG | 32365 AACAGAAGCGCAGCCAGAA | 43349 |
| 9724 CCCTCTTGCTTACATCTCCATTTAGGTT | 21382 GTCCAGCCTAAAGGTTCTGTTGT | 32366 CCTCCAGTTACCGTCTGTTTACATC | 43350 |
| 9725 CACTCTTCACTATCTCAGCCCATGAA | 21383 CTGACAACCATCTAACTGGGAACACA | 32367 CTCCATTACAGATAGCACTCTTCACT | 43351 |
| 9726 TCCCTTCAGCAGAGCAGTCA | 21384 GGCCATGCAGGCTGACAGATT | 32368 CCACAACCCACAGTCCCTTCA | 43352 |
| 9727 GACAGAGATGGTGCATGGATGT | 21385 GTACCCATTGTGAGTGTGAATGAAG | 32369 GATTTGGACCTGATCAGTCTTGACA | 43353 |
| 9728 GTGCCTGCCTGTTAATGAGTGT | 21386 CAGGAACCAGAATAGGGTGAT | 32370 TGGACTAGTGCCTGCCTGTT | 43354 |
| 9729 CCCTCCTTGGTGAATGTGTCGTGACAATGA | 21387 CCATGGATGTGTCGTGACAATGA | 32371 CCATCTGCCCCTCTTGGTGAATG | 43355 |
| 9730 GTGGTAAGTTTGGAAGGAGGCTTA | 21388 CAGCTCATACAGATACGTGGTTATATCTTG | 32372 GCATAGCCAAAGTGGTAAGTTTGGAA | 43356 |
| 9731 GCGCAGGAATGCTGTCATGA | 21389 AGACATAGGGTGTGACGTGTCT | 32373 CAATCCTTTATGGCGCAGGAATG | 43357 |
| 9732 CACCTCCTTGCTGCTACCATA | 21390 TCAGTGAGGTGGTGATGGAAGA | 32374 CTCCAAAATCTGGTCACCTCCTTTG | 43358 |
| 9733 GGGGCCCAGATACACTCTTCTTC | 21391 TGTGCTCTCACTTGTCACCATT | 32375 ATCTGCAGGGGCCCAGATACA | 43359 |
| 9734 CCTGCTTTGGAAATCCGACCACTA | 21392 CCAGGTGGAGCCACAGTA | 32376 CCCATCAAAATCCTGTCTTTGGAA | 43360 |
| 9735 GCTTTCCCGAACAAGGTTCACT | 21393 TCTCCTGTGCTGTTCCTTTGT | 32377 GCCAACCAAGCTTTCCCGAACA | 43361 |
| 9736 GGGGAGAGGAGAAGTGGGTTT | 21394 CCAGTGAAATTTTCTGCCTCCAAGA | 32378 CCTGCACTGTGGGCTGGAA | 43362 |
| 9737 GGGCTTGGGTATCCTAACCTCAT | 21395 GACTGGGTACAGATGTGATATTGGAAGAA | 32379 AAGTCCAAAGGGCCTGGGTATC | 43363 |
| 9738 TCAGCGCATTACCAGTCCTTTAG | 21396 AGCGGGGAAGCTCCAGTCA | 32380 GGAATCACCTTCAGCGCATTAC | 43364 |
| 9739 GGGGATTGTTAGGACTTATCACACT | 21397 GCCCCTTGGGCTTCCAGTTT | 32381 GGAGCAACATACAGAGGGGATTG | 43365 |
| 9740 TGGGGCTGAAGGGTTGACTGTA | 21398 GCTGAGCTCCCAACCATGTGA | 32382 AAATGGTGCCTGGGGCTGAA | 43366 |
| 9741 CCTTTGCCATTCCTGGACACTCT | 21399 TCTGAAACCTGTCAGGGGACTT | 32383 GCCCACACACTTCACCTTTG | 43367 |
| 9742 GGAACACCTACCCTTTATCTGTAACT | 21400 GACAGGGCAGAGTGAAAGGTATTC | 32384 AGGGGAGCAGGAAATAGGAACA | 43368 |
| 9743 GCCTGACCAAAGTAAGTTAGGGTTCT | 21401 TGCCTTTTGCTATATGAGGCTGGAT | 32385 CAGGAAGCCTGAGCAAAGTAAGT | 43369 |
| 9744 TCCTAGGGCTGAGTTTGAGATTTG | 21402 GCTTACCAGGTGTATAATACCTGCAGTTCT | 32386 GTGCAATGTCCTAGGGCTGAGT | 43370 |
| 9745 GGATGGGAGGGTCCTTCATTTTCT | 21403 GCTAGGCACGATGAGTAGTGATT | 32387 AGGTGGGGTGTGGAAGGAT | 43371 |
| 9746 GCCTGGGAAACCAAATGATTGTCAAAGA | 21404 TCCTTTGCTGTGAGCTGTTGTA | 32388 CCCCAGAGAGCCTGGAAACCAA | 43372 |
| 9747 GTGGGACTCAAAGATCTTCCAGAAT | 21405 GGCTGTCACAAATTATATCCCAATCCCTTT | 32389 GGATACAGATGTGGGGACTCAAAGAT | 43373 |

| | | | |
|---|---|---|---|
| 10073 GCCTTACTTTCCTAGTGGGATGA | 21731 GGCAGAGGCTTGGTGGATAGAAG | 32715 CCTGCCCACATGCCTTTACTTTC | 43699 |
| 10074 CAGGGAAATGGGAGCTTAGAAGGTT | 21732 CCCTTCTTCCAAGCCAAGTGA | 32716 CCCGCTTCATAGACCAGGAAATG | 43700 |
| 10075 ACCTAGTTACAGACTGGGCTCTAC | 21733 GCATGTTCCTCTCCCCTCTTCT | 32717 GCCAACGAACCGAACCTAAAC | 43701 |
| 10076 AAGAGCAAGAATCATCCGTATCTGT | 21734 CCGTGAGAATGAAGGTGCTTTG | 32718 CCTTCCCAACCAAGAGCAAGA | 43702 |
| 10077 CCTAGAGATAGGAGCATCCTACTTCTCACAA | 21735 CCAGGCATTAACTTAGCAGTGGAT | 32719 GGCTGTGCCTAGAAGATAGGAGCAT | 43703 |
| 10078 TCCCCTGGCATATGGTGGTTCA | 21736 CTGAGAGGGCCTTTAGGGAAAGAATG | 32720 GCAGGATTAACTGTCCCCTGGCATA | 43704 |
| 10079 TTCACCACATTGTCCTGATTACTGT | 21737 GGGTAAAGTTGGAGGAACTATACTACTTG | 32721 GTGTCTGTCCCTTCACCACAT | 43705 |
| 10080 GTGGGTTAGGATGGTAGGTGCTT | 21738 GGCAGGCTCTGTGGAAGTCAA | 32722 GGCCACTACACTGTGGGTTAGGAT | 43706 |
| 10081 CCTTAAGCGCATGCCAGACA | 21739 CAGGCCTGATTCATTCTCCTGCAA | 32723 GGGCAGAGAATCACGACTCCTT | 43707 |
| 10082 TTGTCAGTGGCCACGCCTTTC | 21740 GGGGAAAAGCCCTGGCCTTATAG | 32724 CTCCTGAAGCGCAAATTGTCAGT | 43708 |
| 10083 CCTAAGGAAGGGTCTCTCCTTCT | 21741 AAACTGTGGGTCACGCTGAT | 32725 ACGGCTGCCAACCTAAGGAA | 43709 |
| 10084 TGCCTCACTCCAGGGCTTTAC | 21742 GCTCCATGGGGAAGGACTCTTA | 32726 TTTGGGGTTCCTGCCTCACT | 43710 |
| 10085 TCCTTGGCCTCAGCGACCTT | 21743 CCACGTGGAGGGGCATTCTA | 32727 CGGTTGCCCAATCTCTCCTT | 43711 |
| 10086 GGAGACCATGGCTGCTGTTG | 21744 CCACCCAGAAGGGGTTATCCAT | 32728 ACTCCGATCGTCGGGAGACCAT | 43712 |
| 10087 CCCCAAGTCTTTTCTAGAGGGATGA | 21745 GGTACTGGATTCAGTTCAGTCTAACTTC | 32729 CTTTGGGAACCCCAAGTCTTTTC | 43713 |
| 10088 CCCTTGTGGGAAGTGAGAAACA | 21746 TGCCACCGATGCCAGACAGA | 32730 TGGAGAGTGGCTCCCTTGT | 43714 |
| 10089 AGGACATGACCTACCCCAGATTC | 21747 GCAGCCAGGTGCACAGAGCATT | 32731 GGGTGCGCTTGTGATAGGACAT | 43715 |
| 10090 CCACTTGGCTCTCATTTCTCTCTTTC | 21748 GGCGGAAAGCTAAAGGCATGT | 32732 ACCTCTTCCACTTGGCTCTCA | 43716 |
| 10091 CGTTTCCACACTCCCCATTATACTTACA | 21749 GCTCTTTGGTGAGCTGAACTCTTTT | 32733 GCACGTTTCCACACTCCCCATT | 43717 |
| 10092 CAAAAGTAGTCCTGGTGCTGATTG | 21750 CTTAGCCTGTGGCACTCAACT | 32734 CCAGCAGCAGACCACTTCAA | 43718 |
| 10093 GGTGACTGTGTACTGGGCTTCT | 21751 CTGCTGACCCCTTCACCTGTAT | 32735 GGAATGGCGTTGGTGACTGT | 43719 |
| 10094 GCCTTGAATGACGGCTCTTTCCTT | 21752 CTTTAGGGGCTGGCACTTTTCA | 32736 CCACGCTGTGTAAGCCTTGA | 43720 |
| 10095 AGAAACCGTTATGGTGGATTGCTT | 21753 CAGCTGTTTTGTGCCGCAAAGAT | 32737 GAAAGCCACCAAGAAACCGTTATG | 43721 |
| 10096 TGGTCCCACATTTCCAAGCAA | 21754 GCCCAGCCTTGTAAAGTGGTT | 32738 AGCCCGTTGGTCCCACATT | 43722 |
| 10097 GAGCAGAGATGGCTGTAAGTCAAAC | 21755 GGTGGATGGGCTGGTATACAAATG | 32739 CCTCTTTCTGTAGTGAGAGCAGAGA | 43723 |
| 10098 GGCATATCCCACCAGAAATGGGTTT | 21756 AGTATACTGCGGGGCCATTTC | 32740 CTGCTGGCACTGGAAGGCATATC | 43724 |
| 10099 CCGGGGCCTATCCTAGCATGT | 21757 AAAAGGTTCGCTCTGGATGGAT | 32741 TCCACGGGGATGACGCAGATG | 43725 |
| 10100 TTCCTCCAATCCAGTTGTCTCTTC | 21758 TTTGAAGCCACTGCAGTCTGA | 32742 ACCGGTCTGTCCTTCCTCCAATC | 43726 |
| 10101 GGAGGAAGGTGTGGACACATA | 21759 CTCAACAGGCTGGCAGTTGTAA | 32743 GGATCTCACCATCCAGGAGGAA | 43727 |
| 10102 GGGTTTGTAGTCGGAGCTCTTG | 21760 CGGCTGTGTTTGCTGCTTGT | 32744 CCCATCAGCACTGGGGTTGTA | 43728 |
| 10103 GCTCCACCTAAGTGTAAATGGAGTTCA | 21761 AGCAGAAGATCCTTAATGGCAGAA | 32745 ACTCTTCCTTGCTCCACCTAA | 43729 |
| 10104 CTGTTGTGGTCTTATGGAAACTTGATCTGA | 21762 GCTCAGTGCATCCCTTCTACCTAGT | 32746 GGCTTTCTGTTGTGGTCTTATGGAAAC | 43730 |
| 10105 TCCCCAAAACCCAGGTCCATGA | 21763 GCTCTGGGCTCTGCAGGATTT | 32747 AGGACCGGGCACCTCATTTGT | 43731 |
| 10106 GAGGAAGGCCAGATTGAGGGTAAC | 21764 CCACTTGTCAAGAACACGCAAGGATT | 32748 ACTGTCTGAGGAAGGCCAGAT | 43732 |
| 10107 AGACAGTTGCCAGAAGTCACAA | 21765 GGGGACCTATTGCTCACAGGAAGA | 32749 GGCTTCCTCGGAAAAGACAGTTG | 43733 |
| 10108 GCATCTGCTCAACAGATGTGTGA | 21766 GCAAAGGAATCAAGTGGTGTCAAGT | 32750 ATCTTGCCTTCTGCCAGCAT | 43734 |
| 10109 GGTGCTACCCACTTCCAAGGTT | 21767 TGGCCCGGTTCAGACTGT | 32751 TGTCCCAGCAAAGGGTGCTA | 43735 |
| 10110 TCCACCTCCAATCCACCTCAA | 21768 CCGAAAATGAAGTTACAGGGGAAA | 32752 TCATCCACCTATCCACCTCCAAT | 43736 |
| 10111 ACAGGTGGCCTTTTAGAGAGTTTC | 21769 GCGAAAATTCCTTCTTGCCTTCCTTAG | 32753 GGGTTCATGCTACAGGTGGCCTTT | 43737 |
| 10112 CCTCCCCTCTTACCCTGTTCTTCT | 21770 GCATTCCTTGGTGCAGGCTTTAAT | 32754 AGCCCAGCCCTCCCCTCTTA | 43738 |
| 10113 TCCAAGTGGAGTCGGGAGAA | 21771 GGTTGCAGTGGAGGAGTTCA | 32755 CCCTCATGGCTCCATTCCAAGT | 43739 |
| 10114 GACCCTACAGAGAAAGTTGTGAACAT | 21772 CCACACACTCAACCCACCTAATG | 32756 TGTTTGCAATTCTGTGACCCTACA | 43740 |
| 10115 GGGCAGAAATGCCCAATGTGAAG | 21773 CACCCTGCAGTCCAGTCAAA | 32757 GGAAGACATTACCAGGGCAGAA | 43741 |
| 10116 CACTCAGCAGATGAGGAGATGTGT | 21774 GGTCTGCTGTGCAGATTCCTACT | 32758 GCAAACAACACACTCAGCAGAT | 43742 |
| 10117 ACACAGGTGCCTTCCACTATG | 21775 CCATGCCCAGTCCATACTTGCTT | 32759 TGACGTGAGAGGGGTACACA | 43743 |
| 10118 TTGGCGGCGTCCACTGAGA | 21776 CCTCTCTTCCGTCTCCTTCCATA | 32760 ACTTCCTGTGGGCCAGTGTTG | 43744 |
| 10119 CGGGCCTCTTGGTTATTCTAGA | 21777 CTGTGGTAGCTTGTTTCGTGCAA | 32761 AGACACCACGGCCTCCTT | 43745 |
| 10120 CGAGGCAGGACTTCCCTTTGTT | 21778 GCTGTTTCCCAGCAGTATGGAAATG | 32762 AGGGAACGAGGCAGGACTT | 43746 |
| 10121 CTTCCTGGATGGCTGGACTTAAA | 21779 GGGCCAGAATCTAGTTAAGGAGAGTTTAT | 32763 CTTTGGAATCTGTGCCTCCTGGAT | 43747 |
| 10122 CAAGTCCAGCCTACTCAATTTACGTT | 21780 AAGCCAGCCAGGGCACTA | 32764 ACACTGCAAGTCCAGCCTACT | 43748 |
| 10123 CCACCTTTCCTCTGTTTCAGCCTTA | 21781 GAGAACCGAGACTCACAACATTAAGA | 32765 GATTTCGTACCACCTTTCCTCTGT | 43749 |
| 10124 CAGCACATGGGAGCTGGTTTTG | 21782 CTGGCCACATTCACCAACCAAAG | 32766 TGCAGCTGGGGTGTTCTCA | 43750 |
| 10125 CAGCAGCCATGCTTCATCATC | 21783 AAGCCAGCTCAGCAGGATTG | 32767 CAGCCAGCAGCCATGCTT | 43751 |
| 10126 ACCTCCCGCCATATTCCTCTCA | 21784 TCTCCACAGCTCACGCTGGTA | 32768 TCTCAGAACCTTCCCGCCATA | 43752 |
| 10127 GCAGGGGAAATGTGTGCCTTATTCA | 21785 CTCAGCACAGCCCATACAGTAG | 32769 GGCAGAGAAGCATGCAAGGGAAA | 43753 |
| 10128 CCTATGCGTTTCCGGTCTGTGCAT | 21786 AGGAAACAGGTGCCCCTACA | 32770 GGCTGCCTTCCACCTATGGTTT | 43754 |
| 10129 GTGCTTATCATCCAAACCCAGTCAAC | 21787 CAAAGTGAGGCACGCATACTCATA | 32771 CATTGGGACCAAGTGCTTATCATC | 43755 |
| 10130 GGGAGTGGATGCAGCTCAACA | 21788 GGGGAGGCAGCATGGAAAA | 32772 CTGTTGAGATCAGAGGGAGTGGAT | 43756 |
| 10131 CCTAAGGATGTCTGCTAAGCACAAA | 21789 AGAGGCGTCCACGCGTTTC | 32773 AGGGCCACCCGTAATCGTGTCT | 43757 |
| 10132 GCAGTTAAGTGGTTTAAGTGGTGTTAG | 21790 GCACCAGCCCTTCCTCACTTT | 32774 GCACAATGGCAGAATGCAGTTA | 43758 |
| 10133 GGCGGCTCTTTAAACAAACTCGTTCT | 21791 GCCCGCTTAATAGCTGAGGTCACA | 32775 AGCCAGATGGCGGCTCTTTA | 43759 |
| 10134 CAGTTTGACTTGTGATCCATTCCACTTTG | 21792 CACAGCTTTTACCTCCTAAGGAACTTG | 32776 TGTGCTGATACTCAGTTTGACTTGT | 43760 |
| 10135 GGAGTCTTCAGTGGTTTTTAGGTTCAAG | 21793 CTCTGGACCTCGGTTTCTTTGTTTC | 32777 CCTCCTAAGAGGAGTCTTCAGTGGTTT | 43761 |
| 10136 GAGAGGTAACTATCACTCTTGCCTTTT | 21794 GCCACCTGCCATAGCCACTTA | 32778 GCAAAGACCCTTTGAGAGGTAAC | 43762 |
| 10137 CCACCAAAACTTGGACTGCCATA | 21795 CCCTAAGAACCAGCACCTTCTATTG | 32779 GGCCTGTTCCACCAAAACTTG | 43763 |

FIG. 36P6

| | | | |
|---|---|---|---|
| 10138 CGGGGCTTCTGTGGGTCATT | 21796 CTCAAAACCGAAATGTGACCCTTTTC | 32780 GGCATAAAGGCGGGGCTTCT | 43764 |
| 10139 GACGCTGATCTTTACGCCCAAT | 21797 CGGTACTCGGCCACACCAA | 32781 CTGCATGGAGACGCTGATCT | 43765 |
| 10140 GCAGTGGGATAAGTGGCTTCAA | 21798 CTCAGTGGCCTGATAATTACATTGAGT | 32782 GCAGAAATCTTGCAGTGGGATAAG | 43766 |
| 10141 GGGATCTGAACCTCTTTGGGAT | 21799 CAGCCACCAGCTCTGTATAGTAGTA | 32783 TGAGAGGAGCACTGGGATCTGA | 43767 |
| 10142 GAGGAACAGGCTCTCACTAGACATTG | 21800 GGCCAGGAAGTCCACAATCA | 32784 GCAGGAAGTCTCCATCTATGAGGAACA | 43768 |
| 10143 GCCCAGTTTCATGGTCCTAGAGAA | 21801 GCTTCCCATACTGGTCTTGATGGAT | 32785 TGAAGAGGATTCAGCCCAGTTTC | 43769 |
| 10144 CCGAGGACTATAGAAGAGTGAGCTTTC | 21802 ACGGAGCCGGAATCTCTGA | 32786 CTCAGAAGTTTTACCGAGGACTATAGAAG | 43770 |
| 10145 GAAGGGGAATGAACAAGACGAGAGA | 21803 CCCCTAAAAATGGGTGCAGGAATC | 32787 GGCCAAGAAGGCGAATGAACA | 43771 |
| 10146 GCTCAGCTCACAGTCCCTACAA | 21804 GACCCTTCCTAATCATGCAAGTCTTT | 32788 ACCCCACCTCCATTCTCCTTAG | 43772 |
| 10147 GCTTTTGGTTGGTTACAGTGGGTTAC | 21805 GTCTTACAAAGTCGTTGATCCCACAA | 32789 TGGTGGCTTTTGGTTGAGTTACA | 43773 |
| 10148 GGACTGTGTCCACATCTGCAGCTT | 21806 TCGGGCCATGTCATCTGAGGAT | 32790 CGGTAGGTGAAGGGACTGTGT | 43774 |
| 10149 GCTCCATCAGCTTAATCTACCCTACT | 21807 GGACTGGCTGCCTAAACTGTCA | 32791 GGTGAGGCTTTCTGCTCCAT | 43775 |
| 10150 CTGGGAGTGTCTCTCTCTTGAGT | 21808 GCAAAGTGAATCTCCACCGAAGT | 32792 CAAGCCCCTCTCGGACTGT | 43776 |
| 10151 GAGAGGGGAGAAGCAGGAGATA | 21809 AGAGGGTTGCGTGGATGGTTAC | 32793 ATGCGGGAGAGCGGGACAAG | 43777 |
| 10152 CCAGCCCAAGATGTCTGTGGAT | 21810 GCTCACCACTGCTCTTGTTCCTT | 32794 CTGAACTCTGCCAGCCCAAGAT | 43778 |
| 10153 CCAGCATTCCCCTCCTCTCAAAATC | 21811 GCCCCAGGAAATGTAGCCCTAT | 32795 TGCCACCACGCCAGCATT | 43779 |
| 10154 TGGAAAGACAAGCCCCAGACA | 21812 AGATGCTTTCTCGCATGTAGTTTG | 32796 CTGGGAGTGGGAGGAATGGAAA | 43780 |
| 10155 CCACATTCCAAAGCCAGGGAAAA | 21813 TCCATTACTCGGCCTTGACCTTTG | 32797 TGCTATTGCCTTTGAACCACATTC | 43781 |
| 10156 CCACTTTTGAGTGGAAAATGCATCCAA | 21814 AGCCACCACGTTGCTGTGAT | 32798 CCCCTGTAGCCACTTTTGAGTGGAAAA | 43782 |
| 10157 CTGCTGATTGCTGACAATTTGGATT | 21815 AGTGACAGCTCAATTCTGATGCTA | 32799 GGAGTTACTGCTGATTGCCTTGACA | 43783 |
| 10158 ACCAGGGACTGAGCATTACCAA | 21816 CTGCAGGTCCATGTCTCTCTTC | 32800 ACACTGGGAACCAGGGACTGA | 43784 |
| 10159 CCATCTCAACACTCACCTCCATTG | 21817 CAACCCAACAGAACCCAAGACT | 32801 TGGGGCCACCATCTCAACACT | 43785 |
| 10160 GCGTGTGGAAAACTTGGCTCTCA | 21818 TGATGCTTGCATGAAGTCATGCTT | 32802 GCCTGGTTTTCTGCGTGTGCAA | 43786 |
| 10161 ACCTCAGCCTCCAGCACCTTA | 21819 ACACAGCAGCTCCCTCTTGT | 32803 AAGCGGCTGCAGGCTGGAA | 43787 |
| 10162 ACCAGCACAACCATGAAAACTCT | 21820 GCCAACTACCAGTCACTGTATCA | 32804 CTCTTCCTACCAGCACAACCAT | 43788 |
| 10163 GCTGCAATGGAAGCCACTTGA | 21821 AGGAGCTAAACATACAATGGTGACA | 32805 CCACCTCTGCTGCAATGGAA | 43789 |
| 10164 CCCGCGCACACATCAAAGCGAA | 21822 CGGTTTGGGCTCTGTTTCACCTCTA | 32806 ACACCACAGGCCCGCACACA | 43790 |
| 10165 GGGTCAGTGGGAGTCCTGTCT | 21823 GCAGAAGAAGCATGGGGTTTAAGT | 32807 TGATGTAGGAACCAAGGGTCAGT | 43791 |
| 10166 AGGCTTCTCCTTCCCAGTCA | 21824 CCCCAAGCCTATTGAGACATCTGTA | 32808 AGCGCTCTCCAGCCCTTGAA | 43792 |
| 10167 GCCTGGGTTCTAGGTAACAAAGCAA | 21825 TCTGCCTGGCTCCCGAAA | 32809 AGAGGGCCTGGGTTCTAGGTA | 43793 |
| 10168 GCCCCAGACTGATTTGGACTT | 21826 GAATGCATGTGGGATCCATTACTCA | 32810 AAGGCCAGTTAGCCCCAGACT | 43794 |
| 10169 CAGAAGCCTCCGACCAGATCAGT | 21827 TGACCAGGGAAGGAAGCAAACT | 32811 ACCAGTTGGCCATCCTACACAA | 43795 |
| 10170 GGAACTGTCCCTGCTGGCAAT | 21828 TGATGGAAGATGAACACTCCACTCG | 32812 CTCCATTTGCACTTTGGAACTGT | 43796 |
| 10171 AACCCATCACACTGTCTTAACTTGA | 21829 GTTTCATGTGGGTTTTTGGCAGTT | 32813 CAGGCACAATTTAACCCATCACACT | 43797 |
| 10172 TCTTGCTTGCCAGCATCAGTAG | 21830 AGAGCTGCCTAAAGCTATCCTCTCA | 32814 GCTCGCCCTACACTCTTGCTT | 43798 |
| 10173 CACCTCGCTTCAAAATCCTCTTC | 21831 ACTTGGCTAGGGCCTTCAGA | 32815 TCTTCCAAACACCTCGCTTCAA | 43799 |
| 10174 GCAAATACCGACCCCACTATGTCA | 21832 GTGTTCCCATCACATTTTCGGTATG | 32816 TGTAGTCCACACGCTGCAAATAC | 43800 |
| 10175 CAGGGTGGAGTGAAGGGCTTTT | 21833 GGTGCAAAATCTCATTCTCCTTGAA | 32817 AGACTGCCAGGCTGGAGTGA | 43801 |
| 10176 GCAGGTGTTTTCTTTCCACCTGTAG | 21834 TGAAGGTGGGGAGGGTAAAGT | 32818 TGAGTTCTTCTCTGCAGGTGTT | 43802 |
| 10177 GCTCACACAGGCTATGGGTCCTA | 21835 GGTGAGTTCCTCGAATGGTGCAT | 32819 TTTGCCCAGAGGCTCACACA | 43803 |
| 10178 TCCACTTGTCTATGTGCCTCATTC | 21836 AGCAGGCCCTGAGTTCTGT | 32820 CTTGCTTCATCCTCCCACTTGTCT | 43804 |
| 10179 TCTGCAGCCCAAAAATCTCATCT | 21837 CAGGCTCATGGGCAGAAAGT | 32821 CTGAAAAGTCTCAGCCCAAAA | 43805 |
| 10180 CCCAGCGATTGTGTATCTAGGTGTT | 21838 TGCCCGGCCTGTGAACAT | 32822 CCTCTTAATATGACCCAGCGATTGTGT | 43806 |
| 10181 CCTCCCTAGAAGGAACTGTAGTTAATCA | 21839 ATGCACGGAATACCTCTGGAAAT | 32823 GGTTTCTCCTCCCTAGAAGGAACTGT | 43807 |
| 10182 GCCAGCAGCTGAAGCTAAACCAA | 21840 CGTGGCCCATGAAGGGTCAA | 32824 CTCCATTGCCAGCAGCTGAA | 43808 |
| 10183 TCATGCGTGCTGGGCAAA | 21841 TCCTGCCACCCCTTCTCCAT | 32825 TCCTTGGGACCTGGGGTCAT | 43809 |
| 10184 GCTTGGTTTACGCCCAGGAA | 21842 AGACTCCACCTTGCTTCTGATCT | 32826 TCCTCCATGGTTAGCTTGGTTTAC | 43810 |
| 10185 GGCCACAGTCTCTGCTTGAA | 21843 AGAACAGCCTGATTGCAAAGATGA | 32827 AGCCATGGCCACAGTCTCT | 43811 |
| 10186 CTCAGATATGGGTATGTGACCATCAA | 21844 AAATTGGTGGGATACCATGTCCAA | 32828 ACACAAACAACAGTCCTTCTCAGAT | 43812 |
| 10187 CCCTCCATCCACTCGCTACT | 21845 TCCATGCCCACCTAACATCTCA | 32829 CAGGGTTCCAGCCCTCCAT | 43813 |
| 10188 CCTTATAGCTGCTTGCTAACCAAAAGT | 21846 GGATGGGCAAGTGGTTGTATCT | 32830 GGTCCACTTCCTTATAGCTGCTT | 43814 |
| 10189 GCTATCCTCCTCACCCAGTCA | 21847 TGAGTGTCCCTGACCTCAAGT | 32831 CCAAGTGTGCAAAAAGAAAGGCTAT | 43815 |
| 10190 GGAGCAGTCAGGTGAGAGGTAAGA | 21848 AGGCCAAGTCCACGATCT | 32832 GCACTATGAGAAGGGGAGCAGTCA | 43816 |
| 10191 GCCCTGGGAAAGAAAAGTCAGA | 21849 GGTGGGGAGCACTGTTCTCAAG | 32833 AGGGAATCTAGCCCTCGGGAAA | 43817 |
| 10192 CAGCAAGTCATGGCAGGGAAA | 21850 TGCAGAGCAGGACAGGGATT | 32834 CCGGGGATTAACCAACAGCAAGT | 43818 |
| 10193 GTCACGATCCCTATTCACCTCATC | 21851 CGGCTCTTCCTGCCTTCA | 32835 CCCTGATGAAAACACAACTCTCACCAT | 43819 |
| 10194 GTGAGTGTGGCACCATGGATGTA | 21852 GCACTCCTGAAAAGTGGACCCAAAT | 32836 TACCCCGTAGCCTGACTGT | 43820 |
| 10195 CCAGCCATGAACCTTCCTGT | 21853 GACCCACAAAGCTGAAGATGTTTAC | 32837 ACCATGCCCAGCCATGAAC | 43821 |
| 10196 CTCTGTATGCCAGCTCCCTTC | 21854 AGGGATTCACGCTGTCTTCCATTC | 32838 CCTCTCTTGCCACATGATCTCTGTATG | 43822 |
| 10197 GGTGGAAGGAACATAGAGTTGCAT | 21855 CAGTCTTTACTTAGTGGGCCCAAATC | 32839 GGGTATGGGATAATGCTGGAAGGAACA | 43823 |
| 10198 GCATCCATTGCTATCTCACCATCAGT | 21856 CGAAATCAGCAAGCTGATGTGTCA | 32840 CATGCGTCATCCAAACGATCCAT | 43824 |
| 10199 GCTATGCCACTTCCTCTGAGACT | 21857 ACAGCAGGGACAAAAGGATCA | 32841 CTCTCCTTTGGTTTTCGATCTGCTATG | 43825 |
| 10200 GCACAGCACTGAGGACAGCTT | 21858 TTTCCCAACGGCCTCTCACA | 32842 CGTATTCTGTACCACAGCACTGA | 43826 |
| 10201 AGAAACACCAAAGGCCAGACA | 21859 TGGTCCTCTGGCTAGAAACAGT | 32843 AGCTGGAAACCTAGAAACACCAA | 43827 |
| 10202 GCACTGTGAGCACAGGTTCTTC | 21860 GCTGTGCAGTGAGATACAGGTAA | 32844 TGCCACCCAGCACTGTGA | 43828 |

FIG. 36P7

| | | | |
|---|---|---|---|
| 10203 GACCCTTCAATCTGAGCTGAGTT | 21861 CACAGTCCCAGGCTGACTTCATT | 32845 CCTGCTGGAGACCCTTCAATCT | 43829 |
| 10204 GCTGGGCCCCATAATTGAAGGTA | 21862 CCAAGCCCTGCTGGTTCA | 32846 AGGCTGTGCTGGGCCCCATA | 43830 |
| 10205 GACCTTCTGGGAACCAGTTTTCT | 21863 GGAGGAGAAGACTCATCCAGTCAA | 32847 CAGCTGGACATACCAAGACCTTCT | 43831 |
| 10206 CACTGGAGGATCACAAACTGTATTTTC | 21864 CCATTAAGTCCAAGATAGAGGAGCCATT | 32848 GTCTGGTAFTACACTGGAGGATCACA | 43832 |
| 10207 CGCAAAACTTGCAAGGAAGGAGAAG | 21865 ACAACTCAGCGGCCTGTAAG | 32849 ACTAGCAAGTCGGCAAAACTTGGAA | 43833 |
| 10208 GAACTCCCGGCTTTGAACAATTC | 21866 CTCACGCTTGTGAAACCAACAT | 32850 ACCCTGAACTCCCGGCTTT | 43834 |
| 10209 GCCTCTCAGGGCGCATTTGTAT | 21867 ACAGCTCCAGGGGCACTAAACT | 32851 TGACATTGCACAGCGTCTCA | 43835 |
| 10210 GCCACTGTGTCGAGTCCTTCAA | 21868 GGCCCACCTCCTCAGGATTAGA | 32852 AAGGCTGGGCCACTGTGT | 43836 |
| 10211 TGAGGAAGAGCGAGCTTTCTTAG | 21869 CTGGAGCTAGAGGAAAGGGTGAA | 32853 GTGCATGCATGTGCTGAGGAA | 43837 |
| 10212 CCTAGAGGCCACTGTTACTCTGAA | 21870 GCAGGCACACAAGCTTTCTTC | 32854 CAGACGTTGGGCATCACCTAGA | 43838 |
| 10213 AGCTGTCCAAATCCAGCTCTAC | 21871 GCAACCTTGGTGAGTGAGCT | 32855 GGTTGGCACACCTGCATTGA | 43839 |
| 10214 GGAAAGGCTTATCGGGAGGTTGT | 21872 ACCATGTGGGGCTCAGAATG | 32856 GCCCTCCGTGGAAAGGCTTA | 43840 |
| 10215 CAGGCACCAAAGATGTAACTACTAGA | 21873 CCGCTAGAAAATTTCGCAGGATTAG | 32857 GAGATCCTCAGGCACCAAAGATGT | 43841 |
| 10216 CGTCCTCCTAACCTGGTGGTCTT | 21874 CCCTTTCCCAAAACTAAACCACCTTTG | 32858 AGGTGCCTCTCGTCCTCCTAAC | 43842 |
| 10217 GLTGAGTTCTGGCAAATGGGAAA | 21875 TLAAGAGGGCAGTCCAGGAA | 32859 CCTGACCTTGGTGCTGAGTTCT | 43843 |
| 10218 GCCATCTTCACAGAGTTCATGGTCTA | 21876 ACGGACCCATGTGACTGTCT | 32860 CCCCTGCTATGTGCCATCTTC | 43844 |
| 10219 GCAAAGGCCCTGCTAATTTTCTCTGT | 21877 GCTCCCTTCAGAAGCATGTACACTAA | 32861 CTTGTGCAAAGGCCCTGCTA | 43845 |
| 10220 CCGGAGTGAGAAGACAAGGAGTCT | 21878 ATTAGGCCCAAGCTGGCCAGAAG | 32862 ATGCCACCGGAGTGAGAAGA | 43846 |
| 10221 GCTAAGAAGAAAGGCTCACTGAAAGT | 21879 GTCAATGCCTGCAACAATGACAA | 32863 CCCAAACATGGGTGGGCTAA | 43847 |
| 10222 CCTTCAACCCGGGATGCTA | 21880 TGGGTCTCAAAGTGGTTGGATTC | 32864 AGCTGGCACACCCCTTCAAA | 43848 |
| 10223 CAGGGCTTCTCTGCTTTTCCAA | 21881 GAGAACTTCTAGAGAAACAGGGCTAGTT | 32865 AGTCGTTAAATCTTCAGGGCTTCT | 43849 |
| 10224 CCCTCCACTACTCCCTGGATTT | 21882 GAGTCCCAGGACTACAGATCTAGTGAAA | 32866 CTCTTAACCACTACCCTCCACTACT | 43850 |
| 10225 CAAAACCGTTCACCCACACATTG | 21883 CCAGCTTAACTCCCAGCTGTCAA | 32867 GGCAGCAGAGGACCATTTACAA | 43851 |
| 10226 AAGCCTTCAGAACCTGAGACTTC | 21884 AGCTCCCCTCTGGGTGAGTATT | 32868 GCAGTGTGTAAAAAGCCTTCAGAAC | 43852 |
| 10227 GGAGCCAGTTGTCAGTTGCGTTA | 21885 CCCCACAATGGLAGGATCTACAAC | 32869 CAGAGGGTGGGAGCCAGTT | 43853 |
| 10228 TGGTAGCCTCACTCCTGCAA | 21886 TGGTACCACAAAGTGAGAAACGTA | 32870 CAGATGGCCACTAGACTCTTCGTA | 43854 |
| 10229 CCAACACCACAGTTACCAGGAA | 21887 GGTCCCTCAGTGTTGCAGCTAT | 32871 GGCCCTGGTGTCATTTCCAA | 43855 |
| 10230 GGCAGTAACCATAGTCCATGCAA | 21888 GCTCTGTACCCACACTAAGGABAG | 32872 GGGAAGTAGGAGTGGCAGTAAC | 43856 |
| 10231 GCTGTGGTTGGCTGGTAACT | 21889 GCCAGACAAGTAGCCCACAGA | 32873 CTCATTCCATTGCTTGCTGTGGTT | 43857 |
| 10232 CCTCTTCCACCCTTTACTTTCAGT | 21890 GCCTTCAAGAGACTCATCTAACACA | 32874 TGATGCCTTCCLACCCCTTT | 43858 |
| 10233 GGAAGTCCCAGAATGAGGTTCA | 21891 GCTGCCAAAGTGAGCACAATTCA | 32875 TGGGCAGGAAGTCCCAGAAT | 43859 |
| 10234 CTGGGAAGGGTTACAGTGAGTCAT | 21892 TTGCCAGTGCTTCCAACTCA | 32876 GCATCCTCTGGGAAGGGTTACA | 43860 |
| 10235 AGCTTGGAGCTCTGGGGTCTT | 21893 CCCATCACTCCGCAAGAGACA | 32877 TCTGGCACCCTGAGAGCTT | 43861 |
| 10236 CCACCAAGACGGGTCTCTCTGTAA | 21894 TGTCTGCCGGAGGGCTTATAGT | 32878 CCTCTGCTTTCTAGTTCCACCAA | 43862 |
| 10237 GCTGTTCACTCCTCCTGCTCTA | 21895 GGACAGGGTACTATGTGGAAAG | 32879 CCTGGTCACATTAGGCTGTTCACT | 43863 |
| 10238 GTCACTTAGAAGCACCCATCTGT | 21896 CAGATGGAATCTGCTTAGATGTGGATGT | 32880 GCTTGGCCTGCAGTCACTTAGA | 43864 |
| 10239 GGAGCAGGGCTAACTCACATGAAG | 21897 GAGAGATGCCAAGAGTCCATACATTG | 32881 TCCTTGTGGAGCAGGGCTAACT | 43865 |
| 10240 CGTGCTGTTAGGAGCAAGAGA | 21898 CTCACGGGGCTCCTTTTGA | 32882 AGGAATAGGGGCCGTGCTGTTA | 43866 |
| 10241 CCTGAATCTGTTGTGGATCAAGTGT | 21899 GTGGGATGGAAGGTCCAGAAAC | 32883 CCCCTGGTCTGCAATCCTGAATC | 43867 |
| 10242 TGGGATGGAGGCAGAGGCTTGAA | 21900 TGCACCTAGGCGGCTGTGA | 32884 TGCAGAGAGCCTTGGGATGA | 43868 |
| 10243 GGGCACTACACTCCAAGATGCAA | 21901 GGGACACAATACATGCCTTGTTA | 32885 GCAAGGATGGGAGCACTACACT | 43869 |
| 10244 CAAACGTGGGTAGACCCGACACT | 21902 CGTGCAGGACTTGTCGTTCT | 32886 GCAACATCACAGACAAACGTGGTA | 43870 |
| 10245 ACTTCTGGCCTTAAAATGGAGTGTCTAC | 21903 GCCCTCTCTGTATTGCCGTTTG | 32887 GCAGAAACCAACTTCTGGGCTTA | 43871 |
| 10246 CGGTGGCTATGCGTGTAAAGA | 21904 GACTAGAAGACCACTTTTCCCAAATG | 32888 TCCTCCCCATAACGTGGCTAT | 43872 |
| 10247 GCTGAACCAATCAATCTGAGAGTCTT | 21905 CTGAGGTTCACACTGAAAGGAACAA | 32889 CCTGTCTTGGGAGCTGAACCAA | 43873 |
| 10248 GGCTGCCATCAAGTCTCTCTCTGT | 21906 GACAAGTTACGAAGTCACTGGAATCCTCTTT | 32890 CTGCGTTGGGCTGGGATCAAGTTC | 43874 |
| 10249 TGCTCTTGTTTCATTTGTGCTATG | 21907 GTGCCATGTTTCCTGCCACTT | 32891 GCTTCGCTTGCTCTTGTTTCA | 43875 |
| 10250 CCAGCTACAGTGATCTGCTT | 21908 AAAGTCCTCAGAGACCAAGAGTTG | 32892 GCTTCAGATCCAGCCACAGT | 43876 |
| 10251 GGTTCTTCATTTTGGAGAGCACGATTG | 21909 CCTCTCCCTTTCCTCTTGTCTTTA | 32893 CGAGGGATCATAGGTTCTTCATTTTG | 43877 |
| 10252 GGCTGAGTCCATTTTATAACCGTGTGT | 21910 GGCTATGTATGCCCTTGTGTGTCATATTC | 32894 GGCACCTGGCTGAGTCCATTT | 43878 |
| 10253 GGGGCTGTCTCAGCTCTTTGT | 21911 CAGGGGCCTGATAGTGAACTAAAC | 32895 GAGACAGAGAGGGGGCTGTCTCA | 43879 |
| 10254 CCCACTGGAAGAGTGACTTAGCTT | 21912 TGTAAGCCTAGTTCCTTCCTCATTC | 32896 TCCACCAACTCACCCACTGGAA | 43880 |
| 10255 CTTGCCCAAACCCACTCCTT | 21913 CTCCTTCTTTCTCCAGGAACCATTAG | 32897 GTGGGAAGTAAGAATCTTGCCCAAAC | 43881 |
| 10256 CCCCAGTGCCTCTTGTCTCTGATA | 21914 GGGTCCTACAGGGCACAGAT | 32898 TTTCTGGCCCCAGTGCCTCTT | 43882 |
| 10257 GTGAAAGGGGAAGCGAAGATG | 21915 TGGGTTTCTGTTGCAGTTTGACT | 32899 TCCTTGGGATCAACACATGTGAAA | 43883 |
| 10258 PTTCTCTTCCCTCTCAACTGATT | 21916 CTCCCAGCTTCATGGGAGTTTC | 32900 ACCAGGACTGGGTTCTCTCTC | 43884 |
| 10259 CCTGCCTTACTACCCCAATCATC | 21917 AGCAGACTCTTAAAATCCGATCTGT | 32901 CAAGTACCATCCCTGCCTTACTAC | 43885 |
| 10260 AGGCTCAGAGGCAAGACAGA | 21918 TGCAGCCATAGGTAAATGGCTTT | 32902 AGCAGGGACAAAGGCTCAGA | 43886 |
| 10261 CCCAGGACCACAAGCACACTTT | 21919 GACAGCCTTTCCAGTGCTATTCA | 32903 CCTGCACCCAGGACCACAA | 43887 |
| 10262 CACGGAGGTGAGCATGATGCAA | 21920 TCTTTCCCGCCTGAGTGTCA | 32904 GGTTGATGGCTGTGGGGAACA | 43888 |
| 10263 CTGGGGTCTGTCTGTGGATGATCT | 21921 TGCTGCCAGGTAAGATGCGA | 32905 TAGGTGCGTGGGGTCTGTCTCT | 43889 |
| 10264 GCCTCTCCACCTTTTTAGAATAAGGGTATC | 21922 GGTGACTCAGGAACAGGAGAACT | 32906 GGGATTACAGCCTCTCCACCTT | 43890 |
| 10265 CTCCTGCAATATCCTTATTCAAGAGT | 21923 GCTCACCACCATCAACACT | 32907 CACGGCAGTTAGACTCCTGCAAT | 43891 |
| 10266 CCAAGCACACATTTGCCTCTCTACT | 21924 CTGCAGTTGCTTCTCCTCACA | 32908 AGTCCAGACCTCTTTCCAAGACA | 43892 |
| 10267 CTTTCACCGTTAACCTGCGTTT | 21925 GTTCCCAGTGTACTTGGATCACAT | 32909 CCAGTCTCTTTCCTTTCACCGTTA | 43893 |

FIG. 36P8

| | | | |
|---|---|---|---|
| 10268 GCCCTGTATTACTCCACAGTGTATG | 21926 CTTGAGTGTGACTGAGGTAAATGAAAG | 32910 CCACTGTTCAAGTGAGCCCTGTA | 43894 |
| 10269 GCCTGGATGGTTCTAGGGCTTTC | 21927 CTCCTTGTGGACACTCGACTACA | 32911 TGCACAGCCTGGATGGTTCT | 43895 |
| 10270 CTTGCACACAGAGGGTGGTCATT | 21928 CCTCATTTCCACCATCCTGTCCTT | 32912 GCCATGCCTTGCACACAGA | 43896 |
| 10271 GACACTGACTCTCTTCTGTCTCAGATT | 21929 AGAGTCTGGCCAAATTCCAGTAAA | 32913 GGGACCTTGACACTGACTCTCTTC | 43897 |
| 10272 CCCTCTTCTCCTTCCACCAGTT | 21930 GGCAGCAATGCCTGCTACAT | 32914 ACATCCGCCCCTCTTCTCCTT | 43898 |
| 10273 GAGGTGGCAATAGCCTTGTGTT | 21931 TGCCAGGGTCAATGGAGGAA | 32915 TGGTGGAAAGAGGTGGCAATAG | 43899 |
| 10274 GCACACTTCCCATCTTGCTT | 21932 CAGCCAAACAGAATACTCCAGCTT | 32916 AGCTAGTGCCCTCTTGCACAAC | 43900 |
| 10275 GCCACCCTGCATATTGCCTTCA | 21933 TCAACCTCCCCTGCCATGGTTA | 32917 TCCCCATGCCACCCTGCATA | 43901 |
| 10276 GTTCCCCACATACCCTTGCTTGT | 21934 AGCCGGATGGTCCAGAGATGA | 32918 CCACTGGATAGAAGAAGTTCCCCACATA | 43902 |
| 10277 GCCGATGGATGCTAACCCAGTT | 21935 TTTGCCAGAAGTTCAGCAGTCT | 32919 GCTGGTTTGCGGATGGATGTCT | 43903 |
| 10278 AGCGTTTGGCCTTGGGTAAG | 21936 GGGGACAAGCAAGGCATTAGTGT | 32920 ATGACCAGGTCGGAGCGTTT | 43904 |
| 10279 CCGGAATATCAGCCCCATATTTATCTACA | 21937 TCCCAAATGAGACCAGAGTTGAAG | 32921 AGTCGGAATATCAGCCCCATA | 43905 |
| 10280 CTGTGTGGTTGCATTCCCTTGA | 21938 GACGAATGTCCTCGACAGCATACA | 32922 GCGTCTGACCCTGTGTTGGTT | 43906 |
| 10281 CTGCCTGCTACTGCAAGCAA | 21939 TGTTTAACACGAGACAGAACCCAAA | 32923 TCCTCCCTTCTGGCTGTCTAC | 43907 |
| 10282 GGGACACAGAACAATTCAGGACTCT | 21940 CCAGCTCACGTGTGTGGCTTA | 32924 ACCCTGACTTTGGAGGGACACA | 43908 |
| 10283 CCTGGGGCAAGTTTTCAAGCCTATC | 21941 CCTCAACAGCCCTGAGTCTGTTTC | 32925 GGTAGCCTGGGGCAAGTTTT | 43909 |
| 10284 GTCACCCAGTTCCTACTTGACAGT | 21942 CGAAGAGGGGATCCAGCTCTAAT | 32926 GAATCTAACAAGTCACCCAGTTCCTA | 43910 |
| 10285 GTCACAAACCCCACAGTTACTCCTT | 21943 CCATGCCAGCAGAACTTTCACT | 32927 CCCGTAGTCACAAACCCCTACA | 43911 |
| 10286 AGTGCTTGATTCCACGTATCTTT | 21944 GTAGGATAAATTAAGGCAAGCGTCTTC | 32928 GCCTGGCTTAAAATAAGTGCTTGA | 43912 |
| 10287 GTTAGGTGCCATTAGCAGCAGTA | 21945 CATTTCCCATCATCCTGGTTCTTTC | 32929 AGCAACCATGTTAGGTGCCATT | 43913 |
| 10288 GCCCCTGGTTAGTTACAGGAAGAAG | 21946 GGCTTCAGGCACCAGAATACACA | 32930 TTTTGTGAGCCCCTGGTTAGTT | 43914 |
| 10289 CCTACCAGATAAGCCTTGAGCAAT | 21947 GGCTGAGGGGCCTTCAATCAACA | 32931 GGGCACCTTTACTCATCCTACCAGATA | 43915 |
| 10290 GCAGACCTGTCTCGCTTAGTTC | 21948 GTGCAGTCGCGATGGTAGT | 32932 TAGCCACCCTGCAGACCTTGT | 43916 |
| 10291 GCCAGAAGTGCCTATTCCTAAACCAATC | 21949 GTTCACACCAGGCAGTGATCT | 32933 ACTGGCCAGAAGTGCCTATTC | 43917 |
| 10292 GCCTCCAGTTGGTTCAGAAAATGA | 21950 GCTCTTGACACAGTCTAT | 32934 CGTTTTCTTGCCTCCAGTTGGTT | 43918 |
| 10293 CGCTACCATGTCCAGCTAGGTT | 21951 GCCTAGGCAGCATAGTGAGATTC | 32935 CTACAGGCACACGCTACCAT | 43919 |
| 10294 ACAGACACCAGCCAGCTTCA | 21952 CACAGAAAACTAAGTCGCCCAGAGT | 32936 GCCCAACGCTCAGACAGACA | 43920 |
| 10295 GTGGACTCTGGTCTACATGGGAAA | 21953 ACCTGGACTCCTGCTTGCTT | 32937 GAGGGTTAGTGGACTCTGGTCTA | 43921 |
| 10296 GCAGTTCTTCACACTCCTTGCTAT | 21954 GGAGGTTATTGGCTTCTGCTTCT | 32938 ACAACAGAGTTAGCAGTTCTTCACA | 43922 |
| 10297 TGCCAAGAACCTTAGGGACATC | 21955 AGCAAGGTTCAGTCTGGAAATGA | 32939 CCCCAGATGCCAAGAACCTT | 43923 |
| 10298 GGCACCCAACCCATAAAAACCATCA | 21956 GTTCAGACCCACGAAAAGTACTTGAA | 32940 AAGGCACGTATGGCCTCAAC | 43924 |
| 10299 CTCATTCCTAACCCAGGACTGAAC | 21957 CAGCAACTAAGGCTTTGCCATT | 32941 CAACCAGAAAGCACTCATTCCTAAC | 43925 |
| 10300 GCAGGCACCTAGTATCAAGCCCAAAG | 21958 CCCTCTGGGTCATCCCTTCATTTC | 32942 GCACTTGGCAGGCACCTAGTAT | 43926 |
| 10301 CCATATGACTGGCAGGTCCTCAA | 21959 CCTCCCCTCCTCAGCATCATTG | 32943 GGTGAAGAGCCAATCAGGCCATA | 43927 |
| 10302 CCACAACCAGCTCTTGTAGTGAAAGTA | 21960 CTGGGAGCAGAACCCAGCATTT | 32944 ATCCCCAAAGTGGCCACAAC | 43928 |
| 10303 GCAACCCAGGGAAGAATCCAGTTG | 21961 GAGGAGTCAGGTCAGGAGTGAAAAC | 32945 GGCCACATTCATGCTGCAA | 43929 |
| 10304 GGGTGATGCAACTTCCAATCTTAG | 21962 GCTCGAGAGTTGGTTGCAGTTG | 32946 CCATCGTGACTATCTCATGGGTGATG | 43930 |
| 10305 GCTAATGTTGGTCCTCCAGTTCT | 21963 TCAGACAGGCCATGGGATCTA | 32947 GGGAGGTCCTGTTGCTAATGTTG | 43931 |
| 10306 GTCCTCCTTTTGAAGCACACTTCTTTG | 21964 GCAATGGAAGGGTAGTGGTACT | 32948 GGACTATGTTCTGTGTCCTCCTTTTGAA | 43932 |
| 10307 CTGGGAGGCTGGGAAATTGATAGT | 21965 CTGACGCTGGATGGCCAAAT | 32949 TCCACTGGGAGGCTGGGAAA | 43933 |
| 10308 GACGGGGCTTAAAGCTGTTTG | 21966 GCCACTGGACTTACTTCGCAAAT | 32950 CCAGTTTGGTGACGGGGCTTA | 43934 |
| 10309 TTCCCAGCTAGGGGAAGCTAAC | 21967 CTGAACTGGCTTACAAAAACACA | 32951 CCCTTTGGTTCCCAGCTAGGGCAGCTA | 43935 |
| 10310 GCTGCTGTTGCCCGTTCTTC | 21968 GCCGCAGCAGCTTCTCATTC | 32952 ACTCGAGCCCGCTGCTGTT | 43936 |
| 10311 GTCTGTTTGCTGATTCCTCCTCCAT | 21969 GTTCTAGCATTGGAGGAAATCCAAAGT | 32953 CCCTTGTTGTCCTTCCTCGTCTGT | 43937 |
| 10312 AGCCACCAAAGGGAAATGTTCT | 21970 ACTTGAGTGTTTGGGTCAACAAGA | 32954 GCCAACTCTCAGCCACCAAA | 43938 |
| 10313 CCGGTATAACATTGCCTCCCTAAG | 21971 AGAGCCCTGCTCCTAGTCTCT | 32955 GGGCGCAAGTACCGGTATAACA | 43939 |
| 10314 AAGAAGGCAGGACTGAATGTCAA | 21972 GCCATCTGGAGGCAGCTGAAAT | 32956 AGGCAGTCTCTCAGTGTAAAGAAG | 43940 |
| 10315 ACAACATGGCTGTCTTCCTGAAA | 21973 CCCCAATACCTTTAAAGCTGGAGCAA | 32957 CCCTTGGTTCCCATACTGTAAACAACA | 43941 |
| 10316 TGCTGAGAGTTTTCGCTGTCA | 21974 AGACTAGCTGAGGGAAAGTGTGA | 32958 CCCCTGTTGTGCTGAGAGTTT | 43942 |
| 10317 TGTCCCATCTCTGCCAGTGAAC | 21975 CCTGGATTGCCCACACATTCCAT | 32959 GAACTGATAAACAGTGTCCCATCTCT | 43943 |
| 10318 AGAGAAAGCAGGCCTGGAATG | 21976 GGCCTCGTAAAAGGCAGGAT | 32960 TCCCACGGACAGTGAAGAGAAA | 43944 |
| 10319 AGGCGTCACTTTCTGCTGTT | 21977 TGACGACTGGATTGTCCAACAAA | 32961 TGGCTGCAGGCGTCACTT | 43945 |
| 10320 CCAATGCTGGGACCGGATCT | 21978 TGAGTCCAGGTGACTGTAGGAA | 32962 ACTGCCTCGAATCAGCCAATG | 43946 |
| 10321 TCCCTCCATTCCCATGCTTCA | 21979 AGACCCAGGCCACTTCTGAT | 32963 TCCTCACTCCATTCTCCATT | 43947 |
| 10322 CTGCCTTAGAAGAAATCTCTGGGAAA | 21980 CTCATCTCTGGGTCTCTCCTTTAGATG | 32964 TCCCTGCTGGTTCTGCCTTAGA | 43948 |
| 10323 ACAGCACATAGTCTCAGGGTCA | 21981 AGGTGTCCTCCTCCCATTCTAG | 32965 GTCACGGGTACAGCACATAGTCT | 43949 |
| 10324 GGGCCCTGAAATATGGAGCCTTT | 21982 TGAGGTTGCAATTCACCCAGAA | 32966 CACTGTGTTGGGCCCTGAAATA | 43950 |
| 10325 GCCATAGGGTCACCAGCCATCT | 21983 GGTGTGCATCTGTGGGCATATC | 32967 AGGCTGGAGCCATAGGGATCA | 43951 |
| 10326 GCTCTCAAACTCTGGGGACCTT | 21984 GTGCCCTAATGATCAGTCTTCAGT | 32968 AGCCTAGGGCTCTCAAACCCT | 43952 |
| 10327 CCCACGACATGCATTCCCTCTA | 21985 AGCCACAGGCGAGCACATAG | 32969 GGCTTAACATGCCCACGAGAT | 43953 |
| 10328 GGATTCAGGCAAAAGCCAACAGA | 21986 CCCCAAACCCTTCGGTTTTCA | 32970 CAAGGCAGGGATTGAGGCAAA | 43954 |
| 10329 GGGGTTGGGCAAAGCAGTTAGA | 21987 AGGATAATGCTTGGCAAAGACACA | 32971 AAAAACGGCGGGTGGGCAAA | 43955 |
| 10330 TGCAGTGAAAATGCAGCAGATG | 21988 CTCTGTAACTTTCTGGCATTGGAGTCT | 32972 CCTCAGGAGACAGATGCAGTGA | 43956 |
| 10331 CACATGCTGCCATTATACCTTGTTC | 21989 TGCAGCTGGGCTTAGCAACT | 32973 GCTTTAAAGATCACATGCTGCCATT | 43957 |
| 10332 TCCACGTAGTCTGTCTCCATGAT | 21990 ACCCCTACCCCAGGAGTTTTG | 32974 GGAGTCAAAGCTTCCACGTAGT | 43958 |

| | | | |
|---|---|---|---|
| 10528 CCACAGGTTGTAAGACAGGTCAA | 22186 CCATTATTCCTGCAACGCTCTTTC | 33170 CGGTTCAGCCACAGGTTGTAAG | 44154 |
| 10529 GAGGTGTTGCCTATCAGGTTGACA | 22187 GGGCCTTGCATGGCTAACTTTG | 33171 ACAAAGGATTGACGTGTTGCCTAT | 44155 |
| 10530 CAAACGAGCTTTTGGTGATGGAT | 22188 CAGACAACTTGTTCCTGGGAAACAAAAG | 33172 GCAGGATAAGGCTTTCAAACGAGCTT | 44156 |
| 10531 TGCACTGGACAGTTCATGAGATG | 22189 AGCGAGGACACCCTGGTCAAA | 33173 CCTTCAGATGCACTCGACAGTTC | 44157 |
| 10532 CACCCGTACCCTAACTCACCATAC | 22190 CCTCTGCCAGTATAGGCAGTCTCT | 33174 GCCAAAGCACCCGTACCCTAA | 44158 |
| 10533 GGAACTTTCAAAGCAATAGCCTCCTT | 22191 TCTAGTAGGGCTCTGACCAACA | 33175 GCACTGGTGGAACTTTCAAAGCAAT | 44159 |
| 10534 GTGTTCCAAAACCGGATTGTAGTGA | 22192 CTGCCCCAATGGCGTTAACAGAGAT | 33176 AGGGCATGGAAGTGTTCCAAA | 44160 |
| 10535 GCTCCACAAAGGGCAACCAA | 22193 GTTGAATACGCAGTACCCTACGTT | 33177 CACATTCCAGTGCTCCACAAAG | 44161 |
| 10536 GTCTTCCCTTTTAGTGGAACCCATT | 22194 ACACGTAGAGTGCAAGGAATCAT | 33178 GTCTCAATTCTGAACGAGTCTTCCCTTT | 44162 |
| 10537 AGCTCGCCACAATCTTCTTGA | 22195 CACAGCTGAAACTACCAGAGAAACTA | 33179 GGAGCAAAAGCTCGCCACAA | 44163 |
| 10538 GCGTAAAGTCAAGGAAAACCCCTTAC | 22196 CGTAGTAATCAGGTGCAGCCAATAG | 33180 ACTTCTGTGCCGTAAAGTCAAGGAA | 44164 |
| 10539 CGGACCCGAAAGGCAGCATAG | 22197 GCAGTAGCCAGAGAGTGGTTACA | 33181 GTGAACTGAGTCGGACCGAAAG | 44165 |
| 10540 GCCCCAAAAGCTTGGAGGGTAA | 22198 AGGGGTTCCACCACCAGATG | 33182 GTTAGGCTCCTTTGCCCCAAAA | 44166 |
| 10541 GCAAGTTAGCTCACTGTCACCTT | 22199 GCCAGAGAGGCTACATGCAGTAAT | 33183 GACACCTTGGCTGATAGAAAATGCAA | 44167 |
| 10542 GCTGACCTTTGCCCCTGTAA | 22200 ACTACGTGAGTATGAGGCACAAG | 33184 GGGGCAGAACAATGCTGACCTT | 44168 |
| 10543 GCAGCGATTGTGAGGAAAGAGT | 22201 GAACTCCTTATGAGCTTTGCCTTGT | 33185 GCAGGTGTTATTATTCTTGCAGCGATTG | 44169 |
| 10544 CCATGAAAGCCTGGCATCCTGTT | 22202 GCAGACAAAAGCGGCAAGAAG | 33186 CTGCCTCAATCTCCCCATGAAAG | 44170 |
| 10545 CTTGCTTAAAGGGCCTCCCTCATC | 22203 CTTTGCATGGGAATGTTCCTCTTT | 33187 GTCAAGAGCACACCACTTGCTT | 44171 |
| 10546 GACATCTGGAGTAGCAGGAGACA | 22204 ACGTGAAGAGGGCCTGAGACT | 33188 CAGCAGGTGACATCTGGAGTAG | 44172 |
| 10547 GGTGCGAAGAAAGTGCATTGGTTTG | 22205 ACCAGTCGTCAGGGACTCGAA | 33189 CCCTTTGGTAGGTGCGGACAAA | 44173 |
| 10548 GAGACAAACCTCTCCCTTTATGGACTT | 22206 TGCCCAGTCCCCTGCTTTC | 33190 GGGATCAGAACCCATGGAGACAAC | 44174 |
| 10549 GCCCATGTGCCAAGGAGACA | 22207 CGTTATAACCTGGGCTTCCACAA | 33191 ACCTCACCTACAAACACACACTTG | 44175 |
| 10550 TTCACGCTTCTCAATACCCCTATTT | 22208 ACAAGGAAAGTTACTTGGAGTCCTT | 33192 CCCCAGCTTCACGCTTCTCAAT | 44176 |
| 10551 GCCAGGCCTTAGGTTTTACTCATG | 22209 GGGAAAGAAGGCACAGGTACA | 33193 CCTCATACTGCCAGGCCTTAGGTT | 44177 |
| 10552 CCTCCTCGACAGAAGCTGAACA | 22210 CCAGGCAGGACATGATACACACA | 33194 AGGCATCACCTCCTCGACAGA | 44178 |
| 10553 CTGTTCCTCTGATCCTGAGTAGT | 22211 GAAAAACTGCAGGCTGACAGAGA | 33195 GCACTAGGCACTGTTCCTCTGA | 44179 |
| 10554 GTGAAATATTGCCCCATGCTAGGTT | 22212 CGCGAGGAAACTTCGCTTGTGTT | 33196 AAGTAGTTGGCCACCTGTGAAA | 44180 |
| 10555 CTCTCAGGCATAACTGCACAGTTCTT | 22213 CTTCCTAGGAGGAAAAATAGGCCATAA | 33197 CCATATAAAGTCAGTCCTCTCAGGCATA | 44181 |
| 10556 TGGAGGGAAAGTGGTGTGTGT | 22214 CTGTGAAGCAGTCAGGGCAAA | 33198 CTGTGGTGAGTTGGAGGGAAAGT | 44182 |
| 10557 CCAGCCCAAATAGCGGTAGCTT | 22215 GGCTGATGCAAGGATGCAACACA | 33199 CTCAAAGTGAACCAGCCCAAATAG | 44183 |
| 10558 GGTCTCTGTTGGACCTCCAATATTCT | 22216 CCCCATGTAGGAGGACTGAGGAT | 33200 AGCCACAGGCTGTCTCTCTT | 44184 |
| 10559 GCTGTGAGGTTGGTTAGAATCATTGT | 22217 GACATCAGTCACCCTCTCTTTCAA | 33201 GGTTGAAGCTGTGAGGTTGGTTAG | 44185 |
| 10560 GGTTGGAGTAGCTTGTCCAGTCTT | 22218 CACTGAAGGAGAGGCAAGACAGAAAT | 33202 AAAATGTACCTGGTTGGAGTAGCTT | 44186 |
| 10561 GCCTCAGCACTCTGTGGGCTTTT | 22219 GATTAGGAAGGGCTTTGGCATTG | 33203 GTCCTTCCAGAAGCCTCAGCAT | 44187 |
| 10562 GGTGTCCTAAGAATGACTAAGGTCTGA | 22220 CATGGTTAAGGCAGCAAAGTGTAA | 33204 GCCTGTAGGTGTCCTAAGAATGACT | 44188 |
| 10563 GTGAGAGTAAGGAGTGCTTTACAAC | 22221 GTTGGTAGGGACTCTTGAAGTTTTG | 33205 CATTCTAGGCATGTGAGAGTAAGGAA | 44189 |
| 10564 TGCTCCTCAAAGCTCCCAAAC | 22222 CACAGGAGAGTCTGGGTTGACT | 33206 GCCAGATCCATATGCTCCTCAAAG | 44190 |
| 10565 CTGCATTTTTCCAGAAGCCCACTAT | 22223 GGCCAGAACTGGGCCGAAA | 33207 GCTGACTACCAGACAATTACTGCATTT | 44191 |
| 10566 CTGGGGCTGTAACTTCATCTGTTT | 22224 GGATGGGTACAGTTGGAGAACAA | 33208 TGCTGTACTCTGGGGCTGTA | 44192 |
| 10567 CCCCTTCAGGATAGAAAGGACCTAAG | 22225 AGACCAACTGGCTACCTGATGT | 33209 TGCTGTCCCCTTCAGGATAGAA | 44193 |
| 10568 CAAGGGCCTACCTACATCCGTTT | 22226 GGCTAAGAGGAGCAGTGACCAT | 33210 CACTCAGTTTCAAGGGCCTACCTA | 44194 |
| 10569 GCACAGAGCACATCCTGGCATA | 22227 GGTGCTCAGGGGAGTGAGAAAA | 33211 TACCACAGCCCATGGCACAGA | 44195 |
| 10570 TGGCATTGAGACACTTCTTGGAT | 22228 GAGAATGTGAACAGGGGAAATAGGAA | 33212 AGCCATTATTCTGGGCATTGAGACA | 44196 |
| 10571 GGGAGACCAAATCCTTTGTAATAGACACAT | 22229 ACTTCAAAGTGTATGACGCTTGCTA | 33213 GCCAGGGAGACCAAATCCTTTGT | 44197 |
| 10572 CACCAATGACTTTGACTGTGGGAGAA | 22230 GCTGGGCTAGATTAGCCATTCAAC | 33214 GCCAGCCATCACCAATGACTT | 44198 |
| 10573 CAGTGGTGCTACTTTGGTGTCT | 22231 TGGCAGCTCAGGGCAATC | 33215 CGCTGTCAGTGGTGCTACTT | 44199 |
| 10574 GCCAACCCTGTAAAAACTTTGTGT | 22232 CTCCTCAACTCCTCACTACGGAACTT | 33216 GGAGACAATTAGCCAACCCTGTAA | 44200 |
| 10575 ATGGCTCCAGCAGGGGAAA | 22233 GGGAAGGGCAGCAGACATCTTT | 33217 ACCAAGCCATCCAGCCTCCAT | 44201 |
| 10576 ACCCAGCACCTAGGGTTCCAA | 22234 GGCCTGTGATTATGTCAGAGGGTTT | 33218 TCCAATGCCACCCAGCACCTA | 44202 |
| 10577 GCCACCTTGGCTCATTATGACT | 22235 GGGAATACAATTGGAGTCAGTGGAAAG | 33219 GTTGTGACCATTTTTGCCACCTT | 44203 |
| 10578 CACCAGGCTGTCCTAACCTCCTCTT | 22236 GAGGAAAGACCTTTGCTGTTCAGGTA | 33220 CTTCCTCCACAGGCTGTCCTA | 44204 |
| 10579 GTGGTGCAAGTTCTATACCGGAGAA | 22237 GCCACCTGGCAGAGAGATGAAA | 33221 CTGCCCCTTGTGGTGGAAGT | 44205 |
| 10580 CCAATCAGGGAATGGCAGAAAG | 22238 GGAGGCAAGGTTAAAAACGTGACTAGGAA | 33222 CCACAGGCCTTAGCTCCAATCA | 44206 |
| 10581 TCGCCCCAGTTTGTGCCTAAG | 22239 GCTAGGCTGCTATTGCAGTAGTTC | 33223 CCATTCCTATCGCCCCAGTTT | 44207 |
| 10582 GAGGCTACTTCACATGGCCTAAT | 22240 CCCCAGTTGACCCCTCTTTTCAGA | 33224 ACTTAGCAAGCTATGAGGCTACTTC | 44208 |
| 10583 GCATGATTCAGAACTGCTAGAGCAT | 22241 TTGGGCTCCTGCCTGCACAAC | 33225 CCACGAACTATGCATGATTCAGAAC | 44209 |
| 10584 GCCGTGTTGTGGTCAATGT | 22242 TGGGAGGAGGCGCGAGACTA | 33226 ACGTCTGGCGCGTGTTGT | 44210 |
| 10585 CACCCTTTCAACTTCACCTCTCGTTA | 22243 ACCCACAAGCCTCAACCATTTC | 33227 GCCCAGTCACACCTTTCAACTTC | 44211 |
| 10586 GGTGGACATTTTCCCTTGCACTTG | 22244 GGCACACCTGTGTTCTGTTGA | 33228 GGCCAAGATGAGAAAGTAGGTGGACAT | 44212 |
| 10587 CCCACTTGGATGCCAGAACA | 22245 GCCACAACCTCCTGTTTGAGAGA | 33229 TGACATTCTAACCCTATTTCCCACTTG | 44213 |
| 10588 GGGTGCAAGGAAGCAAAAGGAAGA | 22246 GTTTCCTGCTTGGACTTGAACAA | 33230 CAGAAATGGGTGCAAGGAAGCAA | 44214 |
| 10589 GAAGAATGACAAGGCATTAGCTAGGAT | 22247 GAJACTATTAACCACCACCGTTCCTT | 33231 CCTAGAAAATGTGAGCCATGAAGA | 44215 |
| 10590 GGCCATTAAAGGAATGACGTGGAT | 22248 CCATCCCATCCGTCCAATACGTTAG | 33232 CCCAAGGTGGCCATTAAGGAA | 44216 |
| 10591 GCTCCTCTGAACTACAACAACCTT | 22249 GGAGCAGCTAGAGCCTGAACAA | 33233 GACCACCATTATTGCTCCTCTGAAC | 44217 |
| 10592 CTTTCTGTGGCCTGTGATAGT | 22250 CCCCTTTCCTAAGGTAGAGGAGTCT | 33234 GGTACCCTGGCAGTACTTTCTGT | 44218 |

FIG. 36Q3

| | | | |
|---|---|---|---|
| 10593 CAACCGTCTTCCCACAAGCTCTGA | 22251 GGGTTTCAGAAAGTTAGAGCCATTCA | 33235 AFTCTCCATGTGTCAACCGTCTT | 44219 |
| 10594 AGGTACTCAGGGCTCAAAGGAA | 22252 GGAAATGGATCATCAGCAGAAGCAA | 33236 CAGGGGATAACTGCTCATGTAAGGTACT | 44220 |
| 10595 GAAATGGTTAGGCTTCTCTCTGCTT | 22253 ACAGCATTGGCCTTATTTCCAAAAG | 33237 CGGACCAATGACAGAAATGGTTAG | 44221 |
| 10596 GGGGAGTGAGGGAGGAGCTTA | 22254 GGCTCTCTGCGCATCAGAAGGA | 33238 GGACGGCTGGGTTTCCTTT | 44222 |
| 10597 GGGAATGGCATGTCATGATTGTT | 22255 GCATGGTCTTGTCTAGGGAGGAA | 33239 TGGTCAATGGGAATGGCATGT | 44223 |
| 10598 GTCACAGCCTCCAAGGTCAGT | 22256 GGAGCAGGACCTATTATTAGTCTTCGATT | 33240 CCTGAAACTAGTCACAGCCTCTCA | 44224 |
| 10599 CAGTGTCAGCTTCTTCCGTGGAT | 22257 CAGGACATTCCTCCTCCTCAGACA | 33241 GGTAATGGACAGTGTCAGCTTCT | 44225 |
| 10600 GCCACCCAATGGTGAATGCTAA | 22258 CACCCACATCAAGGCTCTACCAT | 33242 ACTTCTCCAGCCACCCAATG | 44226 |
| 10601 GACGTGAAGGCAGACATGTCGGA | 22259 GGGCAGGAGGCATTCATCAACT | 33243 TCCAGATAGCCCAAAGAGGTGAA | 44227 |
| 10602 TGGGGTCAAATACAACAAGAGACA | 22260 CCTGGTAGTCTTAAACAGGAATCTCTCA | 33244 GCCATAGACAGTTGGGGTCAA | 44228 |
| 10603 GGCTTGGAGCATGGCAGGAAAT | 22261 GGAGCTGCTGTGTTGGAGTT | 33245 GCTTATGGGTGGCTTGGAGCAT | 44229 |
| 10604 CTGCTCCTTGACATTGCAGACACT | 22262 CTCAGCGAAGTTTAAAGCACATCATTC | 33246 CCAATCCCCTGCTCCTTGACAT | 44230 |
| 10605 CCTTAGCTGCAAGAGAGCCTGTA | 22263 GAACCTCTCTTCCCAGAGATTGAAA | 33247 GTCCATGCCTTAGCTGCAAGA | 44231 |
| 10606 CTTTGTAGAGGTGGCAGGAACA | 22264 TCTTCCTTAGCACTATGGTAGAGAT | 33248 GGTGAGGGCATGGACTTTGTAG | 44232 |
| 10607 CACCCTCGCTTACTGGTATATTGA | 22265 GGAAACCAAAGCTCTCCAGTAAGTT | 33249 TTCTGGCCACACCCTCGCTTA | 44233 |
| 10608 GGTAGCCCAGTAATTGGTACTTG | 22266 GCTTTATGAGGGTAGGGCTTTCA | 33250 TGTGCTAGGTAGGCCCAGTAA | 44234 |
| 10609 CAGTACCCTTTTATAGGCAGCAACTT | 22267 AGTCCACATCTCCCTTGAAGACA | 33251 GGGGAGGTTTATCAGTACCCTTTA | 44235 |
| 10610 GTTCCCAAATCTGCAACCCAAAG | 22268 AGGGTGGGGAAAGATAAATGCAA | 33252 GGAAAGACACAGTGGTTCCCAAATC | 44236 |
| 10611 GTTGCCTCACACACTAGACCTTTG | 22269 TGCAGACCATCACACATCTCAAC | 33253 GTCTTTTAAACAGTTGCCTCACACA | 44237 |
| 10612 TCCATCAGGGAAGAACCACTTATG | 22270 CAGACACTAAGCCAAGCTCTGAAG | 33254 CTGTGCAGTTCCATCAGGGAAGAA | 44238 |
| 10613 CCTGCTGTATTGGGGCAATGCTT | 22271 CAAGAGCCCCAAGTAATGTGTGT | 33255 GGATGATGGGGAGAGTCCTGTGTATT | 44239 |
| 10614 GACAGGATTCCATAGGGTCTTGTTT | 22272 CTCCCACCTTAAAGGCACAGAGTAG | 33256 GGTCTCTTGAAGACAGGATTCCAT | 44240 |
| 10615 CAGAGAGCAAGTCACAGAGTCAT | 22273 GGTGGGGAGAGGCAGGATTG | 33257 GCCTGACACAGACAGAGAGCAA | 44241 |
| 10616 TCTGCATGTCCAACACTGAACT | 22274 AAATGTGTGTTTGCGTCTGGAA | 33258 TGTACTTCAAACTCTGCATGTCCAA | 44242 |
| 10617 GCACTGCCAATGTGGCAAGA | 22275 GGCCTAAACGCTGCTCACCTAT | 33259 CTGAGGCTAGAGCAGTGGCAAT | 44243 |
| 10618 GCTCTCCACAAGAAGATGGCAGTT | 22276 GGAAACCGGCATTTGGACACA | 33260 GCTGGGTTGCTCTCCACAAGAA | 44244 |
| 10619 ACTTTGGGTCTCTGGTTCCTGTA | 22277 GTGACTGTGCGCTTCAGAGTCATG | 33261 GCCCTACAGAAACTTTGGGTCTCT | 44245 |
| 10620 GGCTCCCAAPGCAAAGACCTTCA | 22278 GAGCACAAAAGGTAGGAGTGAGAA | 33262 GCCATCTTGGCTCCCAATGCAA | 44246 |
| 10621 GGGTGCAGGAACATTACCTGGAGTA | 22279 TCATAACGTGGAGGAGAACTGTTG | 33263 CCTCACTAAAGTTTGGGTGCAGGAA | 44247 |
| 10622 GCAAGGGGTATATTGAGTTTCAGTGACTA | 22280 GCCTAAAACTTTCATGGGGTGTTTG | 33264 TTCCATGCAAAGCAAGGGGTAT | 44248 |
| 10623 CCAGGGCCATTGATGGGTT | 22281 ACAGACCTCAAGCTCGCTCAGA | 33265 GCAAGGGAATCCAGGGGCATT | 44249 |
| 10624 CAGCAAAACCAATGCAGTGTGA | 22282 AGCCTGGGGCCTTCTCTCGA | 33266 ACCCTCAGTGAGCCAGCAAA | 44250 |
| 10625 AGATCTTAGATCAAGGGAACACTA | 22283 CACTGCAACATGACCTCTGAGA | 33267 AGGAAGCAAAGAGATCTTAGGATCAAG | 44251 |
| 10626 GGCCCAGTCTCACTATCTAAGTACAGA | 22284 GACGTTTAGGTTTCCATGGCCAAA | 33268 AACAGCCCAGTCTCACTATCT | 44252 |
| 10627 TGGAAGCAGGCTGGATCACT | 22285 TCCCAGGAGAGGAAGGCCAAT | 33269 CCCGAGGGAAAACAAGAGCTGGAA | 44253 |
| 10628 AGCAGGAAATGGGCCTGAAG | 22286 CTCCTTAGGGTGGCATCACAAAC | 33270 GGCAGGTTAGGTATTAGGAGGAAATG | 44254 |
| 10629 GGCCTCATTACTTTGTTGCCTTT | 22287 CAGAGAAGGAATCCCTGCTATCAAA | 33271 GGCTGCTGGCCTCATTACT | 44255 |
| 10630 CTGTAGAAGACGGACCTCAACAATCA | 22288 GGTTTGAGAGGCACCTAGAATCACT | 33272 GTCTTGACAGATAGCCTTCTGTAG | 44256 |
| 10631 GGGTGACTGCCAAGTCCAGAAA | 22289 GTGTGAAAGCCAGGTGAGCAT | 33273 TGTCAGAAGGAAGGGGTGACT | 44257 |
| 10632 AGGTGCAAGGTATGCACTGATT | 22290 GGACCACAATCTTCATGAGACGAA | 33274 GTGCTGTGCTAGGTGCAAGGTA | 44258 |
| 10633 ACGGCCTTGAAAACACCATTCA | 22291 CTCATTGATGCCTTCGTCTTTTCAGT | 33275 ACAAGGTTTATGTAACGGCCTTGAA | 44259 |
| 10634 CCATGAGGACACAATCAGTCTCAA | 22292 GTATTGGCCGTAGGTTTATTGACTTC | 33276 GGGAAATCTATGCCATGAGGACACA | 44260 |
| 10635 GCCCATATCGGTGAGGATGGAT | 22293 CCAGATAGTGGGCAGATTGCTT | 33277 TGACACACAGGGAGGCCCATATC | 44261 |
| 10636 GCCAAGTTCCTCTGTTAACAAGTT | 22294 AGTAGGCAGCAACAGTTGTCAT | 33278 GGGATTGGGATTGTTGCCAAGTTC | 44262 |
| 10637 GGTGGTGGCTACTACCAAAATGT | 22295 TCTCCAGCACTGGCTCAGAT | 33279 GACTAGCATATGGTGGTGGCTACT | 44263 |
| 10638 CACAAACACCCCTAGCTGGTAA | 22296 ATGTCAAGACAGCCTAGGTTCAAA | 33280 GGTGGGTACCTAGATTCAGAAACA | 44264 |
| 10639 CCCAGGACATCTCTTCCACTGCTT | 22297 TGGAGGGAGCTGCTTCTAGCTT | 33281 CCACAAACTCCCAGGACATCTCT | 44265 |
| 10640 ACGAGCCACGACGGCTCTGA | 22298 CGTGACCGGCTAACACTGA | 33282 TACCACCGCCGAGAATGGAA | 44266 |
| 10641 GTCAAGCAGGTAACAGCAGACT | 22299 TGCTGTGCGTTGGGTCCCATT | 33283 AGGGTCCCAGTCAAGCAGGTAA | 44267 |
| 10642 CCACAAAPAGGCAGTTACAGCATGAA | 22300 GTGAAATCCCTGAAGTGTTTGCTT | 33284 GCCATGGCCACAAATAGGCAGTT | 44268 |
| 10643 GKKCTTTCACAGTCAGCAGAT | 22301 AGGGTAAAPGGGAGTGCTTCTCT | 33285 GGGCAGAGGGGCTTTGACA | 44269 |
| 10644 CCTCCTTTAGGGGAGTTT | 22302 GTACGTGGTCAGGAGATAAAGT | 33286 CAGATGAGGGTGCTGCCTTT | 44270 |
| 10645 CCAGCATCTGTGAGAAAACTTCGTT | 22303 CGCTGGCTTCCAGAAGGGTTT | 33287 GGACTCCTTCCAGCATCTGTCAGA | 44271 |
| 10646 GAGTGGCCAGCTGCATAAAAG | 22304 TGGGTCTTCTTGAAGACGAAGATC | 33288 TGCCCACATTTAAAAGGCATAGAGT | 44272 |
| 10647 GCACAGTTTGCAAGCCACTTC | 22305 CTCTGAGAAGACGTGTCTCATTTCCAA | 33289 CTGGGTTTGGGGAAGCACAGT | 44273 |
| 10648 CGTGTTTCTGGGATGAGTTAGTCTGT | 22306 CCCTCTTCAGCTAGGCACACA | 33290 CCTGCTCGTGTTTCGGGATGA | 44274 |
| 10649 GGGACATTGTAGGAGACAAAGAGT | 22307 ATCGGCCCTCCTCCACCTTTCA | 33291 GGGAGAACAGGGTAGGGACATTG | 44275 |
| 10650 GTAGCGAGAGCTTAGCACATCT | 22308 CCCAGGCCCATGACTACTCCTT | 33292 TGGCTGGCAGCGAGAGCTT | 44276 |
| 10651 GTTTGGTCACTGGCAAGAGA | 22309 CCTTAAGGATTCAGCCCTCTTCTAAA | 33293 CTGAGGCAGAAAGTTTGGTCAGT | 44277 |
| 10652 GACAGAGTGAAACCGGGGAAACT | 22310 CCCTCCCTCCCCTTCAAATAGACTT | 33294 TGTCCCAGTTTTGACAGAGGGAAAC | 44278 |
| 10653 GTGGAGGGGATGATGCAGTTCAGA | 22311 GTCCAGGAAGACTGGAGCCTAGAA | 33295 GGGGAATGTGGAGGGGATGA | 44279 |
| 10654 GGGCAGAAGATTAGGGAGGTCTT | 22312 GGCTTCTGGTTTTGGAACAGGTTGA | 33296 GACAGTTGCTTAGGGCAGAAGATT | 44280 |
| 10655 TGGGCTTGGATCCTATGGGAAA | 22313 GGGGCTTTGTACTCACAAGTCA | 33297 CCCAGATAACTATGGGCTTGGAT | 44281 |
| 10656 CATTCAGGACTTGGTTTTTCTTACA | 22314 CCTTGCGCTTGGCATTGTT | 33298 CAAGGAAAACATTCAGGACTTGGTT | 44282 |
| 10657 CACAGGGGTCTAGGCAAATCTCA | 22315 CAGAGGACACTGACAATCAAGTCA | 33299 CAACGGAAACACAGGGGTCTA | 44283 |

| | | | |
|---|---|---|---|
| 10788 GCGGGCAGTGATCATTGGAA | 22446 TCCTTCTTCAGTCCTGTTGAAAGTAG | 33430 AACTGCTATGCGGGCAGTGA | 44414 |
| 10789 GGTGAGGGTGAAATCAATAGCAGAAG | 22447 ATCCTCAGGGGCTCCAGGATCT | 33431 GCAGCTAGAGAGGTGAGGGTGAAATC | 44415 |
| 10790 CACAGACCCAAAACGCAACACA | 22448 GGTGGAGACCAGTAGGTGTTATTGT | 33432 CCCTTGTTCCTTATCTCACAGACCCAAA | 44416 |
| 10791 GACCTCCTGGATTTTCTCCCTTTG | 22449 CCAGGAAAATATCAGGCTCAGTTCA | 33433 TCCCCAATTGACCTCCTGGAT | 44417 |
| 10792 GCATGGGAGGGGTAGTCTATTAGCAA | 22450 GGTGAAATGTAAGCTCTCTGGTTCTTTC | 33434 GTGGCATGGGAGGGGTAGT | 44418 |
| 10793 GTGGTGGTTAGGACAGTGGAACCAA | 22451 GGGTGCTGAAATGGTTGGAATGAGT | 33435 GCATCTGGGAAAGAAGTGGTGGTT | 44419 |
| 10794 ACAGCTACCCCTCCCATGACA | 22452 GGCCCAGCCTATAAAACCACAT | 33436 ATGTCAGAGGTCTCCACAGCTA | 44420 |
| 10795 GGACAGTTGTTGACCTAGGCTGCTA | 22453 GGTTAAAAACATGGGCCTTACAGTCA | 33437 ACCTAACAGAGCTGGACAGTTG | 44421 |
| 10796 GGGGCAGACTGAGTGTATAGGAA | 22454 CCCACAGCTAGGGCAATCTGA | 33438 AGAGCTTGGGGCAGACTGA | 44422 |
| 10797 CCCACATGACAACATCTATCCTGGAA | 22455 GCAGAGGGCACTCATAAGTCAGT | 33439 CCCACCTTCCCACATGACAACA | 44423 |
| 10798 CCTGACTGGGTCAGCTTTCAA | 22456 GTCCGGGCACACATTCTACTTTC | 33440 TGTAACGTCGCGTCCCTGACT | 44424 |
| 10799 CCTGGTTTCCCCTTCATGCAAA | 22457 CTAAAGACCTAAGCCTGTTCACATCT | 33441 CCTGGTTTGGGTCACCTGGTTT | 44425 |
| 10800 GGAACACAGGACTGGTTCAGAAA | 22458 GTGCCACCTTACTGGCCAAACA | 33442 CACCAAACCTAGCATGGAACACA | 44426 |
| 10801 CCGCTCTTCAGAGTGACTACCCTAAC | 22459 CCAGCTGCAGATGAAGCTCAA | 33443 CCAAGGCTAACAATTCCGCTCTTC | 44427 |
| 10802 TGGTCCTTGTAGATGGGAAGACA | 22460 GTAAGTCAAGTCACACCAATTCCTTAC | 33444 AGGGGCCTTGATGGTCCTTGTAG | 44428 |
| 10803 CCAGAGGACTTCAGCCAGTTGT | 22461 CAGATCCCAGTGTTCTGAACTTGA | 33445 GGTTTATTTAAAGCCCCAGAGGACTTC | 44429 |
| 10804 CCTGGCCCTCATAGGGAGATAGA | 22462 GCCTGTACCACCTCCTGCTAAT | 33446 GTATAGTATTGTACCTGGCCCTCATAG | 44430 |
| 10805 CTGGCTGCGTATTTTGGCATGT | 22463 CTGAACATGCACCGAGACAGA | 33447 TACGTGGCTGGCTGCGTAT | 44431 |
| 10806 GGCAAAACTGTTATGGTGACAAGACAGA | 22464 AGCCAGGCCTCCTGTTCT | 33448 AGGGGCTTGGATCCTGGCAAA | 44432 |
| 10807 GGGGCACAAAATGCACCACAGA | 22465 GCAAGCCCCATCAACCATCT | 33449 CGGAGATCTCTGGGGCACAAAA | 44433 |
| 10808 TGGATGGAGTTCACCACTCAATG | 22466 GATGCCTCAAAACGCCTCATAGAT | 33450 GACTGACTTAGTCCAGGGAAAGCAT | 44434 |
| 10809 CCCCGGTTTTTCACAGTACACA | 22467 CAGTCAATGAATACTGCACCCTCTT | 33451 ACACTCCCCCGGTTTTTCA | 44435 |
| 10810 CCAGACAGACGCCTTCCAGTT | 22468 CCCAGGGAATCTGCTGGAATGTAG | 33452 ACAAGCCAGAGACCCAGACA | 44436 |
| 10811 CAGCCTCAAAATATATACAGGGACCATAC | 22469 AAAATGGACCCTAACTGCCAGAA | 33453 GGCAACCTTTGACAGGCCTCAAAAT | 44437 |
| 10812 GCGTGCTCCAACCAGTCCTG | 22470 GGATCCCTGCCTCTAACTCTGA | 33454 AACTGAGTGCGTGCTCCAA | 44438 |
| 10813 CGTGTGCAATCTGGAGCATGT | 22471 GTTCCAGAAATCTATGAGGCCATGA | 33455 CCTGAGCACGTGTGCAATCT | 44439 |
| 10814 GGGTTCAAGTCCTCATCGTGTCT | 22472 GGGAAGGCCAGAGAGTAAGCTACA | 33456 GCTTCCCAAGCATGGGTTCAAG | 44440 |
| 10815 TCTGTGTCTGACCTTCCACTTTCT | 22473 GATTGGAAGGACATAGGCAGTTCA | 33457 GCCCCTGGTTCCTGTTTGTTT | 44441 |
| 10816 CGGTACAGTGAGTTTCTGCATAGATTT | 22474 GTCCCTTGACAAAGTTCCCCTAGA | 33458 ACCAATTCGGTACAGTGAGTTTCT | 44442 |
| 10817 CCTGCTACTAAAGTTACTCTCCCATTG | 22475 GAGAGTCTGGGAAGGCTGAACT | 33459 TGGCCACAGCAGCACTAATTC | 44443 |
| 10818 AGTCCAGGGAAAGCATGATGATAG | 22476 CACTATTTTCCACACTGAGGGCATCT | 33460 GACTGACTTAGTCCAGGGAAAGCAT | 44444 |
| 10819 ACCCATCCCACAAAACCAGATG | 22477 CGTAGAACCAAGCCTGAGATATGA | 33461 GACTTTTCAAAACCCATCCCACAA | 44445 |
| 10820 CCGACTGTCCAGCTTTTTCGTAAG | 22478 TCGAGGAGCCCAGCACATCTA | 33462 GACTTTTCCGACTGTCCAGCTT | 44446 |
| 10821 GGACCATCTTTTCCAACACTATGAATC | 22479 TGATGTCTTTGCCACAGTGTTTTAC | 33463 CTCACCCTTGGACCATCTTTTC | 44447 |
| 10822 ACCTAAGCCACAGATCCCTTATC | 22480 CTAGCCCTCAGCATCAAGCAT | 33464 CCAACCTGACAGCAGCTCTA | 44448 |
| 10823 CCCAACTGTGTTCTGCCTACAAG | 22481 CCCTTGTAGCCTATGTTTATCGTTGA | 33465 AAAACAGAGCCAACTGTGTTC | 44449 |
| 10824 CTGCAGGCAGATCATCCCAAT | 22482 CCCAAACTGGGTCTCCTCTTTGAT | 33466 CTGCAGTGGGTAGCTCCTTTCT | 44450 |
| 10825 GGAGTAGCAGGTTTCCGTGATG | 22483 CCCACCTCCCAGACAGCATTT | 33467 TCCCCTTGGAGTAGCAGGTT | 44451 |
| 10826 GACTGAACAGGTAAGGGAAAG | 22484 TTCACATTACTCGCAAGGTCAGT | 33468 CACCTCTAATAGAAGACTGGAACAGGTA | 44452 |
| 10827 TCAATTCAGTCTTCCTGAGTGCAA | 22485 TGATGACCATGCCACATCTGTAA | 33469 GTCAGGACTGCAACACACTCT | 44453 |
| 10828 CCACAGTCAGTCCAGTCTCCA | 22486 GGGGAAAACAGTGACAAGTCACGAA | 33470 TCAGGCTGCCACAGTCAGT | 44454 |
| 10829 CTCATAGCCAGGATTCACAGATCCAT | 22487 GAGTGGTGCCACTTCTGCTTCA | 33471 GGTACTATTTCTCTCATAGCCAGGATTC | 44455 |
| 10830 GACAGTGCAGGATTGAGTAAATGCAA | 22488 GCACTTGGGAGAGGGAAAAATGCAA | 33472 CTGCTATGACAGTGCAGGATTGA | 44456 |
| 10831 GCAGGTATGCTGGCTGGTGAAA | 22489 CCCTCATTTGTAGGTCTACCCTGAT | 33473 GGGTTAGTTTTCATGCAGCAGGTATG | 44457 |
| 10832 GACAAATGGCTTTGCATATCCCCATAC | 22490 CCCTGCCATGTTGCCAGATA | 33474 GTCTGCCAATTAAGACAAATGGCTTTGCAT | 44458 |
| 10833 ACCAACGGGAAATCCCAGTTAATC | 22491 GGGTCGGACTCTTGGCATCTTC | 33475 GGCACAAAAACACCAACGGGAAATC | 44459 |
| 10834 GCTCCAGGCTTGCTTAGGCTAGAA | 22492 AGGAGCTACCACGGGTATGAA | 33476 TCTCGCTCCAGGCTTGCTT | 44460 |
| 10835 GCTTGGAAAGGCAGTAGGAAAGTGT | 22493 GCTTTCCCCTTTCCTGAAAAACCAA | 33477 CACTCAAAGTAGCTTGGAAAGGCAGTA | 44461 |
| 10836 TGGCCATGAAAGGAGGTACAATTC | 22494 CAGCTGAGATCATCCTGCCCTTCAA | 33478 GCGTAAGTCCAATGGCCATGAAAG | 44462 |
| 10837 GCCGTGTGTTTCCAGAGCTT | 22495 ACAAATCCTAACACAGCACGTGAA | 33479 CCCTAGTTTGGGCCGTGTGTTT | 44463 |
| 10838 GGGACTTATTGTAGCCCTTAGTCA | 22496 CTGTTTTCGAGCAGCTAGGGATT | 33480 GGGGTGAGTAAGGGACTTATTGTAG | 44464 |
| 10839 ATAGGAGGTGCGGGCAGATTC | 22497 TGGAATCCTTTCCCCTGTAAGATAAC | 33481 ATAGGCCCAGTGGCCAGGATA | 44465 |
| 10840 AATGTGATGACGAAGTGGCATCT | 22498 GCCAGACCACTTCAGGAACA | 33482 GTCCAGCAAGAATGTGATGAGGAA | 44466 |
| 10841 GGAAGGGATTAAGTGGCAGGTT | 22499 CTGTTAGAAGGTTCCCTCTCATGGTT | 33483 GAGGGTTGGTTGGAAGGGATTAAG | 44467 |
| 10842 GCAGACACTGATATCCCCTACCCATT | 22500 CCAGCTGAATGCTGGAGATGGTT | 33484 GGCTTCTCCTACATGGCAGACA | 44468 |
| 10843 CTCCCTCAGCTAAGCTATACAGTCAGT | 22501 CACTGCAGAGAAGTTGGGCTTT | 33485 GGTCTCCAGATCTCCCTCAGCTA | 44469 |
| 10844 CCTCCAAAGAGTCTGTCCACAATGA | 22502 GTGAGATGACTCACCCTTTTTGCTTAG | 33486 TGCCAAACTGGCCCTCCAAAG | 44470 |
| 10845 GCCAGCACCATGGAAGAGCTA | 22503 CTGTGGGGCAGTCAGTTTTCCT | 33487 GTTGCCAGCCAGCACCAT | 44471 |
| 10846 GTCATGGAATCCTCTCCTTAGCCATA | 22504 ACCTAACCCTATCTCAGCTGTTTTC | 33488 GCTGATGAAGTCATGGAATCCTCTTCT | 44472 |
| 10847 ACTCCACCAACCTGCCCTTC | 22505 CAGATACAGAGATCAATTCCAGCTAGT | 33489 GCTTGCACCACAACTCCACCAA | 44473 |
| 10848 AGAACCGTGGTGTTCAAATACCAT | 22506 CCCTCTCAGATGGGTTTATCTAACTCT | 33490 GTAGTTTGTTAGAACCGTGCTCTTC | 44474 |
| 10849 AGCAAGAGTTGAGGGGCATTG | 22507 GCTCCTCTCTGAAGTTGGGTT | 33491 GGTGGTCTGAATATTAAGCAAGAGTTG | 44475 |
| 10850 CCCACTAACAGCGCCAAGTT | 22508 GGCCTGAGGCAGGTTTGATTT | 33492 CCCACAGTGCCCCACTAACA | 44476 |
| 10851 GACTCCTTGGCTTTCACAAAGAGA | 22509 TACCCAGGAAGCCGCCTGAA | 33493 GGCCTTTTGACTCCTTGGCTTT | 44477 |
| 10852 CAGCCGTGCATAATTGGGTGTAG | 22510 AGGCTGCCTAGGGGCTATTT | 33494 CTGGCCAGCCGTGCATAAT | 44478 |

FIG. 36Q7

| | | | |
|---|---|---|---|
| 10853 CCCTCCTGTATCTCATCCCAGTC | 22511 TGGGGAGGAGGGACTCTAGTTT | 33495 CCTTCTGCCCTCCTGTATCTCA | 44479 |
| 10854 CACCATGCCATTTTGCTGTGA | 22512 AGGTGCCAGAGACTGCAGAAAC | 33496 CGACATCCTTCACCATGCCATT | 44480 |
| 10855 CAGACATGAAGCTCACTGAAGGTGTAA | 22513 CCACTGCACCTGGCCTATCA | 33497 TGAAGCAGACATGAAGCTCACT | 44481 |
| 10856 GCACAGCTAACATACTCAGTGGTGAA | 22514 TCCTTGTCATGTTCCTTCCTCTTTT | 33498 ACACATACGCACAGCTAACATACT | 44482 |
| 10857 CAGAGCCTTTGCTCATCCCACTAC | 22515 CAGATATCCAGGAATCAACAGTTTC | 33499 GTACTGACCTTGCAGAGCCTTT | 44483 |
| 10858 GTGAATCCAGCGGGTTACAAG | 22516 TGTGCTTTCACTTCCTGGAAACTT | 33500 GCTGGAGGTGTTGTGGTGAATC | 44484 |
| 10859 GCACGTGCTGGTGCTCAGA | 22517 GCCCCAGTTCAAAATCTCTTGTCA | 33501 CCCTGGCTTTGGGTTGGTGAT | 44485 |
| 10860 CCCTACTCCAGCCAATTTCCAT | 22518 GGAAGACCAAAAAGGGATAAAGGTTGA | 33502 CCAGCCTCTTCTAGCACCCTACT | 44486 |
| 10861 GTCTACACACACAGCCTCACTATG | 22519 GCCTAGAGGGGTGGAAAGCAAAG | 33503 CACAGAGCAGTCTACACACACA | 44487 |
| 10862 GGCACATACTGTACTCTTGCATGTTG | 22520 TGCGTCTGCATGGTGGTTT | 33504 GGGTGGAGGCACATACTGTACT | 44488 |
| 10863 CCTAATCCACGATCTCCTCATCTGT | 22521 GACAGCCCTGTGACGTAGGAAT | 33505 GGCACTGCTTCCTAATCCACGAT | 44489 |
| 10864 GCAATTCCCTGAAGATACCTGCTA | 22522 GAGAAACAGTAGGGTCAAAGGAACAGA | 33506 CCTTGACCTTGCAATTCCCTGAA | 44490 |
| 10865 CGGGTACACAATTGTCCCCAGTT | 22523 GGAGCAAATTTGTGGATTAAGGATAG | 33507 TGTCCCCTCGGGTACACAAT | 44491 |
| 10866 ACTTGGGTGAGGTGGCTAAG | 22524 CCTCCTGCCGCAAAACTCTA | 33508 GGCTACAGGCCTGGCACTT | 44492 |
| 10867 TCACTGGTGTATGTCTGGGAAAGTTG | 22525 TGCCTCCACCTTGCTGCTA | 33509 GGTTTCAAGCCTCACTGGTATGTCT | 44493 |
| 10868 GCACCCAAGTGGAGGGTAAATC | 22526 GAGCAAAGAGGTTAAGGTCACAGT | 33510 GAAGGACAGTGCACCCAAGT | 44494 |
| 10869 CCCAAGAAGCTCTCTGTGCTATG | 22527 GGCACCTGCAGACCAGTTCTT | 33511 GGGCTAAGGCTCCCTACACAT | 44495 |
| 10870 GCTCCTGCACAAGCACAGATG | 22528 CGATCCCCTTGGTGTCAGAGTTG | 33512 CCTGTTAGCTTTGCTCCTGCACAA | 44496 |
| 10871 CTGAACACCTCCTTGAGTACAGTTC | 22529 CCTAGGATAGCCCACTGGATGTAG | 33513 CCTTGGATCACTGAACACCTCCTT | 44497 |
| 10872 CCCAGTTTGCAAGAAGCATGAAAG | 22530 CCCTCCAAGGACGTCTTCCCCTAA | 33514 GCCTGTAAGACTTTAACCCAGTTTG | 44498 |
| 10873 GGTTATTCCGTGTTCTTGATCTTGCTT | 22531 CTTTGTGTCCAGGCTCACCAT | 33515 GCCCCTGTGTTCTAACCAGTGGTTC | 44499 |
| 10874 GCAGTGGCAGAAGGGCATTTG | 22532 AGTCCCGCCTCCTCTATAGTCATC | 33516 CCGGATAGGCAGTGGCAGAA | 44500 |
| 10875 CTCCTCTAAGAAACTAAGGGCAACA | 22533 GCCAGGGATAGCTAACAATGACA | 33517 CTGCAAACTCTTCTTCCTCTAAGAAAC | 44501 |
| 10876 CGCTAGGTTGTGTACTGGGAACA | 22534 GTGGACTCCTCTAGGTCAAGCTATTTG | 33518 AGCCGTACGCTAGGTTGTGT | 44502 |
| 10877 GCCCATAGCCTTGTCCCATTGACTGTT | 22535 ACATCATGTGGATAGAATGGGGATTAG | 33519 GTATCCAGATTGCCCATAGCCTTGT | 44503 |
| 10878 CCCTAAGCTTTACCTTAGATGGAGAGAAAG | 22536 CCACCCTGAGGTTCCTTGCAGAT | 33520 GAGCTAGGAACCTCAAGCTTTAC | 44504 |
| 10879 CACACTGGAACCAAAGACCTTTATC | 22537 GCGAGCTATCTTGCAGGCTAGTAA | 33521 AGTTACCCACACTGGAACCAAAG | 44505 |
| 10880 GGGCTGAGTAACAAGAGTGGTTCT | 22538 AAGTAATGCAGGATGAGTGATGCAT | 33522 AGAATCTTGTGGGCTGAGTAACAA | 44506 |
| 10881 GGTTCCCTGTAGCTAAGAACCAT | 22539 GGGGTGGCTCAGAAACCCTTT | 33523 CCCTCTGTATAGGTTCCCTGTAGCTT | 44507 |
| 10882 GGTGGAGAATGACAACATGCAGAA | 22540 CTCTACTGAGAGACAAGCAAAGTTTCA | 33524 GCTAGGCTATGTAAGTAGGTGGAGAATG | 44508 |
| 10883 ACCAGTGGGATTCATGAGACAAAA | 22541 CCCCCTACTTCATTCGTTGTTCTG | 33525 GCCCCTGTATTCTAACCAGTGGGATTG | 44509 |
| 10884 CCACAGAGCCTAGCAAGGTGTT | 22542 GGGAGGCTATCCAACCAGTAAGT | 33526 AGAGCACAGGGACCACAGA | 44510 |
| 10885 CCCTTCTGTGCAATGGGACTTG | 22543 CCCACCCCTGCCCATCTTAC | 33527 CAGCTTCCCCTTCTGTGCAA | 44511 |
| 10886 TGTTGGCTTCTGCAGTGTGA | 22544 TGGGCTCCCACACCTGTTTC | 33528 AGGACTTTCTGGGCATGTGTTG | 44512 |
| 10887 CCAACTGAGAACTTGCTTCCCAAAAG | 22545 GGCTGTGAAGAAGCACTGAGGAT | 33529 GCCACAACCCTACCAACTGAGA | 44513 |
| 10888 CTGCCCAAGCCTTTTGACTTTTG | 22546 CCTCAATGAATAGTTCCCACCTCAA | 33530 AAGGTTTCTGCCCAGGCTTT | 44514 |
| 10889 GTGAAAGCCTAGCCATCTGGGGTTT | 22547 CTTTAAACTGGGATCGCTACAGAAAAG | 33531 GCAAAAGTACTCGCACTGTGAAAGCTA | 44515 |
| 10890 CAAAATCCTGGGGATACAGACTCTT | 22548 TGCCCAGGCAGAGGGAGCAA | 33532 CCTCTGCCCCAGCATATATCAAA | 44516 |
| 10891 GAACCCACTGGAATACGTCCTT | 22549 CCCAAAGTGCCTTGTTTTCTCTGATCA | 33533 CACACCCAAGAACCCACTGGAA | 44517 |
| 10892 GACATGATCTGACCCTTGACACA | 22550 GGCTGCAGCAGAGTGAATAAGA | 33534 GCCCAGAGGCTTGACATGATCT | 44518 |
| 10893 AGGGAGCTTAGAGGGAAGGTCAA | 22551 CACTCTGACAGTGAGGTTCTTGGTA | 33535 GTCATTGCCTCAAAGGGAAGGCTTAG | 44519 |
| 10894 CAGCCACATTCCAGAGGCAATC | 22552 GCCATCCTCCTCTGGGTTACT | 33536 CTAGCCTCCTGCTGGCTCACAGTC | 44520 |
| 10895 GTGTGTGTGGGCTTTATGAAGAAAA | 22553 TGCATACAGCATACTCTGTTCACAT | 33537 GCTCACAGTGTGTGTGGGCTTT | 44521 |
| 10896 GAAGTGAAGAAGAGTGGTCAGCTA | 22554 TCCTACAGGCCCCTGAACTT | 33538 CCTACTTTTGGGAGGGGAAGTGA | 44522 |
| 10897 ACCATGGTTCCTTGTCAGCATAA | 22555 CCGAAAAGAGGTAGGCAGAGCTAAT | 33539 GCCCCTTGATTCCTCTAAACCAT | 44523 |
| 10898 GAAATCAGCTCTCTCTCCACTCAGTT | 22556 GTGATTGGGGCACAGAACTCCTA | 33540 GAGCCCTGAAATCAGCTTCTCTCT | 44524 |
| 10899 TGTGGTAGAAGAAGTGTCTCCATTG | 22557 CTGAAGGGTAGGTCAGATCAAGCAA | 33541 GGTGGTTCAGTGTATTGTGGTAGAAG | 44525 |
| 10900 GCCTAGCTTCAAGAGCTCCTTCT | 22558 ATTCCAGCCAGCCACCAATG | 33542 GGCCTGTGCCTAGCTTCAAGA | 44526 |
| 10901 GTGGCTTACCCACCAGCAAACT | 22559 ACTGTCATGTGTCTCTCTGCTTTT | 33543 AACGGGCAGCAGGTGGCTTA | 44527 |
| 10902 CTGCAGTGTTCTGGGGCTAGTTT | 22560 GCCTTGCACCACTACACAGAGA | 33544 GAGGCAAGCCTGAGTGTTCT | 44528 |
| 10903 CAGAGGGCTAGTGTATCTCCAAGA | 22561 GGGGAGTATTACAAAGACCTAAGGAGGTA | 33545 TCACCCATCAGACGGCTAGTGT | 44529 |
| 10904 GTCTCTGGGCTTAATGTGCAAGT | 22562 GCAATGTGTCCCGGTTCTGTACT | 33546 TCCCAGCCTGCTGCCTGGGCTTA | 44530 |
| 10905 CACAGTGGACTTGTTGTTCTTGAGT | 22563 GGGTCTGTTCATCACTCAATCATTC | 33547 CAGATTCTGACTCACAGTGGACTTGTT | 44531 |
| 10906 GCTCCATTTATGTTCCATTGTGTCT | 22564 GACACTGCCTAGCCTTTGTCATTG | 33548 CCTGCCACCTTGATTGCTCCAT | 44532 |
| 10907 GCTTATTTGGTAACGACTAGGCAGAT | 22565 TGCTGGGCTGTGGATTGGTA | 33549 CCACATACAATTACCGTCTGCTATTTG | 44533 |
| 10908 TCTCCAGAGCCTTTGCTTCCTA | 22566 AGCCAAGAGGAGTTGGGCACTTG | 33550 CGAACCCAAGCAGTCTTCTGTCT | 44534 |
| 10909 CACCAGCATTCAAGTGCAAGTA | 22567 GCACTCACACAAGGGCAGGTAA | 33551 GCTAGGACATCCACCAGCATTCA | 44535 |
| 10910 ACCTTCCAGGTCTCAGCTCTCT | 22568 GCTGGTGGGAGAGGAGTATAGAT | 33552 CTGTGTTTTGCCATGGACACTTT | 44536 |
| 10911 CACCCTTGAGACAATGGGTTCTAG | 22569 GACCCACTGGGAAGGTATCCTA | 33553 GCCCCTCAATCACCCTTGAGACA | 44537 |
| 10912 GGACATGTGAAAGATTGGGACAGGTT | 22570 TCCTATGGGGTCCCATCATTTTCT | 33554 GCTGGCTGAATAGGGACATGGAA | 44538 |
| 10913 CCAGTGTCAGCTGGGTTTTGT | 22571 CATTAAACTCAGTGCTGTCCTGTTAG | 33555 TCCTTCCATGGCCAGTGTCA | 44539 |
| 10914 AGGTAAAGGGTGGAAAAAGACATC | 22572 GTGTCTGATATTCCTGCTACTTTTG | 33556 CACAAACTTAAGGTAAAGGGTGGAA | 44540 |
| 10915 CCTTCTAACACCCCTTCTCTGTGAGAT | 22573 CATTCCCAACAGCATGCCTAGATA | 33557 AGAGTTTCCTTCTAACACCCCTTCT | 44541 |
| 10916 GACTGAAGACCAGCAGACAGAAG | 22574 GGTTAGCTTCACTTCTTGGGAGTA | 33558 GGAAATGATCCACCATGAGTGAAGA | 44542 |
| 10917 GGTGGAACCAAAGAAGAAAGGGTTT | 22575 GCATCTCAGCCTTTGGGTTTTG | 33559 TTTGGACAGGTGGAACCAAAGA | 44543 |

| Description | MAPPED_READS | TOTAL_READS | %Mapped Reads |
|---|---|---|---|
| gMother | 3,633,900 | 3,647,446 | 100% |
| gMother | 3,567,685 | 3,578,549 | 100% |
| gMother | 3,733,706 | 3,747,692 | 100% |
| gChild | 3,725,554 | 3,737,742 | 100% |
| gChild | 3,816,989 | 3,829,450 | 100% |
| gChild | 3,524,956 | 3,536,569 | 100% |
| 1 mother | 3,467,493 | 7,564,869 | 46% |
| 1 mother | 3,868,210 | 7,107,028 | 54% |
| 1 mother | 4,918,140 | 7,613,240 | 65% |
| 1 child | 361,390 | 6,507,434 | 6% |
| 1 child | 1,885,864 | 6,496,348 | 29% |
| 1 child | 2,789,647 | 6,259,288 | 45% |

FIG. 37

| Description | MAPPED_READS | TOTAL_READS | %Mapped Reads |
|---|---|---|---|
| case 1 blastoceol | 68,123 | 8,470,872 | 1% |
| case 1 cell 1 | 4,340,613 | 8,248,598 | 53% |
| case 1 cell 2 | 5,480,580 | 8,230,870 | 67% |
| case 1 cell 3 | 4,664,577 | 7,846,040 | 59% |
| case 2 blastoceol | 45,794 | 6,302,957 | 1% |
| case 2 cell 1 | 6,988,854 | 8,622,495 | 81% |
| case 2 cell 2 | 7,083,600 | 8,843,495 | 80% |
| case 2 cell 3 | 5,811,364 | 8,256,310 | 70% |

FIG. 39

|  | gDNA | Single Cell |
|---|---|---|
| Count | 75 | 510 |
| Mean | 0.15 % | 0.51 % |
| Median | 0.09 % | 0.33 % |
| Max | 1.03 % | 10 % |
| Standard Deviation | 0.16% | 0.79 % |
| 95th percentile | 0.43 % | 1.22 % |
| 90th percentile | 0.37 % | 0.92 % |

FIG. 46

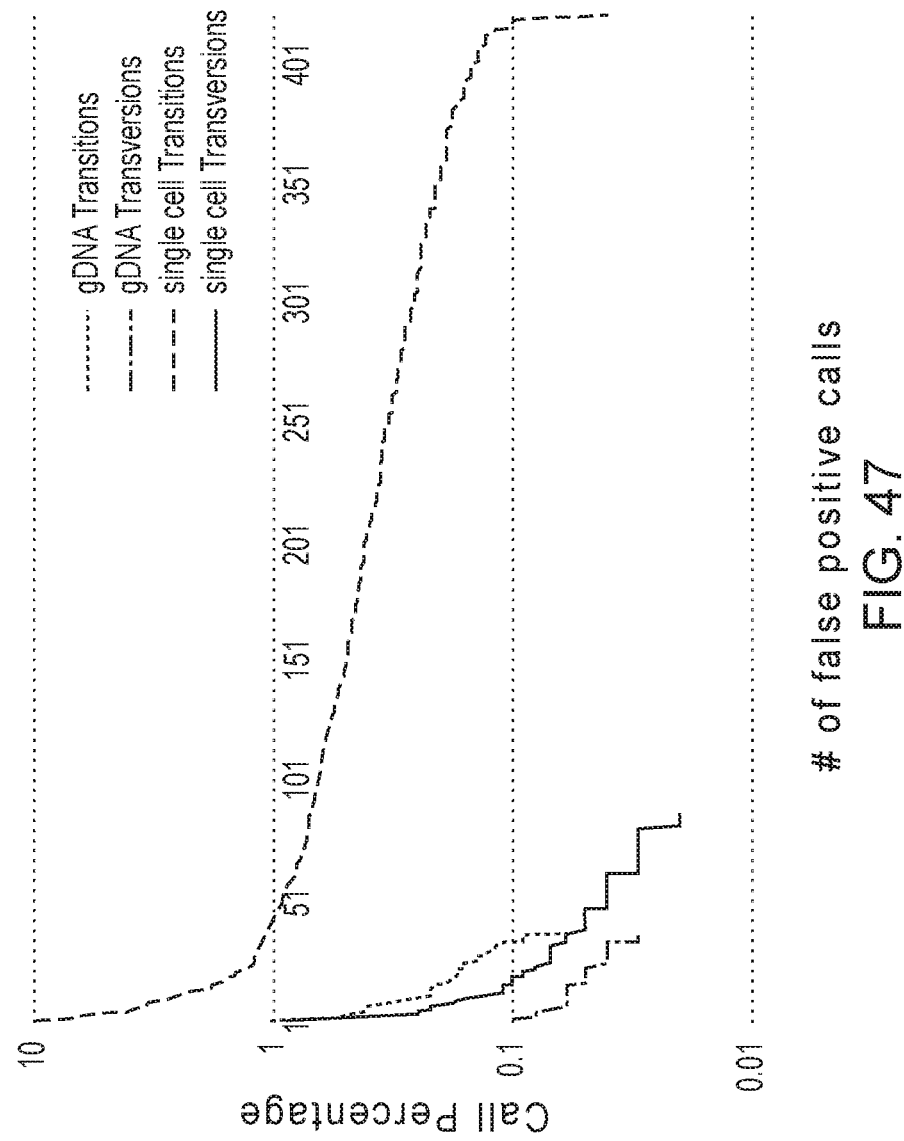

| DOE1 | Mapped READS | TOTAL READS | % Mapped | Dropout Count | Median DOR All | NOR | Error Rate (%) |
|---|---|---|---|---|---|---|---|
| 1xMM | 1,112,007 | 1,262,558 | 80.0% | 436 | 26.25 | 1,043,539 | 0.107% |
| 2xMM | 3,412,593 | 3,615,347 | 94.4% | 105 | 147.75 | 3,206,478 | 0.141% |
| F-A | 449,074 | 635,571 | 70.6% | 1379 | 9.625 | 421,228 | 0.077% |
| F-B | 3,293,944 | 3,519,378 | 93.7% | 105 | 142.5 | 3,106,520 | 0.072% |
| F-D | 4,028,128 | 4,109,448 | 98.0% | 122 | 142.5 | 3,796,213 | 0.064% |
| F-J | 3,676,617 | 3,922,330 | 93.7% | 102 | 159.25 | 3,461,304 | 0.079% |

F-A is : 25 mM Tris pH 7.8, 3 mM MgCl$_2$, 0 mM KCl, 10 mM (NH$_4$)$_2$SO$_4$, 50 U/mL Taq Gold    aka F-A Gold F-B is : 75 mM Tris pH 7.8, 6 mM MgCl$_2$, 0 mM KCl, 40 mM (NH$_4$)$_2$SO$_4$, 150 U/mL Taq Gold    aka F-B Gold F-D is : 25 mM Tris pH 8.2, 3 mM MgCl$_2$, 30 mM KCl, 40 mM (NH$_4$)$_2$SO$_4$, 150 U/mL Taq Gold F-J is : 75 mM Tris pH 7.8, 6 mM MgCl$_2$, 0 mM KCl, 40 mM (NH$_4$)$_2$SO$_4$, 150 U/mL Qiagen HS Taq    aka F-B Qiagen

FIG. 48

METHODS FOR SIMULTANEOUS AMPLIFICATION OF TARGET LOCI

CROSS-REFERENCE TO RELATED APPLICATIONS

This application is a continuation of U.S. Utility application Ser. No. 14/538,982 filed Nov. 24, 2014, which claims the benefit of U.S. Provisional Application Ser. No. 61/982, 245, filed Apr. 21, 2014; U.S. Provisional Application Ser. No. 61/987,407, filed May 1, 2014, U.S. Provisional Application Ser. No. 61/994,791, filed May 16, 2014; and U.S. Provisional Application Ser. No. 62/066,514 filed Oct. 21, 2014. The entireties of all these applications are each hereby incorporated by reference in their entireties.

SEQUENCE LISTING

The instant application contains a Sequence Listing which has been submitted electronically in ASCII format and is hereby incorporated by reference in its entirety. Said ASCII copy, created on Jan. 31, 2017, is named N_012_US_06_SL.txt and is 8,724,145 bytes in size.

FIELD OF THE INVENTION

The present invention generally relates to methods and compositions for simultaneously amplifying multiple nucleic acid regions of interest in one reaction volume.

BACKGROUND OF THE INVENTION

To increase assay throughput and allow more efficient use of nucleic acid samples, simultaneous amplification of many target nucleic acids in a sample of interest can be carried out by combining many oligonucleotide primers with the sample and then subjecting the sample to polymerase chain reaction (PCR) conditions in a process known in the art as multiplex PCR. Use of multiplex PCR can significantly simplify experimental procedures and shorten the time required for nucleic acid analysis and detection. However, when multiple pairs are added to the same PCR reaction, non-target amplification products may be generated, such as amplified primer dimers. The risk of generating such products increases as the number of primers increases. These non-target amplicons significantly limit the use of the amplified products for further analysis and/or assays. Thus, improved methods are needed to reduce the formation of non-target amplicons during multiplex PCR.

Improved multiplex PCR methods would be useful for a variety of application, such as Non-Invasive Prenatal Genetic Diagnosis (NPD). In particular, current methods of prenatal diagnosis can alert physicians and parents to abnormalities in growing fetuses. Without prenatal diagnosis, one in 50 babies is born with serious physical or mental handicap, and as many as one in 30 will have some form of congenital malformation. Unfortunately, standard methods have either poor accuracy, or involve an invasive procedure that carries a risk of miscarriage. Methods based on maternal blood hormone levels or ultrasound measurements are non-invasive, however, they also have low accuracies. Methods such as amniocentesis, chorion villus biopsy and fetal blood sampling have high accuracy, but are invasive and carry significant risks. Amniocentesis was performed in approximately 3% of all pregnancies in the US, though its frequency of use has been decreasing over the past decade and a half.

Normal humans have two sets of 23 chromosomes in every healthy, diploid cell, with one copy coming from each parent. Aneuploidy, a condition in a nuclear cell where the cell contains too many and/or too few chromosomes is believed to be responsible for a large percentage of failed implantations, miscarriages, and genetic diseases. Detection of chromosomal abnormalities can identify individuals or embryos with conditions such as Down syndrome, Klinefelter's syndrome, and Turner syndrome, among others, in addition to increasing the chances of a successful pregnancy. Testing for chromosomal abnormalities is especially important as the mother's age, between the ages of 35 and 40 it is estimated that at least 40% of the embryos are abnormal, and above the age of 40, more than half of the embryos are abnormal.

It has recently been discovered that cell-free fetal DNA and intact fetal cells can enter maternal blood circulation. Consequently, analysis of this genetic material can allow early NPD. Improved methods are desired to improve the sensitivity and specificity and reduce the time and cost required for NPD.

SUMMARY OF THE INVENTION

In one aspect, the invention features methods of amplifying target loci in a nucleic acid sample. In some embodiments, the method involves (i) contacting the nucleic acid sample with a library of test primers (such as non-immobilized primers) that simultaneously hybridize to at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci to produce a reaction mixture; and (ii) subjecting the reaction mixture to primer extension reaction conditions to produce amplified products that include target amplicons. In some embodiments, the method also includes determining the presence or absence of at least one target amplicon (such as at least 50, 60, 70, 80, 90, 95, 96, 97, 98, 99, or 99.5% of the target amplicons). In some embodiments, the method also includes determining the sequence of at least one target amplicon (such as at least 50, 60, 70, 80, 90, 95, 96, 97, 98, 99, or 99.5% of the target amplicons). In some embodiments, the method involves multiplex PCR and sequencing (such as high throughput sequencing). In some embodiments, the method includes selecting the test primers from a library of candidate primers by removing one or more of the candidate primers based at least in part on the likelihood of dimer formation between candidate primers (such as ΔG values, undesirability scores, or interaction scores) prior to contacting the nucleic acid sample with the library of test primers.

In some embodiments, the method involves (i) contacting a sample comprising target human loci with a library of at least 50 (such as at least 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000) non-immobilized, non-identical primers that simultaneously hybridize to at least 50 (such as at least 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000) non-identical target human loci to produce a reaction mixture; wherein the primers do not include molecular inversion probes (MIPs); (ii) subjecting the reaction mixture to primer extension reaction conditions to produce amplified products comprising target amplicons; wherein the annealing temperature for the reaction conditions is greater than a melting temperature (such as the empirically measured or calculated $T_m$) of at least 50 (such as at least 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000) of the non-identical primers and/or the length of the annealing step of the reaction conditions is greater than 5 minutes (such as at least 8, 10, 15, 20, 30, 45, 60, 75, 90, 120, 150, or 180 minutes, and wherein at least 50 (such as at least 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000) non-identical target human loci are simultaneously amplified, and (iii) detecting the amplified products such as by sequencing the amplified products or hybridizing the amplified products to an array. In some embodiments, the method includes empirically measuring or calculating (such as calculating with a computer) the melting temperature of at least 25, 50, 80, 90, 92, 94, 96, 98, 99, or 100% of the primers in the library and selecting an annealing temperature that satisfies any of these embodiments for PCR amplification of target loci.

In some embodiments, the method involves (i) contacting a sample comprising target human loci with a library of at least 2 (such as at least 5, 10, 25 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000) non-immobilized, non-identical primers that simultaneously hybridize to at least 2 (such as at least 5, 10, 25 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000) non-identical target human loci to produce a reaction mixture; wherein the primers do not include molecular inversion probes (MIPs); (ii) subjecting the reaction mixture to primer extension reaction conditions to produce amplified products comprising target amplicons; wherein at least 2 (such as at least 5, 10, 25 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000) non-identical target human loci are simultaneously amplified; and (iii) detecting the amplified products such as by sequencing the amplified products or hybridizing the amplified products to an array. In various embodiments, (i) the annealing temperature is at least 1, 2, 3, 4, 5, 6, 7, 8, 9, 10, 11, 12, 13, or 15° C. greater than the melting temperature (such as the empirically measured or calculated $T_m$) of at least 2, 5, 10, 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers; (ii) the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the melting temperature (such as the empirically measured or calculated $T_m$) of at least 2, 5, 10, 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers; (iii) the annealing temperature is at least 1, 2, 3, 4, 5, 6, 7, 8, 9, 10, 11, 12, 13, or 15° C., greater than the highest melting temperature (such as the empirically measured or calculated $T_m$) of the primers; (iv) the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the highest melting temperature (such as the empirically measured or calculated $T_m$) of the primers; (v) the annealing temperature is at least 1, 2, 3, 4, 5, 6, 7, 8, 9, 10, 11, 12, 13, or 15° C. greater than the average melting temperature (such as the empirically measured or calculated $T_m$) of at least 2, 5, 10, 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers, or (vi) the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the average melting temperature (such as the empirically measured or calculated $T_m$) of at least 2, 5, 10, 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers. In various embodiments, (i) the length of the annealing step (per PCR cycle) is greater than 1, 3, 5, 8, 10, 15, 20, 30, 45, 60, 75, 90, 120, 150, or 180 minutes or (ii) the length of the annealing step (per PCR cycle) is between 5 and 180 minutes, such as 5 to 60, 10 to 60, 5 to 30, or 10 to 30 minutes, inclusive. In various embodiments, any of the embodiments for annealing temperature are combined with any of the embodiments for annealing time. In various embodiments, the annealing temperature is at least 3° C. greater than the melting temperature of at least 50 of the non-identical primers, the annealing temperature is at least 3° C. greater than the highest melting temperature of the primers, the annealing temperature is at least 8° C. greater than the highest melting temperature of the primers, the annealing temperature is at least 3° C. greater than the average melting temperature of the primers, the annealing temperature is at least 8° C. greater than the average melting temperature of the primers, the range of melting temperature of the primers is between 1 to 5° C., inclusive, the range of melting temperatures of the primers is less than 5° C., or any combination thereof. In some embodiments, the method includes empirically measuring or calculating (such as calculating with a computer) the melting temperature of at least 25, 50, 80, 90, 92, 94, 96, 98, 99, or 100% of the primers in the library and selecting an annealing temperature that satisfies any of these embodiments for PCR amplification of target loci. In some embodiments, a crowding agent, such as PEG or glycerol is included in the reaction mixture.

In various embodiments of any of the aspects of the invention, the method includes non-specifically amplifying nucleic acids in a sample comprising target human loci; contacting the amplified nucleic acids with a library of non-identical primers (such as non-immobilized primers) that simultaneously hybridize to at least 1,000 non-identical target human loci to produce a reaction mixture; wherein the primers do not include molecular inversion probes (MIPs); subjecting the reaction mixture to primer extension reaction conditions to produce amplified products comprising target amplicons; wherein at least 1,000 non-identical target human loci are simultaneously amplified; and sequencing the amplified products. In some embodiments, the non-specific amplification comprises universal polymerase chain reaction (PCR), whole genome application, ligation-mediated PCR, degenerate oligonucleotide primer PCR, or multiple displacement amplification. In some embodiments, the method includes contacting a sample comprising target human loci with a library of non-identical primers (such as non-immobilized primers) that simultaneously hybridize to at least 1,000 non-identical target human loci to produce a reaction mixture, wherein the primers do not include molecular inversion probes (MIPs); subjecting the reaction mixture to primer extension reaction conditions to produce amplified products comprising target amplicons; wherein the annealing temperature for the reaction conditions is greater than the melting temperature of at least 1,000 of the non-identical primers; and wherein at least 1,000 non-identical target human loci are simultaneously amplified; and sequencing the amplified products. In some embodiments, the method includes contacting a sample comprising target human loci with a library of non-identical primers (such as non-immobilized primers) that simultaneously hybridize to at least 1,000 non-identical target human loci to produce a reaction mixture in which the concentration of each primer is less than 20 nM; wherein the primers do not include molecular inversion probes (MIPs), subjecting the reaction mixture to primer extension reaction conditions to produce amplified products comprising target amplicons, wherein the length of the annealing step of the reaction conditions is greater than 10 minutes; and wherein at least 1,000 non-identical target human loci are simultaneously amplified; and sequencing the amplified products. In some embodiments, the method includes contacting a sample comprising target human loci with a library of non-identical primers (such as non-immobilized primers) that simultaneously hybridize to at least 1,000 non-identical target human loci to produce a reaction mixture, wherein the guanine-cytosine (GC) content of the primers is between 30% and 80%, inclusive; wherein the range of melting temperatures of the primers is less than 5° C.; wherein the length of the primers is between 15 to 75 nucleotides, inclusive; and wherein the primers do not include molecular inversion probes (MIPs); subjecting the reaction mixture to primer extension reaction conditions to produce amplified products comprising target amplicons; wherein at least 1,000 non-identical target human loci are simultaneously amplified; and sequencing the amplified products. In some embodiments, the method does not comprise using a microarray. In some embodiments, the library includes a least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different primers. In some embodiments, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified.

In various embodiments of any of the aspects of the invention, the ΔG values for each possible combination of two primers in the library are all equal to or greater than −5 kcal/mol. In some embodiments, the method simultaneously PCR-amplifying at least 1,000 non-identical target human loci in the sample using at least 1,000 non-identical primer pairs (such as non-immobilized primer pairs) to produce a first set of amplified products; wherein each primer pair includes a forward primer and a reverse primer that hybridize to the same target human locus. In some embodiments, the method also includes simultaneously PCR-amplifying at least 1,000 non-identical target human loci in the first set of amplified products using at least 1,000 non-identical primer pairs (such as non-immobilized primer pairs) to produce a second set of amplified products; wherein each primer pair includes a forward primer and a reverse primer that hybridize to the same target human locus. In some embodiments, the primer pairs used in the first and second round of PCR are the same. In some embodiments, the primer pairs used in the first and second round of PCR are different. In some embodiments, the forward primers used in the first and second round of PCR are the same, and the reverse primers used in the first and second round of PCR are different. In some embodiments, the forward primers used in the first and second round of PCR are different, and the reverse primers used in the first and second round of PCR are the same. In some embodiments, the method simultaneously PCR-amplifying at least 1,000 non-identical target human loci in the sample using at least 1,000 non-identical primer pairs (such as non-immobilized primer pairs) to produce a first set of amplified products; wherein each primer pair includes an outer forward primer and an outer reverse primer that hybridize to the same target human locus; and simultaneously PCR-amplifying at least 1,000 non-identical target human loci in the first set of amplified products using a universal reverse primer and at least 1,000 non-identical inner forward primers to produce a second set of amplified products; wherein each inner forward primer hybridizes to a region downstream from the corresponding outer forward primer. In some embodiments, the method includes simultaneously PCR-amplifying at least 1,000 non-identical target human loci in the sample using at least 1,000 non-identical primer pairs to produce a first set of amplified products; wherein each primer pair includes an outer forward primer and an outer reverse primer that hybridize to the same target human locus; and simultaneously PCR-amplifying at least 1,000 non-identical target human loci in the first set of amplified products using a universal forward primer and at least 1,000 non-identical inner reverse primers to produce a second set of amplified products; wherein each inner reverse primer hybridizes to a region upstream from the corresponding outer reverse primer. In some embodiments, the method includes simultaneously PCR-amplifying at least 1,000 non-identical target human loci in the sample using at least 1,000 non-identical forward primers and a universal reverse primer to produce a first set of amplified products; and simultaneously PCR-amplifying at least 1,000 non-identical target human loci in the first set of amplified products using a universal forward primer and at least 1,000 non-identical reverse primers to produce a second set of amplified products. In some embodiments, the method includes simultaneously PCR-amplifying at least 1,000 non-identical target human loci in the sample using at least 1,000 non-identical reverse primers and a universal forward primer to produce a first set of amplified products; and simultaneously PCR-amplifying at least 1,000 non-identical target human loci in the first set of amplified products using a universal reverse primer and at least 1,000 non-identical forward primers to produce a second set of amplified products. In some embodiments, at least 96% of the primer molecules are extended to form amplified products. In some embodiments, the annealing temperature is at least 1, 2, 3, 4, 5, 6, 7, 8, 9, 10, 11, 12, 13, or 15° C. greater than the melting temperature of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers. In some embodiments, the annealing temperature is at least 1, 2, 3, 4, 5, 6, 7, 8, 9, 10, 11, 12, 13, or 15° C. greater than the highest melting temperature of the non-identical primers. In some embodiments, the annealing temperature is at least 1, 2, 3, 4, 5, 6, 7, 8, 9, 10, 11, 12, 13, or 15° C. greater than the average melting temperature of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers. In some embodiments, the range of melting temperature of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers is between 1 to 5° C., inclusive. In some embodiments, at least 25; 50; 75; 100; 300; 500; 750; 1,000; 2,000; 5,000; 7,500; 10,000; 15,000; 19,000; 20,000; 25,000; 27,000; 28,000;

30,000; 40,000; 50,000; 75,000; 100,000; or all of the non-identical primers have 2, 1, or 0 guanines or cytosines in the last 5 bases at the 3' end of the primers. In some embodiments, the sample comprises maternal DNA from the pregnant mother of a fetus and fetal DNA, and wherein the method comprises determining the presence or absence of a fetal chromosome abnormality from the sequencing data. In some embodiments, the sample is from an individual suspected of having cancer or an above normal risk for cancer and wherein one or more of the target human loci comprises a polymorphism or other mutation associated with an above normal risk for cancer or associated with cancer.

In various embodiments of any of the aspects of the invention, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified. In some embodiments, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified at least 5, 10, 20, 40, 50, 60, 80, 100, 120, 150, 200, 300, or 400-fold. In some embodiments, at least 50, 60, 70, 80, 90, 95, 96, 97, 98, 99, or 99.5% of the amplified products are target amplicons. In some embodiments, at least 50, 60, 70, 80, 90, 95, 96, 97, 98, 99, or 99.5% of the target loci are amplified. In some embodiments, at least 50, 60, 70, 80, 90, 95, 96, 97, 98, 99, or 99.5% of the target loci are amplified at least 5, 10, 20, 40, 50, 60, 80, 100, 120, 150, 200, 300, or 400-fold. In various embodiments, less than 60, 50, 40, 30, 20, 10, 5, 4, 3, 2, 1, 0.5, 0.25, 0.1, or 0.05% of the amplified products are primer dimers. In some embodiments, the library of test primers includes at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 test primer pairs, wherein each pair of primers includes a forward test primer and a reverse test primer that hybridize to the same target locus. In some embodiments, the library of test primers includes at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 individual test primers that hybridize to different target loci, wherein the individual primers are not part of primer pairs.

In various embodiments of any of the aspects of the invention, the concentration of each test primer is less than 100, 75, 50, 25, 10, 5, 2, 1, 0.5, 0.1, or 0.05 nM. In various embodiments, the guanine-cytosine (GC) content of the test primers is between 30 to 80%, such as between 20 to 70%, 40 to 70%, or 50 to 60%, inclusive. In some embodiments, the range of GC content (e.g., the maximum GC content minus minimum GC content, such as 80%–60%=a range of 20%) of the test primers is less than 30, 20, 10, or 5%. In some embodiments, there are at least 2 (such as 3, 4, or 5) guanines or cytosines in the last 5 bases at the 3' end of the primers. In some embodiments, a maximum of 2 (such as 2, 1, or 0) of the bases in the last 5 bases at the 3' end of the primers are guanines or cytosines. In some embodiments, there are at least 1 (such as 2 or 3) guanines or cytosines in the last 3 bases at the 3' end of the primers. In some embodiments, the melting temperature ($T_m$) of the test primers is between 40 to 80° C., such as 50 to 70° C., 55 to 65° C., 54 to 60.5° C., or 57 to 60.5° C., inclusive. In some embodiments, the range of melting temperatures of the test primers is less than 20, 15, 10, 5, 3, or 1° C. In some embodiments, the length of the test primers is between 15 to 100 nucleotides, such as between 15 to 75 nucleotides, 15 to 40 nucleotides, 17 to 35 nucleotides, 18 to 30 nucleotides, or 20 to 65 nucleotides, inclusive. In some embodiments, the test primers include a tag that is not target specific, such as a tag that forms an internal loop structure. In some embodiments, the tag is between two DNA binding regions. In various embodiments, the test primers include a 5' region that is specific for a target locus, an internal region that is not specific for the target locus and forms a loop structure, and a 3' region that is specific for the target locus. In various embodiments, the length of the 3' region is at least 7 nucleotides. In some embodiments, the length of the 3' region is between 7 and 20 nucleotides, such as between 7 to 15 nucleotides, or 7 to 10 nucleotides, inclusive. In various embodiments, the test primers include a 5' region that is not specific for a target locus (such as a tag or a universal primer binding site) followed by a region that is specific for a target locus, an internal region that is not specific for the target locus and forms a loop structure, and a 3' region that is specific for the target locus. In some embodiments, the range of the length of the test primers is less than 50, 40, 30, 20, 10, or 5 nucleotides. In some embodiments, the length of the target amplicons is between 50 and 100 nucleotides, such as between 60 and 80 nucleotides, or 60 to 75 nucleotides, inclusive. In some embodiments, the length of the target amplicons is at least 100; 200; 300; 400; 500; 600; 700; 800; 900; 1,000; 1,200; 1,500; 2,000; or 3,000 nucleotides. In some embodiments, the length of the target amplicons is between 100 and 1,500 nucleotides, such as between 100 to 1,000, 100 to 500, 500 to 750, or 750 to 1,000 nucleotides, inclusive. In some embodiments, the range of the length of the target amplicons is less than 50, 25, 15, 10, or 5 nucleotides. In some embodiments, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 or all of the target amplicons have a length that falls within the range of the average length of the amplicons ±5% of the average length, average length ±20%, average length ±20%, average length ±30%, or average length ±50%.

In various embodiments of any of the aspects of the invention, the primer extension reaction conditions are polymerase chain reaction conditions (PCR). In various embodiments, the length of the annealing step is greater than 3, 5, 8, 10, 15, 20, 30, 45, 60, 75, 90, 120, 150, or 180 minutes. In various embodiments, the length of the extension step is greater than 0.2, 0.5, 1, 3, 5, 8, 10, or 15 minutes.

In various embodiments of any of the aspects of the invention, the test primers are used to simultaneously amplify at least 300 different target loci in a sample that includes maternal DNA from the pregnant mother of a fetus and fetal DNA to determine the presence or absence of a fetal chromosome abnormality. In various embodiments, the method includes ligating a universal primer binding site to the DNA molecules in the sample; amplifying the ligated DNA molecules using at least 300 specific primers and a universal primer to produce a first set of amplified products; and amplifying the first set of amplified products using at least 300 pairs of specific primers to produce a second set of amplified products.

In various embodiments of any of the aspects of the invention, the test primers are used to simultaneously amplify e.g. at least 100 (e.g., at least 300 or 1,000) different target loci in sample includes DNA from an alleged father of a fetus and to simultaneously amplify the target loci in a sample that includes maternal DNA from the pregnant mother of the fetus and fetal DNA to establish whether the alleged father is the biological father of the fetus.

In various embodiments of any of the aspects of the invention, the test primers are used to simultaneously amplify e.g. at least 100 (e.g., at least 300 or 1,000) different target loci in one cell or multiple cells from an embryo to determine the presence or absence of a chromosome abnormality. In various embodiments, cells from a set of two or more embryos are analyzed, and one embryo is selected for in vitro fertilization.

In various embodiments of any of the aspects of the invention, the test primers are used to simultaneously amplify e.g. at least 100 (e.g., at least 300 or 1,000) different target loci in a forensic nucleic acid sample. In various embodiments, the length of the annealing step is greater than 3, 5, 8, 10, 15, 20, 30, 45, 60, 75, 90, 120, 150, or 180 minutes.

In various embodiments of any of the aspects of the invention, the method involves using the test primers to simultaneously amplify e.g. at least 100 (e.g., at least 300 or 1,000) different target loci in a control nucleic acid sample to produce a first set of target amplicons and to simultaneously amplify the target loci in a test nucleic acid sample to produce a second set of target amplicons, and comparing the first and second sets of target amplicons to determine whether a target locus is present in one sample but absent in the other, or whether a target locus is present at different levels in the control sample and the test sample. In various embodiments, the test sample is from an individual suspected of having a disease or phenotype of interest (such as cancer), or an increased risk (such as an above normal level of risk) for a disease or phenotype of interest; and wherein one or more of the target loci include a sequence (e.g., a polymorphism or other mutation) associated with an increased risk (such as an above normal level of risk) for the disease or phenotype of interest, or associated with the disease or phenotype of interest. In various embodiments, the method involves using the test primers to simultaneously amplify e.g. at least 100 (e.g., at least 300 or 1,000) different target loci in a control sample that includes RNA to produce a first set of target amplicons and to simultaneously amplify the target loci in a test sample that includes RNA to produce a second set of target amplicons, and comparing the first and second sets of target amplicons to determine the presence or absence of a difference in the RNA expression levels between the control sample and the test sample. In various embodiments, the RNA is mRNA. In various embodiments, the test sample is from an individual suspected of having a disease or phenotype of interest (such as cancer) or an increased risk for the disease or phenotype of interest (such as cancer), and wherein one or more of the target loci includes a sequence (e.g., a polymorphism or other mutation) associated with an increased risk for the disease or phenotype of interest or associated with the disease or phenotype of interest. In some embodiments, the test sample is from an individual diagnosed with a disease or phenotype of interest (such as cancer); and wherein a difference in the RNA expression level between the control sample and test sample indicates a target locus includes a sequence (e.g., a polymorphism or other mutation) associated with an increased or decreased risk for the disease or phenotype of interest.

In some embodiments of any of the aspects of the invention, the test primers are selected from a library of candidate primers based on one or more parameters, such as the selection of primers using any of the methods of the invention. In some embodiments, the test primers are selected from a library of candidate primers based at least in part on the ability of the candidate primers to form primer dimers.

In one aspect, the invention features methods of selecting test primers from a library of candidate primers. In various embodiments, the selection involves (i) calculating on a computer a score (such as an undesirability score) for most or all of the possible combinations of two candidate primers from the library, wherein each score (such as an undesirability score) is based at least in part on the likelihood of dimer formation between the two candidate primers; (ii) removing the candidate primer with the highest score (such as an undesirability score) from the library of candidate primers; and (iii) if the candidate primer removed in step (ii) is a member of a primer pair, then removing the other member of the primer pair from the library of candidate primers, and (iv) optionally repeating steps (ii) and (iii), thereby selecting a library of test primers. In some embodiments, the selection method is performed until the score (such as the undesirability score) for the candidate primer combinations remaining in the library are all equal to or below a minimum threshold. In some embodiments, the selection method is performed until the number of candidate primers remaining in the library is reduced to a desired number. In various embodiments, a score (such as an undesirability score) is calculated for at least 80, 90, 95, 98, 99, or 99.5% of the possible combinations of candidate primers in the library. In various embodiments, the candidate primers remaining in the library are capable of simultaneously amplifying at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci. In various embodiments, the method also includes (v) contacting a nucleic acid sample that includes target loci with the candidate primers remaining in the library to produce a reaction mixture, and (vi) subjecting the reaction mixture to primer extension reaction conditions to produce amplified products that includes target amplicons.

In one aspect, the invention features methods of selecting test primers from a library of candidate primers. In various embodiments, the selection of test primers are selected from a library of candidate primers involves (i) calculating on a computer a score (such as an undesirability score) for most or all of the possible combinations of two candidate primers from the library, wherein each score (such as an undesirability score) is based at least in part on the likelihood of dimer formation between the two candidate primers; (ii) removing from the library of candidate primers the candidate primer that is part of the greatest number of combinations of two candidate primers with a score (such as an undesirability score) above a first minimum threshold; (iii) if the candidate primer removed in step (ii) is a member of a primer pair, then removing the other member of the primer pair from the library of candidate primers; and (iv) optionally repeating steps (ii) and (iii), thereby selecting a library of test primers. In some embodiments, the selection method is performed until the score (such as the undesirability score) for the candidate primer combinations remaining in the library are all equal to or below the first minimum threshold. In some embodiments, the selection method is performed until the number of candidate primers remaining in the library is reduced to a desired number. In various embodiments, a score (such as an undesirability score) is calculated for at least 80, 90, 95, 98, 99, or 99.5% of the possible combinations of candidate primers in the library. In various embodiments, the candidate primers remaining in the library are capable of simultaneously amplifying at least 25; 50; 75; 100; 300; 500; 750; 1,000; 2,000; 5,000; 7,500; 10,000; 15,000; 19,000; 20,000; 25,000; 27,000; 28,000; 30,000;

40,000; 50,000; 75,000; or 100,000 different target loci. In various embodiments, the method also includes (v) contacting a nucleic acid sample that includes target loci with the candidate primers remaining in the library to produce a reaction mixture; and (vi) subjecting the reaction mixture to primer extension reaction conditions to produce amplified products that includes target amplicons.

In various embodiments of any of the aspects of the invention, the selection method involves further reducing the number of candidate primers remaining in the library by decreasing the first minimum threshold used in step (ii) to a lower second minimum threshold and optionally repeating steps (ii) and (iii). In some embodiments, the selection method involves increasing the first minimum threshold used in step (ii) to a higher second minimum threshold and optionally repeating steps (ii) and (iii). In some embodiments, the selection method is performed until the score (such as the undesirability score) for the candidate primer combinations remaining in the library are all equal to or below the second minimum threshold, or until the number of candidate primers remaining in the library is reduced to a desired number.

In various embodiments of any of the aspects of the invention, the method involves, prior to step (i), identifying or selecting primers that hybridize to the target loci. In some embodiments, multiple primers (or primer pairs) hybridize to the same target locus, and the selection method is used to select a one primer (or one primer pair) for this target locus based on one or more parameters. In various embodiments, the method involves, prior to step (ii), removing a primer pair from the library that produces a target amplicon that overlaps with a target amplicon produced by another primer pair. In various embodiments, a candidate primer is selected out of a group of two or more candidate primers with equal scores (such as undesirability scores) for removal from the library of candidate primers based on one or more other parameters. In some embodiments, the candidate primers remaining in the library are used as a library of test primers in any of the methods of the invention. In some embodiments, the resulting library of test primers includes any of the primer libraries of the invention.

In various embodiments of any of the aspects of the invention, the selection method selects candidate primers and divides them into different pools (e.g., 2, 3, 4, 5, 6, or more different pools). Each pool can be used to simultaneously amplify a large number of target loci (or a subset of target loci) in a single reaction volume. In some embodiments, a graph coloring algorithm is used to divide candidate primers into different pools. If desired, this method can be used to minimize the number of different pools needed to amplify most or all of the target loci.

In some embodiments, most or all of the target loci (such as at least 70, 80, 90, 92, 94, 96, 98, 99, or 100% of the target loci) are amplified by at least 2, 3, 4, 5, 6, or more different pools. In some embodiments, most or all of the bases in the target loci (such as at least 70, 80, 90, 92, 94, 96, 98, 99, or 100% of the bases in the target loci) are amplified by at least 2, 3, 4, 5, 6, or more different pools. In some embodiments, most or all of the bases in the target loci (such as at least 70, 80, 90, 92, 94, 96, 98, 99, or 100% of the bases in the target loci) are amplified by at least 2, 3, 4, 5, 6, or more different primers or primer pairs in different pools. For example, a particular base in a target locus may be amplified by at least 2, 3, 4, 5, 6, or more different primers or primer pairs, wherein each different primer or primer pair is in a different pool. Using different primers or primer pairs to amplify each base allows multiple independent measurements of the base to be made, thereby increasing the accuracy of the method. Dividing the different primers or primer pairs that amplify the same base into different pools prevents interference due to overlapping amplicons being formed by different primers or primer pairs.

In one aspect, the invention features methods of selecting test primers from a library of candidate primers to form 2 or more different primer pools. In various embodiments, the selection involves (i) calculating on a computer a score (such as an undesirability score) for most or all of the possible combinations of two candidate primers from the library, wherein each score (such as an undesirability score) is based at least in part on the likelihood of dimer formation between the two candidate primers; (ii) removing the candidate primer with the highest score (such as an undesirability score) from the library of candidate primers, and (iii) if the candidate primer removed in step (ii) is a member of a primer pair, then removing the other member of the primer pair from the library of candidate primers and (iv) optionally repeating steps (ii) and (iii), thereby selecting a first pool. In some embodiments, the selection method is performed until the score (such as the undesirability score) for the candidate primer combinations remaining in the library are all equal to or below a minimum threshold for the first pool. In some embodiments, the selection method is performed until the number of candidate primers remaining in the library is reduced to a desired number for the first pool. In some embodiments, after the first pool is selected those primers are removed from further consideration and steps of the method (such as steps (ii) and (iii)) are repeated with the remaining primers to select a second pool. If desired, this method may be repeated to select the desired number of primer pools. In various embodiments, a score (such as an undesirability score) is calculated for at least 80, 90, 95, 98, 99, or 99.5% of the possible combinations of candidate primers in the library. In some embodiments, the score is based at least in part on the current coverage of the bases in the target locus (such as the number of other primer pools that have a primer or primer pair that amplifies a particular base in the target locus). In various embodiments, one or more of the pools are each capable of simultaneously amplifying at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci. In various embodiments, the method also includes separately contacting a nucleic acid sample that includes target loci with two or more of the pools to produce separate reaction mixtures; and (vi) subjecting the reaction mixtures to primer extension reaction conditions to produce amplified products that includes target amplicons.

In one aspect, the invention features methods of selecting test primers from a library of candidate primers to form 2 or more different primer pools. In various embodiments, the selection of test primers are selected from a library of candidate primers involves (i) calculating on a computer a score (such as an undesirability score) for most or all of the possible combinations of two candidate primers from the library, wherein each score (such as an undesirability score) is based at least in part on the likelihood of dimer formation between the two candidate primers, (ii) removing from the library of candidate primers the candidate primer that is part of the greatest number of combinations of two candidate primers with a score (such as an undesirability score) above a first minimum threshold, (iii) if the candidate primer removed in step (ii) is a member of a primer pair, then removing the other member of the primer pair from the library of candidate primers; and (iv) optionally repeating steps (ii) and (iii), thereby selecting a first pool. In some embodiments, the selection method is performed until the score (such as the undesirability score) for the candidate primer combinations remaining in the library are all equal to or below the first minimum threshold for the first pool. In some embodiments, the selection method is performed until the number of candidate primers remaining in the library is reduced to a desired number for the first pool. In various embodiments, the selection method involves further reducing the number of candidate primers remaining in the library by decreasing the first minimum threshold used in step (ii) to a lower second minimum threshold and optionally repeating steps (ii) and (iii). In some embodiments, the selection method involves increasing the first minimum threshold used in step (ii) to a higher second minimum threshold and optionally repeating steps (ii) and (iii). In some embodiments, the selection method is performed until the score (such as the undesirability score) for the candidate primer combinations remaining in the library are all equal to or below the second minimum threshold, or until the number of candidate primers remaining in the library is reduced to a desired number for the first pool. In some embodiments, after the first pool is selected those primers are removed from further consideration and steps of the method (such as steps (ii) and (iii)) are repeated with the remaining primers to select a second pool. If desired, this method may be repeated to select the desired number of primer pools. In various embodiments, a score (such as an undesirability score) is calculated for at least 80, 90, 95, 98, 99, or 99.5% of the possible combinations of candidate primers in the library. In some embodiments, the score is based at least in part on the current coverage of the bases in the target locus (such as the number of other primer pools that have a primer or primer pair that amplifies a particular base in the target locus). In various embodiments, one or more of the pools are each capable of simultaneously amplifying at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci. In various embodiments, the method also includes separately contacting a nucleic acid sample that includes target loci with two or more of the pools to produce separate reaction mixtures; and (vi) subjecting the reaction mixtures to primer extension reaction conditions to produce amplified products that includes target amplicons.

In some embodiments, at least 70, 80, 85, 90, 95, or 100% of the nucleotides in a region of interest (such as an exon) are included in at least 1, 2, 3, or 4 different amplicons (i.e., amplicons with non-identical sequences that are formed by different primers or primer pairs). In some embodiments, at least 70, 80, 85, 90, 95, or 100% of the nucleotides in at least 70, 80, 85, 90, 95, or 100% of the regions of interest are amplified by at least 1, 2, 3, or 4 different amplicons. In some embodiments in which 2-fold coverage is desired, the primers are divided into at least two different pools such the amplicons in each pool do not overlap with each other (which would cause interference during amplification).

In various embodiments of any of the aspects of the invention, the score (such as the undesirability score) are based at least in part on one or more parameters selected from the group consisting of heterozygosity rate of the target locus, disease prevalence associated with a sequence (e.g., a polymorphism) at the target locus, disease penetrance associated with a sequence (e.g., a polymorphism) at the target locus, specificity of the candidate primer for the target locus, size of the candidate primer, melting temperature of the candidate primer, melting temperature of the target amplicon, GC content of the target amplicon, GC content of the 3' end of the candidate primer, homopolymer length in the candidate primer, amplification efficiency of the target amplicon, and size of the target amplicon.

In various embodiments of any of the aspects of the invention, the score (such as the undesirability score) are based at least in part on one or more parameters selected from the group consisting of heterozygosity rate of the target locus, specificity of the candidate primer for the target locus; size of the candidate primer, melting temperature of the candidate primer, melting temperature of the target amplicon, GC content of the target amplicon. GC content of the 3' end of the candidate primer, homopolymer length in the candidate primer, amplification efficiency of the target amplicon, and size of the target amplicon; and the test primers are used to simultaneously amplify e.g. at least 100 (e.g., at least 300 or 1,000) different target loci in a sample that includes maternal DNA from the pregnant mother of a fetus and fetal DNA to determine the presence or absence of a fetal chromosome abnormality. In various embodiments, the method includes ligating a universal primer binding site to the DNA molecules in the sample; amplifying the ligated DNA molecules using e.g. at least 100 (e.g., at least 300 or 1,000) specific primers and a universal primer to produce a first set of amplified products; and amplifying the first set of amplified products using e.g. at least 100 (e.g., at least 300 or 1,000) pairs of specific primers to produce a second set of amplified products. In various embodiments, at least 500; 750; 1,000; 2,000; 5,000; 7,500; 10,000; 15,000; 19,000; 20,000; 25,000; 27,000; 28,000; 30,000; 40,000; 50,000; 75,000; or 100,000 different primer pairs are used. In various embodiments, at least 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified. In some embodiments, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified at least 5, 10, 20, 40, 50, 60, 80, 100, 120, 150, 200, 300, or 400-fold. In some embodiments, at least 50, 60, 70, 80, 90, 95, 96, 97, 98, 99, 99.5, or 100% of the target loci are amplified at least 5, 10, 20, 40, 50, 60, 80, 100, 120, 150, 200, 300, or 400-fold.

In various embodiments of any of the aspects of the invention, the score (such as the undesirability score) are based at least in part on one or more parameters selected from the group consisting of heterozygosity rate of the target locus, specificity of the candidate primer for the target locus, size of the candidate primer, melting temperature of the candidate primer, melting temperature of the target amplicon, GC content of the target amplicon, GC content of the 3' end of the candidate primer, homopolymer length in the candidate primer, amplification efficiency of the target amplicon, and size of the target amplicon; and the test primers are used to simultaneously amplify e.g. at least 100 (e.g., at least 300 or 1,000) different target loci in sample includes DNA from an alleged father of a fetus and to simultaneously amplify the target loci in a sample that includes maternal DNA from the pregnant mother of a fetus and fetal DNA to establish whether the alleged father is the biological father of the fetus. In various embodiments, at least 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified. In some embodiments, at least 25; 50; 75; 100; 300; 500; 750; 1,000; 2,000; 5,000; 7,500; 10,000; 15,000;

19,000; 20,000; 25,000; 27,000; 28,000; 30,000; 40,000; 50,000; 75,000; or 100,000 different target loci are amplified at least 5, 10, 20, 40, 50, 60, 80, 100, 120, 150, 200, 300, or 400-fold. In some embodiments, at least 50, 60, 70, 80, 90, 95, 96, 97, 98, 99, 99.5, or 100% of the target loci are amplified at least 5, 10, 20, 40, 50, 60, 80, 100, 120, 150, 200, 300, or 400-fold.

In various embodiments of any of the aspects of the invention, the score (such as the undesirability score) are based at least in part on one or more parameters selected from the group consisting of heterozygosity rate of the target locus, specificity of the candidate primer for the target locus; size of the candidate primer, melting temperature of the candidate primer, melting temperature of the target amplicon, GC content of the target amplicon, GC content of the 3' end of the candidate primer, homopolymer length in the candidate primer, amplification efficiency of the target amplicon, and size of the target amplicon; and the test primers are used to simultaneously amplify e.g. at least 100 (e.g., at least 300 or 1,000) different target loci in one cell or multiple cells from an embryo to determine the presence or absence of a chromosome abnormality. In various embodiments, cells from a set of two or more embryos are analyzed, and one embryo is selected for in vitro fertilization. In various embodiments, at least 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified. In some embodiments, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified at least 5, 10, 20, 40, 50, 60, 80, 100, 120, 150, 200, 300, or 400-fold. In some embodiments, at least 50, 60, 70, 80, 90, 95, 96, 97, 98, 99, 99.5, or 100% of the target loci are amplified at least 5, 10, 20, 40, 50, 60, 80, 100, 120, 150, 200, 300, or 400-fold.

In various embodiments of any of the aspects of the invention, the scores (such as the undesirability scores) are based at least in part on one or more parameters selected from the group consisting of heterozygosity rate of the target locus, specificity of the candidate primer for the target locus; size of the candidate primer, melting temperature of the candidate primer, melting temperature of the target amplicon. GC content of the target amplicon, GC content of the 3' end of the candidate primer, homopolymer length in the candidate primer, amplification efficiency of the target amplicon, and size of the target amplicon, and the test primers are used to simultaneously amplify e.g. at least 100 (e.g., at least 300 or 1,000) different target loci in a forensic nucleic acid sample. In various embodiments, the length of the annealing step is greater than 3, 5, 8, 10, 15, 20, 30, 45, 60, 75, 90, 120, 150, or 180 minutes. In various embodiments, at least 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified. In some embodiments, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified at least 5, 10, 20, 40, 50, 60, 80, 100, 120, 150, 200, 300, or 400-fold. In some embodiments, at least 50, 60, 70, 80, 90, 95, 96, 97, 98, 99, 99.5, or 100% of the target loci are amplified at least 5, 10, 20, 40, 50, 60, 80, 100, 120, 150, 200, 300, or 400-fold.

In various embodiments of any of the aspects of the invention, the scores (such as the undesirability scores) are based at least in part on one or more parameters selected from the group consisting of heterozygosity rate of the target locus, disease prevalence associated with a sequence (e.g., a polymorphism) at the target locus, disease penetrance associated with a sequence (e.g., a polymorphism) at the target locus, specificity of the candidate primer for the target locus, size of the candidate primer, melting temperature of the candidate primer, melting temperature of the target amplicon, GC content of the target amplicon, GC content of the 3' end of the candidate primer, homopolymer length in the candidate primer, amplification efficiency of the target amplicon, and size of the target amplicon; and the method involves using the test primers to simultaneously amplify e.g. at least 100 (e.g., at least 300 or 1,000) different target loci in a control nucleic acid sample to produce a first set of target amplicons and to simultaneously amplify the target loci in a test nucleic acid sample to produce a second set of target amplicons; and comparing the first and second sets of target amplicons to determine whether a target locus is present in one sample but absent in the other, or whether a target locus is present at different levels in the control sample and the test sample. In various embodiments, the test sample is from an individual suspected of having a disease or phenotype of interest, or an increased risk for a disease or phenotype of interest; and wherein one or more of the target loci include a sequence (e.g., a polymorphism) at the target locus associated with an increased risk for the disease or phenotype of interest, or associated with the disease or phenotype of interest. In various embodiments, at least 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified. In some embodiments, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified at least 5, 10, 20, 40, 50, 60, 80, 100, 120, 150, 200, 300, or 400-fold. In some embodiments, at least 50, 60, 70, 80, 90, 95, 96, 97, 98, 99, 99.5, or 100% of the target loci are amplified at least 5, 10, 20, 40, 50, 60, 80, 100, 120, 150, 200, 300, or 400-fold.

In various embodiments of any of the aspects of the invention, the scores (such as the undesirability scores) are based at least in part on one or more parameters selected from the group consisting of heterozygosity rate of the target locus, disease prevalence associated with a sequence (e.g., a polymorphism) at the target locus, disease penetrance associated with a sequence (e.g., a polymorphism) at the target locus, specificity of the candidate primer for the target locus, size of the candidate primer, melting temperature of the candidate primer, melting temperature of the target amplicon, GC content of the target amplicon, GC content of the 3' end of the candidate primer, homopolymer length in the candidate primer, amplification efficiency of the target amplicon, and size of the target amplicon, and the method involves using the test primers to simultaneously amplify e.g. at least 100 (e.g., at least 300 or 1,000); different target loci in a control sample that includes RNA to produce a first set of target amplicons and to simultaneously amplify the target loci in a test sample that includes RNA to produce a second set of target amplicons; and comparing the first and second sets of target amplicons to determine the presence or absence of a difference in the RNA expression levels between the control sample and the test sample. In various embodiments, the RNA is mRNA. In various embodiments, the test sample is from an individual suspected of having a disease or phenotype of interest (such as cancer) or an increased risk for the disease or phenotype of interest (such as cancer); and wherein one or more of the target loci includes a sequence (e.g., a polymorphism or other mutation) associated with an increased risk for the disease or phenotype of interest or associated with the disease or phenotype of interest. In some embodiments, the test sample is from an individual diagnosed with a disease or phenotype of interest (such as cancer), and wherein a difference in the RNA expression level between the control sample and test sample indicates a target locus includes a sequence (e.g., a polymorphism or other mutation) associated with an increased or decreased risk for the disease or phenotype of interest. In various embodiments, at least 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified. In some embodiments, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified at least 5, 10, 20, 40, 50, 60, 80, 100, 120, 150, 200, 300, or 400-fold. In some embodiments, at least 50, 60, 70, 80, 90, 95, 96, 97, 98, 99, 99.5, or 100% of the target loci are amplified at least 5, 10, 20, 40, 50, 60, 80, 100, 120, 150, 200, 300, or 400-fold.

In one aspect, the invention features libraries of primers (such as non-immobilized primers). In some embodiments, the primers are selected from a library of candidate primers using any of the methods of the invention. In some embodiments, the library includes primers that simultaneously hybridize to at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci. In some embodiments, the library includes primers that simultaneously amplify at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci. In some embodiments, the library includes primers that simultaneously amplify at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci such that less than 60, 40, 30, 20, 10, 5, 4, 3, 2, 1, 0.5, 0.25, 0.1, or 0.05% of the amplified products are primer dimers. In some embodiments, the library includes primers that simultaneously amplify at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci such that at least 50, 60, 70, 80, 90, 95, 96, 97, 98, 99, or 99.5% of the amplified products are target amplicons. In some embodiments, the library includes primers that simultaneously amplify target loci such that at least 50, 60, 70, 80, 90, 95, 96, 97, 98, 99, or 99.5% of the target loci out of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified. In some embodiments, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified at least 5, 10, 20, 40, 50, 60, 80, 100, 120, 150, 200, 300, or 400-fold. In some embodiments, at least 50, 60, 70, 80, 90, 95, 96, 97, 98, 99, 99.5, or 100% of the target loci are amplified at least 5, 10, 20, 40, 50, 60, 80, 100, 120, 150, 200, 300, or 400-fold. In some embodiments, the library of primers includes at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical primers or primer pairs. In some embodiments, the library of primers includes at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 primer pairs, wherein each pair of primers includes a forward test primer and a reverse test primer where each pair of test primers hybridize to a target locus. In some embodiments, the library of primers includes at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 individual primers that each hybridize to a different target locus, wherein the individual primers are not part of primer pairs. In some embodiments, the primers in the library are not immobilized (such as not immobilized to a solid support) or not part of a microarray. In some embodiments, the primers are dissolved in solution (such as dissolved in the liquid phase). In some embodiments, the library of primers consists essentially of, or consists of primers.

In some embodiments, $\Delta G$ values for each possible combination of two primers (each possible primer dimer) in a library are all equal to or greater than −20, −18, −16, −14, −12, −10, −9, −8, −7, −6, −5, −4, −3, −2, or −1 kcal/mol. In some embodiments, $\Delta G$ values for at least 80, 85, 90, 92, 94, 96, 98, 99, or 100% of the primers in the library for possible combinations of that primer with other primers in the library are all equal to or greater than −20, −18, −16, −14, −12, −10, −9, −8, −7, −6, −5, −4, −3, −2, or −1 kcal/mol.

In various embodiments of any of the aspects of the invention, the library of primers includes one or more primers (e.g., at least 10; 20; 50; 25; 50; 75; 100; 300; 500; 750; 1,000; 2,000; 5,000; 7,500; 10,000; 15,000; 20,000; 25,000; 30,000; 40,000; or 50,000 different primers) with at least 60, 70, 80, 90, 95, 96, 97, 98, 99, 99.5, or 100% identity to the corresponding region (e.g., a region of at least 10, 20, 30, 40, 50, or more contiguous nucleotides) of a primer in FIG. 34 (SEQ ID NOs. 1-3,600), FIG. 35 (SEQ ID NOs. 3,601-11,658), or FIG. 36 (SEQ ID NOs 11,659-44,610). In some embodiments, the library of primers includes one or more primers (e.g., at least 10; 20; 50; 25; 50; 75; 100; 300; 500; 750; 1,000; 2,000; 5,000; 7,500; 10,000; 15,000; 20,000; 25,000; 30,000; 40,000; or 50,000 different primers) with at least 60, 70, 80, 90, 95, 96, 97, 98, 99, 99.5, or 100% identity over the entire length of a primer in FIG. 34 (SEQ ID NOs. 1-3,600), FIG. 35 (SEQ ID NOs. 3,601-11,658), or FIG. 36 (SEQ ID NOs 11,659-44,610). In some embodiments, the library of primers includes at least 10; 20; 50; 75; 100; 300; 500; 750; 1,000; 2,000; 5,000; 7,500; 10,000; 15,000; 20,000; 25,000; 30,000; 40,000; or 50,000 different primers from the primers in FIG. 34 (SEQ ID NOs. 1-3,600), FIG. 35 (SEQ ID NOs. 3,601-11,658), or FIG. 36 (SEQ ID NOs 11,659-44,610. In some embodiments, the library of primers includes one or more primers (e.g., at least 10; 20; 50; 75; 100; 300; 500; 750; 1,000; 2,000; 5,000; 7,500; 10,000; 15,000; 20,000; 25,000; 30,000; 40,000; or 50,000 different primers) that hybridize to the complement of a primer in FIG. 34 (SEQ ID NOs. 1-3,600), FIG. 35 (SEQ ID NOs. 3,601-11,658), or FIG. 36 (SEQ ID NOs 11,659-44, 610) under very high stringency hybridization conditions or under high stringency hybridization conditions.

In various embodiments of any of the aspects of the invention, the concentration of each primer is less than 100, 75, 50, 25, 10, 5, 2, 1, 0.5, 0.1, or 0.05 nM. In various embodiments, the GC content of the primers is between 30 to 80%, such as between 40 to 70%, 20 to 70%, or 50 to 60%, inclusive. In some embodiments, the range of GC content of the primers is less than 30, 20, 10, or 5%. In some embodiments, there are at least 2 (such as 3, 4, or 5) guanines or cytosines in the last 5 bases at the 3' end of the primers. In some embodiments, there are at least 1 (such as 2 or 3) guanines or cytosines in the last 3 bases at the 3' end of the primers. In some embodiments, a maximum of 2 (such as 2, 1, or 0) bases in the last 5 bases at the 3' end of the primers are guanines or cytosines. In some embodiments, the melting temperature of the primers is between 40 to 80° C., such as 50 to 70° C., 55 to 65° C., 54 to 60.5° C., or 57 to 60.5° C., inclusive. In some embodiments, the range of melting temperature of the primers is less than 15, 10, 5, 3, or 1° C. In some embodiments, the length of the primers is between 15 to 100 nucleotides, such as between 15 to 75 nucleotides, 15 to 40 nucleotides, 17 to 35 nucleotides, 18 to 30 nucleotides, or 20 to 65 nucleotides, inclusive. In some embodiments, the primers include a tag that is not target specific, such as a tag that forms an internal loop structure. In some embodiments, the tag is between two DNA binding regions. In various embodiments, the primers include a 5' region that is specific for a target locus, an internal region that is not specific for the target locus and forms a loop structure, and a 3' region that is specific for the target locus. In various embodiments, the length of the 3' region is at least 7 nucleotides. In some embodiments, the length of the 3' region is between 7 and 20 nucleotides, such as between 7 to 15 nucleotides, or 7 to 10 nucleotides, inclusive. In various embodiments, the primers include a 5' region that is not specific for a target locus (such as another tag or a universal primer binding site) followed by a region that is not specific for a target locus, an internal region that is not specific for the target locus and forms a loop structure, and a 3' region that is specific for the target locus. In some embodiments, the range of the length of the primers is less than 50, 40, 30, 20, 10, or 5 nucleotides. In some embodiments, the length of the target amplicons is between 50 and 100 nucleotides, such as between 60 and 80 nucleotides, or 60 to 75 nucleotides, inclusive. In some embodiments, the range of the length of the target amplicons is less than 50, 25, 15, 10, or 5 nucleotides. In some embodiments, the target loci are on two or more different chromosomes, such as two or more of chromosomes 13, 18, 21, X and Y. In some embodiments, the target loci are target human loci. In some embodiments, the target loci include a sequence (e.g., a polymorphism or other mutation) associated with an increased risk for the disease or phenotype of interest (such as cancer), or associated with the disease or phenotype of interest (such as cancer). In some embodiments, the polymorphism or mutation is a driver mutation that has a causative role in the disease or phenotype of interest (such as cancer). In some embodiments, the polymorphism or mutation is not a causative mutation. For example, in some cancers, multiple mutations accumulate but some of them are not causative mutations. Polymorphisms or mutations (such as those that are present at a higher frequency in subjects with a disease or phenotype of interest such as cancer than subjects without the disease or phenotype of interest such as cancer) that are not causative can still be useful for diagnosing the disease or phenotype. In some embodiments, the polymorphisms or mutation is present at a higher frequency in subjects with a disease or disorder (such as cancer) than subjects (such as healthy or normal subjects) without the disease or disorder (such as cancer). In some embodiments, the polymorphisms or mutation is indicative of cancer, such as a causative mutation. In some embodiments, the polymorphism(s) or mutation(s) are directly detected. In some embodiments, the polymorphism(s) or mutation(s) are indirectly detected by detection of one or more sequences (e.g., a polymorphic locus such as a SNP) that are linked to the polymorphism or mutation).

In one aspect, the invention provides a composition that includes any of the primer libraries of the invention (such as non-immobilized primers). In some embodiments, the composition includes one or more free nucleotides (such as deoxynucleotides, ATP, CTP, GTP, TTP, UTP, dATP, dCTP, dGTP, dTTP, dUTP an activated nucleotide or deoxynucleotide, or a non-naturally occurring nucleotide or deoxynucleotide). In some embodiments, the composition includes at least one primer (e.g., at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical primers) with a polynucleotide sequence of a human nucleic acid and at least one primer (e.g., at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical primers) with a polynucleotide sequence that is not found in a human (such as a universal primer, a primer that comprises a region or consists entirely of random nucleotides, or a primer with a region such as a tag or barcode of one or more nucleotides that are not found in a human or are not found in nature as part of the polynucleotide sequence of the primer). In some embodiments, the composition includes at least one primer (e.g., at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical primers) with the polynucleotide sequence of a human nucleic acid and one or more non-human or non-naturally occurring enzymes (e.g., ligase or polymerase from a species other than a human, such as a bacterial or non-naturally-occurring ligase or polymerase). In some embodiments, the composition includes at least one primer (e.g., at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical primers) with the polynucleotide sequence of a human nucleic acid and a buffer or additive that is non-naturally-occurring or is not found in a human. In some embodiments, the composition comprises, consists essentially of, or consists of one or more of the following: primer(s), amplicon(s) free nucleotide(s), non-human or non-naturally occurring enzyme(s), buffer(s), additive(s), or any combination thereof. In some embodiments, the composition comprises, consists essentially of, or consists of primers and one or more non-human or non-naturally occurring enzymes. Exemplary non-naturally occurring enzymes contain at least one sequence difference compared to naturally occurring (wild-type) enzymes.

In one aspect, the invention provides a composition comprising at least 100 different amplicons (e.g., at least 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical amplicons) in solution in one reaction volume. In some embodiments, the amplicons are produced from the simultaneous PCR amplification of at least 100 different target loci (e.g., at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical target loci) using at least 100 different primers or primer pairs (e.g., at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical primers or primer pairs) in one reaction volume. In some embodiments, (i) less than 60% of the amplified products are primer dimers and at least 40% of the amplified products are target amplicons, (ii) less than 40% of the amplified products are primer dimers and at least 60% of the amplified products are target amplicons, (iii) less than 20% of the amplified products are primer dimers and at least 80% of the amplified products are target amplicons, (iv) less than 10% of the amplified products are primer dimers and at least 90% of the amplified products are target amplicons, or (v) less than 5% of the amplified products are primer dimers and at least 95% of the amplified products are target amplicons. In some embodiments, the length of the target amplicons is between 50 and 100 nucleotides, such as between 60 and 80 nucleotides, or 60 and 75 nucleotides, inclusive. In some embodiments, the range of the length of the target amplicons is less than 50, 25, 15, 10, or 5 nucleotides. In some embodiments, the range of the length of the target amplicons is between 5 to 50 nucleotides, such as 5 to 25 nucleotides, 5 to 15 nucleotides, or 5 to 10 nucleotides, inclusive. In some embodiments, the composition includes at least 1,000 different amplicons in solution in one reaction volume. In some embodiments, the amplicons are produced from the simultaneous PCR amplification of at least 1,000 different target human loci using at least 1,000 different primers in one reaction volume; wherein (i) less than 20% of the amplicons are primer dimers, and (ii) at least 80% of the amplicons comprise one of the target human loci and are between 50 and 100 nucleotides in length, inclusive. In some embodiments, the composition consists essentially of, or consists of one or more of the following: amplicons, primers (such as any of the primers disclosed herein), free nucleotide(s), non-human or non-naturally occurring enzyme(s), buffer(s), or any combination thereof. In some embodiments, at least one amplicon or primer has a non-human or non-naturally occurring sequence, nucleotide, or linkage between nucleotides.

In one aspect, the invention provides a composition comprising at least 100 different primers or primer pairs (e.g., at least 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical primers or primer pairs) and at least 100 different amplicons (e.g., at least 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical amplicons) in solution in one reaction volume. In some embodiments, the amplicons are produced from the simultaneous PCR amplification of at least 100 different target loci (e.g., at least 300; 500; 750; 1,000; 2,000; 5,000; 7,500; 10,000; 15,000; 19,000; 20,000; 25,000; 27,000; 28,000; 30,000; 40,000, 50,000; 75,000; or 100,000 non-identical target loci) using the primers or primer pairs in one reaction volume. In some embodiments, (i) less than 60% of the amplified products are primer dimers and at least 40% of the amplified products are target amplicons, (ii) less than 40% of the amplified products are primer dimers and at least 60% of the amplified products are target amplicons, (iii) less than 20% of the amplified products are primer dimers and at least 80% of the amplified products are target amplicons, (iv) less than 10% of the amplified products are primer dimers and at least 90% of the amplified products are target amplicons, or (v) less than 5% of the amplified products are primer dimers and at least 95% of the amplified products are target amplicons. In some embodiments, the length of the target amplicons is between 50 and 100 nucleotides, such as between 60 and 80 nucleotides, or 60 and 75 nucleotides, inclusive. In some embodiments, the range of the length of the target amplicons is less than 50, 25, 15, 10, or 5 nucleotides. In some embodiments, the range of the length of the target amplicons is between 5 to 50 nucleotides, such as 5 to 25 nucleotides, 5 to 15 nucleotides, or 5 to 10 nucleotides, inclusive. In some embodiments, the composition comprising at least 1,000 different primers and at least 1,000 different amplicons in solution in one reaction volume. In some embodiments, the amplicons are produced from the simultaneous PCR amplification of at least 1,000 different target human loci with the primers in one reaction volume; wherein (i) less than 20% of the amplicons are primer dimers, and (ii) at least 80% of the amplicons comprise one of the target loci and are between 50 and 100 nucleotides in length, inclusive. In some embodiments, the composition consists essentially of, or consists of one or more of the following: amplicons, primers (such as any of the primers disclosed herein), free nucleotide(s), non-human or non-naturally occurring enzyme(s), buffer(s), or any combination thereof. In some embodiments, at least one amplicon or primer has a non-human or non-naturally occurring sequence, nucleotide, or linkage between nucleotides.

In one aspect, the invention provides kits that include any of the primer libraries or compositions of the invention for amplifying target loci in a nucleic acid sample. In some embodiments, the kits consist essentially of, or consists of primers, primers and instructions for using the primers, a composition of the invention, or a composition of the invention and instructions for using the composition. In some embodiments, the kit includes instructions for using the library to amplify the target loci.

In one aspect, the invention provides an apparatus, device, or composition that includes any of the primer libraries or compositions of the invention. In some embodiments, the apparatus, device, or composition includes a physical structure (such as one or more reaction vessels, reaction chambers, or wells) that contains the primer library or composition of the invention (for example, the primers may be dissolved in a solution that is in the physical structure). In some embodiments, the physical structure is a non-naturally occurring physical structure or a physical structure that does not naturally contain a primer library or composition of the invention (such as a physical structure that is not found in nature with nucleic acids in it). In one aspect, the invention features methods for determining a ploidy status of chromosome in a gestating fetus. In some embodiments, the method involves contacting a nucleic acid sample with a library of primers that simultaneously hybridize to at least 25; 50; 75; 100; 300; 500; 750; 1,000; 2,000; 5,000; 7,500; 10,000; 15,000; 19,000; 20,000; 25,000; 27,000; 28,000; 30,000; 40,000, 50,000; 75,000; or 100,000 different polymorphic loci to produce a reaction mixture; wherein the nucleic acid sample includes maternal DNA from the mother of the fetus and fetal DNA from the fetus. In some embodiments, the reaction mixture is subjected to primer extension reaction conditions to produce amplified products; the amplified products are measured with a high throughput sequencer to produce sequencing data; allele counts at the polymorphic loci are calculated on a computer based on the sequencing data; a plurality of ploidy hypotheses each pertaining to a different possible ploidy state of the chromosome are created on a computer, a joint distribution model for the expected allele counts at the polymorphic loci on the chromosome is built on a computer for each ploidy hypothesis; a relative probability of each of the ploidy hypotheses is determined on a computer using the joint distribution model and the allele counts, and the ploidy state of the fetus is called by selecting the ploidy state corresponding to the hypothesis with the greatest probability.

In one aspect, the invention features methods for determining a ploidy status of a chromosome in a gestating fetus. In an embodiment a method for determining a ploidy status of a chromosome in a gestating fetus includes obtaining a first sample of DNA that comprises maternal DNA from the mother of the fetus and fetal DNA from the fetus, preparing the first sample by isolating the DNA so as to obtain a prepared sample, measuring the DNA in the prepared sample at a plurality of polymorphic loci on the chromosome, calculating, on a computer, allele counts at the plurality of polymorphic loci from the DNA measurements made on the prepared sample, creating, on a computer, a plurality of ploidy hypotheses each pertaining to a different possible ploidy state of the chromosome, building on a computer, a joint distribution model for the expected allele counts at the plurality of polymorphic loci on the chromosome for each ploidy hypothesis, determining, on a computer, a relative probability of each of the ploidy hypotheses using the joint distribution model and the allele counts measured on the prepared sample, and calling the ploidy state of the fetus by selecting the ploidy state corresponding to the hypothesis with the greatest probability.

In one aspect, the invention features methods of testing for an abnormal distribution of a chromosome in a sample that includes a mixture of maternal and fetal DNA. In some embodiments, the method involves (i) contacting the sample with a library of primers that simultaneously hybridize to at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci to produce a reaction mixture; wherein the target loci are from a plurality of different chromosomes; and wherein the plurality of different chromosomes include at least one first chromosome suspected of having an abnormal distribution in the sample and at least one second chromosome presumed to be normally distributed in the sample; (ii) subjecting the reaction mixture to primer extension reaction conditions to produce amplified products; (iii) sequencing the amplified products to obtain a plurality of sequence tags aligning to the target loci; wherein the sequence tags are of sufficient length to be assigned to a specific target locus; (iv) assigning on a computer the plurality of sequence tags to their corresponding target loci, (v) determining on a computer a number of sequence tags aligning to the target loci of the first chromosome and a number of sequence tags aligning to the target loci of the second chromosome; and (vi) comparing on a computer the numbers from step (v) to determine the presence or absence of an abnormal distribution of the first chromosome.

In one aspect, the invention provides methods for detecting the presence or absence of a fetal aneuploidy. In some embodiments, the method involves (i) contacting a sample that includes a mixture of maternal and fetal DNA with a library of primers that simultaneously hybridize to at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different non-polymorphic target loci to produce a reaction mixture, wherein the target loci are from a plurality of different chromosomes; (ii) subjecting the reaction mixture to primer extension reaction conditions to produce amplified products that includes target amplicons; (iii) quantifying on a computer a relative frequency of the target amplicons from the first and second chromosomes of interest; (iv) comparing on a computer the relative frequency of the target amplicons from the first and second chromosomes of interest; and (v) identifying the presence or absence of an aneuploidy based on the compared relative frequencies of the first and second chromosome of interest. In some embodiments, the first chromosome is a chromosome suspected of being euploid. In some embodiments, the second chromosome is a chromosome suspected of being aneuploidy.

In one aspect, a method is disclosed for determining presence or absence of fetal aneuploidy in a maternal tissue sample comprising fetal and maternal genomic DNA, the method including (a) obtaining a mixture of fetal and maternal genomic DNA from said maternal tissue sample, (b) conducting massively parallel DNA sequencing of DNA fragments randomly selected from the mixture of fetal and maternal genomic DNA of step (a) to determine the sequence of said DNA fragments, (c) identifying chromosomes to which the sequences obtained in step (b) belong, (d) using the data of step (c) to determine an amount of at least one first chromosome in said mixture of maternal and fetal genomic DNA, wherein said at least one first chromosome is presumed to be euploid in the fetus, (e) using the data of step (c) to determine an amount of a second chromosome in said mixture of maternal and fetal genomic DNA, wherein said second chromosome is suspected to be aneuploid in the fetus, (f) calculating the fraction of fetal DNA in the mixture of fetal and maternal DNA, (g) calculating an expected distribution of the amount of the second target chromosome if the second target chromosome is euploid, using the number in step (d), (h) calculating an expected distribution of the amount of the second target chromosome if the second target chromosome is aneuploid, using the first number is step (d) and the calculated fraction of fetal DNA in the mixture of fetal and maternal DNA in step (f), and (i) using a maximum likelihood or maximum a posteriori approach to determine whether the amount of the second chromosome as determined in step (e) is more likely to be part of the distribution calculated in step (g) or the distribution calculated in step (h); thereby indicating the presence or absence of a fetal aneuploidy.

In various embodiments of any of the aspects of the invention, the target loci include one or more SNPs in the homologous non-recombining region of chromosome X and/or chromosome Y. In some embodiments, the method includes determining the relative amount of chromosome X and chromosome Y. In some embodiments, the method includes determining the number of copies of chromosome X and/or chromosome Y.

In some embodiments, the method also includes obtaining genotypic data from one or both parents of the fetus. In some embodiments, obtaining genotypic data from one or both parents of the fetus includes preparing the DNA from the parents where the preparing comprises preferentially enriching the DNA at the plurality of polymorphic loci to give prepared parental DNA, optionally amplifying the prepared parental DNA, and measuring the parental DNA in the prepared sample at the plurality of polymorphic loci.

In various embodiments of any of the aspects of the invention, building a joint distribution model for the expected allele count probabilities of the plurality of polymorphic loci on the chromosome is done using the obtained genetic data from the one or both parents. In some embodiments, the sample (e.g., the first sample) has been isolated from maternal plasma and where the obtaining genotypic data from the mother is done by estimating the maternal genotypic data from the DNA measurements made on the prepared sample.

In one aspect, a diagnostic box is disclosed for helping to determine a ploidy status of a chromosome in a gestating fetus where the diagnostic box is capable of executing the preparing and measuring steps of any of the methods of the invention.

In various embodiments of any of the aspects of the invention, the allele counts are probabilistic rather than binary. In some embodiments, measurements of the DNA in the prepared sample at the plurality of polymorphic loci are also used to determine whether or not the fetus has inherited one or a plurality of disease linked haplotypes.

In various embodiments of any of the aspects of the invention, building a joint distribution model for allele count probabilities is done by using data about the probability of chromosomes crossing over at different locations in a chromosome to model dependence between polymorphic alleles on the chromosome. In some embodiments, building a joint distribution model for allele counts and the step of determining the relative probability of each hypothesis are done using a method that does not require the use of a reference chromosome.

In various embodiments of any of the aspects of the invention, determining the relative probability of each hypothesis makes use of an estimated fraction of fetal DNA in the prepared sample. In some embodiments, the DNA measurements from the prepared sample used in calculating allele count probabilities and determining the relative probability of each hypothesis comprise primary genetic data. In some embodiments, selecting the ploidy state corresponding to the hypothesis with the greatest probability is carried out using maximum likelihood estimates or maximum a posteriori estimates.

In various embodiments of any of the aspects of the invention, calling the ploidy state of the fetus also includes combining the relative probabilities of each of the ploidy hypotheses determined using the joint distribution model and the allele count probabilities with relative probabilities of each of the ploidy hypotheses that are calculated using statistical techniques taken from a group consisting of a read count analysis, comparing heterozygosity rates, a statistic that is only available when parental genetic information is used, the probability of normalized genotype signals for certain parent contexts, a statistic that is calculated using an estimated fetal fraction of the sample (e.g., the first sample) or the prepared sample, and combinations thereof. In various embodiments of any of the aspects of the invention, a confidence estimate is calculated for the called ploidy state. In some embodiments, the method also includes taking a clinical action based on the called ploidy state of the fetus, wherein the clinical action is selected from one of terminating the pregnancy or maintaining the pregnancy.

In various embodiments of any of the aspects of the invention, the method may be performed for fetuses at between 4 and 5 weeks gestation; between 5 and 6 weeks gestation; between 6 and 7 weeks gestation; between 7 and 8 weeks gestation; between 8 and 9 weeks gestation; between 9 and 10 weeks gestation; between 10 and 12 weeks gestation; between 12 and 14 weeks gestation; between 14 and 20 weeks gestation, between 20 and 40 weeks gestation; in the first trimester; in the second trimester; in the third trimester, or combinations thereof.

In various embodiments of any of the aspects of the invention, a report displaying a determined ploidy status of a chromosome in a gestating fetus generated using the method. In some embodiments, a kit is disclosed for determining a ploidy status of a target chromosome in a gestating fetus designed to be used with any of the methods of the invention, the kit including a plurality of inner forward primers and optionally the plurality of inner reverse primers, where each of the primers is designed to hybridize to the region of DNA immediately upstream and/or downstream from one of the polymorphic sites on the target chromosome, and optionally additional chromosomes, where the region of hybridization is separated from the polymorphic site by a small number of bases, where the small number is selected from the group consisting of 1, 2, 3, 4, 5, 6 to 10, 11 to 15, 16 to 20, 21 to 25, 26 to 30, 31 to 60, and combinations thereof. In one aspect, the invention features methods for establishing whether an alleged father is the biological father of a fetus that is gestating in a pregnant mother. In some embodiments the method involves, (i) simultaneously amplifying a plurality of polymorphic loci that includes at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different polymorphic loci on genetic material from the alleged father to produce a first set of amplified products; (ii) simultaneously amplifying the corresponding plurality of polymorphic loci on a mixed sample of DNA originating from a blood sample from the pregnant mother to produce a second set of amplified products; wherein the mixed sample of DNA includes fetal DNA and maternal DNA; (iii) determining on a computer the probability that the alleged father is the biological father of the fetus using genotypic measurements based on the first and second sets of amplified products; and (iv) establishing whether the alleged father is the biological father of the fetus using the determined probability that the alleged father is the biological father of the fetus. In various embodiments, the method further includes simultaneously amplifying the corresponding plurality of polymorphic loci on genetic material from the mother to produce a third set of amplified products; wherein the probability that the alleged father is the biological father of the fetus is determined using genotypic measurements based on the first, second, and third sets of amplified products.

In one aspect, the invention provides methods of estimating relative likelihoods that each embryo from a set of embryos will develop as desired. In some embodiments, the method involves contacting a sample from each embryo with a library of primers that simultaneously hybridize to at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci to produce a reaction mixture for each embryo, wherein the samples are each derived from one or more cells from an embryo. In some embodiments, each reaction mixture is subjected to primer extension reaction conditions to produce amplified products. In some embodiments, the method includes determining on a computer one or more characteristics of at least one cell from each embryo based on the amplified products; and estimating on a computer the relative likelihoods that each embryo will develop as desired, based on the one or more characteristics of the at least one cell for each embryo.

In one aspect, the invention features methods of measuring the amount of two or more target loci in a nucleic acid sample. In some embodiments, the method involves (i) using PCR to amplify a nucleic acid sample that includes a first standard locus, a second standard locus, a first target locus, and a second target locus to form amplified products; wherein the first standard locus and the first target locus have the same number of nucleotides but have a sequence that differs at one or more nucleotides; and wherein the second standard locus and the second target locus have the same number of nucleotides but have a sequence that differs at one or more nucleotides; (ii) sequencing the amplified products to determine a standard ratio that compares the relative amount of the amplified first standard locus compared to the amplified second standard locus; wherein the standard ratio indicates the difference in PCR efficiency for the amplification of the first standard locus and the second standard locus, (iii) determining a target ratio that compares the relative amount of the amplified first target locus compared to the amplified second target locus; and (iv) adjusting the target ratio from step (iii) based on the standard ratio from step (ii) to determine the relative amount of the first target locus and the second target locus in the sample. In various embodiments, the method involves determining the absolute amount of the first target locus and the second target locus in the sample. In various embodiments, the method further includes determining the presence or absence of a target locus (e.g., at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci) in the sample. In various embodiments, the method involves using any of the primer libraries of the invention. In various embodiments, the method involves simultaneously amplifying at least 25; 50; 75; 100; 300; 500; 750; 1,000; 2,000; 5,000; 7,500; 10,000; 15,000; 19,000; 20,000; 25,000; 27,000; 28,000; 30,000; 40,000, 50,000; 75,000; or 100,000 different target loci.

In one aspect, the invention features methods of quantitatively measuring a plurality of genetic targets in a sample for analysis. In some embodiments, the method includes (i) mixing genetic material derived from the sample for analysis with a plurality of target specific amplification reagents, and a plurality of standard sequences corresponding to the target specific amplification reagent targets, (ii) amplifying target regions of the genetic material and the standard sequences to produce target amplicons and standard sequence amplicons; and (iii) measuring the quantity of target amplicons and standard sequence amplicons produced. In some embodiments, the genetic material is present in a genetic library. In some embodiments, the genetic targets are polymorphic loci (such as SNPs). In some embodiments, the measuring of quantity is achieved by counting sequences. In some embodiments, the method further includes determining the estimated copy number of at least one chromosome in a sample from which the genetic library was derived, wherein the determination involves comparing the number of sequence reads of a target amplicon with the number of sequence reads of a standard amplicon. In some embodiments, the standard sequences and the genetic library include universal priming sites cable of being primed by the same primer. In some embodiments, the mixing step includes at least 10; 100; 500; 1,000; 2,000; 5,000; 7,500; 10,000; 15,000; 19,000; 20,000; 25,000; 27,000; 28,000; 30,000; 40,000; 50,000; 75,000; or 100,000 different target specific amplification reagents and at least 10; 100; 500; 1,000; 2,000; 5,000; 7,500; 10,000; 15,000; 19,000; 20,000; 25,000; 27,000; 28,000; 30,000; 40,000; 50,000; 75,000; or 100,000 standard sequences. In various embodiments, the method involves using any of the primer libraries of the invention. In various embodiments, the method involves simultaneously amplifying at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target regions. In some embodiments, the relative amounts of each of the standard sequences are known. In some embodiments, the relative amounts of each of the sequences is has been calibrated with respect to a reference genome. In some embodiments, the sample for analysis includes a mixture of fetal and maternal genomes. In some embodiments, the sample for analysis is derived from the blood of a pregnant woman or derived from blood plasma. In some embodiments, the reference genome has at least one aneuploidy, such as an aneuploidy at chromosome 13, 18, 21, X, or Y. In some embodiments, the reference genome is diploid.

In one aspect, the invention features a mixture that includes a plurality of genetic standard sequences, wherein the relative amount of each genetic standard sequence in the mixture has been determined by calibration to a reference genome. In various embodiments, the mixture includes at least 10; 100; 500; 1,000; 2,000; 5,000; 7,500; 10,000; 15,000; 19,000; 20,000; 25,000; 27,000; 28,000; 30,000; 40,000, 50,000; 75,000; or 100,000 genetic standard sequences. In various embodiments, the genetic standard sequences include a first universal priming site, a second universal priming site, a first target specific priming site, a second target specific priming site, and a marker sequence located between the first and second target specific priming sites, wherein the first target specific site and the second target specific priming site are located between the first and second universal priming sites. In various embodiments, the calibration involves using any of the primer libraries of the invention. In various embodiments, the calibration involves simultaneously amplifying at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target regions. In some embodiments, the reference genome has at least one aneuploidy, such as an aneuploidy at chromosome 13, 18, 21, X, or Y. In some embodiments, the reference genome is diploid.

In one aspect, the invention features methods of producing a set of calibrated genetic standard sequences. In some embodiments, the method includes (i) forming an amplification reaction mixture that includes a genetic library prepared from a reference genome, a plurality of target-specific amplification primer reagent sets, and a plurality of genetic standard sequences corresponding to the target specific amplification reagent sets, (ii) amplifying the genetic library and the genetic standard sequences to produce amplicons from the target sequences and amplicons from the genetic standard sequences, (iii) measuring the quantity of the amplicons from the target sequences and amplicons from the genetic standard sequences, and (iv) determining the relative amount of each of genetic standard sequences with respect to each other, whereby the plurality of genetic standard sequences is calibrated. In various embodiments, at least 10; 100; 500; 1,000; 2,000; 5,000; 7,500; 10,000; 15,000; 19,000; 20,000; 25,000; 27,000; 28,000; 30,000; 40,000; 50,000; 75,000; or 100,000 genetic standard sequences are used. In various embodiments, the method involves using any of the primer libraries of the invention. In various embodiments, the method involves simultaneously amplifying at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different sequences. In some embodiments, the reference genome has at least one aneuploidy, such as an aneuploidy at chromosome 13, 18, 21, X, or Y. In some embodiments, the reference genome is diploid.

In one aspect, the invention provides a set of genetic standard sequences that have been calibrated according to any of the methods of the invention. In one aspect, the invention provides a set of genetic standard sequences that may be calibrated either before, during or after the method is performed.

In one aspect, the invention features methods of measuring the number of copies of a gene of interest having at least one allele that has a deletion. In some embodiments, the method includes (i) mixing genetic material derived from a sample for analysis with an amplification reagent specific for the gene of interest and not capable of significantly amplifying the deletion comprising allele of the gene of interest, a standard sequence corresponding to gene of interest, an amplification reagent specific for a reference sequence, and a standard sequence corresponding to the reference sequence, (ii) amplifying the gene sequence of interest, the standard sequence corresponding to the gene of interest, the reference sequence, and the standard sequence corresponding to the reference sequence to produce gene of interest amplicons, reference sequence amplicons, and standard sequence amplicons; and (iii) measuring the quantity of target amplicons and standard sequence amplicons produced. In some embodiments, the measuring of quantity is achieved by counting sequence reads. In some embodiments, the method further includes determining the estimated copy number of at least one chromosome in the sample from which the genetic library was derived, wherein the determination involves comparing the number of sequences of target amplicons with the number of sequences of standard amplicons. In some embodiments, the standard sequences and the genetic library include universal priming sites capable of being primed by the same primer. In some embodiments, the relative amounts of each of the sequences have been calibrated with respect to a reference genome. In various embodiments, at least 10; 100; 500; 1,000; 2,000; 5,000; 7,500; 10,000; 15,000; 19,000; 20,000; 25,000; 27,000; 28,000; 30,000; 40,000; 50,000; 75,000; or 100,000 genetic standard sequences are used. In various embodiments, the method involves using any of the primer libraries of the invention. In various embodiments, the method involves simultaneously amplifying at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target regions. In some embodiments, the reference genome is diploid. In some embodiments, the sample for analysis is derived from blood.

In some embodiments of any of the aspects of the invention, preferentially enriching the DNA in the sample (e.g., the first sample) at the target loci (e.g., the plurality of polymorphic loci) includes obtaining a plurality of pre-circularized probes where each probe targets one of the loci (e.g., polymorphic loci), where the 3' and 5' end of the probes are preferably designed to hybridize to a region of DNA that is separated from the polymorphic site of the locus by a small number of bases, where the small number is 1, 2, 3, 4, 5, 6, 7, 8, 9, 10, 11, 12, 13, 14, 15, 16, 17, 18, 19, 20, 21 to 25, 26 to 30, 31 to 60, or a combination thereof, hybridizing the pre-circularized probes to DNA from the sample (e.g., the first sample), filling the gap between the hybridized probe ends using DNA polymerase, circularizing the pre-circularized probe, and amplifying the circularized probe.

In some embodiments of any of the aspects of the invention, the preferentially enriching the DNA at the target loci (e.g., the plurality of polymorphic loci) includes obtaining a plurality of ligation-mediated PCR probes where each PCR probe targets one of the target loci (e.g., the polymorphic loci), and where the upstream and downstream PCR probes are designed to hybridize to a region of DNA on one strand of DNA that is preferably separated from the polymorphic site of the locus by a small number of bases, where the small number is 1, 2, 3, 4, 5, 6, 7, 8, 9, 10, 11, 12, 13, 14, 15, 16, 17, 18, 19, 20, 21 to 25, 26 to 30, 31 to 60, or a combination thereof, hybridizing the ligation-mediated PCR probes to the DNA from the sample (e.g., the first sample), filling the gap between the ligation-mediated PCR probe ends using DNA polymerase, ligating the ligation-mediated PCR probes, and amplifying the ligated ligation-mediated PCR probes.

In some embodiments of various aspects of the invention, preferentially enriching the DNA at the target loci (e.g., plurality of polymorphic loci) includes obtaining a plurality of hybrid capture probes that target the loci (e.g., the polymorphic loci), hybridizing the hybrid capture probes to the DNA in the sample (e.g., the first sample) and physically removing some or all of the unhybridized DNA from the sample (e.g., the first sample) of DNA.

In some embodiments of any of the aspects of the invention, the hybrid capture probes are designed to hybridize to a region that is flanking but not overlapping the polymorphic site. In some embodiments, the hybrid capture probes are designed to hybridize to a region that is flanking but not overlapping the polymorphic site, and where the length of the flanking capture probe may be selected from the group consisting of less than about 120 bases, less than about 110 bases, less than about 100 bases, less than about 90 bases, less than about 80 bases, less than about 70 bases, less than about 60 bases, less than about 50 bases, less than about 40 bases, less than about 30 bases, and less than about 25 bases. In some embodiments, the hybrid capture probes are designed to hybridize to a region that overlaps the polymorphic site, and where the plurality of hybrid capture probes comprise at least two hybrid capture probes for each polymorphic loci, and where each hybrid capture probe is designed to be complementary to a different allele at that polymorphic locus.

In some embodiments of any of the aspects of the invention, preferentially enriching the DNA a plurality of polymorphic loci includes obtaining a plurality of inner forward primers where each primer targets one of the polymorphic loci, and where the 3' end of the inner forward primers are designed to hybridize to a region of DNA upstream from the polymorphic site, and separated from the polymorphic site by a small number of bases, where the small number is selected from the group consisting of 1, 2, 3, 4, 5, 6 to 10, 11 to 15, 16 to 20, 21 to 25, 26 to 30, or 31 to 60 base pairs, optionally obtaining a plurality of inner reverse primers where each primer targets one of the polymorphic loci, and where the 3' end of the inner reverse primers are designed to hybridize to a region of DNA upstream from the polymorphic site, and separated from the polymorphic site by a small number of bases, where the small number is selected from the group consisting of 1, 2, 3, 4, 5, 6 to 10, 11 to 15, 16 to 20, 21 to 25, 26 to 30, or 31 to 60 base pairs, hybridizing the inner primers to the DNA, and amplifying the DNA using the polymerase chain reaction to form amplicons.

In some embodiments of any of the aspects of the invention, the method also includes obtaining a plurality of outer forward primers where each primer targets one of the target (e.g., polymorphic loci), and where the outer forward primers are designed to hybridize to the region of DNA upstream from the inner forward primer, optionally obtaining a plurality of outer reverse primers where each primer targets one of the target loci (e.g., polymorphic loci), and where the outer reverse primers are designed to hybridize to the region of DNA immediately downstream from the inner reverse primer, hybridizing the first primers to the DNA, and amplifying the DNA using the polymerase chain reaction.

In some embodiments of any of the aspects of the invention, the method also includes obtaining a plurality of outer reverse primers where each primer targets one of the polymorphic loci, and where the outer reverse primers are designed to hybridize to the region of DNA immediately downstream from the inner reverse primer, optionally obtaining a plurality of outer forward primers where each primer targets one of the target loci (e.g., the polymorphic loci), and where the outer forward primers are designed to hybridize to the region of DNA upstream from the inner forward primer, hybridizing the first primers to the DNA, and amplifying the DNA using the polymerase chain reaction.

In some embodiments of any of the aspects of the invention, preparing the sample (e.g., the first sample) further includes appending universal adapters to the DNA in the sample (e.g., the first sample) and amplifying the DNA in the sample (e.g., the first sample) using the polymerase chain reaction. In some embodiments, at least a fraction of the amplicons that are amplified are less than 100 bp, less than 90 bp, less than 80 bp, less than 70 bp, less than 65 bp, less than 60 bp, less than 55 bp, less than 50 bp, or less than 45 bp, and where the fraction is 10%, 20%, 30%, 40%, 50%, 60%, 70%, 80%, 90%, or 99%.

In some embodiments of any of the aspects of the invention, amplifying the DNA is done in one or a plurality of individual reaction volumes, and where each individual reaction volume contains more than 100 different forward and reverse primer pairs, more than 200 different forward and reverse primer pairs, more than 500 different forward and reverse primer pairs, more than 1,000 different forward and reverse primer pairs, more than 2,000 different forward and reverse primer pairs, more than 5,000 different forward and reverse primer pairs, more than 10,000 different forward and reverse primer pairs, more than 20,000 different forward and reverse primer pairs, more than 50,000 different forward and reverse primer pairs, or more than 100,000 different forward and reverse primer pairs. In various embodiments of any of the aspects of the invention, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different primer pairs are used.

In some embodiments of any of the aspects of the invention, preparing the sample (e.g., the first sample) further comprises dividing the sample (e.g., the first sample) into a plurality of portions, and where the DNA in each portion is preferentially enriched at a subset of the target loci (e.g., plurality of polymorphic loci). In some embodiments, the inner primers are selected by identifying primer pairs likely to form undesired primer duplexes and removing from the plurality of primers at least one of the pair of primers identified as being likely to form undesired primer duplexes. In some embodiments, the inner primers contain a region that is designed to hybridize either upstream or downstream of the targeted locus (e.g., the polymorphic locus), and optionally contain a universal priming sequence designed to allow PCR amplification. In some embodiments, at least some of the primers additionally contain a random region that differs for each individual primer molecule. In some embodiments, at least some of the primers additionally contain a molecular barcode.

In some embodiments of any of the aspects of the invention, preferential enrichment results in average degree of allelic bias between the prepared sample and the sample (e.g., the first sample) of a factor selected from the group consisting of no more than a factor of 2, no more than a factor of 1.5, no more than a factor of 1.2, no more than a factor of 1.1, no more than a factor of 1.05, no more than a factor of 1.02, no more than a factor of 1.01, no more than a factor of 1.005, no more than a factor of 1.002, no more than a factor of 1.001 and no more than a factor of 1.0001. In some embodiments, the plurality of polymorphic loci are SNPs. In some embodiments, measuring the DNA in the prepared sample is done by sequencing.

In some embodiments, the nucleic acids in the sample are non-specifically amplified prior to amplification of the target loci (such as specific amplification of the target loci with a primer library of the invention). In some embodiments, the non-specific amplification includes whole genome application (WGA), such as ligation-mediated PCR (LM-PCR), degenerate oligonucleotide primer PCR (DOP-PCR), or multiple displacement amplification (MDA). In some embodiments, the non-specific amplification includes universal PCR, such as adaptor-mediated universal PCR.

In some embodiments of any of the aspects of the invention, the target loci are present on the same nucleic acid of interest (e.g., the same chromosome or the same region of a chromosome). In some embodiments, at least some of the target loci are present on different nucleic acids of interest (e.g., different chromosomes). In some embodiments, the nucleic acid sample includes fragmented or digested nucleic acids. In some embodiments, the nucleic acid sample includes DNA, such as genomic DNA, cDNA, cell-free DNA (cfDNA), cell-free mitochondrial DNA (cf mDNA), cell-free DNA that originated from nuclear DNA (cf nDNA), cellular DNA, or mitochondrial DNA. In some embodiments, nucleic acid sample includes RNA, such as cfRNA, cellular RNA, cytoplasmic RNA, coding cytoplasmic RNA, non-coding cytoplasmic RNA, mRNA, miRNA, mitochondrial RNA, rRNA, or tRNA. In some embodiments, the nucleic acid sample includes DNA from a single cell, 2 cells, 3 cells, 4 cells, 5 cells, 6 cells, 7 cells, 8 cells, 9 cell, 10 cells, or more than 10 cells. In some embodiments, the nucleic acid sample is a blood or plasma sample that is substantially free of cells. In some embodiments, the nucleic acid sample includes or is derived from blood, plasma, saliva, semen, sperm, cell culture supernatant, mucus secretion, dental plaque, gastrointestinal tract tissue, stool, urine, hair, bone, body fluids, tears, tissue, skin, fingernails, blastomeres, embryos, amniotic fluid, chorionic villus samples, bile, lymph, cervical mucus, or a forensic sample. In some embodiments, the target loci are segments of human nucleic acids. In some embodiments, the target loci are segments of human nucleic acids found in the human genome. In some embodiments, the target loci comprise or consist of single nucleotide polymorphisms (SNPs). In some embodiments, the primers are DNA molecules.

In some embodiments of any of the aspects of the invention, the DNA in the sample (e.g., the first sample) originates from maternal plasma. In some embodiments, preparing the sample (e.g., the first sample) further comprises amplifying the DNA. In some embodiments, preparing the sample (e.g., the first sample) further comprises preferentially enriching the DNA in the sample (e.g., the first sample) at the target loci (e.g., a plurality of polymorphic loci).

In various embodiments, the primer extension reaction or the polymerase chain reaction includes the addition of one or more nucleotides by a polymerase. In some embodiments, greater than or equal to 5, 10, 20, 30, 40, 50, or 60 cycles of PCR are performed. In some embodiments, the amplification of loci is performed using a polymerase (e.g., a DNA polymerase, RNA polymerase, or reverse transcriptase) with low 5'→3' exonuclease and/or low strand displacement activity. In some embodiments, a DNA polymerase is used produce DNA amplicons using DNA as a template. In some embodiments, a RNA polymerase is used produce RNA amplicons using DNA as a template. In some embodiments, a reverse transcriptase is used produce cDNA amplicons using RNA as a template.

In various embodiments, the primer extension reaction or the polymerase chain reaction does not include ligation-mediated PCR. In various embodiments, the primer extension reaction or the polymerase chain reaction does not include the joining of two primers by a ligase. In various embodiments, the primers do not include Linked Inverted Probes (LIPs), which can also be called pre-circularized probes, pre-circularizing probes, circularizing probes, Padlock Probes, or Molecular Inversion Probes (MIPs). In some embodiments, the primers are not loopable primers. In some embodiments, the primers do not form a loop structure, for example, the primers do not comprise a 3' target specific portion, a stem (comprising a first loop forming region and a second loop forming region), and a loop portion. In various embodiments, the primer library, composition, kit, or method does not include an array (such as a microarray) or do no use an array (such as a microarray). In some embodiments, multiplex PCR and/or sequencing is performed without use of an array (such as a microarray). In some embodiments, the primer library, composition, kit, or method comprises a microarray. In some embodiments, the primers or the target loci do not comprise an STR allele (for example, the target loci may be non-polymorphic loci or the loci may comprise a polymorphism other than an STR allele). In some embodiments, some or all of the target loci comprise an STR allele.

It is understood that all of the aspects and embodiments of the invention described herein include "comprising," "consisting," and "consisting essentially of" aspects and embodiments. It is understood that aspects and embodiments of the invention described herein include combinations of any two or more of the aspects or embodiments of the invention.

Definitions

Single Nucleotide Polymorphism (SNP) refers to a single nucleotide that may differ between the genomes of two members of the same species. The usage of the term should not imply any limit on the frequency with which each variant occurs.

Sequence refers to a DNA sequence or a genetic sequence. It may refer to the primary, physical structure of the DNA molecule or strand in an individual. It may refer to the sequence of nucleotides found in that DNA molecule, or the complementary strand to the DNA molecule. It may refer to the information contained in the DNA molecule as its representation in silico.

Locus refers to a particular region of interest on the DNA (or corresponding RNA) of an individual, which may refer to a SNP, the site of a possible insertion or deletion, or the site of some other relevant genetic variation. Disease-linked SNPs may also refer to disease-linked loci.

Polymorphic Allele, also "Polymorphic Locus," refers to an allele or locus where the genotype varies between individuals within a given species. Some examples of polymorphic alleles include single nucleotide polymorphisms, short tandem repeats, deletions, duplications, and inversions.

Polymorphic Site refers to the specific nucleotides found in a polymorphic region that vary between individuals.

Allele refers to the genes that occupy a particular locus

Genetic Data also "Genotypic Data" refers to the data describing aspects of the genome of one or more individuals. It may refer to one or a set of loci, partial or entire sequences, partial or entire chromosomes, or the entire genome. It may refer to the identity of one or a plurality of nucleotides; it may refer to a set of sequential nucleotides, or nucleotides from different locations in the genome, or a combination thereof. Genotypic data is typically in silic, however, it is also possible to consider physical nucleotides in a sequence as chemically encoded genetic data. Genotypic Data may be said to be "on," "of," "at," "from" or "on" the individual(s). Genotypic Data may refer to output measurements from a genotyping platform where those measurements are made on genetic material.

Genetic Material also "Genetic Sample" refers to physical matter, such as tissue or blood, from one or more individuals comprising DNA or RNA.

Noisy Generic Data refers to genetic data with any of the following: allele dropouts, uncertain base pair measurements, incorrect base pair measurements, missing base pair measurements, uncertain measurements of insertions or deletions, uncertain measurements of chromosome segment copy numbers, spurious signals, missing measurements, other errors, or combinations thereof Confidence refers to the statistical likelihood that the called SNP, allele, set of alleles, ploidy call, or determined number of chromosome segment copies correctly represents the real genetic state of the individual.

Ploidy Calling, also "Chromosome Copy Number Calling," or "Copy Number Calling" (CNC), may refer to the act of determining the quantity and/or chromosomal identity of one or more chromosomes present in a cell.

Aneuploidy refers to the state where the wrong number of chromosomes (e.g., the wrong number of full chromosomes or the wrong number of chromosome segments, such as the presence of deletions or duplications of a chromosome segment) is present in a cell. In the case of a somatic human cell it may refer to the case where a cell does not contain 22 pairs of autosomal chromosomes and one pair of sex chromosomes. In the case of a human gamete, it may refer to the case where a cell does not contain one of each of the 23 chromosomes. In the case of a single chromosome type, it may refer to the case where more or less than two homologous but non-identical chromosome copies are present, or where there are two chromosome copies present that originate from the same parent. In some embodiments, the deletion of a chromosome segment is a microdeletion.

Ploidy State refers to the quantity and/or chromosomal identity of one or more chromosomes types in a cell.

Chromosome may refer to a single chromosome copy, meaning a single molecule of DNA of which there are 46 in a normal somatic cell; an example is 'the maternally derived chromosome 18'. Chromosome may also refer to a chromosome type, of which there are 23 in a normal human somatic cell; an example is 'chromosome 18'.

Chromosomal Identity may refer to the referent chromosome number, i.e. the chromosome type. Normal humans have 22 types of numbered autosomal chromosome types, and two types of sex chromosomes. It may also refer to the parental origin of the chromosome. It may also refer to a specific chromosome inherited from the parent. It may also refer to other identifying features of a chromosome.

The State of the Genetic Material or simply "Genetic State" may refer to the identity of a set of SNPs on the DNA, to the phased haplotypes of the genetic material, and to the sequence of the DNA, including insertions, deletions, repeats and mutations. It may also refer to the ploidy state of one or more chromosomes, chromosomal segments, or set of chromosomal segments.

Allelic Data refers to a set of genotypic data concerning a set of one or more alleles. It may refer to the phased, haplotypic data. It may refer to SNP identities, and it may refer to the sequence data of the DNA, including insertions, deletions, repeats and mutations. It may include the parental origin of each allele.

Allelic State refers to the actual state of the genes in a set of one or more alleles. It may refer to the actual state of the genes described by the allelic data.

Allelic Ratio or allele ratio, refers to the ratio between the amount of each allele at a locus that is present in a sample or in an individual. When the sample was measured by sequencing, the allelic ratio may refer to the ratio of sequence reads that map to each allele at the locus. When the sample was measured by an intensity based measurement method, the allele ratio may refer to the ratio of the amounts of each allele present at that locus as estimated by the measurement method.

Allele Count refers to the number of sequences that map to a particular locus, and if that locus is polymorphic, it refers to the number of sequences that map to each of the alleles. If each allele is counted in a binary fashion, then the allele count will be whole number. If the alleles are counted probabilistically, then the allele count can be a fractional number.

Allele Count Probability refers to the number of sequences that are likely to map to a particular locus or a set of alleles at a polymorphic locus, combined with the probability of the mapping. Note that allele counts are equivalent to allele count probabilities where the probability of the mapping for each counted sequence is binary (zero or one). In some embodiments, the allele count probabilities may be binary. In some embodiments, the allele count probabilities may be set to be equal to the DNA measurements.

Allelic Distribution, or 'allele count distribution' refers to the relative amount of each allele that is present for each locus in a set of loci. An allelic distribution can refer to an individual, to a sample, or to a set of measurements made on a sample. In the context of sequencing, the allelic distribution refers to the number or probable number of reads that map to a particular allele for each allele in a set of polymorphic loci. The allele measurements may be treated probabilistically, that is, the likelihood that a given allele is present for a give sequence read is a fraction between 0 and 1, or they may be treated in a binary fashion, that is, any given read is considered to be exactly zero or one copies of a particular allele.

Allelic Distribution Pattern refers to a set of different allele distributions for different parental contexts. Certain allelic distribution patterns may be indicative of certain ploidy states.

Allelic Bias refers to the degree to which the measured ratio of alleles at a heterozygous locus is different to the ratio that was present in the original sample, such as a sample of DNA. The degree of allelic bias at a particular locus is equal to the observed allelic ratio at that locus, as measured, divided by the ratio of alleles in the original DNA or RNA sample at that locus. Allelic bias may be defined to be greater than one, such that if the calculation of the degree of allelic bias returns a value, x, that is less than 1, then the degree of allelic bias may be restated as 1/x. Allelic bias may be due to amplification bias, purification bias, or some other phenomenon that affects different alleles differently.

Primer, also "PCR probe" refers to a single DNA molecule (a DNA oligomer) or a collection of DNA molecules (DNA oligomers) where the DNA molecules are identical, or nearly so, and where the primer contains a region that is designed to hybridize to a targeted locus (e.g. a targeted polymorphic locus or a nonpolymorphic locus), and may contain a priming sequence designed to allow PCR amplification. A primer may also contain a molecular barcode. A primer may contain a random region that differs for each individual molecule. The terms "test primer" and "candidate primer" are not meant to be limiting and may refer to any of the primers disclosed herein.

Library of primers refers to a population of two or more primers. In various embodiments, the library includes at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different primers. In various embodiments, the library includes at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different primer pairs, wherein each pair of primers includes a forward test primer and a reverse test primer where each pair of test primers hybridize to a target locus. In some embodiments, the library of primers includes at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different individual primers that each hybridize to a different target locus, wherein the individual primers are not part of primer pairs. In some embodiments, the library has both (i) primer pairs and (ii) individual primers (such as universal primers) that are not part of primer pairs.

Different primers refers to non-identical primers.

Different pools refers to non-identical pools.

Different target loci refers to non-identical target loci.

Different amplicons refers to non-identical amplicons.

Hybrid Capture Probe refers to any nucleic acid sequence, possibly modified, that is generated by various methods such as PCR or direct synthesis and intended to be complementary to one strand of a specific target DNA sequence in a sample. The exogenous hybrid capture probes may be added to a prepared sample and hybridized through a denature-reannealing process to form duplexes of exogenous-endogenous fragments. These duplexes may then be physically separated from the sample by various means Sequence Read refers to data representing a sequence of nucleotide bases that were measured using a clonal sequencing method. Clonal sequencing may produce sequence data representing single, or clones, or clusters of one original DNA molecule. A sequence read may also have associated quality score at each base position of the sequence indicating the probability that nucleotide has been called correctly.

Mapping a sequence read is the process of determining a sequence read's location of origin in the genome sequence of a particular organism. The location of origin of sequence reads is based on similarity of nucleotide sequence of the read and the genome sequence.

Matched Copy Error, also "Matching Chromosome Aneuploidy" (MCA), refers to a state of aneuploidy where one cell contains two identical or nearly identical chromosomes. This type of aneuploidy may arise during the formation of the gametes in meiosis, and may be referred to as a meiotic non-disjunction error. This type of error may arise in mitosis. Matching trisomy may refer to the case where three copies of a given chromosome are present in an individual and two of the copies are identical Unmatched Copy Error, also "Unique Chromosome Aneuploidy" (UCA), refers to a state of aneuploidy where one cell contains two chromosomes that are from the same parent, and that may be homologous but not identical. This type of aneuploidy may arise during meiosis, and may be referred to as a meiotic error. Unmatching trisomy may refer to the case where three copies of a given chromosome are present in an individual and two of the copies are from the same parent, and are homologous, but are not identical. Note that unmatching trisomy may refer to the case where two homologous chromosomes from one parent are present, and where some segments of the chromosomes are identical while other segments are merely homologous.

Homologous Chromosomes refers to chromosome copies that contain the same set of genes that normally pair up during meiosis.

Identical Chromosomes refers to chromosome copies that contain the same set of genes, and for each gene they have the same set of alleles that are identical, or nearly identical.

Allele Drop Out (ADO) refers to the situation where at least one of the base pairs in a set of base pairs from homologous chromosomes at a given allele is not detected.

Locus Drop Out (LDO) refers to the situation where both base pairs in a set of base pairs from homologous chromosomes at a given allele are not detected.

Homozygous refers to having similar alleles as corresponding chromosomal loci.

Heterozygous refers to having dissimilar alleles as corresponding chromosomal loci.

Heterozygosity Rate refers to the rate of individuals in the population having heterozygous alleles at a given locus. The heterozygosity rate may also refer to the expected or measured ratio of alleles, at a given locus in an individual, or a sample of DNA.

Highly Informative Single Nucleotide Polymorphism (HISNP) refers to a SNP where the fetus has an allele that is not present in the mother's genotype.

Chromosomal Region refers to a segment of a chromosome, or a full chromosome.

Segment of a Chromosome refers to a section of a chromosome that can range in size from one base pair to the entire chromosome.

Chromosome refers to either a full chromosome, or a segment or section of a chromosome.

Copies refers to the number of copies of a chromosome segment. It may refer to identical copies, or to non-identical, homologous copies of a chromosome segment wherein the different copies of the chromosome segment contain a substantially similar set of loci, and where one or more of the alleles are different. Note that in some cases of aneuploidy, such as the M2 copy error, it is possible to have some copies of the given chromosome segment that are identical as well as some copies of the same chromosome segment that are not identical.

Haplotype refers to a combination of alleles at multiple loci that are typically inherited together on the same chromosome. Haplotype may refer to as few as two loci or to an entire chromosome depending on the number of recombination events that have occurred between a given set of loci. Haplotype can also refer to a set of single nucleotide polymorphisms (SNPs) on a single chromatid that are statistically associated.

Haplotypic Data, also "Phased Data" or "Ordered Genetic Data," refers to data from a single chromosome in a diploid or polyploid genome, i.e. either the segregated maternal or paternal copy of a chromosome in a diploid genome.

Phasing refers to the act of determining the haplotypic genetic data of an individual given unordered, diploid (or polyploidy) genetic data. It may refer to the act of determining which of two genes at an allele, for a set of alleles found on one chromosome, are associated with each of the two homologous chromosomes in an individual.

Phased Data refers to genetic data where one or more haplotypes have been determined.

Hypothesis refers to a possible ploidy state at a given set of chromosomes, or a set of possible allelic states at a given set of loci. The set of possibilities may comprise one or more elements.

Copy Number Hypothesis, also "Ploidy State Hypothesis," refers to a hypothesis concerning the number of copies of a chromosome in an individual. It may also refer to a hypothesis concerning the identity of each of the chromosomes, including the parent of origin of each chromosome, and which of the parent's two chromosomes are present in the individual. It may also refer to a hypothesis concerning which chromosomes, or chromosome segments, if any, from a related individual correspond genetically to a given chromosome from an individual.

Target Individual refers to the individual whose genetic state is being determined. In some embodiments, only a limited amount of DNA is available from the target individual. In some embodiments, the target individual is a fetus. In some embodiments, there may be more than one target individual. In some embodiments, each fetus that originated from a pair of parents may be considered to be target individuals. In some embodiments, the genetic data that is being determined is one or a set of allele calls. In some embodiments, the genetic data that is being determined is a ploidy call.

Related Individual refers to any individual who is genetically related to, and thus shares haplotype blocks with, the target individual. In one context, the related individual may be a genetic parent of the target individual, or any genetic material derived from a parent, such as a sperm, a polar body, an embryo, a fetus, or a child. It may also refer to a sibling, parent or a grandparent.

Sibling refers to any individual whose genetic parents are the same as the individual in question. In some embodiments, it may refer to a born child, an embryo, or a fetus, or one or more cells originating from a born child, an embryo, or a fetus. A sibling may also refer to a haploid individual that originates from one of the parents, such as a sperm, a polar body, or any other set of haplotypic genetic matter. An individual may be considered to be a sibling of itself.

Fetal refers to "of the fetus," or "of the region of the placenta that is genetically similar to the fetus". In a pregnant woman, some portion of the placenta is genetically similar to the fetus, and the free floating fetal DNA found in maternal blood may have originated from the portion of the placenta with a genotype that matches the fetus. Note that the genetic information in half of the chromosomes in a fetus is inherited from the mother of the fetus. In some embodiments, the DNA from these maternally inherited chromosomes that came from a fetal cell is considered to be "of fetal origin," not "of maternal origin."

DNA of Fetal Origin refers to DNA that was originally part of a cell whose genotype was essentially equivalent to that of the fetus.

DNA of Maternal Origin refers to DNA that was originally part of a cell whose genotype was essentially equivalent to that of the mother.

Child may refer to an embryo, a blastomere, or a fetus. Note that in the presently disclosed embodiments, the concepts described apply equally well to individuals who are a born child, a fetus, an embryo or a set of cells therefrom. The use of the term child may simply be meant to connote that the individual referred to as the child is the genetic offspring of the parents.

Parent refers to the genetic mother or father of an individual. An individual typically has two parents, a mother and a father, though this may not necessarily be the case such as in genetic or chromosomal chimerism. A parent may be considered to be an individual.

Parental Context refers to the genetic state of a given SNP, on each of the two relevant chromosomes for one or both of the two parents of the target.

Develop As Desired, also "Develop Normally," refers to a viable embryo implanting in a uterus and resulting in a pregnancy, and/or to a pregnancy continuing and resulting in a live birth, and/or to a born child being free of chromosomal abnormalities, and/or to a born child being free of other undesired genetic conditions such as disease-linked genes. The term "develop as desired" is meant to encompass anything that may be desired by parents or healthcare facilitators. In some cases, "develop as desired" may refer to an unviable or viable embryo that is useful for medical research or other purposes.

Insertion into a Uterus refers to the process of transferring an embryo into the uterine cavity in the context of in vitro fertilization Maternal Plasma refers to the plasma portion of the blood from a female who is pregnant.

Clinical Decision refers to any decision to take or not take an action that has an outcome that affects the health or survival of an individual. In the context of prenatal diagnosis, a clinical decision may refer to a decision to abort or not abort a fetus. A clinical decision may also refer to a decision to conduct further testing, to take actions to mitigate an undesirable phenotype, or to take actions to prepare for the birth of a child with abnormalities.

Diagnostic Box refers to one or a combination of machines designed to perform one or a plurality of aspects of the methods disclosed herein. In an embodiment, the diagnostic box may be placed at a point of patient care. In an embodiment, the diagnostic box may perform targeted amplification followed by sequencing. In an embodiment the diagnostic box may function alone or with the help of a technician.

Informatics Based Method refers to a method that relies heavily on statistics to make sense of a large amount of data. In the context of prenatal diagnosis, it refers to a method designed to determine the ploidy state at one or more chromosomes or the allelic state at one or more alleles by statistically inferring the most likely state, rather than by directly physically measuring the state, given a large amount of genetic data, for example from a molecular array or sequencing. In an embodiment of the present disclosure, the informatics based technique may be one disclosed in this patent. In an embodiment of the present disclosure it may be PARENTAL SUPPORT™.

Primary Genetic Data refers to the analog intensity signals that are output by a genotyping platform. In the context of SNP arrays, primary genetic data refers to the intensity signals before any genotype calling has been done. In the context of sequencing, primary genetic data refers to the analog measurements, analogous to the chromatogram, that comes off the sequencer before the identity of any base pairs have been determined, and before the sequence has been mapped to the genome.

Secondary Genetic Data refers to processed genetic data that are output by a genotyping platform. In the context of a SNP array, the secondary genetic data refers to the allele calls made by software associated with the SNP array reader, wherein the software has made a call whether a given allele is present or not present in the sample. In the context of sequencing, the secondary genetic data refers to the base pair identities of the sequences have been determined, and possibly also where the sequences have been mapped to the genome.

Non-Invasive Prenatal Diagnosis (NPD), or also "Non-Invasive Prenatal Screening" (NPS), refers to a method of determining the genetic state of a fetus that is gestating in a mother using genetic material found in the mother's blood, where the genetic material is obtained by drawing the mother's intravenous blood.

Preferential Enrichment of DNA that corresponds to a locus, or preferential enrichment of DNA at a locus, refers to any method that results in the percentage of molecules of DNA in a post-enrichment DNA mixture that correspond to the locus being higher than the percentage of molecules of DNA in the pre-enrichment DNA mixture that correspond to the locus. The method may involve selective amplification of DNA molecules that correspond to a locus. The method may involve removing DNA molecules that do not correspond to the locus. The method may involve a combination of methods. The degree of enrichment is defined as the percentage of molecules of DNA in the post-enrichment mixture that correspond to the locus divided by the percentage of molecules of DNA in the pre-enrichment mixture that correspond to the locus. Preferential enrichment may be carried out at a plurality of loci. In some embodiments of the present disclosure, the degree of enrichment is greater than 20. In some embodiments of the present disclosure, the degree of enrichment is greater than 200. In some embodiments of the present disclosure, the degree of enrichment is greater than 2,000. When preferential enrichment is carried out at a plurality of loci, the degree of enrichment may refer to the average degree of enrichment of all of the loci in the set of loci.

Amplification refers to a method that increases the number of copies of a molecule, such as a molecule of DNA.

Selective Amplification may refer to a method that increases the number of copies of a particular molecule of DNA, or molecules of DNA that correspond to a particular region of DNA. It may also refer to a method that increases the number of copies of a particular targeted molecule of DNA, or targeted region of DNA more than it increases non-targeted molecules or regions of DNA. Selective amplification may be a method of preferential enrichment.

Universal Priming Sequence refers to a DNA sequence that may be appended to a population of target DNA molecules, for example by ligation, PCR, or ligation mediated PCR. Once added to the population of target molecules, primers specific to the universal priming sequences can be used to amplify the target population using a single pair of amplification primers. Universal priming sequences are typically not related to the target sequences.

Universal Adapters, or 'ligation adaptors' or 'library tags' are DNA molecules containing a universal priming sequence that can be covalently linked to the 5-prime and 3-prime end of a population of target double stranded DNA molecules. The addition of the adapters provides universal priming sequences to the 5-prime and 3-prime end of the target population from which PCR amplification can take place, amplifying all molecules from the target population, using a single pair of amplification primers.

Targeting refers to a method used to selectively amplify or otherwise preferentially enrich those molecules of DNA that correspond to a set of loci, in a mixture of DNA.

Joint Distribution Model refers to a model that defines the probability of events defined in terms of multiple random variables, given a plurality of random variables defined on the same probability space, where the probabilities of the variable are linked. In some embodiments, the degenerate case where the probabilities of the variables are not linked may be used.

Percent identity in reference to nucleic acid sequences refers to the degree of sequence identity between nucleic acid sequences.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 12: An example of some primers with internal tags (SEQ ID NOs: 44,610-44,622).

FIGS. 29A-29E: Cartoon depiction of a method of the invention for the determination of a fetal aneuploidy (FIG. 29A). Maternal and paternal genotype data (from blood or buccal swabs) and crossover frequency data from the HapMap database are utilized to generate (FIG. 29B) multiple independent hypotheses for each potential fetal ploidy state in silico (FIG. 29C). Each of these hypotheses is expanded to include sub-hypotheses with take into consideration the different possible crossover points. The data model predicts what the sequencing data would look like (the expected allele distributions) given each hypothetical fetal genotype and at different fetal cfDNA fractions, and is compared to the actual sequencing data; the likelihood for each hypothesis is determined using Bayesian statistics. In this hypothetical example, the hypotheses with the highest likelihoods (euploidy) are determined (FIG. 29D and FIG. 29E). The individual likelihoods from FIG. 29C are summed for each copy number hypothesis family (monosomy, disomy, or triploidy). The hypothesis with the maximum likelihood is called as the ploidy state, reveals the fetal fraction, and represents the sample-specific calculated accuracy.

FIG. 30A: Generated plots when two chromosomes are present and the fetal cfDNA fraction is 0%. This plot is from a non-pregnant woman, and thus represents the pattern when the genotype is entirely maternal. Allele clusters are thus centered around 1 (AA alleles), 0.5 (AB alleles), and 0 (BB alleles). FIG. 30B: Generated plot when two chromosomes are present and the fetal fraction is 12%. The contribution of fetal alleles to the fraction of A allele reads shifts the position of some allele spots up or down along the y-axis, such that the bands are centered around 1 (AA|AA alleles), 0.94 (AA|AB alleles), 0.56 (AB|AA alleles), 0.50 (AB|AB alleles), 0.44 (AB|BB alleles), 0.06 (BB|AB alleles), and 0 (BB|BB alleles). FIG. 30C. Generated plot when two chromosomes are present and the fetal fraction is 26%. The pattern, including two red and two blue peripheral bands and a trio of central green bands, is readily apparent. Bands are centered around 1 (AA|AA alleles), 0.87 (AA|AB alleles), 0.63 (AB|AA alleles), 0.50 (AB|AB alleles), 0.37 (AB|BB alleles), 0.13 (BB|AB alleles), and 0 (BB|BB alleles). FIG. 30D: Generated plot when one chromosome is present and the fetal fraction is 26%. The hallmark pattern of one external red and one external blue peripheral band as well as two central green bands indicated maternally-inherited monosomy. Because the fetus only contributes a single allele (A or B) to the allele reads, the internal peripheral red and blue bands are not present, and the center trio of bands condenses into two bands. Bands that are centered around 1 (AA|A alleles), 0.57 (AB|A alleles), 0.43 (AB|B alleles), and 0 (BB|B alleles). FIG. 30E: Generated plot when three chromosomes are present and the fetal fraction is 27%. This pattern of two red and two blue peripheral bands as well as two central green bands indicates maternally-inherited meiotic trisomy. Bands are centered around 1 (AA|AAA alleles), 0.88 (AA|AAB alleles), 0.56 (AB|AAB alleles), 0.44 (AB|ABB alleles), 0.12 (BB|ABB alleles), and 0 (BB|BBB alleles). FIG. 30F: Generated plot when three chromosomes are present and the fetal fraction is 14%. This pattern of three red and three blue peripheral bands, as well as two central green bands, indicates paternally-inherited meiotic trisomy. Bands are centered around 1 (AA|AAA alleles), 0.93 (AA|AAB alleles), 0.87 (AA|ABB alleles), 0.60 (AB|AAA alleles), 0.53 (AB|AAB alleles), 0.47 (AB|ABB alleles), 0.40 (AB|BBB alleles), 0.13 (BB|AAB alleles), 0.07 (BB|ABB alleles), and 0 (BB|BBB alleles). FIG. 30G: Generated plot when three chromosomes are present and the fetal fraction is 35%. This pattern of two red and two blue peripheral bands and four central green bands indicates maternally-inherited mitotic trisomy. Bands are centered around 1 (AA|AAA alleles), 0.85 (AA|AAB alleles), 0.72 (AB|AAA alleles), 0.57 (AB|AAB alleles), 0.43 (AB|ABB alleles), 0.28 (AB|BBB alleles), 0.15 (BB|ABB alleles), and 0 (BB|BBB alleles). FIG. 30H: Generated plot when three chromosomes are present and the fetal fraction is 25%. This pattern of two red and two blue peripheral bands as well as four central green bands indicates paternally-inherited mitotic trisomy. This pattern can be distinguished from that of maternally-inherited mitotic trisomy (as in FIG. 30G) by the position of the internal peripheral bands. Specifically, bands are centered around 1 (AA|AAA alleles), 0.78 (AA|ABB alleles), 0.67 (AB|AAA alleles), 0.56 (AB|AAB alleles), 0.44 (AB|ABB alleles), 0.33 (AB|BBB alleles), 0.22 (BB|AAB alleles), and 0 (BB|BBB alleles).

FIG. 33A shows the first two bases (dinucleotide) of a primer that align to the other primer for calculation of ΔG. Iterate over the remainder of the primer that aligns with the other primer by sliding the bases being observing one base to the right. Continue until ΔG has been calculated for all pairs of bases that align (FIG. 33B). Shift the alignment of the two primers (FIGS. 33C and 33D). Determine ΔG for the new alignment (FIGS. 33E and 33F).

Figure 34A3:
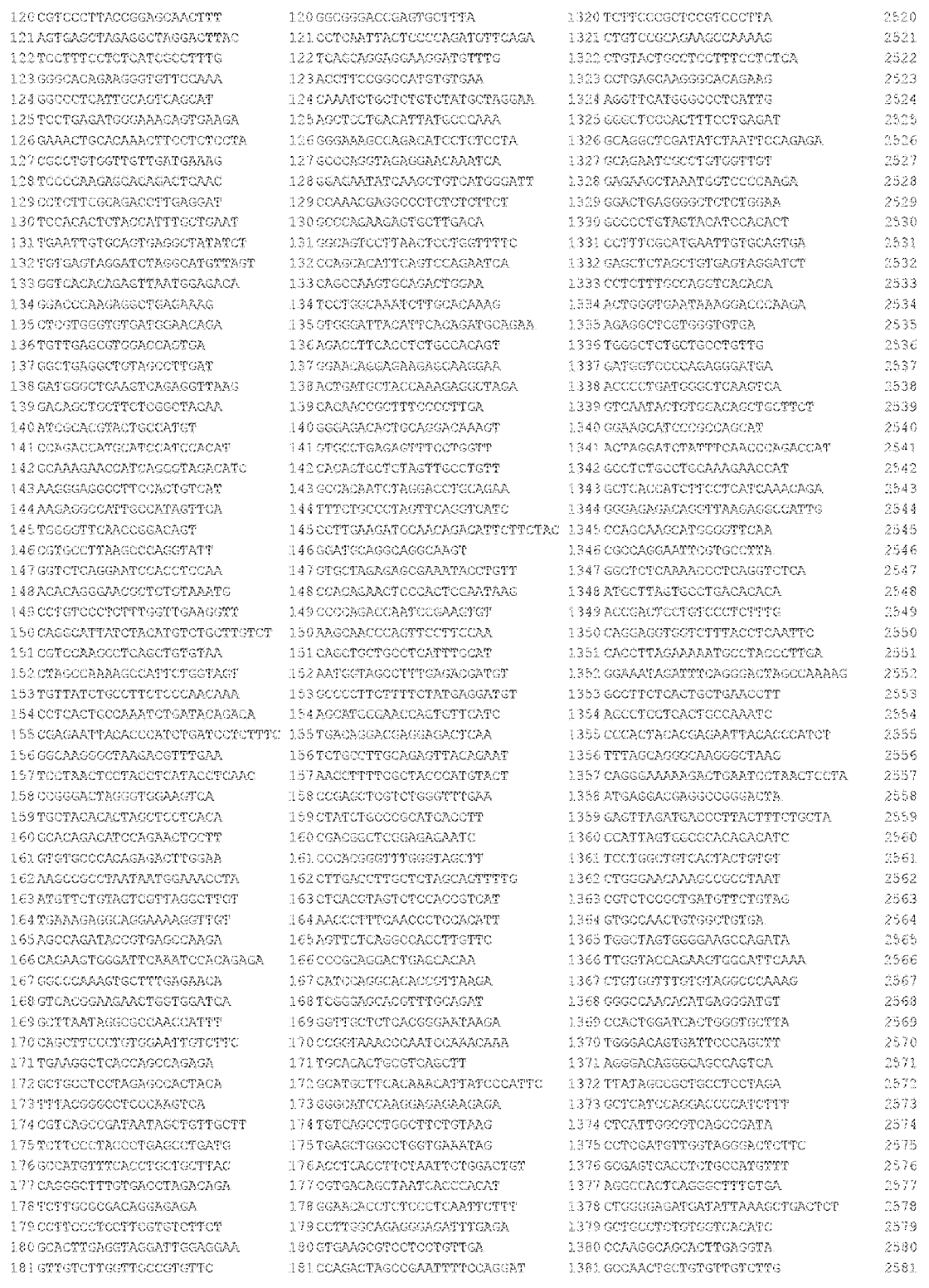
Figure 34A8:
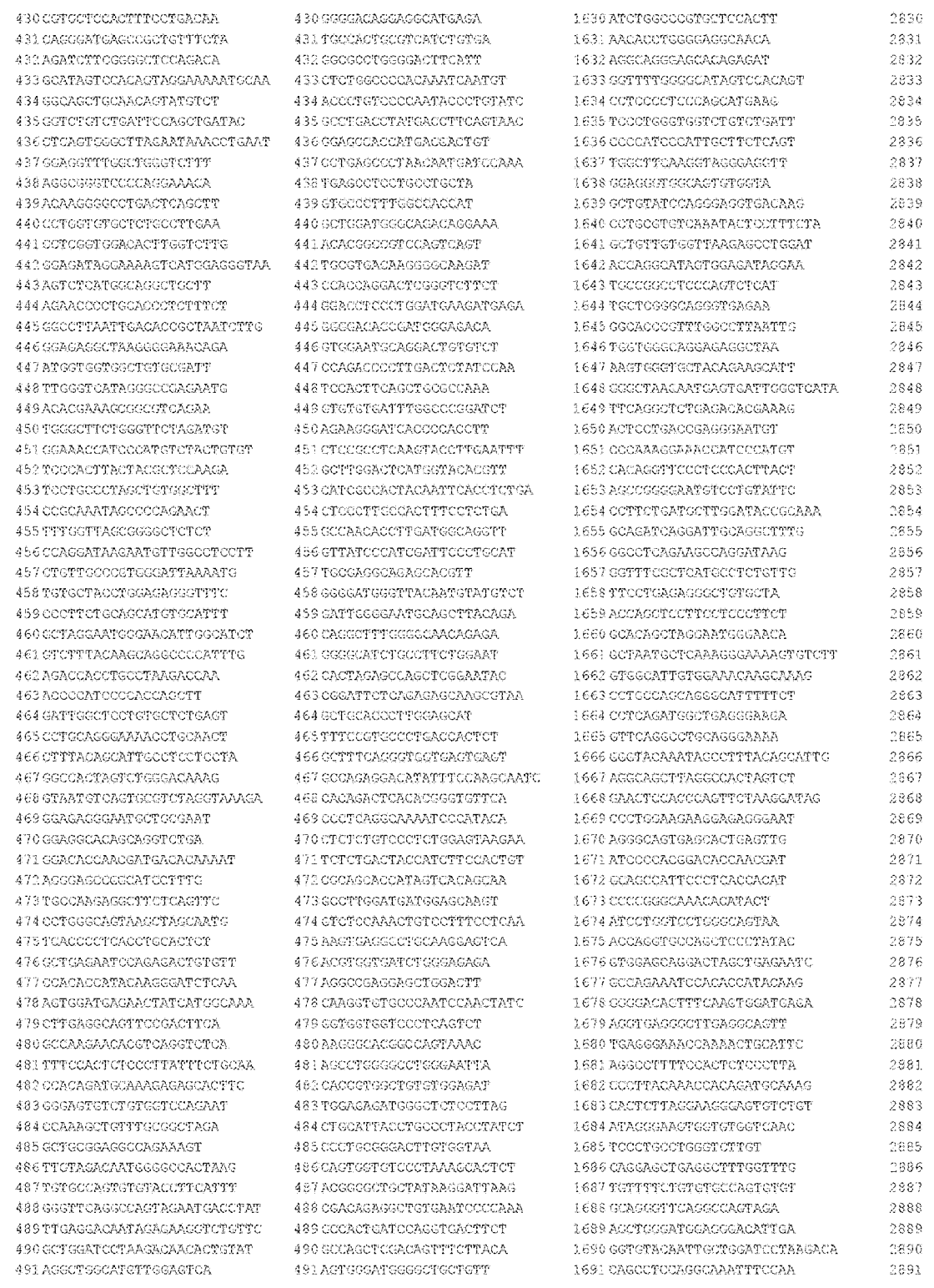
Figure 34A10:
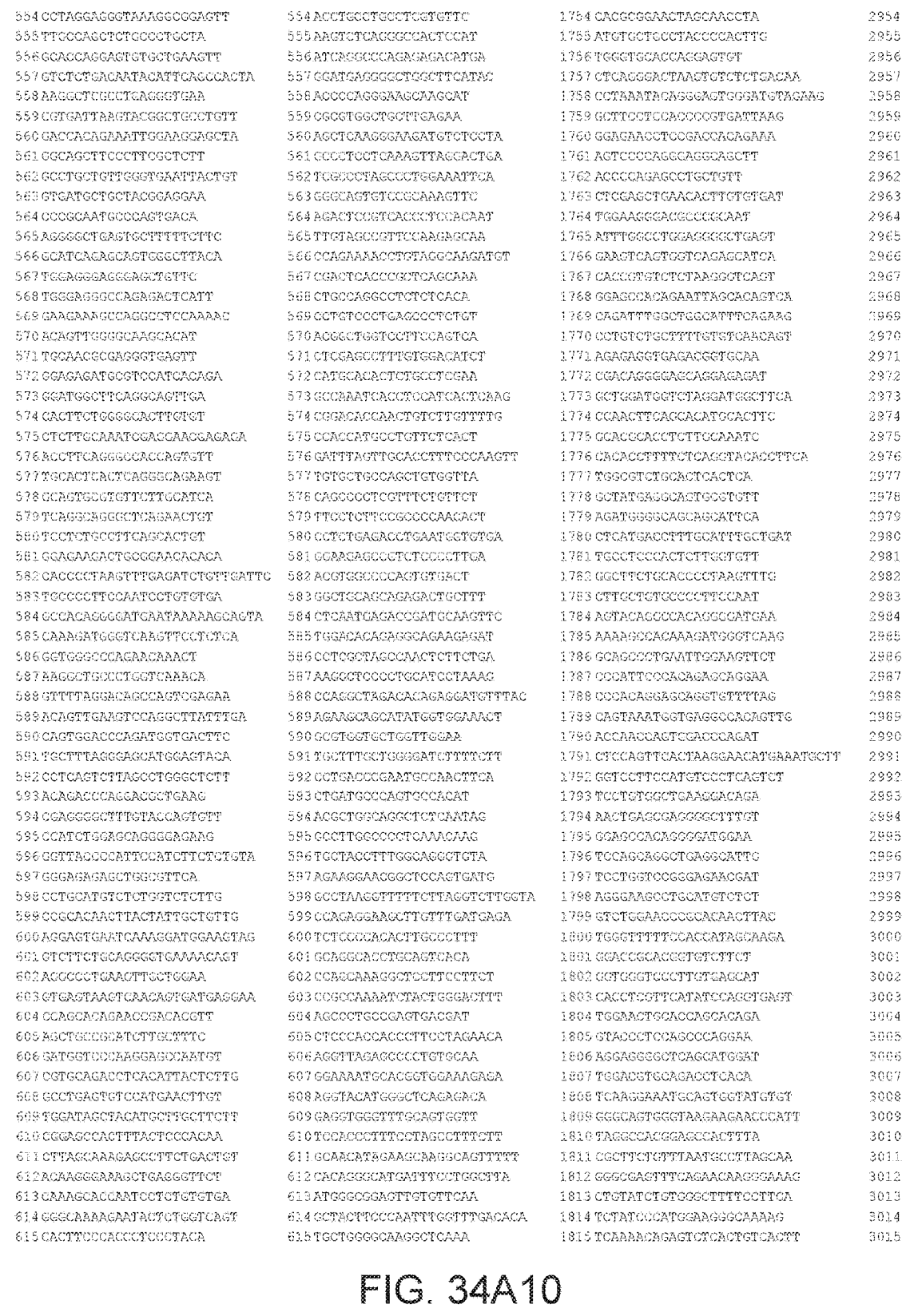
Figure 34B1:
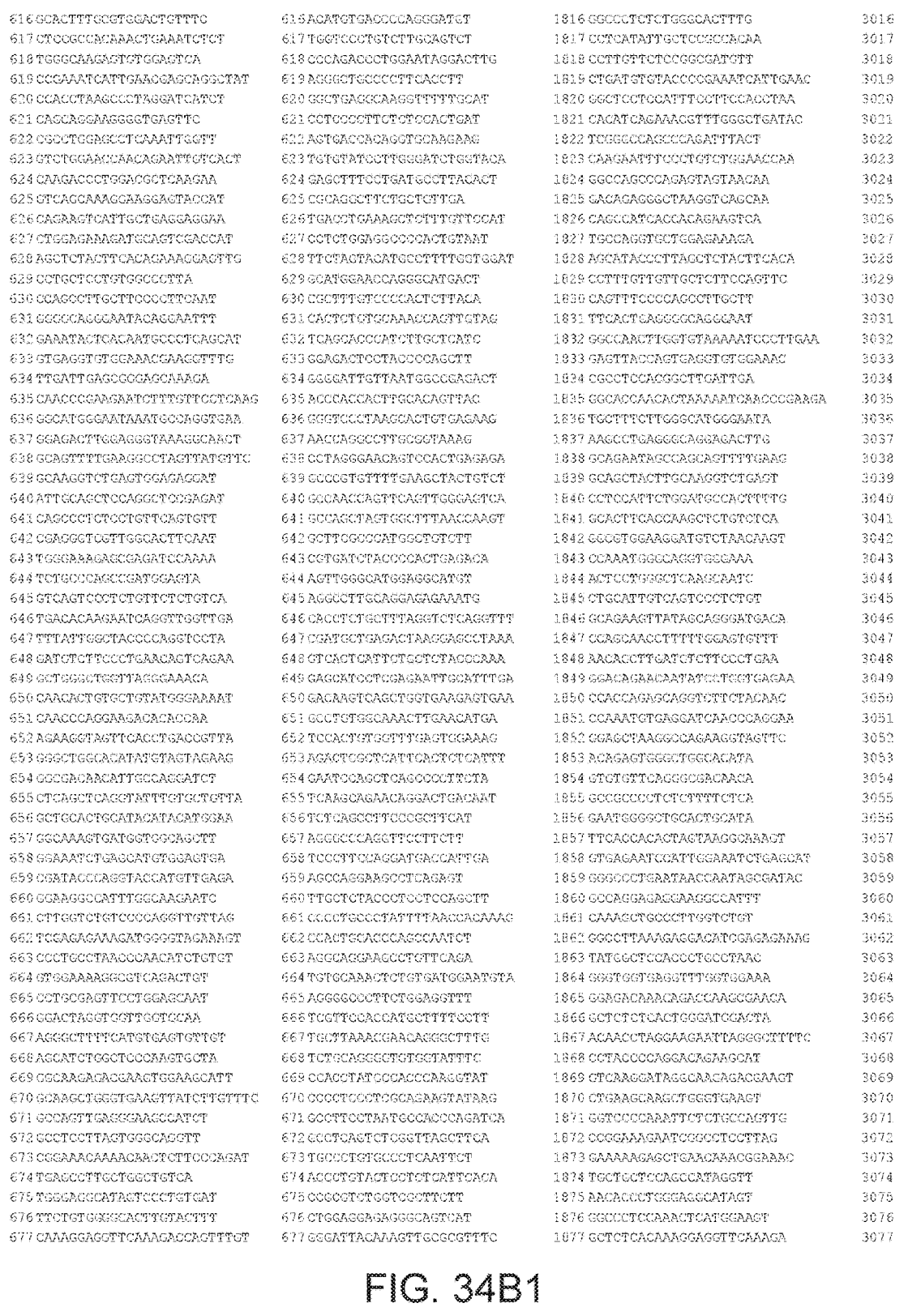
Figure 34B5:
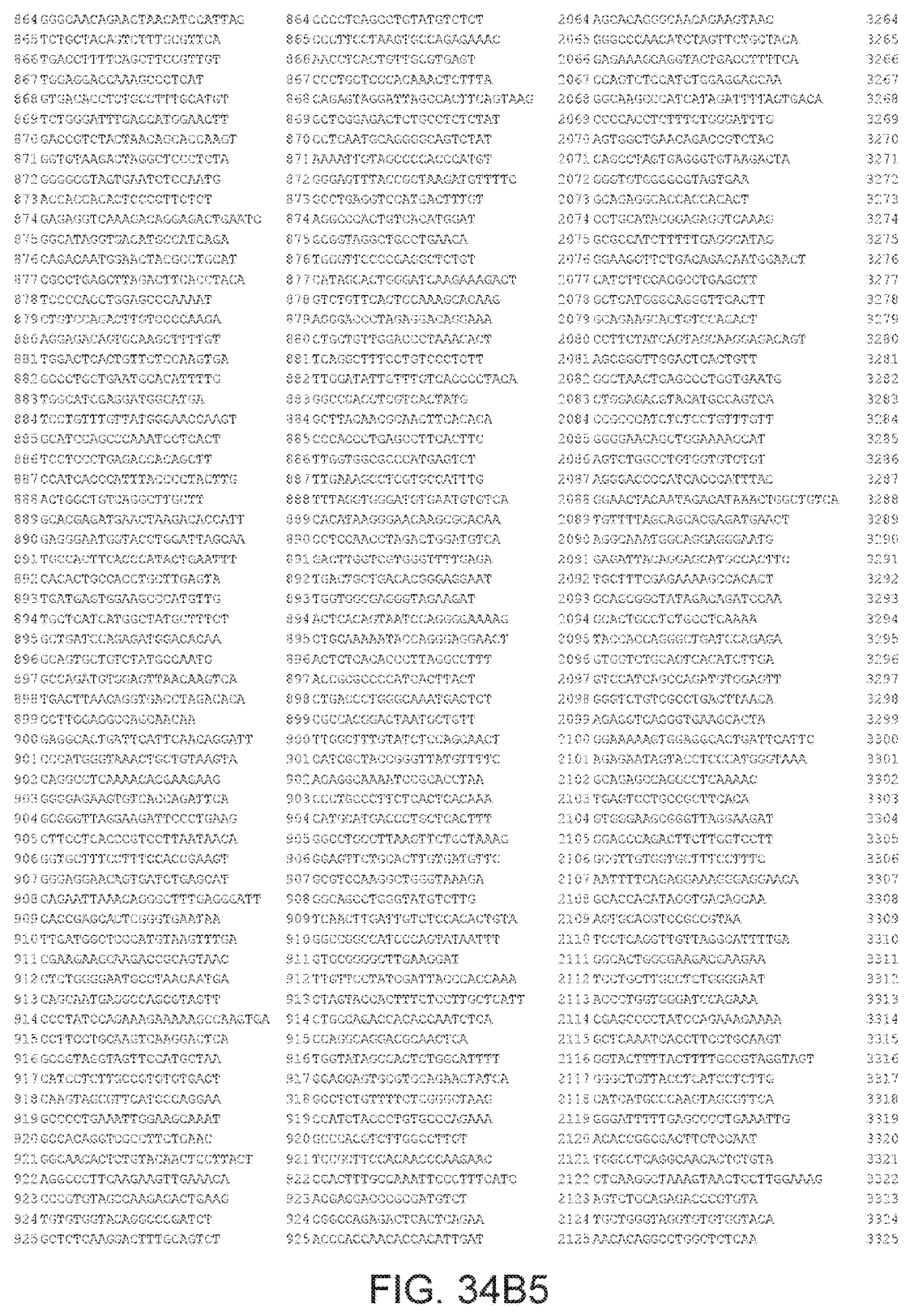
Figure 34B7:
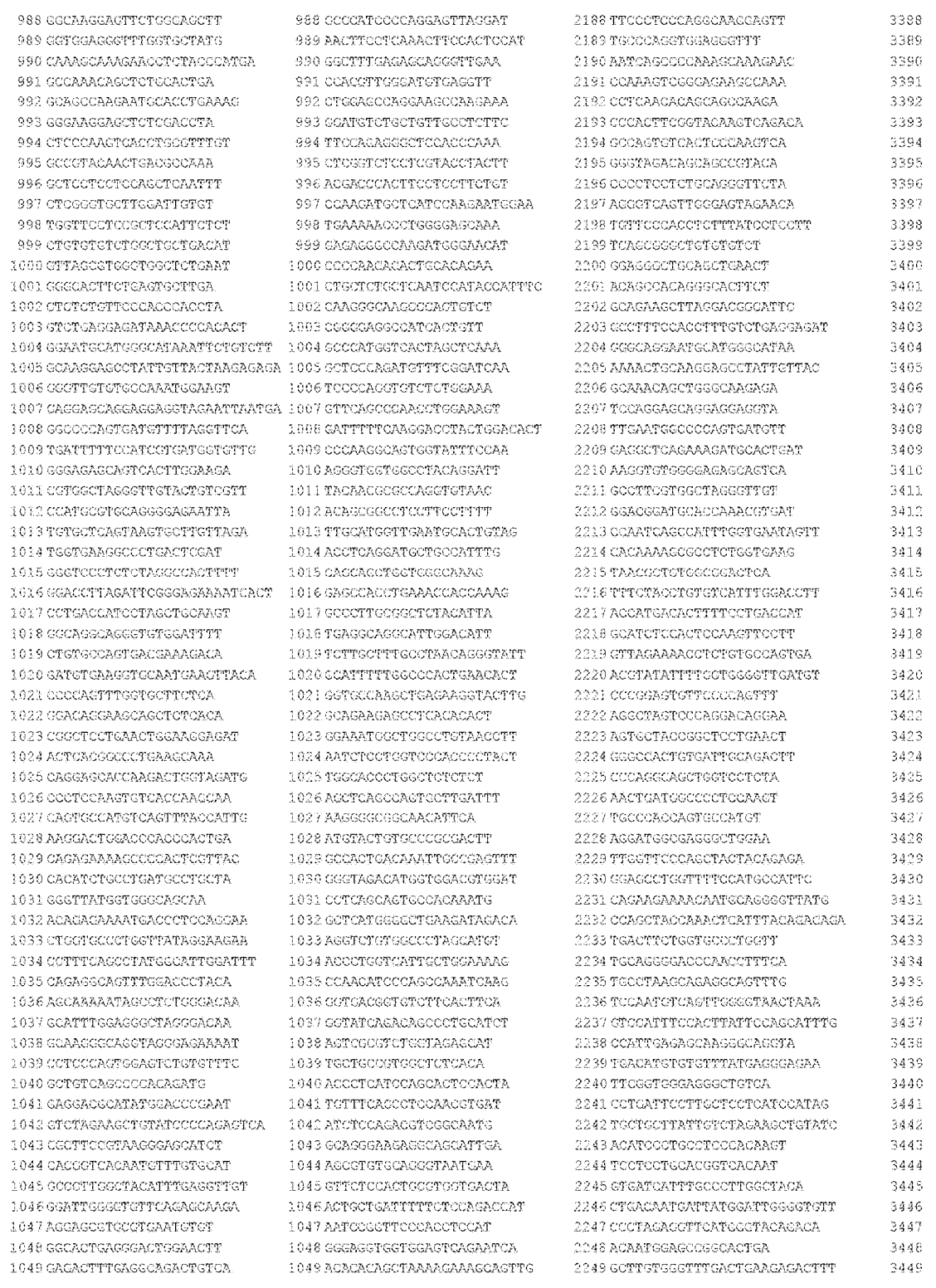

FIG. 34A1-A10, FIG. 34B1-B10: Sequences of an exemplary 1,200-plex primer library (SEQ ID NOs. 1-3,600). The three primers (one from pool A, one from pool B, and one from pool C) in each row all hybridize to the same target locus.

Figure 35A3:
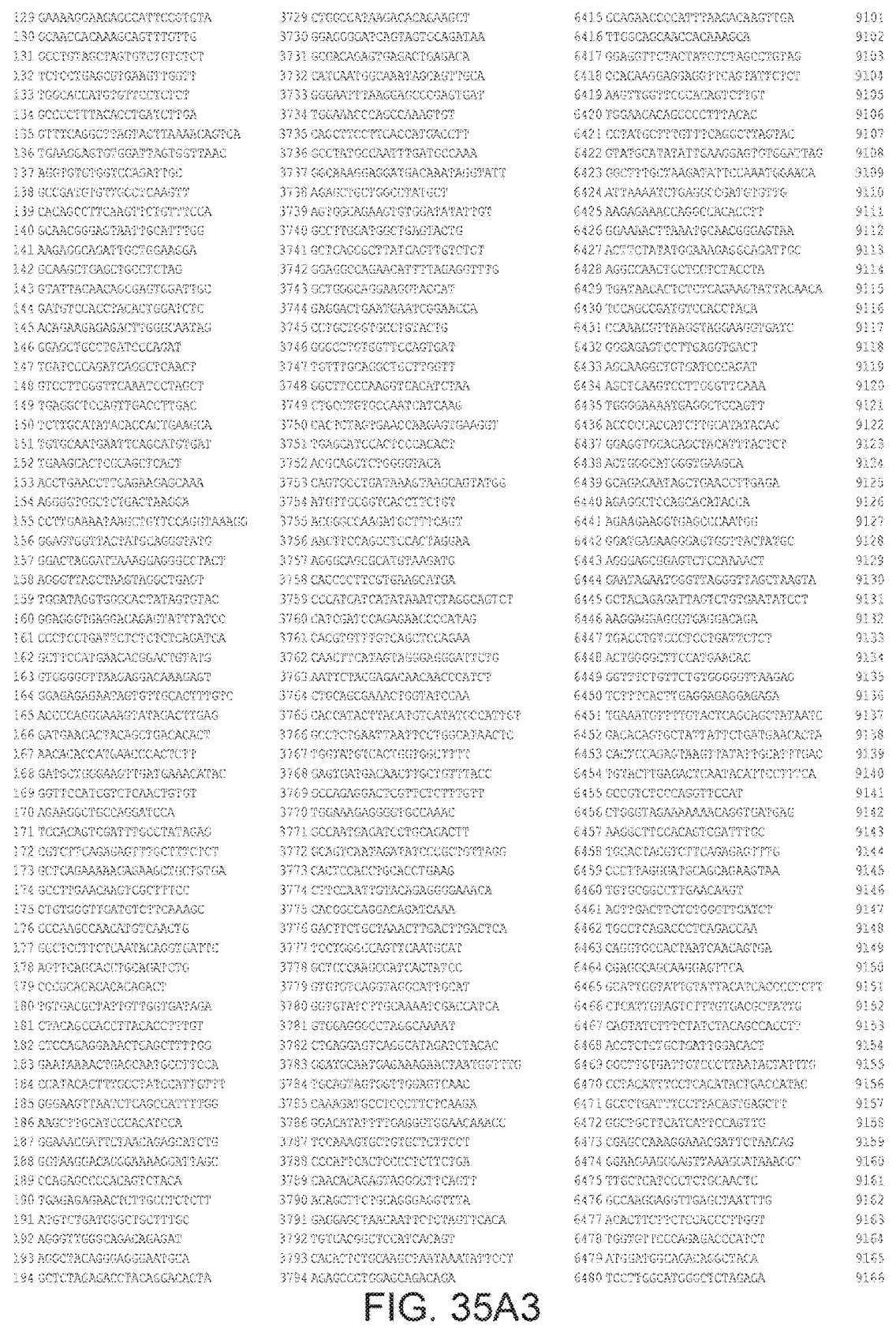
Figure 35A4:
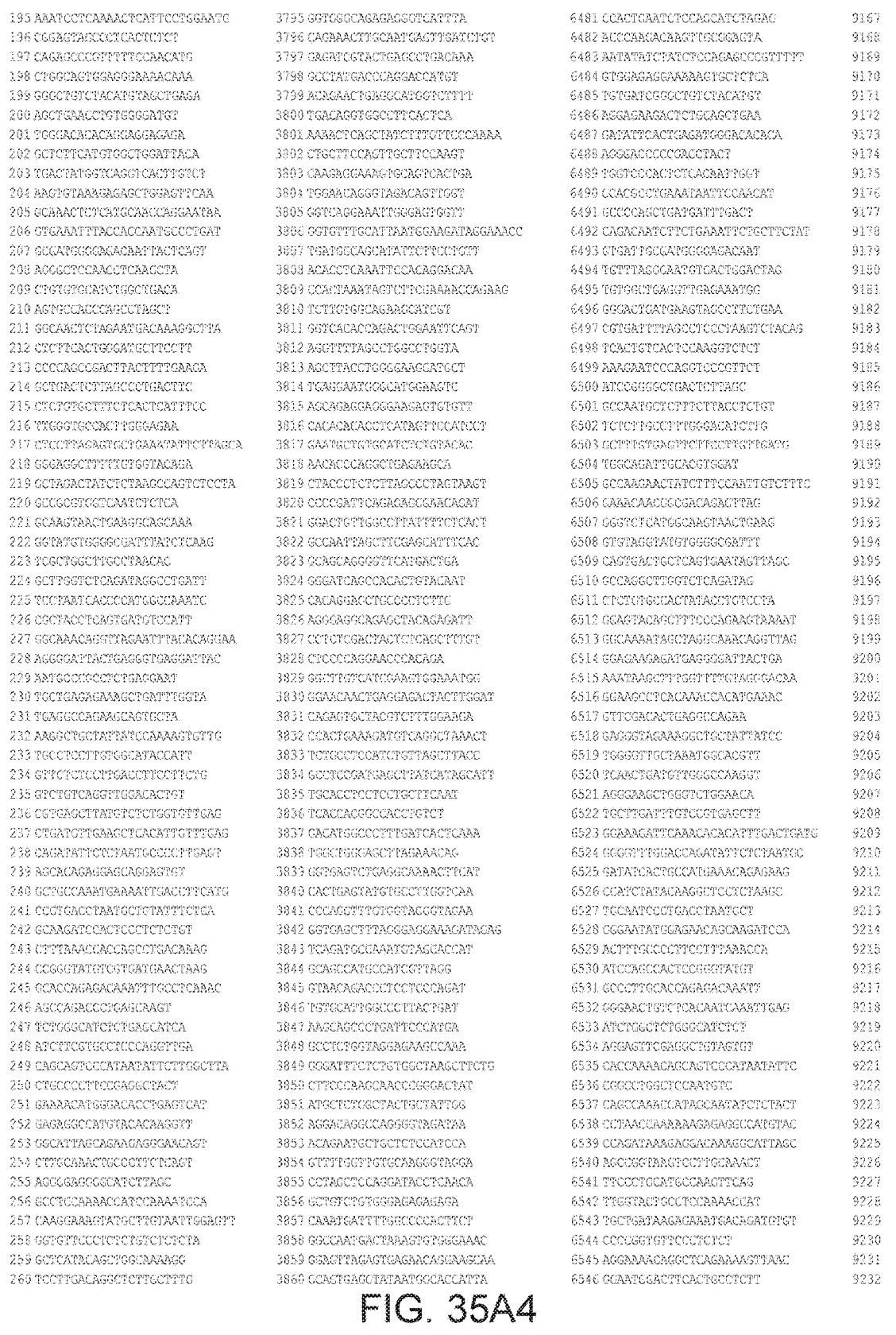
Figure 35A5:
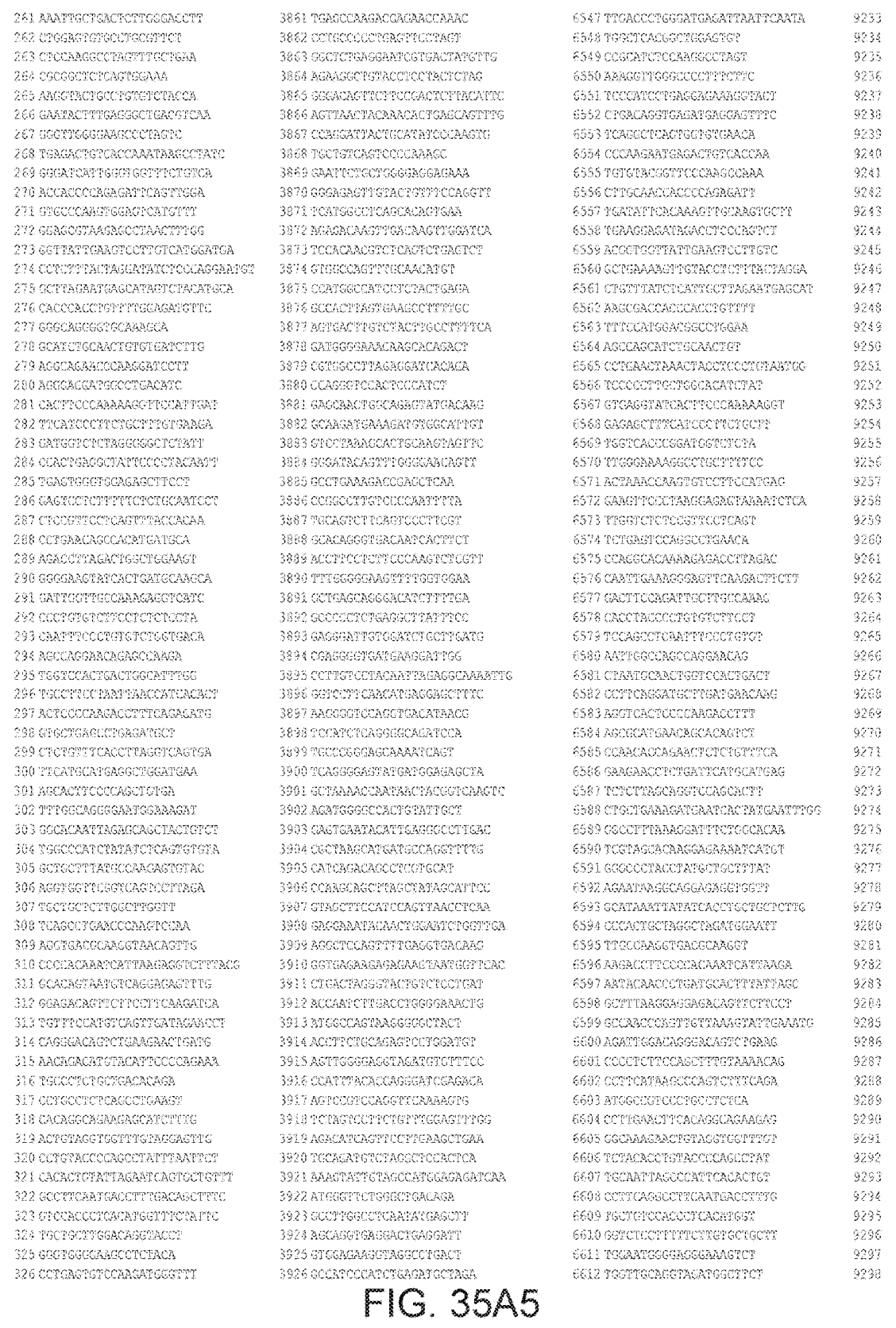
Figure 35A6:
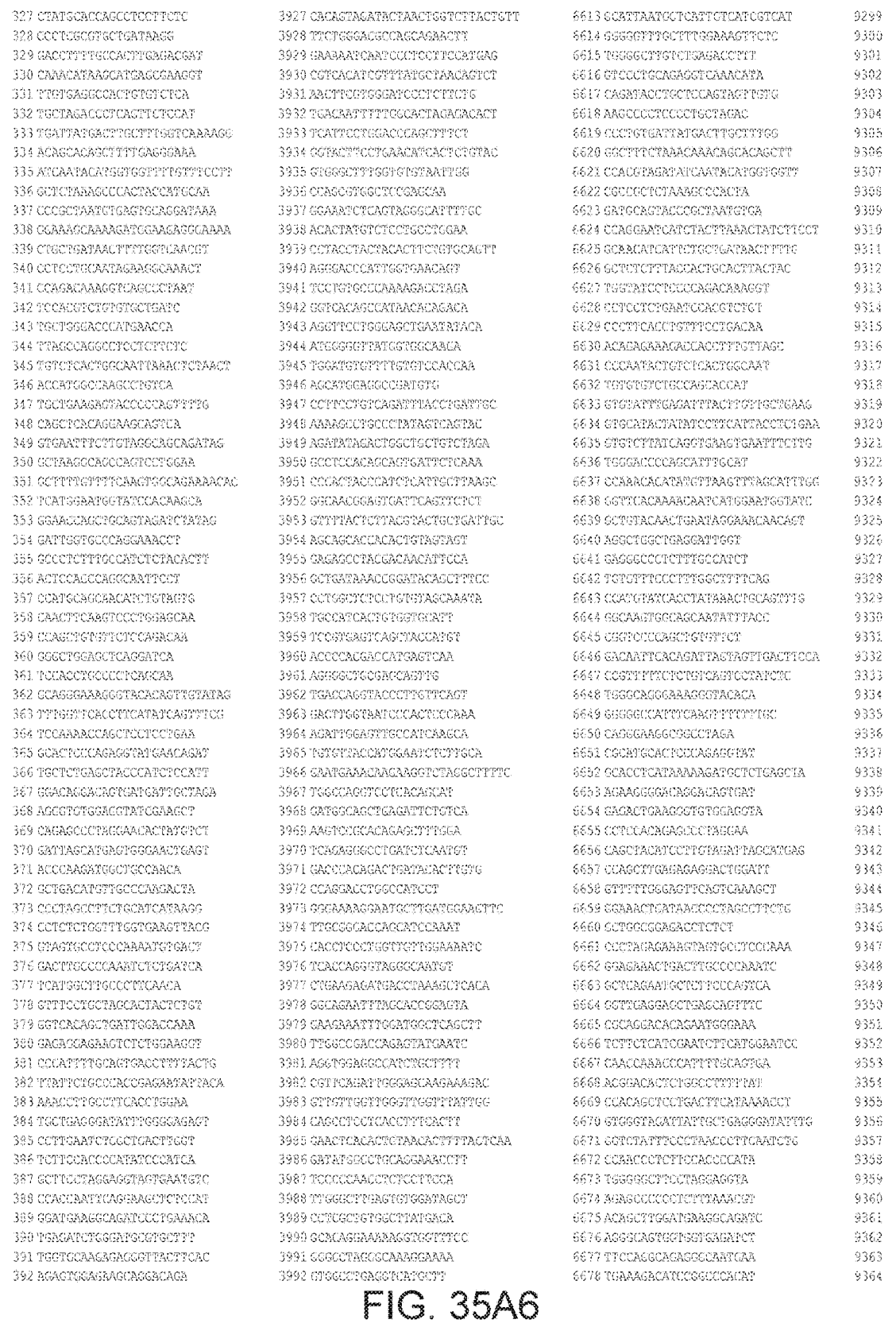
Figure 35A7:
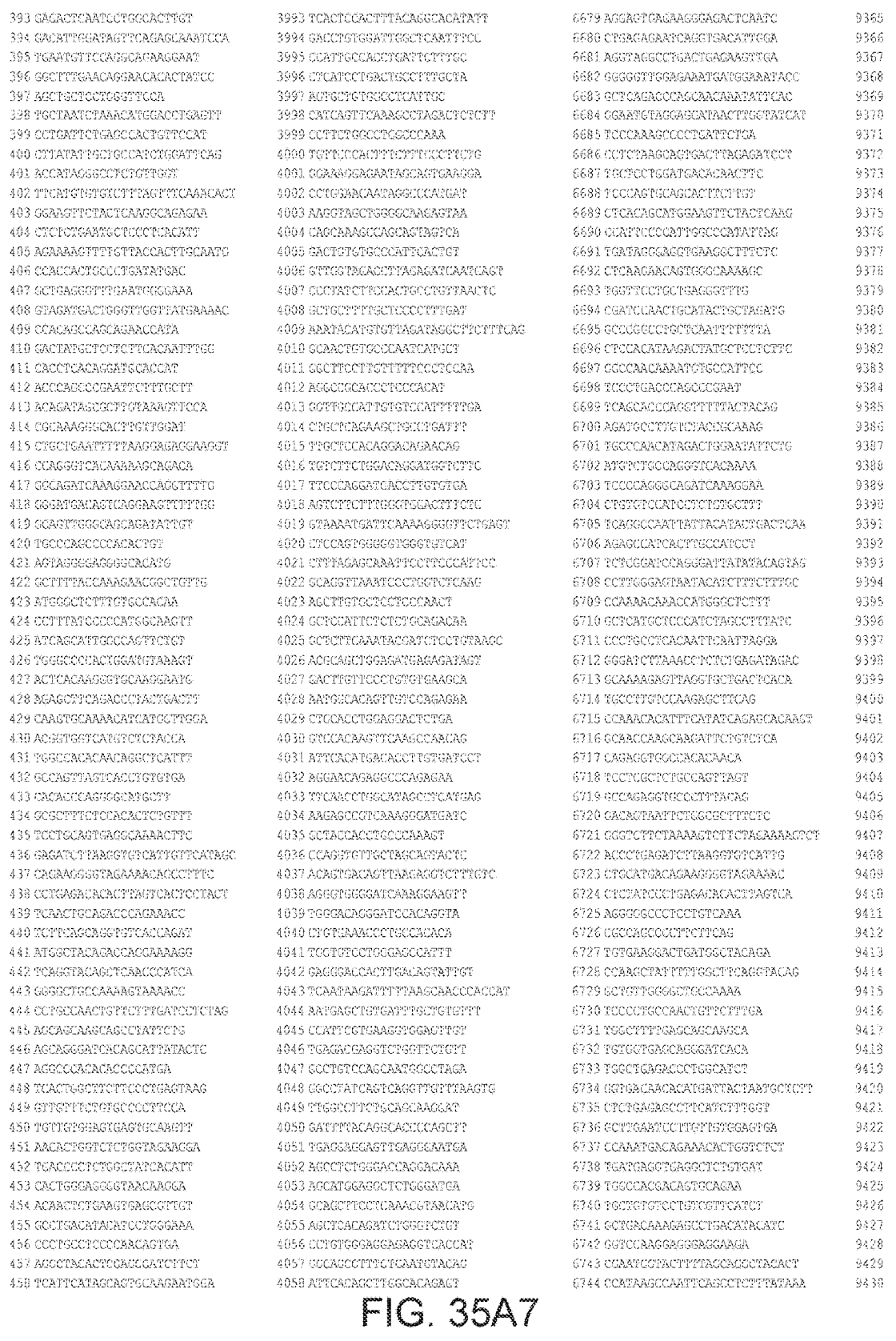
Figure 35A9:
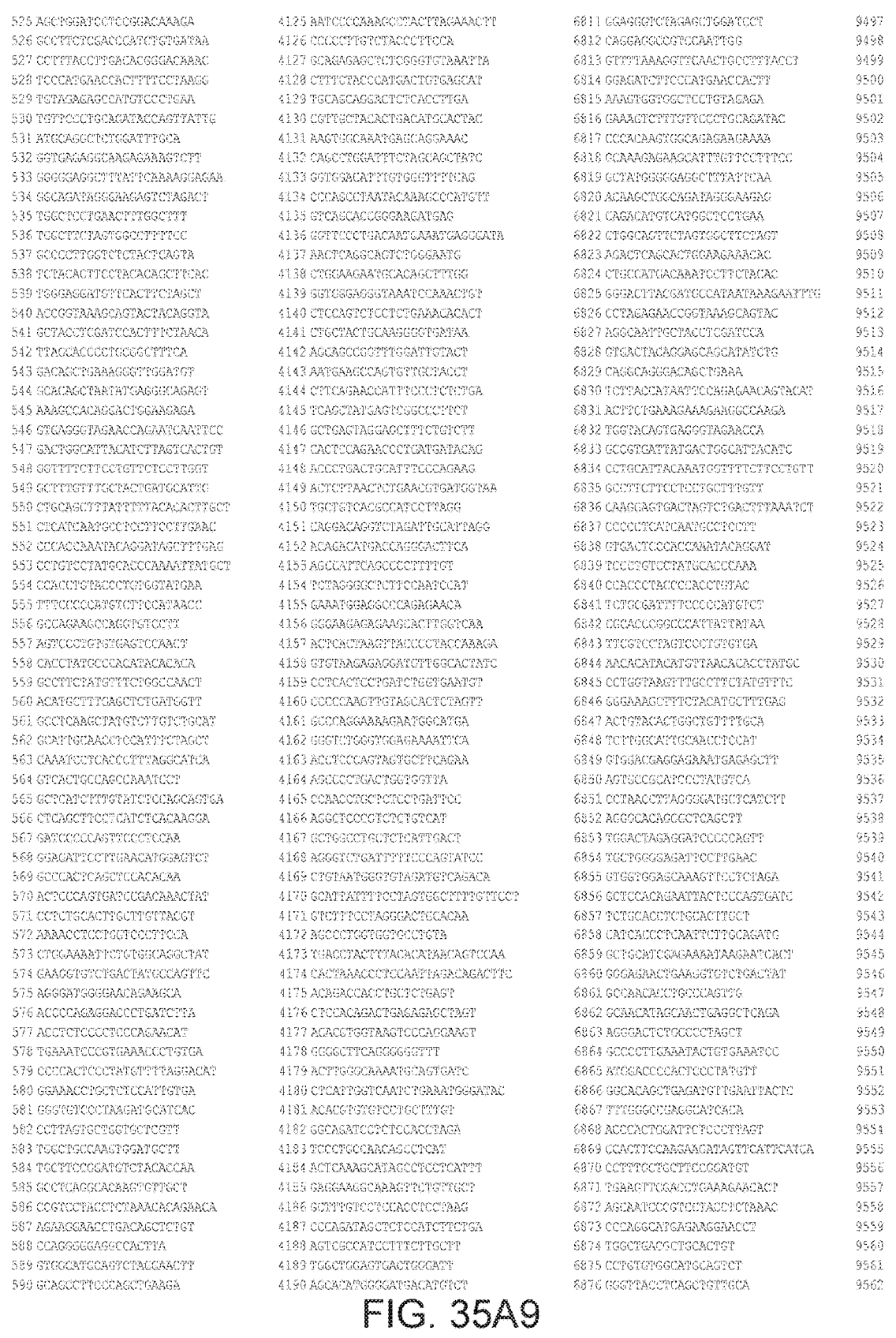
Figure 35A10:
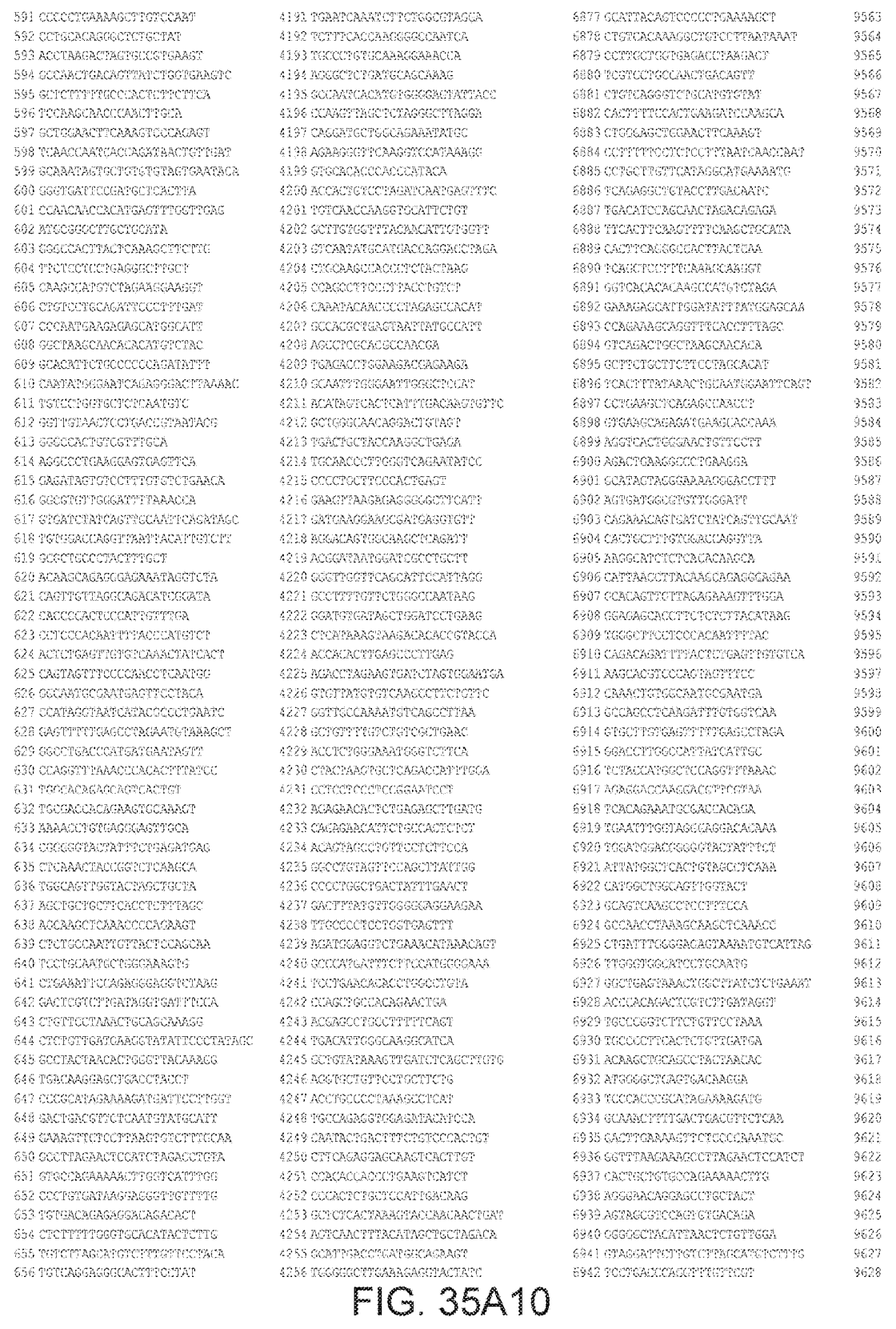
Figure 35B1:
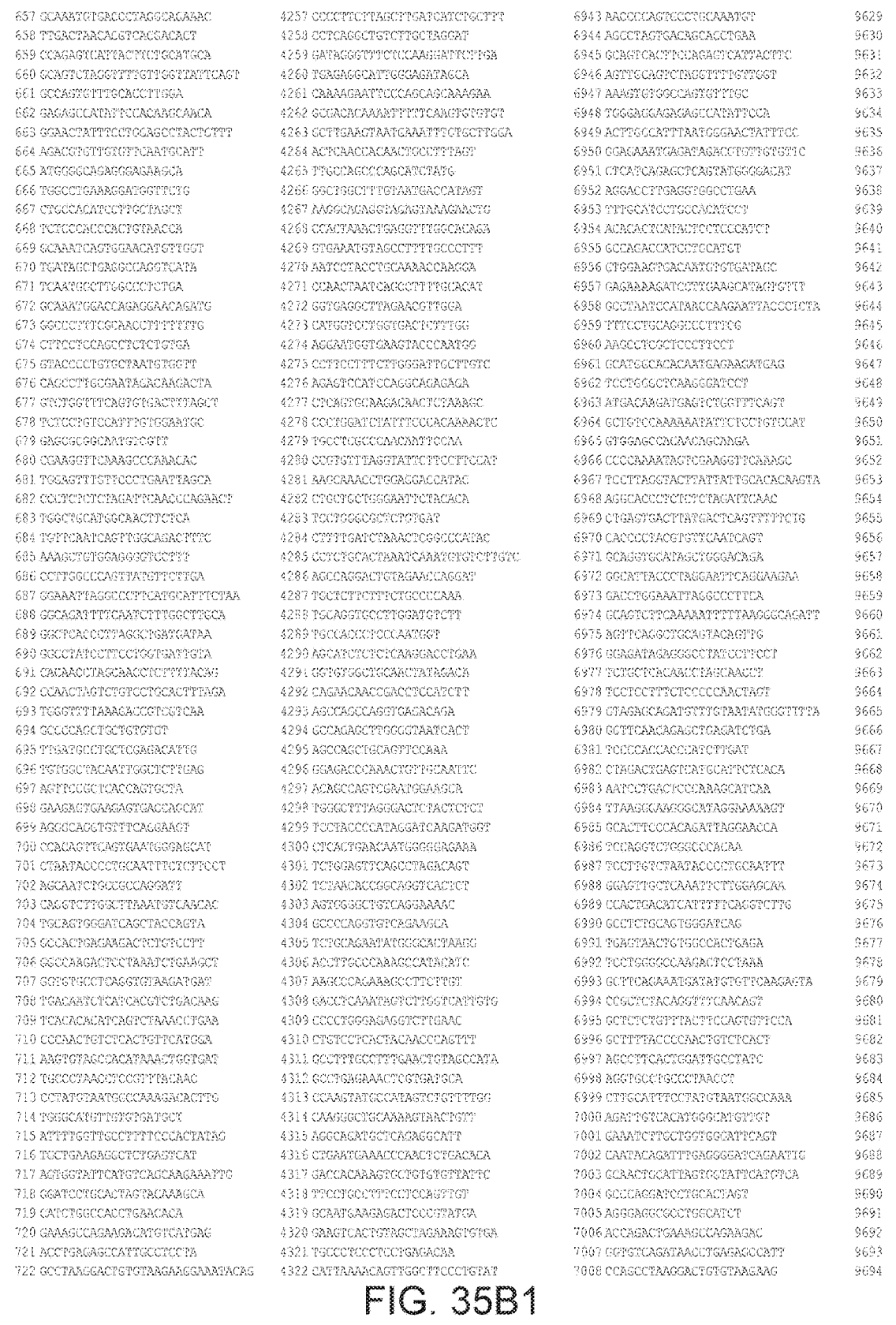
Figure 35B5:
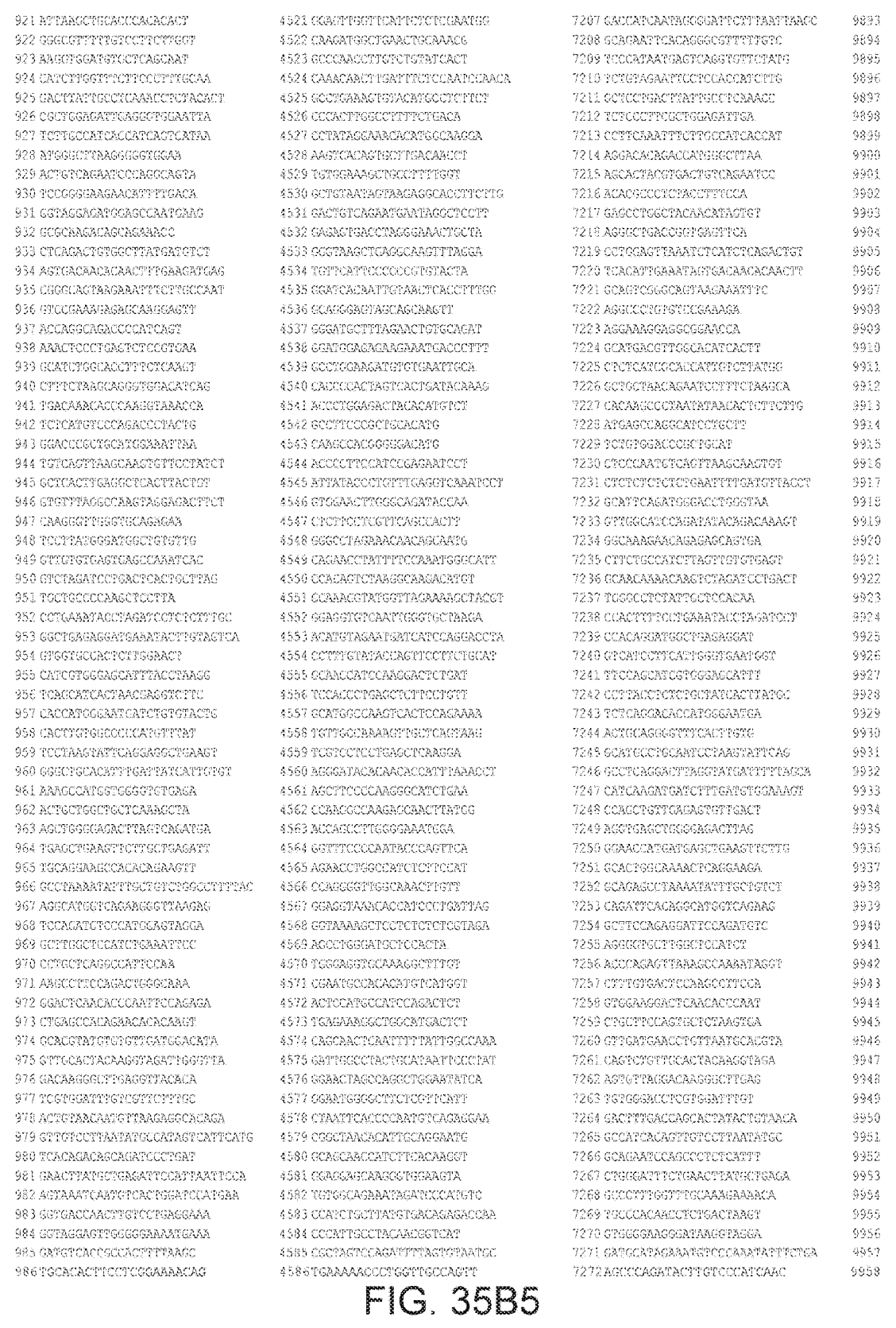
Figure 35C1:
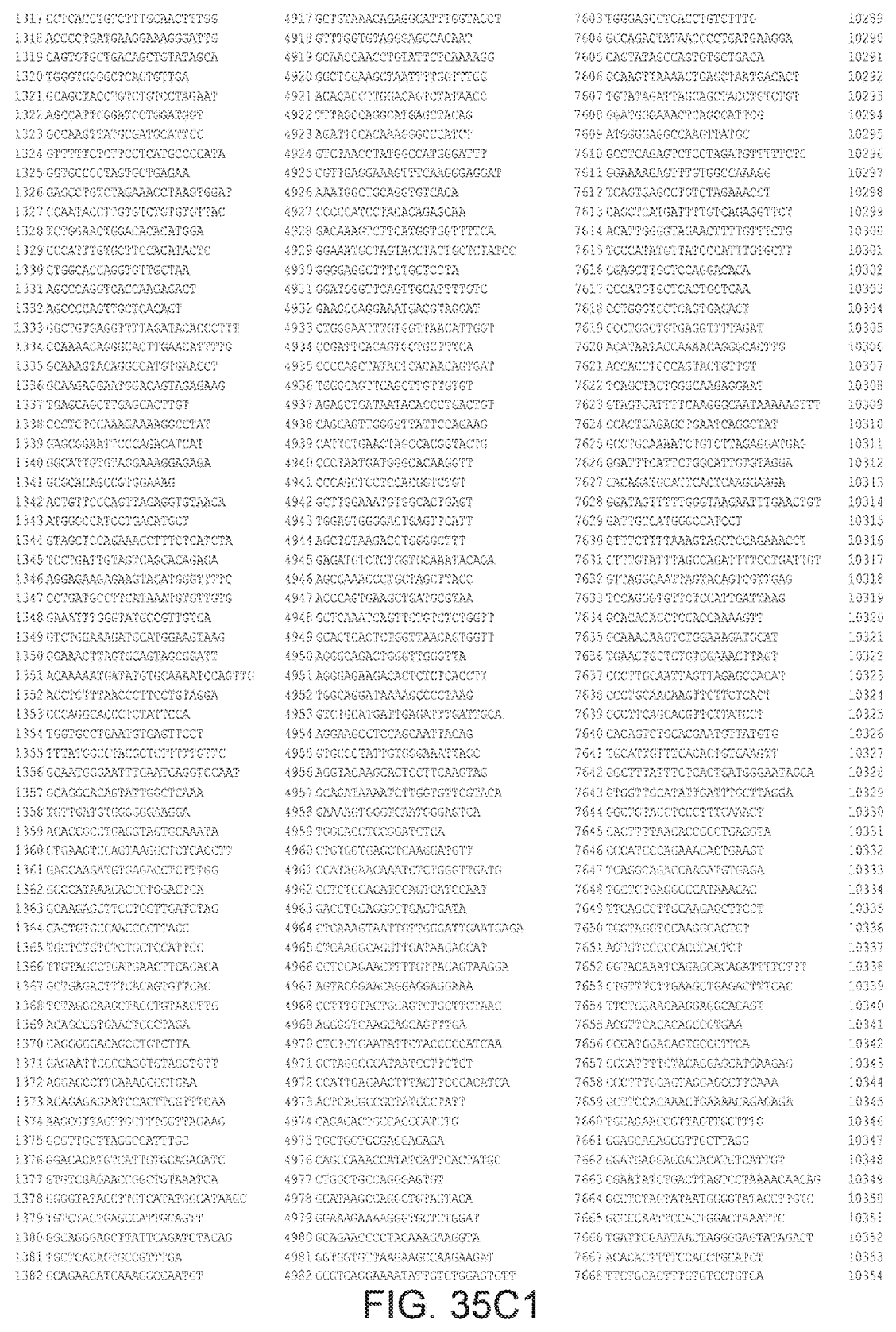
Figure 35C3:
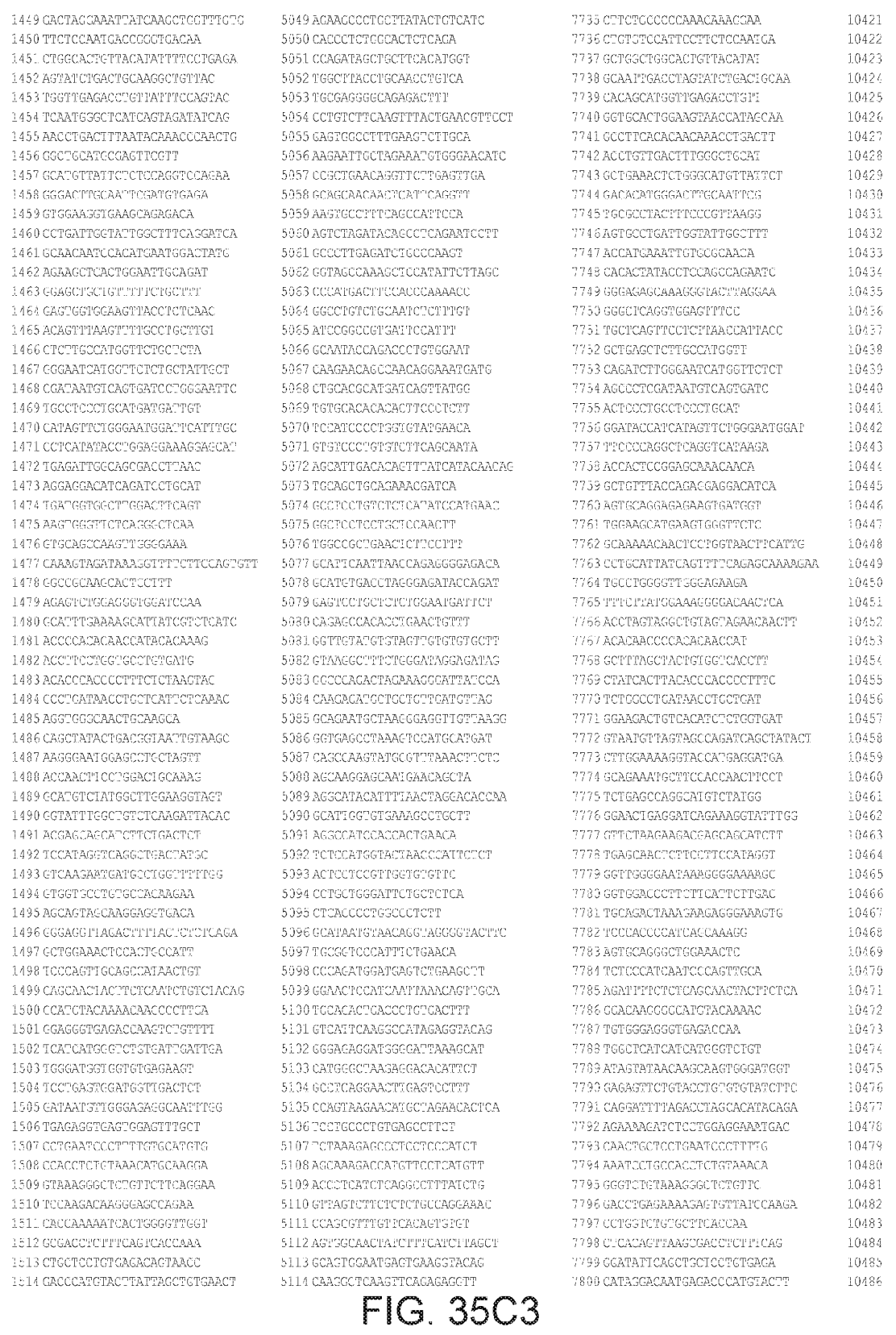
Figure 35C4:
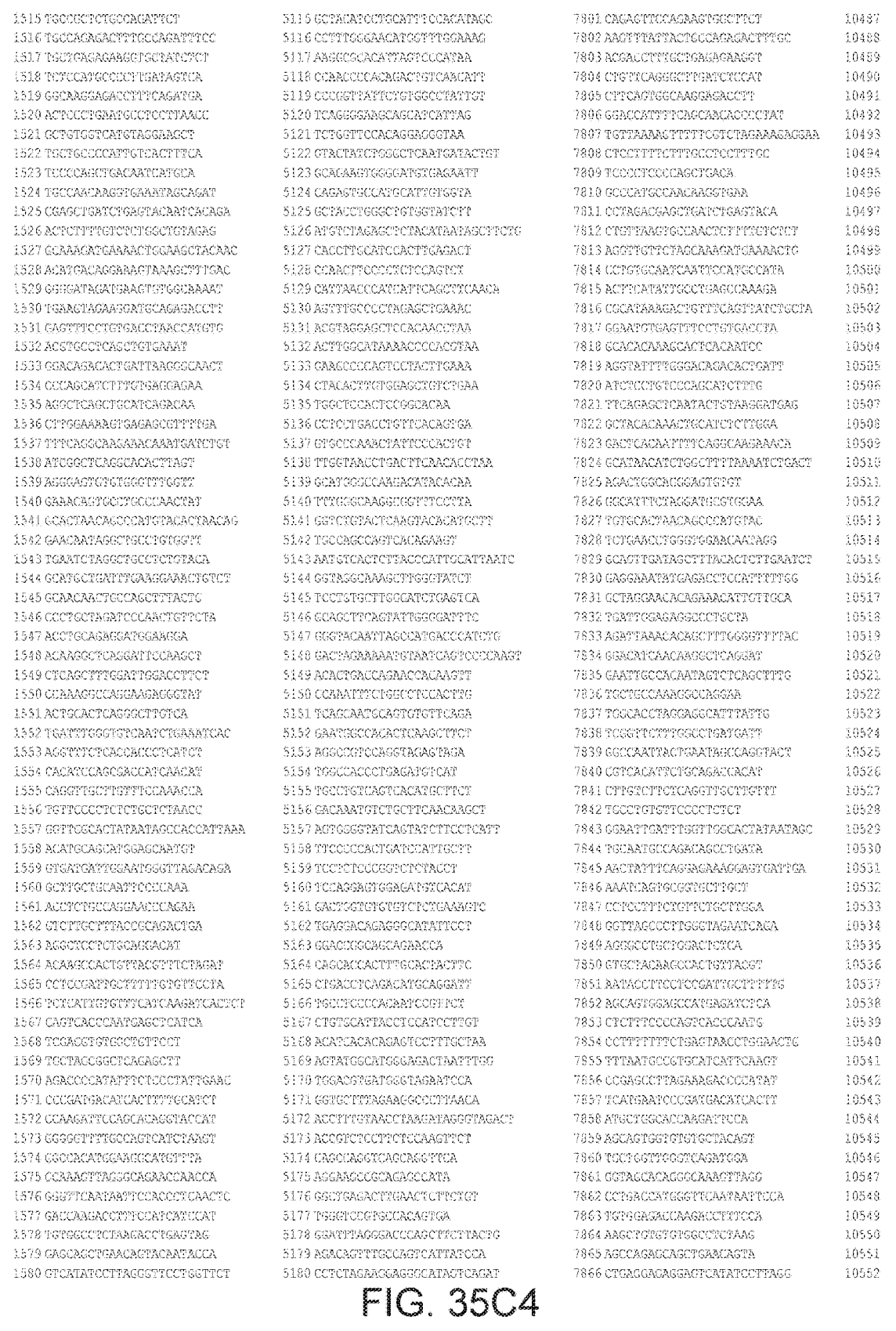
Figure 35C8:
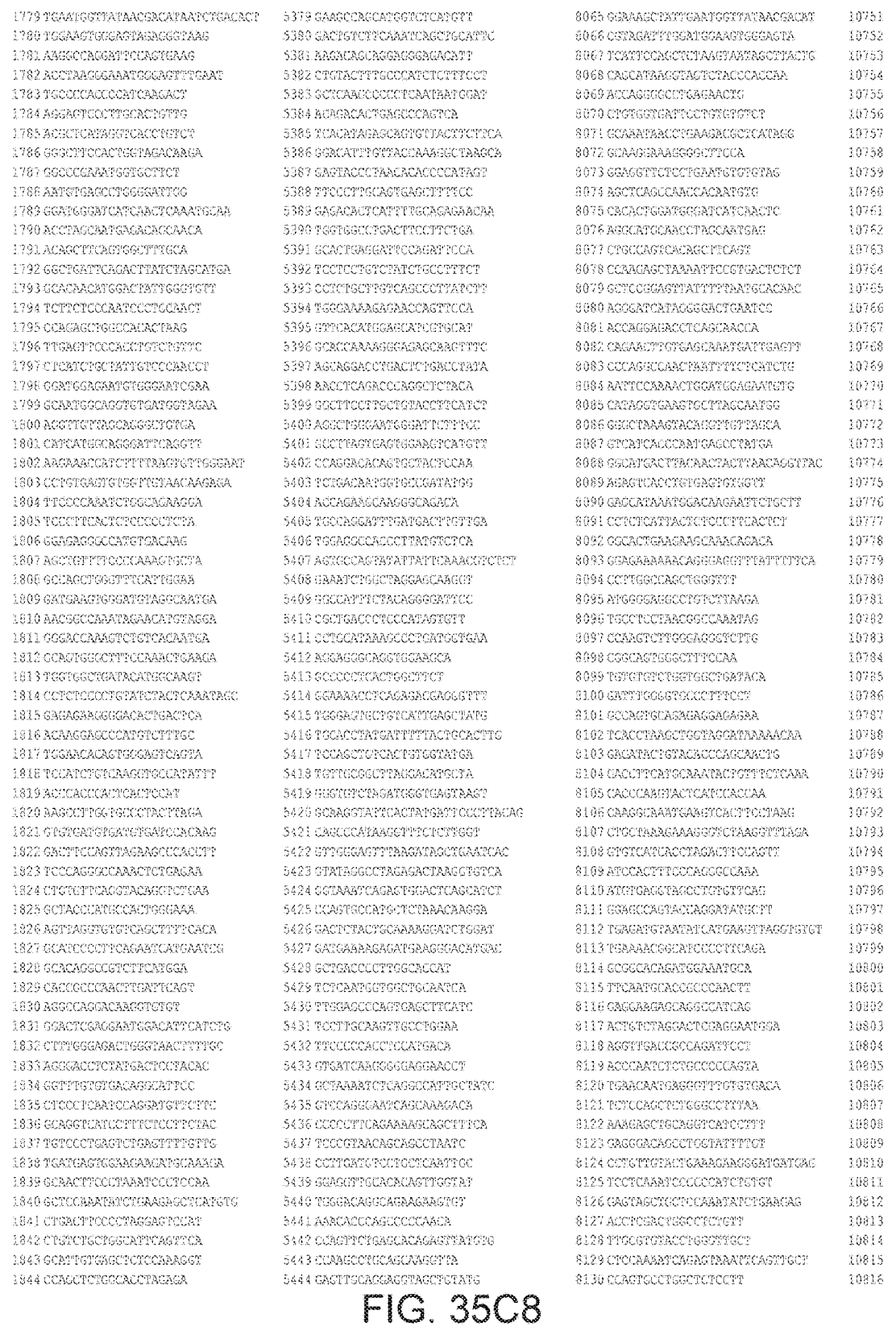
Figure 35D3:
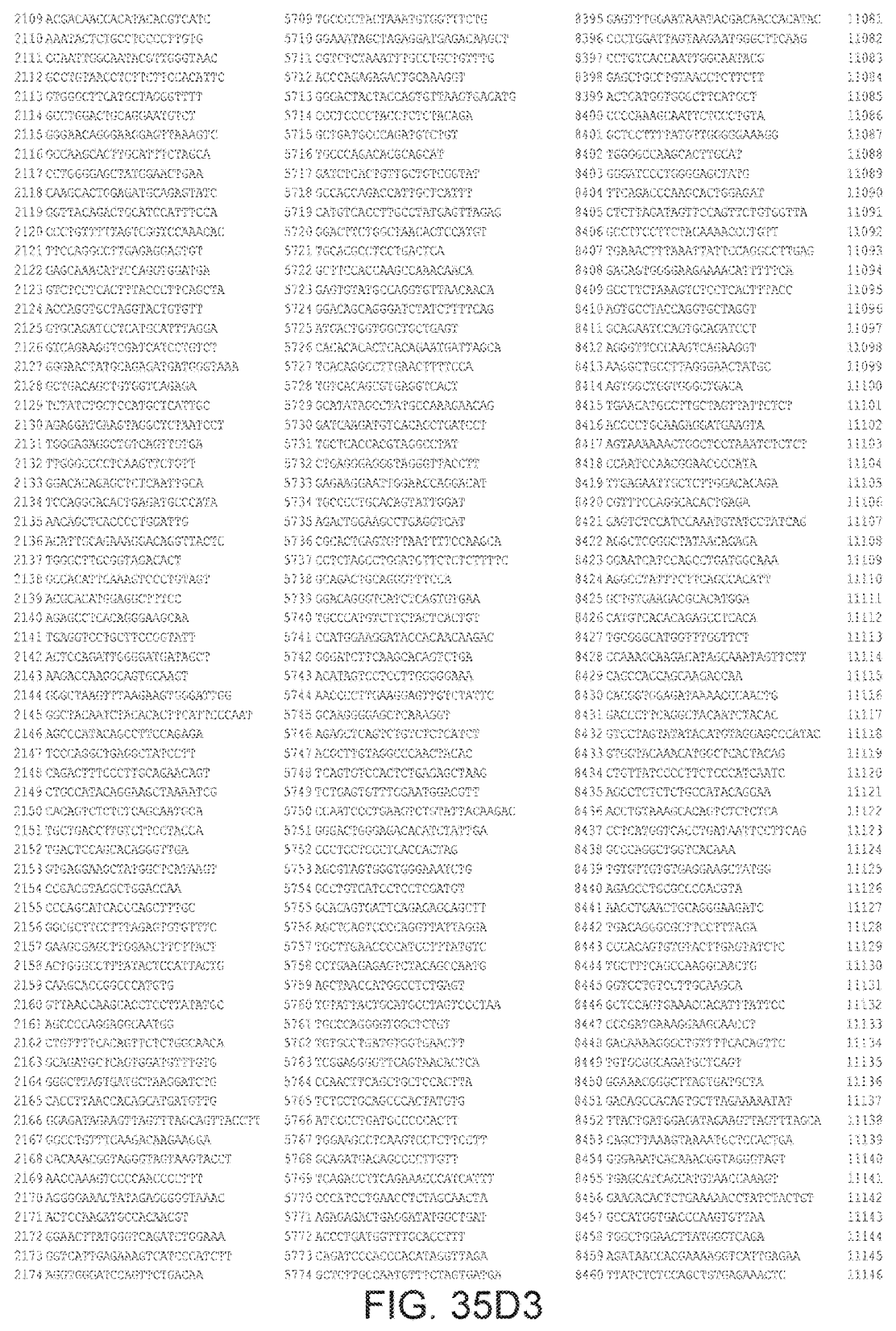
Figure 35D6:
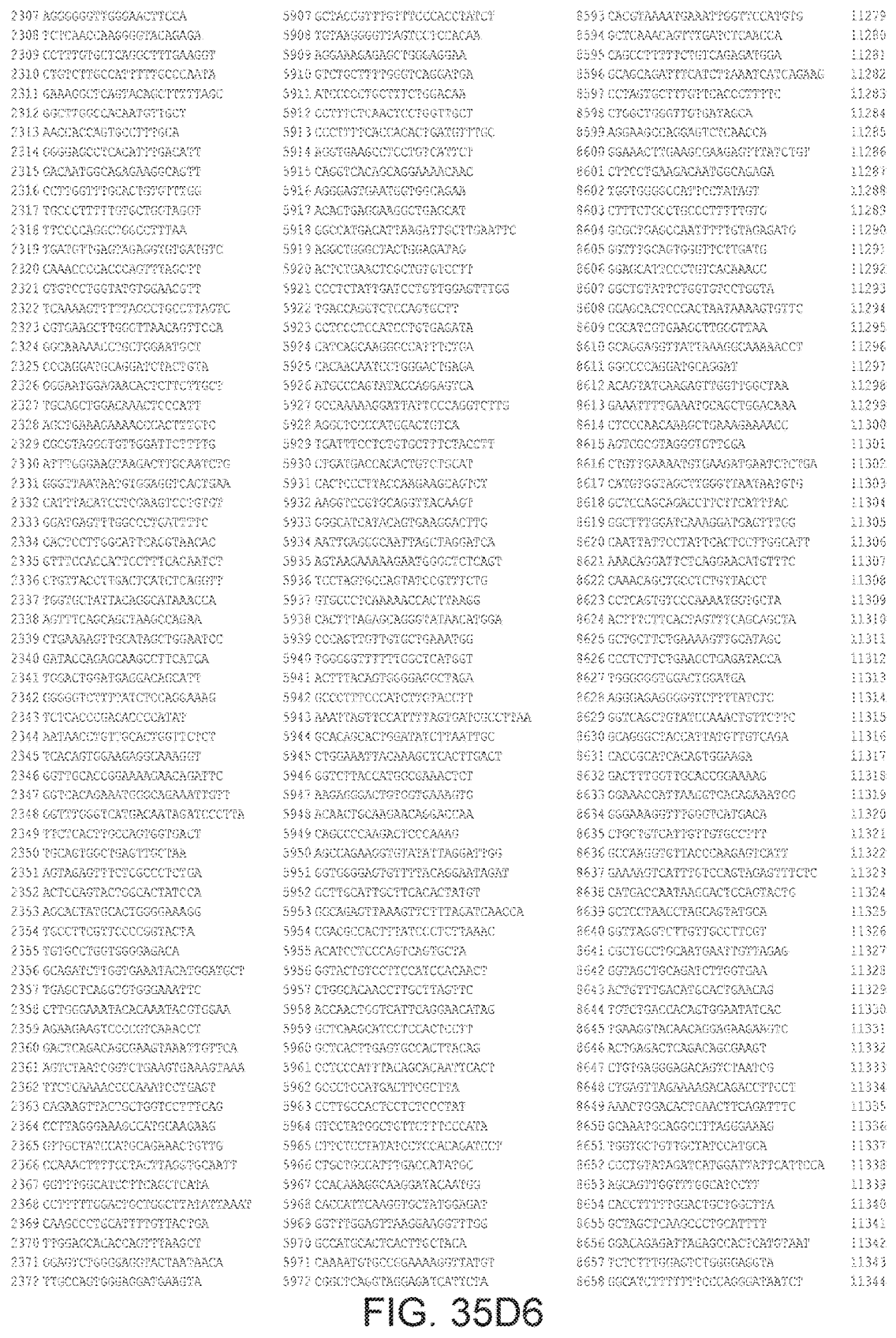

FIG. 35A1-E1: Sequences of an exemplary 2,686-plex primer library (SEQ ID NOs. 3,601-11,658). The three primers (one from pool A, one from pool B, and one from pool C) in each row all hybridize to the same target locus.

Figure 36A2:
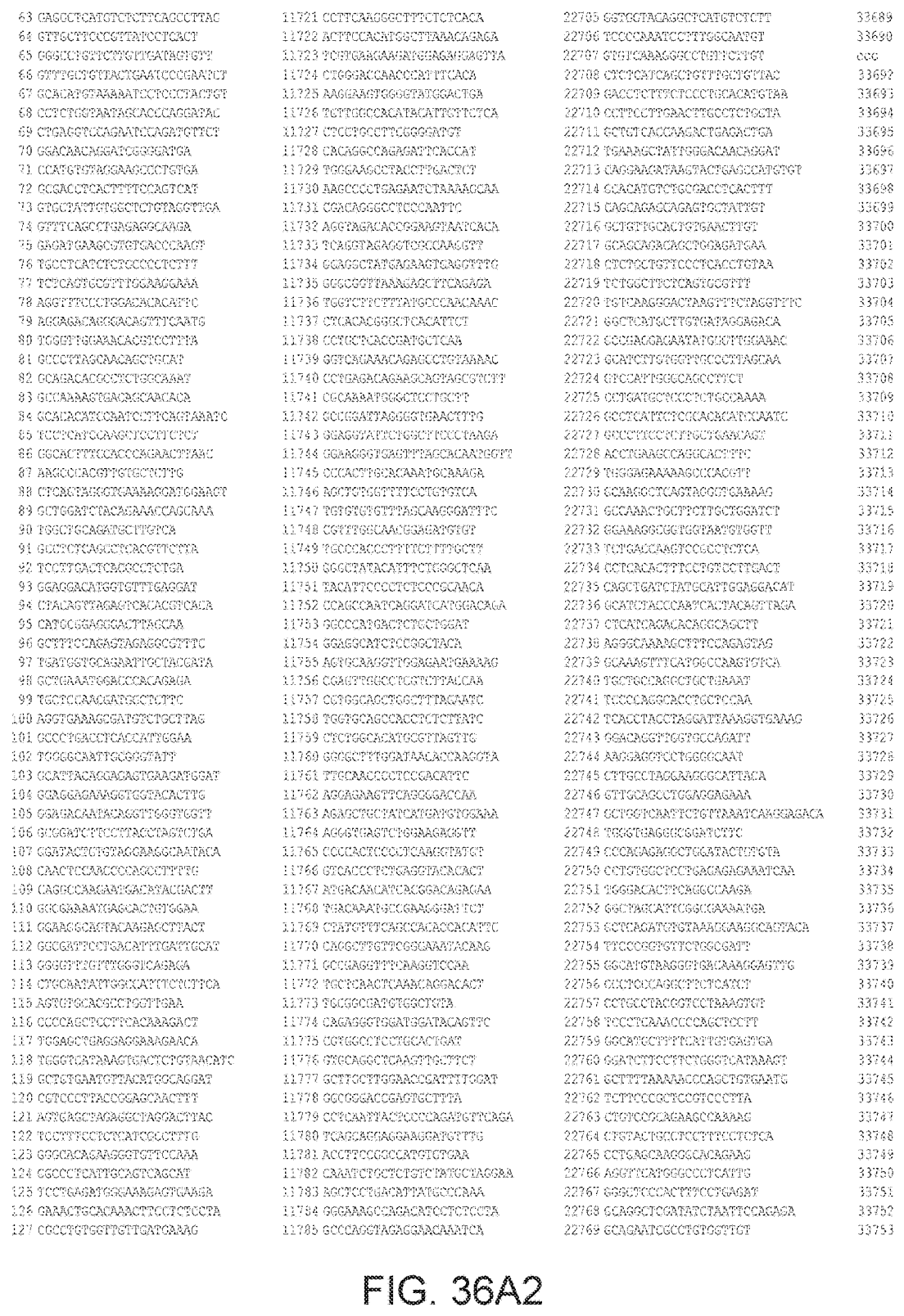
Figure 36A3:
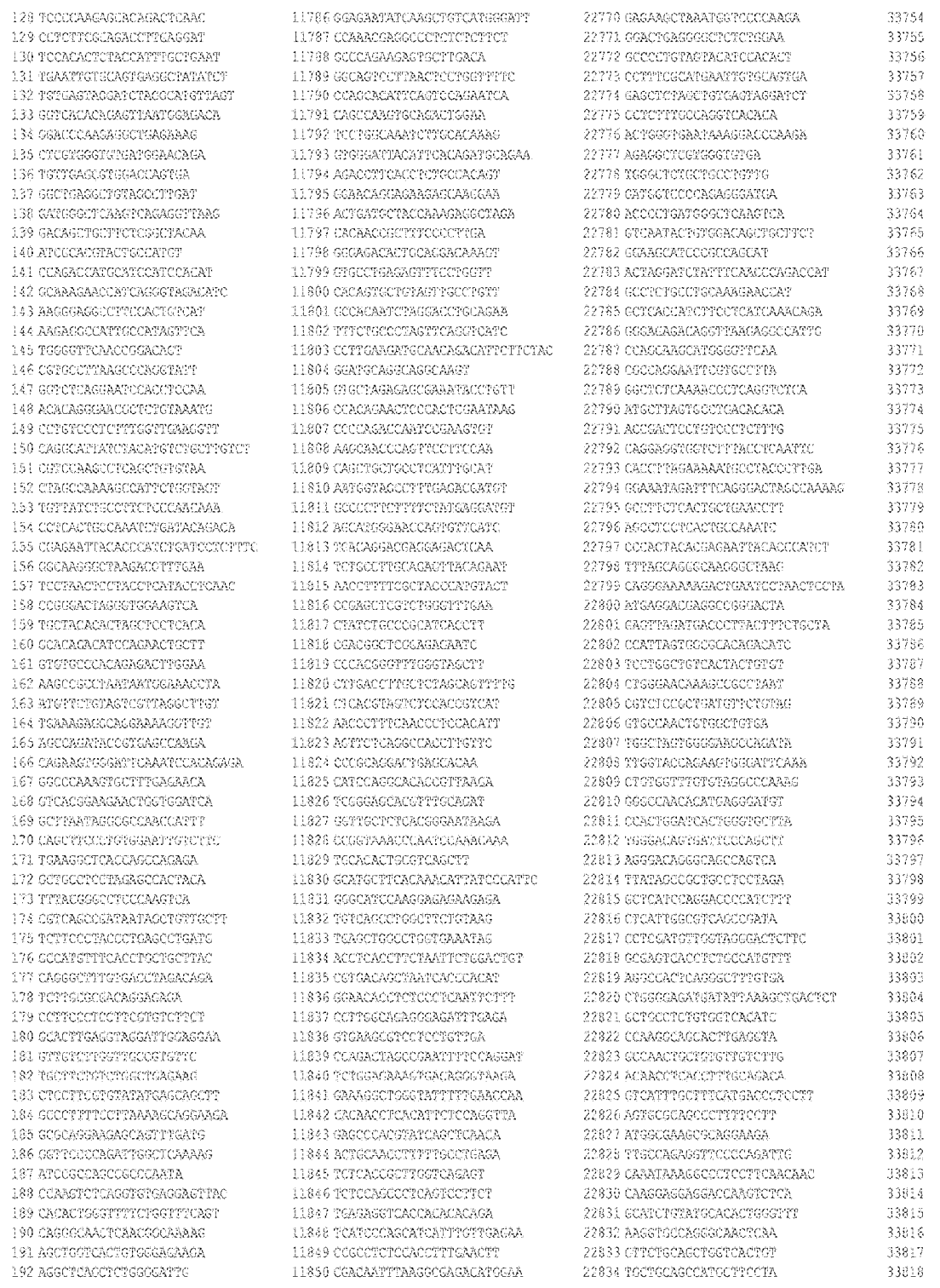
Figure 36A4:
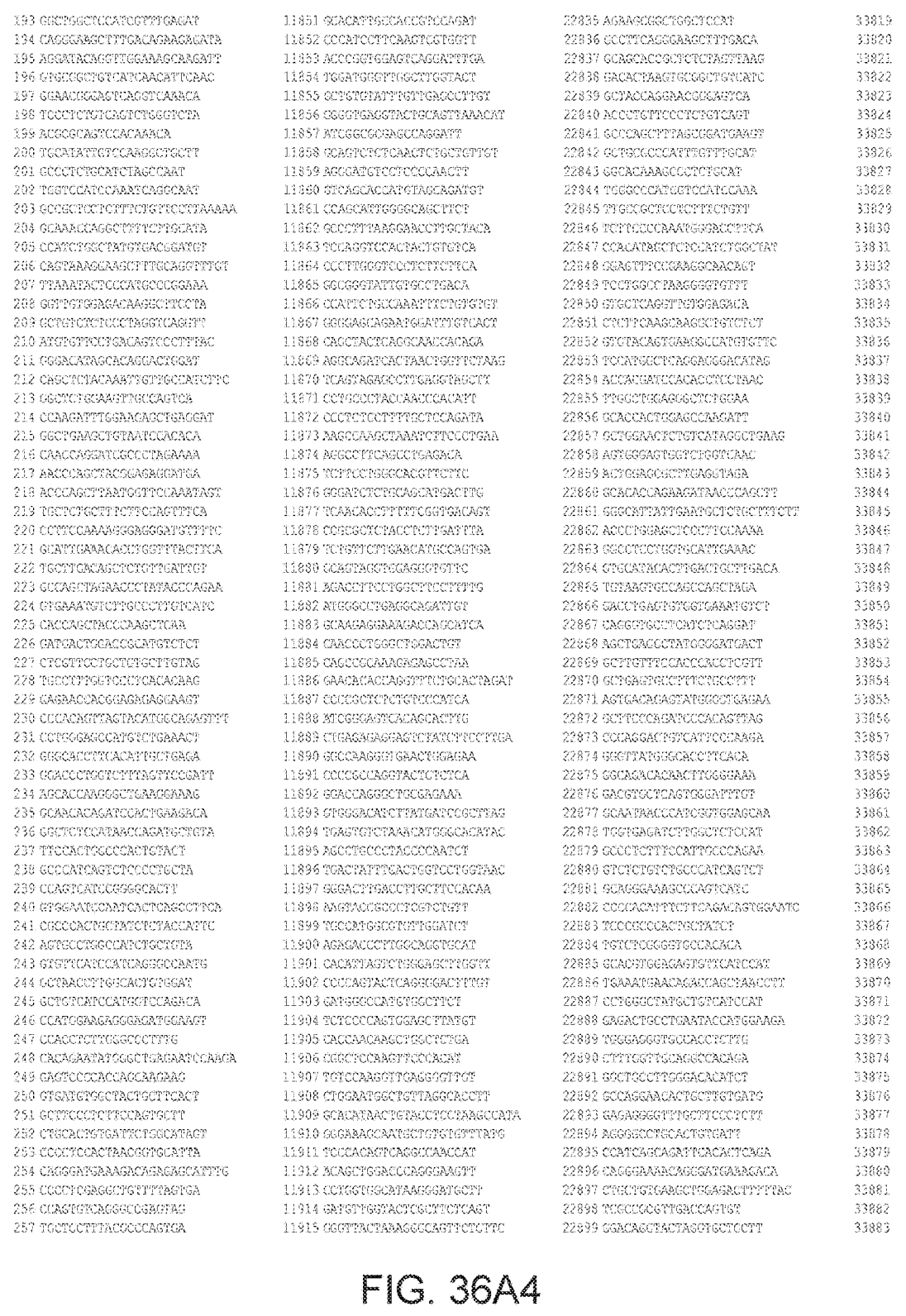
Figure 36A6:
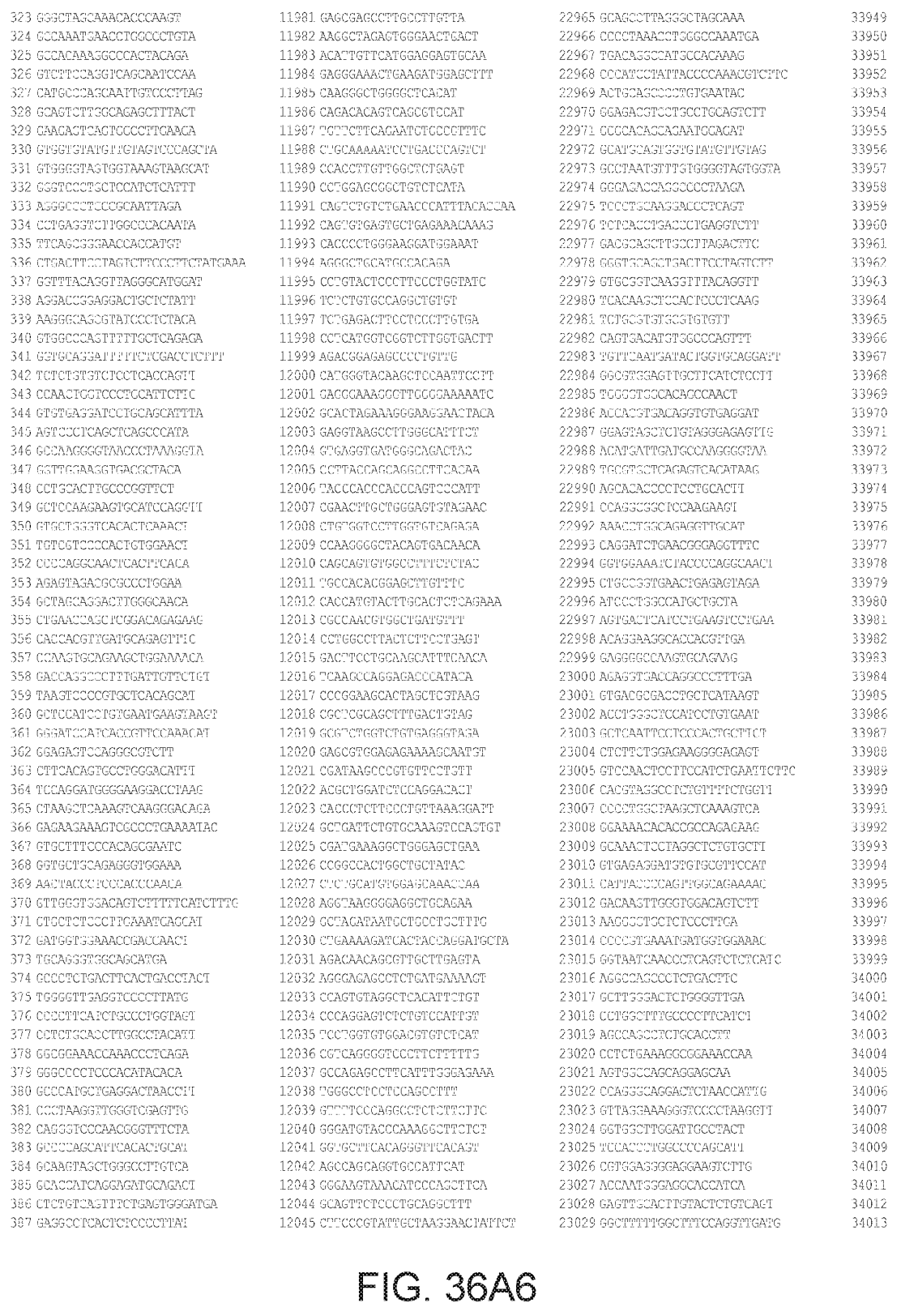
Figure 36A8:
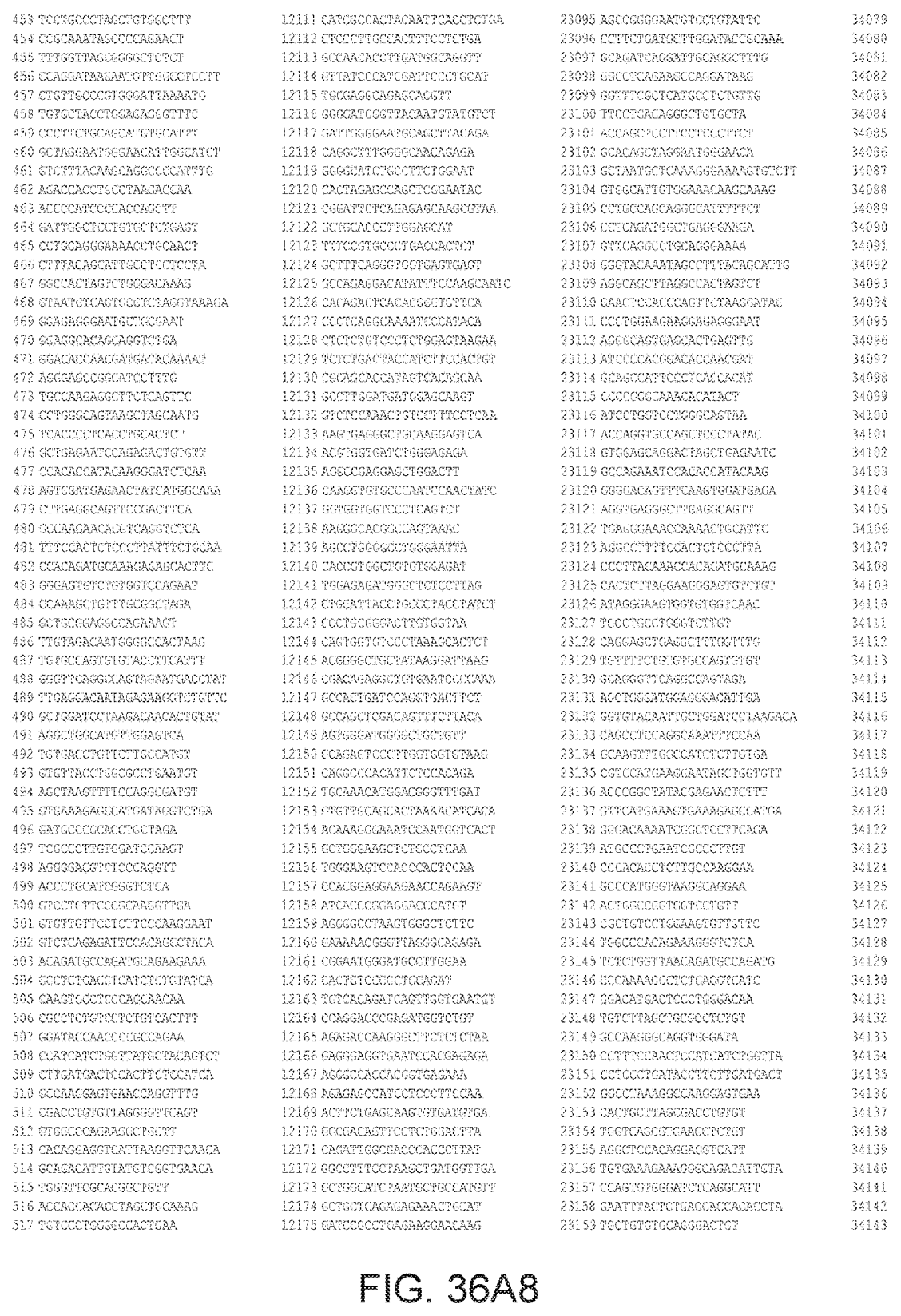
Figure 36A9:
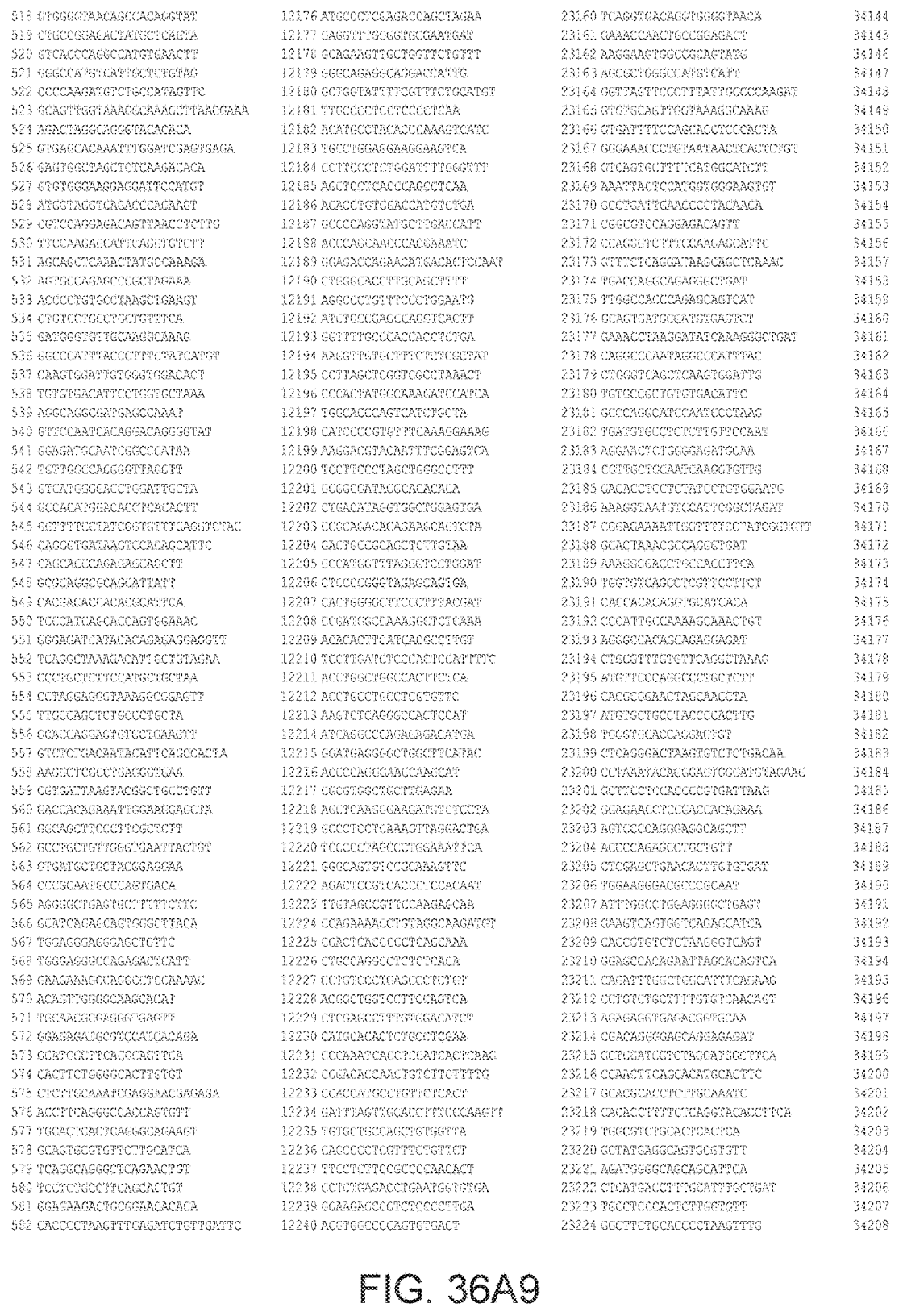
Figure 36A10:
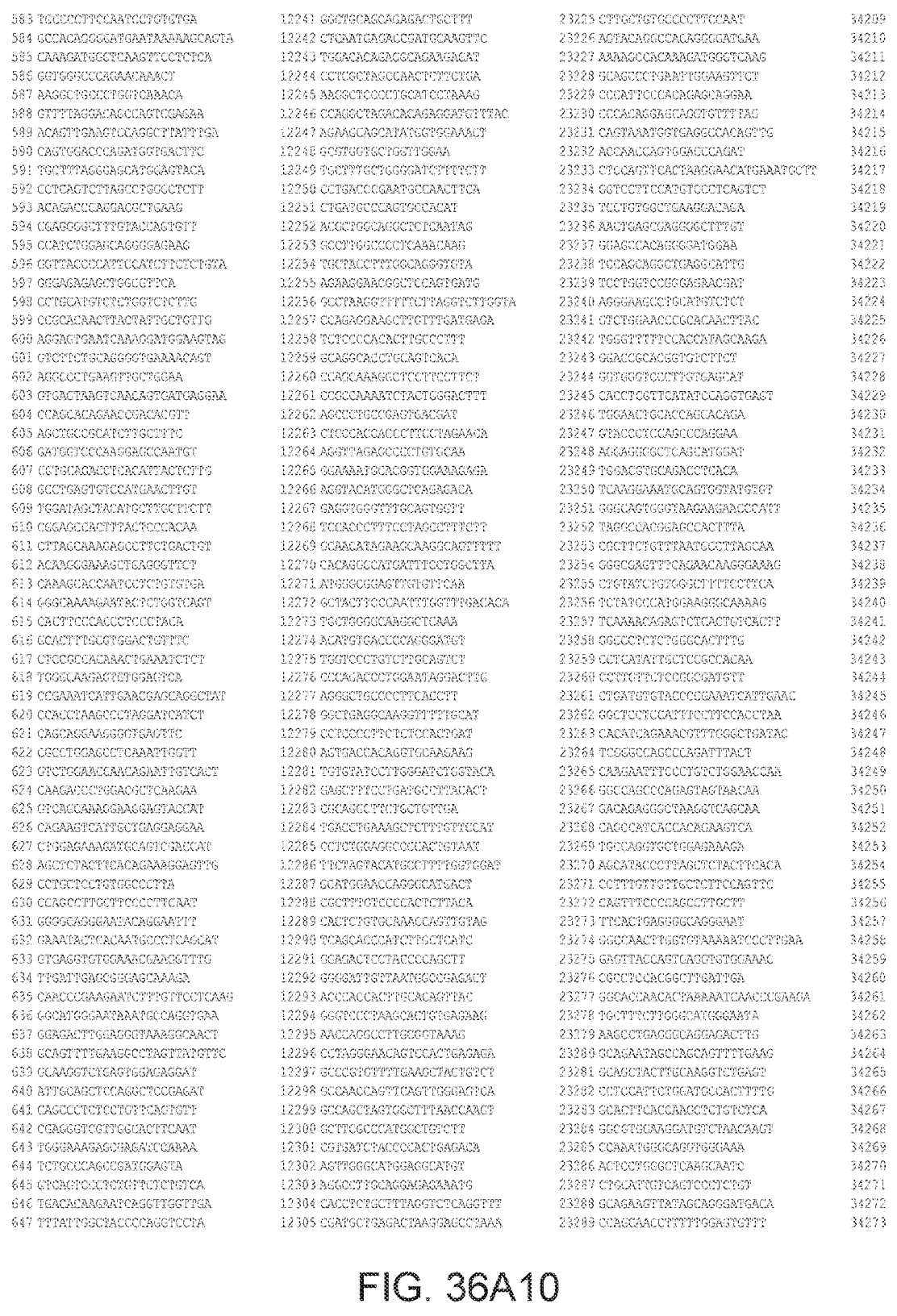
Figure 36B1:
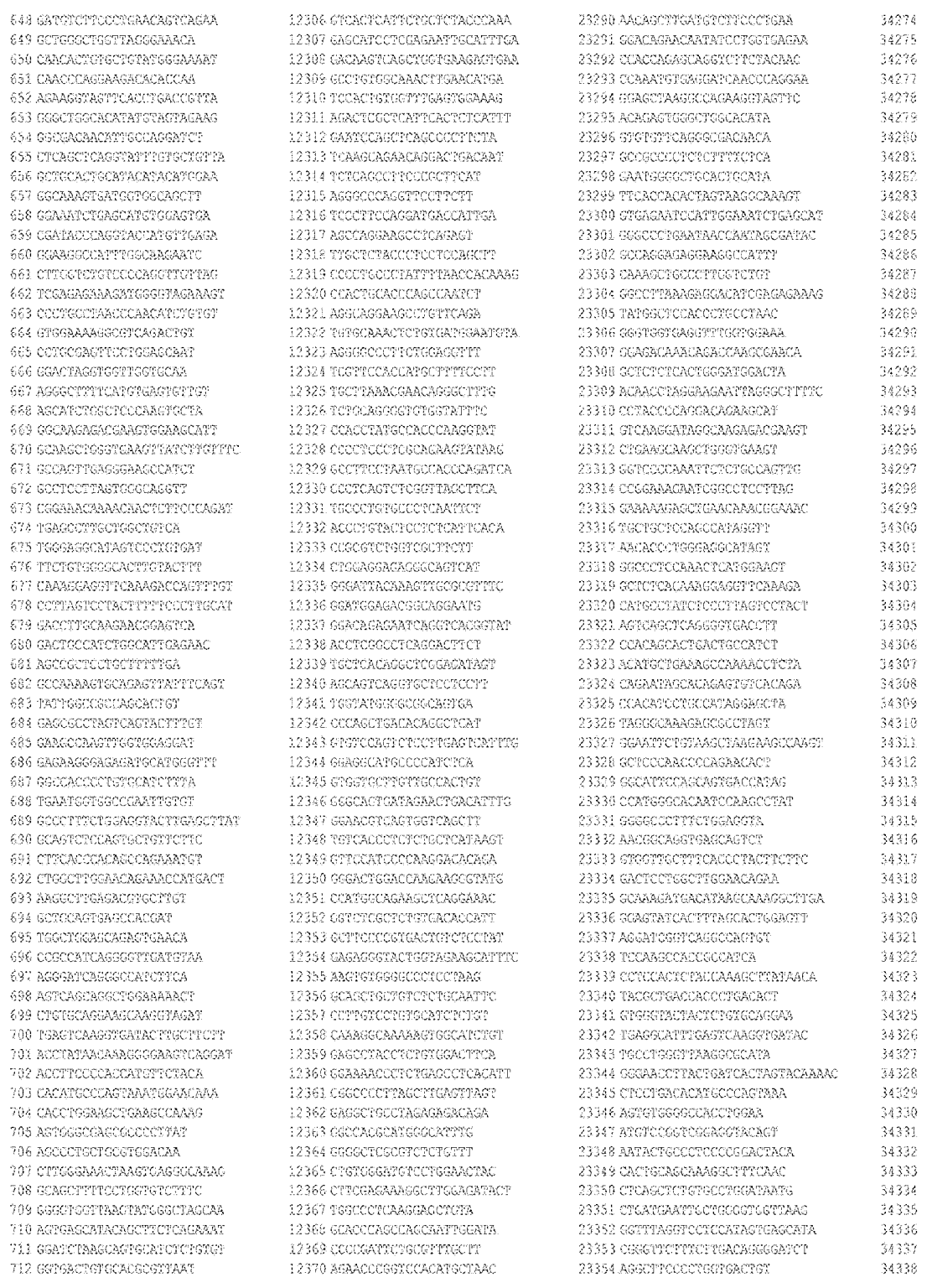
Figure 36B3:
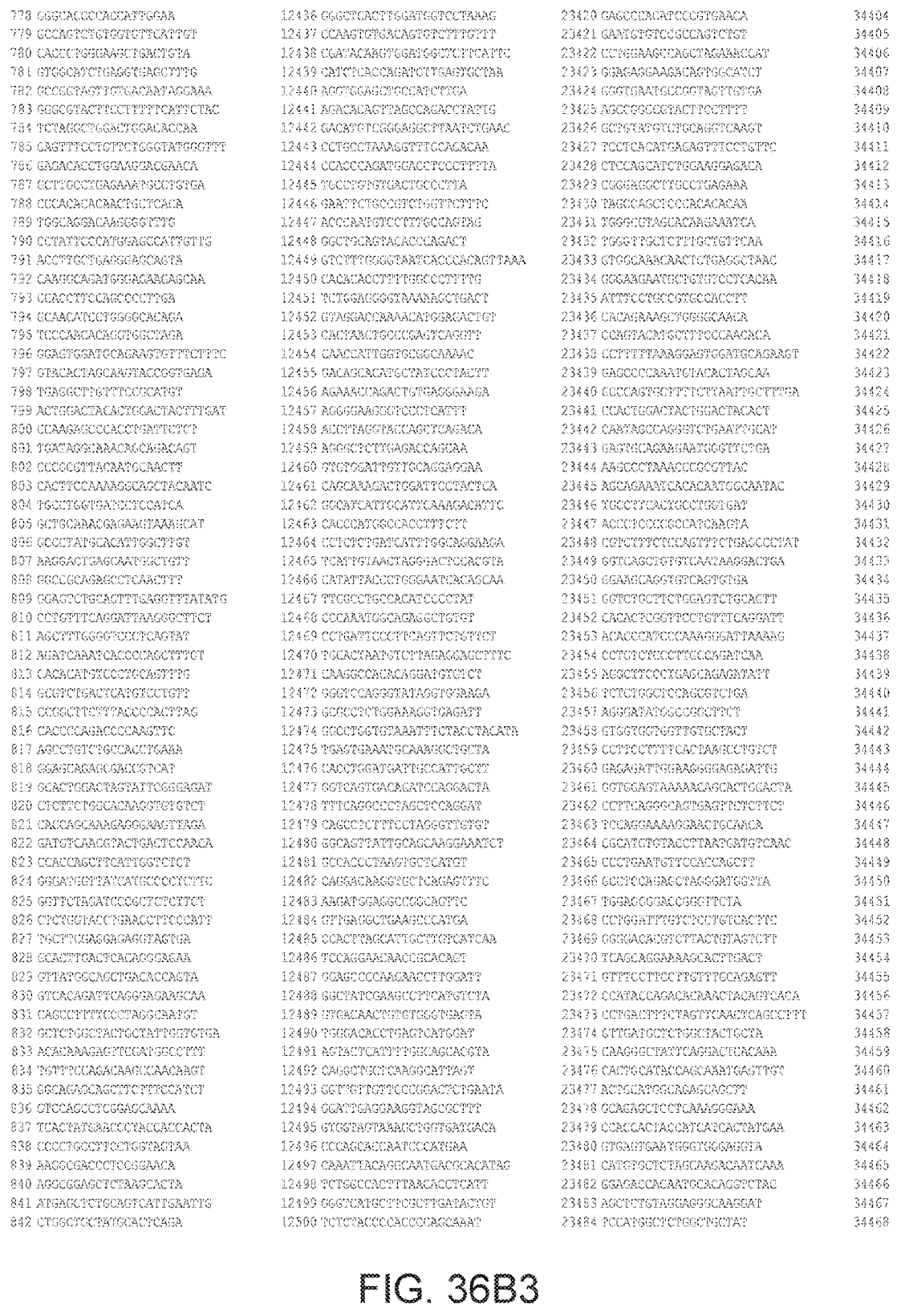
Figure 36B4:
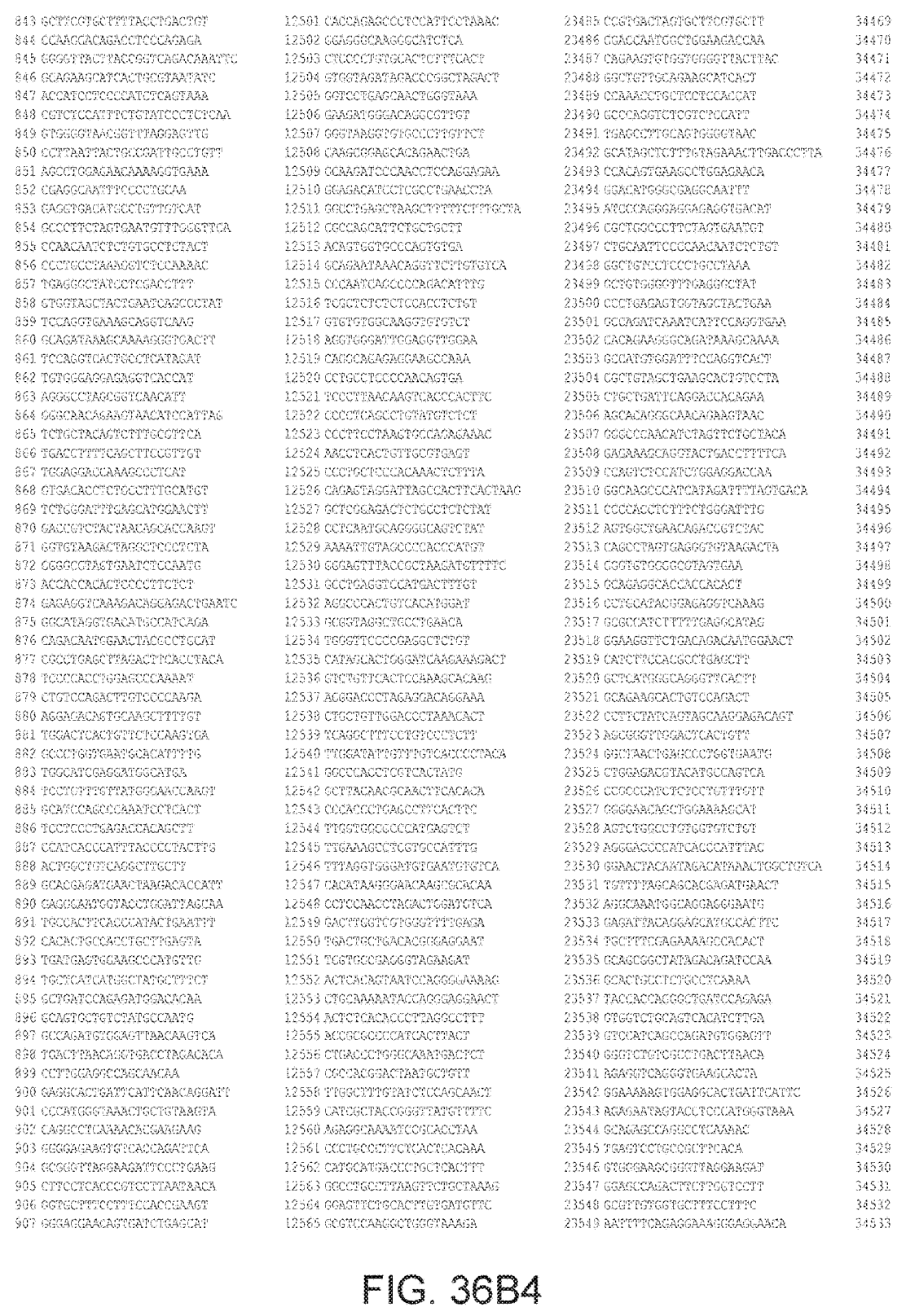
Figure 36B5:
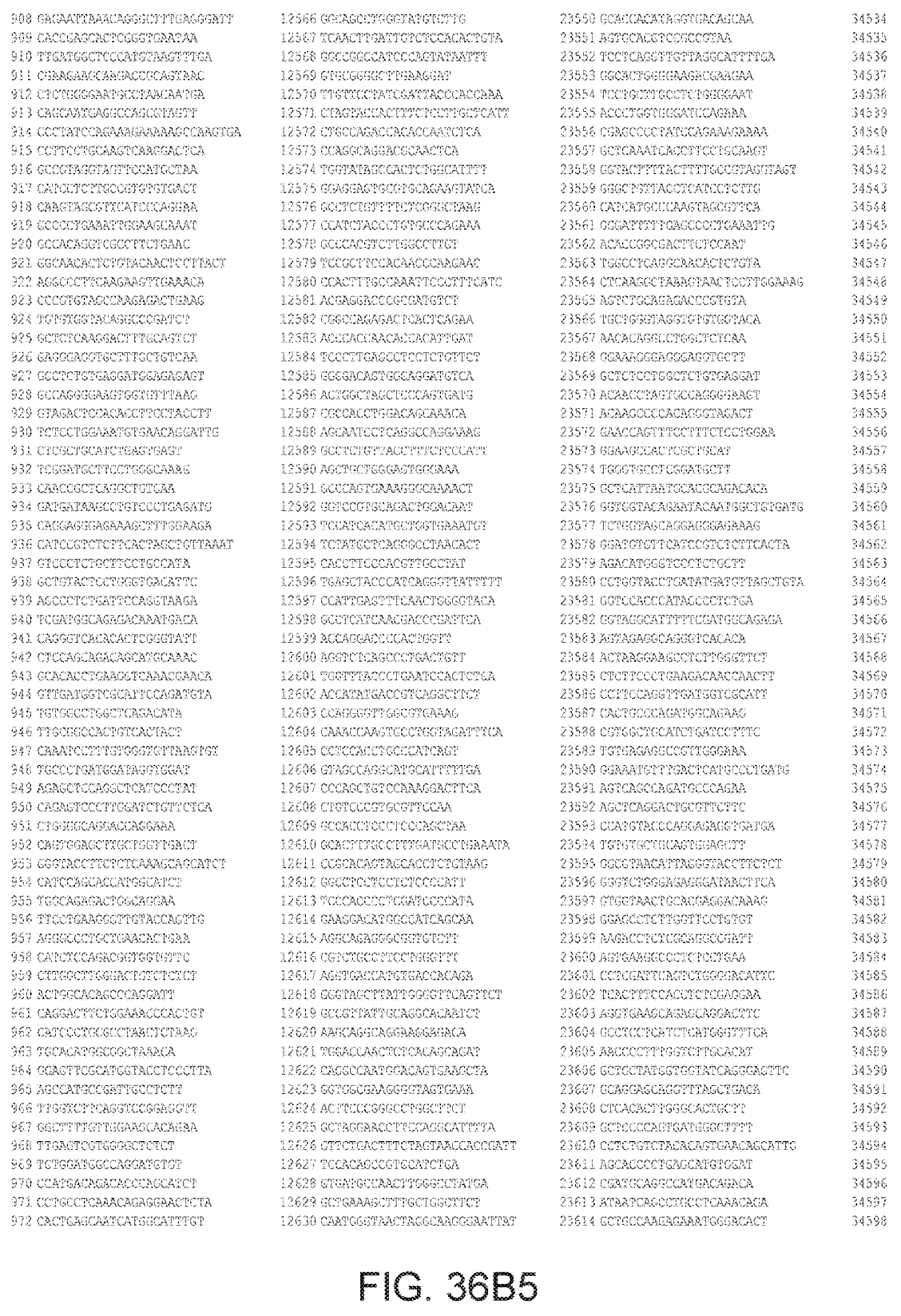
Figure 36B6:
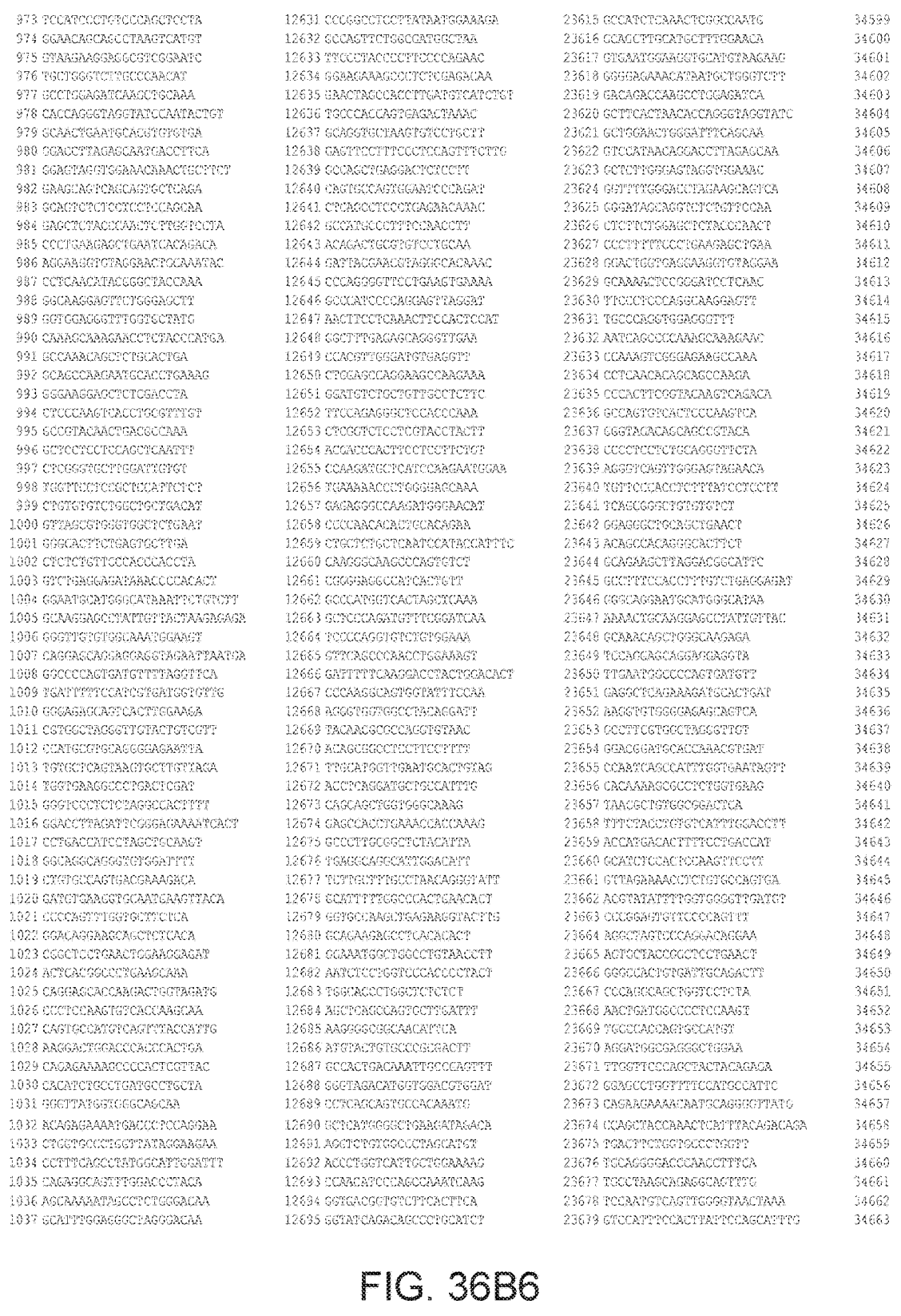
Figure 36B7:
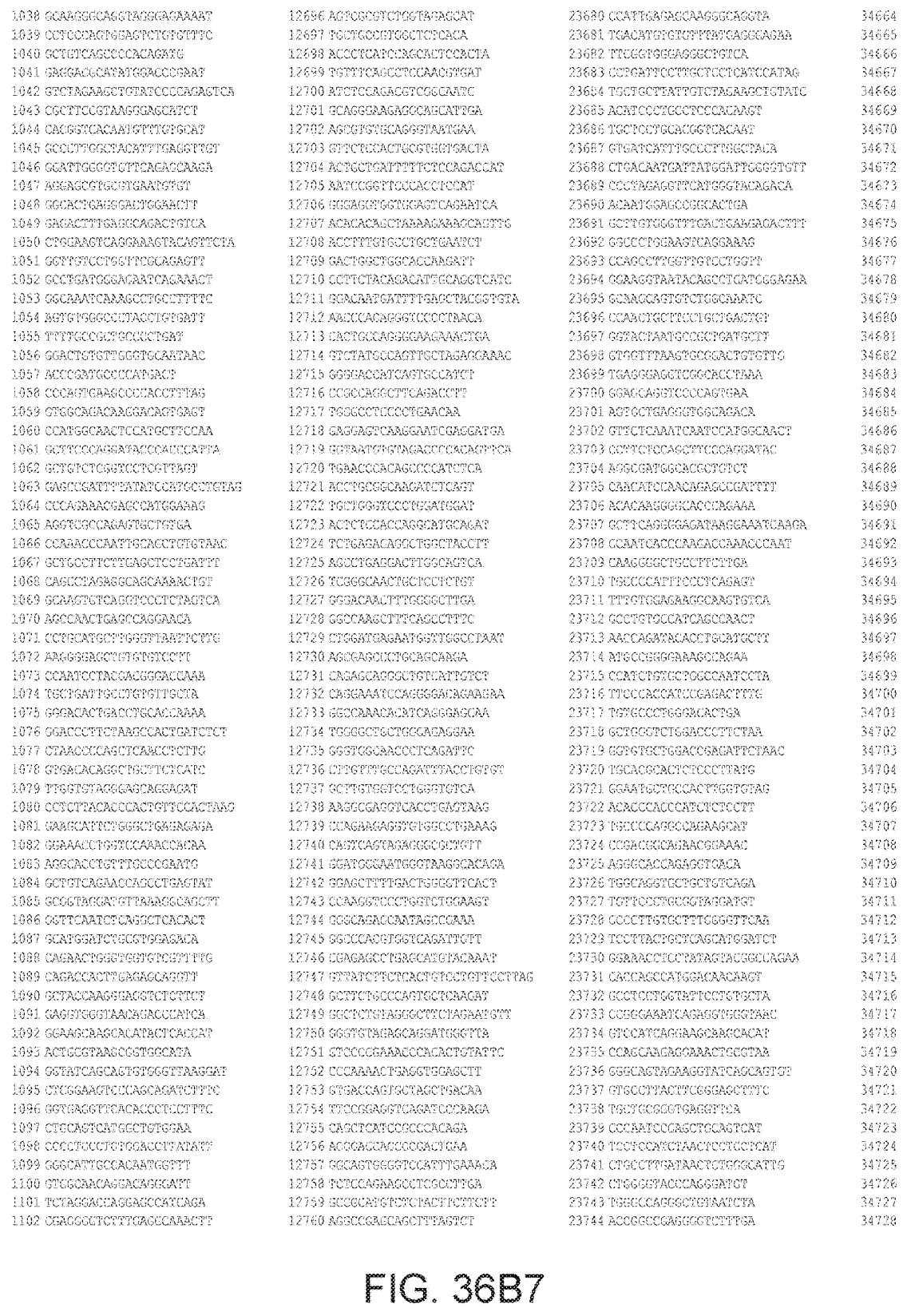
Figure 36B8:
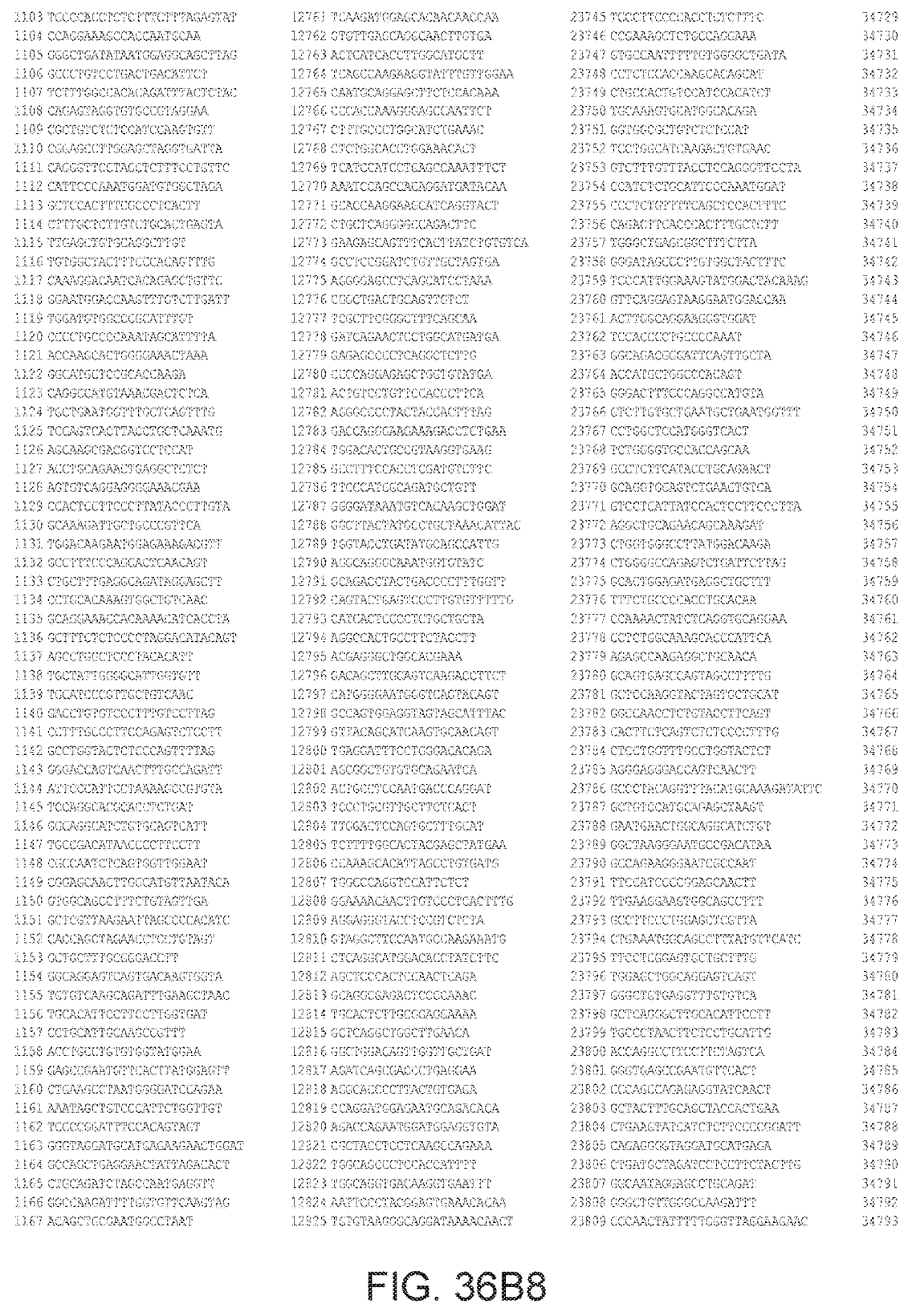
Figure 36B10:
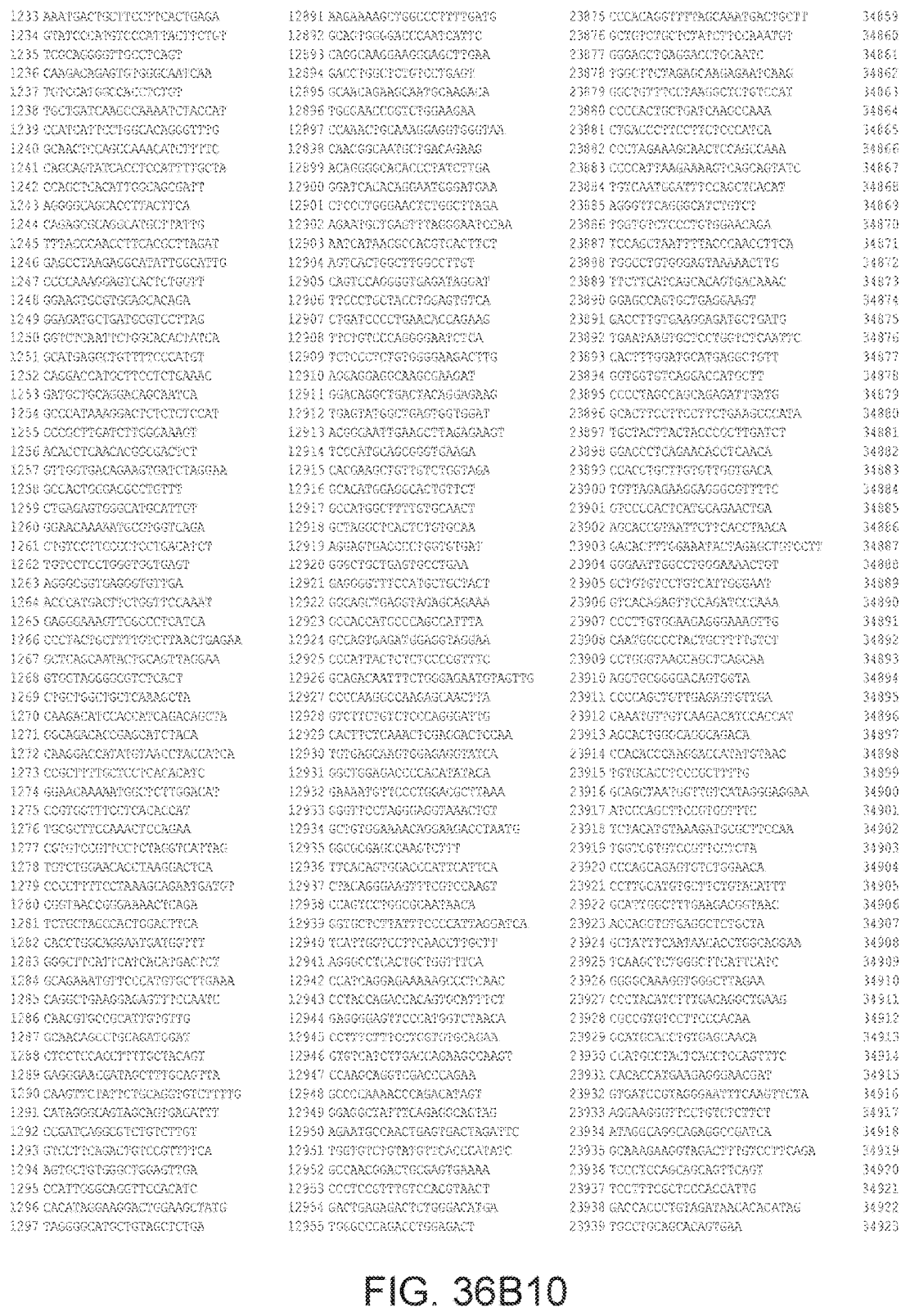
Figure 36C1:
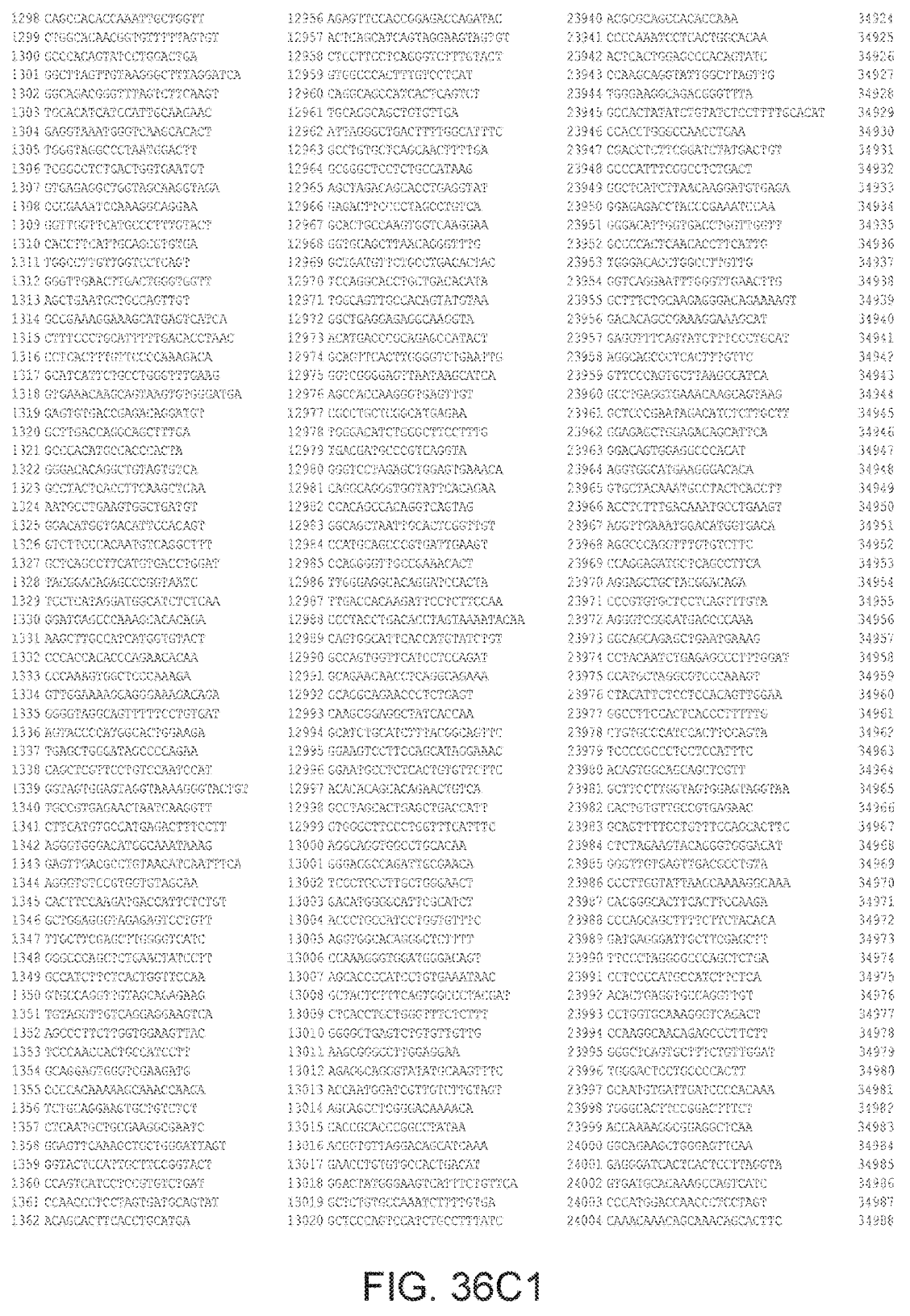
Figure 36C4:
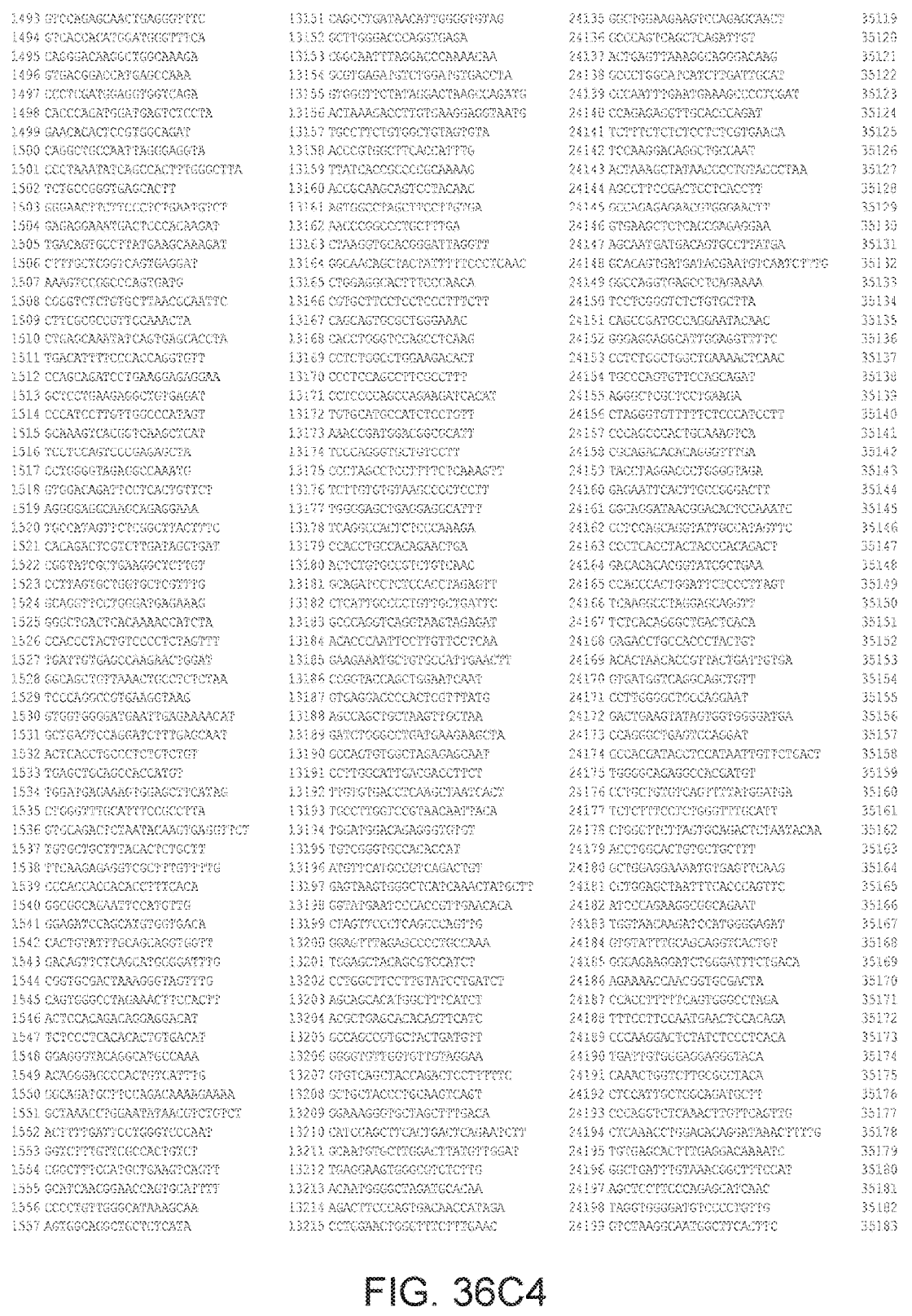
Figure 36C6:
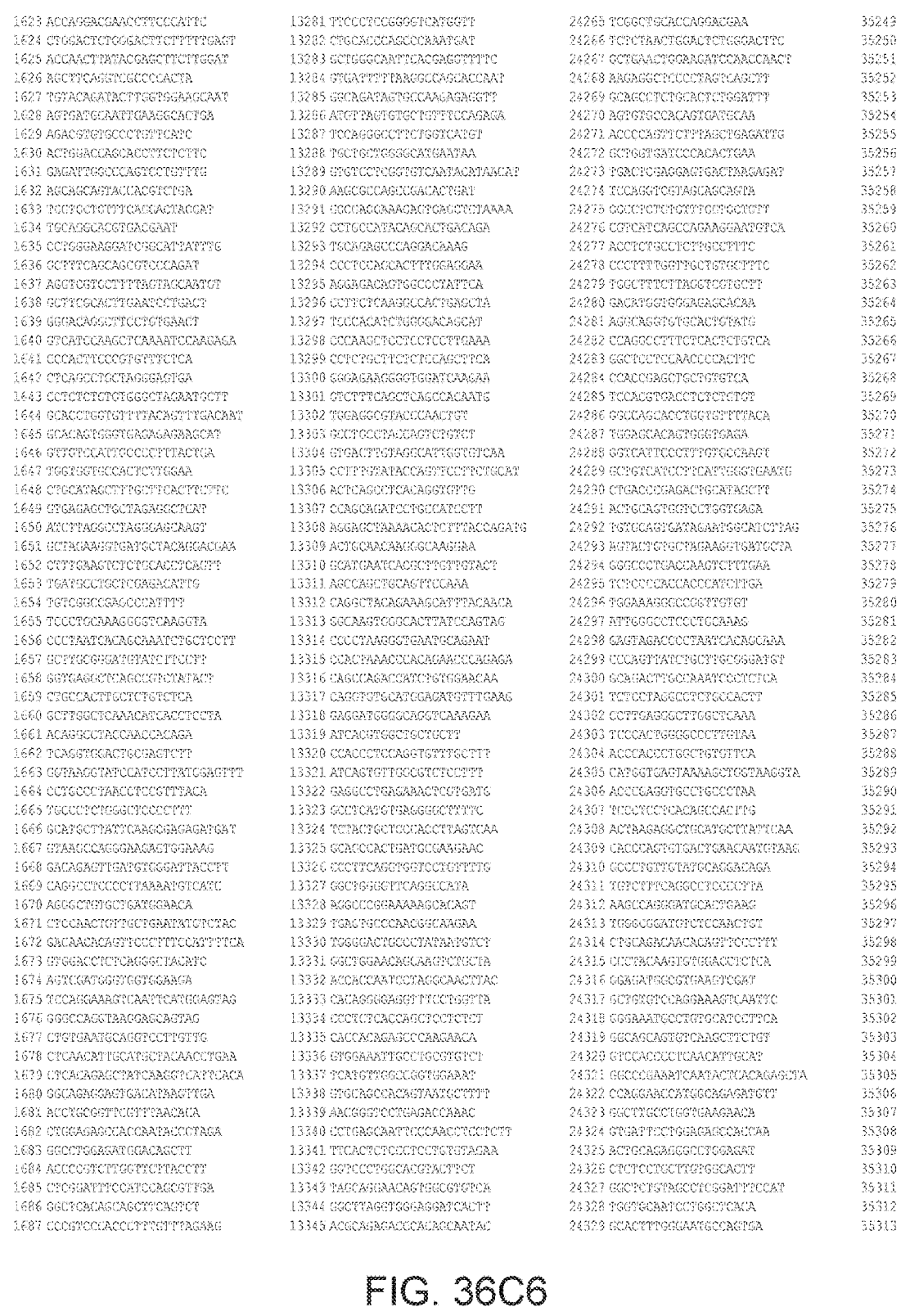
Figure 36C7:
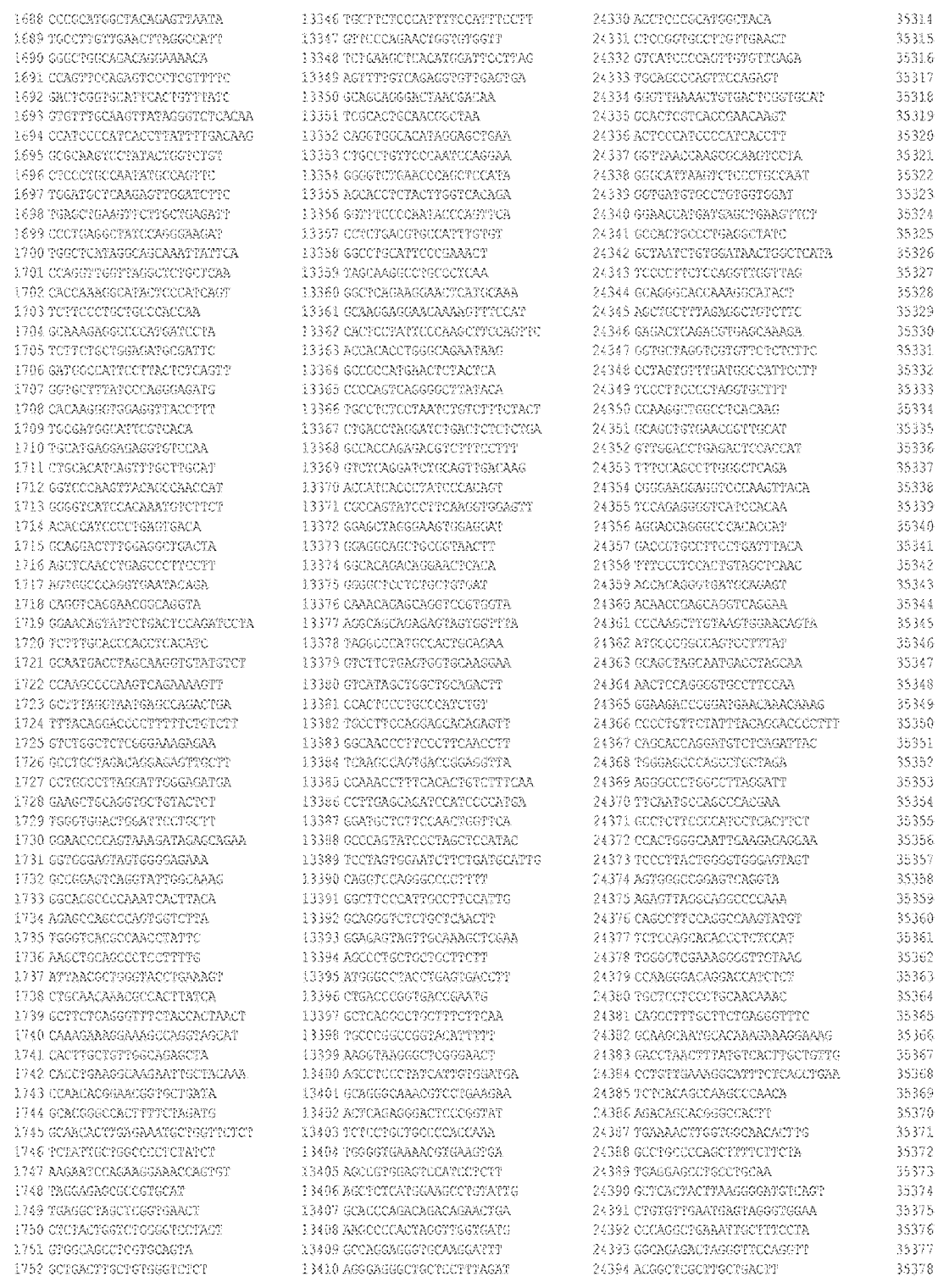
Figure 36C8:
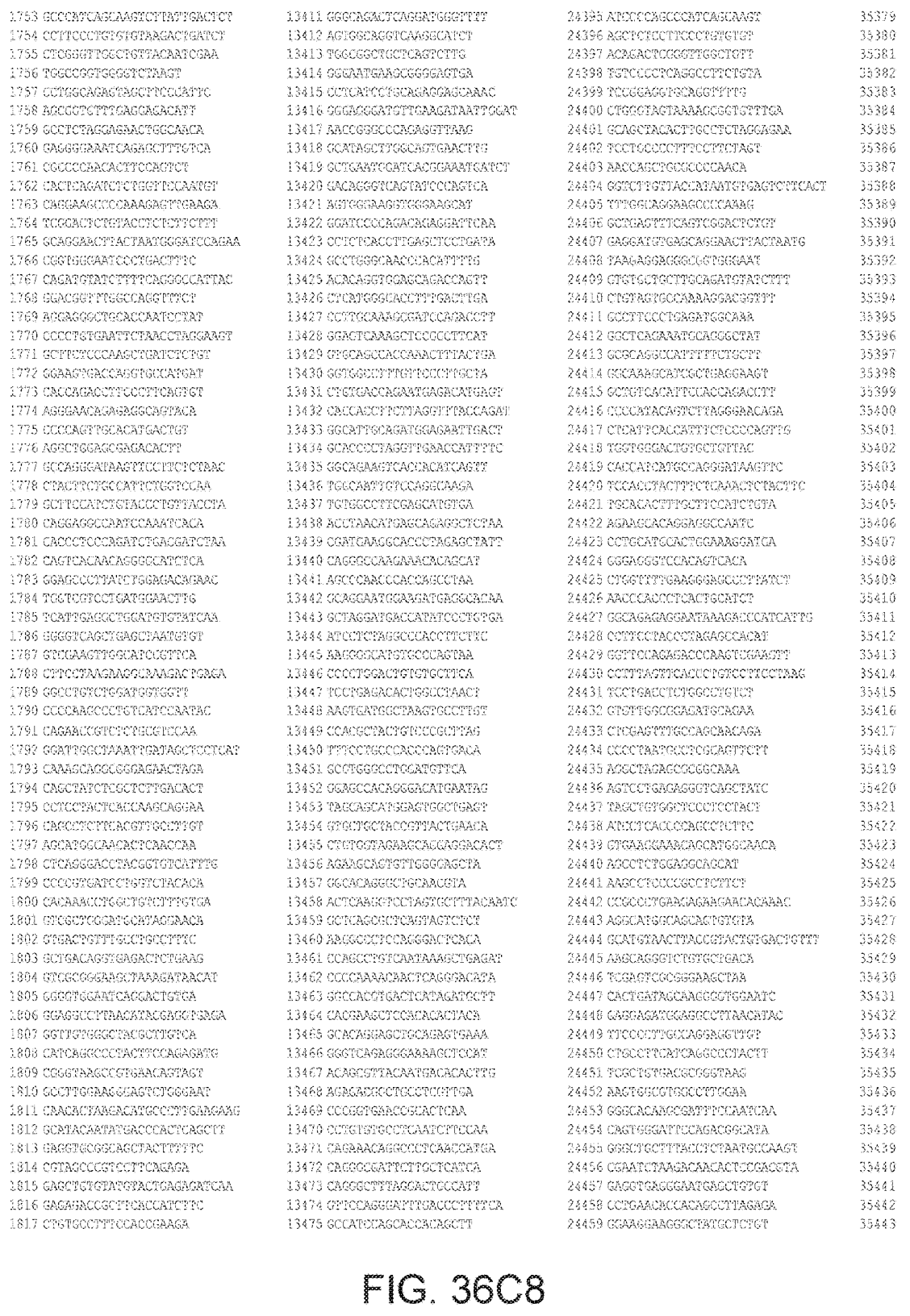
Figure 36C9:
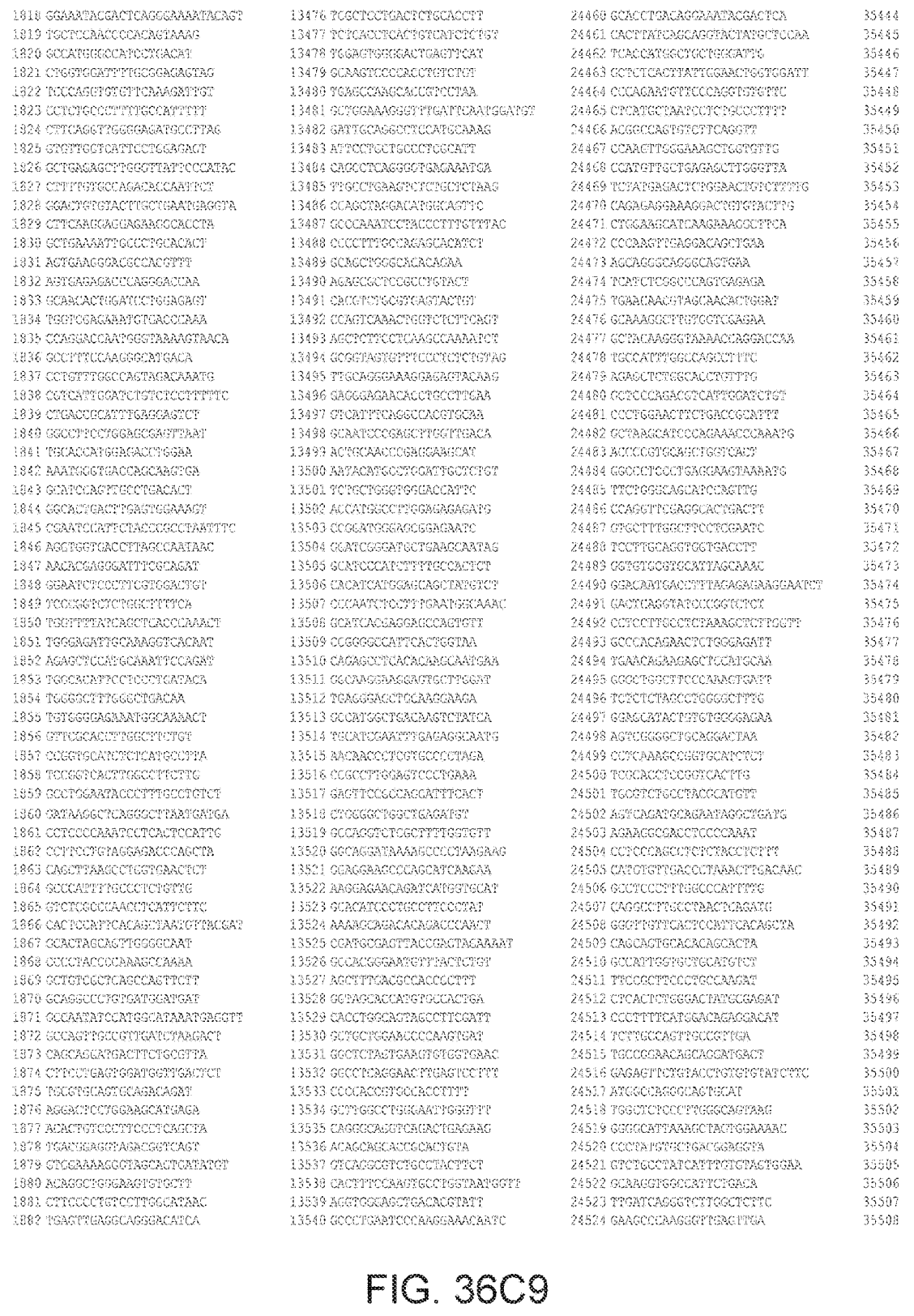
Figure 36C10:
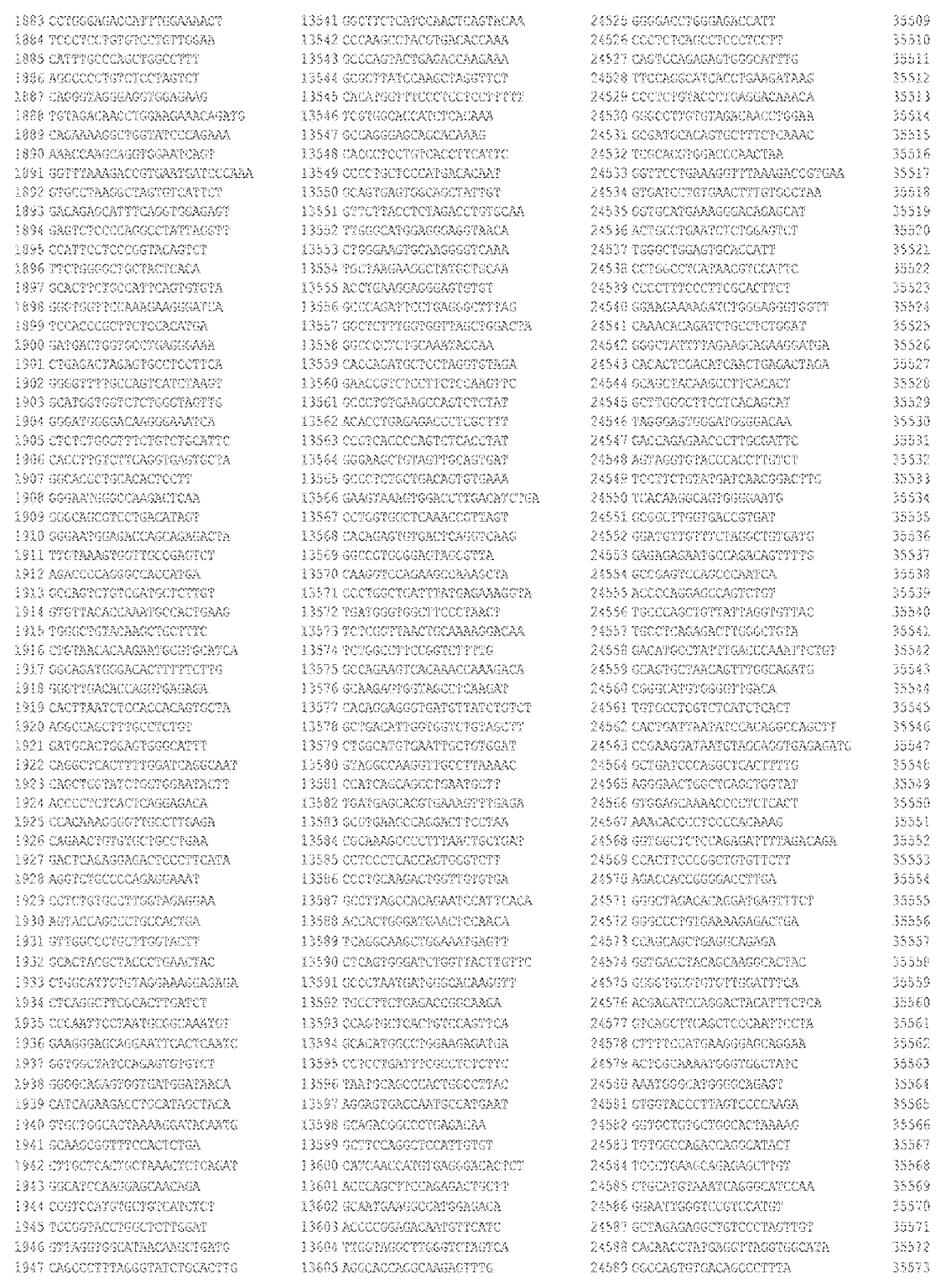
Figure 36D1:
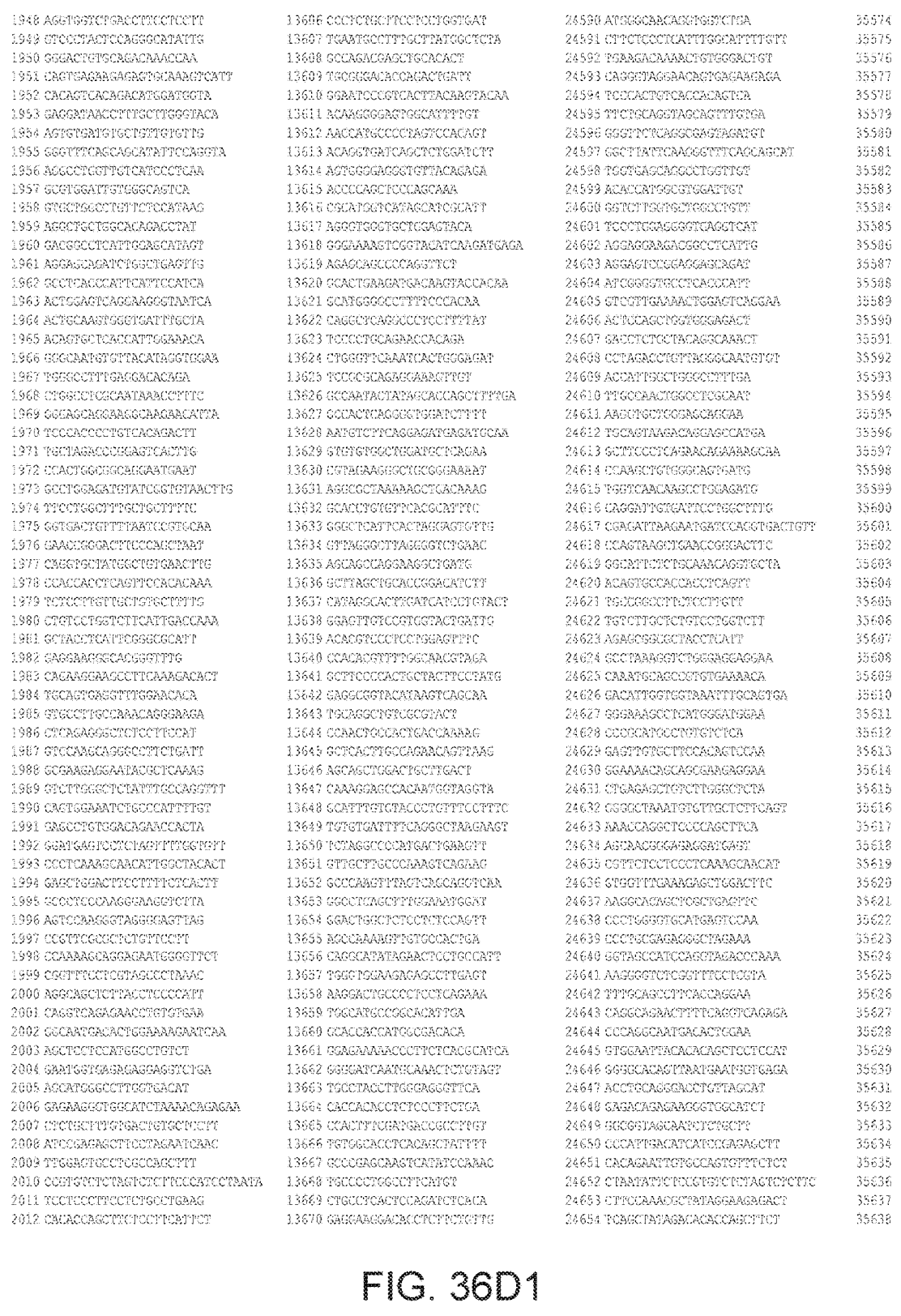
Figure 36D2:
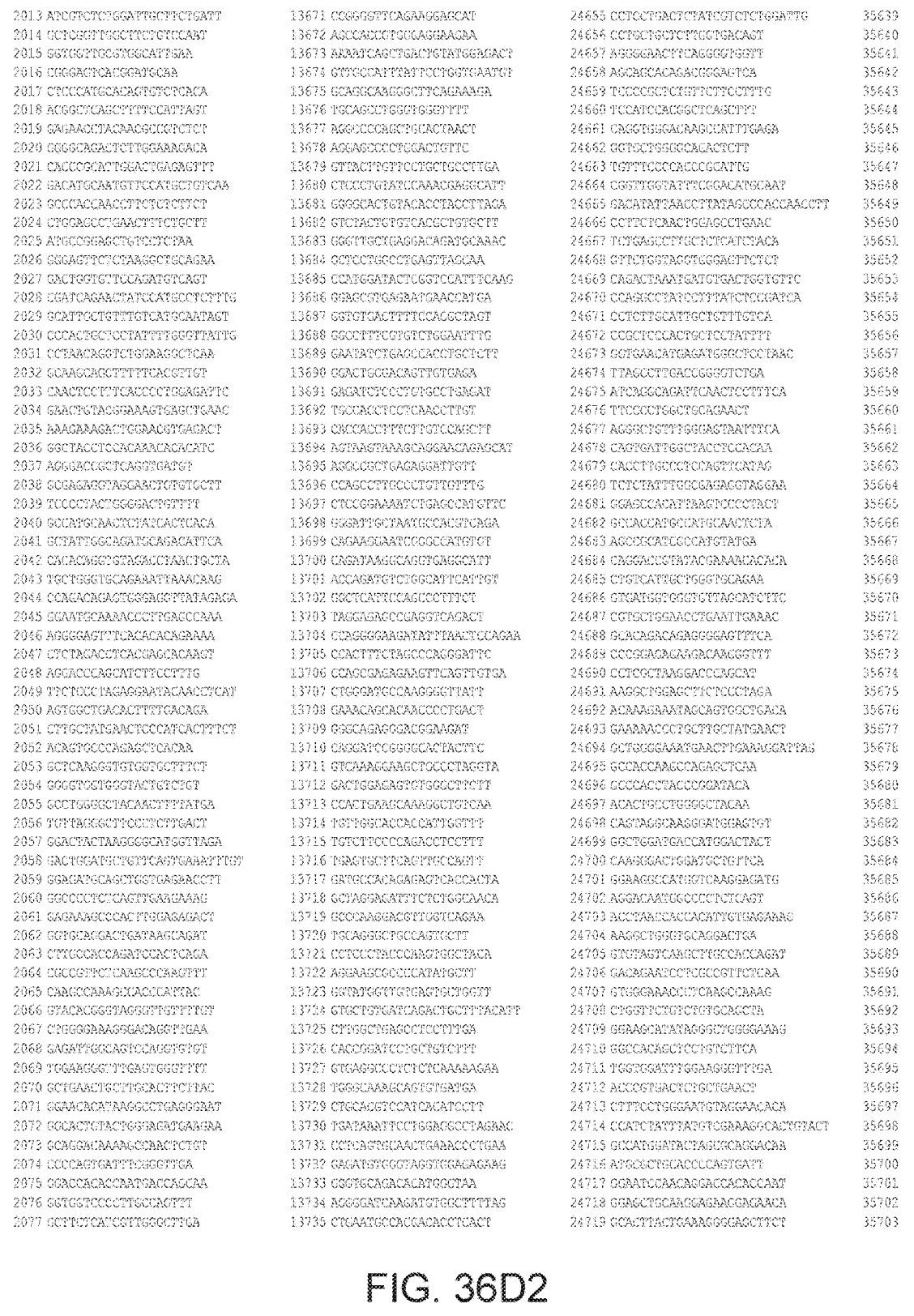
Figure 36D3:
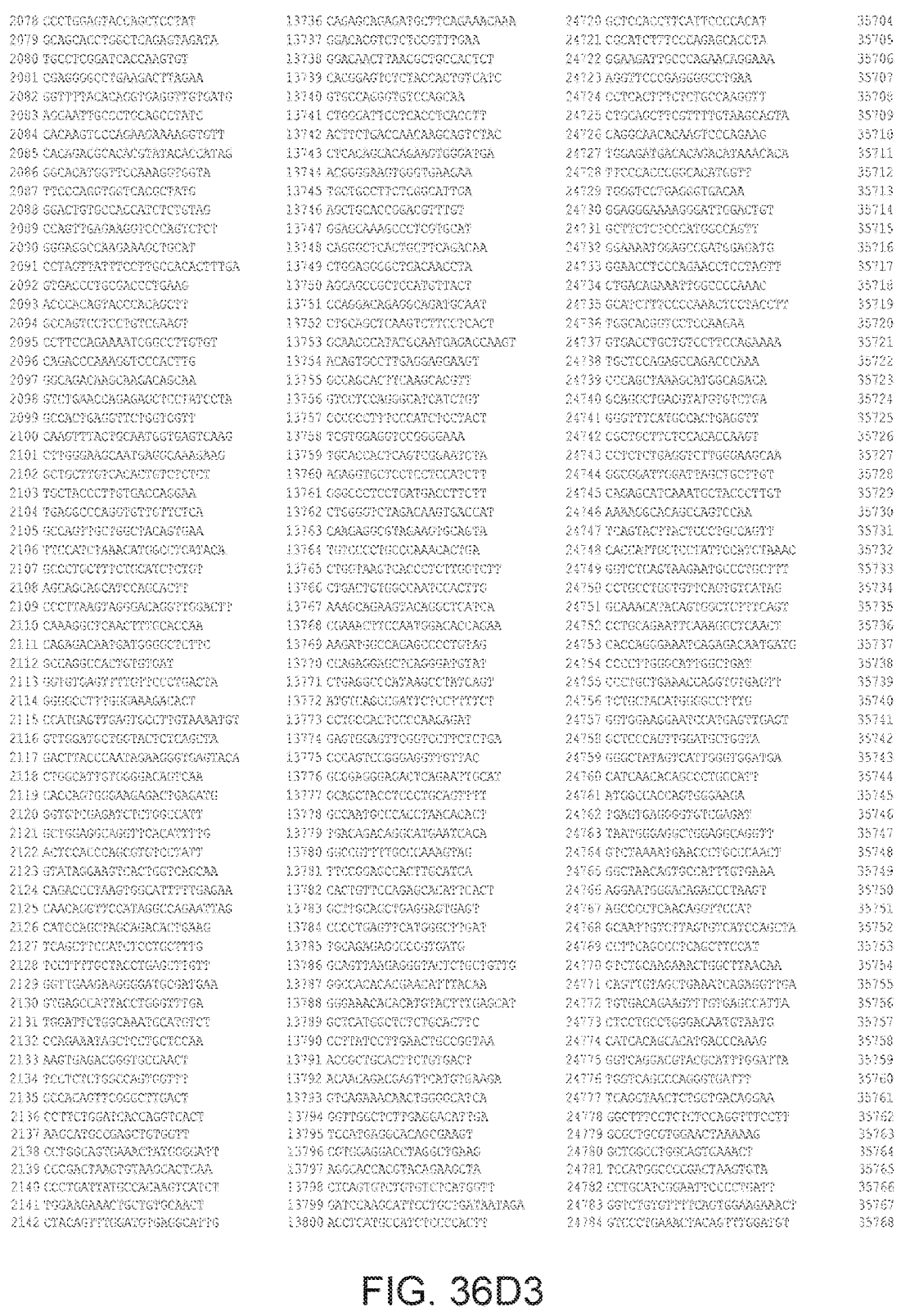
Figure 36D4:
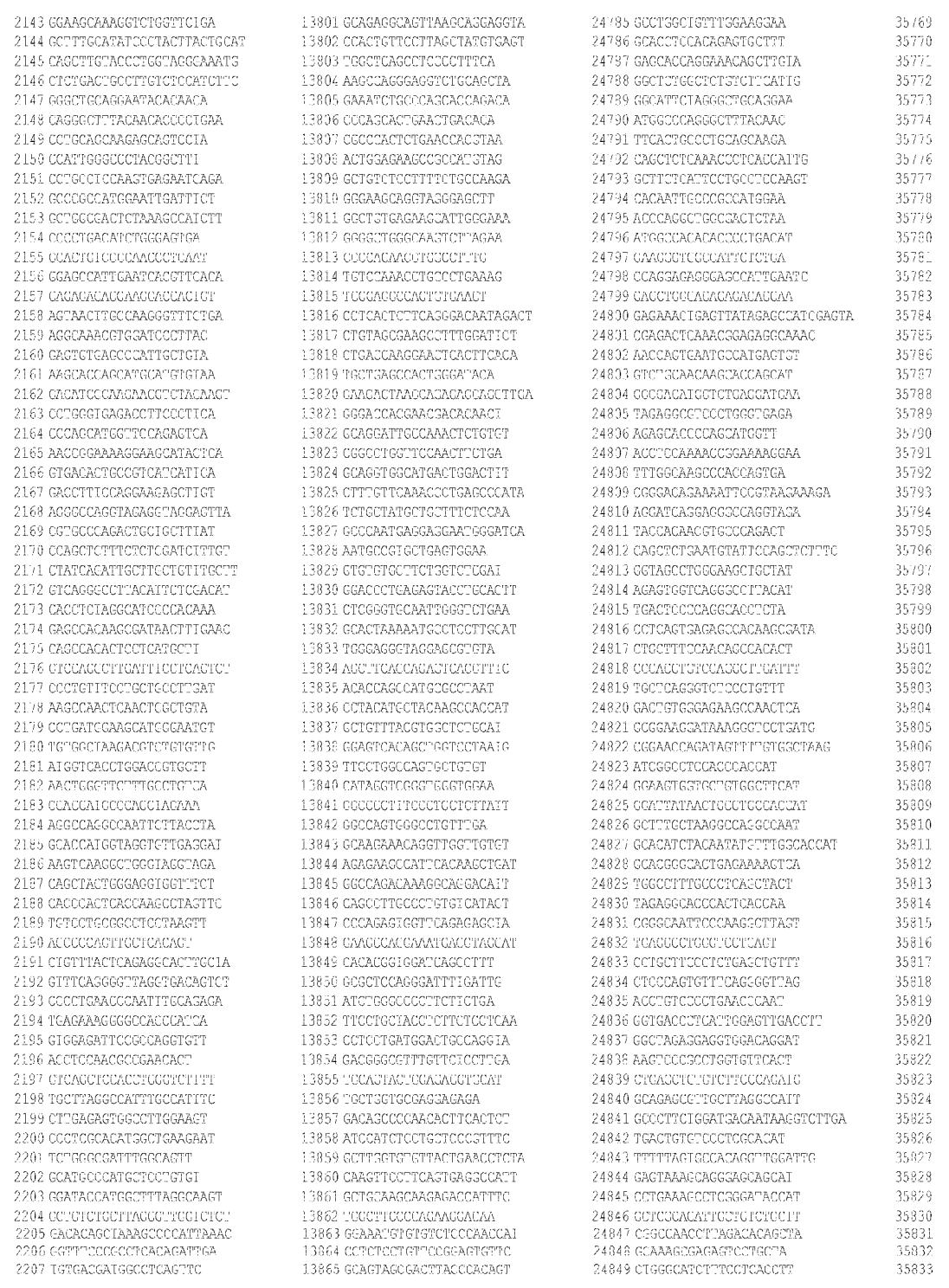
Figure 36D6:
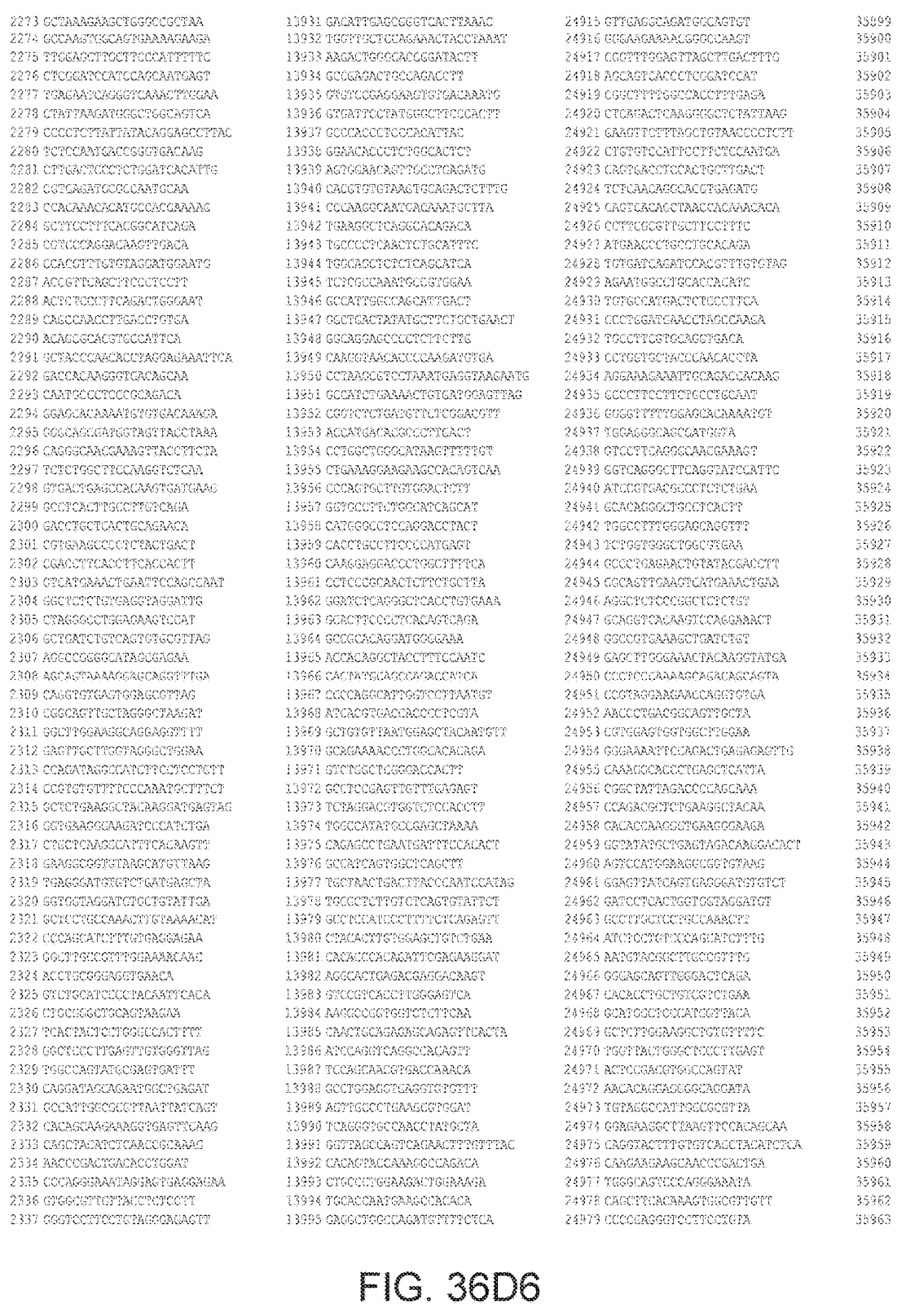
Figure 36D7:
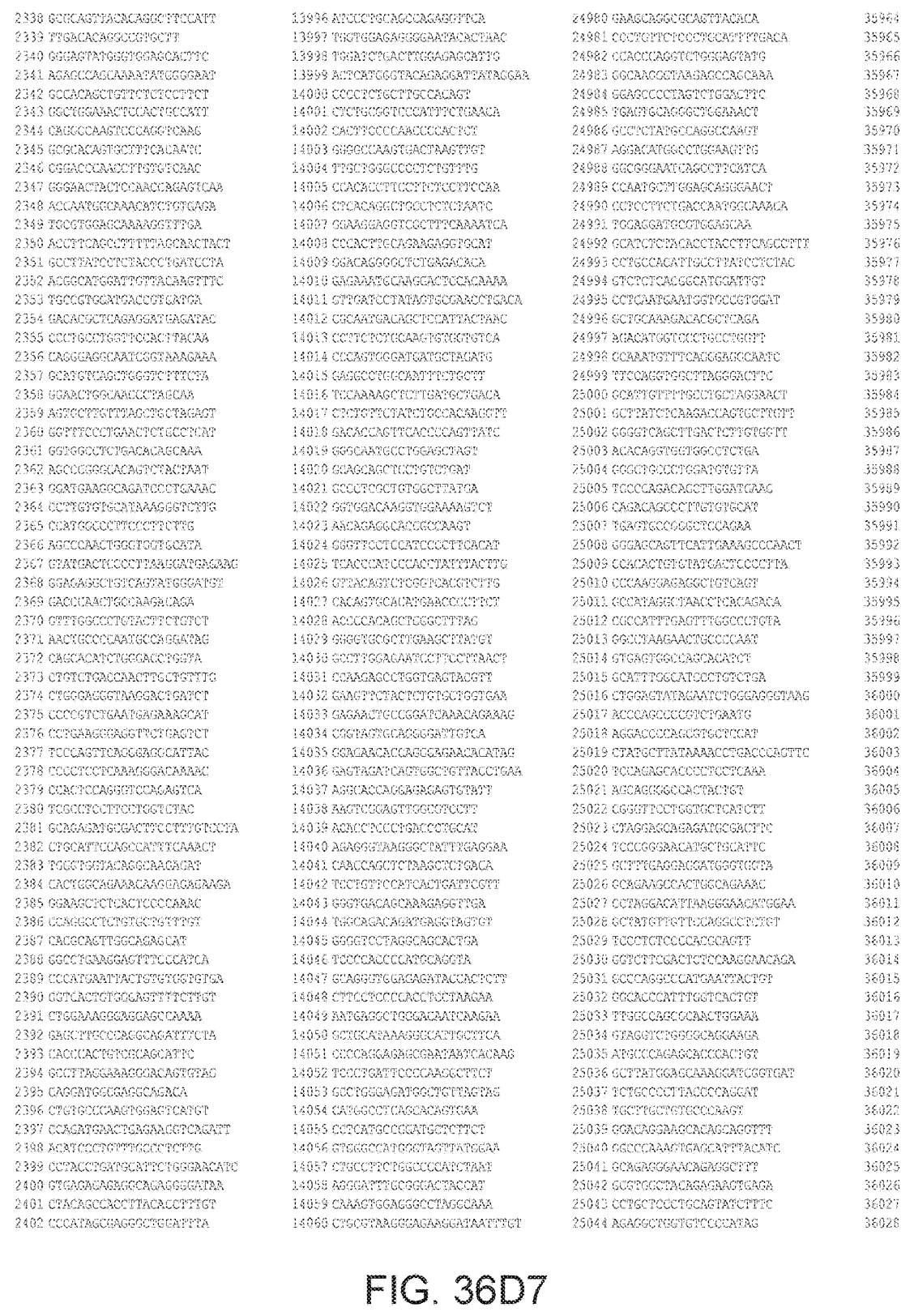
Figure 36D8:
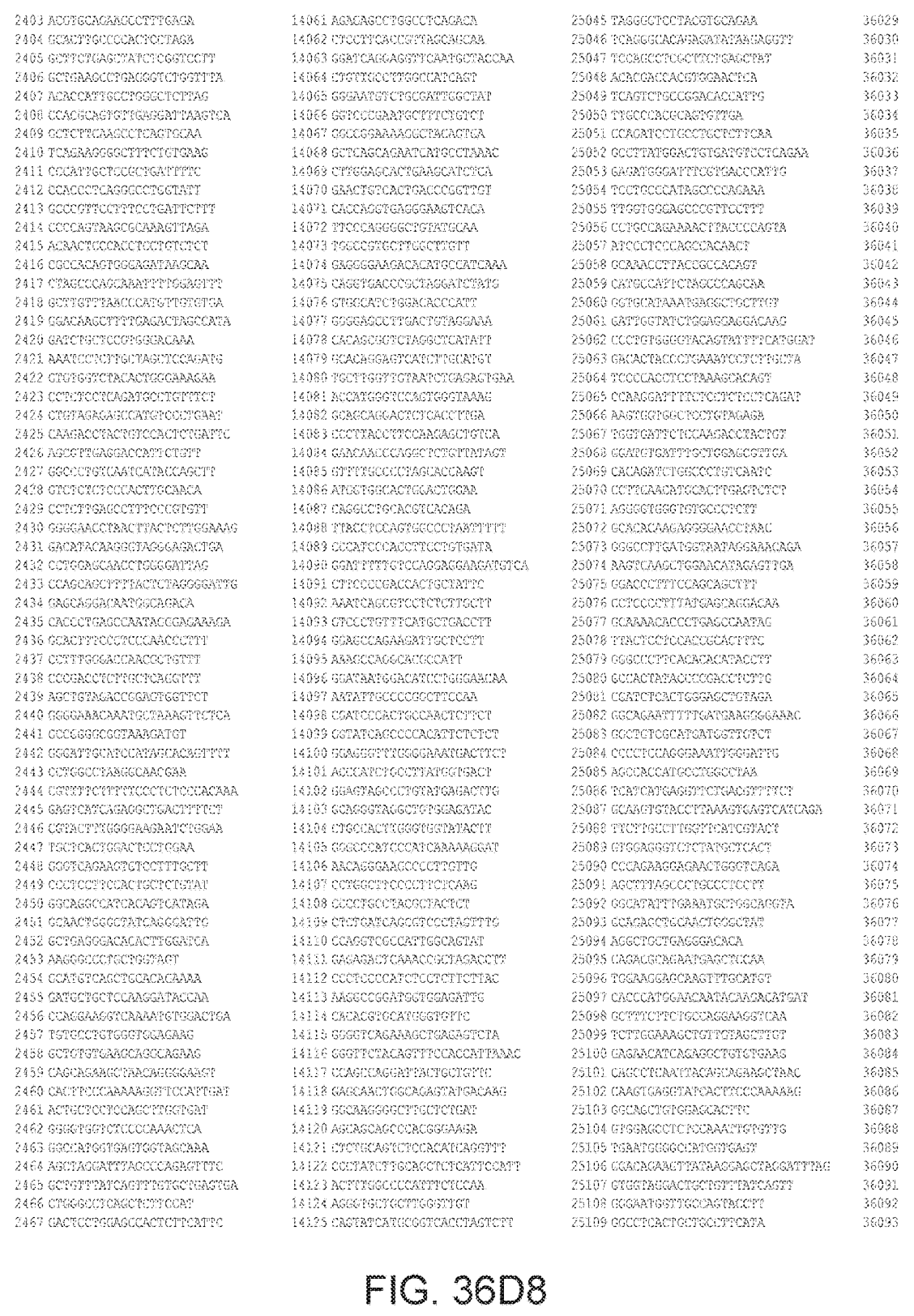
Figure 36D10:
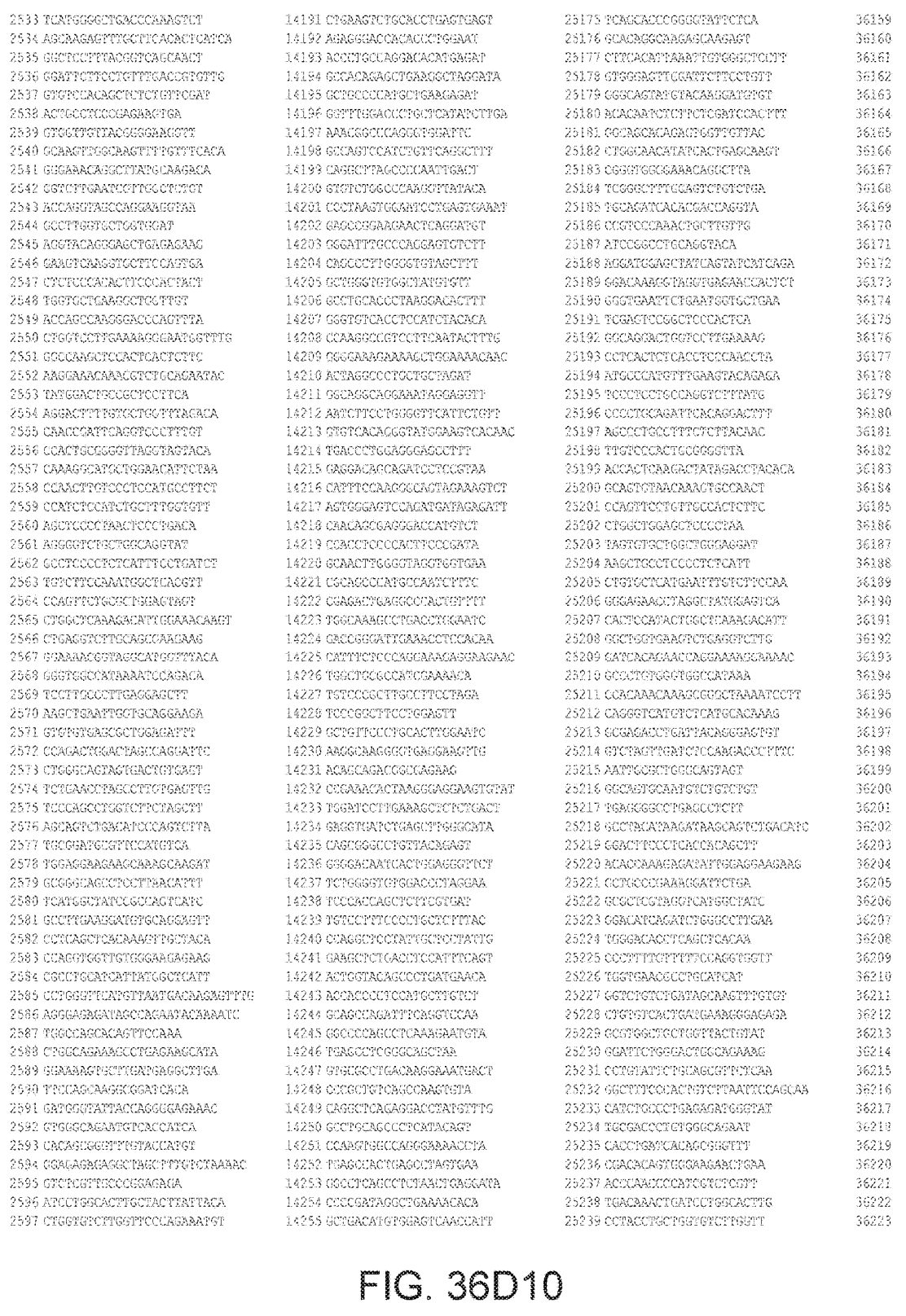
Figure 36E2:
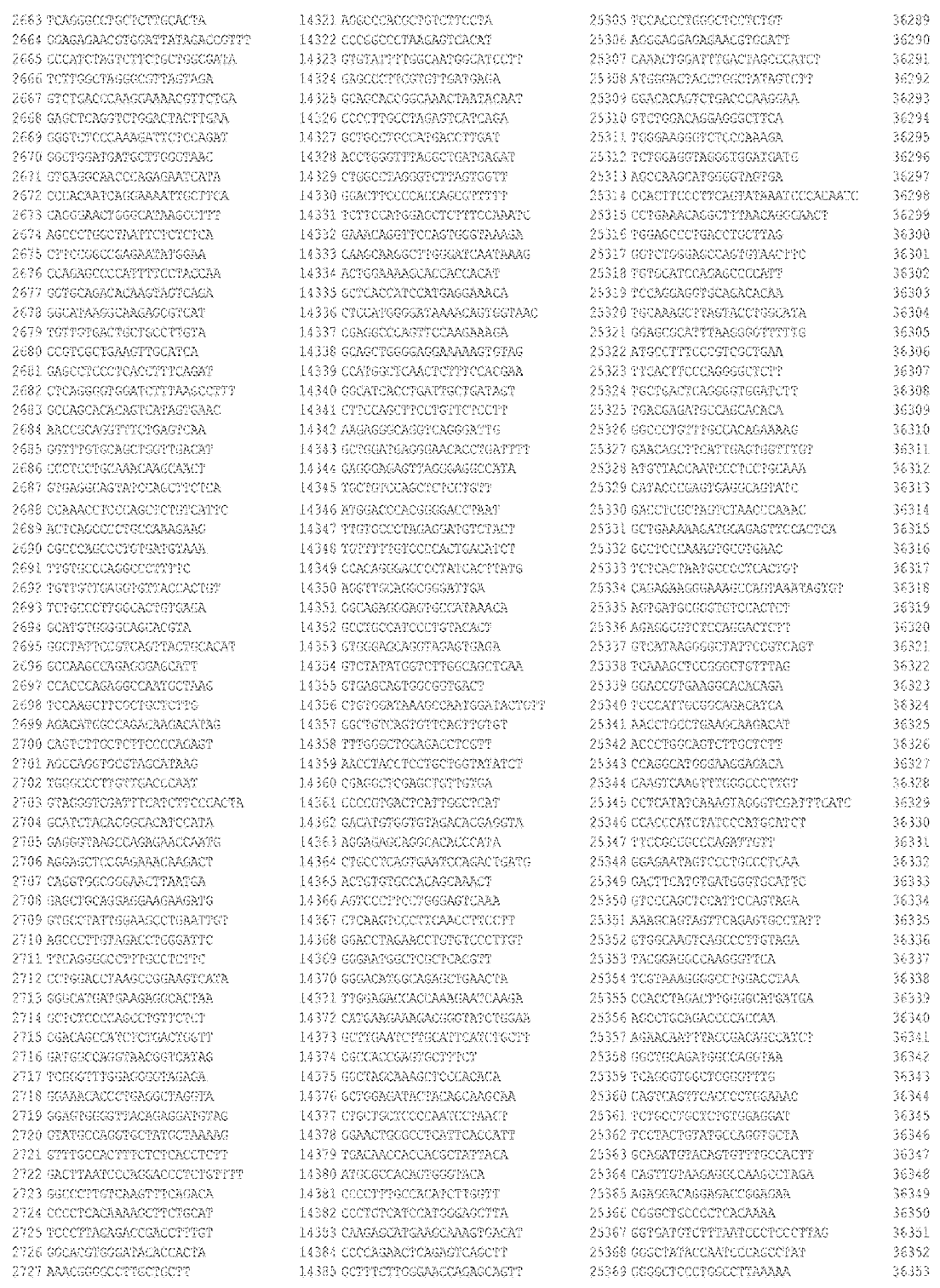
Figure 36E3:
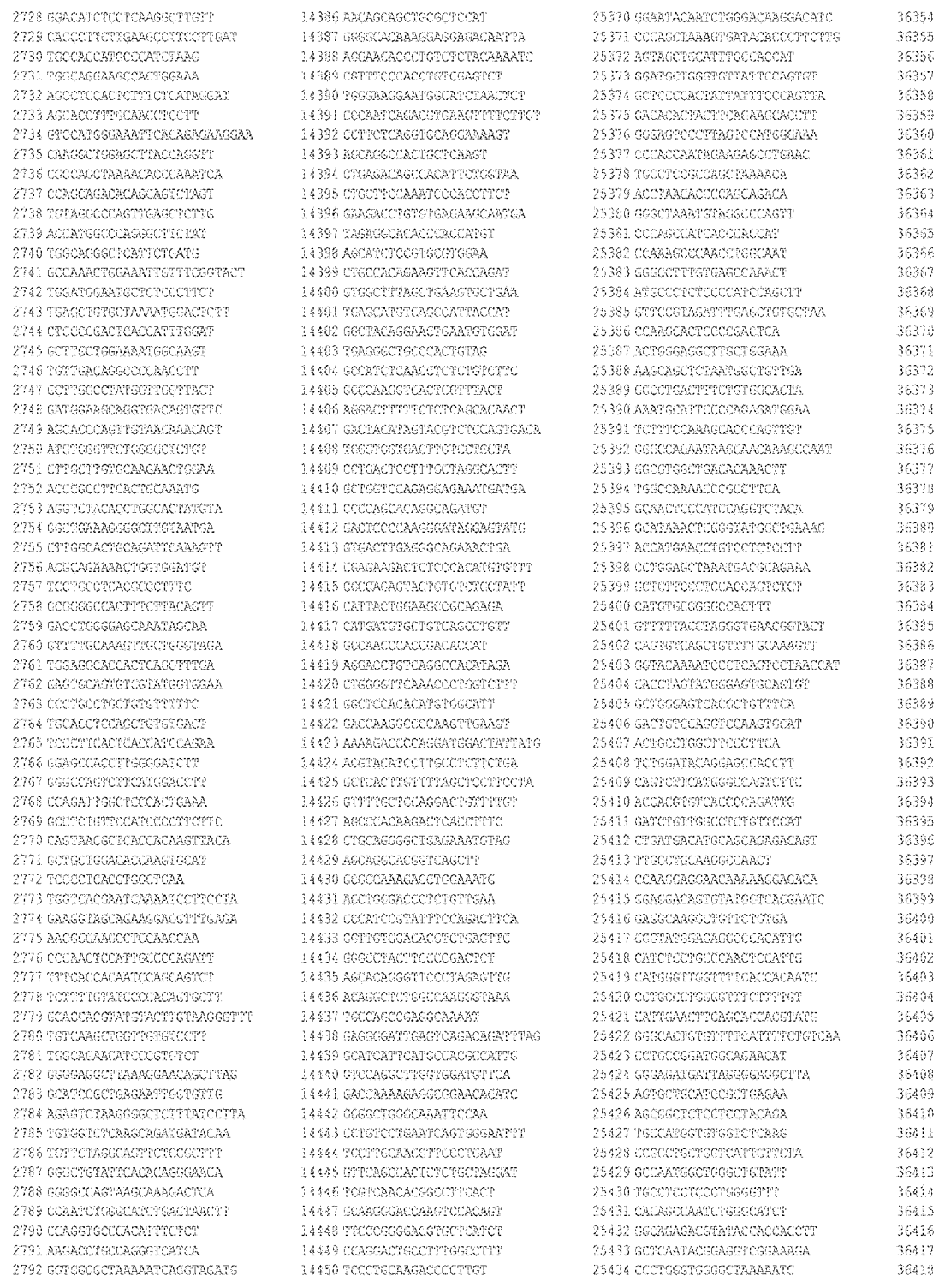
Figure 36E4:
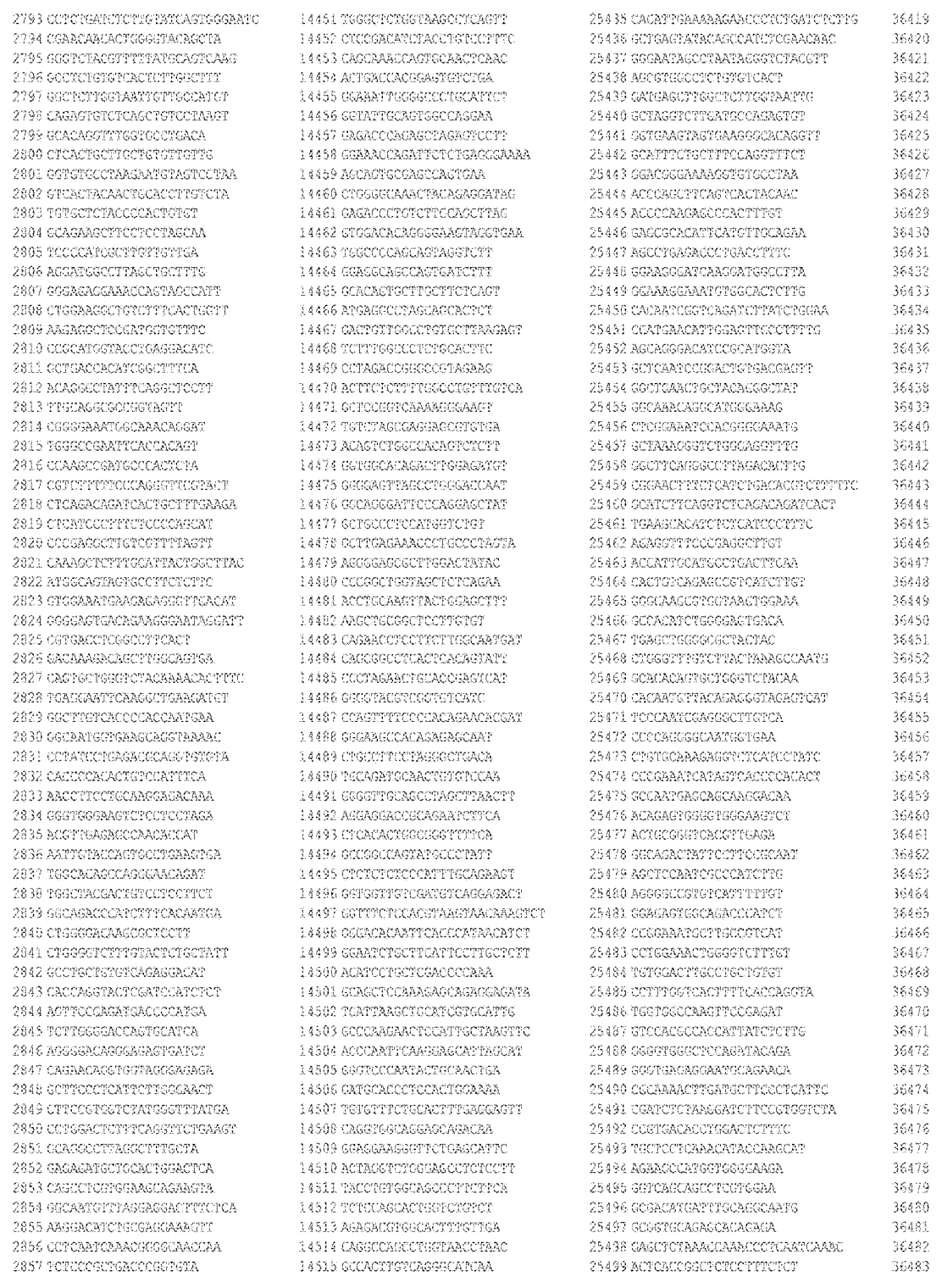
Figure 36E7:
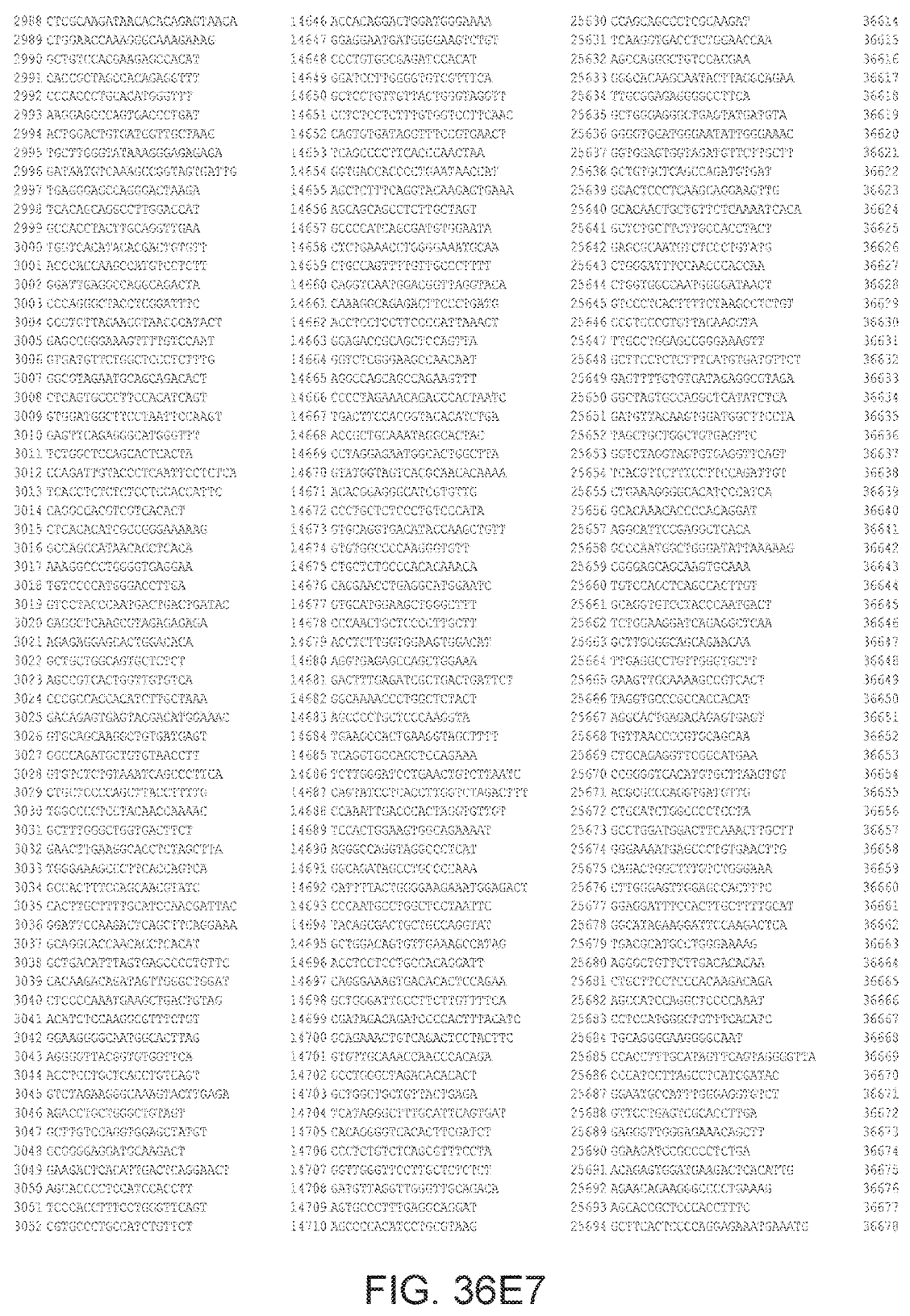
Figure 36E9:
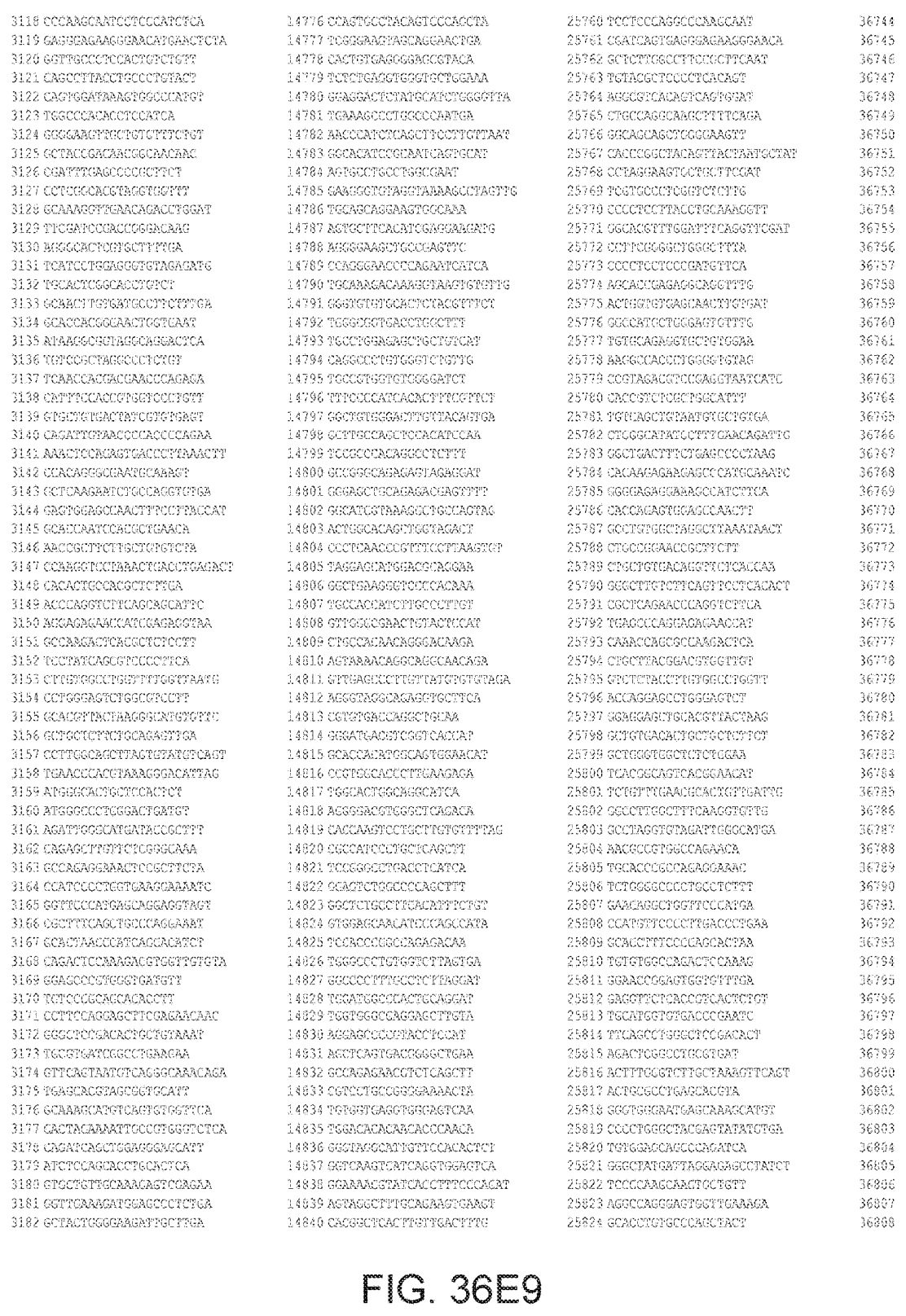
Figure 36F3:
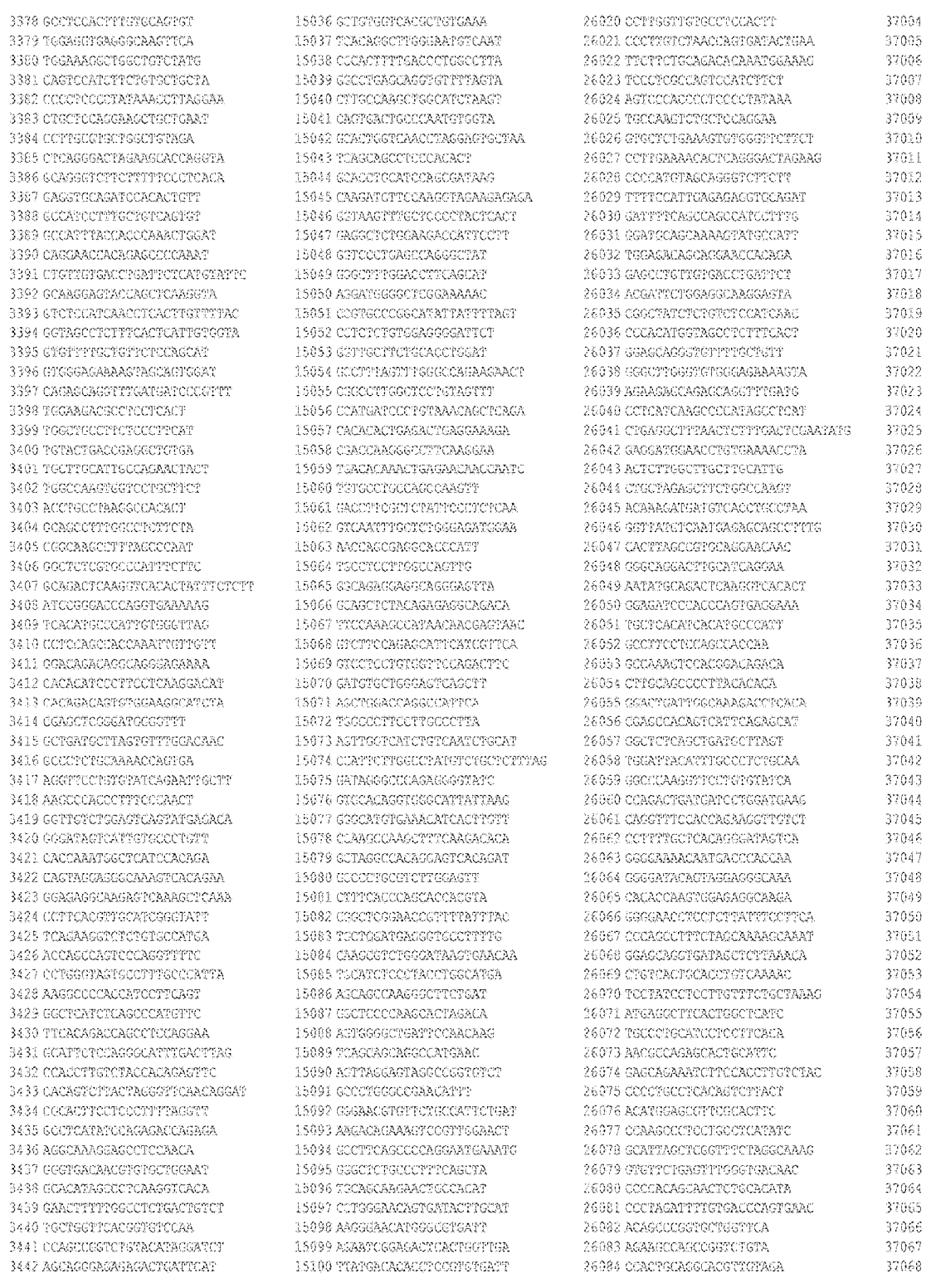
Figure 36F4:
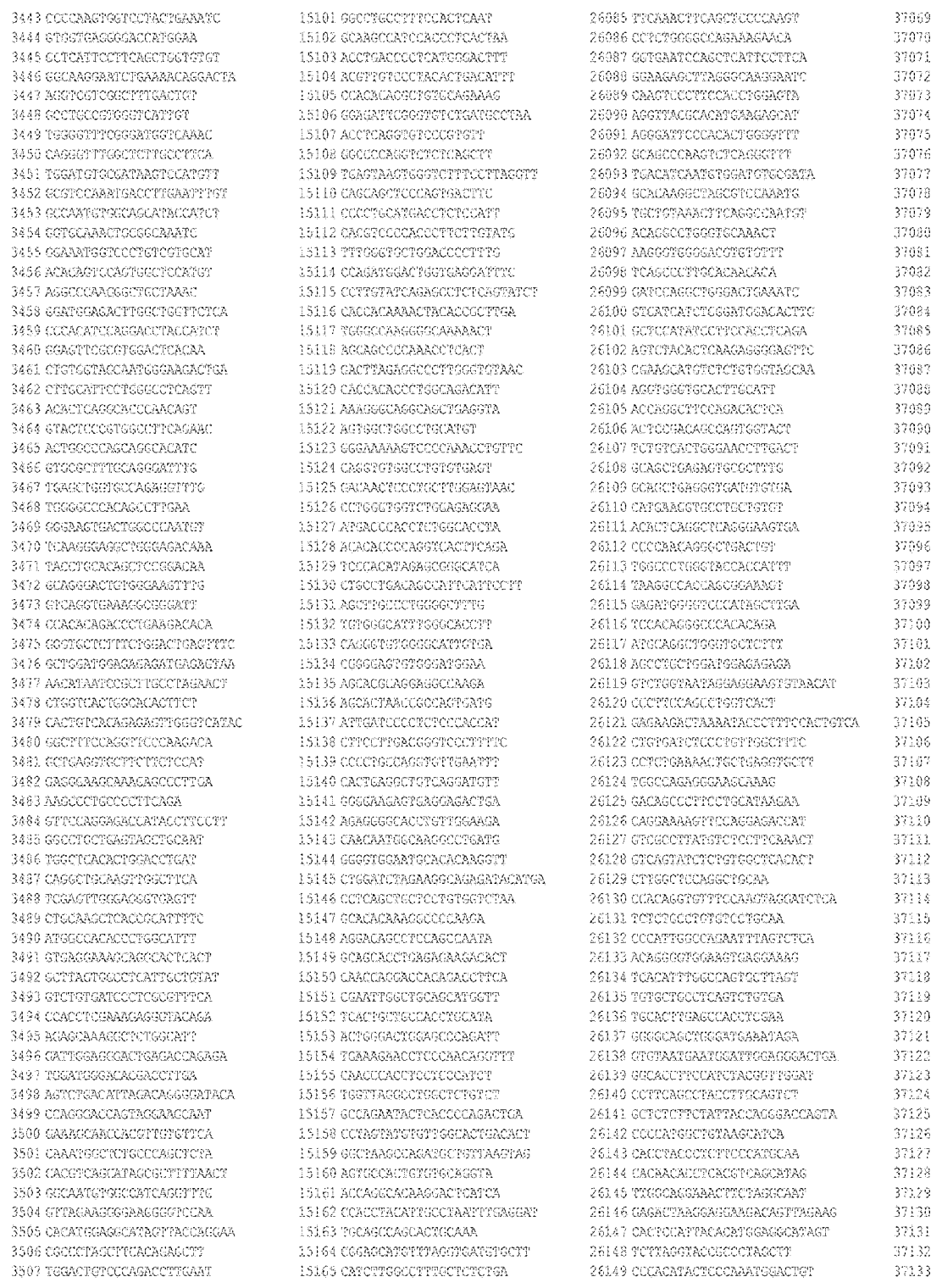
Figure 36F5:
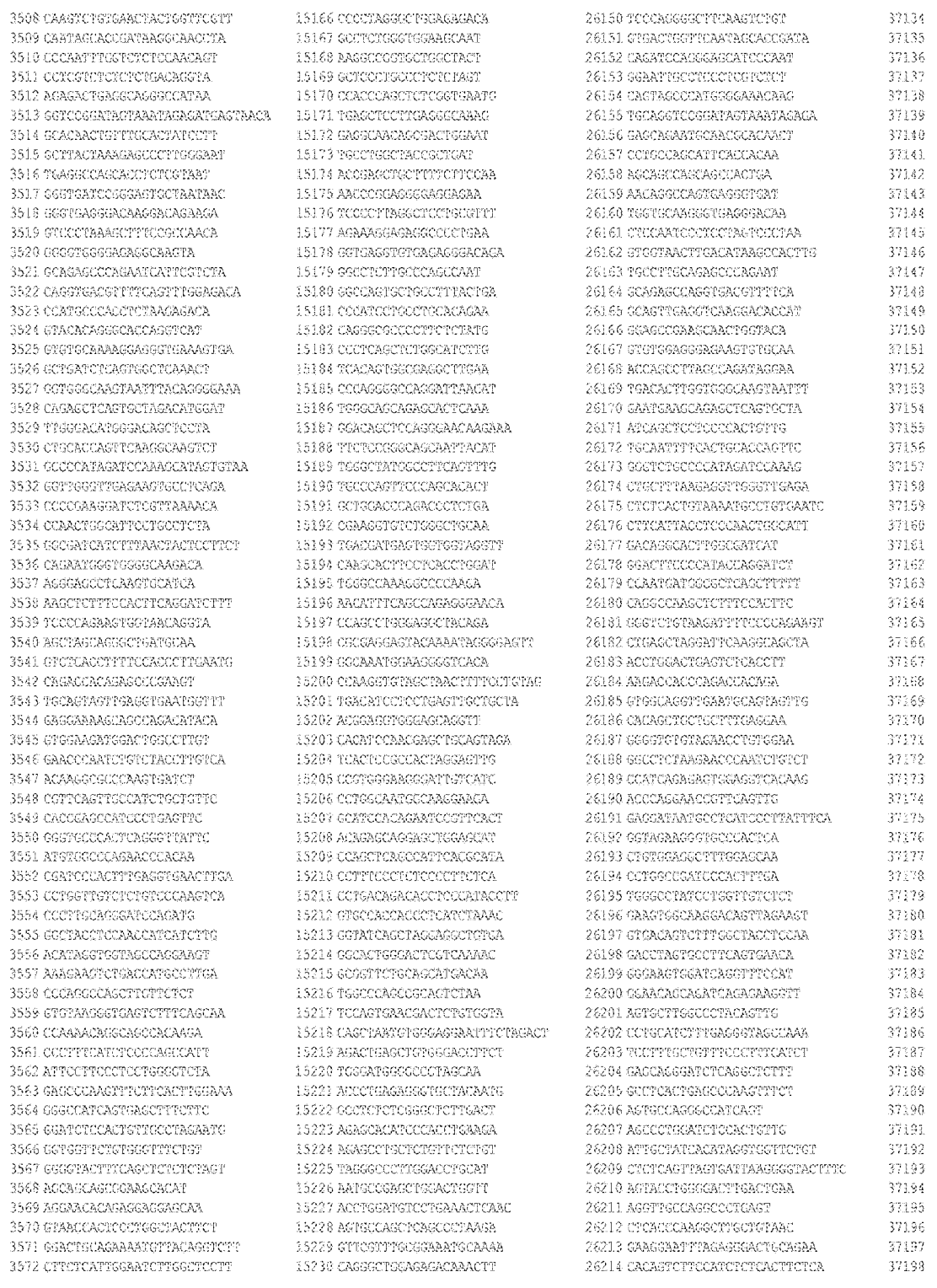
Figure 36F7:
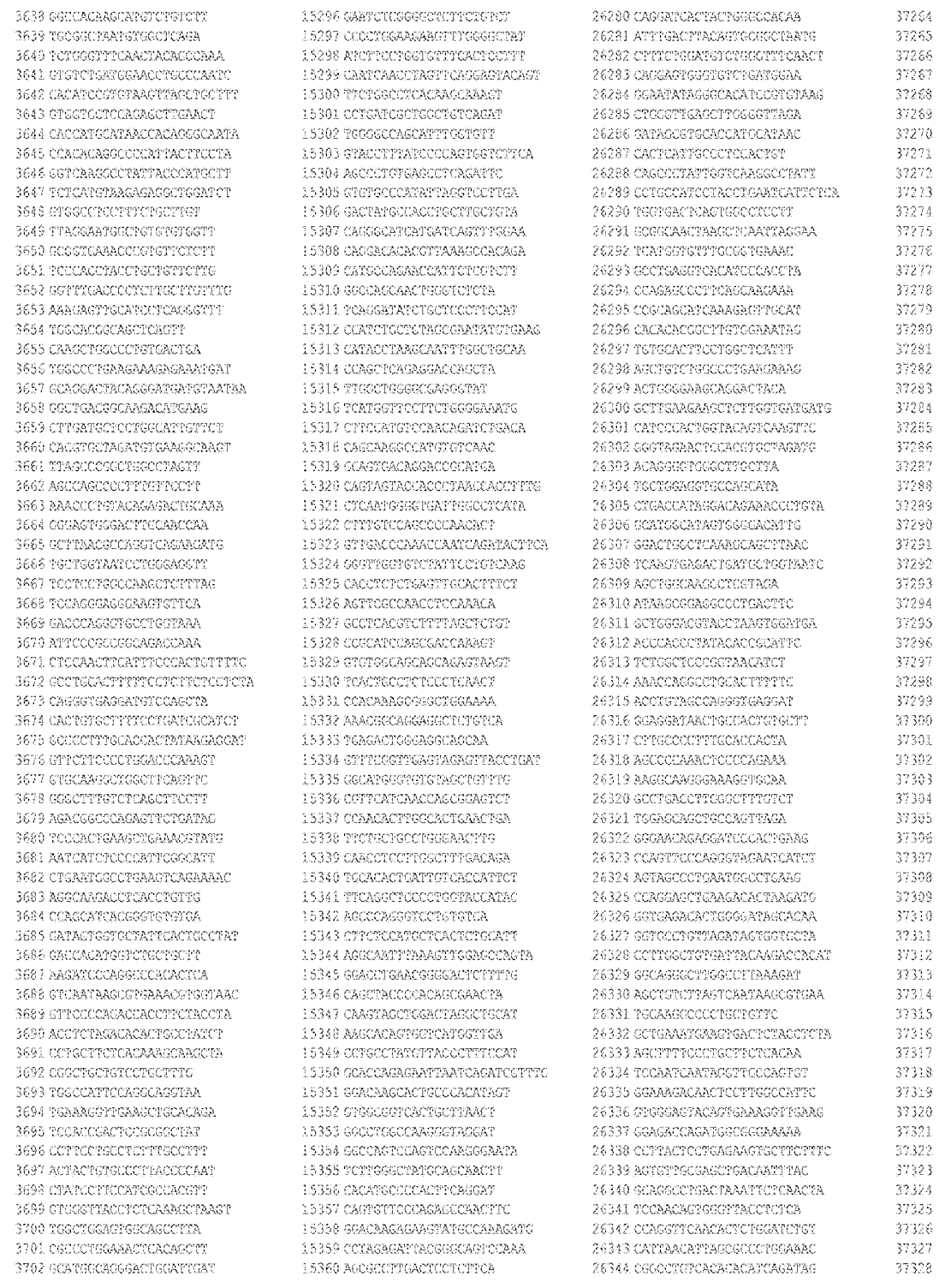
Figure 36F8:
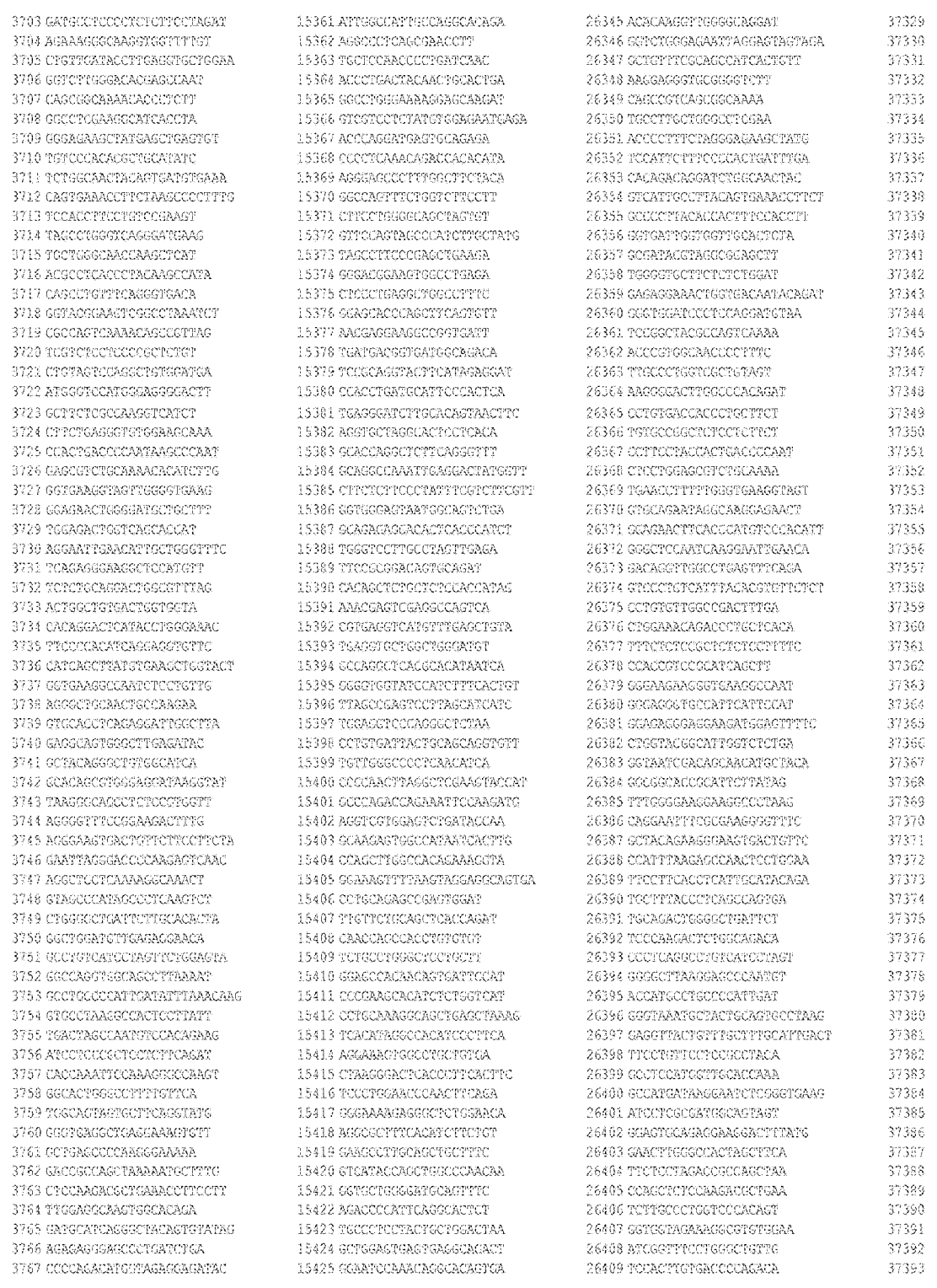
Figure 36F9:
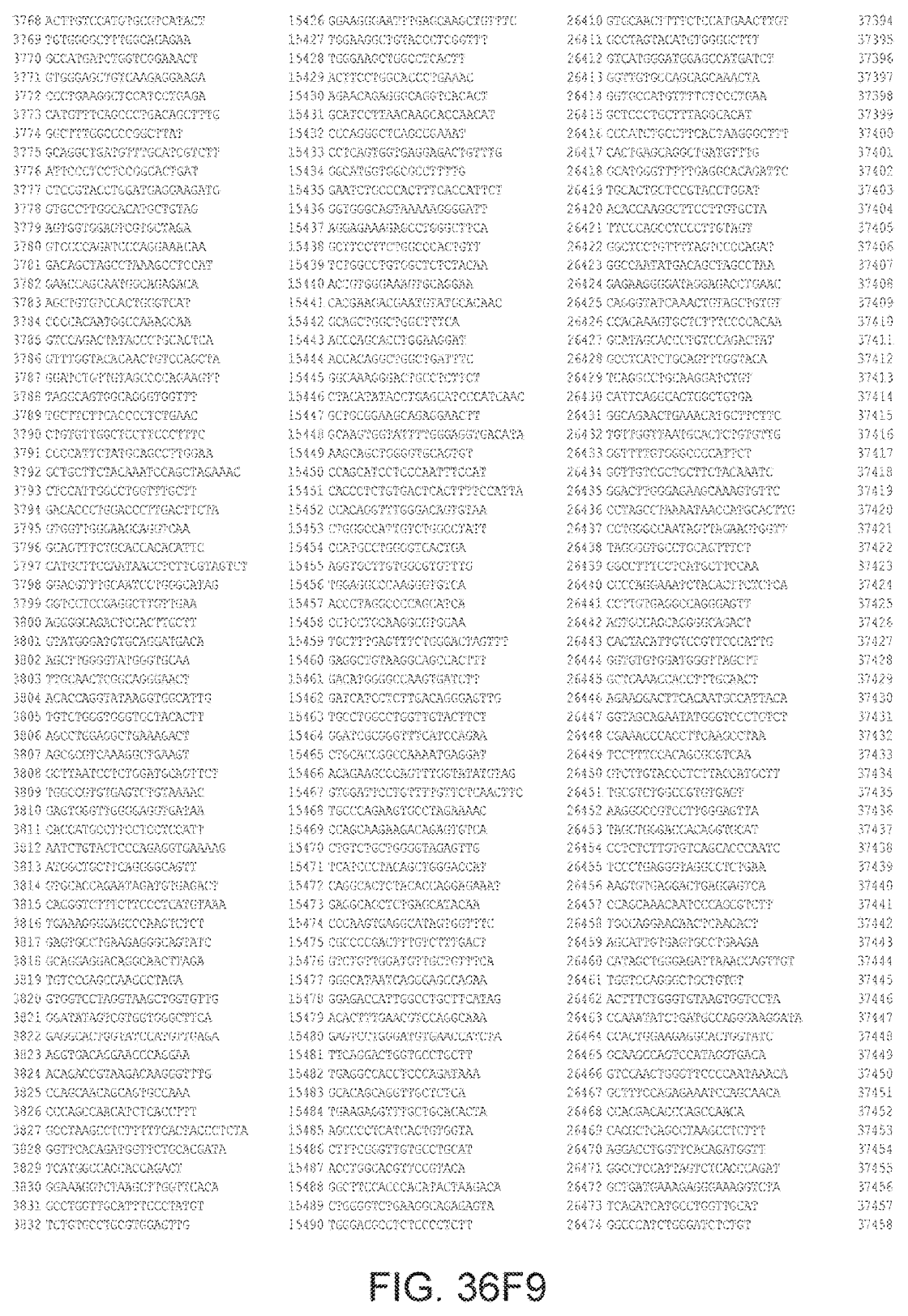
Figure 36G1:
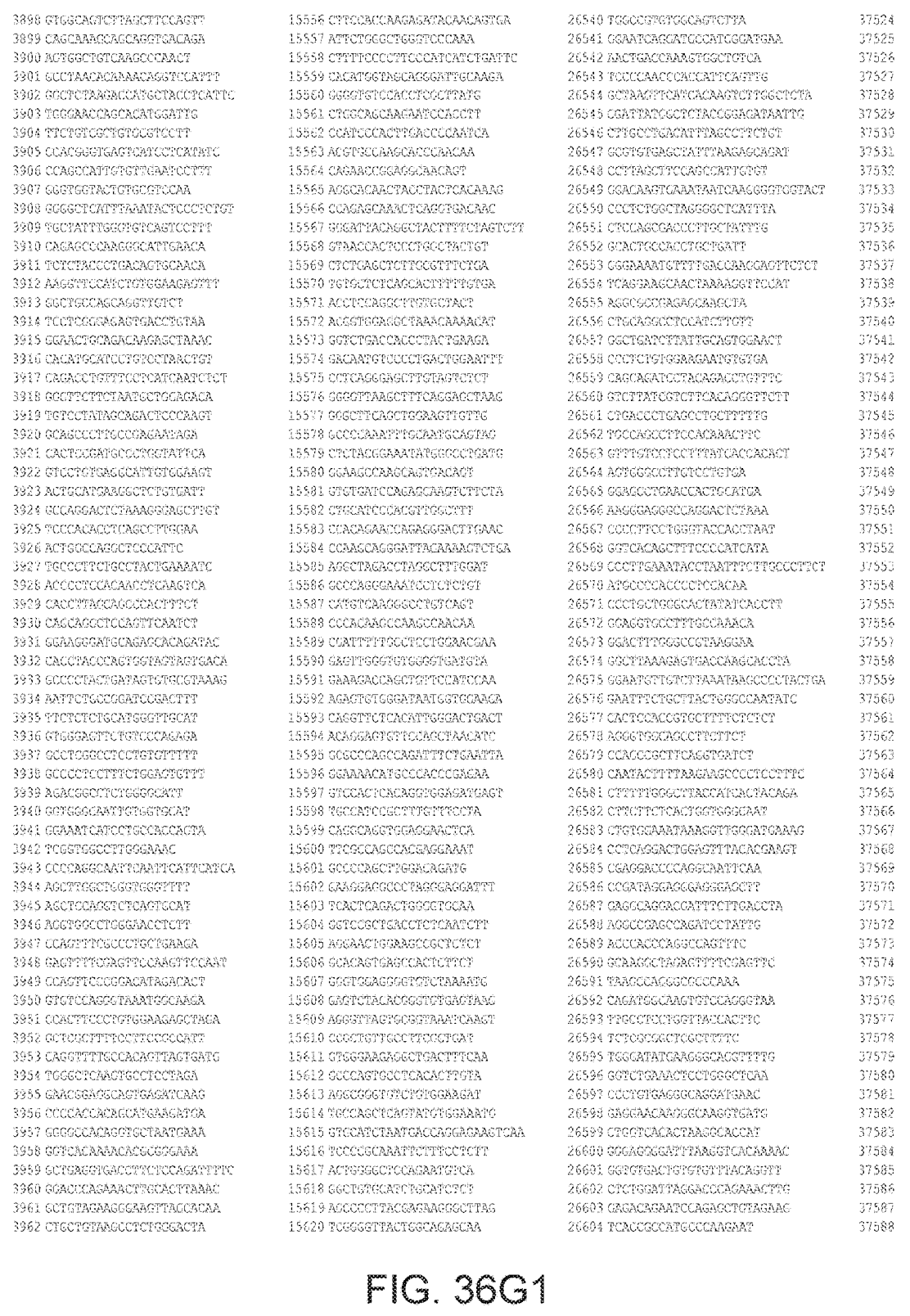
Figure 36G3:
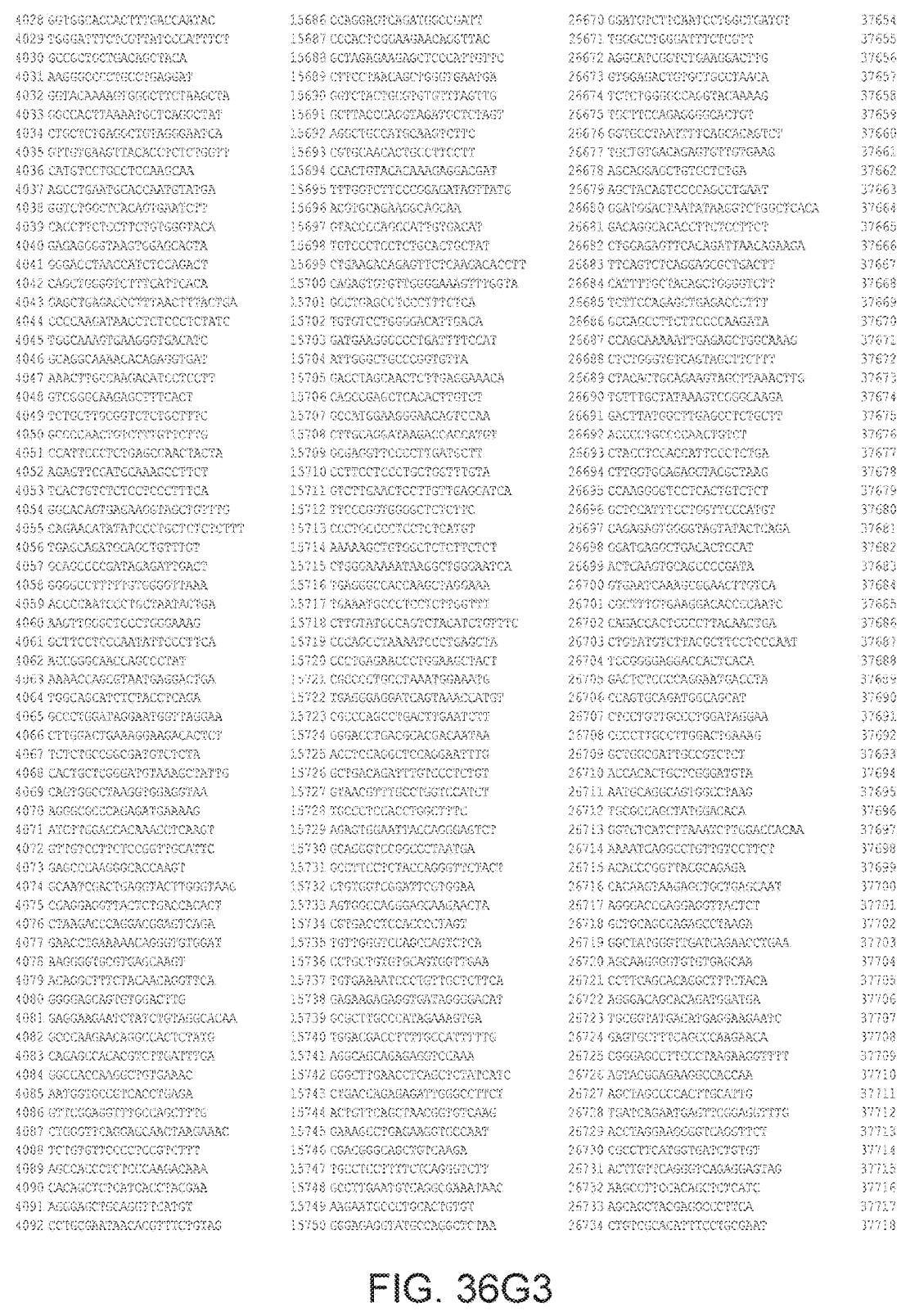
Figure 36G4:
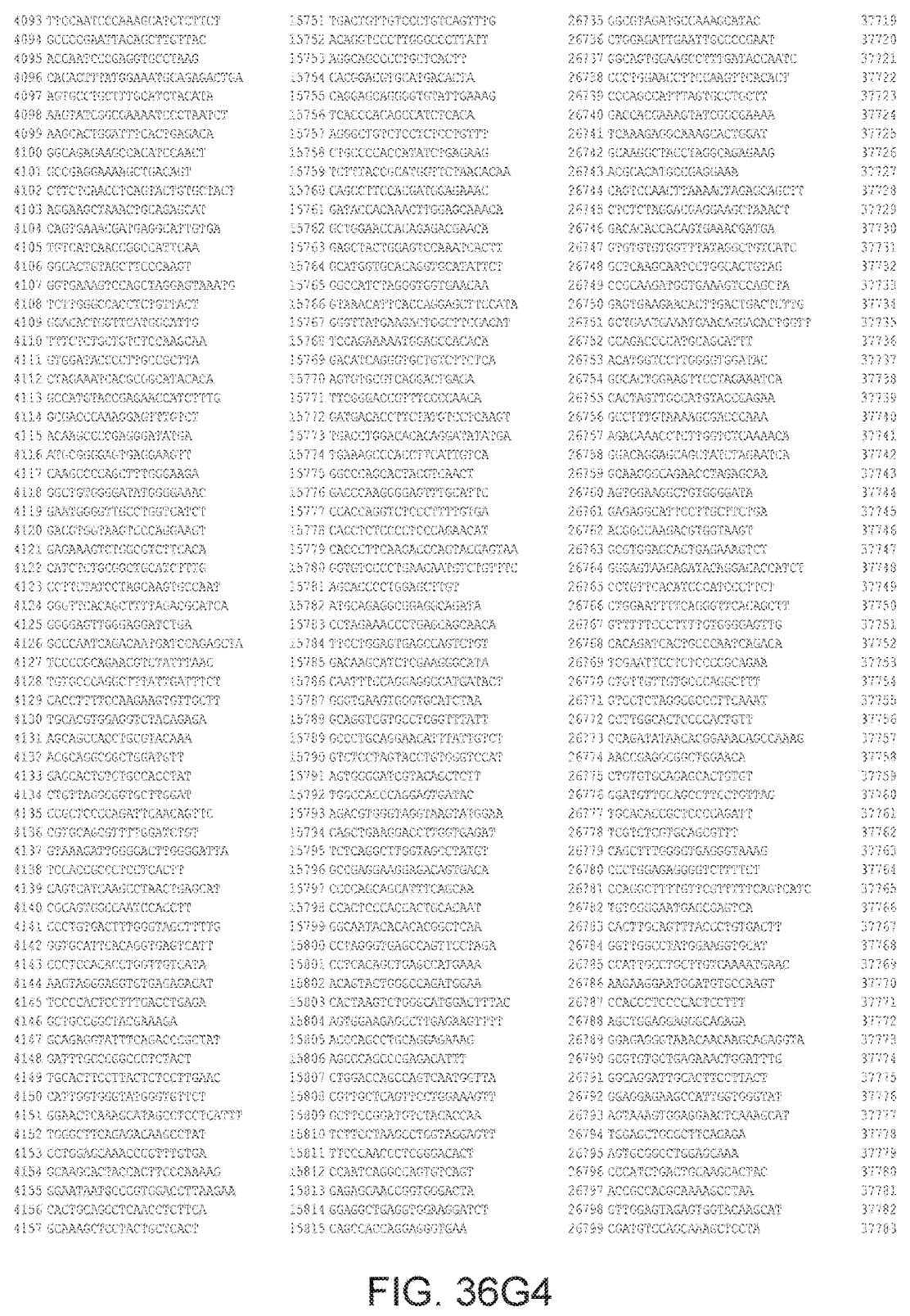
Figure 36G5:
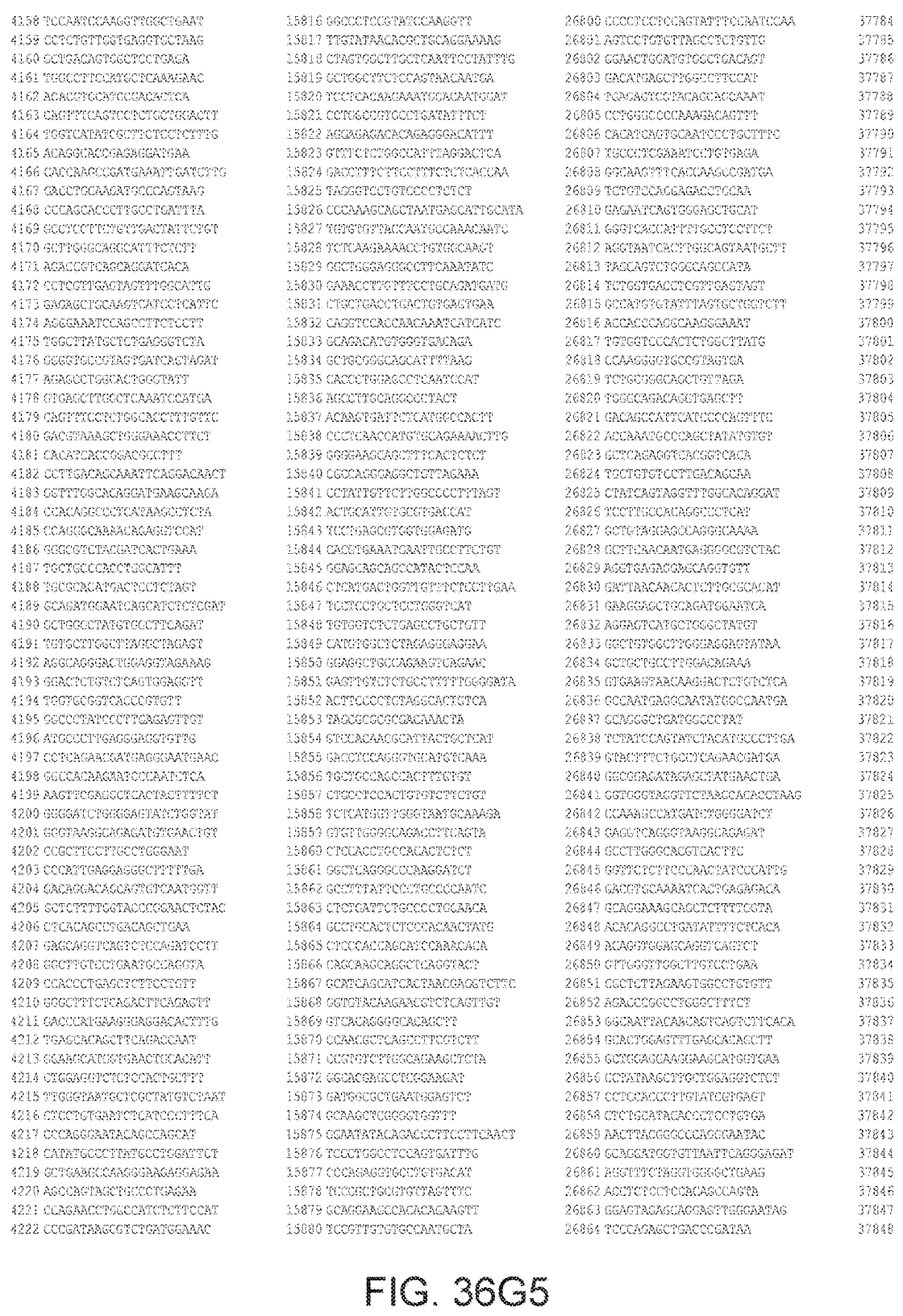
Figure 36G7:
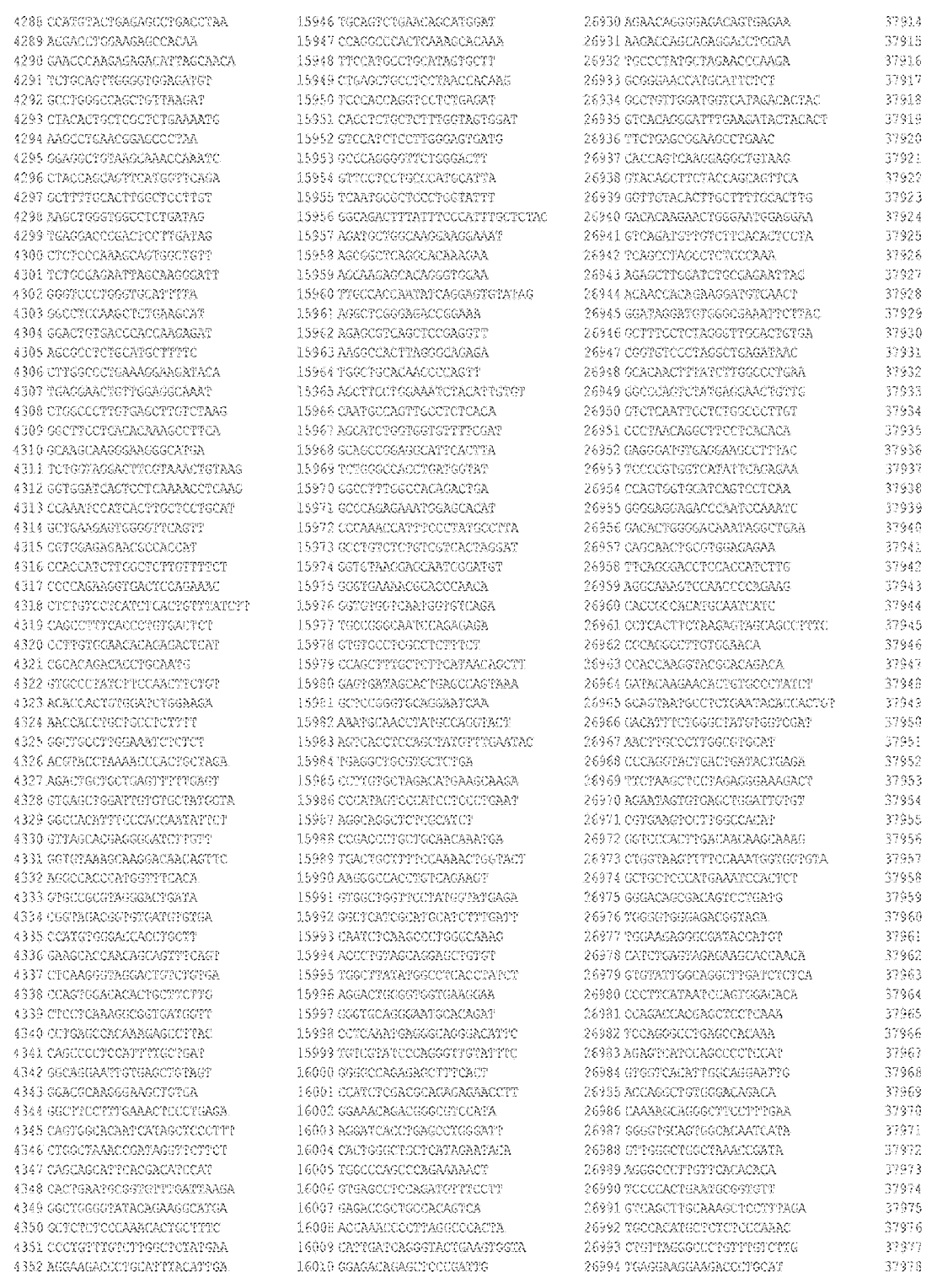
Figure 36G10:
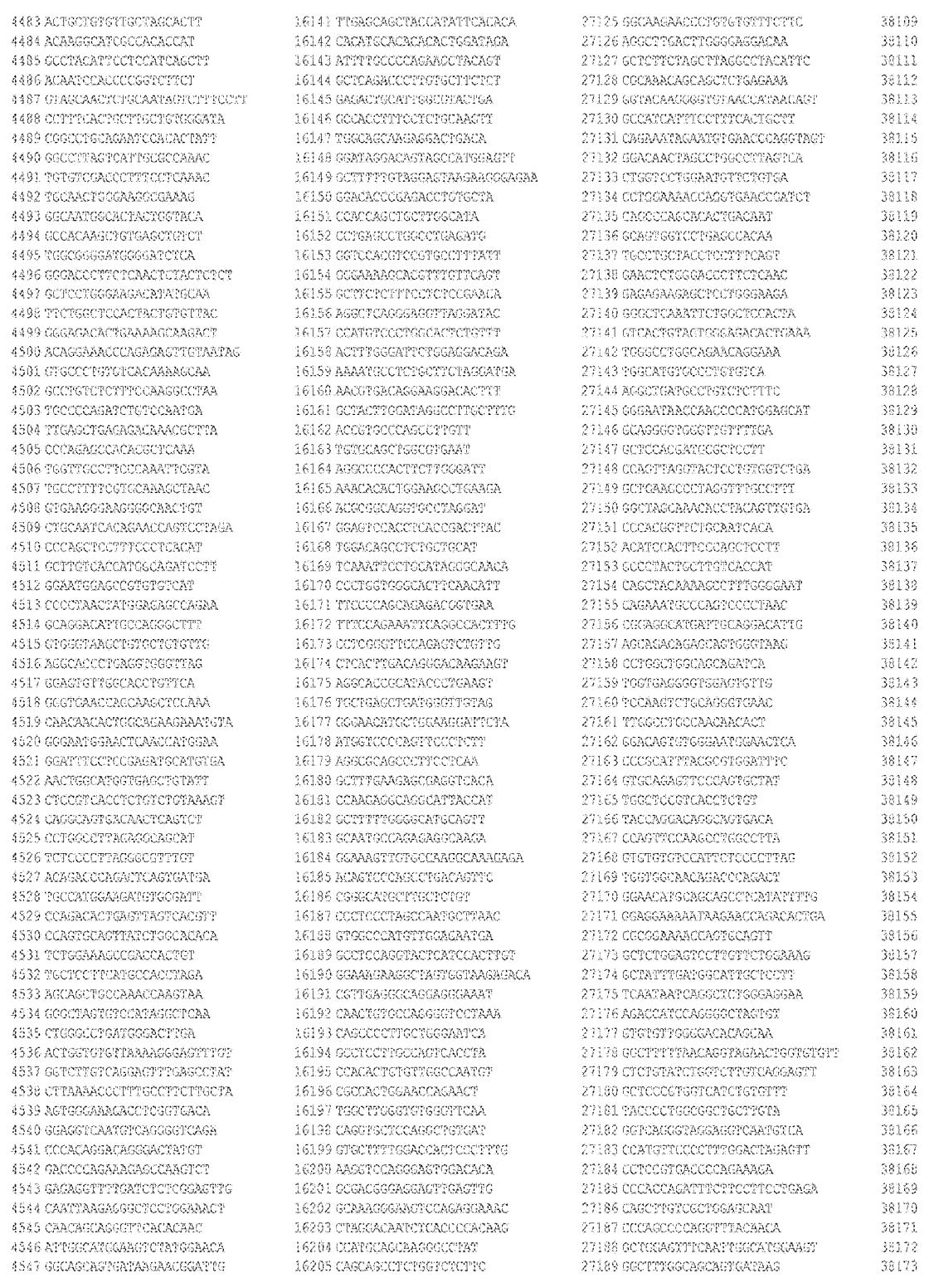
Figure 36H1:
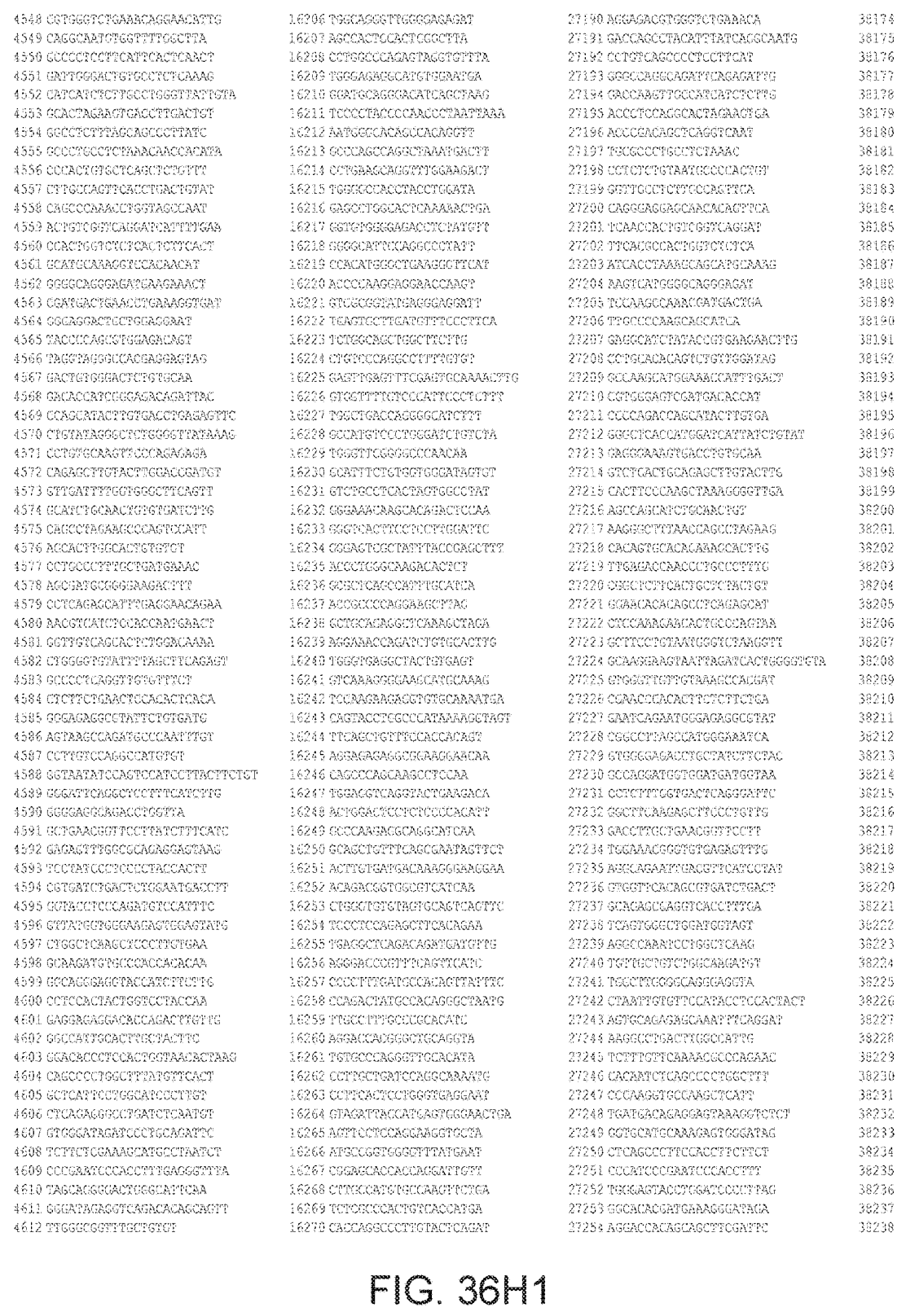
Figure 36H2:
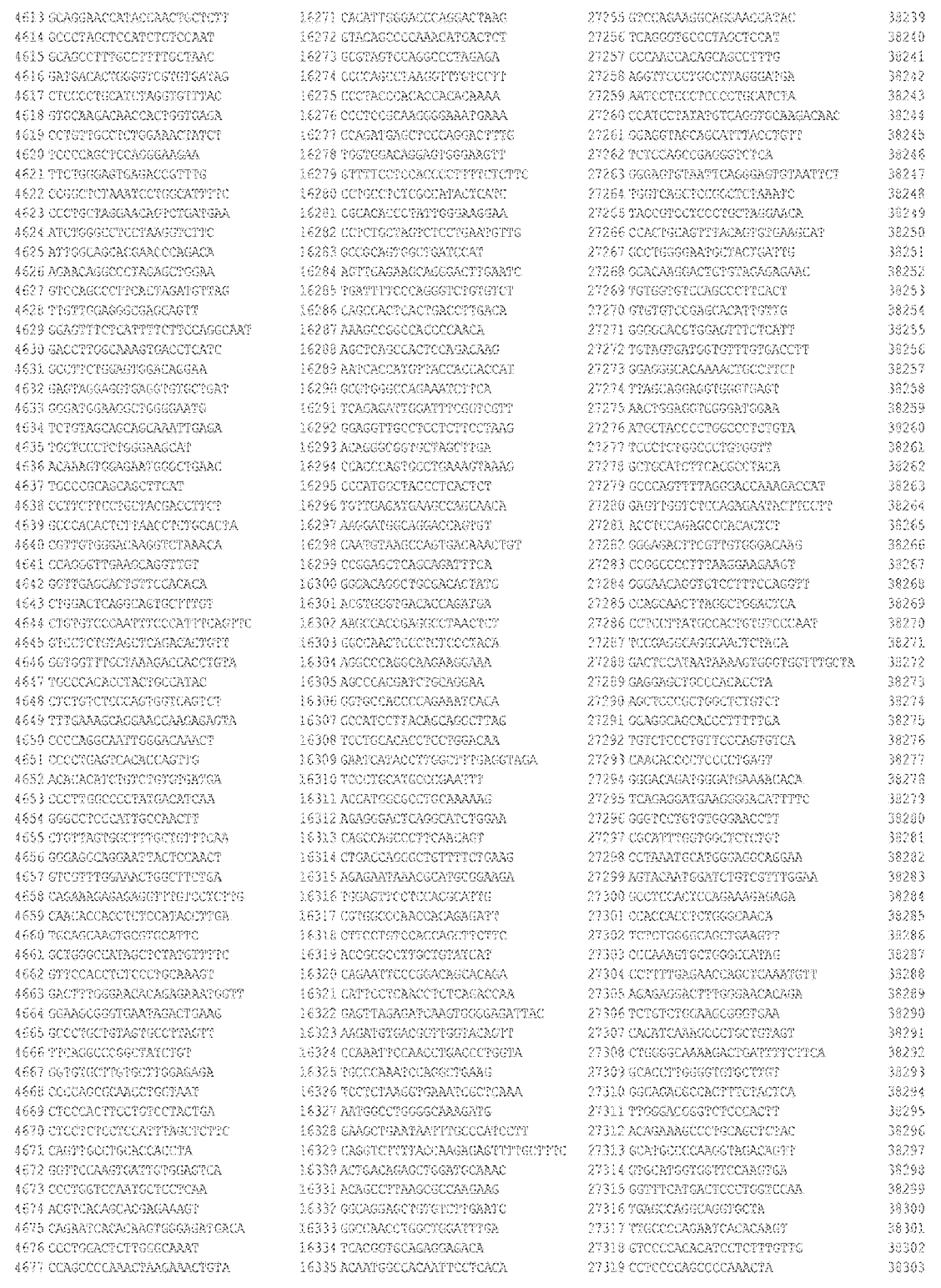
Figure 36H5:
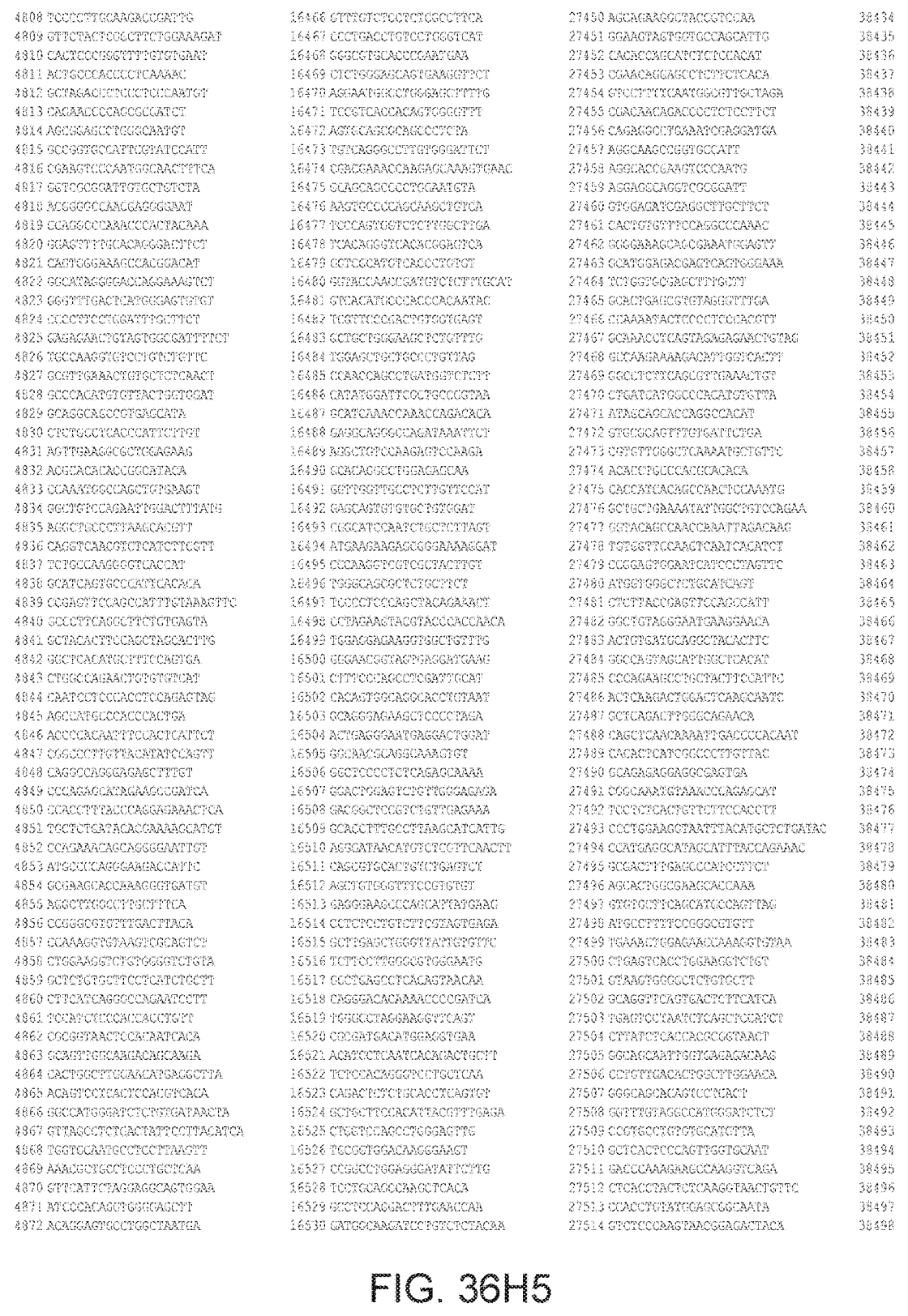
Figure 36H6:
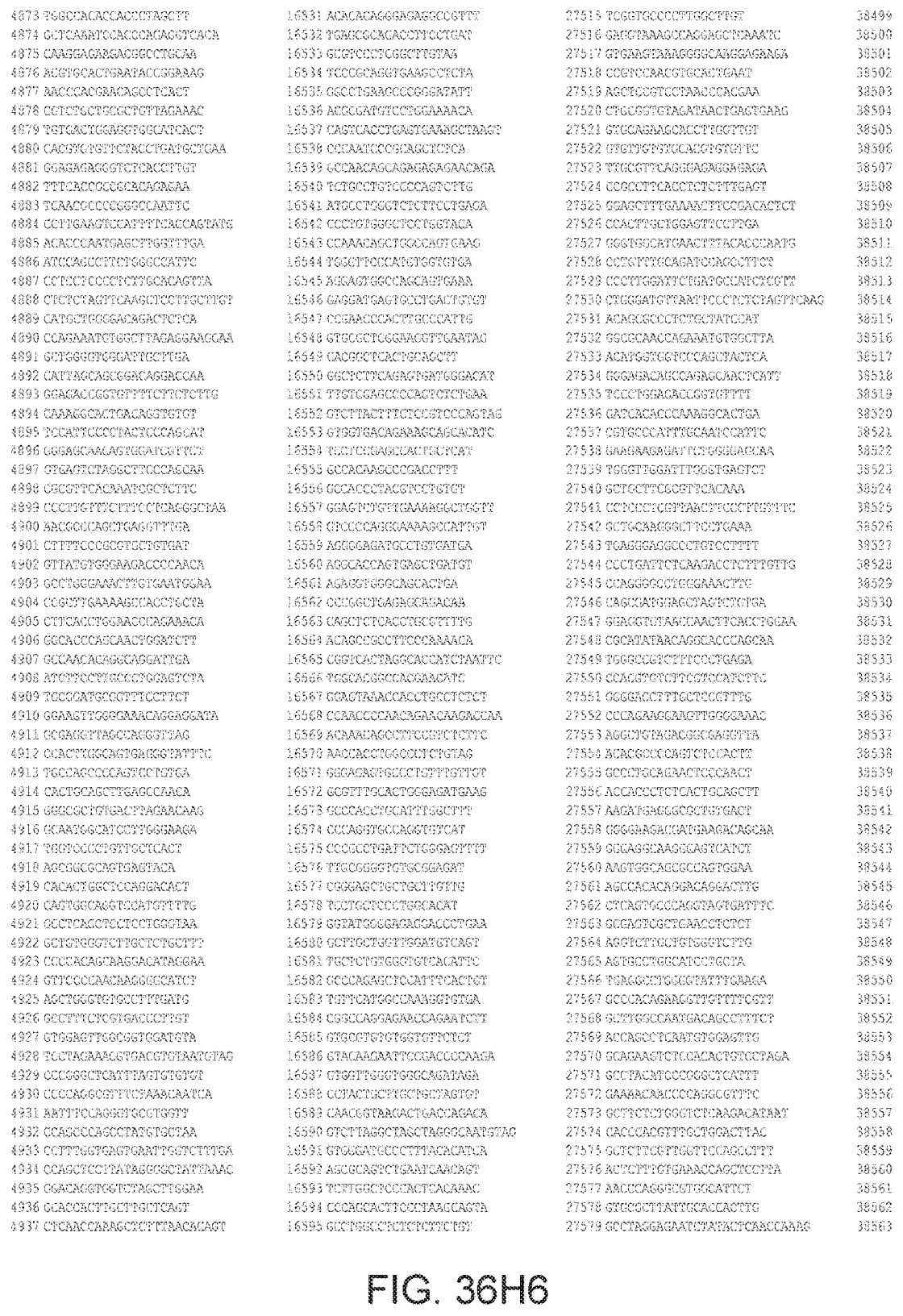
Figure 36H10:
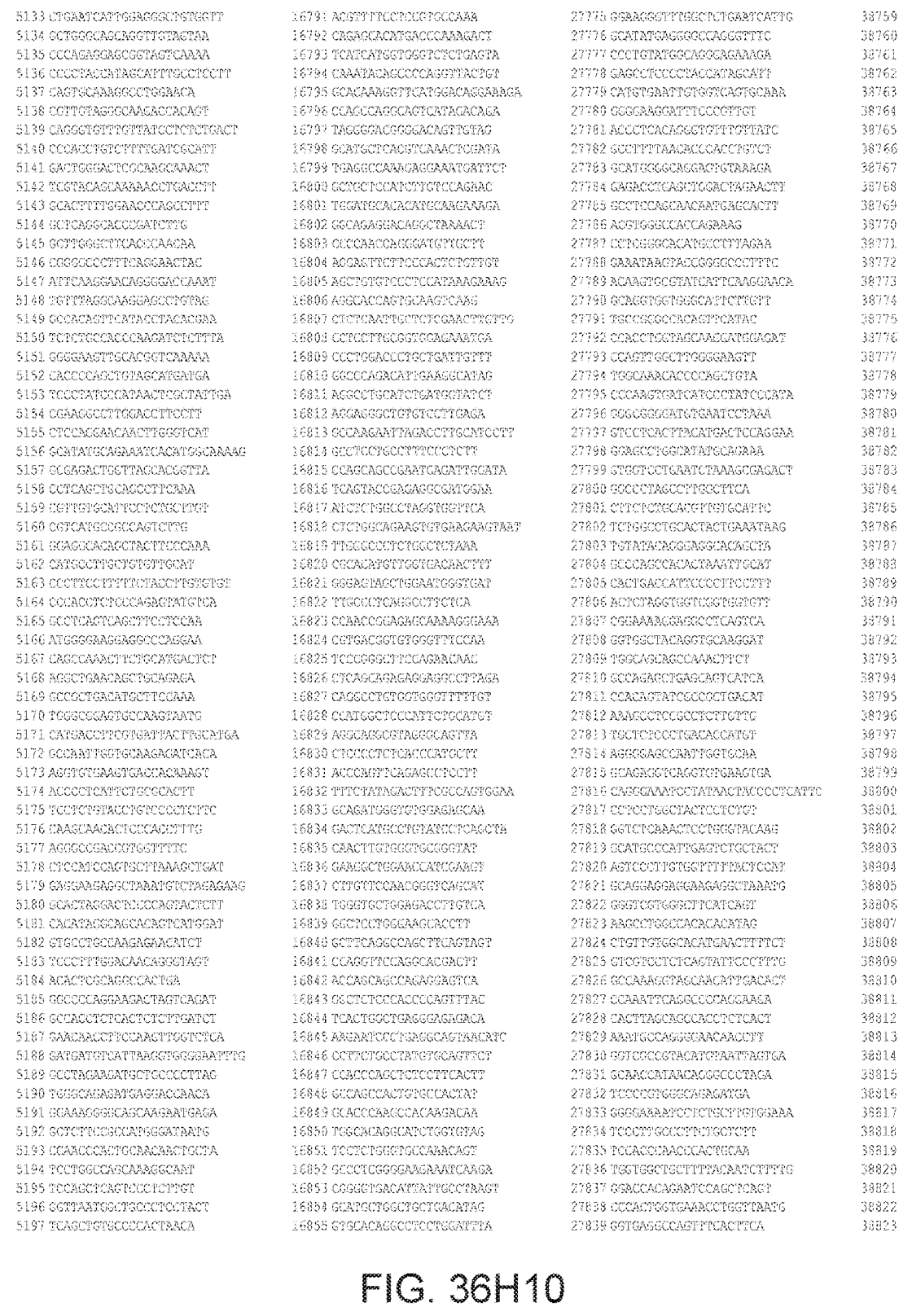
Figure 36I1:
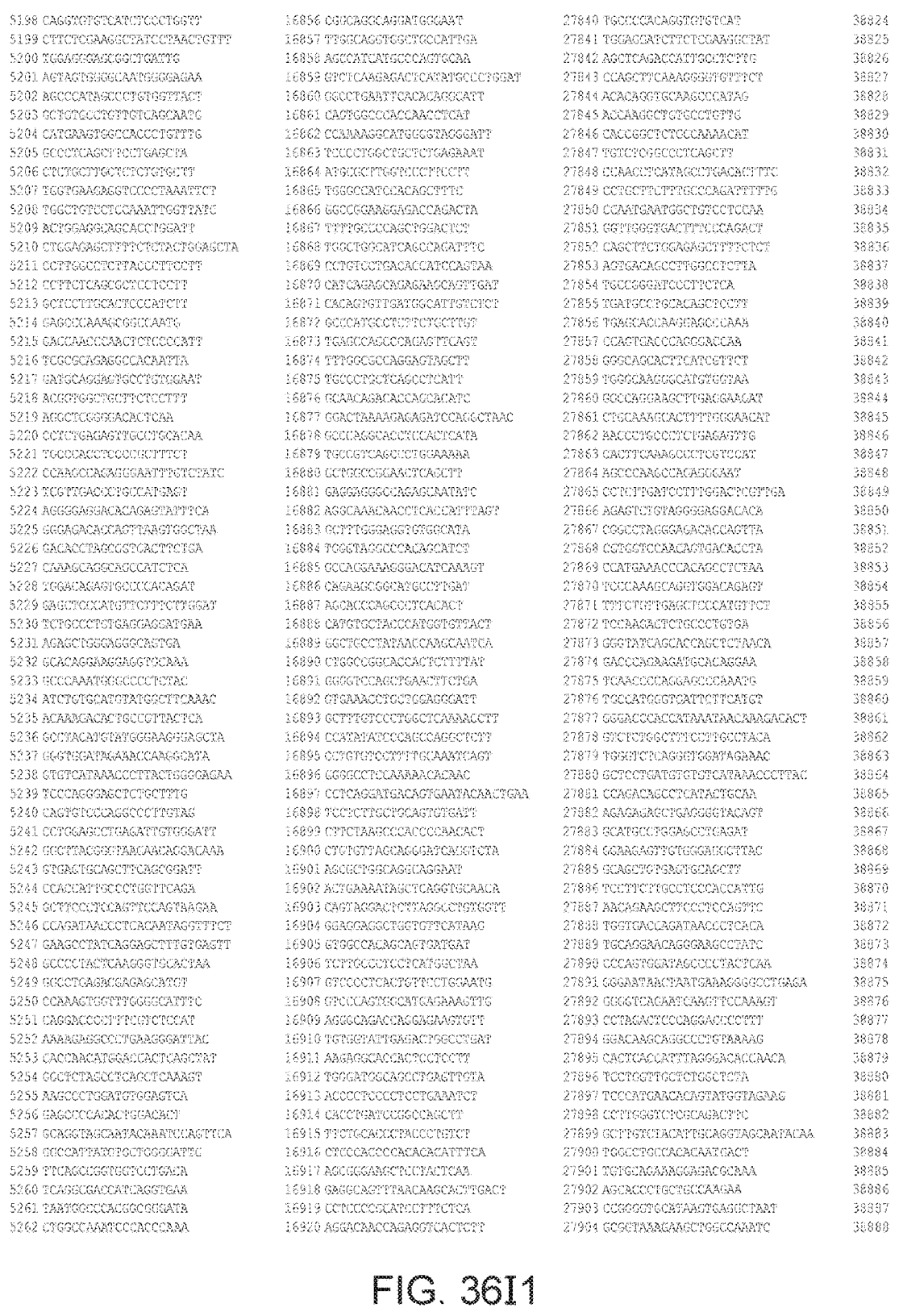
Figure 36I2:
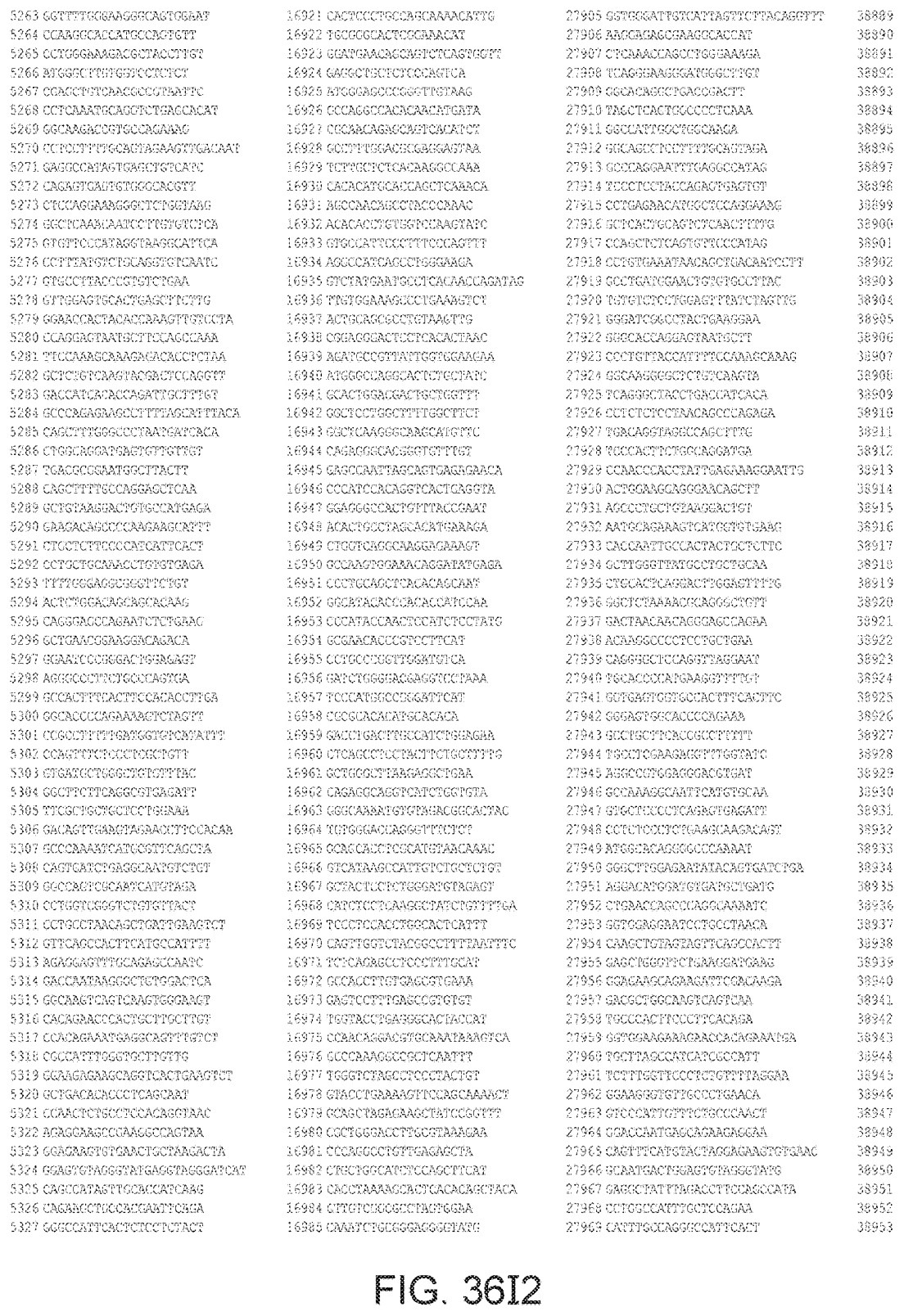
Figure 36I6:
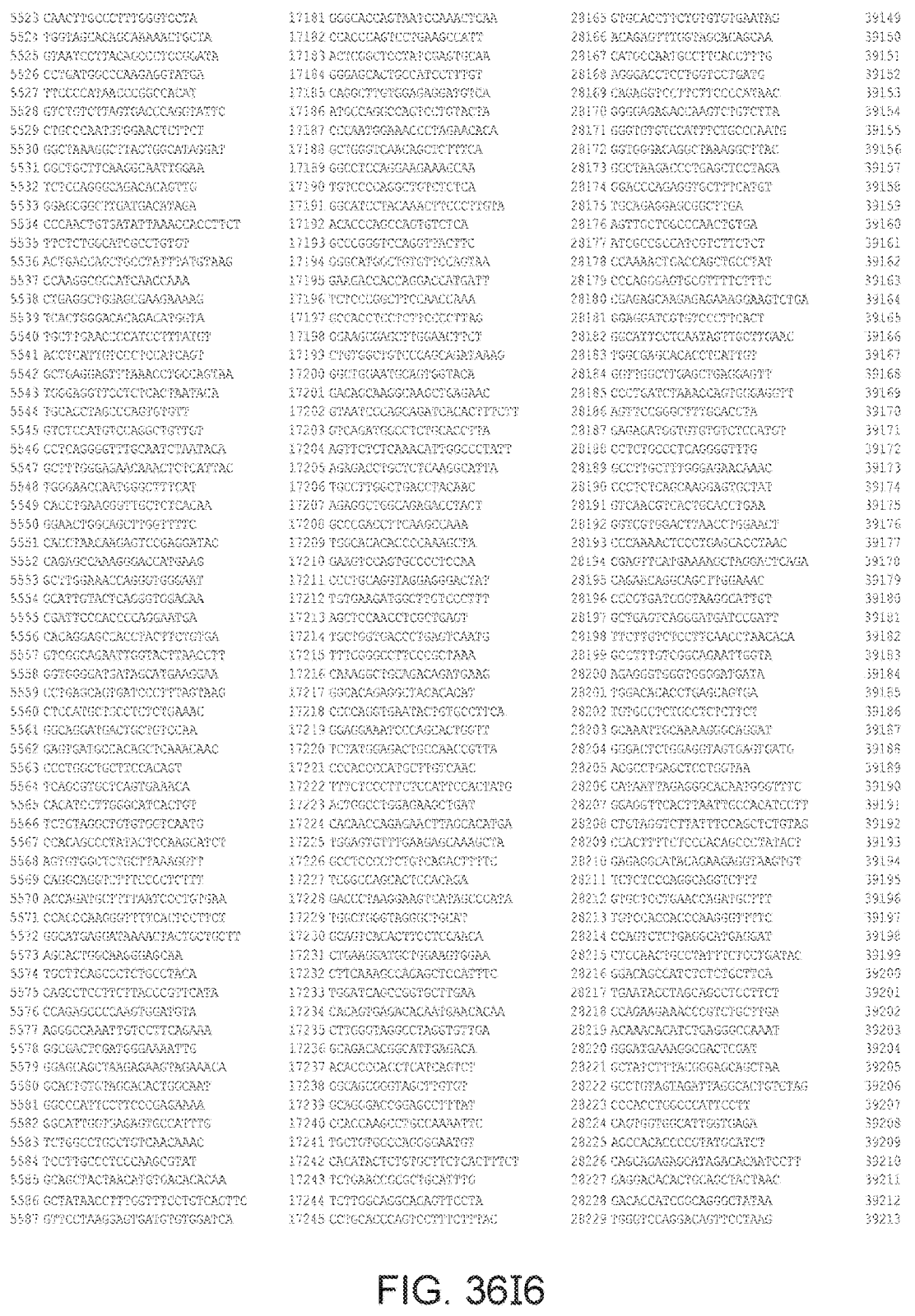
Figure 36I8:
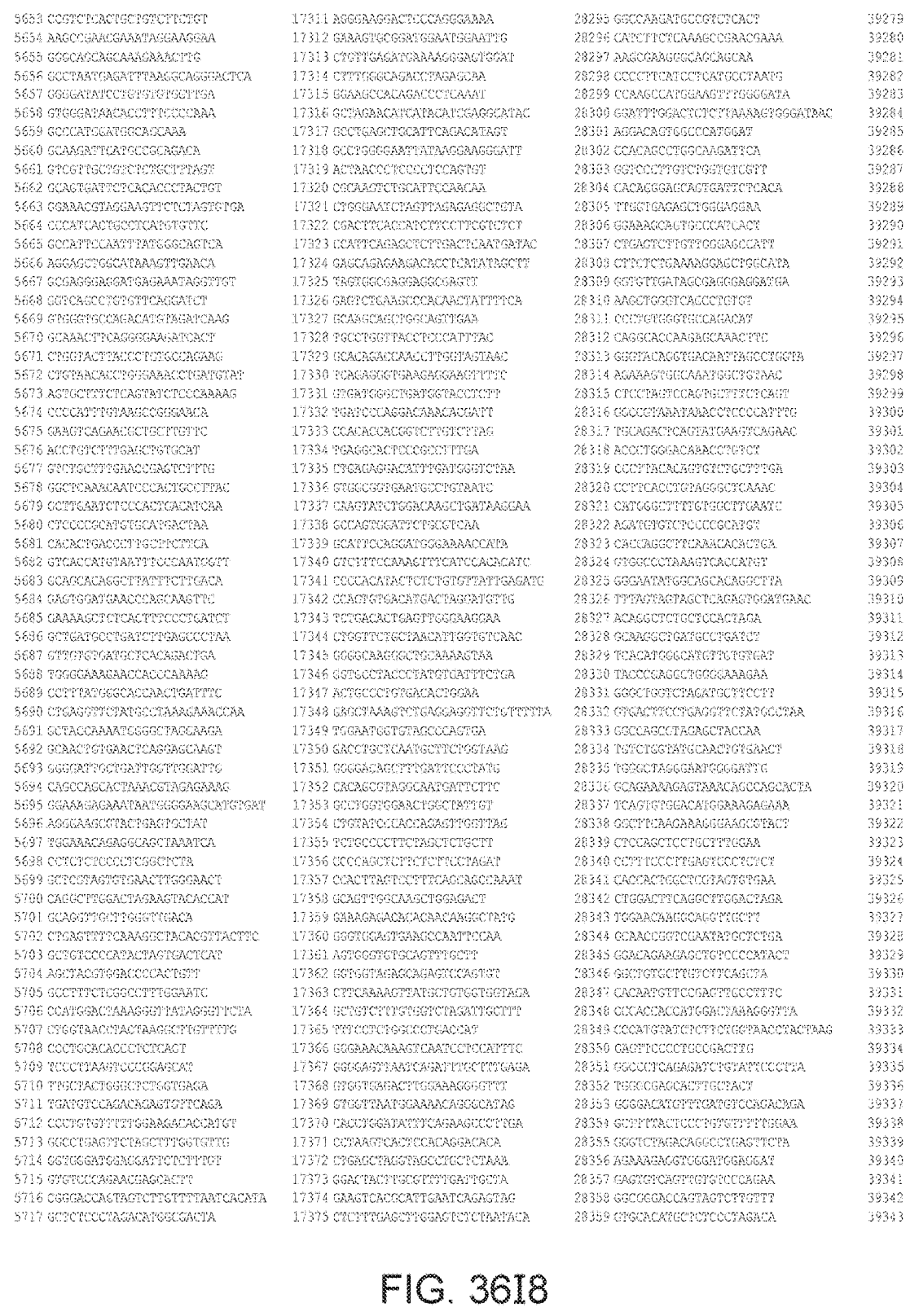
Figure 36I9:
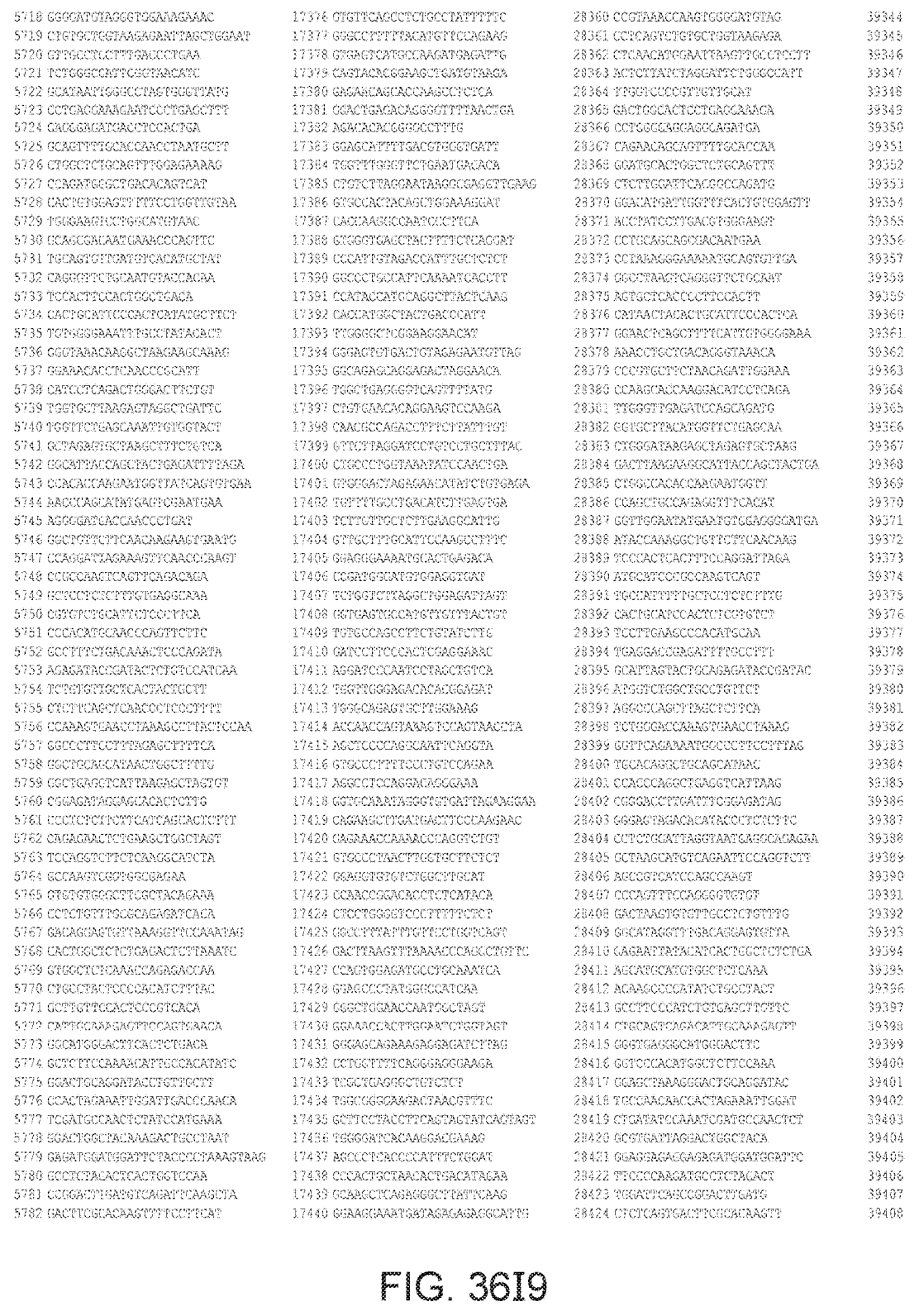
Figure 36I10:
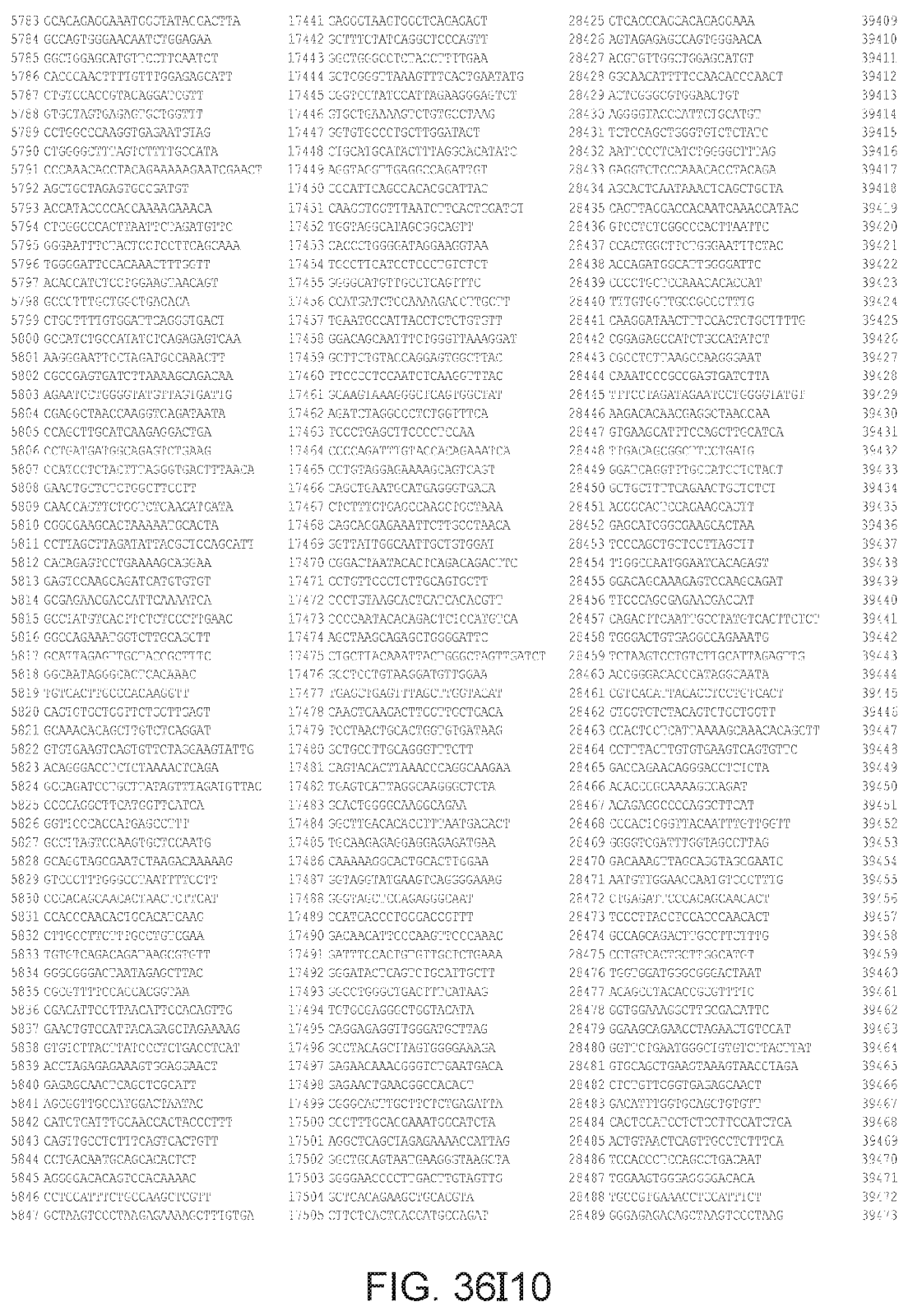
Figure 36J1:
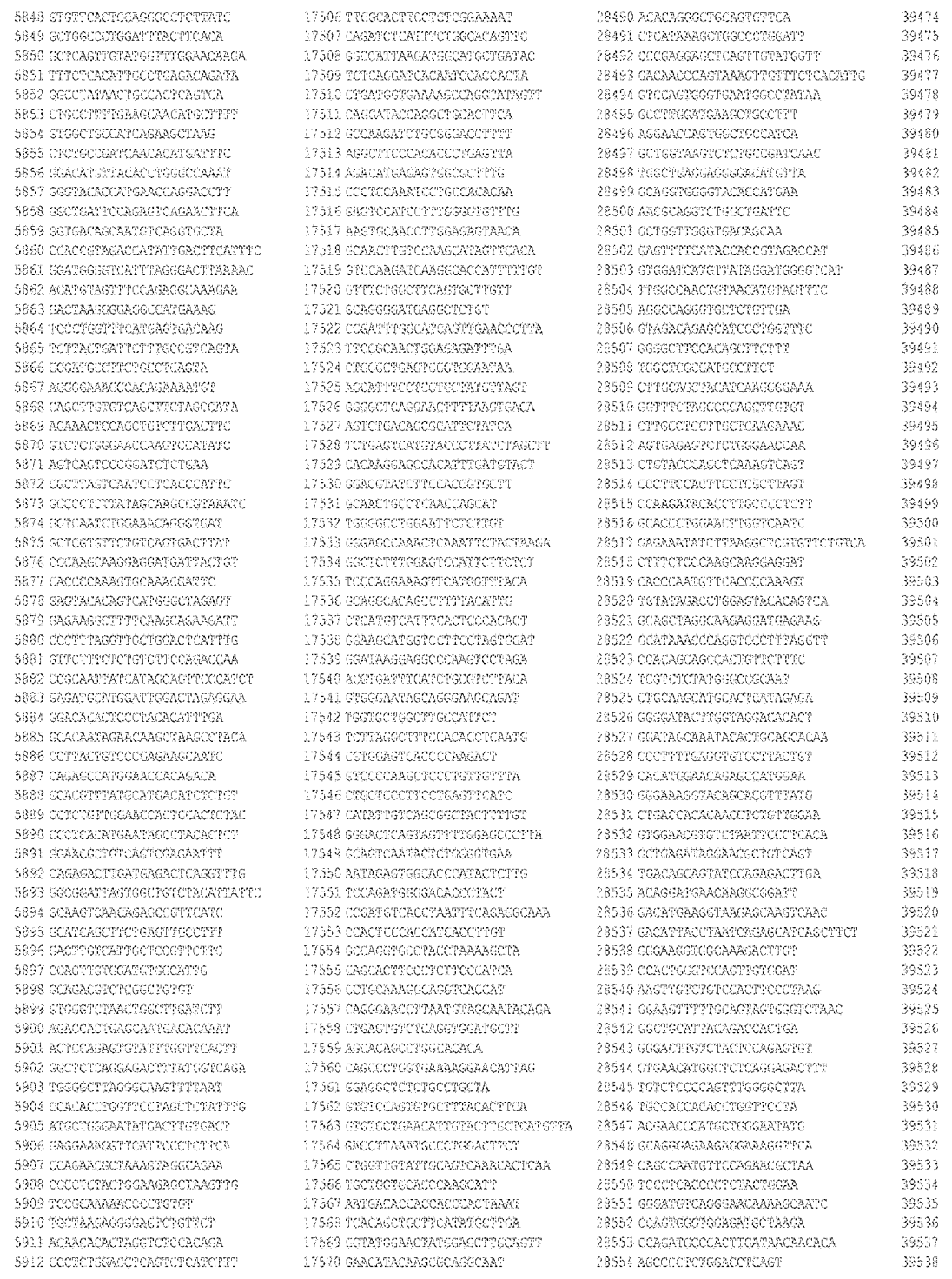
Figure 36J4:
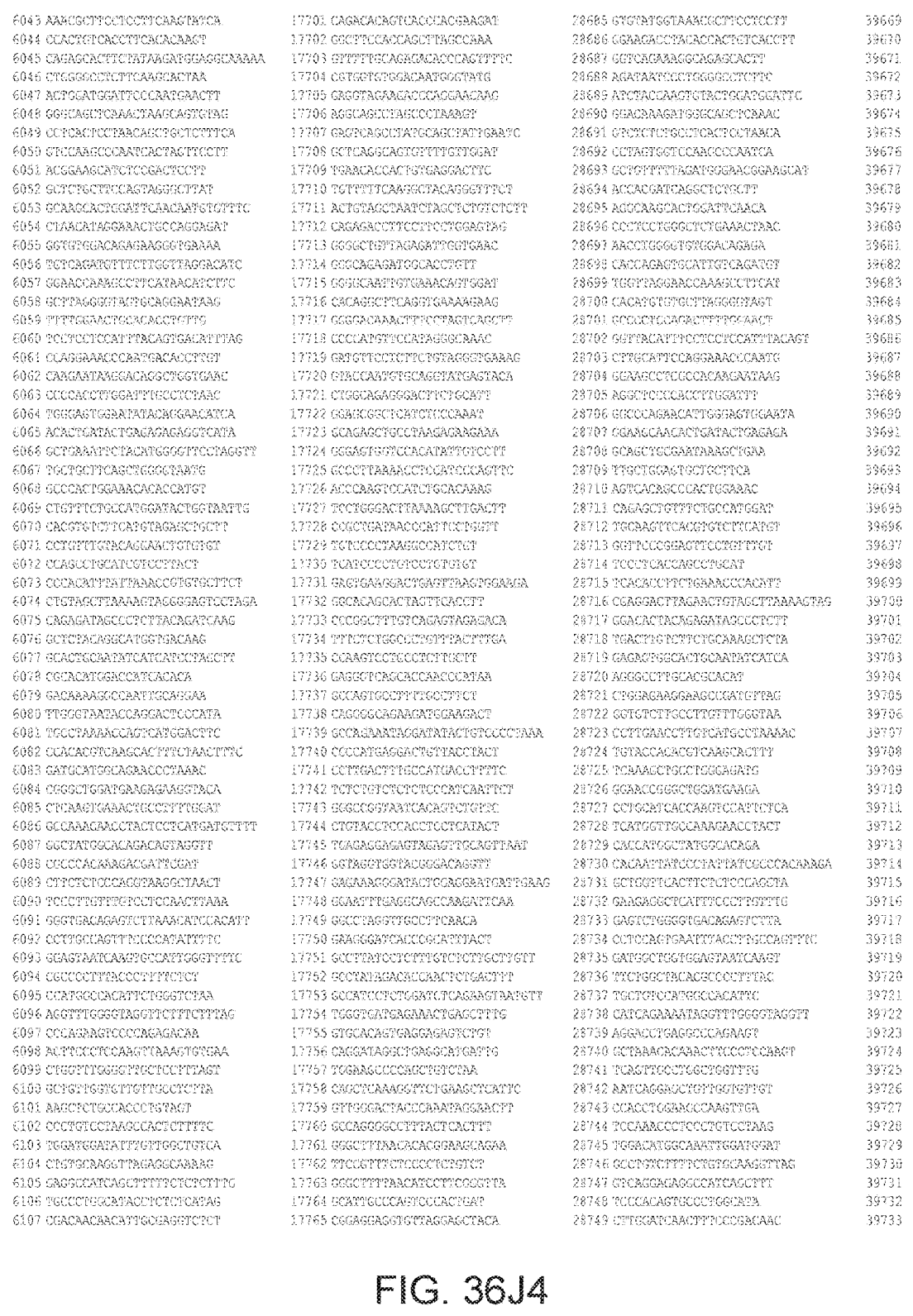
Figure 36J5:
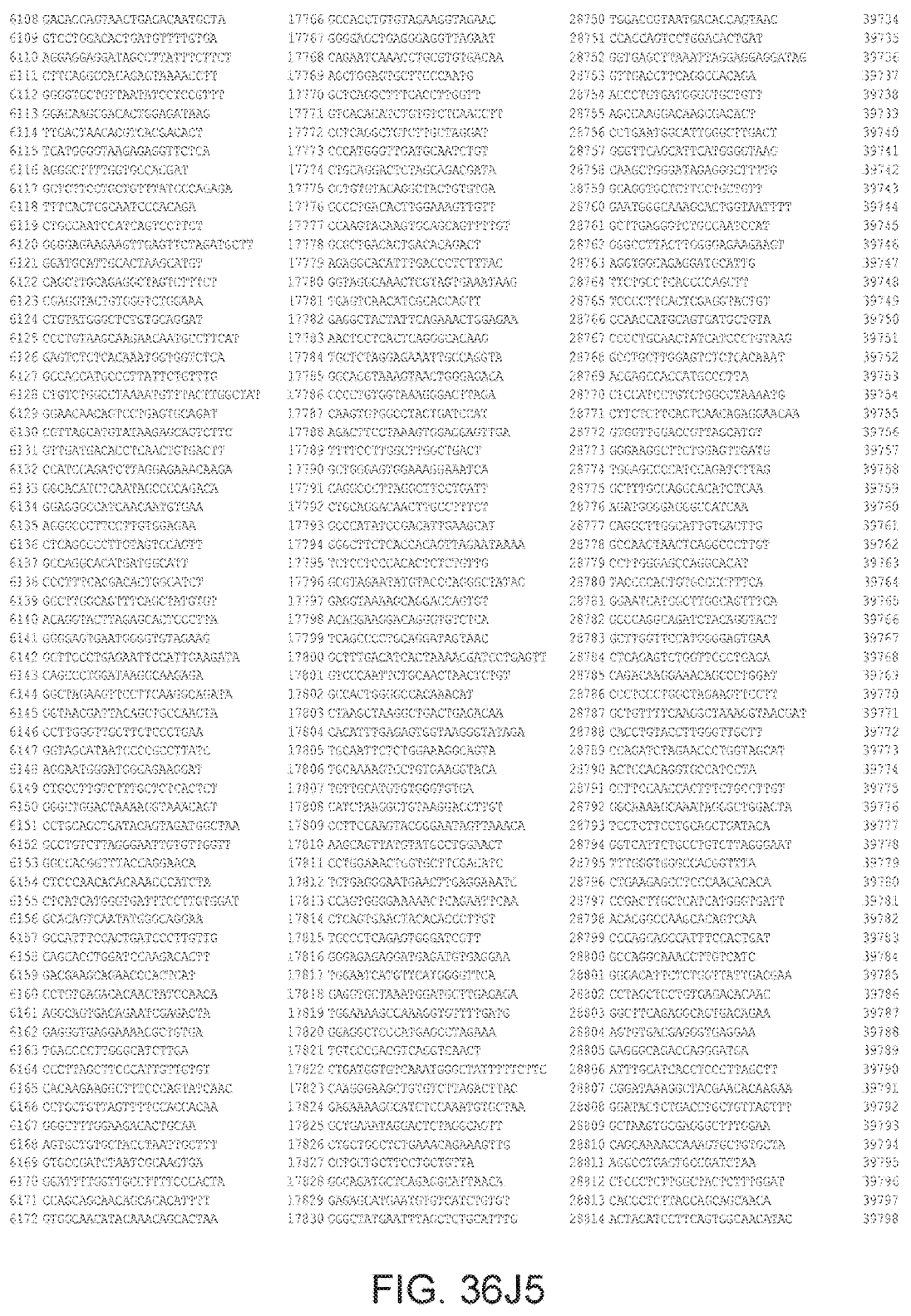
Figure 36J6:
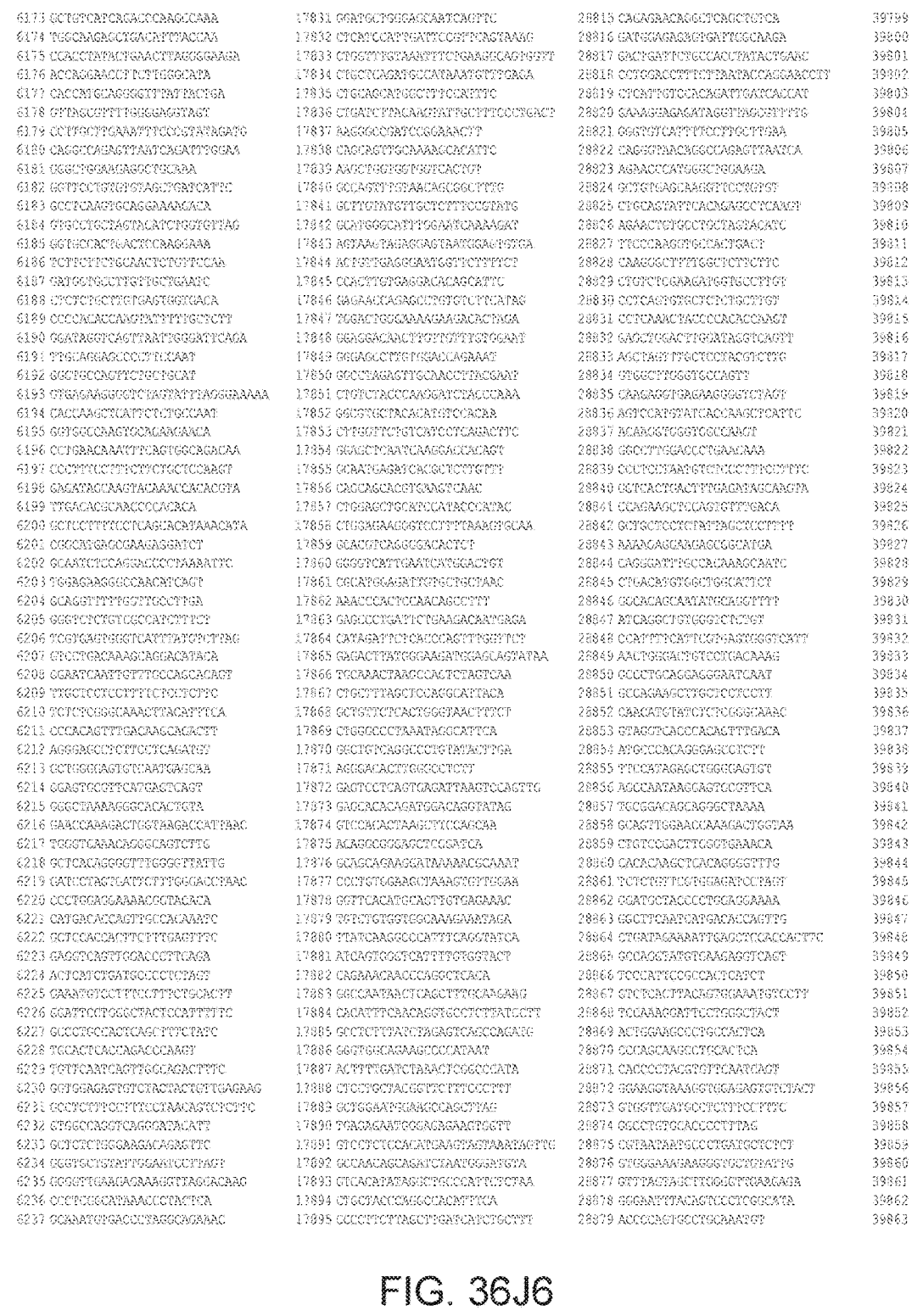
Figure 36J7:
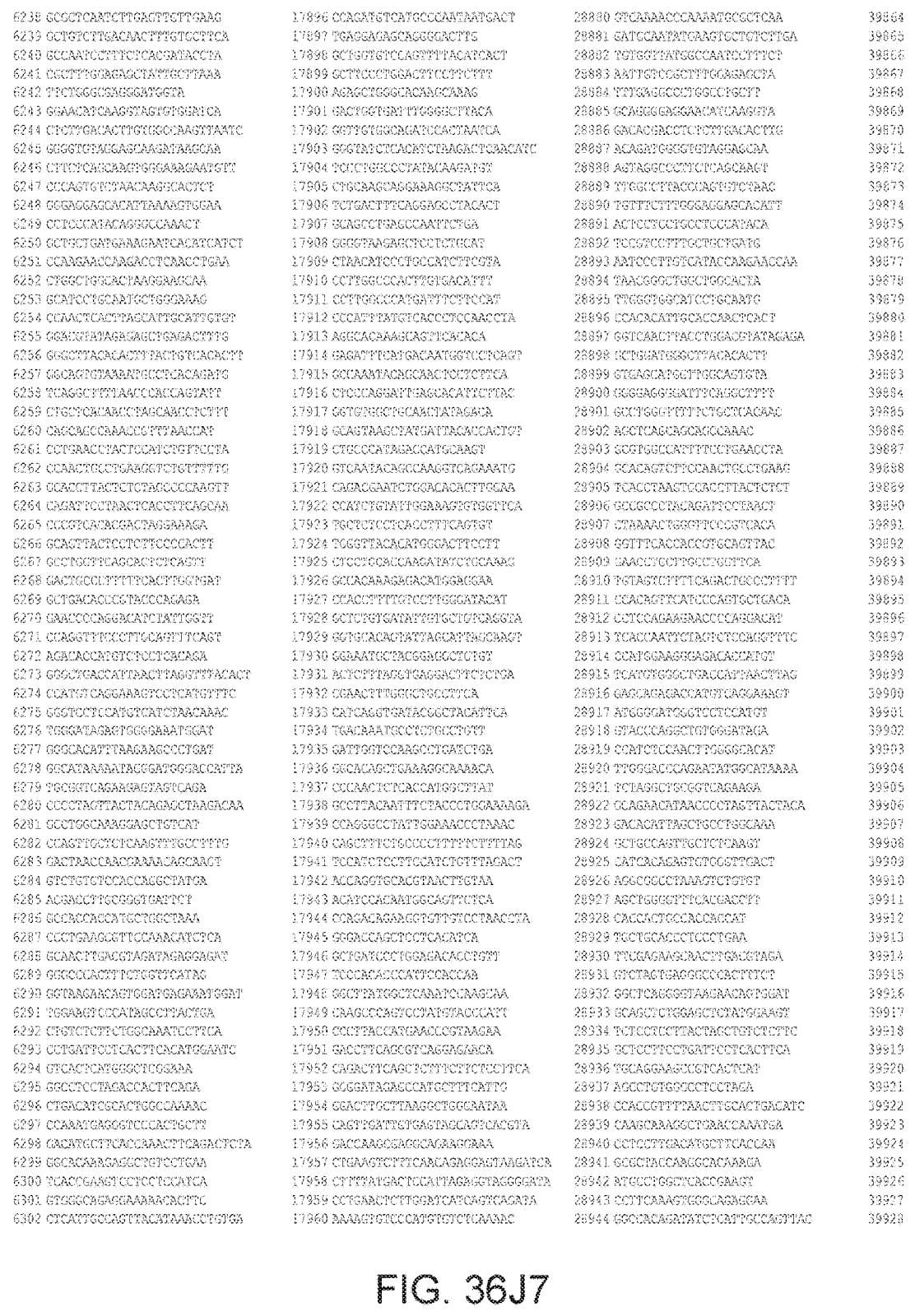
Figure 36J8:
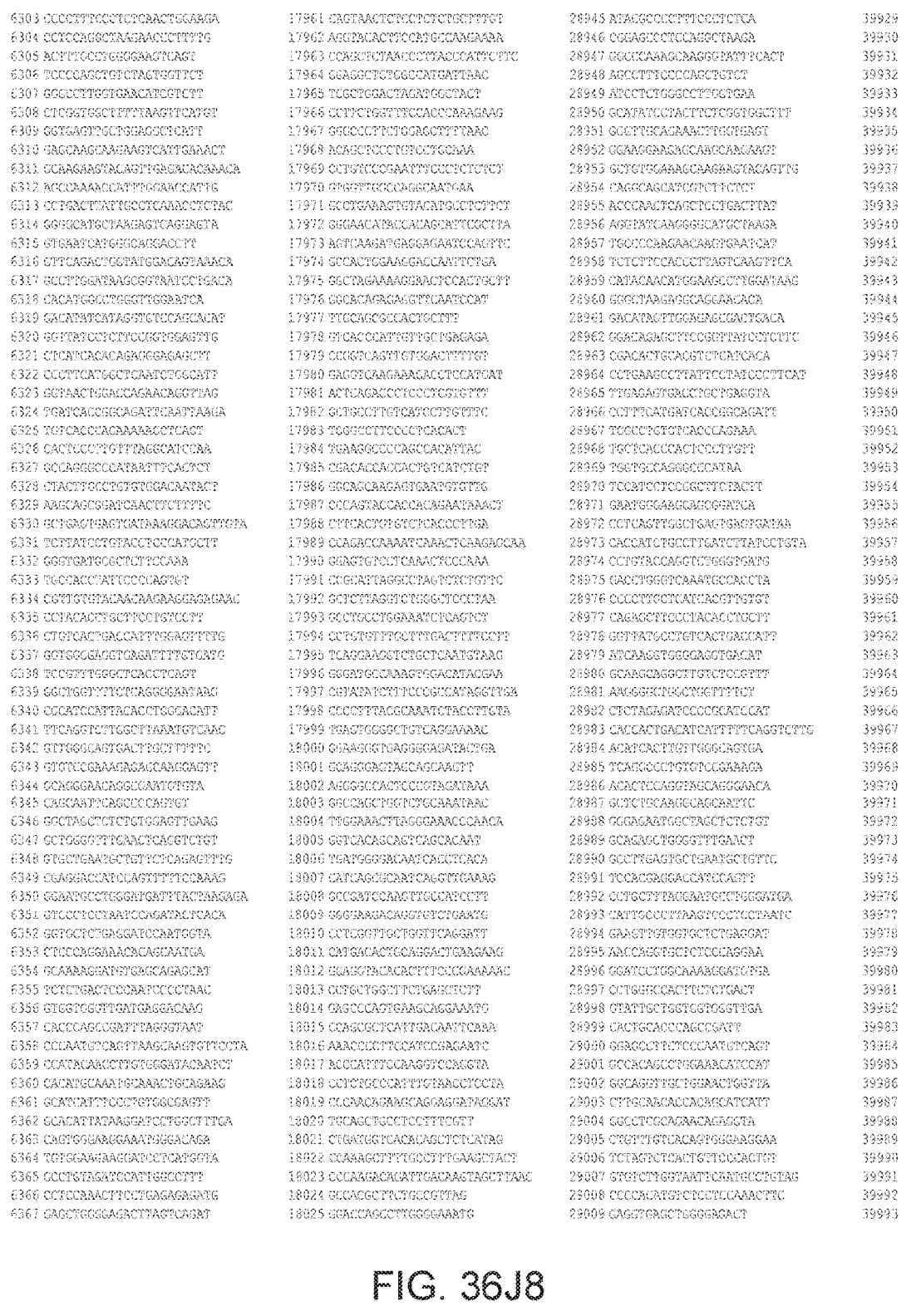
Figure 36K1:
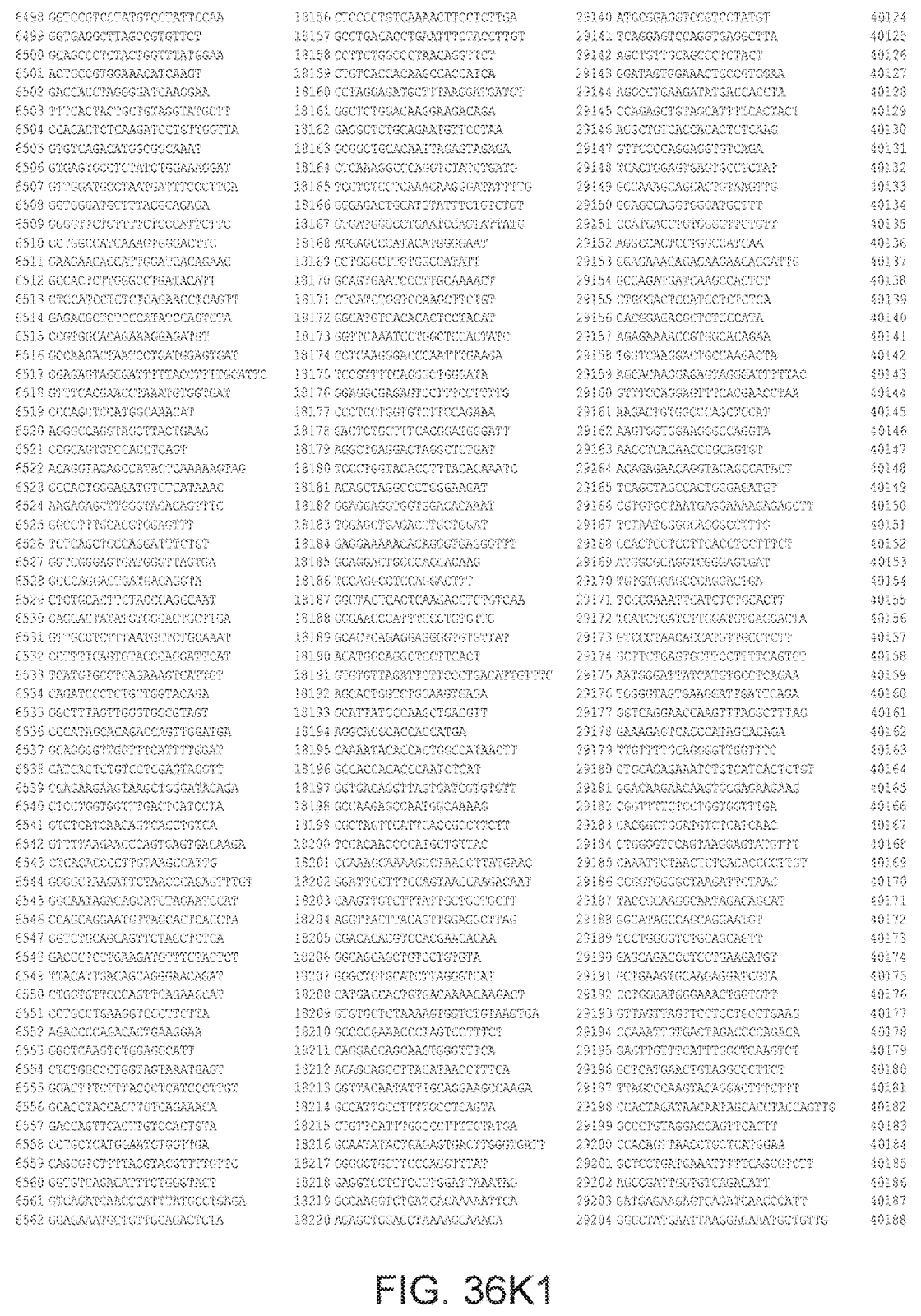
Figure 36K3:
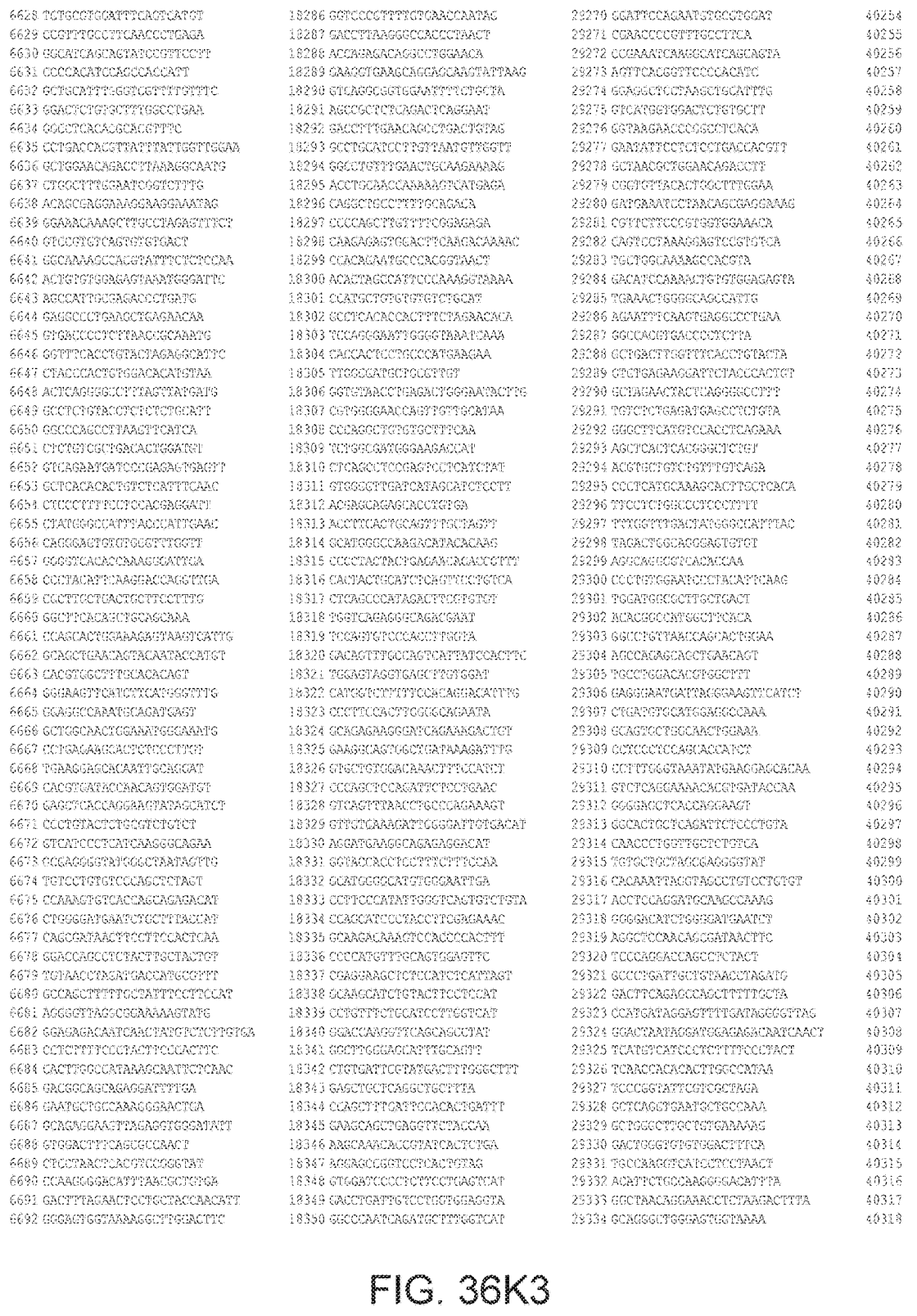
Figure 36K4:
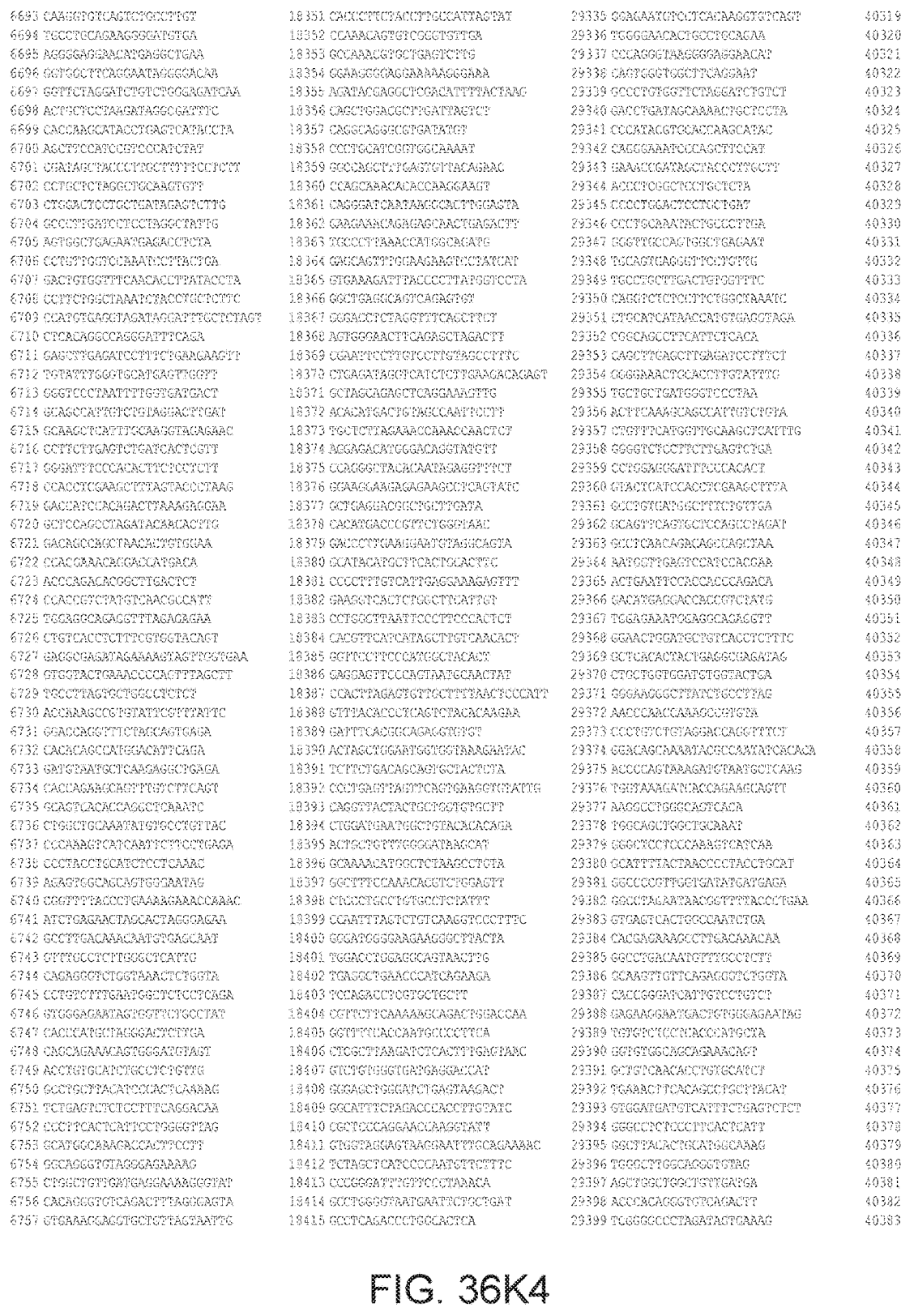
Figure 36K5:
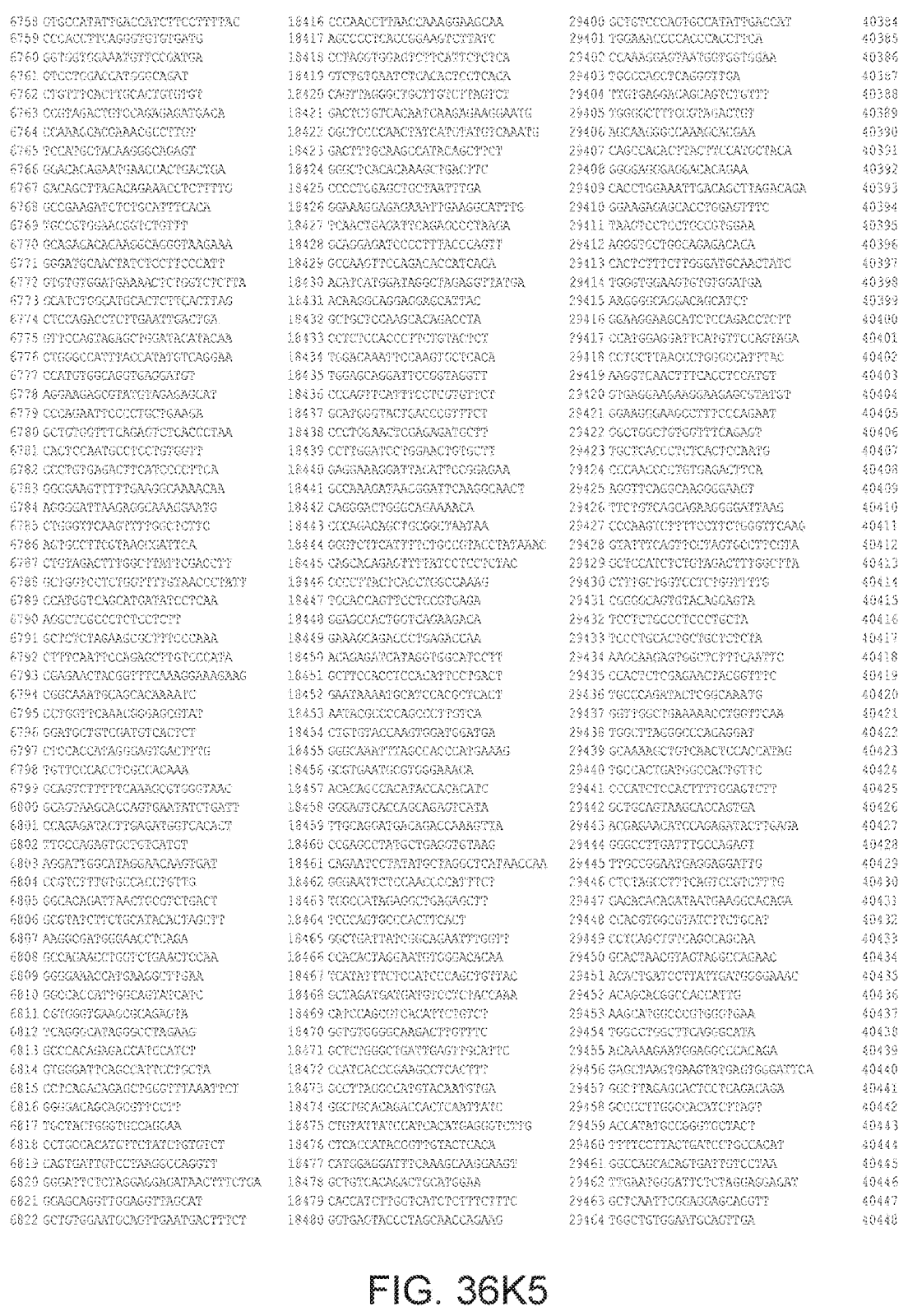
Figure 36K9:
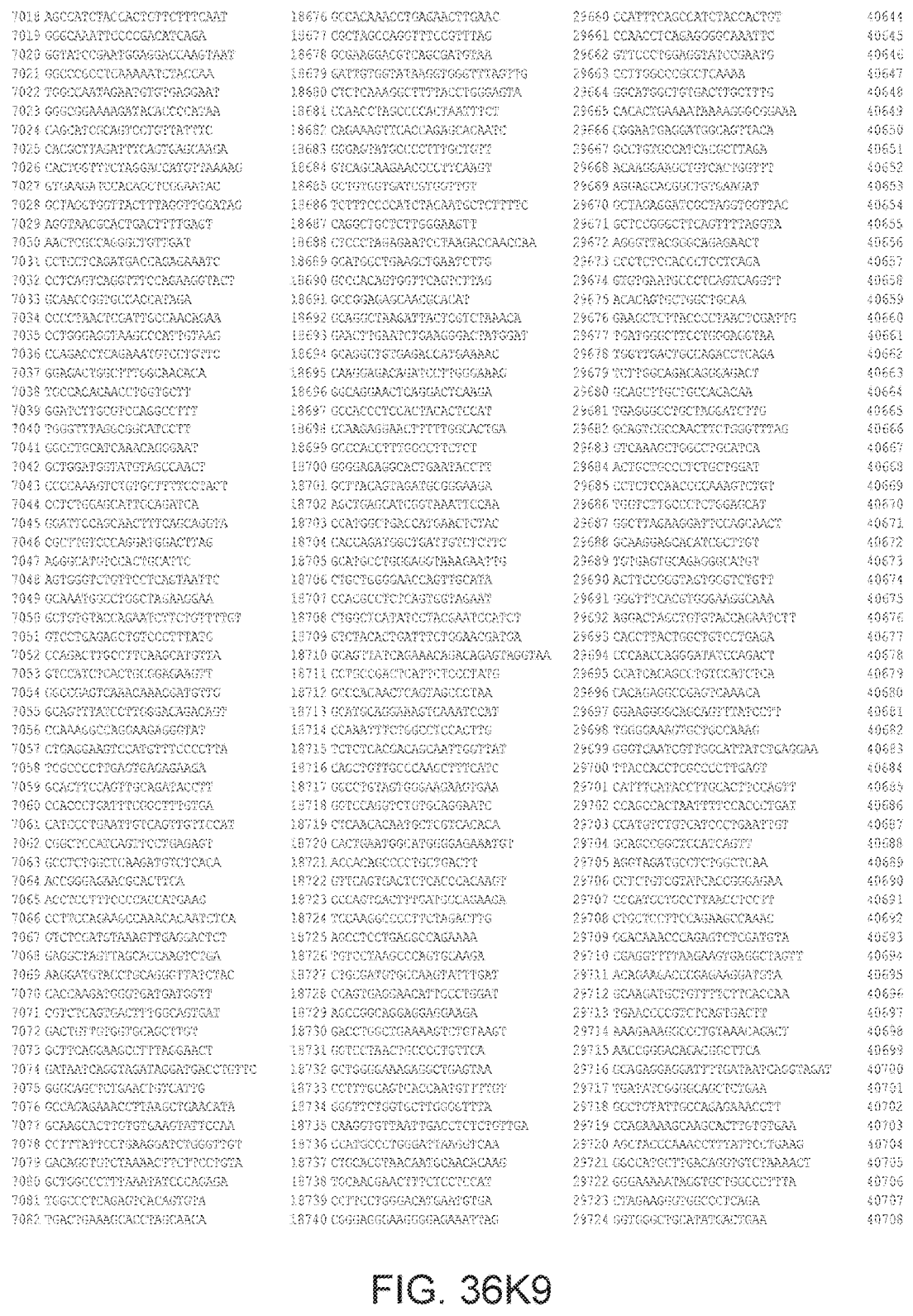
Figure 36K10:
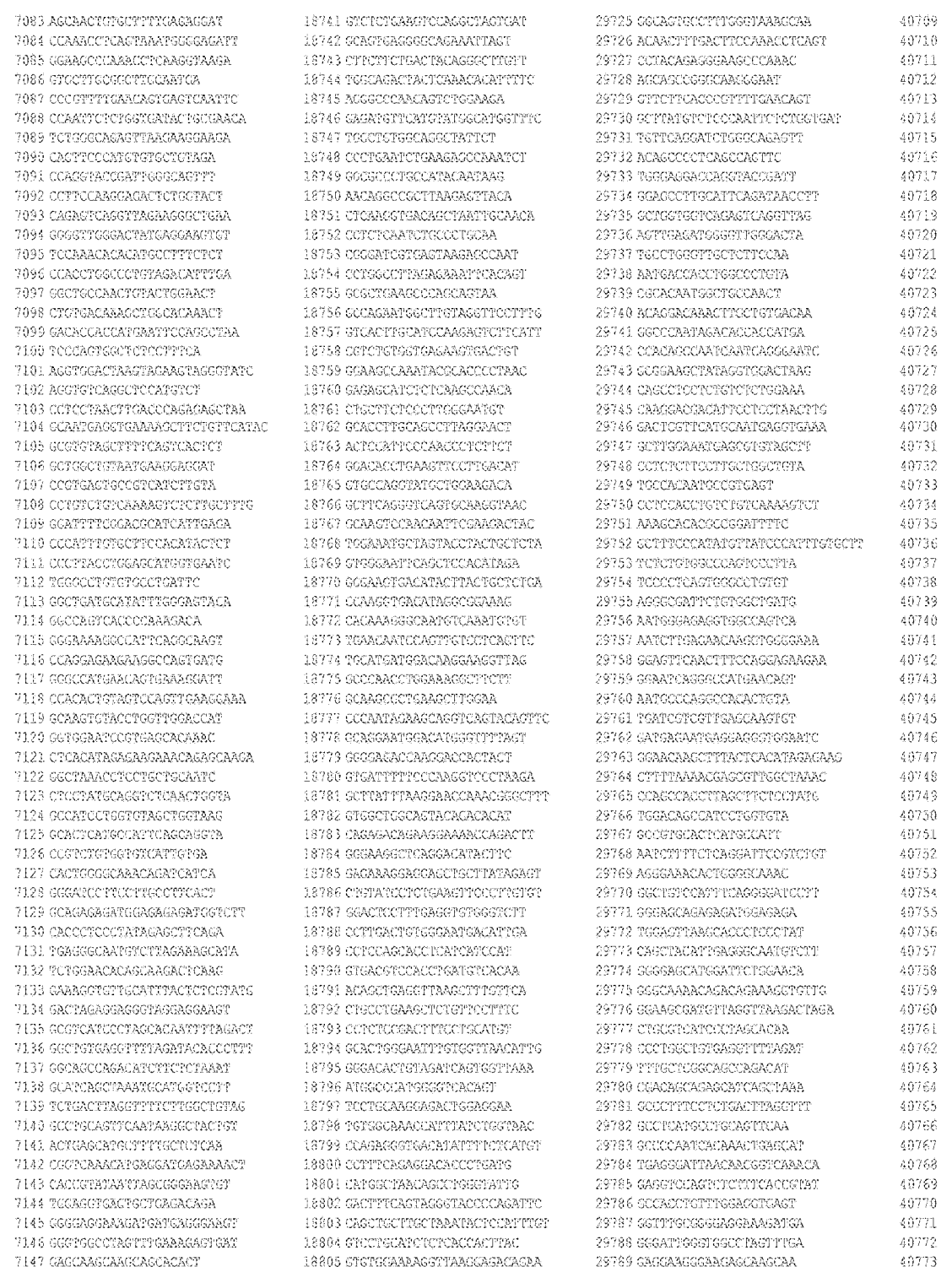
Figure 36L1:
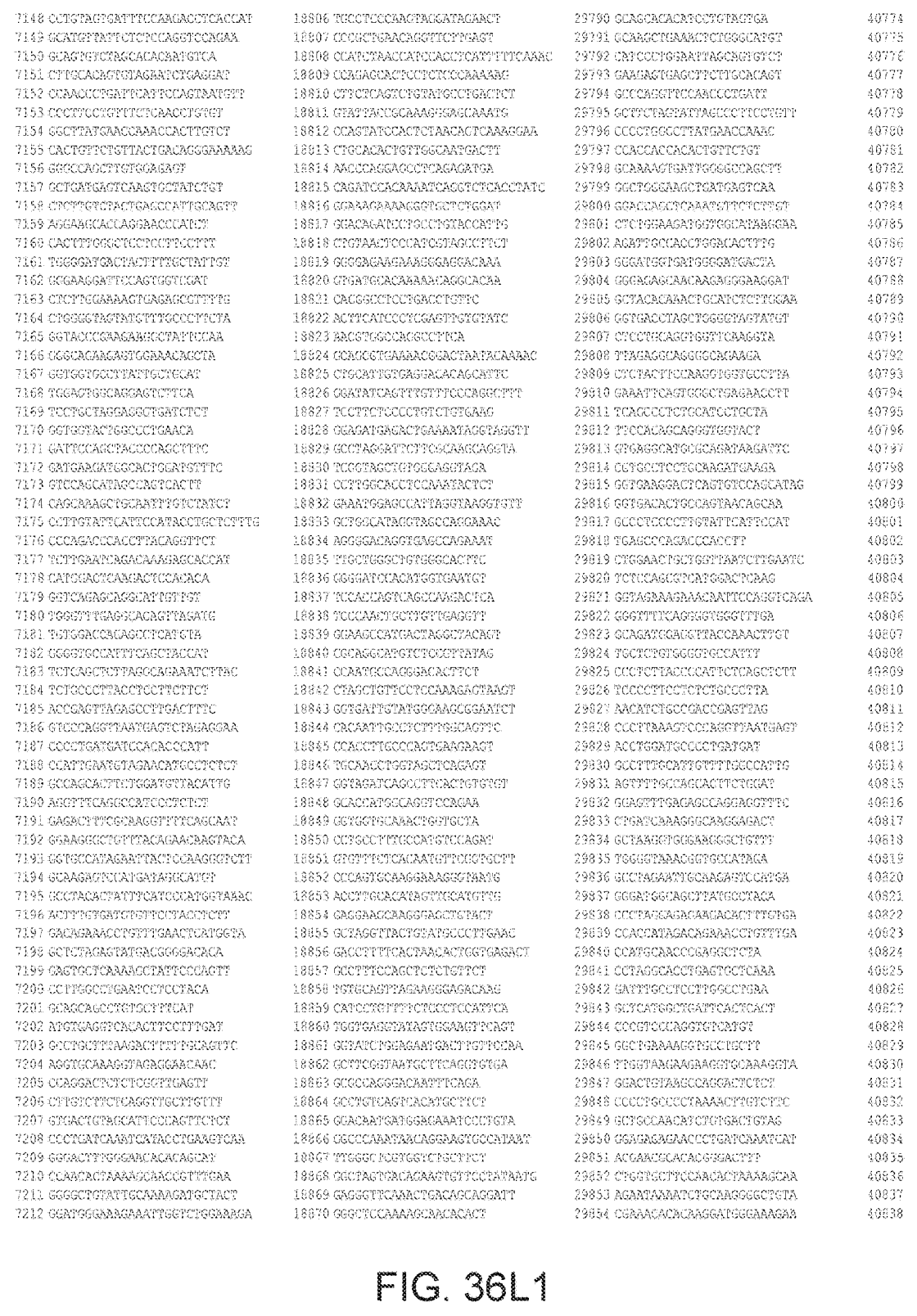
Figure 36L2:
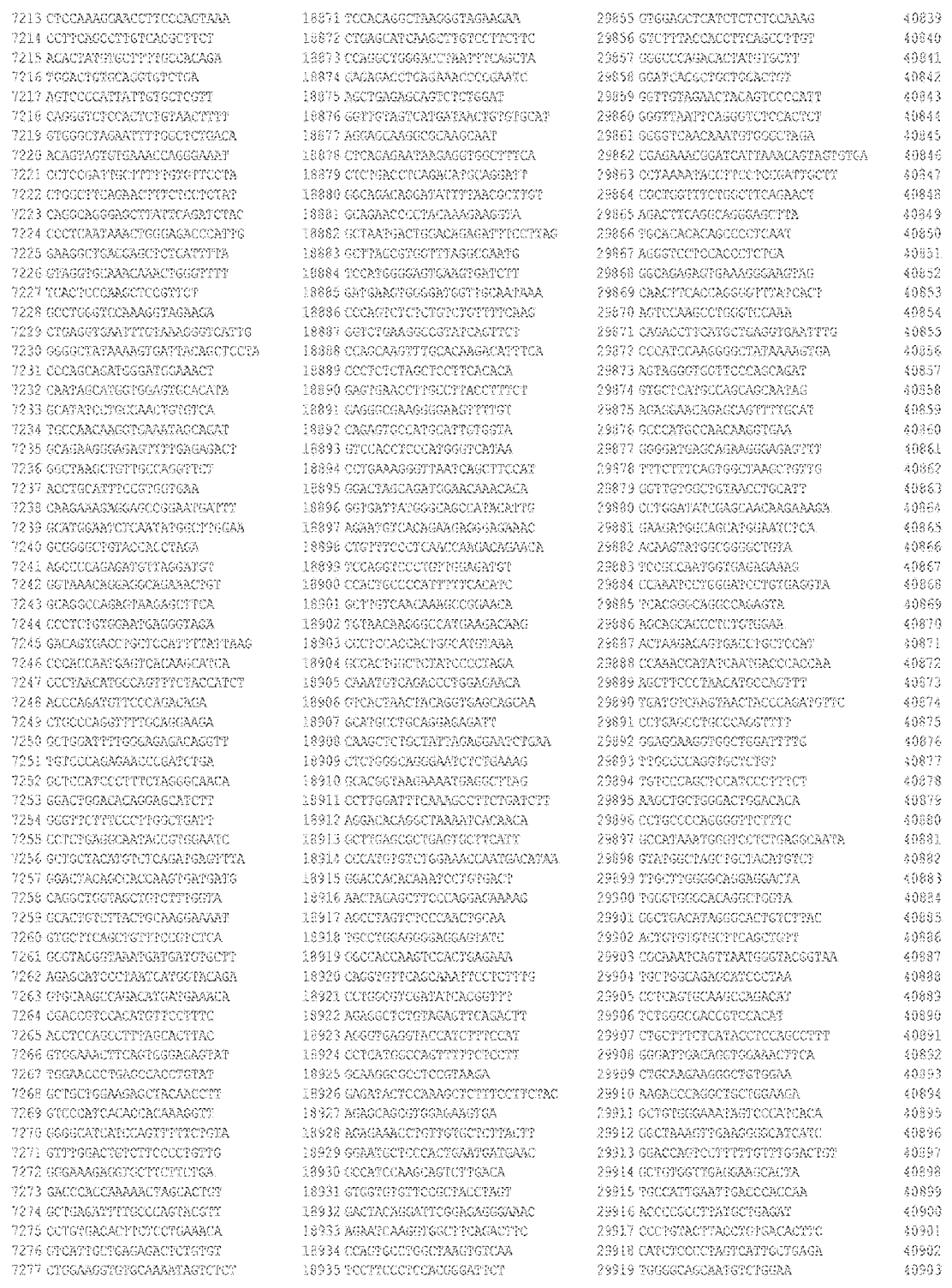
Figure 36L3:
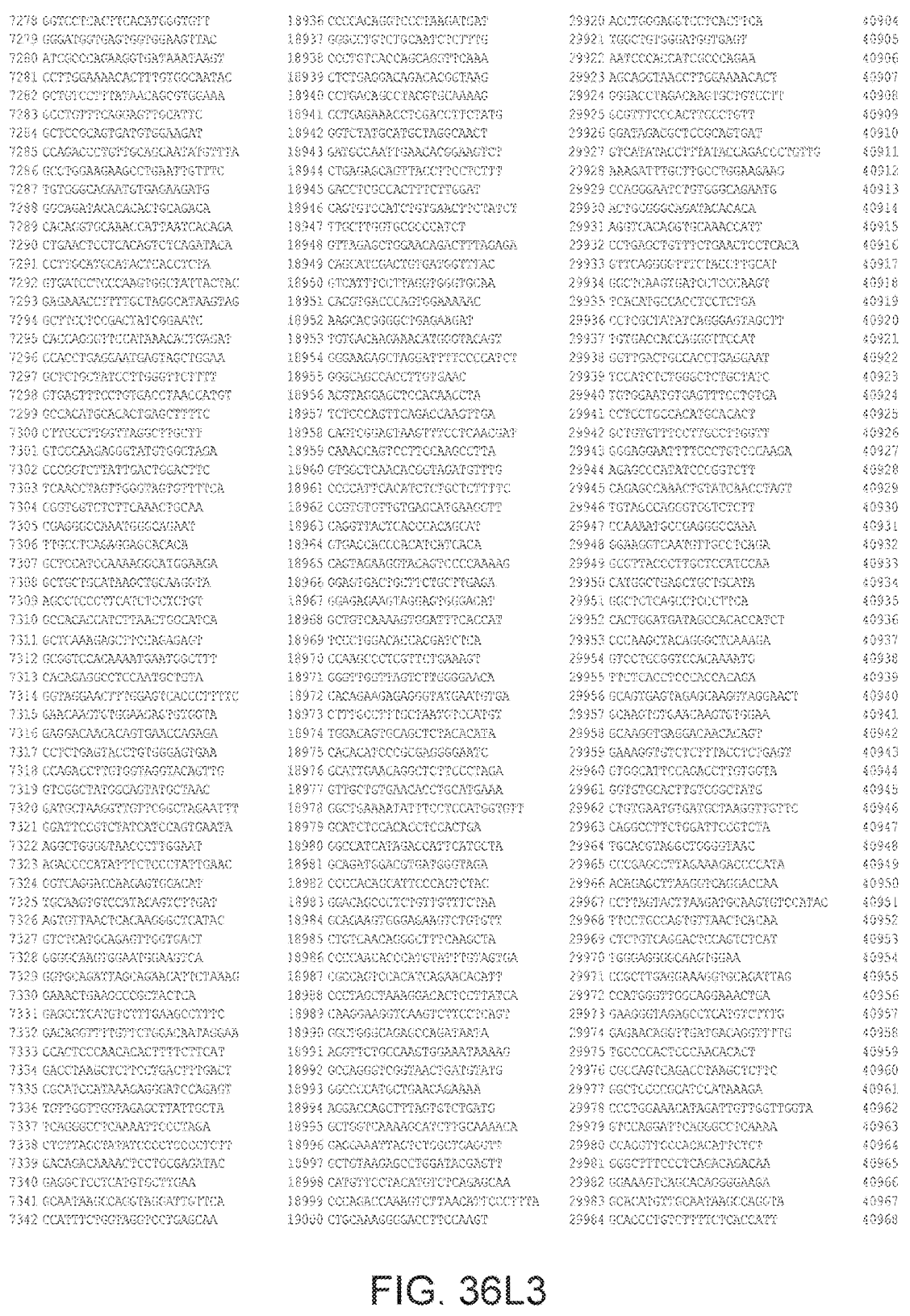
Figure 36L4:
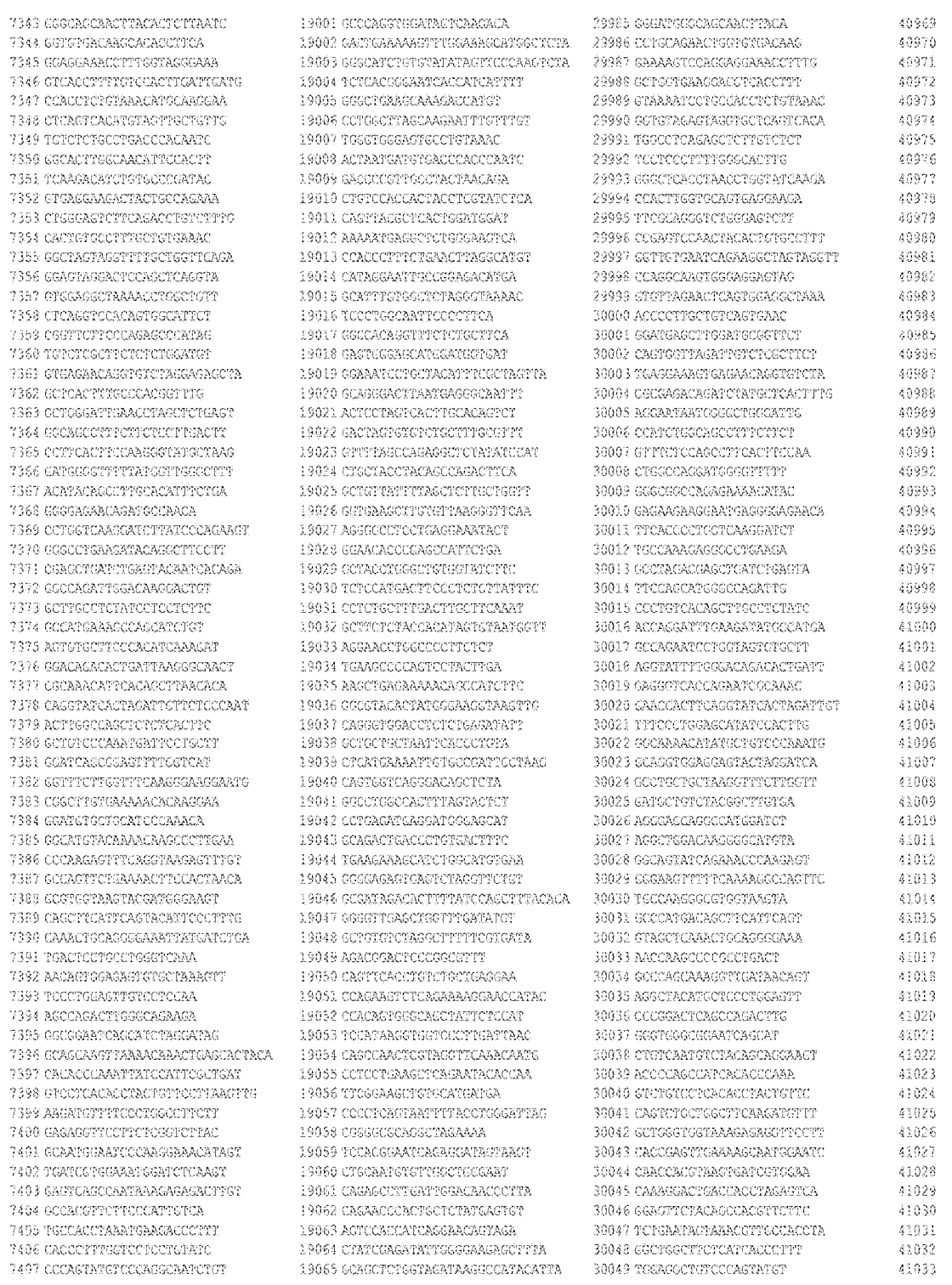
Figure 36L8:
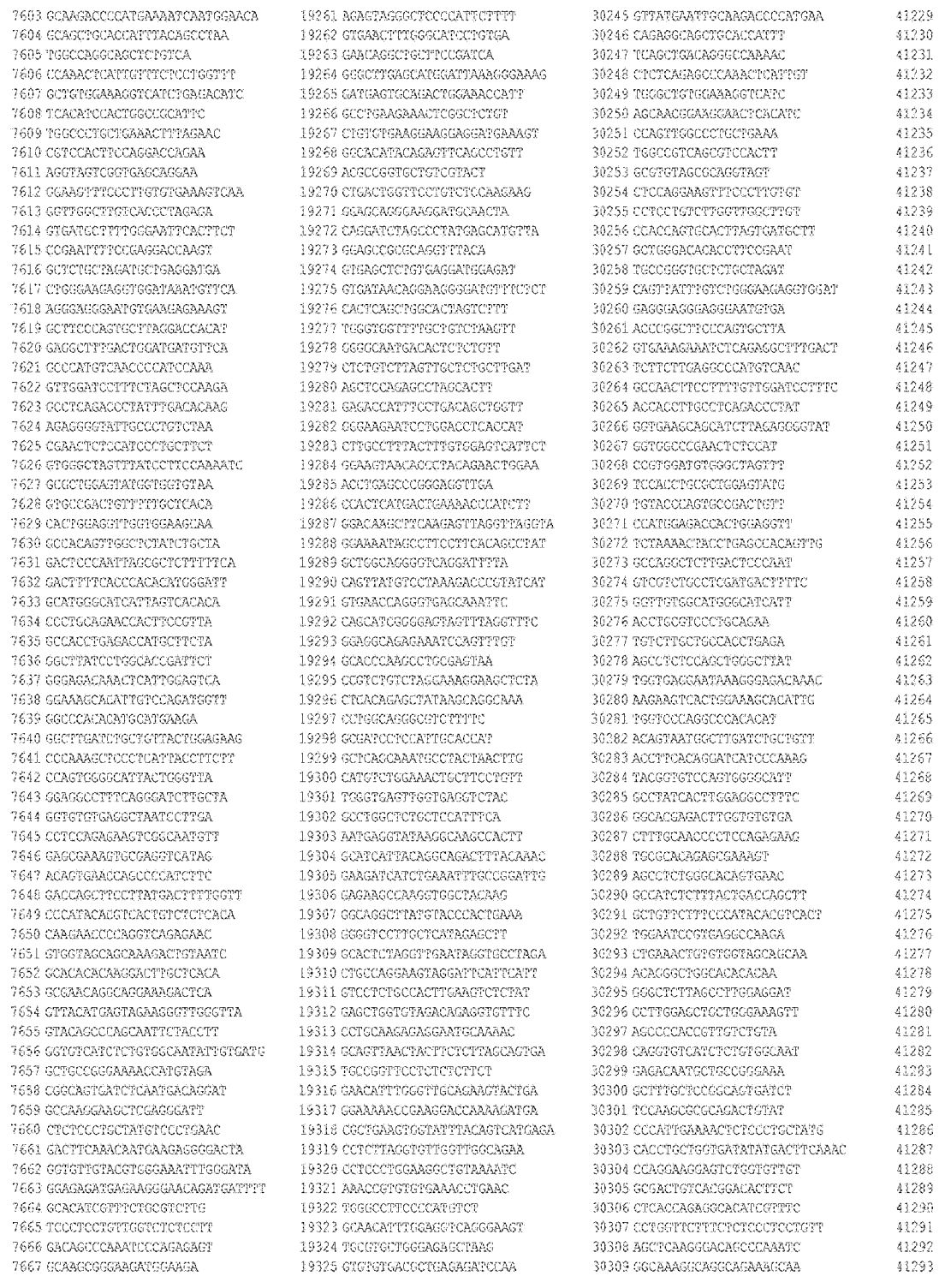
Figure 36M4:
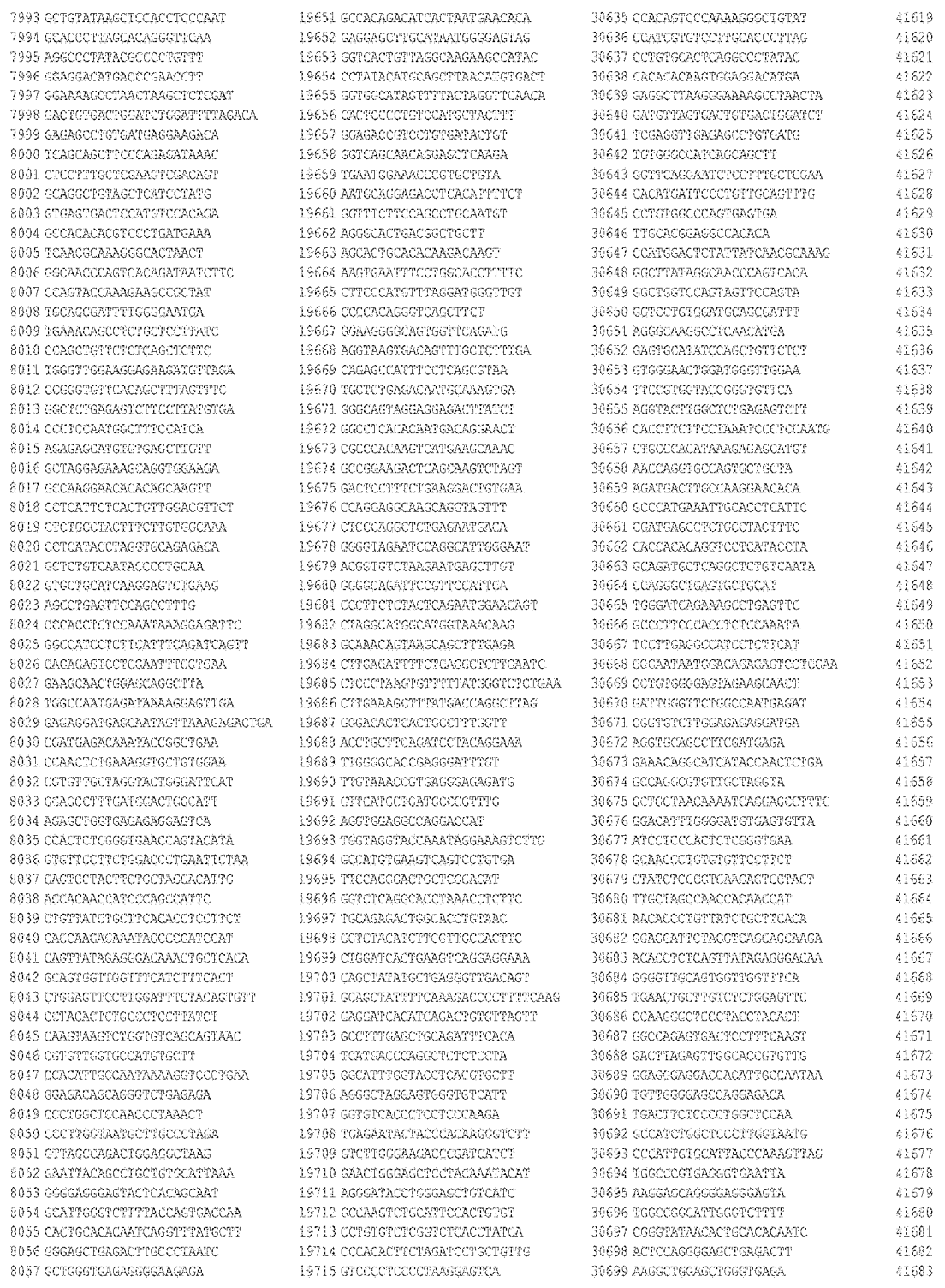
Figure 36M6:
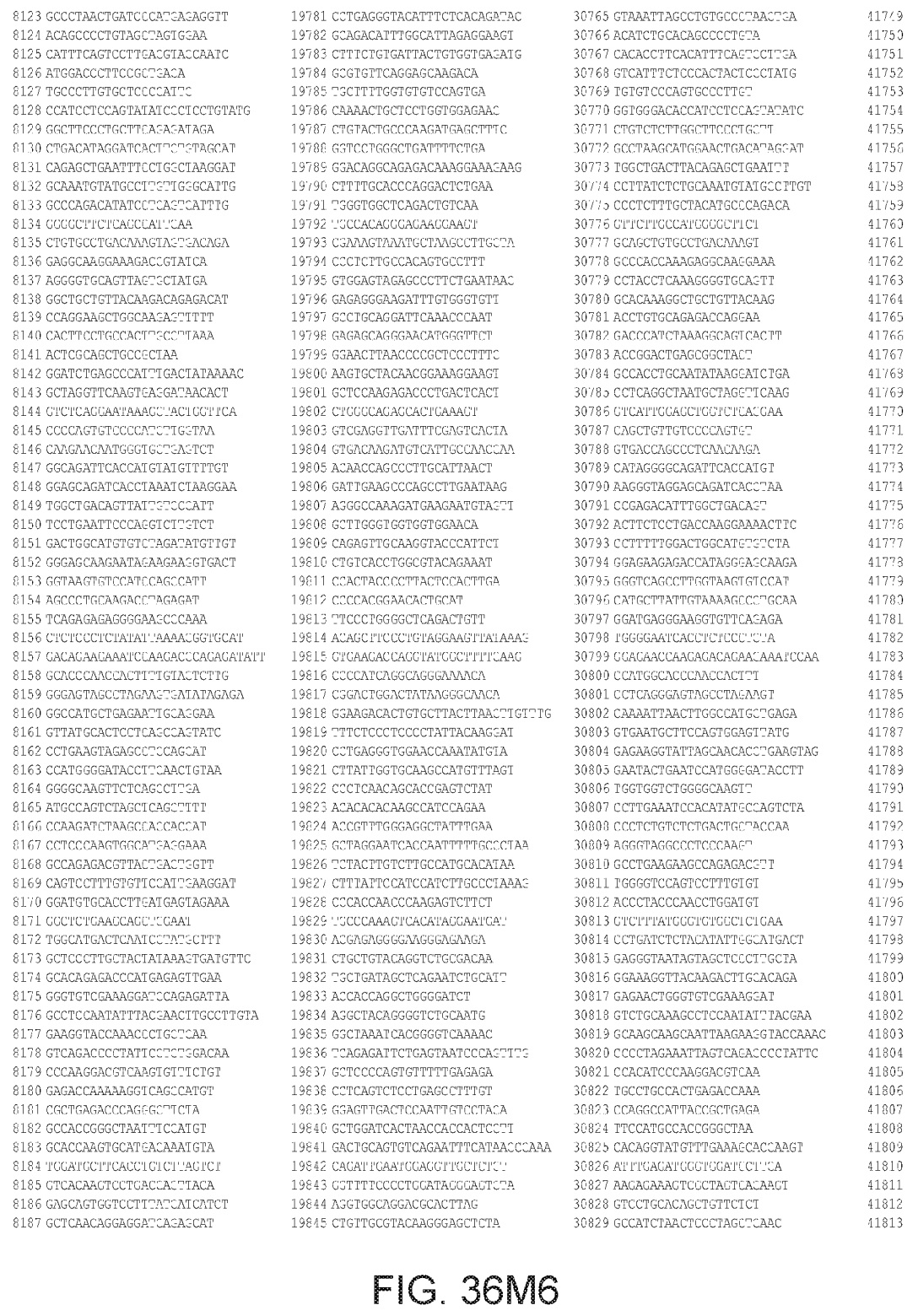
Figure 36N3:
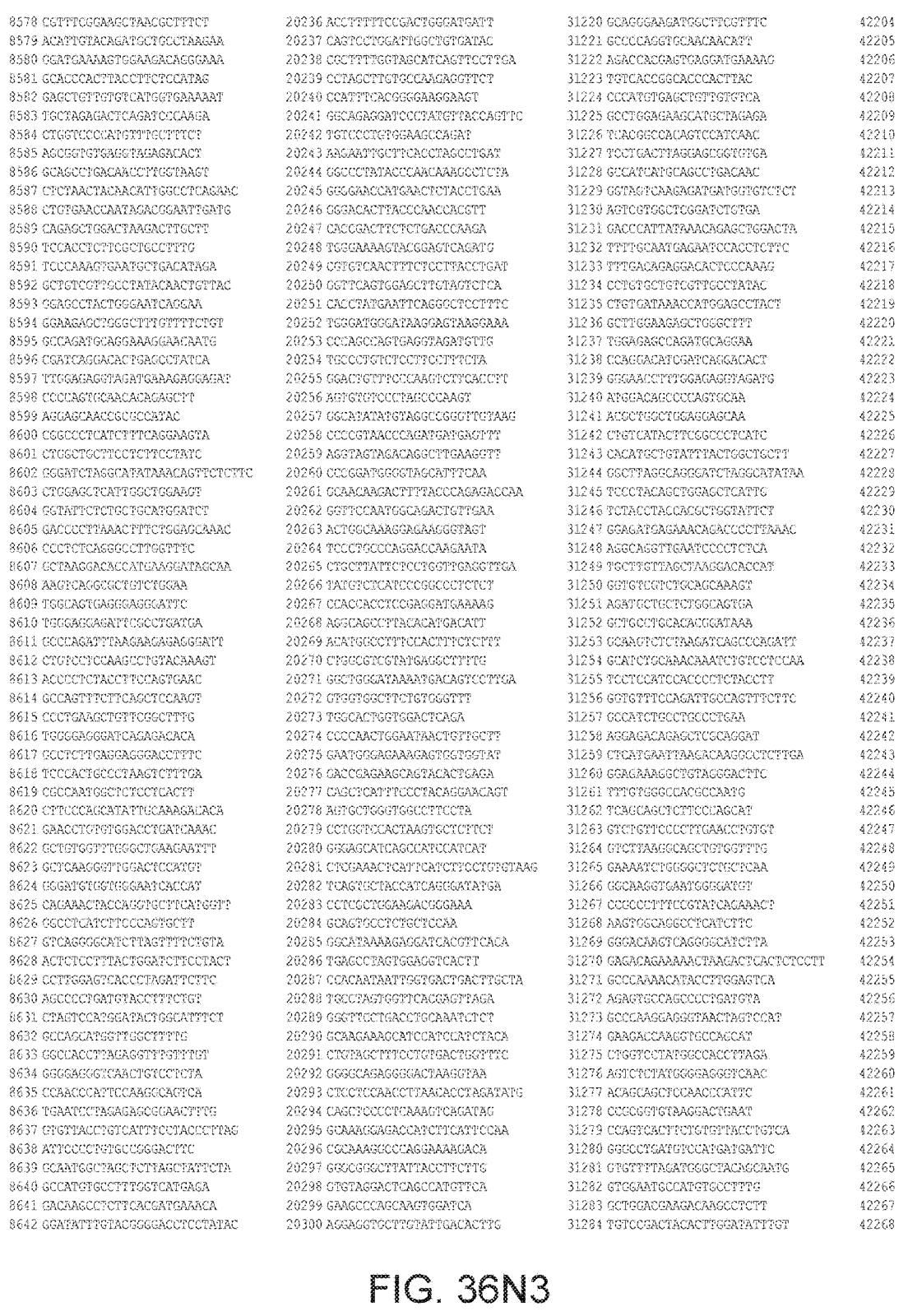
Figure 36N4:
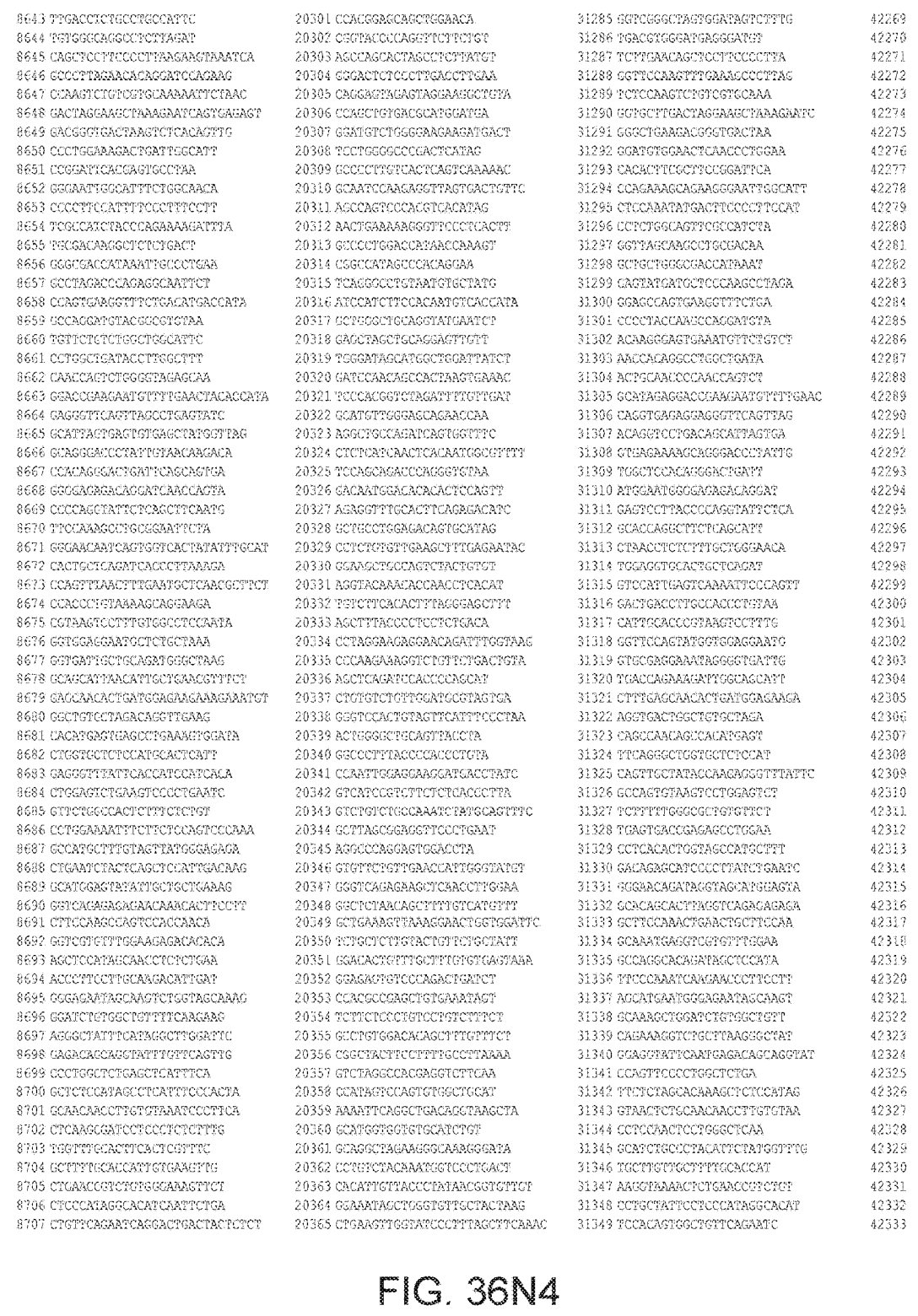
Figure 36O1:
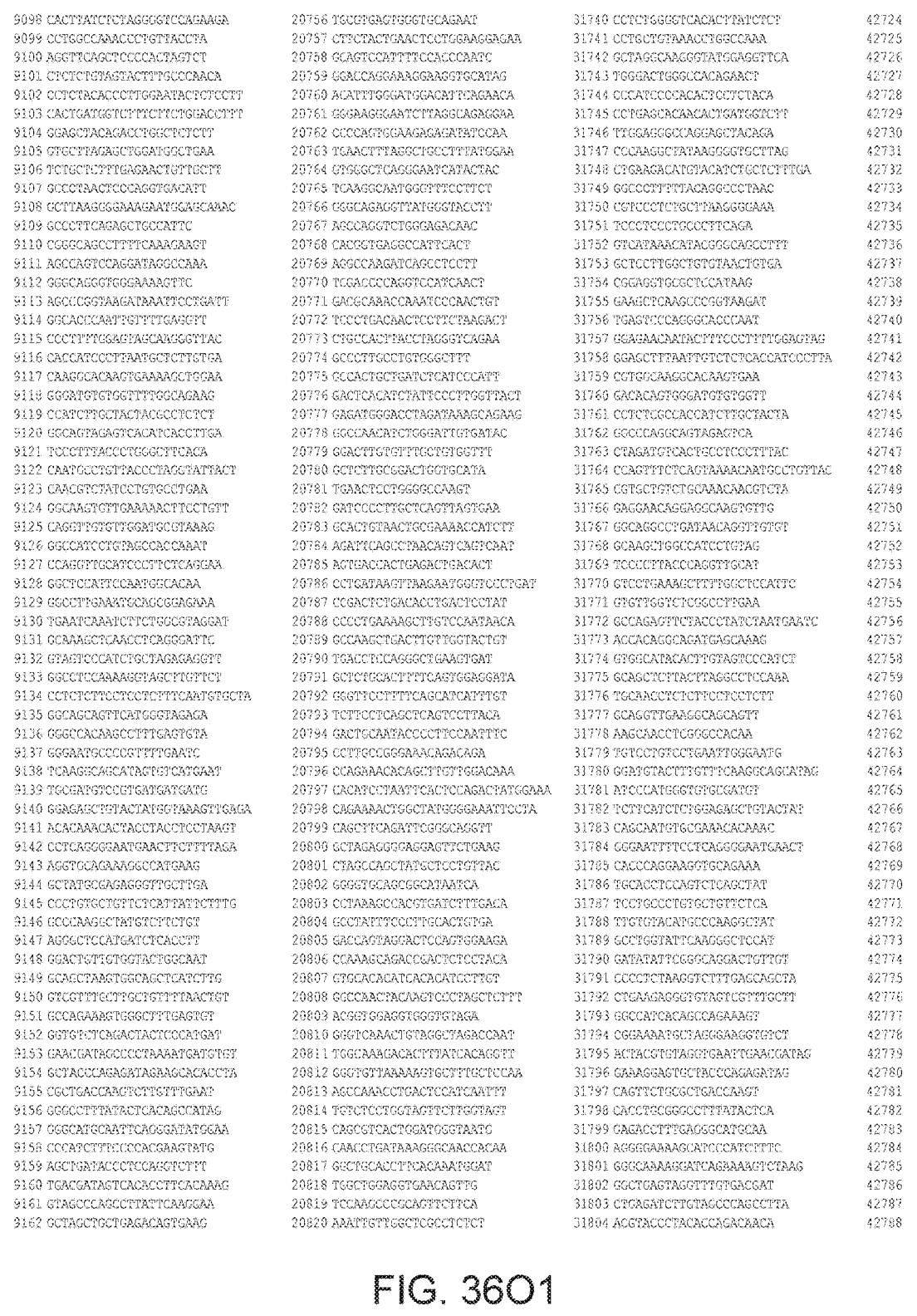
Figure 36O7:
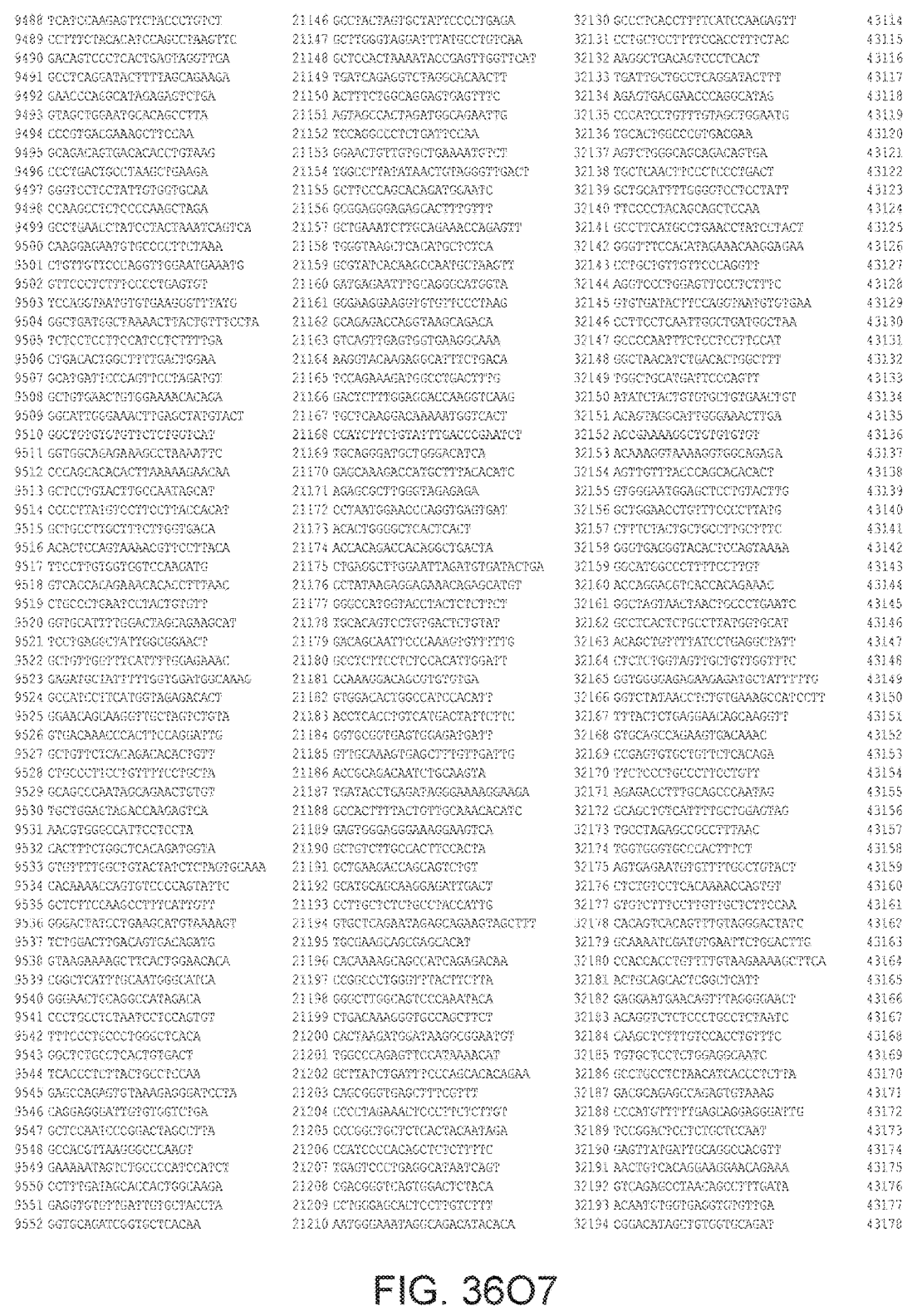
Figure 36P1:
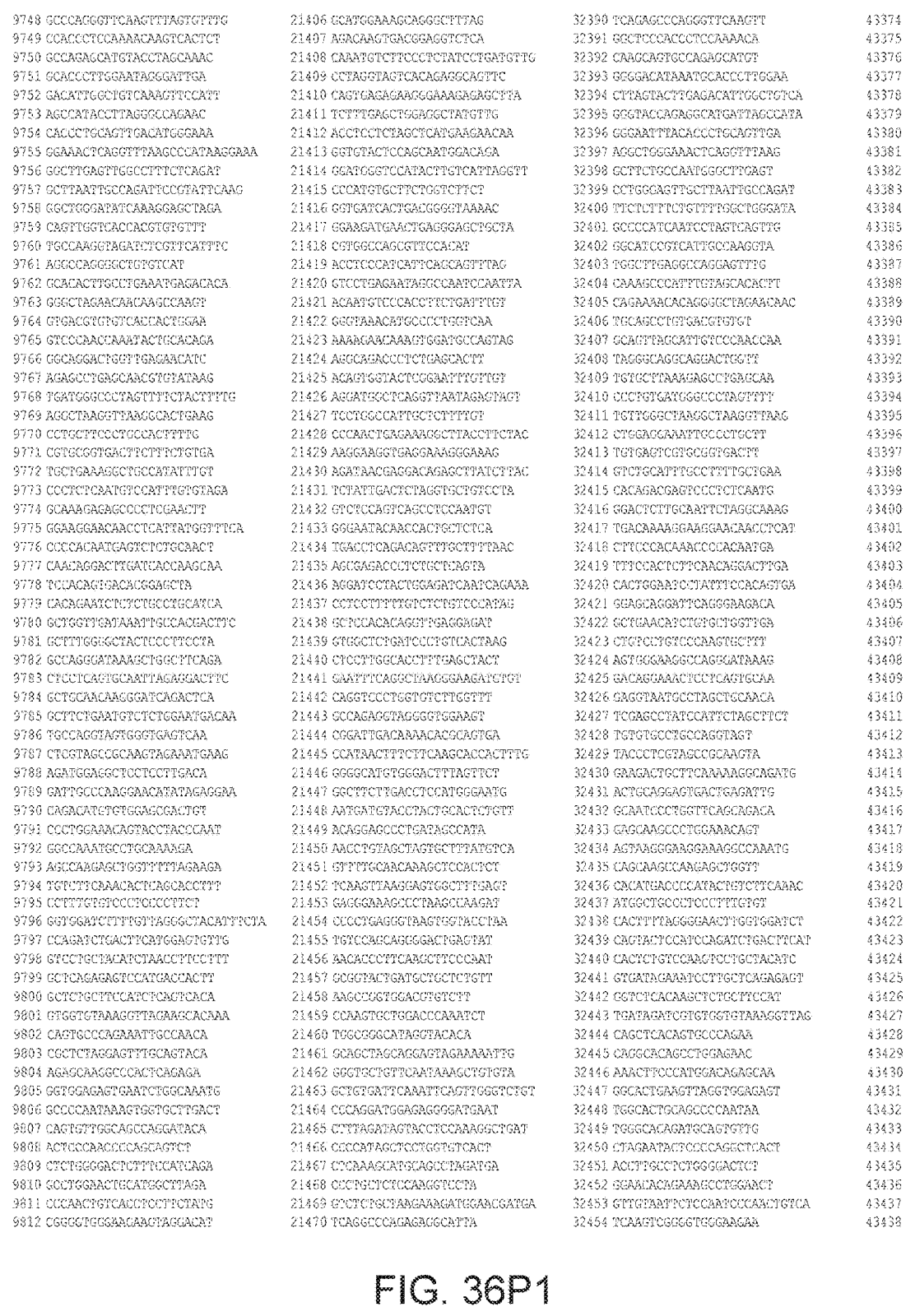
Figure 36P10:
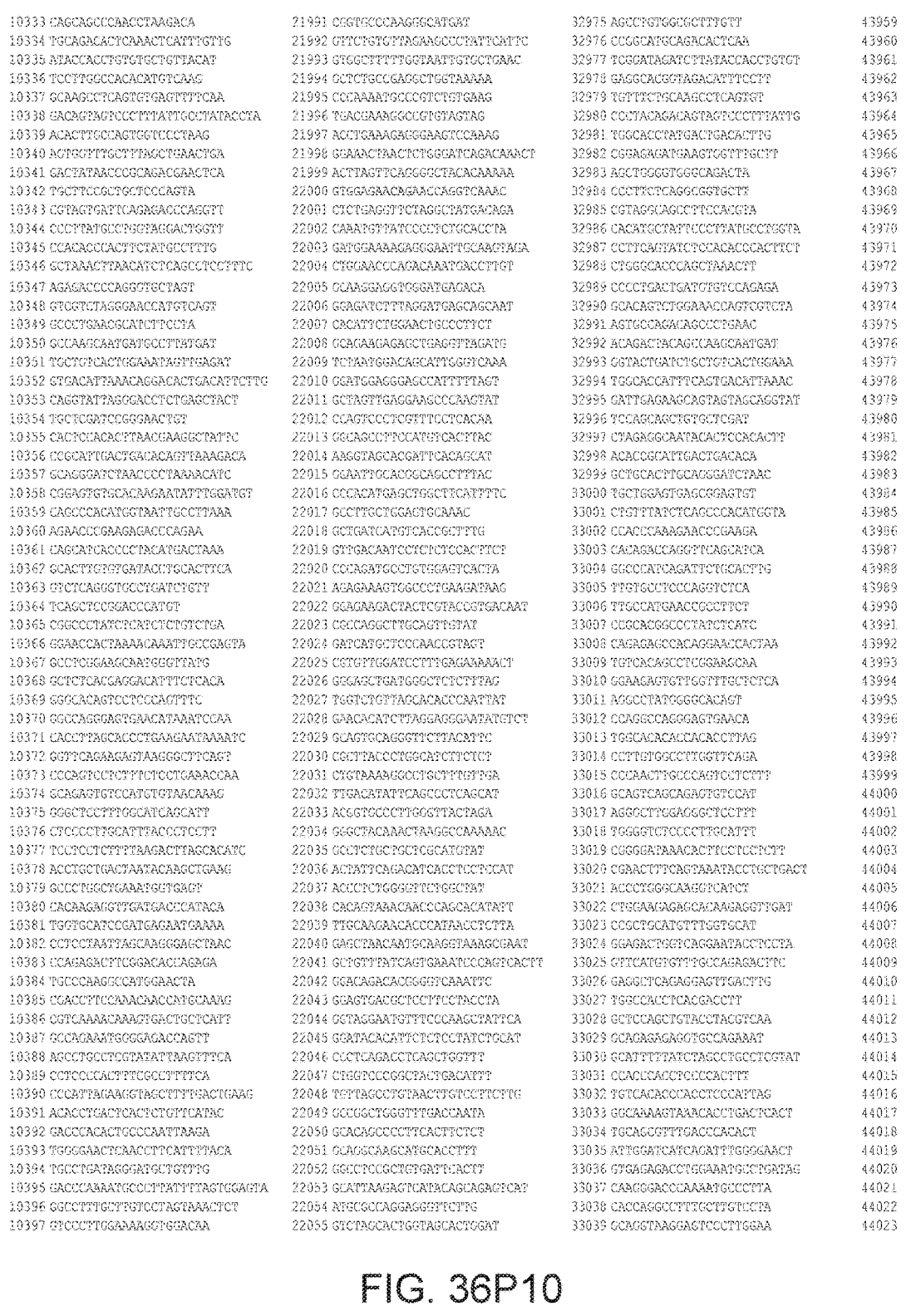
Figure 36Q1:
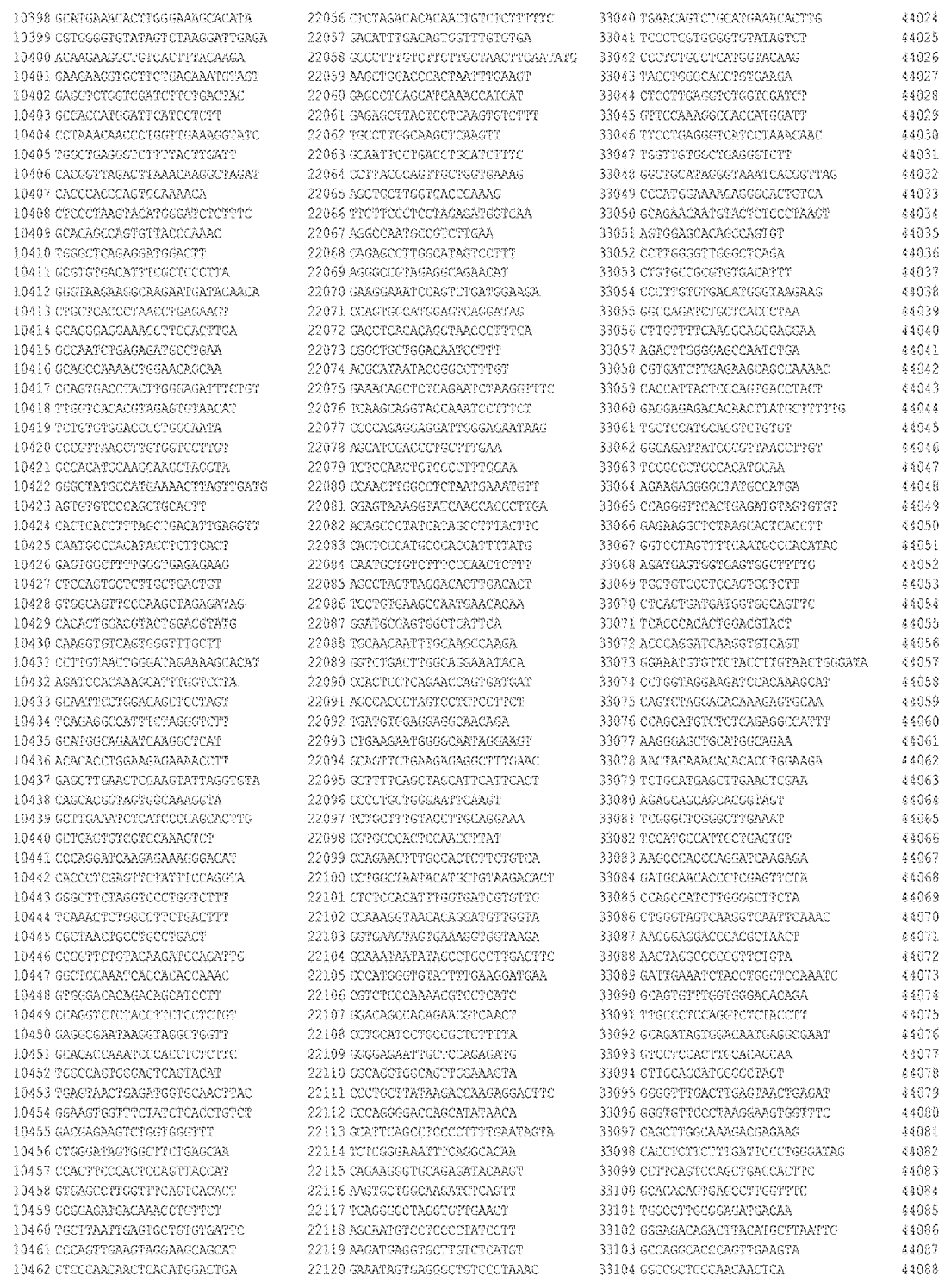
Figure 36Q2:
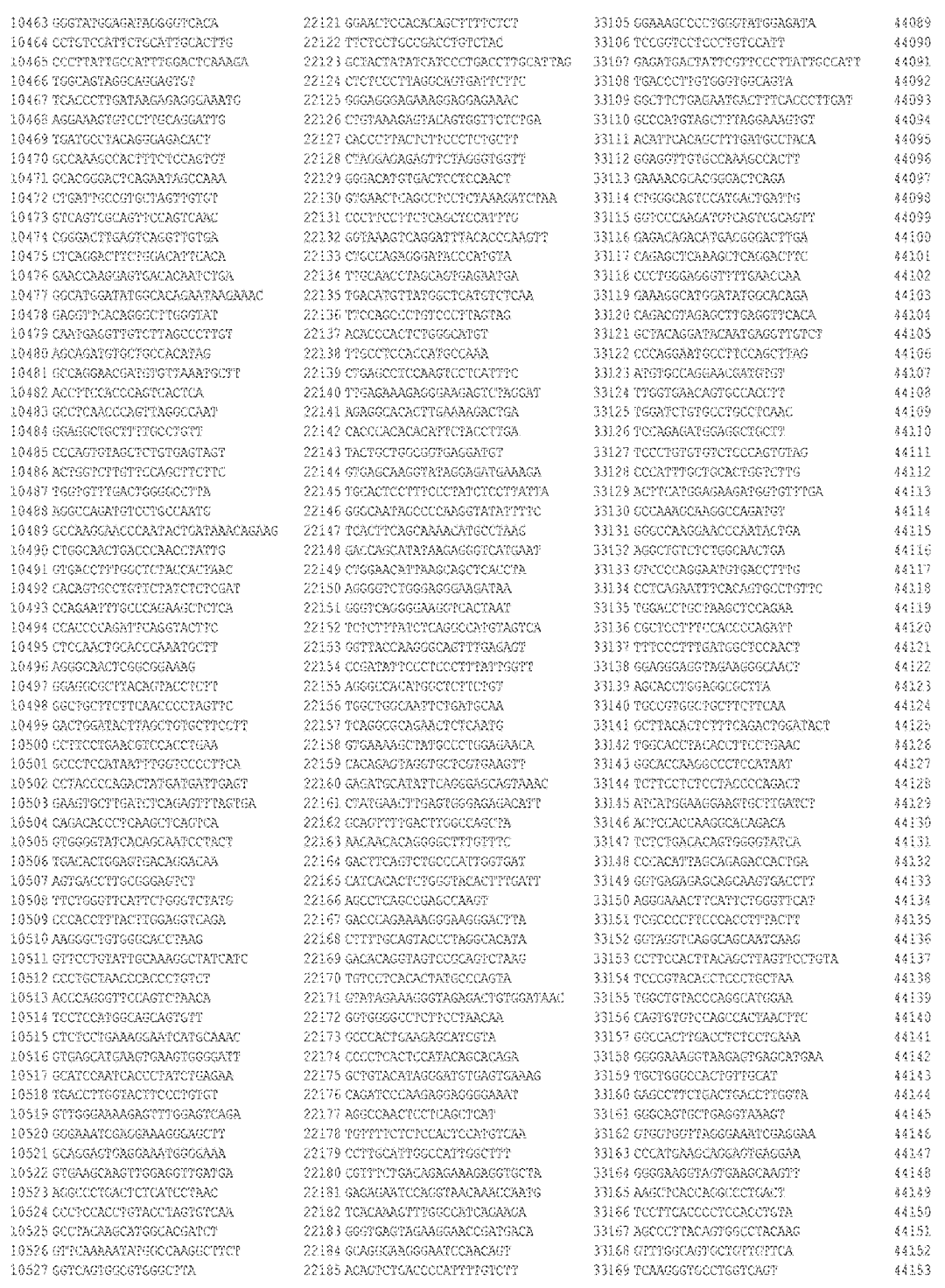
Figure 36Q5:
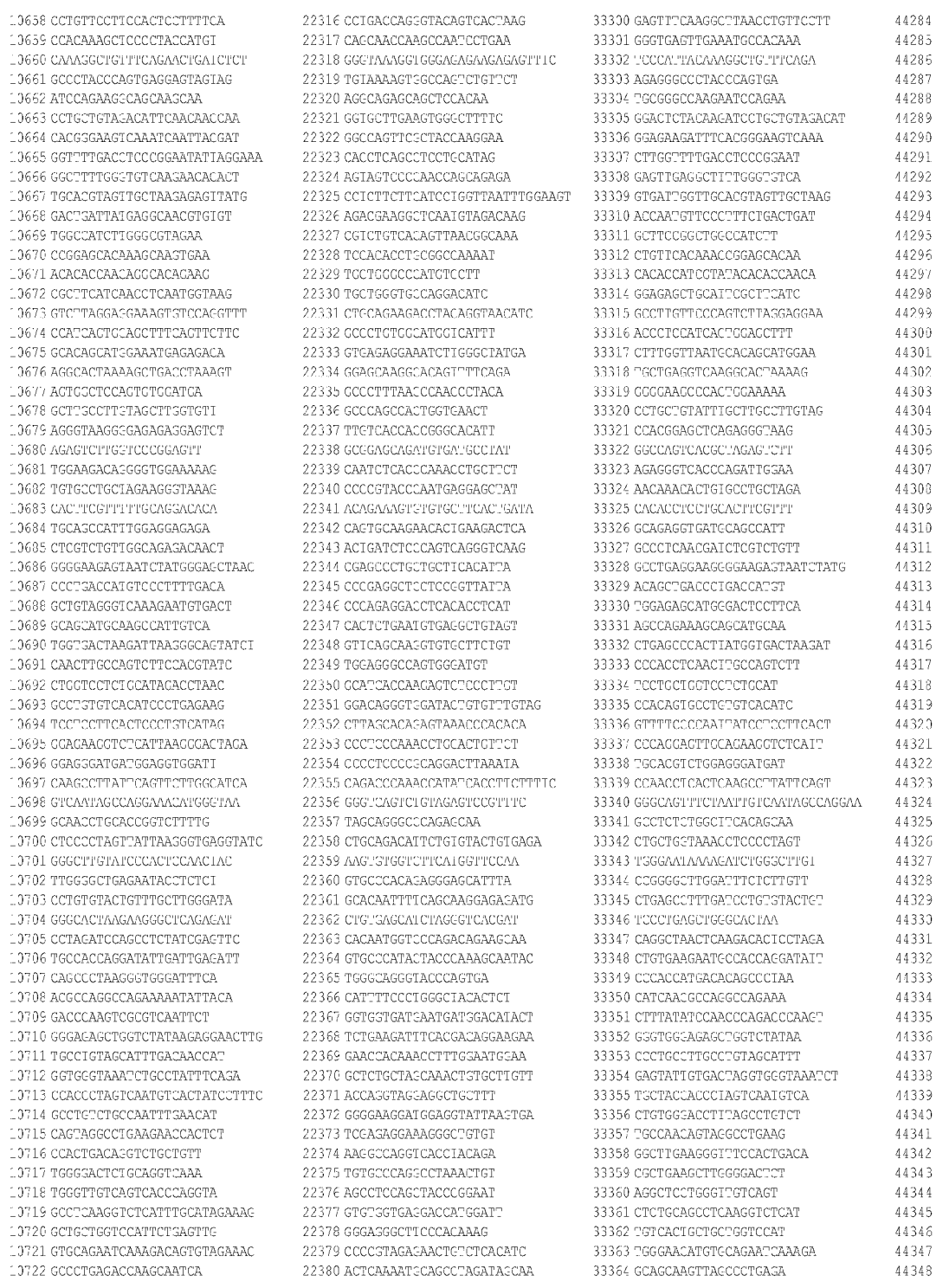
Figure 36Q6:
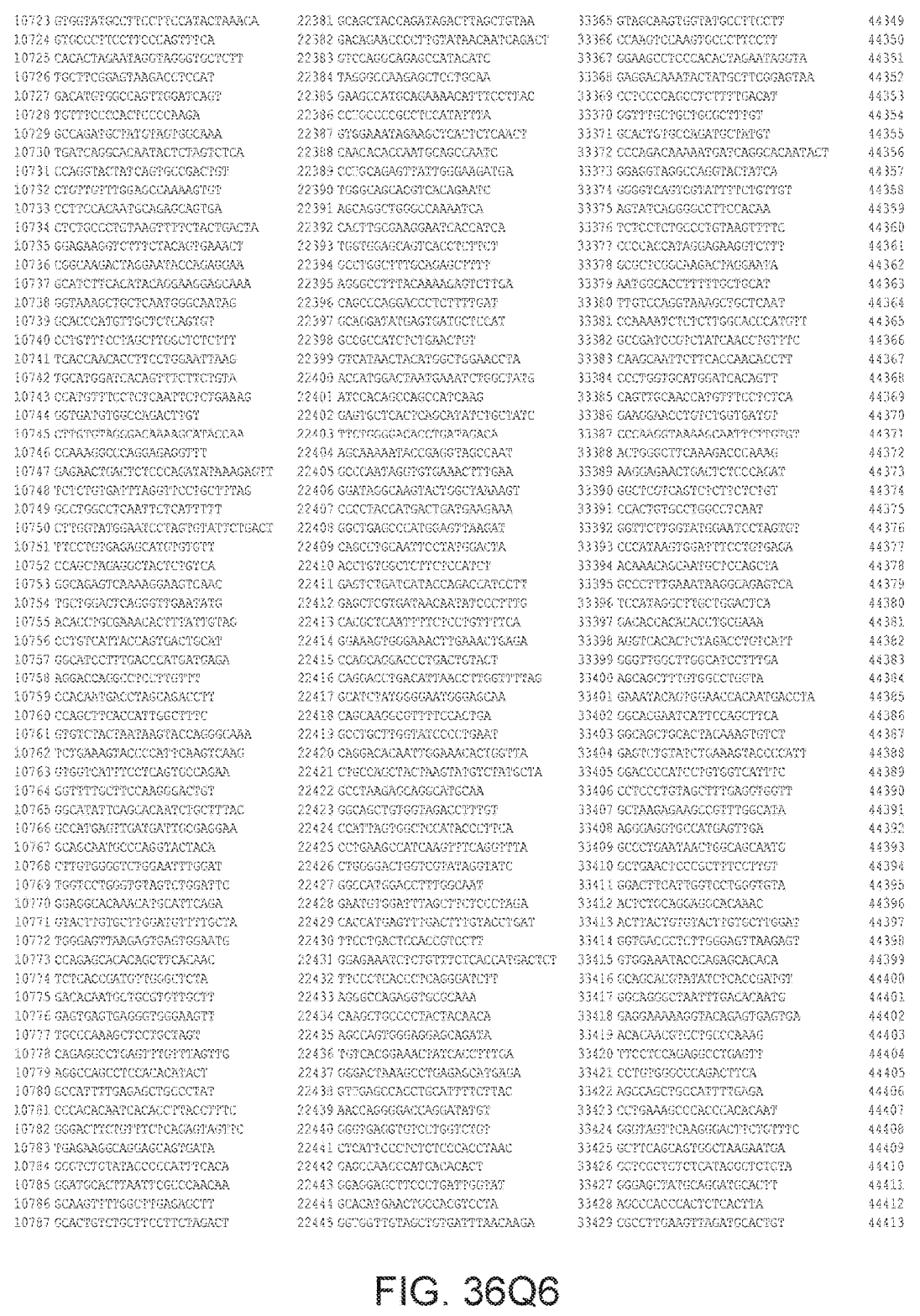
Figure 36Q9:
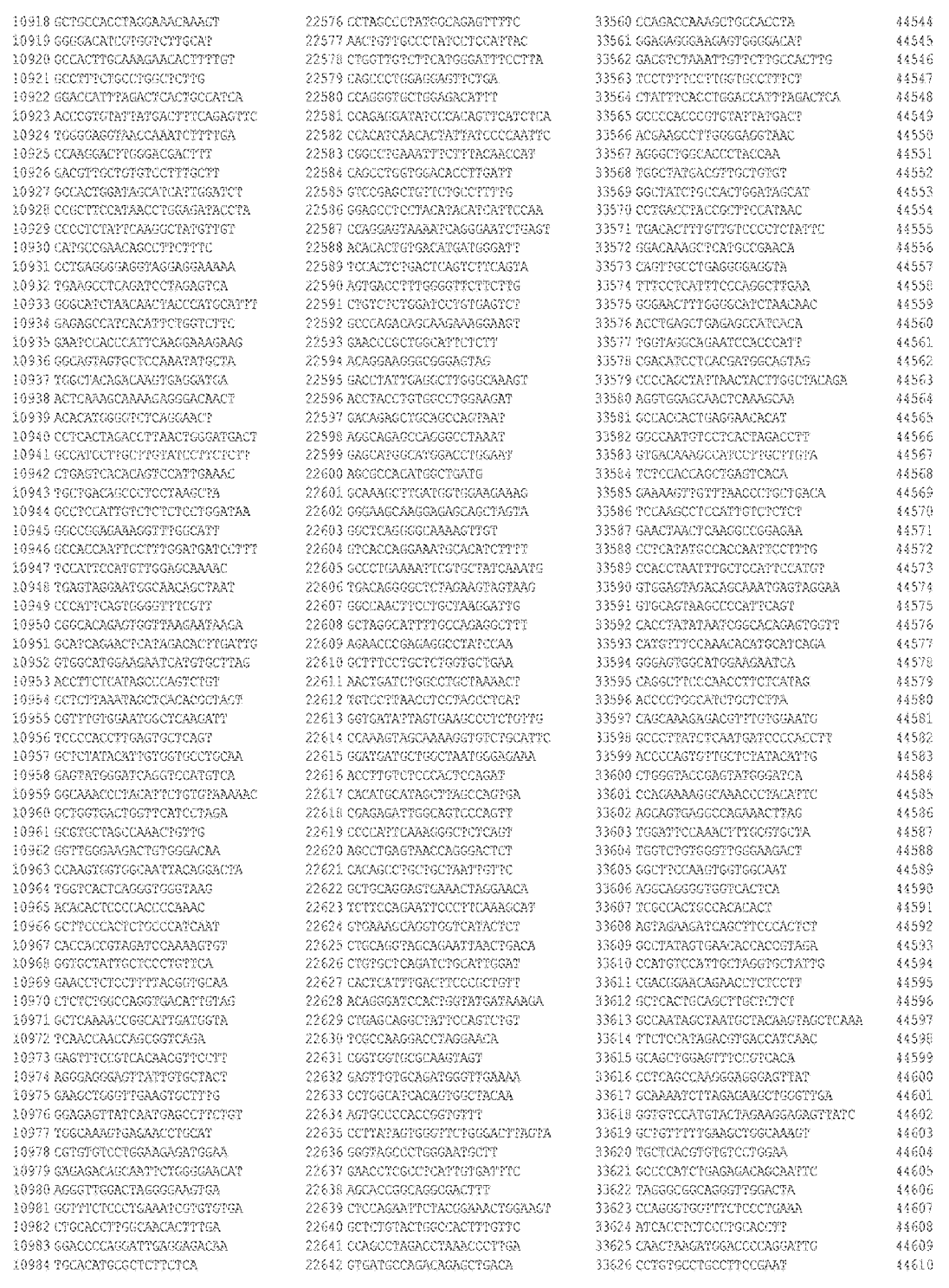

FIG. 36A1-Q9: Sequences of an exemplary 10,984-plex primer library (SEQ ID NOs 11,659-44,610). The three primers (one from pool A, one from pool B, and one from pool C) in each row all hybridize to the same target locus.

FIG. 37: Table of the percentage of reads that map to target loci for genomic DNA samples and for samples of a single cell from a cell line for both mother and child samples.

FIG. 39: Table of the percentage of reads that map to target loci for blastoceol fluid and for a single blastocyst cell.

FIG. 46 is a table comparing error call metrics for genomic DNA and DNA from a single cell.

FIG. 47 is a graph of error rates for transition mutations and transversion mutations.

FIG. 48 is a table of data (such as percent mapped reads and error rate) from multiplex PCR with various buffers.

Figure 1:
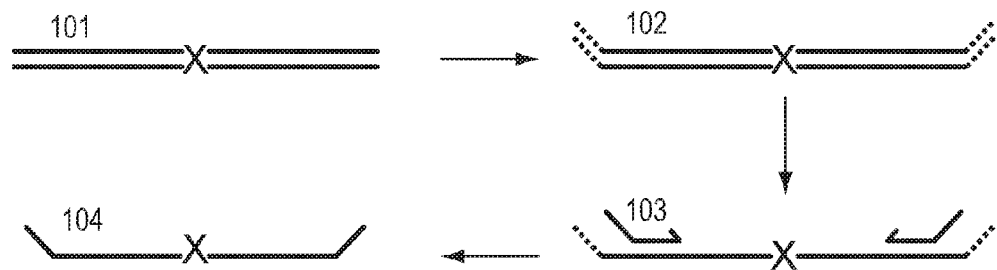
FIG. 1: Graphical representation of direct multiplexed mini-PCR method.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The present invention is based in part on the surprising discovery that often only a relatively small number of primers in a library of primers are responsible for a substantial amount of the amplified primer dimers that form during multiplex PCR reactions. Methods have been developed to select the most undesirable primers for removal from a library of candidate primers. By reducing the amount of primer dimers to a negligible amount (~0.1% of the PCR products), these methods allow the resulting primer libraries to simultaneously amplify a large number of target loci in a single multiplex PCR reaction. Because the primers hybridize to the target loci and amplify them rather than hybridizing to other primers and forming amplified primer dimers, the number of different target loci that can be amplified is increased. It was also discovered that using lower primer concentrations and much longer annealing times than normal increases the likelihood that the primers hybridize to the target loci instead of hybridizing to each other and forming primer dimers (see, e.g., U.S. Ser. No. 13/683,604, filed Nov. 21, 2012, which is hereby incorporated by reference in its entirety). The methods can also be used to amplify a large number of target loci even if the primers have a relatively large range of melting temperatures (in contrast to other methods that require primers to have very similar melting temperatures to successfully amplify multiple loci simultaneously due to the need for the primers to be functional under the same reaction conditions). Additionally, it was discovered that the annealing temperature can optionally be higher than the melting temperatures of the primers (in contrast to other methods that use an annealing temperature below the melting temperatures of the primers). A higher annealing temperature improves the specificity of the PCR amplification and reduces or prevents amplification of non-target loci.

During the PCR amplification and sequencing of 19,488 target loci in a genomic sample, 99.4-99.7% of the sequencing reads mapped to the genome, of those, 99.999% of the mapped to target loci. For plasma samples with 10 million sequencing reads, typically at least 19,350 of the 19,488 target loci (99.3%) were amplified and sequenced. This primer library has even been used to amplify the nucleic acids in a single cell (FIGS. 37-40).

During the PCR amplification and sequencing of ~28,000 target loci in a genomic sample, 99% of the sequencing reads mapped to target loci. This primer library has also been used to amplify nucleic acids in a single cell.

Being able to simultaneously amplify such a large number of target loci at once greatly decreases the amount of time and the amount of DNA required to analyze thousands of target loci. For example, DNA from a single cell is sufficient to simultaneously analyze thousands of target loci, which is important for applications in which the amount of DNA is low, such as genetic testing of a single cell from an embryo prior to in vitro fertilization or genetic testing of a forensic sample with little DNA. In addition, being able to analyze the target loci in one reaction volume (such as in one chamber, well, or vessel) rather than splitting the sample into multiple different reactions reduces variability that can occur between reactions. In addition, methods have been developed to use reference standards to correct for amplification bias that may occur between different target loci. For example, differences in amplification efficiency between target loci due to factors such as GC content may cause differing amounts of PCR products to be produced for target loci that are actually present in the same amount. The use of reference standards similar to the target loci allows the detection of such amplification bias so that it can be corrected for during the quantitation of the target loci.

During sequencing of PCR products, artifacts such as primer dimers are detected and thus inhibit the detection of target amplicons. Because of this limitation, microarrays with hybridization probes are often used for detection since microarrays are less sensitive to interference from primer dimers (for example, microarrays can be used as a target specific detection that uses probes to hybridize to target amplicons but does not have probes to hybridize to undesired primer dimers). The high level of multiplexing with minimal non-target amplicons that has now been achieved allows PCR followed by sequencing to be used as an alternative to microarrays. For example, the present multiplex PCR methods can be used with a non-target specific method of detection, such as sequencing that detects all amplified products (including both target amplicons and primer dimers, if any). The small amount of primer dimers that are produced allows detection of target amplicons by methods that detect all amplicons. Thus, in some embodiments, the method includes multiplex PCR followed by sequencing without use of an array. In other embodiments, the method includes multiplex PCR followed by an array for detection of the amplified products.

The multiplex-PCR methods of the invention can be in a variety of applications, such as genotyping, detection of chromosomal abnormalities (such as a fetal chromosome aneuploidy), gene mutation and polymorphism (such as single nucleotide polymorphisms, SNPs) analysis, gene deletion analysis, determination of paternity, analysis of genetic differences among populations, forensic analysis, measuring predisposition to disease, quantitative analysis of mRNA, and detection and identification of infectious agents (such as bacteria, parasite, and viruses). The multiplex PCR methods can also be used for non-invasive prenatal testing, such as paternity testing or the detection of fetal chromosome abnormalities.

Exemplary Primer Design Methods

Highly multiplexed PCR can often result in the production of a very high proportion of product DNA that results from unproductive side reactions such as primer dimer formation. In an embodiment, the particular primers that are most likely to cause unproductive side reactions may be removed from the primer library to give a primer library that will result in a greater proportion of amplified DNA that maps to the genome. The step of removing problematic primers, that is, those primers that are particularly likely to firm dimers has unexpectedly enabled extremely high PCR multiplexing levels for subsequent analysis by sequencing. In systems such as sequencing, where performance significantly degrades by primer dimers and/or other mischief products, greater than 10, greater than 50, and greater than 100 times higher multiplexing than other described multiplexing has been achieved. Note this is opposed to probe based detection methods, e.g. microarrays, TAQMAN, PCR etc. where an excess of primer dimers will not affect the outcome appreciably. Also note that the general belief in the an is that multiplexing PCR for sequencing is limited to about 100 assays in the same well. Fluidigm and Rain Dance offer platforms to perform 48 or 1000 s of PCR assays in parallel reactions for one sample.

There are a number of ways to choose primers for a library where the amount of non-mapping primer dimer or other primer mischief products are minimized. Empirical data indicate that a small number of 'bad' primers are responsible for a large amount of non-mapping primer dimer side reactions. Removing these 'bad' primers can increase the percent of sequence reads that map to targeted loci. One way to identify the 'bad' primers is to look at the sequencing data of DNA that was amplified by targeted amplification; those primer dimers that are seen with greatest frequency can be removed to give a primer library that is significantly less likely to result in side product DNA that does not map to the genome. There are also publicly available programs that can calculate the binding energy of various primer combinations, and removing those with the highest binding energy will also give a primer library that is significantly less likely to result in side product DNA that does not map to the genome.

In some embodiments for selecting primers, an initial library of candidate primers is created by designing one or more primers or primer pairs to candidate target loci. A set of candidate target loci (such as SNPs) can selected based on publically available information about desired parameters for the target loci, such as frequency of the SNPs within a target population or the heterozygosity rate of the SNPs. In one embodiment, the PCR primers may be designed using the Primer3 program (the worldwide web at primer3.sourceforge.net; libprimer3 release 2.2.3, which is hereby incorporated by reference in its entirety). If desired, the primers can be designed to anneal within a particular annealing temperature range, have a particular range of GC contents, have a particular size range, produce target amplicons in a particular size range, and/or have other parameter characteristics. Starting with multiple primers or primer pairs per candidate target locus increases the likelihood that a primer or prime pair will remain in the library for most or all of the target loci. In one embodiment, the selection criteria may require that at least one primer pair per target locus remains in the library. That way, most or all of the target loci will be amplified when using the final primer library. This is desirable for applications such as screening for deletions or duplications at a large number of locations in the genome or screening for a large number of sequences (such as polymorphisms or other mutations) associated with a disease or an increased risk for a disease. If a primer pair from the library would produces a target amplicon that overlaps with a target amplicon produced by another primer pair, one of the primer pairs may be removed from the library to prevent interference.

In some embodiments, a score such as an "undesirability score" (higher score representing least desirability) is calculated (such as calculation on a computer) for most or all of the possible combinations of two primers from a library of candidate primers. In various embodiments, a score (such as an undesirability score) is calculated for at least 80, 90, 95, 98, 99, or 99.5% of the possible combinations of candidate primers in the library. Each score (such as an undesirability score) is based at least in part on the likelihood of dimer formation between the two candidate primers. If desired, the score (such as the undesirability score) may also be based on one or more other parameters selected from the group consisting of heterozygosity rate of the target locus, disease prevalence associated with a sequence (e.g., a polymorphism) at the target locus, disease penetrance associated with a sequence (e.g., a polymorphism) at the target locus, specificity of the candidate primer for the target locus, size of the candidate primer, melting temperature of the candidate primer, melting temperature of the target amplicon, GC content of the target amplicon, GC content of the 3' end of the candidate primer, homopolymer length in the candidate primer, amplification efficiency of the target amplicon, size of the target amplicon, number of SNPs within the candidate primer, location of SNPs within the candidate primer, distance from an end of the amplicon to the target bases within the amplicon, and the number of target loci in an amplicon. In some embodiments, the lower the number of SNPs with the candidate primer (such as 2, 1 or 0 SNPs) the better. In some embodiments, there are no SNPs in the candidate primer. In some embodiments, SNPs (if any) are preferably not in the last 5 nucleotides in the 3' end of the candidate primer. In some embodiments, the target bases (the bases of interest in a target locus) are preferably near an end (the 3' or 5' end) of the amplicon, this may improve the quality of sequencing data (since bases near the end of an amplicon are sequenced more accurately), and/or allow shorter sequencing reads to be performed. In some embodiments, a single amplicon includes 2 or more target loci (such as 2 or more nearby SNPs or variants). In some embodiments, the specificity of the candidate primer for the target locus includes the likelihood that the candidate primer will mis-prime by binding and amplifying a locus other than the target locus it was designed to amplify. In some embodiments, one or more or all the candidate primers that mis-prime are removed from the library. In some embodiments to increase the number of candidate primers to choose from, candidate primers that may mis-prime are not removed from the library. In some embodiments, the optimal melting temperature for selection of the candidate primers is 57° C. In some embodiments, the optimal size for selection of the candidate primers is a length of 24 nucleotides. In some embodiments, the optimal GC content for selection of the candidate primers is 50%. If multiple factors are considered, the score (such as the undesirability score) may be calculated based on a weighted average of the various parameters. The parameters may be assigned different weights based on their importance for the particular application that the primers will be used for. An exemplary score (such as an undesirability score) for a primer is shown below in which the parameters are weighted by various factors.

score=(1)(total number of targets−number of targets covered)+(100)(number of SNPs in GC clamp)+(10)(number of SNPs in primer binding site)+(10)(number of similar primer pair designs)+(0.1)(distance of target base from amplicon end)+(0.1)(amplicon length)+(100)(interaction score)

where interaction score=max(−1*ΔG value) as described herein.

Another exemplary score for a primer is shown below.

score=(100)(number of SNPs in GC clamp)+(10)(number of SNPs in primer binding site)+(0.1)(distance of target base from amplicon end)+(0.1)(amplicon length)+(100)(interaction score)

where interaction score=max(−1*ΔG value) as described herein.

In some embodiments, the score for a primer pair is the worse score out of the scores for the two primers in the pair. An exemplary score (such as an undesirability score or the score in Experiment 20) for a pairs of designs (in which each design is one primer pair so that a pair of designs includes two primer pairs with a total of 4 primers) is shown below.

score=(10000000)(amplicon overlap)+(100)(distance between designs)+(1)(total number of targets−number of targets covered)+(100)(number of SNPs in GC clamp)+(10)(number of SNPs in primer binding site)+(10)(number of similar primer pair designs)+(0.1)(distance of target base from amplicon end)+(0.1)(amplicon length)+(100)(interaction score)

where interaction score=max(−1*ΔG value) as described herein;

where amplicon overlap=overlap between the two amplicons formed by a pair of designs.

In some embodiments, the score for a pair of designs is the worse score out of the scores for the four primers in the pair of designs.

In some embodiments, the primer with the highest score (such as the undesirability score) or any score representing least desirability is removed from the library. If the removed primer is a member of a primer pair that hybridizes to one target locus, then the other member of the primer pair may be removed from the library. The process of removing primers may be repeated as desired. In some embodiments, the selection method is performed until the score (such as the undesirability score) for the candidate primer combinations remaining in the library are all equal to or below a minimum threshold (such as any threshold for which the primers remaining in the library all have at least that level of desirability). In some embodiments, the selection method is performed until the number of candidate primers remaining in the library is reduced to a desired number.

In various embodiments, after the score (such as the undesirability score) are calculated, the candidate primer that is part of the greatest number of combinations of two candidate primers with a score (such as an undesirability score) above a first minimum threshold (such as any threshold for which the primers remaining in the library all have at least that level of desirability) is removed from the library. This step ignores interactions equal to or below the first minimum threshold since these interactions are less significant. If the removed primer is a member of a primer pair that hybridizes to one target locus, then the other member of the primer pair may be removed from the library. The process of removing primers may be repeated as desired. In some embodiments, the selection method is performed until the score (such as the undesirability score) for the candidate primer combinations remaining in the library are all equal to or below the first minimum threshold. If the number of candidate primers remaining in the library is higher than desired, the number of primers may be reduced by decreasing the first minimum threshold to a lower second minimum threshold (such as any threshold with a stricter cutoff than the first minimum threshold so that some of the least desirable primers are removed from the library) and repeating the process of removing primers. If the number of candidate primers remaining in the library is lower than desired, the method can be continued by increasing the first minimum threshold to a higher second minimum threshold (such as any threshold with a less strict cutoff than the first minimum threshold) and repeating the process of removing primers using the original candidate primer library, thereby allowing more of the candidate primers to remain in the library. In some embodiments, the selection method is performed until the score (such as the undesirability score) for the candidate primer combinations remaining in the library are all equal to or below the second minimum threshold, or until the number of candidate primers remaining in the library is reduced to a desired number.

If desired, primer pairs that produce a target amplicon that overlaps with a target amplicon produced by another primer pair can be divided into separate amplification reactions. Multiple PCR amplification reactions may be desirable for applications in which it is desirable to analyze all of the candidate target loci (instead of omitting candidate target loci from the analysis due to overlapping target amplicons).

In various embodiments of any of the aspects of the invention, the selection method selects candidate primers and divides them into different pools (e.g., 2, 3, 4, 5, 6, or more different pools). Each pool can be used to simultaneously amplify a large number of target loci (or a subset of target loci) in a single reaction volume. In some embodiments, a graph coloring algorithm is used to divide candidate primers into different pools. If desired, this method can be used to minimize the number of different pools needed to amplify most or all of the target loci. In some embodiments, most or all of the target loci (such as at least 70, 80, 90, 92, 94, 96, 98, 99, or 100% of the target loci) are amplified by at least 2, 3, 4, 5, 6, or more different pools. In some embodiments, most or all of the bases in the target loci (such as at least 70, 80, 90, 92, 94, 96, 98, 99, or 100% of the bases in the target loci) are amplified by at least 2, 3, 4, 5, 6, or more different pools. In some embodiments, most or all of the bases in the target loci (such as at least 70, 80, 90, 92, 94, 96, 98, 99, or 100% of the bases in the target loci) are amplified by at least 2, 3, 4, 5, 6, or more different primers or primer pairs in different pools. For example, a particular base in a target locus may be amplified by at least 2, 3, 4, 5, 6, or more different primers or primer pairs; wherein each different primer or primer pair is in a different pool. Using different primers or primer pairs to amplify each base allows multiple independent measurements of the base to be made, thereby increasing the accuracy of the method. Dividing the different primers or primer pairs that amplify the same base into different pools prevents interference due to overlapping amplicons being formed by different primers or primer pairs.

In one aspect, the invention features methods of selecting test primers from a library of candidate primers to form 2 or more different primer pools. In various embodiments, the selection involves (i) calculating on a computer a score (such as an undesirability score) for most or all of the possible combinations of two candidate primers from the library, wherein each score (such as an undesirability score) is based at least in part on the likelihood of dimer formation between the two candidate primers; (ii) removing the candidate primer with the highest or worst score (such as an undesirability score) from the library of candidate primers, and (iii) if the candidate primer removed in step (ii) is a member of a primer pair, then removing the other member of the primer pair from the library of candidate primers; and (iv) optionally repeating steps (ii) and (iii), thereby selecting a first pool. In some embodiments, the selection method is performed until the score (such as the undesirability score) for the candidate primer combinations remaining in the library are all equal to or below a minimum threshold for the first pool. In some embodiments, the selection method is performed until the number of candidate primers remaining in the library is reduced to a desired number for the first pool. In some embodiments, after the first pool is selected those primers are removed from further consideration and steps of the method (such as steps (ii) and (iii)) are repeated with the remaining primers to select a second pool. If desired, this method may be repeated to select the desired number of primer pools. In some embodiments, the score is based at least in part on the current coverage of the bases in the target locus (such as the number of other primer pools that have a primer or primer pair that amplifies a particular base in the target locus).

In one aspect, the invention features methods of selecting test primers from a library of candidate primers to form 2 or more different primer pools. In various embodiments, the selection of test primers are selected from a library of candidate primers involves (i) calculating on a computer a score (such as an undesirability score) for most or all of the possible combinations of two candidate primers from the library, wherein each score (such as an undesirability score) is based at least in part on the likelihood of dimer formation between the two candidate primers; (ii) removing from the library of candidate primers the candidate primer that is part of the greatest number of combinations of two candidate primers with a score (such as an undesirability score) above a first minimum threshold; (iii) if the candidate primer removed in step (ii) is a member of a primer pair, then removing the other member of the primer pair from the library of candidate primers; and (iv) optionally repeating steps (ii) and (iii), thereby selecting a first pool. In some embodiments, the selection method is performed until the score (such as the undesirability score) for the candidate primer combinations remaining in the library are all equal to or below the first minimum threshold for the first pool. In some embodiments, the selection method is performed until the number of candidate primers remaining in the library is reduced to a desired number for the first pool. In various embodiments, the selection method involves further reducing the number of candidate primers remaining in the library by decreasing the first minimum threshold used in step (ii) to a lower second minimum threshold and optionally repeating steps (ii) and (iii). In some embodiments, the selection method involves increasing the first minimum threshold used in step (ii) to a higher second minimum threshold and optionally repeating steps (ii) and (iii). In some embodiments, the selection method is performed until the score (such as the undesirability score) for the candidate primer combinations remaining in the library are all equal to or below the second minimum threshold, or until the number of candidate primers remaining in the library is reduced to a desired number for the first pool. In some embodiments, after the first pool is selected those primers are removed from further consideration and steps of the method (such as steps (ii) and (iii)) are repeated with the remaining primers to select a second pool. If desired, this method may be repeated to select the desired number of primer pools. In some embodiments, the score is based at least in part on the current coverage of the bases in the target locus (such as the number of other primer pools that have a primer or primer pair that amplifies a particular base in the target locus).

As discussed above, in some embodiments, a library is formed by starting with a library of candidate primers and removing primers until the primers remaining in the library have the desired characteristics for use as a final primer library.

In other embodiments, candidate primers are added to a library (such as a library starting with no primers) to form a library with the desired characteristics. In some embodiments, the candidate primer or primer pair with the most desirable score (such as the lowest undesirability score) is added to a library (such as a library starting with no primers). The process of adding candidate primers may be repeated as desired. In some embodiments, the selection method is performed until the score (such as the undesirability score) for the candidate primers that have not been added to the library are all above a minimum threshold (such that all the candidate primers that have not been chosen for the library all have worse scores than the threshold). In some embodiments, the selection method is performed until the number of candidate primers that have been added to the library reaches a desired number. The library of selected primers can then be used in any of the methods of the invention.

In some embodiments, most (such as at least 50, 60, 70, 80, 90, 95, 96, 97, 98, 99, or 99.5%) or all of the possible sets of two primer pairs (two primer pairs with a total of 4 primers) are considered for inclusion in a library. In some embodiments, the set of two different candidate primer pair with the most desirable score (such as the lowest undesirability score) is added to a first pool (such as a first pool starting with no primers). In some embodiments, the set of two different candidate primer pairs with the next most desirable score is added to the first pool if it is connected to at most two sets of two different candidate primer pairs in the first pool. By "connected" for purposes of this step is meant that a single candidate primer pair in one set of two different candidate primer pairs is the same as a single candidate primer pair in another set of two different candidate primer pairs. If the set of two different candidate primer pairs is connected to more than two sets, it may be added to a different pool than the first pool. The process of set of two different candidate primer pair to pool(s) may be repeated as desired for the next set of two different candidate primer pairs with the next most desirable score. In some embodiments, the selection method is performed until the score (such as the undesirability score) for the candidate primers that have not been added to the pool(s) are all above a minimum threshold (such that all the candidate primers that have not been chosen for the pool(s) all have worse scores than the threshold). In some embodiments, the selection method is performed until the number of candidate primers that have been added to the pool(s) reaches a desired number. In some embodiments, the method involves storing designs in N number of doubly linked list data structures with the design pairs. N represents the current number of different primer pools. Initially, N=1, since there is only one primer pool. In some embodiments, a second pool is only created if necessary to include the desired target loci or the desired level of coverage of target loci. The library of selected primers can then be used in any of the methods of the invention.

In some embodiments, the minimum threshold, the first minimum threshold, or the second minimum threshold is an interaction score equal to or about 20, 18, 16, 14, 12, 10, 9, 8, 7, 6, 5, 4, 3, 2, or 1 kcal/mol. In some embodiments, the interaction score is calculated as followed as described further herein:

Interaction score=max(−1*ΔG value); or interaction_score=max(−deltaG_2,0.8*(−deltaG_1))

where
deltaG_2=Gibbs energy (energy required to break the dimer) for a dimer that is extensible by PCR on both ends, i.e., the 3' end of each primer anneals to the other primer, and
deltaG_1=Gibbs energy for a dimer that is extensible by PCR on at least one end.

These selection methods minimize the number of candidate primers that have to be removed from the library to achieve the desired reduction in primer dimers. By removing a smaller number of candidate primers from the library, more (or all) of the target loci can be amplified using the resulting primer library.

Multiplexing large numbers of primers imposes considerable constraint on the assays that can be included. Assays that unintentionally interact result in spurious amplification products. The size constraints of miniPCR may result in further constraints. In an embodiment, it is possible to begin with a very large number of potential SNP targets (between about 500 to greater than 1 million) and attempt to design primers to amplify each SNP. Where primers can be designed it is possible to attempt to identify primer pairs likely to form spurious products by evaluating the likelihood of spurious primer duplex formation between all possible pairs of primers using published thermodynamic parameters for DNA duplex formation. Primer interactions may be ranked by a scoring function related to the interaction and primers with the worst interaction scores are eliminated until the number of primers desired is met. In cases where SNPs likely to be heterozygous are most useful, it is possible to also rank the list of assays and select the most heterozygous compatible assays. Experiments have validated that primers with high interaction scores are most likely to form primer dimers. At high multiplexing it is not possible to eliminate all spurious interactions, but it is essential to remove the primers or pairs of primers with the highest interaction scores in silico as they can dominate an entire reaction, greatly limiting amplification from intended targets. We have performed this procedure to create multiplex primer sets of up to and in some cases more than 10,000 primers. The improvement due to this procedure is substantial, enabling amplification of more than 80%, more than 90%, more than 95%, more than 98%, and even more than 99% on target products as determined by sequencing of all PCR products, as compared to 10% from a reaction in which the worst primers were not removed. When combined with a partial semi-nested approach as previously described, more than 90%, and even more than 95% of amplicons may map to the targeted sequences.

Note that there are other methods for determining which PCR probes are likely to form dimers. In an embodiment, analysis of a pool of DNA that has been amplified using a non-optimized set of primers may be sufficient to determine problematic primers. For example, analysis may be done using sequencing, and those dimers which are present in the greatest number are determined to be those most likely to form dimers, and may be removed.

This method has a number of potential application, for example to SNP genotyping, heterozygosity rate determination, copy number measurement, and other targeted sequencing applications. In an embodiment, the method of primer design may be used in combination with the mini-PCR method described elsewhere in this document. In some embodiments, the primer design method may be used as part of a massive multiplexed PCR method.

The use of tags on the primers may reduce amplification and sequencing of primer dimer products. In some embodiments, the primer contains an internal region that forms a loop structure with a tag. In particular embodiments, the primers include a 5' region that is specific for a target locus, an internal region that is not specific for the target locus and forms a loop structure, and a 3' region that is specific for the target locus. In some embodiments, the loop region may lie between two binding regions where the two binding regions are designed to bind to contiguous or neighboring regions of template DNA. In various embodiments, the length of the 3' region is at least 7 nucleotides. In some embodiments, the length of the 3' region is between 7 and 20 nucleotides, such as between 7 to 15 nucleotides, or 7 to 10 nucleotides, inclusive. In various embodiments, the primers include a 5' region that is not specific for a target locus (such as a tag or a universal primer binding site) followed by a region that is specific for a target locus, an internal region that is not specific for the target locus and forms a loop structure, and a 3' region that is specific for the target locus. Tag-primers can be used to shorten necessary target-specific sequences to below 20, below 15, below 12, and even below 10 base pairs. This can be serendipitous with standard primer design when the target sequence is fragmented within the primer binding site or, or it can be designed into the primer design. Advantages of this method include: it increases the number of assays that can be designed for a certain maximal amplicon length, and it shortens the "non-informative" sequencing of primer sequence. It may also be used in combination with internal tagging (see elsewhere in this document).

In an embodiment, the relative amount of nonproductive products in the multiplexed targeted PCR amplification can be reduced by raising the annealing temperature. In cases where one is amplifying libraries with the same tag as the target specific primers, the annealing temperature can be increased in comparison to the genomic DNA as the tags will contribute to the primer binding. In some embodiments we are using considerably lower primer concentrations than previously reported along with using longer annealing times than reported elsewhere. In some embodiments the annealing times may be longer than 3 minutes, longer than 5 minutes, longer than 8 minutes, longer than 10 minutes, longer than 15 minutes, longer than 20 minutes, longer than 30 minutes, longer than 60 minutes, longer than 120 minutes, longer than 240 minutes, longer than 480 minutes, and even longer than 960 minutes. In an embodiment, longer annealing times are used than in previous reports, allowing lower primer concentrations. In various embodiments, longer than normal extension times are used, such as greater than 3, 5, 8, 10, or 15 minutes. In some embodiments, the primer concentrations are as low as 50 nM, 20 nM, 10 nM, 5 nM, 1 nM, and lower than 1 uM. This surprisingly results in robust performance for highly multiplexed reactions, for example 1,000-plex reactions, 2,000-plex reactions, 5,000-plex reactions, 10,000-plex reactions, 20,000-plex reactions, 50,000-plex reactions, and even 100,000-plex reactions. In an embodiment, the amplification uses one, two, three, four or five cycles run with long annealing times, followed by PCR cycles with more usual annealing times with tagged primers.

To select target locations, one may start with a pool of candidate primer pair designs and create a thermodynamic model of potentially adverse interactions between primer pairs, and then use the model to eliminate designs that are incompatible with other the designs in the pool.

In an embodiment, the invention features a method of decreasing the number of target loci (such as loci that may contain a polymorphism or mutation associated with a disease or disorder or an increased risk for a disease or disorder such as cancer) that need to be detected for a diagnosis and/or increasing the disease load that is detected (e.g., increasing the number of polymorphisms or mutations that are detected). In some embodiments, the method includes ranking (such as ranking from highest to lowest) loci by frequency or reoccurrence of a polymorphism or mutation (such as a single nucleotide variation, insertion, or deletion, or any of the other variations described herein) in each locus among subjects with the disease or disorder such as cancer. In some embodiments. PCR primers are designed to some or all of the loci. During selection of PCR primers for a library of primers, primers to loci that have a higher frequency or reoccurrence (higher ranking loci) are favored over those with a lower frequency or reoccurrence (lower ranking loci). In some embodiments, this parameter is included as one of the parameters in the calculation of the scores (such as the undesirability scores) described herein. If desired, primers (such as primers to high ranking loci) that are incompatible with other designs in the library can be included in a different PCR library/pool. In some embodiments, multiple libraries/pools (such as 2, 3, 4, 5 or more) are used in separate PCR reactions to enable amplification of all (or a majority) of the loci represented by all the libraries/pools. In some embodiment, this method is continued until sufficient primers are included in one or more libraries/pools such that the primers, in aggregate, enable the desired disease load to be captured for the disease or disorder (e.g., such as by detection of at least 80, 85, 90, 95, or 99% of the disease load).

In some embodiments, the library of candidate primers includes at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different primers or different primer pairs. In some embodiments, only a relatively small number of candidate primers need to be removed from the library to achieve the desired reduction in primer dimers. In some embodiments, less than 30, 20, 15, 10, 5, or 2% of the candidate primers are removed from the library prior to use of the resulting library for multiplex PCR amplification of target loci. In some embodiments, a relatively large number of candidate primers are removed from the library to achieve the desired characteristics for the resulting library. In some embodiments, at least 20, 30, 40, 50, 60, 70, 80, or 90% of the candidate primers are removed from the library prior to use of the resulting library for multiplex PCR amplification of target loci. In some embodiments, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different primers or different primer pairs remain in the library (after removal of some candidate primers from the library).

After the selection process, the primers remaining in the library may be used in any of the methods of the invention.

Exemplary Methods for Determining Interaction Scores

Exemplary methods of determining a ΔG value (such as the change in Gibbs free energy for primer dimer formation) or an interaction score that indicates the likelihood of dimer formation between candidate primers are described below. In some embodiments, a thermodynamic Nearest-Neighbors approach is used to calculate the likelihood of dimer formation between any two primers (see, e.g., Rahmann and Grafe (2004). "Mean and variance of the Gibbs free energy of oligonucleotides in the nearest neighbor model under varying conditions" Bioinformatics 20, 2928-2933; Allawi, H. T. & SantaLucia, J., Jr. (1998), "Thermodynamics of Internal C-T Mismatches in DNA", *Nucleic Acids Res.* 26, 2694-2701; Peyret, N., Seneviratne, P. A., Allawi, H. T. & SantaLucia, J., Jr. (1999), "Nearest-Neighbor Thermodynamics and NMR of DNA Sequences with Internal A-A, C-C, G-G, and T-T Mismatches", *Biochemistry* 38, 3468-3477; Allawi, H. T. & SantaLucia, J., Jr. (1998), "Nearest-Neighbor Thermodynamics of Internal A-C Mismatches in DNA-Sequence Dependence and pH Effects", *Biochemistry* 37, 9435-9444; Allawi, H. T. & SantaLucia, J., Jr. (1998), "Nearest Neighbor Thermodynamic Parameters for Internal G-A Mismatches in DNA", *Biochemistry* 37, 2170-2179; and Allawi, H. T. & SantaLucia, J., Jr. (1997), "Thermodynamics and NMR of Internal G-T Mismatches in DNA", *Biochemistry* 36, 10581-10594; MultiPLX 2.1 (Kaplinski L, Andreson R, Puurand T, Remm M. MultiPLX: automatic grouping and evaluation of PCR primers. Bioinformatics. 2005 Apr. 15; 21(8):1701-2, which are each hereby incorporated by reference in its entirety).

In some embodiments, the following steps are performed.

Step 1

Figure 33A:
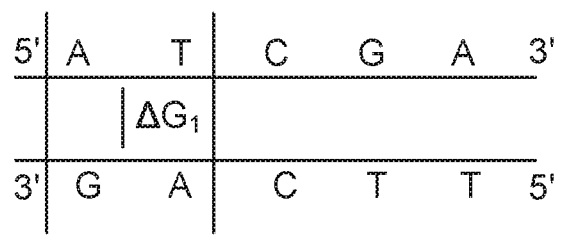
FIGS. 33A-33F: Illustrations of the calculation of an interaction score between primers in a primer library.

For each primer in a set of candidate primers, compare to every other candidate primer in the following way. Implement an ungapped thermodynamic alignment between the two primers, matching the 5' end of the first primer to the 3' end of the second primer. Taking the first two bases (dinucleotide) that align to the other primer and vice versa, determine the ΔH and ΔS values for the dinucleotide in one primer hybridizing to the dinucleotide in the other primer (see the "AT" hybridizing to "GA" in FIG. 33A). ΔH and ΔS values for various combinations of dinucleotides are known and can be determined, for example, using a thermodynamic look up table (such as the Unified NN model parameters according to Allawi and SantaLucia (1997) "Thermodynamics and NMR of internal G-T mismatches in DNA". *Biochemistry*, 36: 10581-10594, which is hereby incorporated by reference in its entirety). Use the ΔH and ΔS values to calculate ΔG for that interaction as follows or as described in any known equation for this.

$$\Delta G=(1000.0*\Delta H-(\text{temperature}*(\Delta S+0.368*(\text{numPhosphates}/2)*\log(\text{saltConcentration}))))/1000.0$$

Figure 33B:
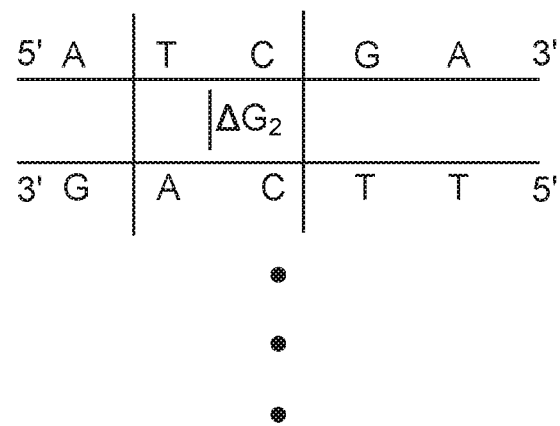

In some embodiments, one or more of the following conditions are assumed for this calculation: temperature: of 60.0° C., primer concentration of 100 nM, or salt concentration of 100 mM. In some embodiments, other conditions are assumed for this calculation, such as the conditions that will be used for multiplex PCR with the pool. Iterate over the remainder of the primer that aligns with the other primer by sliding the bases being observing one base to the right. Continue until ΔG has been calculated for all dinucleotides that align (FIG. 33B). The ΔG for that alignment of the primer pair is the sum of the ΔG values for the various dinucleotides.

Step 2

Figure 33C:
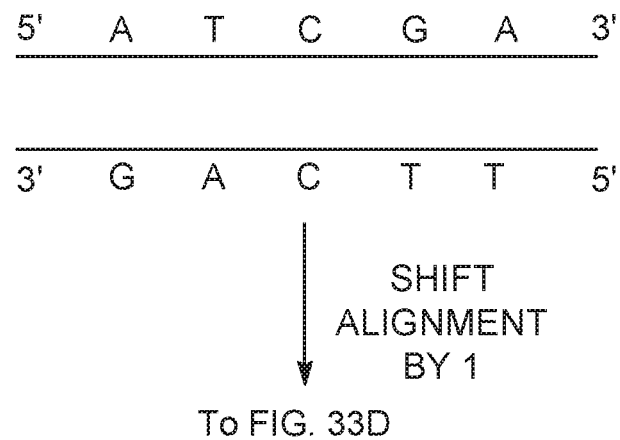
Figure 33D:
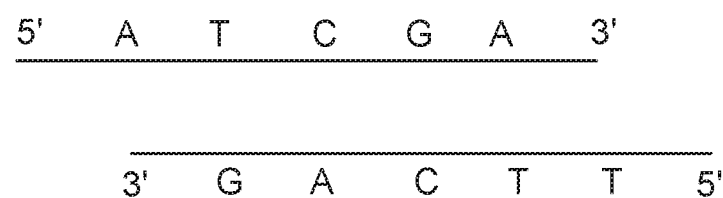

Shift the alignment of the two primers (FIGS. 33C and 33D).

Step 3

Figure 33E:
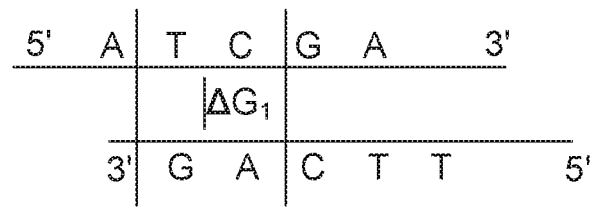
Figure 33F:
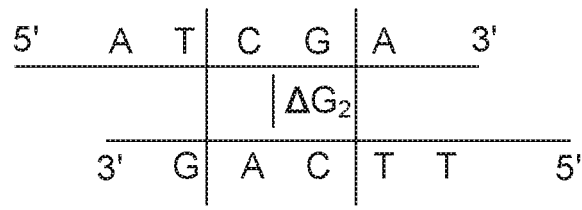

Repeat step 1 again for the new alignment (FIGS. 33E and 33F).

Step 4

After aligning all possible alignments between the two primers, determine the final ΔG value and the interaction score.

In some embodiments, the ΔG value for a combination of primers is the lowest ΔG value (the lowest numerical value, which is indicative of the greatest likelihood of primer dimer formation) out of the ΔG values for all possible alignments between the two primers. For example, if one alignment has a ΔG value of −12 kcal/mol and another alignment has a ΔG value of ~2 kcal/mol then ~12 kcal/mol (worse value) is used as the ΔG value for that combination of primers.

For algorithms such as the one in Experiment 16 in which it is easiest to rank primers based on assigning the worse combination of primers (those with the greatest likelihood of dimer formation) the highest interaction score, then the interaction score can be calculated as follows.

$$\text{Interaction score}=\max(-1*\Delta G\text{ value})$$

For example, if one alignment has a ΔG value of −12 kcal/mol and another alignment has a ΔG value of −2 kcal/mol, then 12 kcal/mol is used as the interaction score. In this case, the interaction score with the largest numerical positive number indicates the least desirable combination of primers due to the greatest likelihood of primer dimer formation.

In some embodiments, the interaction score is calculated as follows (this score weights the ΔG values depending on the number of ends that a dimer can be extended by PCR).

$$\text{interaction\_score}=\max(-\text{delta}G\_2, 0.8*(-\text{delta}G\_1))$$

where deltaG_2=Gibbs energy (energy required to break the dimer) for a dimer that is extensible by PCR on both ends, i.e., the 3' end of each primer anneals to the other primer, and deltaG_1=Gibbs energy for a dimer that is extensible by PCR on at least one end.

In some embodiments, deltaG_2 is determined by performing steps 1-4 above for all the alignments in which a dimer is extensible by PCR on both ends. The deltaG_2 value is the lowest ΔG value (the lowest numerical value, which is indicative of the greatest likelihood of primer dimer formation) for all the alignments in which a dimer is extensible by PCR on both ends.

In some embodiments, deltaG_1 is determined by performing steps 1-4 above for all the alignments in which a dimer is extensible by PCR on at least one end (such as by PCR on one end or by PCR on both ends). The deltaG_1 value is the lowest ΔG value (the lowest numerical value, which is indicative of the greatest likelihood of primer dimer formation) for all the alignments in which a dimer is extensible by PCR on at least one end.

In some embodiments, possible loop structures or gaps in alignment between primers are also considered.

In some embodiments, ΔG values from step 4 for each possible combination of two primers (each possible primer dimer) in a library are all equal to or greater than −20, −18, −16, −14, −12, −10, −9, −8, −7, −6, −5, −4, −3, −2, or −1 kcal/mol. In some embodiments, ΔG values from step 4 for at least 80, 85, 90, 92, 94, 96, 98, 99, or 100% of the primers in the library for possible combinations of that primer with other primers in the library are all equal to or greater than −20, −18, −16, −14, −12, −10, −9, −8, −7, −6, −5, −4, −3, −2, or −1 kcal/mol. In some embodiments, possible combinations of two primers in a library that have positive ΔG values are ignored since these values are indicative of no likelihood to for primer dimers. In some embodiments for the possible combination of two primers in a library that have negative ΔG values, the ΔG values are between −20 and 0 kcal/mol, such as between −15 and 0 kcal/mol, −10 and 0 kcal/mol, −8 and 0 kcal/mol, −7 and 0 kcal/mol, −6 and 0 kcal/mol, −5.5 and 0 kcal/mol, −5 and 0 kcal/mol, −4.5 and 0 kcal/mol, −4 and 0 kcal/mol, −3.5 and 0 kcal/mol, −3 and 0 kcal/mol, −2.5 and 0 kcal/mol, −2 and 0 kcal/mol, or −1.5 and 0 kcal/mol, inclusive.

In some embodiments, the interaction scores from step 4 for each possible combination of two primers in a library are all equal to or less than 20, 18, 16, 14, 12, 10, 9, 8, 7, 6, 5, 4, 3, 2, or 1 kcal/mol. In some embodiments, the interaction scores from step 4 for at least 80, 85, 90, 92, 94, 96, 98, 99, or 100% of the primers in the library for possible combinations of that primer with other primers in the library are all equal to or less than 20, 18, 16, 14, 12, 10, 9, 8, 7, 6, 5, 4, 3, 2, or 1 kcal/mol. In some embodiments, possible combination of two primers in a library that have negative interaction scores are ignored since these values are indicative of no likelihood to for primer dimers. In some embodiments for the possible combination of two primers in a library that have positive interaction scores, the interaction scores are between 20 and 0 kcal/mol, such as between 15 and 0 kcal/mol, 10 and 0 kcal/mol, 8 and 0 kcal/mol, 7 and 0 kcal/mol, 6 and 0 kcal/mol, 5.5 and 0 kcal/mol, 5 and 0 kcal/mol, 4.5 and 0 kcal/mol, 4 and 0 kcal/mol, 3.5 and 0 kcal/mol, 3 and 0 kcal/mol, 2.5 and 0 kcal/mol, 2 and 0 kcal/mol, or 1.5 and 0 kcal/mol, inclusive.

In some embodiments, the score (such as the undesirability score) for candidate primers is based at least in part on the ΔG value or the interaction score that indicates the likelihood of dimer formation between candidate primers as calculated using any of these methods.

Exemplary Primer Libraries

In one aspect, the invention features libraries of primers, such as primers selected from a library of candidate primers using any of the methods of the invention. In some embodiments, the library includes primers that simultaneously hybridize (or are capable of simultaneously hybridizing) to or that simultaneously amplify (or are capable of simultaneously amplifying) at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci in one reaction volume. In various embodiments, the library includes primers that simultaneously amplify (or are capable of simultaneously amplifying) between 1,000 to 2,000; 2,000 to 5,000; 5,000 to 7,500; 7,500 to 10,000; 10,000 to 20,000; 20,000 to 25,000; 25,000 to 30,000; 30,000 to 40,000; 40,000 to 50,000; 50,000 to 75,000; or 75,000 to 100,000 different target loci in one reaction volume, inclusive. In various embodiments, the library includes primers that simultaneously amplify (or are capable of simultaneously amplifying) between 1,000 to 100,000 different target loci in one reaction volume, such as between 1,000 to 50,000; 1,000 to 30,000; 1,000 to 20,000; 1,000 to 10,000; 2,000 to 30,000; 2,000 to 20,000; 2,000 to 10,000; 5,000 to 30,000; 5,000 to 20,000; or 5,000 to 10,000 different target loci, inclusive. In some embodiments, the library includes primers that simultaneously amplify (or are capable of simultaneously amplifying) the target loci in one reaction volume such that less than 60, 40, 30, 20, 10, 5, 4, 3, 2, 1, 0.5, 0.25, 0.1, or 0.5% of the amplified products are primer dimers. The various embodiments, the amount of amplified products that are primer dimers is between 0.5 to 60%, such as between 0.1 to 40%, 0.1 to 20%, 0.25 to 20%, 0.25 to 10%, 0.5 to 20%, 0.5 to 10%, 1 to 20%, or 1 to 10%, inclusive. In some embodiments, the primers simultaneously amplify (or are capable of simultaneously amplifying) the target loci in one reaction volume such that at least 50, 60, 70, 80, 90, 95, 96, 97, 98, 99, or 99.5% of the amplified products are target amplicons. In various embodiments, the amount of amplified products that are target amplicons is between 50 to 99.5%, such as between 60 to 99%, 70 to 98%, 80 to 98%, 90 to 99.5%, or 95 to 99.5%, inclusive. In some embodiments, the primers simultaneously amplify (or are capable of simultaneously amplifying) the target loci in one reaction volume such that at least 50, 60, 70, 80, 90, 95, 96, 97, 98, 99, or 99.5% of the target loci are amplified. In various embodiments, the amount target loci that are amplified is between 50 to 99.5%, such as between 60 to 99%, 70 to 98%, 80 to 99%, 90 to 99.5%, 95 to 99.9%, or 98 to 99.99% inclusive. In some embodiments, at least 50, 60, 70, 80, 90, 95, 96, 97, 98, 99, or 99.5% of the target loci are amplified at least 5, 10, 20, 40, 50, 60, 80, 100, 120, 150, 200, 300, or 400-fold. In some embodiments, the library of primers includes at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 primer pairs, wherein each pair of primers includes a forward test primer and a reverse test primer where each pair of test primers hybridize to a target locus. In some embodiments, the library of primers includes at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 individual primers that each hybridize to a different target locus, wherein the individual primers are not part of primer pairs.

In some embodiments, the library includes primers (such as at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different primers or different primer pairs) that simultaneously amplify (or are capable of simultaneously amplifying) the target loci (such as at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci) in one reaction volume such that one or more of the following: (i) less than 60, 40, 30, 20, 10, 5, 4, 3, 2, 1, 0.5, 0.25, 0.1, or 0.5% of the amplified products are primer dimers, (ii) at least 50, 60, 70, 80, 90, 95, 96, 97, 98, 99, or 99.5% of the amplified products are target amplicons, (iii) at least 50, 60, 70, 80, 90, 95, 96, 97, 98, 99, or 99.5% of the target loci are amplified, (iv) at least 50, 60, 70, 80, 90, 95, 96, 97, 98, 99, or 99.5% of the target loci are amplified at least 5, 10, 20, 40, 50, 60, 80, 100, 120, 150, 200, 300, or 400-fold, (v) at least 60, 70, 80, 90, 95, 96, 97, 98, 99, 99.5, or 100% of the amplified products map to the human genome, or (vi) any combination thereof.

In some embodiments, the library includes at least 1,000 different primers or different primer pairs (such as at least 2,000; 5,000; 7,500; 10,000; 15,000; 19,000; 20,000; 25,000; 27,000; 28,000; 30,000; 40,000; 50,000; 75,000; or 100,000 different primers or different primer pairs) that simultaneously amplify (or are capable of simultaneously amplifying) at least 1,000 different target loci (such as at least 2,000; 5,000; 7,500; 10,000; 15,000; 19,000; 20,000; 25,000; 27,000; 28,000; 30,000; 40,000; 50,000; 75,000; or 100,000 different target loci) in one reaction volume such that one or more of the following: (i) less than 60% of the amplified products are primer dimers and at least 40% of the amplified products are target amplicons, (ii) less than 40% of the amplified products are primer dimers and at least 60% of the amplified products are target amplicons, (iii) less than 20% of the amplified products are primer dimers and at least 80% of the amplified products are target amplicons, (iv) less than 10% of the amplified products are primer dimers and at least 90% of the amplified products are target amplicons, or (v) less than 5% of the amplified products are primer dimers and at least 95% of the amplified products are target amplicons. In some embodiments for the amplification of nucleic acids (such as DNA or RNA) from a single cell (such as a fetal or embryonic cell), the library includes at least 1,000 different primers or different primer pairs (such as at least 2,000; 5,000; 7,500; 10,000; 15,000; 19,000; 20,000; 25,000; 27,000; 28,000; 30,000; 40,000; 50,000; 75,000; or 100,000 different primers or different primer pairs) that simultaneously amplify (or are capable of simultaneously amplifying) at least 1,000 different target loci (such as at least 2,000; 5,000; 7,500; 10,000; 15,000; 19,000; 20,000; 25,000; 27,000; 28,000; 30,000; 40,000; 50,000; 75,000; or 100,000 different target loci) in one reaction volume such that one or more of the following: (i) less than 60% of the amplified products are primer dimers and at least 10% of the amplified products are target amplicons, (ii) less than 40% of the amplified products are primer dimers and at least 10% of the amplified products are target amplicons, (iii) less than 20% of the amplified products are primer dimers and at least 10% of the amplified products are target amplicons, (iv) less than 10% of the amplified products are primer dimers and at least 10% of the amplified products are target amplicons, (v) less than 5% of the amplified products are primer dimers and at least 15% of the amplified products are target amplicons, (vi) less than 60% of the amplified products are primer dimers and at least 20% of the amplified products are target amplicons, (vii) less than 40% of the amplified products are primer dimers and at least 20% of the amplified products are target amplicons, (viii) less than 20% of the amplified products are primer dimers and at least 20% of the amplified products are target amplicons, (ix) less than 10% of the amplified products are primer dimers and at least 20% of the amplified products are target amplicons, (x) less than 5% of the amplified products are primer dimers and at least 20% of the amplified products are target amplicons, (xi) less than 60% of the amplified products are primer dimers and at least 40% of the amplified products are target amplicons, (xii) less than 40% of the amplified products are primer dimers and at least 40% of the amplified products are target amplicons, (xiii) less than 20% of the amplified products are primer dimers and at least 40% of the amplified products are target amplicons, (xiv) less than 10% of the amplified products are primer dimers and at least 40% of the amplified products are target amplicons, (xv) less than 5% of the amplified products are primer dimers and at least 45% of the amplified products are target amplicons, (xvi) less than 40% of the amplified products are primer dimers and at least 60% of the amplified products are target amplicons, (xvii) less than 20% of the amplified products are primer dimers and at least 80% of the amplified products are target amplicons, (xviii) less than 10% of the amplified products are primer dimers and at least 90% of the amplified products are target amplicons, or (xviiii) less than 5% of the amplified products are primer dimers and at least 95% of the amplified products are target amplicons. In some embodiments, at least 50, 60, 70, 80, 90, 95, 96, 97, 98, 99, or 99.5% of the target loci are amplified at least 5, 10, 20, 40, 50, 60, 80, 100, 120, 150, 200, 300, or 400-fold. In some embodiments, one or more of these embodiments (e.g., percent of primer dimers, target amplicons, or amplified target loci) is achieved after greater than or equal to 5, 10, 20, 30, 40, 50, or 60 cycles of PCR are performed. In some embodiments for a library that amplifies human target loci, at least 60, 70, 80, 90, 95, 96, 97, 98, 99, 99.5, or 100% of the amplified products map to the human genome.

In various embodiments, the concentration of each primer is less than 100, 75, 50, 25, 20, 10, 5, 2, 1, 0.5, 0.1, or 0.05 nM, or less than 500, 100, 10, or 1 uM. In various embodiments, the concentration of each primer is between 1 uM to 100 nM, such as between 1 uM to 1 nM, 1 to 75 nM, 1 to 20 nM, 1 to 10 nM, 2 to 50 nM or 5 to 50 nM, inclusive. In some embodiments, the concentration of one or more universal primers is between 0.2 to 3 µM, such as between 0.5 and 2.5 µM, 0.5 to 1 µM, or 1 to 2.5 µM per primer, inclusive, and the concentration of each primer except the universal primer(s) is between 1 uM to 100 nM, such as between 1 uM to 1 nM, 1 to 75 nM, 1 to 20 nM, 1 to 10 nM, 2 to 50 nM or 5 to 50 nM, inclusive. In various embodiments, the GC content of the primers is between 30 to 80%, such as between 20 to 70%, 40 to 70%, or 50 to 60%, inclusive. In some embodiments, the range of GC content of the primers is less than 30, 20, 10, or 5%. In some embodiments, the range of GC content of the primers is between 5 to 30%, such as 5 to 20% or 5 to 10%, inclusive. In some embodiments, there is a high GC content in the 3' end of the primers. In some embodiments, there are at least 2 (such as 3, 4, or 5) guanines or cytosines in the last 5 bases at the 3' end of the primers. In some embodiments, there are at least 1 (such as 2 or 3) guanines or cytosines in the last 3 bases at the 3' end of the primers. In some embodiments, a maximum of 2 (such as 2, 1, or 0) bases in the last 5 bases at the 3' end of the primers are guanines or cytosines. In some embodiments, a maximum of 1 (such as 1 or 0) base in the last 5 bases at the 3' end of the primers is a guanine or cytosine. In some embodiments, the maximum length of a homopolymer (the same base in a row) in the primers is 12, 10, 8, 6, 5, 4, 3, or 2 consecutive nucleotides. In some embodiments, the melting temperature ($T_m$) of the test primers is between 40 to 80° C., such as 50 to 70° C., 55 to 65° C., 54 to 60.5° C., or 57 to 60.5° C., inclusive. In some embodiments, the $T_m$ is calculated using the Primer3 program (libprimer3 release 2.2.3) using the built-in SantaLucia parameters (the world wide web at primer3.sourceforge.net). In some embodiments, the range of melting temperature of the primers is less than 15, 10, 5, 3, or 1° C. In some embodiments, the range of melting temperature of the primers is between 1 to 15° C., such as between 1 to 10° C., 1 to 5° C., or 1 to 3° C., inclusive. In some embodiments, the range of melting temperatures of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the primers is between 1 to 15° C., such as between 1 to 10° C., 1 to 5° C., 1 to 3° C., 2 to 5° C., 3 to 10° C., or 3 to 5° C., inclusive. In some embodiments, the length of the primers is between 15 to 100 nucleotides, such as between 15 to 75 nucleotides, 15 to 40 nucleotides, 17 to 35 nucleotides, 18 to 30 nucleotides, 20 to 65 nucleotides, inclusive. In some embodiments, the range of the length of the primers is less than 50, 40, 30, 20, 10, or 5 nucleotides. In some embodiments, the range of the length of the primers is between 5 to 50 nucleotides, such as 5 to 40 nucleotides, 5 to 20 nucleotides, or 5 to 10 nucleotides, inclusive. In some embodiments, the length of the target amplicons is between 50 and 100 nucleotides, such as between 60 and 80 nucleotides, or 60 to 75 nucleotides, inclusive. In some embodiments, the length of the target amplicons is between 30 and 400 nucleotides, such as between 30 and 200 nucleotides, or 100 and 400 nucleotides, inclusive. In some embodiments, the length of the target amplicons is at least 100; 200; 300, 400; 500; 600; 700; 800; 900; 1,000; 1,200; 1,500; 2,000; or 3,000 nucleotides. In some embodiments, the length of the target amplicons is between 100 and 1,500 nucleotides, such as between 100 to 1,000; 100 to 500, 500 to 750, or 750 to 1,000 nucleotides, inclusive. Longer amplicons may be desirable, e.g., for applications in which is it desirable to screen for multiple potential mutations in one amplicon, such as carrier screening. In some embodiments, one round of PCR is performed to produce relatively long amplicons (such as at least 250 or 500 nucleotides in length) and then a second round of PCR is performed to produce shorter amplicons (to amplify regions within the amplicons amplified in the first round of PCR, such as regions of less than 200 or 100 nucleotides in length). In some embodiments, the range of the length of the target amplicons is less than 50, 25, 15, 10, or 5 nucleotides. In some embodiments, the range of the length of the target amplicons is between 5 to 50 nucleotides, such as 5 to 25 nucleotides, 5 to 15 nucleotides, or 5 to 10 nucleotides, inclusive. In some embodiments, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 or all of the target amplicons have a length that falls within the range of the average length of the amplicons ±5% of the average length, average length ±20%, average length ±20%, or average length ±30%, or average length ±50%.

In some embodiments, library includes at least at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different primers that each includes a target specific sequence, such as a sequence that binds a target locus but does not substantially bind to other nucleic acids (such as non-target loci) in a sample, e.g., a biological sample, which naturally includes other nucleic acids. In some embodiments, each primer binds and amplifies a target locus by at least 2, 4, 6, 8, 10, 20, 50-fold or more than one or more (or all) other nucleic acids (such as non-target loci) in a sample. In some embodiments, the library includes at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target specific primers (e.g., primers that are specific for a target locus). In some embodiments, part or all of the polynucleotide sequence is a non-random sequence for at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different primers in the library. In some embodiments, library also includes a universal primer, a random primer, a primer with a non-naturally occurring polynucleotide sequence, or a primer with a polynucleotide sequence not naturally found in a human. In some embodiments, the universal or random primer has a non-naturally occurring polynucleotide sequence or a polynucleotide sequence not naturally found in a human.

In some embodiments, the composition includes at least one primer (e.g., at least 25; 50; 75; 100; 300; 500; 750; 1,000; 2,000; 5,000; 7,500; 10,000; 15,000; 19,000; 20,000; 25,000; 27,000; 28,000; 30,000; 40,000, 50,000; 75,000; or 100,000 non-identical primers) with a polynucleotide sequence of a human nucleic acid and at least one primer (e.g., at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical primers) with a polynucleotide sequence that is not found in a human (such as a universal primer, a primer that comprises a region or consists entirely of random nucleotides, or a primer with a region such as a tag or barcode of one or more nucleotides that are not found in a human or are not found in nature as part of the polynucleotide sequence of the primer). In some embodiments, at least one primer (e.g., at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical primers) includes a region of one or more nucleotides that is not naturally part of the primer sequence (such as a region added to the 5' end of the target specific sequence in the primer or an internal region added between the 5' and 3' ends of the primer). In some embodiments, the primer is free of the nucleic acids (such as genes) which, in the naturally-occurring genome of the organism from which the nucleic acid of the invention is derived, flank the gene. In some embodiments, the primer has been separated from one or more components that naturally accompany the corresponding sequence in nature (such as in the genome of a human). Typically, each primer is at least 90, 95, 98, 99, 99.9, or 100%, by weight, free from the molecules (such as proteins, nucleic acids, and naturally-occurring organic molecules) that naturally accompany the corresponding sequence in nature (such as in the genome of a human). Purity can be assayed by any appropriate method, e.g., by electrophoresis or HPLC analysis.

In some embodiments, the primers in the library are not immobilized (such as not immobilized to a solid support) or not part of a microarray. In some embodiments, the primers are dissolved in solution (such as dissolved in the liquid phase). In some embodiments, the library comprises a microarray. In some embodiments, the amplified products are detected using an array, such as an array with probes to one or more chromosomes of interest (e.g., chromosome 13, 18, 21, X, Y, or any combination thereof).

In some embodiments, at least one of the primers (such as at least 20, 40, 80, 90, 95, 98, 99, 99.5, or 100% of the primers) in a library are nucleic acid analogs that have a lower likelihood of primer dimerization compared to the naturally-occurring nucleic acids (see, e.g., U.S. Pat. Nos. 7,414,118 and 6,001,611; which are each hereby incorporated by reference in its entirety). Exemplary nucleic acid analogs have a modified pyrimidine nucleobase, or a purine or pyrimidine base that contains an exocyclic amine.

In some embodiments, the primer library includes a small number of primers (such as less than 5, 2, 1, or 0.5% of the primers in the library) that do not have one or more of the properties described herein. In various embodiments, at least 80, 90, 95, 96, 97, 98, 99, 99.5, or 100% of the primers in the library have one or more of the following properties: (i) ΔG values for possible combinations of that primer with other primers in the library are all equal to or greater than −20, −18, −16, −14, −12, −10, −9, −8, −7, −6, −5, −4, −3, −2, or −1 kcal/mol; (ii) ΔG values for the possible combination of that primer with other primers in the library that have negative ΔG are between −20 and 0 kcal/mol, such as between −15 and 0 kcal/mol, −10 and 0 kcal/mol, −8 and 0 kcal/mol, −7 and 0 kcal/mol, −6 and 0 kcal/mol, −5.5 and 0 kcal/mol, −5 and 0 kcal/mol, −4.5 and 0 kcal/mol, −4 and 0 kcal/mol, −3.5 and 0 kcal/mol, −3 and 0 kcal/mol, −2.5 and 0 kcal/mol, −2 and 0 kcal/mol, or −1.5 and 0 kcal/mol, inclusive; (iii) the GC content is between 30 to 80%, such as between 20 to 70%, 40 to 70%, or 50 to 60%, inclusive; (iv) the range of GC content is less than 30, 20, 10, or 5% or the range of GC content of the primers is between 5 to 30%, such as 5 to 20%, or 5 to 10%, inclusive; (v) a maximum of 2 (such as 2, 1, or 0) bases in the last 5 bases at the 3' end of the primers are guanines or cytosines; (vi) the melting temperature ($T_m$) of the primers is between 40 to 80° C., such as 50 to 70° C., 55 to 65° C., 54 to 60.5° C., or 57 to 60.5° C., inclusive, (vii) the range of melting temperature of the primers is less than 15, 10, 5, 3, or 1° C.; (viii) the range of melting temperature of the primers is between 1 to 15° C., such as between 1 to 10° C., 1 to 5° C., 1 to 3° C., 2 to 5° C., 3 to 10° C., or 3 to 5° C., inclusive, (ix) the length of the primers is between 15 to 100 nucleotides, such as between 15 to 75 nucleotides, 15 to 40 nucleotides, 17 to 35 nucleotides, 18 to 30 nucleotides, or 20 to 65 nucleotides, inclusive; (x) the range of the length of the primers is less than 50, 40, 30, 20, 10, or 5 nucleotides; (xi) the range of the length of the primers is between 5 to 50 nucleotides, such as 5 to 40 nucleotides, 5 to 20 nucleotides, or 5 to 10 nucleotides, (xii) the length of the target amplicons is between 50 and 100 nucleotides, such as between 60 and 80 nucleotides, or 60 to 75 nucleotides; (xiii) the length of the target amplicons is between 30 and 400 nucleotides, such as between 30 and 200 nucleotides, or 100 and 400 nucleotides; (xiv) the range of the length of the target amplicons is less than 50, 25, 15, 10, or 5 nucleotides; (xv) the range of the length of the target amplicons is between 5 to 50 nucleotides, such as 5 to 25 nucleotides, 5 to 15 nucleotides, or 5 to 10 nucleotides, (xvi) the maximum length of a homopolymer in the primers is 12, 10, 8, 6, 5, 4, 3, or 2 consecutive nucleotides; (xvii) the concentration of each primer is less than 100, 75, 50, 25, 20, 10, 5, 2, 1, 0.5, 0.1, or 0.05 nM, or less than 500, 100, 10, or 1 uM; (xviii) the concentration of each primer is between 1 uM to 100 nM, such as between 1 uM to 1 nM, 1 to 75 nM, 1 to 20 nM, 1 to 10 nM, 2 to 50 nM, or 5 to 50 nM, inclusive; (xix) at least 80, 90, 92, 94, 96, 98, 99, or 100% of the molecules of that primer are extended to form amplified products; (xx) SNPs (if any) are not in the last 5 nucleotides in the 3' end of the candidate primer; (xxi) the target bases (the bases of interest in a target locus) are near an end (the 3' or 5' end) of the amplicon; (xxii) the region of hybridization is separated from the polymorphic site by a small number of bases, where the small number is selected from the group consisting of 1, 2, 3, 4, 5, 6 to 10, 11 to 15, 16 to 20, 21 to 25, 26 to 30, and 31 to 60; (xxiii) the length of the annealing step is greater than 1, 3, 5, 8, 10, 15, 20, 30, 45, 60, 75, 90, 120, 150, or 180 minutes, (xxiv) the length of the annealing step (per PCR cycle) is between 5 and 180 minutes, such as 5 to 60, 10 to 60, 5 to 30, or 10 to 30 minutes, inclusive, (xxv) the length of the annealing step is greater than 5 minutes (such greater than 10, or 15 minutes), and the concentration of each primer is less than 20 nM, (xxvi) the length of the annealing step is greater than 5 minutes (such greater than 10, or 15 minutes), and the concentration of each primer is between 1 to 20 nM, or 1 to 10 nM, inclusive; (xxvii) the length of the annealing step is greater than 20 minutes (such as greater than 30, 45, 60, or 90 minutes), and the concentration of each primer is less than 1 nM; (xxviii) the annealing temperature is at least 1, 2, 3, 4, 5, 6, 7, 8, 9, 10, 11, 12, 13, or 15° C. greater than the melting temperature (such as the empirically measured or calculated $T_m$) of the primers; (xxix) the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the melting temperature (such as the empirically measured or calculated $T_m$) of the primers; (xxx) the annealing temperature is at least 1, 2, 3, 4, 5, 6, 7, 8, 9, 10, 11, 12, 13, or 15° C. greater than the highest melting temperature of the primers; (xxxi) the annealing temperature is at least 1, 2, 3, 4, 5, 6, 7, 8, 9, 10, 11, 12, 13, or 15° C. greater than the average melting temperature of the primers, (xxxii) the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the average melting temperature of the primers; and (xxviii) any combination thereof. In various embodiments, at least 80, 90, 95, 96, 97, 98, 99, 99.5, or 100% of the primers in the library have one or more of the following properties: (i) $\Delta G$ values for possible combinations of that primer with other primers in the library are all equal to or greater than −20, −18, −16, −14, −12, −10, −9, −8, −7, −6, −5, −4, −3, −2, or −1 kcal/mol; (ii) $\Delta G$ values for the possible combination of that primer with other primers in the library that have negative $\Delta G$ are between −20 and 0 kcal/mol, such as between −15 and 0 kcal/mol, −10 and 0 kcal/mol, −8 and 0 kcal/mol, −7 and 0 kcal/mol, −6 and 0 kcal/mol, −5.5 and 0 kcal/mol, −5 and 0 kcal/mol, −4.5 and 0 kcal/mol, −4 and 0 kcal/mol, −3.5 and 0 kcal/mol, −3 and 0 kcal/mol, −2.5 and 0 kcal/mol, −2 and 0 kcal/mol, or −1.5 and 0 kcal/mol, inclusive; (iii) the melting temperature ($T_m$) of the primers is between 40 to 80° C., such as 50 to 70° C., 55 to 65° C., 54 to 60.5° C., or 57 to 60.5° C., inclusive; (iv) the range of melting temperature of the primers is less than 15, 10, 5, 3, or 1° C.; (v) the range of melting temperature of the primers is between 1 to 15° C., such as between 1 to 10° C., 1 to 5° C., 1 to 3° C., 2 to 5° C., 3 to 10° C., or 3 to 5° C., inclusive, (vi) the length of the target amplicons is between 50 and 100 nucleotides, such as between 60 and 80 nucleotides, or 60 to 75 nucleotides; (vii) the length of the target amplicons is between 30 and 400 nucleotides, such as between 30 and 200 nucleotides, or 100 and 400 nucleotides; (viii) the range of the length of the target amplicons is less than 50, 25, 15, 10, or 5 nucleotides; (ix) the range of the length of the target amplicons is between 5 to 50 nucleotides, such as 5 to 25 nucleotides, 5 to 15 nucleotides, or 5 to 10 nucleotides; (x) the concentration of each primer is less than 100, 75, 50, 25, 20, 10, 5, 2, 1, 0.5, 0.1, or 0.05 nM, or less than 500, 100, 10, or 1 uM; (xi) the concentration of each primer is between 1 uM to 100 nM, such as between 1 uM to 1 nM, 1 to 75 nM, 1 to 20 nM, 1 to 10 nM, 2 to 50 nM, or 5 to 50 nM, inclusive; (xii) the annealing temperature is at least 1, 2, 3, 4, 5, 6, 7, 8, 9, 10, 11, 12, 13, or 15° C. greater than the melting temperature (such as the empirically measured or calculated $T_m$) of the primers; (xiii) the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the melting temperature (such as the empirically measured or calculated $T_m$) of the primers; (xiv) the annealing temperature is at least 1, 2, 3, 4, 5, 6, 7, 8, 9, 10, 11, 12, 13, or 15° C. greater than the highest melting temperature of the primers; (xv) the annealing temperature is at least 1, 2, 3, 4, 5, 6, 7, 8, 9, 10, 11, 12, 13, or 15° C. greater than the average melting temperature of the primers, (xvi) the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the average melting temperature of the primers; and (xvii) any combination thereof.

In various embodiments, at least 80, 90, 95, 96, 97, 98, 99, 99.5, or 100% of the primers in the library have one or more of the following properties: (i) $\Delta G$ values for possible combinations of that primer with other primers in the library are all equal to or greater than −10 kcal/mol, (ii) the range of melting temperature of the primers is between 1 to 15° C., (iii) the length of the target amplicons is between 50 and 100 nucleotides, (iv) the concentration of each primer is less than 20 nM, (v) the length of the annealing step is greater than 5 minutes (such as greater than 10 minutes), (vi) the length of the annealing step is greater than 5 minutes (such greater than 10 minutes), and the concentration of each primer is less than 20 nM, and (vii) any combination thereof. In various embodiments, at least 80, 90, 95, 96, 97, 98, 99, 99.5, or 100% of the primers in the library have the following properties: (i) $\Delta G$ values for possible combinations of that primer with other primers in the library are all equal to or greater than −10 kcal/mol and (ii) the range of melting temperature of the primers is between 1 to 15° C. In various embodiments, at least 80, 90, 95, 96, 97, 98, 99, 99.5, or 100% of the primers in the library have the following properties: (i) the length of the target amplicons is between 50 and 100 nucleotides, and (ii) the concentration of each primer is less than 20 nM. In various embodiments, at least 80, 90, 95, 96, 97, 98, 99, 99.5, or 100% of the primers in the library have the following properties: (i) the length of the target amplicons is between 50 and 100 nucleotides and (ii) the length of the annealing step is greater than 5 minutes (such as greater than 10 minutes). In various embodiments, at least 80, 90, 95, 96, 97, 98, 99, 99.5, or 100% of the primers in the library have the following properties: (i) the length of the target amplicons is between 50 and 100 nucleotides, (ii) the length of the annealing step is greater than 5 minutes (such greater than 10 minutes), and (iii) the concentration of each primer is less than 20 nM, and (vii) any combination thereof.

In various embodiments, at least 80, 90, 95, 96, 97, 98, 99, 99.5, or 100% of the primers in the library have one or more of the following properties: (i) the annealing temperature is at least 5° C. (such as at least 6, 8, or 10° C.) greater than the melting temperature (such as the empirically measured or calculated $T_m$) of the primers; (ii) the annealing temperature is between 5 and 15° C., inclusive greater than the melting temperature of the primers; (iii) the annealing temperature is at least 5° C. (such as at least 6, 8, or 10° C.) greater than the highest melting temperature of the primers; (iv) the annealing temperature is at least 5° C. (such as at least 6, 8, or 10° C.) greater than the average melting temperature of the primers, (v) the annealing temperature is between 4 and 15° C., inclusive greater than the average melting temperature of the primers; and (vi) any combination thereof. In various embodiments, at least 80, 90, 95, 96, 97, 98, 99, 99.5, or 100% of the primers in the library have one or more of the following properties: (i) the annealing temperature is at least 5° C. (such as at least 6, 8, or 10° C.) greater than the melting temperature (such as the empirically measured or calculated $T_m$) of the primers and the length of the annealing step is greater than 5 minutes (such greater than 10 minutes); (ii) the annealing temperature is between 5 and 15° C., inclusive greater than the melting temperature of the primers and the length of the annealing step is greater than 5 minutes (such greater than 10 minutes); (iii) the annealing temperature is at least 5° C. (such as at least 6, 8, or 10° C.) greater than the highest melting temperature of the primers and the length of the annealing step is greater than 5 minutes (such greater than 10 minutes); (iv) the annealing temperature is at least 5° C. (such as at least 6, 8, or 10° C.) greater than the average melting temperature of the primers and the length of the annealing step is greater than 5 minutes (such greater than 10 minutes), (v) the annealing temperature is between 4 and 15° C., inclusive greater than the average melting temperature of the primers and the length of the annealing step is greater than 5 minutes (such greater than 10 minutes), and (vii) any combination thereof. In some embodiments, the guanine-cytosine (GC) content of the primers is between 30% and 80%, inclusive, the range of melting temperatures of the primers is less than 5° C.; and the length of the primers is between 15 to 75 nucleotides, inclusive;

In some embodiments, some (such as at least 80, 90, or 95%) or all of the adaptors or primers include one or more linkages between adjacent nucleotides other than a naturally-occurring phosphodiester linkage. Examples of such linkages include phosphoramide, phosphorothioate, and phosphorodithioate linkages. In some embodiments, some (such as at least 80, 90, or 95%) or all of the adaptors or primers include a thiophosphate (such as a monothiophosphate) between the last 3' nucleotide and the second to last 3' nucleotide. In some embodiments, some (such as at least 80, 90, or 95%) or all of the adaptors or primers include a thiophosphate (such as a monothiophosphate) between the last 2, 3, 4, or 5 nucleotides at the 3' end. In some embodiments, some (such as at least 80, 90, or 95%) or all of the adaptors or primers include a thiophosphate (such as a monothiophosphate) between at least 1, 2, 3, 4, or 5 nucleotides out of the last 10 nucleotides at the 3' end. In some embodiments, such primers are less likely to be cleaved or degraded, such primers may be desirable if a polymerase with proof-reading ability is used (to reduce or prevent the polymerase from removing nucleotides from the primers). In some embodiments, any of the embodiments involving primers with at least one linkage other than a naturally-occurring phosphodiester linkage are used with a polymerase having proof-reader activity. In some embodiments, the primers do not contain an enzyme cleavage site (such as a protease cleavage site). In some embodiments, equal to or greater than 1, 10, 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 primers in the library are non-naturally occurring nucleic acids (such nucleic acids with one or more linkages between adjacent nucleotides other than a naturally-occurring phosphodiester linkage).

In some embodiments, the primers have any combination of two or more of the aspects or embodiments disclosed herein.

These primer libraries can be used in any of the methods of the invention.

Exemplary Primers

The primer design methods of the invention have been used to generate several exemplary primer libraries to human target loci. For example, the primer design methods of the invention were used to generate the primer libraries shown in FIG. 34 (SEQ ID NOs. 1-3,600), FIG. 35 (SEQ ID NOs. 3,601-11,658), and FIG. 36 (SEQ ID NOs 11,659-44, 610). Each of these libraries is composed of three primers (one each from pool A, pool B, and pool C in the same row of each figure) per target locus for 1,200; 2,686; or 10,984 different target loci, respectively. The methods of the invention can also be used to generate libraries to non-human target loci.

For an experiment using the 2,686-plex library FIG. 35 (SEQ ID NOs. 3,601-11,658) for multiplex PCR followed by sequencing, the percent of the amplified products that were primer dimers was 11.13%, the median depth of read per target that was amplified was 799.5× coverage, the percent of amplified products that were target amplicons out of the amplified products that were not primer dimers was 93.15% (this is the percent of on target reads when reads for amplified primer dimers are ignored); the number of target loci that were not amplified (failed assay count) was 246; the percent of target loci that were not amplified (failed assay percentage) was 9.16%; the percent of target loci that were amplified was 90.84%, and the total number of reads was 2,522,742. For this primer library, the ΔG values for each possible combination of two primers (each possible primer dimer) in the library are all equal to or greater than −3.86 kcal/mol. This −3.86 kcal/mol value was used as a threshold value to select candidate primer that all had a value equal to or greater than (more desirable than) this value from an initial library of candidate primers.

For an experiment using the 10.984-plex library FIG. 36 (SEQ ID NOs 11,659-44,610), for multiplex PCR followed by sequencing, the percent of the amplified products that were primer dimers was 5.50%, the median depth of read per target that was amplified was 1,286.5× coverage, the percent of amplified products that were target amplicons out of the amplified products that were not primer dimers was 60.16% (this is the percent of on target reads when reads for amplified primer dimers were ignored); the number of target loci that were not amplified (failed assay count) was 3,712; the percent of target loci that were not amplified (failed assay percentage) was 33.79%; the percent of target loci that were amplified was 66.21%; and the total number of reads was 25,372,858.

For an experiment using the 1,200-plex library FIG. 34 (SEQ ID NOs. 1-3,600), for multiplex PCR of a sample of only a single cell followed by sequencing, the percent of the amplified products that were primer dimers was 24.13%. This library has primers to human target loci on chromosome 1, chromosome 21, and the X chromosome. For chromosomes 1 and 21, the median depth of read per target that was amplified was 436× coverage; the percent of target loci that were not amplified (failed assay percentage) was 32.69%; and the percent of target loci that were amplified was 67.31%. The total number of reads was 808,106.

The primer design methods of the invention were also used to generate a library for ~11,000 different target loci (such as amplifying 10,732 different target human loci using 10,732 different primer pairs). For an experiment using this library for multiplex PCR followed by sequencing, the percent of the amplified products that were primer dimers was 14.75%, the median depth of read per target that was amplified was 72.27× coverage, the percent of the amplified products that were target amplicons was 84.32%; the number of target loci that were not amplified (failed assay count) was 118; the percent of target loci that were not amplified (failed assay percentage) was 1.10%; the percent of target loci that were amplified was 98.9%; and the total number of reads was 6,345,782. For this primer library, the ΔG values for each possible combination of two primers (each possible primer dimer) in the library are all equal to or greater than −4.28 kcal/mol. This −4.28 kcal/mol value was used as a threshold value to select candidate primer that all had a value equal to or greater than (more desirable than) this value from an initial library of candidate primers. For the initial candidate primers that were used to select primers for this library, the following interaction cost histogram shows the number of candidate primers for each of the following ranges of ΔG values. This illustrates how the values for the candidate primers compares to the −4.28 kcal/mol threshold value for the final library.

0 to −0.497 kcal/mol: 88357
−0.497 to −0.993 kcal/mol: 30529
−0.993 to −1.49 kcal/mol: 7862
−1.49 to −1.99 kcal/mol: 2639
−1.99 to −2.48 kcal/mol: 1086
−2.48 to −2.98 kcal/mol: 393
−2.98 to −3.48 kcal/mol: 148
−3.48 to −3.97 kcal/mol: 58

−3.97 to −4.47 kcal/mol: 18
−4.47 to −4.97 kcal/mol: 4
−4.97 to −5.46 kcal/mol: 3
−5.46 to −5.96 kcal/mol: 0
−5.96 to −6.46 kcal/mol: 2
−6.46 to −6.95 kcal/mol: 3

The primer design methods of the invention were also used to generate a library for ~14,000 different target loci (such as amplify 13,392 different target human loci with 13,392 different primer pairs). For an experiment using this library for multiplex PCR followed by sequencing, the percent of the amplified products that were primer dimers was 0.56%, the median depth of read per target that was amplified was 69.09× coverage, the percent of the amplified products that were target amplicons was 99.42%; the number of target loci that were not amplified (failed assay count) was 44; the percent of target loci that were not amplified (failed assay percentage) was 0.33%; the percent of target loci that were amplified was 99.67% and the total number of reads was 7,772,454.

Figure 38:
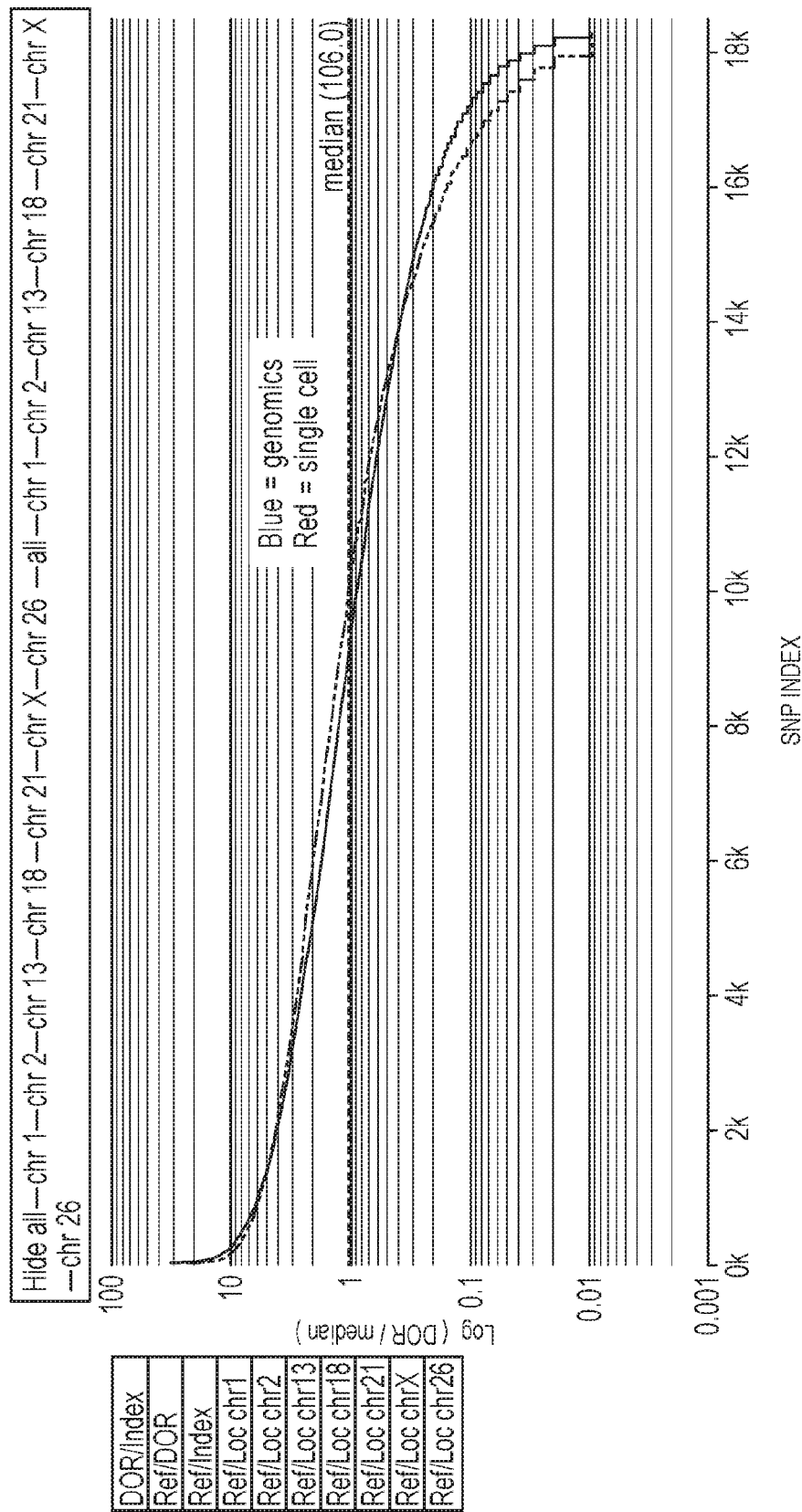
FIG. 38: Overlay of depth of read for a genomic (blue) and a single cell (red) sample for different SNPs.
Figure 40:
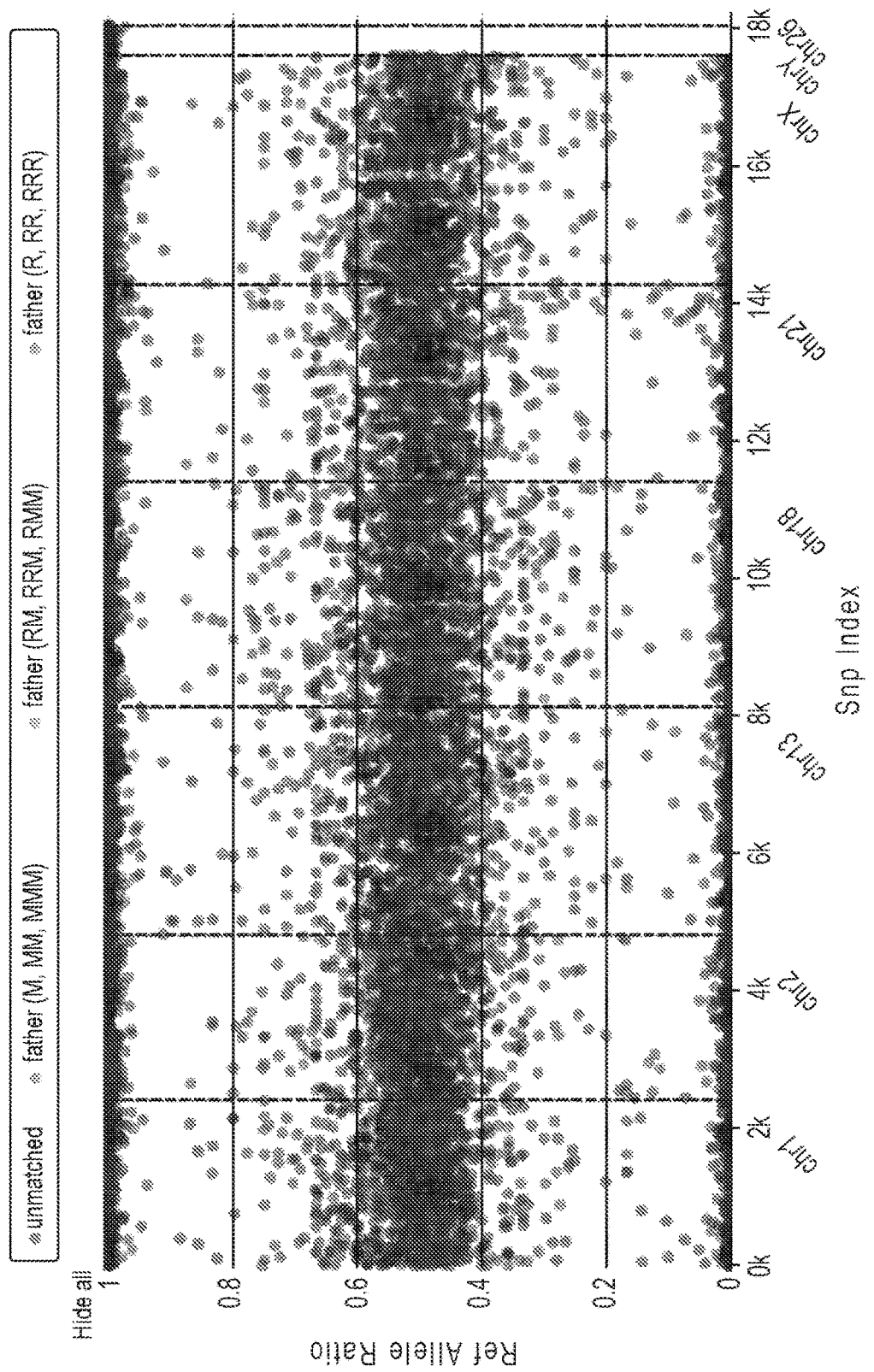
FIG. 40. Graph of reference counts (counts of one allele, such as the "A" allele) divided by total counts for that locus for a single blastocyst cell.

The primer design methods of the invention were also used to generate a library composed of three primers per target locus for 19,488 different target loci. Experiments 15, 18, and 19 describe the use of this library. During the PCR amplification and sequencing of a genomic sample, 99.4-99.7% of the sequencing reads mapped to the genome, of those, 99.99% of the mapped to target loci. For plasma samples with 10 million sequencing reads, typically at least 19,350 of the 19,488 target loci (99.3%) were amplified and sequenced. For another experiment, the percent of the amplified products that were primer dimers was 1.62%, the median depth of read per target that was amplified was 30× coverage, the percent of the amplified products that were target amplicons was 98.15%; the number of target loci that were not amplified (failed assay count) was 736; the percent of target loci that were not amplified (failed assay percentage) was 0.56%; the percent of target loci that were amplified was 99.44%; and the total number of reads was 6,476,975. For this 19,488-plex library, FIG. 37 is a table of the percentage of reads that map to target loci for genomic DNA samples and for samples of a single cell from a cell line for both mother and child samples using this primer library. There was variability in the single cell data which may have resulted from some dead cells being selected, which may have had most of the DNA leaked out. FIG. 38 is an overlay of depth of read for genomic (blue) and a single cell (red) sample for different SNPs. FIG. 39 is a table of the percentage of reads that map to target loci for blastoceol fluid and for a single blastocyst cell. The blastoceol fluid produced no mapped reads, possibly due to no DNA being detected. For a single blastocyst, 50-80% of the reads mapped to target loci. FIG. 40 is a graph of reference counts (counts of one allele, such as the "A" allele) divided by total counts for that locus for a single blastocyst cell. For this primer library, the ΔG values for each possible combination of two primers (each possible primer dimer) in the library are all equal to or greater than −3.86 kcal/mol. This −3.86 kcal/mol value was used as a threshold value to select candidate primer that all had a value equal to or greater than (more desirable than) this value from an initial library of candidate primers.

The primer design methods of the invention were used to generate a library for ~28,000 different target loci (such as amplifying 27,744 different loci with 27,744 different primer pairs). For multiplex PCR and sequencing of genomic DNA samples, 99% of the sequencing reads mapped to target loci. The number of different target human loci that were amplified was 23,776.

For an experiment using this library, the percent of the amplified products that were primer dimers was 0.63%, the median depth of read per target that was amplified was 20× coverage, the percent of the amplified products that were target amplicons was 99.33%; the number of target loci that were not amplified (failed assay count) was 3,968; the percent of target loci that were not amplified (failed assay percentage) was 14.29%; the percent of target loci that were amplified was 85.71%; and the total number of reads was 4,456,636. For a single cell from a cell line, between 2 and 8% of the reads mapped to target loci.

The primer design methods of the invention were used to generate a library for ~9,600 different target loci. As described in Experiment 10, 7.6 million (97%) of reads mapped to the genome, and 6.3 million (80%) of the reads mapped to the targeted SNPs. The average depth of read was 751, and the median depth of read was 396. As described in Experiment 9, another experiment produced 3.7 million reads mapping to the genome (94%), and of those, 2.9 million reads (74%) mapped to targeted SNPs with an average depth of read of 344 and a median depth of read of 255.

The primer design methods of the invention were used to generate a library for ~2,400 different target loci. As described in Experiment 12, when four portions were each amplified with ~2,400 primers, 4.5 million reads mapped to targeted SNPs, the average depth of read was 535 and the median depth of read was 412.

If desired, any of the results may be improved by increasing the number of cells or the amount of nucleic acid template used for the analysis or by optimizing the conditions. For example, if results from single cell samples are not as good as desired for a particular application, a sample with more cells or more nucleic acids may be used instead (such as to decrease the percentage of primer dimers, increase the percentage of target amplicons, or increase the percentage of target loci that are amplified). Samples with more nucleic acids have more template molecules for the primers to bind (instead of primers binding each other and forming primer dimers).

These primer libraries can be used in any of the PCR methods of the invention. In some embodiments, primers from one of the primer pools in FIG. 34, 35, or 36 (either pool A, pool B, or pool C) are used in combination with a universal primer to amplify the target loci. In some embodiments, multiple rounds of PCR are performed in which each round of PCR uses primers from one of the primer pools of FIG. 34, 35, or 36 and a universal primer. In some embodiments, primer from two of the primer pools (such as primers from pools C and B or primers from pools A and C) are used to amplify the target loci. In some embodiments, multiple rounds of PCR are performed. In some embodiments, primers from pools C and B are used for the first round of PCR and then primers from pools A and C are used for the second of PCR. In some embodiments, primers from pools C and B are used for the first round of PCR and then primers from pools A and B are used for the second of PCR. In some embodiments, at least 60, 70, 80, 90, 95, or 100% of the primers from one or more of the primer pools in FIG. 34, 35, or 36 (e.g., pool A, pool B, and/or pool C) are used for the PCR amplification. In some embodiments, primers from FIG. 34, 35, or 36 are combined with other primers that are not included in FIG. 34, 35, or 36.

In one aspect, the invention features one or more primers (e.g., at least 10; 20; 50; 75; 100; 300; 500; 750; 1,000; 2,000; 5,000; 7,500; 10,000; 15,000; 20,000; 25,000; 30,000; 40,000; or 50,000 different primers) with at least 60, 70, 80, 90, 95, 96, 97, 98, 99, 99.5, or 100% identity to the corresponding region (e.g., a region of at least 10, 20, 30, 40, 50 or more contiguous nucleotides) of a primer in pool A, pool B, and/or pool C in FIG. 34, 35, or 36 (SEQ ID NOs 1-44,610). In one aspect, the invention features one or more primers (e.g., at least 10; 20; 50; 75; 100; 300; 500; 750; 1,000; 2,000; 5,000; 7,500; 10,000; 15,000; 20,000; 25,000; 30,000; 40,000; or 50,000 different primers) with at least 60, 70, 80, 90, 95, 96, 97, 98, 99, 99.5, or 100% identity over the entire length of a primer in pool A, pool B, and/or pool C in FIG. 34, 35, or 36. If desired, the primers in FIG. 34, 35, or 36 can be modified by the insertion, deletion, or substitution of one or more nucleotides (e.g., at least 1, 2, 3, 4, 5, 6, 8, 10, 20, or more nucleotides). In some embodiments, a region that is not specific for a target locus (such as a tag, bar code, or universal binding site) is added to one or more primers in FIG. 34, 35, or 36. In various embodiments, the nonspecific region is added to the 5' end of the primer, to the 3' end of the primer, or to an internal region of the primer. In some embodiments, the primers are fragments (such as fragments of at least 10, 20, 30, 40, 50 or more contiguous nucleotides that are less than full-length) of primers in FIG. 34, 35, or 36.

In some embodiments, the invention provides a library of primers that includes at least 10; 20; 50; 75; 100; 300; 500; 750; 1,000; 2,000; 5,000; 7,500; 10,000; 15,000; 20,000; 25,000; 30,000; 40,000, or 50,000 different primers that comprise the polynucleotide sequence of a primer in pool A, pool B, and/or pool C in FIG. 34, 35, or 36. In some embodiments, the invention provides a library of primers that includes at least 10; 20; 50; 75; 100; 300; 500; 750; 1,000; 2,000; 5,000; 7,500; 10,000; 15,000; 20,000; 25,000; 30,000; 40,000; or 50,000 different primers or all of the primer from pool A, pool B, and/or pool C in one of FIG. 34, 35, or 36.

In some embodiment, some or all of the primers in two or three of the primer libraries of FIG. 34, 35, or 36 are combined.

Percent identity in reference to nucleic acid sequences refers to the degree of sequence identity between nucleic acid sequences. Percent identity can be determined in various ways that are within the skill in the art, for instance, using publicly available computer software with the default parameters such as Smith Waterman Alignment (Smith and Waterman J. Mol. Biol. 147:195-7, 1981), "BestFit" (Smith and Waterman, Advances in Applied Mathematics, 482-489, 1981); Basic Local Alignment Search Tool (BLAST, Altschul, S. F., W. Gish, et al., J. Mol. Biol. 215: 403-410, 1990; available through the U.S. government's National Center for Biotechnology Information web site at the world wide web at ncbi.nlm.nih.gov), BLAST-2, BLAST-N, WU-BLAST, WU-BLAST-2, ENTREZ (available through the National Center for Biotechnology Information), CLUSTALW, CLUSTAL Omega, or Megalign (DNASTAR, Inc. Madison, Wis.) software. In addition, those skilled in the art can determine appropriate parameters for measuring alignment, including any algorithms needed to achieve maximal alignment over the length of the sequences being compared. In general, the length of comparison will generally be at least 20, 30, 40, 45, 50, or more nucleotides.

In some embodiments, percent identity is calculated by determining the number of matched positions in aligned nucleic acid sequences, dividing the number of matched positions by the total number of aligned nucleotides, and multiplying by 100. A matched position refers to a position in which identical nucleotides occur at the same position in aligned nucleic acid sequences. The percent identity over a particular length is determined by counting the number of matched positions over that length and dividing that number by the length followed by multiplying the resulting value by 100. For example, if (i) a 500-nucleotide nucleic acid target sequence is compared to a subject nucleic acid sequence, (ii) an alignment program presents 200 nucleotides from the target sequence aligned with a region of the subject sequence where the first and last nucleotides of that 200-nucleotide region are matches, and (iii) the number of matches over those 200 aligned nucleotides is 180, then the 500-nucleotide nucleic acid target sequence contains a length of 200 and a sequence identity over that length of 90% (i.e., 180, 200×100=90).

In one aspect, the invention features one or more primers (e.g., at least 10; 20; 50; 75; 100; 300; 500; 750; 1,000; 2,000; 5,000; 7,500; 10,000; 15,000; 20,000; 25,000; 30,000; 40,000; or 50,000 different primers) that comprise a polynucleotide sequence that hybridizes to the complement of a primer in pool A, pool B, and/or pool C in FIG. 34, 35, or 36 under very high stringency hybridization conditions, high stringency hybridization conditions, or low stringency hybridization conditions. In some embodiments, one or more primers (e.g., at least 10; 20; 50; 75; 100; 300; 500; 750; 1,000; 2,000; 5,000; 7,500; 10,000; 15,000; 20,000; 25,000; 30,000; 40,000; or 50,000 different primers) hybridize to the complement of a primer in pool A, pool B, and/or pool C in FIG. 34, 35, or 36 under very high stringency hybridization conditions, high stringency hybridization conditions, or low stringency hybridization conditions. Hybridization conditions resulting in a particular degree of stringency will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 1); Nucleic Acid Hybridization, A Practical Approach, Ed. Hames, B. D. and Higgins, S. J., IRL Press, 1985; Ausubel et al. Current Protocols in Molecular Biology, Wiley, New York 1994; and U.S. Pat. No. 8,357,488, filed May 16, 2008. In some embodiments, very high stringency hybridization conditions include an overnight incubation at 42° C. in a solution comprising 50% formamide, 5×SSC (750 mM NaCl, 75 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C. The following is an exemplary set of hybridization conditions and is not limiting:

Very High Stringency (Detects Sequences that Share at Least 90% Identity)

a) Hybridization: 5×SSC at 65° C. for 16 hours b) Wash twice: 2×SSC at room temperature for 15 minutes each c) Wash twice: 0.5×SSC at 65° C. for 20 minutes each High Stringency (Detects Sequences that Share at Least 80% Identity)

a) Hybridization: 5×-6×SSC at 65° C.-70° C. for 16-20 hours b) Wash twice: 2×SSC at room temperature for 5-20 minutes each c) Wash twice: 1×SSC at 55° C.-70° C. for 30 minutes each Low Stringency (Detects Sequences that Share at Least 50% Identity)
  a) Hybridization: 6×SSC at room temperature to 55' C. for 16-20 hours
  b) Wash at least twice: 2×-3×SSC at room temperature to 55° C. for 20-30 minutes each These primers can be used in any of the primer libraries or methods of the invention. In some embodiments, the library of primers consists essentially of, or consists of primers from any one of FIGS. 34-36.

Exemplary Primer Libraries for Detection of Recombination

In some embodiments, primers in the primer library are designed to determine whether or not recombination occurred at one or more known recombination hotspots (such as crossovers between homologous human chromosomes). Knowing what crossovers occurred between chromosomes allows more accurate phased genetic data to be determined for an individual. Recombination hotspots are local regions of chromosomes in which recombination events tend to be concentrated. Often they are flanked by "coldspots," regions of lower than average frequency of recombination. Recombination hotspots tend to share a similar morphology and are approximately 1 to 2 kb in length. The hotspot distribution is positively correlated with GC content and repetitive element distribution. A partially degenerated 13-mer motif CCNCCNTNNCCNC plays a role in some hotspot activity. It has been shown that the zinc finger protein called PRDM9 binds to this motif and initiates recombination at its location. The average distance between the centers of recombination hot spots is reported to be ~80 kb. In some embodiments, the distance between the centers of recombination hot spots ranges between ~3 kb to ~100 kb. Public databases include a large number of known human recombination hotspots, such as the HUMHOT and International HapMap Project databases (see, for example, Nishant et al., "HUMHOT: a database of human meiotic recombination hot spots," Nucleic Acids Research, 34: D25-D28, 2006, Database issue; Mackiewicz et al., "Distribution of Recombination Hotspots in the Human Genome—A Comparison of Computer Simulations with Real Data" PLoS ONE 8(6): e65272, doi:10.1371/journal.pone.0065272; and the world wide web at hapmap.ncbi.nlm.nih.gov/downloads/index.html.en, which are each hereby incorporated by reference in its entirety).

In some embodiments, primers in the primer library are clustered at or near recombination hotspots (such as known human recombination hotspots). In some embodiments, the corresponding amplicons are used to determine the sequence within or near a recombination hotspot to determine whether or not recombination occurred at that particular hotspot (such as whether the sequence of the amplicon is the sequence expected if a recombination had occurred or the sequence expected if a recombination had not occurred). In some embodiments, primers are designed to amplify part or all of a recombination hotspot (and optionally sequence flanking a recombination hotspot). In some embodiments, long read sequencing (such as sequencing using the Moleculo Technology developed by Illumina to sequence up to ~10 kb) or paired end sequencing is used to sequence part or all of a recombination hotspot. Knowledge of whether or not a recombination event occurred can be used to determine which haplotype blocks flank the hotspot. If desired, the presence of particular haplotype blocks can be confirmed using primers specific to regions within the haplotype blocks. In some embodiments, it is assumed there are no crossovers between known recombination hotspots. In some embodiments, primers in the primer library are clustered at or near the ends of chromosomes. For example, such primers can be used to determine whether or not a particular arm or section at the end of a chromosome is present. In some embodiments, primers in the primer library are clustered at or near recombination hotspots and at or near the ends of chromosomes.

In some embodiments, the primer library includes one or more primers (such as at least 5; 10; 50; 100; 200; 500; 750; 1,000; 2,000; 5,000; 7,500; 10,000; 20,000; 25,000; 30,000; 40,000; or 50,000 different primers or different primer pairs) that are specific for a recombination hotspot (such as a known human recombination hotspot) and/or are specific for a region near a recombination hotspot (such as within 10, 8, 5, 3, 2, 1, or 0.5 kb of the 5' or 3' end of a recombination hotspot). In some embodiments, at least 1, 5, 10, 20, 40, 60, 80, 100, or 150 different primers (or primer pairs) are specific for the same recombination hotspot, or are specific for the same recombination hotspot or a region near the recombination hotspot. In some embodiments, at least 1, 5, 10, 20, 40, 60, 80, 100, or 150 different primers (or primer pairs) are specific for a region between recombination hotspots (such as a region unlikely to have undergone recombination); these primers can be used to confirm the presence of haplotype blocks (such as those that would be expected depending on whether or not recombination has occurred). In some embodiments, at least 10, 20, 30, 40, 50, 60, 70, 80, or 90% of the primers in the primer library are specific for a recombination hotspot and/or are specific for a region near a recombination hotspot (such as within 10, 8, 5, 3, 2, 1, or 0.5 kb of the 5' or 3' end of the recombination hotspot). In some embodiments, the primer library is used to determine whether or not recombination has occurred at greater than or equal to 5; 10; 50; 100; 200; 500; 750; 1,000; 2,000; 5,000; 7,500; 10,000; 20,000; 25,000; 30,000; 40,000; or 50,000 different recombination hotspots (such as known human recombination hotspots). In some embodiments, the regions targeted by primers to a recombination hotspot or nearby region are approximately evenly spread out along that portion of the genome. In some embodiments, at least 1, 5, 10, 20, 40, 60, 80, 100, or 150 different primers (or primer pairs) are specific for a region at or near the end of a chromosome (such as a region within 20, 10, 5, 1, 0.5, 0.1, 0.01, or 0.001 mb from the end of a chromosome). In some embodiments, at least 10, 20, 30, 40, 50, 60, 70, 80, or 90% of the primers in the primer library are specific for a region at or near the end of a chromosome (such as a region within 20, 10, 5, 1, 0.5, 0.1, 0.01, or 0.001 mb from the end of a chromosome). In some embodiments, at least 1, 5, 10, 20, 40, 60, 80, 100, or 150 different primers (or primer pairs) are specific for a region within a potential microdeletion in a chromosome. In some embodiments, at least 10, 20, 30, 40, 50, 60, 70, 80, or 90% of the primers in the primer library are specific for a region within a potential microdeletion in a chromosome. In some embodiments, at least 10, 20, 30, 40, 50, 60, 70, 80, or 90% of the primers in the primer library are specific for a recombination hotspot, a region near a recombination hotspot, a region at or near the end of a chromosome, or a region within a potential microdeletion in a chromosome. In some embodiments, the primers have one or more of the properties described herein. Other embodiments are disclosed in U.S. Ser. No. 61/987,407, filed May 1, 2014 and 62/066,514, filed Oct. 21, 2014.

Exemplary Primer Kits

In one aspect, the invention features a kit (such as kits for amplifying target loci in a nucleic acid sample) the includes any of the primer libraries of the invention. In some embodiments, a kit may be formulated that comprises a plurality of primers designed to achieve the methods described in this disclosure. The primers may be outer forward and reverse primers, inner forward and reverse primers as disclosed herein, they could be primers that have been designed to have low binding affinity to other primers in the kit as disclosed in the section on primer design, they could be hybrid capture probes or pre-circularized probes as described in the relevant sections, or some combination thereof. In an embodiment, a kit may be formulated for determining a ploidy status of a target chromosome in a gestating fetus designed to be used with the methods disclosed herein, the kit comprising a plurality of inner forward primers and optionally the plurality of inner reverse primers, and optionally outer forward primers and outer reverse primers, where each of the primers is designed to hybridize to the region of DNA immediately upstream and/or downstream from one of the target sites (e.g., polymorphic sites) on the target chromosome, and optionally additional chromosomes. In an embodiment, the primer kit may be used in combination with the diagnostic box described elsewhere in this document. In some embodiments, the kit includes instructions for using the library to amplify the target loci. In some embodiments, the kit consists essentially of, or consists of primers (or of primers and instructions for using the primers).

Exemplary Amplicons

In one aspect, the invention provides a composition comprising at least 100 different amplicons (e.g., at least 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical amplicons) in solution in one reaction volume. In some embodiments, the amplicons are produced from the simultaneous PCR amplification of at least 100 different target loci (e.g., at least 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical target loci) using at least 100 different primers or primer pairs (e.g., at least 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical primers or primer pairs) in one reaction volume. In some embodiments, (i) less than 60% of the amplified products are primer dimers and at least 40% of the amplified products are target amplicons, (ii) less than 40% of the amplified products are primer dimers and at least 60% of the amplified products are target amplicons, (iii) less than 20% of the amplified products are primer dimers and at least 80% of the amplified products are target amplicons, (iv) less than 10% of the amplified products are primer dimers and at least 90% of the amplified products are target amplicons, or (v) less than 5% of the amplified products are primer dimers and at least 95% of the amplified products are target amplicons. In some embodiments, the length of the target amplicons is between 50 and 100 nucleotides, such as between 60 and 80 nucleotides, or 60 to 75 nucleotides, inclusive. In some embodiments, the range of the length of the target amplicons is less than 50, 25, 15, 10, or 5 nucleotides. In some embodiments, the range of the length of the target amplicons is between 5 to 50 nucleotides, such as 5 to 25 nucleotides, 5 to 15 nucleotides, or 5 to 10 nucleotides, inclusive. In some embodiments, the composition includes at least 1,000 different amplicons in solution in one reaction volume; wherein the amplicons are produced from the simultaneous PCR amplification of at least 1,000 different target human loci using at least 1,000 different primers in one reaction volume; wherein (i) less than 20% of the amplicons are primer dimers, and (ii) at least 80% of the amplicons comprise one of the target human loci and are between 50 and 100 nucleotides in length, inclusive. In some embodiments, the composition consists essentially of, or consists of one or more of the following: amplicons, primers (such as any of the primers disclosed herein), free nucleotide(s), non-human or non-naturally occurring enzyme(s), buffer(s), or any combination thereof.

In some embodiments, a large percentage or substantially all of the primers used for the multiplex PCR method are consumed during the PCR reaction or are removed from the reaction volume after the PCR amplification. In some embodiments, at least 80, 90, 92, 94, 96, 98, 99, or 100% of the primer molecules are extended to form amplified products. In some embodiments, for at least 80, 90, 92, 94, 96, 98, 99, or 100% of target loci, at least 80, 90, 92, 94, 96, 98, 99, or 100% of the primer molecules to that target loci are extended to form amplified products. In some embodiments, multiple cycles are performed until all or substantially all of the primers are consumed. If desired, a higher percentage of the primers can be consumed by decreasing the initial primer concentration and/or increasing the number of PCR cycles that are performed. In some embodiments, at least 80, 90, 95, 96, 97, 98, 99, or 100% of the nucleic acids in the composition are amplicons (instead of unextended dimers).

In one aspect, the invention provides a composition comprising at least 100 different primers or primer pairs (e.g., at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical primers or primer pairs) and at least 100 different amplicons (e.g., at least 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical amplicons) in solution in one reaction volume. In some embodiments, the amplicons are produced from the simultaneous PCR amplification of at least 100 different target loci (e.g., at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical target loci) using the primers or primer pairs in one reaction volume. In some embodiments, (i) less than 60% of the amplified products are primer dimers and at least 40% of the amplified products are target amplicons, (ii) less than 40% of the amplified products are primer dimers and at least 60% of the amplified products are target amplicons, (iii) less than 20% of the amplified products are primer dimers and at least 80% of the amplified products are target amplicons, (iv) less than 10% of the amplified products are primer dimers and at least 90% of the amplified products are target amplicons, or (v) less than 5% of the amplified products are primer dimers and at least 95% of the amplified products are target amplicons. In some embodiments, the length of the target amplicons is between 50 and 100 nucleotides, such as between 60 and 80 nucleotides, or 60 to 75 nucleotides, inclusive. In some embodiments, the range of the length of the target amplicons is less than 50, 25, 15, 10, or 5 nucleotides. In some embodiments, the range of the length of the target amplicons is between 5 to 50 nucleotides, such as 5 to 25 nucleotides, 5 to 15 nucleotides, or 5 to 10 nucleotides, inclusive. In some embodiments, the composition comprising at least 1,000 different primers and at least 1,000 different amplicons in solution in one reaction volume; wherein the amplicons are produced from the simultaneous PCR amplification of at least 1,000 different target human loci with the primers in one reaction volume; wherein (i) less than 20% of the amplicons are primer dimers, and (ii) at least 80% of the amplicons comprise one of the target loci and are between 50 and 100 nucleotides in length, inclusive. In some embodiments, the composition consists essentially of, or consists of one or more of the following: amplicons, primers (such as any of the primers disclosed herein), free nucleotide(s), non-human or non-naturally occurring enzyme(s), buffer(s), or any combination thereof.

In some embodiments, the amplification of different target loci is substantially uniform. In some embodiments, target loci (such as nonpolymorphic target loci or polymorphic target loci that are amplified regardless of what allele is present at the polymorphic site) that were present in the same amount (or substantially the same amount) in the initial unamplified sample are also present in substantially the same amount in the PCR-amplified products. In some embodiments, for at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different targets, the target loci that is amplified the most out of these targets (which can be all of the targets or a subset of the targets for a library) is amplified less than 2,000; 1,500; 1,000; 500; 400; 300; 200; 100%, 50, 20, 10, 5, or 2% more than the target loci that is amplified the least out of these targets. In some embodiments, for at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target amplicons, the target amplicon in greatest abundance out of these target amplicons (which can be all of the target amplicons or a subset of the target amplicons produced by a library) is present in an amount that is less than 2,000; 1,500; 1,000; 500; 400; 300; 200; 100%, 50, 20, 10, 5, or 2% more than the target amplicon in least abundance out of these target amplicons. In some embodiments, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target amplicons are present in an amount that is at least 5, 10, 15, 20, 40, 50, 60, 70, 80, or 90% of the amount of the target amplicon in greatest abundance. In some embodiments, for at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different amplicons that are produced by multiplex PCR and then sequenced, at least 80, 90, 95, 96, 97, 98, 99, or 99.5% of the target amplicons produce a number of sequencing reads within 20, 30, 50, or 80% above or below the mean number of sequences for target amplicons. If desired, the uniformity can be increased by using primers with more similar primer lengths, target amplicon lengths, GC contents, melting temperatures, or any combination thereof. In some embodiments, the uniformity can be increased by using TMAC in the reaction volume during amplification. In some embodiments, having most or all the primers consumed in the PCR reaction increases the uniformity of amplification.

If desired, the uniformity in DOR can be measured using standard methods such as depth of read slope (DOR slope), normalized median depth of read (nmDOR), or breadth of read (BOR). DOR slope represents the slope of the line in the linear portion of a list of loci sorted in descending DOR order. Closer to zero is better, as it represents a flat line. In some embodiments, the uniformity in DOR can be measured using the Percent of reads in the $90^{th}$-$95^{th}$ Percentile. For this measurement, the loci are sorted in descending DOR order. In the ideal DOR distribution, the $90^{th}$-$95^{th}$ percentile should contain 5% of reads. The reads of all loci between the $90^{th}$ Percentile and $95^{th}$ percentile are counted and divided by the total reads for all loci. In one experiment, the DOR slope versus percent of reads in the $90^{th}$-$95^{th}$ percentile for all samples had an $R^2$=0.81.

In some embodiments, the magnitude of the DOR slope is less than 0.005, 0.001, 0.0005, 0.0001, 0.00005, 0.00001, 0.000005, or 0.000001. In some embodiments, the magnitude of the DOR slope is between 0 and 0.005, such as 0.000001 to 0.005, such as between 0.000005 to 0.00001, 0.00001 to 0.00005, 0.00005 to 0.0001, 0.0001 to 0.0005, 0.0005 to 0.001, or 0.001 to 0.005, inclusive. In some embodiments, the percent of reads in the $90^{th}$-$95^{th}$ percentile is between 0.2 and 9%, such as between 1 to 8%, 2 to 7%, 0.2 to 1.0%, 1 to 2%, 2 to 3%, 2 to 4%, 3 to 4%, 4 to 5%, 5 to 6%, or 6 to 8%, or 7 to 9% inclusive. In some embodiments, the invention features a composition comprising at least 100 different amplicons (e.g., at least 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical amplicons) with the magnitude of the DOR slope in any of these ranges or with a percent of reads in the $90^{th}$-$95^{th}$ percentile in any of these ranges. In some embodiments, the amplification method produces at least 100 different amplicons (e.g., at least 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical amplicons) with the magnitude of the DOR slope in any of these ranges or with a percent of reads in the $90^{th}$-$95^{th}$ percentile in any of these ranges.

Exemplary Multiplex PCR Methods

In one aspect, the invention features methods of amplifying target loci in a nucleic acid sample that involve (i) contacting the nucleic acid sample with a library of primers that simultaneously hybridize to least 1,000; 2,000; 5,000; 7,500; 10,000; 15,000; 19,000; 20,000; 25,000; 27,000; 28,000; 30,000; 40,000; 50,000; 75,000; or 100,000 different target loci to produce a reaction mixture; and (ii) subjecting the reaction mixture to primer extension reaction conditions (such as PCR conditions) to produce amplified products that include target amplicons. In some embodiments, the method also includes determining the presence or absence of at least one target amplicon (such as at least 50, 60, 70, 80, 90, 95, 96, 97, 98, 99, or 99.5% of the target amplicons). In some embodiments, the method also includes determining the sequence of at least one target amplicon (such as at least 50, 60, 70, 80, 90, 95, 96, 97, 98, 99, or 99.5% of the target amplicons). In some embodiments, at least 50, 60, 70, 80, 90, 95, 96, 97, 98, 99, or 99.5% of the target loci are amplified. In some embodiments, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified at least 5, 10, 20, 40, 50, 60, 80, 100, 120, 150, 200, 300, or 400-fold. In some embodiments, at least 50, 60, 70, 80, 90, 95, 96, 97, 98, 99, 99.5, or 100% of the target loci are amplified at least 5, 10, 20, 40, 50, 60, 80, 100, 120, 150, 200, 300, or 400-fold. In various embodiments, less than 60, 50, 40, 30, 20, 10, 5, 4, 3, 2, 1, 0.5, 0.25, 0.1, or 0.05% of the amplified products are primer dimers. In some embodiments, the method involves multiplex PCR and sequencing (such as high throughput sequencing).

In various embodiments, long annealing times and/or low primer concentrations are used. In various embodiments, the length of the annealing step is greater than 3, 5, 8, 10, 15, 20, 30, 45, 60, 75, 90, 120, 150, or 180 minutes. In various embodiments, the length of the annealing step (per PCR cycle) is between 5 and 180 minutes, such as 5 to 60, 10 to 60, 5 to 30, or 10 to 30 minutes, inclusive. In various embodiments, the length of the annealing step is greater than 5 minutes (such greater than 10, or 15 minutes), and the concentration of each primer is less than 20 nM. In various embodiments, the length of the annealing step is greater than 5 minutes (such greater than 10, or 15 minutes), and the concentration of each primer is between 1 to 20 nM, or 1 to 10 nM, inclusive. In various embodiments, the length of the annealing step is greater than 20 minutes (such as greater than 30, 45, 60, or 90 minutes), and the concentration of each primer is less than 1 nM.

At high level of multiplexing, the solution may become viscous due to the large amount of primers in solution. If the solution is too viscous, one can reduce the primer concentration to an amount that is still sufficient for the primers to bind the template DNA. In various embodiments, less than 60,000 different primers are used and the concentration of each primer is less than 20 nM, such as less than 10 nM or between 1 and 10 nM, inclusive. In various embodiments, more than 60,000 different primers (such as between 60,000 and 120,000 different primers) are used and the concentration of each primer is less than 10 nM, such as less than 5 nM or between 1 and 10 nM, inclusive.

It was discovered that the annealing temperature can optionally be higher than the melting temperatures of some or all of the primers (in contrast to other methods that use an annealing temperature below the melting temperatures of the primers) (Experiment 25). The melting temperature ($T_m$) is the temperature at which one-half (50%) of a DNA duplex of an oligonucleotide (such as a primer) and its perfect complement dissociates and becomes single strand DNA. The annealing temperature ($T_A$) is the temperature one runs the PCR protocol at. For prior methods, it is usually 5 C below the lowest $T_m$ of the primers used, thus close to all possible duplexes are formed (such that essentially all the primer molecules bind the template nucleic acid). While this is highly efficient, at lower temperatures there are more unspecific reactions bound to occur. One consequence of having too low a $T_A$ is that primers may anneal to sequences other than the true target, as internal single-base mismatches or partial annealing may be tolerated. In some embodiments of the present inventions, the $T_A$ is higher than ($T_m$), where at a given moment only a small fraction of the targets have a primer annealed (such as only ~1-5%). If these get extended, they are removed from the equilibrium of annealing and dissociating primers and target (as extension increases $T_m$ quickly to above 70 C), and a new ~1-5% of targets has primers. Thus, by giving the reaction long time for annealing, one can get ~100% of the targets copied per cycle. Thus, the most stable molecule pairs (those with perfect DNA pairing between the primer and the template DNA) are preferentially extended to produce the correct target amplicons. For example, the same experiment was performed with 57° C. as the annealing temperature and with 63° C. as the annealing temperature with primers that had a melting temperature below 63° C. When the annealing temperature was 57° C., the percent of mapped reads for the amplified PCR products was as low as 50% (with ~50% of the amplified products being primer-dimer). When the annealing temperature was 63° C., the percentage of amplified products that were primer dimer dropped to ~2%.

In various embodiments, the annealing temperature is at least 1, 2, 3, 4, 5, 6, 7, 8, 9, 10, 11, 12, 13, or 15° C. greater than the melting temperature (such as the empirically measured or calculated $T_m$) of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers. In some embodiments, the annealing temperature is at least 1, 2, 3, 4, 5, 6, 7, 8, 9, 10, 11, 12, 13, or 15° C. greater than the melting temperature (such as the empirically measured or calculated $T_m$) of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers, and the length of the annealing step (per PCR cycle) is greater than 1, 3, 5, 8, 10, 15, 20, 30, 45, 60, 75, 90, 120, 150, or 180 minutes.

In various embodiments, the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the melting temperature (such as the empirically measured or calculated $T_m$) of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers. In various embodiments, the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the melting temperature (such as the empirically measured or calculated $T_m$) of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers, and the length of the annealing step (per PCR cycle) is between 5 and 180 minutes, such as 5 to 60, 10 to 60, 5 to 30, or 10 to 30 minutes, inclusive.

In some embodiments, the annealing temperature is at least 1, 2, 3, 4, 5, 6, 7, 8, 9, 10, 11, 12, 13, or 15° C. greater than the highest melting temperature (such as the empirically measured or calculated $T_m$) of the primers. In some embodiments, the annealing temperature is at least 1, 2, 3, 4, 5, 6, 7, 8, 9, 10, 11, 12, 13, or 15° C. greater than the highest melting temperature (such as the empirically measured or calculated $T_m$) of the primers, and the length of the annealing step (per PCR cycle) is greater than 1, 3, 5, 8, 10, 15, 20, 30, 45, 60, 75, 90, 120, 150, or 180 minutes.

In some embodiments, the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the highest melting temperature (such as the empirically measured or calculated $T_m$) of the primers. In some embodiments, the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the highest melting temperature (such as the empirically measured or calculated $T_m$) of the primers, and the length of the annealing step (per PCR cycle) is between 5 and 180 minutes, such as 5 to 60, 10 to 60, 5 to 30, or 10 to 30 minutes, inclusive.

In some embodiments, the annealing temperature is at least 1, 2, 3, 4, 5, 6, 7, 8, 9, 10, 11, 12, 13, or 15° C. greater than the average melting temperature (such as the empirically measured or calculated $T_m$) of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers. In some embodiments, the annealing temperature is at least 1, 2, 3, 4, 5, 6, 7, 8, 9, 10, 11, 12, 13, or 15° C. greater than the average melting temperature (such as the empirically measured or calculated $T_m$) of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers, and the length of the annealing step (per PCR cycle) is greater than 1, 3, 5, 8, 10, 15, 20, 30, 45, 60, 75, 90, 120, 150, or 180 minutes.

In some embodiments, the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the average melting temperature (such as the empirically measured or calculated $T_m$) of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers. In some embodiments, the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the average melting temperature (such as the empirically measured or calculated $T_m$) of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers, and the length of the annealing step (per PCR cycle) is between 5 and 180 minutes, such as 5 to 60, 10 to 60, 5 to 30, or 10 to 30 minutes, inclusive.

In some embodiments, the annealing temperature is between 50 to 70° C., such as between 55 to 60, 60 to 65, or 65 to 70° C., inclusive. In some embodiments, the annealing temperature is between 50 to 70° C. such as between 55 to 60, 60 to 65, or 65 to 70° C., inclusive, and either (i) the length of the annealing step (per PCR cycle) is greater than 3, 5, 8, 10, 15, 20, 30, 45, 60, 75, 90, 120, 150, or 180 minutes or (ii) the length of the annealing step (per PCR cycle) is between 5 and 180 minutes, such as 5 to 60, 10 to 60, 5 to 30, or 10 to 30 minutes, inclusive.

In some embodiments, one or more of the following conditions are used for empirical measurement of $T_m$ or are assumed for calculation of $T_m$: temperature: of 60.0° C., primer concentration of 100 nM, and/or salt concentration of 100 mM. In some embodiments, other conditions are used, such as the conditions that will be used for multiplex PCR with the library. In some embodiments, 100 mM KCl, 50 mM $(NH_4)_2SO_4$, 3 mM $MgCl_2$, 7.5 nM of each primer, and 50 mM TMAC, at pH 8.1 is used. In some embodiments, the $T_m$ is calculated using the Primer3 program (libprimer3 release 2.2.3) using the built-in SantaLucia parameters (the world wide web at primer3.sourceforge.net, which is hereby incorporated by reference in its entirety). For example, the $T_m$ values may be calculated using the method in Experiment 25. In some embodiments, the calculated melting temperature for a primer is the temperature at which half of the primers molecules are expected to be annealed. As discussed above, even at a temperature higher than the calculated melting temperature, a percentage of primers will be annealed, and therefore PCR extension is possible. In some embodiments, the empirically measured Tm (the actual Tm) is determined by using a thermostatted cell in a UV spectrophotometer. In some embodiments, temperature is plotted vs. absorbance, generating an S-shaped curve with two plateaus. The absorbance reading halfway between the plateaus corresponds to Tm.

In some embodiments, the absorbance at 260 nm is measured as a function of temperature on an ultrospec 2100 pr UV/visible spectrophotometer (Amershambiosciences) (see, e.g., Takiya et al., "An empirical approach for thermal stability (Tm) prediction of PNA/DNA duplexes," Nucleic Acids Symp Ser (Oxf); (48): 131-2, 2004, which is hereby incorporated by reference in its entirety). In some embodiments, absorbance at 260 nm is measured by decreasing the temperature in steps of 2° C. per minute from 95 to 20° C. In some embodiments, a primer and its perfect complement (such as 2 uM of each paired oligomer) are mixed and then annealing is performed by heating the sample to 95° C., keeping it there for 5 minutes, followed by cooling to room temperature during 30 minutes, and keeping the samples at 95° C. for at least 60 minutes. In some embodiments, melting temperature is determined by analyzing the data using SWIFT Tm software. In some embodiments of any of the methods of the invention, the method includes empirically measuring or calculating (such as calculating with a computer) the melting temperature for at least 50, 80, 90, 92, 94, 96, 98, 99, or 100% of the primers in the library either before or after the primers are used for PCR amplification of target loci.

In some embodiments, the library comprises a microarray. In some embodiments, the library does not comprise a microarray.

In some embodiments, most or all of the primers are extended to form amplified products. Having all the primers consumed in the PCR reaction increases the uniformity of amplification of the different target loci since the same or similar number of primer molecules are converted to target amplicons for each target loci. In some embodiment, at least 80, 90, 92, 94, 96, 98, 99, or 100% of the primer molecules are extended to form amplified products. In some embodiments, for at least 80, 90, 92, 94, 96, 98, 99, or 100% of target loci, at least 80, 90, 92, 94, 96, 98, 99, or 100% of the primer molecules to that target loci are extended to form amplified products. In some embodiments, multiple cycles are performed until this percentage of the primers are consumed. In some embodiments, multiple cycles are performed until all or substantially all of the primers are consumed. If desired, a higher percentage of the primers can be consumed by decreasing the initial primer concentration and/or increasing the number of PCR cycles that are performed.

In some embodiments, the PCR methods may be performed with microliter reaction volumes, for which it can be harder to achieve specific PCR amplification (due to the lower local concentration of the template nucleic acids) compared to nanoliter or picoliter reaction volumes used in microfluidics applications. In some embodiments, the reaction volume is between 1 and 60 uL, such as between 5 and 50 uL, 10 and 50 uL, 10 and 20 uL, 20 and 30 uL, 30 and 40 uL, or 40 to 50 uL, inclusive.

In an embodiment, a method disclosed herein uses highly efficient highly multiplexed targeted PCR to amplify DNA followed by high throughput sequencing to determine the allele frequencies at each target locus. The ability to multiplex more than about 50 or 100 PCR primers in one reaction volume in a way that most of the resulting sequence reads map to targeted loci is novel and non-obvious. One technique that allows highly multiplexed targeted PCR to perform in a highly efficient manner involves designing primers that are unlikely to hybridize with one another. The PCR probes, typically referred to as primers, are selected by creating a thermodynamic model of potentially adverse interactions between at least 300; at least 500; at least 750; at least 1,000; at least 2,000; at least 5,000; at least 7,500; at least 10,000; at least 20,000; at least 25,000; at least 30,000; at least 40,000; at least 50,000; at least 75,000; or at least 100,000 potential primer pairs, or unintended interactions between primers and sample DNA, and then using the model to eliminate designs that are incompatible with other the designs in the pool. Another technique that allows highly multiplexed targeted PCR to perform in a highly efficient manner is using a partial or full nesting approach to the targeted PCR. Using one or a combination of these approaches allows multiplexing of at least 300, at least 800, at least 1,200, at least 4,000 or at least 10,000 primers in a single pool with the resulting amplified DNA comprising a majority of DNA molecules that, when sequenced, will map to targeted loci. Using one or a combination of these approaches allows multiplexing of a large number of primers in a single pool with the resulting amplified DNA comprising greater than 50%, greater than 60%, greater than 67%, greater than 80%, greater than 90%, greater than 95%, greater than 96%, greater than 97%, greater than 98%, greater than 99%, or greater than 99.5% DNA molecules that map to targeted loci.

In some embodiments the detection of the target genetic material may be done in a multiplexed fashion. The number of genetic target sequences that may be run in parallel can range from one to ten, ten to one hundred, one hundred to one thousand, one thousand to ten thousand, ten thousand to one hundred thousand, one hundred thousand to one million, or one million to ten million. Prior attempts to multiplex more than 100 primers per pool have resulted in significant problems with unwanted side reactions such as primer-dimer formation.

Targeted PCR

In some embodiments, PCR can be used to target specific locations of the genome. In plasma samples, the original DNA is highly fragmented (typically less than 500 bp, with an average length less than 200 bp). In PCR, both forward and reverse primers anneal to the same fragment to enable amplification. Therefore, if the fragments are short, the PCR assays must amplify relatively short regions as well. Like MIPS, if the polymorphic positions are too close the polymerase binding site, it could result in biases in the amplification from different alleles. Currently, PCR primers that target polymorphic regions, such as those containing SNPs, are typically designed such that the 3' end of the primer will hybridize to the base immediately adjacent to the polymorphic base or bases. In an embodiment of the present disclosure, the 3' ends of both the forward and reverse PCR primers are designed to hybridize to bases that are one or a few positions away from the variant positions (polymorphic sites) of the targeted allele. The number of bases between the polymorphic site (SNP or otherwise) and the base to which the 3' end of the primer is designed to hybridize may be one base, it may be two bases, it may be three bases, it may be four bases, it may be five bases, it may be six bases, it may be seven to ten bases, it may be eleven to fifteen bases, or it may be sixteen to twenty bases. The forward and reverse primers may be designed to hybridize a different number of bases away from the polymorphic site.

PCR assay can be generated in large numbers, however, the interactions between different PCR assays makes it difficult to multiplex them beyond about one hundred assays. Various complex molecular approaches can be used to increase the level of multiplexing, but it may still be limited to fewer than 100, perhaps 200, or possibly 500 assays per reaction. Samples with large quantities of DNA can be split among multiple sub-reactions and then recombined before sequencing. For samples where either the overall sample or some subpopulation of DNA molecules is limited, splitting the sample would introduce statistical noise. In an embodiment, a small or limited quantity of DNA may refer to an amount below 10 pg, between 10 and 100 pg, between 100 pg and 1 ng, between 1 and 10 ng, or between 10 and 100 ng. Note that while this method is particularly useful on small amounts of DNA where other methods that involve splitting into multiple pools can cause significant problems related to introduced stochastic noise, this method still provides the benefit of minimizing bias when it is run on samples of any quantity of DNA. In these situations, a universal pre-amplification step may be used to increase the overall sample quantity. Ideally, this pre-amplification step should not appreciably alter the allelic distributions.

In an embodiment, a method of the present disclosure can generate PCR products that are specific to a large number of targeted loci, specifically 1,000 to 5,000 loci, 5,000 to 10,000 loci or more than 10,000 loci, for genotyping by sequencing or some other genotyping method, from limited samples such as single cells or DNA from body fluids. Currently, performing multiplex PCR reactions of more than 5 to 10 targets presents a major challenge and is often hindered by primer side products, such as primer dimers, and other artifacts. When detecting target sequences using microarrays with hybridization probes, primer dimers and other artifacts may be ignored, as these are not detected. However, when using sequencing as a method of detection, the vast majority of the sequencing reads would sequence such artifacts and not the desired target sequences in a sample. Methods described in the prior art used to multiplex more than 50 or 100 reactions in one reaction volume followed by sequencing will typically result in more than 20%, and often more than 50%, in many cases more than 80% and in some cases more than 90% off-target sequence reads.

In general, to perform targeted sequencing of multiple (n) targets of a sample (greater than 50, greater than 100, greater than 500, or greater than 1,000), one can split the sample into a number of parallel reactions that amplify one individual target. This has been performed in PCR multiwell plates or can be done in commercial platforms such as the FLUIDIGM ACCESS ARRAY (48 reactions per sample in microfluidic chips) or DROPLET PCR by RAIN DANCE TECHNOLOGY (100 s to a few thousands of targets). Unfortunately, these split-and-pool methods are problematic for samples with a limited amount of DNA, as there is often not enough copies of the genome to ensure that there is one copy of each region of the genome in each well. This is an especially severe problem when polymorphic loci are targeted, and the relative proportions of the alleles at the polymorphic loci are needed, as the stochastic noise introduced by the splitting and pooling will cause very poorly accurate measurements of the proportions of the alleles that were present in the original sample of DNA. Described here is a method to effectively and efficiently amplify many PCR reactions that is applicable to cases where only a limited amount of DNA is available. In an embodiment, the method may be applied for analysis of single cells, body fluids, mixtures of DNA such as the free floating DNA found in maternal plasma, biopsies, environmental and/or forensic samples.

In an embodiment, the targeted sequencing may involve one, a plurality, or all of the following steps: a) Generate and amplify a library with adaptor sequences on both ends of DNA fragments. b) Divide into multiple reactions after library amplification. c) Generate and optionally amplify a library with adaptor sequences on both ends of DNA fragments. d) Perform 1000- to 10,000-plex amplification of selected targets using one target specific "Forward" primer per target and one tag specific primer. e) Perform a second amplification from this product using "Reverse" target specific primers and one (or more) primer specific to a universal tag that was introduced as part of the target specific forward primers in the first round. f) Perform a 1000-plex preamplification of selected target for a limited number of cycles. g) Divide the product into multiple aliquots and amplify subpools of targets in individual reactions (for example, 50 to 500-plex, though this can be used all the way down to singleplex. h) Pool products of parallel subpools reactions. i) During these amplifications primers may carry sequencing compatible tags (partial or full length) such that the products can be sequenced.

Highly Multiplexed PCR

Disclosed herein are methods that permit the targeted amplification of over a hundred to tens of thousands of target sequences (e.g., SNP loci) from a nucleic acid sample such as genomic DNA obtained from plasma. The amplified sample may be relatively free of primer dimer products and have low allelic bias at target loci. If during or after amplification the products are appended with sequencing compatible adaptors, analysis of these products can be performed by sequencing.

Performing a highly multiplexed PCR amplification using methods known in the art results in the generation of primer dimer products that are in excess of the desired amplification products and not suitable for sequencing. These can be reduced empirically by eliminating primers that form these products, or by performing in silico selection of primers. However, the larger the number of assays, the more difficult this problem becomes.

One solution is to split the 5000-plex reaction into several lower-plexed amplifications. e.g. one hundred 50-plex or fifty 100-plex reactions, or to use microfluidics or even to split the sample into individual PCR reactions. However, if the sample DNA is limited, such as in non-invasive prenatal diagnostics from pregnancy plasma, dividing the sample between multiple reactions should be avoided as this will result in bottlenecking.

Described herein are methods to first globally amplify the plasma DNA of a sample and then divide the sample up into multiple multiplexed target enrichment reactions with more moderate numbers of target sequences per reaction. In an embodiment, a method of the present disclosure can be used for preferentially enriching a DNA mixture at a plurality of loci, the method comprising one or more of the following steps: generating and amplifying a library from a mixture of DNA where the molecules in the library have adaptor sequences ligated on both ends of the DNA fragments, dividing the amplified library into multiple reactions, performing a first round of multiplex amplification of selected targets using one target specific "forward" primer per target and one or a plurality of adaptor specific universal "reverse" primers. In an embodiment, a method of the present disclosure further includes performing a second amplification using "reverse" target specific primers and one or a plurality of primers specific to a universal tag that was introduced as part of the target specific forward primers in the first round. In an embodiment, the method may involve a fully nested, hemi-nested, semi-nested, one sided fully nested, one sided hemi-nested, or one sided semi-nested PCR approach. In an embodiment, a method of the present disclosure is used for preferentially enriching a DNA mixture at a plurality of loci, the method comprising performing a multiplex preamplification of selected targets for a limited number of cycles, dividing the product into multiple aliquots and amplifying subpools of targets in individual reactions, and pooling products of parallel subpools reactions. Note that this approach could be used to perform targeted amplification in a manner that would result in low levels of allelic bias for 50-500 loci, for 500 to 5,000 loci, for 5,000 to 50,000 loci, or even for 50,000 to 500,000 loci. In an embodiment, the primers carry partial or full length sequencing compatible tags.

The workflow may entail (1) extracting DNA such as plasma DNA, (2) preparing fragment library with universal adaptors on both ends of fragments, (3) amplifying the library using universal primers specific to the adaptors, (4) dividing the amplified sample "library" into multiple aliquots, (5) performing multiplex (e.g. about 100-plex, 1,000, or 10,000-plex with one target specific primer per target and a tag-specific primer) amplifications on aliquots, (6) pooling aliquots of one sample, (7) barcoding the sample, (8) mixing the samples and adjusting the concentration, (9) sequencing the sample. The workflow may comprise multiple sub-steps that contain one of the listed steps (e.g. step (2) of preparing the library step could entail three enzymatic steps (blunt ending, dA tailing and adaptor ligation) and three purification steps). Steps of the workflow may be combined, divided up or performed in different order (e.g. bar coding and pooling of samples).

It is important to note that the amplification of a library can be performed in such a way that it is biased to amplify short fragments more efficiently. In this manner it is possible to preferentially amplify shorter sequences, e.g. mono-nucleosomal DNA fragments as the cell free fetal DNA (of placental origin) found in the circulation of pregnant women. Note that PCR assays can have the tags, for example sequencing tags, (usually a truncated form of 15-25 bases). After multiplexing, PCR multiplexes of a sample are pooled and then the tags are completed (including bar coding) by a tag-specific PCR (could also be done by ligation). Also, the full sequencing tags can be added in the same reaction as the multiplexing. In the first cycles targets may be amplified with the target specific primers, subsequently the tag-specific primers take over to complete the SQ-adaptor sequence. The PCR primers may carry no tags. The sequencing tags may be appended to the amplification products by ligation.

In an embodiment, highly multiplex PCR followed by evaluation of amplified material by clonal sequencing may be used for various applications such as the detection of fetal aneuploidy. Whereas traditional multiplex PCRs evaluate up to fifty loci simultaneously, the approach described herein may be used to enable simultaneous evaluation of more than 50 loci simultaneously, more than 100 loci simultaneously, more than 500 loci simultaneously, more than 1,000 loci simultaneously, more than 5,000 loci simultaneously, more than 10,000 loci simultaneously, more than 50,000 loci simultaneously, and more than 100,000 loci simultaneously. Experiments have shown that up to, including and more than 10,000 distinct loci can be evaluated simultaneously, in a single reaction, with sufficiently good efficiency and specificity to make non-invasive prenatal aneuploidy diagnoses and/or copy number calls with high accuracy. Assays may be combined in a single reaction with the entirety of a sample such as a cfDNA sample isolated from maternal plasma, a fraction thereof, or a further processed derivative of the cfDNA sample. The sample (e.g., cfDNA or derivative) may also be split into multiple parallel multiplex reactions. The optimum sample splitting and multiplex is determined by trading off various performance specifications. Due to the limited amount of material, splitting the sample into multiple fractions can introduce sampling noise, handling time, and increase the possibility of error. Conversely, higher multiplexing can result in greater amounts of spurious amplification and greater inequalities in amplification both of which can reduce test performance.

Two crucial related considerations in the application of the methods described herein are the limited amount of original sample (e.g., plasma) and the number of original molecules in that material from which allele frequency or other measurements are obtained. If the number of original molecules falls below a certain level, random sampling noise becomes significant, and can affect the accuracy of the test. Typically, data of sufficient quality for making non-invasive prenatal aneuploidy diagnoses can be obtained if measurements are made on a sample comprising the equivalent of 500-1000 original molecules per target locus. There are a number of ways of increasing the number of distinct measurements, for example increasing the sample volume. Each manipulation applied to the sample also potentially results in losses of material. It is essential to characterize losses incurred by various manipulations and avoid, or as necessary improve yield of certain manipulations to avoid losses that could degrade performance of the test.

In an embodiment, it is possible to mitigate potential losses in subsequent steps by amplifying all or a fraction of the original sample (e.g., cfDNA sample). Various methods are available to amplify all of the genetic material in a sample, increasing the amount available for downstream procedures. In an embodiment, ligation mediated PCR (LM-PCR) DNA fragments are amplified by PCR after ligation of either one distinct adaptors, two distinct adapters, or many distinct adaptors. In an embodiment, multiple displacement amplification (MDA) phi-29 polymerase is used to amplify all DNA isothermally. In DOP-PCR and variations, random priming is used to amplify the original material DNA. Each method has certain characteristics such as uniformity of amplification across all represented regions of the genome, efficiency of capture and amplification of original DNA, and amplification performance as a function of the length of the fragment.

In an embodiment LM-PCR may be used with a single heteroduplexed adaptor having a 3-prime tyrosine. The heteroduplexed adaptor enables the use of a single adaptor molecule that may be converted to two distinct sequences on 5-prime and 3-prime ends of the original DNA fragment during the first round of PCR. In an embodiment, it is possible to fractionate the amplified library by size separations, or products such as AMPURE, TASS or other similar methods. Prior to ligation, sample DNA may be blunt ended, and then a single adenosine base is added to the 3-prime end. Prior to ligation the DNA may be cleaved using a restriction enzyme or some other cleavage method. During ligation the 3-prime adenosine of the sample fragments and the complementary 3-prime tyrosine overhang of adaptor can enhance ligation efficiency. The extension step of the PCR amplification may be limited from a time standpoint to reduce amplification from fragments longer than about 200 bp, about 300 bp, about 400 bp, about 500 bp or about 1,000 bp. Since longer DNA found in the maternal plasma is nearly exclusively maternal, this may result in the enrichment of fetal DNA by 10-50% and improvement of test performance. A number of reactions were run using conditions as specified by commercially available kits, the resulted in successful ligation of fewer than 10% of sample DNA molecules. A series of optimizations of the reaction conditions for this improved ligation to approximately 70%.

Mini-PCR

The following Mini-PCR method is desirable for samples containing short nucleic acids, digested nucleic acids, or fragmented nucleic acids, such as cfDNA. Traditional PCR assay design results in significant losses of distinct fetal molecules, but losses can be greatly reduced by designing very short PCR assays, termed mini-PCR assays. Fetal cfDNA in maternal serum is highly fragmented and the fragment sizes are distributed in approximately a Gaussian fashion with a mean of 160 bp, a standard deviation of 15 bp, a minimum size of about 100 bp, and a maximum size of about 220 bp. The distribution of fragment start and end positions with respect to the targeted polymorphisms, while not necessarily random, vary widely among individual targets and among all targets collectively and the polymorphic site of one particular target locus may occupy any position from the start to the end among the various fragments originating from that locus. Note that the term mini-PCR may equally well refer to normal PCR with no additional restrictions or limitations.

During PCR, amplification will only occur from template DNA fragments comprising both forward and reverse primer sites. Because fetal cfDNA fragments are short, the likelihood of both primer sites being present the likelihood of a fetal fragment of length L comprising both the forward and reverse primers sites is ratio of the length of the amplicon to the length of the fragment. Under ideal conditions, assays in which the amplicon is 45, 50, 55, 60, 65, or 70 bp will successfully amplify from 72%, 69%, 66%, 63%, 59%, or 56%, respectively, of available template fragment molecules. The amplicon length is the distance between the 5-prime ends of the forward and reverse priming sites. Amplicon length that is shorter than typically used by those known in the art may result in more efficient measurements of the desired polymorphic loci by only requiring short sequence reads. In an embodiment, a substantial fraction of the amplicons should be less than 100 bp, less than 90 bp, less than 80 bp, less than 70 bp, less than 65 bp, less than 60 bp, less than 55 bp, less than 50 bp, or less than 45 bp.

Note that in methods known in the prior an, short assays such as those described herein are usually avoided because they are not required and they impose considerable constraint on primer design by limiting primer length, annealing characteristics, and the distance between the forward and reverse primer.

Also note that there is the potential for biased amplification if the 3-prime end of the either primer is within roughly 1-6 bases of the polymorphic site. This single base difference at the site of initial polymerase binding can result in preferential amplification of one allele, which can alter observed allele frequencies and degrade performance. All of these constraints make it very challenging to identify primers that will amplify a particular locus successfully and furthermore, to design large sets of primers that are compatible in the same multiplex reaction. In an embodiment, the 3' end of the inner forward and reverse primers are designed to hybridize to a region of DNA upstream from the polymorphic site, and separated from the polymorphic site by a small number of bases. Ideally, the number of bases may be between 6 and 10 bases, but may equally well be between 4 and 15 bases, between three and 20 bases, between two and 30 bases, or between 1 and 60 bases, and achieve substantially the same end.

Multiplex PCR may involve a single round of PCR in which all targets are amplified or it may involve one round of PCR followed by one or more rounds of nested PCR or some variant of nested PCR. Nested PCR consists of a subsequent round or rounds of PCR amplification using one or more new primers that bind internally, by at least one base pair, to the primers used in a previous round. Nested PCR reduces the number of spurious amplification targets by amplifying, in subsequent reactions, only those amplification products from the previous one that have the correct internal sequence. Reducing spurious amplification targets improves the number of useful measurements that can be obtained, especially in sequencing. Nested PCR typically entails designing primers completely internal to the previous primer binding sites, necessarily increasing the minimum DNA segment size required for amplification. For samples such as maternal plasma cfDNA, in which the DNA is highly fragmented, the larger assay size reduces the number of distinct cfDNA molecules from which a measurement can be obtained. In an embodiment, to offset this effect, one may use a partial nesting approach where one or both of the second round primers overlap the first binding sites extending internally some number of bases to achieve additional specificity while minimally increasing in the total assay size.

In an embodiment, a multiplex pool of PCR assays are designed to amplify potentially heterozygous SNP or other polymorphic or non-polymorphic loci on one or more chromosomes and these assays are used in a single reaction to amplify DNA. The number of PCR assays may be between 50 and 200 PCR assays, between 200 and 1,000 PCR assays, between 1,000 and 5,000 PCR assays, or between 5,000 and 20,000 PCR assays (50 to 200-plex, 200 to 1,000-plex, 1,000 to 5,000-plex, 5,000 to 20,000-plex, more than 20,000-plex respectively). In an embodiment, a multiplex pool of about 10,000 PCR assays (10,000-plex) are designed to amplify potentially heterozygous SNP loci on chromosomes X, Y, 13, 18, and 21 and 1 or 2 and these assays are used in a single reaction to amplify cfDNA obtained from a material plasma sample, chorion villus samples, amniocentesis samples, single or a small number of cells, other bodily fluids or tissues, cancers, or other genetic matter. The SNP frequencies of each locus may be determined by clonal or some other method of sequencing of the amplicons. Statistical analysis of the allele frequency distributions or ratios of all assays may be used to determine if the sample contains a trisomy of one or more of the chromosomes included in the test. In another embodiment the original cfDNA samples is split into two samples and parallel 5,000-plex assays are performed. In another embodiment the original cfDNA samples is split into n samples and parallel (~10,000/n)-plex assays are performed where n is between 2 and 12, or between 12 and 24, or between 24 and 48, or between 48 and 96. Data is collected and analyzed in a similar manner to that already described. Note that this method is equally well applicable to detecting translocations, deletions, duplications, and other chromosomal abnormalities.

In an embodiment, tails with no homology to the target genome may also be added to the 3-prime or 5-prime end of any of the primers. These tails facilitate subsequent manipulations, procedures, or measurements. In an embodiment, the tail sequence can be the same for the forward and reverse target specific primers. In an embodiment, different tails may be used for the forward and reverse target specific primers. In an embodiment, a plurality of different tails may be used for different loci or sets of loci. Certain tails may be shared among all loci or among subsets of loci. For example, using forward and reverse tails corresponding to forward and reverse sequences required by any of the current sequencing platforms can enable direct sequencing following amplification. In an embodiment, the tails can be used as common priming sites among all amplified targets that can be used to add other useful sequences. In some embodiments, the inner primers may contain a region that is designed to hybridize either upstream or downstream of the targeted locus (e.g., a polymorphic locus). In some embodiments, the primers may contain a molecular barcode. In some embodiments, the primer may contain a universal priming sequence designed to allow PCR amplification.

In an embodiment, a 10,000-plex PCR assay pool is created such that forward and reverse primers have tails corresponding to the required forward and reverse sequences required by a high throughput sequencing instrument such as the HISEQ, GAIIX, or MYSEQ available from ILLUMINA. In addition, included 5-prime to the sequencing tails is an additional sequence that can be used as a priming site in a subsequent PCR to add nucleotide barcode sequences to the amplicons, enabling multiplex sequencing of multiple samples in a single lane of the high throughput sequencing instrument.

In an embodiment, a 10,000-plex PCR assay pool is created such that reverse primers have tails corresponding to the required reverse sequences required by a high throughput sequencing instrument. After amplification with the first 10,000-plex assay, a subsequent PCR amplification may be performed using another 10,000-plex pool having partly nested forward primers (e.g. 6-bases nested) for all targets and a reverse primer corresponding to the reverse sequencing tail included in the first round. This subsequent round of partly nested amplification with just one target specific primer and a universal primer limits the required size of the assay, reducing sampling noise, but greatly reduces the number of spurious amplicons. The sequencing tags can be added to appended ligation adaptors and/or as part of PCR probes, such that the tag is part of the final amplicon.

Fetal fraction affects performance of the test. There are a number of ways to enrich the fetal fraction of the DNA found in maternal plasma. Fetal fraction can be increased by the previously described LM-PCR method already discussed as well as by a targeted removal of long maternal fragments. In an embodiment, prior to multiplex PCR amplification of the target loci, an additional multiplex PCR reaction may be carried out to selectively remove long and largely maternal fragments corresponding to the loci targeted in the subsequent multiplex PCR. Additional primers are designed to anneal a site a greater distance from the polymorphism than is expected to be present among cell free fetal DNA fragments. These primers may be used in a one cycle multiplex PCR reaction prior to multiplex PCR of the target polymorphic loci. These distal primers are tagged with a molecule or moiety that can allow selective recognition of the tagged pieces of DNA. In an embodiment, these molecules of DNA may be covalently modified with a biotin molecule that allows removal of newly formed double stranded DNA comprising these primers after one cycle of PCR. Double stranded DNA formed during that first round is likely maternal in origin. Removal of the hybrid material may be accomplished by the use of magnetic streptavidin beads. There are other methods of tagging that may work equally well. In an embodiment, size selection methods may be used to enrich the sample for shorter strands of DNA, for example, those less than about 800 bp, less than about 500 bp, or less than about 300 bp. Amplification of short fragments can then proceed as usual.

The mini-PCR method described in this disclosure enables highly multiplexed amplification and analysis of hundreds to thousands or even millions of loci in a single reaction, from a single sample. At the same, the detection of the amplified DNA can be multiplexed; tens to hundreds of samples can be multiplexed in one sequencing lane by using barcoding PCR. This multiplexed detection has been successfully tested up to 49-plex, and a much higher degree of multiplexing is possible. In effect, this allows hundreds of samples to be genotyped at thousands of SNPs in a single sequencing run. For these samples, the method allows determination of genotype and heterozygosity rate and simultaneously determination of copy number, both of which may be used for the purpose of aneuploidy detection. This method is particularly useful in detecting aneuploidy of a gestating fetus from the free floating DNA found in maternal plasma. This method may be used as part of a method for sexing a fetus, and/or predicting the paternity of the fetus. It may be used as part of a method for mutation dosage. This method may be used for any amount of DNA or RNA, and the targeted regions may be SNPs, other polymorphic regions, non-polymorphic regions, and combinations thereof.

In some embodiments, ligation mediated universal-PCR amplification of fragmented DNA may be used. The ligation mediated universal-PCR amplification can be used to amplify plasma DNA, which can then be divided into multiple parallel reactions. It may also be used to preferentially amplify short fragments, thereby enriching fetal fraction. In some embodiments the addition of tags to the fragments by ligation can enable detection of shorter fragments, use of shorter target sequence specific portions of the primers and/or annealing at higher temperatures which reduces unspecific reactions.

The methods described herein may be used for a number of purposes where there is a target set of DNA that is mixed with an amount of contaminating DNA. In some embodiments, the target DNA and the contaminating DNA may be from individuals who are genetically related. For example, genetic abnormalities in a fetus (target) may be detected from maternal plasma which contains fetal (target) DNA and also maternal (contaminating) DNA, the abnormalities include whole chromosome abnormalities (e.g. aneuploidy) partial chromosome abnormalities (e.g. deletions, duplications, inversions, translocations), polynucleotide polymorphisms (e.g. STRs), single nucleotide polymorphisms, and/or other genetic abnormalities or differences. In some embodiments, the target and contaminating DNA may be from the same individual, but where the target and contaminating DNA are different by one or more mutations, for example in the case of cancer. (see e.g. H. Mamon et al. *Preferential Amplification of Apoptotic DNA from Plasma: Potential for Enhancing Detection of Minor DNA Alterations in Circulating DNA*. Clinical Chemistry 54:9 (2008). In some embodiments, the DNA may be found in cell culture (apoptotic) supernatant. In some embodiments, it is possible to induce apoptosis in biological samples (e.g., blood) for subsequent library preparation, amplification and/or sequencing. A number of enabling workflows and protocols to achieve this end are presented elsewhere in this disclosure.

In some embodiments, the target DNA may originate from single cells, from samples of DNA consisting of less than one copy of the target genome, from low amounts of DNA, from DNA from mixed origin (e.g. pregnancy plasma, placental and maternal DNA; cancer patient plasma and tumors: mix between healthy and cancer DNA, transplantation etc), from other body fluids, from cell cultures, from culture supernatants, from forensic samples of DNA, from ancient samples of DNA (e.g. insects trapped in amber), from other samples of DNA, and combinations thereof.

In some embodiments, a short amplicon size may be used. Short amplicon sizes are especially suited for fragmented DNA (see e.g. A. Sikora, et al. Detection of increased amounts of cell-free fetal DNA with short PCR amplicons. Clin Chem 2010 January; 56(1):136-8).

The use of short amplicon sizes may result in some significant benefits. Short amplicon sizes may result in optimized amplification efficiency. Short amplicon sizes typically produce shorter products, therefore there is less chance for nonspecific priming. Shorter products can be clustered more densely on sequencing flow cell, as the clusters will be smaller. Note that the methods described herein may work equally well for longer PCR amplicons. Amplicon length may be increased if necessary, for example, when sequencing larger sequence stretches. Experiments with 146-plex targeted amplification with assays of 100 bp to 200 bp length as first step in a nested-PCR protocol were run on single cells and on genomic DNA with positive results.

In some embodiments, the methods described herein may be used to amplify and/or detect SNPs, copy number, nucleotide methylation, mRNA levels, other types of RNA expression levels, other genetic and/or epigenetic features. The mini-PCR methods described herein may be used along with next-generation sequencing; it may be used with other downstream methods such as microarrays, counting by digital PCR, real-time PCR, Mass-spectrometry analysis etc.

In some embodiment, the mini-PCR amplification methods described herein may be used as part of a method for accurate quantification of minority populations. It may be used for absolute quantification using spike calibrators. It may be used for mutation/minor allele quantification through very deep sequencing, and may be run in a highly multiplexed fashion. It may be used for standard paternity and identity testing of relatives or ancestors, in human, animals, plants or other creatures. It may be used for forensic testing. It may be used for rapid genotyping and copy number analysis (CN), on any kind of material, e.g. amniotic fluid and CVS, sperm, product of conception (POC). It may be used for single cell analysis, such as genotyping on samples biopsied from embryos. It may be used for rapid embryo analysis (within less than one, one, or two days of biopsy) by targeted sequencing using min-PCR.

In some embodiments, it may be used for tumor analysis: tumor biopsies are often a mixture of health and tumor cells. Targeted PCR allows deep sequencing of SNPs and loci with close to no background sequences. It may be used for copy number and loss of heterozygosity analysis on tumor DNA. Said tumor DNA may be present in many different body fluids or tissues of tumor patients. It may be used for detection of tumor recurrence, and/or tumor screening. It may be used for quality control testing of seeds. It may be used for breeding, or fishing purposes. Note that any of these methods could equally well be used targeting non-polymorphic loci for the purpose of ploidy calling.

Some literature describing some of the fundamental methods that underlie the methods disclosed herein include: (1) Wang H Y, Luo M, Tereshchenko I V, Frikker D M, Cui X, Li J Y, Hu G, Chu Y, Azaro M A, Lin Y, Shen L, Yang Q, Kambouris M E, Gao R, Shih W, Li H. Genome Res. 2005 February; 15(2):276-83 Department of Molecular Genetics, Microbiology and Immunology/The Cancer Institute of New Jersey, Robert Wood Johnson Medical School, New Brunswick, N.J. 08903, USA. (2) High-throughput genotyping of single nucleotide polymorphisms with high sensitivity. Li H, Wang H Y, Cui X, Luo M, Hu G, Greenawalt D M, Tereshchenko I V, Li J Y, Chu Y, Gao R. Methods Mol Biol. 2007; 396—PubMed PMID: 18025699. (3) A method comprising multiplexing of an average of 9 assays for sequencing is described in: Nested Patch PCR enables highly multiplexed mutation discovery in candidate genes. Varley K E, Mitra R D. Genome Res 2008 November; 18(11);

1844-50. Epub 2008 Oct. 10. Note that the methods disclosed herein allow multiplexing of orders of magnitude more than in the above references.

Targeted PCR Variants—Nesting

There are many workflows that are possible when conducting PCR; some workflows typical to the methods disclosed herein are described. The steps outlined herein are not meant to exclude other possible steps nor does it imply that any of the steps described herein are required for the method to work properly. A large number of parameter variations or other modifications are known in the literature, and may be made without affecting the essence of the invention. One particular generalized workflow is given below followed by a number of possible variants. The variants typically refer to possible secondary PCR reactions, for example different types of nesting that may be done (step 3). It is important to note that variants may be done at different times, or in different orders than explicitly described herein. Examples that use polymorphic loci for illustration can be readily adapted for the amplification of nonpolymorphic loci if desired.

1. The DNA in the sample may have ligation adapters, often referred to as library tags or ligation adaptor tags (LTs), appended, where the ligation adapters contain a universal priming sequence, followed by a universal amplification. In an embodiment, this may be done using a standard protocol designed to create sequencing libraries after fragmentation. In an embodiment, the DNA sample can be blunt ended, and then an A can be added at the 3' end. A Y-adaptor with a T-overhang can be added and ligated. In some embodiments, other sticky ends can be used other than an A or T overhang. In some embodiments, other adaptors can be added, for example looped ligation adaptors. In some embodiments, the adaptors may have tag designed for PCR amplification.

2. Specific Target Amplification (STA): Pre-amplification of hundreds to thousands to tens of thousands and even hundreds of thousands of targets may be multiplexed in one reaction volume. STA is typically run from 10 to 30 cycles, though it may be run from 5 to 40 cycles, from 2 to 50 cycles, and even from 1 to 100 cycles. Primers may be tailed, for example for a simpler workflow or to avoid sequencing of a large proportion of dimers. Note that typically, dimers of both primers carrying the same tag will not be amplified or sequenced efficiently. In some embodiments, between 1 and 10 cycles of PCR may be carried out; in some embodiments between 10 and 20 cycles of PCR may be carried out; in some embodiments between 20 and 30 cycles of PCR may be carried out; in some embodiments between 30 and 40 cycles of PCR may be carried out; in some embodiments more than 40 cycles of PCR may be carried out. The amplification may be a linear amplification. The number of PCR cycles may be optimized to result in an optimal depth of read (DOR) profile. Different DOR profiles may be desirable for different purposes. In some embodiments, a more even distribution of reads between all assays is desirable; if the DOR is too small for some assays, the stochastic noise can be too high for the data to be too useful, while if the depth of read is too high, the marginal usefulness of each additional read is relatively small.

Primer tails may improve the detection of fragmented DNA from universally tagged libraries. If the library tag and the primer-tails contain a homologous sequence, hybridization can be improved (for example, melting temperature ($T_M$) is lowered) and primers can be extended if only a portion of the primer target sequence is in the sample DNA fragment. In some embodiments, 13 or more target specific base pairs may be used. In some embodiments, 10 to 12 target specific base pairs may be used. In some embodiments, 8 to 9 target specific base pairs may be used. In some embodiments, 6 to 7 target specific base pairs may be used. In some embodiments, STA may be performed on pre-amplified DNA, e.g. MDA, RCA, other whole genome amplifications, or adaptor-mediated universal PCR. In some embodiments, STA may be performed on samples that are enriched or depleted of certain sequences and populations, e.g. by size selection, target capture, directed degradation.

3. In some embodiments, it is possible to perform secondary multiplex PCRs or primer extension reactions to increase specificity and reduce undesirable products. For example, full nesting, semi-nesting, hemi-nesting, and/or subdividing into parallel reactions of smaller assay pools are all techniques that may be used to increase specificity. Experiments have shown that splitting a sample into three 400-plex reactions resulted in product DNA with greater specificity than one 1,200-plex reaction with exactly the same primers. Similarly, experiments have shown that splitting a sample into four 2,400-plex reactions resulted in product DNA with greater specificity than one 9,600-plex reaction with exactly the same primers. In an embodiment, it is possible to use target-specific and tag specific primers of the same and opposing directionality.

4. In some embodiments, it is possible to amplify a DNA sample (dilution, purified or otherwise) produced by an STA reaction using tag-specific primers and "universal amplification", i.e. to amplify many or all pre-amplified and tagged targets. Primers may contain additional functional sequences, e.g. barcodes, or a full adaptor sequence necessary for sequencing on a high throughput sequencing platform.

These methods may be used for analysis of any sample of DNA, and are especially useful when the sample of DNA is particularly small, or when it is a sample of DNA where the DNA originates from more than one individual, such as in the case of maternal plasma. These methods may be used on DNA samples such as a single or small number of cells, genomic DNA, plasma DNA, amplified plasma libraries, amplified apoptotic supernatant libraries, or other samples of mixed DNA. In an embodiment, these methods may be used in the case where cells of different genetic constitution may be present in a single individual, such as with cancer or transplants. In an embodiment, some of the DNA is from the recipient of a transplant (such as recipient cell-free or cellular DNA) and some of the DNA is from the donor of the transplant (such as cell-free or cellular DNA from the transplant). In an embodiment, the method is used to amplify one or more loci that differ between the recipient and the donor (such as loci for which a different combination of alleles are present in the recipient compared to the donor). In some embodiments, the recipient is homozygous for a first allele (such as AA) and the donor is homozygous for a second allele (such as BB) or is heterozygous with the first allele and a second allele (such as AB) at one or more loci. In some embodiments, the method is used to measure the absolute or relative amount of DNA from the donor of the transplant (such as cell-free or cellular DNA from the transplant). In some embodiments, this method is used to prognose, diagnose, detect, or monitor a transplant status or outcome, such as transplant rejection, tolerance, non-rejection based allograft injury, transplant function, transplant survival, chronic transplant injury, or tittering of pharmacological immunosuppression.

Protocol Variants (Variants and or Additions to the Workflow Above)

Direct Multiplexed Mini-PCR:

Specific target amplification (STA) of a plurality of target sequences with tagged primers is shown in FIG. 1. 101 denotes double stranded DNA with a polymorphic locus of interest at X. 102 denotes the double stranded DNA with ligation adaptors added for universal amplification. 103 denotes the single stranded DNA that has been universally amplified with PCR primers hybridized. 104 denotes the final PCR product. In some embodiments, STA may be done on more than 100, more than 200, more than 500, more than 1,000, more than 2,000, more than 5,000, more than 10,000, more than 20,000, more than 50,000, more than 100,000 or more than 200,000 targets. In a subsequent reaction, tag-specific primers amplify all target sequences and lengthen the tags to include all necessary sequences for sequencing, including sample indexes. In an embodiment, primers may not be tagged or only certain primers may be tagged. Sequencing adaptors may be added by conventional adaptor ligation. In an embodiment, the initial primers may carry the tags.

In an embodiment, primers are designed so that the length of DNA amplified is unexpectedly short. Prior art demonstrates that ordinary people skilled in the art typically design 100+ bp amplicons. In an embodiment, the amplicons may be designed to be less than 80 bp. In an embodiment, the amplicons may be designed to be less than 70 bp. In an embodiment, the amplicons may be designed to be less than 60 bp. In an embodiment, the amplicons may be designed to be less than 50 bp. In an embodiment, the amplicons may be designed to be less than 45 bp. In an embodiment, the amplicons may be designed to be less than 40 bp. In an embodiment, the amplicons may be designed to be less than 35 bp. In an embodiment, the amplicons may be designed to be between 40 and 65 bp.

An experiment was performed using this protocol using 1200-plex amplification. Both genomic DNA and pregnancy plasma were used, about 70% of sequence reads mapped to targeted sequences. Details are given elsewhere in this document. Sequencing of a 1042-plex without design and selection of assays resulted in >99% of sequences being primer dimer products.

Sequential PCR:

After STA1 multiple aliquots of the product may be amplified in parallel with pools of reduced complexity with the same primers. The first amplification can give enough material to split. This method is especially good for small samples, for example those that are about 6-100 pg, about 100 pg to 1 ng, about 1 ng to 10 ng, or about 10 ng to 100 ng. The protocol was performed with 1200-plex into three 400-plexes. Mapping of sequencing reads increased from around 60 to 70% in the 1200-plex alone to over 95%.

Figure 2:
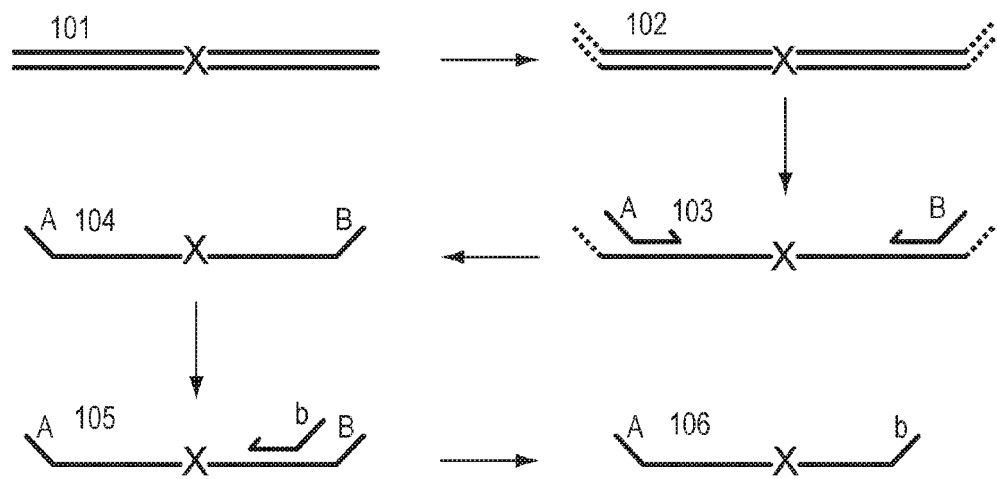
FIG. 2: Graphical representation of semi-nested mini-PCR method.

Semi-Nested Mini-PCR:

(see FIG. 2) After STA 1 a second STA is performed comprising a multiplex set of internal nested Forward primers (103 B, 105 b) and one (or few) tag-specific Reverse primers (103 A). 101 denotes double stranded DNA with a polymorphic locus of interest at X. 102 denotes the double stranded DNA with ligation adaptors added for universal amplification. 103 denotes the single stranded DNA that has been universally amplified with Forward Primer B and Reverse Primer A hybridized. 104 denotes the PCR product from 103. 105 denotes the product from 104 with nested Forward primer b hybridized, and Reverse tag A already pan of the molecule from the PCR that occurred between 103 and 104. 106 denotes the final PCR product. With this workflow usually greater than 95% of sequences map to the intended targets. The nested primer may overlap with the outer Forward primer sequence but introduces additional 3'-end bases. In some embodiments it is possible to use between one and 20 extra 3' bases. Experiments have shown that using 9 or more extra 3' bases in a 1200-plex designs works well. As readily apparent, the primers for the second STA can alternatively be considered a multiplex set of internal nested Reverse primers and one (or a few) tag-specific Forward primers.

Figure 3:
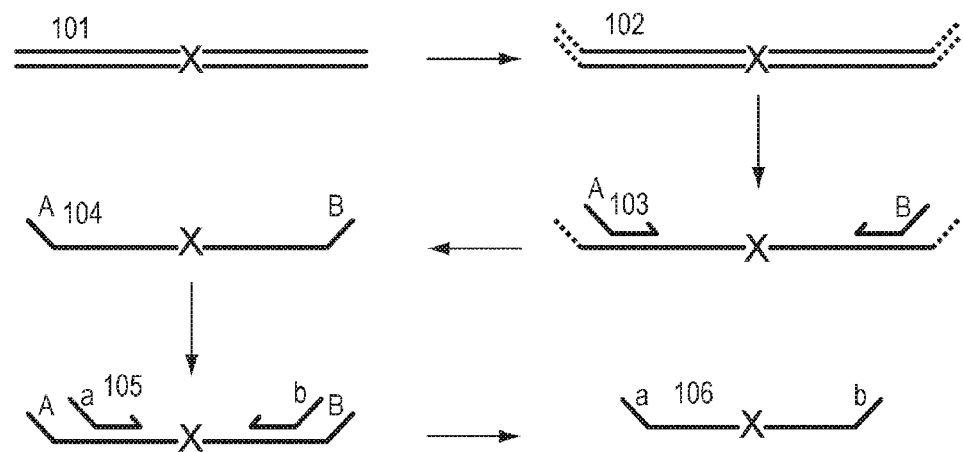
FIG. 3: Graphical representation of fully nested mini-PCR method.

Fully Nested Mini-PCR:

(see FIG. 3) After STA step 1, it is possible to perform a second multiplex PCR (or parallel m.p. PCRs of reduced complexity) with two nested primers carrying tags (A, a, B, b). 101 denotes double stranded DNA with a polymorphic locus of interest at X. 102 denotes the double stranded DNA with ligation adaptors added for universal amplification. 103 denotes the single stranded DNA that has been universally amplified with Forward Primer B and Reverse Primer A hybridized. 104 denotes the PCR product from 103. 105 denotes the product from 104 with nested Forward primer b and nested Reverse primer a hybridized. 106 denotes the final PCR product. In some embodiments, it is possible to use two full sets of primers. Experiments using a fully nested mini-PCR protocol were used to perform 146-plex amplification on single and three cells without step 102 of appending universal ligation adaptors and amplifying.

Figure 4:
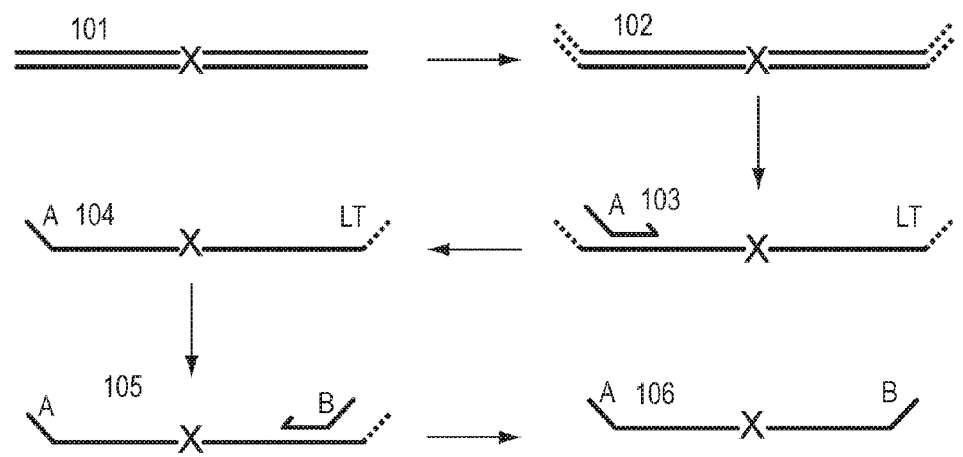
FIG. 4: Graphical representation of hemi-nested mini-PCR method.

Hemi-Nested Mini-PCR:

(see FIG. 4) It is possible to use target DNA that has and adaptors at the fragment ends. STA is performed comprising a multiplex set of Forward primers (B) and one (or few) tag-specific Reverse primers (A). A second STA can be performed using a universal tag-specific Forward primer and target specific Reverse primer. 101 denotes double stranded DNA with a polymorphic locus of interest at X. 102 denotes the double stranded DNA with ligation adaptors added for universal amplification. 103 denotes the single stranded DNA that has been universally amplified with Reverse Primer A hybridized. 104 denotes the PCR product from 103 that was amplified using Reverse primer A and ligation adaptor tag primer LT. 105 denotes the product from 104 with Forward primer B hybridized. 106 denotes the final PCR product. In this workflow, target specific Forward and Reverse primers are used in separate reactions, thereby reducing the complexity of the reaction and preventing dimer formation of forward and reverse primers. Note that in this example, primers A and B may be considered to be first primers, and primers 'a' and 'b' may be considered to be inner primers. This method is a big improvement on direct PCR as it is as good as direct PCR, but it avoids primer dimers. After first round of hemi nested protocol one typically sees ~99% non-targeted DNA, however, after second round there is typically a big improvement. As readily apparent, the primers for the first STA can be considered a multiplex set of Reverse primers and one (or few) tag-specific Forward primers, and the primers for the second STA can be considered a universal tag-specific Reverse primer and target specific Forward primer(s).

Figure 5:
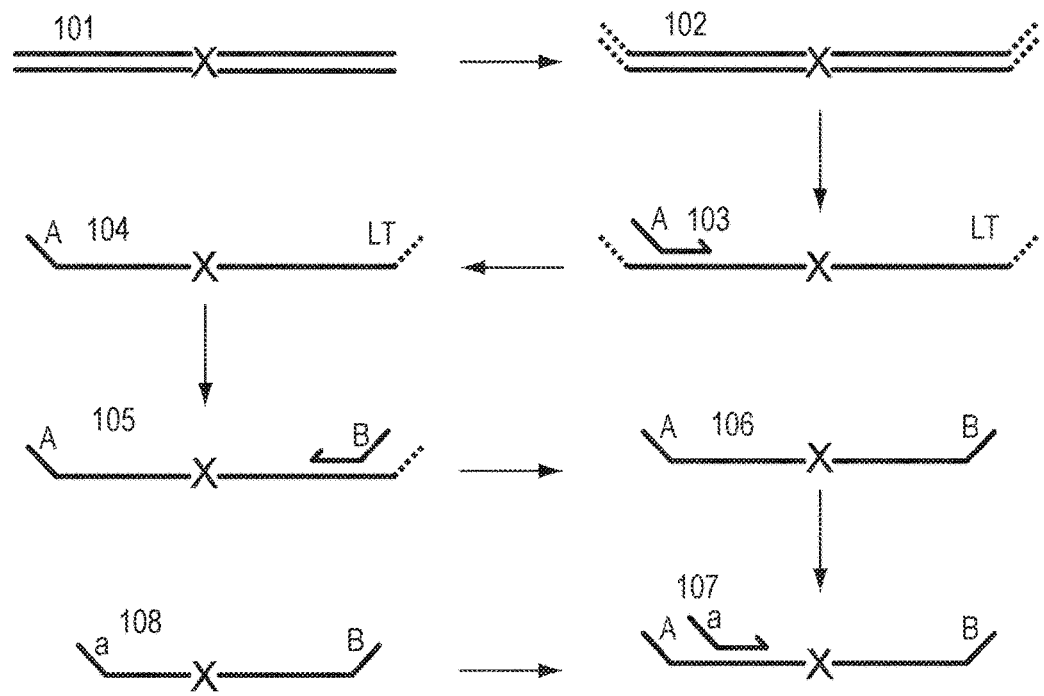
FIG. 5: Graphical representation of triply hemi-nested mini-PCR method.

Triply Hemi-Nested Mini-PCR:

(see FIG. 5) It is possible to use target DNA that has and adaptor at the fragment ends. STA is performed comprising a multiplex set of Forward primers (B) and one (or few) tag-specific Reverse primers (A) and (a). A second STA can be performed using a universal tag-specific Forward primer and target specific Reverse primer. 101 denotes double stranded DNA with a polymorphic locus of interest at X. 102 denotes the double stranded DNA with ligation adaptors added for universal amplification. 103 denotes the single stranded DNA that has been universally amplified with Reverse Primer A hybridized. 104 denotes the PCR product from 103 that was amplified using Reverse primer A and ligation adaptor tag primer LT. 105 denotes the product from 104 with Forward primer B hybridized. 106 denotes the PCR product from 105 that was amplified using Reverse primer A and Forward primer B. 107 denotes the product from 106 with Reverse primer 'a' hybridized. 108 denotes the final PCR product. Note that in this example, primers 'a' and B may be considered to be inner primers, and A may be considered to be a first primer. Optionally, both A and B may be considered to be first primers, and 'a' may be considered to be an inner primer. The designation of reverse and forward primers may be switched. In this workflow, target specific Forward and Reverse primers are used in separate reactions, thereby reducing the complexity of the reaction and preventing dimer formation of forward and reverse primers. This method is a big improvement on direct PCR as it is as good as direct PCR, but it avoids primer dimers. After first round of hemi nested protocol one typically sees ~99% non-targeted DNA, however, after second round there is typically a big improvement.

Figure 6:
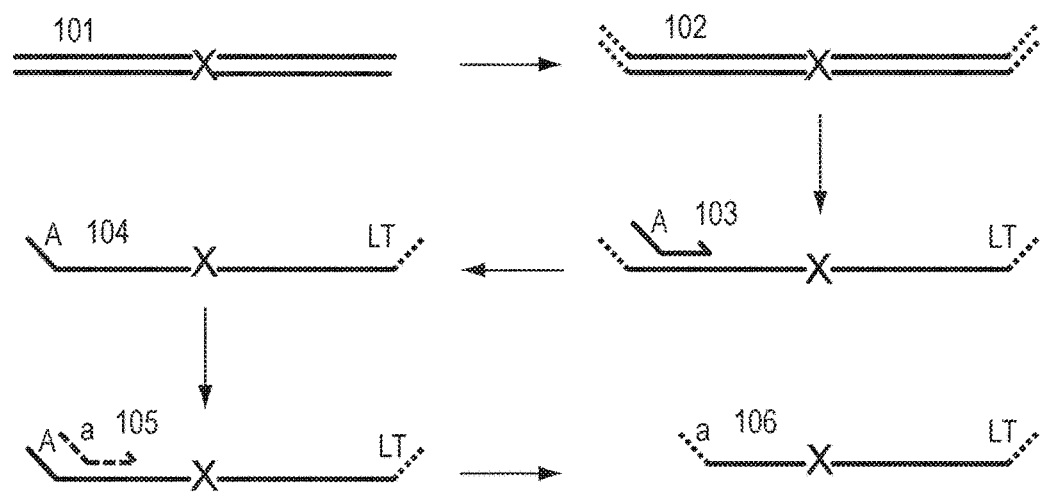
FIG. 6: Graphical representation of one-sided nested mini-PCR method.

One-Sided Nested Mini-PCR:

(see FIG. 6) It is possible to use target DNA that has an adaptor at the fragment ends. STA may also be performed with a multiplex set of nested Forward primers and using the ligation adapter tag as the Reverse primer. A second STA may then be performed using a set of nested Forward primers and a universal Reverse primer. 101 denotes double stranded DNA with a polymorphic locus of interest at X. 102 denotes the double stranded DNA with ligation adaptors added for universal amplification. 103 denotes the single stranded DNA that has been universally amplified with Forward Primer A hybridized. 104 denotes the PCR product from 103 that was amplified using Forward primer A and ligation adaptor tag Reverse primer LT. 105 denotes the product from 104 with nested Forward primer a hybridized. 106 denotes the final PCR product. This method can detect shorter target sequences than standard PCR by using overlapping primers in the first and second STAs. The method is typically performed off a sample of DNA that has already undergone STA step 1 above—appending of universal tags and amplification; the two nested primers are only on one side, the other side uses the library tag. The method was performed on libraries of apoptotic supernatants and pregnancy plasma. With this workflow around 60% of sequences mapped to the intended targets. Note that reads that contained the reverse adaptor sequence were not mapped, so this number is expected to be higher if those reads that contain the reverse adaptor sequence are mapped.

Figure 7:
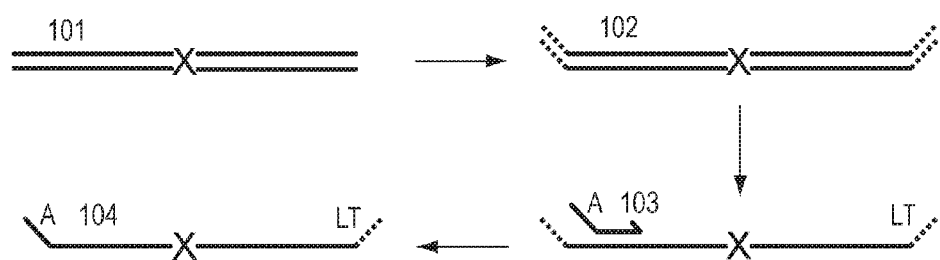
FIG. 7: Graphical representation of one-sided mini-PCR method.

One-Sided Mini-PCR:

It is possible to use target DNA that has an adaptor at the fragment ends (see FIG. 7). STA may be performed with a multiplex set of Forward primers and one (or few) tag-specific Reverse primer. 101 denotes double stranded DNA with a polymorphic locus of interest at X. 102 denotes the double stranded DNA with ligation adaptors added for universal amplification. 103 denotes the single stranded DNA with Forward Primer A hybridized. 104 denotes the PCR product from 103 that was amplified using Forward primer A and ligation adaptor tag Reverse primer LT, and which is the final PCR product. This method can detect shorter target sequences than standard PCR. However it may be relatively unspecific, as only one target specific primer is used. This protocol is effectively half of the one sided nested mini PCR.

Figure 8:
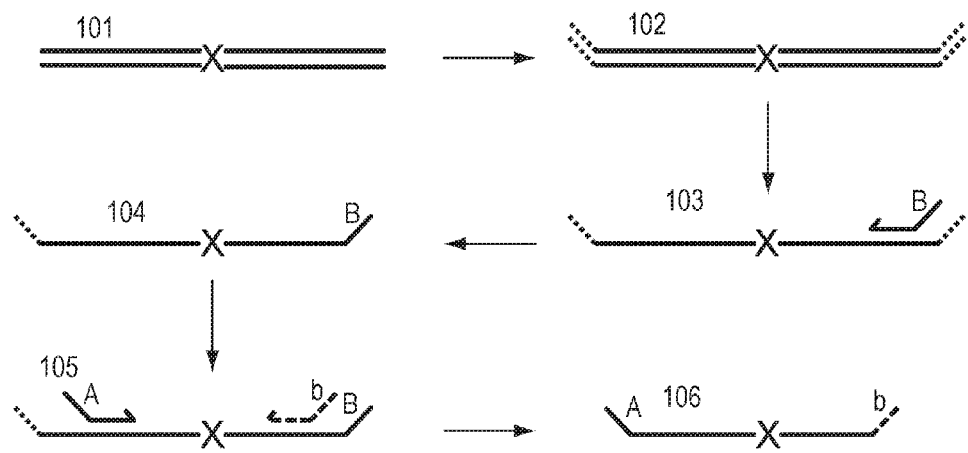
FIG. 8: Graphical representation of reverse semi-nested mini-PCR method.

Reverse Semi-Nested Mini-PCR:

It is possible to use target DNA that has an adaptor at the fragment ends (see FIG. 8). STA may be performed with a multiplex set of Forward primers and one (or few) tag-specific Reverse primer. 101 denotes double stranded DNA with a polymorphic locus of interest at X. 102 denotes the double stranded DNA with ligation adaptors added for universal amplification. 103 denotes the single stranded DNA with Reverse Primer B hybridized. 104 denotes the PCR product from 103 that was amplified using Reverse primer B and ligation adaptor tag Forward primer LT. 105 denotes the PCR product 104 with hybridized Forward Primer A, and inner Reverse primer 'b'. 106 denotes the PCR product that has been amplified from 105 using Forward primer A and Reverse primer 'b', and which is the final PCR product. This method can detect shorter target sequences than standard PCR.

There also may be more variants that are simply iterations or combinations of the above methods such as doubly nested PCR, where three sets of primers are used. Another variant is one-and-a-half sided nested mini-PCR, where STA may also be performed with a multiplex set of nested Forward primers and one (or few) tag-specific Reverse primer.

Note that in all of these variants, the identity of the Forward primer and the Reverse primer may be interchanged. Note that in some embodiments, the nested variant can equally well be run without the initial library preparation that comprises appending the adapter tags, and a universal amplification step. Note that in some embodiments, additional rounds of PCR may be included, with additional Forward and/or Reverse primers and amplification steps; these additional steps may be particularly useful if it is desirable to further increase the percent of DNA molecules that correspond to the targeted loci.

Nesting Workflows

Figure 9:
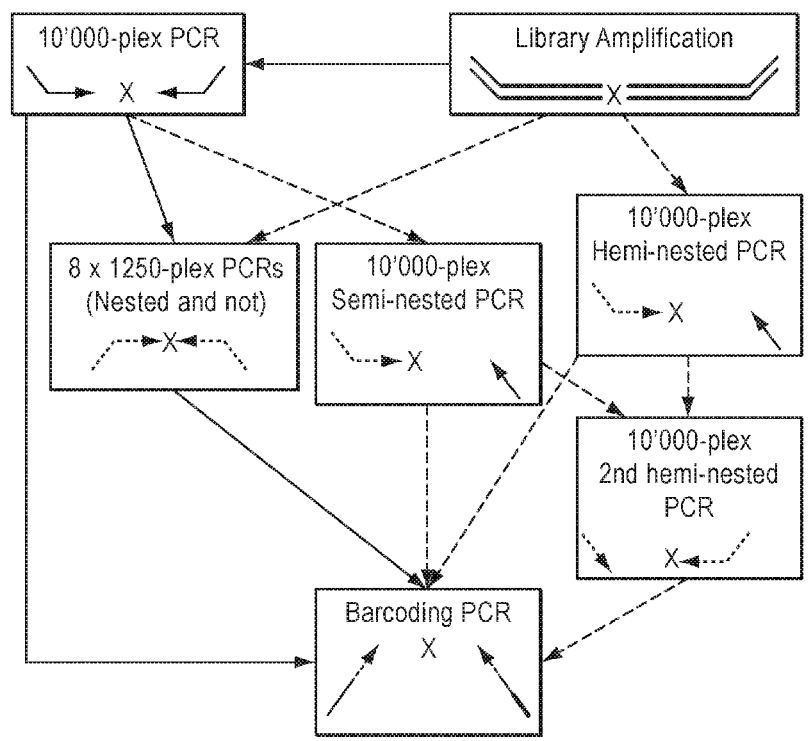
FIG. 9: Some possible workflows for semi-nested methods.

There are many ways to perform the amplification, with different degrees of nesting, and with different degrees of multiplexing. In FIG. 9, a flow chart is given with some of the possible workflows. Note that the use of 10,000-plex PCR is only meant to be an example; these flow charts would work equally well for other degrees of multiplexing.

Looped Ligation Adaptors

When adding universal tagged adaptors for example for the purpose of making a library for sequencing, there are a number of ways to ligate adaptors. One way is to blunt end the sample DNA, perform A-tailing, and ligate with adaptors that have a T-overhang. There are a number of other ways to ligate adaptors. There are also a number of adaptors that can be ligated. For example, a Y-adaptor can be used where the adaptor consists of two strands of DNA where one strand has a double strand region, and a region specified by a forward primer region, and where the other strand specified by a double strand region that is complementary to the double strand region on the first strand, and a region with a reverse primer. The double stranded region, when annealed, may contain a T-overhang for the purpose of ligating to double stranded DNA with an A overhang.

In an embodiment, the adaptor can be a loop of DNA where the terminal regions are complementary, and where the loop region contains a forward primer tagged region (LFT), a reverse primer tagged region (LRT), and a cleavage site between the two (See FIG. 10). 101 refers to the double stranded, blunt ended target DNA. 102 refers to the A-tailed target DNA. 103 refers to the looped ligation adaptor with T overhang 'T' and the cleavage site 'Z'. 104 refers to the target DNA with appended looped ligation adaptors. 105 refers to the target DNA with the ligation adaptors appended cleaved at the cleavage site. LFT refers to the ligation adaptor Forward tag, and the LRT refers to the ligation adaptor Reverse tag. The complementary region may end on a T overhang, or other feature that may be used for ligation to the target DNA. The cleavage site may be a series of uracils for cleavage by UNG, or a sequence that may be recognized and cleaved by a restriction enzyme or other method of cleavage or just a basic amplification. These adaptors can be uses for any library preparation, for example, for sequencing. These adaptors can be used in combination with any of the other methods described herein, for example the mini-PCR amplification methods.

Internally Tagged Primers

Figure 11:
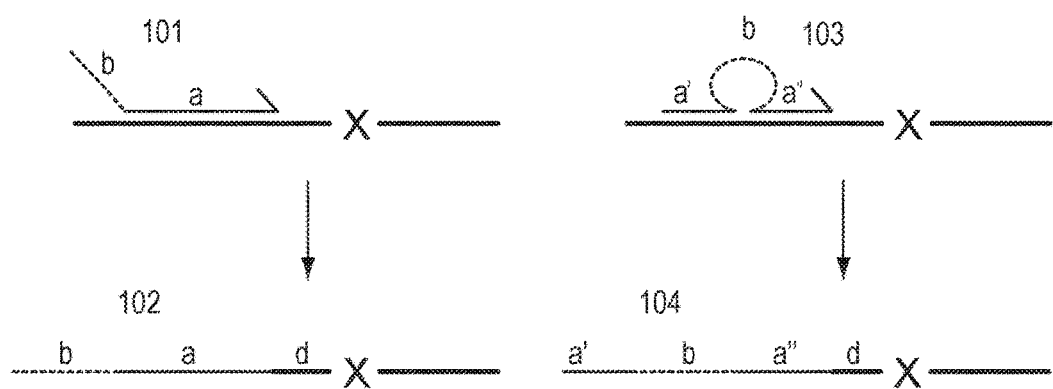
FIG. 11: Graphical representation of internally tagged primers.

When using sequencing to determine the allele present at a given polymorphic locus, the sequence read typically begins upstream of the primer binding site (a), and then to the polymorphic site (X). Tags are typically configured as shown in FIG. 11, left. 101 refers to the single stranded target DNA with polymorphic locus of interest 'X', and primer'a' with appended tag 'b'. In order to avoid nonspecific hybridization, the primer binding site (region of target DNA complementary to 'a') is typically 18 to 30 bp in length. Sequence tag 'b' is typically about 20 bp, in theory these can be any length longer than about 15 bp, though many people use the primer sequences that are sold by the sequencing platform company. The distance 'd' between 'a' and 'X' may be at least 2 bp so as to avoid allele bias. When performing multiplexed PCR amplification using the methods disclosed herein or other methods, where careful primer design is necessary to avoid excessive primer interaction, the window of allowable distance 'd' between 'a' and 'X' may vary quite a bit: from 2 bp to 10 bp, from 2 bp to 20 bp, from 2 bp to 30 bp, or even from 2 bp to more than 30 bp. Therefore, when using the primer configuration shown in FIG. 11, left, sequence reads must be a minimum of 40 bp to obtain reads long enough to measure the polymorphic locus, and depending on the lengths of 'a' and 'd' the sequence reads may need to be up to 60 or 75 bp. Usually, the longer the sequence reads, the higher the cost and time of sequencing a given number of reads, therefore, minimizing the necessary read length can save both time and money. In addition, since, on average, bases read earlier on the read are read more accurately than those read later on the read, decreasing the necessary sequence read length can also increase the accuracy of the measurements of the polymorphic region.

In an embodiment, termed internally tagged primers, the primer binding site (a) is split in to a plurality of segments (a', a'', a''' . . . ), and the sequence tag (b) is on a segment of DNA that is in the middle of two of the primer binding sites, as shown in FIG. 11, 103. This configuration allows the sequencer to make shorter sequence reads. In an embodiment, a'+a'' should be at least about 18 bp, and can be as long as 30, 40, 50, 60, 80, 100 or more than 100 bp. In an embodiment, a'' should be at least about 6 bp, and in an embodiment is between about 8 and 16 bp. All other factors being equal, using the internally tagged primers can cut the length of the sequence reads needed by at least 6 bp, as much as 8 bp, 10 bp, 12 bp, 15 bp, and even by as many as 20 or 30 bp. This can result in a significant money, time and accuracy advantage. An example of internally tagged primers is given in FIG. 12.

Primers with Ligation Adaptor Binding Region

Figure 10:
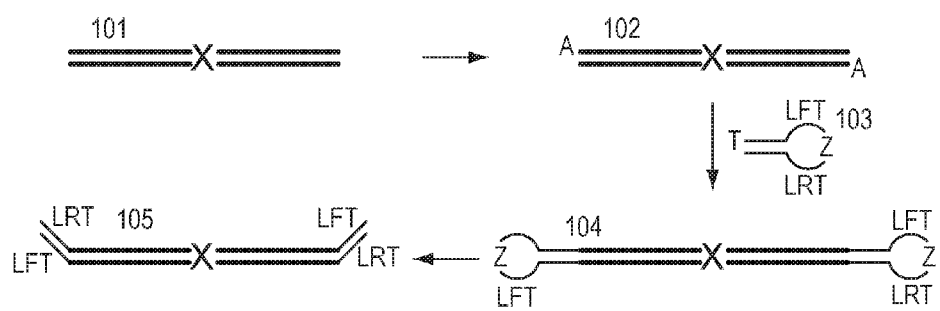
FIG. 10: Graphical representation of looped ligation adaptors.
Figure 13:
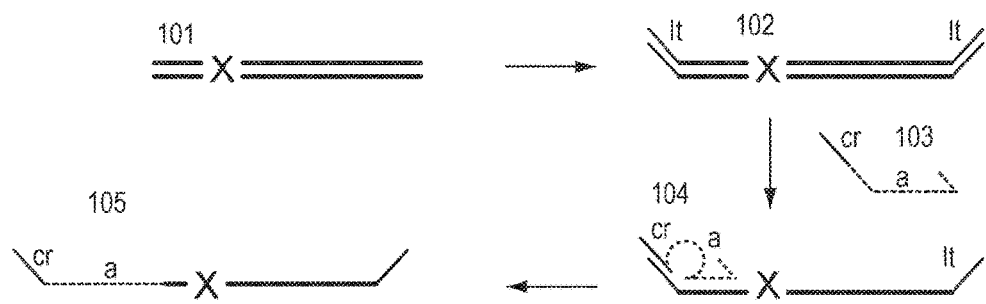
FIG. 13: Graphical representation of a method using primers with a ligation adaptor binding region.

One issue with fragmented DNA is that since it is short in length, the chance that a polymorphism is close to the end of a DNA strand is higher than for a long strand (e.g. 101, FIG. 10). Since PCR capture of a polymorphism requires a primer binding site of suitable length on both sides of the polymorphism, a significant number of strands of DNA with the targeted polymorphism will be missed due to insufficient overlap between the primer and the targeted binding site. In an embodiment, the target DNA 101 can have ligation adaptors appended 102, and the target primer 103 can have a region (cr) that is complementary to the ligation adaptor tag (lt) appended upstream of the designed binding region (a) (see FIG. 13); thus in cases where the binding region (region of 101 that is complementary to a) is shorter than the 18 bp typically required for hybridization, the region (cr) on the primer than is complementary to the library tag is able to increase the binding energy to a point where the PCR can proceed. Note that any specificity that is lost due to a shorter binding region can be made up for by other PCR primers with suitably long target binding regions. Note that this embodiment can be used in combination with direct PCR, or any of the other methods described herein, such as nested PCR, semi nested PCR, hemi nested PCR, one sided nested or semi or hemi nested PCR, or other PCR protocols.

When using the sequencing data to determine ploidy in combination with an analytical method that involves comparing the observed allele data to the expected allele distributions for various hypotheses, each additional read from alleles with a low depth of read will yield more information than a read from an allele with a high depth of read. Therefore, ideally, one would wish to see uniform depth of read (DOR) where each locus will have a similar number of representative sequence reads. Therefore, it is desirable to minimize the DOR variance. In an embodiment, it is possible to decrease the coefficient of variance of the DOR (this may be defined as the standard deviation of the DOR/the average DOR) by increasing the annealing times. In some embodiments the annealing temperatures may be longer than 2 minutes, longer than 4 minutes, longer than ten minutes, longer than 30 minutes, and longer than one hour, or even longer. Since annealing is an equilibrium process, there is no limit to the improvement of DOR variance with increasing annealing times. In an embodiment, increasing the primer concentration may decrease the DOR variance.

Exemplary Amplification Methods

Improved PCR amplification methods have also been developed that minimize or prevent interference due to the amplification of nearby or adjacent target loci in the same reaction volume (such as part of the sample multiplex PCR reaction that simultaneously amplifies all the target loci) (see, U.S. Ser. No. 61/982,245, filed Apr. 21, 2014; U.S. Ser. No. 61/987,407, filed May 1, 2014, and U.S. Ser. No. 62/066,514, filed Oct. 21, 2014, which are each hereby incorporated by reference in its entirety). These methods can be used to simultaneously amplify nearby or adjacent target loci, which is faster and cheaper than having to separate nearby target loci into different reaction volumes so that they can be amplified separately to avoid interference. In particular embodiments, these methods are used to tile a region such that the amplicons include all the nucleotides in the region (such as an exon or all the exons of a gene such as cystic fibrosis).

In some embodiments, the amplification of target loci is performed using a polymerase (e.g., a DNA polymerase, RNA polymerase, or reverse transcriptase) with low 5'→3' exonuclease and/or low strand displacement activity. In some embodiments, the low level of 5'→3' exonuclease reduces or prevents the degradation of a nearby primer (e.g., an unextended primer or a primer that has had one or more nucleotides added to during primer extension). In some embodiments, the low level of strand displacement activity reduces or prevents the displacement of a nearby primer (e.g., an unextended primer or a primer that has had one or more nucleotides added to it during primer extension). In some embodiments, target loci that are adjacent to each other (e.g., no bases between the target loci) or nearby (e.g., loci are within 50, 40, 30, 20, 15, 10, 9, 8, 7, 6, 5, 4, 3, 2, or 1 base) are amplified. In some embodiments, the 3' end of one locus is within 50, 40, 30, 20, 15, 10, 9, 8, 7, 6, 5, 4, 3, 2, or 1 base of the 5' end of next downstream locus.

In some embodiments, at least 100, 200, 500, 750, 1,000; 2,000; 5,000; 7,500; 10,000; 15,000; 19,000; 20,000; 25,000; 27,000; 28,000; 30,000; 40,000; 50,000; 75,000; or 100,000 different target loci are amplified, such as by the simultaneous amplification in one reaction volume. In some embodiments, at least 50, 60, 70, 80, 90, 95, 96, 97, 98, 99, or 99.5% of the amplified products are target amplicons. In various embodiments, the amount of amplified products that are target amplicons is between 50 to 99.5%, such as between 60 to 99%, 70 to 98%, 80 to 98%, 90 to 99.5%, or 95 to 99.5%, inclusive. In some embodiments, at least 50, 60, 70, 80, 90, 95, 96, 97, 98, 99, or 99.5% of the target loci are amplified (e.g. amplified at least 5, 10, 20, 30, 50, or 100-fold compared to the amount prior to amplification), such as by the simultaneous amplification in one reaction volume. In various embodiments, the amount target loci that are amplified (e.g., amplified at least 5, 10, 20, 30, 50, or 100-fold compared to the amount prior to amplification) is between 50 to 99.5%, such as between 60 to 99%, 70 to 98%, 80 to 99%, 90 to 99.5%, 95 to 99.9%, or 98 to 99.99% inclusive. In some embodiments, fewer non-target amplicons are produced, such as fewer amplicons formed from a forward primer from a first primer pair and a reverse primer from a second primer pair. Such undesired non-target amplicons can be produced using prior amplification methods if, e.g., the reverse primer from the first primer pair and/or the forward primer from the second primer pair are degraded and/or displaced.

In some embodiments, these methods allow longer extension times to be used since the polymerase bound to a primer being extended is less likely to degrade and/or displace a nearby primer (such as the next downstream primer) given the low 5'→3' exonuclease and/or low strand displacement activity of the polymerase. In various embodiments, reaction conditions (such as the extension time and temperature) are used such that the extension rate of the polymerase allows the number of nucleotides that are added to a primer being extended to be equal to or greater than 80, 90, 95, 100, 110, 120, 130, 140, 150, 175, or 200% of the number of nucleotides between the 3' end of the primer binding site and the 5' end of the next downstream primer binding site on the same strand.

In some embodiments, a DNA polymerase is used produce DNA amplicons using DNA as a template. In some embodiments, a RNA polymerase is used produce RNA amplicons using DNA as a template. In some embodiments, a reverse transcriptase is used produce cDNA amplicons using RNA as a template.

In some embodiments, the low level of 5'→3' exonuclease of the polymerase is less than 80, 70, 60, 50, 40, 30, 20, 10, 5, 1, or 0.1% of the activity of the same amount of Thermas aquaticus polymerase ("Taq" polymerase, which is a commonly used DNA polymerase from a thermophilic bacterium, PDB IBGX, EC 2.7.7.7, Murali et al, "Crystal structure of Taq DNA polymerase in complex with an inhibitory Fab: the Fab is directed against an intermediate in the helix-coil dynamics of the enzyme," Proc. Natl. Acad Sci. USA 95:12562-12567, 1998, which is hereby incorporated by reference in its entirety) under the same conditions. In some embodiments, the low level of strand displacement activity of the polymerase is less than 80, 70, 60, 50, 40, 30, 20, 10, 5, 1, or 0.1% of the activity of the same amount of Taq polymerase under the same conditions.

In some embodiments, the polymerase is a PUSHION DNA polymerase, such as PHUSION High Fidelity DNA polymerase (M0530S, New England BioLabs, Inc.) or PHUSION Hot Start Flex DNA polymerase (M0535S, New England BioLabs, Inc.; Frey and Suppman *Bio Chemica.* 2:34-35, 1995; Chester and Marshak *Analytical Biochemistry.* 209:284-290, 1993, which are each hereby incorporated by reference in its entirety). The PHUSION DNA polymerase is a *Pyrococcus*-like enzyme fused with a processivity-enhancing domain. PHUSION DNA polymerase possesses 5'→3' polymerase activity and 3'→5' exonuclease activity, and generates blunt-ended products. PHUSION DNA polymerase lacks 5'→3' exonuclease activity and strand displacement activity.

In some embodiments, the polymerase is a Q5® DNA Polymerase, such as Q5® High-Fidelity DNA Polymerase (M0491S, New England BioLabs, Inc.) or Q5® Hot Start High-Fidelity DNA Polymerase (M0493S, New England BioLabs, Inc.). Q5® High-Fidelity DNA polymerase is a high-fidelity, thermostable, DNA polymerase with 3'→5' exonuclease activity, fused to a processivity-enhancing Sso7d domain. Q5@ High-Fidelity DNA polymerase lacks 5'→3' exonuclease activity and strand displacement activity.

In some embodiments, the polymerase is a T4 DNA polymerase (M0203S, New England BioLabs, Inc., Tabor and Struh. (1989). "DNA-Dependent DNA Polymerases," In Ausebel et al (Ed.), *Current Protocols in Molecular Biology.* 3.5.10-3.5.12. New York. John Wiley & Sons, Inc., 1989; Sambrook et al. *Molecular Cloning: A Laboratory Manual.* (2nd ed.), 5.44-5.47 Cold Spring Harbor Cold Spring Harbor Laboratory Press, 1989, which are each hereby incorporated by reference in its entirety). T4 DNA Polymerase catalyzes the synthesis of DNA in the 5'→3' direction and requires the presence of template and primer. This enzyme has a 3'→5' exonuclease activity which is much more active than that found in DNA Polymerase I. T4 DNA polymerase lacks 5'→3' exonuclease activity and strand displacement activity.

In some embodiments, the polymerase is a Sulfolobus DNA Polymerase IV (M0327S, New England BioLabs, Inc.; (Boudsocq, et al. (2001). *Nucleic Acids Res.,* 29:4607-4616, 2001; McDonald, et al. (2006). *Nucleic Acids Res.,* 34:1102-1111, 2006, which are each hereby incorporated by reference in its entirety). Sulfolobus DNA Polymerase IV is a thermostable Y-family lesion-bypass DNA Polymerase that efficiently synthesizes DNA across a variety of DNA template lesions McDonald, J. P. et al. (2006) *Nucleic Acids Res.,* 34, 1102-1111, which is hereby incorporated by reference in its entirety). Sulfolobus DNA Polymerase IV lacks 5'→3' exonuclease activity and strand displacement activity.

In some embodiments, if a primer binds a region with a SNP, the primer may bind and amplify the different alleles with different efficiencies or may only bind and amplify one allele. For subjects who are heterozygous, one of the alleles may not be amplified by the primer. In some embodiments, a primer is designed for each allele. For example, if there are two alleles (e.g., a biallelic SNP), then two primers can be used to bind the same location of a target locus (e.g., a forward primer to bind the "A" allele and a forward primer to bind the "B" allele). Standard methods, such as the dbSNP database, can be used to determine the location of known SNPs, such as SNP hot spots that have a high heterozygosity rate.

In some embodiments, the amplicons are similar in size. In some embodiments, the range of the length of the target amplicons is less than 100, 75, 50, 25, 15, 10, or 5 nucleotides. In some embodiments (such as the amplification of target loci in fragmented DNA or RNA), the length of the target amplicons is between 50 and 100 nucleotides, such as between 60 and 80 nucleotides, or 60 and 75 nucleotides, inclusive. In some embodiments (such as the amplification of multiple target loci throughout an exon or gene), the length of the target amplicons is between 100 and 500 nucleotides, such as between 150 and 450 nucleotides, 200 and 400 nucleotides, 200 and 300 nucleotides, or 300 and 400 nucleotides, inclusive.

In some embodiments, multiple target loci are simultaneously amplified using a primer pair that includes a forward and reverse primer for each target locus to be amplified in that reaction volume. In some embodiments, one round of PCR is performed with a single primer per target locus, and then a second round of PCR is performed with a primer pair per target locus. For example, the first round of PCR may be performed with a single primer per target locus such that all the primers bind the same strand (such as using a forward primer for each target locus). This allows the PCR to amplify in a linear manner and reduces or eliminates amplification bias between amplicons due to sequence or length differences. In some embodiments, the amplicons are then amplified using a forward and reverse primer for each target locus.

Exemplary Whole Genome Amplification Methods

In some embodiments, a method of the present disclosure may involve amplifying DNA, such as the use of whole genome application to amplify a nucleic acid sample before amplifying just the target loci. Amplification of the DNA, a process which transforms a small amount of genetic material to a larger amount of genetic material that comprises a similar set of genetic data, can be done by a wide variety of methods, including, but not limited to polymerase chain reaction (PCR). One method of amplifying DNA is whole genome amplification (WGA). There are a number of methods available for WGA: ligation-mediated PCR (LM-PCR), degenerate oligonucleotide primer PCR (DOP-PCR), and multiple displacement amplification (MDA). In LM-PCR, short DNA sequences called adapters are ligated to blunt ends of DNA. These adapters contain universal amplification sequences, which are used to amplify the DNA by PCR. In DOP-PCR, random primers that also contain universal amplification sequences are used in a first round of annealing and PCR. Then, a second round of PCR is used to amplify the sequences further with the universal primer sequences. MDA uses the phi-29 polymerase, which is a highly processive and non-specific enzyme that replicates DNA and has been used for single-cell analysis. The major limitations to amplification of material from a single cell are (1) necessity of using extremely dilute DNA concentrations or extremely small volume of reaction mixture, and (2) difficulty of reliably dissociating DNA from proteins across the whole genome. Regardless, single-cell whole genome amplification has been used successfully for a variety of applications for a number of years. There are other methods of amplifying DNA from a sample of DNA. The DNA amplification transforms the initial sample of DNA into a sample of DNA that is similar in the set of sequences, but of much greater quantity. In some cases, amplification may not be required.

In some embodiments. DNA may be amplified using a universal amplification, such as WGA or MDA. In some embodiments. DNA may be amplified by targeted amplification, for example using targeted PCR, or circularizing probes. In some embodiments, the DNA may be preferentially enriched using a targeted amplification method, or a method that results in the full or partial separation of desired from undesired DNA, such as capture by hybridization approaches. In some embodiments, DNA may be amplified by using a combination of a universal amplification method and a preferential enrichment method. A fuller description of some of these methods can be found elsewhere in this document.

Exemplary Enrichment and Sequencing Methods

In an embodiment, a method disclosed herein uses selective enrichment techniques that preserve the relative allele frequencies that are present in the original sample of DNA at each target loci (e.g., each polymorphic locus) from a set of target loci (e.g., polymorphic loci). While enrichment is particularly advantageous for methods for analyzing polymorphic loci, these enrichment methods can be readily adapted for nonpolymorphic loci if desired. In some embodiments the amplification and/or selective enrichment technique may involve PCR such as ligation mediated PCR, fragment capture by hybridization, Molecular Inversion Probes, or other circularizing probes. In some embodiments, methods for amplification or selective enrichment may involve using probes where, upon correct hybridization to the target sequence, the 3-prime end or 5-prime end of a nucleotide probe is separated from the polymorphic site of the allele by a small number of nucleotides. This separation reduces preferential amplification of one allele, termed allele bias. This is an improvement over methods that involve using probes where the 3-prime end or 5-prime end of a correctly hybridized probe are directly adjacent to or very near to the polymorphic site of an allele. In an embodiment, probes in which the hybridizing region may or certainly contains a polymorphic site are excluded. Polymorphic sites at the site of hybridization can cause unequal hybridization or inhibit hybridization altogether in some alleles, resulting in preferential amplification of certain alleles. These embodiments are improvements over other methods that involve targeted amplification and/or selective enrichment in that they better preserve the original allele frequencies of the sample at each polymorphic locus, whether the sample is pure genomic sample from a single individual or mixture of individuals.

The use of a technique to enrich a sample of DNA at a set of target loci followed by sequencing as part of a method for non-invasive prenatal allele calling or ploidy calling may confer a number of unexpected advantages. In some embodiments of the present disclosure, the method involves measuring genetic data for use with an informatics based method, such as PARENTAL SUPPORT™ (PS). The ultimate outcome of some of the embodiments is the actionable genetic data of an embryo or a fetus. There are many methods that may be used to measure the genetic data of the individual and/or the related individuals as part of embodied methods. In an embodiment, a method for enriching the concentration of a set of targeted alleles is disclosed herein, the method comprising one or more of the following steps: targeted amplification of genetic material, addition of loci specific oligonucleotide probes, ligation of specified DNA strands, isolation of sets of desired DNA, removal of unwanted components of a reaction, detection of certain sequences of DNA by hybridization, and detection of the sequence of one or a plurality of strands of DNA by DNA sequencing methods. In some cases the DNA strands may refer to target genetic material, in some cases they may refer to primers, in some cases they may refer to synthesized sequences, or combinations thereof. These steps may be carried out in a number of different orders.

For example, a universal amplification step of the DNA prior to targeted amplification may confer several advantages, such as removing the risk of bottlenecking and reducing allelic bias. The DNA may be mixed an oligonucleotide probe that can hybridize with two neighboring regions of the target sequence, one on either side. After hybridization, the ends of the probe may be connected by adding a polymerase, a means for ligation, and any necessary reagents to allow the circularization of the probe. After circularization, an exonuclease may be added to digest to non-circularized genetic material, followed by detection of the circularized probe. The DNA may be mixed with PCR primers that can hybridize with two neighboring regions of the target sequence, one on either side. After hybridization, the ends of the probe may be connected by adding a polymerase, a means for ligation, and any necessary reagents to complete PCR amplification. Amplified or unamplified DNA may be targeted by hybrid capture probes that target a set of loci, after hybridization, the probe may be localized and separated from the mixture to provide a mixture of DNA that is enriched in target sequences.

The use of a method to target certain loci followed by sequencing as part of a method for allele calling or ploidy calling may confer a number of unexpected advantages. Some methods by which DNA may be targeted, or preferentially enriched, include using circularizing probes, linked inverted probes (LIPs, MIPs), capture by hybridization methods such as SURESELECT, and targeted PCR or ligation-mediated PCR amplification strategies.

In some embodiments, a method of the present disclosure involves measuring genetic data for use with an informatics based method, such as PARENTAL SUPPORT™ (PS), which is described further herein. PARENTAL SUPPORT™ is an informatics based approach to manipulating genetic data, aspects of which are described herein. The ultimate outcome of some of the embodiments is the actionable genetic data of an embryo or a fetus followed by a clinical decision based on the actionable data. The algorithms behind the PS method take the measured genetic data of the target individual, often an embryo or fetus, and the measured genetic data from related individuals, and are able to increase the accuracy with which the genetic state of the target individual is known. In an embodiment, the measured genetic data is used in the context of making ploidy determinations during prenatal genetic diagnosis. In an embodiment, the measured genetic data is used in the context of making ploidy determinations or allele calls on embryos during in vitro fertilization. There are many methods that may be used to measure the genetic data of the individual and/or the related individuals in the aforementioned contexts. The different methods comprise a number of steps, those steps often involving amplification of genetic material, addition of oligonucleotide probes, ligation of specified DNA strands, isolation of sets of desired DNA, removal of unwanted components of a reaction, detection of certain sequences of DNA by hybridization, detection of the sequence of one or a plurality of strands of DNA by DNA sequencing methods. In some cases the DNA strands may refer to target genetic material, in some cases they may refer to primers, in some cases they may refer to synthesized sequences, or combinations thereof. These steps may be carried out in a number of different orders.

Note that in theory it is possible to target any number loci in the genome, anywhere from one loci to well over one million loci. If a sample of DNA is subjected to targeting, and then sequenced, the percentage of the alleles that are read by the sequencer will be enriched with respect to their natural abundance in the sample. The degree of enrichment can be anywhere from one percent (or even less) to ten-fold, a hundred-fold, a thousand-fold or even many million-fold. In the human genome there are roughly 3 billion base pairs, and nucleotides, comprising approximately 75 million polymorphic loci. The more loci that are targeted, the smaller the degree of enrichment is possible. The fewer the number of loci that are targeted, the greater degree of enrichment is possible, and the greater depth of read may be achieved at those loci for a given number of sequence reads.

In an embodiment of the present disclosure, the targeting or preferential may focus entirely on SNPs. In an embodiment, the targeting or preferential may focus on any polymorphic site. A number of commercial targeting products are available to enrich exons. Surprisingly, targeting exclusively SNPs, or exclusively polymorphic loci, is particularly advantageous when using a method for NPD that relies on allele distributions. There are also published methods for NPD using sequencing, for example U.S. Pat. No. 7,888,017, involving a read count analysis where the read counting focuses on counting the number of reads that map to a given chromosome, where the analyzed sequence reads do not focus on regions of the genome that are polymorphic. Those types of methodology that do not focus on polymorphic alleles would not benefit as much from targeting or preferential enrichment of a set of alleles.

In an embodiment of the present disclosure, it is possible to use a targeting method that focuses on SNPs to enrich a genetic sample in polymorphic regions of the genome. In an embodiment, it is possible to focus on a small number of SNPs, for example between 1 and 100 SNPs, or a larger number, for example, between 100 and 1,000, between 1,000 and 10,000, between 10,000 and 100,000 or more than 100,000 SNPs. In an embodiment, it is possible to focus on one or a small number of chromosomes that are correlated with live trisomic births, for example chromosomes 13, 18, 21, X and Y, or some combination thereof. In an embodiment, it is possible to enrich the targeted SNPs by a small factor, for example between 1.01 fold and 100 fold, or by a larger factor, for example between 100 fold and 1,000,000 fold, or even by more than 1,000,000 fold. In an embodiment of the present disclosure, it is possible to use a targeting method to create a sample of DNA that is preferentially enriched in polymorphic regions of the genome. In an embodiment, it is possible to use this method to create a mixture of DNA with any of these characteristics where the mixture of DNA contains maternal DNA and also free floating fetal DNA. In an embodiment, it is possible to use this method to create a mixture of DNA that has any combination of these factors. For example, the method described herein may be used to produce a mixture of DNA that comprises maternal DNA and fetal DNA, and that is preferentially enriched in DNA that corresponds to 200 SNPs, all of which are located on either chromosome 18 or 21, and which are enriched an average of 1000 fold. In another example, it is possible to use the method to create a mixture of DNA that is preferentially enriched in 10,000 SNPs that are all or mostly located on chromosomes 13, 18, 21, X and Y, and the average enrichment per loci is greater than 500 fold. Any of the targeting methods described herein can be used to create mixtures of DNA that are preferentially enriched in certain loci.

In some embodiments, a method of the present disclosure further includes measuring the DNA in the mixed fraction using a high throughput DNA sequencer, where the DNA in the mixed fraction contains a disproportionate number of sequences from one or more chromosomes, wherein the one or more chromosomes are taken from the group comprising chromosome 13, chromosome 18, chromosome 21, chromosome X, chromosome Y and combinations thereof.

Described herein are three methods: multiplex PCR, targeted capture by hybridization, and linked inverted probes (LIPs), which may be used to obtain and analyze measurements from a sufficient number of polymorphic loci from a maternal plasma sample in order to detect fetal aneuploidy, this is not meant to exclude other methods of selective enrichment of targeted loci. Other methods may equally well be used without changing the essence of the method. In each case the polymorphism assayed may include single nucleotide polymorphisms (SNPs), small indels, or STRs. A preferred method involves the use of SNPs. Each approach produces allele frequency data, allele frequency data for each targeted locus and/or the joint allele frequency distributions from these loci may be analyzed to determine the ploidy of the fetus. Each approach has its own considerations due to the limited source material and the fact that maternal plasma consists of mixture of maternal and fetal DNA. This method may be combined with other approaches to provide a more accurate determination. In an embodiment, this method may be combined with a sequence counting approach such as that described in U.S. Pat. No. 7,888,017. The approaches described could also be used to detect fetal paternity noninvasively from maternal plasma samples. In addition each approach may be applied to other mixtures of DNA or pure DNA samples to detect the presence or absence of aneuploid chromosomes, to genotype a large number of SNP from degraded DNA samples, to detect segmental copy number variations (CNVs), to detect other genotypic states of interest, or some combination thereof.

Accurately Measuring the Allelic Distributions in a Sample

Current sequencing approaches can be used to estimate the distribution of alleles in a sample. One such method involves randomly sampling sequences from a pool DNA, termed shotgun sequencing. The proportion of a particular allele in the sequencing data is typically very low and can be determined by simple statistics. The human genome contains approximately 3 billion base pairs. So, if the sequencing method used make 100 bp reads, a particular allele will be measured about once in every 30 million sequence reads.

In an embodiment, a method of the present disclosure is used to determine the presence or absence of two or more different haplotypes that contain the same set of loci in a sample of DNA from the measured allele distributions of loci from that chromosome. The different haplotypes could represent two different homologous chromosomes from one individual, three different homologous chromosomes from a trisomic individual, three different homologous haplotypes from a mother and a fetus where one of the haplotypes is shared between the mother and the fetus, three or four haplotypes from a mother and fetus where one or two of the haplotypes are shared between the mother and the fetus, or other combinations. Alleles that are polymorphic between the haplotypes tend to be more informative, however any alleles where the mother and father are not both homozygous for the same allele will yield useful information through measured allele distributions beyond the information that is available from simple read count analysis.

Shotgun sequencing of such a sample, however, is extremely inefficient as it results in many sequences for regions that are not polymorphic between the different haplotypes in the sample, or are for chromosomes that are not of interest, and therefore reveal no information about the proportion of the target haplotypes. Described herein are methods that specifically target and/or preferentially enrich segments of DNA in the sample that are more likely to be polymorphic in the genome to increase the yield of allelic information obtained by sequencing. Note that for the measured allele distributions in an enriched sample to be truly representative of the actual amounts present in the target individual, it is critical that there is little or no preferential enrichment of one allele as compared to the other allele at a given loci in the targeted segments. Current methods known in the art to target polymorphic alleles are designed to ensure that at least some of any alleles present are detected. However, these methods were not designed for the purpose of measuring the unbiased allelic distributions of polymorphic alleles present in the original mixture. It is non-obvious that any particular method of target enrichment would be able to produce an enriched sample wherein the measured allele distributions would accurately represent the allele distributions present in the original unamplified sample better than any other method. While many enrichment methods may be expected, in theory, to accomplish such an aim, an ordinary person skilled in the art is well aware that there is a great deal of stochastic or deterministic bias in current amplification, targeting and other preferential enrichment methods. One embodiment of a method described herein allows a plurality of alleles found in a mixture of DNA that correspond to a given locus in the genome to be amplified, or preferentially enriched in a way that the degree of enrichment of each of the alleles is nearly the same. Another way to say this is that the method allows the relative quantity of the alleles present in the mixture as a whole to be increased, while the ratio between the alleles that correspond to each locus remains essentially the same as they were in the original mixture of DNA. For some reported methods, preferential enrichment of loci can result in allelic biases of more than 1%, more than 2%, more than 5% and even more than 10%. This preferential enrichment may be due to capture bias when using a capture by hybridization approach, or amplification bias which may be small for each cycle, but can become large when compounded over 20, 30 or 40 cycles. For the purposes of this disclosure, for the ratio to remain essentially the same means that the ratio of the alleles in the original mixture divided by the ratio of the alleles in the resulting mixture is between 0.95 and 1.05, between 0.98 and 1.02, between 0.99 and 1.01, between 0.995 and 1.005, between 0.998 and 1.002, between 0.999 and 1.001, or between 0.9999 and 1.0001. Note that the calculation of the allele ratios presented here may not be used in the determination of the ploidy state of the target individual, and may only a metric to be used to measure allelic bias.

In an embodiment, once a mixture has been preferentially enriched at the set of target loci, it may be sequenced using any one of the previous, current, or next generation of sequencing instruments that sequences a clonal sample (a sample generated from a single molecule; examples include ILLUMINA GAIIx, ILLUMINA HiSeq, LIFE TECHNOLOGIES SOLiD, 5500XL). The ratios can be evaluated by sequencing through the specific alleles within the targeted region. These sequencing reads can be analyzed and counted according the allele type and the rations of different alleles determined accordingly. For variations that are one to a few bases in length, detection of the alleles will be performed by sequencing and it is essential that the sequencing read span the allele in question in order to evaluate the allelic composition of that captured molecule. The total number of captured molecules assayed for the genotype can be increased by increasing the length of the sequencing read. Full sequencing of all molecules would guarantee collection of the maximum amount of data available in the enriched pool. However, sequencing is currently expensive, and a method that can measure allele distributions using a lower number of sequence reads will have great value. In addition, there are technical limitations to the maximum possible length of read as well as accuracy limitations as read lengths increase. The alleles of greatest utility will be of one to a few bases in length, but theoretically any allele shorter than the length of the sequencing read can be used. While allele variations come in all types, the examples provided herein focus on SNPs or variants contained of just a few neighboring base pairs. Larger variants such as segmental copy number variants can be detected by aggregations of these smaller variations in many cases as whole collections of SNP internal to the segment are duplicated. Variants larger than a few bases, such as STRs require special consideration and some targeting approaches work while others will not.

There are multiple targeting approaches that can be used to specifically isolate and enrich a one or a plurality of variant positions in the genome. Typically, these rely on taking advantage of the invariant sequence flanking the variant sequence. There are reports by others related to targeting in the context of sequencing where the substrate is maternal plasma (see, e.g., Liao et al., Clin. Chem. 2011; 57(1): pp. 92-101). However, these approaches use targeting probes that target exons, and do not focus on targeting polymorphic regions of the genome. In an embodiment, a method of the present disclosure involves using targeting probes that focus exclusively or almost exclusively on polymorphic regions. In an embodiment, a method of the present disclosure involves using targeting probes that focus exclusively or almost exclusively on SNPs. In some embodiments of the present disclosure, the targeted polymorphic sites consist of at least 10% SNPs, at least 20% SNPs, at least 30% SNPs, at least 40% SNPs, at least 50% SNPs, at least 60% SNPs, at least 70% SNPs, at least 80% SNPs, at least 90% SNPs, at least 95% SNPs, at least 98%. SNPs, at least 99% SNPs, at least 99.9% SNPs, or exclusively SNPs.

In an embodiment, a method of the present disclosure can be used to determine genotypes (base composition of the DNA at specific loci) and relative proportions of those genotypes from a mixture of DNA molecules, where those DNA molecules may have originated from one or a number of genetically distinct individuals. In an embodiment, a method of the present disclosure can be used to determine the genotypes at a set of polymorphic loci, and the relative ratios of the amount of different alleles present at those loci. In an embodiment the polymorphic loci may consist entirely of SNPs. In an embodiment, the polymorphic loci can comprise SNPs, single tandem repeats, and other polymorphisms. In an embodiment, a method of the present disclosure can be used to determine the relative distributions of alleles at a set of polymorphic loci in a mixture of DNA, where the mixture of DNA comprises DNA that originates from a mother, and DNA that originates from a fetus. In an embodiment, the joint allele distributions can be determined on a mixture of DNA isolated from blood from a pregnant woman. In an embodiment, the allele distributions at a set of loci can be used to determine the ploidy state of one or more chromosomes on a gestating fetus.

In an embodiment, the mixture of DNA molecules could be derived from DNA extracted from multiple cells of one individual. In an embodiment, the original collection of cells from which the DNA is derived may comprise a mixture of diploid or haploid cells of the same or of different genotypes, if that individual is mosaic (germline or somatic). In an embodiment, the mixture of DNA molecules could also be derived from DNA extracted from single cells. In an embodiment, the mixture of DNA molecules could also be derived from DNA extracted from mixture of two or more cells of the same individual, or of different individuals. In an embodiment, the mixture of DNA molecules could be derived from DNA isolated from biological material that has already liberated from cells such as blood plasma, which is known to contain cell free DNA. In an embodiment, the biological material may be a mixture of DNA from one or more individuals, as is the case during pregnancy where it has been shown that fetal DNA is present in the mixture. In an embodiment, the biological material could be from a mixture of cells that were found in maternal blood, where some of the cells are fetal in origin. In an embodiment, the biological material could be cells from the blood of a pregnant which have been enriched in fetal cells.

Circularizing Probes

Some embodiments of the present disclosure involve the use of "Linked Inverted Probes" (LIPs), which have been previously described in the literature, to amplify the target loci before or after amplification using primers that are not LIPs in the multiplex PCR methods of the invention. LIPs is a generic term meant to encompass technologies that involve the creation of a circular molecule of DNA, where the probes are designed to hybridize to targeted region of DNA on either side of a targeted allele, such that addition of appropriate polymerases and/or ligases, and the appropriate conditions, buffers and other reagents, will complete the complementary, inverted region of DNA across the targeted allele to create a circular loop of DNA that captures the information found in the targeted allele. LIPs may also be called pre-circularized probes, pre-circularizing probes, or circularizing probes. The LIPs probe may be a linear DNA molecule between 50 and 500 nucleotides in length, and in an embodiment between 70 and 100 nucleotides in length; in some embodiments, it may be longer or shorter than described herein. Others embodiments of the present disclosure involve different incarnations, of the LIPs technology, such as Padlock Probes and Molecular Inversion Probes (MIPs).

One method to target specific locations for sequencing is to synthesize probes in which the 3' and 5' ends of the probes anneal to target DNA at locations adjacent to and on either side of the targeted region, in an inverted manner, such that the addition of DNA polymerase and DNA ligase results in extension from the 3' end, adding bases to single stranded probe that are complementary to the target molecule (gap-fill), followed by ligation of the new 3' end to the 5' end of the original probe resulting in a circular DNA molecule that can be subsequently isolated from background DNA. The probe ends are designed to flank the targeted region of interest. One aspect of this approach is commonly called MIPS and has been used in conjunction with array technologies to determine the nature of the sequence filled in. One drawback to the use of MIPs in the context of measuring allele ratios is that the hybridization, circularization and amplification steps do not happed at equal rates for different alleles at the same loci. This results in measured allele ratios that are not representative of the actual allele ratios present in the original mixture.

In an embodiment, the circularizing probes are constructed such that the region of the probe that is designed to hybridize upstream of the targeted polymorphic locus and the region of the probe that is designed to hybridize downstream of the targeted polymorphic locus are covalently connected through a non-nucleic acid backbone. This backbone can be any biocompatible molecule or combination of biocompatible molecules. Some examples of possible biocompatible molecules are poly(ethylene glycol), polycarbonates, polyurethanes, polyethylenes, polypropylenes, sulfone polymers, silicone, cellulose, fluoropolymers, acrylic compounds, styrene block copolymers, and other block copolymers.

In an embodiment of the present disclosure, this approach has been modified to be easily amenable to sequencing as a means of interrogating the filled in sequence. In order to retain the original allelic proportions of the original sample at least one key consideration must be taken into account. The variable positions among different alleles in the gap-fill region must not be too close to the probe binding sites as there can be initiation bias by the DNA polymerase resulting in differential of the variants. Another consideration is that additional variations may be present in the probe binding sites that are correlated to the variants in the gap-fill region which can result unequal amplification from different alleles. In an embodiment of the present disclosure, the 3' ends and 5' ends of the pre-circularized probe are designed to hybridize to bases that are one or a few positions away from the variant positions (polymorphic sites) of the targeted allele. The number of bases between the polymorphic site (SNP or otherwise) and the base to which the 3' end and/or 5' of the pre-circularized probe is designed to hybridize may be one base, it may be two bases, it may, be three bases, it may be four bases, it may be five bases, it may be six bases, it may be seven to ten bases, it may be eleven to fifteen bases, or it may be sixteen to twenty bases, twenty to thirty bases, or thirty to sixty bases. The forward and reverse primers may be designed to hybridize a different number of bases away from the polymorphic site. Circularizing probes can be generated in large numbers with current DNA synthesis technology allowing very large numbers of probes to be generated and potentially pooled, enabling interrogation of many loci simultaneously. It has been reported to work with more than 300,000 probes. Two papers that discuss a method involving circularizing probes that can be used to measure the genomic data of the target individual include: Porreca et al., Nature Methods, 2007 4(11), pp. 931-936; and also Turner et al., Nature Methods, 2009, 6(5), pp. 315-316. The methods described in these papers may be used in combination with other methods described herein. Certain steps of the method from these two papers may be used in combination with other steps from other methods described herein.

In some embodiments of the methods disclosed herein, the genetic material of the target individual is optionally amplified, followed by hybridization of the pre-circularized probes, performing a gap fill to fill in the bases between the two ends of the hybridized probes, ligating the two ends to form a circularized probe, and amplifying the circularized probe, using, for example, rolling circle amplification. Once the desired target allelic genetic information is captured by circularizing appropriately designed oligonucleotide probes, such as in the LIPs system, the genetic sequence of the circularized probes may be being measured to give the desired sequence data. In an embodiment, the appropriately designed oligonucleotides probes may be circularized directly on unamplified genetic material of the target individual, and amplified afterwards. Note that a number of amplification procedures may be used to amplify the original genetic material, or the circularized LIPs, including rolling circle amplification, MDA, or other amplification protocols.

Different methods may be used to measure the genetic information on the target genome, for example using high throughput sequencing, Sanger sequencing, other sequencing methods, capture-by-hybridization, capture-by-circularization, multiplex PCR, other hybridization methods, and combinations thereof.

Once the genetic material of the individual has been measured using one or a combination of the above methods, an informatics based method, such as the PARENTAL SUPPORT™ method, along with the appropriate genetic measurements, can then be used to determination the ploidy state of one or more chromosomes on the individual, and/or the genetic state of one or a set of alleles, specifically those alleles that are correlated with a disease or genetic state of interest. Note that the use of LIPs has been reported for multiplexed capture of genetic sequences, followed by genotyping with sequencing. However, the use of sequencing data resulting from a LIPs-based strategy for the amplification of the genetic material found in a single cell, a small number of cells, or extracellular DNA, has not been used for the purpose of determining the ploidy state of a target individual.

Applying an informatics based method to determine the ploidy state of an individual from genetic data as measured by hybridization arrays, such as the ILLUMINA INFINIUM array, or the AFFYMETRIX gene chip has been described in documents references elsewhere in this document. However, the method described herein shows improvements over methods described previously in the literature. For example, the LIPs based approach followed by high throughput sequencing unexpectedly provides better genotypic data due to the approach having better capacity for multiplexing better capture specificity, better uniformity, and low allelic bias. Greater multiplexing allows more alleles to be targeted, giving more accurate results. Better uniformity results in more of the targeted alleles being measured, giving more accurate results. Lower rates of allelic bias result in lower rates of miscalls, giving more accurate results. More accurate results result in an improvement in clinical outcomes, and better medical care.

It is important to note that LIPs may be used as a method for targeting specific loci in a sample of DNA for genotyping by methods other than sequencing. For example, LIPs may be used to target DNA for genotyping using SNP arrays or other DNA or RNA based microarrays.

Ligation-Mediated PCR

Ligation-mediated PCR may be used to amplify the target loci before or after PCR amplification using primers that are not ligated. Ligation-mediated PCR is a method of PCR used to preferentially enrich a sample of DNA by amplifying one or a plurality of loci in a mixture of DNA, the method comprising: obtaining a set of primer pairs, where each primer in the pair contains a target specific sequence and a non-target sequence, where the target specific sequence is preferably designed to anneal to a target region, one upstream and one downstream from the polymorphic site, and which can be separated from the polymorphic site by 0, 1, 2, 3, 4, 5, 6, 7, 8, 9, 10, 11-20, 21-30, 31-40, 41-50, 51-100, or more than 100; polymerization of the DNA from the 3-prime end of upstream primer to the fill the single strand region between it and the 5-prime end of the downstream primer with nucleotides complementary to the target molecule, ligation of the last polymerized base of the upstream primer to the adjacent 5-prime base of the downstream primer, and amplification of only polymerized and ligated molecules using the non-target sequences contained at the 5-prime end of the upstream primer and the 3-prime end of the downstream primer. Pairs of primers to distinct targets may be mixed in the same reaction. The non-target sequences serve as universal sequences such that of all pairs of primers that have been successfully polymerized and ligated may be amplified with a single pair of amplification primers.

Capture by Hybridization

In some embodiments, a method of the present disclosure may involve using any of the following capture by hybridization methods in addition to using multiplex PCR to amplify the target loci. Preferential enrichment of a specific set of sequences in a target genome can be accomplished in a number of ways. Elsewhere in this document is a description of how LIPs can be used to target a specific set of sequences, but in all of those applications, other targeting and/or preferential enrichment methods can be used equally well for the same ends. One example of another targeting method is the capture by hybridization approach. Some examples of commercial capture by hybridization technologies include AGILENT's SURE SELECT and ILLUMINA's TRUSEQ. In capture by hybridization, a set of oligonucleotides that is complimentary or mostly complimentary to the desired targeted sequences is allowed to hybridize to a mixture of DNA, and then physically separated from the mixture. Once the desired sequences have hybridized to the targeting oligonucleotides, the effect of physically removing the targeting oligonucleotides is to also remove the targeted sequences. Once the hybridized oligos are removed, they can be heated to above their melting temperature and they can be amplified. Some ways to physically remove the targeting oligonucleotides is by covalently bonding the targeting oligos to a solid support, for example a magnetic bead, or a chip. Another way to physically remove the targeting oligonucleotides is by covalently bonding them to a molecular moiety with a strong affinity for another molecular moiety. An example of such a molecular pair is biotin and streptavidin, such as is used in SURE SELECT. Thus that targeted sequences could be covalently attached to a biotin molecule, and after hybridization, a solid support with streptavidin affixed can be used to pull down the biotinylated oligonucleotides, to which are hybridized to the targeted sequences.

Hybrid capture involves hybridizing probes that are complementary to the targets of interest to the target molecules. Hybrid capture probes were originally developed to target and enrich large fractions of the genome with relative uniformity between targets. In that application, it was important that all targets be amplified with enough uniformity that all regions could be detected by sequencing, however, no regard was paid to retaining the proportion of alleles in original sample. Following capture, the alleles present in the sample can be determined by direct sequencing of the captured molecules. These sequencing reads can be analyzed and counted according the allele type. However, using the current technology, the measured allele distributions the captured sequences are typically not representative of the original allele distributions.

In an embodiment, detection of the alleles is performed by sequencing. In order to capture the allele identity at the polymorphic site, it is essential that the sequencing read span the allele in question in order to evaluate the allelic composition of that captured molecule. Since the capture molecules are often of variable lengths upon sequencing cannot be guaranteed to overlap the variant positions unless the entire molecule is sequenced. However, cost considerations as well as technical limitations as to the maximum possible length and accuracy of sequencing reads make sequencing the entire molecule unfeasible. In an embodiment, the read length can be increased from about 30 to about 50 or about 70 bases can greatly increase the number of reads that overlap the variant positions within the targeted sequences.

Another way to increase the number of reads that interrogate the position of interest is to decrease the length of the probe, as long as it does not result in bias in the underlying enriched alleles. The length of the synthesized probe should be long enough such that two probes designed to hybridize to two different alleles found at one locus will hybridize with near equal affinity to the various alleles in the original sample. Currently, methods known in the art describe probes that are typically longer than 120 bases. In a current embodiment, if the allele is one or a few bases then the capture probes may be less than about 110 bases, less than about 100 bases, less than about 90 bases, less than about 80 bases, less than about 70 bases, less than about 60 bases, less than about 50 bases, less than about 40 bases, less than about 30 bases, and less than about 25 bases, and this is sufficient to ensure equal enrichment from all alleles. When the mixture of DNA that is to be enriched using the hybrid capture technology is a mixture comprising free floating DNA isolated from blood, for example maternal blood, the average length of DNA is quite short, typically less than 200 bases. The use of shorter probes results in a greater chance that the hybrid capture probes will capture desired DNA fragments. Larger variations may require longer probes. In an embodiment, the variations of interest are one (a SNP) to a few bases in length. In an embodiment, targeted regions in the genome can be preferentially enriched using hybrid capture probes wherein the hybrid capture probes are of a length below 90 bases, and can be less than 80 bases, less than 70 bases, less than 60 bases, less than 50 bases, less than 40 bases, less than 30 bases, or less than 25 bases. In an embodiment, to increase the chance that the desired allele is sequenced, the length of the probe that is designed to hybridize to the regions flanking the polymorphic allele location can be decreased from above 90 bases, to about 80 bases, or to about 70 bases, or to about 60 bases, or to about 50 bases, or to about 40 bases, or to about 30 bases, or to about 25 bases.

There is a minimum overlap between the synthesized probe and the target molecule in order to enable capture. This synthesized probe can be made as short as possible while still being larger than this minimum required overlap. The effect of using a shorter probe length to target a polymorphic region is that there will be more molecules that overlap the target allele region. The state of fragmentation of the original DNA molecules also affects the number of reads that will overlap the targeted alleles. Some DNA samples such as plasma samples are already fragmented due to biological processes that take place in vivo. However, samples with longer fragments by benefit from fragmentation prior to sequencing library preparation and enrichment. When both probes and fragments are short (~60-80 bp) maximum specificity may be achieved relatively few sequence reads failing to overlap the critical region of interest.

In an embodiment, the hybridization conditions can be adjusted to maximize uniformity in the capture of different alleles present in the original sample. In an embodiment, hybridization temperatures are decreased to minimize differences in hybridization bias between alleles. Methods known in the art avoid using lower temperatures for hybridization because lowering the temperature has the effect of increasing hybridization of probes to unintended targets. However, when the goal is to preserve allele ratios with maximum fidelity, the approach of using lower hybridization temperatures provides optimally accurate allele ratios, despite the fact that the current art teaches away from this approach. Hybridization temperature can also be increased to require greater overlap between the target and the synthesized probe so that only targets with substantial overlap of the targeted region are captured. In some embodiments of the present disclosure, the hybridization temperature is lowered from the normal hybridization temperature to about 40° C., to about 45° C., to about 50° C. to about 55° C. to about 60° C., to about 65, or to about 70° C.

In an embodiment, the hybrid capture probes can be designed such that the region of the capture probe with DNA that is complementary to the DNA found in regions flanking the polymorphic allele is not immediately adjacent to the polymorphic site. Instead, the capture probe can be designed such that the region of the capture probe that is designed to hybridize to the DNA flanking the polymorphic site of the target is separated from the portion of the capture probe that will be in van der Waals contact with the polymorphic site by a small distance that is equivalent in length to one or a small number of bases. In an embodiment, the hybrid capture probe is designed to hybridize to a region that is flanking the polymorphic allele but does not cross it; this may be termed a flanking capture probe. The length of the flanking capture probe may be less than about 120 bases, less than about 110 bases, less than about 100 bases, less than about 90 bases, and can be less than about 80 bases, less than about 70 bases, less than about 60 bases, less than about 50 bases, less than about 40 bases, less than about 30 bases, or less than about 25 bases. The region of the genome that is targeted by the flanking capture probe may be separated by the polymorphic locus by 1, 2, 3, 4, 5, 6, 7, 8, 9, 10, 11-20, or more than 20 base pairs.

Description of a targeted capture based disease screening test using targeted sequence capture. Custom targeted sequence capture, like those currently offered by AGILENT (SURE SELECT), ROCHE-NIMBLEGEN, or ILLUMINA. Capture probes could be custom designed to ensure capture of various types of mutations. For point mutations, one or more probes that overlap the point mutation should be sufficient to capture and sequence the mutation.

For small insertions or deletions, one or more probes that overlap the mutation may be sufficient to capture and sequence fragments comprising the mutation. Hybridization may be less efficient between the probe-limiting capture efficiency, typically designed to the reference genome sequence. To ensure capture of fragments comprising the mutation one could design two probes, one matching the normal allele and one matching the mutant allele. A longer probe may enhance hybridization. Multiple overlapping probes may enhance capture. Finally, placing a probe immediately adjacent to, but not overlapping, the mutation may permit relatively similar capture efficiency of the normal and mutant alleles.

For Simple Tandem Repeats (STRs), a probe overlapping these highly variable sites is unlikely to capture the fragment well. To enhance capture a probe could be placed adjacent to, but not overlapping the variable site. The fragment could then be sequenced as normal to reveal the length and composition of the STR.

For large deletions, a series of overlapping probes, a common approach currently used in exon capture systems may work. However, with this approach it may be difficult to determine whether or not an individual is heterozygous. Targeting and evaluating SNPs within the captured region could potentially reveal loss of heterozygosity across the region indicating that an individual is a carrier. In an embodiment, it is possible to place non-overlapping or singleton probes across the potentially deleted region and use the number of fragments captured as a measure of heterozygosity. In the case where an individual caries a large deletion, one-half the number of fragments are expected to be available for capture relative to a non-deleted (diploid) reference locus. Consequently, the number of reads obtained from the deleted regions should be roughly half that obtained from a normal diploid locus. Aggregating and averaging the sequencing read depth from multiple singleton probes across the potentially deleted region may enhance the signal and improve confidence of the diagnosis. The two approaches, targeting SNPs to identify loss of heterozygosity and using multiple singleton probes to obtain a quantitative measure of the quantity of underlying fragments from that locus can also be combined. Either or both of these strategies may be combined with other strategies to better obtain the same end.

If during testing cfDNA detection of a male fetus, as indicated by the presence of the Y-chromosome fragments, captured and sequenced in the same test, and either an X-linked dominant mutation where mother and father are unaffected, or a dominant mutation where mother is not affected would indicated heighted risk to the fetus. Detection of two mutant recessive alleles within the same gene in an unaffected mother would imply the fetus had inherited a mutant allele from father and potentially a second mutant allele from mother. In all cases, follow-up testing by amniocentesis or chorionic villus sampling may be indicated.

A targeted capture based disease screening test could be combined with a targeted capture based non-invasive prenatal diagnostic test for aneuploidy.

There are a number of ways to decrease depth of read (DOR) variability: for example, one could increase primer concentrations, one could use longer targeted amplification probes, or one could run more STA cycles (such as more than 25, more than 30, more than 35, or even more than 40). Exemplary Methods of Determining the Number of DNA Molecules in a Sample.

A method is described herein to determine the number of DNA molecules in a sample by generating a uniquely identified molecule for each original DNA molecules in the sample during the first round of DNA amplification. Described here is a procedure to accomplish the above end followed by a single molecule or clonal sequencing method.

The approach entails targeting one or more specific loci and generating a tagged copy of the original molecules such manner that most or all of the tagged molecules from each targeted locus will have a unique tag and can be distinguished from one another upon sequencing of this barcode using clonal or single molecule sequencing. Each unique sequenced barcode represents a unique molecule in the original sample. Simultaneously, sequencing data is used to ascertain the locus from which the molecule originates. Using this information one can determine the number of unique molecules in the original sample for each locus.

This method can be used for any application in which quantitative evaluation of the number of molecules in an original sample is required. Furthermore, the number of unique molecules of one or more targets can be related to the number of unique molecules to one or more other targets to determine the relative copy number, allele distribution, or allele ratio. Alternatively, the number of copies detected from various targets can be modeled by a distribution in order to identify the mostly likely number of copies of the original targets. Applications include but are not limited to detection of insertions and deletions such as those found in carriers of Duchenne Muscular Dystrophy, quantitation of deletions or duplications segments of chromosomes such as those observed in copy number variants; chromosome copy number of samples from born individuals; chromosome copy number of samples from unborn individuals such as embryos or fetuses.

The method can be combined with simultaneous evaluation of variations contained in the targeted by sequence. This can be used to determine the number of molecules representing each allele in the original sample. This copy number method can be combined with the evaluation of SNPs or other sequence variations to determine the chromosome copy number of born and unborn individuals; the discrimination and quantification of copies from loci which have short sequence variations, but in which PCR may amplifies from multiple target regions such as in carrier detection of Spinal Muscle Atrophy; determination of copy number of different sources of molecules from samples consisting of mixtures of different individual such as in detection of fetal aneuploidy from free floating DNA obtained from maternal plasma.

In an embodiment, the method as it pertains to a single target locus may comprise one or more of the following steps: (1) Designing a standard pair of oligomers for PCR amplification of a specific locus. (2) Adding, during synthesis, a sequence of specified bases with no or minimal complimentarity to the target locus or genome to the 5' end of the one of the target specific oligomer. This sequence, termed the tail, is a known sequence, to be used for subsequent amplification, followed by a sequence of random nucleotides. These random nucleotides comprise the random region. The random region comprises a randomly generated sequence of nucleic acids that probabilistically differ between each probe molecule. Consequently, following synthesis, the tailed oligomer pool will consist of a collection of oligomers beginning with a known sequence followed by unknown sequence that differs between molecules, followed by the target specific sequence. (3) Performing one round of amplification (denaturation, annealing, extension) using only the tailed oligomer. (4) adding exonuclease to the reaction, effectively stopping the PCR reaction, and incubating the reaction at the appropriate temperature to remove forward single stranded oligos that did not anneal to temple and extend to form a double stranded product. (5) Incubating the reaction at a high temperature to denature the exonuclease and eliminate its activity. (6) Adding to the reaction a new oligonucleotide that is complementary to tail of the oligomer used in the first reaction along with the other target specific oligomer to enable PCR amplification of the product generated in the first round of PCR. (7) Continuing amplification to generate enough product for downstream clonal sequencing (8) Measuring the amplified PCR product by a multitude of methods, for example, clonal sequencing, to a sufficient number of bases to span the sequence.

In an embodiment, a method of the present disclosure involves targeting multiple loci in parallel or otherwise. Primers to different target loci can be generated independently and mixed to create multiplex PCR pools. In an embodiment, original samples can be divided into sub-pools and different loci can be targeted in each sub-pool before being recombined and sequenced. In an embodiment, the tagging step and a number of amplification cycles may be performed before the pool is subdivided to ensure efficient targeting of all targets before splitting, and improving subsequent amplification by continuing amplification using smaller sets of primers in subdivided pools.

One example of an application where this technology would be particularly useful is non-invasive prenatal aneuploidy diagnosis where the ratio of alleles at a given locus or a distribution of alleles at a number of loci can be used to help determine the number of copies of a chromosome present in a fetus. In this context, it is desirable to amplify the DNA present in the initial sample while maintaining the relative amounts of the various alleles. In some circumstances, especially in cases where there is a very small amount of DNA, for example, fewer than 5,000 copies of the genome, fewer than 1,000 copies of the genome, fewer than 500 copies of the genome, and fewer than 100 copies of the genome, one can encounter a phenomenon called bottlenecking. This is where there are a small number of copies of any given allele in the initial sample, and amplification biases can result in the amplified pool of DNA having significantly different ratios of those alleles than are in the initial mixture of DNA. By applying a unique or nearly unique set of barcodes to each strand of DNA before standard PCR amplification, it is possible to exclude n−1 copies of DNA from a set of n identical molecules of sequenced DNA that originated from the same original molecule.

For example, imagine a heterozygous SNP in the genome of an individual, and a mixture of DNA from the individual where ten molecules of each allele are present in the original sample of DNA. After amplification there may be 100,000 molecules of DNA corresponding to that locus. Due to stochastic processes, the ratio of DNA could be anywhere from 1:2 to 2:1, however, since each of the original molecules was tagged with a unique tag, it would be possible to determine that the DNA in the amplified pool originated from exactly 10 molecules of DNA from each allele. This method would therefore give a more accurate measure of the relative amounts of each allele than a method not using this approach. For methods where it is desirable for the relative amount of allele bias to be minimized, this method will provide more accurate data.

Association of the sequenced fragment to the target locus can be achieved in a number of ways. In an embodiment, a sequence of sufficient length is obtained from the targeted fragment to span the molecule barcode as well a sufficient number of unique bases corresponding to the target sequence to allow unambiguous identification of the target locus. In another embodiment, the molecular bar-coding primer that contains the randomly generated molecular barcode can also contain a locus specific barcode (locus barcode) that identifies the target to which it is to be associated. This locus barcode would be identical among all molecular bar-coding primers for each individual target and hence all resulting amplicons, but different from all other targets. In an embodiment, the tagging method described herein may be combined with a one-sided nesting protocol.

In an embodiment, the design and generation of molecular barcoding primers may be reduced to practice as follows: the molecular barcoding primers may consist of a sequence that is not complementary to the target sequence followed by random molecular barcode region followed by a target specific sequence. The sequence 5' of molecular barcode may be used for subsequence PCR amplification and may comprise sequences useful in the conversion of the amplicon to a library for sequencing. The random molecular barcode sequence could be generated in a multitude of ways. The preferred method synthesizes the molecule tagging primer in such a way as to include all four bases to the reaction during synthesis of the barcode region. All or various combinations of bases may be specified using the IUPAC DNA ambiguity codes. In this manner the synthesized collection of molecules will contain a random mixture of sequences in the molecular barcode region. The length of the barcode region will determine how many primers will contain unique barcodes. The number of unique sequences is related to the length of the barcode region as $N^L$ where N is the number of bases, typically 4, and L is the length of the barcode A barcode of five bases can yield up to 1024 unique sequences; a barcode of eight bases can yield 65536 unique barcodes. In an embodiment, the DNA can be measured by a sequencing method, where the sequence data represents the sequence of a single molecule. This can include methods in which single molecules are sequenced directly or methods in which single molecules are amplified to form clones detectable by the sequence instrument, but that still represent single molecules, herein called clonal sequencing.

Exemplary Methods and Reagents for Quantification of Amplification Products

Quantitation of specific nucleic acid sequences of interest is typically done by quantitative real-time PCR techniques such as TAQMAN (LIFE TECHNOLOGIES), INVADER probes (THIRD WAVE TECHNOLOGIES), and the like. Such techniques suffer from numerous shortcomings such as limited ability to achieve the simultaneous analysis of multiple sequences in parallel (multiplexation) and the ability to provide accurate quantitative data for only a narrow range of possible amplification cycles (e.g., when the logarithm of PCR amplification production quantity versus the number of cycles is in the linear range). DNA sequencing techniques, particularly high throughput next-generation sequencing techniques (often referred to as massively parallel sequencing techniques) such as those employed in MYSEQ (ILLUMINA), HISEQ (ILLUMINA), ION TORRENT (LIFE TECHNOLOGIES), GENOME ANALYZER ILX (ILLUMINA), GS FLEX+(ROCHE 454) etc., can be used for by quantitative measurements of the number of copies of sequence of interest present in sample, thereby providing quantitative information about the starting materials, e.g., copy number or transcription levels. High throughput genetic sequencers are amenable to the use of bar coding (i.e., sample tagging with distinctive nucleic acid sequences) so as to identify specific samples from individuals thereby permitting the simultaneous analysis of multiple samples in a single run of the DNA sequencer. The number of times a given region of the genome in a library preparation (or other nucleic preparation of interest) is sequenced (number of reads) will be proportional to the number of copies of that sequence in the genome of interest (or expression level in the case of cDNA containing preparations). However, the preparation and sequencing of genetic libraries (and similar genome derived preparations) can introduce numerous biases that interfere with obtaining an accurate quantitative reading for the nucleic acid sequence of interest. For example, different nucleic acid sequences can amplify with different efficiencies during nucleic amplification steps that take place during the genetic library preparation or sample preparation.

The problem with differential amplification efficiencies can be mitigated by using certain embodiments of the subject invention. The subject invention includes various methods and compositions that relate to the use of standards for inclusion in amplification processes that can be used to improve the accuracy of quantitation. The invention is of use in, among other areas, the detection of aneuploidy in a fetus by analyzing free floating fetal DNA in maternal blood, as described herein and as described, among other places, U.S. Pat. Nos. 8,008,018, 7,332,277: PCT Published Application WO 2012/078792A2; and PCT Published Application WO 2011/146632 A1, which are each herein incorporated by reference in its entirety. Embodiments of the invention are also of use in the detection of aneuploidy in an in vitro generated embryos. Commercially significant aneuploidies that may be detected include aneuploidy of the human chromosomes 13, 18, 21, X and Y.

Embodiments of the invention may be used with either human or non-human nucleic acids, and may be applied to both animal and plant derived nucleic acids. Embodiments of the invention may also be used to detect and/or quantitate alleles for other genetic disorders characterized by deletions or insertions. The deletion containing alleles can be detected in suspected carriers of the allele of interest.

One embodiment of the subject invention includes standards that are present in a known quantity (relative or absolute). For example, consider a genetic library made from a genetic source that is diploid for chromosome 8 (containing locus A) and triploid for chromosome 21 (containing locus B). A genetic library can be produced from this sample that will contain sequences in quantities that are a function of the number of chromosomes present in the sample, e.g., 200 copies of locus A and 300 copies of locus B. However, if locus A amplifies much more efficiently than locus B, after PCR there may be 60,000 copies of the A amplicon and 30,000 copies of the B amplicon, thus obscuring the true chromosomal copy number of the initial genomic sample when analysis by high throughput DNA sequencing (or other quantitative nucleic acid detection techniques). To mitigate this problem a standard sequence for locus A is employed, wherein the standard sequence amplifies with essentially the same efficiency as locus A. Similarly, a standard sequence for locus B is created, wherein the standard sequence amplifies with the essentially the same efficiency as locus B. A standard sequence of locus A and a standard sequence for locus B are added to the mixture prior to PCR (or other amplification techniques). These standard sequences are present in known quantities, either relative quantities or absolute quantities. Thus if a 1:1 mixture of standard sequence A and standard sequence B were added (prior to amplification) to the mixture in the previous example, 3000 copies of the standard A amplicon would be produced and 1000 copies of the standard B amplicon would be produced, showing that locus A is amplified 3 times more efficiently than locus B, under the same set of conditions.

In various embodiments one or more selected regions of a genome containing a SNP (or other polymorphism) of interest can be specifically amplified and subsequently sequenced. This target specific amplification can take place during the formation of a genetic library for sequencing. The library can contain numerous targeted regions for amplification. In some embodiments at least 10; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 regions of interest. Examples of such libraries are described herein and can be found in U.S. Patent Application No. 2012/0270212, filed Nov. 18, 2011, which is herein incorporated by reference in its entirety.

Many high throughput DNA sequencing techniques require the modification of the genetic starting material, e.g., the litigation of universal priming sites and/or barcodes, so as to form libraries to facilitate the clonal amplification of small nucleic acid fragments prior to performing subsequent sequencing reactions. In some embodiments, one or more standard sequences are added during genetic library formation or added to a precursor component of a genetic library prior to amplification of the library. The standard sequences can be selected so as to mimic (yet be distinguishable based on nucleotide base sequence) target genomic fragments to be prepared for sequencing by a high throughput genetic sequencing technique. In one embodiment, the standard sequence can be identical to the target genomic fragment excepting one, two, three, four to ten, or eleven to twenty nucleotides. In some embodiments, when the target genetic sequence contains a SNP, the standard sequence can be identical to the SNP excepting the nucleotide at the polymorphic base, which may be chosen to be one of the four nucleotides that is not observed at that location in nature. The standard sequences can be used in a highly multiplexed analysis of multiple target loci (such as polymorphic loci). Standard sequences can be added during the process of library formation (prior to amplification) in known quantities (relative or absolute) so as to provide a standard metric for greater accuracy in determining the amount of target sequence of interest in the sample of analysis. The combination of knowledge of the known quantities of the standard sequences used in conjunction with the knowledge of the ploidy level formation of library for sequencing formed from a genome of previously characterized ploidy level, e.g., known to be diploid for all autosomal chromosomes, can be used to calibrate the amplification properties of each standard sequence with respect to its corresponding target sequence and account for variations between batches of mixtures comprising multiple standard sequences. Given that it is often necessary to simultaneously analyze a large number of loci, it is useful to produce a mixture comprising a large set standard sequences. Embodiments of the invention include mixtures comprising multiple standard sequences. Ideally the amount of each standard sequence in the mixture is known with high precision. However, it is extremely difficult to achieve this ideal because as a practical matter there is a significant amount of variation in the quantity of each standard sequence in the mixture, particularly for mixtures comprising a large number of different synthetic oligonucleotides. This variation has numerous sources, e.g., variations in in vitro oligonucleotide synthesis reaction efficiencies between batch, inaccuracies in volume measurement, variations in pipetting. Furthermore, this variation can occur between different batches of that theoretically contain the exact same set of standard sequences in the exact same amounts. Accordingly, it is of interest to calibrate each batch of standard sequences independently. Batches of standard sequences can be calibrated against reference genomes of known chromosomal composition. Batched of standard sequences can be calibrated by sequencing the batch of standard sequences with minimal or no amplifications steps included in the sequencing protocol. Embodiments of the invention include calibrated mixtures of different standard sequences. Other embodiments of the invention include methods of calibrating mixtures of different standard sequences and calibrated mixtures of different standard sequences made by the subject methods.

Various embodiments of the subject mixtures of standard sequences and methods for using them can comprise at least 10; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 or more standards sequences, as well as various intermediate amounts. The number of the standard sequences can be the same as the number of target sequences selected for analysis during the generation of a targeted library for DNA sequencing. However, in some embodiments, it may be advantageous to use a lower number of standard sequences than the number of targeted regions in the library being constructed. It may be advantageous to use the lower number so as avoid coming up against the limits of the sequencing capacity of the high throughput DNA sequencer being employed. The number of standard sequences can be 50% or less than the number of targeted regions, 40% or less than the number of targeted regions, be 30% or less than the number of targeted regions, 20% or less than the number of targeted regions, be 10% or less than the number of targeted regions, 5% or less than the number of targeted regions, 1% or less than the number of targeted regions, as well as various intermediate values. For example, if a genetic library is created using 15,000 pairs of primers targeted to specific SNP containing loci, a suitable mixture containing 1500 standard sequences corresponding to 1500 of the 15,000 targeted loci can be added prior to the amplification step of library constructions.

The amount of standard sequences added during library construction can vary considerably among different embodiments. In some embodiments, the amount of each standard sequence can be approximately the same as the predicted amount of the target sequence present in the genomic material sample used for library preparation. In other embodiments, the amount of each standard sequence can be greater or less than the predicted amount of the target sequence present in the genomic material sample used for library preparation. While the initial relative amounts of the target sequence and the standard sequence are not critical for the function of the invention, it is preferable that the amount be within the range 100 times greater to 100 times less than the amount of the target sequence present in the genomic material sample used for library preparation. Excessive amounts of standard may use too much sequencing capacity of the DNA sequencer in a given run of the instrument. Using too low an amount of standard sequences will produce insufficient data to aid in the analysis of variation in amplification efficiency.

The standard sequences may be selected to be very similar in nucleotide base sequence to the amplified regions of interest; preferably the standard sequence has the exact same primer-binding sites as the analyzed genomic region, i.e., the "target sequence." The standard sequence must be distinguishable from the corresponding target sequence at a given locus. For the sake of convenience, this distinguishable region of the standard sequence will be referred to as a "marker sequence." In some embodiments, the marker sequence region of the target sequences contains the polymorphic region, e.g., a SNP, and can be flanked on both sides by primer binding regions. The standard sequence may be selected to closely match the GC content of the corresponding target sequence. In some embodiments, the primer binding regions of the standard sequence are flanked by universal priming sites. These universal priming sites are selected to match universal priming sites used in a genomic library for analysis. In other embodiments, the standard sequences do not have universal priming sites and the universal priming sites are added during the creation of a library. Standard sequences are typically provided in single stranded form. A standard sequence is defined with respect to a corresponding target sequence and the sequence specific reagents used to amplify the target sequence. In some embodiments, the target sequence contains the polymorphism of interest, e.g., a SNP, a deletion, or insertion, present in the nucleic acid sample for analysis. The standard sequence is a synthetic polynucleotide that is similar in nucleotide base sequence to the target sequence, but is nonetheless distinguishable from the target sequence by virtue of at least one nucleotide base difference, thereby providing a mechanism for distinguishing amplicon sequences derived from the standard sequence form amplicon sequences derived from the target sequence. Standard sequences are selected so as to have essentially the same amplification properties as the corresponding target sequence when amplified with the same set of amplification reagents, e.g., PCR primers. In some embodiments, the standard sequences can have the same primer sequence binding sites than the corresponding target sequences. In other embodiments, the standard sequences can have a different primer sequence binding sites than the corresponding target sequences. In some embodiments, the standard sequences can be selected to produce amplicons that have the same length as the length of amplicons produced from the corresponding target sequences. In other embodiments, the standard sequences can be selected to produce amplicons that have the slightly different lengths than the length of amplicons produced from the corresponding target sequences.

After the amplification reactions have been completed, the library is sequenced on a high throughput DNA sequencer where individual molecule are clonally amplified and sequenced. The number of sequence reads for each allele of the target sequence is counted, also counted are the number of sequence reads for the standard sequence corresponding to the target sequence. The process is also carried out for at least one other pair of target sequences and corresponding standard sequences. Consider for example, locus A. $X_{A1}$ reads for allele 1 of locus A are produced; $X_{A2}$ reads for allele 2 of locus A are produced, and $X_{AC}$ reads for standard sequence A are produced. The ratio of ($X_{A1}$ plus $X_{A2}$) to $X_{AC}$ is determined for each locus of interest. As discussed earlier, the process can be performed on a reference genome, e.g., a genome that is known to be diploid for all chromosomes. The process can be repeated many times in order to provide a large number of read values so as to determine a mean number of reads and the standard deviation in the number of reads. The process is performed with a mixture comprising a large number of different standard sequences corresponding to different loci. By assuming that (1) $X_{A1}$ plus $X_{A2}$ corresponds to the known number of chromosome, e.g., 2 for the normal human female genome and (2) the standard sequences have similar amplification (and detectability) properties as their corresponding natural loci, the relative amounts of the different standard sequences in the multiplex standard mixture can be determined. The calibrated multiplex standard sequence mixture can then be used to adjust for the variability in amplification efficiency between the different loci in a multiplex amplification reaction.

Other embodiments of the invention include methods and compositions for measuring the copy number of specific genes of interest, including duplications and mutant genes characterized by large deletions that would interfere with quantitation by sequencing. Sequencing would have problems detecting alleles having such deletions. Standard sequences included the amplification process can be used to reduce this problem.

In one embodiment of the invention the target sequence for analysis is a gene having a wild type (i.e. functional) form and a mutant form characterized by a deletion. Exemplary of such genes is SMN 1, an allele having deletion being responsible for the genetic disease spinal muscular atrophy (SMA). It is of interest to detect an individual carrying the mutant form of the gene by means of high throughput genetic sequencing techniques. The application of such techniques to the detection of deletion mutations can be problematic because, among other reasons, the lack of sequences observed in sequencing (as opposed to detecting a simple point mutation or SNP). Such embodiments employ (1) a pair of amplification primers specific for the gene of interest, where in the amplification primers will amplify the gene of interest (or a portion thereof) and will not significantly amplify the mutant allele, (2) a standard sequence corresponding to the wild type allele of the gene of interest (i.e., a target sequence), but differing by at least one detectable nucleotide base, (3) a pair of amplification primers specific for a second target sequence that serves as a reference sequence, and (4) a standard sequence corresponding to the reference sequence.

In one embodiment of the invention is provided a method for measuring the number of copies of the gene of interest, where in the gene of interest has one meaning allele that comprises a deletion. The method can employ amplification reagent specific for the gene of interest, e.g., PCR primers, that are specific for the gene of interest by amplifying at least a portion of the gene of interest, or the entire gene of interest, or a region adjacent to the gene of interest, while not amplifying the deletion comprising allele of the gene of interest. Additionally, the subject method employs a standard sequence corresponding to the gene of interest, wherein the standard sequence differs by at least one nucleotide base from the gene of interest (so that the sequence of the standard sequence can be readily distinguished from the naturally occurring gene of interest). Typically, the standard sequence will contain the same primer binding sites as the gene of interest so as to minimize any amplification discrimination between the gene of interest and the standard sequence corresponding to the gene of interest. The reaction will also comprises amplification reagents specific for a reference sequence. The reference sequence is a sequence of known (or at least assumed to be known) copy number in the genome to be analyzed. The reaction further comprises a standard sequence corresponding to the reference sequence. Typically, the standard sequence corresponding to the reference sequence will contain the same primer binding sites as the reference sequence so as to minimize any amplification discrimination between the reference sequence and the standard sequence corresponding to the reference sequence.

Exemplary PCR Conditions

If desired, any of the PCR conditions disclosed herein or any standard PCR conditions can be used to test a primer library to determine, e.g., the percent of primer dimers, percent of target amplicons, and percent of target loci that are amplified. If desired, standard methods can be used to optimize the reaction conditions to improve the performance of a primer library. Any of these PCR conditions may also be used in any of the methods of the invention to amplify target loci. It was determined that high ionic strength solutions can surprisingly be used for multiplex PCR. In some embodiments, monovalent cations are used to increase the ionic strength to, e.g., help the primers bind the template.

In some embodiments, the reaction volume includes ethylenediaminetetraacetic acid (EDTA), magnesium, tetramethyl ammonium chloride (TMAC), or any combination thereof. In some embodiments, the concentration of TMAC is between 20 and 80 mM, such as between 25 and 70 mM, 30 and 60 mM, 30 and 40 mM, 40 and 50 mM, 50 and 60 mM, or 60 and 70 mM, inclusive. While not meant to be bound to any particular theory, it is believed that TMAC binds to DNA, stabilizes duplexes, increases primer specificity, and/or equalizes the melting temperatures of different primers. In some embodiments, TMAC increases the uniformity in the amount of amplified products for the different targets. In some embodiments, the concentration of magnesium (such as magnesium from magnesium chloride) is between 1 and 10 mM, such as between 1 and 8 mM, 1 and 5 mM, 1 and 3 mM, 3 and 5 mM, 3 and 6 mM, or 5 and 8 mM, inclusive.

In some embodiments, the concentration of available magnesium (the concentration of magnesium that is assumed to be available for binding the polymerase and not bound to molecules other than the polymerase), such as the magnesium that is not bound by phosphate groups on dNTPs, primers, or nucleic acid templates, or carboxylic acid groups on magnetic or other beads, if present) is between 0.5 to 10 mM, such as between 1 and 8 mM, 1 and 5 mM, 1 and 3 mM, 3 and 5 mM, 3 and 6 mM, 4 and 6 mM, or 5 and 8 mM, inclusive. The large number of primers used for multiplex PCR of a large number of targets may chelate a lot of the magnesium (2 phosphates in the primers chelate 1 magnesium). For example, if enough primers are used such that the concentration of phosphate from the primers is ~9 mM, then the primers may reduce the effective magnesium concentration by ~4.5 mM. In some embodiments, EDTA is used to decrease the amount of magnesium available as a cofactor for the polymerase since high concentrations of magnesium can result in PCR errors, such as amplification of non-target loci. In some embodiments, the concentration of EDTA reduces the amount of available magnesium to between 1 and 5 mM (such as between 3 and 5 mM).

In some embodiments, the pH is between 7.5 and 8.5, such as between 7.5 and 8, 8 and 8.3, or 8.3 and 8.5, inclusive. In some embodiments. Tris is used at, for example, a concentration of between 10 and 100 mM, such as between 10 and 25 mM, 25 and 50 mM, 50 and 75 mM, or 25 and 75 mM, inclusive. In some embodiments, any of these concentrations of Tris are used at a pH between 7.5 and 8.5. In some embodiments, a combination of KCl and $(NH_4)_2SO_4$ is used, such as between 50 and 150 mM KCl and between 10 and 90 mM $(NH_4)_2SO_4$, inclusive. In some embodiments, the concentration of KCl is between 0 and 30 mM, between 50 and 100 mM, or between 100 and 150 mM, inclusive. In some embodiments, the concentration of $(NH_4)_2SO_4$ is between 10 and 50 mM, 50 and 90 mM, 10 and 20 mM, 20 and 40 mM, 40 mM and 60, or 60 mM and 80 mM $(NH_4)_2SO_4$, inclusive. In some embodiments, the ammonium $[NH_4^+]$ concentration is between 0 and 160 mM, such as between 0 to 50, 50 to 100, or 100 to 160 mM, inclusive. In some embodiments, the sum of the potassium and ammonium concentration ($[K^+]+[NH_4^+]$) is between 0 and 160 mM, such as between 0 to 25, 25 to 50, 50 to 150, 50 to 75, 75 to 100, 100 to 125, or 125 to 160 mM, inclusive. An exemplary buffer with $[K^+]+[NH_4^+]=120$ mM is 20 mM KCl and 50 mM $(NH_4)_2SO_4$. In some embodiments, the buffer includes 25 to 75 mM Tris, pH 7.2 to 8, 0 to 50 mM KCL, 10 to 80 mM ammonium sulfate, and 3 to 6 mM magnesium, inclusive. In some embodiments, the buffer includes 25 to 75 mM Tris pH 7 to 8.5, 3 to 6 mM $MgCl_2$, 10 to 50 mM KCl, and 20 to 80 mM $(NH_4)_2SO_4$, inclusive. In some embodiments, 100 to 200 Units/mL of polymerase are used. In some embodiments, 100 mM KCl, 50 mM $(NH_4)_2SO_4$, 3 mM $MgCl_2$, 7.5 nM of each primer in the library, 50 mM TMAC, and 7 ul DNA template in a 20 ul final volume at pH 8.1 is used.

In some embodiments, a crowding agent is used, such as polyethylene glycol (PEG, such as PEG 8,000) or glycerol. In some embodiments, the amount of PEG (such as PEG 8,000) is between 0.1 to 20%, such as between 0.5 to 15%, 1 to 10%, 2 to 8%, or 4 to 8%, inclusive. In some embodiments, the amount of glycerol is between 0.1 to 20%, such as between 0.5 to 15%, 1 to 10%, 2 to 8%, or 4 to 8%, inclusive. In some embodiments, a crowding agent allows either a low polymerase concentration and/or a shorter annealing time to be used. In some embodiments, a crowding agent improves the uniformity of the DOR and/or reduces dropouts (undetected alleles). For example, at 8% PEG, and 50 U/mL polymerase, the uniformity was as good as 150 U/mL polymerase and no PEG. If the error rate increases when PEG is included, a higher magnesium chloride concentration (such greater than or about 4, 5, 6, 7, 8, 9, or 10 $MgCl_2$) can be used to reduce or prevent the increase in error rate. Inclusion of 8% PEG 8,000 allowed successful multiplexing with an annealing time of only 1 minute at an annealing temperature of 63° C.

In some embodiments, a polymerase with proof-reading activity, a polymerase without (or with negligible) proof-reading activity, or a mixture of a polymerase with proof-reading activity and a polymerase without (or with negligible) proof-reading activity is used. In some embodiments, a hot start polymerase, a non-hot start polymerase, or a mixture of a hot start polymerase and a non-hot start polymerase is used. In some embodiments, a HotStarTaq DNA polymerase is used (see, for example, QIAGEN catalog No. 203203, see, e.g., information available at the world wide web at qiagen.com/us/products/catalog/assay-technologies/end-point-pcr-and-rt-pcr-reagents/hotstartaq-dna-polymerase/, which is hereby incorporated by reference in its entirety). In some embodiments, AmpliTaq Gold® DNA Polymerase is used; it is a chemically modified form of AmpliTaq® DNA Polymerase requiring thermal activation (see, for example, Applied Biosystems catalog No. N8080241 see, e.g., information available at the world wide web at lifetechnologies.com/order/catalog/product/N8080241, which is hereby incorporated by reference in its entirety). In some embodiments. KAPA Taq DNA Polymerase or KAPA Taq HotStart DNA Polymerase is used, they are based on the single-subunit, wild-type Taq DNA polymerase of the thermophilic bacterium *Thermus aquaticus*. KAPA Taq and KAPA Taq HotStart DNA Polymerase have 5'-3' polymerase and 5'-3' exonuclease activities, but no 3' to 5' exonuclease (proofreading) activity (see, for example, KAPA BIOSYSTEMS catalog No. BK1000 see, e.g., information available at the world wide web at kapabiosystems.com/product-applications/products/pcr-2/kapa-taq-pcr-kits/, which is hereby incorporated by reference in its entirety). In some embodiments, Pfu DNA polymerase is used; it is a highly thermostable DNA polymerase from the hyperthermophilic archaeum *Pyrococcus furiosus*. The enzyme catalyzes the template-dependent polymerization of nucleotides into duplex DNA in the 5'→3' direction Pfu DNA Polymerase also exhibits 3'→5' exonuclease (proofreading) activity that enables the polymerase to correct nucleotide incorporation errors. It has no 5'→3' exonuclease activity (see, for example, Thermo Scientific catalog No. EP0501 see, e.g. information available at the world wide web at thermoscientificbio.com/pcr-enzymes-master-mixes-and-reagents/pfu-dna-polymerase/, which is hereby incorporated by reference in its entirety). In some embodiments Klentaq1 is used; it is a Klenow-fragment analog of Taq DNA polymerase, it has no exonuclease or endonuclease activity (see, for example, DNA POLYMERASE TECHNOLOGY, Inc, St. Louis, Mo., catalog No. 100 see, e.g., information available at the world wide web at klentaq.com/products/klentaq, which is hereby incorporated by reference in its entirety). In some embodiments, the polymerase is a PUSHION DNA polymerase, such as PHUSION High Fidelity DNA polymerase (M0530S, New England BioLabs, Inc.) or PHUSION Hot Start Flex DNA polymerase (M0535S, New England BioLabs. Inc.; Frey and Suppman *BioChemica*. 2:34-35, 1995; Chester and Marshak *Analytical Biochemistry* 209:284-290, 1993, which are each hereby incorporated by reference in its entirety). In some embodiments, the polymerase is a Q5® DNA Polymerase, such as Q5' High-Fidelity DNA Polymerase (M0491S, New England BioLabs, Inc) or Q5® Hot Start High-Fidelity DNA Polymerase (M0493S, New England BioLabs, Inc.). In some embodiments, the polymerase is a T4 DNA polymerase (M0203S. New England BioLabs, Inc., Tabor and Struh, (1989). "DNA-Dependent DNA Polymerases," In Ausebel et al. (Ed.), *Current Protocols in Molecular Biology*. 3.5.10-3.5.12. New York: John Wiley & Sons, Inc., 1989, Sambrook et al. *Molecular Cloning: A laboratory Manual*. (2nd ed.), 5.44-5.47. Cold Spring Harbor: Cold Spring Harbor Laboratory Press, 1989, which are each hereby incorporated by reference in its entirety).

In some embodiment, between 5 and 600 Units/mL (Units per 1 mL of reaction volume) of polymerase is used, such as between 5 to 100, 100 to 200, 200 to 300, 300 to 400, 400 to 500, or 500 to 600 Units/mL, inclusive. One unit is commonly defined as the amount of enzyme that will incorporate 15 nmol of dNTP into acid-insoluble material in 30 minutes at 75° C. Exemplary assay conditions for measuring unit activity include 1×THERMOPOL Reaction Buffer, 200 µM dNTPs including [$^3$H]-dTTP and 200 µg/ml activated Calf Thymus DNA (see, e.g., information available at the world wide web at neb.com/products/m0267-taq-dna-polymerase-with-thermopol-buffer, which is hereby incorporated by reference in its entirety). 1× THERMOPOL® Reaction Buffer contains 20 mM Tris-HCl, 10 mM (NH$_4$)$_2$SO$_4$, 10 mM KCl, 2 mM MgSO$_4$, and 0.1% TRITON® X-100, pH 8.8.

In some embodiments, hot-start PCR is used to reduce or prevent polymerization prior to PCR thermocycling. Exemplary hot-start PCR methods include initial inhibition of the DNA polymerase, or physical separation of reaction components reaction until the reaction mixture reaches the higher temperatures. In some embodiments, the enzyme is spatially separated from the reaction mixture by wax that melts when the reaction reaches high temperature. In some embodiments, slow release of magnesium is used DNA polymerase requires magnesium ions for activity, so the magnesium is chemically separated from the reaction by binding to a chemical compound, and is released into the solution only at high temperature. In some embodiments, non-covalent binding of an inhibitor is used. In this method a peptide, antibody, or aptamer are non-covalently bound to the enzyme at low temperature and inhibit its activity. After incubation at elevated temperature, the inhibitor is released and the reaction starts. In some embodiments, a cold-sensitive Taq polymerase is used, such as a modified DNA polymerase with almost no activity at low temperature. In some embodiments, chemical modification is used. In this method, a molecule is covalently bound to the side chain of an amino acid in the active site of the DNA polymerase. The molecule is released from the enzyme by incubation of the reaction mixture at elevated temperature. Once the molecule is released, the enzyme is activated.

In some embodiments, the amount to template nucleic acids (such as an RNA or DNA sample) is between 20 and 5,000 ng, such as between 20 to 200, 200 to 400, 400 to 600, 600 to 1,000; 1,000 to 1,500; or 2,000 to 3,000 ng, inclusive.

In some embodiments QIAGEN Multiplex PCR Kit is used (QIAGEN catalog No. 206143, see, e.g., information available at the world wide web at qiagen.com/products/catalog/assay-technologies/end-point-pcr-and-rt-pcr-reagents/qiagen-multiplex-pcr-kit, which is hereby incorporated by reference in its entirety). For 100×50 µl multiplex PCR reactions, the kit includes 2×QIAGEN Multiplex PCR Master Mix (providing a final concentration of 3 mM MgCl$_2$, 3×0.85 ml), 5× Q-Solution (1×2.0 ml), and RNase-Free Water (2×1.7 ml). The QIAGEN Multiplex PCR Master Mix (MM) contains a combination of KCl and (NH$_4$)$_2$SO$_4$ as well as the PCR additive, Factor MP, which increases the local concentration of primers at the template. Factor MP stabilizes specifically bound primers, allowing efficient primer extension by HotStarTaq DNA Polymerase. HotStarTaq DNA Polymerase is a modified form of Taq DNA polymerase and has no polymerase activity at ambient temperatures. In some embodiments, HotStarTaq DNA Polymerase is activated by a 15-minute incubation at 95° C. which can be incorporated into any existing thermal-cycler program.

In some embodiments, 1×QIAGEN MM final concentration (the recommended concentration), 7.5 nM of each primer in the library, 50 mM TMAC, and 7 ul DNA template in a 20 ul final volume is used. In some embodiments, the PCR thermocycling conditions include 95° C. for 10 minutes (hot start); 20 cycles of 96° C. for 30 seconds; 65° C. for 15 minutes; and 72° C. for 30 seconds, followed by 72° C. for 2 minutes (final extension); and then a 4° C. hold.

In some embodiments, 2×QIAGEN MM final concentration (twice the recommended concentration), 2 nM of each primer in the library, 70 mM TMAC, and 7 ul DNA template in a 20 ul total volume is used. In some embodiments, up to 4 mM EDTA is also included. In some embodiments, the PCR thermocycling conditions include 95° C. for 10 minutes (hot start); 25 cycles of 96° C. for 30 seconds; 65° C. for 20 minutes; and 72° C. for 30 seconds); followed by 72° C. for 2 minutes (final extension); and then a 4° C. hold.

Another exemplary set of PCR thermocycling conditions includes 95° C. for 10 minutes, 15 cycles of 95° C. for 30 seconds, 65° C. for 1 minute, 60° C. for 5 minutes, 65° C. for 5 minutes and 72° C. for 30 seconds; and then 72° C. for 2 minutes. In some embodiments, this set of PCR thermocycling conditions is used with the following reaction conditions: 100 mM KCl, 50 mM (Nh$_4$)$_2$SO$_4$. 3 mM MgCl$_2$, 7.5 nM of each primer in the library, 50 mM TMAC, and 7 ul DNA template in a 20 ul final volume at pH 8.1.

Another exemplary set of conditions includes a semi-nested PCR approach. The first PCR reaction uses 20 ul a reaction volume with 2×QIAGEN MM final concentration, 1.875 nM of each primer in the library (outer forward and reverse primers), and DNA template. Thermocycling parameters include 95° C. for 10 minutes; 25 cycles of 96° C. for 30 seconds, 65° C. for 1 minute, 58° C. for 6 minutes, 60° C. for 8 minutes, 65° C. for 4 minutes, and 72° C. for 30 seconds; and then 72° C. for 2 minutes, and then a 4° C. hold. Next, 2 ul of the resulting product, diluted 1:200, is as input in a second PCR reaction. This reaction uses a 10 ul reaction volume with 1×QIAGEN MM final concentration, 20 nM of each inner forward primer, and 1 uM of reverse primer tag. Thermocycling parameters include 95° C. for 10 minutes; 15 cycles of 95° C. for 30 seconds, 65° C. for 1 minute, 60° C. for 5 minutes, 65° C. for 5 minutes, and 72° C. for 30 seconds; and then 72° C. for 2 minutes, and then a 4° C. hold.

Any of the methods disclosed herein or any standard methods can be used to test a primer library to determine, e.g., the percent of primer dimers, percent of target amplicons, and percent of target loci that are amplified. In some embodiments, the PCR products are sequenced as described in Experiment 15 or using standard sequencing methods. In some embodiments, the percentage of primer dimers can be determined by measuring the number of sequencing reads from primer dimers, the percentage of amplified products that are target amplicons can be determined by measuring the number of sequencing reads that map to target loci; the percent of target loci that are amplified can be determined by measuring the number of target loci for which there are sequencing reads that map to the target loci; the number of copies of a particular amplified target loci can be determined based on the number of sequencing reads that map to that target loci (such as by comparing the number of sequencing reads compared to the sequences reads from a standard of known concentration or amount).

Figure 49:
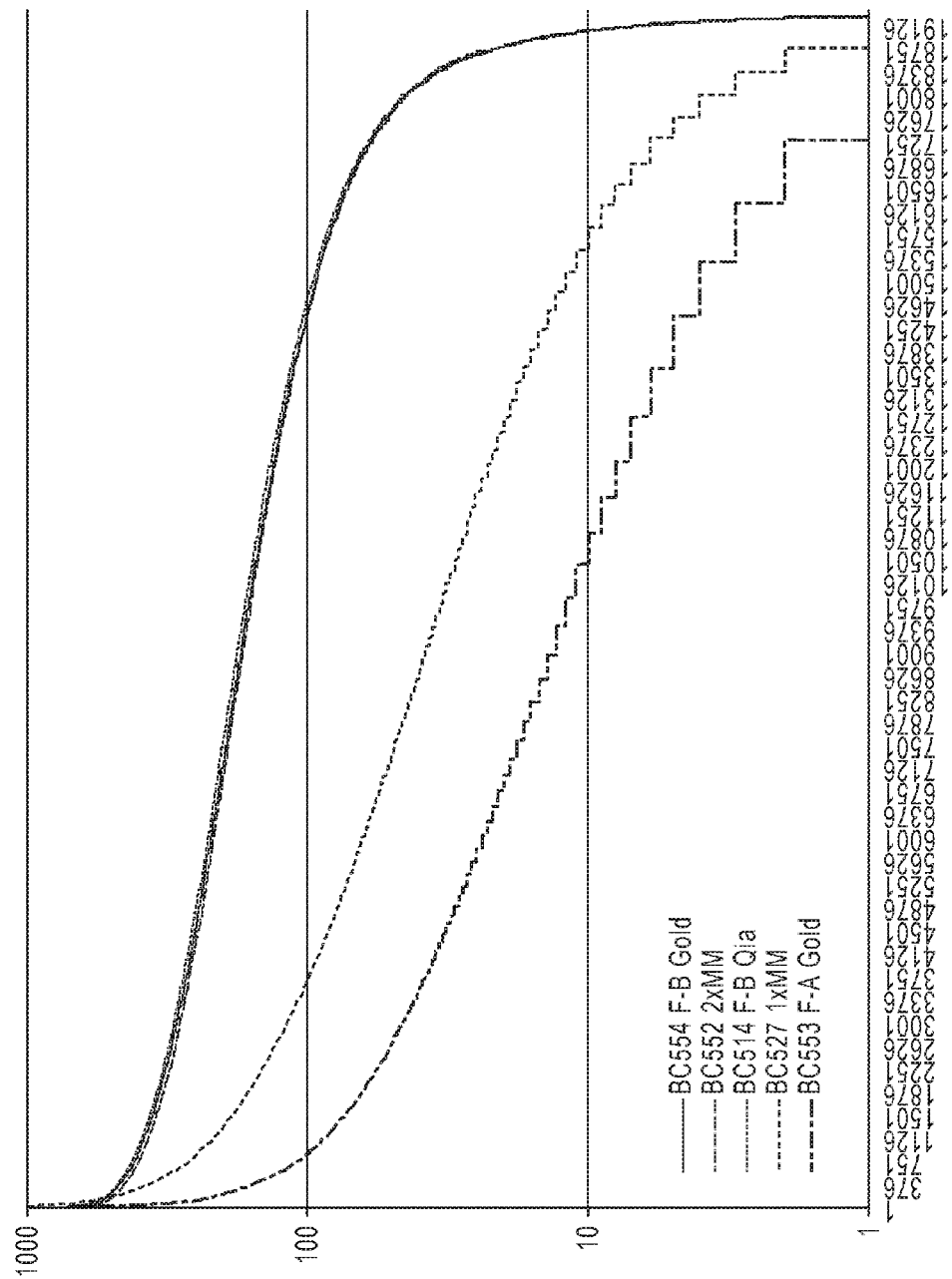
FIG. 49 is a graph illustrating the uniformity in DOR for multiplex PCR with buffers from FIG. 48.
Figure 50:
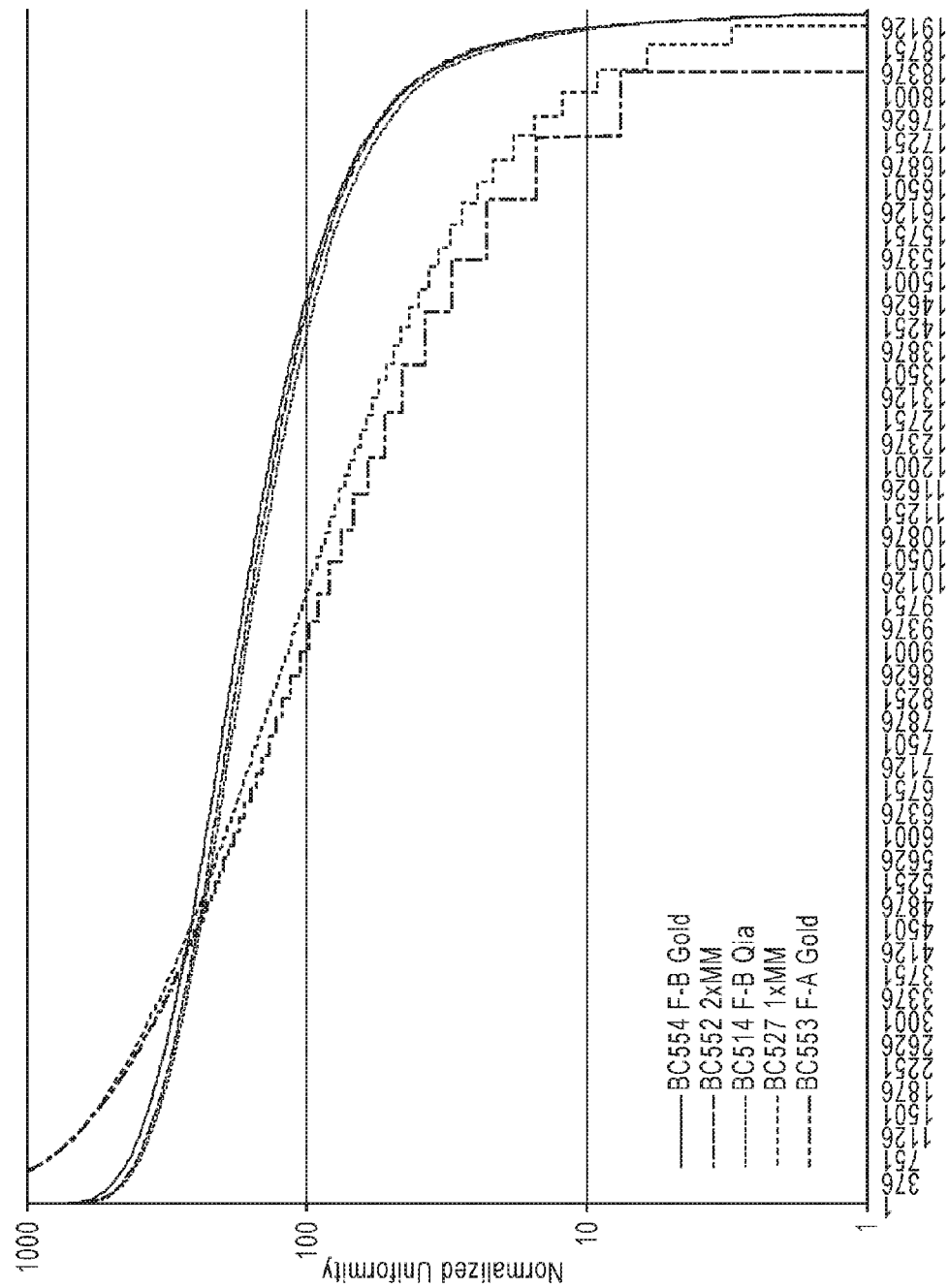
FIG. 50 is a graph illustrating the normalized depth of read (DOR) for multiplex PCR with buffers from FIG. 48 with the DOR normalized to that of buffer 2×MM.

FIG. 48 contains data (such as percent mapped reads and error rate) from multiplex PCR with various buffers. In this figure, "1×MM" denotes 1×QIAGEN Master Mix (the recommended concentration) discussed above, and "2×MM" denotes 2×QIAGEN Master Mix (twice the recommended concentration). FIG. 48 also lists the components of buffer F-A (also called F-A Gold), F-B (also called F-B Gold), F-D, and F-J (also called F-B Qiagen or F-B Qia) as well as the amount and type of polymerase used to generate the data. FIG. 49 is a graph illustrating the uniformity in DOR for multiplex PCR with buffers from FIG. 48. FIG. 50 is a graph illustrating the normalized depth of read (DOR) for multiplex PCR with buffers from FIG. 48 with the DOR normalized to that of buffer 2×MM.

Limit of Detection

In some embodiments, a limit of detection of a mutation (such as an SNV or CNV) of a method of the invention is less than or equal to 10, 5, 2, 1, 0.5, 0.1, 0.05, 0.01, or 0.005%. In some embodiments, a limit of detection of a mutation (such as an SNV or CNV) of a method of the invention is between 15 to 0.005%, such as between 10 to 0.005%, 10 to 0.01%, 10 to 0.1%, 5 to 0.005%, 5 to 0.01%, 5 to 0.1%, 1 to 0.005%, 1 to 0.01%, 1 to 0.1%, 0.5 to 0.005%, 0.5 to 0.01%, 0.5 to 0.1%, or 0.1 to 0.01%, inclusive.

In some embodiments, a limit of detection is such that a mutation (such as an SNV or CNV) that is present in less than or equal to 10, 5, 2, 1, 0.5, 0.1, 0.05, 0.01, or 0.005% of the DNA or RNA molecules with that locus in a sample (such as a sample that has undergone PCR amplification with any of the methods of the invention, such as a sample of PCR-amplified cfDNA or cfRNA) is detected (or is capable of being detected). For example, the mutation can be detected even if less than or equal to 10, 5, 2, 1, 0.5, 0.1, 0.05, 0.01, or 0.005% of the DNA or RNA molecules that have that locus have that mutation in the locus (instead of, for example, a wild-type or non-mutated version of the locus or a different mutation at that locus). In some embodiments, a limit of detection is such that a mutation (such as an SNV or CNV) that is present in less than or equal to 10, 5, 2, 1, 0.5, 0.1, 0.05, 0.01, or 0.005% of the DNA or RNA molecules in a sample (such as a sample that has undergone PCR amplification with any of the methods of the invention, such as a sample of PCR-amplified cfDNA or cfRNA) is detected (or is capable of being detected). In some embodiments in which the CNV is a deletion, the deletion can be detected even if it is only present in less than or equal to 10, 5, 2, 1, 0.5, 0.1, 0.05, 0.01, or 0.005% of the DNA or RNA molecules that have a region of interest that may or may not contain the deletion in a sample. In some embodiments in which the CNV is a deletion, the deletion can be detected even if it is only present in less than or equal to 10, 5, 2, 1, 0.5, 0.1, 0.05, 0.01, or 0.005% of the DNA or RNA molecules in a sample. In some embodiments in which the CNV is a duplication, the duplication can be detected even if the extra duplicated DNA or RNA that is present is less than or equal to 10, 5, 2, 1, 0.5, 0.1, 0.05, 0.01, or 0.005% of the DNA or RNA molecules that have a region of interest that may or may not be duplicated in a sample (such as a sample that has undergone PCR amplification, such as a sample of PCR-amplified cfDNA or cfRNA from, e.g., a blood sample). In some embodiments in which the CNV is a duplication, the duplication can be detected even if the extra duplicated DNA or RNA that is present is less than or equal to 10, 5, 2, 1, 0.5, 0.1, 0.05, 0.01, or 0.005% of the DNA or RNA molecules in a sample (such as a sample that has undergone PCR amplification, such as a sample of PCR-amplified cfDNA or cfRNA from, e.g., a blood sample) is detected (or is capable of being detected). In some embodiments, a mutation (such as an SNV or CNV) that is present in less than 1,000, 500, 100, 50, 20, 10, 5, 4, 3, or 2 DNA or RNA molecules after PCR amplification with any of the methods of the invention in a sample (such as a sample that has undergone PCR amplification, such as a sample of PCR-amplified cfDNA or cfRNA from, e.g., a blood sample) is detected (or is capable of being detected). In some embodiments, a mutation (such as an SNV or CNV) that is present in less than 1,000, 500, 100, 50, 20, 10, 5, 4, 3, or 2 original DNA or RNA molecules (before amplification) in a sample (such as a sample of cfDNA or cfRNA from, e.g., a blood sample) is detected (or is capable of being detected). In some embodiments, a mutation (such as an SNV or CNV) that is present in only 1 original DNA or RNA molecule (before amplification) in a sample (such as a sample of cfDNA or cfRNA from, e.g., a blood sample) is detected (or is capable of being detected). Experiment 23 provides exemplary methods for calculating the limit of detection. In some embodiments, the "LOD-zs5.0-mr5" method of Experiment 23 is used.

Exemplary Nucleic Acid Samples

In some embodiments, the genetic sample may be prepared and/or purified. There are a number of standard procedures known in the art to accomplish such an end. In some embodiments, the sample may be centrifuged to separate various layers. In some embodiments, the DNA may be isolated using filtration. In some embodiments, the preparation of the DNA may involve amplification, separation, purification by chromatography, liquid separation, isolation, preferential enrichment, preferential amplification, targeted amplification, or any of a number of other techniques either known in the art or described herein.

In some embodiments, a method disclosed herein could be used in situations where there is a very small amount of DNA present, such as in in vitro fertilization, or in forensic situations, where one or a few cells are available (typically less than ten cells, less than twenty cells or less than 40 cells.) In these embodiments, a method disclosed herein serves to make ploidy calls from a small amount of DNA that is not contaminated by other DNA, but where the ploidy calling very difficult the small amount of DNA. In some embodiments, a method disclosed herein could be used in situations where the target DNA is contaminated with DNA of another individual, for example in maternal blood in the context of prenatal diagnosis, paternity testing, or products of conception testing. Some other situations where these methods would be particularly advantageous would be in the case of cancer testing where only one or a small number of cells were present among a larger amount of normal cells. The genetic measurements used as part of these methods could be made on any sample comprising DNA or RNA, for example but not limited to: blood, plasma, body fluids, urine, hair, tears, saliva, tissue, skin, fingernails, blastomeres, embryos, fetal cells, amniotic fluid, chorionic villus samples, feces, bile, lymph, cervical mucus, semen, or other cells or materials comprising nucleic acids. In an embodiment, a method disclosed herein could be run with nucleic acid detection methods such as sequencing, microarrays, qPCR, digital PCR, or other methods used to measure nucleic acids. If for some reason it were found to be desirable, the ratios of the allele count probabilities at a locus could be calculated, and the allele ratios could be used to determine ploidy state in combination with some of the methods described herein, provided the methods are compatible. In some embodiments, a method disclosed herein involves calculating, on a computer, allele ratios at the plurality of polymorphic loci from the DNA measurements made on the processed samples. In some embodiments, a method disclosed herein involves calculating, on a computer, allele ratios at the plurality of polymorphic loci from the DNA measurements made on the processed samples along with any combination of other improvements described in this disclosure. Exemplary methods for isolating fetal cells, such as a single fetal cell are disclosed in U.S. Ser. No. 61/978,648, filed Apr. 11, 2014 and U.S. Ser. No. 61/984,546, filed Apr. 25, 2014. Fetal cells or fetal nucleic acids can be isolated from a pregnant mother using invasive (such as CVS or amniocentesis) or noninvasive methods (such as from a maternal blood sample).

In some embodiments, this method may be used to genotype a single cell, a small number of cells, two to five cells, six to ten cells, ten to twenty cells, twenty to fifty cells, fifty to one hundred cells, one hundred to one thousand cells, or a small amount of extracellular DNA, for example from one to ten picograms, from ten to one hundred pictograms, from one hundred pictograms to one nanogram, from one to ten nanograms, from ten to one hundred nanograms, from 30 to 500 nanograms, or from one hundred nanograms to one microgram. In some embodiments, nucleic acids (such as DNA and/or RNA) from less than 100, 75, 50, 40, 30, 20, 10, 8, 6, 4, 2, or 1 cell is amplified with any of the methods of the invention. In some embodiments, the nucleic acid sample includes less than 80, 60, 40, 20, or 10% of the nucleic acids (such as DNA and/or RNA) from a single cell. In some embodiments, in which a small number of cells (such as one cell) or a small amount of nucleic acids is used, nested PCR such as hemi-nested or semi-nested PCR is used and/or the number of PCR cycles is increased compare to that used for samples with a larger amount of cells or nucleic acids. In some embodiments, a large amount of cells or nucleic acids are used (such as in cases in which a larger amount is desired to improve performance of any of the methods of the invention. In some embodiments, a sample with at least 2, 5, 10, 15, 20, 30, 50, 100, or more cells (or DNA or RNA from such cells) is used in any of the methods of the invention. In some embodiments, at least 0.5, 1, 10, 25, 50, 100, 500, 1,000; or 5,000 ng of DNA or RNA is used.

In some embodiments, the cells in the sample are lysed prior to PCR. In some embodiments, the Arcturus PicoPure DNA extraction kit from Applied Biosystems is used. (Applied Biosystems cat No KIT0103, see, e.g., information available at the world wide web at lifetechnologies.com/order/catalog/product/KIT0103?ICID=search-product, which is hereby incorporated by reference in its entirety). This kit contains Arcturus reconstitution buffer and Protease K. In some embodiments, the following cell lysis thermocycling protocol is used 56° C. for 1 hour, 95° C. for 10 minutes, 25° C. for 15 minutes, and then a 4° C. hold.

In some embodiments, the nucleic acids are processed using the consecutive steps of end-repairing, dA-tailing, and adaptor ligating the nucleic acids. The consecutive steps exclude purifying the end-repaired products prior to the dA-tailing step and exclude purifying the dA-tailing products prior to the adaptor ligating step. The resulting products are amplified in any of the multiplex PCR methods of the invention. In some embodiments, the amplified products are then sequenced.

Exemplary Nucleic Acid Studies

The multiplex PCR methods of the invention can be used to increase the number of target loci that can be evaluated to measure the amount of one or more specific nucleic acid molecules of interest or of one or more types of nucleic acids. In some embodiments, there is a change in the total amount or concentration of one or more types of DNA (such as cfDNA cf mDNA, cf nDNA, cellular DNA, or mitochondrial DNA) or RNA (cfRNA, cellular RNA, cytoplasmic RNA, coding cytoplasmic RNA, non-coding cytoplasmic RNA, mRNA, miRNA, mitochondrial RNA, rRNA, or tRNA). In some embodiments, there is a change in the amount or concentration of one or more specific DNA (such as cfDNA cf mDNA, cf nDNA, cellular DNA, or mitochondrial DNA) or RNA (cfRNA, cellular RNA, cytoplasmic RNA, coding cytoplasmic RNA, non-coding cytoplasmic RNA, mRNA, miRNA, mitochondrial RNA, rRNA, or tRNA) molecules. In some embodiments, one allele is expressed more than another allele of a locus of interest. Exemplary miRNAs are short 20-22 nucleotide RNA molecules that regulate the expression of a gene. In some embodiments, there is a change in the transcriptome, such as a change in the identity or amount of one or more RNA molecules.

In some embodiments, an increase in the total amount or concentration of cfDNA or cfRNA is associated with a disease such as cancer, or an increased risk for a disease such as cancer. In some embodiments, the total concentration of a type of DNA (such as cfDNA cf mDNA, cf nDNA, cellular DNA, or mitochondrial DNA) or RNA (cfRNA, cellular RNA, cytoplasmic RNA, coding cytoplasmic RNA, non-coding cytoplasmic RNA. mRNA, miRNA, mitochondrial RNA, rRNA, or tRNA) increases by at least 2, 3, 4, 5, 6, 7, 8, 9, 10-fold, or more compared to the total concentration of that type of DNA or RNA in healthy (such as non-cancerous) subjects. In some embodiments, a total concentration of cfDNA between 75 to 100 ng/mL, 100 to 150 ng/mL, 150 to 200 ng/mL, 200 to 300 ng/mL, 300 to 400 ng/mgL, 400 to 600 ng/mL, 600 to 800 ng/mL, 800 to 1,000 ng/mL, inclusive, or a total concentration of cfDNA of more than 100 ng, mL, such as more than 200, 300, 400, 500, 600, 700, 800, 900, or 1,000 ng/mL is indicative of cancer, an increased risk for cancer, an increased risk of a tumor being malignant rather than benign, a decreased probably of the cancer going into remission, or a worse prognosis for the cancer. In some embodiments, the amount of a type of DNA (such as cfDNA cf mDNA, cf nDNA, cellular DNA, or mitochondrial DNA) or RNA (cfRNA, cellular RNA, cytoplasmic RNA, coding cytoplasmic RNA, non-coding cytoplasmic RNA, mRNA, miRNA, mitochondrial RNA, rRNA, or tRNA) having one or more polymorphisms/mutations (such as deletions or duplications) associated with a disease such as cancer or an increased risk for a disease such as cancer is at least 2, 3, 4, 5, 6, 7, 8, 9, 10, 11, 12, 14, 16, 18, 20, or 25% of the total amount of that type of DNA or RNA. In some embodiments, at least 2, 3, 4, 5, 6, 7, 8, 9, 10, 11, 12, 14, 16, 18, 20, or 25% of the total amount of a type of DNA (such as cfDNA cf mDNA, cf nDNA, cellular DNA, or mitochondrial DNA) or RNA (cfRNA, cellular RNA, cytoplasmic RNA, coding cytoplasmic RNA, non-coding cytoplasmic RNA, mRNA, miRNA, mitochondrial RNA, rRNA, or tRNA) has a particular polymorphism or mutation (such as a deletion or duplication) associated with a disease such as cancer or an increased risk for a disease such as cancer.

Exemplary RNA Expression Studies

The multiplex PCR methods of the invention can be used to increase the number of target loci that can be evaluated during gene expression profiling experiments. For example, the expression levels of thousands of genes can be simultaneously monitored to determine whether a person has a sequence (such as a polymorphism or other mutation) associated with a disease (such as cancer) or an increased risk of a disease. These methods can be used to identify sequences (such as polymorphisms or other mutations) associated with an increased or decreased risk for a disease such as cancer by comparing gene expression (such as the expression of particular mRNA alleles) in samples from patients with and without the disease. Additionally, the effect of particular treatments, diseases, or developmental stages on gene expression can be determined. Similarly, these methods can be used to identify genes whose expression is changed in response to pathogens or other organisms by comparing gene expression in infected and uninfected cells or tissues. In these methods the number of sequencing reads can be adjusted based on the frequency of the polymorphisms that are being analyzed such that sufficient reads are performed for the polymorphisms to be detected if they are present. In some embodiments, the polymorphisms or mutation is present at a higher frequency in subjects with a disease or disorder (such as cancer) than subjects without the disease or disorder (such as cancer). In some embodiments, the polymorphisms or mutation is indicative of cancer, such as a causative mutation.

In some embodiments, a sample containing RNA (such as mRNA) is amplified using a reverse transcriptase (RT) and the resulting DNA (such as cDNA) is then amplified using a DNA polymerase (PCR). The RT and PCR steps may be carried out sequentially in the same reaction volume or separately. Any of the primer libraries of the invention can be used in this reverse transcription polymerase chain reaction (RT-PCR) method. In various embodiments, the reverse transcription is performed using oligo-dT, random primers, a mixture of oligo-dT and random primers, or primers specific to the target loci. To avoid amplification of contaminating genomic DNA, primers for RT-PCR can be designed so that part of one primer hybridizes to the 3' end of one exon and the other part of the primer hybridizes to the 5' end of the adjacent exon. Such primers anneal to cDNA synthesized from spliced mRNAs, but not to genomic DNA. To detect amplification of contaminating DNA, RT-PCR primer pairs may be designed to flank a region that contains at least one intron. Products amplified from cDNA (no introns) are smaller than those amplified from genomic DNA (containing introns). Size difference in products is used to detect the presence of contaminating DNA. In some embodiments when only the mRNA sequence is known, primer annealing sites are chosen that are at least 300-400 base pairs apart since it is likely that fragments of this size from eukaryotic DNA contain splice junctions. Alternatively, the sample can be treated with DNase to degrade contaminating DNA.

Exemplary Methods for Paternity Testing

The multiplex PCR methods of the invention can be used to improve the accuracy of paternity testing since so many target loci can be analyzed at once (see, e.g. U.S. Publication No. 2012/0122701, filed Dec. 22, 2011, is which is hereby incorporated by reference in its entirety). For example, the multiplex PCR method can allow thousands of polymorphic loci (such as SNPs) to be analyzed for use in the PARENTAL SUPPORT algorithm described herein to determine whether an alleged father in is the biological father of a fetus. In some embodiments the method involves (i) simultaneously amplifying a plurality of polymorphic loci that includes at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different polymorphic loci on genetic material from the alleged father to produce a first set of amplified products; (ii) simultaneously amplifying the corresponding plurality of polymorphic loci on a mixed sample of DNA originating from a blood sample from the pregnant mother to produce a second set of amplified products wherein the mixed sample of DNA comprises fetal DNA and maternal DNA; (iii) determining on a computer the probability that the alleged father is the biological father of the fetus using genotypic measurements based on the first and second sets of amplified products; and (iv) establishing whether the alleged father is the biological father of the fetus using the determined probability that the alleged father is the biological father of the fetus. In various embodiments, the method further includes simultaneously amplifying the corresponding plurality of polymorphic loci on genetic material from the mother to produce a third set of amplified products; wherein the probability that the alleged father is the biological father of the fetus is determined using genotypic measurements based on the first, second, and third sets of amplified products.

Exemplary Methods for Embryo Characterization and Selection

The multiplex PCR methods of the invention can be used to improve the selection of embryos for in vitro fertilization by allowing thousands of target loci to be analyzed at once (see. e.g. U.S. Pub. No 2011/0092763, filed May 27, 2008, filed Dec. 22, 2011, is which is hereby incorporated by reference in its entirety). For example, the multiplex PCR method can allow thousands of polymorphic loci (such as SNPs) to be analyzed for use in the PARENTAL SUPPORT algorithm described herein to select an embryo out of a set of embryos for in vitro fertilization.

In some embodiments, the invention provides methods of estimating relative likelihoods that each embryo from a set of embryos will develop as desired. In some embodiments, the method involves contacting a sample from each embryo with a library of primers that simultaneously hybridize to at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci to produce a reaction mixture for each embryo, wherein the samples are each derived from one or more cells from an embryo. In some embodiments, each reaction mixture is subjected to primer extension reaction conditions to produce amplified products. In some embodiments, the method includes determining on a computer one or more characteristics of at least one cell from each embryo based on the amplified products; and estimating on a computer the relative likelihoods that each embryo will develop as desired, based on the one or more characteristics of the at least one cell for each embryo. In some embodiments, the method includes using an informatics based method to determine the at least one characteristic, such as the PARENTAL SUPPORT algorithm described herein. In some embodiments, the characteristic includes a ploidy state. In some embodiments, the characteristic is selected from the group consisting of aneuploid, euploid, mosaic, nullsomy, monosomy, uniparental disomy, trisomy, tetrasomy, a type of aneuploidy, unmatched copy error trisomy, matched copy error trisomy, maternal origin of aneuploidy, paternal origin of aneuploidy, a presence or absence of a disease-linked gene, a chromosomal identity of any aneuploid chromosome, an abnormal genetic condition, a deletion or duplication, a likelihood of a characteristic, and combinations thereof. The characteristic may be associated with a chromosome taken from the group consisting of chromosome one, chromosome two, chromosome three, chromosome four, chromosome five, chromosome six, chromosome seven, chromosome eight, chromosome nine, chromosome ten, chromosome eleven, chromosome twelve, chromosome thirteen, chromosome fourteen, chromosome fifteen, chromosome sixteen, chromosome seventeen, chromosome eighteen, chromosome nineteen, chromosome twenty, chromosome twenty-one, chromosome twenty-two, X chromosome or Y chromosome, and combinations thereof.

Exemplary Prenatal Diagnostic Methods

The multiplex PCR methods of the present invention can be used to improve prenatal diagnostic methods, such as the determination of the ploidy status of fetal chromosomes. Given that the large number of target loci that can be simultaneously amplified, more accurate determinations can be made.

In an embodiment, the present disclosure provides ex vivo methods for determining the ploidy status of a chromosome in a gestating fetus from genotypic data measured from a mixed sample of DNA (i.e., DNA from the mother of the fetus, and DNA from the fetus) and optionally from genotypic data measured from a sample of genetic material from the mother and possibly also from the father, wherein the determining is done by using a joint distribution model to create a set of expected allele distributions for different possible fetal ploidy states given the parental genotypic data, and comparing the expected allelic distributions to the actual allelic distributions measured in the mixed sample, and choosing the ploidy state whose expected allelic distribution pattern most closely matches the observed allelic distribution pattern. In an embodiment, the mixed sample is derived from maternal blood, or maternal serum or plasma. In an embodiment, the mixed sample of DNA may be preferentially enriched at a target loci (e.g., plurality of polymorphic loci). In an embodiment, the preferential enrichment is done in a way that minimizes the allelic bias. In an embodiment, the present disclosure relates to a composition of DNA that has been preferentially enriched at a plurality of loci such that the allelic bias is low. In an embodiment, the allelic distribution(s) are measured by sequencing the DNA from the mixed sample. In an embodiment, the joint distribution model assumes that the alleles will be distributed in a binomial fashion. In an embodiment, the set of expected joint allele distributions are created for genetically linked loci while considering the extant recombination frequencies from various sources, for example, using data from the International HapMap Consortium.

In an embodiment, the present disclosure provides methods for non-invasive prenatal diagnosis (NPD), specifically, determining the aneuploidy status of a fetus by observing allele measurements at a plurality of polymorphic loci in genotypic data measured on DNA mixtures, where certain allele measurements are indicative of an aneuploid fetus, while other allele measurements are indicative of a euploid fetus. In an embodiment, the genotypic data is measured by sequencing DNA mixtures that were derived from maternal plasma. In an embodiment, the DNA sample may be preferentially enriched in molecules of DNA that correspond to the plurality of loci whose allele distributions are being calculated. In an embodiment a sample of DNA comprising only or almost only genetic material from the mother and possibly also a sample of DNA comprising only or almost only genetic material from the father are measured. In an embodiment, the genetic measurements of one or both parents along with the estimated fetal fraction are used to create a plurality of expected allele distributions corresponding to different possible underlying genetic states of the fetus, the expected allele distributions may be termed hypotheses. In an embodiment, the maternal genetic data is not determined by measuring genetic material that is exclusively or almost exclusively maternal in nature, rather, it is estimated from the genetic measurements made on maternal plasma that comprises a mixture of maternal and fetal DNA. In some embodiments the hypotheses may comprise the ploidy of the fetus at one or more chromosomes, which segments of which chromosomes in the fetus were inherited from which parents, and combinations thereof. In some embodiments, the ploidy state of the fetus is determined by comparing the observed allele measurements to the different hypotheses where at least some of the hypotheses correspond to different ploidy states, and selecting the ploidy state that corresponds to the hypothesis that is most likely to be true given the observed allele measurements. In an embodiment, this method involves using allele measurement data from some or all measured SNPs, regardless of whether the loci are homozygous or heterozygous, and therefore does not involve using alleles at loci that are only heterozygous. This method may not be appropriate for situations where the genetic data pertains to only one polymorphic locus. This method is particularly advantageous when the genetic data comprises data for more than ten polymorphic loci for a target chromosome or more than twenty polymorphic loci. This method is especially advantageous when the genetic data comprises data for more than 50 polymorphic loci for a target chromosome, more than 100 polymorphic loci or more than 200 polymorphic loci for a target chromosome. In some embodiments, the genetic data may comprise data for more than 500 polymorphic loci for a target chromosome, more than 1,000 polymorphic loci, more than 2,000 polymorphic loci, or more than 5,000 polymorphic loci for a target chromosome.

In an embodiment, a method disclosed herein yields a quantitative measure of the number of independent observations of each allele at a polymorphic locus. This is unlike most methods such as microarrays or qualitative PCR which provide information about the ratio of two alleles but do not quantify the number of independent observations of either allele. With methods that provide quantitative information regarding the number of independent observations, only the ratio is utilized in ploidy calculations, while the quantitative information by itself is not useful. To illustrate the importance of retaining information about the number of independent observations consider the sample locus with two alleles, A and B. In a first experiment twenty A alleles and twenty B alleles are observed, in a second experiment 200 A alleles and 200 B alleles are observed. In both experiments the ratio (A/(A+B)) is equal to 0.5, however the second experiment conveys more information than the first about the certainty of the frequency of the A or B allele. Some methods by others involve averaging or summing allele ratios (channel ratios) (i.e. $x_i/y_i$) from individual allele and analyzes this ratio, either comparing it to a reference chromosome or using a rule pertaining to how this ratio is expected to behave in particular situations. No allele weighting is implied in such methods, where it is assumed that one can ensure about the same amount of PCR product for each allele and that all the alleles should behave the same way. Such a method has a number of disadvantages, and more importantly, precludes the use a number of improvements that are described elsewhere in this disclosure.

In an embodiment, a method disclosed herein explicitly models the allele frequency distributions expected in disomy as well as a plurality of allele frequency distributions that may be expected in cases of trisomy resulting from nondisjunction during meiosis I, nondisjunction during meiosis II, and/or nondisjunction during mitosis early in fetal development. To illustrate why this is important, imagine a case where there were no crossovers: nondisjunction during meiosis I would result a trisomy in which two different homologs were inherited from one parent; in contrast, nondisjunction during meiosis II or during mitosis early in fetal development would result in two copies of the same homolog from one parent. Each scenario would result in different expected allele frequencies at each polymorphic locus and also at all loci considered jointly, due to genetic linkage. Crossovers, which result in the exchange of genetic material between homologs, make the inheritance pattern more complex; in an embodiment, the instant method accommodates for this by using recombination rate information in addition to the physical distance between loci. In an embodiment, to enable improved distinction between meiosis I nondisjunction and meiosis II or mitotic nondisjunction the instant method incorporate into the model an increasing probability of crossover as the distance from the centromere increases. Meiosis II and mitotic nondisjunction can be distinguished by the fact that mitotic nondisjunction typically results in identical or nearly identical copies of one homolog while the two homologs present following a meiosis II nondisjunction event often differ due to one or more crossovers during gametogenesis.

In some embodiments, a method disclosed herein involves comparing the observed allele measurements to theoretical hypotheses corresponding to possible fetal genetic aneuploidy, and does not involve a step of quantitating a ratio of alleles at a heterozygous locus. Where the number of loci is lower than about 20, the ploidy determination made using a method comprising quantitating a ratio of alleles at a heterozygous locus and a ploidy determination made using a method comprising comparing the observed allele measurements to theoretical allele distribution hypotheses corresponding to possible fetal genetic states may give a similar result. However, where the number of loci is above 50 these two methods is likely to give significantly different results; where the number of loci is above 400, above, 1,000 or above 2,000 these two methods are very likely to give results that are increasingly significantly different. These differences are due to the fact that a method that comprises quantitating a ratio of alleles at a heterozygous locus without measuring the magnitude of each allele independently and aggregating or averaging the ratios precludes the use of techniques including using a joint distribution model, performing a linkage analysis, using a binomial distribution model, and/or other advanced statistical techniques, whereas using a method comprising comparing the observed allele measurements to theoretical allele distribution hypotheses corresponding to possible fetal genetic states may use these techniques which can substantially increase the accuracy of the determination.

In an embodiment, a method disclosed herein involves determining whether the distribution of observed allele measurements is indicative of a euploid or an aneuploid fetus using a joint distribution model. The use of a joint distribution model is a different from and a significant improvement over methods that determine heterozygosity rates by treating polymorphic loci independently in that the resultant determinations are of significantly higher accuracy. Without being bound by any particular theory, it is believed that one reason they are of higher accuracy is that the joint distribution model takes into account the linkage between SNPs, and likelihood of crossovers having occurred during the meiosis that gave rise to the gametes that formed the embryo that grew into the fetus. The purpose of using the concept of linkage when creating the expected distribution of allele measurements for one or more hypotheses is that it allows the creation of expected allele measurements distributions that correspond to reality considerably better than when linkage is not used. For example, imagine that there are two SNPs, 1 and 2 located nearby one another, and the mother is A at SNP 1 and A at SNP 2 on one homolog, and B at SNP 1 and B at SNP 2 on homolog two. If the father is A for both SNPs on both homologs, and a B is measured for the fetus SNP 1, this indicates that homolog two has been inherited by the fetus, and therefore that there is a much higher likelihood of a B being present on the fetus at SNP 2. A model that takes into account linkage would predict this, while a model that does not take linkage into account would not. Alternately, if a mother was AB at SNP 1 and AB at nearby SNP 2, then two hypotheses corresponding to maternal trisomy at that location could be used—one involving a matching copy error (nondisjunction in meiosis II or mitosis in early fetal development), and one involving an unmatching copy error (nondisjunction in meiosis I). In the case of a matching copy error trisomy, if the fetus inherited an AA from the mother at SNP 1, then the fetus is much more likely to inherit either an AA or BB from the mother at SNP 2, but not AB. In the case of an unmatching copy error, the fetus would inherit an AB from the mother at both SNPs. The allele distribution hypotheses made by a ploidy calling method that takes into account linkage would make these predictions, and therefore correspond to the actual allele measurements to a considerably greater extent than a ploidy calling method that did not take into account linkage. Note that a linkage approach is not possible when using a method that relies on calculating allele ratios and aggregating those allele ratios.

One reason that it is believed that ploidy determinations that use a method that comprises comparing the observed allele measurements to theoretical hypotheses corresponding to possible fetal genetic states are of higher accuracy is that when sequencing is used to measure the alleles, this method can glean more information from data from alleles where the total number of reads is low than other methods; for example, a method that relies on calculating and aggregating allele ratios would produce disproportionately weighted stochastic noise. For example, imagine a case that involved measuring the alleles using sequencing, and where there was a set of loci where only five sequence reads were detected for each locus. In an embodiment, for each of the alleles, the data may be compared to the hypothesized allele distribution, and weighted according to the number of sequence reads; therefore the data from these measurements would be appropriately weighted and incorporated into the overall determination. This is in contrast to a method that involved quantitating a ratio of alleles at a heterozygous locus, as this method could only calculate ratios of 0%, 20%, 40%, 60%, 80% or 100% as the possible allele ratios; none of these may be close to expected allele ratios. In this latter case, the calculated allele rations would either have to be discarded due to insufficient reads or else would have disproportionate weighting and introduce stochastic noise into the determination, thereby decreasing the accuracy of the determination. In an embodiment, the individual allele measurements may be treated as independent measurements, where the relationship between measurements made on alleles at the same locus is no different from the relationship between measurements made on alleles at different loci.

In an embodiment, a method disclosed herein involves determining whether the distribution of observed allele measurements is indicative of a euploid or an aneuploid fetus without comparing any metrics to observed allele measurements on a reference chromosome that is expected to be disomic (termed the RC method). This is a significant improvement over methods, such as methods using shotgun sequencing which detect aneuploidy by evaluating the proportion of randomly sequenced fragments from a suspect chromosomes relative to one or more presumed disomic reference chromosome. This RC method yields incorrect results if the presumed disomic reference chromosome is not actually disomic. This can occur in cases where aneuploidy is more substantial than trisomy of a single chromosome or where the fetus is triploid and all autosomes are trisomic. In the case of a female triploid (69, XXX) fetus there are in fact no disomic chromosomes at all. The method described herein does not require a reference chromosome and would be able to correctly identify trisomic chromosomes in a female triploid fetus. For each chromosome, hypothesis, child fraction and noise level, a joint distribution model may be fit, without any of: reference chromosome data, an overall child fraction estimate, or a fixed reference hypothesis.

In an embodiment, a method disclosed herein demonstrates how observing allele distributions at polymorphic loci can be used to determine the ploidy state of a fetus with greater accuracy than methods in the prior art. In an embodiment, the method uses the targeted sequencing to obtain mixed maternal-fetal genotypes and optionally mother and/or father genotypes at a plurality of SNPs to first establish the various expected allele frequency distributions under the different hypotheses, and then observing the quantitative allele information obtained on the maternal-fetal mixture and evaluating which hypothesis fits the data best, where the genetic state corresponding to the hypothesis with the best fit to the data is called as the correct genetic state. In an embodiment, a method disclosed herein also uses the degree of fit to generate a confidence that the called genetic state is the correct genetic state. In an embodiment, a method disclosed herein involves using algorithms that analyze the distribution of alleles found for loci that have different parental contexts, and comparing the observed allele distributions to the expected allele distributions for different ploidy states for the different parental contexts (different parental genotypic patterns). This is different from and an improvement over methods that do not use methods that enable the estimation of the number of independent instances of each allele at each locus in a mixed maternal-fetal sample. In an embodiment, a method disclosed herein involves determining whether the distribution of observed allele measurements is indicative of a euploid or an aneuploid fetus using observed allelic distributions measured at loci where the mother is heterozygous. This is different from and an improvement over methods that do not use observed allelic distributions at loci where the mother is heterozygous because, in cases where the DNA is not preferentially enriched or is preferentially enriched for loci that are not known to be highly informative for that particular target individual, it allows the use of about twice as much genetic measurement data from a set of sequence data in the ploidy determination, resulting in a more accurate determination.

In an embodiment, a method disclosed herein uses a joint distribution model that assumes that the allele frequencies at each locus are multinomial (and thus binomial when SNPs are biallelic) in nature. In some embodiments the joint distribution model uses beta-binomial distributions. When using a measuring technique, such as sequencing, provides a quantitative measure for each allele present at each locus, binomial model can be applied to each locus and the degree underlying allele frequencies and the confidence in that frequency can be ascertained. With methods known in the art that generate ploidy calls from allele ratios, or methods in which quantitative allele information is discarded, the certainty in the observed ratio cannot be ascertained. The instant method is different from and an improvement over methods that calculate allele ratios and aggregate those ratios to make a ploidy call, since any method that involves calculating an allele ratio at a particular locus, and then aggregating those ratios, necessarily assumes that the measured intensities or counts that are indicative of the amount of DNA from any given allele or locus will be distributed in a Gaussian fashion. The method disclosed herein does not involve calculating allele ratios. In some embodiments, a method disclosed herein may involve incorporating the number of observations of each allele at a plurality of loci into a model. In some embodiments, a method disclosed herein may involve calculating the expected distributions themselves, allowing the use of a joint binomial distribution model which may be more accurate than any model that assumes a Gaussian distribution of allele measurements. The likelihood that the binomial distribution model is significantly more accurate than the Gaussian distribution increases as the number of loci increases. For example, when fewer than 20 loci are interrogated, the likelihood that the binomial distribution model is significantly better is low. However, when more than 100, or especially more than 400, or especially more than 1,000, or especially more than 2,000 loci are used, the binomial distribution model will have a very high likelihood of being significantly more accurate than the Gaussian distribution model, thereby resulting in a more accurate ploidy determination. The likelihood that the binomial distribution model is significantly more accurate than the Gaussian distribution also increases as the number of observations at each locus increases. For example, when fewer than 10 distinct sequences are observed at each locus are observed, the likelihood that the binomial distribution model is significantly better is low. However, when more than 50 sequence reads, or especially more than 100 sequence reads, or especially more than 200 sequence reads, or especially more than 300 sequence reads are used for each locus, the binomial distribution model will have a very high likelihood of being significantly more accurate than the Gaussian distribution model, thereby resulting in a more accurate ploidy determination.

In an embodiment, a method disclosed herein uses sequencing to measure the number of instances of each allele at each locus in a DNA sample. Each sequencing read may be mapped to a specific locus and treated as a binary sequence read; alternately, the probability of the identity of the read and/or the mapping may be incorporated as part of the sequence read, resulting in a probabilistic sequence read, that is, the probable whole or fractional number of sequence reads that map to a given loci. Using the binary counts or probability of counts it is possible to use a binomial distribution for each set of measurements, allowing a confidence interval to be calculated around the number of counts. This ability to use the binomial distribution allows for more accurate ploidy estimations and more precise confidence intervals to be calculated. This is different from and an improvement over methods that use intensities to measure the amount of an allele present, for example methods that use microarrays, or methods that make measurements using fluorescence readers to measure the intensity of fluorescently tagged DNA in electrophoretic bands.

In an embodiment, a method disclosed herein uses aspects of the present set of data to determine parameters for the estimated allele frequency distribution for that set of data. This is an improvement over methods that utilize training set of data or prior sets of data to set parameters for the present expected allele frequency distributions, or possibly expected allele ratios. This is because there are different sets of conditions involved in the collection and measurement of every genetic sample, and thus a method that uses data from the instant set of data to determine the parameters for the joint distribution model that is to be used in the ploidy determination for that sample will tend to be more accurate.

In an embodiment, a method disclosed herein involves determining whether the distribution of observed allele measurements is indicative of a euploid or an aneuploid fetus using a maximum likelihood technique. The use of a maximum likelihood technique is different from and a significant improvement over methods that use single hypothesis rejection technique in that the resultant determinations will be made with significantly higher accuracy. One reason is that single hypothesis rejection techniques set cut off thresholds based on only one measurement distribution rather than two, meaning that the thresholds are usually not optimal. Another reason is that the maximum likelihood technique allows the optimization of the cut off threshold for each individual sample instead of determining a cut off threshold to be used for all samples regardless of the particular characteristics of each individual sample. Another reason is that the use of a maximum likelihood technique allows the calculation of a confidence for each ploidy call. The ability to make a confidence calculation for each call allows a practitioner to know which calls are accurate, and which are more likely to be wrong. In some embodiments, a wide variety of methods may be combined with a maximum likelihood estimation technique to enhance the accuracy of the ploidy calls. In an embodiment, the maximum likelihood technique may be used in combination with the method described in U.S. Pat. No. 7,888,017 In an embodiment, the maximum likelihood technique may be used in combination with the method of using targeted PCR amplification to amplify the DNA in the mixed sample followed by sequencing and analysis using a read counting method such as used by TANDEM DIAGNOSTICS, as presented at the International Congress of Human Genetics 2011, in Montreal in October 2011. In an embodiment, a method disclosed herein involves estimating the fetal fraction of DNA in the mixed sample and using that estimation to calculate both the ploidy call and the confidence of the ploidy call. Note that this is both different and distinct from methods that use estimated fetal fraction as a screen for sufficient fetal fraction, followed by a ploidy call made using a single hypothesis rejection technique that does not take into account the fetal fraction nor does it produce a confidence calculation for the call.

In an embodiment, a method disclosed herein takes into account the tendency for the data to be noisy and contain errors by attaching a probability to each measurement. The use of maximum likelihood techniques to choose the correct hypothesis from the set of hypotheses that were made using the measurement data with attached probabilistic estimates makes it more likely that the incorrect measurements will be discounted, and the correct measurements will be used in the calculations that lead to the ploidy call. To be more precise, this method systematically reduces the influence of data that is incorrectly measured on the ploidy determination. This is an improvement over methods where all data is assumed to be equally correct or methods where outlying data is arbitrarily excluded from calculations leading to a ploidy call. Existing methods using channel ratio measurements claim to extend the method to multiple SNPs by averaging individual SNP channel ratios. Not weighting individual SNPs by expected measurement variance based on the SNP quality and observed depth of read reduces the accuracy of the resulting statistic, resulting in a reduction of the accuracy of the ploidy call significantly, especially in borderline cases.

In an embodiment, a method disclosed herein does not presuppose the knowledge of which SNPs or other polymorphic loci are heterozygous on the fetus. This method allows a ploidy call to be made in cases where paternal genotypic information is not available. This is an improvement over methods where the knowledge of which SNPs are heterozygous must be known ahead of time in order to appropriately select loci to target, or to interpret the genetic measurements made on the mixed fetal/maternal DNA sample.

The methods described herein are particularly advantageous when used on samples where a small amount of DNA is available, or where the percent of fetal DNA is low. This is due to the correspondingly higher allele dropout rate that occurs when only a small amount of DNA is available and/or the correspondingly higher fetal allele dropout rate when the percent of fetal DNA is low in a mixed sample of fetal and maternal DNA. A high allele dropout rate, meaning that a large percentage of the alleles were not measured for the target individual, results in poorly accurate fetal fractions calculations, and poorly accurate ploidy determinations. Since methods disclosed herein may use a joint distribution model that takes into account the linkage in inheritance patterns between SNPs, significantly more accurate ploidy determinations may be made. The methods described herein allow for an accurate ploidy determination to be made when the percent of molecules of DNA that are fetal in the mixture is less than 40%, less than 30%, less than 20%, less than 10%, less than 8%, and even less than 6%.

In an embodiment, it is possible to determine the ploidy state of an individual based on measurements when that individual's DNA is mixed with DNA of a related individual. In an embodiment, the mixture of DNA is the free floating DNA found in maternal plasma, which may include DNA from the mother, with known karyotype and known genotype, and which may be mixed with DNA of the fetus, with unknown karyotype and unknown genotype. It is possible to use the known genotypic information from one or both parents to predict a plurality of potential genetic states of the DNA in the mixed sample for different ploidy states, different chromosome contributions from each parent to the fetus, and optionally, different fetal DNA fractions in the mixture. Each potential composition may be referred to as a hypothesis. The ploidy state of the fetus can then be determined by looking at the actual measurements, and determining which potential compositions are most likely given the observed data.

Further discussion of the points above may be found elsewhere in this document.

Non-Invasive Prenatal Diagnosis (NPD)

The process of non-invasive prenatal diagnosis involves a number of steps. Some of the steps may include: (1) obtaining the genetic material from the fetus; (2) enriching the genetic material of the fetus that may be in a mixed sample, ex vivo; (3) amplifying the genetic material, ex vivo; (4) preferentially enriching specific loci in the genetic material, ex vivo, (5) measuring the genetic material, ex vivo; and (6) analyzing the genotypic data, on a computer, and ex vivo. Methods to reduce to practice these six and other relevant steps are described herein. At least some of the method steps are not directly applied on the body. In an embodiment, the present disclosure relates to methods of treatment and diagnosis applied to tissue and other biological materials isolated and separated from the body. At least some of the method steps are executed on a computer.

Some embodiments of the present disclosure allow a clinician to determine the genetic state of a fetus that is gestating in a mother in a non-invasive manner such that the health of the baby is not put at risk by the collection of the genetic material of the fetus, and that the mother is not required to undergo an invasive procedure. Moreover, in certain aspects, the present disclosure allows the fetal genetic state to be determined with high accuracy, significantly greater accuracy than, for example, the non-invasive maternal serum analyte based screens, such as the triple test, that are in wide use in prenatal care.

The high accuracy of the methods disclosed herein is a result of an informatics approach to analysis of the genotype data, as described herein. Modern technological advances have resulted in the ability to measure large amounts of genetic information from a genetic sample using such methods as high throughput sequencing and genotyping arrays. The methods disclosed herein allow a clinician to take greater advantage of the large amounts of data available, and make a more accurate diagnosis of the fetal genetic state. The details of a number of embodiments are given below. Different embodiments may involve different combinations of the aforementioned steps. Various combinations of the different embodiments of the different steps may be used interchangeably.

In an embodiment, a blood sample is taken from a pregnant mother, and the free floating DNA in the plasma of the mother's blood, which contains a mixture of both DNA of maternal origin, and DNA of fetal origin, is isolated and used to determine the ploidy status of the fetus. In an embodiment, a method disclosed herein involves preferential enrichment of those DNA sequences in a mixture of DNA that correspond to polymorphic alleles in a way that the allele ratios and/or allele distributions remain mostly consistent upon enrichment. In an embodiment, a method disclosed herein involves the highly efficient targeted PCR based amplification such that a very high percentage of the resulting molecules correspond to targeted loci. In an embodiment, a method disclosed herein involves sequencing a mixture of DNA that contains both DNA of maternal origin, and DNA of fetal origin. In an embodiment, a method disclosed herein involves using measured allele distributions to determine the ploidy state of a fetus that is gestating in a mother. In an embodiment, a method disclosed herein involves reporting the determined ploidy state to a clinician. In an embodiment, a method disclosed herein involves taking a clinical action, for example, performing follow up invasive testing such as chorionic villus sampling or amniocentesis, preparing for the birth of a trisomic individual or an elective termination of a trisomic fetus.

This application makes reference to U.S. Utility application Ser. No. 11/603,406, filed Nov. 28, 2006 (US Publication No. 20070184467); U.S. Utility application Ser. No. 12/076,348, filed Mar. 17, 2008 (US Publication No.: 20080243398); PCT Application Serial No. PCT/US09/52730, filed Aug. 4, 2009 (PCT Publication No: WO/2010/017214); PCT Application Serial No. PCT/US10/050824, filed Sep. 30, 2010 (PCT Publication No.: WO/2011/041485), U.S. Utility application Ser. No. 13/110,685, filed May 18, 2011, and PCT Application Serial No. PCT/12/58578, filed Oct. 3, 2012, which are each herein incorporated by reference in its entirety. Some of the vocabulary used in this filing may have its antecedents in these references. Some of the concepts described herein may be better understood in light of the concepts found in these references.

Screening Maternal Blood Comprising Free Floating Fetal DNA

The methods described herein may be used to help determine the genotype of a child, fetus, or other target individual where the genetic material of the target is found in the presence of a quantity of other genetic material. In some embodiments the genotype may refer to the ploidy state of one or a plurality of chromosomes, it may refer to one or a plurality of disease linked alleles, or some combination thereof. In this disclosure, the discussion focuses on determining the genetic state of a fetus where the fetal DNA is found in maternal blood, but this example is not meant to limit to possible contexts that this method may be applied to. In addition, the method may be applicable in cases where the amount of target DNA is in any proportion with the non-target DNA; for example, the target DNA could make up anywhere between 0.000001 and 99.999999% of the DNA present. In addition, the non-target DNA does not necessarily need to be from one individual, or even from a related individual, as long as genetic data from some or all of the relevant non-target individual(s) is known. In an embodiment, a method disclosed herein can be used to determine genotypic data of a fetus from maternal blood that contains fetal DNA. It may also be used in a case where there are multiple fetuses in the uterus of a pregnant woman, or where other contaminating DNA may be present in the sample, for example from other already born siblings.

This technique may make use of the phenomenon of fetal blood cells gaining access to maternal circulation through the placental villi. Ordinarily, only a very small number of fetal cells enter the maternal circulation in this fashion (not enough to produce a positive Kleihauer-Betke test for fetal-maternal hemorrhage). The fetal cells can be sorted out and analyzed by a variety of techniques to look for particular DNA sequences, but without the risks that invasive procedures inherently have. This technique may also make use of the phenomenon of free floating fetal DNA gaining access to maternal circulation by DNA release following apoptosis of placental tissue where the placental tissue in question contains DNA of the same genotype as the fetus. The free floating DNA found in maternal plasma has been shown to contain fetal DNA in proportions as high as 30-40% fetal DNA.

In an embodiment, blood may be drawn from a pregnant woman. Research has shown that maternal blood may contain a small amount of free floating DNA from the fetus, in addition to free floating DNA of maternal origin. In addition, there also may be enucleated fetal blood cells comprising DNA of fetal origin, in addition to many blood cells of maternal origin, which typically do not contain nuclear DNA. There are many methods know in the art to isolate fetal DNA, or create fractions enriched in fetal DNA. For example, chromatography has been show to create certain fractions that are enriched in fetal DNA.

Once the sample of maternal blood, plasma, or other fluid, drawn in a relatively non-invasive manner, and that contains an amount of fetal DNA, either cellular or free floating, either enriched in its proportion to the maternal DNA, or in its original ratio, is in hand, one may genotype the DNA found in said sample. In some embodiments, the blood may be drawn using a needle to withdraw blood from a vein, for example, the basilica vein. The method described herein can be used to determine genotypic data of the fetus. For example, it can be used to determine the ploidy state at one or more chromosomes, it can be used to determine the identity of one or a set of SNPs, including insertions, deletions, and translocations. It can be used to determine one or more haplotypes, including the parent of origin of one or more genotypic features.

Note that this method will work with any nucleic acids that can be used for any genotyping and/or sequencing methods, such as the ILLUMINA INFINIUM ARRAY platform, AFFYMETRIX GENECHIP, ILLUMINA GENOME ANALYZER, or LIFE TECHNOLOGIES' SOLID SYSTEM. This includes extracted free-floating DNA from plasma or amplifications (e.g. whole genome amplification, PCR) of the same; genomic DNA from other cell types (e.g. human lymphocytes from whole blood) or amplifications of the same. For preparation of the DNA, any extraction or purification method that generates genomic DNA suitable for the one of these platforms will work as well. This method could work equally well with samples of RNA. In an embodiment, storage of the samples may be done in a way that will minimize degradation (e.g. below freezing, at about −20 C, or at a lower temperature).

Parental Support

Some embodiments may be used in combination with the PARENTAL SUPPORT™ (PS) method, embodiments of which are described in U.S. application Ser. No. 11/603,406 (US Publication No.: 20070184467), U.S. application Ser. No. 12/076,348 (US Publication No.: 20080243398). U.S. application Ser. No. 13/110,685, PCT Application PCT/US09/52730 (PCT Publication No.: WO/2010/017214), and PCT Application No. PCT/US10/050824 (PCT Publication No. WO/2011/041485) which are incorporated herein by reference in their entirety. PARENTAL SUPPORT™ is an informatics based approach that can be used to analyze genetic data. In some embodiments, the methods disclosed herein may be considered as part of the PARENTAL SUPPORT™ method. In some embodiments. The PARENTAL SUPPORT™ method is a collection of methods that may be used to determine the genetic data of a target individual, with high accuracy, of one or a small number of cells from that individual, or of a mixture of DNA consisting of DNA from the target individual and DNA from one or a plurality of other individuals, specifically to determine disease-related alleles, other alleles of interest, and/or the ploidy state of one or a plurality of chromosomes in the target individual. PARENTAL SUPPORT™ may refer to any of these methods. PARENTAL SUPPORT™ is an example of an informatics based method. Exemplary embodiments of the PARENTAL SUPPORT™ method are illustrated in FIGS. 29-31G and described in Experiment 19.

The PARENTAL SUPPORT™ method makes use of known parental genetic data, i.e. haplotypic and/or diploid genetic data of the mother and/or the father, together with the knowledge of the mechanism of meiosis and the imperfect measurement of the target DNA, and possibly of one or more related individuals, along with population based crossover frequencies, in order to reconstruct, in silico, the genotype at a plurality of alleles, and/or the ploidy state of an embryo or of any target cell(s), and the target DNA at the location of key loci with a high degree of confidence. The PARENTAL SUPPORT™ method can reconstruct not only single nucleotide polymorphisms (SNPs) that were measured poorly, but also insertions and deletions, and SNPs or whole regions of DNA that were not measured at all. Furthermore, the PARENTAL SUPPORT™ method can both measure multiple disease-linked loci as well as screen for aneuploidy, from a single cell. In some embodiments, the PARENTAL SUPPORT™ method may be used to characterize one or more cells from embryos biopsied during an IVF cycle to determine the genetic condition of the one or more cells.

The PARENTAL SUPPORT™ method allows the cleaning of noisy genetic data. This may be done by inferring the correct genetic alleles in the target genome (embryo) using the genotype of related individuals (parents) as a reference. PARENTAL SUPPORT™ may be particularly relevant where only a small quantity of genetic material is available (e.g. PGD) and where direct measurements of the genotypes are inherently noisy due to the limited amounts of genetic material. PARENTAL SUPPORT™ may be particularly relevant where only a small fraction of the genetic material available is from the target individual (e.g. NPD) and where direct measurements of the genotypes are inherently noisy due to the contaminating DNA signal from another individual. The PARENTAL SUPPORT™ method is able to reconstruct highly accurate ordered diploid allele sequences on the embryo, together with copy number of chromosomes segments, even though the conventional, unordered diploid measurements may be characterized by high rates of allele dropouts, drop-ins, variable amplification biases and other errors. The method may employ both an underlying genetic model and an underlying model of measurement error. The genetic model may determine both allele probabilities at each SNP and crossover probabilities between SNPs. Allele probabilities may be modeled at each SNP based on data obtained from the parents and model crossover probabilities between SNPs based on data obtained from the HapMap database, as developed by the International HapMap Project. Given the proper underlying genetic model and measurement error model, maximum a posteriori (MAP) estimation may be used, with modifications for computationally efficiency, to estimate the correct, ordered allele values at each SNP in the embryo.

The techniques outlined above, in some cases, are able to determine the genotype of an individual given a very small amount of DNA originating from that individual. This could be the DNA from one or a small number of cells, or it could be from the small amount of fetal DNA found in maternal blood.

Hypotheses

In the context of this disclosure, a hypothesis refers to a possible genetic state. It may refer to a possible ploidy state. It may refer to a possible allelic state. A set of hypotheses may refer to a set of possible genetic states, a set of possible allelic states, a set of possible ploidy states, or combinations thereof. In some embodiments, a set of hypotheses may be designed such that one hypothesis from the set will correspond to the actual genetic state of any given individual. In some embodiments, a set of hypotheses may be designed such that every possible genetic state may be described by at least one hypothesis from the set. In some embodiments of the present disclosure, one aspect of a method is to determine which hypothesis corresponds to the actual genetic state of the individual in question.

In another embodiment of the present disclosure, one step involves creating a hypothesis. In some embodiments it may be a copy number hypothesis. In some embodiments it may involve a hypothesis concerning which segments of a chromosome from each of the related individuals correspond genetically to which segments, if any, of the other related individuals. Creating a hypothesis may refer to the act of setting the limits of the variables such that the entire set of possible genetic states that are under consideration are encompassed by those variables.

A "copy number hypothesis," also called a "ploidy hypothesis," or a "ploidy state hypothesis," may refer to a hypothesis concerning a possible ploidy state for a given chromosome copy, chromosome type, or section of a chromosome, in the target individual. It may also refer to the ploidy state at more than one of the chromosome types in the individual. A set of copy number hypotheses may refer to a set of hypotheses where each hypothesis corresponds to a different possible ploidy state in an individual. A set of hypotheses may concern a set of possible ploidy states, a set of possible parental haplotypes contributions, a set of possible fetal DNA percentages in the mixed sample, or combinations thereof. In some embodiments, the copy number hypotheses include all fetuses in a multiple pregnancy being euploid, all fetuses in a multiple pregnancy being aneuploid (such as any of the aneuploidies disclosed herein), and/or one or more fetuses in a multiple pregnancy being euploid and one or more fetuses in a multiple pregnancy being aneuploidy. In some embodiments, the copy number hypotheses include identical twins (also referred to as monozygotic twins) or fraternal twins (also referred to as dizygotic twins). In some embodiments, the copy number hypotheses include a molar pregnancy, such as a complete or partial molar pregnancy.

A normal individual contains one of each chromosome type from each parent. However, due to errors in meiosis and mitosis, it is possible for an individual to have 0, 1, 2, or more of a given chromosome type from each parent. In practice, it is rare to see more than two of a given chromosome from a parent. In this disclosure, some embodiments only consider the possible hypotheses where 0, 1, or 2 copies of a given chromosome come from a parent; it is a trivial extension to consider more or less possible copies originating from a parent. In some embodiments, for a given chromosome, there are nine possible hypotheses: the three possible hypothesis concerning 0, 1, or 2 chromosomes of maternal origin, multiplied by the three possible hypotheses concerning 0, 1, or 2 chromosomes of paternal origin. Let (m,f) refer to the hypothesis where m is the number of a given chromosome inherited from the mother, and f is the number of a given chromosome inherited from the father. Therefore, the nine hypotheses are (0,0), (0,1), (0,2), (1,0), (1,1), (1,2), (2,0), (2,1), and (2,2). These may also be written as $H_{00}$, $H_{01}$, $H_{02}$, $H_{10}$, $H_{12}$, $H_{20}$, $H_{21}$, and $H_{22}$. The different hypotheses correspond to different ploidy states. For example, (1,1) refers to a normal disomic chromosome; (2,1) refers to a maternal trisomy, and (0,1) refers to a paternal monosomy. In some embodiments, the case where two chromosomes are inherited from one parent and one chromosome is inherited from the other parent may be further differentiated into two cases: one where the two chromosomes are identical (matched copy error), and one where the two chromosomes are homologous but not identical (unmatched copy error). In these embodiments, there are sixteen possible hypotheses. It should be understood that it is possible to use other sets of hypotheses, and a different number of hypotheses.

In some embodiments of the present disclosure, the ploidy hypothesis refers to a hypothesis concerning which chromosome from other related individuals correspond to a chromosome found in the target individual's genome. In some embodiments, a key to the method is the fact that related individuals can be expected to share haplotype blocks, and using measured genetic data from related individuals, along with a knowledge of which haplotype blocks match between the target individual and the related individual, it is possible to infer the correct genetic data for a target individual with higher confidence than using the target individual's genetic measurements alone. As such, in some embodiments, the ploidy hypothesis may concern not only the number of chromosomes, but also which chromosomes in related individuals are identical, or nearly identical, with one or more chromosomes in the target individual.

Once the set of hypotheses have been defined, when the algorithms operate on the input genetic data, they may output a determined statistical probability for each of the hypotheses under consideration. The probabilities of the various hypotheses may be determined by mathematically calculating, for each of the various hypotheses, the value that the probability equals, as stated by one or more of the expert techniques, algorithms, and/or methods described elsewhere in this disclosure, using the relevant genetic data as input.

Once the probabilities of the different hypotheses are estimated, as determined by a plurality of techniques, they may be combined. This may entail, for each hypothesis, multiplying the probabilities as determined by each technique. The product of the probabilities of the hypotheses may be normalized. Note that one ploidy hypothesis refers to one possible ploidy state for a chromosome.

The process of "combining probabilities," also called "combining hypotheses," or combining the results of expert techniques, is a concept that should be familiar to one skilled in the art of linear algebra. One possible way to combine probabilities is as follows: When an expert technique is used to evaluate a set of hypotheses given a set of genetic data, the output of the method is a set of probabilities that are associated, in a one-to-one fashion, with each hypothesis in the set of hypotheses. When a set of probabilities that were determined by a first expert technique, each of which are associated with one of the hypotheses in the set, are combined with a set of probabilities that were determined by a second expert technique, each of which are associated with the same set of hypotheses, then the two sets of probabilities are multiplied. This means that, for each hypothesis in the set, the two probabilities that are associated with that hypothesis, as determined by the two expert methods, are multiplied together, and the corresponding product is the output probability. This process may be expanded to any number of expert techniques. If only one expert technique is used, then the output probabilities are the same as the input probabilities. If more than two expert techniques are used, then the relevant probabilities may be multiplied at the same time. The products may be normalized so that the probabilities of the hypotheses in the set of hypotheses sum to 100%.

In some embodiments, if the combined probabilities for a given hypothesis are greater than the combined probabilities for any of the other hypotheses, then it may be considered that that hypothesis is determined to be the most likely. In some embodiments, a hypothesis may be determined to be the most likely, and the ploidy state, or other genetic state, may be called if the normalized probability is greater than a threshold. In an embodiment, this may mean that the number and identity of the chromosomes that are associated with that hypothesis may be called as the ploidy state. In an embodiment, this may mean that the identity of the alleles that are associated with that hypothesis may be called as the allelic state. In some embodiments, the threshold may be between about 50% and about 80. In some embodiments the threshold may be between about 80% and about 90%. In some embodiments the threshold may be between about 90% and about 95%. In some embodiments the threshold may be between about 95% and about 99%. In some embodiments the threshold may be between about 99% and about 99.9%. In some embodiments the threshold may be above about 99.9%.

Parental Contexts

The parental context refers to the genetic state of a given allele, on each of the two relevant chromosomes for one or both of the two parents of the target. Note that in an embodiment, the parental context does not refer to the allelic state of the target, rather, it refers to the allelic state of the parents. The parental context for a given SNP may consist of four base pairs, two paternal and two maternal; they may be the same or different from one another. It is typically written as "$m_1m_2|f_1f_2$," where $m_1$ and $m_2$ are the genetic state of the given SNP on the two maternal chromosomes, and $f_1$ and $f_2$ are the genetic state of the given SNP on the two paternal chromosomes. In some embodiments, the parental context may be written as "$f_1f_2|m_1m_2$" Note that subscripts "1" and "2" refer to the genotype, at the given allele, of the first and second chromosome; also note that the choice of which chromosome is labeled "1" and which is labeled "2" is arbitrary.

Note that in this disclosure, A and B are often used to generically represent base pair identities; A or B could equally well represent C (cytosine). G (guanine), A (adenine) or T (thymine). For example, if, at a given SNP based allele, the mother's genotype was T at that SNP on one chromosome, and G at that SNP on the homologous chromosome, and the father's genotype at that allele is G at that SNP on both of the homologous chromosomes, one may say that the target individual's allele has the parental context of AB|BB, it could also be said that the allele has the parental context of AB|AA. Note that, in theory, any of the four possible nucleotides could occur at a given allele, and thus it is possible, for example, for the mother to have a genotype of AT, and the father to have a genotype of GC at a given allele. However, empirical data indicate that in most cases only two of the four possible base pairs are observed at a given allele. It is possible, for example when using single tandem repeats, to have more than two parental, more than four and even more than ten contexts. In this disclosure the discussion assumes that only two possible base pairs will be observed at a given allele, although the embodiments disclosed herein could be modified to take into account the cases where this assumption does not hold.

A "parental context" may refer to a set or subset of target SNPs that have the same parental context. For example, if one were to measure 1000 alleles on a given chromosome on a target individual, then the context AA|BB could refer to the set of all alleles in the group of 1,000 alleles where the genotype of the mother of the target was homozygous, and the genotype of the father of the target is homozygous, but where the maternal genotype and the paternal genotype are dissimilar at that locus. If the parental data is not phased, and thus AB=BA, then there are nine possible parental contexts: AA|AA, AA|AB, AA|BB, AB|AA, AB|AB, AB|BB, BB|AA, BB|AB, and BB|BB. If the parental data is phased, and thus AB≠BA, then there are sixteen different possible parental contexts: AA|AA, AA|AB, AA|BA, AA|BB, AB|AA, AB|AB, AB|BA, AB|BB, BA|AA, BA|AB, BA|BA, BA|BB, BB|AA, BB|AB, BB|BA, and BB|BB. Every SNP allele on a chromosome, excluding some SNPs on the sex chromosomes, has one of these parental contexts. The set of SNPs wherein the parental context for one parent is heterozygous may be referred to as the heterozygous context.

Use of Parental Contexts in NPD

Non-invasive prenatal diagnosis is an important technique that can be used to determine the genetic state of a fetus from genetic material that is obtained in a non-invasive manner, for example from a blood draw on the pregnant mother. The blood could be separated and the plasma isolated, followed by isolation of the plasma DNA. Size selection could be used to isolate the DNA of the appropriate length. The DNA may be preferentially enriched at a set of loci. This DNA can then be measured by a number of means, such as by hybridizing to a genotyping array and measuring the fluorescence, or by sequencing on a high throughput sequencer.

When sequencing is used for ploidy calling of a fetus in the context of non-invasive prenatal diagnosis, there are a number of ways to use the sequence data. The most common way one could use the sequence data is to simply count the number of reads that map to a given chromosome. For example, imagine if you are trying to determine the ploidy state of chromosome 21 on the fetus. Further imagine that the DNA in the sample is comprised of 10% DNA of fetal origin, and 90% DNA of maternal origin. In this case, you could look at the average number of reads on a chromosome which can be expected to be disomic, for example chromosome 3, and compare that to the number of read on chromosome 21, where the reads are adjusted for the number of base pairs on that chromosome that are part of a unique sequence. If the fetus were euploid, one would expect the amount of DNA per unit of genome to be about equal at all locations (subject to stochastic variations). On the other hand, if the fetus were trisomic at chromosome 21, then one would expect there to be more slightly more DNA per genetic unit from chromosome 21 than the other locations on the genome. Specifically one would expect there to be about 5% more DNA from chromosome 21 in the mixture. When sequencing is used to measure the DNA, one would expect about 5% more uniquely mappable reads from chromosome 21 per unique segment than from the other chromosomes. One could use the observation of an amount of DNA from a particular chromosome that is higher than a certain threshold, when adjusted for the number of sequences that are uniquely mappable to that chromosome, as the basis for an aneuploidy diagnosis. Another method that may be used to detect aneuploidy is similar to that above, except that parental contexts could be taken into account.

When considering which alleles to target, one may consider the likelihood that some parental contexts are likely to be more informative than others. For example, AA|BB and the symmetric context BB|AA are the most informative contexts, because the fetus is known to carry an allele that is different from the mother. For reasons of symmetry, both AA|BB and BB|AA contexts may be referred to as AA|BB Another set of informative parental contexts are AA|AB and BB|AB, because in these cases the fetus has a 50% chance of carrying an allele that the mother does not have. For reasons of symmetry, both AA|AB and BB|AB contexts may be referred to as AA|AB. A third set of informative parental contexts are AB|AA and AB|BB, because in these cases the fetus is carrying a known paternal allele, and that allele is also present in the maternal genome. For reasons of symmetry, both AB|AA and AB|BB contexts may be referred to as AB|AA. A fourth parental context is AB|AB where the fetus has an unknown allelic state, and whatever the allelic state, it is one in which the mother has the same alleles. The fifth parental context is AA|AA, where the mother and father are heterozygous.

Different Implementations of the Presently Disclosed Embodiments

Methods are disclosed herein for determining the ploidy state of a target individual. The target individual may be a blastomere, an embryo, or a fetus. In some embodiments of the present disclosure, a method for determining the ploidy state of one or more chromosome in a target individual may include any of the steps described in this document, and combinations thereof.

In some embodiments the source of the genetic material to be used in determining the genetic state of the fetus may be fetal cells, such as nucleated fetal red blood cells, isolated from the maternal blood. The method may involve obtaining a blood sample from the pregnant mother. The method may involve isolating a fetal red blood cell using visual techniques, based on the idea that a certain combination of colors are uniquely associated with nucleated red blood cells, and a similar combination of colors is not associated with any other present cell in the maternal blood. The combination of colors associated with the nucleated red blood cells may include the red color of the hemoglobin around the nucleus, which color may be made more distinct by staining, and the color of the nuclear material which can be stained, for example, blue. By isolating the cells from maternal blood and spreading them over a slide, and then identifying those points at which one sees both red (from the Hemoglobin) and blue (from the nuclear material) one may be able to identify the location of nucleated red blood cells. One may then extract those nucleated red blood cells using a micromanipulator, use genotyping and/or sequencing techniques to measure aspects of the genotype of the genetic material in those cells.

In an embodiment, one may stain the nucleated red blood cell with a die that only fluoresces in the presence of fetal hemoglobin and not maternal hemoglobin, and so remove the ambiguity between whether a nucleated red blood cell is derived from the mother or the fetus. Some embodiments of the present disclosure may involve staining or otherwise marking nuclear material. Some embodiments of the present disclosure may involve specifically marking fetal nuclear material using fetal cell specific antibodies.

There are many other ways to isolate fetal cells from maternal blood, or fetal DNA from maternal blood, or to enrich samples of fetal genetic material in the presence of maternal genetic material. Some of these methods are listed here, but this is not intended to be an exhaustive list. Some appropriate techniques are listed here for convenience: using fluorescently or otherwise tagged antibodies, size exclusion chromatography, magnetically or otherwise labeled affinity tags, epigenetic differences, such as differential methylation between the maternal and fetal cells at specific alleles, density gradient centrifugation succeeded by CD45/14 depletion and CD71-positive selection from CD45/14 negative-cells, single or double Percoil gradients with different osmolalities, or galactose specific lectin method.

In an embodiment of the present disclosure, the target individual is a fetus, and the different genotype measurements are made on a plurality of DNA samples from the fetus. In some embodiments of the present disclosure, the fetal DNA samples are from isolated fetal cells where the fetal cells may be mixed with maternal cells. In some embodiments of the present disclosure, the fetal DNA samples are from free floating fetal DNA, where the fetal DNA may be mixed with free floating maternal DNA. In some embodiments, the fetal DNA samples may be derived from maternal plasma or maternal blood that contains a mixture of maternal DNA and fetal DNA. In some embodiments, the fetal DNA may be mixed with maternal DNA in maternal:fetal ratios ranging from 99.9:0.1% to 99:1%; 99:1% to 90:10%; 90:10% to 80:20%; 80:20% to 70:30%; 70:30% to 50:50%; 50:50% to 10:90%; or 10:90% to 1:99%; 1:99% to 0.1:99.9%.

The genetic data of the target individual and/or of the related individual can be transformed from a molecular state to an electronic state by measuring the appropriate genetic material using tools and or techniques taken from a group including, but not limited to: genotyping microarrays, and high throughput sequencing. Some high throughput sequencing methods include Sanger DNA sequencing, pyrosequencing, the ILLUMINA SOLEXA platform, ILLUMINA's GENOME ANALYZER, or APPLIED BIOSYSTEM's 454 sequencing platform, HELICOS's TRUE SINGLE MOLECULE SEQUENCING platform, HALCYON MOLECULAR's electron microscope sequencing method, or any other sequencing method. All of these methods physically transform the genetic data stored in a sample of DNA into a set of genetic data that is typically stored in a memory device in route to being processed.

A relevant individual's genetic data may be measured by analyzing substances taken from a group including, but not limited to: the individual's bulk diploid tissue, one or more diploid cells from the individual, one or more haploid cells from the individual, one or more blastomeres from the target individual, extra-cellular genetic material found on the individual, extra-cellular genetic material from the individual found in maternal blood, cells from the individual found in maternal blood, one or more embryos created from (a) gamete(s) from the related individual, one or more blastomeres taken from such an embryo, extra-cellular genetic material found on the related individual, genetic material known to have originated from the related individual, and combinations thereof.

In some embodiments, a set of at least one ploidy state hypothesis may be created for each of the chromosomes types of interest of the target individual. Each of the ploidy state hypotheses may refer to one possible ploidy state of the chromosome or chromosome segment of the target individual. The set of hypotheses may include some or all of the possible ploidy states that the chromosome of the target individual may be expected to have. Some of the possible ploidy states may include nullsomy, monosomy, disomy, uniparental disomy, euploidy, trisomy, matching trisomy, unmatching trisomy, maternal trisomy, paternal trisomy, tetrasomy, balanced (2:2) tetrasomy, unbalanced (3:1) tetrasomy, pentasomy, hexasomy, other aneuploidy, and combinations thereof. Any of these aneuploidy states may be mixed or partial aneuploidy such as unbalanced translocations, balanced translocations, Robertsonian translocations, recombinations, deletions, insertions, crossovers, and combinations thereof.

In some embodiments, the knowledge of the determined ploidy state may be used to make a clinical decision. This knowledge, typically stored as a physical arrangement of matter in a memory device, may then be transformed into a report. The report may then be acted upon. For example, the clinical decision may be to terminate the pregnancy; alternately, the clinical decision may be to continue the pregnancy. In some embodiments the clinical decision may involve an intervention designed to decrease the severity of the phenotypic presentation of a genetic disorder, or a decision to take relevant steps to prepare for a special needs child. In an embodiment of the present disclosure, any of the methods described herein may be modified to allow for multiple targets to come from same target individual, for example, multiple blood draws from the same pregnant mother. This may improve the accuracy of the model, as multiple genetic measurements may provide more data with which the target genotype may be determined. In an embodiment, one set of target genetic data served as the primary data which was reported, and the other served as data to double-check the primary target genetic data. In an embodiment, a plurality of sets of genetic data, each measured from genetic material taken from the target individual, are considered in parallel, and thus both sets of target genetic data serve to help determine which sections of parental genetic data, measured with high accuracy, composes the fetal genome.

In an embodiment, the method may be used for the purpose of paternity testing. For example, given the SNP-based genotypic information from the mother, and from a man who may or may not be the genetic father, and the measured genotypic information from the mixed sample, it is possible to determine if the genotypic information of the male indeed represents that actual genetic father of the gestating fetus. A simple way to do this is to simply look at the contexts where the mother is AA, and the possible father is AB or BB. In these cases, one may expect to see the father contribution half (AA|AB) or all (AA|BB) of the time, respectively. Taking into account the expected ADO, it is straightforward to determine whether or not the fetal SNPs that are observed are correlated with those of the possible father.

One embodiment of the present disclosure could be as follows: a pregnant woman wants to know if her fetus is afflicted with Down Syndrome, and/or if it will suffer from Cystic Fibrosis, and she does not wish to bear a child that is afflicted with either of these conditions. A doctor takes her blood, and stains the hemoglobin with one marker so that it appears clearly red, and stains nuclear material with another marker so that it appears clearly blue. Knowing that maternal red blood cells are typically anuclear, while a high proportion of fetal cells contain a nucleus, the doctor is able to visually isolate a number of nucleated red blood cells by identifying those cells that show both a red and blue color. The doctor picks up these cells off the slide with a micromanipulator and sends them to a lab which amplifies and genotypes ten individual cells. By using the genetic measurements, the PARENTAL SUPPORT™ method is able to determine that six of the ten cells are maternal blood cells, and four of the ten cells are fetal cells. If a child has already been born to a pregnant mother, PARENTAL SUPPORT™ can also be used to determine that the fetal cells are distinct from the cells of the born child by making reliable allele calls on the fetal cells and showing that they are dissimilar to those of the born child. Note that this method is similar in concept to the paternal testing embodiment of the present disclosure. The genetic data measured from the fetal cells may be of very poor quality, comprising many allele drop outs, due to the difficulty of genotyping single cells. The clinician is able to use the measured fetal DNA along with the reliable DNA measurements of the parents to infer aspects of the genome of the fetus with high accuracy using PARENTAL SUPPORT™, thereby transforming the genetic data contained on genetic material from the fetus into the predicted genetic state of the fetus, stored on a computer. The clinician is able to determine both the ploidy state of the fetus, and the presence or absence of a plurality of disease-linked genes of interest. It turns out that the fetus is euploid, and is not a carrier for cystic fibrosis, and the mother decides to continue the pregnancy.

In an embodiment of the present disclosure, a pregnant mother would like to determine if her fetus is afflicted with any whole chromosomal abnormalities. She goes to her doctor, and gives a sample of her blood, and she and her husband gives samples of their own DNA from cheek swabs. A laboratory researcher genotypes the parental DNA using the MDA protocol to amplify the parental DNA, and ILLUMINA INFINIUM arrays to measure the genetic data of the parents at a large number of SNPs. The researcher then spins down the blood, takes the plasma, and isolates a sample of free-floating DNA using size exclusion chromatography. Alternately, the researcher uses one or more fluorescent antibodies, such as one that is specific to fetal hemoglobin to isolate a nucleated fetal red blood cell. The researcher then takes the isolated or enriched fetal genetic material and amplifies it using a library of 70-mer oligonucleotides appropriately designed such that two ends of each oligonucleotide corresponded to the flanking sequences on either side of a target allele. Upon addition of a polymerase, ligase, and the appropriate reagents, the oligonucleotides underwent gap-filling circularization, capturing the desired allele. An exonuclease was added, heat-inactivated, and the products were used directly as a template for PCR amplification. The PCR products were sequenced on an ILLUMINA GENOME ANALYZER. The sequence reads were used as input for the PARENTAL SUPPORT™ method, which then predicted the ploidy state of the fetus.

In another embodiment, a couple—where the mother, who is pregnant, and is of advanced maternal age—wants to know whether the gestating fetus has Down syndrome, Turner Syndrome, Prader Willi syndrome, or some other whole chromosomal abnormality. The obstetrician takes a blood draw from the mother and father. The blood is sent to a laboratory, where a technician centrifuges the maternal sample to isolate the plasma and the buffy coat. The DNA in the buffy coat and the paternal blood sample are transformed through amplification and the genetic data encoded in the amplified genetic material is further transformed from molecularly stored genetic data into electronically stored genetic data by running the genetic material on a high throughput sequencer to measure the parental genotypes. The plasma sample is preferentially enriched at a set of loci using a 5,000-plex hemi-nested targeted PCR method. The mixture of DNA fragments is prepared into a DNA library suitable for sequencing. The DNA is then sequenced using a high throughput sequencing method, for example, the ILLUMINA GAIIx GENOME ANALYZER. The sequencing transforms the information that is encoded molecularly in the DNA into information that is encoded electronically in computer hardware. An informatics based technique that includes the presently disclosed embodiments, such as PARENTAL SUPPORT™, may be used to determine the ploidy state of the fetus. This may involve calculating, on a computer, allele count probabilities at the plurality of polymorphic loci from the DNA measurements made on the prepared sample; creating, on a computer, a plurality of ploidy hypotheses each pertaining to a different possible ploidy state of the chromosome; building, on a computer, a joint distribution model for the expected allele counts at the plurality of polymorphic loci on the chromosome for each ploidy hypothesis; determining, on a computer, a relative probability of each of the ploidy hypotheses using the joint distribution model and the allele counts measured on the prepared sample; and calling the ploidy state of the fetus by selecting the ploidy state corresponding to the hypothesis with the greatest probability. It is determined that the fetus has Down syndrome. A report is printed out, or sent electronically to the pregnant woman's obstetrician, who transmits the diagnosis to the woman. The woman, her husband, and the doctor sit down and discuss their options. The couple decides to terminate the pregnancy based on the knowledge that the fetus is afflicted with a trisomic condition.

In an embodiment, a company may decide to offer a diagnostic technology designed to detect aneuploidy in a gestating fetus from a maternal blood draw. Their product may involve a mother presenting to her obstetrician, who may draw her blood. The obstetrician may also collect a genetic sample from the father of the fetus. A clinician may isolate the plasma from the maternal blood, and purify the DNA from the plasma. A clinician may also isolate the buffy coat layer from the maternal blood, and prepare the DNA from the buffy coat. A clinician may also prepare the DNA from the paternal genetic sample. The clinician may use molecular biology techniques described in this disclosure to append universal amplification tags to the DNA in the DNA derived from the plasma sample. The clinician may amplify the universally tagged DNA. The clinician may preferentially enrich the DNA by a number of techniques including capture by hybridization and targeted PCR. The targeted PCR may involve nesting, hemi-nesting or semi-nesting, or any other approach to result in efficient enrichment of the plasma derived DNA. The targeted PCR may be massively multiplexed, for example with 10,000 primers in one reaction volume, where the primers target SNPs on chromosomes 13, 18, 21, X and those loci that are common to both X and Y, and optionally other chromosomes as well. The selective enrichment and/or amplification may involve tagging each individual molecule with different tags, molecular barcodes, tags for amplification, and/or tags for sequencing. The clinician may then sequence the plasma sample, and also possibly also the prepared maternal and/or paternal DNA. The molecular biology steps may be executed either wholly or partly by a diagnostic box. The sequence data may be fed into a single computer, or to another type of computing platform such as may be found in 'the cloud'. The computing platform may calculate allele counts at the targeted polymorphic loci from the measurements made by the sequencer. The computing platform may create a plurality of ploidy hypotheses pertaining to nullsomy, monosomy, disomy, matched trisomy, and unmatched trisomy for each of chromosomes 13, 18, 21, X and Y. The computing platform may build a joint distribution model for the expected allele counts at the targeted loci on the chromosome for each ploidy hypothesis for each of the five chromosomes being interrogated. The computing platform may determine a probability that each of the ploidy hypotheses is true using the joint distribution model and the allele counts measured on the preferentially enriched DNA derived from the plasma sample. The computing platform may call the ploidy state of the fetus, for each of chromosome 13, 18, 21, X and Y by selecting the ploidy state corresponding to the germane hypothesis with the greatest probability. A report may be generated comprising the called ploidy states, and it may be sent to the obstetrician electronically, displayed on an output device, or a printed hard copy of the report may be delivered to the obstetrician. The obstetrician may inform the patient and optionally the father of the fetus, and they may decide which clinical options are open to them, and which is most desirable.

In another embodiment, a pregnant woman, hereafter referred to as "the mother" may decide that she wants to know whether or not her fetus(es) are carrying any genetic abnormalities or other conditions. She may want to ensure that there are not any gross abnormalities before she is confident to continue the pregnancy. She may go to her obstetrician, who may take a sample of her blood. He may also take a genetic sample, such as a buccal swab, from her cheek. He may also take a genetic sample from the father of the fetus, such as a buccal swab, a sperm sample, or a blood sample. He may send the samples to a clinician. The clinician may enrich the fraction of free floating fetal DNA in the maternal blood sample. The clinician may enrich the fraction of enucleated fetal blood cells in the maternal blood sample. The clinician may use various aspects of the methods described herein to determine genetic data of the fetus. That genetic data may include the ploidy state of the fetus, and/or the identity of one or a number of disease linked alleles in the fetus. A report may be generated summarizing the results of the prenatal diagnosis. The report may be transmitted or mailed to the doctor, who may tell the mother the genetic state of the fetus. The mother may decide to discontinue the pregnancy based on the fact that the fetus has one or more chromosomal, or genetic abnormalities, or undesirable conditions. She may also decide to continue the pregnancy based on the fact that the fetus does not have any gross chromosomal or genetic abnormalities, or any genetic conditions of interest. Another example may involve a pregnant woman who has been artificially inseminated by a sperm donor, and is pregnant. She wants to minimize the risk that the fetus she is carrying has a genetic disease. She has blood drawn at a phlebotomist, and techniques described in this disclosure are used to isolate three nucleated fetal red blood cells, and a tissue sample is also collected from the mother and genetic father. The genetic material from the fetus and from the mother and father are amplified as appropriate and genotyped using the ILLUMINA INFINIUM BEADARRAY, and the methods described herein clean and phase the parental and fetal genotype with high accuracy, as well as to make ploidy calls for the fetus. The fetus is found to be euploid, and phenotypic susceptibilities are predicted from the reconstructed fetal genotype, and a report is generated and sent to the mother's physician so that they can decide what clinical decisions may be best.

In an embodiment, the raw genetic material of the mother and the father is transformed by way of amplification to an amount of DNA that is similar in sequence, but larger in quantity. Then, by way of a genotyping method, the genotypic data that is encoded by nucleic acids is transformed into genetic measurements that may be stored physically and/or electronically on a memory device, such as those described above. The relevant algorithms that makeup the PARENTAL SUPPORT™ algorithm, relevant parts of which are discussed in detail herein, are translated into a computer program, using a programming language. Then, through the execution of the computer program on the computer hardware, instead of being physically encoded bits and bytes, arranged in a pattern that represents raw measurement data, they become transformed into a pattern that represents a high confidence determination of the ploidy state of the fetus. The details of this transformation will rely on the data itself and the computer language and hardware system used to execute the method described herein. Then, the data that is physically configured to represent a high quality ploidy determination of the fetus is transformed into a report which may be sent to a health care practitioner. This transformation may be carried out using a printer or a computer display. The report may be a printed copy, on paper or other suitable medium, or else it may be electronic. In the case of an electronic report, it may be transmitted, it may be physically stored on a memory device at a location on the computer accessible by the health care practitioner; it also may be displayed on a screen so that it may be read. In the case of a screen display, the data may be transformed to a readable format by causing the physical transformation of pixels on the display device. The transformation may be accomplished by way of physically firing electrons at a phosphorescent screen, by way of altering an electric charge that physically changes the transparency of a specific set of pixels on a screen that may lie in front of a substrate that emits or absorbs photons. This transformation may be accomplished by way of changing the nanoscale orientation of the molecules in a liquid crystal, for example, from nematic to cholesteric or smectic phase, at a specific set of pixels. This transformation may be accomplished by way of an electric current causing photons to be emitted from a specific set of pixels made from a plurality of light emitting diodes arranged in a meaningful pattern. This transformation may be accomplished by any other way used to display information, such as a computer screen, or some other output device or way of transmitting information. The health care practitioner may then act on the report, such that the data in the report is transformed into an action. The action may be to continue or discontinue the pregnancy, in which case a gestating fetus with a genetic abnormality is transformed into non-living fetus. The transformations listed herein may be aggregated, such that, for example, one may transform the genetic material of a pregnant mother and the father, through a number of steps outlined in this disclosure, into a medical decision consisting of aborting a fetus with genetic abnormalities, or consisting of continuing the pregnancy. Alternately, one may transform a set of genotypic measurements into a report that helps a physician treat his pregnant patient.

In an embodiment of the present disclosure, the method described herein can be used to determine the ploidy state of a fetus even when the host mother, i.e. the woman who is pregnant, is not the biological mother of the fetus she is carrying. In an embodiment of the present disclosure, the method described herein can be used to determine the ploidy state of a fetus using only the maternal blood sample, and without the need for a paternal genetic sample.

Some of the math in the presently disclosed embodiments makes hypotheses concerning a limited number of states of aneuploidy. In some cases, for example, only zero, one or two chromosomes are expected to originate from each parent. In some embodiments of the present disclosure, the mathematical derivations can be expanded to take into account other forms of aneuploidy, such as quadrosomy, where three chromosomes originate from one parent, pentasomy, hexasomy etc., without changing the fundamental concepts of the present disclosure. At the same time, it is possible to focus on a smaller number of ploidy states, for example, only trisomy and disomy. Note that ploidy determinations that indicate a non-whole number of chromosomes may indicate mosaicism in a sample of genetic material.

In some embodiments, the genetic abnormality is a type of aneuploidy, such as Down syndrome (or trisomy 21), Edwards syndrome (trisomy 18), Patau syndrome (trisomy 13), Turner Syndrome (45X), Klinefelter's syndrome (a male with 2 X chromosomes), Prader-Willi syndrome, and DiGeorge syndrome (UPD 15). Congenital disorders, such as those listed in the prior sentence, are commonly undesirable, and the knowledge that a fetus is afflicted with one or more phenotypic abnormalities may provide the basis for a decision to terminate the pregnancy, to take necessary precautions to prepare for the birth of a special needs child, or to take some therapeutic approach meant to lessen the severity of a chromosomal abnormality.

In some embodiments, the methods described herein can be used at a very early gestational age, for example as early as four weeks, as early as five weeks, as early as six weeks, as early as seven weeks, as early as eight weeks, as early as nine weeks, as early as ten weeks, as early as eleven weeks, and as early as twelve weeks.

In some embodiments, a method disclosed herein is used in the context of pre-implantation genetic diagnosis (PGD) for embryo selection during in vitro fertilization, where the target individual is an embryo, and the parental genotypic data can be used to make ploidy determinations about the embryo from sequencing data from a single or two cell biopsy from a day 3 embryo or a trophectoderm biopsy from a day 5 or day 6 embryo. In a PGD setting, only the child DNA is measured, and only a small number of cells are tested, generally one to five but as many as ten, twenty or fifty. The total number of starting copies of the A and B alleles (at a SNP) are then trivially determined by the child genotype and the number of cells. In NPD, the number of starting copies is very high and so the allele ratio after PCR is expected to accurately reflect the starting ratio. However, the small number of starting copies in PGD means that contamination and imperfect PCR efficiency have a non-trivial effect on the allele ratio following PCR. This effect may be more important than depth of read in predicting the variance in the allele ratio measured after sequencing. The distribution of measured allele ratio given a known child genotype may be created by Monte Carlo simulation of the PCR process based on the PCR probe efficiency and probability of contamination. Given an allele ratio distribution for each possible child genotype, the likelihoods of various hypotheses can be calculated as described for NIPD.

Maximum Likelihood Estimates

Most methods known in the art for detecting the presence or absence of biological phenomenon or medical condition involve the use of a single hypothesis rejection test, where a metric that is correlated with the condition is measured, and if the metric is on one side of a given threshold, the condition is present, while of the metric falls on the other side of the threshold, the condition is absent. A single-hypothesis rejection test only looks at the null distribution when deciding between the null and alternate hypotheses. Without taking into account the alternate distribution, one cannot estimate the likelihood of each hypothesis given the observed data and therefore cannot calculate a confidence on the call. Hence with a single-hypothesis rejection test, one gets a yes or no answer without a feeling for the confidence associated with the specific case.

In some embodiments, the method disclosed herein is able to detect the presence or absence of biological phenomenon or medical condition using a maximum likelihood method. This is a substantial improvement over a method using a single hypothesis rejection technique as the threshold for calling absence or presence of the condition can be adjusted as appropriate for each case. This is particularly relevant for diagnostic techniques that aim to determine the presence or absence of aneuploidy in a gestating fetus from genetic data available from the mixture of fetal and maternal DNA present in the free floating DNA found in maternal plasma. This is because as the fraction of fetal DNA in the plasma derived fraction changes, the optimal threshold for calling aneuploidy vs. euploidy changes. As the fetal fraction drops, the distribution of data that is associated with an aneuploidy becomes increasingly similar to the distribution of data that is associated with a euploidy.

The maximum likelihood estimation method uses the distributions associated with each hypothesis to estimate the likelihood of the data conditioned on each hypothesis. These conditional probabilities can then be convened to a hypothesis call and confidence. Similarly, maximum a posteriori estimation method uses the same conditional probabilities as the maximum likelihood estimate, but also incorporates population priors when choosing the best hypothesis and determining confidence.

Therefore, the use of a maximum likelihood estimate (MLE) technique, or the closely related maximum a posteriori (MAP) technique give two advantages, first it increases the chance of a correct call, and it also allows a confidence to be calculated for each call. In an embodiment, selecting the ploidy state corresponding to the hypothesis with the greatest probability is carried out using maximum likelihood estimates or maximum a posteriori estimates. In an embodiment, a method is disclosed for determining the ploidy state of a gestating fetus that involves taking any method currently known in the art that uses a single hypothesis rejection technique and reformulating it such that it uses a MLE or MAP technique. Some examples of methods that can be significantly improved by applying these techniques can be found in U.S. Pat. Nos. 8,008,018, 7,888,017, or 7,332,277.

In an embodiment, a method is described for determining presence or absence of fetal aneuploidy in a maternal plasma sample comprising fetal and maternal genomic DNA, the method comprising, obtaining a maternal plasma sample; measuring the DNA fragments found in the plasma sample with a high throughput sequencer, mapping the sequences to the chromosome and determining the number of sequence reads that map to each chromosome; calculating the fraction of fetal DNA in the plasma sample; calculating an expected distribution of the amount of a target chromosome that would be expected to be present if that if the second target chromosome were euploid and one or a plurality of expected distributions that would be expected if that chromosome were aneuploid, using the fetal fraction and the number of sequence reads that map to one or a plurality of reference chromosomes expected to be euploid; and using a MLE or MAP determine which of the distributions is most likely to be correct, thereby indicating the presence or absence of a fetal aneuploidy. In an embodiment, the measuring the DNA from the plasma may involve conducting massively parallel shotgun sequencing. In an embodiment, the measuring the DNA from the plasma sample may involve sequencing DNA that has been preferentially enriched, for example through targeted amplification, at a plurality of polymorphic or non-polymorphic loci. The plurality of loci may be designed to target one or a small number of suspected aneuploid chromosomes and one or a small number of reference chromosomes. The purpose of the preferential enrichment is to increase the number of sequence reads that are informative for the ploidy determination.

Ploidy Calling Informatics Method

Described herein is a method for determining the ploidy state of a fetus given sequence data. In some embodiments, this sequence data may be measured on a high throughput sequencer. In some embodiments, the sequence data may be measured on DNA that originated from free floating DNA isolated from maternal blood, wherein the free floating DNA comprises some DNA of maternal origin, and some DNA of fetal/placental origin. This section will describe one embodiment of the present disclosure in which the ploidy state of the fetus is determined assuming that fraction of fetal DNA in the mixture that has been analyzed is not known and will be estimated from the data. It will also describe an embodiment in which the fraction of fetal DNA ("fetal fraction") or the percentage of fetal DNA in the mixture can be measured by another method, and is assumed to be known in determining the ploidy state of the fetus. In some embodiments the fetal fraction can be calculated using only the genotyping measurements made on the maternal blood sample itself, which is a mixture of fetal and maternal DNA. In some embodiments the fraction may be calculated also using the measured or otherwise known genotype of the mother and/or the measured or otherwise known genotype of the father. In another embodiment ploidy state of the fetus can be determined solely based on the calculated fraction of fetal DNA for the chromosome in question compared to the calculated fraction of fetal DNA for the reference chromosome assumed disomic.

In the preferred embodiment, suppose that, for a particular chromosome, we observe and analyze N SNPs, for which we have:

Set of NR free floating DNA sequence measurements $S=(s_1, \ldots, s_{NR})$. Since this method utilizes the SNP measurements, all sequence data that corresponds to non-polymorphic loci can be disregarded. In a simplified version, where we have (A,B) counts on each SNP, where A and B correspond to the two alleles present at a given locus, S can be written as $S=((a_1,b_1), \ldots, (a_N,b_N))$, where $a_i$ is the A count on SNP i, $b_i$ is the B count on SNP i, and $\Sigma_{i=1..N}(a_i+b_i)=NR$ Parent data consisting of
genotypes from a SNP microarray or other intensity based genotyping platform: mother $M=(m_1, \ldots, m_N)$, father $F=(f_1, \ldots, f_N)$, where $m_i, f_i \epsilon$(AA, AB, BB).

AND/OR sequence data measurements: NRM mother measurements $SM=(sm_1, \ldots, sm_{mm})$, NRF father measurements $SF=(sf_1, \ldots, sf_{mf})$. Similar to the above simplification, if we have (A,B) counts on each SNP $SM=((am_1,bm_1), \ldots, (am_N,bm_N))$, $SF=((af_1,bf_1), \ldots, (af_N,bf_N))$.

Collectively, the mother, father child data are denoted as D=(M, F, SM, SF, S). Note that the parent data is desired and increases the accuracy of the algorithm, but is NOT necessary, especially the father data. This means that even in the absence of mother and/or father data, it is possible to get very accurate copy number results.

It is possible to derive the best copy number estimate (H*) by maximizing the data log likelihood LIK(D|H) over all hypotheses (H) considered. In particular, it is possible to determine the relative probability of each of the ploidy hypotheses using the joint distribution model and the allele counts measured on the prepared sample, and using those relative probabilities to determine the hypothesis most likely to be correct as follows.

$$H^* = \underset{H}{\mathrm{argmax}} LIK(D \mid H)$$

Similarly the a posteriori hypothesis likelihood given the data may be written as:

$$H^* = \underset{H}{\mathrm{argmax}} LIK(D \mid H) * priorprob(H)$$

Where priorprob(H) is the prior probability assigned to each hypothesis H, based on model design and prior knowledge. It is also possible to use priors to find the maximum a posteriori estimate:

$$H_{MA} = \underset{H}{\mathrm{argmax}} LIK(D \mid H)$$

In an embodiment, the copy number hypotheses that may be considered are.
Monosomy:
    maternal H10 (one copy from mother)
    paternal H01 (one copy from father)
Disomy H11 (one copy each mother and father)
Simple trisomy, no crossovers considered:
    Maternal: H21_matched (two identical copies from mother, one copy from father), H21_unmatched (BOTH copies from mother, one copy from father)
    Paternal: H12_matched (one copy from mother, two identical copies from father), H12_unmatched (one copy from mother, both copies from father)
Composite trisomy, allowing for crossovers (using a joint distribution model).
    maternal H21 (two copies from mother, one from father),
    paternal H12 (one copy from mother, two copies from father)

In other embodiments, other ploidy states, such as nullsomy (H00), uniparental disomy (H20 and H02), and tetrasomy (H04, H13, H22, H31 and H40), may be considered.

If there are no crossovers, each trisomy, whether the origin was mitosis, meiosis I, or meiosis II, would be one of the matched or unmatched trisomies. Due to crossovers, true trisomy is usually a combination of the two. First, a method to derive hypothesis likelihoods for simple hypotheses is described. Then a method to derive hypothesis likelihoods for composite hypotheses is described, combining individual SNP likelihood with crossovers.

LIK(D|H) for a Simple Hypothesis

In an embodiment, LIK(D|H) may be determined for simple hypotheses, as follows. For simple hypotheses H, LIK(H), the log likelihood of hypothesis H on a whole chromosome, may be calculated as the sum of log likelihoods of individual SNPs, assuming known or derived child fraction cf. In an embodiment it is possible to derive cf from the data.

$$LIK(D \mid H) = \sum_i LIK(D \mid H, cf, i)$$

This hypothesis does not assume any linkage between SNPs, and therefore does not utilize a joint distribution model.

In some embodiments, the Log Likelihood may be determined on a per SNP basis. On a particular SNP i, assuming fetal ploidy hypothesis H and percent fetal DNA cf, log likelihood of observed data D is defined as:

$$LIK(D \mid H, i) = \log P(D \mid H, cf, i) =$$
$$\log\left(\sum_{m,f,c} P(D \mid m, f, c, H, cf, i) P(c \mid m, f, H) P(m \mid i) P(f \mid i)\right)$$

where m are possible true mother genotypes, f are possible true father genotypes, where $m, f \in \{AA, AB, BB\}$, and c are possible child genotypes given the hypothesis H. In particular, for monosomy $c \in \{A, B\}$, for disomy $c \in \{AA, AB, BB\}$, for trisomy $c \in \{AAA, AAB, ABB, BBB\}$.

Genotype prior frequency: p(m|i) is the general prior probability of mother genotype m on SNP i, based on the known population frequency at SNP I, denoted $pA_i$. In particular $$p(AA \mid pA_i) = (pA_i)^2, p(AB \mid pA_i) = 2(pA_i)*(1-pA_i), p(BB \mid pA_i) = (1-pA_i)^2$$

Father genotype probability, p(f|i), may be determined in an analogous fashion.

True child probability: p(c|m, f, H) is the probability of getting true child genotype=c, given parents m, f, and assuming hypothesis H, which can be easily calculated. For example, for H11, H21 matched and H21 unmatched, p(c|m, f, H) is given below.

| | | P(c\|m, f, H) | | | | | | | | | | |
|---|---|---|---|---|---|---|---|---|---|---|---|---|
| | | H11 | | | H21 matched | | | | H21 unmatched | | | |
| m | f | AA | AB | BB | AAA | AAB | ABB | BBB | AAA | AAB | ABB | BBB |
| AA | AA | 1 | 0 | 0 | 1 | 0 | 0 | 0 | 1 | 0 | 0 | 0 |
| AB | AA | 0.5 | 0.5 | 0 | 0.5 | 0 | 0.5 | 0 | 0 | 1 | 0 | 0 |
| BB | AA | 0 | 1 | 0 | 0 | 0 | 1 | 0 | 0 | 0 | 1 | 0 |
| AA | AB | 0.5 | 0.5 | 0 | 0.5 | 0.5 | 0 | 0 | 0.5 | 0.5 | 0 | 0 |
| AB | AB | 0.25 | 0.5 | 0.25 | 0.25 | 0.25 | 0.25 | 0.25 | 0 | 0.5 | 0.5 | 0 |
| BB | AB | 0 | 0.5 | 0.5 | 0 | 0 | 0.5 | 0.5 | 0 | 0 | 0.5 | 0.5 |
| AA | BB | 0 | 1 | 0 | 0 | 1 | 0 | 0 | 0 | 1 | 0 | 0 |
| AB | BB | 0 | 0.5 | 0.5 | 0 | 0.5 | 0 | 0.5 | 0 | 0 | 1 | 0 |
| BB | BB | 0 | 0 | 1 | 0 | 0 | 0 | 1 | 0 | 0 | 0 | 1 |

Data likelihood: P(D|m, f, c, H, i, cf) is the probability of given data D on SNP i, given true mother genotype m, true father genotype f, true child genotype c, hypothesis H and child fraction cf. It can be broken down into the probability of mother, father and child data as follows:

$$P(D \mid m,f,c,H,cf,i) = P(SM \mid m,i) P(M \mid m,i) P(SF \mid f,i) P(F \mid f,i) P(S \mid m,c,H,cf,i)$$

Mother SNP array data likelihood: Probability of mother SNP array genotype data $m_t$ at SNP i compared to true genotype m, assuming SNP array genotypes are correct, is simply $$P(M \mid m, i) = \begin{cases} 1 & m_i = m \\ 0 & m_i \neq m \end{cases}$$

Mother sequence data likelihood: the probability of the mother sequence data at SNP i, in the case of counts $S_i=(am_i,bm_i)$, with no extra noise or bias involved, is the binomial probability defined as $P(SM|m,i)=P_{X|m}(am_i)$ where $X|m\sim\text{Binom}(p_m(A), am_i+bm_i)$ with $p_m(A)$ defined as

|  | m | | | | | |
|---|---|---|---|---|---|---|
|  | AA | AB | BB | A | B | nocall |
| p(A) | 1 | 0.5 | 0 | 1 | 0 | 0.5 |

Father data likelihood: a similar equation applies for father data likelihood.

Note that it is possible to determine the child genotype without the parent data, especially father data. For example if no father genotype data F is available, one may just use $P(F|f,i)=1$. If no father sequence data SF is available, one may just use $P(SF|f,i)=1$.

In some embodiments, the method involves building a joint distribution model for the expected allele counts at a plurality of polymorphic loci on the chromosome for each ploidy hypothesis; one method to accomplish such an end is described here. Free fetal DNA data likelihood. P(S|m, c, H, cf, i) is the probability of free fetal DNA sequence data on SNP i, given true mother genotype m, true child genotype c, child copy number hypothesis H, and assuming child fraction cf. It is in fact the probability of sequence data S on SNP I, given the true probability of A content on SNP i $\mu(m, c, cf, H)$.

$$P(S|m,c,H,cf,i)=P(S|\mu(m,c,cf,H),i)$$

For counts, where $S_i=(a_i,b_i)$, with no extra noise or bias in data involved, $$P(S|\mu(m,c,cf,H),i)=P_x(a_i)$$

where $X\sim\text{Binom}(p(A), a_i+b_i)$ with $p(A)=\mu(m, c, cf, H)$. In a more complex case where the exact alignment and (A,B) counts per SNP are not known. $P(S|\mu(m, c, cf, H), i)$ is a combination of integrated binomials.

True A content probability: $\mu(m, c, cf, H)$, the true probability of A content on SNP i in this mother/child mixture, assuming that true mother genotype=m, true child genotype=c, and overall child fraction=cf, is defined as $$\mu(m, c, cf, H) = \frac{\#A(m)*(1-cf) + \#A(c)*cf}{n_m*(1-cf) + n_c*cf}$$

where #A(g)=number of A's in genotype g, $n_m=2$ is somy of mother and $n_c$ is ploidy of the child under hypothesis H (1 for monosomy, 2 for disomy, 3 for trisomy).

Using A Joint Distribution Model: LIK(D|H) for a Composite Hypothesis

In some embodiments, the method involves building a joint distribution model for the expected allele counts at the plurality of polymorphic loci on the chromosome for each ploidy hypothesis; one method to accomplish such an end is described here. In many cases, trisomy is usually not purely matched or unmatched, due to crossovers, so in this section results for composite hypotheses H21 (maternal trisomy) and H12 (paternal trisomy) are derived, which combine matched and unmatched trisomy, accounting for possible crossovers.

In the case of trisomy, if there were no crossovers, trisomy would be simply matched or unmatched trisomy. Matched trisomy is where child inherits two copies of the identical chromosome segment from one parent. Unmatched trisomy is where child inherits one copy of each homologous chromosome segment from the parent. Due to crossovers, some segments of a chromosome may have matched trisomy, and other parts may have unmatched trisomy. Described in this section is how to build a joint distribution model for the heterozygosity rates for a set of alleles; that is, for the expected allele counts at a number of loci for one or more hypotheses.

Suppose that on SNP i, LIK(D|Hm,i) is the fit for matched hypothesis $H_m$, and LIK(D|Hu, i) is the fit for unmatched hypothesis $H_u$, and pc(i)=probability of crossover between SNPs i–1 and i. One may then calculate the full likelihood as:

$$LIK(D|H)=\Sigma_E LIK(D|E,1:N)$$

where LIK(D|E, 1:N) is the likelihood of ending in hypothesis E, for SNPs 1:N. E=hypothesis of the last SNP, E∈(Hm, Hu). Recursively, one may calculate:

$$LIK(D|E,1:i)=LIK(D|E,i)+\log(\exp(LIK(D|E,1:i-1))* (1-pc(i))+\exp(LIK(D|\sim E,1:i-1))*pc(i))$$

where ~E is the hypothesis other than E (not E), where hypotheses considered are $H_m$ and $H_n$. In particular, one may calculate the likelihood of 1:i SNPs, based on likelihood of 1 to (i–1) SNPs with either the same hypothesis and no crossover, or the opposite hypothesis and a crossover, multiplied by the likelihood of the SNP i For SNP 1, $i=1$, LIK(D|E,1:1)=LIK(D|E,1).

For SNP 2, $i=2$, LIK(D|E,1:2)=LIK(D|E,2)+log(exp (LIK(D|E,1))*(1-pc(2))+exp(LIK(D|~E,1))*pc (2)).

and so on for i=3:N.

In some embodiments, the child fraction may be determined. The child fraction may refer to the proportion of sequences in a mixture of DNA that originate from the child. In the context of non-invasive prenatal diagnosis, the child fraction may refer to the proportion of sequences in the maternal plasma that originate from the fetus or the portion of the placenta with fetal genotype. It may refer to the child fraction in a sample of DNA that has been prepared from the maternal plasma, and may be enriched in fetal DNA. One purpose of determining the child fraction in a sample of DNA is for use in an algorithm that can make ploidy calls on the fetus, therefore, the child fraction could refer to whatever sample of DNA was analyzed by sequencing for the purpose of non-invasive prenatal diagnosis.

Some of the algorithms presented in this disclosure that are part of a method of non-invasive prenatal aneuploidy diagnosis assume a known child fraction, which may not always the case. In an embodiment, it is possible to find the most likely child fraction by maximizing the likelihood for disomy on selected chromosomes, with or without the presence of the parental data.

In particular, suppose that LIK(D|H11, cf, chr)=log likelihood as described above, for the disomy hypothesis, and for child fraction cf on chromosome chr. For selected chromosomes in Cset (usually 1:16), assumed to be euploid, the full likelihood is:

$$LIK(cf) = \Sum_{chr \in Cset} Lik(D|H11, cf, chr)$$

The most likely child fraction (cf*) is derived as $$cf^* = \underset{cf}{\mathrm{argmax}} LIK(cf).$$

It is possible to use any set of chromosomes. It is also possible to derive child fraction without assuming euploidy on the reference chromosomes. Using this method it is possible to determine the child fraction for any of the following situations: (1) one has array data on the parents and shotgun sequencing data on the maternal plasma; (2) one has array data on the parents and targeted sequencing data on the maternal plasma; (3) one has targeted sequencing data on both the parents and maternal plasma; (4) one has targeted sequencing data on both the mother and the maternal plasma fraction; (5) one has targeted sequencing data on the maternal plasma fraction; (6) other combinations of parental and child fraction measurements.

In some embodiments the informatics method may incorporate data dropouts; this may result in ploidy determinations of higher accuracy. Elsewhere in this disclosure it has been assumed that the probability of getting an A is a direct function of the true mother genotype, the true child genotype, the fraction of the child in the mixture, and the child copy number. It is also possible that mother or child alleles can drop out, for example instead of measuring true child AB in the mixture, it may be the case that only sequences mapping to allele A are measured. One may denote the parent dropout rate for genomic illumina data $d_{pg}$, parent dropout rate for sequence data $d_{ps}$ and child dropout rate for sequence data $d_{cs}$. In some embodiments, the mother dropout rate may be assumed to be zero, and child dropout rates are relatively low; in this case, the results are not severely affected by dropouts. In some embodiments the possibility of allele dropouts may be sufficiently large that they result in a significant effect of the predicted ploidy call. For such a case, allele dropouts have been incorporated into the algorithm here:

Parent SNP array data dropouts: For mother genomic data M, suppose that the genotype after the dropout is $m_d$, then $$P(M | m, i) = \sum_{m_d} P(M | m_d, i) P(m_d | m)$$

$$\text{where } P(M | m_d, i) = \begin{cases} 1 & m_i = m_d \\ 0 & m_i \neq m_d \end{cases}$$

as before, and $P(m_d|m)$ is the likelihood of genotype $m_d$ after the possible dropout given the true genotype m, defined as below, for dropout rate d

| m | AA | AB | BB | A | B | nocall |
|---|---|---|---|---|---|---|
| AA | $(1-d)^2$ | 0 | 0 | $2d(1-d)$ | 0 | $d^2$ |
| AB | 0 | $(1-d)^2$ | 0 | $d(1-d)$ | $d(1-d)$ | $d^2$ |
| BB | 0 | 0 | $(1-d)^2$ | 0 | $2d(1-d)$ | $d^2$ |

A similar equation applies for father SNP array data.

Parent sequence data dropouts: For mother sequence data SM $$P(SM | m, i) = \sum_{m_d} P_{X|m_d}(am_i) P(m_d | m)$$

where $P(m_d|m)$ is defined as in previous section and $P_{X|m_d}(am_i)$ probability from a binomial distribution is defined as before in the parent data likelihood section. A similar equation applies to the paternal sequence data.

Free floating DNA sequence data dropout:

$$P(S | m, c, H, cf, i) = \sum_{m_d, c_d} P(S | \mu(m_d, c_d, cf, H), i) P(m_d | m) P(c_d | c)$$

where $P(S|\mu(m_d, c_d, cf, H), i)$ is as defined in the section on free floating data likelihood.

In an embodiment, $p(m_d|m)$ is the probability of observed mother genotype $m_d$, given true mother genotype m, assuming dropout rate $d_{ps}$, and $p(c_d|c)$ is the probability of observed child genotype $c_d$, given true child genotype c, assuming dropout rate $d_{cs}$. If $nA_T$=number of A alleles in true genotype c, $nA_D$=number of A alleles in observed genotype $c_d$, where $nA_T \geq nA_D$, and similarly $nB_T$=number of B alleles in true genotype c, $nB_D$=number of B alleles in observed genotype $c_d$, where $nB_T \geq nB_D$ and d=dropout rate, then $$p(c_d | c) = \binom{nA_T}{nA_D} * d^{nA_T - nA_D} * (1-d)^{nA_D} * \binom{nB_T}{nB_D} * d^{nB_T - nB_D} * (1-d)^{nB_D}$$

In an embodiment, the informatics method may incorporate random and consistent bias. In an ideal word there is no per SNP consistent sampling bias or random noise (in addition to the binomial distribution variation) in the number of sequence counts. In particular, on SNP i, for mother genotype m, true child genotype c and child fraction cf, and X=the number of A's in the set of (A+B) reads on SNP i, X acts like a X~Binomial(p, A+B), where p=μ(m, c, cf, H)=true probability of A content.

In an embodiment, the informatics method may incorporate random bias. As is often the case, suppose that there is a bias in the measurements, so that the probability of getting an A on this SNP is equal to q, which is a bit different than p as defined above. How much different p is from q depends on the accuracy of the measurement process and number of other factors and can be quantified by standard deviations of q away from p. In an embodiment, it is possible to model q as having a beta distribution, with parameters α, β depending on the mean of that distribution being centered at p, and some specified standard deviation s. In particular, this gives $X|q \sim \text{Bin}(q, D_i)$, where $q \sim \text{Beta}(\alpha, \beta)$. If we let $E(q)=p$, $V(q)=s^2$, and parameters $\alpha$, $\beta$ can be derived as $\alpha=pN$, $\beta=(1-p)N$, where $$N = \frac{p(1-p)}{s^2} - 1.$$

This is the definition of a beta-binomial distribution, where one is sampling from a binomial distribution with variable parameter q, where q follows a beta distribution with mean p. So, in a setup with no bias, on SNP i, the parent sequence data (SM) probability assuming true mother genotype (m), given mother sequence A count on SNP i ($am_i$) and mother sequence B count on SNP i ($bm_i$) may be calculated as:

$P(SM|m,i)=P_{X|m}(am_i)$ where $X|m \sim \text{Binom}(p_m(A),am_i+bm_i)$

Now, including random bias with standard deviation s, this becomes:

$X|m \sim \text{BetaBinom}(p_m(A),am_i+bm_i,s)$

In the case with no bias, the maternal plasma DNA sequence data (S) probability assuming true mother genotype (m), true child genotype (c), child fraction (cf), assuming child hypothesis H, given free floating DNA sequence A count on SNP i ($a_i$) and free floating sequence B count on SNP i ($b_i$) may be calculated as $P(S|m,c,cf,H,i)=P_x(a_1)$ where $X \sim \text{Binom}(p(A), a_i+b_i)$ with $p(A)=\mu(m, c, cf, H)$.

In an embodiment, including random bias with standard deviation s, this becomes $X \sim \text{BetaBinom}(p(A),a_i+b_i,s)$, where the amount of extra variation is specified by the deviation parameter s, or equivalently N. The smaller the value of s (or the larger the value of N) the closer this distribution is to the regular binomial distribution. It is possible to estimate the amount of bias, i.e. estimate N above, from unambiguous contexts AA|AA, BB|BB, AA|BB, BB|AA and use estimated $\hat{N}$ in the above probability. Depending on the behavior of the data, N may be made to be a constant irrespective of the depth of read $a_i+b_i$, or a function of $a_i+b_i$, making bias smaller for larger depths of read.

In an embodiment, the informatics method may incorporate consistent per-SNP bias. Due to artifacts of the sequencing process, some SNPs may have consistently lower or higher counts irrespective of the true amount of A content. Suppose that SNP i consistently adds a bias of $w_i$ percent to the number of A counts. In some embodiments, this bias can be estimated from the set of training data derived under same conditions, and added back in to the parent sequence data estimate as:

$P(SM|m,i)=P_{X|m}(am_i)$ where $X|m \sim \text{BetaBinom}(p_m(A)+w_i,am_i+bm_i,s)$ and with the free floating DNA sequence data probability estimate as:

$P(S|m,c,cf,H,i)=P_x(a_1)$ where $X \sim \text{BetaBinom}(p(A)+w_i,a_i+b_i,s)$,

In some embodiments, the method may be written to specifically take into account additional noise, differential sample quality, differential SNP quality, and random sampling bias. An example of this is given here. This method has been shown to be particularly useful in the context of data generated using the massively multiplexed mini-PCR protocol, and was used in Experiments 7 through 13. The method involves several steps that each introduce different kind of noise and/or bias to the final model:

(1) Suppose the first sample that comprises a mixture of maternal and fetal DNA contains an original amount of DNA of size=$N_0$ molecules, usually in the range 1,000-40,000, where p=true % refs (2) In the amplification using the universal ligation adaptors, assume that $N_1$ molecules are sampled; usually $N_1 \sim N_0/2$ molecules and random sampling bias is introduced due to sampling. The amplified sample may contain a number of molecules $N_2$ where $N_2 \gg N_1$. Let $X_1$ represent the amount of reference loci (on per SNP basis) out of $N_1$ sampled molecules, with a variation in $p_1=X_1/N_1$ that introduces random sampling bias throughout the rest of protocol. This sampling bias is included in the model by using a Beta-Binomial (BB) distribution instead of using a simple Binomial distribution model. Parameter N of the Beta-Binomial distribution may be estimated later on per sample basis from training data after adjusting for leakage and amplification bias, on SNPs with $0<p<1$. Leakage is the tendency for a SNP to be read incorrectly.

(3) The amplification step will amplify any allelic bias, thus amplification bias introduced due to possible uneven amplification. Suppose that one allele at a locus is amplified f times another allele at that locus is amplified g times, where $f=ge^b$, where b=0 indicates no bias. The bias parameter, b, is centered at 0, and indicates how much more or less the A allele get amplified as opposed to the B allele on a particular SNP. The parameter b may differ from SNP to SNP. Bias parameter b may be estimated on per SNP basis, for example from training data.

(4) The sequencing step involves sequencing a sample of amplified molecules. In this step there may be leakage, where leakage is the situation where a SNP is read incorrectly. Leakage may result from any number of problems, and may result in a SNP being read not as the correct allele A, but as another allele B found at that locus or as an allele C or D not typically found at that locus. Suppose the sequencing measures the sequence data of a number of DNA molecules from an amplified sample of size $N_3$, where $N_3<N_2$. In some embodiments, $N_3$ may be in the range of 20,000 to 100,000; 100,000 to 500,000; 500,000 to 4,000,000; 4,000,000 to 20,000,000; or 20,000,000 to 100,000,000. Each molecule sampled has a probability $p_g$ of being read correctly, in which case it will show up correctly as allele A. The sample will be incorrectly read as an allele unrelated to the original molecule with probability $1-p_g$, and will look like allele A with probability $p_r$, allele B with probability $p_m$ or allele C or allele D with probability $p_o$, where $p_r+p_m+p_o=1$. Parameters $p_g$, $p_r$, $p_m$, $p_o$ are estimated on per SNP basis from the training data.

Different protocols may involve similar steps with variations in the molecular biology steps resulting in different amounts of random sampling, different levels of amplification and different leakage bias. The following model may be equally well applied to each of these cases. The model for the amount of DNA sampled, on per SNP basis, is given by:

$X_3 \sim \text{BetaBinomial}(L(F(p,b),p_r,p_g),N*H(p,b))$ where p=the true amount of reference DNA, b=per SNP bias, and as described above, $p_g$ is the probability of a correct read, $p_r$ is the probability of read being read incorrectly but serendipitously looking like the correct allele, in case of a bad read, as described above, and:

$F(p,b)=pe^b/(pe^b+(1-p)),H(p,b)=(e^bp+(1-p))^2/e^b,L(p,p_r,p_g)=p*p_g+p_r*(1-p_g).$

In some embodiments, the method uses a Beta-Binomial distribution instead of a simple binomial distribution; this takes care of the random sampling bias. Parameter N of the Beta-Binomial distribution is estimated on per sample basis on an as needed basis. Using bias correction F(p,b), H(p,b), instead of just p, takes care of the amplification bias. Parameter b of the bias is estimated on per SNP basis from training data ahead of time.

In some embodiments the method uses leakage correction $L(p, p_r, p_g)$, instead of just p; this takes care of the leakage bias, i.e. varying SNP and sample quality. In some embodiments, parameters $p_g$, $p_r$, $p_o$ are estimated on per SNP basis from the training data ahead of time. In some embodiments, the parameters $p_g$, $p_r$, $p_o$ may be updated with the current sample on the go, to account for varying sample quality.

The model described herein is quite general and can account for both differential sample quality and differential SNP quality. Different samples and SNPs are treated differently, as exemplified by the fact that some embodiments use Beta-Binomial distributions whose mean and variance are a function of the original amount of DNA, as well as sample and SNP quality.

Platform Modeling

Consider a single SNP where the expected allele ratio present in the plasma is r (based on the maternal and fetal genotypes). The expected allele ratio is defined as the expected fraction of A alleles in the combined maternal and fetal DNA. For maternal genotype $g_m$ and child genotype $g_c$, the expected allele ratio is given by equation 1, assuming that the genotypes are represented as allele ratios as well.

$$r = f g_c + (1-f) g_m \quad (1)$$

The observation at the SNP consists of the number of mapped reads with each allele present, $n_a$ and $n_b$, which sum to the depth of read d. Assume that thresholds have already been applied to the mapping probabilities and phred scores such that the mappings and allele observations can be considered correct. A phred score is a numerical measure that relates to the probability that a particular measurement at a particular base is wrong. In an embodiment, where the base has been measured by sequencing, the phred score may be calculated from the ratio of the dye intensity corresponding to the called base to the dye intensity of the other bases. The simplest model for the observation likelihood is a binomial distribution which assumes that each of the d reads is drawn independently from a large pool that has allele ratio r. Equation 2 describes this model.

$$P(n_a, n_b \mid r) = p_{bino}(n_a; n_a + n_b, r) = \binom{n_a + n_b}{n_a} r^{n_a} (1-r)^{n_b} \quad (2)$$

The binomial model can be extended in a number of ways. When the maternal and fetal genotypes are either all A or all B, the expected allele ratio in plasma will be 0 or 1, and the binomial probability will not be well-defined. In practice, unexpected alleles are sometimes observed in practice. In an embodiment, it is possible to use a corrected allele ratio $\hat{r} = 1/(n_a + n_b)$ to allow a small number of the unexpected allele. In an embodiment, it is possible to use training data to model the rate of the unexpected allele appearing on each SNP, and use this model to correct the expected allele ratio. When the expected allele ratio is not 0 or 1, the observed allele ratio may not converge with a sufficiently high depth of read to the expected allele ratio due to amplification bias or other phenomena. The allele ratio can then be modeled as a beta distribution centered at the expected allele ratio, leading to a beta-binomial distribution for $P(n_a, n_b \mid r)$ which has higher variance than the binomial.

The platform model for the response at a single SNP will be defined as $F(a, b, g_c, g_m, f)$ (3), or the probability of observing $n_a = a$ and $n_b = b$ given the maternal and fetal genotypes, which also depends on the fetal fraction through equation 1. The functional form of F may be a binomial distribution, beta-binomial distribution, or similar functions as discussed above.

$$F(a, b, g_c, g_m, f) = P(n_a = a, n_b = b \mid g_c, g_m, f) = P(n_a = a, n = b \mid r(g_c, g_m, f)) \quad (3)$$

In an embodiment, the child fraction may be determined as follows. A maximum likelihood estimate of the fetal fraction f for a prenatal test may be derived without the use of paternal information. This may be relevant where the paternal genetic data is not available, for example where the father of record is not actually the genetic father of the fetus. The fetal fraction is estimated from the set of SNPs where the maternal genotype is 0 or 1, resulting in a set of only two possible fetal genotypes. Define $S_0$ as the set of SNPs with maternal genotype 0 and $S_1$ as the set of SNPs with maternal genotype 1. The possible fetal genotypes on $S_0$ are 0 and 0.5, resulting in a set of possible allele ratios $R_0(f) = (0, f/2)$. Similarly, $R_1(f) = \{1-f/2, 1\}$. This method can be trivially extended to include SNPs where maternal genotype is 0.5, but these SNPs will be less informative due to the larger set of possible allele ratios.

Define $N_{a0}$ and $N_{b0}$ As the vectors formed by $n_{as}$ and $n_{bs}$ for SNPs s in $S_0$, and $N_{a1}$ and $N_{b1}$ similarly for $S_1$. The maximum likelihood estimate $\hat{f}$ of f is defined by equation 4.

$$\hat{f} = \arg\max_f P(N_{a0}, N_{b0} \mid f) P(N_{a1}, N_{b1} \mid f) \quad (4)$$

Assuming that the allele counts at each SNP are independent conditioned on the SNP's plasma allele ratio, the probabilities can be expressed as products over the SNPs in each set (5).

$$P(N_{a0}, N_{b0} \mid f) = \Pi_{s \in S_0} P(n_{as}, n_{bs} \mid f)$$

$$P(N_{a1}, N_{b1} \mid f) = \Pi_{s \in S_1} P(n_{as}, n_{bs} \mid f) \quad (5)$$

The dependence on f is through the sets of possible allele ratios $R_0(f)$ and $R_1(f)$. The SNP probability $P(n_{as}, n_{bs} \mid f)$ can be approximated by assuming the maximum likelihood genotype conditioned on f. At reasonably high fetal fraction and depth of read, the selection of the maximum likelihood genotype will be high confidence. For example, at fetal fraction of 10 percent and depth of read of 1000, consider a SNP where the mother has genotype zero. The expected allele ratios are 0 and 5 percent, which will be easily distinguishable at sufficiently high depth of read. Substitution of the estimated child genotype into equation 5 results in the complete equation (6) for the fetal fraction estimate.

$$\hat{f} = \mathrm{argmax}_f \left[ \prod_{s \in S_0} \left( \max_{r_s \in R_0(f)} P(n_{as}, n_{bs} \mid r_s) \right) \prod_{s \in S_1} \left( \max_{r_s \in R_1(f)} P(n_{as}, n_{bs} \mid r_s) \right) \right] \quad (6)$$

The fetal fraction must be in the range [0, 1] and so the optimization can be easily implemented by a constrained one-dimensional search.

In the presence of low depth of read or high noise level, it may be preferable not to assume the maximum likelihood genotype, which may result in artificially high confidences. Another method would be to sum over the possible genotypes at each SNP, resulting in the following expression (7) for $P(n_a, n_b|f)$ for a SNP in $S_0$. The prior probability $P(r)$ could be assumed uniform over $R_0(f)$, or could be based on population frequencies. The extension to group $S_1$ is trivial.

$$P(n_a, n_b|f) = \Sigma_{r \in R_0(f)} P(n_a, n_a|r) P(r) \quad (7)$$

In some embodiments the probabilities may be derived as follows. A confidence can be calculated from the data likelihoods of the two hypotheses $H_t$ and $H_f$. The likelihood of each hypothesis is derived based on the response model, the estimated fetal fraction, the mother genotypes, allele population frequencies, and the plasma allele counts.

Define the following notation:
$G_m$, $G_c$ true maternal and child genotypes
$G_{af}$, $G_{tf}$ true genotypes of alleged father and of true father
$G(g_c, g_m, g_{tf}) = P(G_c = g_c | G_m = g_m, G_{tf} = g_{tf})$ inheritance probabilities
$P(g) = P(G_{tf} = g)$ population frequency of genotype $g$ at particular SNP Assuming that the observation at each SNP is independent conditioned on the plasma allele ratio, the likelihood of a paternity hypothesis is the product of the likelihoods on the SNPs. The following equations derive the likelihood for a single SNP. Equation 8 is a general expression for the likelihood of any hypothesis h, which will then be broken down into the specific cases of $H_t$ and $H_f$.

$$P(n_a, n_b | h, G_m, G_{tf}, f) = \sum_{g_c \in (0, 0.5, 1)} P(n_a, n_b | G_c = g_c, G_m, G_{tf}, h, f) \quad (8)$$

$$P(G_c = g_c, G_m, G_{tf}, h, f)$$

$$= \sum_{g_c \in (0, 0.5, 1)} P(n_a, n_b | G_c = g_c, G_m, f)$$

$$P(G_c = g_c | G_m, G_{tf}, h)$$

$$= \sum_{g_c \in (0, 0.5, 1)} F(n_a, n_b, g_c, g_m, f)$$

$$P(G_c = g_c | G_m, G_{tf}, h)$$

In the case of $H_t$, the alleged father is the true father and the fetal genotypes are inherited from the maternal genotypes and alleged father genotypes according to equation 9.

$$P(n_a, n_b | H_t, G_m, G_{tf}, f) = \sum_{g_c \in (0, 0.5, 1)} F(n_a, n_b, g_c, g_m, f) \quad (9)$$

$$P(G_c = g_c | G_m, G_{tf}, H_t)$$

$$= \sum_{g_c \in (0, 0.5, 1)} F(n_a, n_b, g_c, g_m, f)$$

$$G(g_c, G_m, G_{tf})$$

In the case of $H_f$, the alleged father is not the true father. The best estimate of the true father genotypes are given by the population frequencies at each SNP. Thus, the probabilities of child genotypes are determined by the known mother genotypes and the population frequencies, as in equation 10.

$$P(n_a, n_b | H_f, G_{tf}, f) = \sum_{g_c \in (0, 0.5, 1)} F(n_a, n_b, g_c, g_m, f)$$

$$P(G_c = g_c | G_m, G_{tf}, H_f)$$

$$= \sum_{g_c \in (0, 0.5, 1)} F(n_a, n_b, g_c, g_m, f)$$

$$P(G_c = g_c | G_m)$$

$$= \sum_{g_c \in (0, 0.5, 1)} \sum_{g_{tf} \in (0, 0.5, 1)} F(n_a, n_b, g_c, g_m, f)$$

$$P(G_c = g_c | G_m, G_{tf} = g_{tf}) P(G_{tf} = g_{tf})$$

$$= \sum_{g_c \in (0, 0.5, 1)} \sum_{g_{tf} \in (0, 0.5, 1)} F(n_a, n_b, g_c, g_m, f)$$

$$G(g_c, G_m, g_{tf}) P(g_{tf})$$

The confidence $C_p$ on correct paternity is calculated from the product over SNPs of the two likelihoods using Bayes rule (11).

$$C_p = \frac{\Pi_s P(n_{as}, n_{bs} | H_t, G_{ms}, G_{tf}, f)}{\Pi_s P(n_{as}, n_{bs} | H_t, G_{ms}, G_{tf}, f) + \Pi_s P(n_{as}, n_{bs} | H_f, G_{ms}, G_{tf}, f)} \quad (11)$$

Exemplary Methods for Identifying and Analyzing Multiple Pregnancies

In some embodiments, any of the methods of the present invention are used to detect the presence of a multiple pregnancy, such as a twin pregnancy, where at least one of the fetuses is genetically different from at least one other fetus. In some embodiments, fraternal twins are identified based on the presence of two fetus with different allele, different allele ratios, or different allele distributions at some (or all) of the tested loci. In some embodiments, fraternal twins are identified by determining the expected allele ratio at each locus (such as SNP loci) for two fetuses that may have the same or different fetal fractions in the sample (such as a plasma sample). In some embodiments, the likelihood of a particular pair of fetal fractions (where f1 is the fetal fraction for fetus 1, and f2 is the fetal fraction for fetus 2) is calculated by considering some or all of the possible genotypes of the two fetuses, conditioned on the mother's genotype and genotype population frequencies. The mixture of two fetal and one maternal genotype, combined with the fetal fractions, determine the expected allele ratio at a SNP. For example, if the mother is AA, fetus 1 is AA, and fetus 2 is AB, the overall fraction of B allele at the SNP is one-half of f2. The likelihood calculation asks how well all of the SNPs together match the expected allele ratios based on all of the possible combinations of fetal genotypes. The fetal fraction pair (f1, f2) that best matches the data is selected. It is not necessary to calculated specific genotypes of the fetuses, instead, one can, for example, considered all of the possible genotypes in a statistical combination. In some embodiments, if the method does not distinguish between singleton and identical twins, an ultrasound can be performed to determine whether there is a singleton or identical twin pregnancy. If the ultrasound detects a twin pregnancy it can be assumed that the pregnancy is an identical twin pregnancy because a fraternal twin pregnancy would have been detected based on the SNP analysis discussed above.

In some embodiments, a pregnant mother is known to have a multiple pregnancy (such as a twin pregnancy) based on prior testing, such as an ultrasound. Any of the methods of the present invention can be used to determine whether the multiple pregnancy includes identical or fraternal twins.

For example, the measured allele ratios can be compared to what would be expected for identical twins (the same allele ratios as a singleton pregnancy) or for fraternal twins (such as the calculation of allele ratios as described above). Some identical twins are monochorionic twins, which have a risk of twin-to-twin transfusion syndrome. Thus, twins determined to be identical twins using a method of the invention are desirably tested (such as by ultrasound) to determine if they are monochorionic twins, and if so, these twins can be monitored (such as bi-weekly ultrasounds from 16 weeks) for signs of win-to-twin transfusion syndrome.

In some embodiments, any of the methods of the present invention are used to determine whether any of the fetuses in a multiple pregnancy, such as a twin pregnancy, are aneuploid. Aneuploidy testing for twins begins with the fetal fraction estimate. In some embodiments, the fetal fraction pair (f1, f2) that best matches the data is selected as described above. In some embodiments, a maximum likelihood estimate is performed for the parameter pair (f1, f2) over the range of possible fetal fractions. In some embodiments, the range of f2 is from 0 to f1 because f2 is defined as the smaller fetal fraction. Given a pair (f1, f2), data likelihood is calculated from the allele ratios observed at a set of loci such as SNP loci. In some embodiments, the data likelihood reflects the genotypes of the mother, the father if available, population frequencies, and the resulting probabilities of fetal genotypes. In some embodiments, SNPs are assumed independent. The estimated fetal fraction pair is the one that produces the highest data likelihood. If f2 is 0 then the data is best explained by only one set of fetal genotypes, indicating identical twins, where f1 is the combined fetal fraction. Otherwise f1 and f2 are the estimates of the individual twin fetal fractions. Having established the best estimate of (f1, f2), one can predict the overall fraction of B allele in the plasma for any combination of maternal and fetal genotypes, if desired. It is not necessary to assign individual sequence reads to the individual fetuses. Ploidy testing is performed using another maximum likelihood estimate which compares the data likelihood of two hypotheses. In some embodiments for identical twins, one considers the hypotheses (i) both twins are euploid, and (ii) both twins are trisomic. In some embodiments for fraternal twins, one considers the hypotheses (i) both twins are euploid and (ii) at least one twin is trisomic. The trisomy hypotheses for fraternal twins are based on the lower fetal fraction, since a trisomy in the twin with a higher fetal fraction would also be detected. Ploidy likelihoods are calculated using a method which predicts the expected number of reads at each targeted genome locus conditioned on either the disomy or trisomy hypothesis. There is no requirement for a disomy reference chromosome. The variance model for the expected number of reads takes into account the performance of individual target loci as well as the correlation between loci (see, for example, U.S. Ser. No. 62/008,235, filed Jun. 5, 2014, and U.S. Ser. No. 62/032,785, filed Aug. 4, 2014, which are each hereby incorporated by reference in its entirety). If the smaller twin has fetal fraction f1, our ability to detect a trisomy in that twin is equivalent to our ability to detect a trisomy in a singleton pregnancy at the same fetal fraction. This is because the part of the method that detects the trisomy in some embodiments does not depend on genotypes and does not distinguish between multiple or singleton pregnancy. It simply looks for an increased number of reads in accordance with the determined fetal fraction.

In some embodiments, the method includes detecting the presence of twins based on SNP loci (such as described above). If twins are detected, SPNs are used to determine the fetal fraction of each fetus (f1, f2) such as described above. In some embodiments, samples that have high confidence disomy calls are used to determine the amplification bias on a per-SNP basis. In some embodiments, these samples with high confidence disomy calls are analyzed in the same run as one or more samples of interest. In some embodiments, the amplification bias on a per-SNP basis is used to model the distribution of reads for one or more chromosomes or chromosome segments of interest such as chromosome 21 that are expected or the disomy hypothesis and the trisomy hypothesis given the lower of the two twin fetal fraction. The likelihood or probability of disomy or trisomy is calculated given the two models and the measured quantity of the chromosome or chromosome segment of interest.

In some embodiments, the threshold for a positive aneuploidy call (such as a trisomy call) is set based on the twin with the lower fetal fraction. This way, if the other twin is positive, or if both are positive, the total chromosome representation is definitely above the threshold.

Maximum Likelihood Model Using Percent Fetal Fraction

Determining the ploidy status of a fetus by measuring the free floating DNA contained in maternal serum, or by measuring the genotypic material in any mixed sample, is a non-trivial exercise. There are a number of methods, for example, performing a read count analysis where the presumption is that if the fetus is trisomic at a particular chromosome, then the overall amount of DNA from that chromosome found in the maternal blood will be elevated with respect to a reference chromosome. One way to detect trisomy in such fetuses is to normalize the amount of DNA expected for each chromosome, for example, according to the number of SNPs in the analysis set that correspond to a given chromosome, or according to the number of uniquely mappable portions of the chromosome. Once the measurements have been normalized, any chromosomes for which the amount of DNA measured exceeds a certain threshold are determined to be trisomic. This approach is described in Fan, et al. PNAS, 2008; 105(42); pp. 16266-16271, and also in Chiu et al. BMJ 2011; 342:c7401. In the Chiu et al. paper, the normalization was accomplished by calculating a Z score as follows:

> Z score for percentage chromosome 21 in test case=
> ((percentage chromosome 21 in test case)−
> (mean percentage chromosome 21 in reference
> controls))/(standard deviation of percentage
> chromosome 21 in reference controls).

These methods determine the ploidy status of the fetus using a single hypothesis rejection method. However, they suffer from some significant shortcomings. Since these methods for determining ploidy in the fetus are invariant according to the percentage of fetal DNA in the sample, they use one cut off value; the result of this is that the accuracies of the determinations are not optimal, and those cases where the percentage of fetal DNA in the mixture are relatively low will suffer the worst accuracies.

In an embodiment, a method of the present disclosure is used to determine the ploidy state of the fetus involves taking into account the fraction of fetal DNA in the sample. In another embodiment of the present disclosure, the method involves the use of maximum likelihood estimations. In an embodiment, a method of the present disclosure involves calculating the percent of DNA in a sample that is fetal or placental in origin. In an embodiment, the threshold for calling aneuploidy is adaptively adjusted based on the calculated percent fetal DNA. In some embodiments, the method for estimating the percentage of DNA that is of fetal origin in a mixture of DNA, comprises obtaining a mixed sample that comprises genetic material from the mother, and genetic material from the fetus, obtaining a genetic sample from the father of the fetus, measuring the DNA in the mixed sample, measuring the DNA in the father sample, and calculating the percentage of DNA that is of fetal origin in the mixed sample using the DNA measurements of the mixed sample, and of the father sample.

In an embodiment of the present disclosure, the fraction of fetal DNA, or the percentage of fetal DNA in the mixture can be measured. In some embodiments the fraction can be calculated using only the genotyping measurements made on the maternal plasma sample itself, which is a mixture of fetal and maternal DNA. In some embodiments the fraction may be calculated also using the measured or otherwise known genotype of the mother and/or the measured or otherwise known genotype of the father. In some embodiments the percent fetal DNA may be calculated using the measurements made on the mixture of maternal and fetal DNA along with the knowledge of the parental contexts. In an embodiment, the fraction of fetal DNA may be calculated using population frequencies to adjust the model on the probability on particular allele measurements.

In an embodiment of the present disclosure, a confidence may be calculated on the accuracy of the determination of the ploidy state of the fetus. In an embodiment, the confidence of the hypothesis of greatest likelihood ($H_{major}$) may be calculated as $(1-H_{major})/\Sigma(\text{all H})$. It is possible to determine the confidence of a hypothesis if the distributions of all of the hypotheses are known. It is possible to determine the distribution of all of the hypotheses if the parental genotype information is known. It is possible to calculate a confidence of the ploidy determination if the knowledge of the expected distribution of data for the euploid fetus and the expected distribution of data for the aneuploid fetus are known. It is possible to calculate these expected distributions if the parental genotype data are known. In an embodiment one may use the knowledge of the distribution of a test statistic around a normal hypothesis and around an abnormal hypothesis to determine both the reliability of the call as well as refine the threshold to make a more reliable call. This is particularly useful when the amount and/or percent of fetal DNA in the mixture is low. It will help to avoid the situation where a fetus that is actually aneuploid is found to be euploid because a test statistic, such as the Z statistic does not exceed a threshold that is made based on a threshold that is optimized for the case where there is a higher percent fetal DNA.

In an embodiment, a method disclosed herein can be used to determine a fetal aneuploidy by determining the number of copies of maternal and fetal target chromosomes in a mixture of maternal and fetal genetic material. This method may entail obtaining maternal tissue comprising both maternal and fetal genetic material, in some embodiments this maternal tissue may be maternal plasma or a tissue isolated from maternal blood. This method may also entail obtaining a mixture of maternal and fetal genetic material from said maternal tissue by processing the aforementioned maternal tissue. This method may entail distributing the genetic material obtained into a plurality of reaction samples, to randomly provide individual reaction samples that comprise a target sequence from a target chromosome and individual reaction samples that do not comprise a target sequence from a target chromosome, for example, performing high throughput sequencing on the sample. This method may entail analyzing the target sequences of genetic material present or absent in said individual reaction samples to provide a first number of binary results representing presence or absence of a presumably euploid fetal chromosome in the reaction samples and a second number of binary results representing presence or absence of a possibly aneuploid fetal chromosome in the reaction samples. Either of the number of binary results may be calculated, for example, by way of an informatics technique that counts sequence reads that map to a particular chromosome, to a particular region of a chromosome, to a particular locus or set of loci. This method may involve normalizing the number of binary events based on the chromosome length, the length of the region of the chromosome, or the number of loci in the set. This method may entail calculating an expected distribution of the number of binary results for a presumably euploid fetal chromosome in the reaction samples using the first number. This method may entail calculating an expected distribution of the number of binary results for a presumably aneuploid fetal chromosome in the reaction samples using the first number and an estimated fraction of fetal DNA found in the mixture, for example, by multiplying the expected read count distribution of the number of binary results for a presumably euploid fetal chromosome by $(1+n/2)$ where n is the estimated fetal fraction. In some embodiments, the sequence reads may be treated at probabilistic mappings rather than binary results; this method would yield higher accuracies, but require more computing power. The fetal fraction may be estimated by a plurality of methods, some of which are described elsewhere in this disclosure. This method may involve using a maximum likelihood approach to determine whether the second number corresponds to the possibly aneuploid fetal chromosome being euploid or being aneuploid. This method may involve calling the ploidy status of the fetus to be the ploidy state that corresponds to the hypothesis with the maximum likelihood of being correct given the measured data.

Note that the use of a maximum likelihood model may be used to increase the accuracy of any method that determines the ploidy state of a fetus. Similarly, a confidence may be calculated for any method that determines the ploidy state of the fetus. The use of a maximum likelihood model would result in an improvement of the accuracy of any method where the ploidy determination is made using a single hypothesis rejection technique. A maximum likelihood model may be used for any method where a likelihood distribution can be calculated for both the normal and abnormal cases. The use of a maximum likelihood model implies the ability to calculate a confidence for a ploidy call.

Further Discussion of the Method

In an embodiment, a method disclosed herein utilizes a quantitative measure of the number of independent observations of each allele at a polymorphic locus, where this does not involve calculating the ratio of the alleles. This is different from methods, such as some microarray based methods, which provide information about the ratio of two alleles at a locus but do not quantify the number of independent observations of either allele. Some methods known in the art can provide quantitative information regarding the number of independent observations, but the calculations leading to the ploidy determination utilize only the allele ratios, and do not utilize the quantitative information. To illustrate the importance of retaining information about the number of independent observations consider the sample locus with two alleles, A and B. In a first experiment twenty A alleles and twenty B alleles are observed, in a second experiment 200 A alleles and 200 B alleles are observed. In both experiments the ratio $(A/(A+B))$ is equal to 0.5, however the second experiment conveys more information than the first about the certainty of the frequency of the A or B allele. The instant method, rather than utilizing the allele ratios, uses the quantitative data to more accurately model the most likely allele frequencies at each polymorphic locus.

In an embodiment, the instant methods build a genetic model for aggregating the measurements from multiple polymorphic loci to better distinguish trisomy from disomy and also to determine the type of trisomy. Additionally, the instant method incorporates genetic linkage information to enhance the accuracy of the method. This is in contrast to some methods known in the art where allele ratios are averaged across all polymorphic loci on a chromosome. The method disclosed herein explicitly models the allele frequency distributions expected in disomy as well as and trisomy resulting from nondisjunction during meiosis I, nondisjunction during meiosis II, and nondisjunction during mitosis early in fetal development. To illustrate why this is important, if there were no crossovers nondisjunction during meiosis I would result a trisomy in which two different homologs were inherited from one parent; nondisjunction during meiosis II or during mitosis early in fetal development would result in two copies of the same homolog from one parent. Each scenario results in different expected allele frequencies at each polymorphic locus and also at all physically linked loci (i.e. loci on the same chromosome) considered jointly. Crossovers, which result in the exchange of genetic material between homologs, make the inheritance pattern more complex, but the instant method accommodates for this by using genetic linkage information, i.e. recombination rate information and the physical distance between loci. To better distinguish between meiosis I nondisjunction and meiosis II or mitotic nondisjunction the instant method incorporates into the model an increasing probability of crossover as the distance from the centromere increases. Meiosis II and mitotic nondisjunction can be distinguished by the fact that mitotic nondisjunction typically results in identical or nearly identical copies of one homolog while the two homologs present following a meiosis II nondisjunction event often differ due to one or more crossovers during gametogenesis.

In an embodiment, a method of the present disclosure may not determine the haplotypes of the parents if disomy is assumed. In an embodiment, in case of trisomy, the instant method can make a determination about the haplotypes of one or both parents by using the fact that plasma takes two copies from one parent, and parent phase information can be determined by noting which two copies have been inherited from the parent in question. In particular, a child can inherit either two of the same copies of the parent (matched trisomy) or both copies of the parent (unmatched trisomy). At each SNP one can calculate the likelihood of the matched trisomy and of the unmatched trisomy. A ploidy calling method that does not use the linkage model accounting for crossovers would calculate the overall likelihood of the trisomy as a simple weighted average of the matched and unmatched trisomies over all chromosomes. However, due to the biological mechanisms that result in disjunction error and crossing over, trisomy can change from matched to unmatched (and vice versa) on a chromosome only if a crossover occurs. The instant method probabilistically takes into account the likelihood of crossover, resulting in ploidy calls that are of greater accuracy than those methods that do not.

In an embodiment, a reference chromosome is used to determine the child fraction and noise level amount or probability distribution. In an embodiment, the child fraction, noise level, and/or probability distribution is determined using only the genetic information available from the chromosome whose ploidy state is being determined. The instant method works without the reference chromosome, as well as without fixing the particular child fraction or noise level. This is a significant improvement and point of differentiation from methods known in the art where genetic data from a reference chromosome is necessary to calibrate the child fraction and chromosome behavior.

In an embodiment where a reference chromosome is not needed to determine the fetal fraction, determining the hypothesis is done as follows:

$$H^* = \underset{H}{\operatorname{argmax}} LIK(D \mid H) * priorprob(H)$$

With the algorithm with reference chromosome, one typically assumes that the reference chromosome is a disomy, and then one may either (a) fix the most likely child fraction and random noise level N based on this assumption and reference chromosome data:

$$[cfr^*, N^*] = \underset{cfr,N}{\operatorname{argmax}} LIK(D(ref.chrom) \mid H11, cfr, N)$$

And then reduce $$LIK(D|H)=LIK(D|H,cfr^*,N^*)$$

or (b) estimate the child fraction and noise level distribution based on this assumption and reference chromosome data. In particular, one would not fix just one value for cfr and N, but assign probability p(cfr, N) for the wider range of possible cfr, N values:

$$p(cfr,N) \sim LIK(D(ref,chrom)|H11,cfr,N)*priorprob(cfr, N)$$

where priorprob(cfr, N) is the prior probability of particular child fraction and noise level, determined by prior knowledge and experiments. If desired, just uniform over the range of cfr. N. One may then write:

$$LIK(D \mid H) = \sum_{cfr,N} LIK(D \mid H, cfr, N) * p(cfr, N)$$

Both methods above give good results.

Note that in some instances using a reference chromosome is not desirable, possible or feasible. In such a case, it is possible to derive the best ploidy call for each chromosome separately. In particular:

$$LIK(D \mid H) = \sum_{cfr,N} LIK(D \mid H, cfr, N) * p(cfr, N \mid H)$$

p(cfr, N|H) may be determined as above, for each chromosome separately, assuming hypothesis H, not just for the reference chromosome assuming disomy. It is possible, using this method, to keep both noise and child fraction parameters fixed, fix either of the parameters, or keep both parameters in probabilistic form for each chromosome and each hypothesis.

Measurements of DNA are noisy and/or error prone, especially measurements where the amount of DNA is small, or where the DNA is mixed with contaminating DNA.

This noise results in less accurate genotypic data, and less accurate ploidy calls. In some embodiments, platform modeling or some other method of noise modeling may be used to counter the deleterious effects of noise on the ploidy determination. The instant method uses a joint model of both channels, which accounts for the random noise due to the amount of input DNA, DNA quality, and/or protocol quality.

This is in contrast to some methods known in the art where the ploidy determinations are made using the ratio of allele intensities at a locus. This method precludes accurate SNP noise modeling. In particular, errors in the measurements typically do not specifically depend on the measured channel intensity ratio, which reduces the model to using one-dimensional information. Accurate modeling of noise, channel quality and channel interaction requires a two-dimensional joint model, which can not be modeled using allele ratios.

In particular, projecting two channel information to the ratio r where f(x,y) is r=x/y, does not lend itself to accurate channel noise and bias modeling. Noise on a particular SNP is not a function of the ratio, i.e. noise(x,y)≠f(x,y) but is in fact a joint function of both channels. For example, in the binomial model, noise of the measured ratio has a variance of r(1−r)/(x+y) which is not a function purely of r. In such a model, where any channel bias or noise is included, suppose that on SNP i, the observed channel X value is x=$a_i$X+$b_i$, where X is the true channel value, $b_i$ is the extra channel bias and random noise. Similarly, suppose that y=$c_i$Y+$d_i$. The observed ratio r=x/y can not accurately predict the true ratio X/Y or model the leftover noise, since (aiX+bi)/(ciY+di) is not a function of X/Y.

The method disclosed herein describes an effective way to model noise and bias using joint binomial distributions of all of the measurement channels individually. Relevant equations may be found elsewhere in the document in sections which speaks of per SNP consistent bias, P(good) and P(ref|bad), P(mut|bad) which effectively adjust SNP behavior. In an embodiment, a method of the present disclosure uses a BetaBinomial distribution, which avoids the limiting practice of relying on the allele ratios only, but instead models the behavior based on both channel counts.

In an embodiment, a method disclosed herein can call the ploidy of a gestating fetus from genetic data found in maternal plasma by using all available measurements. In an embodiment, a method disclosed herein can call the ploidy of a gestating fetus from genetic data found in maternal plasma by using the measurements from only a subset of parental contexts. Some methods known in the art only use measured genetic data where the parental context is from the AA|BB context, that is, where the parents are both homozygous at a given locus, but for a different allele. One problem with this method is that a small proportion of polymorphic loci are from the AA|BB context, typically less than 10%. In an embodiment of a method disclosed herein, the method does not use genetic measurements of the maternal plasma made at loci where the parental context is AA|BB. In an embodiment, the instant method uses plasma measurements for only those polymorphic loci with the AA|AB, AB|AA, and AB|AB parental context.

Some methods known in the art involve averaging allele ratios from SNPs in the AA|BB context, where both parent genotypes are present, and claim to determine the ploidy calls from the average allele ratio on these SNPs. This method suffers from significant inaccuracy due differential SNP behavior. Note that this method assumes that have both parent genotypes are known. In contrast, in some embodiments, the instant method uses a joint channel distribution model that does not assume the presence of either of the parents, and does not assume the uniform SNP behavior. In some embodiments, the instant method accounts for the different SNP behavior/weighing. In some embodiments, the instant method does not require the knowledge of one or both parental genotypes. An example of how the instant method may accomplish this follows:

In some embodiments, the log likelihood of a hypothesis may be determined on a per SNP basis. On a particular SNP i, assuming fetal ploidy hypothesis H and percent fetal DNA cf, the log likelihood of observed data D is defined as:

$$LIK(D \mid H, i) = \log P(D \mid H, cf, i) = \log\left(\sum_{m,f,c} P(D \mid m, f, c, H, cf, i) P(c \mid m, f, H) P(m \mid i) P(f \mid i)\right)$$

where m are possible true mother genotypes, f are possible true father genotypes, where m,f∈{AA, AB, BB}, and where c are possible child genotypes given the hypothesis H. In particular, for monosomy c {A, B}, for disomy c∈{AA, AB, BB}, for trisomy c∈{AAA, AAB, ABB, BBB}. Note that including parental genotypic data typically results in more accurate ploidy determinations, however, parental genotypic data is not necessary for the instant method to work well.

Some methods known in the art involve averaging allele ratios from SNPs where the mother is homozygous but a different allele is measured in the plasma (either AA|AB or AA|BB contexts), and claim to determine the ploidy calls from the average allele ratio on these SNPs. This method is intended for cases where the paternal genotype is not available. Note that it is questionable how accurately one can claim that plasma is heterozygous on a particular SNP without the presence of homozygous and opposite father BB: for cases with low child fraction, what looks like presence of B allele could be just presence of noise, additionally, what looks like no B present could be simple allele drop out of the fetal measurements. Even in a case where one can actually determine heterozygosity of the plasma, this method will not be able to distinguish paternal trisomies. In particular, for SNPs where mother is AA, and where some B is measured in the plasma, if the father is GG, the resulting child genotype is AGG, resulting in an average ratio of 33% A (for child fraction=100%). But in the case where the father is AG, the resulting child genotype could be AGG for matched trisomy, contributing to the 33% A ratio, or AAG for unmatched trisomy, drawing the average ratio more toward 66% A. Given that many trisomies are on chromosomes with crossovers, the overall chromosome can have anywhere between no unmatched trisomy and all unmatched trisomy, this ratio can vary anywhere between 33-66%. For a plain disomy, the ratio should be around 50%. Without the use of a linkage model or an accurate error model of the average, this method would miss many cases of paternal trisomy. In contrast, the method disclosed herein assigns parental genotype probabilities for each parental genotypic candidate, based on available genotypic information and population frequency, and does not explicitly require parental genotypes. Additionally, the method disclosed herein is able to detect trisomy even in the absence or presence of parent genotypic data, and can compensate by identifying the points of possible crossovers from matched to unmatched trisomy using a linkage model.

Some methods known in the art claim a method for averaging allele ratios from SNPs where neither the maternal or paternal genotype is known, and for determining the ploidy calls from average ratio on these SNPs. However, a method to accomplish these ends is not disclosed. The method disclosed herein is able to make accurate ploidy calls in such a situation, and the reduction to practice is disclosed elsewhere in this document, using a joint probability maximum likelihood method and optionally utilizes SNP noise and bias models, as well as a linkage model.

Some methods known in the art involve averaging allele ratios and claim to determine the ploidy calls from the average allele ratio at one or a few SNPs. However, such methods do not utilize the concept of linkage. The methods disclosed herein do not suffer from these drawbacks.

Using Sequence Length as a Prior to Determine the Origin of DNA

It has been reported that the distribution of length of sequences differ for maternal and fetal DNA, with fetal generally being shorter. In an embodiment of the present disclosure, it is possible to use previous knowledge in the form of empirical data, and construct prior distribution for expected length of both mother($P(X|maternal)$) and fetal DNA ($P(X|fetal)$). Given new unidentified DNA sequence of length x, it is possible to assign a probability that a given sequence of DNA is either maternal or fetal DNA, based on prior likelihood of x given either maternal or fetal. In particular if $P(x|maternal) > P(x|fetal)$, then the DNA sequence can be classified as maternal, with $P(x|maternal) = P(x|maternal)/[(P(x|maternal) + P(x|fetal)]$, and if $p(x|maternal) < p(x|fetal)$, then the DNA sequence can be classified as fetal, $P(x|fetal) = P(x|fetal)/[(P(x|maternal) + P(x|fetal)]$. In an embodiment of the present disclosure, a distributions of maternal and fetal sequence lengths can be determined that is specific for that sample by considering the sequences that can be assigned as maternal or fetal with high probability, and then that sample specific distribution can be used as the expected size distribution for that sample.

Variable Read Depth to Minimize Sequencing Cost

In many clinical trials concerning a diagnostic, for example, in Chiu et al. BMJ 2011; 342:c7401, a protocol with a number of parameters is set, and then the same protocol is executed with the same parameters for each of the patients in the trial. In the case of determining the ploidy status of a fetus gestating in a mother using sequencing as a method to measure genetic material one pertinent parameter is the number of reads. The number of reads may refer to the number of actual reads, the number of intended reads, fractional lanes, full lanes, or full flow cells on a sequencer. In these studies, the number of reads is typically set at a level that will ensure that all or nearly all of the samples achieve the desired level of accuracy. Sequencing is currently an expensive technology, a cost of roughly $200 per 5 mappable million reads, and while the price is dropping, any method which allows a sequencing based diagnostic to operate at a similar level of accuracy but with fewer reads will necessarily save a considerable amount of money.

The accuracy of a ploidy determination is typically dependent on a number of factors, including the number of reads and the fraction of fetal DNA in the mixture. The accuracy is typically higher when the fraction of fetal DNA in the mixture is higher. At the same time, the accuracy is typically higher if the number of reads is greater. It is possible to have a situation with two cases where the ploidy state is determined with comparable accuracies wherein the first case has a lower fraction of fetal DNA in the mixture than the second, and more reads were sequenced in the first case than the second. It is possible to use the estimated fraction of fetal DNA in the mixture as a guide in determining the number of reads necessary to achieve a given level of accuracy.

In an embodiment of the present disclosure, a set of samples can be run where different samples in the set are sequenced to different reads depths, wherein the number of reads run on each of the samples is chosen to achieve a given level of accuracy given the calculated fraction of fetal DNA in each mixture. In an embodiment of the present disclosure, this may entail making a measurement of the mixed sample to determine the fraction of fetal DNA in the mixture; this estimation of the fetal fraction may be done with sequencing, it may be done with TAQMAN, it may be done with qPCR, it may be done with SNP arrays, it may be done with any method that can distinguish different alleles at a given loci. The need for a fetal fraction estimate may be eliminated by including hypotheses that cover all or a selected set of fetal fractions in the set of hypotheses that are considered when comparing to the actual measured data. After the fraction fetal DNA in the mixture has been determined, the number of sequences to be read for each sample may be determined.

In an embodiment of the present disclosure, 100 pregnant women visit their respective OB's, and their blood is drawn into blood tubes with an anti-lysant and/or something to inactivate DNAase. They each take home a kit for the father of their gestating fetus who gives a saliva sample. Both sets of genetic materials for all 100 couples are sent back to the laboratory, where the mother blood is spun down and the buffy coat is isolated, as well as the plasma. The plasma comprises a mixture of maternal DNA as well as placentally derived DNA. The maternal buffy coat and the paternal blood is genotyped using a SNP array, and the DNA in the maternal plasma samples are targeted with SURESELECT hybridization probes. The DNA that was pulled down with the probes is used to generate 100 tagged libraries, one for each of the maternal samples, where each sample is tagged with a different tag. A fraction from each library is withdrawn, each of those fractions are mixed together and added to two lanes of a ILLUMINA HISEQ DNA sequencer in a multiplexed fashion, wherein each lane resulted in approximately 50 million mappable reads, resulting in approximately 100 million mappable reads on the 100 multiplexed mixtures, or approximately 1 million reads per sample. The sequence reads were used to determine the fraction of fetal DNA in each mixture. 50 of the samples had more than 15% fetal DNA in the mixture, and the 1 million reads were sufficient to determine the ploidy status of the fetuses with a 99.9% confidence.

Of the remaining mixtures, 25 had between 10 and 15% fetal DNA; a fraction of each of the relevant libraries prepped from these mixtures were multiplexed and run down one lane of the HISEQ generating an additional 2 million reads for each sample. The two sets of sequence data for each of the mixture with between 10 and 15% fetal DNA were added together, and the resulting 3 million reads per sample which were sufficient to determine the ploidy state of those fetuses with 99.9% confidence.

Of the remaining mixtures, 13 had between 6 and 10% fetal DNA; a fraction of each of the relevant libraries prepped from these mixtures were multiplexed and run down one lane of the HISEQ generating an additional 4 million reads for each sample. The two sets of sequence data for each of the mixture with between 6 and 10% fetal DNA were added together, and the resulting 5 million total reads per mixture which were sufficient to determine the ploidy state of those fetuses with 99.9% confidence.

Of the remaining mixtures, 8 had between 4 and 6% fetal DNA; a fraction of each of the relevant libraries prepped from these mixtures were multiplexed and run down one lane of the HISEQ generating an additional 6 million reads for each sample. The two sets of sequence data for each of the mixture with between 4 and 6% fetal DNA were added together, and the resulting 7 million total reads per mixture which were sufficient to determine the ploidy state of those fetuses with 99.9% confidence.

Of the remaining four mixtures, all of them had between 2 and 4% fetal DNA; a fraction of each of the relevant libraries prepped from these mixtures were multiplexed and run down one lane of the HISEQ generating an additional 12 million reads for each sample. The two sets of sequence data for each of the mixture with between 2 and 4% fetal DNA were added together, and the resulting 13 million total reads per mixture which were sufficient to determine the ploidy state of those fetuses with 99.9% confidence.

This method required six lanes of sequencing on a HISEQ machine to achieve 99.9% accuracy over 100 samples. If the same number of runs had been required for every sample, to ensure that every ploidy determination was made with a 99.9% accuracy, it would have taken 25 lanes of sequencing, and if a no-call rate or error rate of 4% was tolerated, it could have been achieved with 14 lanes of sequencing.

Using Raw Genotyping Data

There are a number of methods that can accomplish NPD using fetal genetic information measured on fetal DNA found in maternal blood. Some of these methods involve making measurements of the fetal DNA using SNP arrays, some methods involve untargeted sequencing, and some methods involve targeted sequencing. The targeted sequencing may target SNPs, it may target STRs, it may target other polymorphic loci, it may target non-polymorphic loci, or some combination thereof. Some of these methods may involve using a commercial or proprietary allele caller that calls the identity of the alleles from the intensity data that comes from the sensors in the machine doing the measuring. For example, the ILLUMINA INFINIUM system or the AFFYMETRIX GENECHIP microarray system involves beads or microchips with attached DNA sequences that can hybridize to complementary segments of DNA; upon hybridization, there is a change in the fluorescent properties of the sensor molecule that can be detected. There are also sequencing methods, for example the ILLUMINA SOLEXA GENOME SEQUENCER or the ABI SOLID GENOME SEQUENCER, wherein the genetic sequence of fragments of DNA are sequenced: upon extension of the strand of DNA complementary to the strand being sequenced, the identity of the extended nucleotide is typically detected via a fluorescent or radio tag appended to the complementary nucleotide. In all of these methods the genotypic or sequencing data is typically determined on the basis of fluorescent or other signals, or the lack thereof. These systems are typically combined with low level software packages that make specific allele calls (secondary genetic data) from the analog output of the fluorescent or other detection device (primary genetic data). For example, in the case of a given allele on a SNP array, the software will make a call, for example, that a certain SNP is present or not present if the fluorescent intensity is measure above or below a certain threshold. Similarly, the output of a sequencer is a chromatogram that indicates the level of fluorescence detected for each of the dyes, and the software will make a call that a certain base pair is A or T or C or G. High throughput sequencers typically make a series of such measurements, called a read, that represents the most likely structure of the DNA sequence that was sequenced. The direct analog output of the chromatogram is defined here to be the primary genetic data, and the base pair/SNP calls made by the software are considered here to be the secondary genetic data. In an embodiment, primary data refers to the raw intensity data that is the unprocessed output of a genotyping platform, where the genotyping platform may refer to a SNP array, or to a sequencing platform. The secondary genetic data refers to the processed genetic data, where an allele call has been made, or the sequence data has been assigned base pairs, and/or the sequence reads have been mapped to the genome.

Many higher level applications take advantage of these allele calls, SNP calls and sequence reads, that is, the secondary genetic data, that the genotyping software produces. For example, DNA NEXUS, ELAND or MAQ will take the sequencing reads and map them to the genome. For example, in the context of non-invasive prenatal diagnosis, complex informatics, such as PARENTAL SUPPORT™, may leverage a large number of SNP calls to determine the genotype of an individual. Also, in the context of preimplantation genetic diagnosis, it is possible to take a set of sequence reads that are mapped to the genome, and by taking a normalized count of the reads that are mapped to each chromosome, or section of a chromosome, it may be possible to determine the ploidy state of an individual. In the context of non-invasive prenatal diagnosis it may be possible to take a set of sequence reads that have been measured on DNA present in maternal plasma, and map them to the genome. One may then take a normalized count of the reads that are mapped to each chromosome, or section of a chromosome, and use that data to determine the ploidy state of an individual. For example, it may be possible to conclude that those chromosomes that have a disproportionately large number of reads are trisomic in the fetus that is gestating in the mother from which the blood was drawn.

However, in reality, the initial output of the measuring instruments is an analog signal. When a certain base pair is called by the software that is associated with the sequencing software, for example the software may call the base pair a T, in reality the call is the call that the software believes to be most likely. In some cases, however, the call may be of low confidence, for example, the analog signal may indicate that the particular base pair is only 90% likely to be a T, and 10% likely to be an A. In another example, the genotype calling software that is associated with a SNP array reader may call a certain allele to be G. However, in reality, the underlying analog signal may indicate that it is only 70% likely that the allele is G, and 30% likely that the allele is T. In these cases, when the higher level applications use the genotype calls and sequence calls made by the lower level software, they are losing some information. That is, the primary genetic data, as measured directly by the genotyping platform, may be messier than the secondary genetic data that is determined by the attached software packages, but it contains more information. In mapping the secondary genetic data sequences to the genome, many reads are thrown out because some bases are not read with enough clarity and or mapping is not clear. When the primary genetic data sequence reads are used, all or many of those reads that may have been thrown out when first converted to secondary genetic data sequence read can be used by treating the reads in a probabilistic manner.

In an embodiment of the present disclosure, the higher level software does not rely on the allele calls, SNP calls, or sequence reads that are determined by the lower level software. Instead, the higher level software bases its calculations on the analog signals directly measured from the genotyping platform. In an embodiment of the present disclosure, an informatics based method such as PARENTAL SUPPORT™ is modified so that its ability to reconstruct the genetic data of the embryo/fetus/child is engineered to directly use the primary genetic data as measured by the genotyping platform. In an embodiment of the present disclosure, an informatics based method such as PARENTAL SUPPORT™ is able to make allele calls, and/or chromosome copy number calls using primary genetic data, and not using the secondary genetic data. In an embodiment of the present disclosure, all genetic calls, SNPs calls, sequence reads, sequence mapping is treated in a probabilistic manner by using the raw intensity data as measured directly by the genotyping platform, rather than converting the primary genetic data to secondary genetic calls. In an embodiment, the DNA measurements from the prepared sample used in calculating allele count probabilities and determining the relative probability of each hypothesis comprise primary genetic data.

In some embodiments, the method can increase the accuracy of genetic data of a target individual which incorporates genetic data of at least one related individual, the method comprising obtaining primary genetic data specific to a target individual's genome and genetic data specific to the genome(s) of the related individual(s), creating a set of one or more hypotheses concerning possibly which segments of which chromosomes from the related individual(s) correspond to those segments in the target individual's genome, determining the probability of each of the hypotheses given the target individual's primary genetic data and the related individual(s)'s genetic data, and using the probabilities associated with each hypothesis to determine the most likely state of the actual genetic material of the target individual. In some embodiments, the method can determining the number of copies of a segment of a chromosome in the genome of a target individual, the method comprising creating a set of copy number hypotheses about how many copies of the chromosome segment are present in the genome of a target individual, incorporating primary genetic data from the target individual and genetic information from one or more related individuals into a data set, estimating the characteristics of the platform response associated with the data set, where the platform response may vary from one experiment to another, computing the conditional probabilities of each copy number hypothesis, given the data set and the platform response characteristics, and determining the copy number of the chromosome segment based on the most probable copy number hypothesis. In an embodiment, a method of the present disclosure can determine a ploidy state of at least one chromosome in a target individual, the method comprising obtaining primary genetic data from the target individual and from one or more related individuals, creating a set of at least one ploidy state hypothesis for each of the chromosomes of the target individual, using one or more expert techniques to determine a statistical probability for each ploidy state hypothesis in the set, for each expert technique used, given the obtained genetic data, combining, for each ploidy state hypothesis, the statistical probabilities as determined by the one or more expert techniques, and determining the ploidy state for each of the chromosomes in the target individual based on the combined statistical probabilities of each of the ploidy state hypotheses. In an embodiment, a method of the present disclosure can determine an allelic state in a set of alleles, in a target individual, and from one or both parents of the target individual, and optionally from one or more related individuals, the method comprising obtaining primary genetic data from the target individual, and from the one or both parents, and from any related individuals, creating a set of at least one allelic hypothesis for the target individual, and for the one or both parents, and optionally for the one or more related individuals, where the hypotheses describe possible allelic states in the set of alleles, determining a statistical probability for each allelic hypothesis in the set of hypotheses given the obtained genetic data, and determining the allelic state for each of the alleles in the set of alleles for the target individual, and for the one or both parents, and optionally for the one or more related individuals, based on the statistical probabilities of each of the allelic hypotheses.

In some embodiments, the genetic data of the mixed sample may comprise sequence data wherein the sequence data may not uniquely map to the human genome. In some embodiments, the genetic data of the mixed sample may comprise sequence data wherein the sequence data maps to a plurality of locations in the genome, wherein each possible mapping is associated with a probability that the given mapping is correct. In some embodiments, the sequence reads are not assumed to be associated with a particular position in the genome. In some embodiments, the sequence reads are associated with a plurality of positions in the genome, and an associated probability belonging to that position.

Counting Method to Determine Chromosome Copy Number

In one aspect, the invention features methods of testing for an abnormal distribution of a fetal chromosome by comparing the number of sequence tags that align to different chromosomes (see, e.g., U.S. Pat. No. 8,296,076, filed Apr. 20, 2012, which is hereby incorporated by reference in its entirety). As is known in the an, the term "sequence tag" refers to a relatively short (e.g., 15-100) nucleic acid sequence that can be used to identify a certain larger sequence, e.g., be mapped to a chromosome or genomic region or gene. In some embodiments, the method involves (i) contacting a sample that includes a mixture of maternal and fetal DNA with a library of primers that simultaneously hybridize to at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci to produce a reaction mixture, wherein the target loci are from a plurality of different chromosomes; and wherein the plurality of different chromosomes comprise at least one first chromosome suspected of having an abnormal distribution in the sample and at least one second chromosome presumed to be normally distributed in the sample; (ii) subjecting the reaction mixture to primer extension reaction conditions to produce amplified products; (iii) sequencing the amplified products to obtain a plurality of sequence tags aligning to the target loci; wherein the sequence tags are of sufficient length to be assigned to a specific target locus; (iv) assigning on a computer the plurality of sequence tags to their corresponding target loci; (v) determining on a computer a number of sequence tags aligning to the target loci of the first chromosome and a number of sequence tags aligning to the target loci of the second chromosome; and (vi) comparing the numbers from step (v) to determine the presence or absence of an abnormal distribution of the first chromosome.

In one aspect, the invention provides methods for detecting the presence or absence of a fetal aneuploidy by comparing the relative frequency of target amplicons between chromosomes (see, e.g., PCT Publ. No. WO 2012/103031, filed Jan. 23, 2012, which is hereby incorporated by reference in its entirety). In some embodiments, the method involves (i) contacting a sample that includes a mixture of maternal and fetal DNA with a library of primers that simultaneously hybridize to at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different non-polymorphic target loci to produce a reaction mixture; wherein the target loci are from a plurality of different chromosomes; (ii) subjecting the reaction mixture to primer extension reaction conditions to produce amplified products that includes target amplicons; (iii) quantifying on a computer a relative frequency of the target amplicons from the first and second chromosomes of interest; (iv) comparing on a computer the relative frequency of the target amplicons from the first and second chromosomes of interest; and (v) identifying the presence or absence of an aneuploidy based on the compared relative frequencies of the first and second chromosome of interest. In some embodiments, the first chromosome is a chromosome suspected of being euploid. In some embodiments, the second chromosome is a chromosome suspected of being aneuploidy.

Combining Methods of Prenatal Diagnosis

There are many methods that may be used for prenatal diagnosis or prenatal screening of aneuploidy or other genetic defects. Described elsewhere in this document, and in U.S. Utility application Ser. No. 11/603,406, filed Nov. 28, 2006, U.S. Utility application Ser. No. 12/076,348, filed Mar. 17, 2008, and PCT Application Serial No. PCT/S09/52730 is one such method that uses the genetic data of related individuals to increase the accuracy with which genetic data of a target individual, such as a fetus, is known, or estimated. Other methods used for prenatal diagnosis involve measuring the levels of certain hormones in maternal blood, where those hormones are correlated with various genetic abnormalities. An example of this is called the triple test, a test wherein the levels of several (commonly two, three, four or five) different hormones are measured in maternal blood. In a case where multiple methods are used to determine the likelihood of a given outcome, where none of the methods are definitive in and of themselves, it is possible to combine the information given by those methods to make a prediction that is more accurate than any of the individual methods. In the triple test, combining the information given by the three different hormones can result in a prediction of genetic abnormalities that is more accurate than the individual hormone levels may predict.

Disclosed herein is a method for making more accurate predictions about the genetic state of a fetus, specifically the possibility of genetic abnormalities in a fetus that comprises combining predictions of genetic abnormalities in a fetus where those predictions were made using a variety of methods. A "more accurate" method may refer to a method for diagnosing an abnormality that has a lower false negative rate at a given false positive rate. In a favored embodiment of the present disclosure, one or more of the predictions are made based on the genetic data known about the fetus, where the genetic knowledge was determined using the PARENTAL SUPPORT™ method, that is, using genetic data of individual related to the fetus to determine the genetic data of the fetus with greater accuracy. In some embodiments the genetic data may include ploidy states of the fetus. In some embodiments, the genetic data may refer to a set of allele calls on the genome of the fetus. In some embodiments some of the predictions may have been made using the triple test. In some embodiments, some of the predictions may have been made using measurements of other hormone levels in maternal blood. In some embodiments, predictions made by methods considered diagnoses may be combined with predictions made by methods considered screening. In some embodiments, the method involves measuring maternal blood levels of alpha-fetoprotein (AFP). In some embodiments, the method involves measuring maternal blood levels of unconjugated estriol ($UE_3$). In some embodiments, the method involves measuring maternal blood levels of beta human chorionic gonadotropin (beta-hCG). In some embodiments, the method involves measuring maternal blood levels of invasive trophoblast antigen (ITA). In some embodiments, the method involves measuring maternal blood levels of inhibin. In some embodiments, the method involves measuring maternal blood levels of pregnancy-associated plasma protein A (PAPP-A). In some embodiments, the method involves measuring maternal blood levels of other hormones or maternal serum markers. In some embodiments, some of the predictions may have been made using other methods. In some embodiments, some of the predictions may have been made using a fully integrated test such as one that combines ultrasound and blood test at around 12 weeks of pregnancy and a second blood test at around 16 weeks. In some embodiments, the method involves measuring the fetal nuchal translucency (NT). In some embodiments, the method involves using the measured levels of the aforementioned hormones for making predictions. In some embodiments the method involves a combination of the aforementioned methods.

There are many ways to combine the predictions, for example, one could convert the hormone measurements into a multiple of the median (MoM) and then into likelihood ratios (LR). Similarly, other measurements could be transformed into LRs using the mixture model of NT distributions. The LRs for NT and the biochemical markers could be multiplied by the age and gestation-related risk to derive the risk for various conditions, such as trisomy 21. Detection rates (DRs) and false-positive rates (FPRs) could be calculated by taking the proportions with risks above a given risk threshold.

In an embodiment, a method to call the ploidy state involves combining the relative probabilities of each of the ploidy hypotheses determined using the joint distribution model and the allele count probabilities with relative probabilities of each of the ploidy hypotheses that are calculated using statistical techniques taken from other methods that determine a risk score for a fetus being trisomic, including but not limited to: a read count analysis, comparing heterozygosity rates, a statistic that is only available when parental genetic information is used, the probability of normalized genotype signals for certain parent contexts, a statistic that is calculated using an estimated fetal fraction of the first sample or the prepared sample, and combinations thereof.

Another method could involve a situation with four measured hormone levels, where the probability distribution around those hormones is known: $p(x_1, x_2, x_3, x_4|e)$ for the euploid case and $p(x_1, x_2, x_3, x_4|a)$ for the aneuploid case. Then one could measure the probability distribution for the DNA measurements, $g(y|e)$ and $g(y|a)$ for the euploid and aneuploid cases respectively. Assuming they are independent given the assumption of euploid/aneuploid, one could combine as $p(x_1, x_2, x_3, x_4|a)g(y|a)$ and $p(x_1, x_2, x_3, x_4|e)g(y|e)$ and then multiply each by the prior $p(a)$ and $p(e)$ given the maternal age. One could then choose the one that is highest.

In an embodiment, it is possible to evoke central limit theorem to assume distribution on $g(y|a$ or $e)$ is Gaussian, and measure mean and standard deviation by looking at multiple samples. In another embodiment, one could assume they are not independent given the outcome and collect enough samples to estimate the joint distribution $p(x_1, x_2, x_3, x_4|a$ or $e)$.

In an embodiment, the ploidy state for the target individual is determined to be the ploidy state that is associated with the hypothesis whose probability is the greatest. In some cases, one hypothesis will have a normalized, combined probability greater than 90%. Each hypothesis is associated with one, or a set of, ploidy states, and the ploidy state associated with the hypothesis whose normalized, combined probability is greater than 90%, or some other threshold value, such as 50%, 80%, 95%, 98%, 99%, or 99.9%, may be chosen as the threshold required for a hypothesis to be called as the determined ploidy state.

DNA from Children from Previous Pregnancies in Maternal Blood

One difficulty to non-invasive prenatal diagnosis is differentiating fetal cells from the current pregnancy from fetal cells from previous pregnancies. Some believe that genetic matter from prior pregnancies will go away after some time, but conclusive evidence has not been shown. In an embodiment of the present disclosure, it is possible to determine fetal DNA present in the maternal blood of paternal origin (that is, DNA that the fetus inherited from the father) using the PARENTAL SUPPORT™ (PS) method, and the knowledge of the paternal genome. This method may utilize phased parental genetic information. It is possible to phase the parental genotype from unphased genotypic information using grandparental genetic data (such as measured genetic data from a sperm from the grandfather), or genetic data from other born children, or a sample of a miscarriage. One could also phase unphased genetic information by way of a HapMap-based phasing, or a haplotyping of paternal cells. Successful haplotyping has been demonstrated by arresting cells at phase of mitosis when chromosomes are tight bundles and using microfluidics to put separate chromosomes in separate wells. In another embodiment it is possible to use the phased parental haplotypic data to detect the presence of more than one homolog from the father, implying that the genetic material from more than one child is present in the blood. By focusing on chromosomes that are expected to be euploid in a fetus, one could rule out the possibility that the fetus was afflicted with a trisomy. Also, it is possible to determine if the fetal DNA is not from the current father, in which case one could use other methods such as the triple test to predict genetic abnormalities.

There may be other sources of fetal genetic material available via methods other than a blood draw. In the case of the fetal genetic material available in maternal blood, there are two main categories: (1) whole fetal cells, for example, nucleated fetal red blood cells or erythroblats, and (2) free floating fetal DNA. In the case of whole fetal cells, there is some evidence that fetal cells can persist in maternal blood for an extended period of time such that it is possible to isolate a cell from a pregnant woman that contains the DNA from a child or fetus from a prior pregnancy. There is also evidence that the free floating fetal DNA is cleared from the system in a matter of weeks. One challenge is how to determine the identity of the individual whose genetic material is contained in the cell, namely to ensure that the measured genetic material is not from a fetus from a prior pregnancy. In an embodiment of the present disclosure, the knowledge of the maternal genetic material can be used to ensure that the genetic material in question is not maternal genetic material. There are a number of methods to accomplish this end, including informatics based methods such as PARENTAL SUPPORT™, as described in this document or any of the patents referenced in this document.

In an embodiment of the present disclosure, the blood drawn from the pregnant mother may be separated into a fraction comprising free floating fetal DNA, and a fraction comprising nucleated red blood cells. The free floating DNA may optionally be enriched, and the genotypic information of the DNA may be measured. From the measured genotypic information from the free floating DNA, the knowledge of the maternal genotype may be used to determine aspects of the fetal genotype. These aspects may refer to ploidy state, and/or a set of allele identities. Then, individual nucleated red blood cells may be genotyped using methods described elsewhere in this document, and other referent patents, especially those mentioned in the first section of this document. The knowledge of the maternal genome would allow one to determine whether or not any given single blood cell is genetically maternal. And the aspects of the fetal genotype that were determined as described above would allow one to determine if the single blood cell is genetically derived from the fetus that is currently gestating. In essence, this aspect of the present disclosure allows one to use the genetic knowledge of the mother, and possibly the genetic information from other related individuals, such as the father, along with the measured genetic information from the free floating DNA found in maternal blood to determine whether an isolated nucleated cell found in maternal blood is either (a) genetically maternal, (b) genetically from the fetus currently gestating, or (c) genetically from a fetus from a prior pregnancy.

Prenatal Sex Chromosome Aneuploidy Determination

In methods known in the art, people attempting to determine the sex of a gestating fetus from the blood of the mother have used the fact that fetal free floating DNA (fffDNA) is present in the plasma of the mother. If one is able to detect Y-specific loci in the maternal plasma, this implies that the gestating fetus is a male. However, the lack of detection of Y-specific loci in the plasma does not always guarantee that the gestating fetus is a female when using methods known in the art, as in some cases the amount of fffDNA is too low to ensure that the Y-specific loci would be detected in the case of a male fetus.

Presented here is a novel method that does not require the measurement of Y-specific nucleic acids, that is, DNA that is from loci that are exclusively paternally derived. The Parental Support method, disclosed previously, uses crossover frequency data, parental genotypic data, and informatics techniques, to determine the ploidy state of a gestating fetus. The sex of a fetus is simply the ploidy state of the fetus at the sex chromosomes. A child that is XX is female, and XY is male. The method described herein is also able to determine the ploidy state of the fetus. Note that sexing is effectively synonymous with ploidy determination of the sex chromosomes; in the case of sexing, an assumption is often made that the child is euploid, therefore there are fewer possible hypotheses.

The method disclosed herein involves looking at loci that are common to both the X and Y chromosome to create a baseline in terms of expected amount of fetal DNA present for a fetus. Then, those regions that are specific only to the X chromosome can be interrogated to determine if the fetus is female or male. In the case of a male, we expect to see less fetal DNA from loci that are specific to the X chromosome than from loci that are specific to both the X and the Y. In contrast, in female fetuses, we expect the amount of DNA for each of these groups to be the same. The DNA in question can be measured by any technique that can quantitate the amount of DNA present on a sample, for example, qPCR, SNP arrays, genotyping arrays, or sequencing. For DNA that is exclusively from an individual we would expect to see the following:

|  | DNA specific to X | DNA specific to X and Y | DNA specific to Y |
|---|---|---|---|
| Male (XY) | A | 2A | A |
| Female (XX) | 2A | 2A | 0 |

In the case of DNA from a fetus that is mixed with DNA from the mother, and where the fraction of fetal DNA in the mixture is F, and where the fraction of maternal DNA in the mixture is M, such that F+M=100%, we would expect to see the following:

|  | DNA specific to X | DNA specific to X and Y | DNA specific to Y |
|---|---|---|---|
| Male fetus (XY) | M + ½F | M + F | ½F |
| Female fetus (XX) | M + F | M + F | 0 |

In the case where F and M are known, the expected ratios can be computed, and the observed data can be compared to the expected data. In the case where M and F are not known, a threshold can be selected based on historical data. In both cases, the measured amount of DNA at loci specific to both X and Y can be used as a baseline, and the test for the sex of the fetus can be based on the amount of DNA observed on loci specific to only the X chromosome. If that amount is lower than the baseline by an amount roughly equal to ½F, or by an amount that causes it to fall below a predefined threshold, the fetus is determined to be male, and if that amount is about equal to the baseline, or if is not lower by an amount that causes it to fall below a predefined threshold, the fetus is determined to be female.

In another embodiment, one can look only at those loci that are common to both the X and the Y chromosomes, often termed the Z chromosome. A subset of the loci on the Z chromosome are typically always A on the X chromosome, and B on the Y chromosome. If SNPs from the Z chromosome are found to have the B genotype, then the fetus is called a male; if the SNPs from the Z chromosome are found to only have A genotype, then the fetus is called a female. In another embodiment, one can look at the loci that are found only on the X chromosome. Contexts such as AA|B are particularly informative as the presence of a B indicates that the fetus has an X chromosome from the father. Contexts such as AB|B are also informative, as we expect to see B present only half as often in the case of a female fetus as compared to a male fetus. In another embodiment, one can look at the SNPs on the Z chromosome where both A and B alleles are present on both the X and the Y chromosome, and where the it is known which SNPs are from the paternal Y chromosome, and which are from the paternal X chromosome.

In an embodiment, it is possible to amplify single nucleotide positions known to varying between the homologous non-recombining (HNR) region shared by chromosome Y and chromosome X. The sequence within this HNR region is largely identical between the X and Y chromosomes. Within this identical region are single nucleotide positions that, while invariant among X chromosomes and among Y chromosomes in the population, are different between the X and Y chromosomes. Each PCR assay could amplify a sequence from loci that are present on both the X and Y chromosomes. Within each amplified sequence would be a single base that can be detected using sequencing or some other method (see, for example, U. S. Publication No. 2011/0178719, filed Feb. 3, 2011, which is hereby incorporated by reference in its entirety).

In an embodiment, the sex of the fetus could be determined from the fetal free floating DNA found in maternal plasma, the method comprising some or all of the following steps: 1) Design PCR (either regular or mini-PCR, plus multiplexing if desired) primers amplify X/Y variant single nucleotide positions within HNR region, 2) obtain maternal plasma, 3) PCR Amplify targets from maternal plasma using HNR X/Y PCR assays, 4) sequence the amplicons, 5) Examine sequence data for presence of Y-allele within one or more of the amplified sequences. The presence of one or more would indicate a male fetus. Absence of all Y-alleles from all amplicons indicates a female fetus.

In an embodiment, one could use targeted sequencing to measure the DNA in the maternal plasma and/or the parental genotypes. In an embodiment, one could ignore all sequences that clearly originate from paternally sourced DNA. For example, in the context AA|AB, one could count the number of A sequences and ignore all the B sequences. In order to determine a heterozygosity rate for the above algorithm, one could compare the number of observed A sequences to the expected number of total sequences for the given probe. There are many ways one could calculate an expected number of sequences for each probe on a per sample basis. In an embodiment, it is possible to use historical data to determine what fraction of all sequence reads belongs to each specific probe and then use this empirical fraction, combined with the total number of sequence reads, to estimate the number of sequences at each probe. Another approach could be to target some known homozygous alleles and then use historical data to relate the number of reads at each probe with the number of reads at the known homozygous alleles. For each sample, one could then measure the number of reads at the homozygous alleles and then use this measurement, along with the empirically derived relationships, to estimate the number of sequence reads at each probe.

In some embodiments, it is possible to determine the sex of the fetus by combining the predictions made by a plurality of methods. In some embodiments the plurality of methods are taken from methods described in this disclosure. In some embodiments, at least one of the plurality of methods are taken from methods described in this disclosure.

In some embodiments the method described herein can be used to determine the ploidy state of the gestating fetus. In an embodiment, the ploidy calling method uses loci that are specific to the X chromosome, or common to both the X and Y chromosome, but does not make use of any Y-specific loci. In an embodiment, the ploidy calling method uses one or more of the following: loci that are specific to the X chromosome, loci that are common to both the X and Y chromosome, and loci that are specific to the Y chromosome. In an embodiment, where the ratios of sex chromosomes are similar, for example 45,X (Turner Syndrome), 46,XX (normal female) and 47,XXX (trisomy X), the differentiation can be accomplished by comparing the allele distributions to expected allele distributions according to the various hypotheses. In another embodiment, this can be accomplished by comparing the relative number of sequence reads for the sex chromosomes to one or a plurality of reference chromosomes that are assumed to be euploid. Also note that these methods can be expanded to include aneuploid cases.

Single Gene Disease Screening

In an embodiment, a method for determining the ploidy state of the fetus may be extended to enable simultaneous testing for single gene disorders. Single-gene disease diagnosis leverages the same targeted approach used for aneuploidy testing, and requires additional specific targets. In an embodiment, the single gene NPD diagnosis is through linkage analysis. In many cases, direct testing of the cfDNA sample is not reliable, as the presence of maternal DNA makes it virtually impossible to determine if the fetus has inherited the mother's mutation. Detection of a unique paternally-derived allele is less challenging, but is only fully informative if the disease is dominant and carried by the father, limiting the utility of the approach. In an embodiment, the method involves PCR or related amplification approaches.

In some embodiments, the method involves phasing the abnormal allele with surrounding very tightly linked SNPs in the parents using information from first-degree relatives. Then Parental Support may be run on the targeted sequencing data obtained from these SNPs to determine which homologs, normal or abnormal, were inherited by the fetus from both parents. As long as the SNPs are sufficiently linked, the inheritance of the genotype of the fetus can be determined very reliably. In some embodiments, the method comprises (a) adding a set of SNP loci to densely flank a specified set of common diseases to our multiplex pool for aneuploidy testing; (b) reliably phasing the alleles from these added SNPs with the normal and abnormal alleles based on genetic data from various relatives; and (c) reconstructing the fetal haplotype, or set of phased SNP alleles on the inherited maternal and paternal homologs in the region surrounding the disease locus to determine fetal genotype. In some embodiments additional probes that are closely linked to a disease linked locus are added to the set of polymorphic locus being used for aneuploidy testing.

Reconstructing fetal diplotype is challenging because the sample is a mixture of maternal and fetal DNA. In some embodiments, the method incorporates relative information to phase the SNPs and disease alleles, then take into account physical distance of the SNPs and recombination data from location specific recombination likelihoods and the data observed from the genetic measurements of the maternal plasma to obtain the most likely genotype of the fetus.

In an embodiment, a number of additional probes per disease linked locus are included in the set of targeted polymorphic loci, the number of additional probes per disease linked locus may be between 4 and 10, between 11 and 20, between 21 and 40, between 41 and 60, between 61 and 80, or combinations thereof.

Phasing the diploid data from the parents can be challenging, and there are a number of ways this can be accomplished. Some are discussed in this disclosure, others are described in greater detail in other disclosures (see, e.g., PCT Publ No WO2009105531, filed Feb. 9, 2009, and PCT Publ. No. WO2010017214, filed Aug. 4, 2009, which are each hereby incorporated by reference in its entirety). In one embodiment, a parent can be phased by inference by measuring tissue from the parent that is haploid, for example by measuring one or more sperm or eggs. In one embodiment the parent can be phased by inference using the measured genotypic data of a first degree relative such as the parent's parent(s) or siblings. In one embodiment, the parent can be phased by dilution where the DNA is diluted, in one or a plurality of wells, to the point where there is expected to be no more than approximately one copy of each haplotype in each well, and then measuring the DNA in the one or more wells. In one embodiment, the parent genotype can be phased by using computer programs that use population based haplotype frequencies to infer the most likely phase. In one embodiment, the parent can be phased if the phased haplotypic data is known for the other parent, along with the unphased genetic data of one or more genetic offspring of the parents. In some embodiments, the genetic offspring of the parents may be one or more embryos, fetuses, and/or born children. Some of these methods and other methods for phasing one or both parents are disclosed in greater detail in, e.g., U.S. Publ. No. 2011/0033862, filed Aug. 19, 2010; U.S. Publ. No. 2011/0178719, filed Feb. 3, 2011, U.S. Publ. No 2007/0184467, filed Nov. 22, 2006, U.S. Publ. No. 2008/0243398, filed Mar. 17, 2008, which are each hereby incorporated by reference in its entirety.

Fetal Genome Reconstruction

In one aspect, the invention features methods for determining a haplotype of a fetus. In various embodiments, this method allows one to determine which polymorphic loci (such as SNPs) were inherited by the fetus and to reconstruct which homologs (including recombination events) are present in the fetus (and thereby interpolate the sequence between the polymorphic loci). If desired, essentially the entire genome of the fetus can be reconstructed. If there is some remaining ambiguity in the genome of the fetus (such as in intervals with a crossover), this ambiguity can be minimized if desired by analyzing additional polymorphic loci. In various embodiments, the polymorphic loci are chosen to cover one or more of the chromosomes at a density to reduce any ambiguity to a desired level. This method has important applications for the detection of polymorphisms or other mutations of interest in a fetus since it enables their detection based on linkage (such as the presence of linked polymorphic loci in the fetal genome) rather than by directing detecting the polymorphism or other mutation of interest in the fetal genome. For example, if a parent is a carrier for a mutation associated with cystic fibrosis (CF), a nucleic acid sample that includes maternal DNA from the mother of the fetus and fetal DNA from the fetus can be analyzed to determine whether the fetal DNA include the haplotype containing the CF mutation. In particular, polymorphic loci can be analyzed to determine whether the fetal DNA includes the haplotype containing the CF mutation without having to detect the CF mutation itself in the fetal DNA. This is useful in screening for one or more mutations, such as disease-linked mutations, without having to directly detect the mutations.

In some embodiments, the method involves determining a parental haplotype (e.g., a haplotype of the mother or father of the fetus). In some embodiments, this determination is made without using data from a relative of the mother or father. In some embodiments, a parental haplotype is determined using a dilution approach followed by SNP genotyping or sequencing as described herein and elsewhere (see, e.g., U.S. Publ. No. 2011/0033862, filed Aug. 19, 2010, which is hereby incorporated by reference in its entirety). Because the DNA is diluted, it is unlikely that more than one haplotype is in the same fraction (or tube). Thus, there may be effectively a single molecule of DNA in the tube, which allows the haplotype on a single DNA molecule to be determined. In some embodiments, the method includes dividing a DNA sample into a plurality of fractions such that at least one of the fractions includes one chromosome or one chromosome segment from a pair of chromosomes, and genotyping (e.g., determining the presence of two or more polymorphic loci) the DNA sample in at least one of the fractions, thereby determining a parental haplotype. In some embodiments, the genotyping involves sequencing (such as shotgun sequencing). In some embodiments, the genotyping involves use of a SNP array to detect polymorphic loci, such as at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different polymorphic loci. In some embodiments, the genotyping involves the use of multiplex PCR. In some embodiments, the method involves contacting the sample in a fraction with a library of primers that simultaneously hybridize to at least 25; 50; 75; 100; 300; 500; 750; 1,000; 2,000; 5,000; 7,500; 10,000; 15,000; 19,000; 20,000; 25,000; 27,000; 28,000; 30,000; 40,000, 50,000; 75,000; or 100,000 different polymorphic loci (such as SNPs) to produce a reaction mixture; and subjecting the reaction mixture to primer extension reaction conditions to produce amplified products that are measured with a high throughput sequencer to produce sequencing data.

In some embodiments, a haplotype of the mother is determined by any of the methods described herein using data from a relative of the mother. In some embodiments, a haplotype of the father is determined by any of the methods described herein using data from a relative of the father. In some embodiments, a haplotype is determined for both the father and the mother. In some embodiments, a SNP array is used to determine the presence of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different polymorphic loci in a DNA sample from the mother (or father) and a relative of the mother (or father). In some embodiments, the method involves contacting a DNA sample from the mother (or father) and/or a relative of the mother (or father) with a library of primers that simultaneously hybridize to at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different polymorphic loci (such as SNPs) to produce a reaction mixture, and subjecting the reaction mixture to primer extension reaction conditions to produce amplified products that are measured with a high throughput sequencer to produce sequencing data. The parental haplotype may be determined based on the SNP array or sequencing data. In some embodiments, parental data may be phased by methods described or referred to elsewhere in this document.

This parental haplotype data can be used to determine if the fetus inherited the parental haplotype. In some embodiments, a nucleic acid sample that includes maternal DNA from the mother of the fetus and fetal DNA from the fetus is analyzed using a SNP array to detect at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different polymorphic loci. In some embodiments, a nucleic acid sample that includes maternal DNA from the mother of the fetus and fetal DNA from the fetus is analyzed by contacting the sample with a library of primers that simultaneously hybridize to at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different polymorphic loci (such as SNPs) to produce a reaction mixture. In some embodiments, the reaction mixture is subjected to primer extension reaction conditions to produce amplified products. In some embodiments, the amplified products are measured with a high throughput sequencer to produce sequencing data. In various embodiments, the SNP array or sequencing data is used to determine a parental haplotype by using data about the probability of chromosomes crossing over at different locations in a chromosome (such as by using recombination data such as may be found in the HapMap database to create a recombination risk score for any interval) to model dependence between polymorphic alleles on the chromosome. In some embodiments, allele counts at the polymorphic loci are calculated on a computer based on the sequencing data. In some embodiments, a plurality of ploidy hypotheses each pertaining to a different possible ploidy state of the chromosome are created on a computer, a model (such as a joint distribution model) for the expected allele counts at the polymorphic loci on the chromosome is built on a computer for each ploidy hypothesis; a relative probability of each of the ploidy hypotheses is determined on a computer using the joint distribution model and the allele counts; and the ploidy state of the fetus is called by selecting the ploidy state corresponding to the hypothesis with the greatest probability. In some embodiments, building a joint distribution model for allele counts and the step of determining the relative probability of each hypothesis are done using a method that does not require the use of a reference chromosome.

In some embodiments, a fetal haplotype is determined for one or more chromosomes taken from the group consisting of chromosomes 13, 18, 21, X, and Y. In some embodiments, a fetal haplotype is determined for all of the fetal chromosomes. In various embodiments, the method determines essentially the entire genome of the fetus. In some embodiments, the haplotype is determined for at least 30, 40, 50, 60, 70, 80, 90, or 95% of the genome of the fetus. In some embodiments, the haplotype determination of the fetus includes information about which allele is present for at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different polymorphic loci.

Compositions of DNA

When performing an informatics analysis on sequencing data measured on a mixture of fetal and maternal blood to determine genomic information pertaining to the fetus, for example the ploidy state of the fetus, it may be advantageous to measure the allele distributions at a set of alleles. Unfortunately, in many cases, such as when attempting to determine the ploidy state of a fetus from the DNA mixture found in the plasma of a maternal blood sample, the amount of DNA available is not sufficient to directly measure the allele distributions with good fidelity in the mixture. In these cases, amplification of the DNA mixture will provide sufficient numbers of DNA molecules that the desired allele distributions may be measured with good fidelity. However, current methods of amplification typically used in the amplification of DNA for sequencing are often very biased, meaning that they do not amplify both alleles at a polymorphic locus by the same amount. A biased amplification can result in allele distributions that are quite different from the allele distributions in the original mixture. For most purposes, highly accurate measurements of the relative amounts of alleles present at polymorphic loci are not needed. In contrast, in an embodiment of the present disclosure, amplification or enrichment methods that specifically enrich polymorphic alleles and preserve allelic ratios is advantageous.

A number of methods are described herein that may be used to preferentially enrich a sample of DNA at a plurality of loci in a way that minimizes allelic bias. Some examples are using circularizing probes to target a plurality of loci where the 3' ends and 5' ends of the pre-circularized probe are designed to hybridize to bases that are one or a few positions away from the polymorphic sites of the targeted allele. Another is to use PCR probes where the 3' end PCR probe is designed to hybridize to bases that are one or a few positions away from the polymorphic sites of the targeted allele. Another is to use a split and pool approach to create mixtures of DNA where the preferentially enriched loci are enriched with low allelic bias without the drawbacks of direct multiplexing. Another is to use a hybrid capture approach where the capture probes are designed such that the region of the capture probe that is designed to hybridize to the DNA flanking the polymorphic site of the target is separated from the polymorphic site by one or a small number of bases.

In the case where measured allele distributions at a set of polymorphic loci are used to determine the ploidy state of an individual, it is desirable to preserve the relative amounts of alleles in a sample of DNA as it is prepared for genetic measurements. This preparation may involve WGA amplification, targeted amplification, selective enrichment techniques, hybrid capture techniques, circularizing probes or other methods meant to amplify the amount of DNA and/or selectively enhance the presence of molecules of DNA that correspond to certain alleles.

In some embodiments of the present disclosure, there is a set of DNA probes designed to target loci where the loci have maximal minor allele frequencies. In some embodiments of the present disclosure, there is a set of probes that are designed to target where the loci have the maximum likelihood of the fetus having a highly informative SNP at those loci. In some embodiments of the present disclosure, there is a set of probes that are designed to target loci where the probes are optimized for a given population subgroup. In some embodiments of the present disclosure, there is a set of probes that are designed to target loci where the probes are optimized for a given mix of population subgroups. In some embodiments of the present disclosure, there is a set of probes that are designed to target loci where the probes are optimized for a given pair of parents which are from different population subgroups that have different minor allele frequency profiles. In some embodiments of the present disclosure, there is a circularized strand of DNA that comprises at least one base pair that annealed to a piece of DNA that is of fetal origin. In some embodiments of the present disclosure, there is a circularized strand of DNA that comprises at least one base pair that annealed to a piece of DNA that is of placental origin. In some embodiments of the present disclosure, there is a circularized strand of DNA that circularized while at least some of the nucleotides were annealed to DNA that was of fetal origin. In some embodiments of the present disclosure, there is a circularized strand of DNA that circularized while at least some of the nucleotides were annealed to DNA that was of placental origin. In some embodiments of the present disclosure, there is a set of probes wherein some of the probes target single tandem repeats, and some of the probes target single nucleotide polymorphisms. In some embodiments, the loci are selected for the purpose of non-invasive prenatal diagnosis. In some embodiments, the probes are used for the purpose of non-invasive prenatal diagnosis. In some embodiments, the loci are targeted using a method that could include circularizing probes, MIPs, capture by hybridization probes, probes on a SNP array, or combinations thereof. In some embodiments, the probes are used as circularizing probes. MIPs, capture by hybridization probes, probes on a SNP array, or combinations thereof. In some embodiments, the loci are sequenced for the purpose of non-invasive prenatal diagnosis.

In the case where the relative informativeness of a sequence is greater when combined with relevant parent contexts, it follows that maximizing the number of sequence reads that contain a SNP for which the parental context is known may maximize the informativeness of the set of sequencing reads on the mixed sample. In an embodiment, the number of sequence reads that contain a SNP for which the parent contexts are known may be enhanced by using qPCR to preferentially amplify specific sequences. In an embodiment, the number of sequence reads that contain a SNP for which the parent contexts are known may be enhanced by using circularizing probes (for example, MIPs) to preferentially amplify specific sequences. In an embodiment, the number of sequence reads that contain a SNP for which the parent contexts are known may be enhanced by using a capture by hybridization method (for example SURESELECT) to preferentially amplify specific sequences. Different methods may be used to enhance the number of sequence reads that contain a SNP for which the parent contexts are known. In an embodiment, the targeting may be accomplished by extension ligation, ligation without extension, capture by hybridization, or PCR.

In a sample of fragmented genomic DNA, a fraction of the DNA sequences map uniquely to individual chromosomes; other DNA sequences may be found on different chromosomes. Note that DNA found in plasma, whether maternal or fetal in origin is typically fragmented, often at lengths under 500 bp. In a typical genomic sample, roughly 3.3% of the mappable sequences will map to chromosome 13; 2.2% of the mappable sequences will map to chromosome 18; 1.35% of the mappable sequences will map to chromosome 21; 4.5% of the mappable sequences will map to chromosome X in a female; 2.25% of the mappable sequences will map to chromosome X (in a male); and 0.73% of the mappable sequences will map to chromosome Y (in a male). These are the chromosomes that are most likely to be aneuploid in a fetus. Also, among short sequences, approximately 1 in 20 sequences will contain a SNP, using the SNPs contained on dbSNP. The proportion may well be higher given that there may be many SNPs that have not been discovered.

In an embodiment of the present disclosure, targeting methods may be used to enhance the fraction of DNA in a sample of DNA that map to a given chromosome such that the fraction significantly exceeds the percentages listed above that are typical for genomic samples. In an embodiment of the present disclosure, targeting methods may be used to enhance the fraction of DNA in a sample of DNA such that the percentage of sequences that contain a SNP are significantly greater than what may be found in typical for genomic samples. In an embodiment of the present disclosure, targeting methods may be used to target DNA from a chromosome or from a set of SNPs in a mixture of maternal and fetal DNA for the purposes of prenatal diagnosis.

Note that a method has been reported (U.S. Pat. No. 7,888,017) for determining fetal aneuploidy by counting the number of reads that map to a suspect chromosome and comparing it to the number of reads that map to a reference chromosome, and using the assumption that an overabundance of reads on the suspect chromosome corresponds to a triploidy in the fetus at that chromosome. Those methods for prenatal diagnosis would not make use of targeting of any sort, nor do they describe the use of targeting for prenatal diagnosis.

By making use of targeting approaches in sequencing the mixed sample, it may be possible to achieve a certain level of accuracy with fewer sequence reads. The accuracy may refer to sensitivity, it may refer to specificity, or it may refer to some combination thereof. The desired level of accuracy may be between 90% and 95%; it may be between 95% and 98%; it may be between 98% and 99%; it may be between 99% and 99.5%; it may be between 99.5% and 99.9%; it may be between 99.9% and 99.99%; it may be between 99.99% and 99.999%, it may be between 99.999% and 100%. Levels of accuracy above 95% may be referred to as high accuracy.

There are a number of published methods in the prior art that demonstrate how one may determine the ploidy state of a fetus from a mixed sample of maternal and fetal DNA, for example: G. J. W. Liao et al. Clinical Chemistry 2011; 57(1) pp 92-101. These methods focus on thousands of locations along each chromosome. The number of locations along a chromosome that may be targeted while still resulting in a high accuracy ploidy determination on a fetus, for a given number of sequence reads, from a mixed sample of DNA is unexpectedly low. In an embodiment of the present disclosure, an accurate ploidy determination may be made by using targeted sequencing, using any method of targeting, for example qPCR, ligand mediated PCR, other PCR methods, capture by hybridization, or circularizing probes, wherein the number of loci along a chromosome that need to be targeted may be between 5,000 and 2,000 loci; it may be between 2,000 and 1,000 loci; it may be between 1,000 and 500 loci; it may be between 500 and 300 loci; it may be between 300 and 200 loci; it may be between 200 and 150 loci; it may be between 150 and 100 loci; it may be between 100 and 50 loci; it may be between 50 and 20 loci; it may be between 20 and 10 loci. Optimally, it may be between 100 and 500 loci. The high level of accuracy may be achieved by targeting a small number of loci and executing an unexpectedly small number of sequence reads. The number of reads may be between 100 million and 50 million reads; the number of reads may be between 50 million and 20 million reads; the number of reads may be between 20 million and 10 million reads; the number of reads may be between 10 million and 5 million reads, the number of reads may be between 5 million and 2 million reads; the number of reads may be between 2 million and 1 million, the number of reads may be between 1 million and 500,000; the number of reads may be between 500,000 and 200,000; the number of reads may be between 200,000 and 100,000; the number of reads may be between 100,000 and 50,000; the number of reads may be between 50,000 and 20,000; the number of reads may be between 20,000 and 10,000; the number of reads may be below 10,000. Fewer number of read are necessary for larger amounts of input DNA.

In some embodiments, there is a composition comprising a mixture of DNA of fetal origin, and DNA of maternal origin, wherein the percent of sequences that uniquely map to chromosome 13 is greater than 4%, greater than 5%, greater than 6%, greater than 7%, greater than 8%, greater than 9%, greater than 10%, greater than 12%, greater than 15%, greater than 20%, greater than 25%, or greater than 30%. In some embodiments of the present disclosure, there is a composition comprising a mixture of DNA of fetal origin, and DNA of maternal origin, wherein the percent of sequences that uniquely map to chromosome 18 is greater than 3%, greater than 4%, greater than 5%, greater than 6%, greater than 7%, greater than 8%, greater than 9%, greater than 10%, greater than 12%, greater than 15%, greater than 20%, greater than 25%, or greater than 30%. In some embodiments of the present disclosure, there is a composition comprising a mixture of DNA of fetal origin, and DNA of maternal origin, wherein the percent of sequences that uniquely map to chromosome 21 is greater than 2%, greater than 3%, greater than 4%, greater than 5%, greater than 6%, greater than 7%, greater than 8%, greater than 9%, greater than 10%, greater than 12%, greater than 15%, greater than 20%, greater than 25%, or greater than 30%. In some embodiments of the present disclosure, there is a composition comprising a mixture of DNA of fetal origin, and DNA of maternal origin, wherein the percent of sequences that uniquely map to chromosome X is greater than 6%, greater than 7%, greater than 8%, greater than 9%, greater than 10%, greater than 12%, greater than 15%, greater than 20%, greater than 25%, or greater than 30%. In some embodiments of the present disclosure, there is a composition comprising a mixture of DNA of fetal origin, and DNA of maternal origin, wherein the percent of sequences that uniquely map to chromosome Y is greater than 1%, greater than 2%, greater than 3%, greater than 4%, greater than 5%, greater than 6%, greater than 7%, greater than 8%, greater than 9%, greater than 10%, greater than 12%, greater than 15%, greater than 20%, greater than 25%, or greater than 30%.

In some embodiments, a composition is described comprising a mixture of DNA of fetal origin, and DNA of maternal origin, wherein the percent of sequences that uniquely map to a chromosome, and that contains at least one single nucleotide polymorphism is greater than 0.2%, greater than 0.3%, greater than 0.4%, greater than 0.5%, greater than 0.6%, greater than 0.7%, greater than 0.8%, greater than 0.9%, greater than 1%, greater than 1.2, greater than 1.4%, greater than 1.6%, greater than 1.8%, greater than 2%, greater than 2.5%, greater than 3%, greater than 4%, greater than 5%, greater than 6%, greater than 7%, greater than 8%, greater than 9%, greater than 10%, greater than 12%, greater than 15%, or greater than 20%, and where the chromosome is taken from the group 13, 18, 21, X, or Y. In some embodiments of the present disclosure, there is a composition comprising a mixture of DNA of fetal origin, and DNA of maternal origin, wherein the percent of sequences that uniquely map to a chromosome and that contain at least one single nucleotide polymorphism from a set of single nucleotide polymorphisms is greater than 0.15%, greater than 0.2%, greater than 0.3%, greater than 0.4%, greater than 0.5%, greater than 0.6%, greater than 0.7%, greater than 0.8%, greater than 0.9%, greater than 1%, greater than 1.2%, greater than 1.4%, greater than 1.6%, greater than 1.8%, greater than 2%, greater than 2.5%, greater than 3%, greater than 4%, greater than 5%, greater than 6%, greater than 7%, greater than 8%, greater than 9%, greater than 10%, greater than 12%, greater than 150%, or greater than 20%, where the chromosome is taken from the set of chromosome 13, 18, 21, X and Y, and where the number of single nucleotide polymorphisms in the set of single nucleotide polymorphisms is between 1 and 10, between 10 and 20, between 20 and 50, between 50 and 100, between 100 and 200, between 200 and 500, between 500 and 1,000, between 1,000 and 2,000, between 2,000 and 5,000, between 5,000 and 10,000, between 10,000 and 20,000, between 20,000 and 50,000, and between 50,000 and 100,000.

In theory, each cycle in the amplification doubles the amount of DNA present; however, in reality, the degree of amplification is slightly lower than two. In theory, amplification, including targeted amplification, will result in bias free amplification of a DNA mixture; in reality, however, different alleles tend to be amplified to a different extent than other alleles. When DNA is amplified, the degree of allelic bias typically increases with the number of amplification steps. In some embodiments, the methods described herein involve amplifying DNA with a low level of allelic bias. Since the allelic bias compounds with each additional cycle, one can determine the per cycle allelic bias by calculating the nth root of the overall bias where n is the base 2 logarithm of degree of enrichment. In some embodiments, there is a composition comprising a second mixture of DNA, where the second mixture of DNA has been preferentially enriched at a plurality of polymorphic loci from a first mixture of DNA where the degree of enrichment is at least 10, at least 100, at least 1,000, at least 10,000, at least 100,000 or at least 1,000,000, and where the ratio of the alleles in the second mixture of DNA at each locus differs from the ratio of the alleles at that locus in the first mixture of DNA by a factor that is, on average, less than 1,000%, 500%, 200%, 100%, 50%, 20%, 10%, 5%, 2%, 1%, 0.5%, 0.2%, 0.1%, 0.05%, 0.02, or 0.01%. In some embodiments, there is a composition comprising a second mixture of DNA, where the second mixture of DNA has been preferentially enriched at a plurality of polymorphic loci from a first mixture of DNA where the per cycle allelic bias for the plurality of polymorphic loci is, on average, less than 10%, 5%, 2%, 1%, 0.5%, 0.2%, 0.1%, 0.05%, or 0.02%. In some embodiments, the plurality of polymorphic loci comprises at least 10 loci, at least 20 loci, at least 50 loci, at least 100 loci, at least 200 loci, at least 500 loci, at least 1,000 loci, at least 2,000 loci, at least 5,000 loci, at least 10,000 loci, at least 20,000 loci, or at least 50,000 loci.

Some Embodiments

In some embodiments, a method is disclosed herein for generating a report disclosing the determined ploidy status of a chromosome in a gestating fetus, the method comprising: obtaining a first sample that contains DNA from the mother of the fetus and DNA from the fetus; obtaining genotypic data from one or both parents of the fetus; preparing the first sample by isolating the DNA so as to obtain a prepared sample; measuring the DNA in the prepared sample at a plurality of polymorphic loci; calculating, on a computer, allele counts or allele count probabilities at the plurality of polymorphic loci from the DNA measurements made on the prepared sample; creating, on a computer, a plurality of ploidy hypotheses concerning expected allele count probabilities at the plurality of polymorphic loci on the chromosome for different possible ploidy states of the chromosome; building, on a computer, a joint distribution model for allele count probability of each polymorphic locus on the chromosome for each ploidy hypothesis using genotypic data from the one or both parents of the fetus, determining, on a computer, a relative probability of each of the ploidy hypotheses using the joint distribution model and the allele count probabilities calculated for the prepared sample; calling the ploidy state of the fetus by selecting the ploidy state corresponding to the hypothesis with the greatest probability; and generating a report disclosing the determined ploidy status.

In some embodiments, the method is used to determine the ploidy state of a plurality of gestating fetuses in a plurality of respective mothers, the method further comprising: determining the percent of DNA that is of fetal origin in each of the prepared samples; and wherein the step of measuring the DNA in the prepared sample is done by sequencing a number of DNA molecules in each of the prepared samples, where more molecules of DNA are sequenced from those prepared samples that have a smaller fraction of fetal DNA than those prepared samples that have a larger fraction of fetal DNA.

In some embodiments, the method is used to determine the ploidy state of a plurality of gestating fetuses in a plurality of respective mothers, and where the measuring the DNA in the prepared sample is done, for each of the fetuses, by sequencing a first fraction of the prepared sample of DNA to give a first set of measurements, the method further comprising: making a first relative probability determination for each of the ploidy hypotheses for each of the fetuses, given the first set of DNA measurements; resequencing a second fraction of the prepared sample from those fetuses where the first relative probability determination for each of the ploidy hypotheses indicates that a ploidy hypothesis corresponding to an aneuploid fetus has a significant but not conclusive probability, to give a second set of measurements; making a second relative probability determination for ploidy hypotheses for the fetuses using the second set of measurements and optionally also the first set of measurements; and calling the ploidy states of the fetuses whose second sample was resequenced by selecting the ploidy state corresponding to the hypothesis with the greatest probability as determined by the second relative probability determination.

In some embodiments, a composition of matter is disclosed, the composition of matter comprising: a sample of preferentially enriched DNA, wherein the sample of preferentially enriched DNA has been preferentially enriched at a plurality of polymorphic loci from a first sample of DNA, wherein the first sample of DNA consisted of a mixture of maternal DNA and fetal DNA derived from maternal plasma, where the degree of enrichment is at least a factor of 2, and wherein the allelic bias between the first sample and the preferentially enriched sample is, on average, selected from the group consisting of less than 2%, less than 1%, less than 0.5%, less than 0.2%, less than 0.1%, less than 0.05%, less than 0.02%, and less than 0.01%. In some embodiments, a method is disclosed to create a sample of such preferentially enriched DNA.

In some embodiment, a method is disclosed for determining the presence or absence of a fetal aneuploidy in a maternal tissue sample comprising fetal and maternal genomic DNA, wherein the method comprises: (a) obtaining a mixture of fetal and maternal genomic DNA from said maternal tissue sample; (b) selectively enriching the mixture of fetal and maternal DNA at a plurality of polymorphic alleles; (c) distributing selectively enriched fragments from the mixture of fetal and maternal genomic DNA of step a to provide reaction samples comprising a single genomic DNA molecule or amplification products of a single genomic DNA molecule; (d) conducting massively parallel DNA sequencing of the selectively enriched fragments of genomic DNA in the reaction samples of step c) to determine the sequence of said selectively enriched fragments; (e) identifying the chromosomes to which the sequences obtained in step d) belong; (f) analyzing the data of step d) to determine i) the number of fragments of genomic DNA from step d) that belong to at least one first target chromosome that is presumed to be diploid in both the mother and the fetus, and ii) the number of fragments of genomic DNA from step d) that belong to a second target chromosome, wherein said second chromosome is suspected to be aneuploid in the fetus; (g) calculating an expected distribution of the number of fragments of genomic DNA from step d) for the second target chromosome if the second target chromosome is euploid, using the number determined in step f) part i); (h) calculating an expected distribution of the number of fragments of genomic DNA from step d) for the second target chromosome if the second target chromosome is aneuploid, using the first number is step f) part i) and an estimated fraction of fetal DNA found in the mixture of step b), and (i) using a maximum likelihood or maximum a posteriori approach to determine whether the number of fragments of genomic DNA determined in step f) part ii) is more likely to be part of the distribution calculated in step g) or the distribution calculated in step h); thereby indicating the presence or absence of a fetal aneuploidy.

Exemplary Cancer Diagnostic Methods

Note that it has been demonstrated that DNA that originated from cancer that is living in a host can be found in the blood of the host. In the same way that genetic diagnoses can be made from the measurement of mixed DNA found in maternal blood, genetic diagnoses can equally well be made from the measurement of mixed DNA found in host blood. The genetic diagnoses may include aneuploidy states, or gene mutations. Any claim in the instant disclosure that reads on determining the ploidy state or genetic state of a fetus from the measurements made on maternal blood can equally well read on determining the ploidy state or genetic state of a cancer from the measurements on host blood.

In some embodiments, a method of the present disclosure allows one to determine the ploidy status of a cancer, the method including obtaining a mixed sample that contains genetic material from the host, and genetic material from the cancer; measuring the DNA in the mixed sample; calculating the fraction of DNA that is of cancer origin in the mixed sample; and determining the ploidy status of the cancer using the measurements made on the mixed sample and the calculated fraction. In some embodiments, the method may further include administering a cancer therapeutic based on the determination of the ploidy state of the cancer. In some embodiments, the method may further include administering a cancer therapeutic based on the determination of the ploidy state of the cancer, wherein the cancer therapeutic is taken from the group comprising a pharmaceutical, a biologic therapeutic, and antibody based therapy and combination thereof.

Exemplary Clinical Actions

In some embodiments, any of the methods include taking a clinical action based on a result of a method of the invention (such as the determination of the presence or absence of a polymorphism or mutation, ploidy state, or paternity). In some embodiments in which an embryo or fetus has one or more one or more polymorphisms or mutations of interest (such as a CNV) based on a result of a method of the invention, the clinical action includes performing additional testing (such as testing to confirm the presence of the polymorphism or mutation), not implanting the embryo for IVF, implanting a different embryo for IVF, terminating a pregnancy, preparing for a special needs child, or undergoing an intervention designed to decrease the severity of the phenotypic presentation of a genetic disorder. In some embodiments, the clinical action is selected from the group consisting of performing an ultrasound, amniocentesis on the fetus, amniocentesis on a subsequent fetus that inherits genetic material from the mother and/or father, chorion villus biopsy on the fetus, chorion villus biopsy on a subsequent fetus that inherits genetic material from the mother and/or father, in vitro fertilization, preimplantation genetic diagnosis on one or more embryos that inherited genetic material from the mother and/or father, karyotyping on the mother, karyotyping on the father, fetal echocardiogram (such as an echocardiogram of a fetus with trisomy 21, 18, or 13, monosomy X, or a microdeletion), and combinations thereof. In some embodiments, the clinical action is selected from the group consisting of administering growth hormone to a born child with monosomy X (such as administration starting at ~9 months), administering calcium to a born child with a 22q deletion (such as DiGeorge syndrome), administering an androgen such as testosterone to a born child with 47,XXY (such as one injection per month for 3 months of 25 mg testosterone enanthate to an infant or toddler), performing a test for cancer on a woman with a complete or partial molar pregnancy (such as a triploid fetus), administering a therapy for cancer such as a chemotherapeutic agent to a woman with a complete or partial molar pregnancy (such as a triploid fetus), screening a fetus determined to be male (such as a fetus determined to be male using a method of the invention) for one or more X-linked genetic disorders such as Duchenne muscular dystrophy (DMD), adrenoleukodystrophy, or hemophilia, performing amniocentesis on a male fetus at risk for an X-linked disorder, administering dexamethasone to a women with a female fetus at risk male (such as a fetus determined to be female using a method of the invention) for congenital adrenal hyperplasia, performing amniocentesis on a female fetus at risk for congenital adrenal hyperplasia, administering killed vaccines (instead of live vaccines) or not administering certain vaccines to a born child who is (or is suspected of being) immune deficient from a 22q11.2 deletion, performing occupational and/or physical therapy, performing early intervention in education, delivering the baby at a tertiary care center with a NICU and/or having pediatric specialists available at delivery, behavioral intervention for born child (such as a child with XXX, XXY, or XYY), and combinations thereof.

In some embodiments, ultrasound or another screening test is performed on a women determined to have multiple pregnancies (such as twins) to determine whether or not two or more of the fetus are monochorionic. Monozygotic twins result from ovulation and fertilization of a single oocyte, with subsequent division of the zygote; placentation may be dichorionic or monochorionic. Dizygotic twins occur from ovulation and fertilization of two oocytes, which usually results in dichorionic placentation. Monochorionic twins have a risk of twin-to-twin transfusion syndrome, which may cause unequal distribution of blood between fetuses that results in differences in their growth and development, sometimes resulting in stillbirth. Thus, twins determined to be monozygotic twins using a method of the invention are desirably tested (such as by ultrasound) to determine if they are monochorionic twins, and if so, these twins can be monitored (such as bi-weekly ultrasounds from 16 weeks) for signs of win-to-twin transfusion syndrome.

In some embodiments in which an embryo or fetus does not have one or more one or more polymorphisms or mutations of interest (such as a CNV) based on a result of a method of the invention, the clinical action includes implanting the embryo for IVF or continuing a pregnancy. In some embodiments, the clinical action is additional testing to confirm the absence of the polymorphism or mutation selected from the group consisting of performing an ultrasound, amniocentesis, chorion villus biopsy, and combinations thereof.

In some embodiments in which an individual has one or more polymorphisms or mutations (such as a polymorphism or mutation associated with a disease or disorder such as cancer or an increased risk for a disease or disorder such as cancer) based on a result of a method of the invention, the clinical action includes performing additional testing or administering one or more therapies for a disease or disorder (such as a therapy for cancer, a therapy for the specific type of cancer or type of mutation the individual is diagnosed with, or any of the therapies disclosed herein). In some embodiments, the clinical action is additional testing to confirm the presence or absence of a polymorphism or mutation selected from the group consisting of biopsy, surgery, medical imaging (such as a mammogram or an ultrasound), and combinations thereof. In some embodiments, the additional testing includes performing the same or a different method (such as any of the methods described herein) to confirm the presence or absence of the polymorphism or mutation (such as a CNV), such as testing either a second fraction of the same sample that was tested or a different sample from the same individual (such as the same pregnant mother, fetus, embryo, or individual at increased risk for cancer). In some embodiments, the additional testing is performed for an individual for whom the probability of a polymorphism or mutation (such as a CNV) is above a threshold value. In some embodiments, the additional testing is performed for an individual for whom the confidence or z-score for the determination of a polymorphism or mutation (such as a CNV) is above a threshold value (such as additional testing to confirm the presence of a likely polymorphism or mutation). In some embodiments, the additional testing is performed for an individual for whom the confidence or z-score for the determination of a polymorphism or mutation (such as a CNV) is between minimum and maximum threshold values (such as additional testing to increase the confidence that the initial result is correct). In some embodiments, the additional testing is performed for an individual for whom the confidence for the determination of the presence or absence of a polymorphism or mutation (such as a CNV) is below a threshold value (such as a "no call" result due to not being able to determine the presence or absence of the CNV with sufficient confidence). An exemplary Z core is calculated in Chiu et al. BMJ 2011; 342:c7401 (which is hereby incorporated by reference in its entirety) in which chromosome 21 is used as an example and can be replaced with any other chromosome or chromosome segment in the test sample.

$$Z \text{ score for percentage chromosome 21 in test case} = ((\text{percentage chromosome 21 in test case}) - (\text{mean percentage chromosome 21 in reference controls}))/(\text{standard deviation of percentage chromosome 21 in reference controls}).$$

In some embodiments, the additional testing is performed for an individual for whom the initial sample did not meet quality control guidelines or had a fetal fraction or a tumor fraction below a threshold value. In some embodiments, the method includes selecting an individual for additional testing based on the result of a method of the invention, the probability of the result, the confidence of the result, or the z-score: and performing the additional testing on the individual (such as on the same or a different sample). In some embodiments, a subject diagnosed with a disease or disorder (such as cancer) undergoes repeat testing using a method of the invention or known testing for the disease or disorder at multiple time points to monitor the progression of the disease or disorder or the remission or reoccurrence of the disease or disorder.

Exemplary Implementation Methods

Any of the embodiments disclosed herein may be implemented in digital electronic circuitry, integrated circuitry, specially designed ASICs (application-specific integrated circuits), computer hardware, firmware, software, or in combinations thereof. Apparatus of the presently disclosed embodiments can be implemented in a computer program product tangibly embodied in a machine-readable storage device for execution by a programmable processor; and method steps of the presently disclosed embodiments can be performed by a programmable processor executing a program of instructions to perform functions of the presently disclosed embodiments by operating on input data and generating output. The presently disclosed embodiments can be implemented advantageously in one or more computer programs that are executable and/or interpretable on a programmable system including at least one programmable processor, which may be special or general purpose, coupled to receive data and instructions from, and to transmit data and instructions to, a storage system, at least one input device, and at least one output device. Each computer program can be implemented in a high-level procedural or object-oriented programming language or in assembly or machine language if desired; and in any case, the language can be a compiled or interpreted language. A computer program may be deployed in any form, including as a stand-alone program, or as a module, component, subroutine, or other unit suitable for use in a computing environment. A computer program may be deployed to be executed or interpreted on one computer or on multiple computers at one site, or distributed across multiple sites and interconnected by a communication network.

Computer readable storage media, as used herein, refers to physical or tangible storage (as opposed to signals) and includes without limitation volatile and non-volatile, removable and non-removable media implemented in any method or technology for the tangible storage of information such as computer-readable instructions, data structures, program modules or other data Computer readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor.

In some embodiments, the invention features a computer configured to accomplish one or more of the in vitro methods described herein. In some embodiments, the data is analyzed by the computer system as described herein. In some embodiments, genetic data (such as sequencing or microarray data) from at least 100; 200; 500; 750; 1,000; 2,000; 5,000; 7,500; 10,000; 20,000; 25,000; 30,000; 40,000; 50,000; 75,000; or 100,000 different loci is analyzed by the computer is less than 200, 100, 60, 30, 20, 10, 5, or 1 minute, or in less than 30 or 10 seconds to detect the present or absence of a mutation (such as a CNV or SNV) at the loci.

Any of the methods described herein may include the output of data in a physical format, such as on a computer screen, or on a paper printout. In explanations of any embodiments elsewhere in this document, it should be understood that the described methods may be combined with the output of the actionable data in a format that can be acted upon by a physician. In addition, the described methods may be combined with the actual execution of a clinical decision that results in a clinical treatment, or the execution of a clinical decision to make no action. Some of the embodiments described in the document for determining genetic data pertaining to a target individual may be combined with the decision to select one or more embryos for transfer in the context of IVF, optionally combined with the process of transferring the embryo to the womb of the prospective mother. Some of the embodiments described in the document for determining genetic data pertaining to a target individual may be combined with the notification of a potential chromosomal abnormality, or lack thereof, with a medical professional, optionally combined with the decision to abort, or to not abort, a fetus in the context of prenatal diagnosis. Some of the embodiments described herein may be combined with the output of the actionable data, and the execution of a clinical decision that results in a clinical treatment, or the execution of a clinical decision to make no action.

Exemplary Diagnostic Boxes

In an embodiment, the present disclosure comprises a diagnostic box that is capable of partly or completely carrying out any of the methods described in this disclosure. In an embodiment, the diagnostic box may be located at a physician's office, a hospital laboratory, or any suitable location reasonably proximal to the point of patient care. The box may be able to run the entire method in a wholly automated fashion, or the box may require one or a number of steps to be completed manually by a technician. In an embodiment, the box may be able to analyze at least the genotypic data measured on the maternal plasma. In an embodiment, the box may be linked to means to transmit the genotypic data measured on the diagnostic box to an external computation facility which may then analyze the genotypic data, and possibly also generate a report. The diagnostic box may include a robotic unit that is capable of transferring aqueous or liquid samples from one container to another. It may comprise a number of reagents, both solid and liquid. It may comprise a high throughput sequencer. It may comprise a computer.

Experimental Section

The presently disclosed embodiments are described in the following Examples, which are set forth to aid in the understanding of the disclosure, and should not be construed to limit in any way the scope of the disclosure as defined in the claims which follow thereafter. The following examples are put forth so as to provide those of ordinary skill in the art with a complete disclosure and description of how to use the described embodiments, and are not intended to limit the scope of the disclosure nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by volume, and temperature is in degrees Centigrade. It should be understood that variations in the methods as described may be made without changing the fundamental aspects that the experiments are meant to illustrate.

Experiment 1

The objective was to show that a Bayesian maximum likelihood estimation (MLE) algorithm that uses parent genotypes to calculate fetal fraction improves accuracy of non-invasive prenatal trisomy diagnosis compared to published methods.

Figure 14:
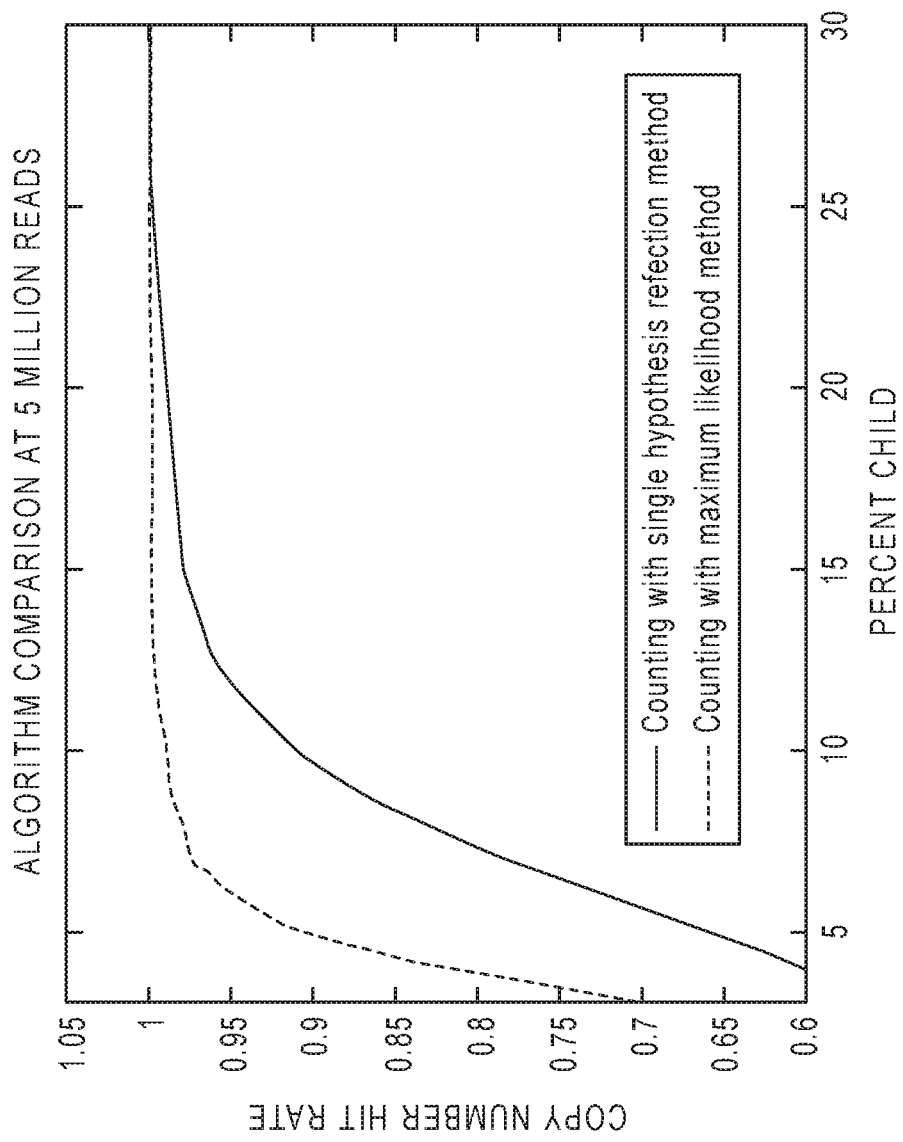
FIG. 14: Simulated ploidy call accuracies for counting method with two different analysis techniques.

Simulated sequencing data for maternal cfDNA was created by sampling reads obtained on trisomy-21 and respective mother cell lines. The rate of correct disomy and trisomy calls were determined from 500 simulations at various fetal fractions for a published method (Chiu et al. BMJ 201; 342:c7401) and our MLE-based algorithm. We validated the simulations by obtaining 5 million shotgun reads from four pregnant mothers and respective fathers collected under an IRB-approved protocol. Parental genotypes were obtained on a 290K SNP array. (See FIG. 14).

In simulations, the MLE-based approach achieved 99.0% accuracy for fetal fractions as low as 9% and reported confidences that corresponded well to overall accuracy. We validated these results using four real samples wherein we obtained all correct calls with a computed confidence exceeding 99%. In contrast, our implementation of the published algorithm for Chiu et al required 18% fetal fraction to achieve 99.0% accuracy, and achieved only 87.8% accuracy at 9% fetal DNA.

Fetal fraction determination from parental genotypes in conjunction with a MLE-based approach achieves greater accuracy than published algorithms at the fetal fractions expected during the 1st and early 2nd trimester. Furthermore, the method disclosed herein produces a confidence metric that is crucial in determining the reliability of the result, especially at low fetal fractions where ploidy detection is more difficult. Published methods use a less accurate threshold method for calling ploidy based on large sets of disomy training data, an approach that predefines a false positive rate. In addition, without a confidence metric, published methods are at risk of reporting false negative results when there is insufficient fetal cfDNA to make a call. In some embodiments, a confidence estimate is calculated for the called ploidy state.

Experiment 2

The objective was to improve non-invasive detection of fetal trisomy 18, 21, and X particularly in samples consisting of low fetal fraction by using a targeted sequencing approach combined with parent genotypes and Hapmap data in a Bayesian Maximum Likelihood Estimation (MLE) algorithm.

Maternal samples from four euploid and two trisomy-positive pregnancies and respective paternal samples were obtained under an IRB-approved protocol from patients where fetal karyotype was known Maternal cfDNA was extracted from plasma and roughly 10 million sequence reads were obtained following preferential enrichment that targeted specific SNPs. Parent samples were similarly sequenced to obtain genotypes.

The described algorithm correctly called chromosome 18 and 21 disomy for all euploid samples and normal chromosomes of aneuploid samples. Trisomy 18 and 21 calls were correct, as were chromosome X copy numbers in male and female fetuses. The confidence produced by the algorithm was in excess of 98% in all cases.

The method described accurately reported the ploidy of all tested chromosomes from six samples, including samples comprised of less than 12% fetal DNA, which account for roughly 30% of $1^{st}$ and early $2^{nd}$-trimester samples. The crucial difference between the instant MLE algorithm and published methods is that it leverages parent genotypes and Hapmap data to improve accuracy and generate a confidence metric. At low fetal fractions, all methods become less accurate; it is important to correctly identify samples without sufficient fetal cfDNA to make a reliable call. Others have used chromosome Y specific probes to estimate fetal fraction of male fetuses, but concurrent parental genotyping enables estimation of fetal fraction for both sexes. Another inherent limitation of published methods using untargeted shotgun sequencing is that accuracy of ploidy calling varies among chromosomes due to differences in factors such as GC richness. The instant targeted sequencing approach is largely independent of such chromosome-scale variations and yields more consistent performance between chromosomes.

Experiment 3

The objective was to determine if uisomy is detectable with high confidence on a triploid fetus, using novel informatics to analyze SNP loci of free floating fetal DNA in maternal plasma.

20 mL of blood was drawn from a pregnant patient following abnormal ultrasound. After centrifugation, maternal DNA was extracted from the buffy coat (DNEASY, QIAGEN), cell-free DNA was extracted from plasma (QIAAMP QIAGEN). Targeted sequencing was applied to SNP loci on chromosomes 2, 21, and X in both DNA samples. Maximum-Likelihood Bayesian estimation selected the most likely hypothesis from the set of all possible ploidy states. The method determines fetal DNA fraction, ploidy state and explicit confidences in the ploidy determination. No assumptions are made about the ploidy of a reference chromosome. The diagnostic uses a test statistic that is independent of sequence read counts, which is the recent state of the art.

The instant method accurately diagnosed trisomy of chromosomes 2 and 21. Child fraction was estimated at 11.9% [CI 11.7-12.1]. The fetus was found to have one maternal and two paternal copies of chromosomes 2 and 21 with confidence of effectively 1 (error probability<$10^{-30}$). This was achieved with 92,600 and 258,100 reads on chromosomes 2 and 21 respectively.

This is the first demonstration of non-invasive prenatal diagnosis of trisomic chromosomes from maternal blood where the fetus was triploid, as confirmed by metaphase karyotype. Extant methods of non-invasive diagnosis would not detect aneuploidy in this sample. Current methods rely on a surplus of sequence reads on a trisomic chromosome relative to disomic reference chromosomes; but a triploid fetus has no disomic reference. Furthermore, extant methods would not achieve similarly high-confidence ploidy determination with this fraction of fetal DNA and number of sequence reads. It is straightforward to extend the approach to all 24 chromosomes.

Experiment 4

Figure 15:
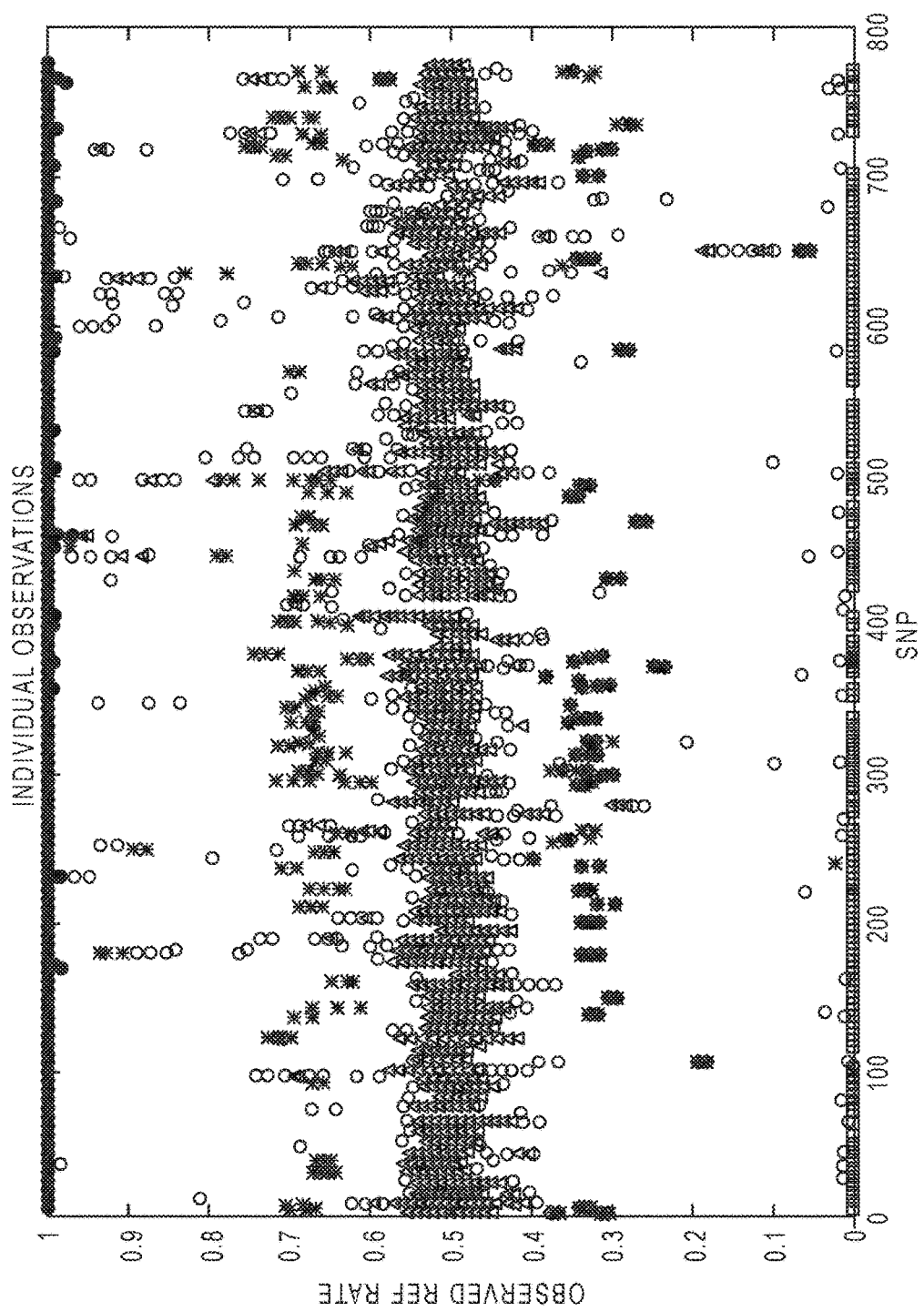
FIG. 15: Ratio of two alleles for a plurality of SNPs in a cell line in Experiment 4.
Figure 16:
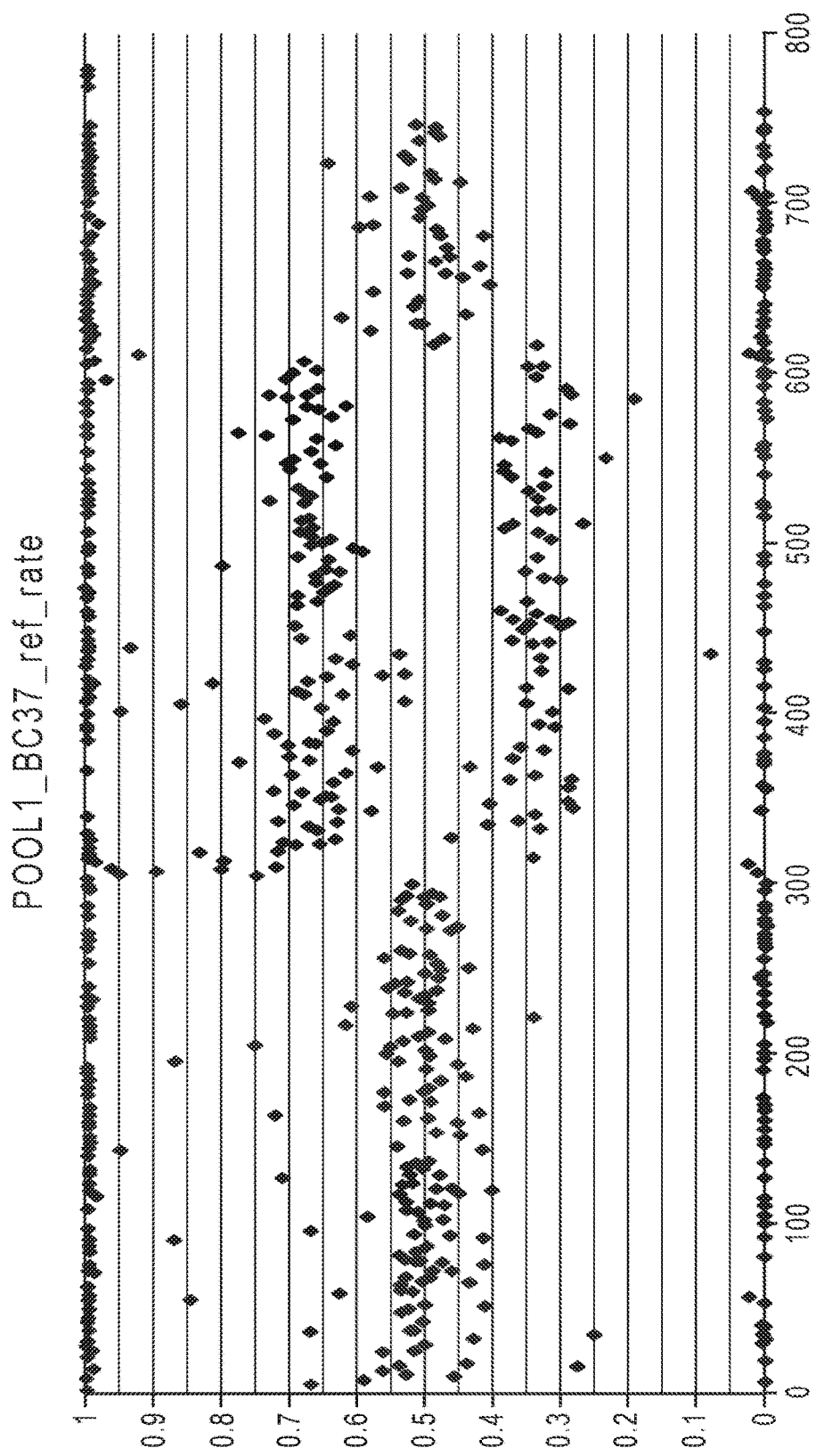
FIG. 16: Ratio of two alleles for a plurality of SNPs in a cell line in Experiment 4 sorted by chromosome.
Figure 17A:
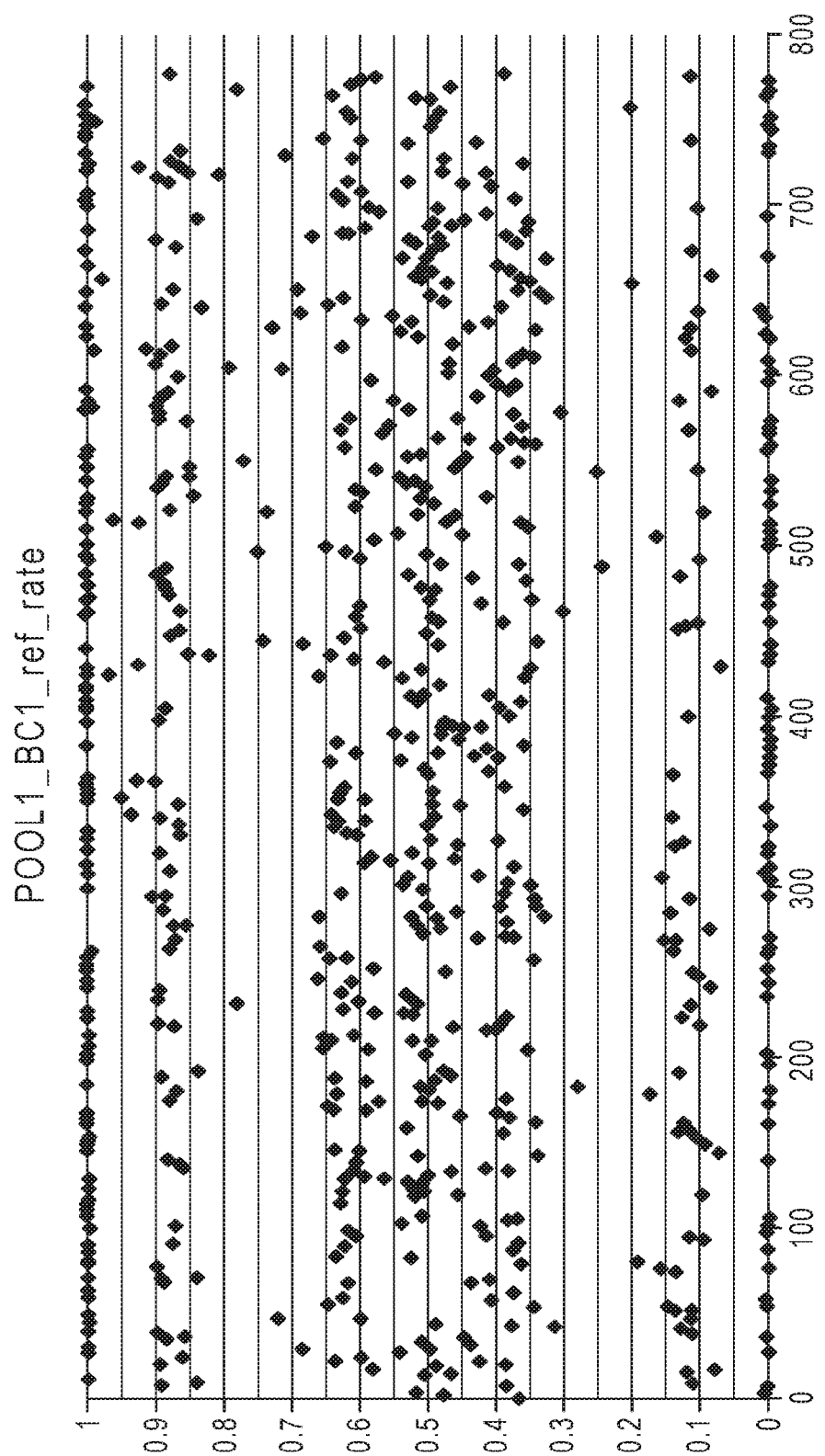
FIGS. 17A-17D: Ratio of two alleles for a plurality of SNPs in four pregnant women plasma samples, sorted by chromosome.
Figure 17B:
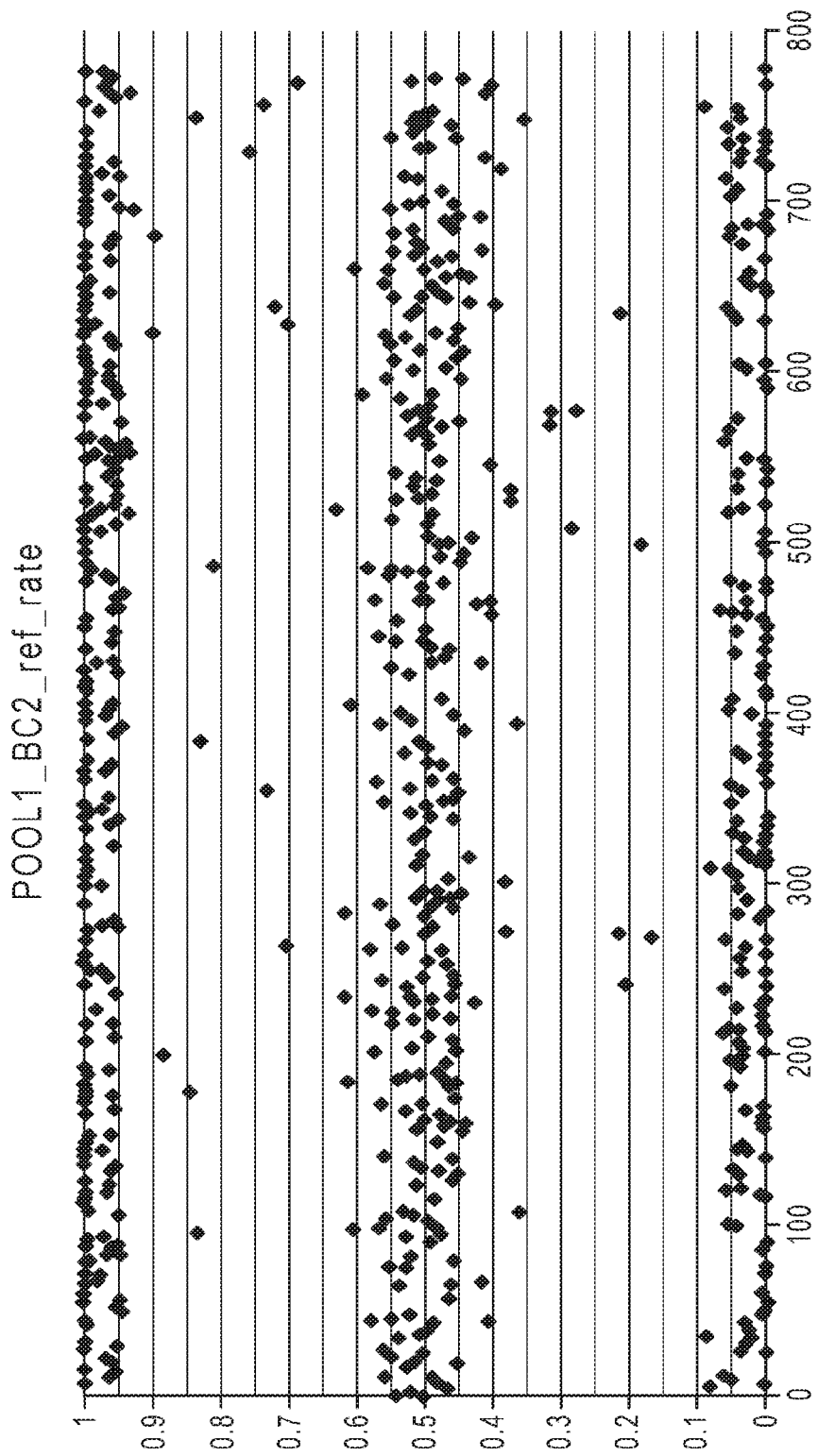
Figure 17C:
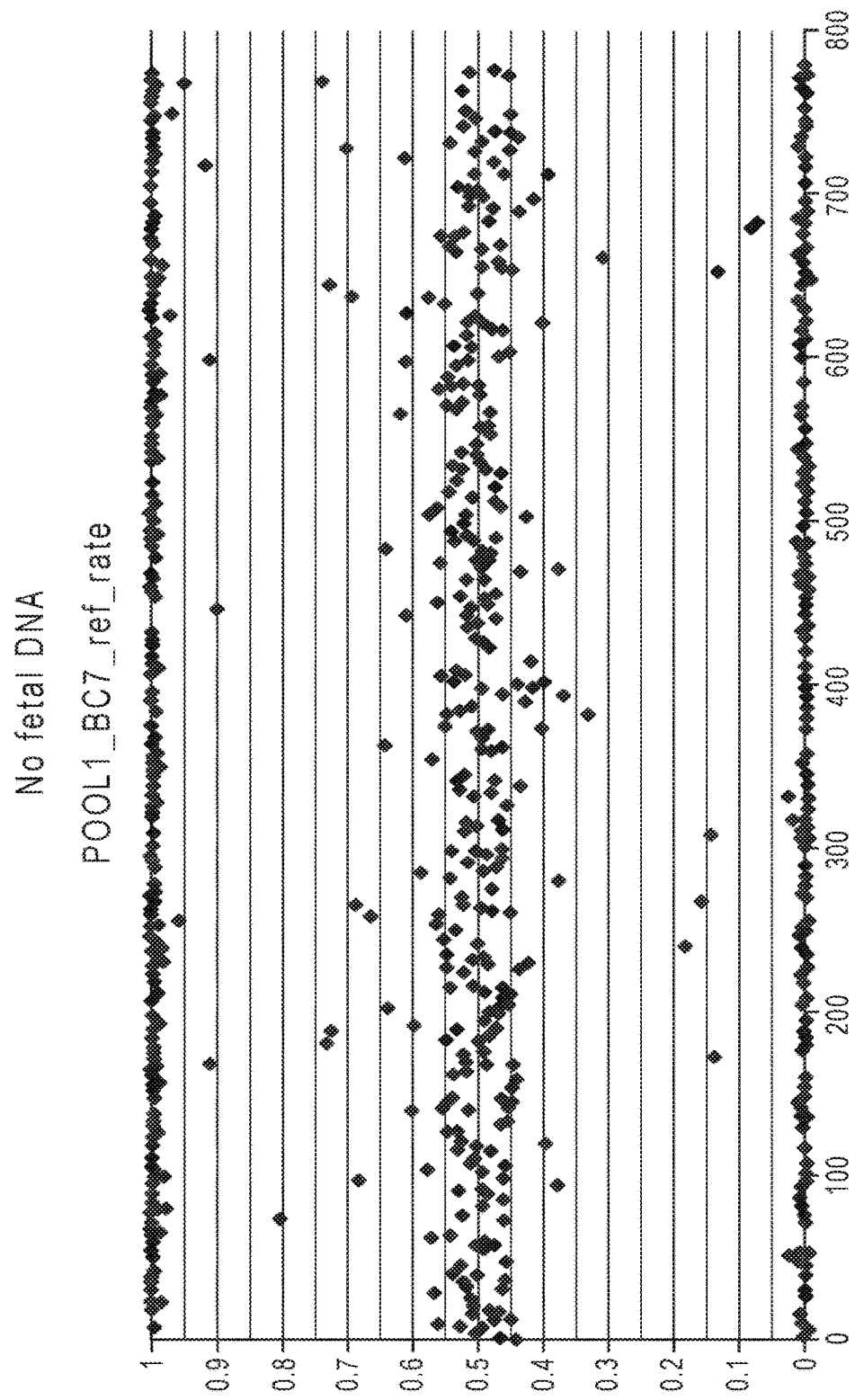
Figure 17D:
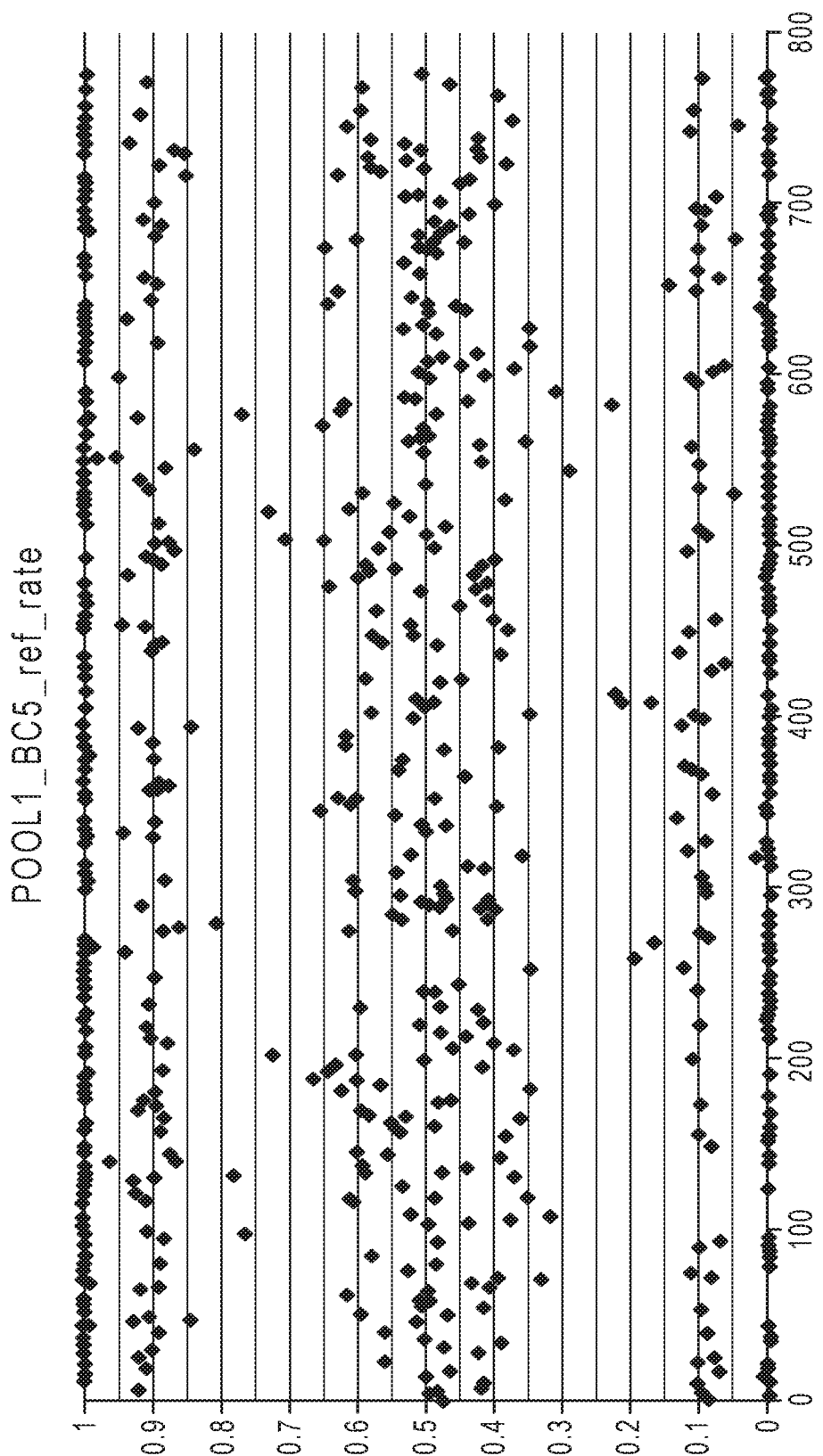

The following protocol was used for 800-plex amplification of DNA isolated from maternal plasma from a euploid pregnancy and also genomic DNA from a triploidy 21 cell line using standard PCR (meaning no nesting was used). Library preparation and amplification involved single tube blunt ending followed by A-tailing. Adaptor ligation was run using the ligation kit found in the AGILENT SURESELECT kit, and PCR was run for 7 cycles. Then, 15 cycles of STA (95° C. for 30 s; 72° C. for 1 min; 60° C. for 4 min; 65° C. for 1 min; 72° C. for 30 s) using 800 different primer pairs targeting SNPs on chromosomes 2, 21 and X. The reaction was run with 12.5 nM primer concentration. The DNA was then sequenced with an ILLUMINA IIGAX sequencer. The sequencer output 1.9 million reads, of which 92% mapped to the genome; of those reads that mapped to the genome, more than 99% mapped to one of the regions targeted by the targeted primers. The numbers were essentially the same for both the plasma DNA and the genomic DNA. FIG. 15 shows the ratio of the two alleles for the ~780 SNPs that were detected by the sequencer in the genomic DNA that was taken from a cell line with known trisomy at chromosome 21. Note that the allele ratios are plotted here for ease of visualization, because the allele distributions are not straightforward to read visually. The circles represent SNPs on disomic chromosomes, while the stars represent SNPs on a trisomic chromosome. FIG. 16 is another representation of the same data as in FIG. X, where the Y-axis is the relative number of A and B measured for each SNP, and where the X-axis is the SNP number where the SNPs are separated by chromosome. In FIG. 16. SNP 1 to 312 are found on chromosome 2, from SNP 313 to 605 are found on chromosome 21 which is trisomic, and from SNP 606 to 800 are on chromosome X. The data from chromosomes 2 and X show a disomic chromosome, as the relative sequence counts lie in three clusters: AA at the top of the graph, BB at the bottom of the graph, and AB in the middle of the graph. The data from chromosome 21, which is trisomic, shows four clusters: AAA at the top of the graph, AAB around the 0.65 line (⅔). ABB around the 0.35 line (⅓), and BBB at the bottom of the graph.

FIGS. 17A-D show data for the same 800-plex protocol, but measured on DNA that was amplified from four plasma samples from pregnant women. For these four samples, we expect to see seven clusters of dots: (1) along the top of the graph are those loci where both the mother and the fetus are AA, (2) slightly below the top of the graph are those loci where the mother is AA and the fetus is AB, (3) slightly above the 0.5 line are those loci where the mother is AB and the fetus is AA, (4) along the 0.5 line are those loci where the mother and the fetus are both AB, (5) slightly below the 0.5 line are those loci where the mother is AB and the fetus is BB, (6) slightly above the bottom of the graph are those loci where the mother is BB and the fetus is AB, (1) along the bottom of the graph are those loci where both the mother and the fetus are BB. The smaller the fetal fraction, the less the separation between clusters (1) and (2), between clusters (3), (4) and (5), and between clusters (6) and (7). The separation is expected to be half of the fraction of DNA that is of fetal origin. For example if the DNA is 20% fetal, and 80% maternal, we expect (1) through (7) to be centered at 1.0, 0.9, 0.6, 0.5, 0.4, 0.1 and 0.0 respectively; see for example FIG. 17D, POOL1_BC5_ref_rate. If, instead the DNA is 8% fetal, and 92% maternal, we expect (1) through (7) to be centered at 1.00, 0.96, 0.54, 0.50, 0.46, 0.04 and 0.00 respectively; see for example FIG. 17B, POOL1_BC2_ref_rate. If there is not fetal DNA detected, we do not expect to see (2), (3), (5), or (6); alternately we could say that the separation is zero, and therefore (1) and (2) are on top of each other, as are (3), (4) and (5), and also (6) and (7); see e.g. FIG. 17C, POOL1_BC7_ref_rate. Note that the fetal fraction for FIG. 17A, POOL1_BC1_ref_rate is about 25%.

Experiment 5

Figure 18:
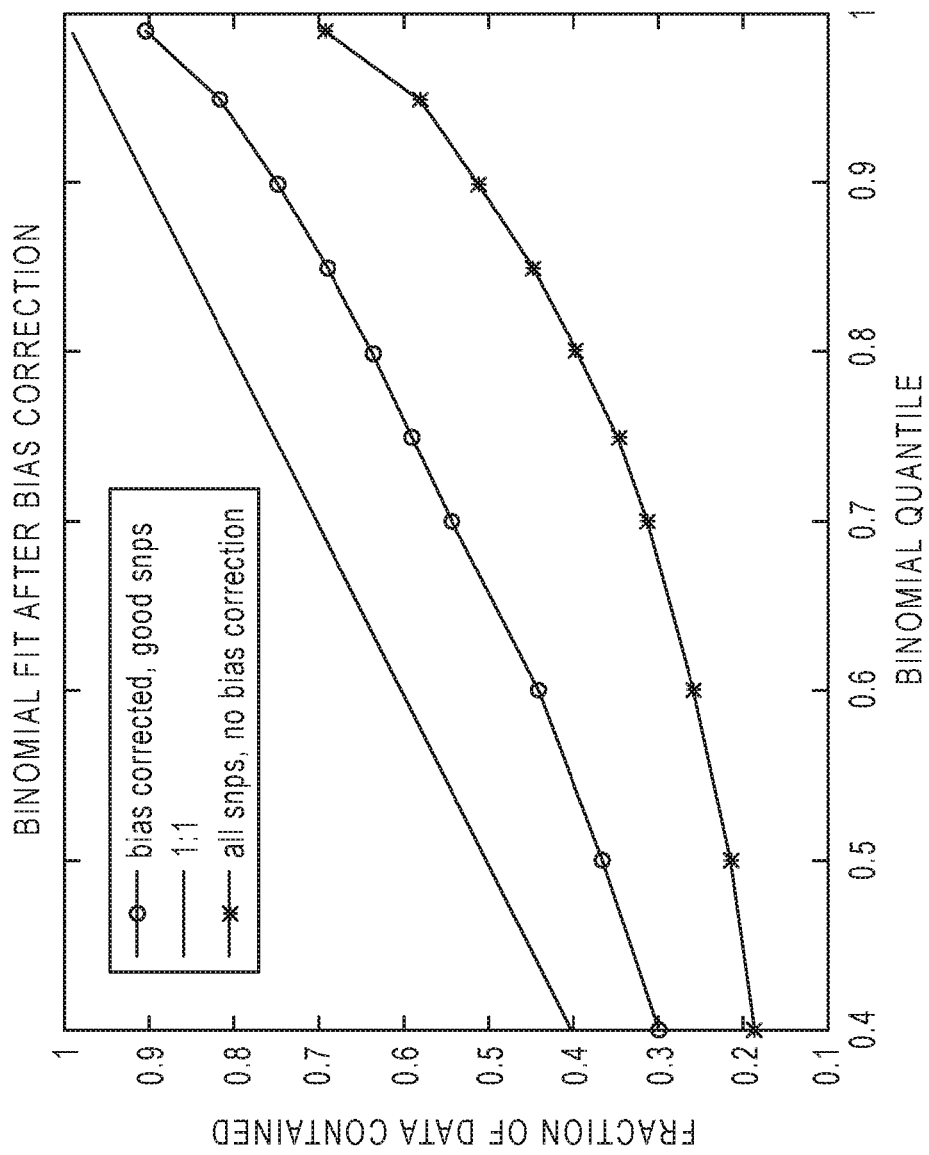
FIG. 18: Fraction of data that can be explained by binomial variance before and after data correction.

Most methods of DNA amplification and measurement will produce some allele bias, wherein the two alleles that are typically found at a locus are detected with intensities or counts that are not representative of the actual amounts of alleles in the sample of DNA. For example, for a single individual, at a heterozygous locus we expect to see a 1:1 ratio of the two alleles, which is the theoretical ratio expected for a heterozygous locus; however due to allele bias, we may see 55:45, or even 60:40. Also note that in the context of sequencing, if the depth of read is low, then simple stochastic noise could result in significant allele bias. In an embodiment, it is possible to model the behavior of each SNP such that if a consistent bias is observed for particular alleles, this bias can be corrected for. FIG. 18 shows the fraction of data that can be explained by binomial variance, before and after bias correction. In FIG. 18, the stars represent the observed allele bias on raw sequence data for the 800-plex experiment, the circles represent the allele bias after correction. Note that if there were no allele bias at all, we would expect the data to fall along the x=y line. A similar set of data that was produced by amplifying DNA using a 150-plex targeted amplification produced data that fell very closely on the 1.1 line after bias correction.

Experiment 6

Figure 19:
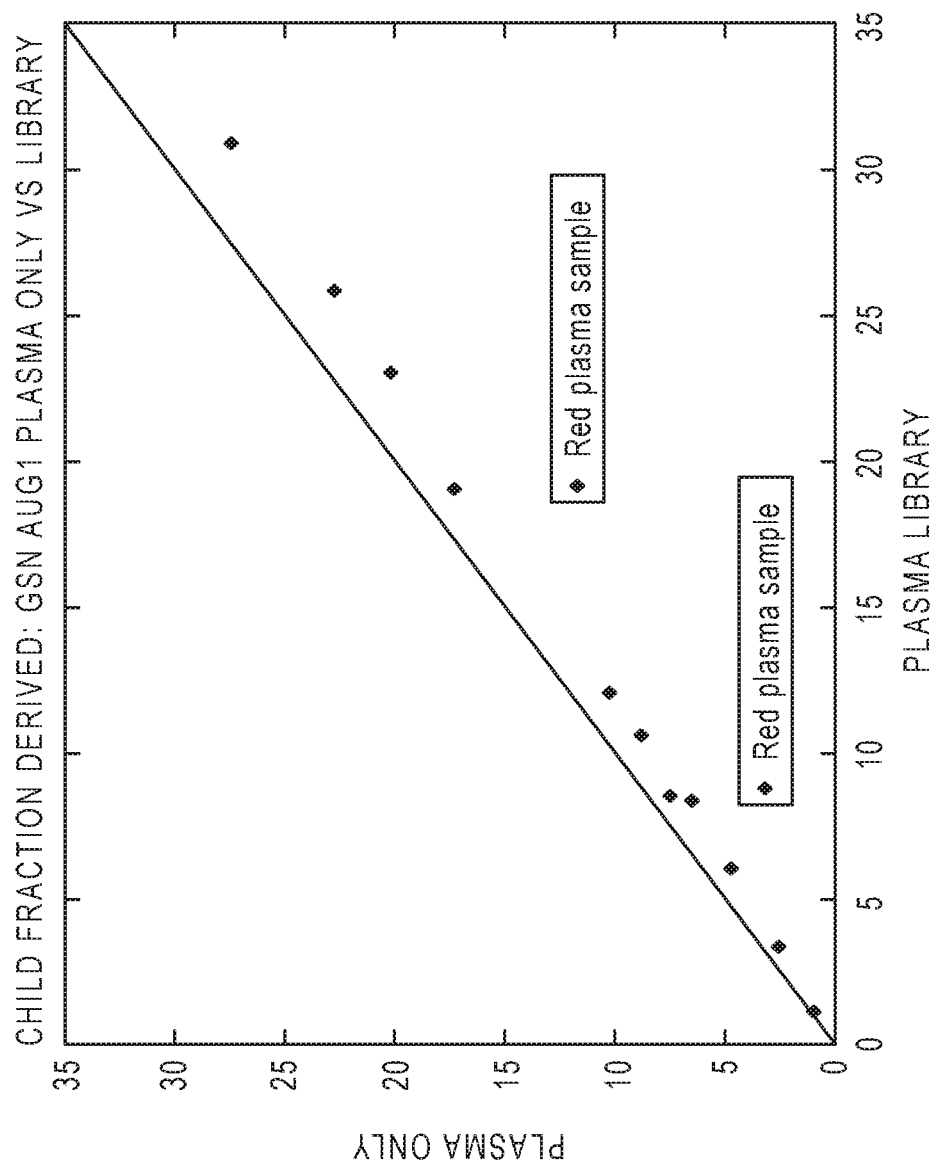
FIG. 19: Graph showing relative enrichment of fetal DNA in samples following a short library preparation protocol.

Universal amplification of DNA using ligated adaptors with primers specific to the adaptor tags, where the primer annealing and extension times are limited to a few minutes has the effect of enriching the proportion of shorter DNA strands. Most library protocols designed for creating DNA libraries suitable for sequencing contain such a step, and example protocols are published and well known to those in the art. In some embodiments of the invention, adaptors with a universal tag are ligated to the plasma DNA, and amplified using primers specific to the adaptor tag. In some embodiments, the universal tag can be the same tag as used for sequencing, it can be a universal tag only for PCR amplification, or it can be a set of tags. Since the fetal DNA is typically short in nature, while the maternal DNA can be both short and long in nature, this method has the effect of enriching the proportion of fetal DNA in the mixture. The free floating DNA, thought to be DNA from apoptotic cells, and which contains both fetal and maternal DNA, is short—mostly under 200 bp. Cellular DNA released by cell lysis, a common phenomenon after phlebotomy, is typically almost exclusively maternal, and is also quite long—mostly above 500 bp. Therefore, blood samples that have sat around for more than a few minutes will contain a mixture of short (fetal+maternal) and longer (maternal) DNA. Performing a universal amplification with relatively short extension times on maternal plasma followed by targeted amplification will tend to increase the relative proportion of fetal DNA when compared to the plasma that has been amplified using targeted amplification alone. This can be seen in FIG. 19 which shows the measured fetal percent when the input is plasma DNA (vertical axis) vs. the measured fetal percent when the input DNA is plasma DNA that has had a library prepared using the ILLUMINA GAIIx library preparation protocol. All the dots fall below the line, indicating that the library preparation step enriches the fraction of DNA that is of fetal origin. Two samples of plasma that were red, indicating hemolysis and therefore that there would be an increased amount of long maternal DNA present from cell lysis, show a particularly significant enrichment of fetal fraction when the library preparation is performed prior to targeted amplification. The method disclosed herein is particularly useful in cases where there is hemolysis or some other situation has occurred where cells comprising relatively long strands of contaminating DNA have lysed, contaminating the mixed sample of short DNA with the long DNA. Typically the relatively short annealing and extension times are between 30 seconds and 2 minutes, though they could be as short as 5 or 10 seconds or less, or as long as 5 or 10 minutes.

Experiment 7

The following protocol was used for 1,200-plex amplification of DNA isolated from maternal plasma from a euploid pregnancy and also genomic DNA from a triploidy 21 cell line using a direct PCR protocol, and also a semi-nested approach. Library preparation and amplification involved single tube blunt ending followed by A-tailing. Adaptor ligation was run using a modification of the ligation kit found in the AGILENT SURESELECT kit, and PCR was run for 7 cycles. In the targeted primer pool, there were 550 assays for SNPs from chromosome 21, and 325 assays for SNPs from each of chromosomes 1 and X. Both protocols involved 15 cycles of STA (95° C. for 30 s; 72° C. for 1 min; 60° C. for 4 min; 65° C. for 30 s; 72° C. for 30 s) using 16 nM primer concentration. The semi-nested PCR protocol involved a second amplification of 15 cycles of STA (95° C. for 30 s; 72° C. for 1 min; 60° C. for 4 min; 65° C. for 30 s; 72° C. for 30 s) using an inner forward tag concentration of 29 nM, and a reverse tag concentration of 1 uM or 0.1 uM. The DNA was then sequenced with an ILLUMINA IIGAX sequencer. For the direct PCR protocol, 73% of the reads map to the genome; for the semi-nested protocol, 97.2% of the sequence reads map to the genome. Therefore, the semi-nested protocol result in approximately 30% more information, presumably mostly due to the elimination of primers that are most likely to cause primer dimers.

Figure 20:
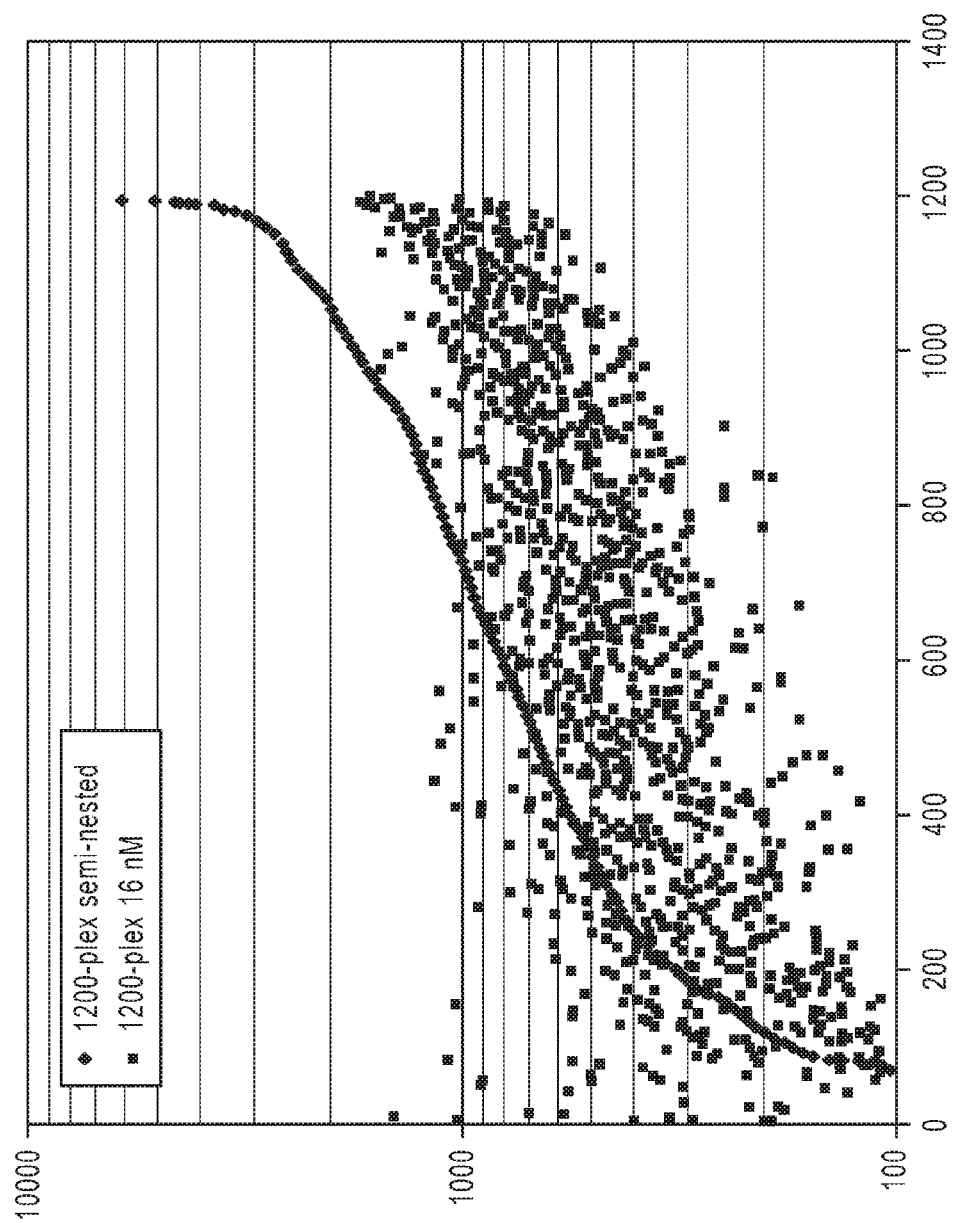
FIG. 20: Depth of read graph comparing direct PCR and semi-nested methods.

The depth of read variability tends to be higher when using the semi-nested protocol than when the direct PCR protocol is used (see FIG. 20) where the diamonds refer to the depth of read for loci run with the semi-nested protocol, and the squares refer to the depth of read for loci run with no nesting. The SNPs are arranged by depth of read for the diamonds, so the diamonds all fall on a curved line, while the squares appear to be loosely correlated, the arrangements of the SNPs is arbitrary, and it is the height of the dot that denotes depth of read rather than its location left to right.

Figure 21:
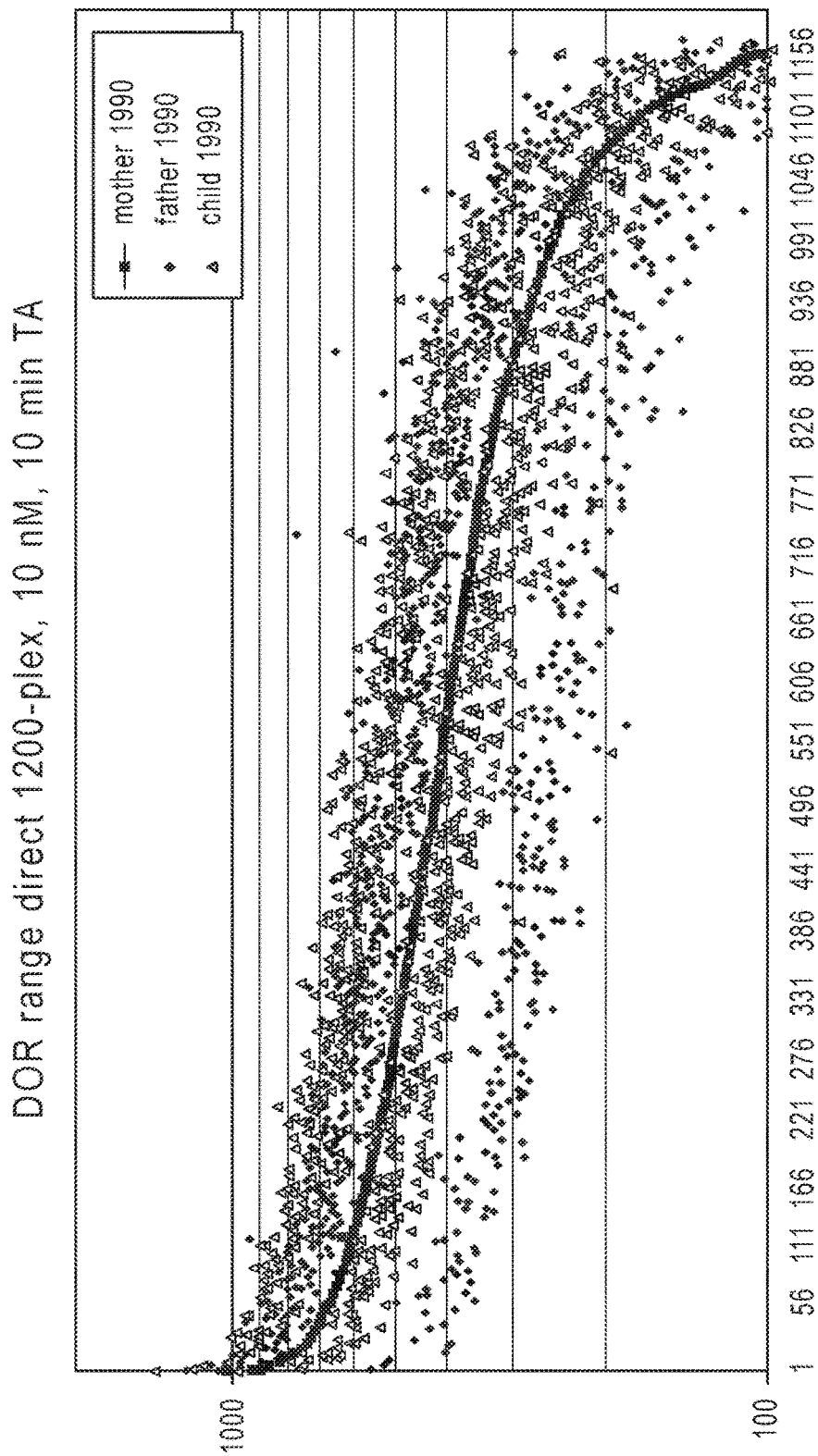
FIG. 21: Comparison of depth of read for direct PCR of three genomic samples.
Figure 22:
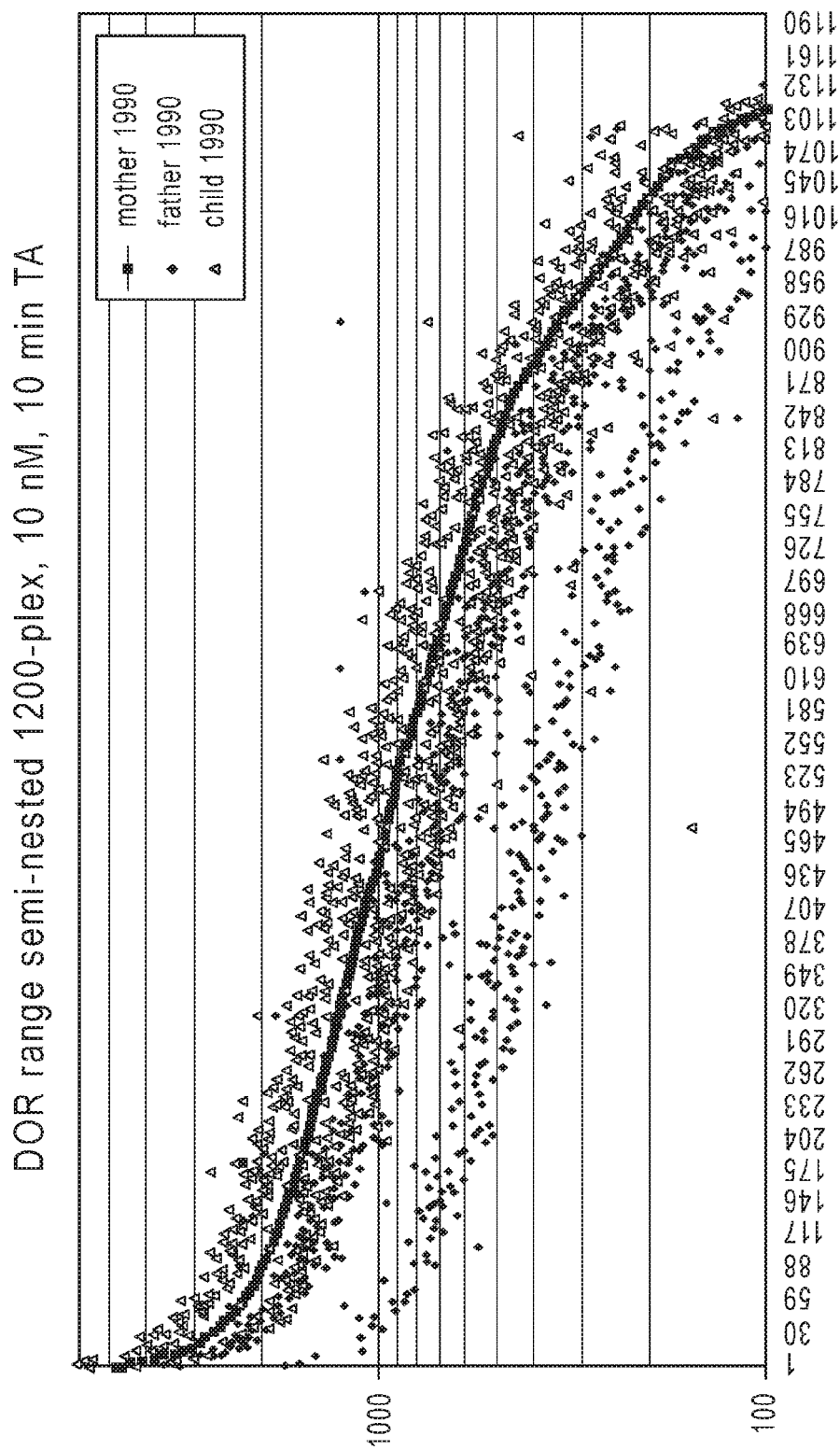
FIG. 22: Comparison of depth of read for semi-nested mini-PCR of three samples.

In some embodiments, the methods described herein can achieve excellent depth of read (DOR) variances. For example, in one version of this experiment (FIG. 21) using a 1,200-plex direct PCR amplification of genomic DNA, of the 1,200 assays: 1186 assays had a DOR greater than 10; the average depth of read was 400; 1063 assays (88.6%) had a depth of read of between 200 and 800, and ideal window where the number of reads for each allele is high enough to give meaningful data, while the number of reads for each allele is not so high that the marginal use of those reads was particularly small. Only 12 alleles had higher depth of read with the highest at 1035 reads. The standard deviation of the DOR was 290, the average DOR was 453, the coefficient of variance of the DOR was 64%, there were 950,000 total reads, and 63.1% of the reads mapped to the genome. In another experiment (FIG. 22) using a 1,200-plex semi-nested protocol, the DOR was higher. The standard deviation of the DOR was 583, the average DOR was 630, the coefficient of variance of the DOR was 93%, there were 870,000 total reads, and 96.3% of the reads mapped to the genome. Note, in both these cases, the SNPs are arranged by the depth of read for the mother, so the curved line represents the maternal depth of read. The differentiation between child and father is not significant; it is only the trend that is significant for the purpose of this explanation.

Experiment 8

In an experiment, the semi-nested 1,200-plex PCR protocol was used to amplify DNA from one cell and from three cells. This experiment is relevant to prenatal aneuploidy testing using fetal cells isolated from maternal blood, or for preimplantation genetic diagnosis using biopsied blastomeres or trophectoderm samples. There were 3 replicates of 1 and 3 cells from 2 individuals (46 XY and 47 XX+21) per condition. Assays targeted chromosomes 1, 21 and X. Three different lysis methods were used: ARCTURUS, MPERv2 and Alkaline lysis. Sequencing was run multiplexing 48 samples in one sequencing lane. The algorithm returned correct ploidy calls for each of the three chromosomes, and for each of the replicates.

Experiment 9

In one experiment, four maternal plasma samples were prepared and amplified using a hemi-nested 9,600-plex protocol. The samples were prepared in the following way. Up to 40 mL of maternal blood were centrifuged to isolate the buffy coat and the plasma. The genomic DNA in the maternal sample was prepared from the buffy coat and paternal DNA was prepared from a blood sample or saliva sample. Cell-free DNA in the maternal plasma was isolated using the QIAGEN CIRCULATING NUCLEIC ACID kit and eluted in 45 uL TE buffer according to manufacturer's instructions. Universal ligation adapters were appended to the end of each molecule of 35 uL of purified plasma DNA and libraries were amplified for 7 cycles using adaptor specific primers. Libraries were purified with AGENCOURT AMPURE beads and eluted in 50 ul water.

3 ul of the DNA was amplified with 15 cycles of STA (95° C. for 10 min for initial polymerase activation, then 15 cycles of 95° C. for 30 s; 72° C. for 10 s; 65° C. for 1 min; 60° C. for 8 min; 65° C. for 3 min and 72° C. for 30 s; and a final extension at 72° C. for 2 min) using 14.5 nM primer concentration of 9600 target-specific tagged reverse primers and one library adaptor specific forward primer at 500 nM.

The hemi-nested PCR protocol involved a second amplification of a dilution of the first STAs product for 15 cycles of STA (95° C. for 10 min for initial polymerase activation, then 15 cycles of 95° C. for 30 s; 65° C. for 1 min; 60° C. for 5 min; 65° C. for 5 min and 72° C. for 30 s; and a final extension at 72° C. for 2 min) using reverse tag concentration of 1000 nM, and a concentration of 16.6 u nM for each of 9600 target-specific forward primers.

An aliquot of the STA products was then amplified by standard PCR for 10 cycles with 1 uM of tag-specific forward and barcoded reverse primers to generate barcoded sequencing libraries. An aliquot of each library was mixed with libraries of different barcodes and purified using a spin column.

In this way, 9,600 primers were used in the single-well reactions; the primers were designed to target SNPs found on chromosomes 1, 2, 13, 18, 21, X and Y. The amplicons were then sequenced using an ILLUMINA GAIIX sequencer. Per sample, approximately 3.9 million reads were generated by the sequencer, with 3.7 million reads mapping to the genome (94%), and of those, 2.9 million reads (74%) mapped to targeted SNPs with an average depth of read of 344 and a median depth of read of 255. The fetal fraction for the four samples was found to be 9.9%, 18.9%, 16.3%, and 21.2%.

Relevant maternal and paternal genomic DNA samples amplified using a semi-nested 9600-plex protocol and sequenced. The semi-nested protocol is different in that it applies 9,600 outer forward primers and tagged reverse primers at 7.3 nM in the first STA. Thermocycling conditions and composition of the second STA, and the barcoding PCR were the same as for the hemi-nested protocol.

The sequencing data was analyzed using informatics methods disclosed herein and the ploidy state was called at six chromosomes for the fetuses whose DNA was present in the 4 maternal plasma samples. The ploidy calls for all 28 chromosomes in the set were called correctly with confidences above 99.2% except for one chromosome that was called correctly, but with a confidence of 83%.

Figure 23:
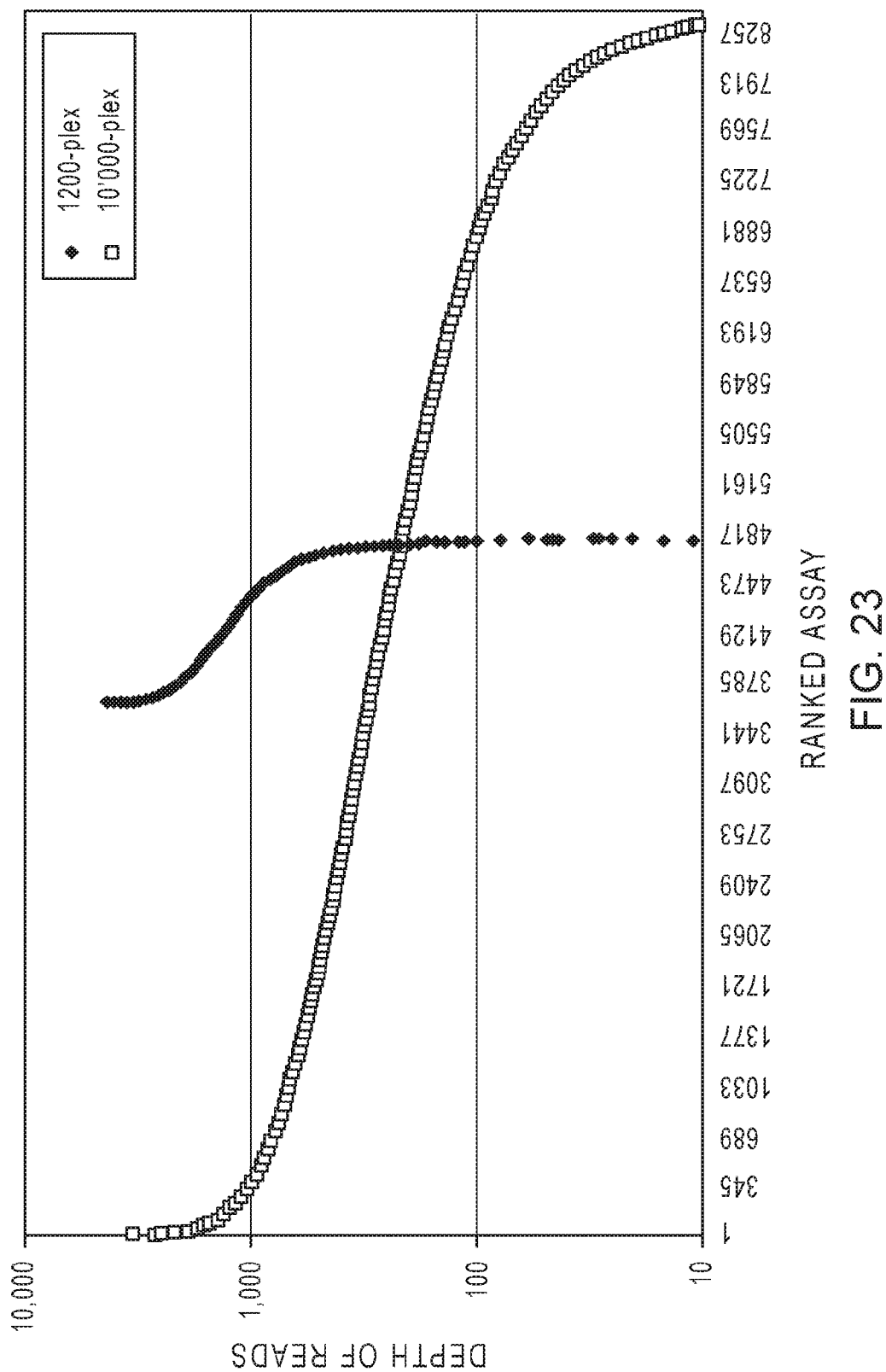
FIG. 23: Comparison of depth of read for 1,200-plex and 9,600-plex reactions.

FIG. 23 shows the depth of read of the 9,600-plex hemi-nesting approach along with the depth of read of the 1,200-plex semi-nested approach described in Experiment 7, though the number of SNPs with a depth of read greater than 100, greater than 200 and greater than 400 was significantly higher than in the 1,200-plex protocol. The number of reads at the $90^{th}$ percentile can be divided by the number of reads at the 100 percentile to give a dimensionless metric that is indicative of the uniformity of the depth of read, the smaller the number, the more uniform (narrow) the depth of read. The average $90^{th}$ percentile/$10^{th}$ percentile ratio is 11.5 for the method run in Experiment 9, while it is 5.6 for the method run in Experiment 7. A narrower depth of read for a given protocol plexity is better for sequencing efficiency, as fewer sequence reads are necessary to ensure that a certain percentage of reads are above a read number threshold.

Experiment 10

In one experiment, four maternal plasma samples were prepared and amplified using a semi-nested 9,600-plex protocol. Details of Experiment 10 were very similar to Experiment 9, the exception being the nesting protocol, and including the identity of the four samples. The ploidy calls for all 28 chromosomes in the set were called correctly with confidences above 99.7%. 7.6 million (97%) of reads mapped to the genome, and 6.3 million (80%) of the reads mapped to the targeted SNPs. The average depth of read was 751, and the median depth of read was 396.

Experiment 11

In one experiment, three maternal plasma samples were split into five equal portions, and each portion was amplified using either 2,400 multiplexed primers (four portions) or 1,200 multiplexed primers (one portion) and amplified using a semi-nested protocol, for a total of 10,800 primers. After amplification, the portions were pooled together for sequencing. Details of Experiment 11 were very similar to Experiment 9, the exception being the nesting protocol, and the split and pool approach. The ploidy calls for all 21 chromosomes in the set were called correctly with confidences above 99.7%, except for one missed call where the confidence was 83%. 3.4 million reads mapped to targeted SNPs, the average depth of read was 404 and the median depth of read was 258.

Experiment 12

In one experiment, four maternal plasma samples were split into four equal portions, and each portion was amplified using 2,400 multiplexed primers and amplified using a semi-nested protocol, for a total of 9,600 primers. After amplification, the portions were pooled together for sequencing. Details of Experiment 12 were very similar to Experiment 9, the exception being the nesting protocol, and the split and pool approach. The ploidy calls for all 28 chromosomes in the set were called correctly with confidences above 97%, except for one missed call where the confidence was 78%. 4.5 million reads mapped to targeted SNPs, the average depth of read was 535 and the median depth of read was 412.

Experiment 13

In one experiment, four maternal plasma samples were prepared and amplified using a 9,600-plex triply hemi-nested protocol, for a total of 9,600 primers. Details of Experiment 12 were very similar to Experiment 9, the exception being the nesting protocol which involved three rounds of amplification, the three rounds involved 15, 10 and 15 STA cycles respectively. The ploidy calls for 27 of 28 chromosomes in the set were called correctly with confidences above 99.9%, except for one that was called correctly with 94.6%, and one missed call with a confidence of 80.8%. 3.5 million reads mapped to targeted SNPs, the average depth of read was 414 and the median depth of read was 249.

Experiment 14

In one experiment 45 sets of cells were amplified using a 1,200-plex semi-nested protocol, sequenced, and ploidy determinations were made at three chromosomes. Note that this experiment is meant to simulate the conditions of performing pre-implantation genetic diagnosis on single-cell biopsies from day 3 embryos, or trophectoderm biopsies from day 5 embryos 15 individual single cells and 30 sets of three cells were placed in 45 individual reaction tubes for a total of 45 reactions where each reaction contained cells from only one cell line, but the different reactions contained cells from different cell lines. The cells were prepared into 5 ul washing buffer and lysed the by adding 5 ul ARCTURUS PICOPURE lysis buffer (APPLIED BIOSYSTEMS) and incubating at 56° C. for 20 min, 95° C. for 10 min.

The DNA of the single/three cells was amplified with 25 cycles of STA (95° C. for 10 min for initial polymerase activation, then 25 cycles of 95° C. for 30 s; 72° C. for 10 s; 65° C. for 1 min; 60° C. for 8 min; 65° C. for 3 min and 72° C. for 30 s; and a final extension at 72° C. for 2 min) using 50 nM primer concentration of 1200 target-specific forward and tagged reverse primers.

The semi-nested PCR protocol involved three parallel second amplification of a dilution of the first STAs product for 20 cycles of STA (95° C. for 10 min for initial polymerase activation, then 15 cycles of 95° C. for 30 s; 65° C. for 1 min; 60° C. for 5 min; 65° C. for 5 min and 72° C. for 30 s; and a final extension at 72° C. for 2 min) using reverse tag specific primer concentration of 1000 nM, and a concentration of 60 nM for each of 400 target-specific nested forward primers. In the three parallel 400-plex reactions the total of 1200 targets amplified in the first STA were thus amplified.

An aliquot of the STA products was then amplified by standard PCR for 15 cycles with 1 uM of tag-specific forward and barcoded reverse primers to generate barcoded sequencing libraries. An aliquot of each library was mixed with libraries of different barcodes and purified using a spin column.

In this way, 1,200 primers were used in the single cell reactions, the primers were designed to target SNPs found on chromosomes 1, 21 and X. The amplicons were then sequenced using an ILLUMINA GAIIX sequencer. Per sample, approximately 3.9 million reads were generated by the sequencer, with 500,000 to 800,000 million reads mapping to the genome (74% to 94% of all reads per sample).

Relevant maternal and paternal genomic DNA samples from cell lines were analyzed using the same semi-nested 1200-plex assay pool with a similar protocol with fewer cycles and 1200-plex second STA, and sequenced.

The sequencing data was analyzed using informatics methods disclosed herein and the ploidy state was called at the three chromosomes for the samples.

Figure 24:
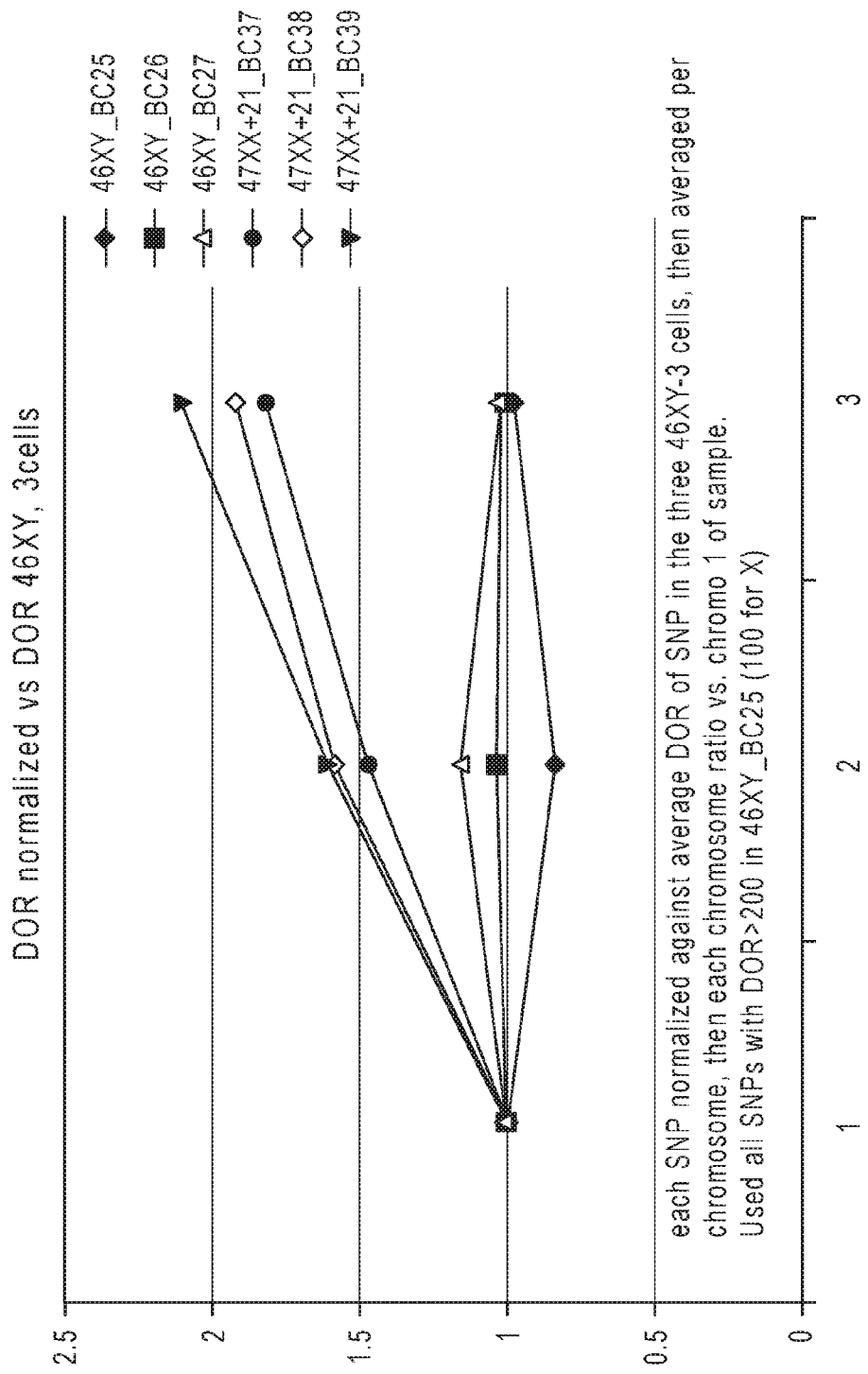
FIG. 24: Read count ratios for six cells at three chromosomes.
Figure 25A:
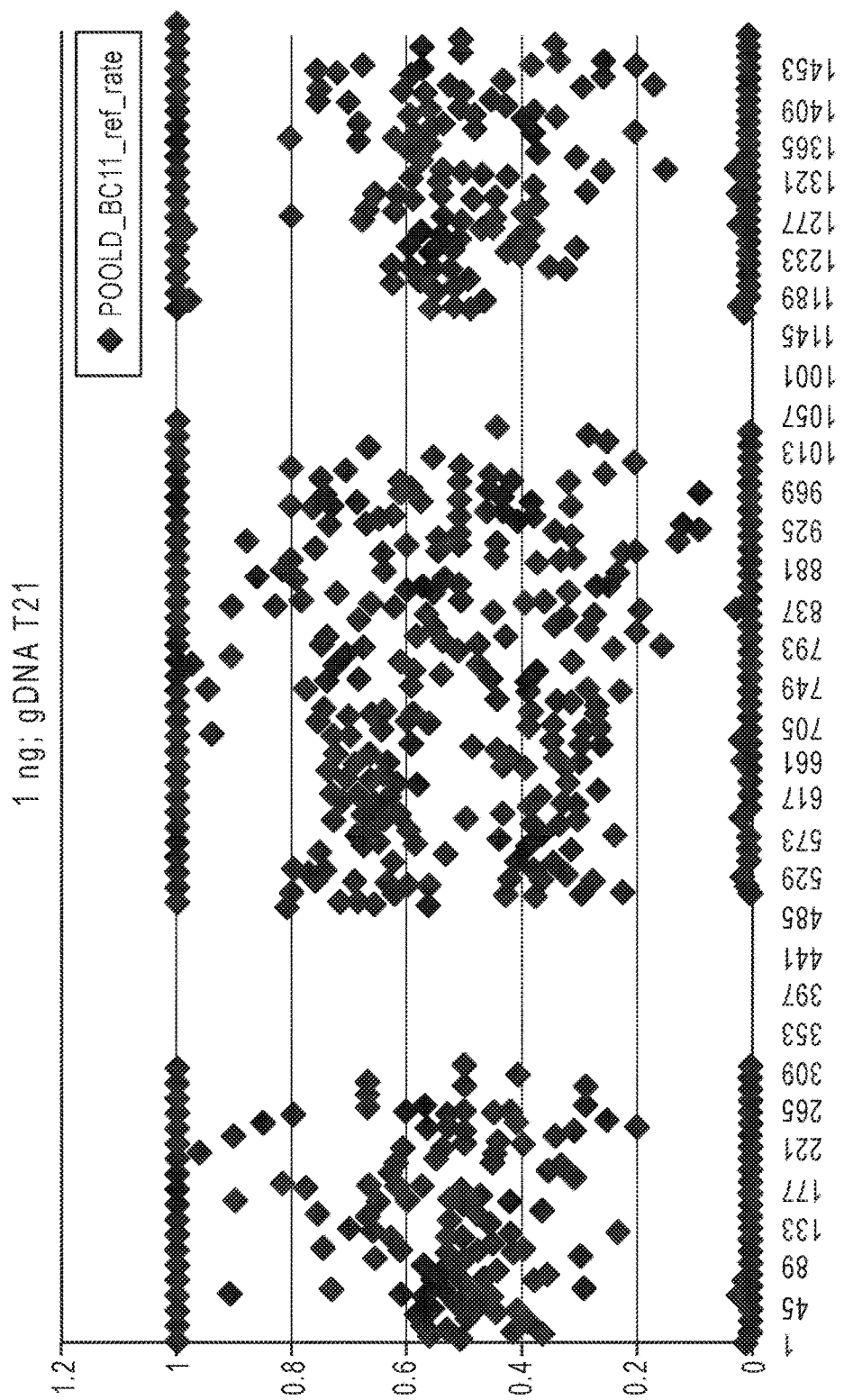
FIGS. 25A-25C: Allele ratios for two three-cell reactions (FIGS. 25B and 25C) and a third reaction run on 1 ng of genomic DNA at three chromosomes (FIG. 25A).
Figure 25B:
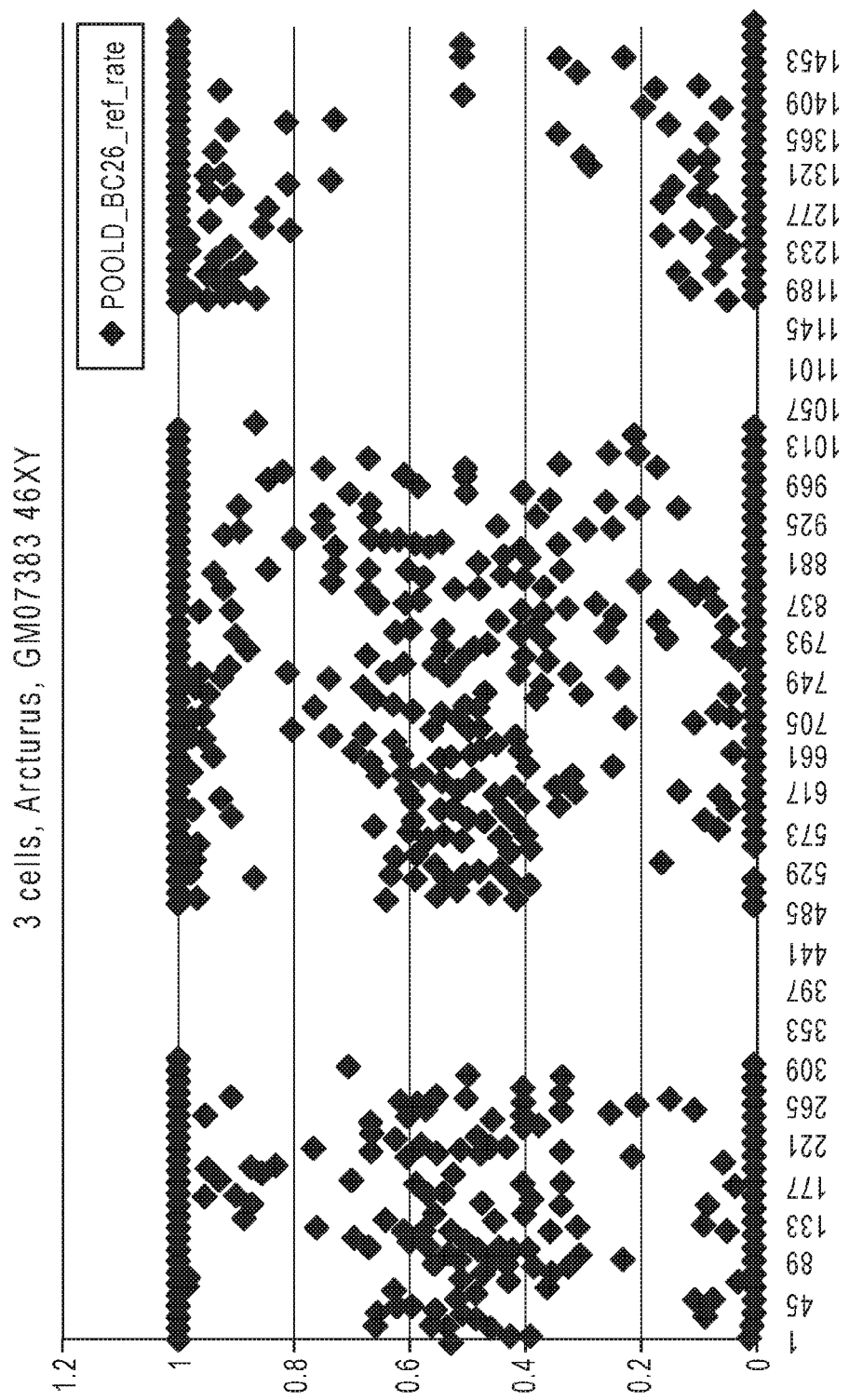
Figure 25C:
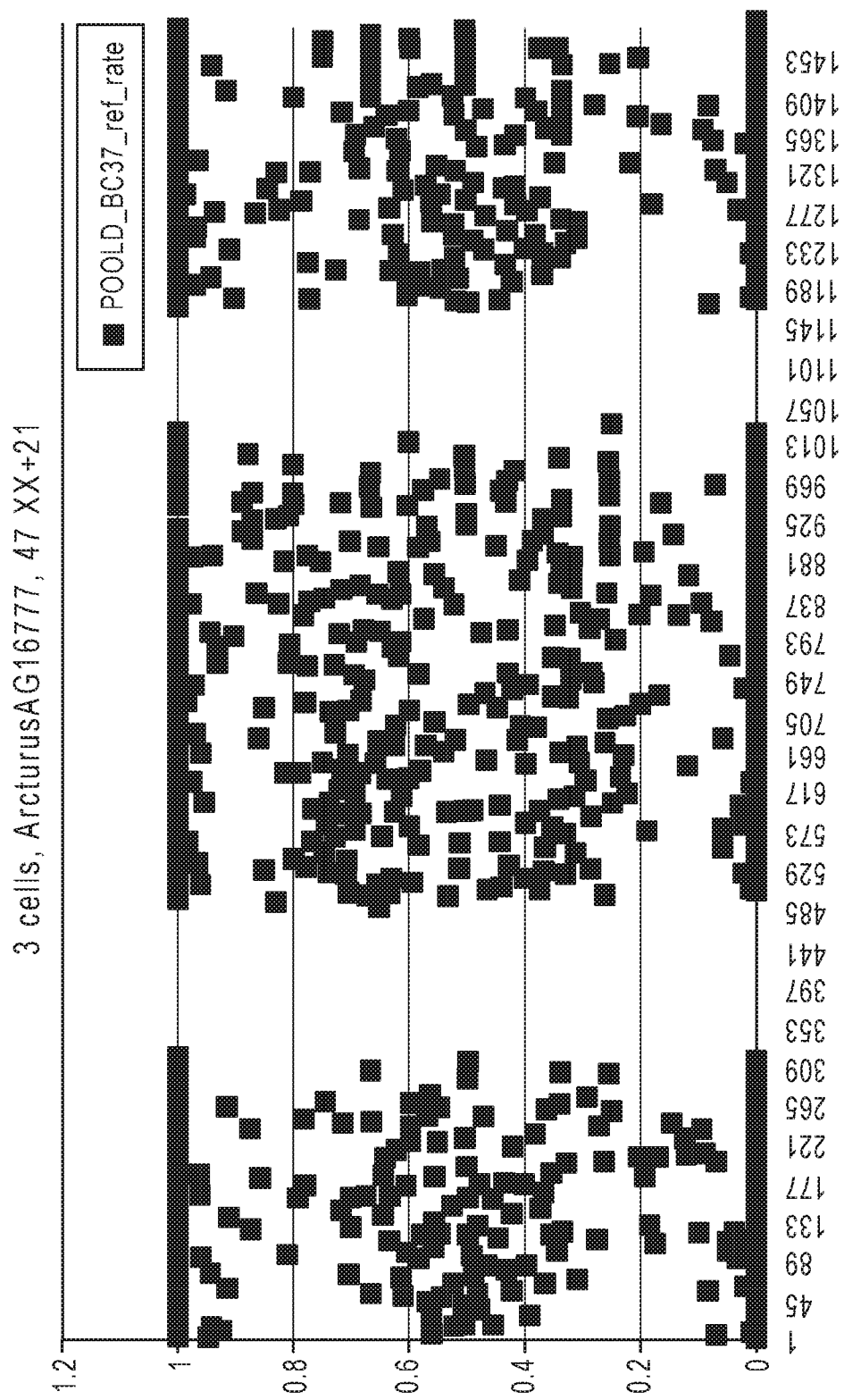
Figures 26A, 26B:
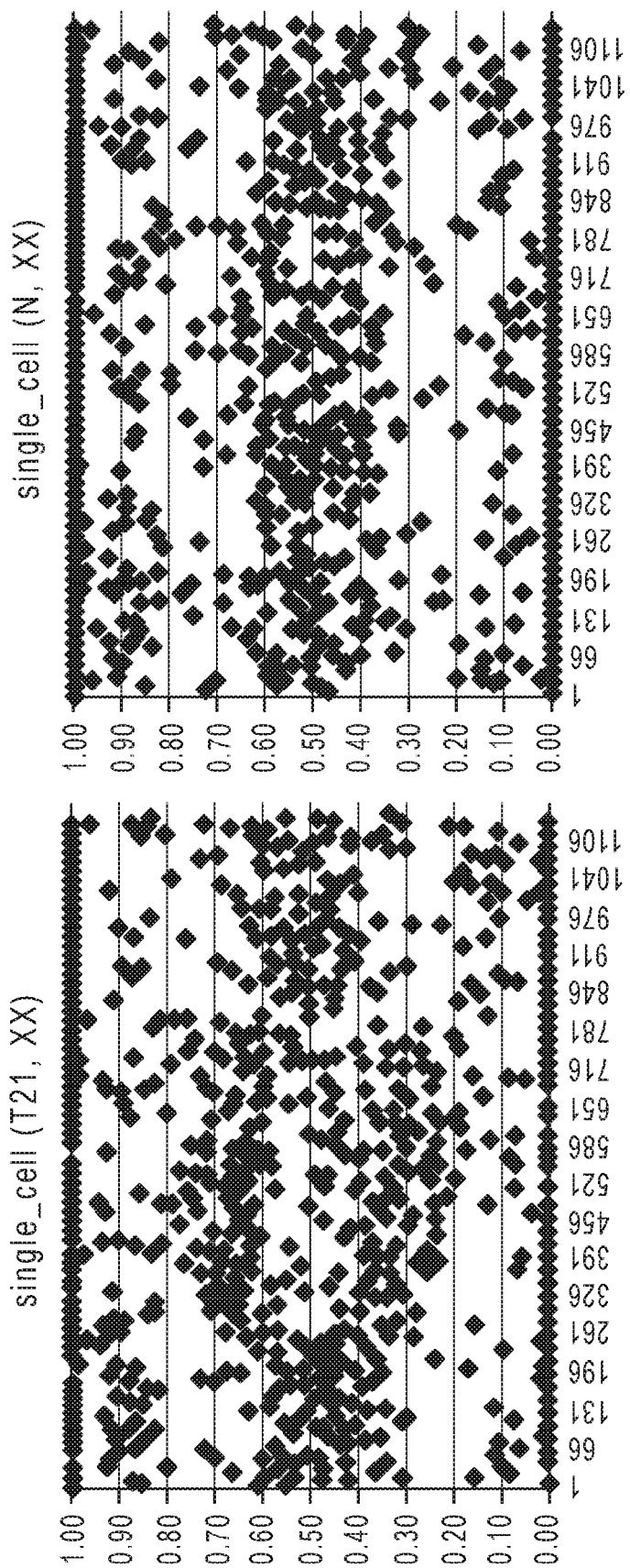
FIGS. 26A and 26B: Allele ratios for two single-cell reactions (FIGS. 26A and 26B) at three chromosomes.

FIG. 24 shows normalized depth of read ratios (vertical axis) for six samples at three chromosomes (1=chrom 1; 2=chrom 21; 3=chrom X) The ratios were set to be equal to the number of reads mapping to that chromosome, normalized, and divided by the number of reads mapping to that chromosome averaged over three wells each comprising three 46XY cells. The three sets of data points corresponding to the 46XY reactions are expected to have ratios of 1:1. The three sets of data points corresponding to the 47XX+21 cells are expected to have ratios of 1:1 for chromosome 1, 1.5.1 for chromosome 21, and 2.1 for chromosome X FIG. 25A-25C show allele ratios plotted for three chromosomes (1, 21, X) for three reactions. The reaction in the lower left shows a reaction on three 46XY cells (FIG. 25B). The left region are the allele ratios for chromosome 1, the middle region are the allele ratios for chromosome 21, and the right region are the allele ratios for chromosome X. For the 46XY cells, for chromosome 1 we expect to see ratios of 1, 0.5 and 0, corresponding to AA, AB and BB SNP genotypes. For the 46XY cells, for chromosome 21 we expect to see ratios of 1, 0.5 and 0, corresponding to AA, AB and BB SNP genotypes. For the 46XY cells, for chromosome X we expect to see ratios of 1 and 0, corresponding to A, and B SNP genotypes. The reaction in the lower right shows a reaction on three 47XX+21 cells (FIG. 25C). The allele ratios are segregated by chromosome as in the lower left graph. For the 47XX+21 cells, for chromosome 1 we expect to see ratios of 1, 0.5 and 0, corresponding to AA. AB and BB SNP genotypes. For the 47XX+21 cells, for chromosome 21 we expect to see ratios of 1, 0.67, 0.33 and 0, corresponding to AAA, AAB, ABB and BBB SNP genotypes. For the 47XX+21 cells, for chromosome X we expect to see ratios of 1, 0.5 and 0, corresponding to AA, AB, and BB SNP genotypes. The plot in the upper right was made on a reaction comprising 1 ng of genomic DNA from the 47XX+21 cell line (FIG. 25A). FIGS. and 26B shows the same graphs as in FIG. 25A-25C, but for reactions performed on only one cell. The left graph was a reaction that contained a 47XX+21 cell (FIG. 26A), and the right graph was for a reaction that contained a 46XX cell (FIG. 26B).

From the graphs shown in FIGS. 25A-25C and FIGS. 26A and 26B, it is visually apparent that there are two clusters of dots for chromosomes where we expect to see ratios of 1 and 0, three clusters of dots for chromosomes where we expect to see ratios of 1, 0.5, and 0, and four clusters of dots for chromosomes where we expect to see ratios of 1, 0.67, 0.33 and 0. The parental support algorithm was able to make correct calls on all of the three chromosomes for all of the 45 reactions.

Experiment 15

In one experiment, maternal plasma samples were prepared and amplified using a hemi-nested 19,488-plex protocol. The samples were prepared in the following way: up to 20 mL of maternal blood were centrifuged to isolate the buffy coat and the plasma. The genomic DNA in the maternal sample was prepared from the buffy coat and paternal DNA was prepared from a blood sample or saliva sample. Cell-free DNA in the maternal plasma was isolated using the QIAGEN CIRCULATING NUCLEIC ACID kit and eluted in 50 uL TE buffer according to manufacturer's instructions. Universal ligation adapters were appended to the end of each molecule of 40 uL of purified plasma DNA and libraries were amplified for 9 cycles using adaptor specific primers. Libraries were purified with AGENCOURT AMPURE beads and eluted in 50 ul DNA suspension buffer.

6 ul of the DNA was amplified with 15 cycles of STAR 1 (95° C. for 10 min for initial polymerase activation, then 15 cycles of 96° C. for 30 s; 65° C. for 1 min; 58° C. for 6 min; 60° C. for 8 min, 65° C. for 4 min and 72° C. for 30 s; and a final extension at 72° C. for 2 min) using 7.5 nM primer concentration of 19,488 target-specific tagged reverse primers and one library adaptor specific forward primer at 500 nM.

The hemi-nested PCR protocol involved a second amplification of a dilution of the STAR 1 product for 15 cycles (STAR 2) (95° C. for 10 min for initial polymerase activation, then 15 cycles of 95° C. for 30 s; 65° C. for 1 min; 60° C. for 5 min; 65° C. for 5 min and 72° C. for 30 s; and a final extension at 72° C. for 2 min) using reverse tag concentration of 1000 nM, and a concentration of 20 nM for each of 19,488 target-specific forward primers.

An aliquot of the STAR 2 products was then amplified by standard PCR for 12 cycles with 1 uM of tag-specific forward and barcoded reverse primers to generate barcoded sequencing libraries. An aliquot of each library was mixed with libraries of different barcodes and purified using a spin column.

In this way, 19,488 primers were used in the single-well reactions; the primers were designed to target SNPs found on chromosomes 1, 2, 13, 18, 21, X and Y. The amplicons were then sequenced using an ILLUMINA GAIIX sequencer. For plasma samples, approximately 10 million reads were generated by the sequencer, with 9.4-9.6 million reads mapping to the genome (94-96%), and of those, 99.95% mapped to targeted SNPs with a mean depth of read of 460 and a median depth of read of 350. For comparison, a perfectly even distribution would be: 10M reads/19,488 targets=513 reads/target. For primer-dimers, 30,000 reads were from sequenced primer-dimers (0.3% of the reads generated by the sequencer). For genomic samples, 99.4-99.7% of the reads mapped to the genome, of those, 99.99% of the mapped to targeted SNPs, and 0.1% of the reads generated by the sequencer were primer-dimers.

For plasma samples with 10 million sequencing reads, typically at least 19,350 of the 19,488 targeted SNPs (99.3%) are amplified and sequenced. For DNA samples with 2M sequencing reads, typically at least 19,000 targeted SNPs (97.5%) are amplified and sequenced. The lower number may be due to sampling noise since the number of reads is lower and the sequencer misses some of the amplified products. If desired, the number of sequencing reads can be increased to increase the number of targeted SNPs that are amplified and sequenced.

Relevant maternal and paternal genomic DNA samples amplified using a semi-nested 19,488 outer forward primers and tagged reverse primers at 7.5 nM in the STAR 1. Thermocycling conditions and composition of STAR 2, and the barcoding PCR were the same as for the hemi-nested protocol.

The average fetal fraction for 407 samples was found to be 14.8%. The sequencing data was analyzed using informatics methods disclosed herein and the ploidy state was called at four chromosomes (13, 18, 21, Y) for the fetuses whose DNA was present in 378 of the 407 maternal plasma samples, and at chromosome X in 375 of the 407 maternal plasma samples. The ploidy calls for all 1,887 chromosomes in the set were called correctly with confidences above 90%. 1882 of the 1887 calls were above 95%; and 1,862 of the 1,887 calls were called with confidences above 99%.

A similar control experiment was performed using water instead of DNA extracted from plasma in the plasma PCR protocol. Based on six such trials of an experiment, 5-6% of the sequenced reads were primer-dimers. Other sequenced reads were due to background noise. This experiment demonstrates that even in the absence of a nucleic acid sample with target loci for the primers to hybridize to (rather than hybridizing to other primers and forming amplified primer dimers) few primer dimers are formed.

Experiment 16

The following experiment illustrates an exemplary method for designing and selecting a library of primers that can be used in any of the multiplexed PCR methods of the invention. The goal is to select primers from an initial library of candidate primers that can be used to simultaneously amplify a large number of target loci (or a subset of target loci) in a single reaction. For an initial set of candidate target loci, primers did not have to be designed or selected for each target locus. Preferably, primers are designed and selected for a large portion of the most desirable target loci.

Step 1

A set of candidate target loci (such as SNPs) were selected based on publically available information about desired parameters for the target loci, such as frequency of the SNPs within a target population or heterozygosity rate of the SNPs (worldwide web at ncbi.nlm.nih.gov/projects/SNP/; Sherry S T, Ward M H, Kholodov M, et al. dbSNP: the NCBI database of genetic variation. *Nucleic Acids Res.* 2001 Jan. 1; 29(1):308-11, which are each incorporated by reference in its entirety). For each candidate locus, one or more PCR primer pairs were designed using the Primer3 program (the worldwide web at primer3.sourceforge.net; libprimer3 release 2.2.3, which is hereby incorporated by reference in its entirety). If there were no feasible designs for PCR primers for a particular target locus, then that target locus was eliminated from further consideration. If desired, a "target locus score" (higher score representing higher desirability) can be calculated for most or all of the target loci, such as a target locus score calculated based on a weighted average of various desired parameters for the target loci. The parameters may be assigned different weights based on their importance for the particular application that the primers will be used for. Exemplary parameters include the heterozygosity rate of the target locus, the disease prevalence associated with a sequence (e.g., a polymorphism) at the target locus, the disease penetrance associated with a sequence (e.g., a polymorphism) at the target locus, the specificity of the candidate primer(s) used to amplify the target locus, the size of the candidate primer(s) used to amply the target locus, and the size of the target amplicon. In some embodiments, the specificity of the candidate primer for the target locus includes the likelihood that the candidate primer will mis-prime by binding and amplifying a locus other than the target locus it was designed to amplify. In some embodiments, one or more or all the candidate primers that mis-prime are removed from the library.

Step 2

A thermodynamic interaction score was calculated between each primer and all primers for all other target loci from Step 1 (see, e.g., Allawi, H. T. & SantaLucia, J., Jr. (1998), "Thermodynamics of Internal C-T Mismatches in DNA", *Nucleic Acids Res.* 26, 2694-2701; Peyret, N, Seneviratne, P. A., Allawi, H. T. & SantaLucia, J., Jr (1999), "Nearest-Neighbor Thermodynamics and NMR of DNA Sequences with Internal A-A, C-C, G-G, and T-T Mismatches", *Biochemistry* 38, 3468-3477; Allawi, H. T. & SantaLucia, J., Jr. (1998), "Nearest-Neighbor Thermodynamics of Internal A-C Mismatches in DNA: Sequence Dependence and pH Effects", *Biochemistry* 37, 9435-9444, Allawi, H. T. & SantaLucia, J., Jr. (1998), "Nearest Neighbor Thermodynamic Parameters for Internal G-A Mismatches in DNA", *Biochemistry* 37, 2170-2179, and Allawi, H. T. & SantaLucia, J., Jr. (1997). "Thermodynamics and NMR of Internal G-T Mismatches in DNA", *Biochemistry* 36, 10581-10594; MultiPLX 2.1 (Kaplinski L, Andreson R, Puurand T, Remm M. MultiPLX: automatic grouping and evaluation of PCR primers. Bioinformatics. 2005 Apr. 15; 21(8):1701-2, which are each hereby incorporated by reference in its entirety). This step resulted in a 2D matrix of interaction scores. The interaction score predicted the likelihood of primer-dimers involving the two interacting primers. The score was calculated as follows:

$$\text{interaction\_score} = \max(-\text{delta}G\_2, 0.8 * (-\text{delta}G\_1))$$

where deltaG_2=Gibbs energy (energy required to break the dimer) for a dimer that is extensible by PCR on both ends, i.e., the 3' end of each primer anneals to the other primer; and deltaG_1=Gibbs energy for a dimer that is extensible by PCR on at least one end.

Step 3:

For each target locus, if there was more than one primer-pair design, then one design was selected using the following method:

1 For each primer-pair design for the locus, find the worst-case (highest) interaction score for the two primers in that design and all primers from all designs for all other target loci.
2 Pick the design with the best (lowest) worst-case interaction score.

Step 4

A graph was built such that each node represented one locus and its associated primer-pair design (e.g., a Maximal Clique problem). One edge was created between every pair of nodes. A weight was assigned to each edge equal to the worst-case (highest) interaction score between the primers associated with the two nodes connected by the edge.

Step 5

If desired, for every pair of designs for two different target loci where one of the primers from one design and one of the primers from the other design would anneal to overlapping target regions, an additional edge was added between the nodes for the two design. The weight of these edges was set equal to the highest weight assigned in Step 4. Thus, Step 5 prevents the library from having primers that would anneal to overlapping target regions, and thus interfere with each other during a multiplex PCR reaction.

Step 6

An initial interaction score threshold was calculated as follows:

$$weight\_threshold=max(edge\_weight)-0.05*(max(edge\_weight)-min(edge\_weight))$$

where max(edge_weight) is the maximum edge weight in the graph; and min(edge_weight) is the minimum edge weight in the graph.

The initial bounds for the threshold were set as follows:

$$max\_weight\_threshold=max(edge\_weight)$$

$$min\_weight\_threshold=min(edge\_weight)$$

Step 7

A new graph was constructed consisting of the same set of nodes as the graph from Step 5, only including edges with weights that exceed weight_threshold. Thus, step ignores interactions with scores equal to or below weight_threshold.

Step 8

Nodes (and all of the edges connected to the removed nodes) were removed from the graph of Step 7 until there were no edges left. Nodes were removed by applying the following procedure repeatedly:
1 Find the node with the highest degree (highest number of edges). If there is more than one then pick one arbitrarily.
2 Define the set of nodes consisting of the node picked above and all of the nodes connected to it, but excluding any nodes that have degree less than the node picked above.
3 Choose the node from the set that has the lowest target locus score (lower score representing lower desirability) from Step 1. Remove that node from the graph.

Step 9

If the number of nodes remaining in the graph satisfies the required number of target loci for the multiplexed PCR pool (within an acceptable tolerance), then the method was continued at Step 10.

If there were too many or too few nodes remaining in the graph, then a binary search was performed to determine what threshold values would result in the desired number of nodes remaining in the graphs. If there were too many nodes in the graph then, the weight threshold bounds were adjusted as follows:

$$max\_weight\_threshold=weight\_threshold$$

Otherwise (if there are two few nodes in the graph), then the weight threshold bounds were adjusted as follows:

$$min\_weight\_threshold=weight\_threshold$$

Then, the weight threshold was adjusted follows:

$$weight\_threshold=(max\_weight\_threshold+min\_weight\_threshold)/2$$

Steps 7-9 were repeated.

Step 10

The primer-pair designs associated with the nodes remaining in the graph were selected for the library of primers. This primer library can be used in any of the methods of the invention.

If desired, this method of designing and selecting primers can be performed for primer libraries in which only one primer (instead of a primer pair) is used for amplification of a target locus. In this case, a node presents one primer per target locus (rather than a primer pair).

Experiment 17

Figure 27:
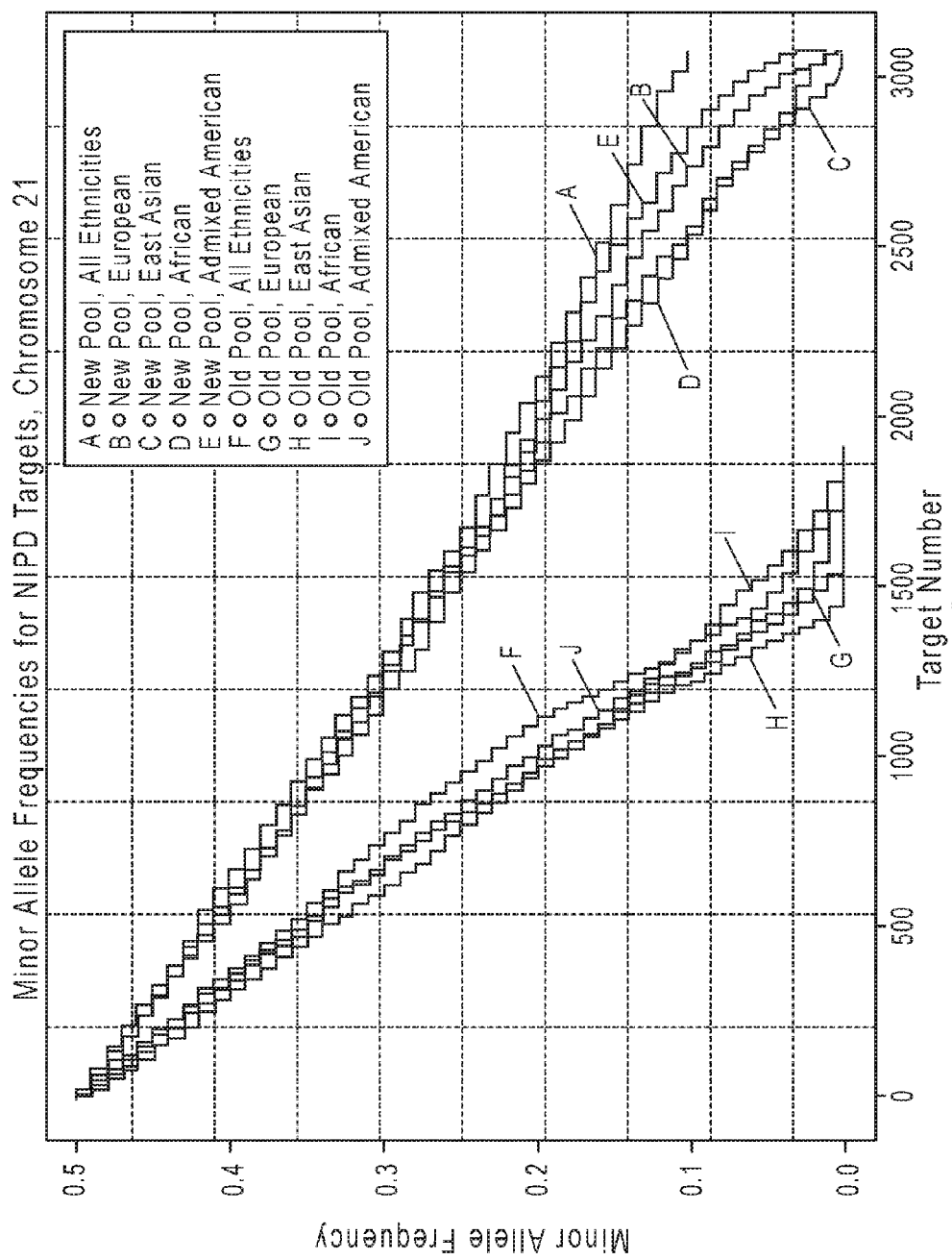
FIG. 27: Comparison of two primer libraries showing the number of loci with a particular minor allele frequency that are targeted by each primer library.
Figure 28A:
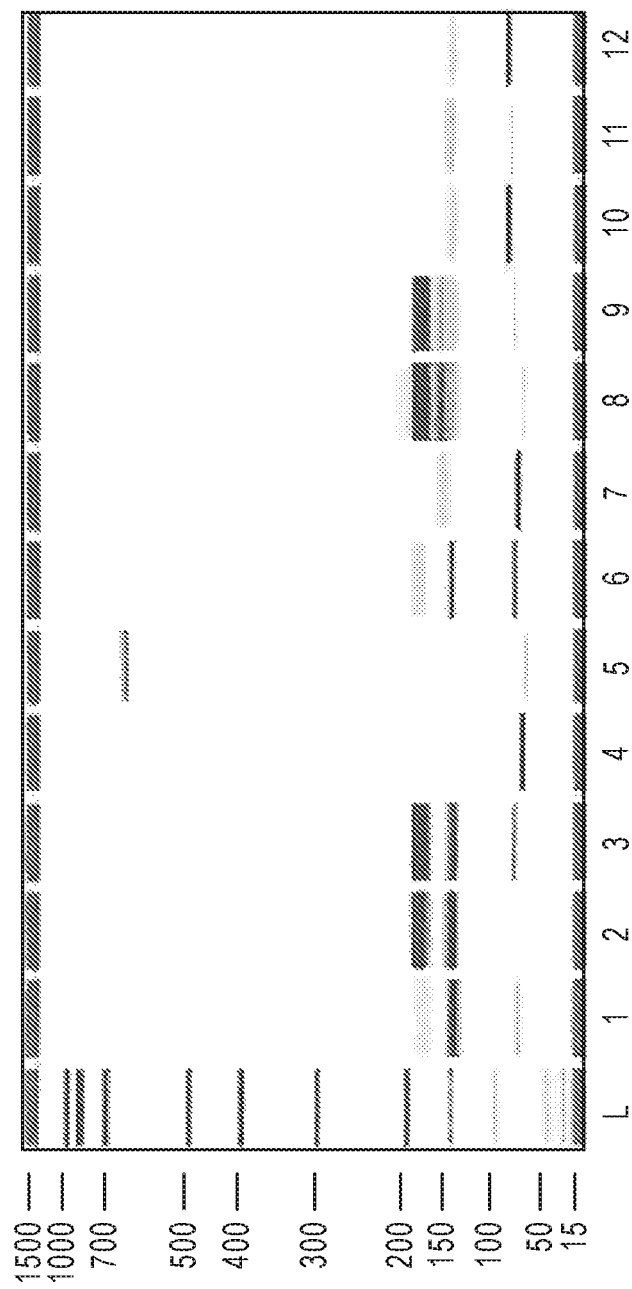
FIG. 28A: Graph of the electrophoresis of PCR products.
Figure 28B:
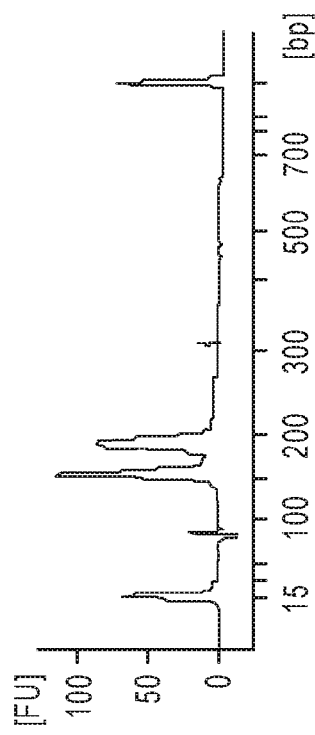
FIGS. 28B-28M are electropherograms of lanes 1-12, respectively, in FIG. 28A.
Figure 28C:
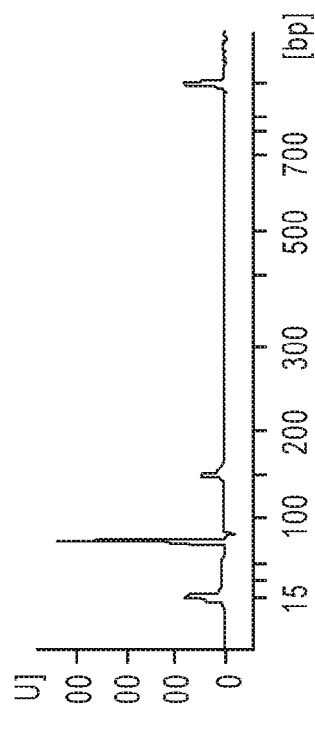
Figure 28D:
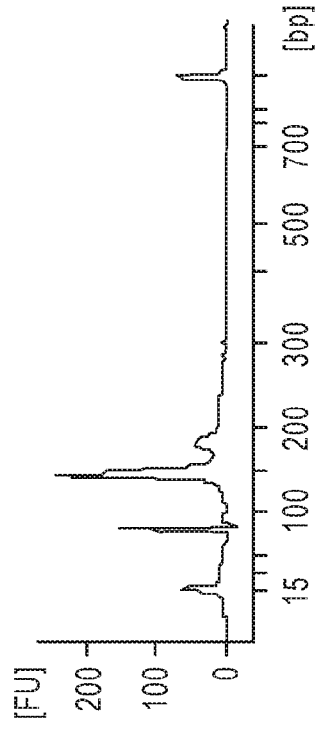
Figure 28E:
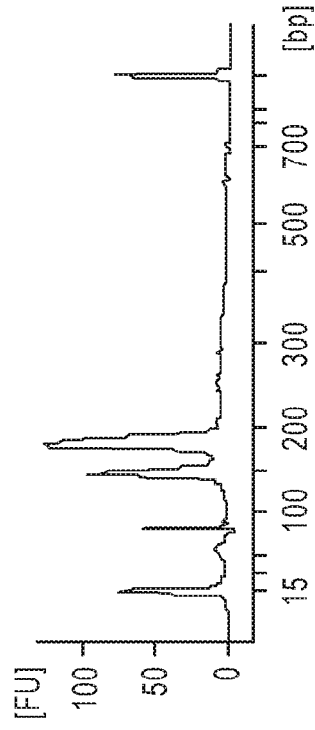
Figure 28F:
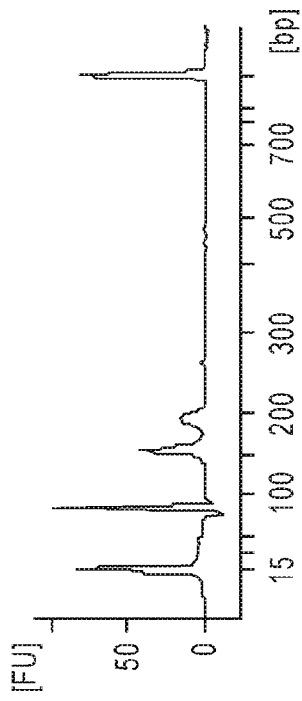
Figure 28G:
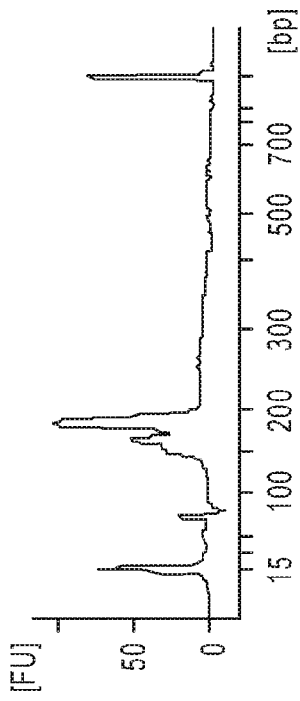
Figure 28H:
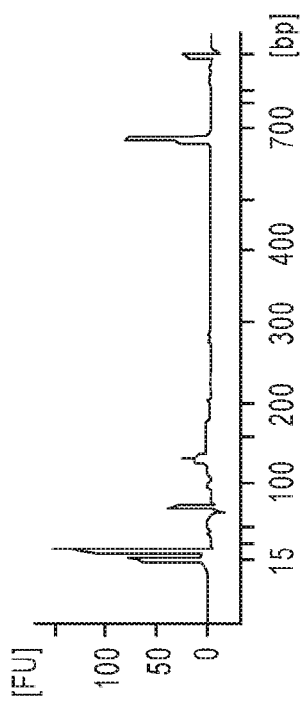
Figure 28I:
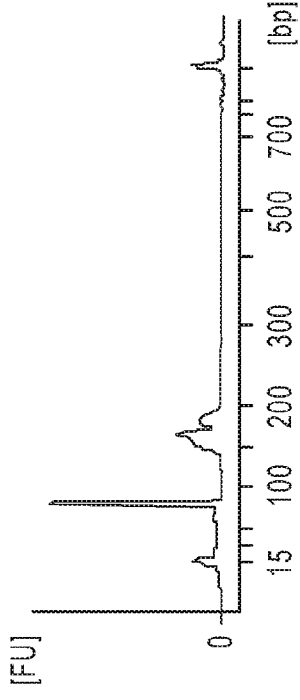
Figures 28J, 28K, 28L, 28M:
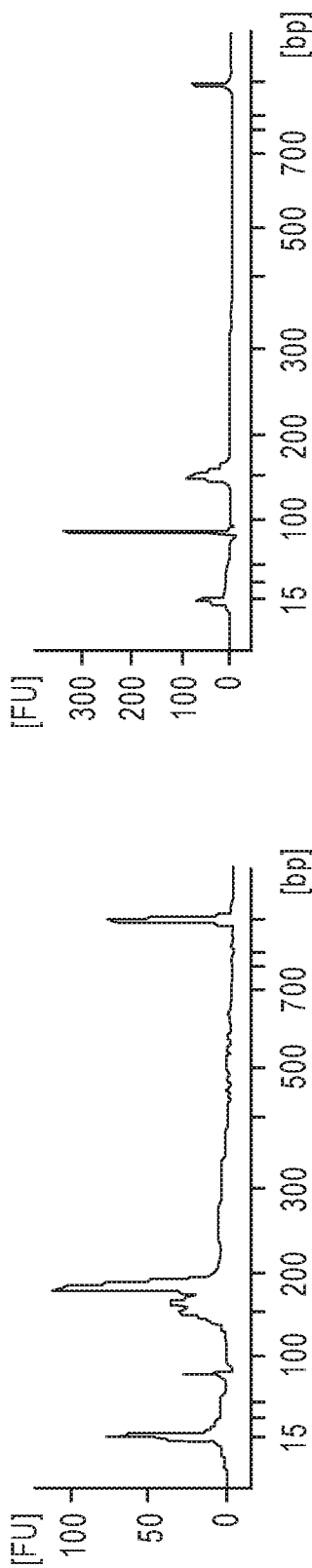

FIG. 27 is a graph comparing two primer libraries designed using the methods of the invention. This graph shows the number of loci with a particular minor allele frequency that are targeted by each primer library. During the selection of the "new pool" library, more primers were retained. This library enables the amplification of more target loci, especially target loci with relatively large minor allele frequencies (which are the more informative alleles for some method of the invention, such as for detecting fetal chromosomal abnormalities).

These primer libraries were used in the following multiplex PCR method. Blood (20-40 mL) was collected from each subject into two to four CELL-FREE™ DNA tubes (Streck). Plasma (a minimum of 7 mL) was isolated from each sample via a double centrifugation protocol of 2,000 g for 20 min, followed by 3,220 g for 30 min, with supernatant transfer following the first spin. cfDNA was isolated from 7-20 mL plasma using the QIAGEN QIAamp Circulating Nucleic Acid kit and eluted in 45 uL TE buffer. Pure maternal genomic DNA was isolated from the buffy coat obtained following the first centrifugation, and pure paternal genomic DNA was prepared similarly from a blood, saliva or buccal sample.

Maternal cfDNA, maternal genomic DNA, and paternal genomic DNA samples were pre-amplified for 15 cycles using 11,000 target-specific assays and an aliquot was transferred to a second PCR reaction of 15 cycles using nested primers. Finally, samples were prepared for sequencing by adding barcoded tags in a third 12-cycle round of PCR. Thus, 11,000 targets were amplified in a single reaction; the targets included SNPs found on chromosomes 13, 18, 21, X, and Y. The amplicons were then sequenced using an ILLUMINA GAIIx or HISEQ sequencer. Parental genotypes were sequenced at a lower read depth (~20% of cfdDNA read depth) than the fetal genotypes.

Experiment 18

If desired, the size and quantity of the PCR products can be analyzed using standard methods, such as the use of the Agilent Technologies 2100 Bioanalyzer (FIG. 28A-M). For example, direct PCR methods described herein without nesting were used in 2,400-plex (FIGS. 28B-28G) and 19,488-plex experiments (FIGS. 28H to 28M). The amount of primer was 10 nM for FIGS. 28B-28D and 28H to 28J. The amount of primer was 1 nM for FIGS. 28E-28G and 28K to 28M. The amount of input DNA was 24 ng for FIGS. 28B, 28E, 28H, and 28K; 80 ng for FIGS. 28C, 28F, 28I, and 28L; and 250 ng for FIGS. 28D, 28G, 28J, and 28M. More input DNA resulted in a greater proportion of the desired 180 base pair product. The peak at 140 base pairs is a primer dimer product.

Experiment 19

A proof-of-principle study demonstrated the detection of T13, T18, T21, 45,X, and 47,XXY with equally high accuracies across all chromosomes.

Patients

Pregnant couples were enrolled at specific prenatal care centers under protocols approved by an Institutional Review Board pursuant to local laws, Inclusion criteria were at least 18 years of age, gestational age of at least nine weeks, singleton pregnancies, and signed informed consent. Blood samples were drawn from pregnant mothers, and a blood or buccal sample was collected from the father. Samples from 2 pregnancies with T13 (Patau Syndrome), 2 with T18 (Edwards Syndrome), 2 with T21 (Down's Syndrome), 2 with 45,X, 2 with 47,XXY, and 90 normal pregnancies were selected prior to testing from a cohort of ~500 women to test which chromosomal abnormalities the method detects. Normal fetal karyotype was confirmed by molecular karyotyping for the samples where post-birth child tissue was available. Euploid sample were drawn prior to invasive testing from low-risk women. Aneuploid samples were drawn at least 7 days after invasive testing and aneuploidy was confirmed via cytogenetic karyotyping or fluorescence in situ hybridization at independent laboratories.

Sample Preparation and Multiplex PCR

For the data in FIGS. 30A-E, 30G, 30H, and 31A-31G, sample preparation and 19,488-plex-PCR were performed as described in Experiment 15. For the data in FIG. 30F, sample preparation and 11,000-plex-PCR were performed as described in Experiment 17.

Methodology and Data Analysis

The algorithm considers parental genotypes and crossover frequency data (such as data from the HapMap database) to calculate expected allele distributions for 19,488 polymorphic loci for a very large number possible fetal ploidy states, and at various fetal cfDNA fractions. (FIGS. 29A-29C). Unlike allele ratio based-methods, it also takes into account linkage disequilibrium, and uses non-Gaussian data models to describe the expected distribution of allele measurements at a SNP given observed platform characteristics and amplification biases. It then compares the various predicted allele distributions to the actual allelic distributions as measured in the cfDNA sample (FIG. 29C), and calculates the likelihood of each hypothesis (monosomy, disomy, or trisomy, for which there are numerous hypotheses based on the various potential crossovers) based on the sequencing data. The algorithm sums the likelihoods of each individual monosomy, disomy, or trisomy hypotheses (FIG. 29D), and calls the ploidy state with the maximum overall likelihood as the copy number and fetal fraction (FIG. 29E). Although laboratory researchers were not blinded to sample karyotype, the algorithm called the ploidy states without human intervention and was blind to the truth.

Data Interpretation

Graphical Representations of the Generated Data

To determine the ploidy state of a chromosome of interest, the algorithm considers the distribution of sequence counts from each of two possible alleles at 3,000 to 4,000 SNPs per chromosome. It is important to note that the algorithm makes ploidy calls using an approach that does not lend itself to visualization. Thus, for the purposes of illustration, the data is displayed here in a simplified fashion as ratios of the two most likely alleles, labeled as A and B, so that the relevant trends can be more readily visualized. This simplified illustration does not take into account some of the features of the algorithm. For example, two important aspects of the algorithm that are not possible to illustrate with a method of visualization that displays allele ratios are: 1) the ability to leverage linkage disequilibrium, i.e. the influence that a measurement at one SNP has on the likely identity of a neighboring SNP, and 2) the use of non-Gaussian data models that describe the expected distribution of allele measurements at a SNP given platform characteristics and amplification biases. Also note that the algorithm only considers the two most common alleles at each SNP, ignoring other possible alleles.

The graphical representations in FIG. 30A-30H include samples for which two, one, or three fetal chromosomes are present. Generally, these indicate euploidy (FIGS. 30A-30C) monosomy (FIG. 30D), and trisomy (FIGS. 30E-30H), respectively. In all plots, each spot represents a single SNP, where the targeted SNPs are plotted sequentially from left to right for one chromosome along the horizontal axes. The vertical axes indicate the number of reads for the A allele as a fraction of the total number of reads for both the A and B alleles for that SNP. Note that the measurements are made on total cfDNA isolated from maternal blood, and the cfDNA includes both maternal and fetal cfDNA; thus, each spot represents the combination of the fetal and maternal DNA contribution for that SNP. Therefore, increasing the proportion of maternal cfDNA from 0% to 100% will gradually shift some spots up or down within the plots, depending on the maternal and fetal genotype. This is described in more detail below with the corresponding plots.

If desired to facilitate visualization, the spots may be color-coded according to maternal genotype, as maternal genotype contributes more to the localization of each spot and the majority of trisomies are maternally-inherited, this assists in visualizing ploidy states. Specifically, SNPs for which the maternal genotype is AA may be indicated in red, those for which the maternal genotype is AB may be indicated in green, and those for which the maternal genotype is BB may be indicated in blue.

In all cases. SNPs that are homozygous for the A allele (AA) in both the mother and the fetus are found tightly associated with the upper limit of the plots, as the fraction of A allele reads is high because there should be no B alleles present. Conversely, SNPs that are homozygous for the B allele in both the mother and the fetus are found tightly associated with the lower limit of the plots, as the fraction of A allele reads is low because there should be only B alleles. The spots that are not tightly associated with the upper and lower limits of the plots represent SNPs for which the mother, the fetus, or both are heterozygous; these spots are useful for identifying fetal ploidy, but can also be informative for determining paternal versus maternal inheritance. These spots segregate based on both maternal and fetal genotypes and fetal fraction, and as such the precise position of each individual spot along the y-axis depends on both stoichiometry and fetal fraction. For example, loci where the mother is AA and the fetus is AB are expected to have a different fraction of A allele reads, and thus different positioning along the y-axis, depending on the fetal fraction.

Two Chromosomes Present

Figure 30A:
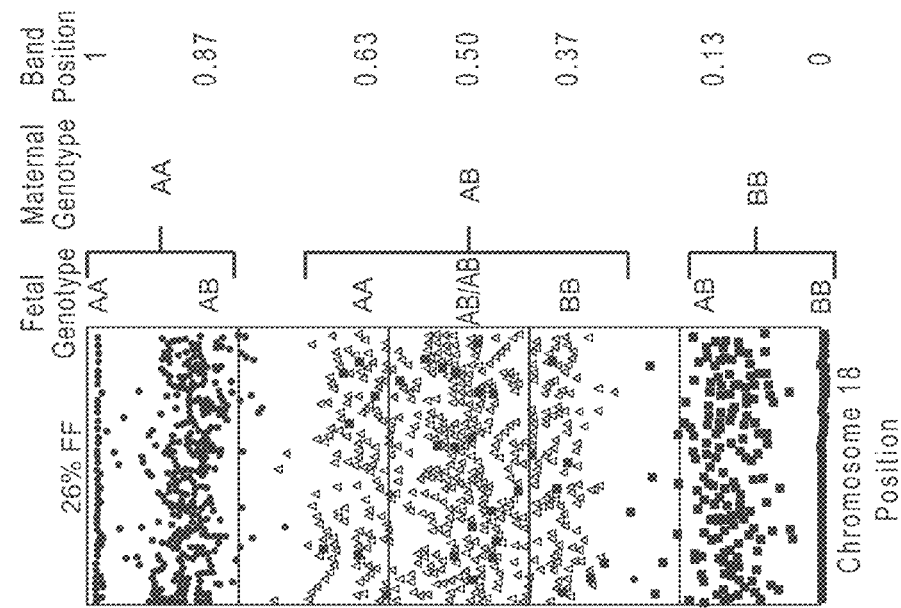
FIGS. 30A-30H: Typical graphical representations of euploidy (FIGS. 30A-30C), monosomy (FIG. 30D), and trisomy (FIGS. 30E-30H). For all plots, the x-axis represents the linear position of the individual polymorphic loci along each chromosome (as indicated below the plots), and the y-axis represents the number of A allele reads as a fraction of the total (A+B) allele reads. Maternal and fetal genotypes, as well as the position on the y-axis around which the bands are centered, are indicated to the right of the plots. If desired to facilitate visualization, the plots may be color-coded according to maternal genotype, such that red indicates a maternal genotype of AA, blue indicates a maternal genotype of BB, and green indicates a maternal genotype of AB. If desired, maternal allele contributions may be indicated in color in the "Fetal Genotype" column. Allele contributions are indicated as maternal|fetal, such that alleles for which the mother is AA and the fetus is AB are indicated as AA|AB.
Figure 30B:
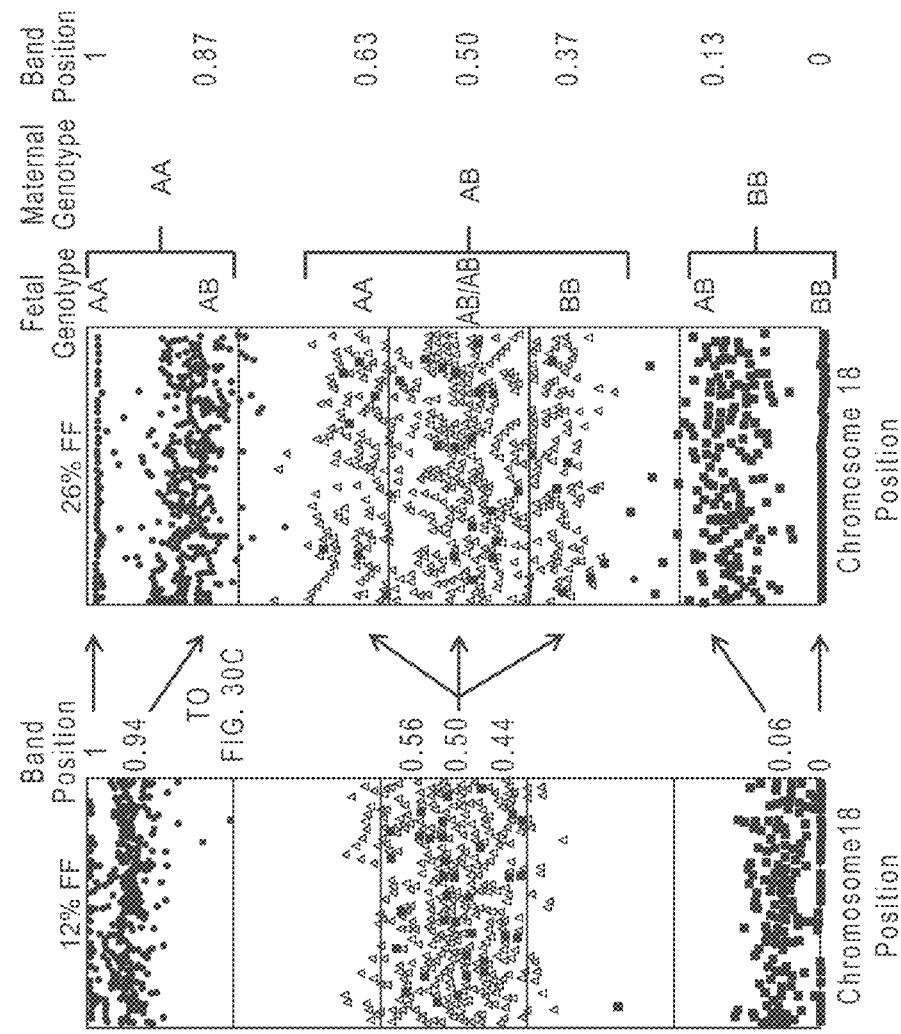
Figure 30C:
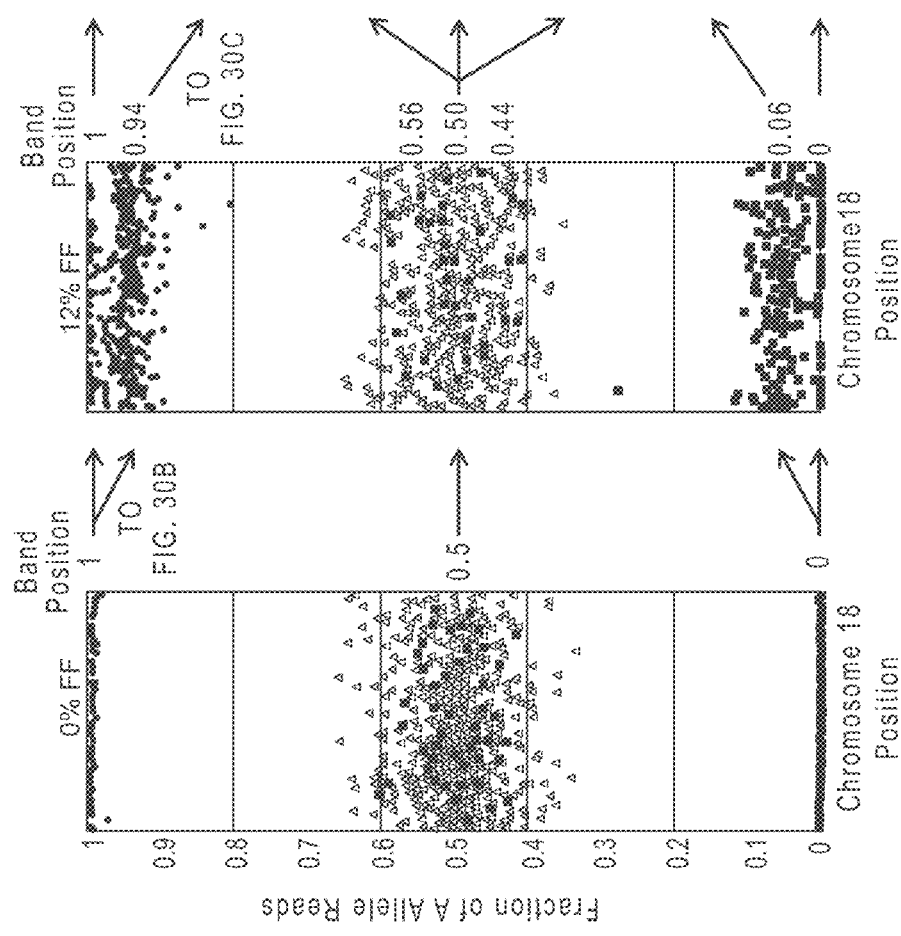

FIGS. 30A-30C depict data that indicate the presence of two chromosomes when the sample is entirely maternal (no fetal cfDNA present, FIG. 30A), contains a moderate fetal cfDNA fraction (FIG. 30B), or contains a high fetal cfDNA fraction (FIG. 30C).

FIG. 30A shows data obtained from cfDNA isolated from the blood of a non-pregnant woman. When there is no fetal cfDNA present and the sample contains only maternal cfDNA, the plots represent purely the euploid maternal genotype; the hallmark pattern includes "clusters" of spots: a red cluster tightly associated with the top of the plot (SNPs where the maternal genotype is AA), a blue cluster tightly associated with the bottom of the plot (SNPs where the maternal genotype is BB), and a single, centered green cluster (SNPs where the maternal genotype is AB).

When fetal cfDNA is present, the location of the spots shifts such that the clusters segregate into discrete "bands". Note that for samples with a fetal fraction of 0%, the groupings of spots are referred to as "clusters" (as in FIG. 30A), and for all samples with a fetal fraction of >0%, the groupings of spots are referred to as "bands" (as in FIGS. 30B-30J). If the fetal fraction is high enough, these discrete bands will be readily visible. Specifically, FIGS. 30B and 30C demonstrate the characteristic pattern associated with two fetal chromosomes present at moderate and high fetal fractions, respectively. This pattern includes three central green bands that correspond to SNPs that are heterozygous in the mother, and two "peripheral" bands each at both the top (red) and bottom (blue) of the plots that correspond to SNPs that are homozygous in the mother.

FIG. 30B shows data obtained from cfDNA isolated from a plasma sample from a woman carrying a euploid fetus and with a 12% fetal cfDNA fraction. Here, the clusters of spots tightly associated with the top and bottom of the plot segregate into two discrete bands each: one red and one blue external peripheral band that remains tightly associated with the upper or lower limit of the plots, and one red and one blue internal peripheral band that has separated from the limits of the plots. These internal peripheral bands, centered around 0.92 and 0.08, represent SNPs for which the maternal genotype is AA and the fetal genotype is AB (indicated in red), and SNPs for which the maternal genotype is BB and the fetal genotype is AB (indicated in blue), respectively. The center cluster of green spots broadens, but at this fetal fraction the segregation into distinct bands is not readily visible.

At a high fetal cfDNA fraction, the typical pattern that indicates the presence of two chromosomes (a trio of green bands as well as two red and two blue peripheral bands) is readily apparent. FIG. 30C displays data obtained from a plasma sample from a woman carrying a euploid fetus at a fetal cfDNA fraction of 26%. Here, the peripheral bands have separated such that the internal band has shifted towards the center of the plot due to the altered levels of B alleles from the increased fetal cfDNA fraction. Significantly, at higher fetal fractions, the separation of the center green cluster into three distinct bands is now readily apparent. This central trio of bands, in this case clustering around 0.37, 0.50 and 0.63, corresponds to those SNPs where the maternal genotype is AB, and the fetal genotype is AA (top), AB (middle) and BB (bottom).

These hallmark patterns, namely three green bands and four peripheral bands (two red and two blue), indicate the presence of two chromosomes, as in autosomal euploidy or for the X chromosome in a female (XX) fetus.

One Chromosome Present

Figures 30D, 30E:
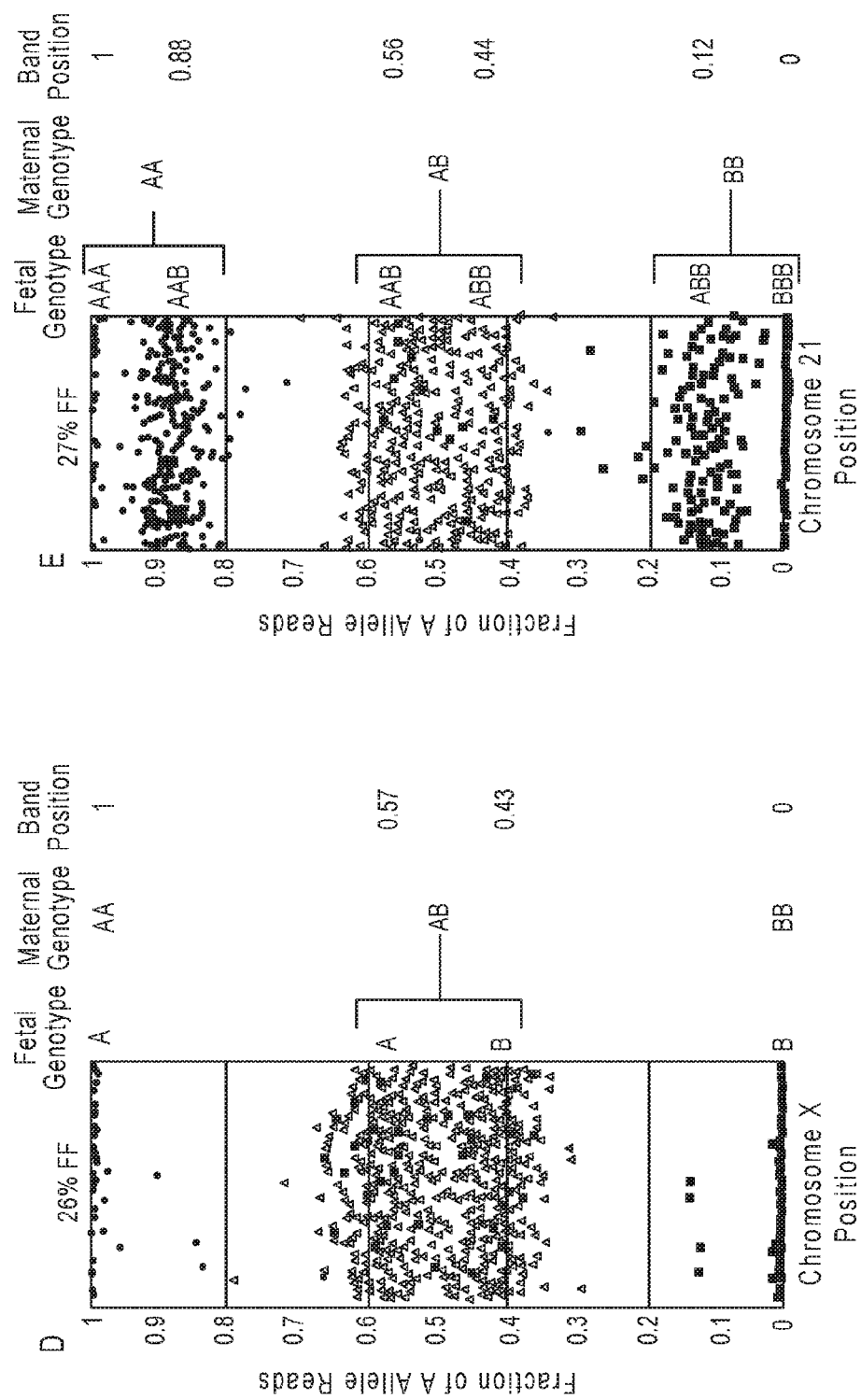
Figure 30F:
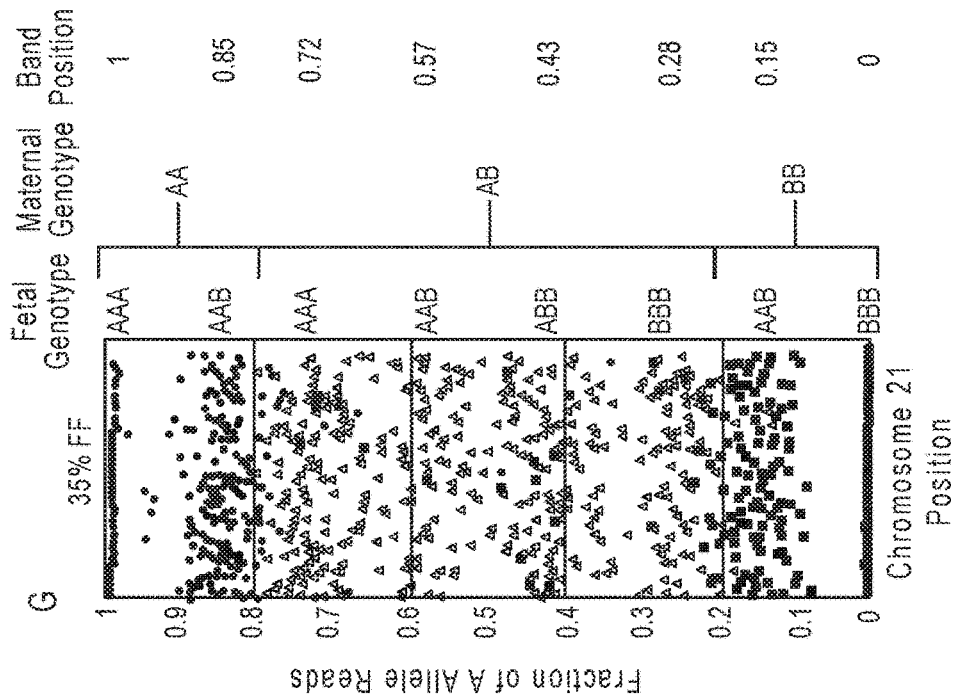
Figure 30G:
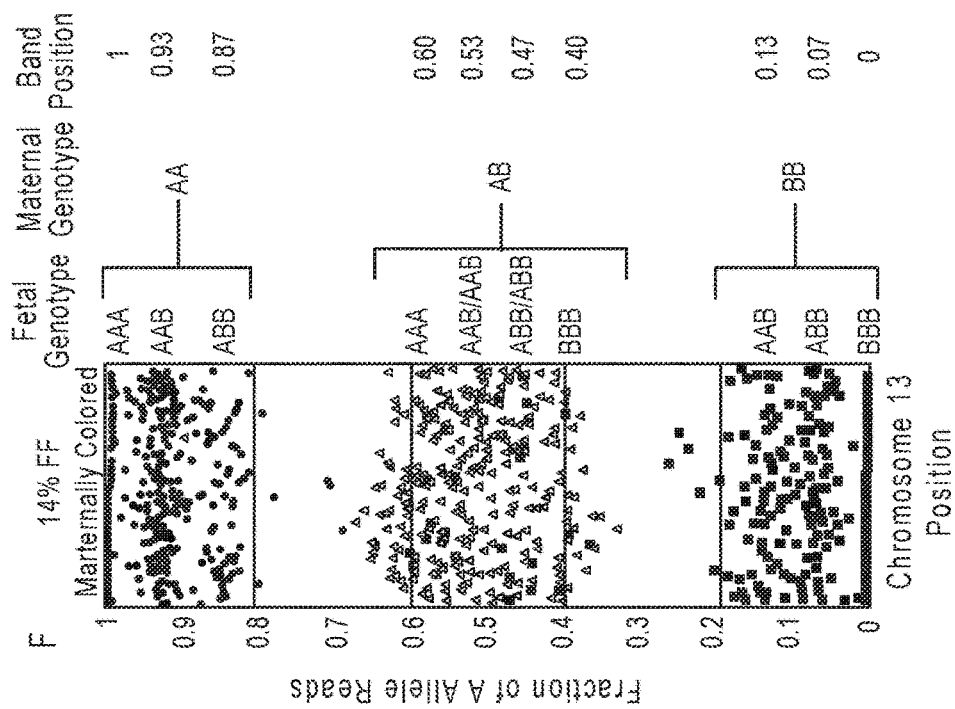
Figure 30H:
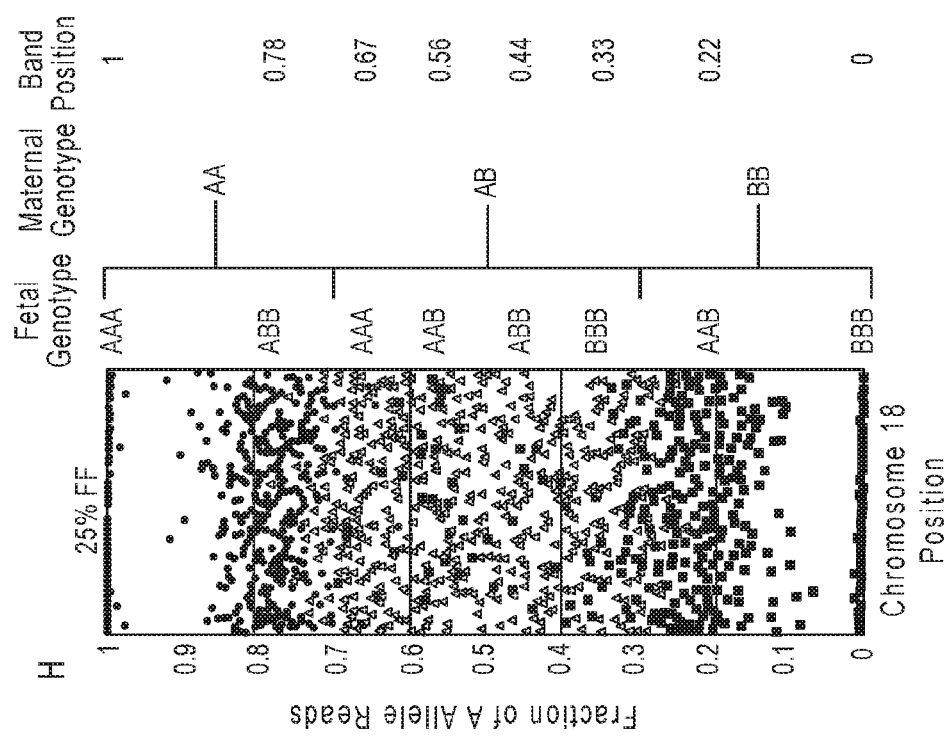

When the fetus only inherits a single chromosome, and thus only inherits a single allele, heterozygosity of the fetus is not possible. As such, the only possible fetal SNP identities are A or B. Thus, maternally-inherited monosomic chromosomes have a characteristic pattern of two central green bands that represent SNPs for which the mother is heterozygous, and only have single peripheral red and blue bands that represent SNPs for which the mother is homozygous, and which remain tightly associated with the upper and lower limits of the plots (1 and 0), respectively (FIG. 30D). Note the absence of internal peripheral bands. This pattern indicates the presence of one chromosome, as in maternally-inherited autosomal monosomy, or for the X chromosome in a male (XY) fetus.

Three Chromosomes Present

Trisomic chromosomes have three characteristic patterns. The first pattern indicates maternally-inherited meiotic trisomy, a meiotic error where the fetus inherited two homologous, non-identical chromosomes from the mother (FIG. 30E); this pattern includes two central green bands with two each of the peripheral red and blue bands. The second pattern indicates paternally-inherited meiotic trisomy, where the fetus inherited two homologous, non-identical chromosomes from the father (FIG. 30F); this pattern includes four central green bands and three each of the peripheral red and blue bands. The third pattern indicates either maternally- (FIG. 30G) or paternally-inherited (FIG. 30H) mitotic trisomy, a mitotic error where the fetus inherited two identical chromosomes from either the mother or the father; this pattern includes four central green bands with two each of the peripheral red and blue bands. Maternally- and paternally-inherited mitotic trisomies can be distinguished by the placement of the flanking red and blue bands, such that the red and blue internal peripheral bands (those not associated with the limits of the plots) are closer to the center in paternally-inherited mitotic trisomy. This is due to the paternal contribution of identical chromosomes. Note that our previous results indicate that at the blastomere stage, 66.7% of maternally-inherited trisomies are meiotic, and that only 10.2% of trisomies are paternally-inherited.

For the Y chromosome, the PS method considers a different set of hypotheses: zero, one, or two chromosomes present. As there is no maternal contribution to the sequence reads at each locus and because heterozygous loci are not possible (cases of two Y chromosomes necessarily involve two identical chromosomes), the bands remain tightly associated with the top (A alleles) or the bottom (B alleles) of the plot (data not shown), and analysis is greatly simplified, relying on quantitative allele count data. Note that since the method interrogates SNPs, it uses homologous non-recombinant SNPs from the Y chromosome, thus obtaining data on both X and Y for one probe pair.

Identifying Aneuploidies

Identification of autosomal aneuploidies using this plot-based visualization method is straightforward given a sufficient fetal fraction, and requires only identifying plots for which there are an abnormal number of chromosomes present, as described above. Combining the knowledge of copy number of the X and Y chromosomes identifies whether sex chromosome aneuploidies are present. Specifically, plots representing a fetus with a 47,XXX genotype will have a typical "three-chromosome" pattern, and plots representing a fetus with a 47,XXY genotype will have the typical "two-chromosome" pattern for the X chromosome, but will also have allele reads indicating the presence of one Y chromosome. The method is similarly able to call 47,XYY, where a "one chromosome" pattern indicates the presence of a single X chromosome, and allele reads indicate the presence of two Y chromosomes. A fetus with a 45,X genotype will have the typical "one-chromosome" pattern for the X chromosome, and data indicating zero Y chromosomes.

Effects of Fetal Fraction

As discussed above, the number of sequence reads from the fetus contributes to the precise location of each spot along the y-axis in the plots. As fetal fraction will affect the proportion of reads that originate from the fetus and the mother, it will also affect the positioning of each spot. At a high fraction of fetal cfDNA (generally above ~20%), as in FIGS. 30C-30E and FIGS. 30G and 30H, it is readily apparent that although the spots cluster based mainly on maternal genotype, the presence of fetal DNA from alleles whose genotype is distinct from the maternal genotype shift the clusters into multiple, distinct bands. However, as the fetal fraction decreases (as in FIGS. 30B and 30F), the spots regress towards the poles and center of the plot, resulting in tighter clusters. Specifically, the set of peripheral red bands, where the maternal genotype is AA, regress towards the top of the plot; the set of peripheral blue bands, where the maternal genotype is BB, regress towards the bottom, the set of central green bands, where the mother is heterozygous, condense into a single cluster at the center of the plot (compare FIGS. 30B and 30C). Although aneuploidy is not readily apparent by eye using this visualization technique for low fetal fraction cases, the algorithm is able to identify ploidy states with a very low fetal fraction, such as 3% fetal fraction. It is able to do this because the statistical technique compares the observed data to very precise data models that predict the allele distributions for a given sample parameter set (including copy number, parental genotypes, and fetal fraction, for example). Data model precision is critical in low fetal fraction cases, as the differences between the allele distributions for different ploidy states are proportional to the fetal fraction. In addition, the algorithm is able to determine when a data set does not contain enough data to make a confident fetal ploidy determination.

Results

Figure 31G:
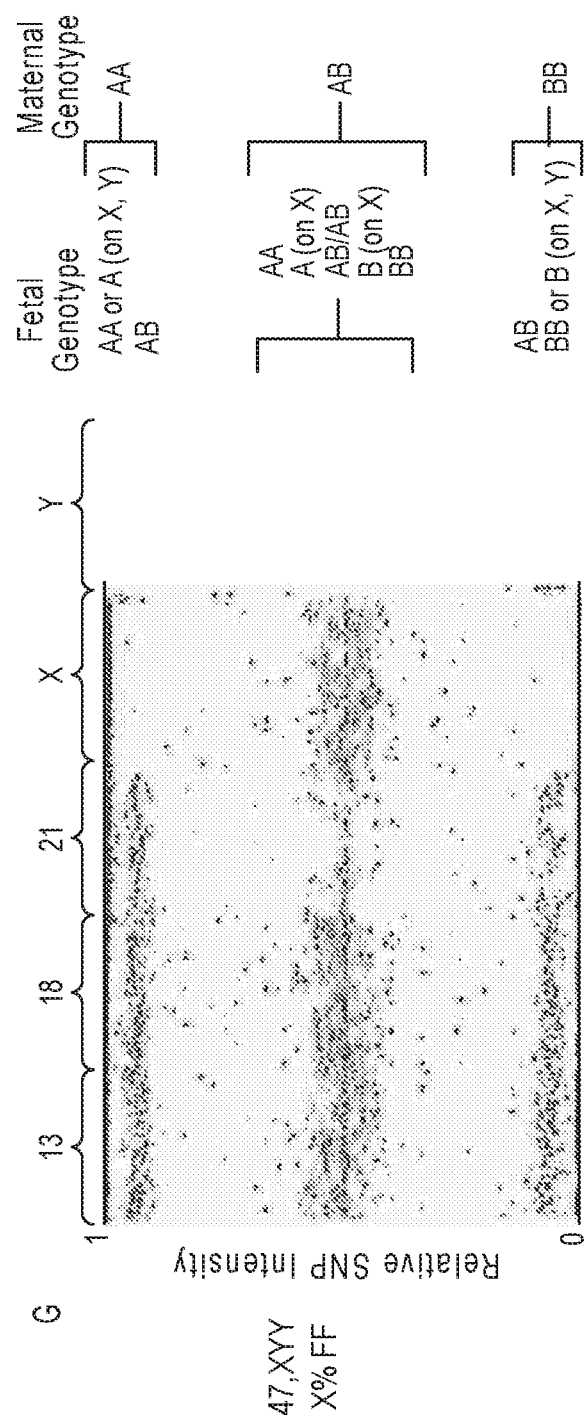
FIG. 31: Graphical representations of (FIG. 31A) euploid, (FIG. 31B) T13, (FIG. 31C) T18, (FIG. 31D) T21, (FIG. 31E) 45,X, (FIG. 31F) 47,XXY, and (FIG. 31G) 47,XYY test samples as indicated. Each chromosome is indicated at the top of the plot, fetal and maternal genotypes are indicated to the right of the plots, the x-axis represents the linear position of the SNPs along each chromosome, and the y-axis indicates the number of A allele reads as a fraction of the total reads. Note the altered cluster positioning based on fetal fraction, as described herein. Each spot represents a single SNP locus. Fetal and maternal genotypes are indicated to the right of the plot, and chromosome identities are indicated at the top of the plots.

Sequencing reads that mapped to targeted SNPs were deemed to be informative and were used by the algorithm. More than 95% of targeted loci were observed in the sequencing results. The plots for visualizing key ploidy calls are depicted in FIG. 31A-31G. FIG. 31A indicates a euploid sample. Here, chromosomes 13, 18, and 21 have the typical "two chromosome" pattern (as described herein). This includes a trio of center green bands, and two red and two blue peripheral bands. This, together with the two center green bands for the X chromosome and the presence of Y chromosome bands along the plots' peripheries, indicate a euploid XY genotype.

The most prevalent autosomal trisomies, T13, T18, and T21, are indicated by the plots in FIGS. 31B, 31C, and 31D, respectively. Specifically, FIG. 31B depicts a T13 sample. Here, chromosomes 18 and 21 display the typical "two chromosome" pattern, chromosome X displays the typical "one chromosome" pattern, and there are reads from the Y chromosome. Together, this indicates disomy at chromosomes 18 and 21, and identifies a fetal XY genotype. However, chromosome 13 depicts a typical "three chromosome" pattern—specifically. Similarly, FIG. 31C depicts a T18 sample, and FIG. 31D depicts a T21 sample.

The method is also able to detect sex chromosome aneuploidies, including 45,X (FIG. 31E), 47,XXY (FIG. 31F), and 47,XYY (FIG. 31G). Note that the method is calling copy number at chromosomes 13, 18, 21, X, and Y; the overall chromosome number is reported assuming disomy at the remaining chromosomes. The X chromosome regions of the plot depicting a 45,X sample reveals the presence of a single chromosome. However, the lack of reads from the Y chromosome, coupled with the "two chromosome" pattern for chromosomes 13, 18, and 21, indicate a 45,X genotype. Conversely, the 47,XXY samples generate a plot revealing the presence of two X chromosomes. The data also revealed reads for alleles from the Y chromosome. Together with the presence of two copies of chromosomes 13, 18, and 21, this indicates a 47,XXY genotype. A 47,XYY genotype is indicated by the presence of a "one chromosome" pattern for the X chromosome, and reads indicating the presence of two Y chromosomes.

Discussion

This method detected T13, T18, T21, 45,X, 47,XXY, and 47,XYY non-invasively from maternal blood. This method interrogates cfDNA from maternal plasma by targeted multiplex PCR amplification and high-throughput sequencing of 19,488 SNPs. This, coupled with the method's sophisticated informatics analyses that take into account parental genotypic information and numerous sample parameters, including fetal fraction and DNA quality, more robustly detects the fetal signal and makes highly accurate ploidy calls at all of the five chromosomes implicated in the seven most common types of at-birth aneuploidy (T13, T18, T21, 45,X 47,XXX, 47,XXY, and 47,XYY). This method offers a number of clinical advantages over previous methods, including and most significantly greater clinical coverage and sample-specific calculated accuracies (analogous to a personalized risk score).

Increased Clinical Coverage

This method offers approximately a two-fold increase in aneuploidy coverage compared to clinically available NIPT methodologies, given its ability to accurately detect autosomal trisomies and sex chromosome aneuploidies. The method presented here is the only noninvasive test that calls ploidy at the sex chromosomes with high accuracy. Prior DNA mixing experiments and separate plasma samples analyzed in our experimental assays suggest that this method will detect a larger cohort of sex chromosome anomalies, including 47,XXX. The method presented here also detects aneuploidies at chromosomes 13, 18, and 21 with high sensitivities and specificities, and with appropriate primer design is expected to be able to detect copy number at the remaining chromosomes as well.

Sample-Specific Calculated Accuracies

Significantly, this method calculates a sample-specific accuracy for ploidy calls on each chromosome in each sample. Accuracies calculated by this method are expected to significantly lower the rate of incorrect calls by identifying and flagging individual samples that have poor quality DNA or low fetal fractions that are likely to result in a poor accuracy test result. By contrast, massively parallel shotgun sequencing (MPSS)-based methods produce a positive or negative call using a single-hypothesis rejection test, and their accuracy estimate is based on a published study cohort rather than on the characteristics of the individual sample, which are assumed to have the same accuracy as the cohort. However, individual accuracies for samples with parameters in the tail of the cohort distribution may differ significantly. This is exacerbated at low fetal fractions, as in early gestational age, or for samples with low DNA quality. These samples are generally not identified and flagged for follow-up, which can result in missed calls. The present method, however, takes into account many parameters, including fetal fraction and a number of DNA quality metrics, to make each chromosome copy number call, calculating a sample-specific accuracy for that call. This allows the method to identify individual samples with low accuracy and flag them for follow-up. This is expected to nearly eliminate missed calls, especially at the early stages of pregnancy when fetal fractions are typically low. The presumption is that a no call is much preferred to a missed call, since a no call simply requires a redraw and reanalysis.

Converting Calculated Accuracies to Traditional Risk Scores

This method can offer an adjusted risk of aneuploidy for high-risk pregnant women, where the adjusted risk takes into account an a priori risk (Benn P, Cuckle H, Pergament E. Non-invasive prenatal diagnosis for Down syndrome: the paradigm will shift, but slowly. Ultrasound *Obstet Gynecol* 2012; 39:127-130, which is hereby incorporated by reference in its entirety). Although the present method offers each patient a customized calculated accuracy, for clinical use these accuracies can be converted to traditional risk scores, which also denote the risk of an aneuploid pregnancy but are expressed as fractions. Traditional risk scores take into account various parameters, including maternal age-related risk and serum levels of biochemical markers, to offer a risk score above which a mother is considered high-risk and for whom follow-up invasive diagnostic procedures are recommended. This method significantly refines this risk score, thus reducing both the false positive and false negative rates, and offering a more accurate assessment of individual maternal risk. A calculated accuracy as used here is the likelihood that the ploidy call is correct, and is expressed as a percentage, but the calculated accuracies used in Experiment 19 do not include an age-related risk. Because calculation of a risk score typically includes an age-related risk, the calculated accuracies and traditional risk scores are not interchangeable; they must be combined to convert into a traditional risk score. The formula to combine the age-related risk with the calculated accuracy is:

$$\frac{R_1 R_2}{R_1 R_2 + [1 - R_1][1 - R_2]}$$

where $R_1$ is the risk score as calculated by the present method and $R_2$ is the risk score as calculated by first trimester screening.

SNP-Based Methods Negate Issues with Amplification Variation

An inherent drawback to the counting methods used by some other methods is that they determine fetal ploidy state by measuring the ratio of the number of reads mapping to the chromosome of interest (e.g., chromosome 21) to those mapping to a reference chromosome. Chromosomes with high or low GC content, including chromosomes 13, X, and Y, amplify with high variability. This can result in signal variation that is comparable in magnitude to the fetal cfDNA signal, which can confound copy number calls by altering the ratio of allele reads from the chromosome-of-interest to those from the reference chromosome. This can result in low accuracy for chromosomes 13, X, and Y. Significantly, this problem is exacerbated at low fetal cfDNA fractions, as tends to be the case at early gestational ages.

In contrast, SNP-based methods do not rely on consistent amplification levels between chromosomes, and are thus expected to provide results that are equally accurate across all chromosomes. Because the present method looks, in part, at relative counts of different alleles at polymorphic loci, which by definition differ only by a single nucleotide, it does not require the use of reference chromosomes, and this obviates the problems with chromosome-to-chromosome amplification variation that are inherent to methods that rely on quantitating read counts. Unlike quantitative methods that require reference chromosomes that are euploid, the present method is expected to be able to detect triploidy as well as copy-number neutral anomalies like uniparental disomy.

The Importance of Early Detection

Figure 32:
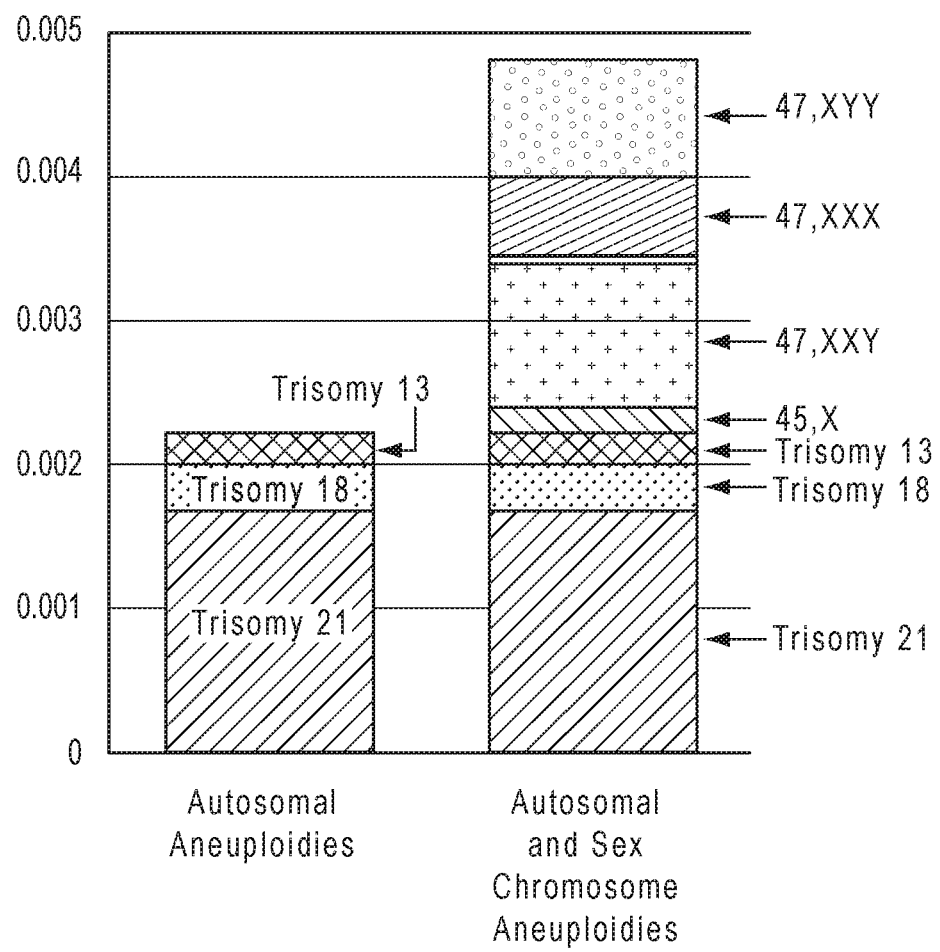
FIG. 32: The combined at-birth prevalence of sex chromosome aneuploidies is greater than that of autosomal aneuploidies.

Significantly, the combined at-birth prevalence of sex chromosome aneuploidies is higher than that of the most common autosomal aneuploidies (FIG. 32). However, there are currently no routine non-invasive screening methods that reliably detect sex chromosome abnormalities. Thus, sex chromosome anomalies are generally detected prenatally as a side-effect of routine testing for Down syndrome or other autosomal aneuploidies; a large proportion of cases are missed entirely. Early and accurate detection is crucial for many of these disorders where early therapeutic intervention improves clinical outcomes. For example, Turner syndrome is often not diagnosed until adolescence, although its overall at-birth prevalence is 1 in 2,500 females. Growth hormone therapy is known to prevent short stature that results from the disorder, but treatments are significantly more effective when initiated prior to the age of 4. Additionally, estrogen replacement therapy can stimulate secondary sexual characteristics in patients with Turner syndrome, but again therapy must be initiated in the pre-teen years, before the syndrome is usually detected Together, this underscores the importance of early, routine, and safe detection of sex chromosome aneuploidies. This method offers the first approach with the potential to serve as a routine screen for sex chromosome anomalies.

Experiment 20

The following experiment illustrates an exemplary method for designing and selecting primers that can be used in any of the multiplexed PCR methods of the invention. In some embodiments, primers from an initial library of candidate primers are selected so that they can be used to simultaneously amplify a large number of target loci (or a subset of target loci) in a single reaction. In some embodiments, primers from an initial library of candidate primers are selected to form multiple primer pools such that each pool can be used to simultaneously amplify a subset of target loci in a single reaction. Preferably, primers are designed and selected for a large portion or all of the most desirable target loci. Preferably, the minimum number of pools needed to amplify the target loci are created.

Step 1

Calculate a first score for each primer pair design using one or more of the following parameters: number of SNPs within the primers, location of SNPs within the primers, distance from an end of the amplicon to the target bases within the amplicon, number of target loci in an amplicon, heterozygosity rate of the target locus, disease prevalence associated with a sequence (e.g., a polymorphism) at the target locus, disease penetrance associated with a sequence (e.g., a polymorphism) at the target locus, specificity of the candidate primer for the target locus, size of the candidate primer, melting temperature of the candidate primer, melting temperature of the target amplicon, GC content of the target amplicon, GC content of the 3' end of the candidate primer, homopolymer length in the candidate primer, amplification efficiency of the target amplicon, and size of the target amplicon.

Step 2

Compare each primer pair to every other primer pair, and calculate a second score for the pair using one or more of the following parameters: likelihood of dimer formation, amplicon overlap, number of primer designs for a particular target locus, and distance between amplicons. In some embodiments, the score is infinite if amplicons overlap so that two different primer pairs that generate overlapping amplicons are not included in the same primer pool.

Step 3

Aggregate the first score and the second score together (such as by using a weighted average of the scores).

Step 4

If desired, order all target loci into one contiguous list based upon their genomic location in ascending order.

Step 5

Build a minimum priority queue data structure that prioritizes the pairs of designs (in which each design is one primer pair so that a pair of designs includes two primer pairs with a total of 4 primers) based on their score (such as the aggregate score from step 3). In some embodiments, the score for a pair of designs is the worse score (such as the worse aggregate score from step 3) out of the scores for all 4 primers in the pair of designs. The pair of designs with the best (most desirable) score is first in the queue, and the pair of designs with the worst (least desirable) score is last in the queue. If desired, pairs of designs with a score above a threshold (least desirable) are removed from the library of candidate primers such that they are not included in the final pool(s) (for example, these primers may be omitted from the queue). In some embodiments, pairs of design with an interaction score above (worse than) 20, 18, 16, 14, 12, 10, 9, 8, 7, 6, 5, 4, 3, 2, or 1 kcal/mol are removed from the library of candidate primers. In some embodiments, pairs of design with a ΔG value below (worse than) −20, −15, −16, −14, −12, −10, −9, −8, −7, −6, −5, −4, −3, −2, or −1 kcal/mol are removed from the library of candidate primers.

Each design pair can be stored as a node of a doubly linked list with initial "next" and "previous" pointers set to NULL.

Step 6

Begin forming all pools simultaneously by doing the following steps. Take the design pair with the best (most desirable) score from the priority queue and add it to "the potential pools." Begin storing designs in N number of doubly linked list data structures with the design pairs. N represents the current number of different primer pools. Initially, N=1, since there is only one primer pool. In some embodiments, a second pool is only created if necessary to include the desired target loci or the desired level of coverage of target loci. Check to see if the design pair removed from the queue is "connected" to any other existing design pair. By "connected" for purposes of this step is meant that a single design in one pair is the same as a single design in another pair. If two pairs are connected, then assign the appropriate next and previous pointers to one another. If two pairs are not connected, then add them to the "potential pools" In some embodiments, a design pair is only placed in a particular pool if it would be connected to at most two other design pairs in that pool (otherwise it can be assigned to a different pool).

Check to see if (i) any linked list spans from the first target to the last target (such that all the desired target loci are included) or (ii) if a pool meets the cutoff for the desired minimum pool level. If it does, that list now forms a pool and can be added to the "final pools" list.

Step 7

If desired, check to see if the desired level of coverage (such as all the bases in the target loci being included in amplicons from 4 different primer pairs) that is desired for each location. Repeat step 6 until achieving the desired level of coverage.

The resulting primer pool(s) can be used in any of the methods of the invention.

Experiment 21

The following experiment illustrates an exemplary method for designing and selecting primers that can be used in any of the multiplexed PCR methods of the invention. In some embodiments, the primers are divided into different pools (e.g., 2, 3, 4, 5, 6, or more different pools) such that each pool is used to amplify target loci in a different reaction volume. Each pool is used to simultaneously amplify a large number of target loci (or a subset of target loci) in a single reaction volume. Preferably, primers are designed and selected for a large portion of the most desirable target loci or for all of the target loci. A set of candidate target loci can be selected as described in Experiments 16 or 20 based on the particular polymorphisms or mutations of interest. In some embodiments, one or more of the following type of target loci are included: SNPs, short indels, long indels, exons, and combinations thereof. In some embodiments for target loci that are short indels, the PCR primer or primer pair targets a sequence of adjacent base pairs; and the indel is completely covered by one sequencing read. In some embodiments for target loci that are large indels, two primer pairs are used to target a pair of breakpoints at the boundaries of the indel. In this case, the two primer pairs are designed such that when the deletion is present there is a PCR product and the two primer pairs are selected together for inclusion in the same pool (the four primers are treated by the algorithm as a single assay rather than two assays). In some embodiments for target loci that are exons, a set of primers pairs are designed to tile the full exon.

For each candidate locus, one or more PCR primer pairs are designed using the Primer3 program (available at the worldwide web at primer3.sourceforge.net; libprimer3 release 2.2.3, which is hereby incorporated by reference in its entirety). If there are no feasible designs for PCR primers for a particular target locus, then that target locus is eliminated from further consideration. In some embodiments, each target base is covered by at least two independent PCR assays (such as two independent primer pairs that will amplify the target base) and preferably by four assays, although not all of the available assays for a target must be used. In some embodiments, no targets are omitted. Desirably, the algorithm produces as few pools as possible but may produce more than one pool. In some embodiments, two different primer pairs that are in close proximity in the genome (such as within 2 kbases or 1 kbase) and whose forward primers are on the same strand are not be assigned to the same pool. This constraint avoids primer interference in the extension-and-ligation amplification method. In some embodiments in which the PCR will be performed using a polymerase with low 5'→3' exonuclease and/or low strand displacement activity, different primer pairs that are in close proximity in the genome and whose forward primers are on the same strand can be assigned to the same pool since the with low 5'→3' exonuclease and/or low strand displacement activity of the polymerase will reduce or prevent primer interference and allow nearby or adjacent amplicons to be produced.

Step 1

Build an interaction graph. Each node represents one assay (such as one primer pair). Each edge represents a conflict between two assays. There are three types. Interaction edges represent a potential primer dimer and have a score indicating the interaction strength. Proximity edges represent physical proximity of the primer binding sites which may result in interference. Target edges represent redundant designs associated with the same target (a special case of a proximity edge).

Step 2

Select an initial value for the maximum interaction score (e.g., 95% of the maximum score).

Step 3

Compute a score such as a utility score for each assay as follows using steps 3A and 3B.

Step 3A

Calculate a score for each assay based on one or more of its intrinsic characteristics. For example, favor assays with amplicons close to the optimal length (such as 300 bp); favor assays with a shorter distance from the beginning of the amplicon to the target; and/or penalize assays with primers overlapping known SNPs. Any other parameter, such as the parameters disclosed herein can also be included.

Step 3B

Multiply the score for each assay by a factor that varies from 0 to 1 according to the current coverage of the assay's target bases. This factor gives lower weight to targets that are already covered by assays. At the beginning of the algorithm this factor is 1 for all assays because none have been covered. Calculate the factor as follows. For each base in the target, compute a coverage score as $1/(2^c)$ where c is the number of previously-selected assays (in other pools) that cover that base. For instance, if three assays cover the base then the coverage score is $1/(2^3)=0.125$. The factor for the target is the maximum value of the coverage score for all bases in the target. For instance, if the target contains 10 bases, 3 bases are covered by 1 target, and 7 bases are covered by 3 targets, then the factor is $MAX(1/(2^1), 1/(2^3))=0.5$. The score in step 3A is then multiplied by this factor.

Step 4

Use a single iteration of the algorithm in Experiment 16 to design a pool given the current maximum interaction score. Construct a new graph with the assays that have not been assigned to a pool yet and with the edges that have weights exceeding the maximum interaction score. Remove nodes (assays) according to the algorithm in Experiment 16 until there are no edges left. The assay utility scores come from step 3 in this experiment rather than the calculation used for Experiment 16.

Step 5

Save the assays selected in step 4 as a new pool and remove them from consideration. Then repeat steps 3 and 4 with the remaining assays, and iterate until all targets have sufficient coverage.

Step 6

If desired, evaluate the result. If the total number of pools meets the design goal then reduce the maximum interaction score, otherwise increase the maximum interaction score. Then go back to step 3. Iterate, using a binary search strategy to find the lowest maximum interaction score that produces the desired number of pools.

Step 7

Output the pools from the final iteration. After the selection process, the primers remaining in the pools may be used in any of the methods of the invention.

Experiment 22

The following experiment illustrates an exemplary method for designing and selecting primers that can be used in any of the multiplexed PCR methods of the invention. In some embodiments, the primers are divided into different pools (e.g., 2, 3, 4, 5, 6, or more different pools) such that each pool is used to amplify target loci in a different reaction volume. Any of the embodiments listed in Experiment 21 can be used for this experiment as well.

This method uses a graph coloring algorithm.

Step 1

Select 2, 3 or 4 of the best assays (such as primer pairs) for each target locus from all of the available assays.

Step 2

Select an initial maximum interaction score.

Step 3

Build an interaction graph containing only edges that exceed the maximum interaction score.

Step 4

Color the graph such that no adjacent nodes have the same color (this is a standard problem with many heuristic solutions). Each color represents a different pool.

Step 5

Go back to step 3 and iterate, refining the maximum interaction score until the desired number of pools is achieved. In some embodiments, after the primers are selected in step 1, the algorithm assumes all assays must be included in a pool.

After the primers are divided into different pools, the pools may be used in any of the methods of the invention.

Experiment 23

This example illustrates there exemplary methods for calculating the limit of detection for any of the methods of the invention. These methods were used to calculate the limit of detection for single nucleotide variants (SNVs) in a tumor biopsy (FIG. 41) and a plasma sample (FIG. 42).

The first method (denoted "LOD-mr5" in FIGS. 41 and 42) calculates the limit of detection based on a minimum of 5 reads being chosen as the minimum number of times a SNV is observed in the sequencing data to have sufficient confidence the SNV is actually present. The limit of detection is based on whether the observed the depth of read (DOR) is above this minimum of 5. The gray lines in FIGS. 41 and 42 indicate SNVs for which the limit of detection is limited by the DOR. In these cases, not enough reads were measured to reach the error limit of the assay. If desired, the limit of detection can be improved (resulting in a lower numerical value) for these SNVs by increasing the DOR.

The second method (denoted "LOD-zs5.0" in FIGS. 41 and 42) calculates the limit of detection based on the z-score. The Z-score is the number of standard deviations an observed error percentage is away from the background mean error. If desired, outliers can be removed and the z-score can be recalculated and this process can be repeated. The final weighted mean and the standard deviation of the error rate are used to calculate the z-score. The mean is weighted by the DOR since the accuracy is higher when the DOR is higher.

For the exemplary z-score calculation used for this example, the background mean error and standard deviation were calculated from all the other samples of the same sequencing run weighted by their depth of read, for each genomic loci and substitution type. Samples were not considered in the background distribution if they were 5 standard deviations away from the background mean. The orange lines in FIGS. 41 and 42 indicate SNVs for which the limit of detection is limited by the error rate. For these SNV's enough reads were taken to reach the 5 read minimum, and the limit of detection was limited by the error rate. If desired, the limit of detection can be improved by optimizing the assay to reduce the error rate.

The third method (denoted "LOD-zs5.0-mr5" in FIGS. 41 and 42) calculates the limit of detection based on the maximum value of the above two metrics.

Figure 41:
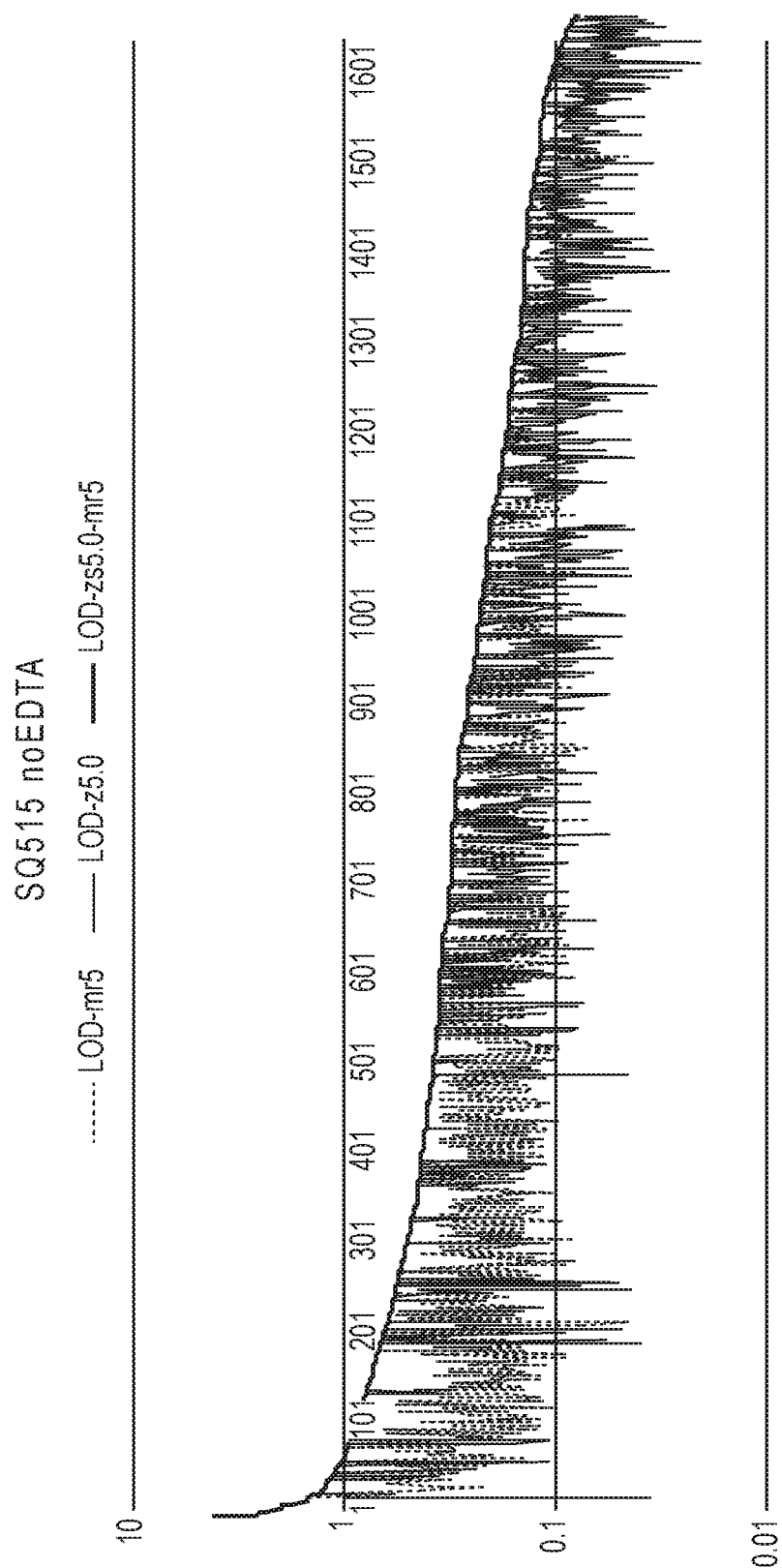
FIG. 41 is a graph showing the limit of detection for single nucleotide variants in a tumor biopsy using three different methods described in Experiment 23.
Figure 42:
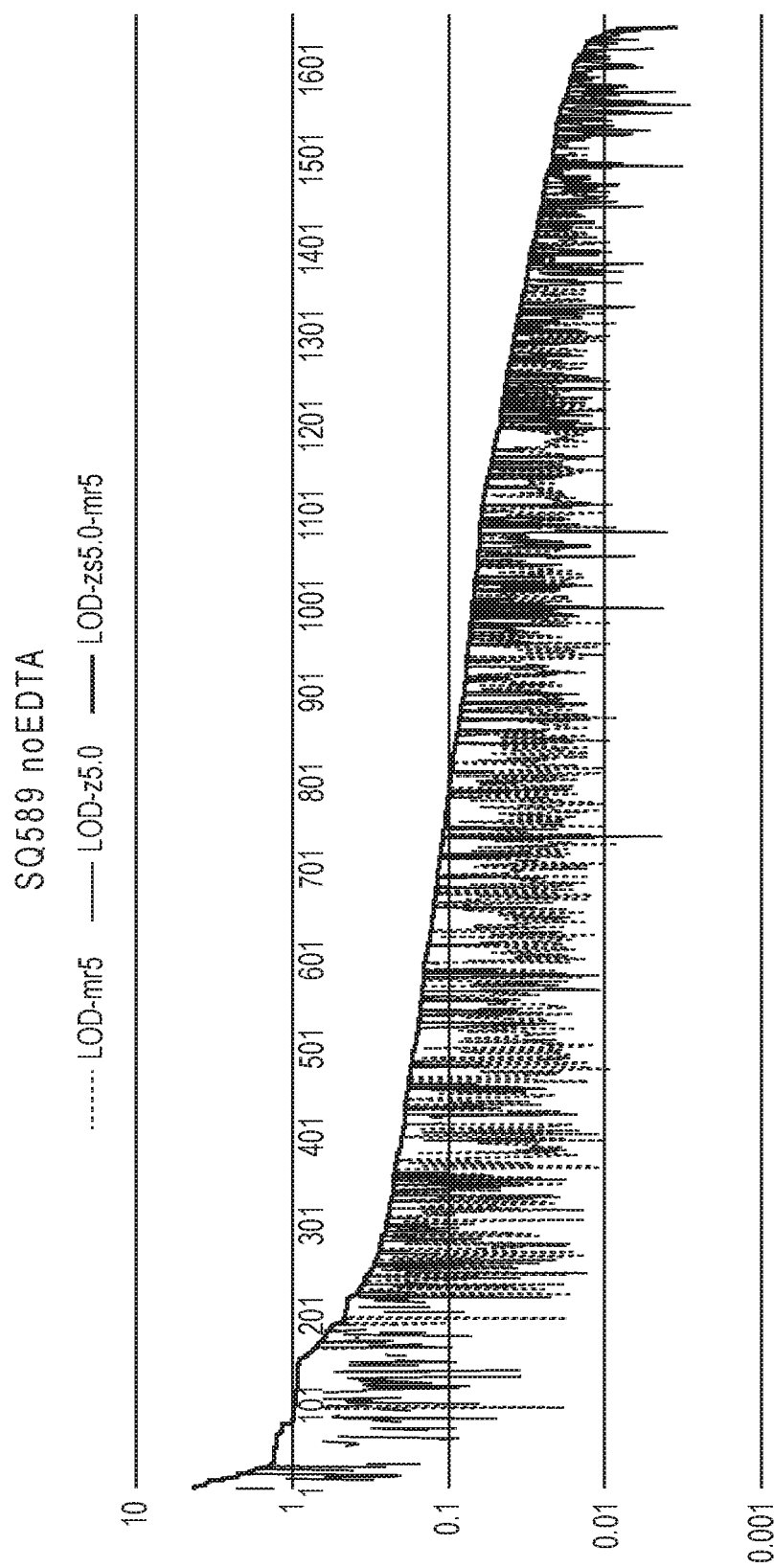
FIG. 42 is a graph showing the limit of detection for single nucleotide variants in a plasma sample using three different methods described in Experiment 23.

For the analysis of a tumor sample shown in FIG. 41, the mean limit of detection was 0.36%, and the median limit of detection was 0.28%. The number of DOR limited (gray lines) SNVs was 934. The number of error rate limited (orange lines) SNVs was 738.

For the analysis of cDNA in a plasma sample shown in FIG. 42, the mean limit of detection was 0.24%, and the median limit of detection was 0.09%. The number of DOR limited (gray lines) SNVs was 732. The number of error rate limited (orange lines) SNVs was 921.

Experiment 24

This example illustrates the detection of CNVs and SNVs from the same single cell. The following primer libraries were used a library of ~28,000 primers for detecting CNVs, a library of ~3,000 primers for detecting CNVs, and library of primers for detecting SNVs. For analysis of a single cell, cells were serial diluted until there were 3 or 4 cells per droplet. An individual cell was pipetted and placed into a PCR tube. The cell was lysed using Protease K, salt, and DTT using the following thermocycling conditions: 56° C. for 20 minutes, 95° C. for 10 minutes, and then a 4° C. hold. For analysis of genomic DNA, DNA from the same cell line as the analyzed single cell was either purchased or obtained by growing the cells and extracting the DNA.

For amplification with the library of ~28,000 primers, the following PCR conditions were used a 40 uL reaction volume, 7.5 nM of each primer, and 2× master mix (MM). In some embodiments QIAGEN Multiplex PCR Kit is used for the master mix (QIAGEN catalog No. 206143; see, e.g., information available at the world wide web at qiagen.com/products/catalog/assay-technologies/end-point-pcr-and-rt-pcr-reagents/qiagen-multiplex-pcr-kit, is which is hereby incorporated by reference in its entirety). The kit includes 2×QIAGEN Multiplex PCR Master Mix (providing a final concentration of 3 mM $MgCl_2$, 3×0.85 ml), 5× Q-Solution (1×2.0 ml), and RNase-Free Water (2×1.7 ml). The QIAGEN Multiplex PCR Master Mix (MM) contains a combination of KCl and $(NH_4)_2SO_4$ as well as the PCR additive, Factor MP, which increases the local concentration of primers at the template. Factor MP stabilizes specifically bound primers, allowing efficient primer extension by, e.g., HotStarTaq DNA Polymerase HotStarTaq DNA Polymerase is a modified form of iaq DNA polymerase and has no polymerase activity at ambient temperatures. The following thermocycling conditions were used for the first round of PCR: 95° C. for 10 minutes; 25 cycles of 96° C. for 30 seconds, 65° C. for 29 minutes, and 72° C. for 30 seconds; and then 72° C. for 2 minutes, and a 4° C. hold. For the second round of PCR a 10 ul reaction volume, 1×MM, and 5 nM of each primer was used. The following thermocycling conditions were used: 95° C. for 15 minutes; 25 cycles of 94° C. for 30 seconds, 65° C. for 1 minute, 60° C. for 5 minutes, 65° C. for 5 minutes, and 72° C. for 30 seconds; and then 72° C. for 2 minutes, and a 4° C. hold.

For the library of ~3,000 primers, exemplary reaction conditions include a 10 ul reaction volume, 2× MM, 70 mM TMAC, and 2 nM primer of each primer. For the library of primers for detecting SNVs, exemplary reaction conditions include a 10 ul reaction volume, 2× MM, 4 mM EDTA, and 7.5 nM primer of each primer. Exemplary thermocycling conditions include 95° C. for 15 minutes, 20 cycles of 94° C. for 30 seconds, 65° C. for 15 minutes, and 72° C. for 30 seconds; and then 72° C. for 2 minutes, and a 4° C. hold.

The amplified products were barcoded. One run of sequencing was performed with an approximately equal number of reads per sample.

Figure 43A:
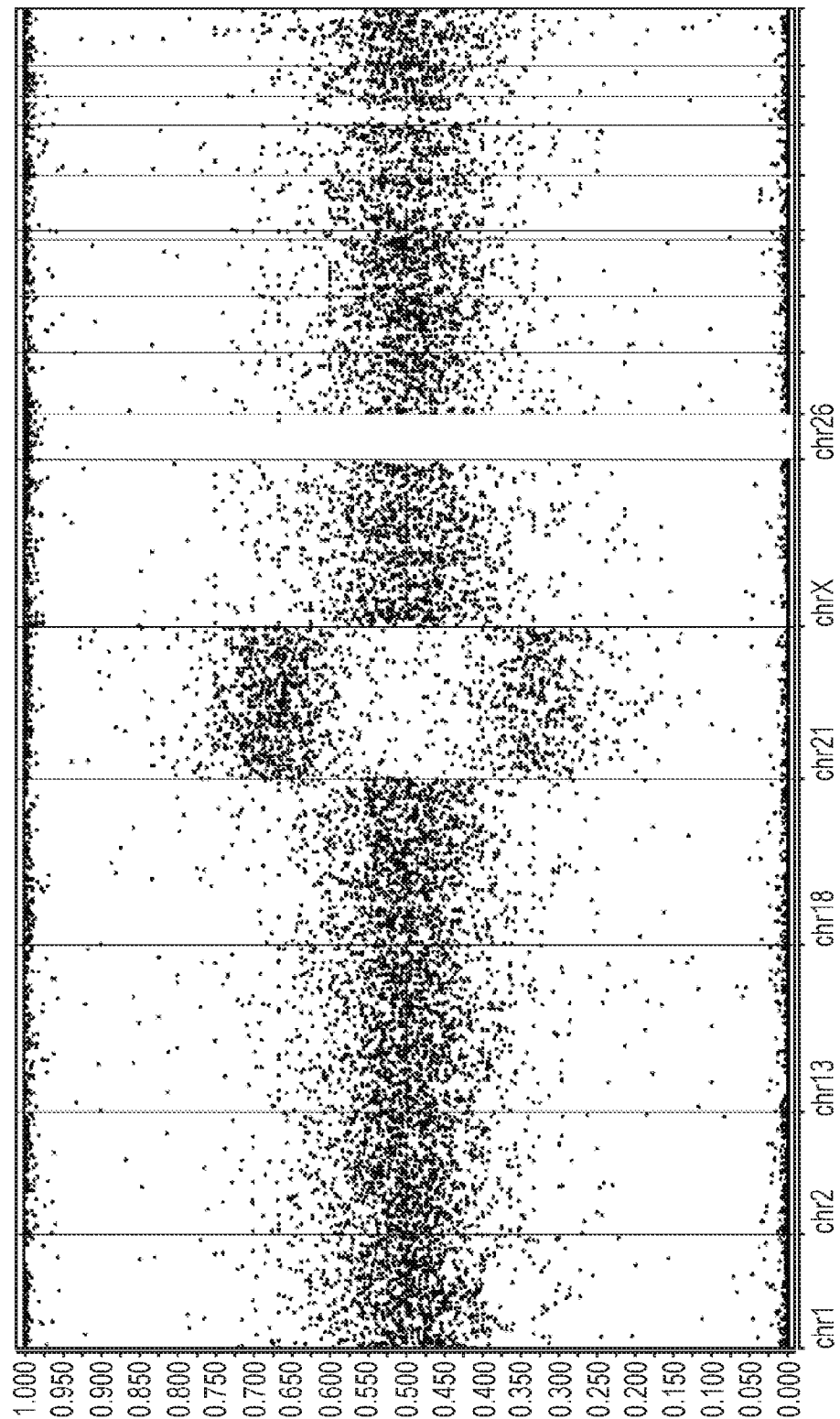
FIGS. 43A and 43B are graphs of the analysis of genomic DNA (FIG. 43A) or DNA from a single cell (FIG. 43B) using a library of approximately 28,000 primers designed to detect CNVs. The presence of two central bands instead of one central band indicates the presence of a CNV. The x-axis represents the linear position of the SNPs, and the y-axis indicates the fraction of A allele reads out of the total reads.
Figure 43B:
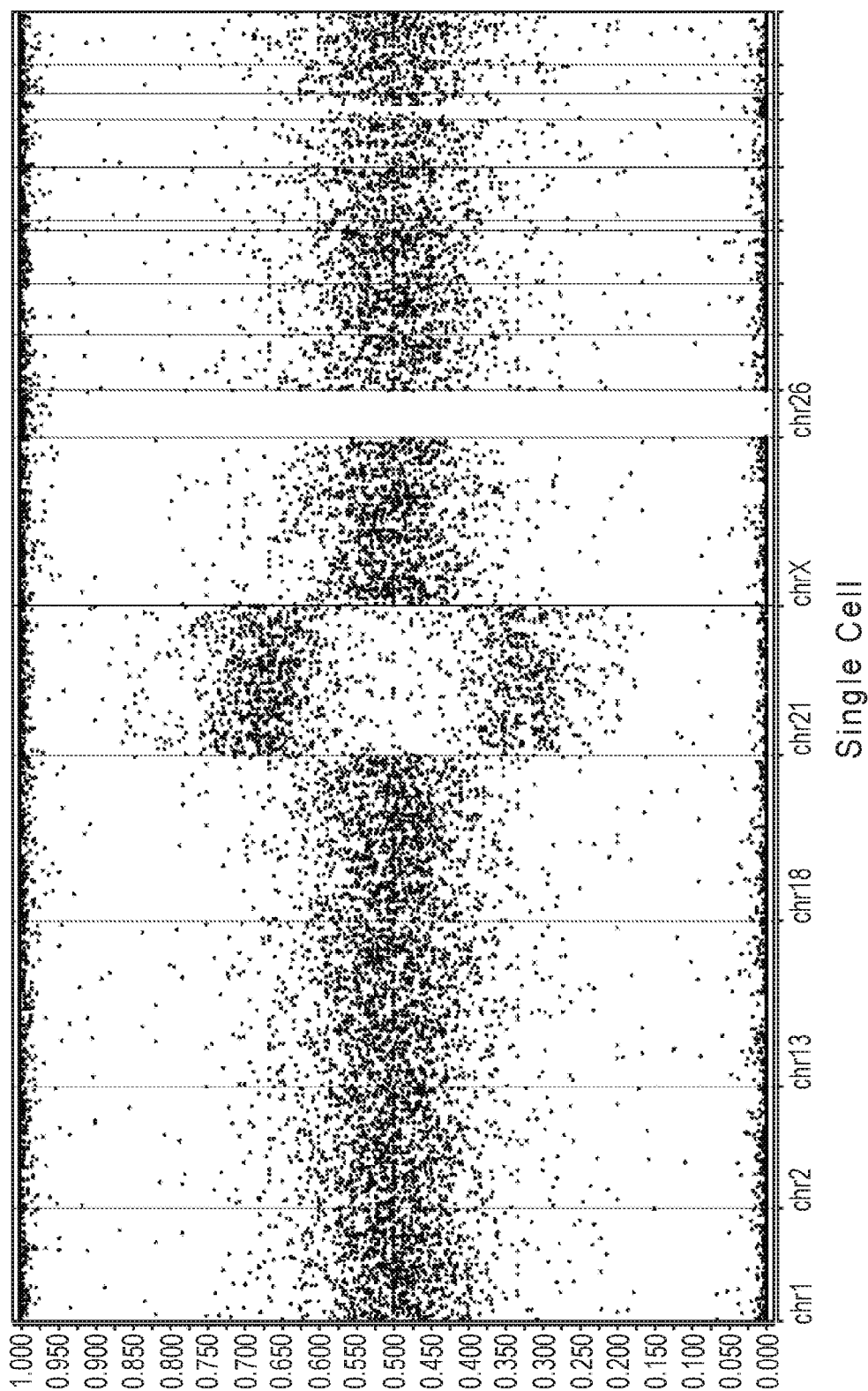

FIGS. 43A and 43B show results from analysis of genomic DNA (FIG. 43A) or DNA from a single cell (FIG. 43B) using a library of approximately 28,000 primers designed to detect CNVs. Approximately 4 million reads were measured per sample. The presence of two central bands instead of one central band indicates the presence of a CNV. For three samples of DNA from a single cell, the percent of mapped reads was 89.9%, 94.0%, and 93.4%, respectively. For two samples of genomic DNA the percent of mapped reads was 99.1% for each sample.

Figure 44A:
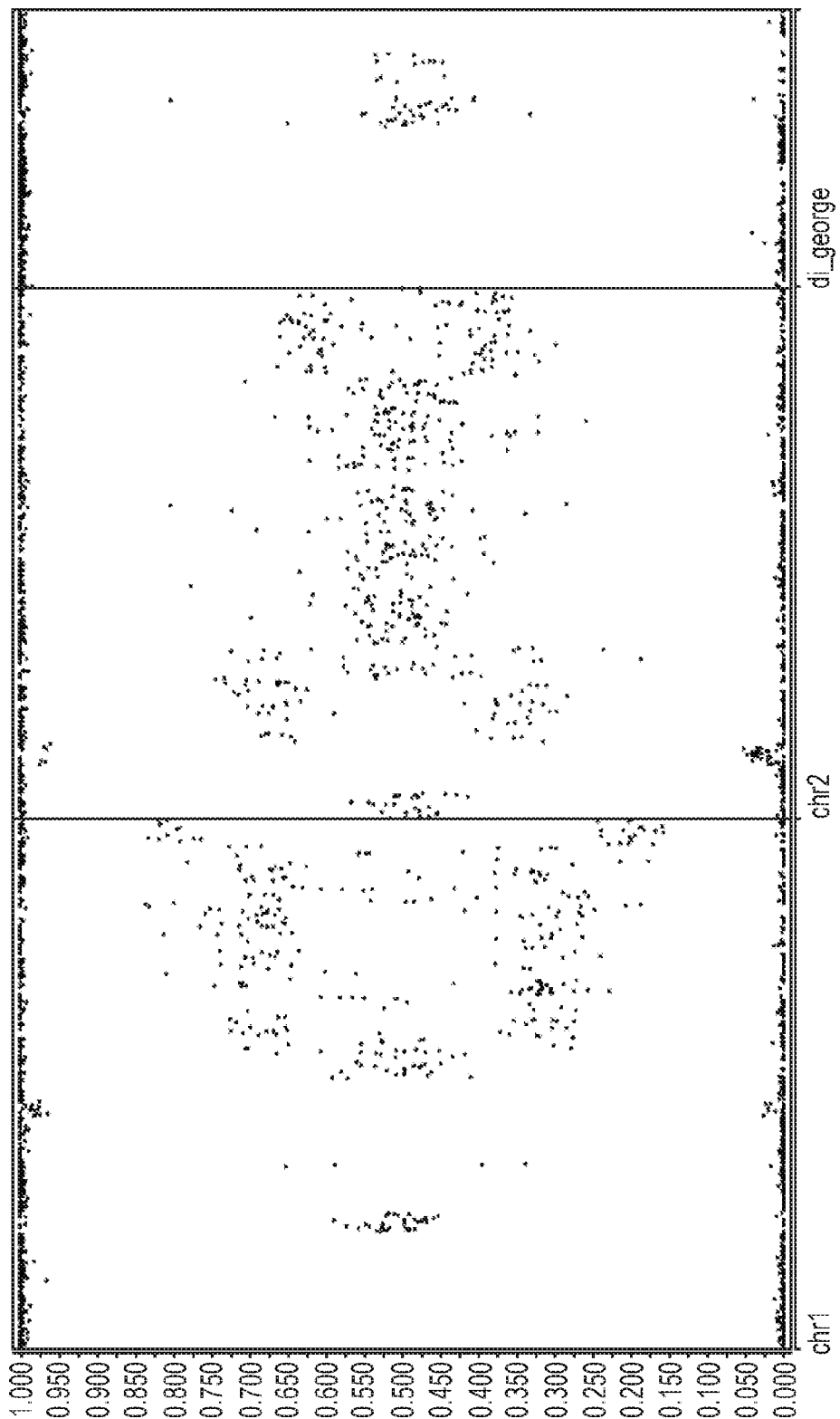
FIGS. 44A and 44B are graphs of the analysis of genomic DNA (FIG. 44A) or DNA from a single cell (FIG. 44B) using a library of approximately 3,000 primers designed to detect CNVs. The presence of two central bands instead of one central band indicates the presence of a CNV. The x-axis represents the linear position of the SNPs, and the y-axis indicates the fraction of A allele reads out of the total reads.
Figure 44B:
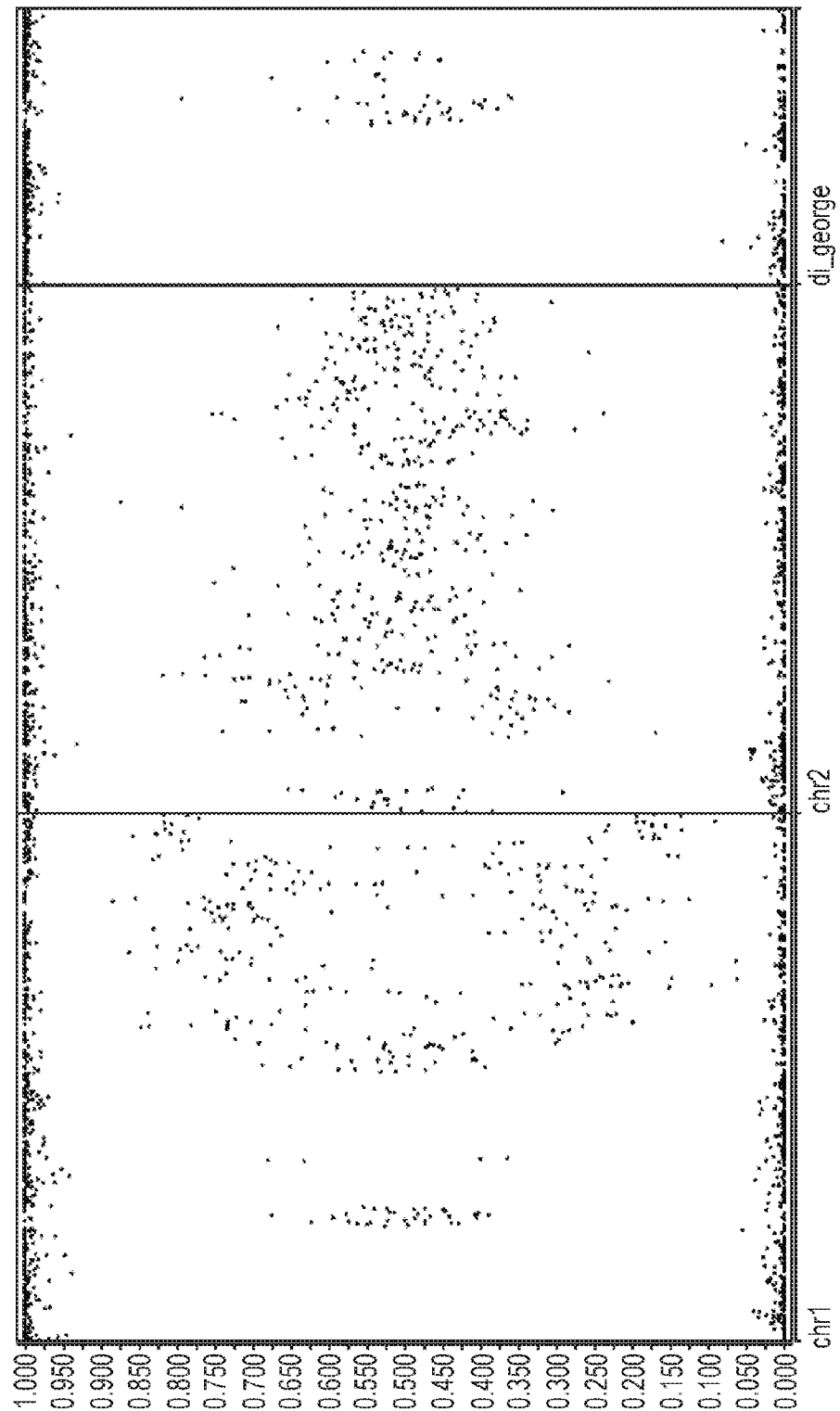
Figure 45:
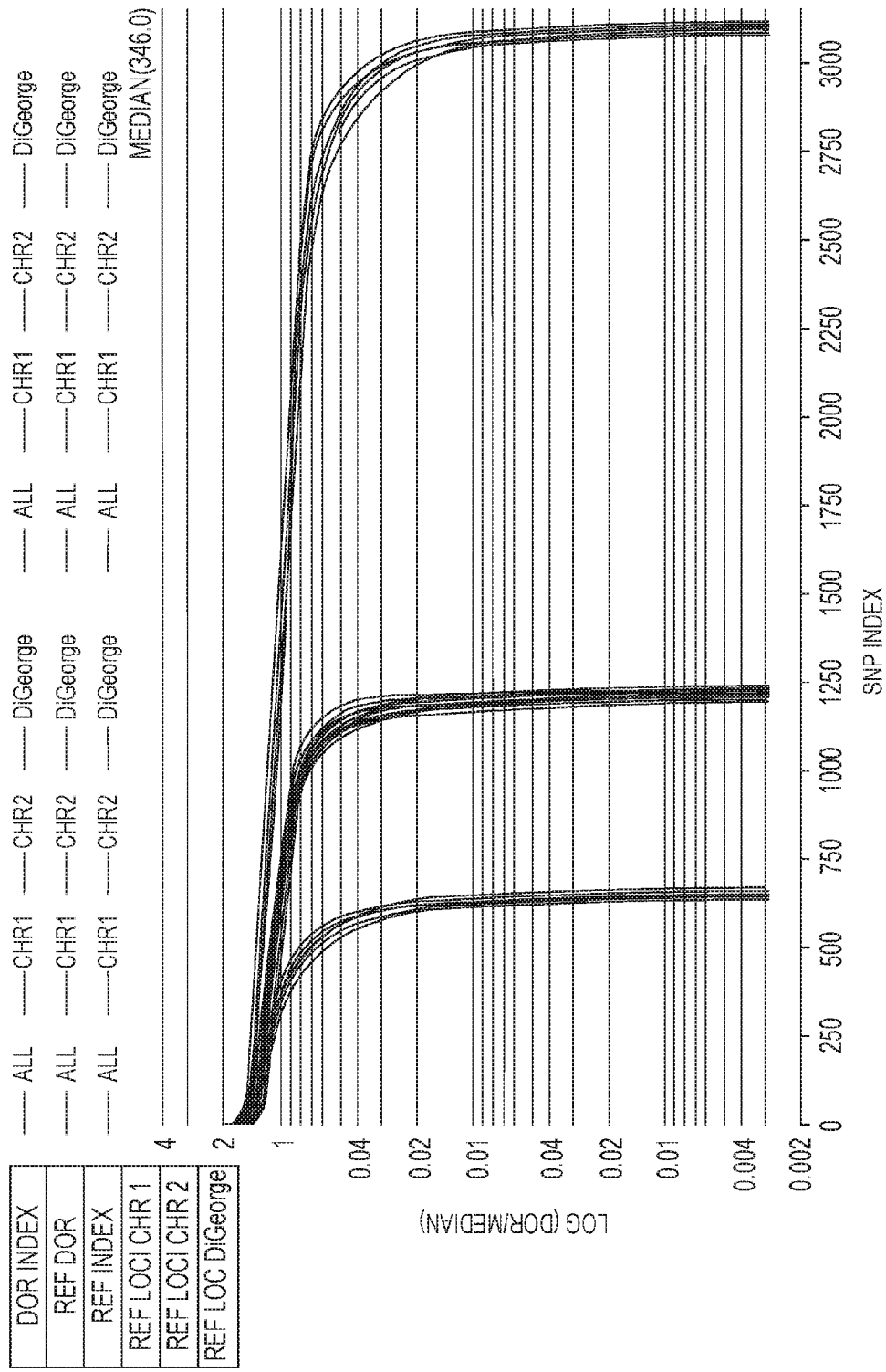
FIG. 45 is a graph illustrating the uniformity in depth of read (DOR) for these ~3,000 loci.

FIGS. 44A and 44B show results from analysis of genomic DNA (FIG. 44A) or DNA from a single cell (FIG. 44B) using a library of approximately 3,000 primers designed to detect CNVs. Approximately 1.2 million reads were measured per sample. The presence of two central bands instead of one central band indicates the presence of a CNV. For three samples of DNA from a single cell, the percent of mapped reads was 98.2%, 98.2%, and 97.9%, respectively. For two samples of genomic DNA the percent of mapped reads was 98.8% for each sample. FIG. 45 illustrates the uniformity in DOR for these ~3,000 loci.

For calling SNVs, the call percent for true positive mutations was similar for DNA from a single cell and genomic DNA. A graph of call percent for true positive mutations for single cells on the y-axis versus that for genomic DNA on the x-axis yielded a curve fit of $y=1.0076x-0.3088$ with $R^2=0.9834$. FIG. 46 shows similar error call metrics for genomic DNA and DNA from a single cell. FIG. 47 shows that the error rate for detecting transition mutations was greater than for detecting transversion mutations, indicating it may be desirable to select transversion mutations for detection rather than transition mutations when possible. In some embodiments, at least 50, 60, 70, 80, 90, 95, 96, 98, 99, or 100% of the SNVs tested for are transversion mutations rather than transition mutations.

Experiment 25

The following is an example of multiplex PCR conditions in which the annealing temperature is significantly higher than the average or maximum melting ($T_m$) of the primers in the library. A 3,168-plex reaction was performed with 3,168 primer pairs to 3,168 different target loci. For the PCR amplification a 20 ul total volume was used with 2 nM of each primer (3,168 pairs of forward and reverse primers), 70 mM TMAC (tetra-methyl ammonium chloride), and 7 ul library DNA or genomic DNA. The following thermocycling conditions were used: 95° C. for 10 minutes and then 25 cycles of 96° C. for 30 seconds, 65° C. for 20 minutes (this annealing temperature is higher than the $T_m$ of the primers, listed above), and 72° C. for 30 seconds. Then, 72° C. for 2 minutes and a 4° C. hold were used.

The minimum $T_m$ (the lowest numerical value for the $T_m$ for any of the primers) for this primer library is 54.0° C. The maximum $T_m$ (the highest numerical value for the $T_m$ for any of the primers) for this primer library is 60.36° C. The average $T_m$ (average value of the $T_m$ values of the primers) for this primer library is 55.25° C. These $T_m$ values were calculated using the following exemplary method for calculating $T_m$ values. This method is used by the Primer3 program (the worldwide web at primer3.sourceforge.net, which is hereby incorporated by reference in its entirety) to calculate $T_m$ values. In some embodiments, one or more of the following conditions are assumed for this calculation: temperature: of 60.0° C., primer concentration of 100 nM, and/or salt concentration of 100 mM. In some embodiments, other conditions are assumed for this calculation, such as the conditions that will be used for multiplex PCR with the library.

$$Tm = deltaH/(deltaS + R*\ln(C/4))$$

Below is documentation from the Primer3 program for its Tm calculations; PRIMER_TM_FORMULA (int; default 0) specifies details of melting temperature calculation. This is new in version 1.1.0, and added by Maido Remm and Triinu Koressaar (the world wide web at primer3.ut.ee/primer3web_help.htm#PRIMER_TM_FORMULA, which is hereby incorporated by reference in its entirety). A value of 0 directs primer3 to a backward compatible calculation (in other words, the only calculation available in previous version of primer3). This backward compatible calculation uses the table of thermodynamic parameters in the paper (Breslauer K J et al. (1986) "Predicting DNA duplex stability from the base sequence" *Proc Natl Acad Sci* 83, 4746-50, dx.doi.org/10.1073/pnas 83.11.3746, which is hereby incorporated by reference in its entirety), and the method in the paper (Rychlik W, Spencer W J and Rhoads R E (1990) "Optimization of the annealing temperature for DNA amplification in vitro", *Nucleic Acids Res* 18:6409-12, dx.doi.org/10.1093/nar/18.21.6409, which is hereby incorporated by reference in its entirety).

A value of 1 (which is recommended) directs primer3 to use the table of thermodynamic values and the method for melting temperature calculation suggested in the following paper (SantaLucia J R (1998) "A unified view of polymer, dumbbell and oligonucleotide DNA nearest-neighbor thermodynamics", *Proc Natl Acad Sci* 95:1460-65, dx.doi.org/10.1073/pnas.95.4.1460, which is hereby incorporated by reference in its entirety). The tag PRIMER_SALT_CORRECTIONS can be used to specify the salt correction method for melting temperature calculation.

The following is an example of calculating the melting temperature of an oligo with PRIMER_TM_FORMULA=1 and PRIMER_SALT_CORRECTIONS=1 recommended values for primer=CGTGACGTGACGGACT.

Using default salt and DNA concentrations gives $$Tm = deltaH/(deltaS + R*\ln(C/4))$$

where R is the gas constant (1.987 cal/K mol) and C is the DNA concentration.

$$deltaH(\text{predicted}) = dH(CG) + dH(GT) + dH(TG) + \ldots + dH(CT) +$$
$$dH(\text{init. w. term. } GC) + dH(\text{init. w. term. } AT)$$
$$= -10.6 + (-8.4) + (-8.5) + \ldots + (-7.8) +$$
$$0.1 + 2.3$$
$$= -128.8 \text{ kcal/mol}$$

where 'init.w.term GC' and 'init.w.term AT' are two initiation parameters for duplex formation: 'initiation with terminal GC' and 'initiation with terminal AT.'

$$deltaS(\text{predicted}) = dS(CG) + dS(GT) + dS(TG) + \ldots + dS(CT) +$$
$$dS(\text{init. w. term. } GC) + dS(\text{init. w. term. } AT)$$
$$= -27.2 + (-22.4) + (-22.7) + \ldots + (-21.0) + (-2.8) + 4.1$$
$$= -345.2 \text{ cal/k} * \text{mol}$$

$$deltaS(\text{salt corrected}) = deltaS(\text{predicted}) + 0.368 * 15(NN \text{ pairs}) *$$
$$\ln(0.05M \text{ monovalent cations})$$
$$= -361.736$$

$$Tm = -128.800/(-361.736 + 1.987*\ln((5*10^{(-8)})/4))$$
$$= 323.704K$$

$$Tm(C) = 323.704 - 273.15 = 50.554C$$

ADDITIONAL APPLICATIONS

Because this method utilizes targeted amplification, it is uniquely poised to detect submicroscopic anomalies, such as microdeletions and microduplications. Although non-targeted methods like MPSS have been shown to detect the DiGeorge microdeletion syndrome, this required a sufficiently high level of genomic coverage so as to make the approach unfeasible. This is because non-targeted amplification will be several orders of magnitude less efficient on submicroscopic regions, as very small fraction of the sequencing reads will be informative. Additionally, the fact that the currently available methods have trouble accurately identifying ploidy state for the sex chromosomes suggests that they will also encounter variable amplification problems on smaller chromosomal segments.

Similarly, SNP based methods can detect UPD disorders, which are copy number-neutral anomalies that will not be detected by either the current noninvasive methods that rely on counting or the traditional invasive methods like amniocentesis and CVS that rely on cytogenetic karyotyping and/or fluorescence in siitu hybridization. This is because SNP-based methods are uniquely able to distinguish individual haplotypes, whereas the clinically available MPSS-based and targeted methods amplify non-polymorphic loci and are thus unable to determine, for example, whether the chromosomes-of-interest originate from the same parent. This means that these microdeletion/microduplication and UPD syndromes, including Prader-Willi. Angelman, and Beckwith-Wiedemann syndromes, are generally not diagnosed prenatally, and are often initially misdiagnosed postnatally. This significantly delays therapeutic intervention. Additionally, because this method targets SNPs, this method will also facilitate parental haplotype reconstruction, allowing for detection of fetal inheritance of individual disease-linked loci (Kitzman J O, Snyder M W, Ventura M, et al. Noninvasive whole-genome sequencing of a human fetus. *Sci Transl Med* 2012; 4:137ra76, which is hereby incorporated by reference in its entirety).

The results presented here confirm the expanded scope of this method for identifying prenatal aneuploidy. Specifically, by amplifying and sequencing 19,488 SNPs, this method is able to determine copy number at chromosomes 13, 18, 21, X, and Y, and is uniquely expected to detect other chromosomal abnormalities, such as triploidy and UPD, that are not detected by any other clinically available non-invasive method. The increased clinical coverage and powerful sample-specific calculated accuracies suggest that this method may offer a viable adjunct to invasive testing for detecting fetal chromosomal aneuploidies.

All patents, patent applications, and published references cited herein are hereby incorporated by reference in their entirety. While the methods of the present disclosure have been described in connection with the specific embodiments thereof, it will be understood that it is capable of further modification. Furthermore, this application is intended to cover any variations, uses, or adaptations of the methods of the present disclosure, including such departures from the present disclosure as come within known or customary practice in the art to which the methods of the present disclosure pertain, and as fall within the scope of the appended claims. For example, any of the methods disclosed herein for DNA can be readily adapted for RNA by including a reverse transcription step to convert the RNA into DNA. Examples that use polymorphic loci for illustration can be readily adapted for the amplification of nonpolymorphic loci if desired. Any of the methods disclosed herein can be used with a low level of multiplexing if desired (such as with less than 1,000, 750, 500, 250, 100, 75, 50, 25, or 10 different primers or different primer pairs to different target loci).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10351906B2). An electronic copy of the "Sequence Listing" will also be available from the USPTO upon request and payment of the fee set forth in 37 CFR 1.19(b)(3).

What is claimed is:

1. A method of amplifying target loci in a nucleic acid sample, the method comprising:
   (a) contacting a sample comprising target loci with a library of at least 50 non-immobilized, non-identical PCR primers that simultaneously hybridize to at least 50 non-identical target loci to produce a reaction mixture; and
   (b) subjecting the reaction mixture to PCR conditions to produce amplified products comprising target amplicons; wherein an annealing temperature for the PCR conditions is greater than a melting temperature for at least 95% of the at least 50 non-identical PCR primers; wherein a length of an annealing step of the PCR conditions is greater than 5 minutes; and wherein at least 50 non-identical target loci are simultaneously amplified.

2. The method of claim 1, wherein the lengths of the target amplicons are between 30 and 200 nucleotides and wherein the concentration of each primer in the library is less than 20 nM.

3. The method of claim 1, wherein the annealing temperature is 1 to 15° C. greater than the highest melting temperature of at least 95% of the at least 50 non-identical primers.

4. The method of claim 1, wherein the library comprises at least 1000 non-immobilized, non-identical primer pairs that simultaneously hybridize to at least 1000 non-identical target human loci, wherein the annealing temperature for the PCR conditions is greater than a melting temperature of at least 90% of the at least 1000 non-identical primers, and wherein the at least 1000 non-identical target loci are simultaneously amplified.

5. The method of claim 1, wherein the length of the annealing step of the PCR conditions is between 10 and 60 minutes.

6. The method of claim 1, wherein the AG values for each possible combination of two primers in the library are all equal to or greater than −5 kcal/mol.

7. The method of claim 1, further comprising performing universal amplification on nucleic acids in the sample prior to step (a), and further comprising sequencing the amplified products comprising target amplicons after step (b).

8. The method of claim 1, wherein at least 90% of the amplified products are target amplicons, and wherein the range of melting temperatures of the at least 50 non-identical primers is less than 5° C.

9. The method of claim 1, wherein at least 90% of the target loci are amplified and wherein less than 20% of the amplified products are primer dimers.

10. A method of amplifying target loci in a nucleic acid sample, the method comprising:
    (a) contacting a sample comprising target loci with a library of at least 50 non-immobilized, non-identical PCR primers that simultaneously hybridize to at least 50 non-identical target loci to produce a reaction mixture, wherein the sample is derived from blood; and
    (b) subjecting the reaction mixture to PCR conditions to produce amplified products comprising target amplicons, wherein the annealing temperature for the PCR conditions is greater than a melting temperature for at least 95% of the at least 50 non-identical PCR primers, wherein the melting temperature is a calculated temperature at which one-half of a DNA duplex of a primer and its perfect complement is predicted to dissociate and become single stranded DNA, wherein the length of an annealing step of the PCR conditions is between 5 and 60 minutes, wherein the length of the target amplicons is between 30 and 200 nucleotides, and wherein at least 50 non-identical target human loci are simultaneously amplified.

11. The method of claim 10, wherein the sample is from an individual suspected of having cancer.

12. The method of claim 10, wherein the sample comprises maternal DNA from the pregnant mother of a fetus and fetal DNA.

13. The method of claim 10, wherein the melting temperature of at least 90% of the primers is between 54 and 60.5, inclusive, and the annealing temperature is between 60° C. and 70° C., inclusive.

14. The method of claim 10, wherein the annealing temperature is 1 to 10° C. greater than the highest melting temperature of at least 95% of the at least 50 non-identical primers.

15. The method of claim 10, wherein the library comprises between 10,000 and 100,000 non-immobilized, non-identical primers or primer pairs that simultaneously hybridize to the at least 10,000 and 100,000 non-identical target human loci, wherein the annealing temperature for the PCR conditions is greater than a melting temperature of at least 90% of the between 10,000 and 100,000 non-identical primers, and wherein between 10,000 and 100,000 non-identical target human loci are simultaneously amplified.

16. A method of amplifying target loci in a nucleic acid sample, the method comprising:
   (a) contacting a sample comprising target loci with a library of between 10,000 and 100,000 non-immobilized, non-identical PCR primers or primer pairs that simultaneously hybridize to between 10,000 and 100,000 non-identical target loci to produce a reaction mixture, wherein the concentration of each primer in the reaction mixture is less than 20 nM; and
   (b) subjecting the reaction mixture to PCR conditions to produce amplified products comprising target amplicons, wherein an annealing temperature for the PCR conditions is greater than a melting temperature for at least 95% of primers of the 10,000 to 100,000 non-identical PCR primers or primer pairs, wherein the length of an annealing step of the PCR conditions is between 5 and 60 minutes, and wherein between 10,000 and 100,000 non-identical target loci are simultaneously amplified.

17. The method of claim 16, wherein the melting temperature of at least 90% of primers of the PCR primers or primer pairs is between 50° C. and 60.5° C., inclusive, and the annealing temperature is between 60° C. and 70° C., inclusive.

18. The method of claim 16, wherein the length of at least 95% of primers of the PCR primers or primer pairs is between 15 to 40 nucleotides, inclusive, the length of at least 95% of the target amplicons is between 30 and 200 nucleotides, and the concentration of at least 95% of primers of the PCR primers or primer pairs is less than 10 nm.

19. The method of claim 16, wherein the annealing temperature is 1 to 10° C. greater than the highest melting temperature of at least 95% of primers of the PCR primers or primer pairs.

20. The method of claim 16, wherein the annealing temperature is at least 3° C. greater than the highest melting temperature of at least 90% of primers of the PCR primers or primer pairs.

* * * * *